United States Patent
Leabman

(10) Patent No.: US 12,166,363 B2
(45) Date of Patent: Dec. 10, 2024

(54) SYSTEM AND METHODS OF USING ELECTROMAGNETIC WAVES TO WIRELESSLY DELIVER POWER TO SECURITY CAMERAS AND ADJUSTING WIRELESS DELIVERY OF POWER TO THE SECURITY CAMERAS AS THEY MOVE

(71) Applicant: Energous Corporation, San Jose, CA (US)

(72) Inventor: Michael A. Leabman, San Ramon, CA (US)

(73) Assignee: Energous Corporation, San Jose, CA (US)

( * ) Notice: Subject to any disclaimer, the term of this patent is extended or adjusted under 35 U.S.C. 154(b) by 22 days.

(21) Appl. No.: 17/987,818

(22) Filed: Nov. 15, 2022

(65) Prior Publication Data

US 2023/0208198 A1 Jun. 29, 2023

Related U.S. Application Data

(63) Continuation of application No. 17/242,194, filed on Apr. 27, 2021, now Pat. No. 11,502,551, which is a
(Continued)

(51) Int. Cl.
*H02J 50/20* (2016.01)
*A61B 8/00* (2006.01)
(Continued)

(52) U.S. Cl.
CPC ............ *H02J 50/20* (2016.02); *A61B 8/56* (2013.01); *H02J 50/80* (2016.02); *H05B 3/342* (2013.01);
(Continued)

(58) Field of Classification Search
CPC ....................................................... H02J 50/20
(Continued)

(56) References Cited

U.S. PATENT DOCUMENTS

| 787,412 A | 4/1905 | Tesla |
| 2,811,624 A | 10/1957 | Haagensen |

(Continued)

FOREIGN PATENT DOCUMENTS

| CN | 1829999 A | 9/2006 |
| CN | 101401312 A | 4/2009 |

(Continued)

OTHER PUBLICATIONS

Energous Corp., IPRP, PCT/US2014/037072, Nov. 10, 2015, 6 pgs.
(Continued)

*Primary Examiner* — Joseph Chang
(74) *Attorney, Agent, or Firm* — Morgan, Lewis & Bockius LLP

(57) ABSTRACT

An example system includes a wireless-power transmitter configured to emit a first set of one or more radio frequency (RB) signals and a security camera coupled to a wireless-power receiver. The wireless-power receiver is configured to receive the first set of one or more RF signals. The security camera includes at least one component for converting energy from the first set of one or more RF signals into usable power to power the security camera. The usable power is a primary source of power for the security camera. The example system can also include a processor in communication with the wireless-power transmitter configured to, in accordance with a determination that the security camera has moved relative to the wireless-power transmitter, adjust the wireless-power transmitter to emit a second set of one or more RF signals from the wireless-power transmitter to continue providing usable power to the security camera.

17 Claims, 311 Drawing Sheets

Related U.S. Application Data continuation of application No. 16/258,358, filed on Jan. 25, 2019, now Pat. No. 10,992,185, which is a continuation-in-part of application No. 14/584,220, filed on Dec. 29, 2014, now Pat. No. 10,291,055, and a continuation-in-part of application No. 13/908,809, filed on Jun. 3, 2013, now Pat. No. 10,206,185, and a continuation-in-part of application No. 14/336,963, filed on Jul. 21, 2014, now Pat. No. 10,381,880, and a continuation-in-part of application No. 13/946,082, filed on Jul. 19, 2013, now Pat. No. 10,211,680, and a continuation-in-part of application No. 15/820,335, filed on Nov. 21, 2017, now Pat. No. 10,291,294, which is a continuation of application No. 14/584,364, filed on Dec. 29, 2014, now Pat. No. 9,825,674, which is a continuation-in-part of application No. 14/286,243, filed on May 23, 2014, now Pat. No. 9,793,758, said application No. 15/820,335 is a continuation-in-part of application No. 14/584,268, filed on Dec. 29, 2014, now Pat. No. 10,141,768, which is a continuation-in-part of application No. 13/908,760, filed on Jun. 3, 2013, now abandoned, said application No. 15/820,335 is a continuation-in-part of application No. 14/584,484, filed on Dec. 29, 2014, now Pat. No. 10,148,097, which is a continuation-in-part of application No. 14/075,376, filed on Nov. 8, 2013, now abandoned, said application No. 15/820,335 is a continuation-in-part of application No. 14/584,449, filed on Dec. 29, 2014, now Pat. No. 9,941,707, which is a continuation-in-part of application No. 13/946,065, filed on Jul. 19, 2013, now abandoned, said application No. 16/258,358 is a continuation-in-part of application No. 16/238,478, filed on Jan. 2, 2019, now abandoned, which is a continuation of application No. 14/586,254, filed on Dec. 30, 2014, now Pat. No. 10,205,239, which is a continuation-in-part of application No. 14/272,265, filed on May 7, 2014, now Pat. No. 10,218,227, said application No. 16/258,358 is a continuation-in-part of application No. 15/860,592, filed on Jan. 2, 2018, now Pat. No. 10,298,133, which is a continuation of application No. 14/584,901, filed on Dec. 29, 2014, now Pat. No. 9,859,797, which is a continuation-in-part of application No. 14/272,247, filed on May 7, 2014, now abandoned, said application No. 16/258,358 is a continuation-in-part of application No. 16/027,182, filed on Jul. 3, 2018, now Pat. No. 11,233,425, which is a continuation of application No. 14/748,043, filed on Jun. 23, 2015, now Pat. No. 10,014,728, which is a continuation of application No. 14/584,964, filed on Dec. 29, 2014, now Pat. No. 9,876,394, which is a continuation-in-part of application No. 14/272,280, filed on May 7, 2014, now abandoned, said application No. 16/258,358 is a continuation-in-part of application No. 14/272,066, filed on May 7, 2014, now Pat. No. 10,211,682, and a continuation-in-part of application No. 14/585,509, filed on Dec. 30, 2014, now Pat. No. 10,223,717, which is a continuation-in-part of application No. 14/286,232, filed on May 23, 2014, now abandoned, said application No. 16/258,358 is a continuation-in-part of application No. 14/586,509, filed on Dec. 30, 2014, now Pat. No. 10,243,414, which is a continuation-in-part of application No. 14/272,066, filed on May 7, 2014, now Pat. No. 10,211,682, said application No. 14/585,509 is a continuation-in-part of application No. 14/272,039, filed on May 7, 2014, now Pat. No. 10,141,791, said application No. 16/258,358 is a continuation-in-part of application No. 16/115,495, filed on Aug. 28, 2018, now Pat. No. 10,523,058, which is a continuation of application No. 14/757,568, filed on Dec. 24, 2015, now Pat. No. 10,063,105, which is a continuation-in-part of application No. 14/861,285, filed on Sep. 22, 2015, now Pat. No. 9,948,135, which is a continuation-in-part of application No. 14/585,341, filed on Dec. 30, 2014, now Pat. No. 9,812,890, which is a continuation-in-part of application No. 13/939,706, filed on Jul. 11, 2013, now Pat. No. 9,143,000, said application No. 16/258,358 is a continuation-in-part of application No. 15/053,124, filed on Feb. 25, 2016, now Pat. No. 10,270,261, which is a continuation-in-part of application No. 14/861,285, filed on Sep. 22, 2015, now Pat. No. 9,948,135, and a continuation-in-part of application No. 14/856,337, filed on Sep. 16, 2015, now Pat. No. 10,312,715, said application No. 16/258,358 is a continuation-in-part of application No. 15/053,292, filed on Feb. 25, 2016, now Pat. No. 10,291,056, which is a continuation-in-part of application No. 14/861,285, filed on Sep. 22, 2015, now Pat. No. 9,948,135, and a continuation-in-part of application No. 14/856,337, filed on Sep. 16, 2015, now Pat. No. 10,312,715, said application No. 16/258,358 is a continuation-in-part of application No. 16/190,071, filed on Nov. 13, 2018, now abandoned, which is a continuation of application No. 15/060,167, filed on Mar. 3, 2016, now Pat. No. 10,128,699, which is a continuation-in-part of application No. 14/856,337, filed on Sep. 16, 2015, now Pat. No. 10,312,715, and a continuation-in-part of application No. 14/584,412, filed on Dec. 29, 2014, now Pat. No. 9,893,554, which is a continuation-in-part of application No. 14/330,939, filed on Jul. 14, 2014, now Pat. No. 10,128,693, said application No. 16/258,358 is a continuation-in-part of application No. 15/046,026, filed on Feb. 17, 2016, now Pat. No. 10,256,657, and a continuation-in-part of application No. 29/669,227, filed on Nov. 6, 2018, now Pat. No. Des. 937,203, which is a continuation of application No. 29/550,049, filed on Dec. 30, 2015, now Pat. No. Des. 832,782, said application No. 16/258,358 is a continuation-in-part of application No. 29/656,147, filed on Jul. 10, 2018, now Pat. No. Des. 851,120, which is a continuation of application No. 29/586,759, filed on Dec. 6, 2016, now Pat. No. Des. 822,701, which is a continuation of application No. 29/513,406, filed on Dec. 30, 2014, now Pat. No. Des. 773,506, said application No. 16/258,358 is a continuation-in-part of application No. 14/587,367, filed on Dec. 31, 2014, now Pat. No. 10,230,266, which is a continuation-in-part of application No. 14/173,936, filed on Feb. 6, 2014, now abandoned, said application No. 16/258,358 is a continuation-in-part of application No. 15/061,473, filed on Mar. 4, 2016, now Pat. No. 10,193,396, which is a continuation-in-part of application No. 14/748,136, filed on Jun. 23, 2015, now Pat. No. 9,882,395, which is a continuation-in-part of application No. 14/587,616, filed on Dec. 31, 2014, now Pat. No. 9,882,430, which is a continuation-in-part of application No. 14/272,124, filed on May 7, 2014, now Pat. No. 9,847,679, said application No. 16/258,358 is a continuation-in-part of application No. 15/058,714, filed on Mar. 2, 2016, now Pat. No. 10,199,835, said application No. 16/258,358 is a continuation-in-part of application No. 15/854,718, filed on Dec. 26, 2017, now Pat. No. 10,396,604, which is a continuation of application No. 14/584,324, filed on Dec. 29, 2014, now Pat. No. 9,853,458, which is a continuation-in-part of application No. 14/272,093, filed on May 7, 2014, now abandoned, said application No. 15/854,718 is a continuation of application No. 14/584,170, filed on Dec. 29, 2014, now Pat. No. 9,853,692, which is a continuation-in-part of application No. 14/286,243, filed on May 23, 2014, now Pat. No. 9,793,758, said application No. 16/258,358 is a continuation-in-part of application No. 15/961,825, filed on Apr. 24, 2018, now Pat. No. 10,992,187, which is a continuation-in-part of application No. 15/725,236, filed on Oct. 4, 2017, now abandoned, which is a continuation-in-part of application No. 13/926,055, filed on Jun. 25, 2013, now Pat. No. 10,128,695, and a continuation-in-part of application No. 14/585,484, filed on Dec. 30, 2014, now Pat. No. 10,263,432, said application No. 15/725,236 is a continuation-in-part of application No. 14/585,506, filed on Dec. 30, 2014, now Pat. No. 9,966,765, which is a continuation-in-part of application No. 13/926,055, filed on Jun. 25, 2013, now Pat. No. 10,128,695, said application No. 15/725,236 is a continuation-in-part of application No. 14/585,387, filed on Dec. 30, 2014, now Pat. No. 10,224,982, which is a continuation-in-part of application No. 13/939,506, filed on Jul. 11, 2013, now abandoned, said application No. 15/725,236 is a continuation-in-part of application No. 14/585,370, filed on Dec. 30, 2014, now Pat. No. 9,876,379, which is a continuation-in-part of application No. 13/939,655, filed on Jul. 11, 2013, now Pat. No. 9,130,397, said application No. 15/725,236 is a continuation-in-part of application No. 14/732,140, filed on Jun. 5, 2015, now abandoned, which is a continuation of application No. 13/939,655, filed on Jul. 11, 2013, now Pat. No. 9,130,397, said application No. 15/725,236 is a continuation-in-part of application No. 14/585,324, filed on Dec. 30, 2014, now Pat. No. 10,124,754, which is a continuation-in-part of application No. 13/946,128, filed on Jul. 19, 2013, now abandoned, said application No. 15/725,236 is a continuation-in-part of application No. 14/585,362, filed on Dec. 30, 2014, now abandoned, which is a continuation-in-part of application No. 13/950,536, filed on Jul. 25, 2013, now abandoned, said application No. 15/725,236 is a continuation-in-part of application No. 14/586,137, filed on Dec. 30, 2014, now Pat. No. 9,876,380, which is a continuation-in-part of application No. 14/026,747, filed on Sep. 13, 2013, now abandoned, said application No. 15/725,236 is a continuation-in-part of application No. 14/586,539, filed on Dec. 30, 2014, now Pat. No. 10,038,337, which is a continuation-in-part of application No. 14/027,446, filed on Sep. 16, 2013, now abandoned, said application No. 15/725,236 is a continuation-in-part of application No. 14/586,603, filed on Dec. 30, 2014, now abandoned, which is a continuation-in-part of application No. 14/027,468, filed on Sep. 16, 2013, now abandoned, said application No. 15/725,236 is a continuation-in-part of application No. 14/051,054, filed on Oct. 10, 2013, now Pat. No. 9,824,815, and a continuation-in-part of application No. 14/586,160, filed on Dec. 30, 2014, now Pat. No. 9,847,677, said application No. 15/725,236 is a continuation-in-part of application No. 14/585,797, filed on Dec. 30, 2014, now Pat. No. 9,893,555, which is a continuation-in-part of application No. 14/051,128, filed on Oct. 10, 2013, now abandoned, said application No. 15/725,236 is a continuation-in-part of application No. 14/585,844, filed on Dec. 30, 2014, now Pat. No. 9,899,861, which is a continuation-in-part of application No. 14/051,170, filed on Oct. 10, 2013, now abandoned, said application No. 15/725,236 is a continuation-in-part of application No. 14/069,983, filed on Nov. 1, 2013, now Pat. No. 9,882,427, and a continuation-in-part of application No. 14/586,197, filed on Dec. 30, 2014, now Pat. No. 10,090,699, said application No. 15/725,236 is a continuation-in-part of application No. 14/586,243, filed on Dec. 30, 2014, now abandoned, which is a continuation-in-part of application No. 14/095,358, filed on Dec. 3, 2013, now abandoned, said application No. 15/725,236 is a continuation-in-part of application No. 14/586,370, filed on Dec. 30, 2014, now abandoned, which is a continuation-in-part of application No. 14/103,528, filed on Dec. 11, 2013, now abandoned, said application No. 15/725,236 is a continuation-in-part of application No. 14/586,400, filed on Dec. 30, 2014, now abandoned, which is a continuation-in-part of application No. 14/104,503, filed on Dec. 12, 2013, now Pat. No. 9,252,628, said application No. 15/725,236 is a continuation-in-part of application No. 15/010,127, filed on Jan. 29, 2016, now Pat. No. 9,847,669, which is a continuation of application No. 14/104,503, filed on Dec. 12, 2013, now Pat. No. 9,252,628, said application No. 15/725,236 is a continuation-in-part of application No. 15/181,242, filed on Jun. 13, 2016, now Pat. No. 10,134,260, which is a continuation of application No. 14/586,448, filed on Dec. 30, 2014, now Pat. No. 9,368,020, which is a continuation-in-part of application No. 14/330,926, filed on Jul. 14, 2014, now abandoned, said application No. 15/725,236 is a continuation-in-part of application No. 14/585,585, filed on Dec. 30, 2014, now abandoned, which is a continuation-in-part of application No. 13/950,492, filed on Jul. 25, 2013, now Pat. No. 9,831,718, said application No. 15/725,236 is a continuation-in-part of application No. 14/584,752, filed on Dec. 29, 2014, now abandoned, which is a continuation-in-part of application No. 13/950,492, filed on Jul. 25, 2013, now Pat. No. 9,831,718, said application No. 15/725,236 is a continuation-in-part of application No. 14/584,800, filed on Dec. 29, 2014, now Pat. No. 9,859,757, which is a continuation-in-part of application No. 13/950,492, filed on Jul. 25, 2013, now Pat. No. 9,831,718, said application No. 15/725,236 is a continuation-in-part of application No. 14/587,294, filed on Dec. 31, 2014, now abandoned, and a continuation-in-part of application No. 14/587,308, filed on Dec. 31, 2014, now abandoned, and a continuation-in-part of application No. 14/069,934, filed on Nov. 1, 2013, now Pat. No. 10,224,758, said application No. 15/961,825 is a continuation-in-part of application No. 15/872,888, filed on Jan. 16, 2018, now Pat. No. 10,396,588, which is a continuation of application No. 14/584,743, filed on Dec. 29, 2014, now Pat. No. 9,871,398, which is a continuation-in-part of application No. 13/932,166, filed on Jul. 1, 2013, now abandoned, said application No. 15/961,825 is a continuation-in-part of application No. 14/585,432, filed on Dec. 30, 2014, now Pat. No. 10,211,674, which is a continuation-in-part of application No. 13/916,233, filed on Jun. 12, 2013, now abandoned, said application No. 15/961,825 is a continuation-in-part of application No. 15/729,574, filed on Oct. 10, 2017, now Pat. No. 10,498,144, which is a continuation of application No. 14/584,375, filed on Dec. 29, 2014, now Pat. No. 9,787,103, which is a continuation-in-part of application No. 13/960,522, filed on Aug. 6, 2013, now abandoned, said application No. 15/961,825 is a continuation-in-part of application No. 14/585,291, filed on Dec. 30, 2014, now Pat. No. 9,954,374, which is a continuation-in-part of application No. 14/286,129, filed on May 23, 2014, now Pat. No. 10,063,106, said application No. 15/961,825 is a continuation-in-part of application No. 14/683,437, filed on Apr. 10, 2015, now Pat. No. 10,056,782, which is a continuation of application No. 14/584,869, filed on Dec. 29, 2014, now Pat. No. 9,438,045, which is a continuation-in-part of application No. 14/272,207, filed on May 7, 2014, now abandoned, said application No. 15/961,825 is a continuation-in-part of application No. 14/587,027, filed on Dec. 31, 2014, now Pat. No. 10,291,066, which is a continuation of application No. 14/584,869, filed on Dec. 29, 2014, now Pat. No. 9,438,045, and a continuation-in-part of application No. 14/272,207, filed on May 7, 2014, now abandoned, and a continuation-in-part of application No. 14/272,287, filed on May 7, 2014, now Pat. No. 9,806,564, and a continuation-in-part of application No. 14/272,280, filed on May 7, 2014, now abandoned, and a continuation-in-part of application No. 14/272,247, filed on May 7, 2014, now abandoned, said application No. 15/961,825 is a continuation-in-part of application No. 15/806,266, filed on Nov. 7, 2017, now Pat. No. 10,305,315, which is a continuation of application No. 14/585,341, filed on Dec. 30, 2014, now Pat. No. 9,812,890, which is a continuation-in-part of application No. 13/939,706, filed on Jul. 11, 2013, now Pat. No. 9,143,000, said application No. 15/961,825 is a continuation-in-part of application No. 14/585,574, filed on Dec. 30, 2014, now Pat. No. 10,063,064, which is a continuation-in-part of application No. 14/286,289, filed on May 23, 2014, now Pat. No. 9,899,873, said application No. 15/961,825 is a continuation-in-part of application No. 14/585,660, filed on Dec. 30, 2014, now Pat. No. 10,075,008, which is a continuation-in-part of application No. 14/330,936, filed on Jul. 14, 2014, now Pat. No. 9,941,747, said application No. 15/961,825 is a continuation-in-part of application No. 14/465,487, filed on Aug. 21, 2014, now Pat. No. 10,439,448, and a continuation-in-part of application No. 14/585,727, filed on Dec. 30, 2014, now Pat. No. 10,199,849, which is a continuation-in-part of application No. 14/465,508, filed on Aug. 21, 2014, now Pat. No. 10,008,889, said application No. 15/961,825 is a continuation-in-part of application No. 14/585,388, filed on Dec. 30, 2014, now Pat. No. 10,050,462, which is a continuation-in-part of application No. 13/960,488, filed on Aug. 6, 2013, now Pat. No. 9,843,213, said application No. 15/961,825 is a continuation-in-part of application No. 14/585,633, filed on Dec. 30, 2014, now Pat. No. 10,090,886, which is a continuation-in-part of application No. 14/330,931, filed on Jul. 14, 2014, now abandoned, said application No. 15/961,825 is a continuation-in-part of application No. 14/587,025, filed on Dec. 31, 2014, now Pat. No. 9,991,741, which is a continuation-in-part of application No. 14/330,931, filed on Jul. 14, 2014, now abandoned, and a continuation-in-part of application No. 14/330,936, filed on Jul. 14, 2014, now Pat. No. 9,941,747, said application No. 15/961,825 is a continuation-in-part of application No. 14/803,672, filed on Jul. 20, 2015, now Pat. No. 10,148,133, which is a continuation of application No. 13/926,020, filed on Jun. 25, 2013, now Pat. No. 9,124,125, said application No. 15/961,825 is a continuation-in-part of application No. 15/839,774, filed on Dec. 12, 2017, now Pat. No. 10,298,024, which is a continuation of application No. 14/747,946, filed on Jun. 23, 2015, now Pat. No. 9,843,201, which is a continuation of application No. 14/586,314, filed on Dec. 30, 2014, now Pat. No. 9,450,449, which is a continuation-in-part of application No. 13/908,839, filed on Jun. 3, 2013, now abandoned, and a continuation-in-part of application No. 13/891,399, filed on May 10, 2013, now Pat. No. 9,912,199, and a continuation-in-part of application No. 13/891,430, filed on May 10, 2013, now abandoned, and a continuation-in-part of application No. 13/891,445, filed on May 10, 2013, now Pat. No. 10,103,582, said application No. 15/961,825 is a continuation-in-part of application No. 15/884,303, filed on Jan. 30, 2018, now Pat. No. 10,554,052, which is a continuation of application No. 14/748,101, filed on Jun. 23, 2015, now Pat. No. 9,882,394, which is a continuation of application No. 14/585,271, filed on Dec. 30, 2014, now Pat. No. 9,867,062, which is a continuation-in-part of application No. 14/337,002, filed on Jul. 21, 2014, now Pat. No. 9,838,083, said application No. 15/884,303 is a continuation of application No. 14/587,025, filed on Dec. 31, 2014, now Pat. No. 9,991,741, which is a continuation-in-part of application No. 14/330,931, filed on Jul. 14, 2014, now abandoned, and a continuation-in-part of application No. 14/330,936, filed on Jul. 14, 2014, now Pat. No. 9,941,747, said application No. 15/961,825 is a continuation-in-part of application No. 15/900,727, filed on Feb. 20, 2018, now Pat. No. 10,790,674, which is a continuation of application No. 14/748,116, filed on Jun. 23, 2015, now Pat. No. 9,899,844, which is a continuation of application No. 14/585,986, filed on Dec. 30, 2014, now Pat. No. 9,887,584, which is a continuation-in-part of application No. 14/465,553, filed on Aug. 21, 2014, now Pat. No. 9,891,669, said application No. 15/900,727 is a continuation of application No. 14/585,923, filed on Dec. 30, 2014, now Pat. No. 9,939,864, which is a continuation-in-part of application No. 14/465,545, filed on Aug. 21, 2014, now Pat. No. 9,876,648.

(60) Provisional application No. 62/387,467, filed on Dec. 24, 2015, provisional application No. 62/272,571, filed on Dec. 29, 2015, provisional application No. 62/387,206, filed on Dec. 24, 2015, provisional application No. 62/387,466, filed on Dec. 24, 2015, provisional application No. 62/272,553, filed on Dec. 29, 2015, provisional application No. 61/978,031, filed on Apr. 10, 2014, provisional application No. 61/978,301, filed on Apr. 11, 2014, provisional application No. 61/720,798, filed on Oct. 31, 2012, provisional application No. 61/677,706, filed on Jul. 31, 2012, provisional application No. 61/668,799, filed on Jul. 6, 2012.

(51) Int. Cl.
  *H02J 50/80* (2016.01)
  *H05B 3/34* (2006.01)
  *A61B 5/145* (2006.01)
  *B60L 55/00* (2019.01)

(52) U.S. Cl.
  CPC ... *A61B 5/14532* (2013.01); *A61B 2560/0214* (2013.01); *B60L 55/00* (2019.02)

(58) Field of Classification Search
  USPC .................................................. 307/104
  See application file for complete search history.

(56) References Cited

U.S. PATENT DOCUMENTS

| | | |
|---|---|---|
| 2,863,148 A | 12/1958 | Gammon et al. |
| 3,167,775 A | 1/1965 | Guertler |
| 3,434,678 A | 3/1969 | Brown et al. |
| 3,696,384 A | 10/1972 | Lester |
| 3,754,269 A | 8/1973 | Clavin |
| 4,101,895 A | 7/1978 | Jones, Jr. |
| 4,360,741 A | 11/1982 | Fitzsimmons et al. |
| 4,944,036 A | 7/1990 | Hyatt |
| 4,995,010 A | 2/1991 | Knight |
| 5,142,292 A | 8/1992 | Chang |
| 5,200,759 A | 4/1993 | McGinnis |
| 5,211,471 A | 5/1993 | Rohrs |
| 5,276,455 A | 1/1994 | Fitzsimmons et al. |
| 5,548,292 A | 8/1996 | Hirshfield et al. |
| 5,556,749 A | 9/1996 | Mitsuhashi et al. |
| 5,568,088 A | 10/1996 | Dent et al. |
| 5,631,572 A | 5/1997 | Sheen et al. |
| 5,646,633 A | 7/1997 | Dahlberg |
| 5,697,063 A | 12/1997 | Kishigami et al. |
| 5,712,642 A | 1/1998 | Hulderman |
| 5,936,527 A | 8/1999 | Isaacman et al. |
| 5,982,139 A | 11/1999 | Parise |
| 6,046,708 A | 4/2000 | MacDonald, Jr. et al. |
| 6,061,025 A | 5/2000 | Jackson et al. |
| 6,127,799 A | 10/2000 | Krishnan |
| 6,127,942 A | 10/2000 | Welle |
| 6,163,296 A | 12/2000 | Lier et al. |
| 6,176,433 B1 | 1/2001 | Uesaka et al. |
| 6,208,115 B1 | 3/2001 | Binder |
| 6,271,799 B1 | 8/2001 | Rief |
| 6,289,237 B1 | 9/2001 | Mickle et al. |
| 6,316,915 B1 | 11/2001 | Fujiwara et al. |
| 6,329,908 B1 | 12/2001 | Frecska |
| 6,400,586 B2 | 6/2002 | Raddi et al. |
| 6,421,235 B2 | 7/2002 | Ditzik |
| 6,437,685 B2 | 8/2002 | Hanaki |
| 6,456,253 B1 | 9/2002 | Rummeli et al. |
| 6,476,769 B1 | 11/2002 | Lehtola |
| 6,476,795 B1 | 11/2002 | Derocher et al. |
| 6,501,414 B2 | 12/2002 | Amdt et al. |
| 6,583,723 B2 | 6/2003 | Watanabe et al. |
| 6,597,897 B2 | 7/2003 | Tang |
| 6,615,074 B2 | 9/2003 | Mickle et al. |
| 6,650,376 B1 | 11/2003 | Obitsu |
| 6,661,197 B2 | 12/2003 | Zink et al. |
| 6,664,920 B1 | 12/2003 | Mott et al. |
| 6,680,700 B2 | 1/2004 | Hilgers |
| 6,798,716 B1 | 9/2004 | Charych |
| 6,803,744 B1 | 10/2004 | Sabo |
| 6,853,197 B1 | 2/2005 | McFarland |
| 6,856,291 B2 | 2/2005 | Mickle et al. |
| 6,911,945 B2 | 6/2005 | Korva |
| 6,960,968 B2 | 11/2005 | Odendaal et al. |
| 6,967,462 B1 | 11/2005 | Landis |
| 6,982,697 B2 | 1/2006 | Wilson et al. |
| 6,988,026 B2 | 1/2006 | Breed et al. |
| 7,003,350 B2 | 2/2006 | Denker et al. |
| 7,012,572 B1 | 3/2006 | Schaffner et al. |
| 7,027,311 B2 | 4/2006 | Vanderelli et al. |
| 7,042,196 B2 | 5/2006 | Ka-Lai et al. |
| 7,068,234 B2 | 6/2006 | Sievenpiper |
| 7,068,991 B2 | 6/2006 | Parise |
| 7,079,079 B2 | 7/2006 | Jo et al. |
| 7,183,748 B1 | 2/2007 | Unno et al. |
| 7,191,013 B1 | 3/2007 | Miranda et al. |
| 7,193,644 B2 | 3/2007 | Carter |
| 7,196,663 B2 | 3/2007 | Bolzer et al. |
| 7,205,749 B2 | 4/2007 | Hagen et al. |
| 7,215,296 B2 | 5/2007 | Abramov et al. |
| 7,222,356 B1 | 5/2007 | Yonezawa et al. |
| 7,274,334 B2 | 9/2007 | O'Riordan et al. |
| 7,274,336 B2 | 9/2007 | Carson |
| 7,351,975 B2 | 4/2008 | Brady et al. |
| 7,359,730 B2 | 4/2008 | Dennis et al. |
| 7,372,408 B2 | 5/2008 | Gaucher |
| 7,392,068 B2 | 6/2008 | Dayan |
| 7,403,803 B2 | 7/2008 | Mickle et al. |
| 7,443,057 B2 | 10/2008 | Nunally |
| 7,451,839 B2 | 11/2008 | Perlman |
| 7,463,201 B2 | 12/2008 | Chiang et al. |
| 7,471,247 B2 | 12/2008 | Saily |
| 7,525,283 B2 | 4/2009 | Cheng et al. |
| 7,535,195 B1 | 5/2009 | Horovitz et al. |
| 7,614,556 B2 | 11/2009 | Overhultz et al. |
| 7,639,994 B2 | 12/2009 | Greene et al. |
| 7,643,312 B2 | 1/2010 | Vanderelli et al. |
| 7,652,577 B1 | 1/2010 | Madhow et al. |
| 7,679,576 B2 | 3/2010 | Riedel et al. |
| 7,702,771 B2 | 4/2010 | Ewing et al. |
| 7,786,419 B2 | 8/2010 | Hyde et al. |
| 7,812,771 B2 | 10/2010 | Greene et al. |
| 7,830,312 B2 | 11/2010 | Choudhury et al. |
| 7,844,306 B2 | 11/2010 | Shearer et al. |
| 7,868,482 B2 | 1/2011 | Greene et al. |
| 7,898,105 B2 | 3/2011 | Greene et al. |
| 7,904,117 B2 | 3/2011 | Doan et al. |
| 7,911,386 B1 | 3/2011 | Ito et al. |
| 7,925,308 B2 | 4/2011 | Greene et al. |
| 7,948,208 B2 | 5/2011 | Partovi et al. |
| 8,010,205 B2 | 8/2011 | Rahman et al. |
| 8,049,676 B2 | 11/2011 | Yoon et al. |
| 8,055,003 B2 | 11/2011 | Mittleman et al. |
| 8,070,595 B2 | 12/2011 | Alderucci et al. |
| 8,072,380 B2 | 12/2011 | Crouch |
| 8,092,301 B2 | 1/2012 | Alderucci et al. |
| 8,099,140 B2 | 1/2012 | Arai |
| 8,115,448 B2 | 2/2012 | John |
| 8,159,090 B2 | 4/2012 | Greene et al. |
| 8,159,364 B2 | 4/2012 | Zeine |
| 8,180,286 B2 | 5/2012 | Yamasuge |
| 8,184,454 B2 | 5/2012 | Mao |
| 8,228,194 B2 | 7/2012 | Mickle |
| 8,234,509 B2 | 7/2012 | Gioscia et al. |
| 8,264,101 B2 | 9/2012 | Hyde et al. |
| 8,264,291 B2 | 9/2012 | Morita |
| 8,276,325 B2 | 10/2012 | Clifton et al. |
| 8,278,784 B2 | 10/2012 | Cook et al. |
| 8,284,101 B2 | 10/2012 | Fusco |
| 8,310,201 B1 | 11/2012 | Wright |
| 8,338,991 B2 | 12/2012 | Von Novak et al. |
| 8,362,745 B2 | 1/2013 | Tinaphong |
| 8,380,255 B2 | 2/2013 | Shearer et al. |
| 8,384,600 B2 | 2/2013 | Huang et al. |
| 8,410,953 B2 | 4/2013 | Zeine |
| 8,411,963 B2 | 4/2013 | Luff |

(56) References Cited

U.S. PATENT DOCUMENTS

| | | |
|---|---|---|
| 8,432,062 B2 | 4/2013 | Greene et al. |
| 8,432,071 B2 | 4/2013 | Huang et al. |
| 8,446,248 B2 | 5/2013 | Zeine |
| 8,447,234 B2 | 5/2013 | Cook et al. |
| 8,451,189 B1 | 5/2013 | Fluhler |
| 8,452,235 B2 | 5/2013 | Kirby et al. |
| 8,457,656 B2 | 6/2013 | Perkins et al. |
| 8,461,817 B2 | 6/2013 | Martin et al. |
| 8,467,733 B2 | 6/2013 | Leabman |
| 8,497,601 B2 | 7/2013 | Hall et al. |
| 8,497,658 B2 | 7/2013 | Von Novak et al. |
| 8,552,597 B2 | 8/2013 | Song et al. |
| 8,558,661 B2 | 10/2013 | Zeine |
| 8,560,026 B2 | 10/2013 | Chanterac |
| 8,564,485 B2 | 10/2013 | Milosavljevic et al. |
| 8,587,154 B2 | 11/2013 | Fells et al. |
| 8,604,746 B2 | 12/2013 | Lee |
| 8,614,643 B2 | 12/2013 | Leabman |
| 8,621,245 B2 | 12/2013 | Shearer et al. |
| 8,626,249 B2 | 1/2014 | Kuusilinna et al. |
| 8,629,576 B2 | 1/2014 | Levine |
| 8,653,966 B2 | 2/2014 | Rao et al. |
| 8,655,272 B2 | 2/2014 | Saunamäki |
| 8,674,551 B2 | 3/2014 | Low et al. |
| 8,686,685 B2 | 4/2014 | Moshfeghi |
| 8,686,905 B2 | 4/2014 | Shtrom |
| 8,712,355 B2 | 4/2014 | Black et al. |
| 8,712,485 B2 | 4/2014 | Tam |
| 8,718,773 B2 | 5/2014 | Wills et al. |
| 8,729,737 B2 | 5/2014 | Schatz et al. |
| 8,736,228 B1 | 5/2014 | Freed et al. |
| 8,760,113 B2 | 6/2014 | Keating |
| 8,770,482 B2 | 7/2014 | Ackermann et al. |
| 8,772,960 B2 | 7/2014 | Yoshida |
| 8,819,659 B2 | 8/2014 | Ramer et al. |
| 8,823,319 B2 | 9/2014 | Von Novak, III et al. |
| 8,832,646 B1 | 9/2014 | Wendling |
| 8,853,891 B2 | 10/2014 | Soar |
| 8,854,176 B2 | 10/2014 | Zeine |
| 8,860,364 B2 | 10/2014 | Low et al. |
| 8,896,315 B1 | 11/2014 | Davies |
| 8,897,770 B1 | 11/2014 | Frolov et al. |
| 8,903,456 B2 | 12/2014 | Chu et al. |
| 8,917,057 B2 | 12/2014 | Hui |
| 8,923,189 B2 | 12/2014 | Leabman |
| 8,928,544 B2 | 1/2015 | Massie et al. |
| 8,937,408 B2 | 1/2015 | Ganem et al. |
| 8,946,940 B2 | 2/2015 | Kim et al. |
| 8,963,486 B2 | 2/2015 | Kirby et al. |
| 8,970,070 B2 | 3/2015 | Sada et al. |
| 8,989,053 B1 | 3/2015 | Skaaksrud et al. |
| 9,000,616 B2 | 4/2015 | Greene et al. |
| 9,001,622 B2 | 4/2015 | Perry |
| 9,006,934 B2 | 4/2015 | Kozakai et al. |
| 9,021,277 B2 | 4/2015 | Shearer et al. |
| 9,030,161 B2 | 5/2015 | Lu et al. |
| 9,059,598 B2 | 6/2015 | Kang et al. |
| 9,059,599 B2 | 6/2015 | Won et al. |
| 9,077,188 B2 | 7/2015 | Moshfeghi |
| 9,083,595 B2 | 7/2015 | Rakib et al. |
| 9,088,216 B2 | 7/2015 | Garrity et al. |
| 9,124,125 B2 | 9/2015 | Leabman et al. |
| 9,130,397 B2 | 9/2015 | Leabman et al. |
| 9,130,602 B2 | 9/2015 | Cook |
| 9,142,998 B2 | 9/2015 | Yu et al. |
| 9,143,000 B2 | 9/2015 | Leabman et al. |
| 9,143,010 B2 | 9/2015 | Urano |
| 9,153,074 B2 | 10/2015 | Zhou et al. |
| 9,178,389 B2 | 11/2015 | Hwang |
| 9,225,196 B2 | 12/2015 | Huang et al. |
| 9,240,469 B2 | 1/2016 | Sun et al. |
| 9,242,411 B2 | 1/2016 | Kritchman et al. |
| 9,244,500 B2 | 1/2016 | Cain et al. |
| 9,252,628 B2 | 2/2016 | Leabman et al. |
| 9,270,344 B2 | 2/2016 | Rosenberg |
| 9,276,329 B2 | 3/2016 | Jones et al. |
| 9,282,582 B1 | 3/2016 | Dunsbergen et al. |
| 9,294,840 B1 | 3/2016 | Anderson et al. |
| 9,297,896 B1 | 3/2016 | Andrews |
| 9,318,898 B2 | 4/2016 | John |
| 9,368,020 B1 | 6/2016 | Bell et al. |
| 9,391,477 B2 | 7/2016 | Sheng |
| 9,401,977 B1 | 7/2016 | Gaw |
| 9,409,490 B2 | 8/2016 | Kawashima |
| 9,419,335 B2 | 8/2016 | Pintos |
| 9,419,443 B2 | 8/2016 | Leabman |
| 9,438,045 B1 | 9/2016 | Leabman |
| 9,438,046 B1 | 9/2016 | Leabman |
| 9,444,283 B2 | 9/2016 | Son et al. |
| 9,450,449 B1 | 9/2016 | Leabman et al. |
| 9,452,296 B2 | 9/2016 | Forsell |
| 9,461,502 B2 | 10/2016 | Lee et al. |
| 9,520,725 B2 | 12/2016 | Masaoka et al. |
| 9,520,748 B2 | 12/2016 | Hyde et al. |
| 9,521,926 B1 | 12/2016 | Leabman et al. |
| 9,522,270 B2 | 12/2016 | Perryman et al. |
| 9,532,748 B2 | 1/2017 | Denison et al. |
| 9,537,354 B2 | 1/2017 | Bell et al. |
| 9,537,357 B2 | 1/2017 | Leabman |
| 9,537,358 B2 | 1/2017 | Leabman |
| 9,538,382 B2 | 1/2017 | Bell et al. |
| 9,544,640 B2 | 1/2017 | Lau |
| 9,559,553 B2 | 1/2017 | Bae |
| 9,564,773 B2 | 2/2017 | Pogorelik et al. |
| 9,571,974 B2 | 2/2017 | Choi et al. |
| 9,590,317 B2 | 3/2017 | Zimmerman et al. |
| 9,590,444 B2 | 3/2017 | Walley |
| 9,620,996 B2 | 4/2017 | Zeine |
| 9,635,625 B2 | 4/2017 | Russell et al. |
| 9,647,328 B2 | 5/2017 | Dobric |
| 9,647,483 B1 | 5/2017 | Bana et al. |
| 9,706,137 B2 | 7/2017 | Scanlon et al. |
| 9,711,999 B2 | 7/2017 | Hietala et al. |
| 9,723,635 B2 | 8/2017 | Nambord et al. |
| 9,787,103 B1 | 10/2017 | Leabman et al. |
| 9,793,758 B2 | 10/2017 | Leabman |
| 9,793,764 B2 | 10/2017 | Perry |
| 9,800,080 B2 | 10/2017 | Leabman et al. |
| 9,800,172 B1 | 10/2017 | Leabman |
| 9,806,564 B2 | 10/2017 | Leabman |
| 9,812,890 B1 | 11/2017 | Leabman et al. |
| 9,819,230 B2 | 11/2017 | Petras et al. |
| 9,824,815 B2 | 11/2017 | Leabman et al. |
| 9,825,674 B1 | 11/2017 | Leabman |
| 9,831,718 B2 | 11/2017 | Leabman et al. |
| 9,838,083 B2 | 12/2017 | Bell et al. |
| 9,843,201 B1 | 12/2017 | Leabman et al. |
| 9,843,213 B2 | 12/2017 | Leabman et al. |
| 9,843,229 B2 | 12/2017 | Leabman |
| 9,843,763 B2 | 12/2017 | Leabman et al. |
| 9,847,669 B2 | 12/2017 | Leabman |
| 9,847,677 B1 | 12/2017 | Leabman |
| 9,847,679 B2 | 12/2017 | Bell et al. |
| 9,853,361 B2 | 12/2017 | Chen et al. |
| 9,853,458 B1 | 12/2017 | Bell et al. |
| 9,853,485 B2 | 12/2017 | Contopanagos |
| 9,853,692 B1 | 12/2017 | Bell et al. |
| 9,859,756 B2 | 1/2018 | Leabman et al. |
| 9,859,757 B1 | 1/2018 | Leabman et al. |
| 9,859,758 B1 | 1/2018 | Leabman |
| 9,859,797 B1 | 1/2018 | Leabman |
| 9,866,279 B2 | 1/2018 | Bell et al. |
| 9,867,032 B2 | 1/2018 | Verma et al. |
| 9,867,062 B1 | 1/2018 | Bell et al. |
| 9,871,301 B2 | 1/2018 | Contopanagos |
| 9,871,387 B1 | 1/2018 | Bell et al. |
| 9,871,398 B1 | 1/2018 | Leabman |
| 9,876,379 B1 | 1/2018 | Leabman et al. |
| 9,876,380 B1 | 1/2018 | Leabman et al. |
| 9,876,394 B1 | 1/2018 | Leabman |
| 9,876,536 B1 | 1/2018 | Bell et al. |
| 9,876,648 B2 | 1/2018 | Bell |
| 9,882,394 B1 | 1/2018 | Bell et al. |
| 9,882,395 B1 | 1/2018 | Leabman et al. |

(56) References Cited

U.S. PATENT DOCUMENTS

| | | |
|---|---|---|
| 9,882,427 B2 | 1/2018 | Leabman et al. |
| 9,882,430 B1 | 1/2018 | Leabman et al. |
| 9,887,584 B1 | 2/2018 | Bell et al. |
| 9,887,739 B2 | 2/2018 | Leabman et al. |
| 9,891,669 B2 | 2/2018 | Bell |
| 9,893,535 B2 | 2/2018 | Leabman |
| 9,893,538 B1 | 2/2018 | Bell et al. |
| 9,893,554 B2 | 2/2018 | Bell et al. |
| 9,893,555 B1 | 2/2018 | Leabman et al. |
| 9,893,564 B2 | 2/2018 | de Rochemont |
| 9,893,768 B2 | 2/2018 | Leabman et al. |
| 9,899,744 B1 | 2/2018 | Contopanagos et al. |
| 9,899,844 B1 | 2/2018 | Bell et al. |
| 9,899,861 B1 | 2/2018 | Leabman et al. |
| 9,899,873 B2 | 2/2018 | Bell et al. |
| 9,906,065 B2 | 2/2018 | Leabman et al. |
| 9,906,275 B2 | 2/2018 | Leabman |
| 9,912,199 B2 | 3/2018 | Leabman et al. |
| 9,916,485 B1 | 3/2018 | Lilly et al. |
| 9,917,477 B1 | 3/2018 | Bell et al. |
| 9,923,386 B1 | 3/2018 | Leabman et al. |
| 9,939,864 B1 | 4/2018 | Bell et al. |
| 9,941,707 B1 | 4/2018 | Leabman |
| 9,941,747 B2 | 4/2018 | Bell et al. |
| 9,954,374 B1 | 4/2018 | Bell et al. |
| 9,965,009 B1 | 5/2018 | Bell et al. |
| 9,966,765 B1 | 5/2018 | Leabman |
| 9,966,784 B2 | 5/2018 | Leabman |
| 9,967,743 B1 | 5/2018 | Bell et al. |
| 9,973,008 B1 | 5/2018 | Leabman |
| 9,991,741 B1 | 6/2018 | Bell et al. |
| 10,003,211 B1 | 6/2018 | Leabman et al. |
| 10,008,777 B1 | 6/2018 | Broyde et al. |
| 10,008,889 B2 | 6/2018 | Bell et al. |
| 10,014,728 B1 | 7/2018 | Leabman |
| 10,027,159 B2 | 7/2018 | Hosseini |
| 10,027,180 B1 | 7/2018 | Hosseini |
| 10,038,337 B1 | 7/2018 | Leabman et al. |
| 10,050,462 B1 | 8/2018 | Leabman et al. |
| 10,056,782 B1 | 8/2018 | Leabman |
| 10,063,064 B1 | 8/2018 | Bell et al. |
| 10,063,105 B2 | 8/2018 | Leabman |
| 10,063,106 B2 | 8/2018 | Bell et al. |
| 10,068,703 B1 | 9/2018 | Contopanagos |
| 10,075,008 B1 | 9/2018 | Bell et al. |
| 10,075,017 B2 | 9/2018 | Leabman et al. |
| 10,079,515 B2 | 9/2018 | Hosseini et al. |
| 10,090,699 B1 | 10/2018 | Leabman |
| 10,090,714 B2 | 10/2018 | Bohn et al. |
| 10,090,886 B1 | 10/2018 | Bell et al. |
| 10,103,552 B1 | 10/2018 | Leabman et al. |
| 10,103,582 B2 | 10/2018 | Leabman et al. |
| 10,110,046 B1 | 10/2018 | Esquibel et al. |
| 10,116,143 B1 | 10/2018 | Leabman et al. |
| 10,116,162 B2 | 10/2018 | Hosseini et al. |
| 10,116,170 B1 | 10/2018 | Leabman |
| 10,122,219 B1 | 11/2018 | Hosseini et al. |
| 10,122,415 B2 | 11/2018 | Bell et al. |
| 10,124,754 B1 | 11/2018 | Leabman |
| 10,128,686 B1 | 11/2018 | Leabman et al. |
| 10,128,693 B2 | 11/2018 | Bell et al. |
| 10,128,695 B2 | 11/2018 | Leabman et al. |
| 10,128,699 B2 | 11/2018 | Leabman |
| 10,134,260 B1 | 11/2018 | Bell et al. |
| 10,135,112 B1 | 11/2018 | Hosseini |
| 10,135,286 B2 | 11/2018 | Hosseini et al. |
| 10,135,294 B1 | 11/2018 | Leabman |
| 10,135,295 B1 | 11/2018 | Leabman |
| 10,141,768 B2 | 11/2018 | Leabman et al. |
| 10,141,771 B1 | 11/2018 | Hosseini et al. |
| 10,141,791 B2 | 11/2018 | Bell et al. |
| 10,148,097 B1 | 12/2018 | Leabman et al. |
| 10,148,133 B2 | 12/2018 | Leabman et al. |
| 10,153,645 B1 | 12/2018 | Bell et al. |
| 10,153,653 B1 | 12/2018 | Bell et al. |
| 10,153,660 B1 | 12/2018 | Leabman et al. |
| 10,158,257 B2 | 12/2018 | Leabman |
| 10,158,259 B1 | 12/2018 | Leabman |
| 10,164,478 B2 | 12/2018 | Leabman |
| 10,170,917 B1 | 1/2019 | Bell et al. |
| 10,177,594 B2 | 1/2019 | Contopanagos |
| 10,181,756 B2 | 1/2019 | Bae et al. |
| 10,186,892 B2 | 1/2019 | Hosseini et al. |
| 10,186,893 B2 | 1/2019 | Bell et al. |
| 10,186,911 B2 | 1/2019 | Leabman |
| 10,186,913 B2 | 1/2019 | Leabman et al. |
| 10,193,396 B1 | 1/2019 | Bell et al. |
| 10,199,835 B2 | 2/2019 | Bell |
| 10,199,849 B1 | 2/2019 | Bell |
| 10,199,850 B2 | 2/2019 | Leabman |
| 10,205,239 B1 | 2/2019 | Contopanagos et al. |
| 10,206,185 B2 | 2/2019 | Leabman et al. |
| 10,211,674 B1 | 2/2019 | Leabman et al. |
| 10,211,680 B2 | 2/2019 | Leabman et al. |
| 10,211,682 B2 | 2/2019 | Bell et al. |
| 10,211,685 B2 | 2/2019 | Bell et al. |
| 10,218,207 B2 | 2/2019 | Hosseini et al. |
| 10,218,227 B2 | 2/2019 | Leabman et al. |
| 10,223,717 B1 | 3/2019 | Bell |
| 10,224,758 B2 | 3/2019 | Leabman et al. |
| 10,224,982 B1 | 3/2019 | Leabman |
| 10,230,266 B1 | 3/2019 | Leabman et al. |
| 10,243,414 B1 | 3/2019 | Leabman et al. |
| 10,256,657 B2 | 4/2019 | Hosseini et al. |
| 10,256,677 B2 | 4/2019 | Hosseini et al. |
| 10,263,432 B1 | 4/2019 | Leabman et al. |
| 10,263,476 B2 | 4/2019 | Leabman |
| 10,270,261 B2 | 4/2019 | Bell et al. |
| 10,277,054 B2 | 4/2019 | Hosseini |
| 10,291,055 B1 | 5/2019 | Bell et al. |
| 10,291,056 B2 | 5/2019 | Bell et al. |
| 10,291,066 B1 | 5/2019 | Leabman |
| 10,291,294 B2 | 5/2019 | Leabman |
| 10,298,024 B2 | 5/2019 | Leabman |
| 10,298,133 B2 | 5/2019 | Leabman |
| 10,305,315 B2 | 5/2019 | Leabman et al. |
| 10,312,715 B2 | 6/2019 | Leabman |
| 10,320,446 B2 | 6/2019 | Hosseini |
| 10,333,332 B1 | 6/2019 | Hosseini |
| 10,333,357 B1 | 6/2019 | Abu Qahouq |
| 10,355,534 B2 | 7/2019 | Johnston et al. |
| 10,381,880 B2 | 8/2019 | Leabman et al. |
| 10,389,161 B2 | 8/2019 | Hosseini et al. |
| 10,396,588 B2 | 8/2019 | Leabman |
| 10,396,604 B2 | 8/2019 | Bell et al. |
| 10,439,442 B2 | 10/2019 | Hosseini et al. |
| 10,439,448 B2 | 10/2019 | Bell et al. |
| 10,447,093 B2 | 10/2019 | Hosseini |
| 10,476,312 B2 | 11/2019 | Johnston et al. |
| 10,490,346 B2 | 11/2019 | Contopanagos |
| 10,491,029 B2 | 11/2019 | Hosseini |
| 10,498,144 B2 | 12/2019 | Leabman et al. |
| 10,509,466 B1 | 12/2019 | Miller et al. |
| 10,511,097 B2 | 12/2019 | Kornaros et al. |
| 10,516,289 B2 | 12/2019 | Leabman et al. |
| 10,516,301 B2 | 12/2019 | Leabman |
| 10,523,033 B2 | 12/2019 | Leabman |
| 10,523,058 B2 | 12/2019 | Leabman |
| 10,554,052 B2 | 2/2020 | Bell et al. |
| 10,594,165 B2 | 3/2020 | Hosseini |
| 10,615,647 B2 | 4/2020 | Johnston et al. |
| 10,616,534 B2 | 4/2020 | Thiel et al. |
| 10,651,670 B1 | 5/2020 | Jiang et al. |
| 10,680,319 B2 | 6/2020 | Hosseini et al. |
| 10,714,984 B2 | 7/2020 | Hosseini et al. |
| 10,734,717 B2 | 8/2020 | Hosseini |
| 10,778,041 B2 | 9/2020 | Leabman |
| 10,790,674 B2 | 9/2020 | Bell et al. |
| 10,840,743 B2 | 11/2020 | Johnston et al. |
| 10,848,853 B2 | 11/2020 | Leabman et al. |
| 10,879,740 B2 | 12/2020 | Hosseini |
| 10,923,954 B2 | 2/2021 | Leabman |
| 10,958,095 B2 | 3/2021 | Leabman et al. |
| 10,965,164 B2 | 3/2021 | Leabman et al. |

(56) References Cited

U.S. PATENT DOCUMENTS

| | | |
|---|---|---|
| 10,985,617 B1 | 4/2021 | Johnston et al. |
| 10,992,185 B2 | 4/2021 | Leabman |
| 10,992,187 B2 | 4/2021 | Leabman |
| 11,011,942 B2 | 5/2021 | Liu |
| 11,018,779 B2 | 5/2021 | Sarajedini |
| 11,056,929 B2 | 7/2021 | Bell et al. |
| 11,114,885 B2 | 9/2021 | Hosseini et al. |
| 11,139,699 B2 | 10/2021 | Johnston et al. |
| 11,159,057 B2 | 10/2021 | Kabiri et al. |
| 11,233,425 B2 | 1/2022 | Leabman |
| 11,245,191 B2 | 2/2022 | Kornaros et al. |
| 11,342,798 B2 | 5/2022 | Johnston et al. |
| 11,355,966 B2 | 6/2022 | Muryanto et al. |
| 11,411,437 B2 | 8/2022 | Johnston et al. |
| 11,411,441 B2 | 8/2022 | Woo |
| 11,437,735 B2 | 9/2022 | Papio-Toda et al. |
| 11,451,096 B2 | 9/2022 | Hoss |
| 11,502,551 B2 | 10/2022 | Leabman |
| 11,515,732 B2 | 11/2022 | Contopanagos et al. |
| 11,539,243 B2 | 12/2022 | Katajamaki et al. |
| 2001/0027876 A1 | 10/2001 | Tsukamoto et al. |
| 2002/0001307 A1 | 1/2002 | Nguyen et al. |
| 2002/0024471 A1 | 2/2002 | Ishitobi |
| 2002/0028655 A1 | 3/2002 | Rosener et al. |
| 2002/0034958 A1 | 3/2002 | Oberschmidt et al. |
| 2002/0054330 A1 | 5/2002 | Jinbo et al. |
| 2002/0065052 A1 | 5/2002 | Pande et al. |
| 2002/0072784 A1 | 6/2002 | Sheppard et al. |
| 2002/0080083 A1 | 6/2002 | Nantz et al. |
| 2002/0095980 A1 | 7/2002 | Breed et al. |
| 2002/0103447 A1 | 8/2002 | Terry |
| 2002/0123776 A1 | 9/2002 | Von Arx |
| 2002/0133592 A1 | 9/2002 | Matsuda |
| 2002/0171594 A1 | 11/2002 | Fang |
| 2002/0172223 A1 | 11/2002 | Stilp |
| 2003/0005759 A1 | 1/2003 | Breed et al. |
| 2003/0027036 A1 | 2/2003 | Emori et al. |
| 2003/0038750 A1 | 2/2003 | Chen |
| 2003/0058187 A1 | 3/2003 | Billiet et al. |
| 2003/0076274 A1 | 4/2003 | Phelan et al. |
| 2003/0179152 A1 | 9/2003 | Watada et al. |
| 2003/0179573 A1 | 9/2003 | Chun |
| 2003/0192053 A1 | 10/2003 | Sheppard et al. |
| 2004/0019624 A1 | 1/2004 | Sukegawa |
| 2004/0020100 A1 | 2/2004 | O'Brian et al. |
| 2004/0036657 A1 | 2/2004 | Forster et al. |
| 2004/0066251 A1 | 4/2004 | Eleftheriades et al. |
| 2004/0107641 A1 | 6/2004 | Walton et al. |
| 2004/0113543 A1 | 6/2004 | Daniels |
| 2004/0119675 A1 | 6/2004 | Washio et al. |
| 2004/0130425 A1 | 7/2004 | Dayan et al. |
| 2004/0130442 A1 | 7/2004 | Breed |
| 2004/0142733 A1 | 7/2004 | Parise |
| 2004/0145342 A1 | 7/2004 | Lyon |
| 2004/0155832 A1 | 8/2004 | Yuanzhu |
| 2004/0196190 A1 | 10/2004 | Mendolia et al. |
| 2004/0203979 A1 | 10/2004 | Attar et al. |
| 2004/0207559 A1 | 10/2004 | Milosavljevic |
| 2004/0218759 A1 | 11/2004 | Yacobi |
| 2004/0241402 A1 | 12/2004 | Kawate |
| 2004/0259604 A1 | 12/2004 | Mickle et al. |
| 2004/0263124 A1 | 12/2004 | Wieck et al. |
| 2005/0007276 A1 | 1/2005 | Barrick et al. |
| 2005/0030118 A1 | 2/2005 | Wang |
| 2005/0046584 A1 | 3/2005 | Breed |
| 2005/0055316 A1 | 3/2005 | Williams |
| 2005/0077872 A1 | 4/2005 | Single |
| 2005/0093766 A1 | 5/2005 | Turner |
| 2005/0116683 A1 | 6/2005 | Cheng |
| 2005/0117660 A1 | 6/2005 | Vialle et al. |
| 2005/0134517 A1 | 6/2005 | Gottl |
| 2005/0171411 A1 | 8/2005 | KenKnight |
| 2005/0198673 A1 | 9/2005 | Kit et al. |
| 2005/0227619 A1 | 10/2005 | Lee et al. |
| 2005/0232469 A1 | 10/2005 | Schofield |
| 2005/0237249 A1 | 10/2005 | Nagel |
| 2005/0237258 A1 | 10/2005 | Abramov et al. |
| 2005/0275983 A1 | 12/2005 | Franklin et al. |
| 2005/0282591 A1 | 12/2005 | Shaff |
| 2006/0013335 A1 | 1/2006 | Leabman |
| 2006/0019712 A1 | 1/2006 | Choi |
| 2006/0030279 A1 | 2/2006 | Leabman et al. |
| 2006/0033674 A1 | 2/2006 | Essig, Jr. et al. |
| 2006/0056855 A1 | 3/2006 | Nakagawa et al. |
| 2006/0071308 A1 | 4/2006 | Tang et al. |
| 2006/0092079 A1 | 5/2006 | de Rochemont |
| 2006/0094425 A1 | 5/2006 | Mickle et al. |
| 2006/0113955 A1 | 6/2006 | Nunally |
| 2006/0119532 A1 | 6/2006 | Yun et al. |
| 2006/0136004 A1 | 6/2006 | Cowan et al. |
| 2006/0160517 A1 | 7/2006 | Yoon |
| 2006/0183473 A1 | 8/2006 | Ukon |
| 2006/0190063 A1 | 8/2006 | Kanzius |
| 2006/0192913 A1 | 8/2006 | Shutou et al. |
| 2006/0199620 A1 | 9/2006 | Greene et al. |
| 2006/0238365 A1 | 10/2006 | Vecchione et al. |
| 2006/0266564 A1 | 11/2006 | Perlman et al. |
| 2006/0266917 A1 | 11/2006 | Baldis et al. |
| 2006/0278706 A1 | 12/2006 | Hatakayama et al. |
| 2006/0281435 A1 | 12/2006 | Shearer et al. |
| 2006/0284593 A1 | 12/2006 | Nagy et al. |
| 2006/0287094 A1 | 12/2006 | Mahaffey et al. |
| 2007/0007821 A1 | 1/2007 | Rossetti |
| 2007/0019693 A1 | 1/2007 | Graham |
| 2007/0021140 A1 | 1/2007 | Keyes |
| 2007/0060185 A1 | 3/2007 | Simon et al. |
| 2007/0070490 A1 | 3/2007 | Tsunoda et al. |
| 2007/0090997 A1 | 4/2007 | Brown et al. |
| 2007/0093269 A1 | 4/2007 | Leabman et al. |
| 2007/0097653 A1 | 5/2007 | Gilliland et al. |
| 2007/0099644 A1 | 5/2007 | Batra et al. |
| 2007/0103110 A1 | 5/2007 | Sagoo |
| 2007/0106894 A1 | 5/2007 | Zhang |
| 2007/0109121 A1 | 5/2007 | Cohen |
| 2007/0139000 A1 | 6/2007 | Kozuma |
| 2007/0149162 A1 | 6/2007 | Greene et al. |
| 2007/0149237 A1 | 6/2007 | Russell et al. |
| 2007/0164868 A1 | 7/2007 | Deavours et al. |
| 2007/0173196 A1 | 7/2007 | Gallic |
| 2007/0173214 A1 | 7/2007 | Mickle et al. |
| 2007/0178857 A1 | 8/2007 | Greene et al. |
| 2007/0178945 A1 | 8/2007 | Cook et al. |
| 2007/0182367 A1 | 8/2007 | Partovi |
| 2007/0191074 A1 | 8/2007 | Harrist et al. |
| 2007/0191075 A1 | 8/2007 | Greene et al. |
| 2007/0197281 A1 | 8/2007 | Stronach |
| 2007/0210960 A1 | 9/2007 | Rofougaran et al. |
| 2007/0222681 A1 | 9/2007 | Greene et al. |
| 2007/0228833 A1 | 10/2007 | Stevens et al. |
| 2007/0229261 A1 | 10/2007 | Zimmerman et al. |
| 2007/0240297 A1 | 10/2007 | Yang et al. |
| 2007/0257634 A1 | 11/2007 | Leschin et al. |
| 2007/0273486 A1 | 11/2007 | Shiotsu |
| 2007/0291165 A1 | 12/2007 | Wang |
| 2007/0296639 A1 | 12/2007 | Hook et al. |
| 2007/0298846 A1 | 12/2007 | Greene et al. |
| 2008/0014897 A1 | 1/2008 | Cook et al. |
| 2008/0024376 A1 | 1/2008 | Norris et al. |
| 2008/0048917 A1 | 2/2008 | Achour et al. |
| 2008/0062062 A1 | 3/2008 | Borau et al. |
| 2008/0062255 A1 | 3/2008 | Gal |
| 2008/0067874 A1 | 3/2008 | Tseng |
| 2008/0074324 A1 | 3/2008 | Puzella et al. |
| 2008/0089277 A1 | 4/2008 | Alexander et al. |
| 2008/0102786 A1 | 5/2008 | Griffin |
| 2008/0110263 A1 | 5/2008 | Klessel et al. |
| 2008/0113816 A1 | 5/2008 | Mahaffey et al. |
| 2008/0122297 A1 | 5/2008 | Arai |
| 2008/0123383 A1 | 5/2008 | Shionoiri |
| 2008/0129536 A1 | 6/2008 | Randall et al. |
| 2008/0140278 A1 | 6/2008 | Breed |
| 2008/0169910 A1 | 7/2008 | Greene et al. |
| 2008/0197802 A1 | 8/2008 | Onishi |
| 2008/0204342 A1 | 8/2008 | Kharadly |

(56) References Cited

U.S. PATENT DOCUMENTS

| | | |
|---|---|---|
| 2008/0204350 A1 | 8/2008 | Tam et al. |
| 2008/0207218 A1 | 8/2008 | Craine et al. |
| 2008/0210762 A1 | 9/2008 | Osada et al. |
| 2008/0211458 A1 | 9/2008 | Lawther et al. |
| 2008/0233890 A1 | 9/2008 | Baker |
| 2008/0248758 A1 | 10/2008 | Schedelbeck et al. |
| 2008/0248846 A1 | 10/2008 | Stronach et al. |
| 2008/0258981 A1 | 10/2008 | Achour et al. |
| 2008/0258993 A1 | 10/2008 | Gummalla et al. |
| 2008/0266191 A1 | 10/2008 | Hilgers |
| 2008/0276879 A1 | 11/2008 | Marsh |
| 2008/0278378 A1 | 11/2008 | Chang et al. |
| 2008/0309452 A1 | 12/2008 | Zeine |
| 2009/0002493 A1 | 1/2009 | Kates |
| 2009/0010316 A1 | 1/2009 | Rofougaran et al. |
| 2009/0019183 A1 | 1/2009 | Wu et al. |
| 2009/0036065 A1 | 2/2009 | Siu |
| 2009/0039828 A1 | 2/2009 | Jakubowski |
| 2009/0047998 A1 | 2/2009 | Alberth, Jr. |
| 2009/0051324 A1 | 2/2009 | Nakatsuji |
| 2009/0058354 A1 | 3/2009 | Harrison |
| 2009/0058361 A1 | 3/2009 | John |
| 2009/0058731 A1 | 3/2009 | Geary et al. |
| 2009/0060012 A1 | 3/2009 | Gresset et al. |
| 2009/0067198 A1 | 3/2009 | Graham et al. |
| 2009/0067208 A1 | 3/2009 | Martin et al. |
| 2009/0073066 A1 | 3/2009 | Jordon et al. |
| 2009/0096412 A1 | 4/2009 | Huang |
| 2009/0096413 A1 | 4/2009 | Partovi |
| 2009/0102292 A1 | 4/2009 | Cook et al. |
| 2009/0102296 A1 | 4/2009 | Greene et al. |
| 2009/0108679 A1 | 4/2009 | Porwal |
| 2009/0122847 A1 | 5/2009 | Nysen et al. |
| 2009/0128262 A1 | 5/2009 | Lee et al. |
| 2009/0152954 A1 | 6/2009 | Le et al. |
| 2009/0157911 A1 | 6/2009 | Aihara |
| 2009/0174604 A1 | 7/2009 | Keskitalo |
| 2009/0180653 A1 | 7/2009 | Sjursen et al. |
| 2009/0200985 A1 | 8/2009 | Zane et al. |
| 2009/0206791 A1 | 8/2009 | Jung |
| 2009/0207090 A1 | 8/2009 | Pettus et al. |
| 2009/0207092 A1 | 8/2009 | Nysen et al. |
| 2009/0218884 A1 | 9/2009 | Soar |
| 2009/0218891 A1 | 9/2009 | McCollough |
| 2009/0219903 A1 | 9/2009 | Alamouti et al. |
| 2009/0243397 A1 | 10/2009 | Cook et al. |
| 2009/0256752 A1 | 10/2009 | Akkermans et al. |
| 2009/0264069 A1 | 10/2009 | Yamasuge |
| 2009/0271048 A1 | 10/2009 | Wakamatsu |
| 2009/0280866 A1 | 11/2009 | Lo et al. |
| 2009/0281678 A1 | 11/2009 | Wakamatsu |
| 2009/0284082 A1 | 11/2009 | Mohammadian |
| 2009/0284083 A1 | 11/2009 | Karalis et al. |
| 2009/0284220 A1 | 11/2009 | Toncich et al. |
| 2009/0284227 A1 | 11/2009 | Mohammadian et al. |
| 2009/0284325 A1 | 11/2009 | Rossiter et al. |
| 2009/0286475 A1 | 11/2009 | Toncich et al. |
| 2009/0286476 A1 | 11/2009 | Toncich et al. |
| 2009/0291634 A1 | 11/2009 | Saarisalo |
| 2009/0299175 A1 | 12/2009 | Bernstein et al. |
| 2009/0303693 A1 | 12/2009 | Mao |
| 2009/0308936 A1 | 12/2009 | Nitzan et al. |
| 2009/0312046 A1 | 12/2009 | Clevenger et al. |
| 2009/0315412 A1 | 12/2009 | Yamamoto et al. |
| 2009/0322281 A1 | 12/2009 | Kamijo et al. |
| 2010/0001683 A1 | 1/2010 | Huang et al. |
| 2010/0007307 A1 | 1/2010 | Baarman et al. |
| 2010/0007569 A1 | 1/2010 | Sim et al. |
| 2010/0019686 A1 | 1/2010 | Gutierrez, Jr. |
| 2010/0019908 A1 | 1/2010 | Cho et al. |
| 2010/0026605 A1 | 2/2010 | Yang et al. |
| 2010/0027379 A1 | 2/2010 | Saulnier et al. |
| 2010/0029383 A1 | 2/2010 | Dai |
| 2010/0033021 A1 | 2/2010 | Bennett |
| 2010/0033390 A1 | 2/2010 | Alamouti et al. |
| 2010/0034238 A1 | 2/2010 | Bennett |
| 2010/0041453 A1 | 2/2010 | Grimm, Jr. |
| 2010/0044123 A1 | 2/2010 | Perlman et al. |
| 2010/0054200 A1 | 3/2010 | Tsai |
| 2010/0060534 A1 | 3/2010 | Oodachi |
| 2010/0066631 A1 | 3/2010 | Puzella et al. |
| 2010/0075607 A1 | 3/2010 | Hosoya |
| 2010/0079005 A1 | 4/2010 | Hyde et al. |
| 2010/0079011 A1 | 4/2010 | Hyde et al. |
| 2010/0082193 A1 | 4/2010 | Chiappetta |
| 2010/0087227 A1 | 4/2010 | Francos et al. |
| 2010/0090524 A1 | 4/2010 | Obayashi |
| 2010/0090656 A1 | 4/2010 | Shearer et al. |
| 2010/0109443 A1 | 5/2010 | Cook et al. |
| 2010/0117596 A1 | 5/2010 | Cook et al. |
| 2010/0117926 A1 | 5/2010 | DeJean, II |
| 2010/0119234 A1 | 5/2010 | Suematsu et al. |
| 2010/0123618 A1 | 5/2010 | Martin et al. |
| 2010/0123624 A1 | 5/2010 | Minear et al. |
| 2010/0124040 A1 | 5/2010 | Diebel et al. |
| 2010/0127660 A1 | 5/2010 | Cook et al. |
| 2010/0134105 A1 | 6/2010 | Zelinski et al. |
| 2010/0141214 A1 | 6/2010 | Yoon et al. |
| 2010/0142418 A1 | 6/2010 | Nishioka et al. |
| 2010/0142509 A1 | 6/2010 | Zhu et al. |
| 2010/0148723 A1 | 6/2010 | Cook et al. |
| 2010/0151808 A1 | 6/2010 | Toncich et al. |
| 2010/0156721 A1 | 6/2010 | Alamouti et al. |
| 2010/0156741 A1 | 6/2010 | Vazquez et al. |
| 2010/0164296 A1 | 7/2010 | Kurs et al. |
| 2010/0164433 A1 | 7/2010 | Janefalker et al. |
| 2010/0167664 A1 | 7/2010 | Szini |
| 2010/0171461 A1 | 7/2010 | Baarman et al. |
| 2010/0171676 A1 | 7/2010 | Tani et al. |
| 2010/0174629 A1 | 7/2010 | Taylor et al. |
| 2010/0176934 A1 | 7/2010 | Chou et al. |
| 2010/0181961 A1 | 7/2010 | Novak et al. |
| 2010/0181964 A1 | 7/2010 | Huggins et al. |
| 2010/0194206 A1 | 8/2010 | Burdo et al. |
| 2010/0201189 A1 | 8/2010 | Kirby et al. |
| 2010/0201201 A1 | 8/2010 | Mobarhan et al. |
| 2010/0201314 A1 | 8/2010 | Toncich et al. |
| 2010/0207572 A1 | 8/2010 | Kirby et al. |
| 2010/0210233 A1 | 8/2010 | Cook et al. |
| 2010/0213895 A1 | 8/2010 | Keating et al. |
| 2010/0214177 A1 | 8/2010 | Parsche |
| 2010/0222010 A1 | 9/2010 | Ozaki et al. |
| 2010/0225270 A1 | 9/2010 | Jacobs et al. |
| 2010/0227570 A1 | 9/2010 | Hendin |
| 2010/0231470 A1 | 9/2010 | Lee et al. |
| 2010/0237709 A1 | 9/2010 | Hall et al. |
| 2010/0244576 A1 | 9/2010 | Hillan et al. |
| 2010/0253281 A1 | 10/2010 | Li |
| 2010/0256831 A1 | 10/2010 | Abramo et al. |
| 2010/0259110 A1 | 10/2010 | Kurs et al. |
| 2010/0259401 A1 | 10/2010 | Azancot et al. |
| 2010/0259447 A1 | 10/2010 | Crouch |
| 2010/0264747 A1 | 10/2010 | Hall et al. |
| 2010/0264748 A1 | 10/2010 | Tucker |
| 2010/0277003 A1 | 11/2010 | Von Novak et al. |
| 2010/0277121 A1 | 11/2010 | Hall et al. |
| 2010/0279606 A1 | 11/2010 | Hillan et al. |
| 2010/0289341 A1 | 11/2010 | Ozaki et al. |
| 2010/0295372 A1 | 11/2010 | Hyde et al. |
| 2010/0308767 A1 | 12/2010 | Rofougaran et al. |
| 2010/0309079 A1 | 12/2010 | Rofougaran et al. |
| 2010/0309088 A1 | 12/2010 | Hyvonen et al. |
| 2010/0315045 A1 | 12/2010 | Zeine |
| 2010/0316163 A1 | 12/2010 | Forenza et al. |
| 2010/0327766 A1 | 12/2010 | Recker et al. |
| 2010/0328044 A1 | 12/2010 | Waffenschmidt et al. |
| 2010/0332401 A1 | 12/2010 | Prahlad et al. |
| 2011/0009057 A1 | 1/2011 | Saunamäki |
| 2011/0013198 A1 | 1/2011 | Shirley |
| 2011/0018360 A1 | 1/2011 | Baarman et al. |
| 2011/0028114 A1 | 2/2011 | Kerselaers |
| 2011/0031928 A1 | 2/2011 | Soar |
| 2011/0032149 A1 | 2/2011 | Leabman |
| 2011/0032866 A1 | 2/2011 | Leabman |

(56) References Cited

U.S. PATENT DOCUMENTS

| | | |
|---|---|---|
| 2011/0034190 A1 | 2/2011 | Leabman |
| 2011/0034191 A1 | 2/2011 | Leabman |
| 2011/0043047 A1 | 2/2011 | Karalis et al. |
| 2011/0043163 A1 | 2/2011 | Baarman et al. |
| 2011/0043327 A1 | 2/2011 | Baarman et al. |
| 2011/0050166 A1 | 3/2011 | Cook et al. |
| 2011/0055037 A1 | 3/2011 | Hayashigawa et al. |
| 2011/0056215 A1 | 3/2011 | Ham |
| 2011/0057607 A1 | 3/2011 | Carobolante |
| 2011/0057853 A1 | 3/2011 | Kim et al. |
| 2011/0062788 A1 | 3/2011 | Chen et al. |
| 2011/0074342 A1 | 3/2011 | MacLaughlin |
| 2011/0074346 A1 | 3/2011 | Hall et al. |
| 2011/0074349 A1 | 3/2011 | Ghovanloo |
| 2011/0074620 A1 | 3/2011 | Wintermantel |
| 2011/0078092 A1 | 3/2011 | Kim et al. |
| 2011/0090126 A1 | 4/2011 | Szini et al. |
| 2011/0092161 A1 | 4/2011 | Dotan |
| 2011/0109167 A1 | 5/2011 | Park et al. |
| 2011/0114401 A1 | 5/2011 | Kanno |
| 2011/0115303 A1 | 5/2011 | Baarman et al. |
| 2011/0115432 A1 | 5/2011 | El-Maleh |
| 2011/0115605 A1 | 5/2011 | Dimig et al. |
| 2011/0121660 A1 | 5/2011 | Azancot et al. |
| 2011/0122018 A1 | 5/2011 | Tarng et al. |
| 2011/0122026 A1 | 5/2011 | DeLaquil et al. |
| 2011/0127845 A1 | 6/2011 | Walley et al. |
| 2011/0127952 A1 | 6/2011 | Walley et al. |
| 2011/0133655 A1 | 6/2011 | Recker et al. |
| 2011/0133691 A1 | 6/2011 | Hautanen |
| 2011/0148578 A1 | 6/2011 | Aloi et al. |
| 2011/0148595 A1 | 6/2011 | Miller et al. |
| 2011/0151789 A1 | 6/2011 | Viglione et al. |
| 2011/0152670 A1 | 6/2011 | Yang |
| 2011/0154429 A1 | 6/2011 | Stantchev |
| 2011/0156493 A1 | 6/2011 | Bennett |
| 2011/0156494 A1 | 6/2011 | Mashinsky |
| 2011/0156640 A1 | 6/2011 | Moshfeghi |
| 2011/0163128 A1 | 7/2011 | Taguchi et al. |
| 2011/0175455 A1 | 7/2011 | Hashiguchi |
| 2011/0175461 A1 | 7/2011 | Tinaphong |
| 2011/0181120 A1 | 7/2011 | Liu et al. |
| 2011/0182245 A1 | 7/2011 | Malkamaki et al. |
| 2011/0184842 A1 | 7/2011 | Melen |
| 2011/0188207 A1 | 8/2011 | Won et al. |
| 2011/0193688 A1 | 8/2011 | Forsell |
| 2011/0194543 A1 | 8/2011 | Zhao et al. |
| 2011/0195722 A1 | 8/2011 | Walter et al. |
| 2011/0199046 A1 | 8/2011 | Tsai et al. |
| 2011/0215086 A1 | 9/2011 | Yeh |
| 2011/0217923 A1 | 9/2011 | Ma |
| 2011/0220634 A1 | 9/2011 | Yeh |
| 2011/0221389 A1 | 9/2011 | Won et al. |
| 2011/0222154 A1 | 9/2011 | Choi et al. |
| 2011/0222272 A1 | 9/2011 | Yeh |
| 2011/0227725 A1 | 9/2011 | Muirhead |
| 2011/0228436 A1 | 9/2011 | Lee et al. |
| 2011/0243040 A1 | 10/2011 | Khan et al. |
| 2011/0243050 A1 | 10/2011 | Yanover |
| 2011/0244913 A1 | 10/2011 | Kim et al. |
| 2011/0248573 A1 | 10/2011 | Kanno et al. |
| 2011/0248575 A1 | 10/2011 | Kim et al. |
| 2011/0249678 A1 | 10/2011 | Bonicatto |
| 2011/0254377 A1 | 10/2011 | Widmer et al. |
| 2011/0254503 A1 | 10/2011 | Widmer et al. |
| 2011/0259953 A1 | 10/2011 | Baarman et al. |
| 2011/0273977 A1 | 11/2011 | Shapira et al. |
| 2011/0278941 A1 | 11/2011 | Krishna et al. |
| 2011/0279226 A1 | 11/2011 | Chen et al. |
| 2011/0281535 A1 | 11/2011 | Low et al. |
| 2011/0282415 A1 | 11/2011 | Eckhoff et al. |
| 2011/0285213 A1 | 11/2011 | Kowalewski |
| 2011/0286374 A1 | 11/2011 | Shin et al. |
| 2011/0291489 A1 | 12/2011 | Tsai et al. |
| 2011/0302078 A1 | 12/2011 | Failing |
| 2011/0304216 A1 | 12/2011 | Baarman |
| 2011/0304437 A1 | 12/2011 | Beeler |
| 2011/0304521 A1 | 12/2011 | Ando et al. |
| 2012/0001644 A1 | 1/2012 | Baarman et al. |
| 2012/0007441 A1 | 1/2012 | John |
| 2012/0013196 A1 | 1/2012 | Kim et al. |
| 2012/0013198 A1 | 1/2012 | Uramoto et al. |
| 2012/0013296 A1 | 1/2012 | Heydari et al. |
| 2012/0019419 A1 | 1/2012 | Prat et al. |
| 2012/0025622 A1 | 2/2012 | Kim et al. |
| 2012/0043887 A1 | 2/2012 | Mesibov |
| 2012/0051109 A1 | 3/2012 | Kim et al. |
| 2012/0051294 A1 | 3/2012 | Guillouard |
| 2012/0056486 A1 | 3/2012 | Endo et al. |
| 2012/0056741 A1 | 3/2012 | Zhu et al. |
| 2012/0068906 A1 | 3/2012 | Asher et al. |
| 2012/0074891 A1 | 3/2012 | Anderson et al. |
| 2012/0075072 A1 | 3/2012 | Pappu |
| 2012/0080944 A1 | 4/2012 | Recker et al. |
| 2012/0080957 A1 | 4/2012 | Cooper et al. |
| 2012/0086284 A1 | 4/2012 | Capanella et al. |
| 2012/0086615 A1 | 4/2012 | Norair |
| 2012/0095617 A1 | 4/2012 | Martin et al. |
| 2012/0098350 A1 | 4/2012 | Campanella et al. |
| 2012/0098485 A1 | 4/2012 | Kang et al. |
| 2012/0099675 A1 | 4/2012 | Kitamura et al. |
| 2012/0103562 A1 | 5/2012 | Clayton |
| 2012/0104849 A1 | 5/2012 | Jackson |
| 2012/0105252 A1 | 5/2012 | Wang |
| 2012/0112532 A1 | 5/2012 | Kesler et al. |
| 2012/0119914 A1 | 5/2012 | Uchida |
| 2012/0126743 A1 | 5/2012 | Rivers, Jr. |
| 2012/0132647 A1 | 5/2012 | Beverly et al. |
| 2012/0133214 A1 | 5/2012 | Yun et al. |
| 2012/0142291 A1 | 6/2012 | Rath et al. |
| 2012/0143383 A1 | 6/2012 | Cooperrider et al. |
| 2012/0146426 A1 | 6/2012 | Sabo |
| 2012/0146576 A1 | 6/2012 | Partovi |
| 2012/0146577 A1 | 6/2012 | Tanabe |
| 2012/0147802 A1 | 6/2012 | Ukita et al. |
| 2012/0149307 A1 | 6/2012 | Terada et al. |
| 2012/0150670 A1 | 6/2012 | Taylor et al. |
| 2012/0153740 A1 | 6/2012 | Soar |
| 2012/0153894 A1 | 6/2012 | Widmer et al. |
| 2012/0157019 A1 | 6/2012 | Li |
| 2012/0161531 A1 | 6/2012 | Kim et al. |
| 2012/0161544 A1 | 6/2012 | Kashiwagi et al. |
| 2012/0169276 A1 | 7/2012 | Wang |
| 2012/0169278 A1 | 7/2012 | Choi |
| 2012/0173418 A1 | 7/2012 | Beardsmore et al. |
| 2012/0179004 A1 | 7/2012 | Roesicke et al. |
| 2012/0181973 A1 | 7/2012 | Lyden |
| 2012/0182427 A1 | 7/2012 | Marshall |
| 2012/0188142 A1 | 7/2012 | Shashi et al. |
| 2012/0187851 A1 | 8/2012 | Huggins et al. |
| 2012/0193999 A1 | 8/2012 | Zeine |
| 2012/0200399 A1 | 8/2012 | Chae |
| 2012/0201153 A1 | 8/2012 | Bharadia et al. |
| 2012/0201173 A1 | 8/2012 | Jian et al. |
| 2012/0206299 A1 | 8/2012 | Valdes-Garcia |
| 2012/0211214 A1 | 8/2012 | Phan |
| 2012/0212071 A1 | 8/2012 | Miyabayashi et al. |
| 2012/0212072 A1 | 8/2012 | Miyabayashi et al. |
| 2012/0214462 A1 | 8/2012 | Chu et al. |
| 2012/0214536 A1 | 8/2012 | Kim et al. |
| 2012/0228392 A1 | 9/2012 | Cameron et al. |
| 2012/0228956 A1 | 9/2012 | Kamata |
| 2012/0231856 A1 | 9/2012 | Lee et al. |
| 2012/0235636 A1 | 9/2012 | Partovi |
| 2012/0242283 A1 | 9/2012 | Kim et al. |
| 2012/0242809 A1 | 9/2012 | White et al. |
| 2012/0248886 A1 | 10/2012 | Kesler et al. |
| 2012/0248888 A1 | 10/2012 | Kesler et al. |
| 2012/0248891 A1 | 10/2012 | Drennen |
| 2012/0249051 A1 | 10/2012 | Son et al. |
| 2012/0262002 A1 | 10/2012 | Widmer et al. |
| 2012/0265272 A1 | 10/2012 | Judkins |
| 2012/0267900 A1 | 10/2012 | Huffman et al. |
| 2012/0268238 A1 | 10/2012 | Park et al. |

(56) References Cited

U.S. PATENT DOCUMENTS

| | | |
|---|---|---|
| 2012/0270592 A1 | 10/2012 | Ngai |
| 2012/0274154 A1 | 11/2012 | DeLuca |
| 2012/0280650 A1 | 11/2012 | Kim et al. |
| 2012/0286582 A1 | 11/2012 | Kim et al. |
| 2012/0292993 A1 | 11/2012 | Mettler et al. |
| 2012/0293021 A1 | 11/2012 | Teggatz et al. |
| 2012/0293119 A1 | 11/2012 | Park et al. |
| 2012/0294054 A1 | 11/2012 | Kim et al. |
| 2012/0299389 A1 | 11/2012 | Lee et al. |
| 2012/0299540 A1 | 11/2012 | Perry |
| 2012/0299541 A1 | 11/2012 | Perry |
| 2012/0299542 A1 | 11/2012 | Perry |
| 2012/0300588 A1 | 11/2012 | Perry |
| 2012/0300592 A1 | 11/2012 | Perry |
| 2012/0300593 A1 | 11/2012 | Perry |
| 2012/0306284 A1 | 12/2012 | Lee et al. |
| 2012/0306433 A1 | 12/2012 | Kim et al. |
| 2012/0306572 A1 | 12/2012 | Hietala et al. |
| 2012/0306705 A1 | 12/2012 | Sakurai et al. |
| 2012/0306707 A1 | 12/2012 | Yang et al. |
| 2012/0306720 A1 | 12/2012 | Tanmi et al. |
| 2012/0307873 A1 | 12/2012 | Kim et al. |
| 2012/0309295 A1 | 12/2012 | Maguire |
| 2012/0309308 A1 | 12/2012 | Kim et al. |
| 2012/0309332 A1 | 12/2012 | Liao |
| 2012/0313446 A1 | 12/2012 | Park et al. |
| 2012/0313449 A1 | 12/2012 | Kurs |
| 2012/0313835 A1 | 12/2012 | Gebretnsae |
| 2012/0326660 A1 | 12/2012 | Lu et al. |
| 2013/0002550 A1 | 1/2013 | Zalewski |
| 2013/0005252 A1 | 1/2013 | Lee et al. |
| 2013/0018439 A1 | 1/2013 | Chow et al. |
| 2013/0024059 A1 | 1/2013 | Miller et al. |
| 2013/0026981 A1 | 1/2013 | Van Der Lee |
| 2013/0026982 A1 | 1/2013 | Rothenbaum |
| 2013/0032589 A1 | 2/2013 | Chung |
| 2013/0033571 A1 | 2/2013 | Steen |
| 2013/0038124 A1 | 2/2013 | Newdoll et al. |
| 2013/0038136 A1 | 2/2013 | Wheatley et al. |
| 2013/0038402 A1 | 2/2013 | Karalis et al. |
| 2013/0043738 A1 | 2/2013 | Park et al. |
| 2013/0044035 A1 | 2/2013 | Zhuang |
| 2013/0049471 A1 | 2/2013 | Oleynik |
| 2013/0049475 A1 | 2/2013 | Kim et al. |
| 2013/0049484 A1 | 2/2013 | Weissentern et al. |
| 2013/0057078 A1 | 3/2013 | Lee |
| 2013/0057205 A1 | 3/2013 | Lee et al. |
| 2013/0057210 A1 | 3/2013 | Negaard et al. |
| 2013/0057364 A1 | 3/2013 | Kesler et al. |
| 2013/0058379 A1 | 3/2013 | Kim et al. |
| 2013/0062959 A1 | 3/2013 | Lee et al. |
| 2013/0063082 A1 | 3/2013 | Lee et al. |
| 2013/0063143 A1 | 3/2013 | Adalsteinsson et al. |
| 2013/0063266 A1 | 3/2013 | Yunker et al. |
| 2013/0063550 A1 | 3/2013 | Ritchey et al. |
| 2013/0069444 A1 | 3/2013 | Waffenschmidt et al. |
| 2013/0076308 A1 | 3/2013 | Niskala et al. |
| 2013/0077650 A1 | 3/2013 | Traxler et al. |
| 2013/0078918 A1 | 3/2013 | Crowley et al. |
| 2013/0082651 A1 | 4/2013 | Park et al. |
| 2013/0082653 A1 | 4/2013 | Lee et al. |
| 2013/0083774 A1 | 4/2013 | Son et al. |
| 2013/0088082 A1 | 4/2013 | Kang et al. |
| 2013/0088090 A1 | 4/2013 | Wu |
| 2013/0088192 A1 | 4/2013 | Eaton |
| 2013/0088331 A1 | 4/2013 | Cho |
| 2013/0093388 A1 | 4/2013 | Partovi |
| 2013/0099389 A1 | 4/2013 | Hong et al. |
| 2013/0099586 A1 | 4/2013 | Kato |
| 2013/0106197 A1 | 5/2013 | Bae et al. |
| 2013/0107023 A1 | 5/2013 | Tanaka et al. |
| 2013/0119777 A1 | 5/2013 | Rees |
| 2013/0119778 A1 | 5/2013 | Jung |
| 2013/0119929 A1 | 5/2013 | Partovi |
| 2013/0120052 A1 | 5/2013 | Siska |
| 2013/0120205 A1 | 5/2013 | Thomson et al. |
| 2013/0120206 A1 | 5/2013 | Biancotto et al. |
| 2013/0120217 A1 | 5/2013 | Ueda et al. |
| 2013/0130621 A1 | 5/2013 | Kim et al. |
| 2013/0132010 A1 | 5/2013 | Winger et al. |
| 2013/0134923 A1 | 5/2013 | Smith |
| 2013/0137455 A1 | 5/2013 | Xia |
| 2013/0141037 A1 | 6/2013 | Jenwatanavet et al. |
| 2013/0148341 A1 | 6/2013 | Williams |
| 2013/0149975 A1 | 6/2013 | Yu et al. |
| 2013/0154387 A1 | 6/2013 | Lee et al. |
| 2013/0155748 A1 | 6/2013 | Sundstrom |
| 2013/0157729 A1 | 6/2013 | Tabe |
| 2013/0162335 A1 | 6/2013 | Kim et al. |
| 2013/0169061 A1 | 7/2013 | Microshnichenko et al. |
| 2013/0169219 A1 | 7/2013 | Gray |
| 2013/0169348 A1 | 7/2013 | Shi |
| 2013/0171939 A1 | 7/2013 | Tian et al. |
| 2013/0175877 A1 | 7/2013 | Abe et al. |
| 2013/0178253 A1 | 7/2013 | Karaoguz |
| 2013/0181881 A1 | 7/2013 | Christie et al. |
| 2013/0187475 A1 | 7/2013 | Vendik |
| 2013/0190031 A1 | 7/2013 | Persson et al. |
| 2013/0193769 A1 | 8/2013 | Mehta et al. |
| 2013/0197320 A1 | 8/2013 | Albert et al. |
| 2013/0200064 A1 | 8/2013 | Alexander |
| 2013/0201316 A1 | 8/2013 | Binder et al. |
| 2013/0207477 A1 | 8/2013 | Nam et al. |
| 2013/0207604 A1 | 8/2013 | Zeine |
| 2013/0207879 A1 | 8/2013 | Rada et al. |
| 2013/0210357 A1 | 8/2013 | Qin et al. |
| 2013/0221757 A1 | 8/2013 | Cho et al. |
| 2013/0222201 A1 | 8/2013 | Ma et al. |
| 2013/0223538 A1 | 8/2013 | Wang et al. |
| 2013/0234530 A1 | 9/2013 | Miyauchi |
| 2013/0234536 A1 | 9/2013 | Chemishkian et al. |
| 2013/0234658 A1 | 9/2013 | Endo et al. |
| 2013/0241306 A1 | 9/2013 | Aber et al. |
| 2013/0241468 A1 | 9/2013 | Moshfeghi |
| 2013/0241474 A1 | 9/2013 | Moshfeghi |
| 2013/0249478 A1 | 9/2013 | Hirano |
| 2013/0249479 A1 | 9/2013 | Partovi |
| 2013/0249682 A1 | 9/2013 | Van Wiemeersch et al. |
| 2013/0250102 A1 | 9/2013 | Scanlon et al. |
| 2013/0254578 A1 | 9/2013 | Huang et al. |
| 2013/0264997 A1 | 10/2013 | Lee et al. |
| 2013/0268782 A1 | 10/2013 | Tam et al. |
| 2013/0270923 A1 | 10/2013 | Cook et al. |
| 2013/0278076 A1 | 10/2013 | Proud |
| 2013/0278209 A1 | 10/2013 | Von Novak |
| 2013/0285464 A1 | 10/2013 | Miwa |
| 2013/0285477 A1 | 10/2013 | Lo et al. |
| 2013/0285606 A1 | 10/2013 | Ben-Shalom et al. |
| 2013/0288600 A1 | 10/2013 | Kuusilinna et al. |
| 2013/0288617 A1 | 10/2013 | Kim et al. |
| 2013/0293423 A1 | 11/2013 | Moshfeghi |
| 2013/0300356 A1 | 11/2013 | Yang |
| 2013/0307751 A1 | 11/2013 | Yu-Juin et al. |
| 2013/0310020 A1 | 11/2013 | Kazuhiro |
| 2013/0311798 A1 | 11/2013 | Sultenfuss |
| 2013/0328417 A1 | 12/2013 | Takeuchi |
| 2013/0334883 A1 | 12/2013 | Kim et al. |
| 2013/0339108 A1 | 12/2013 | Ryder et al. |
| 2013/0343208 A1 | 12/2013 | Sexton et al. |
| 2013/0343251 A1 | 12/2013 | Zhang |
| 2013/0343585 A1 | 12/2013 | Bennett et al. |
| 2014/0001608 A1 | 1/2014 | McPartlin |
| 2014/0001846 A1 | 1/2014 | Mosebrook |
| 2014/0001875 A1 | 1/2014 | Nahidipour |
| 2014/0001876 A1 | 1/2014 | Fujiwara et al. |
| 2014/0002012 A1 | 1/2014 | McCauley et al. |
| 2014/0006017 A1 | 1/2014 | Sen |
| 2014/0008993 A1 | 1/2014 | Leabman |
| 2014/0009110 A1 | 1/2014 | Lee |
| 2014/0011531 A1 | 1/2014 | Burstrom et al. |
| 2014/0015336 A1 | 1/2014 | Weber et al. |
| 2014/0015344 A1 | 1/2014 | Mohamadi |
| 2014/0021907 A1 | 1/2014 | Yu et al. |
| 2014/0021908 A1 | 1/2014 | McCool |

(56) References Cited

U.S. PATENT DOCUMENTS

| | | |
|---|---|---|
| 2014/0024325 A1 | 1/2014 | Iun et al. |
| 2014/0035524 A1 | 2/2014 | Zeine |
| 2014/0035526 A1 | 2/2014 | Tripathi et al. |
| 2014/0035786 A1 | 2/2014 | Ley |
| 2014/0043248 A1 | 2/2014 | Yeh |
| 2014/0049422 A1 | 2/2014 | Von Novak et al. |
| 2014/0054971 A1 | 2/2014 | Kissin |
| 2014/0057618 A1 | 2/2014 | Zirwas et al. |
| 2014/0062395 A1 | 3/2014 | Kwon et al. |
| 2014/0082435 A1 | 3/2014 | Kitgawa |
| 2014/0086125 A1 | 3/2014 | Polo et al. |
| 2014/0086592 A1 | 3/2014 | Nakahara et al. |
| 2014/0091756 A1 | 4/2014 | Ofstein et al. |
| 2014/0091968 A1 | 4/2014 | Harel et al. |
| 2014/0091974 A1 | 4/2014 | Desclos et al. |
| 2014/0103869 A1 | 4/2014 | Radovic |
| 2014/0104157 A1 | 4/2014 | Burns |
| 2014/0111147 A1 | 4/2014 | Soar |
| 2014/0111153 A1 | 4/2014 | Kwon et al. |
| 2014/0113689 A1 | 4/2014 | Lee |
| 2014/0117946 A1 | 5/2014 | Muller et al. |
| 2014/0118140 A1 | 5/2014 | Amis |
| 2014/0128107 A1 | 5/2014 | An |
| 2014/0132210 A1 | 5/2014 | Partovi |
| 2014/0133279 A1 | 5/2014 | Khuri-Yakub |
| 2014/0139034 A1 | 5/2014 | Sankar et al. |
| 2014/0139039 A1 | 5/2014 | Cook et al. |
| 2014/0139180 A1 | 5/2014 | Kim et al. |
| 2014/0141838 A1 | 5/2014 | Cai et al. |
| 2014/0142876 A1 | 5/2014 | John et al. |
| 2014/0143933 A1 | 5/2014 | Low et al. |
| 2014/0145879 A1 | 5/2014 | Pan |
| 2014/0145884 A1 | 5/2014 | Dang et al. |
| 2014/0152117 A1 | 6/2014 | Sanker |
| 2014/0159646 A1 | 6/2014 | Sankar et al. |
| 2014/0159651 A1 | 6/2014 | Von Novak et al. |
| 2014/0159652 A1 | 6/2014 | Hall et al. |
| 2014/0159662 A1 | 6/2014 | Furui |
| 2014/0159667 A1 | 6/2014 | Kim et al. |
| 2014/0169385 A1 | 6/2014 | Hadani et al. |
| 2014/0175876 A1 | 6/2014 | Cheatham, III et al. |
| 2014/0175893 A1 | 6/2014 | Sengupta et al. |
| 2014/0176054 A1 | 6/2014 | Porat et al. |
| 2014/0176061 A1 | 6/2014 | Cheatham, III et al. |
| 2014/0176082 A1 | 6/2014 | Visser |
| 2014/0177399 A1 | 6/2014 | Teng et al. |
| 2014/0183964 A1 | 7/2014 | Walley |
| 2014/0184148 A1 | 7/2014 | Van Der Lee et al. |
| 2014/0184155 A1 | 7/2014 | Cha |
| 2014/0184163 A1 | 7/2014 | Das et al. |
| 2014/0184170 A1 | 7/2014 | Jeong |
| 2014/0191568 A1 | 7/2014 | Partovi |
| 2014/0191818 A1 | 7/2014 | Waffenschmidt et al. |
| 2014/0194092 A1 | 7/2014 | Wanstedt et al. |
| 2014/0194095 A1 | 7/2014 | Wanstedt et al. |
| 2014/0197691 A1 | 7/2014 | Wang |
| 2014/0203629 A1 | 7/2014 | Hoffman et al. |
| 2014/0203768 A1 | 7/2014 | Andic et al. |
| 2014/0206384 A1 | 7/2014 | Kim et al. |
| 2014/0210281 A1 | 7/2014 | Ito et al. |
| 2014/0217955 A1 | 8/2014 | Lin |
| 2014/0217967 A1 | 8/2014 | Zeine et al. |
| 2014/0225805 A1 | 8/2014 | Pan et al. |
| 2014/0229644 A1 | 8/2014 | Thanigasalam et al. |
| 2014/0232320 A1 | 8/2014 | Ento July et al. |
| 2014/0232610 A1 | 8/2014 | Shigemoto et al. |
| 2014/0239733 A1 | 8/2014 | Mach et al. |
| 2014/0241231 A1 | 8/2014 | Zeine |
| 2014/0245036 A1 | 8/2014 | Oishi |
| 2014/0246416 A1 | 9/2014 | White |
| 2014/0247152 A1 | 9/2014 | Proud |
| 2014/0252813 A1 | 9/2014 | Lee et al. |
| 2014/0252866 A1 | 9/2014 | Walsh et al. |
| 2014/0252869 A1 | 9/2014 | Kamiura et al. |
| 2014/0265725 A1 | 9/2014 | Angle et al. |
| 2014/0265727 A1 | 9/2014 | Berte |
| 2014/0265943 A1 | 9/2014 | Angle et al. |
| 2014/0266025 A1 | 9/2014 | Jakubowski |
| 2014/0266160 A1 | 9/2014 | Coza |
| 2014/0266946 A1 | 9/2014 | Bily et al. |
| 2014/0273819 A1 | 9/2014 | Nadakuduti et al. |
| 2014/0273892 A1 | 9/2014 | Nourbakhsh |
| 2014/0281655 A1 | 9/2014 | Angle et al. |
| 2014/0292090 A1 | 10/2014 | Cordeiro et al. |
| 2014/0292269 A1 | 10/2014 | Keating et al. |
| 2014/0292451 A1 | 10/2014 | Zimmerman |
| 2014/0300452 A1 | 10/2014 | Rofe et al. |
| 2014/0312706 A1 | 10/2014 | Fiorello et al. |
| 2014/0312833 A1 | 10/2014 | Won et al. |
| 2014/0325218 A1 | 10/2014 | Shimizu et al. |
| 2014/0327320 A1 | 11/2014 | Muhs et al. |
| 2014/0327390 A1 | 11/2014 | Park et al. |
| 2014/0333142 A1 | 11/2014 | Desrosiers |
| 2014/0346860 A1 | 11/2014 | Aubry et al. |
| 2014/0354063 A1 | 12/2014 | Leabman et al. |
| 2014/0354221 A1 | 12/2014 | Leabman et al. |
| 2014/0355718 A1 | 12/2014 | Guan et al. |
| 2014/0362517 A1 | 12/2014 | Moock et al. |
| 2014/0368048 A1 | 12/2014 | Leabman et al. |
| 2014/0368161 A1 | 12/2014 | Leabman et al. |
| 2014/0368405 A1 | 12/2014 | Ek et al. |
| 2014/0370929 A1 | 12/2014 | Khawand et al. |
| 2014/0375139 A1 | 12/2014 | Tsukamoto |
| 2014/0375253 A1 | 12/2014 | Leabman et al. |
| 2014/0375258 A1 | 12/2014 | Arkhipenkov |
| 2014/0375261 A1 | 12/2014 | Manova-Elssibony et al. |
| 2014/0380403 A1 | 12/2014 | Pearson et al. |
| 2015/0001949 A1 | 1/2015 | Leabman et al. |
| 2015/0002086 A1 | 1/2015 | Matos et al. |
| 2015/0003207 A1 | 1/2015 | Lee et al. |
| 2015/0008980 A1 | 1/2015 | Kim et al. |
| 2015/0011160 A1 | 1/2015 | Uurgovan et al. |
| 2015/0015180 A1 | 1/2015 | Miller et al. |
| 2015/0015182 A1 | 1/2015 | Brandtman et al. |
| 2015/0015192 A1 | 1/2015 | Leabman et al. |
| 2015/0021990 A1 | 1/2015 | Myer et al. |
| 2015/0022008 A1 | 1/2015 | Leabman et al. |
| 2015/0022010 A1 | 1/2015 | Leabman et al. |
| 2015/0022194 A1 | 1/2015 | Almalki et al. |
| 2015/0023204 A1 | 1/2015 | Wil et al. |
| 2015/0028688 A1 | 1/2015 | Masaoka |
| 2015/0028694 A1 | 1/2015 | Leabman et al. |
| 2015/0028697 A1 | 1/2015 | Leabman et al. |
| 2015/0028875 A1 | 1/2015 | Irie et al. |
| 2015/0035378 A1 | 2/2015 | Calhoun et al. |
| 2015/0035709 A1 | 2/2015 | Lim |
| 2015/0035715 A1 | 2/2015 | Kim et al. |
| 2015/0039482 A1 | 2/2015 | Fuinaga |
| 2015/0041459 A1 | 2/2015 | Leabman et al. |
| 2015/0042265 A1 | 2/2015 | Leabman et al. |
| 2015/0042287 A1 | 2/2015 | Liu et al. |
| 2015/0044977 A1 | 2/2015 | Ramasamy et al. |
| 2015/0046526 A1 | 2/2015 | Bush et al. |
| 2015/0061404 A1 | 3/2015 | Lamenza et al. |
| 2015/0076917 A1 | 3/2015 | Leabman et al. |
| 2015/0076927 A1 | 3/2015 | Leabman et al. |
| 2015/0077036 A1 | 3/2015 | Leabman et al. |
| 2015/0077037 A1 | 3/2015 | Leabman et al. |
| 2015/0091520 A1 | 4/2015 | Blum et al. |
| 2015/0091706 A1 | 4/2015 | Chemishkian et al. |
| 2015/0097442 A1 | 4/2015 | Muurinen |
| 2015/0097663 A1 | 4/2015 | Sloo et al. |
| 2015/0102764 A1 | 4/2015 | Leabman et al. |
| 2015/0102769 A1 | 4/2015 | Leabman et al. |
| 2015/0102942 A1 | 4/2015 | Houser et al. |
| 2015/0102973 A1 | 4/2015 | Hand et al. |
| 2015/0108848 A1 | 4/2015 | Joehren |
| 2015/0109181 A1 | 4/2015 | Hyde et al. |
| 2015/0115877 A1 | 4/2015 | Aria et al. |
| 2015/0115878 A1 | 4/2015 | Park |
| 2015/0116153 A1 | 4/2015 | Chen et al. |
| 2015/0128733 A1 | 5/2015 | Taylor et al. |
| 2015/0130285 A1 | 5/2015 | Leabman et al. |
| 2015/0130293 A1 | 5/2015 | Hajimiri et al. |

(56) References Cited

U.S. PATENT DOCUMENTS

| | | |
|---|---|---|
| 2015/0137612 A1 | 5/2015 | Yamakawa et al. |
| 2015/0148664 A1 | 5/2015 | Stolka et al. |
| 2015/0155737 A1 | 6/2015 | Mayo |
| 2015/0155738 A1 | 6/2015 | Leabman et al. |
| 2015/0162662 A1 | 6/2015 | Chen et al. |
| 2015/0162751 A1 | 6/2015 | Leabman et al. |
| 2015/0162779 A1 | 6/2015 | Lee et al. |
| 2015/0171512 A1 | 6/2015 | Chen et al. |
| 2015/0171513 A1 | 6/2015 | Chen et al. |
| 2015/0171516 A1 | 6/2015 | Chen et al. |
| 2015/0171656 A1 | 6/2015 | Leabman et al. |
| 2015/0171658 A1 | 6/2015 | Manova-Elssibony et al. |
| 2015/0171931 A1 | 6/2015 | Won et al. |
| 2015/0177326 A1 | 6/2015 | Chakraborty et al. |
| 2015/0180133 A1 | 6/2015 | Hunt |
| 2015/0180249 A1 | 6/2015 | Jeon et al. |
| 2015/0180284 A1 | 6/2015 | Kang et al. |
| 2015/0181117 A1 | 6/2015 | Park et al. |
| 2015/0187491 A1 | 7/2015 | Yanagawa |
| 2015/0188352 A1 | 7/2015 | Peek et al. |
| 2015/0199665 A1 | 7/2015 | Chu |
| 2015/0201385 A1 | 7/2015 | Mercer et al. |
| 2015/0207333 A1 | 7/2015 | Baarman et al. |
| 2015/0207542 A1 | 7/2015 | Zeine |
| 2015/0222126 A1 | 8/2015 | Leabman et al. |
| 2015/0233987 A1 | 8/2015 | Von Novak, Iii et al. |
| 2015/0234144 A1 | 8/2015 | Cameron et al. |
| 2015/0236520 A1 | 8/2015 | Baarman |
| 2015/0236877 A1 | 8/2015 | Peng et al. |
| 2015/0244070 A1 | 8/2015 | Cheng et al. |
| 2015/0244080 A1 | 8/2015 | Gregoire |
| 2015/0244187 A1 | 8/2015 | Horie |
| 2015/0244201 A1 | 8/2015 | Chu |
| 2015/0244341 A1 | 8/2015 | Ritter et al. |
| 2015/0249484 A1 | 9/2015 | Mach et al. |
| 2015/0255989 A1 | 9/2015 | Walley et al. |
| 2015/0256097 A1 | 9/2015 | Gudan et al. |
| 2015/0260835 A1 | 9/2015 | Widmer et al. |
| 2015/0262465 A1 | 9/2015 | Pritchett |
| 2015/0263534 A1 | 9/2015 | Lee et al. |
| 2015/0263548 A1 | 9/2015 | Cooper |
| 2015/0270618 A1 | 9/2015 | Zhu et al. |
| 2015/0270622 A1 | 9/2015 | Takasaki et al. |
| 2015/0270741 A1 | 9/2015 | Leabman et al. |
| 2015/0278558 A1 | 10/2015 | Priev et al. |
| 2015/0280429 A1 | 10/2015 | Makita et al. |
| 2015/0280484 A1 | 10/2015 | Radziemski et al. |
| 2015/0288074 A1 | 10/2015 | Harper et al. |
| 2015/0288214 A1 | 10/2015 | Borngraber |
| 2015/0288438 A1 | 10/2015 | Maltsev et al. |
| 2015/0306063 A1 | 10/2015 | McGinnis et al. |
| 2015/0311585 A1 | 10/2015 | Church et al. |
| 2015/0312721 A1 | 10/2015 | Singh |
| 2015/0318729 A1 | 11/2015 | Leabman |
| 2015/0326024 A1 | 11/2015 | Bell et al. |
| 2015/0326070 A1 | 11/2015 | Petras et al. |
| 2015/0326072 A1 | 11/2015 | Petras et al. |
| 2015/0326143 A1 | 11/2015 | Petras et al. |
| 2015/0327085 A1 | 11/2015 | Hadani |
| 2015/0333528 A1 | 11/2015 | Leabman |
| 2015/0333573 A1 | 11/2015 | Leabman |
| 2015/0333800 A1 | 11/2015 | Perry et al. |
| 2015/0339497 A1 | 11/2015 | Kurian |
| 2015/0340759 A1 | 11/2015 | Bridgelall et al. |
| 2015/0340903 A1 | 11/2015 | Bell et al. |
| 2015/0341087 A1 | 11/2015 | Moore et al. |
| 2015/0356482 A1 | 12/2015 | Whipple et al. |
| 2015/0358222 A1 | 12/2015 | Berger et al. |
| 2015/0365003 A1 | 12/2015 | Sadwick |
| 2015/0365137 A1 | 12/2015 | Miller et al. |
| 2015/0365138 A1 | 12/2015 | Miller et al. |
| 2016/0001136 A1 | 1/2016 | King et al. |
| 2016/0005068 A1 | 1/2016 | Im et al. |
| 2016/0012695 A1 | 1/2016 | Bell et al. |
| 2016/0013560 A1 | 1/2016 | Daniels |
| 2016/0013661 A1 | 1/2016 | Kurs et al. |
| 2016/0013677 A1 | 1/2016 | Bell et al. |
| 2016/0013855 A1 | 1/2016 | Campos |
| 2016/0020636 A1 | 1/2016 | Khlat |
| 2016/0028403 A1 | 1/2016 | McCaughan et al. |
| 2016/0033254 A1 | 2/2016 | Zeine et al. |
| 2016/0042206 A1 | 2/2016 | Pesavento et al. |
| 2016/0043571 A1 | 2/2016 | Kesler et al. |
| 2016/0043572 A1 | 2/2016 | Cooper et al. |
| 2016/0054440 A1 | 2/2016 | Younis |
| 2016/0056635 A1 | 2/2016 | Bell |
| 2016/0056640 A1 | 2/2016 | Mao |
| 2016/0056664 A1 | 2/2016 | Partovi |
| 2016/0057268 A1 | 2/2016 | Jiang |
| 2016/0062319 A1 | 3/2016 | Kim et al. |
| 2016/0064959 A1 | 3/2016 | Jung et al. |
| 2016/0065005 A1 | 3/2016 | Won et al. |
| 2016/0079799 A1 | 3/2016 | Khlat |
| 2016/0087483 A1 | 3/2016 | Hietala et al. |
| 2016/0087486 A1 | 3/2016 | Pogorelik et al. |
| 2016/0087687 A1 | 3/2016 | Kesler et al. |
| 2016/0089987 A1 | 3/2016 | Ichikawa et al. |
| 2016/0094091 A1 | 3/2016 | Shin et al. |
| 2016/0094092 A1 | 3/2016 | Davlantes et al. |
| 2016/0099601 A1 | 4/2016 | Leabman et al. |
| 2016/0099611 A1 | 4/2016 | Leabman et al. |
| 2016/0099614 A1 | 4/2016 | Leabman et al. |
| 2016/0099755 A1 | 4/2016 | Leabman et al. |
| 2016/0099757 A1 | 4/2016 | Leabman et al. |
| 2016/0112787 A1 | 4/2016 | Rich |
| 2016/0114687 A1 | 4/2016 | Ichikawa et al. |
| 2016/0126749 A1 | 5/2016 | Shichino et al. |
| 2016/0126752 A1 | 5/2016 | Vuori et al. |
| 2016/0126776 A1 | 5/2016 | Kim et al. |
| 2016/0141908 A1 | 5/2016 | Jakl et al. |
| 2016/0164563 A1 | 6/2016 | Khawand et al. |
| 2016/0172890 A1 | 6/2016 | Jeong |
| 2016/0174162 A1 | 6/2016 | Nadakuduti et al. |
| 2016/0181849 A1 | 6/2016 | Govindaraj |
| 2016/0181867 A1 | 6/2016 | Daniel et al. |
| 2016/0181873 A1 | 6/2016 | Mitcheson et al. |
| 2016/0197511 A1 | 7/2016 | Atasoy et al. |
| 2016/0197522 A1 | 7/2016 | Zeine et al. |
| 2016/0202343 A1 | 7/2016 | Okutsu |
| 2016/0204642 A1 | 7/2016 | Oh |
| 2016/0204643 A1 | 7/2016 | Manova-Elssibony |
| 2016/0218545 A1 | 7/2016 | Schroeder et al. |
| 2016/0233582 A1 | 8/2016 | Piskun |
| 2016/0238365 A1 | 8/2016 | Wixey et al. |
| 2016/0240908 A1 | 8/2016 | Strong |
| 2016/0248276 A1 | 8/2016 | Hong et al. |
| 2016/0294225 A1 | 10/2016 | Blum et al. |
| 2016/0299210 A1 | 10/2016 | Zeine |
| 2016/0301240 A1 | 10/2016 | Zeine |
| 2016/0322833 A1 | 11/2016 | Moshfeghi et al. |
| 2016/0322868 A1 | 11/2016 | Akuzawa et al. |
| 2016/0323000 A1 | 11/2016 | Liu et al. |
| 2016/0325680 A1 | 11/2016 | Curtis et al. |
| 2016/0336804 A1 | 11/2016 | Son et al. |
| 2016/0339258 A1 | 11/2016 | Perryman et al. |
| 2016/0344098 A1 | 11/2016 | Ming |
| 2016/0359367 A1 | 12/2016 | Rothschild |
| 2016/0368510 A1 | 12/2016 | Simon et al. |
| 2016/0380464 A1 | 12/2016 | Chin et al. |
| 2016/0380466 A1 | 12/2016 | Yang et al. |
| 2017/0005481 A1 | 1/2017 | Von Novak, III |
| 2017/0005516 A9 | 1/2017 | Leabman et al. |
| 2017/0005524 A1 | 1/2017 | Akuzawa et al. |
| 2017/0005530 A1 | 1/2017 | Zeine et al. |
| 2017/0012448 A1 | 1/2017 | Miller et al. |
| 2017/0025887 A1 | 1/2017 | Hyun et al. |
| 2017/0025903 A1 | 1/2017 | Song et al. |
| 2017/0026087 A1 | 1/2017 | Tanabe |
| 2017/0033611 A1 | 2/2017 | Shin et al. |
| 2017/0040700 A1 | 2/2017 | Leung |
| 2017/0043675 A1 | 2/2017 | Jones et al. |
| 2017/0047784 A1 | 2/2017 | Jung et al. |
| 2017/0063168 A1 | 3/2017 | Uchida |
| 2017/0077733 A1 | 3/2017 | Jeong et al. |

(56) References Cited

U.S. PATENT DOCUMENTS

| | | | |
|---|---|---|---|
| 2017/0077765 A1 | 3/2017 | Bell et al. |
| 2017/0077979 A1 | 3/2017 | Papa et al. |
| 2017/0085120 A1 | 3/2017 | Leabman et al. |
| 2017/0085437 A1 | 3/2017 | Condeixa et al. |
| 2017/0092115 A1 | 3/2017 | Sloo et al. |
| 2017/0093229 A1 | 3/2017 | Sindia et al. |
| 2017/0110886 A1 | 4/2017 | Reynolds et al. |
| 2017/0110910 A1 | 4/2017 | Zeine et al. |
| 2017/0117756 A1 | 4/2017 | Muratov |
| 2017/0118714 A1 | 4/2017 | Kaechi |
| 2017/0127196 A1 | 5/2017 | Blum et al. |
| 2017/0134686 A9 | 5/2017 | Leabman |
| 2017/0141582 A1 | 5/2017 | Adolf et al. |
| 2017/0141583 A1 | 5/2017 | Adolf et al. |
| 2017/0141622 A1 | 5/2017 | Meichle |
| 2017/0163076 A1 | 6/2017 | Park et al. |
| 2017/0168595 A1 | 6/2017 | Sakaguchi et al. |
| 2017/0179763 A9 | 6/2017 | Leabman |
| 2017/0214422 A1 | 7/2017 | Na et al. |
| 2017/0274787 A1 | 9/2017 | Salter et al. |
| 2017/0338695 A1 | 11/2017 | Port |
| 2017/0346349 A1 | 11/2017 | Shimokawa |
| 2018/0006611 A1 | 1/2018 | de Jong et al. |
| 2018/0012082 A1 | 1/2018 | Satazoda et al. |
| 2018/0040929 A1 | 2/2018 | Chappelle |
| 2018/0048178 A1 | 2/2018 | Leabman |
| 2018/0090992 A1 | 3/2018 | Shrivastava et al. |
| 2018/0131449 A1 | 5/2018 | Kare et al. |
| 2018/0205265 A1 | 7/2018 | Park et al. |
| 2018/0227018 A1 | 8/2018 | Moshfeghi |
| 2018/0241255 A1 | 8/2018 | Leabman |
| 2018/0248409 A1 | 8/2018 | Johnston |
| 2018/0262050 A1 | 9/2018 | Yankowitz |
| 2018/0301934 A1 | 10/2018 | Prabhala et al. |
| 2018/0309314 A1 | 10/2018 | White et al. |
| 2018/0343040 A1 | 11/2018 | Luzinski et al. |
| 2019/0044390 A1* | 2/2019 | Hajimiri ............ H02J 50/90 |
| 2019/0044392 A1 | 2/2019 | Chowdhury et al. |
| 2019/0052979 A1 | 2/2019 | Chen et al. |
| 2019/0074722 A1 | 3/2019 | Shahsavari et al. |
| 2019/0074862 A1 | 3/2019 | Wang et al. |
| 2019/0130215 A1 | 5/2019 | Kaestle et al. |
| 2019/0229397 A1 | 7/2019 | Rizzo et al. |
| 2019/0296586 A1 | 9/2019 | Moshfeghi |
| 2019/0326782 A1 | 10/2019 | Graham et al. |
| 2019/0363588 A1 | 11/2019 | Daetwyler et al. |
| 2019/0386522 A1 | 12/2019 | Park et al. |
| 2019/0393928 A1 | 12/2019 | Leabman |
| 2020/0006988 A1 | 1/2020 | Leabman |
| 2020/0091608 A1 | 3/2020 | Alpman et al. |
| 2020/0112204 A1 | 4/2020 | Hosseini et al. |
| 2020/0144846 A1 | 5/2020 | Shin |
| 2020/0202145 A1 | 6/2020 | Mao et al. |
| 2020/0225673 A1 | 7/2020 | Ebrahimi Afrouzi et al. |
| 2020/0235614 A1 | 7/2020 | Swan et al. |
| 2020/0244111 A1 | 7/2020 | Johnston et al. |
| 2020/0274397 A1 | 8/2020 | Hwang et al. |
| 2020/0313464 A1 | 10/2020 | Leabman |
| 2020/0389057 A1* | 12/2020 | Hajimiri ............ B60L 8/003 |
| 2020/0403452 A1 | 12/2020 | Leabman |
| 2021/0104919 A1 | 4/2021 | Leabman |
| 2021/0152922 A1 | 5/2021 | Leabman et al. |
| 2021/0184503 A1 | 6/2021 | Leabman |
| 2021/0313840 A1 | 10/2021 | Leabman et al. |
| 2021/0320529 A1 | 10/2021 | Sengupta et al. |
| 2022/0045554 A1 | 2/2022 | Leabman |

FOREIGN PATENT DOCUMENTS

| | | |
|---|---|---|
| CN | 101465471 A | 6/2009 |
| CN | 101496222 A | 7/2009 |
| CN | 201278367 Y | 7/2009 |
| CN | 101507044 A | 8/2009 |
| CN | 101630357 A | 1/2010 |
| CN | 101699709 A | 4/2010 |
| CN | 102004442 A | 4/2011 |
| CN | 102027690 A | 4/2011 |
| CN | 102089952 A | 6/2011 |
| CN | 102227884 A | 10/2011 |
| CN | 102292896 A | 12/2011 |
| CN | 102474109 A | 5/2012 |
| CN | 202333847 U | 7/2012 |
| CN | 102860037 A | 1/2013 |
| CN | 103151848 A | 6/2013 |
| CN | 103296767 A | 9/2013 |
| CN | 103348563 A | 10/2013 |
| CN | 103594776 A | 2/2014 |
| CN | 103683443 A | 3/2014 |
| CN | 104040789 A | 9/2014 |
| CN | 203826555 U | 9/2014 |
| CN | 104090265 A | 10/2014 |
| CN | 104113814 A | 10/2014 |
| CN | 104167773 A | 11/2014 |
| CN | 104347915 A | 2/2015 |
| CN | 104584449 A | 4/2015 |
| CN | 104617680 A | 5/2015 |
| CN | 104659927 A | 5/2015 |
| CN | 105207373 A | 12/2015 |
| CN | 105491472 A | 4/2016 |
| CN | 105762946 A | 7/2016 |
| CN | 105765821 A | 7/2016 |
| CN | 105932407 A | 9/2016 |
| CN | 106329116 A | 1/2017 |
| CN | 103380561 B | 9/2017 |
| DE | 20016655 U1 | 2/2002 |
| DE | 102013216953 A1 | 2/2015 |
| DE | 102014219679 A1 | 3/2016 |
| EP | 1028482 A2 | 8/2000 |
| EP | 1081506 A1 | 3/2001 |
| EP | 2346136 A1 | 7/2011 |
| EP | 2397973 A1 | 2/2012 |
| EP | 2545635 A2 | 1/2013 |
| EP | 2747195 A1 | 6/2014 |
| EP | 3067983 A1 | 9/2016 |
| EP | 3118970 A1 | 1/2017 |
| EP | 3145052 A1 | 3/2017 |
| GB | 2404497 A | 2/2005 |
| GB | 2556620 A | 6/2018 |
| JP | H 06327172 A | 11/1994 |
| JP | 2000323916 A | 11/2000 |
| JP | 2002209343 A | 7/2002 |
| JP | 2002319816 A | 10/2002 |
| JP | 2006157586 A | 6/2006 |
| JP | 2007043432 A | 2/2007 |
| JP | 2007135335 A | 5/2007 |
| JP | 2008092704 A | 4/2008 |
| JP | 2008167017 A | 7/2008 |
| JP | 2008295176 A | 12/2008 |
| JP | 2009071835 A | 4/2009 |
| JP | 2009525715 A | 7/2009 |
| JP | 2009201328 A | 9/2009 |
| JP | 2009290764 A | 12/2009 |
| JP | 2011083078 A | 4/2011 |
| JP | 2011514781 A | 5/2011 |
| JP | 2012016171 A | 1/2012 |
| JP | 2012023950 A | 2/2012 |
| JP | 2012095226 A | 5/2012 |
| JP | 2012157167 A | 8/2012 |
| JP | 2013099249 A | 5/2013 |
| JP | 2013162624 A | 8/2013 |
| JP | 2014501080 A | 1/2014 |
| JP | 2014075927 A | 4/2014 |
| JP | 2014112063 A | 6/2014 |
| JP | 2014176125 A | 9/2014 |
| JP | 2014176131 A | 9/2014 |
| JP | 2014223018 A | 11/2014 |
| JP | 2015027345 A | 2/2015 |
| JP | 2015128349 A | 7/2015 |
| JP | 2015128370 A | 7/2015 |
| JP | 2015139276 A | 7/2015 |
| JP | 2017034935 A | 2/2017 |
| JP | WO2015177859 A1 | 4/2017 |
| KR | 20060061776 A | 6/2006 |
| KR | 20070044302 A | 4/2007 |

(56) References Cited

FOREIGN PATENT DOCUMENTS

| | | |
|---|---|---|
| KR | 100755144 B1 | 9/2007 |
| KR | 100819604 B1 | 4/2008 |
| KR | 20110132059 A | 12/2011 |
| KR | 20110135540 A1 | 12/2011 |
| KR | 20120009843 A | 2/2012 |
| KR | 20120108759 A | 10/2012 |
| KR | 20130026977 A | 3/2013 |
| KR | 20140023409 A | 2/2014 |
| KR | 20140023410 A | 3/2014 |
| KR | 20140025410 A | 3/2014 |
| KR | 20140085200 A | 7/2014 |
| KR | 20140148270 A | 12/2014 |
| KR | 20150077678 A | 7/2015 |
| KR | 20160018826 A | 2/2016 |
| KR | 20160087671 A | 7/2016 |
| KR | 20180108317 A | 10/2018 |
| KR | 20180114721 A | 10/2018 |
| RU | 2658332 C1 | 6/2018 |
| WO | WO 199508125 A1 | 3/1995 |
| WO | WO 199831070 A1 | 7/1998 |
| WO | WO 199952173 A1 | 10/1999 |
| WO | WO 2000111716 A1 | 2/2001 |
| WO | WO 2003091943 A1 | 11/2003 |
| WO | WO 2004077550 A1 | 9/2004 |
| WO | WO 2006122783 A2 | 11/2006 |
| WO | WO 2007070571 A2 | 6/2007 |
| WO | WO 2008024993 A2 | 2/2008 |
| WO | WO 2008156571 A2 | 12/2008 |
| WO | WO 2010022181 A1 | 2/2010 |
| WO | WO 2010039246 A1 | 4/2010 |
| WO | WO 2010116441 A1 | 10/2010 |
| WO | WO 2010138994 A1 | 12/2010 |
| WO | WO 2011112022 A2 | 9/2011 |
| WO | WO 2012153529 A1 | 11/2012 |
| WO | WO 2012177283 A1 | 12/2012 |
| WO | WO 2013031988 A1 | 3/2013 |
| WO | WO 2013035190 A1 | 3/2013 |
| WO | WO 2013038074 A2 | 3/2013 |
| WO | WO 2013042399 A1 | 3/2013 |
| WO | WO 2013052950 A1 | 4/2013 |
| WO | WO 2013088238 A2 | 6/2013 |
| WO | WO 2013105920 A2 | 7/2013 |
| WO | WO 2013175596 A1 | 11/2013 |
| WO | WO 2014068992 A1 | 5/2014 |
| WO | WO 2014075103 A1 | 5/2014 |
| WO | WO 2014113093 A1 | 7/2014 |
| WO | WO 2014132258 A1 | 9/2014 |
| WO | WO 2014134996 A1 | 9/2014 |
| WO | WO 2014156465 A1 | 10/2014 |
| WO | WO 2014170773 A2 | 10/2014 |
| WO | WO 2014182788 A2 | 11/2014 |
| WO | WO 2014182788 A3 | 11/2014 |
| WO | WO 2014197472 A1 | 12/2014 |
| WO | WO 2014209587 A1 | 12/2014 |
| WO | WO 2015038773 A1 | 3/2015 |
| WO | WO 2015097809 A1 | 7/2015 |
| WO | WO 2015130902 A1 | 9/2015 |
| WO | WO 2015161323 A1 | 10/2015 |
| WO | WO 2016024869 A1 | 2/2016 |
| WO | WO 2016048512 A1 | 3/2016 |
| WO | WO 2016088261 A1 | 6/2016 |
| WO | WO 2016187357 A1 | 11/2016 |

OTHER PUBLICATIONS

Energous Corp., IPRP, PCT/US2014/037109, Apr. 12, 2016, 9 pgs.
Energous Corp., IPRP, PCT/US2014/037170, Nov. 10, 2015, 8 pgs.
Energous Corp., IPRP, PCT/US2014/040648, Dec. 8, 2015, 8 pgs.
Energous Corp., IPRP, PCT/US2014/040697, Dec. 8, 2015, 9 pgs.
Energous Corp., IPRP, PCT/US2014/040705, Dec. 8, 2015, 6 pgs.
Energous Corp., IPRP, PCT/US2014/041323, Dec. 22, 2015, 8 pgs.
Energous Corp., IPRP, PCT/US2014/041342, Dec. 15, 2015, 8 pgs.
Energous Corp., IPRP, PCT/US2014/041534, Dec. 29, 2015, 7 pgs.
Energous Corp., IPRP, PCT/US2014/041546, Dec. 29, 2015, 9 pgs.
Energous Corp., IPRP, PCT/US2014/041558, Dec. 29, 2015, 6 pgs.
Energous Corp., IPRP, PCT/US2014/044810, Jan. 5, 2016, 10 pgs.
Energous Corp., IPRP, PCT/US2014/045102, Jan. 12, 2016, 11 pgs.
Energous Corp., IPRP, PCT/US2014/045119, Jan. 12, 2016, 9 pgs.
Energous Corp., IPRP, PCT/US2014/045237, Jan. 12, 2016, 12 pgs.
Energous Corp., IPRP, PCT/US2014/046941, Jan. 19, 2016, 9 pgs.
Energous Corp., IPRP, PCT/US2014/046956, Jan. 19, 2016, 7 pgs.
Energous Corp., IPRP, PCT/US2014/046961, Jan. 19, 2016, 8 pgs.
Energous Corp., IPRP, PCT/US2014/047963, Jan. 26, 2016, 10 pgs.
Energous Corp., IPRP, PCT/US2014/048002, Feb. 12, 2015 8 pgs.
Energous Corp., IPRP, PCT/US2014/049666, Feb. 9, 2016, 5 pgs.
Energous Corp., IPRP, PCT/US2014/049669, Feb. 9, 2016, 8 pgs.
Energous Corp., IPRP, PCT/US2014/049673, Feb. 9, 2016, 6 pgs.
Energous Corp., IPRP, PCT/US2014/054891, Mar. 15, 2016, 10 pgs.
Energous Corp., IPRP, PCT/US2014/054897, Mar. 15, 2016, 8 pgs.
Energous Corp., IPRP, PCT/US2014/054953, Mar. 22, 2016, 5 pgs.
Energous Corp., IPRP, PCT/US2014/055195, Mar. 22, 2016, 9 pgs.
Energous Corp., IPRP, PCT/US2014/059317, Apr. 12, 2016, 10 pgs.
Energous Corp., IPRP, PCT/US2014/059340, Apr. 12, 2016, 11 pgs.
Energous Corp., IPRP, PCT/US2014/059871, Apr. 12, 2016, 9 pgs.
Energous Corp., IPRP, PCT/US2014/062661, May 3, 2016, 10 pgs.
Energous Corp., IPRP, PCT/US2014/062672, May 10, 2016, 8 pgs.
Energous Corp., IPRP, PCT/US2014/062682, May 3, 2016, 8 pgs.
Energous Corp., IPRP, PCT/US2014/068282, Jun. 7, 2016, 10 pgs.
Energous Corp., IPRP, PCT/US2014/068568, Jun. 14, 2016, 8 pgs.
Energous Corp., IPRP, PCT/US2014/068586, Jun. 14, 2016, 8 pgs.
Energous Corp., IPRP, PCT/US2015/067242, Jun. 27, 2017, 7 pgs.
Energous Corp., IPRP, PCT/US2015/067243, Jun. 27, 2017, 7 pgs.
Energous Corp., IPRP, PCT/US2015/067245, Jun. 27, 2017, 7 pgs.
Energous Corp., IPRP, PCT/US2015/067246, Jun. 27, 2017, 9 pgs.
Energous Corp., IPRP, PCT/US2015/067249, Jun. 27, 2017, 7 pgs.
Energous Corp., IPRP, PCT/US2015/067250, Mar. 30, 2016, 10 pgs.
Energous Corp., IPRP, PCT/US2015/067271, Jul. 4, 2017, 5 pgs.
Energous Corp., IPRP, PCT/US2015/067275, Jul. 4, 2017, 7 pgs.
Energous Corp., IPRP, PCT/US2015/067279, Jul. 4, 2017, 7 pgs.
Energous Corp., IPRP, PCT/US2015/067282, Jul. 4, 2017, 6 pgs.
Energous Corp., IPRP, PCT/US2015/067287, Jul. 4, 2017, 6 pgs.
Energous Corp., IPRP, PCT/US2015/067291, Jul. 4, 2017, 4 pgs.
Energous Corp., IPRP, PCT/US2015/067294, Jul. 4, 2017, 6 pgs.
Energous Corp., IPRP, PCT/US2015/067325, Jul. 4, 2017, 8 pgs.
Energous Corp., IPRP, PCT/US2015/067334, Jul. 4, 2017, 5 pgs.
Energous Corp., IPRP, PCT/US2016/068495, Jun. 26, 2018, 7 pgs.
Energous Corp., IPRP, PCT/US2016/068498, Jun. 26, 2018, 6 pgs.
Energous Corp., IPRP, PCT/US2016/068504, Jun. 26, 2018, 5 pgs.
Energous Corp., IPRP, PCT/US2016/068551, Jun. 26, 2018, 6 pgs.
Energous Corp., IPRP, PCT/US2016/068565, Jun. 26, 2018, 9 pgs.
Energous Corp., IPRP, PCT/US2016/068987, Jul. 3, 2018, 7 pgs.
Energous Corp., IPRP, PCT/US2016/068993, Jul. 3, 2018, 10 pgs.
Energous Corp., IPRP, PCT/US2016/069313, Jul. 3, 2018, 7 pgs.
Energous Corp., IPRP, PCT/US2016/069316, Jul. 3, 2018, 12 pgs.
Energous Corp., IPRP, PCT/US2017/046800, Feb. 12, 2019, 10 pgs.
Energous Corp., IPRP, PCT/US2017/065886, Jun. 18, 2019, 10 pgs.
Energous Corp., IPRP, PCT/US2018/012806, Jul. 9, 2019, 6 pgs.
Energous Corp., IPRP, PCT/US2018/025465, Oct. 1, 2019, 8 pgs.
Energous Corp., IPRP, PCT/US2018/031768, Nov. 12, 2019, 8 pgs.
Energous Corp., IPRP, PCT/US2018/031786, Apr. 14, 2020, 7 pgs.
Energous Corp., IPRP, PCT/US2018/039334, Dec. 24, 2019, 8 pgs.
Energous Corp., IPRP, PCT/US2018/051082, Mar. 17, 2020, 9 pgs.
Energous Corp., IPRP, PCT/US2018/058178, May 5, 2020, 7 pgs.
Energous Corp., IPRP, PCT/US2019/015820, Aug. 4, 2020, 7 pgs.
Energous Corp., IPRP, PCT/US2019/021817, Sep. 15, 2020, 7 pgs.
Energous Corp., IPRP, PCT/US2019/061445, May 18, 2021, 14 pgs.
Energous Corp., IPRP, PCT/US2020/015450, Jul. 27, 2021, 6 pgs.
Energous Corp., IPRP, PCT/US2020/016975, Aug. 10, 2021, 13 pgs.
Energous Corp., IPRP, PCT/US2020/027409, Sep. 28, 2021, 7 pgs.
Energous Corp., ISRWO, PCT/US2014/037072, Sep. 12, 2014, 8 pgs.
Energous Corp., ISRWO, PCT/US2014/037109, Apr. 8, 2016, 12 pgs.

(56) References Cited

OTHER PUBLICATIONS

Energous Corp., ISRWO, PCT/US2014/037170, Sep. 15, 2014, 11 pgs.
Energous Corp., ISRWO, PCT/US2014/040648, Oct. 10, 2014, 11 pgs.
Energous Corp., ISRWO, PCT/US2014/040697, Oct. 1, 2014, 12 pgs.
Energous Corp., ISRWO, PCT/US2014/040705, Sep. 23, 2014, 8 pgs.
Energous Corp., ISRWO, PCT/US2014/041323, Oct. 1, 2014, 10 pgs.
Energous Corp., ISRWO, PCT/US2014/041342, Jan. 27, 2015, 10 pgs.
Energous Corp., ISRWO, PCT/US2014/041534, Oct. 13, 2014, 10 pgs.
Energous Corp., ISRWO, PCT/US2014/041546, Oct. 16, 2014, 12 pgs.
Energous Corp., ISRWO, PCT/US2014/041558, Oct. 10, 2014, 8 pgs.
Energous Corp., ISRWO, PCT/US2014/044810 Oct. 21, 2014, 12 pgs.
Energous Corp., ISRWO, PCT/US2014/045102, Oct. 28, 2014, 14 pgs.
Energous Corp., ISRWO, PCT/US2014/045119, Oct. 13, 2014, 11 pgs.
Energous Corp., ISRWO, PCT/US2014/045237, Oct. 13, 2014, 16 pgs.
Energous Corp., ISRWO, PCT/US2014/046941, Nov. 6, 2014, 11 pgs.
Energous Corp., ISRWO, PCT/US2014/046956, Nov. 12, 2014, 10 pgs.
Energous Corp., ISRWO, PCT/US2014/046961, Nov. 24, 2014, 16 pgs.
Energous Corp., ISRWO, PCT/US2014/047963, Nov. 7, 2014, 13 pgs.
Energous Corp., ISRWO, PCT/US2014/048002, Nov. 13, 2014, 11 pgs.
Energous Corp., ISRWO, PCT/US2014/049666, Nov. 10, 2014, 7 pgs.
Energous Corp., ISRWO, PCT/US2014/049669, Nov. 13, 2014, 10 pgs.
Energous Corp., ISRWO, PCT/US2014/049673, Nov. 18, 2014, 10 pgs.
Energous Corp., ISRWO, PCT/US2014/054891, Dec. 18, 2014, 12 pgs.
Energous Corp., ISRWO, PCT/US2014/054897, Feb. 17, 2015, 10 pgs.
Energous Corp., ISRWO, PCT/US2014/054953, Dec. 4, 2014, 7 pgs.
Energous Corp., ISRWO, PCT/US2014/055195, Dec. 22, 2014, 11 pgs.
Energous Corp., ISRWO, PCT/US2014/059317, Feb. 24, 2015, 13 pgs.
Energous Corp., ISRWO, PCT/US2014/059340, Jan. 15, 2015, 13 pgs.
Energous Corp., ISRWO, PCT/US2014/059871, Jan. 23, 2015, 12 pgs.
Energous Corp., ISRWO, PCT/US2014/062661, Jan. 27, 2015, 12 pgs.
Energous Corp., ISRWO, PCT/US2014/062672, Jan. 26, 2015, 11 pgs.
Energous Corp., ISRWO, PCT/US2014/062682, Feb. 12, 2015, 10 pgs.
Energous Corp., ISRWO, PCT/US2014/068282, Mar. 19, 2015, 13 pgs.
Energous Corp., ISRWO, PCT/US2014/068568, Mar. 20, 2015, 10 pgs.
Energous Corp., ISRWO, PCT/US2014/068586, Mar. 20, 2015, 11 pgs.
Energous Corp., ISRWO, PCT/US2015/067242, Mar. 16, 2016, 9 pgs.
Energous Corp., ISRWO, PCT/US2015/067243, Mar. 10, 2016, 11 pgs.
Energous Corp., ISRWO, PCT/US2015/067245, Mar. 17, 2016, 8 pgs.
Energous Corp., ISRWO, PCT/US2015/067246, May 11, 2016, 18 pgs.
Energous Corp., ISRWO, PCT/US2015/067249, Mar. 29, 2016, 8 pgs.
Energous Corp., ISRWO, PCT/US2015/067250, Mar. 30, 2016, 11 pgs.
Energous Corp., ISRWO, PCT/US2015/067271, Mar. 11, 2016, 6 pgs.
Energous Corp., ISRWO, PCT/US2015/067275, Mar. 3, 2016, 8 pgs.
Energous Corp., ISRWO, PCT/US2015/067279, Mar. 11, 2015, 13 pgs.
Energous Corp., ISRWO, PCT/US2015/067282, Jul. 5, 2016, 7 pgs.
Energous Corp., ISRWO, PCT/US2015/067287, Feb. 2, 2016, 8 pgs.
Energous Corp., ISRWO, PCT/US2015/067291, Mar. 4, 2016, 10 pgs.
Energous Corp., ISRWO, PCT/US2015/067294, Mar. 29, 2016, 7 pgs.
Energous Corp., ISRWO, PCT/US2015/067325, Mar. 10, 2016, 9 pgs.
Energous Corp., ISRWO, PCT/US2015/067334, Mar. 3, 2016, 6 pgs.
Energous Corp., ISRWO, PCT/US2016/068495, Mar. 30, 2017, 9 pgs.
Energous Corp., ISRWO, PCT/US2016/068498, May 17, 2017, 8 pgs.
Energous Corp., ISRWO, PCT/US2016/068504, Mar. 30, 2017, 8 pgs.
Energous Corp., ISRWO, PCT/US2016/068551, Mar. 17, 2017, 8 pgs.
Energous Corp., ISRWO, PCT/US2016/068565, Mar. 8, 2017, 11 pgs.
Energous Corp., ISRWO, PCT/US2016/068987, May 8, 2017, 10 pgs.
Energous Corp., ISRWO, PCT/US2016/068993, Mar. 13, 2017, 12 pgs.
Energous Corp., ISRWO, PCT/US2016/069313, Nov. 13, 2017, 10 pgs.
Energous Corp., ISRWO, PCT/US2016/069316, Mar. 16, 2017, 15 pgs.
Energous Corp., ISRWO, PCT/US2017/046800, Sep. 11, 2017, 13 pgs.
Energous Corp., ISRWO, PCT/US2017/065886, Apr. 6, 2018, 13 pgs.
Energous Corp., ISRWO, PCT/US2018/012806, Mar. 23, 2018, 9 pgs.
Energous Corp., ISRWO, PCT/US2018/025465, Jun. 22, 2018, 9 pgs.
Energous Corp., ISRWO, PCT/US2018/031768, Jul. 3, 2018, 9 pgs.
Energous Corp., ISRWO, PCT/US2018/031786, Aug. 8, 2018, 9 pgs.
Energous Corp., ISRWO, PCT/US2018/039334, Sep. 11, 2018, 9 pgs.
Energous Corp., ISRWO, PCT/US2018/051082, Dec. 12, 2018, 9 pgs.
Energous Corp., ISRWO, PCT/US2018/058178, Mar. 13, 2019, 10 pgs.
Energous Corp., ISRWO, PCT/US2018/064289, Apr. 25, 2019, 12 pgs.
Energous Corp., ISRWO, PCT/US2019/015820, May 14, 2019, 9 pgs.
Energous Corp., ISRWO, PCT/US2019/021817, Apr. 6, 2019, 11 pgs.
Energous Corp., ISRWO, PCT/US2019/039014, Oct. 4, 2019, 15 pgs.

(56) References Cited

OTHER PUBLICATIONS

Energous Corp., ISRWO, PCT/US2019/061445, Jan. 7, 2020, 19 pgs.
Energous Corp., ISRWO, PCT/US2020/015450, May 18, 2020, 8 pgs.
Energous Corp., ISRWO, PCT/US2020/016975, May 15, 2020, 15 pgs.
Energous Corp., ISRWO, PCT/US2020/027409, Jul. 24, 2020, 11 pgs.
Energous Corp., ISRWO, PCT/US2020/064592, Mar. 24, 2021, 10 pgs.
Energous Corp., ISRWO, PCT/US2020/067566, Apr. 27, 2021, 12 pgs.
Energous Corp., ISRWO, PCT/US2021/027140, Jul. 21, 2021, 9 pgs.
Order Granting Reexamination Request, App. No. 90/013,793 Aug. 31, 2016, 23 pgs.
Notice of Intent to Issue Reexam Certificate: 90/013,793 Feb. 2, 2017, 8 pgs.
Ossia Inc. vs Energous Corp., Declaration of Stephen B. Heppe in Support of Petition for Post-Grant Review of U.S. Pat. No. 9,124,125, PGR2016-00023, May 31, 2016, 144 pgs.
Ossia Inc. vs Energous Corp., Declaration of Stephen B. Heppe in Support of Petition for Post-Grant Review of U.S. Pat. No. 9,124,125, PGR2016-00024, May 31, 2016, 122 pgs.
Ossia Inc. vs Energous Corp., Patent Owner Preliminary Response, Sep. 8, 2016, 95 pgs.
Ossia Inc. vs Energous Corp., Petition for Post Grant Review of U.S. Pat. No. 9,124,125, May 31, 2016, 86 pgs.
Ossia Inc. vs Energous Corp., Petition for Post-Grant Review of U.S. Pat. No. 9,124,125, May 31, 2016, 92 pgs.
Ossia Inc. vs Energous Corp., PGR2016-00023-Institution Decision, Nov. 29, 2016, 29 pgs.
Ossia Inc. vs Energous Corp., PGR2016-00024-Institution Decision, Nov. 29, 2016, 50 pgs.
Ossia Inc. vs Energous Corp., PGR2016-00024-Judgement-Adverse, Jan. 20, 2017, 3 pgs.
Extended European Search Report, EP14818136.5, Jul. 21, 2016, 9 pgs.
Extended European Search Report, EP14822971.9, Feb. 10, 2017, 10 pgs.
Extended European Search Report, EP14868901.1, Jul. 17, 2017, 6 pgs.
Extended European Search Report, EP15874273.4, May 11, 2018, 7 pgs.
Extended European Search Report, EP15876033.0, Jun. 13, 2018, 10 pgs.
Extended European Search Report, EP15876036.3, May 3, 2018, 9 pgs.
Extended European Search Report, EP15876043.9, Aug. 9, 2018, 9 pgs.
Extended European Search Report, EP16189052.0, Feb. 10, 2017, 13 pgs.
Extended European Search Report, EP16189300.3, Mar. 24, 2017, 6 pgs.
Extended European Search Report, EP16189319.3, Feb. 10, 2017, 11 pgs.
Extended European Search Report, EP16189974.5, Mar. 13, 2017, 7 pgs.
Extended European Search Report, EP16189982.8, Feb. 7, 2017, 11 pgs.
Extended European Search Report, EP16189987.7, Feb. 9, 2017, 10 pgs.
Extended European Search Report, EP16189988.5, Mar. 13, 2017, 6 pgs.
Extended European Search Report, EP16193743.8, Feb. 8, 2017, 9 pgs.
Extended European Search Report, EP16196205.5, Apr. 7, 2017, 9 pgs.
Extended European Search Report, EP16880139.7, Jul. 12, 2019, 5 pgs.
Extended European Search Report, EP16880153.8, Jul. 2, 2019, 9 pgs.
Extended European Search Report, EP16880158.7, Jul. 15, 2019, 8 pgs.
Extended European Search Report, EP16882597.4, Aug. 7, 2019, 9 pgs.
Extended European Search Report, EP16882696.4, Jul. 3, 2019, 10 pgs.
Extended European Search Report, EP17840412.5, Jul. 15, 2019, 8 pgs.
Extended European Search Report, EP17882087.4, Sep. 17, 2019, 10 pgs.
Extended European Search Report, EP18204043.6, Feb. 14, 2019, 5 pgs.
Extended European Search Report, EP18797695.6, Nov. 19, 2020, 9 pgs.
Extended European Search Report, EP18820206.3, May 17, 2021, 6 pgs.
Extended European Search Report, EP19214719.7, Jan. 17, 2020, 9 pgs.
Extended European Search Report, EP21159553.3, May 31, 2021, 8 pgs.
Extended European Search Report, EP21161278.3, Jun. 28, 2021, 10 pgs.
Extended European Search Report, EP21164951.2, Oct. 7, 2021, 9 pgs.
Adamiuk et al., "Compact, Dual-Polarized UWB-Antanna, Embedded in a Dielectric," IEEE Transactions on Antenna and Propagation, IEEE Service Center, Piscataway, NJ, US vol. 56, No. 2, Feb. 1, 2010, 8 pgs.
Gill et al., "A System for Change Detection and Human Recognition in Voxel Space using the Microsoft Kinect Sensor," 2011 IEEE Applied Imagery Pattern Recognition Workshop. 8 pgs.
Han et al., Enhanced Computer Vision with Microsoft Kinect Sensor: A Review, IEEE Transactions on Cybernetics vol. 43, No. 5., pp. 1318-1334, Oct. 3, 2013.
Hsieh et al., "Development of a Retrodirective Wireless Microwave Power Transmission System", IEEE, 2003, pp. 393-396.
Leabman, "Adaptive Band-partitioning for Interference Cancellation in Communication System," Thesis Massachusetts Institute of Technology, Feb. 1997, pp. 1-70.
Li et al., "High-Efficiency Switching-Mode Charger System Design Considerations with Dynamic Power Path Management," Mar./Apr. 2012 Issue, 8 pgs.
Mao et al., "BeamStar: An Edge-Based Approach to Routing in Wireless Sensors Networks", IEEE Transactions on Mobile Computing, IEEE Service Center, Los Alamitos, CA, vol. 6, No. 11, Nov. 1, 2007, 13 pgs.
Mascarenas et al., "Experimental Studies of Using Wireless Energy Transmission for Powering Embedded Sensor Nodes," Nov. 28, 2009, Journal of Sound and Vibration, 13 pgs.
Mishra et al., "SIW-based Slot Array Antenna and Power Management Circuit for Wireless Energy Harvesting Applications", IEEE APSURSI, Jul. 2012, 2 pgs.
Nenzi et al., "U-Helix: On-Chip Short Conical Antenna", 7th European Conference on Antennas and Propagation (EUCAP), ISBN: 978-1-4673-2187-7, IEEE, Apr. 8, 2013, 5 pgs.
Qing et al., "UHF Near-Field Segmented Loop Antennas with Enlarged Interrogation Zone," 2012 IEEE International Workshop on Antenna Technology (iWAT), Mar. 1, 2012, pp. 132-135, XP055572059, ISBN: 978-1-4673-0035-3.
Singh, "Wireless Power Transfer Using Metamaterial Bonded Microstrip Antenna for Smart Grid WSN", 4th International Conference on Advances in Computing and Communications (ICACC), Aug. 27-29, 2014, 1 pg.
Smolders, "Broadband Microstrip Array Antennas", Institute of Electrical and Electronics Engineers, Digest of the Antennas and Propagation Society International Symposium, Seattle, WA, Jun. 19-24, 1994, 3 pgs.
Van Veen et al., "Beamforming: A Versatile Approach to Spatial Filtering", IEEE, ASSP Magazine, Apr. 1988, pp. 4-24.

(56) References Cited

OTHER PUBLICATIONS

Wei et al., "Design of a Wideband Horizontally Polarized Omnidirectional Printed Loop Antenna," IEEE Antennas and Wireless Propagation Letters, vol. 11, Jan. 3, 2012, 4 pgs.

Zeng et al., "A Compact Fractal Loop Rectenna for RF Energy Harvesting," IEEE Antennas And Wireless Propagation Letters, vol. 16, Jun. 26, 2017, 4 pgs.

Zhai et al., "A Practical Wireless Charging System Based on Ultra-Wideband Retro-Reflective Beamforming", 2010 IEEE Antennas and Propagation Society International Symposium, Toronto, ON, 2010, 4 pgs.

* cited by examiner

Wireless Power Transmission Environment 100

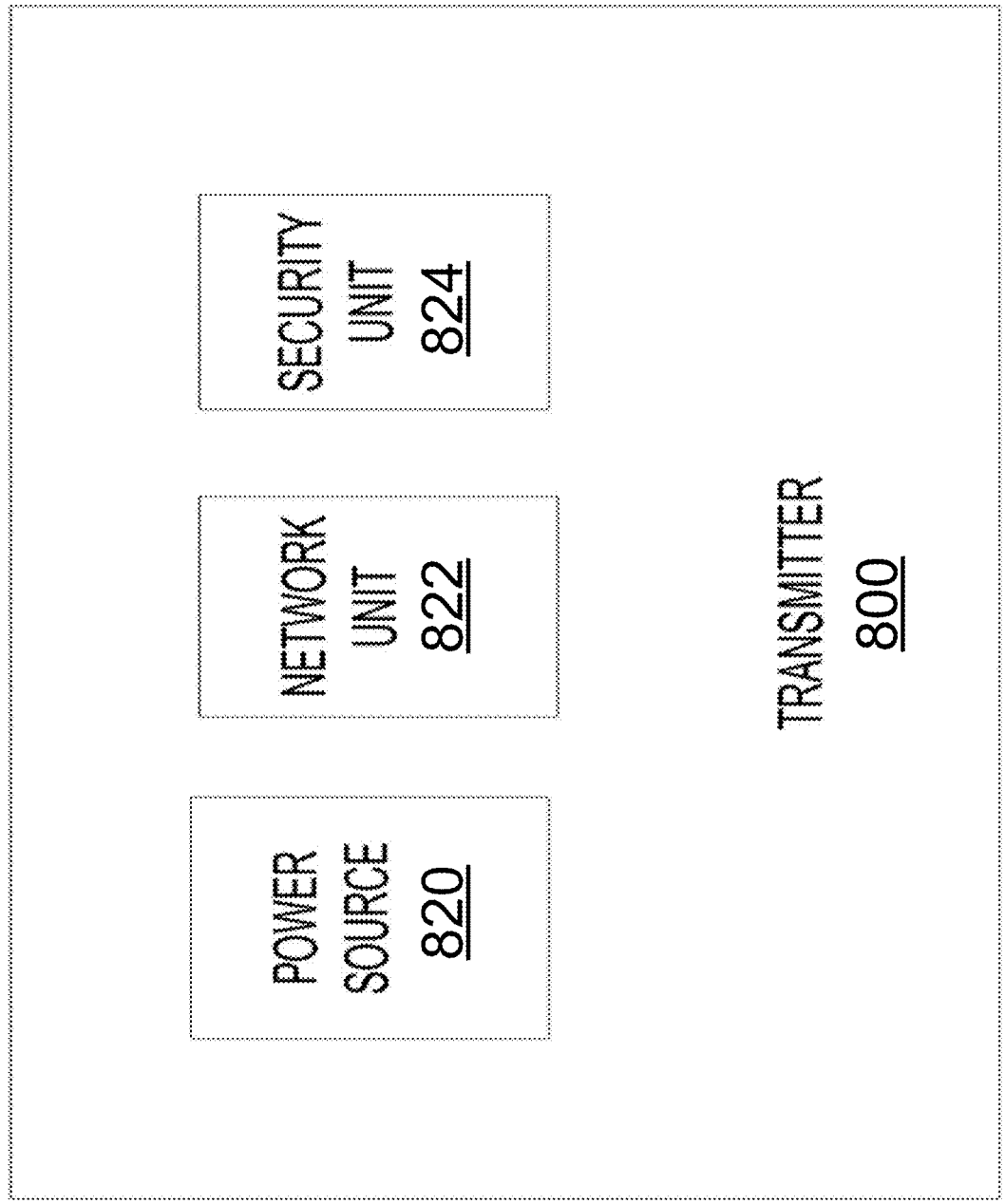

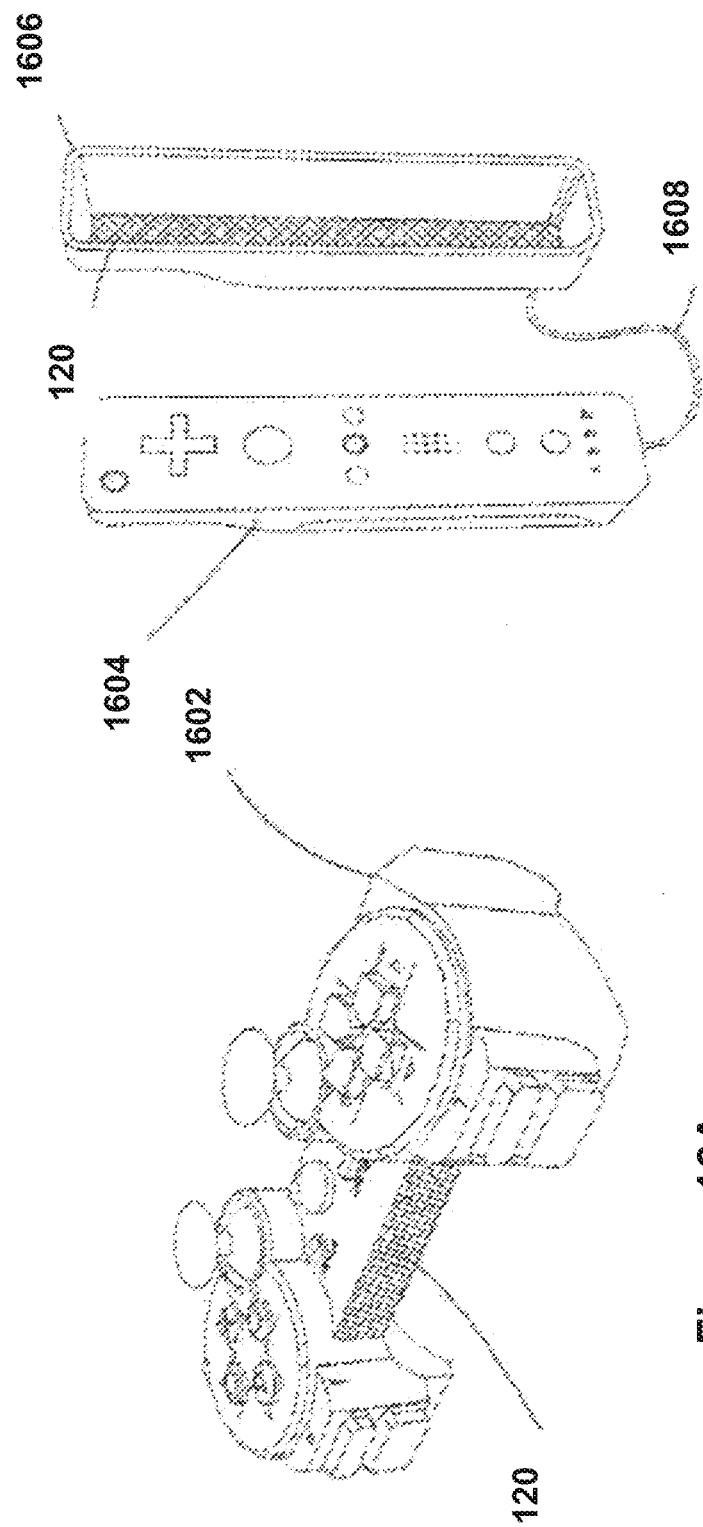

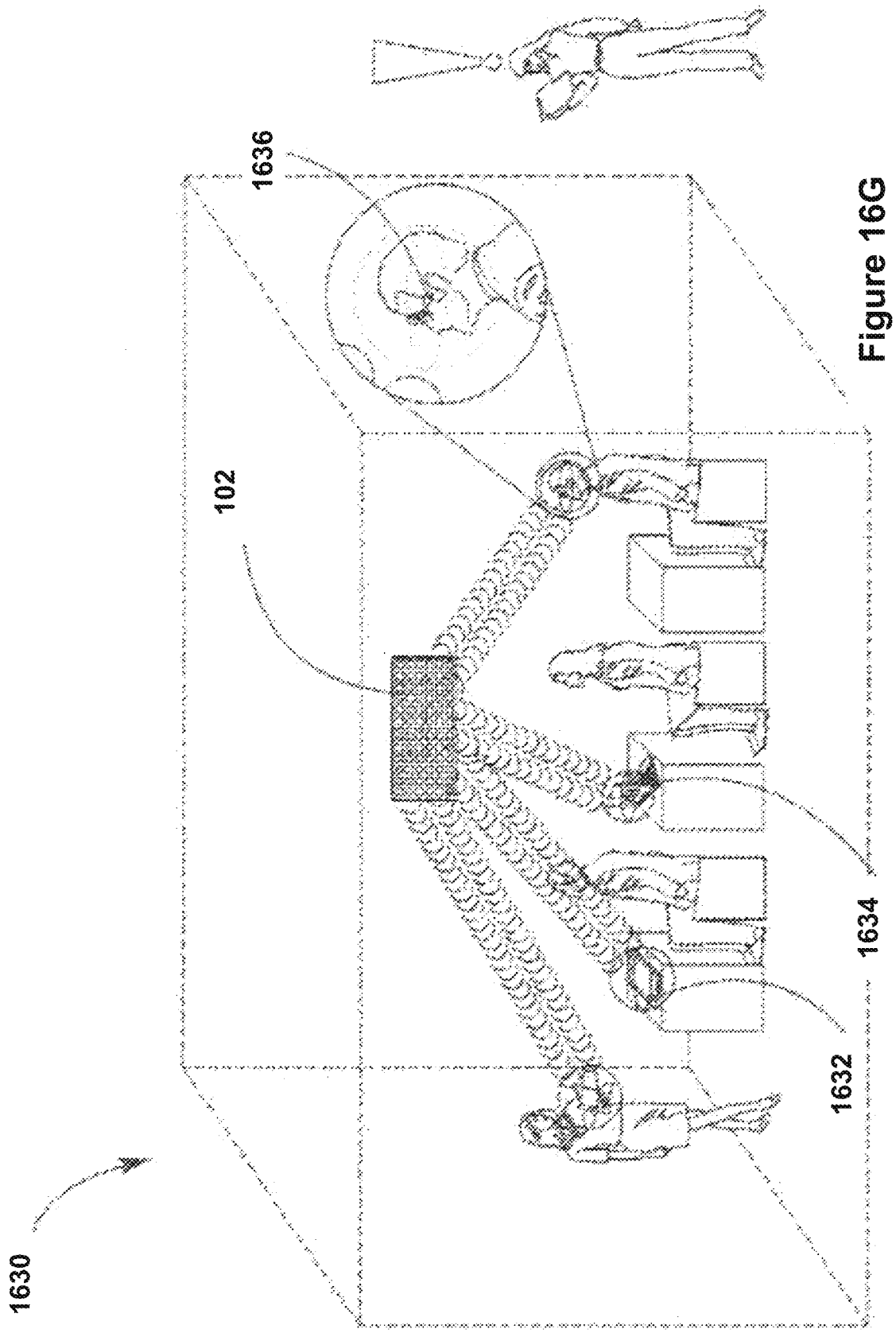

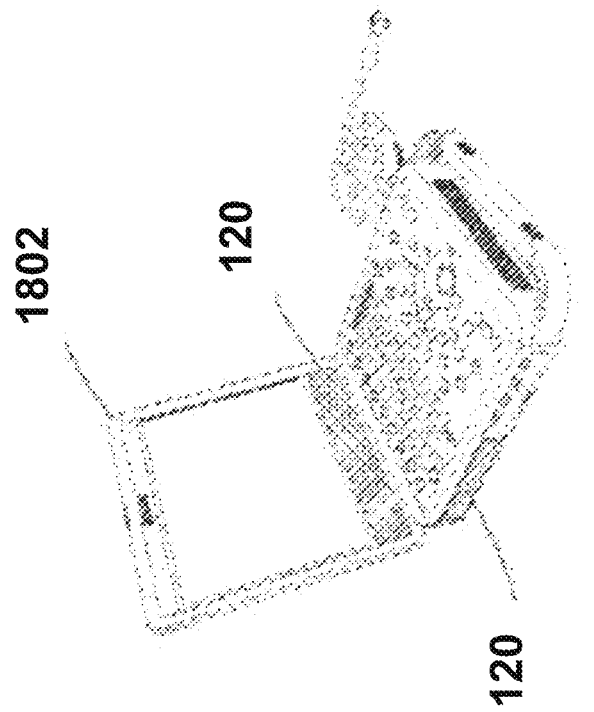
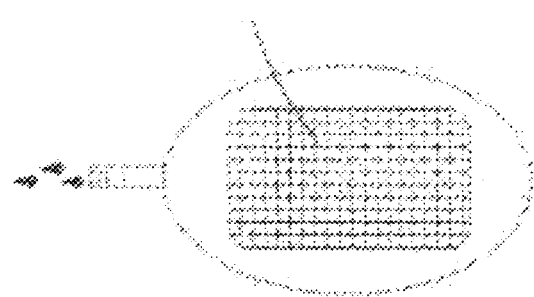
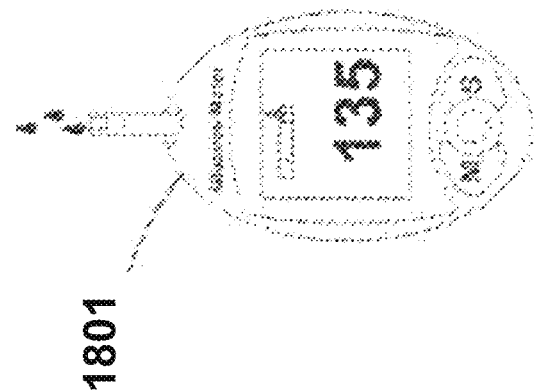
Figure 18A
Figure 18B

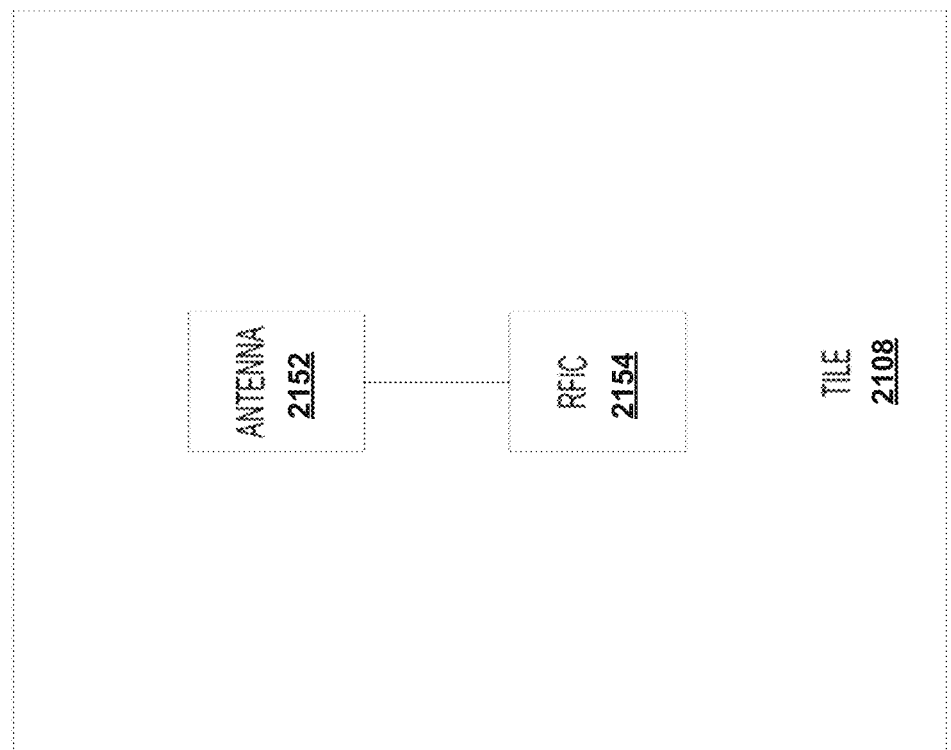

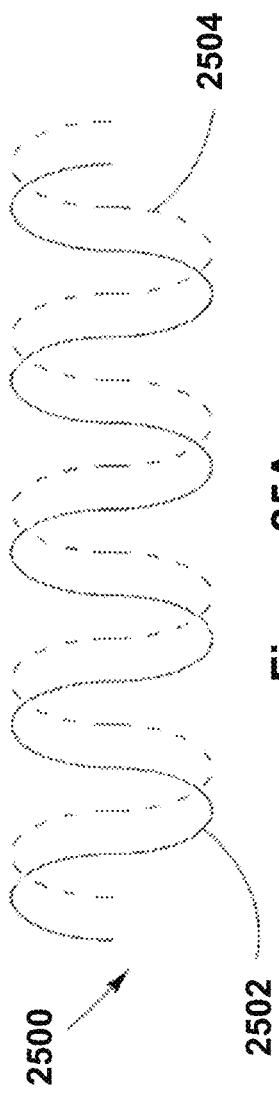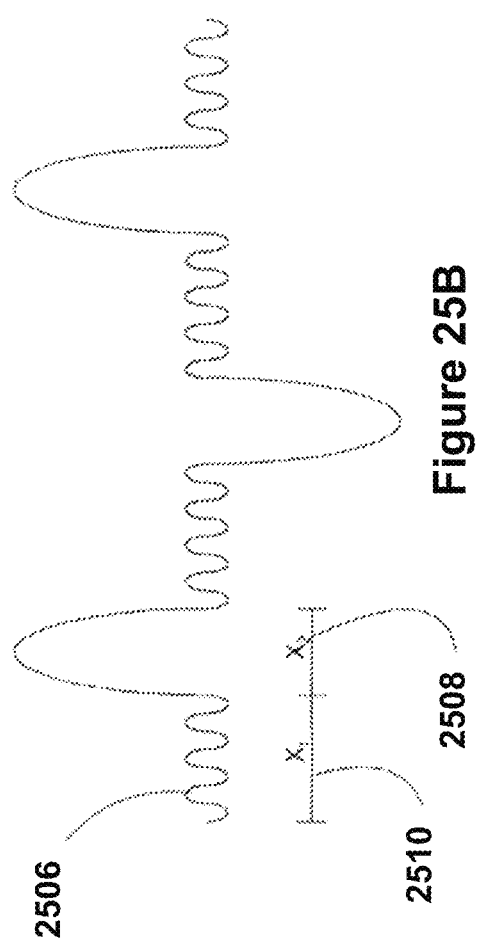
Figure 25A
Figure 25B

02 USAGE STATISTICS

IN THE PAST 5 DAYS ▼

Here's what your WattUp enabled devices have been up to in the past

| POWER RECEIVED | POWER TRANSMITTED | POWER ON THE GO |

- Energy Received 55.3 Wh
- Energy Transmitted 0.3 w
- Peak Incoming energy 0.3 w
- Peak Outgoing energy 0.3 w
- Devices Charged 42

Bar chart values:
- OCT 9: 39.7
- OCT 8: 21.8
- OCT 7: 18.2
- OCT 6: 30.6
- OCT 5: 8.7

Sidebar:
- DASHBOARD
- DEVICES
- LOCATIONS
- TRANSMITTERS
- ACCOUNTS
- SETTINGS

WELCOME
energous_demo

03 POWER UP HISTORY

Here's a record of where your devices have charged up recently

Figure 63C

03 POWER UP HISTORY

Here's a record of where your devices have charged up recently

| Location/Transmitter | Device | Power | Duration | Time & Date |
|---|---|---|---|---|
| Upstars Bedroom | Jane's iPhone | 5.2 Wh | 1h 32min | 11:32PM October 7th, 2014 |
| Living Room | Derrick's iPad Mini | 13.4 Wh | 2h 41min | 4:03PM October 7th, 2014 |
| Living Room | Xbox Controller | 7.5 Wh | 57min | 3:00AM October 7th, 2014 |
| Upstairs Bedroom | Jane's iPhone | 5.2 Wh | 1h 32min | 11:32PM October 6th, 2014 |
| Living Room | Derrick's iPad Mini | 13.4 Wh | 2h 41min | 4:03PM October 6th, 2014 |
| Living Room | Xbox Controller | 7.5 Wh | 57min | 3:00AM October 6th, 2014 |

VIEW ALL POWER UPS

- DASHBOARD
- DEVICES
- LOCATIONS
- TRANSMITTERS
- ACCOUNTS
- SETTINGS

WELCOME
energous_demo

Figure 63D

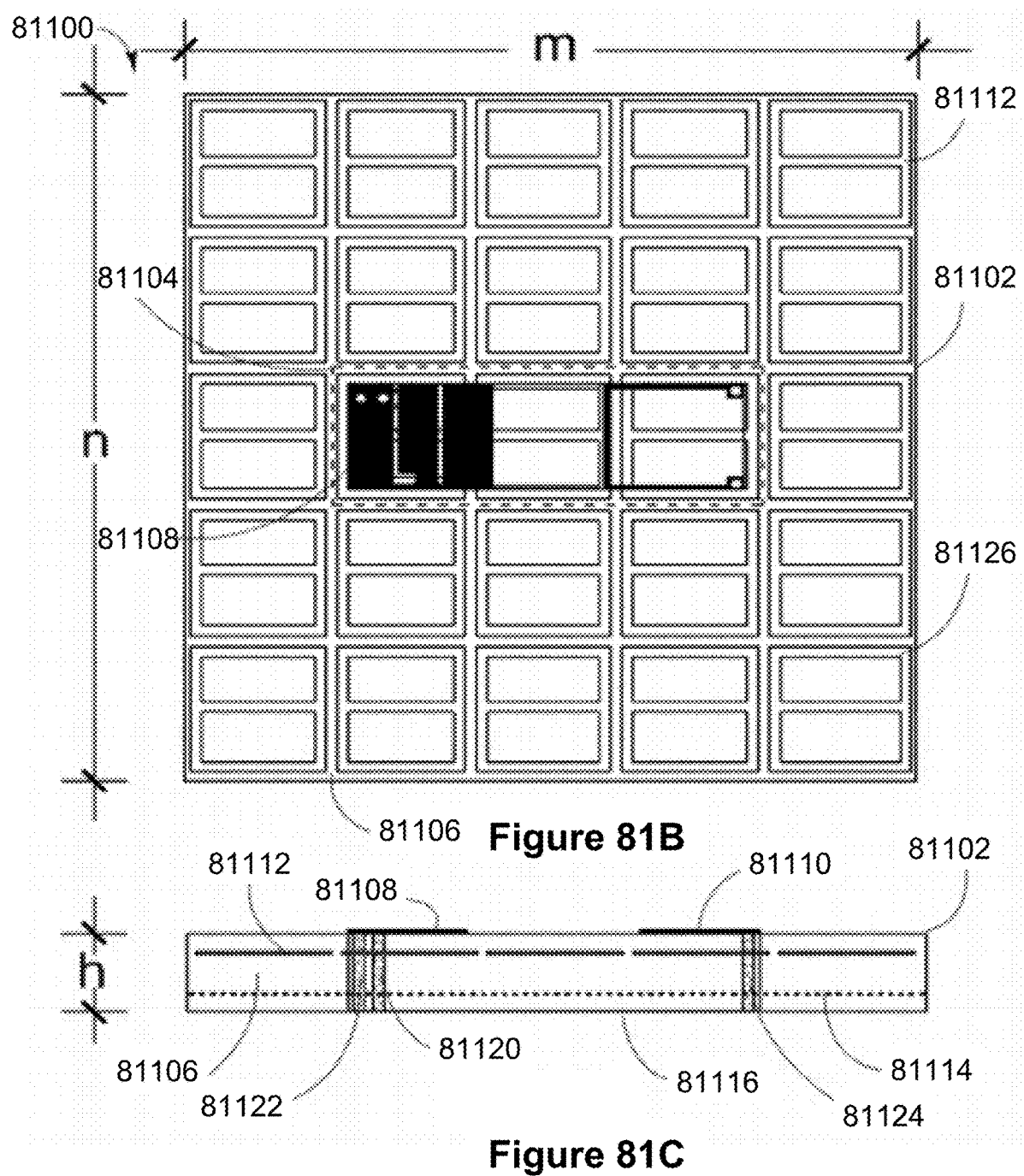

81142

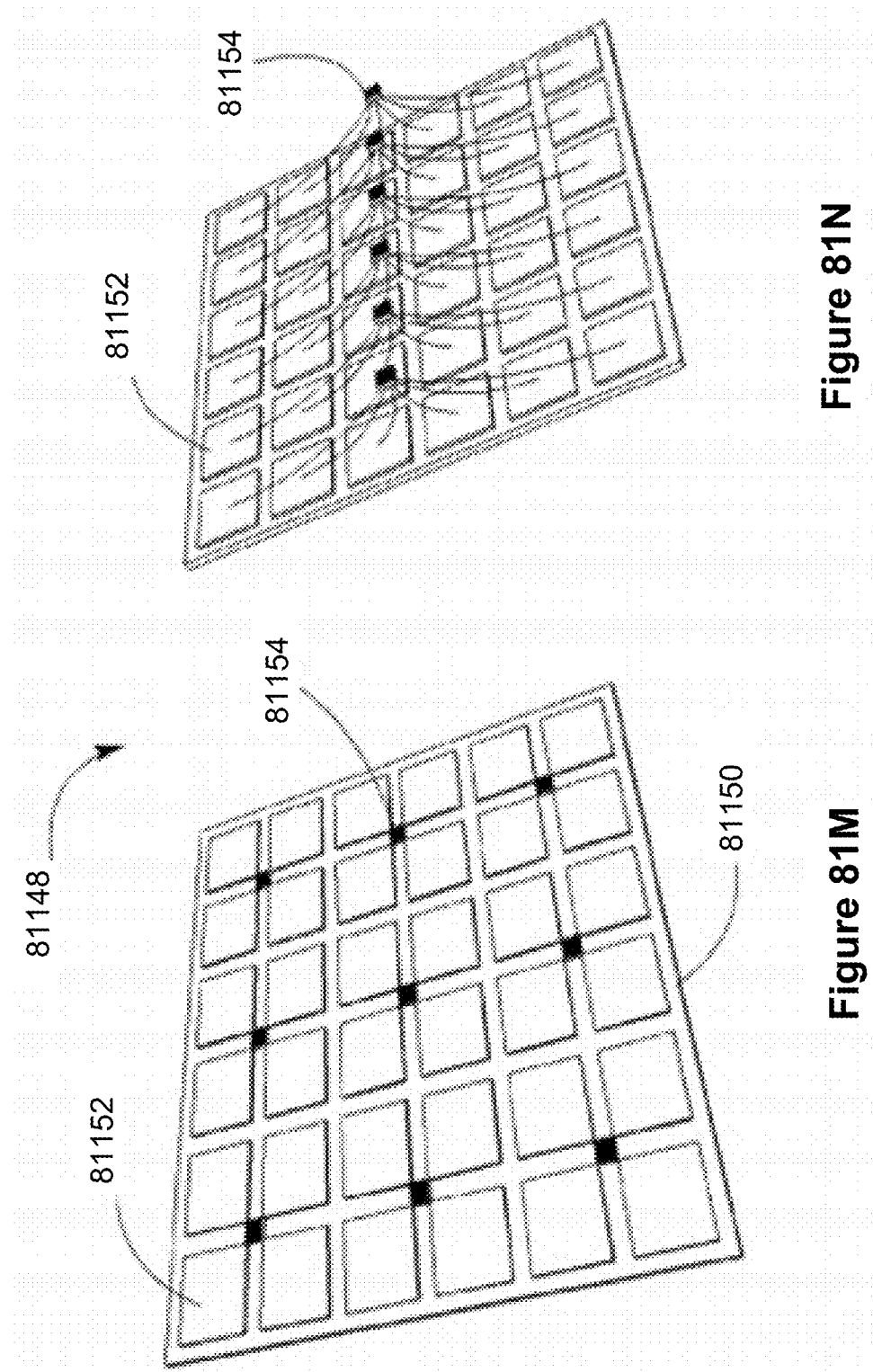

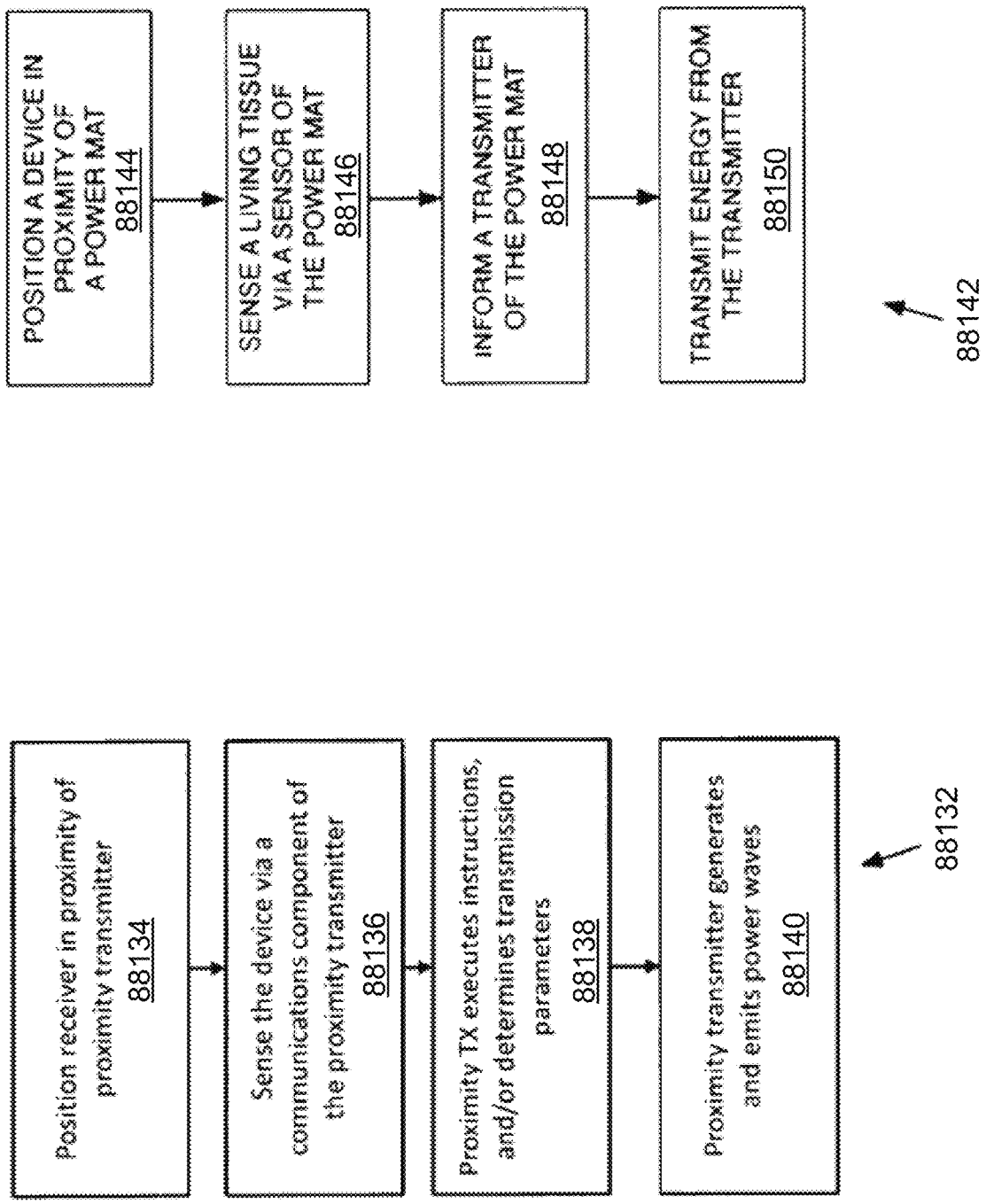

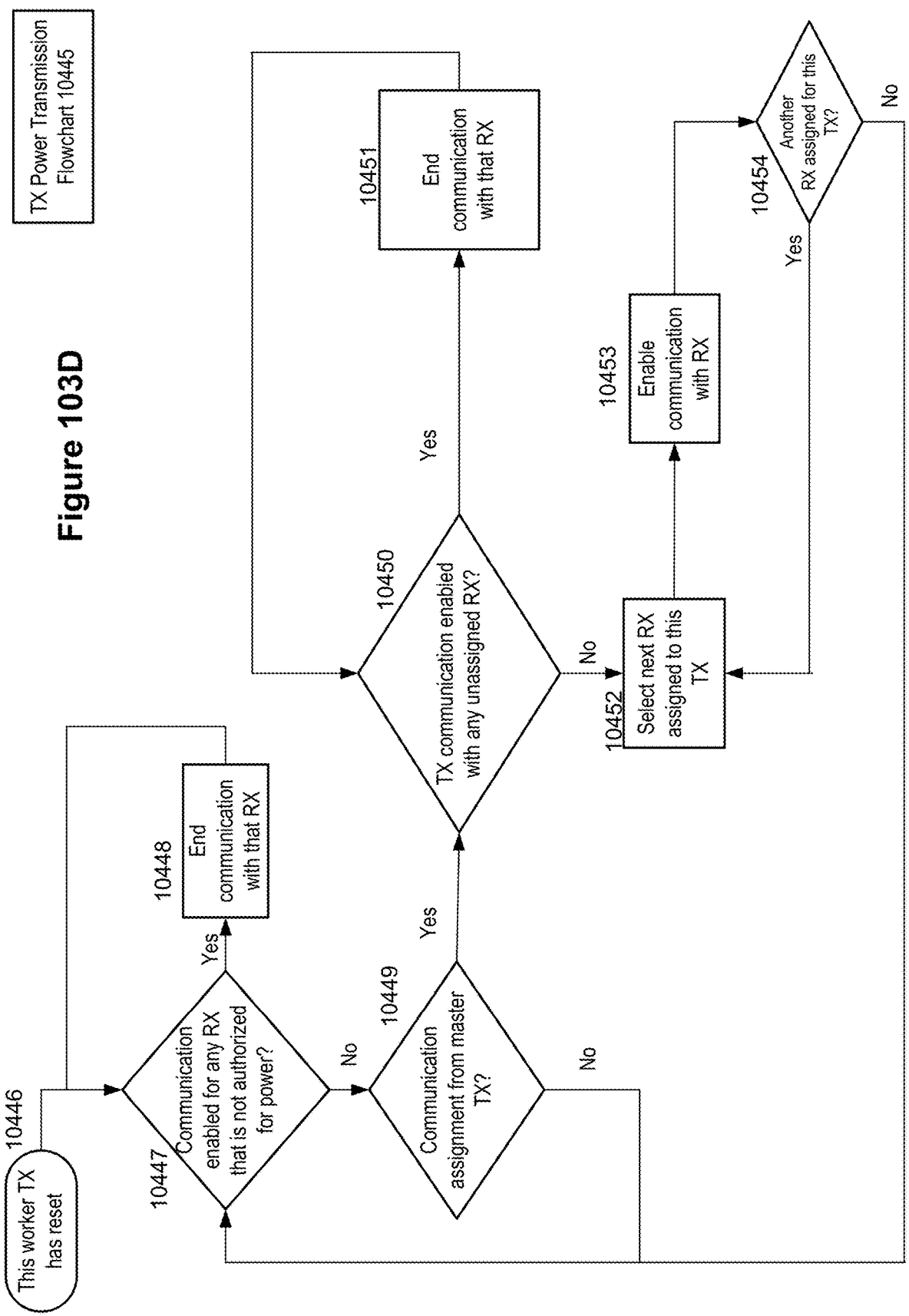

Figure 105I

| | t0 | t1 | t2 | t3 | t4 | t5 | t6 | t7 | t8 | t9 |
|---|---|---|---|---|---|---|---|---|---|---|
| D5 | | | | | | | | | | |
| D4 | | | GC4 | GC4 | GC4 | GC4 | - | GC4 | GC4 | GC4 |
| D3 | | | GC3 | - | GC3 | GC3 | GC3 | GC3 | - | - |
| D2 | | GB2 | GC2 | GC2 | - | GC2 | GC2 | GC2 | GC3 | - |
| D1 | GA | GB1 | GC1 | GC1 | GC1 | GC1 | - | GC1 | GC1 | GC3 |

WPR  
Time

10647

$t_0$ — Group of all antennas of transmitters.
$t_1$ — 2nd device D2 added. Group GB1 is for D1 and GB2 is for D2.
$t_2$ — D3 & D4 added, so GC3 is group for D3 and GC4 is for D4.
$t_8$ — Cycle pattern repeats.

SYSTEM AND METHODS OF USING ELECTROMAGNETIC WAVES TO WIRELESSLY DELIVER POWER TO SECURITY CAMERAS AND ADJUSTING WIRELESS DELIVERY OF POWER TO THE SECURITY CAMERAS AS THEY MOVE

RELATED APPLICATIONS

This application is a continuation application of U.S. patent application Ser. No. 17/242,194, filed Apr. 27, 2021 which is a continuation application of U.S. patent application Ser. No. 16/258,358, filed Jan. 25, 2019, which is a continuation-in-part of U.S. patent application Ser. No. 15/961,825, filed Apr. 24, 2018, which is a continuation-in-part of U.S. patent application Ser. No. 15/725,236, filed Oct. 4, 2017, which is a continuation-in-part of the following applications: U.S. patent application Ser. No. 13/926,055 (U.S. Pat. No. 10,128,695), filed Jun. 25, 2013; U.S. patent application Ser. No. 14/585,484 (U.S. Pat. No. 10,263,432), filed Dec. 30, 2014, which is a continuation-in-part of U.S. patent application Ser. No. 13/926,055 (U.S. Pat. No. 10,128,695), filed Jun. 25, 2013; U.S. patent application Ser. No. 14/585,506 (U.S. Pat. No. 9,966,765), filed Dec. 30, 2014, which is a continuation-in-part of U.S. patent application Ser. No. 13/926,055 (U.S. Pat. No. 10,128,695), filed Jun. 25, 2013; U.S. patent application Ser. No. 14/585,387 (U.S. Pat. No. 10,224,982), filed Dec. 30, 2014, which is a continuation-in-part of U.S. patent application Ser. No. 13/939,506, filed on Jul. 11, 2013; U.S. patent application Ser. No. 14/585,370, filed Dec. 30, 2014, which is a continuation-in-part of U.S. patent application Ser. No. 13/939,655 (U.S. Pat. No. 9,130,397), filed on Jul. 11, 2013; U.S. patent application Ser. No. 14/732,140, filed Jun. 5, 2015, which is a continuation of U.S. patent application Ser. No. 13/939,655 (U.S. Pat. No. 9,130,397), filed Jul. 11, 2014; U.S. patent application Ser. No. 14/585,324 (U.S. Pat. No. 10,124,754), filed Dec. 30, 2014, which is a continuation-in-part of U.S. patent application Ser. No. 13/946,128, filed on Jul. 19, 2013; U.S. patent application Ser. No. 14/585,362, filed Dec. 30, 2014, which is a continuation-in-part of U.S. patent application Ser. No. 13/950,536, filed on Jul. 25, 2013; U.S. patent application Ser. No. 14/586,137 (U.S. Pat. No. 9,876,380), filed Dec. 30, 2014, which is a continuation-in-part of U.S. patent application Ser. No. 14/026,747, filed on Sep. 13, 2013; U.S. patent application Ser. No. 14/586,266, filed Dec. 30, 2014, which is a continuation-in-part of U.S. patent application Ser. No. 14/026,852, filed on Sep. 13, 2013; U.S. patent application Ser. No. 14/586,539, filed Dec. 30, 2014, which is a continuation-in-part of U.S. patent application Ser. No. 14/027,446, filed on Sep. 16, 2013; U.S. patent application Ser. No. 14/586,603, filed Dec. 30, 2014, which is a continuation-in-part of U.S. patent application Ser. No. 14/027,468, filed on Sep. 16, 2013; U.S. patent application Ser. No. 14/051,054 (U.S. Pat. No. 9,824,815), filed Oct. 10, 2013; U.S. patent application Ser. No. 14/586,160 (U.S. Pat. No. 9,847,677), filed Dec. 30, 2014, which is a continuation-in-part of U.S. patent application Ser. No. 14/051,054 (U.S. Pat. No. 9,824,815), filed Oct. 10, 2013; U.S. patent application Ser. No. 14/585,797 (U.S. Pat. No. 9,893,555), filed Dec. 30, 2014, which claims priority to U.S. Patent Provisional Application No. 61/978,031, filed on Apr. 10, 2014, and is a continuation-in-part of U.S. patent application Ser. No. 14/051,128, filed on Oct. 10, 2013; U.S. patent application Ser. No. 14/585,844 (U.S. Pat. No. 9,899,861), filed Dec. 30, 2014, which claims priority to U.S. Patent Provisional Application No. 61/978,031, filed on Apr. 10, 2014, and is a continuation-in-part of U.S. patent application Ser. No. 14/051,170, filed on Oct. 10, 2013; U.S. patent application Ser. No. 14/069,983 (U.S. Pat. No. 9,882,427), filed Nov. 1, 2013; U.S. patent application Ser. No. 14/586,197 (U.S. Pat. No. 10,090,699), filed Dec. 30, 2014, which is a continuation-in-part of U.S. patent application Ser. No. 14/069,983 (U.S. Pat. No. 9,882,427), filed Nov. 1, 2013; U.S. patent application Ser. No. 14/586,243, filed Dec. 30, 2014, which is a continuation-in-part of U.S. patent application Ser. No. 14/095,358, filed Dec. 3, 2013; U.S. patent application Ser. No. 14/586,370, filed Dec. 30, 2014, which claims priority to U.S. Patent Provisional Application No. 61/978,031, filed on Apr. 10, 2014, and is a continuation-in-part of U.S. patent application Ser. No. 14/103,528, filed on Dec. 11, 2013; U.S. patent application Ser. No. 14/586,400, filed Dec. 30, 2014, which claims priority to U.S. Patent Provisional Application No. 61/978,031, filed on Apr. 10, 2014, and is a continuation-in-part of U.S. patent application Ser. No. 14/104,503 (U.S. Pat. No. 9,252,628), filed on Dec. 12, 2013; U.S. patent application Ser. No. 15/010,127 (U.S. Pat. No. 9,847,669), filed Jan. 29, 2016, which is a continuation of U.S. patent application Ser. No. 14/104,503 (U.S. Pat. No. 9,252,628), filed on Dec. 12, 2013; U.S. patent application Ser. No. 15/181,242 (U.S. Pat. No. 10,134,260), filed Jun. 13, 2016, which is a continuation of U.S. patent application Ser. No. 14/586,448 (U.S. Pat. No. 9,368,020), filed Dec. 30, 2014, which is a continuation-in-part of U.S. patent application Ser. No. 14/330,926, filed on Jul. 14, 2014; U.S. patent application Ser. No. 14/585,585, filed Dec. 30, 2014, which claims priority to U.S. Patent Provisional Application No. 61/978,031, filed on Apr. 10, 2014, and is a continuation-in-part of U.S. patent application Ser. No. 13/950,492 (U.S. Pat. No. 9,831,718), filed on Jul. 25, 2013; U.S. patent application Ser. No. 14/584,752, filed Dec. 29, 2014, which claims priority to U.S. Patent Provisional Application No. 61/978,031, filed on Apr. 10, 2014, and is a continuation-in-part of U.S. patent application Ser. No. 13/950,492 (U.S. Pat. No. 9,831,718), filed on Jul. 25, 2013; U.S. patent application Ser. No. 14/584,800 (U.S. Pat. No. 9,859,757), filed Dec. 29, 2014, which claims priority to U.S. Patent Provisional Application No. 61/978,031, filed on Apr. 10, 2014, and is a continuation-in-part of U.S. patent application Ser. No. 13/950,492 (U.S. Pat. No. 9,831,718), filed on Jul. 25, 2013; U.S. patent application Ser. No. 14/587,294, filed Dec. 31, 2014, which claims priority to U.S. Patent Provisional Application No. 61/978,031, filed on Apr. 10, 2014; U.S. patent application Ser. No. 14/587,308, filed Dec. 31, 2014, which claims priority to U.S. Patent Provisional Application No. 61/978,031, filed on Apr. 10, 2014; and U.S. patent application Ser. No. 14/069,934 (U.S. Pat. No. 10,224,758), filed Nov. 1, 2013. Each of these applications is hereby incorporated by reference in its entirety.

U.S. patent application Ser. No. 15/961,825, filed Apr. 24, 2018, is also a continuation-in-part of the following applications:

U.S. patent application Ser. No. 15/872,888 (U.S. Pat. No. 10,396,588), filed Jan. 16, 2018, which is a continuation of U.S. patent application Ser. No. 14/584,743 (U.S. Pat. No. 9,871,398), filed Dec. 29, 2014, which is a continuation-in-part of U.S. patent application Ser. No. 13/932,166, filed on Jul. 1, 2013; U.S. patent application Ser. No. 14/585,432 (U.S. Pat. No. 10,211,674), filed Dec. 30, 2014, which is a continuation-in-part of U.S. patent application Ser. No. 13/916,233, filed Jun. 12, 2013; U.S. patent application Ser. No. 15/729,574 (U.S. Pat. No. 10,498,144), filed Oct. 10, 2017, which is a continuation of U.S. patent application Ser. No. 14/584,375 (U.S. Pat. No. 9,787,103), filed Dec. 29, 2014, which is a continuation-in-part of U.S. patent application Ser. No. 13/960,522, filed Aug. 6, 2013; U.S. patent application Ser. No. 14/585,291 (U.S. Pat. No. 9,954,374), filed Dec. 30, 2014, which is a continuation-in-part of U.S. patent application Ser. No. 14/286,129 (U.S. Pat. No. 10,063,106), filed May 23, 2014; U.S. patent application Ser. No. 14/683,437 (U.S. Pat. No. 10,056,782), filed Apr. 10, 2015, which is a continuation of U.S. patent application Ser. No. 14/584,869 (U.S. Pat. No. 9,438,045), filed Dec. 29, 2014, which is a continuation-in-part of U.S. patent application Ser. No. 14/272,207, filed May 7, 2014, which claims priority to U.S. Patent Provisional Application No. 61/978,031, filed on Apr. 10, 2014; U.S. patent application Ser. No. 14/587,027 (U.S. Pat. No. 10,291,066), filed Dec. 31, 2014, which is a continuation of U.S. patent application Ser. No. 14/584,869 (U.S. Pat. No. 9,438,045), filed Dec. 29, 2014, and is a continuation-in-part of U.S. patent application Ser. No. 14/272,207, filed May 7, 2014, U.S. patent application Ser. No. 14/272,287 (U.S. Pat. No. 9,806,564), filed May 7, 2014, U.S. patent application Ser. No. 14/272,280, filed May 7, 2014, and U.S. patent application Ser. No. 14/272,247, filed May 7, 2014; U.S. patent application Ser. No. 15/806,266 (U.S. Pat. No. 10,305,315), filed Nov. 7, 2017, which is a continuation of U.S. patent application Ser. No. 14/585,341 (U.S. Pat. No. 9,812,890), filed Dec. 30, 2014, which is a continuation-in-part of U.S. patent application Ser. No. 13/939,706 (U.S. Pat. No. 9,143,000), filed Jul. 11, 2013; U.S. patent application Ser. No. 14/585,574 (U.S. Pat. No. 10,063,064), filed Dec. 30, 2014, which is a continuation-in-part of U.S. patent application Ser. No. 14/286,289 (U.S. Pat. No. 9,899,873), filed May 23, 2014; U.S. patent application Ser. No. 14/585,660 (U.S. Pat. No. 10,075,008), filed Dec. 30, 2014, which is a continuation-in-part of U.S. patent application Ser. No. 14/330,936 (U.S. Pat. No. 9,941,747), filed Jul. 14, 2014; U.S. patent application Ser. No. 14/465,487 (U.S. Pat. No. 10,439,448), filed Aug. 21, 2014; U.S. patent application Ser. No. 14/585,727(U.S. Pat. No. 10,199,849), filed Dec. 30, 2014, which is a continuation-in-part of U.S. patent application Ser. No. 14/465,508 (U.S. Pat. No. 10,008,889), filed Aug. 21, 2014; U.S. patent application Ser. No. 14/585,388 (U.S. Pat. No. 10,050,462), filed Dec. 30, 2014, which is a continuation-in-part of U.S. patent application Ser. No. 13/960,488 (U.S. Pat. No. 843,213), filed Aug. 6, 2013; U.S. patent application Ser. No. 14/585,633 (U.S. Pat. No. 10,090,886), filed Dec. 30, 2014, which is a continuation-in-part of U.S. patent application Ser. No. 14/330,931, filed Jul. 14, 2014; U.S. patent application Ser. No. 14/587,025 (U.S. Pat. No. 9,991,741), filed Dec. 31, 2014, which is a continuation-in-part of U.S. patent application Ser. No. 14/330,931, filed Jul. 14, 2014 and U.S. patent application Ser. No. 14/330,936 (U.S. Pat. No. 9,941,747), filed Jul. 14, 2014; and U.S. patent application Ser. No. 14/803,672 (U.S. Pat. No. 10,148,133), filed Jul. 20, 2015, which is a continuation of U.S. patent application Ser. No. 13/926,020 (U.S. Pat. No. 9,124,125), filed Jun. 25, 2013, which claims priority to U.S. Patent Provisional Application No. 61/720,798, filed on Oct. 31, 2012, U.S. Patent Provisional Application No. 61/677,706, filed on Jul. 31, 2012, and U.S. Patent Provisional Application No. 61/668,799, filed on Jul. 6, 2012;

U.S. patent application Ser. No. 15/839,774 (U.S. Pat. No. 10,298,024), filed Dec. 12, 2017, which is a continuation of U.S. patent application Ser. No. 14/747,946 (U.S. Pat. No. 9,843,201), filed on Jun. 23, 2015, which is a continuation of U.S. patent application Ser. No. 14/586,314 (U.S. Pat. No. 9,450,449), filed on Dec. 30, 2014, which is a continuation-in-part of U.S. patent application Ser. No. 13/908,839, filed on Jun. 3, 2013, and U.S. patent application Ser. No. 14/586,314 (U.S. Pat. No. 9,450,449), filed Dec. 30, 2014 is a continuation-in-part of:

U.S. patent application Ser. No. 13/891,399 (U.S. Pat. No. 9,912,199), filed May 10, 2013, which claims priority to U.S. Patent Application Ser. No. 61/720,798, filed Oct. 31, 2012, U.S. Patent Application Ser. No. 61/677,706, filed Jul. 31, 2012, and U.S. Patent Application Ser. No. 61/668,799, filed Jul. 6, 2012;

U.S. patent application Ser. No. 13/891,430, filed May 10, 2013, which claims priority to U.S. Patent Application Ser. No. 61/720,798, filed Oct. 31, 2012, U.S. Patent Application Ser. No. 61/677,706, filed Jul. 31, 2012, and U.S. Patent Application Ser. No. 61/668,799, filed Jul. 6, 2012; and U.S. patent application Ser. No. 13/891,445 (U.S. Pat. No. 10,103,582), filed May 10, 2013, which claims priority to U.S. Patent Application Ser. No. 61/720,798, filed Oct. 31, 2012, U.S. Patent Application Ser. No. 61/677,706, filed Jul. 31, 2012, U.S. Patent Application Ser. No. 61/668,799, filed Jul. 6, 2012;

U.S. patent application Ser. No. 15/884,303, filed Jan. 30, 2018, which is a continuation of:

U.S. patent application Ser. No. 14/748,101 (U.S. Pat. No. 9,882,394), filed on Jun. 23, 2015, which is a continuation of U.S. patent application Ser. No. 14/585,271 (U.S. Pat. No. 9,867,062), filed on Dec. 30, 2014, which is a continuation-in-part of U.S. Non-Provisional patent application Ser. No. 14/337,002 (U.S. Pat. No. 9,838,083) filed Jul. 21, 2014; and U.S. patent application Ser. No. 14/587,025 (U.S. Pat. No. 9,991,741), filed on Dec. 31, 2014, which is a continuation-in-part of U.S. patent application Ser. No. 14/330,931, filed on Jul. 14, 2014; and is also a continuation of U.S. patent application Ser. No. 14/330,936 (U.S. Pat. No. 9,941,747), filed on Jul. 14, 2014; and U.S. patent application Ser. No. 15/900,727 (U.S. Pat. No. 10,790,674), filed Feb. 20, 2018, which is a continuation of:

U.S. patent application Ser. No. 14/748,116 (U.S. Pat. No. 9,899,844), filed on Jun. 23, 2015, which is a continuation of U.S. patent application Ser. No. 14/585,986 (U.S. Pat. No. 9,887,584), filed on Dec. 30, 2014, which is a continuation-in-part of U.S. patent application Ser. No. 14/465,553 (U.S. Pat. No. 9,891,669), filed Aug. 21, 2014; and U.S. patent application Ser. No. 14/585,923 (U.S. Pat. No. 9,939,864), file Dec. 30, 2014, which is a continuation-in-part of U.S. patent application Ser. No. 14/465,545 (U.S. Pat. No. 9,876,648), filed Aug. 21, 2014, each of these applications is hereby incorporated by reference in its entirety.

This application is also a continuation-in-part of the following applications:

U.S. patent application Ser. No. 13/908,809 (U.S. Pat. No. 10,206,185), filed on Jun. 3, 2013;

U.S. patent application Ser. No. 14/336,963 (U.S. Pat. No. 10,381,880) filed on Jul. 21, 2014;

U.S. patent application Ser. No. 13/946,082 (U.S. Pat. No. 10,211,680), filed on Jul. 19, 2013;

U.S. patent application Ser. No. 15/820,335 (U.S. Pat. No. 10,291,294), filed Nov. 21, 2017, which is:
- a continuation of U.S. patent application Ser. No. 14/584,364 (U.S. Pat. No. 9,825,674), filed on Dec. 29, 2014, which is a continuation-in-part of U.S. patent application Ser. No. 14/286,243 (U.S. Pat. No. 9,793,758), filed on May 23, 2014;
- a continuation-in-part of U.S. patent application Ser. No. 14/584,268 (U.S. Pat. No. 10,141,768) filed Dec. 29, 2014, which is a continuation-in-part of U.S. patent application Ser. No. 13/908,760, filed on Jun. 3, 2013;
- a continuation-in-part of U.S. patent application Ser. No. 14/584,484 (U.S. Pat. No. 10,148,097), filed Dec. 29, 2014, which is a continuation-in-part of U.S. patent application Ser. No. 14/075,376, filed Nov. 8, 2013; and
- a continuation-in-part of U.S. patent application Ser. No. 14/584,449 (U.S. Pat. No. 9,941,707), filed Dec. 29, 2014, which is a continuation-in-part of U.S. patent application Ser. No. 13/946,065, filed Jul. 19, 2013;

U.S. patent application Ser. No. 16/238,478, filed Jan. 2, 2019, which is a continuation of U.S. patent application Ser. No. 14/586,254 (U.S. Pat. No. 10,205,239), filed Dec. 30, 2014, which is a continuation-in-part of U.S. patent application Ser. No. 14/272,265 (U.S. Pat. No. 10,218,227), filed on May 7, 2014;

U.S. patent application Ser. No. 15/860,592 (U.S. Pat. No. 10,298,133), filed Jan. 2, 2018, which is a continuation of U.S. patent application Ser. No. 14/584,901 (U.S. Pat. No. 9,859,797), filed on Dec. 29, 2014, which is a continuation-in-part of U.S. patent application Ser. No. 14/272,247, filed on May 7, 2014;

U.S. patent application Ser. No. 16/027,182, filed Jul. 3, 2018, which is a continuation of U.S. patent application Ser. No. 14/748,043 (U.S. Pat. No. 10,014,728), filed Jun. 23, 2015, which is a continuation of U.S. patent application Ser. No. 14/584,964 (U.S. Pat. No. 9,876,394), filed Dec. 29, 2014, which is a continuation-in-part of U.S. patent application Ser. No. 14/272,280, filed May 7, 2014;

U.S. patent application Ser. No. 14/272,066 (U.S. Pat. No. 10,211,682), filed on May 7, 2014;

U.S. patent application Ser. No. 14/585,509 (U.S. Pat. No. 10,223,717), filed Dec. 30, 2014, which is a continuation-in-part of U.S. patent application Ser. No. 14/286,232, filed on May 23, 2014;

U.S. patent application Ser. No. 14/586,509 (U.S. Pat. No. 10,223,717), filed Dec. 30, 2014, which is a continuation-in-part of (i) U.S. patent application Ser. No. 14/272,066 (U.S. Pat. No. 10,211,682), filed May 7, 2014 and (ii) U.S. patent application Ser. No. 14/272,039 (U.S. Pat. No. 10,141,791), filed May 7, 2014;

U.S. patent application Ser. No. 16/115,495 (U.S. Pat. No. 10,523,058), filed Aug. 28, 2018, which is a continuation of U.S. patent application Ser. No. 14/757,568 (U.S. Pat. No. 10,063,105), filed Dec. 24, 2015, which is (i) a continuation-in-part of U.S. patent application Ser. No. 14/861,285 (U.S. Pat. No. 9,948,135), filed Sep. 22, 2015, and (ii) a continuation-in-part of U.S. patent application Ser. No. 14/585,341 (U.S. Pat. No. 9,812,890), filed Dec. 30, 2014, which is a continuation-in-part of U.S. patent application Ser. No. 13/939,706 (U.S. Pat. No. 9,143,000), filed Jul. 11, 2013;

U.S. patent application Ser. No. 15/053,124 (U.S. Pat. No. 10,270,261), filed Feb. 25, 2016, which claims priority to U.S. Patent Provisional Application No. 62/387,467, filed Dec. 24, 2015, and is a continuation-in-part of (i) U.S. patent application Ser. No. 14/861,285 (U.S. Pat. No. 9,948,135), filed Sep. 22, 2015 and (ii) U.S. patent application Ser. No. 14/856,337 (U.S. Pat. No. 10,312,715), filed Sep. 16, 2015;

U.S. patent application Ser. No. 15/053,292 (U.S. Pat. No. 10,291,056), filed Feb. 25, 2016, which claims priority to U.S. Patent Provisional Application No. 62/387,467, filed Dec. 24, 2015, and is a continuation of (i) U.S. patent application Ser. No. 14/861,285 (U.S. Pat. No. 9,948,135), filed Sep. 22, 2015 and (ii) U.S. patent application Ser. No. 14/856,337 (U.S. Pat. No. 10,312,715), filed Sep. 16, 2015;

U.S. patent application Ser. No. 16/190,071, filed Nov. 13, 2018, which is a continuation of U.S. patent application Ser. No. 15/060,167 (U.S. Pat. No. 10,128,699), filed Mar. 3, 2016, which claims priority to U.S. Patent Provisional Application No. 62/272,571, filed Dec. 29, 2015, and is a continuation-in-part of (i) U.S. patent application Ser. No. 14/856,337 (U.S. Pat. No. 10,312,715), filed Sep. 16, 2015, and (ii) U.S. patent application Ser. No. 14/584,412 (U.S. Pat. No. 9,893,554) filed Dec. 29, 2014, which is a continuation-in-part of U.S. patent application Ser. No. 14/330,939 (U.S. Pat. No. 10,128,693), filed Jul. 14, 2014;

U.S. patent application Ser. No. 15/046,026 (U.S. Pat. No. 10,256,657), filed Feb. 17, 2016, which claims priority to U.S. Patent Provisional Application No. 62/387,206, filed Dec. 24, 2015;

U.S. patent application Ser. No. 29/669,227, filed Nov. 6, 2018, which is a continuation of U.S. patent application Ser. No. 29/550,049 (U.S. Pat. D832,782) filed on Dec. 30, 2015; and U.S. patent application Ser. No. 29/656,147 (U.S. Pat. D851,120), filed Jul. 10, 2018, which is a continuation of U.S. patent application Ser. No. 29/586,759 (U.S. Pat. D822,701), filed Dec. 6, 2016, which is a continuation of U.S. patent application Ser. No. 29/513,406 (U.S. Pat. D773,506), filed Dec. 30, 2014.

U.S. patent application Ser. No. 14/587,367 (U.S. Pat. No. 10,230,266), filed Dec. 31, 2014, which is a continuation-in-part of U.S. patent application Ser. No. 14/173,936, filed on Feb. 6, 2014;

U.S. patent application Ser. No. 15/061,473 (U.S. Pat. No. 10,193,396), filed Mar. 4, 2016, which claims priority to U.S. Patent Provisional Application No. 62/387,466, filed Dec. 28, 2015, and is a continuation-in-part of U.S. patent application Ser. No. 14/748,136 (U.S. Pat. No. 9,882,395), filed Jun. 23, 2015, which is a continuation of U.S. patent application Ser. No. 14/587,616 (U.S. Pat. No. 9,882,430), filed Dec. 31, 2014, which is a continuation-in-part of U.S. patent application Ser. No. 14/272,124 (U.S. Pat. No. 9,847,679), filed May 7, 2014; and U.S. patent application Ser. No. 15/058,714 (U.S. Pat. No. 10,199,835), filed Mar. 2, 2016, which claims priority to U.S. Patent Provisional Application No. 62/272,553, filed Dec. 29, 2015;

U.S. patent application Ser. No. 15/854,718 (U.S. Pat. No. 10,396,604), filed Dec. 26, 2017, which is a continuation of (i) U.S. patent application Ser. No. 14/584,324 (U.S. Pat. No. 9,853,458), filed Dec. 29, 2014, which is a continuation-in-part of U.S. patent application Ser. No. 14/272,093, filed May 7, 2014, and (ii) U.S. patent application Ser. No. 14/584,170 (U.S. Pat. No. 9,853,692), filed Dec. 29, 2014, which is a continuation-in-part of U.S. patent application Ser. No. 14/286,243 (U.S. Pat. No. 9,793,758), filed May 23, 2014; and U.S. patent application Ser. No. 14/584,220 (U.S. Pat. No. 10,291,055), filed Dec. 29, 2014, each of these applications is hereby incorporated by reference in its entirety.

TECHNICAL FIELD

The disclosed embodiments relate generally to wireless power transmission systems and, in particular, to wireless power transmitters, wireless power receivers, and other devices that are used in wireless power transmission systems to wirelessly deliver power to an electronic device.

BACKGROUND

Portable electronic devices, such as laptop computers, mobile phones, tablets, and other electronic devices, require frequent charging of a power-storing component (e.g., a battery) to operate. Many electronic devices require charging one or more times per day. Often, charging an electronic device requires manually connecting an electronic device to an outlet or other power source using a wired charging cable. In some cases, the power-storing component is removed from an electronic device and inserted into charging equipment. Accordingly, charging is time consuming, burdensome, and inefficient because users must carry around multiple charging cables and/or other charging devices, and frequently must locate appropriate power sources to charge their electronic devices. Additionally, conventional charging techniques potentially deprive a user of the ability to use the device while it is charging, and/or require the user to remain next to a wall outlet or other power source to which their electronic device or other charging equipment is connected.

Some other conventional charging systems utilize inductive coils to generate a magnetic field that is used to charge a device. However, such inductive coupling has a limited short range, such as a few inches or less. Users typically must place the device at a specific position on a charging pad and are unable to move the device to different positions on the pad, without interrupting or terminating the charging of the device. This results in a frustrating experience for many users as they may be unable to locate the device at the exact right position on the pad to start charging their device.

SUMMARY

There is a need for systems and methods for wirelessly delivering power to electronic devices that address the drawbacks of conventional systems discussed above.

In some embodiments, a method of wirelessly transmitting power is provided. The method includes: (i) receiving, by a communications radio of a wireless power transmitter, a communication signal from a communications radio of a wireless power receiver, the communication signal including data used to determine a location of the wireless power receiver, and (ii) determining, by a processor of the wireless power transmitter, a location of the wireless power receiver based, at least in part, on the data included in the communication signal. The method further includes, in response to determining that the location of the wireless power receiver is within a wireless power transmission range defined by the transmitter, transmitting, by antennas of the wireless power transmitter, radio frequency (RF) power transmission waves towards the wireless power receiver, the RF power transmission waves converging to form controlled constructive interference patterns and destructive interference patterns in proximity to the location of the wireless power receiver, and the destructive interference patterns form a null space that surrounds the controlled constructive interference patterns and the controlled constructive interference patterns are received by an antenna of the wireless power receiver.

In accordance with some implementations, a wireless power transmitter includes one or more processors/cores, memory, and one or more programs; the one or more programs are stored in the memory and configured to be executed by the one or more processors/cores and the one or more programs include instructions for performing the operations of the method described above (and/or any of the other methods described in more detail below). In accordance with some implementations, a computer-readable storage medium has stored therein instructions which when executed by one or more processors/cores of a wireless power transmitter, cause the wireless power transmitter to perform the operations of the method described above (and/or any of the other methods described in more detail below).

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit to other effective features.

FIG. 8C is a block diagram of an example multi-mode transmitter.

FIGS. 16A-16B are illustrations of game controllers that are coupled with wireless power receivers, in accordance with some embodiments.

FIGS. 16C-16G illustrate various wireless power transmission systems in which power is wirelessly delivered to electronic devices, in accordance with some embodiments.

FIGS. 18A-18B are illustrations of medical devices with wireless power receivers coupled thereto, in accordance with some embodiments.

FIG. 21D illustrates an example embodiment of a tile architecture, in accordance with some embodiments.

FIGS. 25A and 25B illustrate waveforms for wireless power transmission with selective range, which may get unified in single waveform, in accordance with some embodiments.

FIGS. 63A-63H are various screenshots of graphical user interfaces for a wireless power transmission management system, in accordance with some embodiments.

FIGS. 78A-78N illustrate examples of the methodology for pocket-forming, in accordance with some embodiments.

FIGS. 79A-79C illustrate examples of tracking surface for determining optimal charging position, in accordance with some embodiments.

FIGS. 80A-80B illustrate examples of protocols for wireless power transmission, in accordance with some embodiments.

FIGS. 81A-81N illustrate examples of integrated antenna arrays for wireless power transmission, in accordance with some embodiments.

FIGS. 82A-82D illustrate examples of devices, apparatus, and methods for 3 dimensional pocket-forming, in accordance with some embodiments.

FIGS. 83A-83C illustrate examples of devices, apparatus, and methods for an enhanced transmitter for wireless power transmission, in accordance with some embodiments.

FIGS. 84A-84B illustrate examples of systems and methods for providing health safety in a wireless power transmission system, in accordance with some embodiments.

FIGS. 85A-85B illustrate examples of devices, apparatus, and methods for a portable transmitter for wireless power transmission, in accordance with some embodiments.

FIGS. 86A-86J illustrate examples of devices, apparatus, and methods for a compact PIFA antenna, in accordance with some embodiments.

FIGS. 87A-87E illustrate examples of devices, apparatus, and methods for a simultaneous power and payload receiver, in accordance with some embodiments.

FIGS. 88A-88M illustrate examples of devices, apparatus, and methods for proximity transmitters for wireless power charging systems, in accordance with some embodiments.

FIGS. 89A-89I and 90A-90F illustrate examples of devices, apparatus, and methods of object detection in wireless power charging systems, in accordance with some embodiments.

FIGS. 91A-91D illustrate examples of devices, apparatus, and methods of providing wireless power using receiver device sensor inputs, in accordance with some embodiments.

Figure 92:
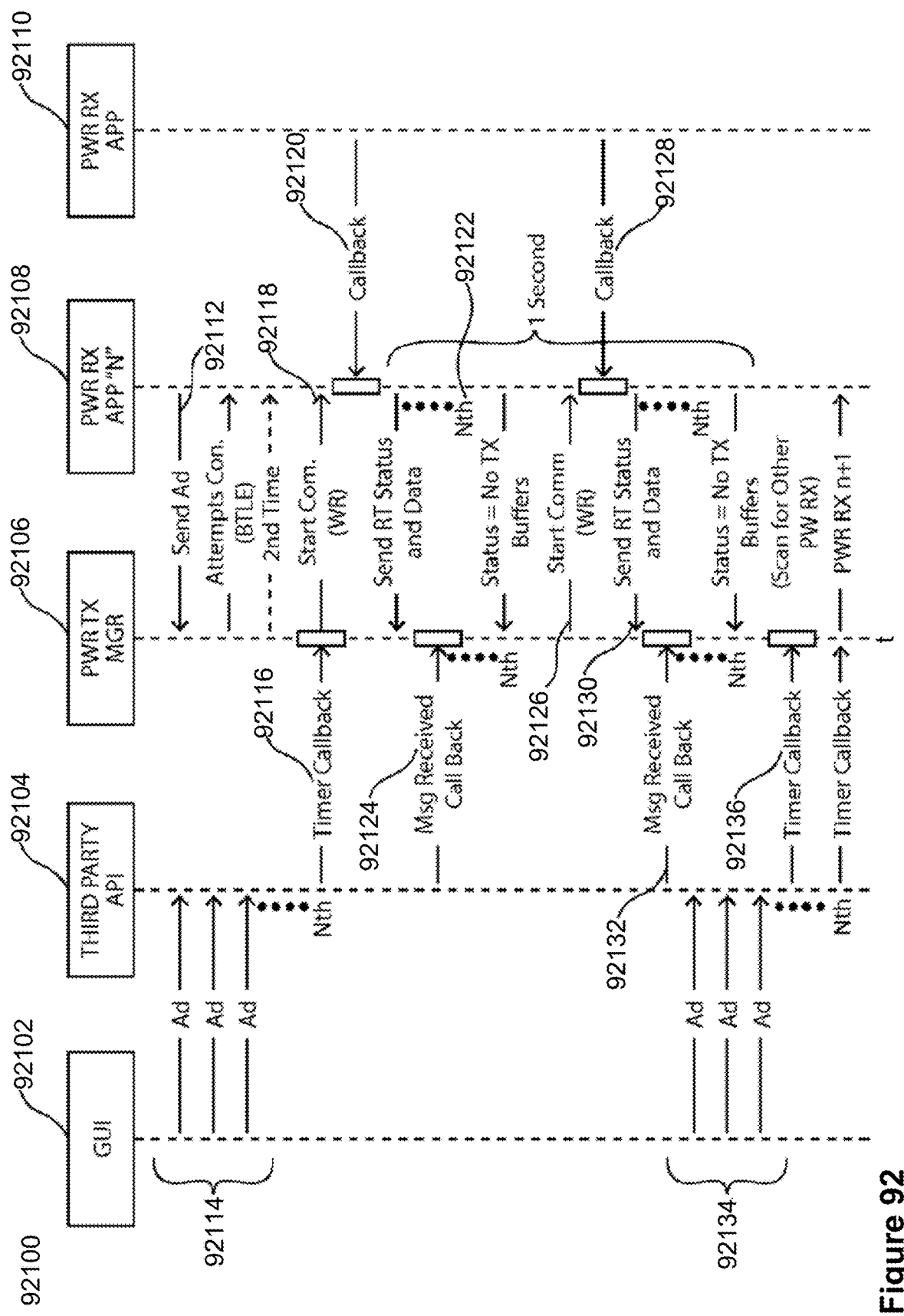

FIG. 92 illustrates examples of systems and methods for wireless transmission of power, in accordance with some embodiments.

Figure 93:
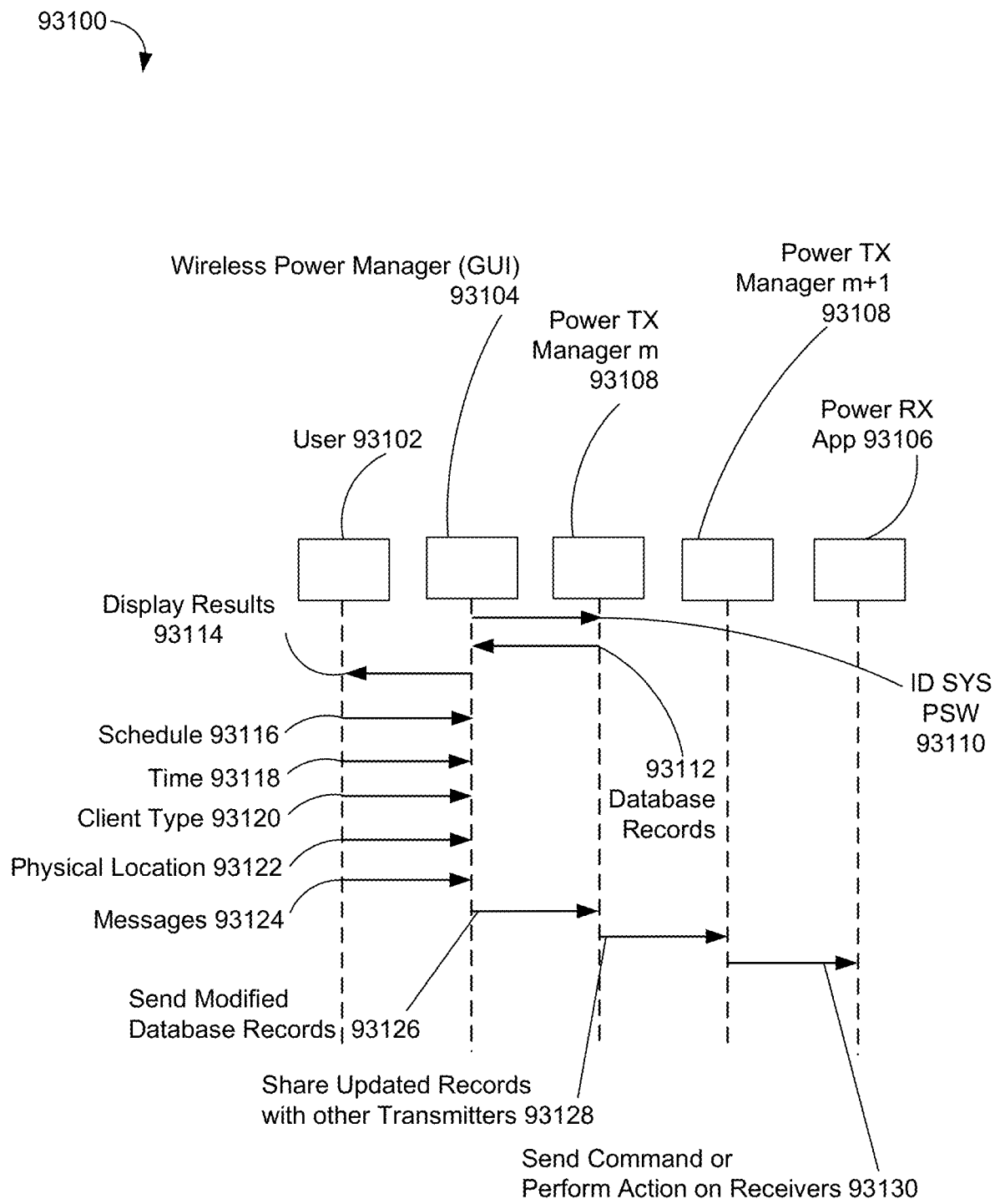

FIG. 93 illustrates examples of systems and methods for managing and controlling a wireless power network, in accordance with some embodiments.

Figure 94:
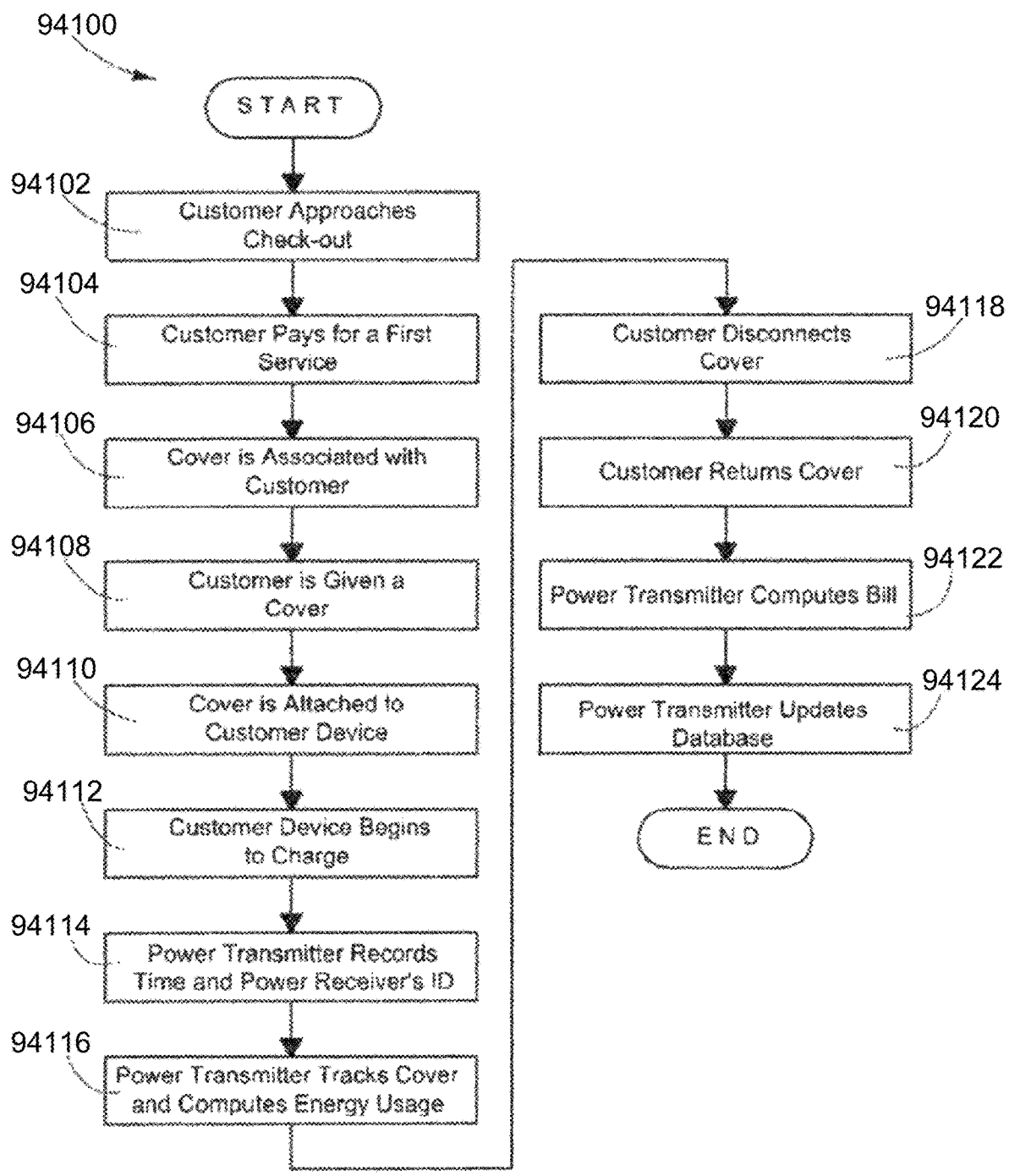
Figure 95:
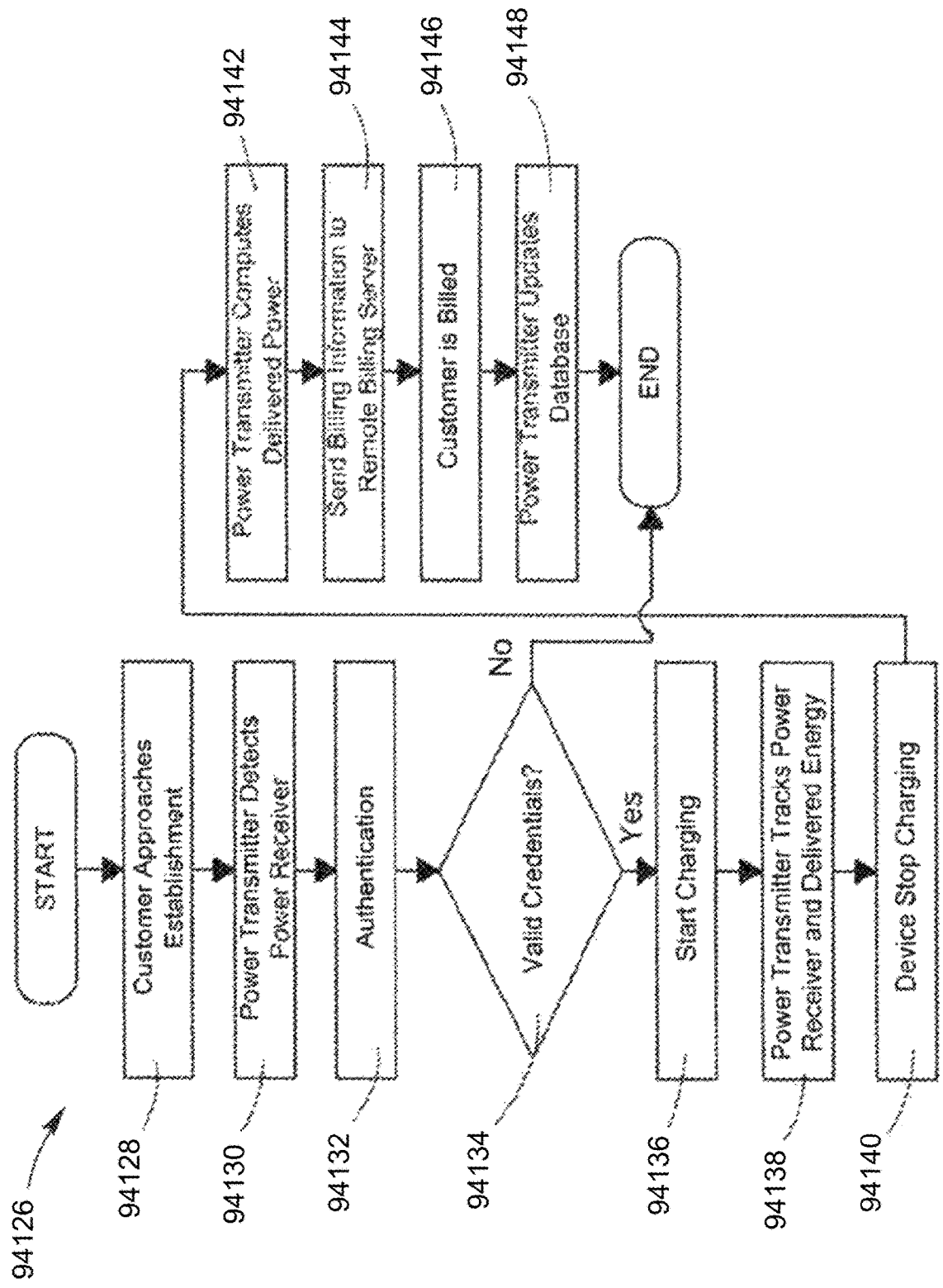

FIGS. 94 and 95 illustrate examples of systems and methods for power payment based on proximity, in accordance with some embodiments.

FIGS. 96A-96H illustrate examples of devices, apparatus, and methods for antenna for near field wireless power charging, in accordance with some embodiments.

FIGS. 97A-97G illustrate examples of electronic devices, in accordance with some embodiments.

Figure 98:
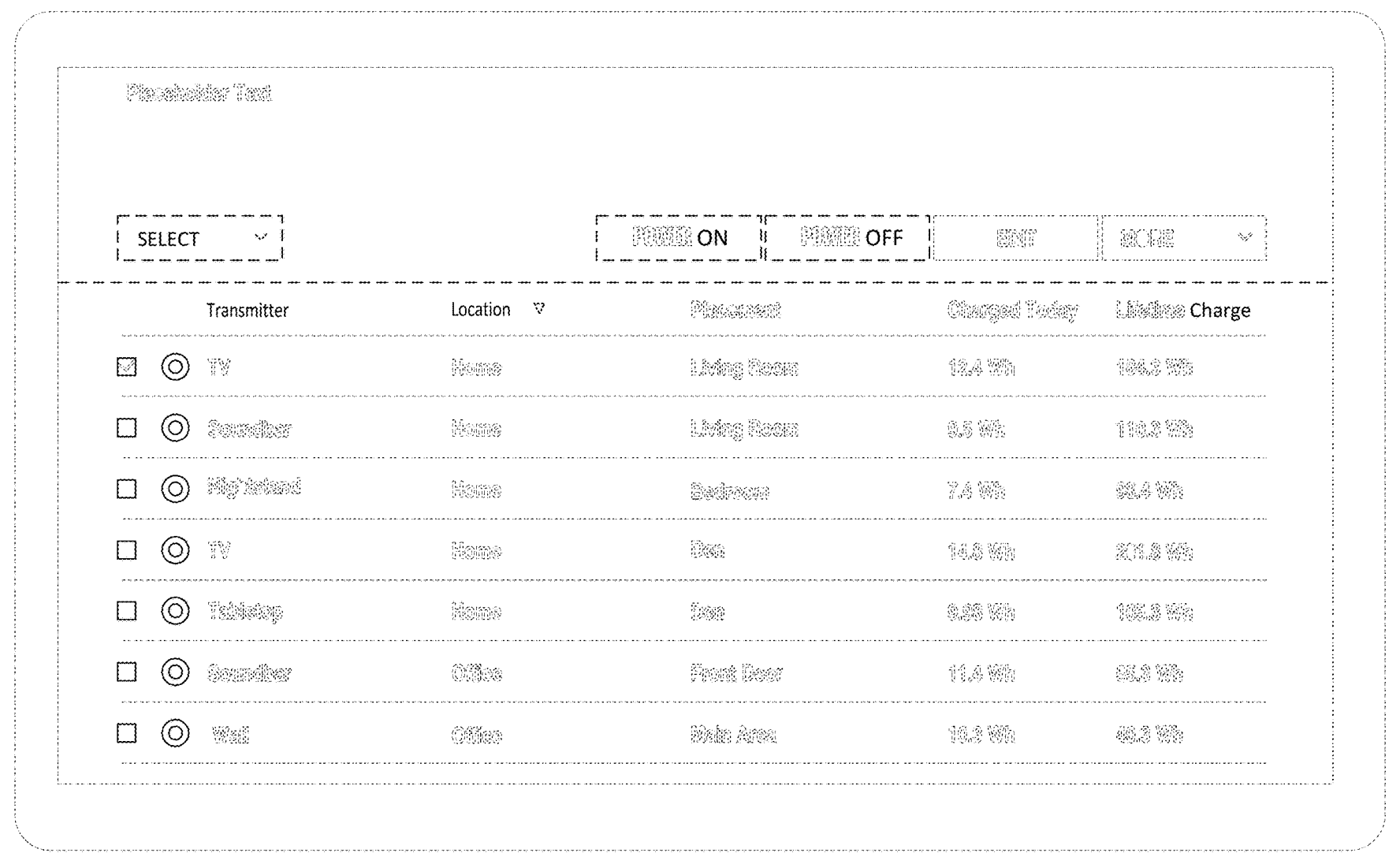

FIG. 98 illustrates an example of display screen or portion thereof with a graphical user interface, in accordance with some embodiments.

Figure 99A:
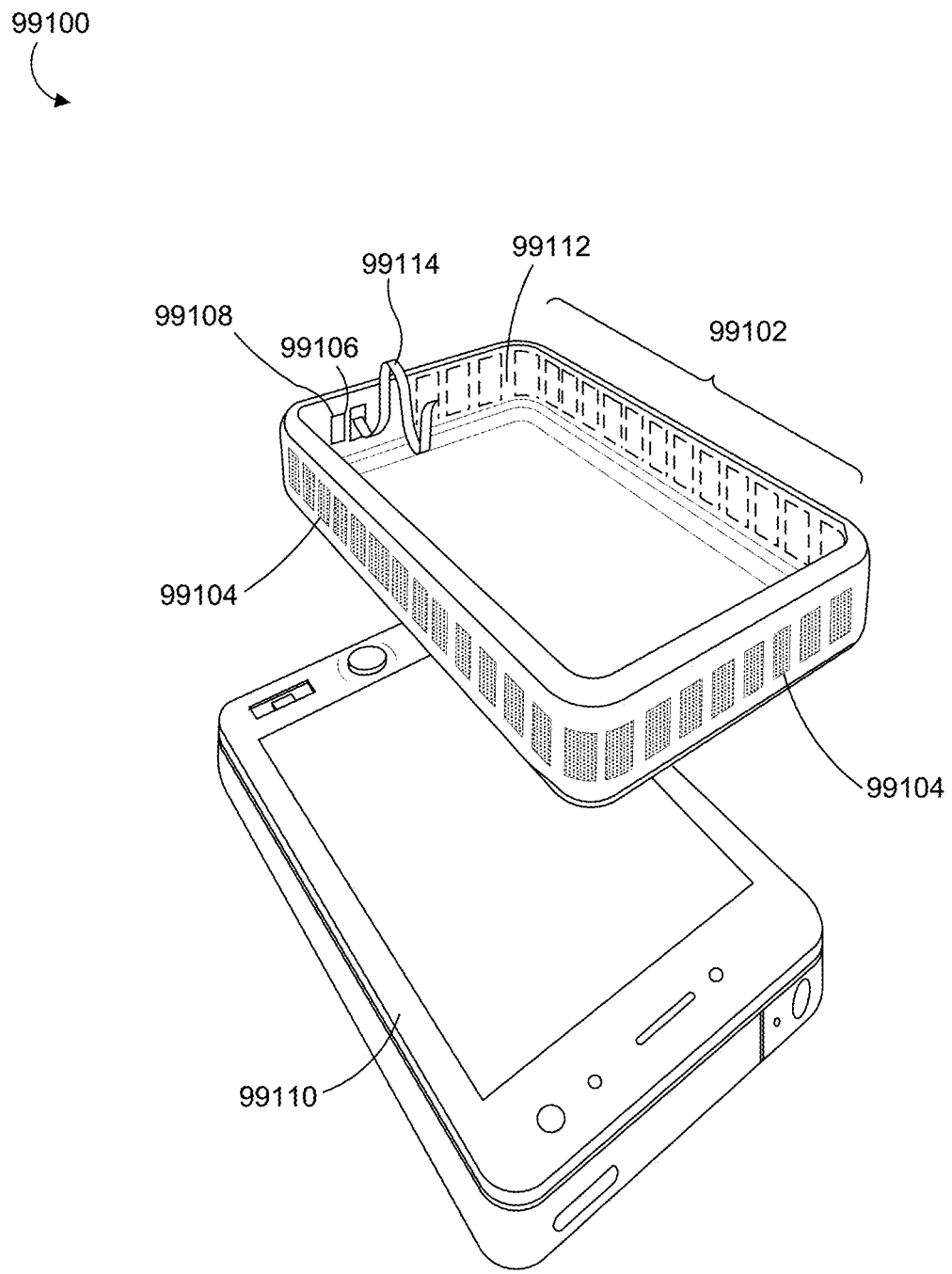
Figure 99B:
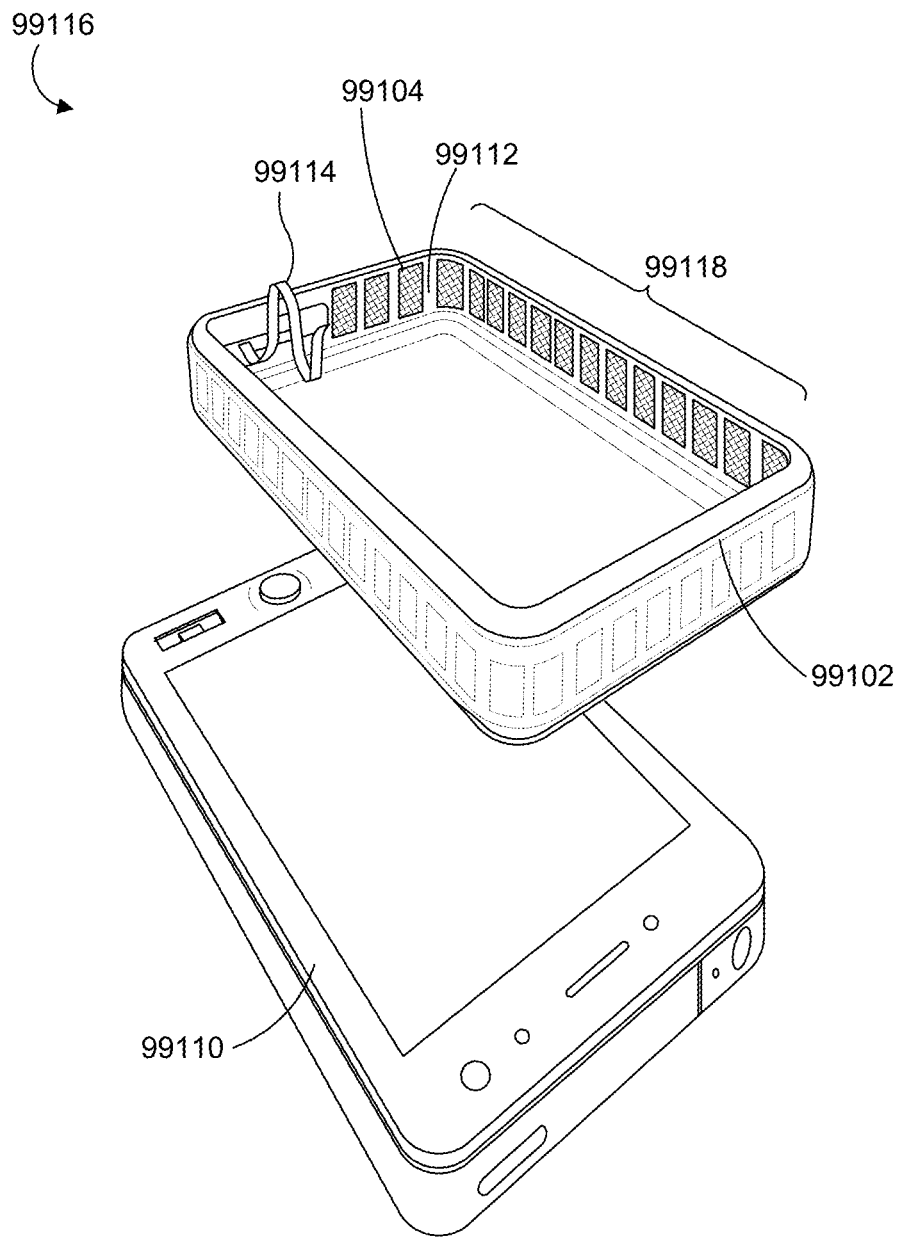

FIGS. 99A and 99B illustrate examples of devices, apparatus, and methods for external or internal receiver for smart mobile devices, in accordance with some embodiments.

Figure 100A:
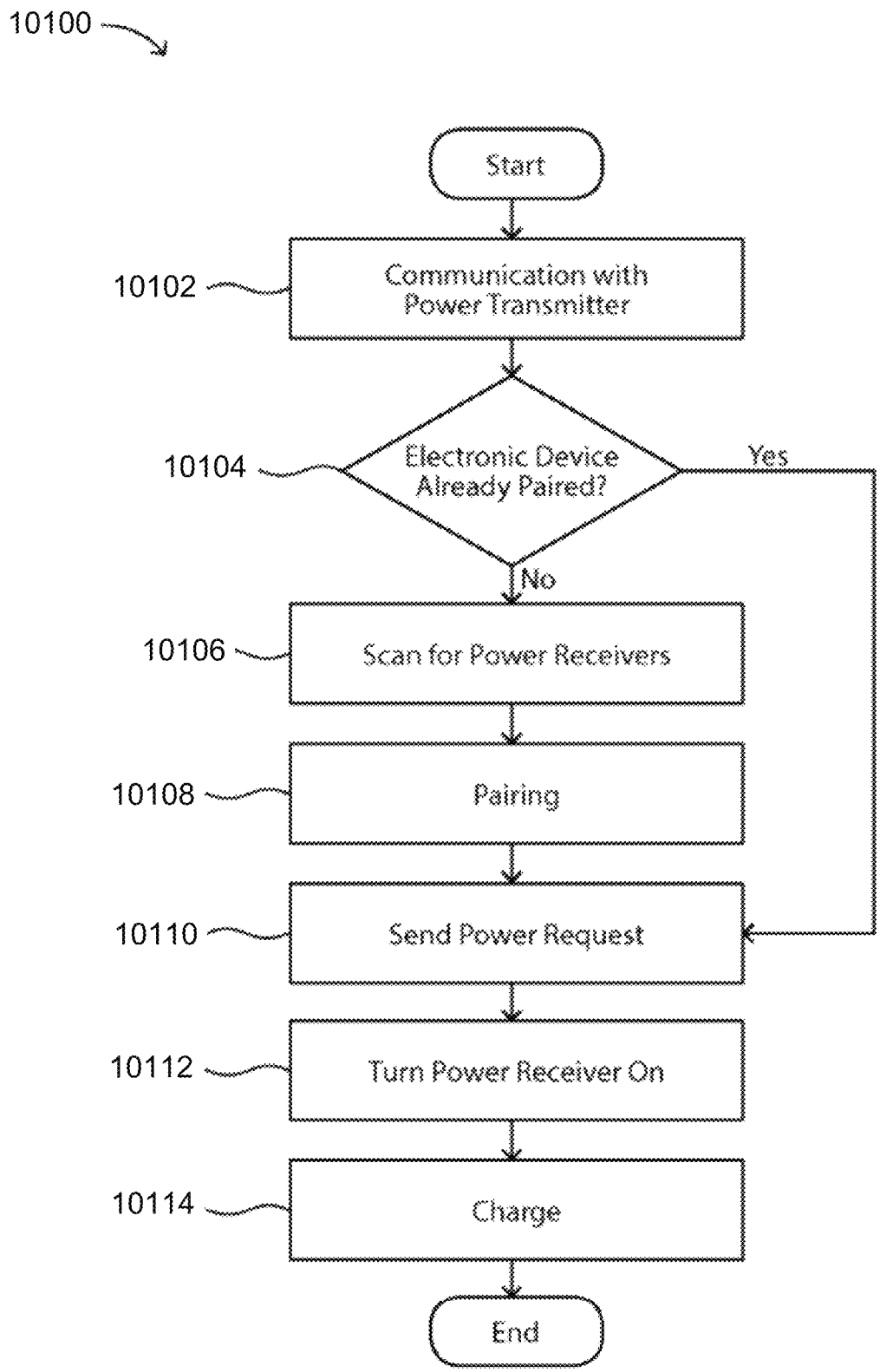
Figure 100B:
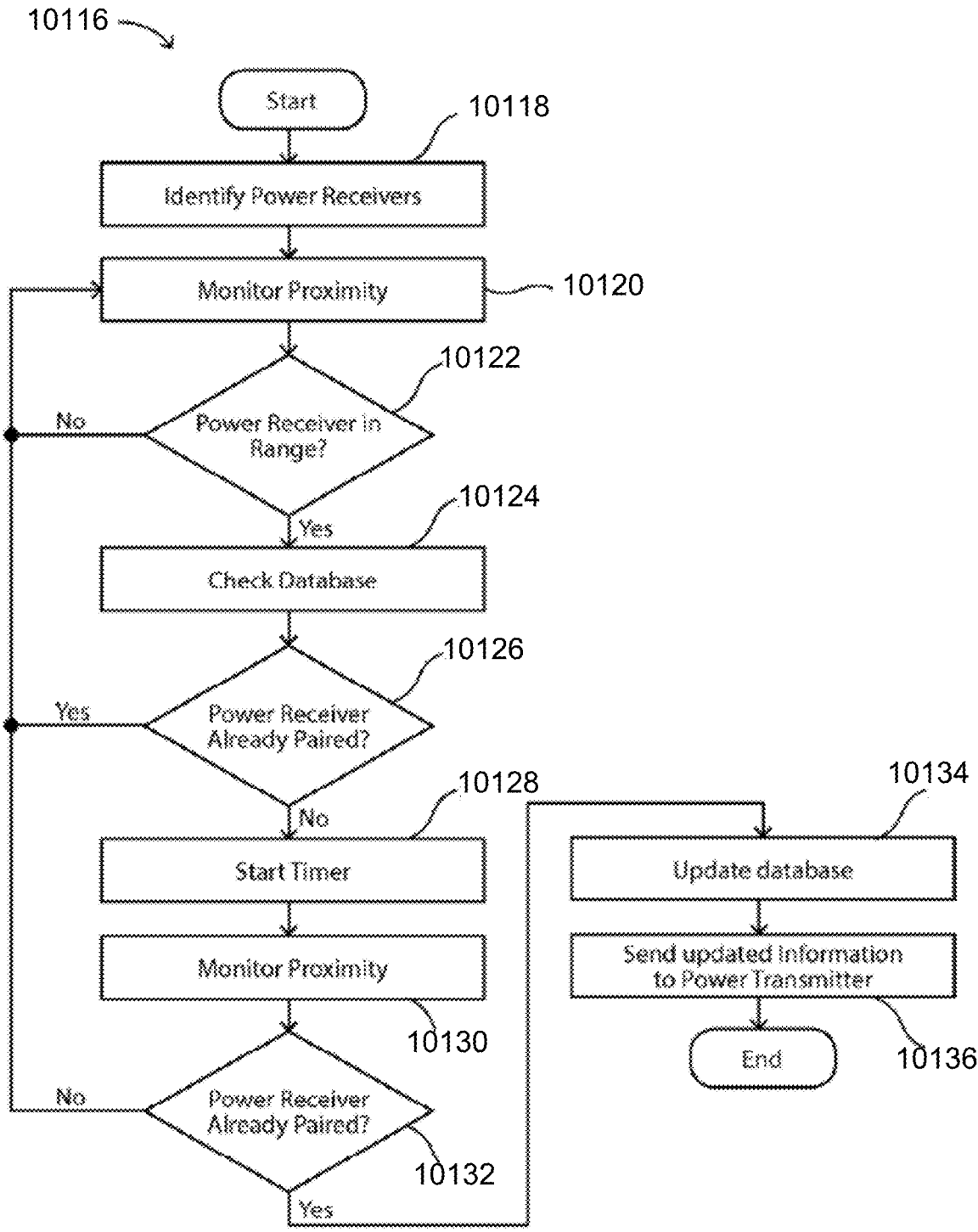
Figure 100C:
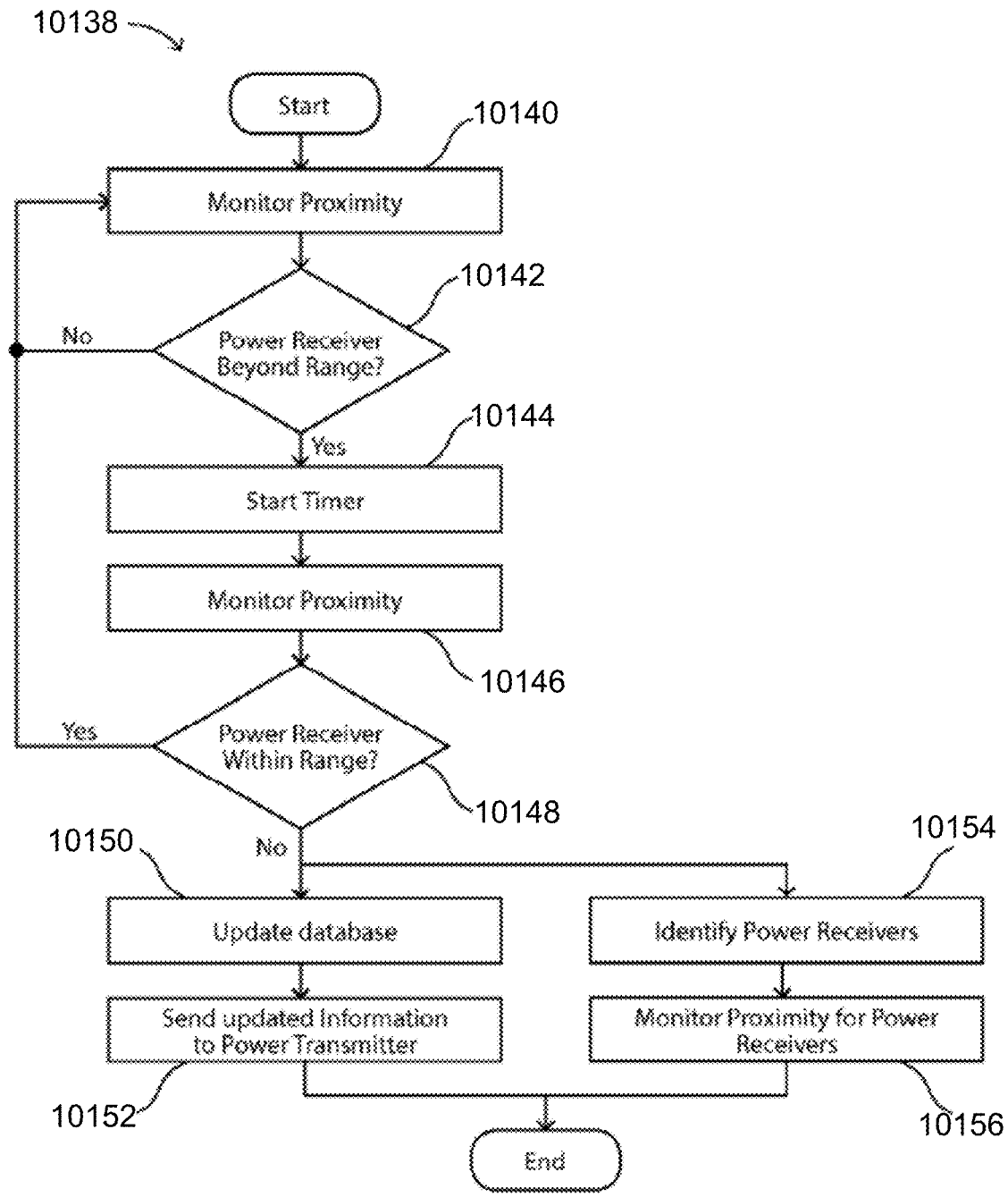

FIGS. 100A-100C illustrate examples of devices, apparatus, and methods for systems and methods for device and power receiver pairing.

FIGS. 101A-101D illustrate examples of devices, apparatus, and methods for home base station for multiple room coverage with multiple transmitters, in accordance with some embodiments.

FIGS. 102A-102K and 103A-103F illustrate examples of devices, apparatus, and methods for cluster management of transmitters in a wireless power transmission system, in accordance with some embodiments.

Figure 104A:
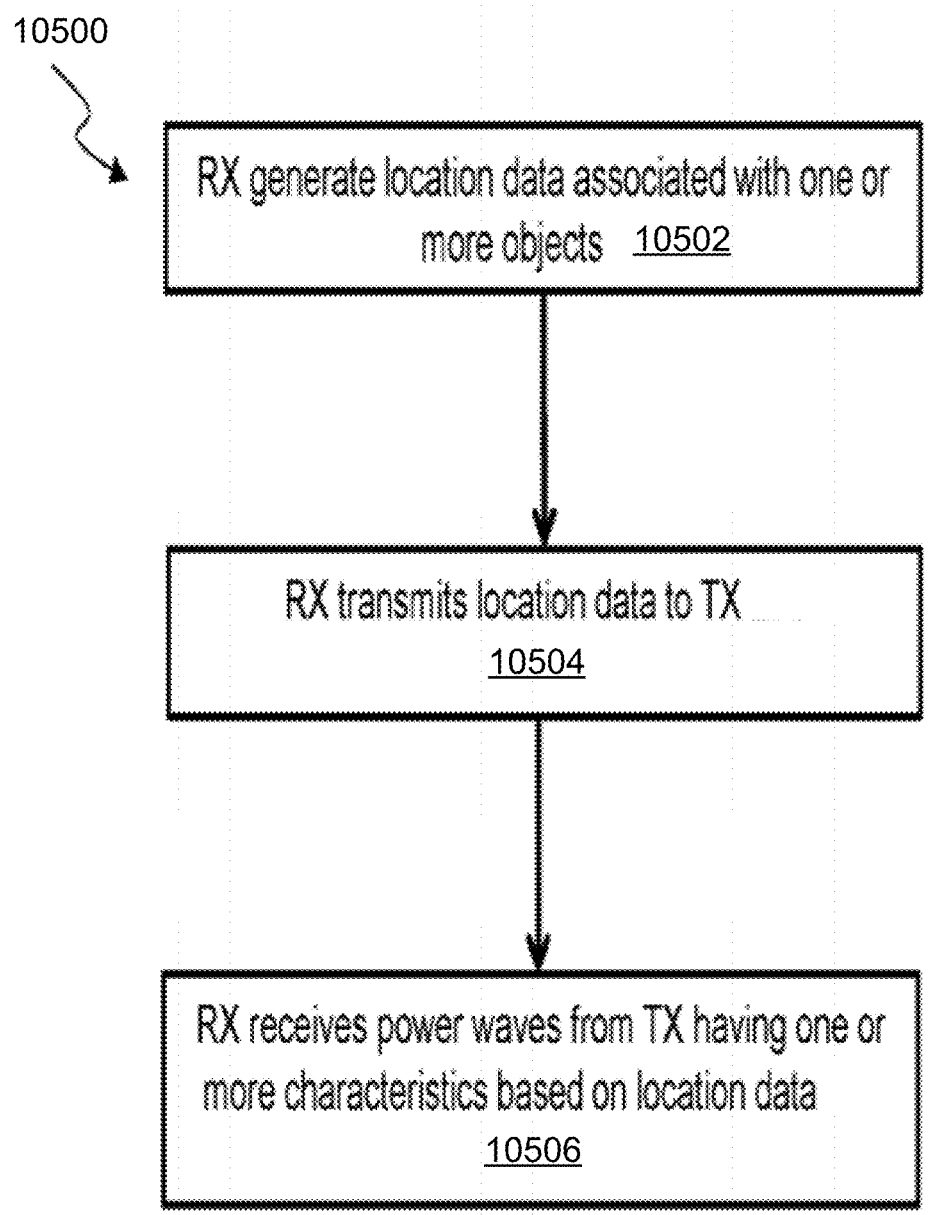
Figure 104B:
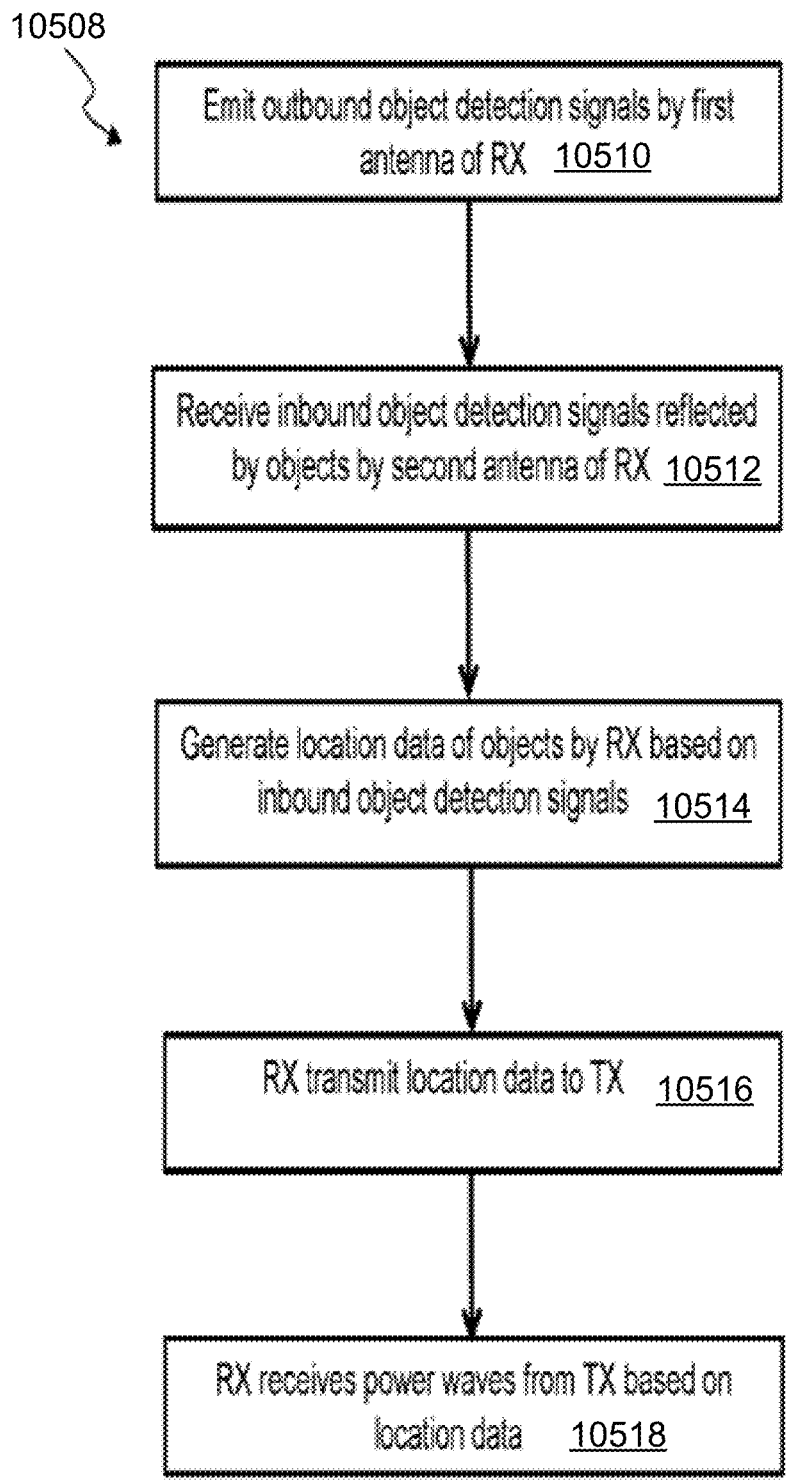

FIGS. 104A-104B illustrate examples of devices, apparatus, and methods for radar motion detection using stepped frequency in wireless power transmission system, in accordance with some embodiments.

FIGS. 105A-105M illustrate examples of devices, apparatus, and methods for systems and methods for wireless power transmission, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as not to unnecessarily obscure pertinent aspects of the embodiments described herein.

As used here, the following terms may have the following definitions:

"Pocket-forming" may refer to generating two or more RF waves which converge in 3-d space, forming controlled constructive and destructive interference patterns.

"Pockets of energy" may refer to areas or regions of space where energy or power may accumulate in the form of constructive interference patterns of RF waves.

"Null-space" may refer to areas or regions of space where pockets of energy do not form because of destructive interference patterns of RF waves.

"Adaptive pocket-forming" may refer to dynamically adjusting pocket-forming to regulate power on one or more targeted receivers.

"FET transistor" refers to a switch used to open or close an analog or digital circuit.

"Delay-locked loop clock" refers to a digital circuit used to change the phase of a clock signal with a periodic waveform to enhance timing characteristics of integrated circuits.

Figure 1:
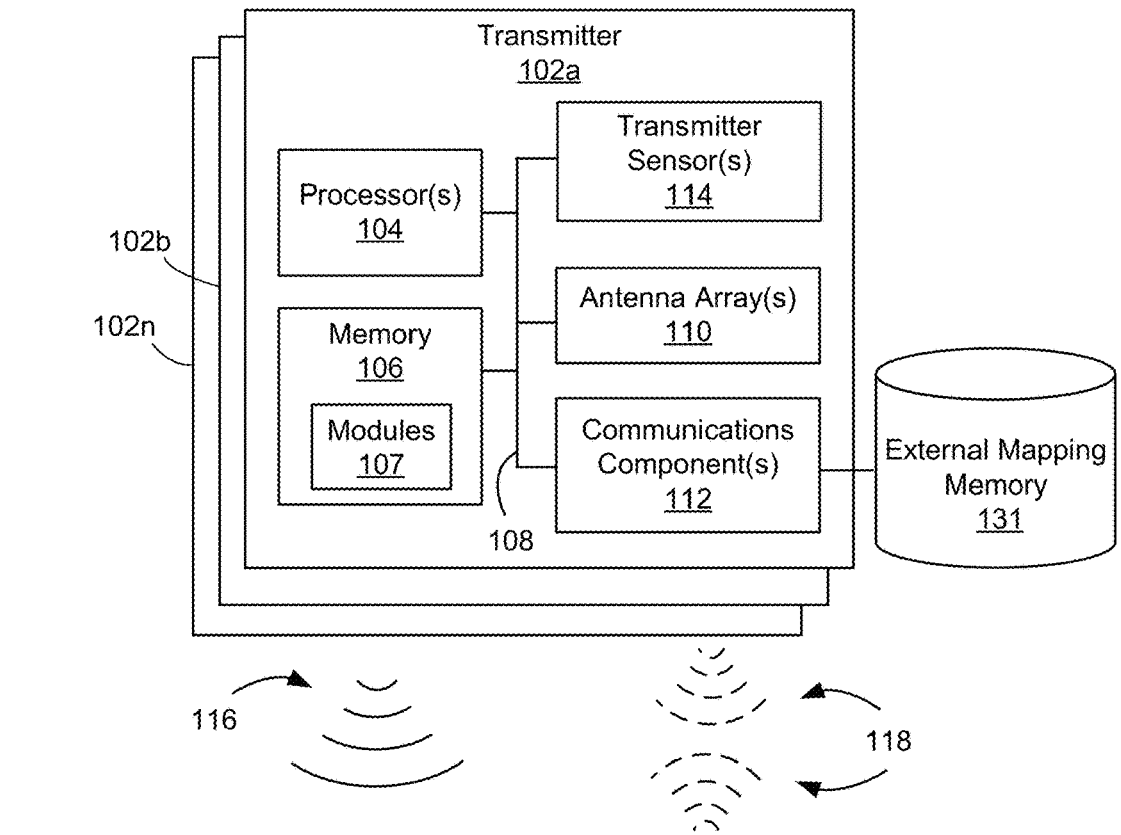
FIG. 1 is a block diagram showing components of a wireless power transmission system, in accordance with some embodiments.
Figure 1:
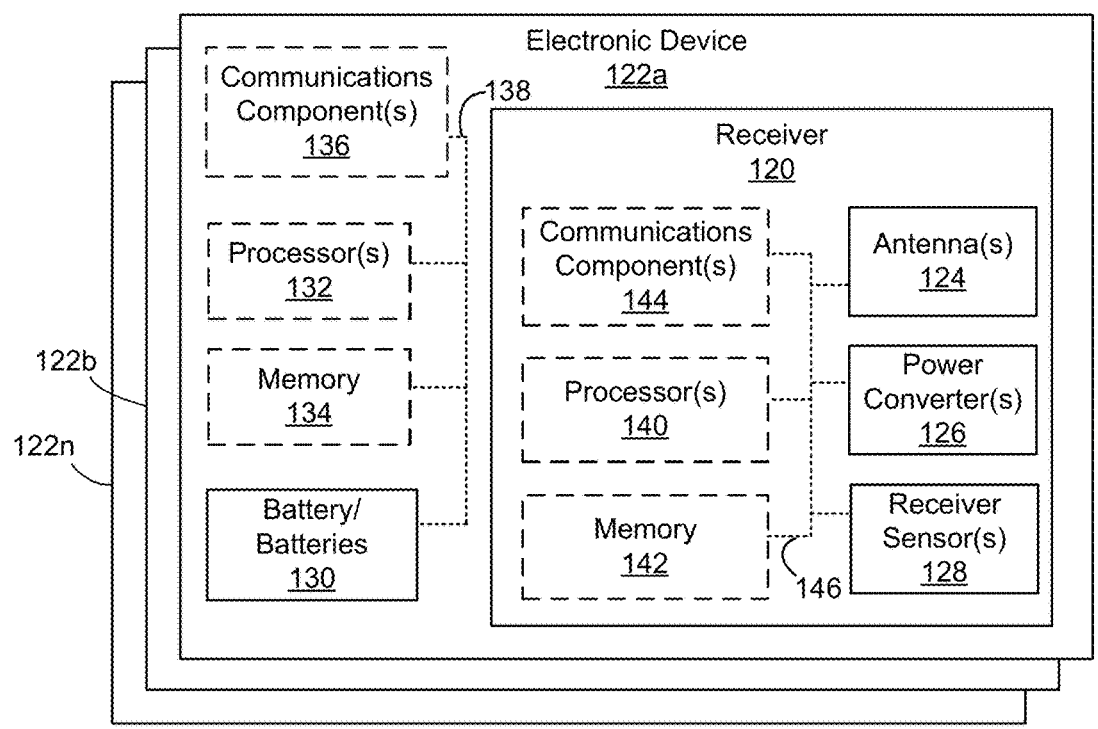

FIG. 1 is a block diagram of components of wireless power transmission environment 100, in accordance with some embodiments. Wireless power transmission environment 100 includes, for example, transmitters 102 (e.g., transmitters 102a, 102b ... 102n) and one or more receivers 120 (e.g., receivers 120a, 120b ... 120n). In some embodiments, each respective wireless power transmission environment 100 includes a number of receivers 120, each of which is associated with a respective electronic device 122.

An example transmitter 102 (e.g., transmitter 102a) includes, for example, one or more processor(s) 104, a memory 106, one or more antenna arrays 110, one or more communications components 112 (also referred to herein as a communications radio), and/or one or more transmitter sensors 114. In some embodiments, these components are interconnected by way of a communications bus 108. References to these components of transmitters 102 cover embodiments in which one or more of these components (and combinations thereof) are included.

In some embodiments, the memory 106 stores one or more programs (e.g., sets of instructions) and/or data structures, collectively referred to as "modules 107" herein. In some embodiments, the memory 106, or the non-transitory computer readable storage medium of the memory 106 stores the following programs, modules, and data structures, or a subset or superset thereof:

information received from receiver 120 (e.g., generated by receiver sensor 128 and then transmitted to the transmitter 102a);
information received from transmitter sensor 114;
an adaptive pocket-forming module that adjusts one or more power waves transmitted by one or more transmitters 102; and/or
a beacon transmitting module that transmits a communication signal 118 for detecting a receiver 120 (e.g., within a transmission field of the transmitter 102).

The above-identified modules (e.g., data structures and/or programs including sets of instructions) need not be implemented as separate software programs, procedures, or modules, and thus various subsets of these modules may be combined or otherwise re-arranged in various embodiments. In some embodiments, the memory 106 stores a subset of the modules identified above. In some embodiments, an external mapping memory 132 that is communicatively connected to communications component 112 stores one or more modules identified above. Furthermore, the memory 106 and/or external mapping memory 132 may store additional modules not described above. In some embodiments, the modules stored in the memory 106, or a non-transitory computer readable storage medium of memory 106, provide instructions for implementing respective operations in the methods described below. In some embodiments, some or all of these modules may be implemented with specialized hardware circuits that subsume part or all of the module functionality. One or more of the above-identified elements may be executed by one or more of processor(s) 104. In some embodiments, one or more of the modules described with regard to the memory 106 is implemented on the memory 104 of a server (not shown) that is communicatively coupled to one or more transmitters 102 and/or by a memory of electronic device 122 and/or receiver 120.

In some embodiments, a single processor 104 (e.g., processor 104 of transmitter 102a) executes software modules for controlling multiple transmitters 102 (e.g., transmitters 102b . . . 102n). In some embodiments, a single transmitter 102 (e.g., transmitter 102a) includes multiple processors 104, such as one or more transmitter processors (configured to, e.g., control transmission of signals 116 by antenna array 110), one or more communications component processors (configured to, e.g., control communications transmitted by communications component 112 and/or receive communications by way of communications component 112) and/or one or more sensor processors (configured to, e.g., control operation of transmitter sensor 114 and/or receive output from transmitter sensor 114).

Wireless power receiver 120 (also referred to as a receiver 120, e.g., a receiver of electronic device 122) receives power transmission signals 116 and/or communications 118 transmitted by transmitters 102. In some embodiments, receiver 120 includes one or more antennas 124 (e.g., an antenna array including multiple antenna elements), power converter 126, receiver sensor 128, and/or other components or circuitry (e.g., processor(s) 140, memory 142, and/or communication component(s) 144). In some embodiments, these components are interconnected by way of a communications bus 146. References to these components of receiver 120 cover embodiments in which one or more of these components (and combinations thereof) are included.

Receiver 120 converts energy from received signals 116 (also referred to herein as RF power transmission signals, or simply, RF signals, RF waves, power waves, or power transmission signals) into electrical energy to power and/or charge electronic device 122. For example, receiver 120 uses power converter 126 to convert captured energy from power waves 116 to alternating current (AC) electricity or direct current (DC) electricity usable to power and/or charge electronic device 122. Non-limiting examples of power converter 126 include rectifiers, rectifying circuits, voltage conditioners, among suitable circuitry and devices.

In some embodiments, receiver 120 is a standalone device that is detachably coupled to one or more electronic devices 122. For example, electronic device 122 has processor(s) 132 for controlling one or more functions of electronic device 122, and receiver 120 has processor(s) 140 for controlling one or more functions of receiver 120.

In some embodiments, receiver 120 is a component of electronic device 122. For example, processor(s) 132 controls functions of electronic device 122 and receiver 120. In addition, in some embodiments, receiver 120 includes processor(s) 140, which communicate(s) with processor(s) 132 of the electronic device 122.

In some embodiments, electronic device 122 includes processor(s) 132, memory 134, communication component(s) 136, and/or battery/batteries 130. In some embodiments, these components are interconnected by way of a communications bus 138. In some embodiments, communications between electronic device 122 and receiver 120 occur via communications component(s) 136 and/or 144. In some embodiments, communications between electronic device 122 and receiver 120 occur via a wired connection between communications bus 138 and communications bus 146. In some embodiments, electronic device 122 and receiver 120 share a single communications bus.

In some embodiments, receiver 120 receives one or more power waves 116 directly from transmitter 102 (e.g., via one or more antennas 124). In some embodiments, receiver 120 harvests power waves from one or more pockets of energy created by one or more power waves 116 transmitted by transmitter 102. In some embodiments, the transmitter 102 is a near-field transmitter that transmits the one or more power waves 116 within a near-field distance (e.g., less than approximately six inches away from the transmitter 102). In some embodiments, the transmitter 102 is a far-field transmitter that transmits the one or more power waves 116 within a far-field distance (e.g., more than approximately six inches to approximately fifteen feet or more away from the transmitter 102).

In some embodiments, after the power waves 116 are received and/or energy is harvested from a pocket of energy, circuitry (e.g., integrated circuits, amplifiers, rectifiers, and/or voltage conditioner) of the receiver 120 converts the energy of the power waves (e.g., radio frequency electromagnetic radiation) to usable power (i.e., electricity), which powers electronic device 122 and/or is stored to battery 130 of electronic device 122. In some embodiments, a rectifying circuit of the receiver 120 translates the electrical energy from AC to DC for use by electronic device 122. In some embodiments, a voltage conditioning circuit increases or decreases the voltage of the electrical energy as required by the electronic device 122. In some embodiments, an electrical relay conveys electrical energy from the receiver 120 to the electronic device 122.

In some embodiments, electronic device 122 obtains power from multiple transmitters 102 and/or using multiple receivers 120. In some embodiments, the wireless power transmission environment 100 includes a plurality of electronic devices 122, each having at least one respective receiver 120 that is used to harvest power waves from the transmitters 102 into usable power for charging the electronic devices 122.

In some embodiments, the one or more transmitters 102 adjust one or more characteristics (e.g., waveform characteristics, such as phase, gain, direction, amplitude, polarization, and/or frequency) of power waves 116. For example, a transmitter 102 selects a subset of one or more antenna elements of antenna array 110 to initiate transmission of power waves 116, cease transmission of power waves 116, and/or adjust one or more characteristics used to transmit power waves 116. In some embodiments, the one or more transmitters 102 adjust power waves 116 such that trajectories of power waves 116 converge at a predetermined location within a transmission field (e.g., a location or region in space), resulting in controlled constructive or destructive interference patterns. The transmitter 102 may adjust sets of characteristics for transmitting the power waves 116 to account for changes at the wireless power receiver that may negatively impact transmission of the power waves 116.

In some embodiments, respective antenna arrays 110 of the one or more transmitters 102 may include antennas having one or more polarizations. For example, a respective antenna array 110 may include vertical or horizontal polarization, right hand or left hand circular polarization, elliptical polarization, or other polarizations, as well as any number of polarization combinations. In some embodiments, antenna array 110 is capable of dynamically varying the antenna polarization (or any other characteristic) to optimize wireless power transmission.

In some embodiments, respective antenna arrays 110 of the one or more transmitters 102 may include a set of one or more antennas configured to transmit the power waves 116 into respective transmission fields of the one or more transmitters 102. Integrated circuits (not shown) of the respective transmitter 102, such as a controller circuit (e.g., a radio frequency integrated circuit (RFIC)) and/or waveform generator, may control the behavior of the antennas. For example, based on the information received from the receiver by way of the communication signal 118, a controller circuit (e.g., processor 104 of the transmitter 102, FIG. 1) may determine a set of one or more waveform characteristics (e.g., amplitude, frequency, trajectory, direction, phase, polarization, among other characteristics) used for transmitting the power waves 116 that would effectively provide power to the receiver 102 and electronic device 122. The controller circuit may also identify a subset of antennas from the antenna arrays 110 that would be effective in transmitting the power waves 116. In some embodiments, a waveform generator circuit (not shown in FIG. 1) of the respective transmitter 102 coupled to the processor 104 may convert energy and generate the power waves 116 having the waveform characteristics identified by the processor 104/ controller circuit, and then provide the power waves to the antenna arrays 110 for transmission.

In some embodiments, constructive interference of power waves occurs when two or more power waves 116 (e.g., RF power transmission signals) are in phase with each other and converge into a combined wave such that an amplitude of the combined wave is greater than amplitude of a single one of the power waves. For example, the positive and negative peaks of sinusoidal waveforms arriving at a location from multiple antennas "add together" to create larger positive and negative peaks. In some embodiments, a pocket of energy is formed at a location in a transmission field where constructive interference of power waves occurs.

In some embodiments, destructive interference of power waves occurs when two or more power waves are out of phase and converge into a combined wave such that the amplitude of the combined wave is less than the amplitude of a single one of the power waves. For example, the power waves "cancel each other out," thereby diminishing the amount of energy concentrated at a location in the transmission field. In some embodiments, destructive interference is used to generate a negligible amount of energy or "null" at a location within the transmission field where the power waves converge.

In some embodiments, the one or more transmitters 102 transmit power waves 116 that create two or more discrete transmission fields (e.g., overlapping and/or non-overlapping discrete transmission fields). In some embodiments, a first transmission field (i.e., an area of physical space into which a first set of power waves is transmitted) is managed by a first processor 104 of a first transmitter (e.g., transmitter 102a) and a second transmission field (i.e., another area of physical space into which a second set of power waves is transmitted) is managed by a second processor 104 of a second transmitter (e.g., transmitter 102b). In some embodiments, the two or more discrete transmission fields (e.g., overlapping and/or non-overlapping) are managed by the transmitter processors 104 as a single transmission field. Moreover, in some embodiments, a single processor 104 manages the first and second transmission fields.

In some embodiments, communications component 112 transmits communication signals 118 by way of a wired and/or wireless communication connection to receiver 120. In some embodiments, communications component 112 generates communication signals 118 used for triangulation of receiver 120. In some embodiments, communication signals 118 are used to convey information between transmitter 102 and receiver 120 for adjusting one or more characteristics used to transmit the power waves 116. In some embodiments, communication signals 118 include information related to status, efficiency, user data, power consumption, billing, geo-location, and other types of information.

In some embodiments, communications component 112 transmits communication signals 118 to receiver 120 by way of the electronic device 122a. For example, communications component 112 may convey information to communications component 136 of the electronic device 122a, which the electronic device 122a may in turn convey to the receiver 120 (e.g., via bus 138).

In some embodiments, communications component 112 includes a communications component antenna for communicating with receiver 120 and/or other transmitters 102 (e.g., transmitters 102b through 102n). In some embodiments, these communication signals 118 are sent using a first channel (e.g., a first frequency band) that is independent and distinct from a second channel (e.g., a second frequency band distinct from the first frequency band) used for transmission of the power waves 116.

In some embodiments, the receiver 120 includes a receiver-side communications component 144 (also referred to herein as a communications radio) configured to communicate various types of data with one or more of the transmitters 102, through a respective communication signal 118 generated by the receiver-side communications component (in some embodiments, a respective communication signal 118 is referred to as an advertising signal). The data may include location indicators for the receiver 102 and/or electronic device 122, a power status of the device 122, status information for the receiver 102, status information for the electronic device 122, status information about the power waves 116, and/or status information for pockets of energy. In other words, the receiver 120 may provide data to the transmitter 102, by way of the communication signal 118, regarding the current operation of the system 100, including: information identifying a present location of the receiver 120 or the device 122, an amount of energy (i.e., usable power) received by the receiver 120, and an amount of usable power received and/or used by the electronic device 122, among other possible data points containing other types of information.

In some embodiments, the data contained within communication signals 118 is used by electronic device 122, receiver 120, and/or transmitters 102 for determining adjustments of the one or more characteristics used by the antenna array 110 to transmit the power waves 116. Using a communication signal 118, the transmitter 102 communicates data that is used, e.g., to identify receivers 120 within a transmission field, identify electronic devices 122, determine safe and effective waveform characteristics for power waves, and/or hone the placement of pockets of energy. In some embodiments, receiver 120 uses a communication signal 118 to communicate data for, e.g., alerting transmitters 102 that the receiver 120 has entered or is about to enter a transmission field, provide information about electronic device 122, provide user information that corresponds to electronic device 122, indicate the effectiveness of received power waves 116, and/or provide updated characteristics or transmission parameters that the one or more transmitters 102 use to adjust transmission of the power waves 116.

In some embodiments, transmitter sensor 114 and/or receiver sensor 128 detect and/or identify conditions of electronic device 122, receiver 120, transmitter 102, and/or a transmission field. In some embodiments, data generated by transmitter sensor 114 and/or receiver sensor 128 is used by transmitter 102 to determine appropriate adjustments to the one or more characteristics used to transmit the power waves 116. Data from transmitter sensor 114 and/or receiver sensor 128 received by transmitter 102 includes, e.g., raw sensor data and/or sensor data processed by a processor 104, such as a sensor processor. Processed sensor data includes, e.g., determinations based upon sensor data output. In some embodiments, sensor data received from sensors that are external to the receiver 120 and the transmitters 102 is also used (such as thermal imaging data, information from optical sensors, and others).

In some embodiments, receiver sensor 128 is a gyroscope that provides raw data such as orientation data (e.g., tri-axial orientation data), and processing this raw data may include determining a location of receiver 120 and/or a location of receiver antenna 124 using the orientation data.

In some embodiments, receiver sensor 128 includes one or more infrared sensors (e.g., that output thermal imaging information), and processing this infrared sensor data includes identifying a person (e.g., indicating presence of the person and/or indicating an identification of the person) or other sensitive object based upon the thermal imaging information.

In some embodiments, receiver sensor 128 includes a gyroscope and/or an accelerometer that indicates an orientation of receiver 120 and/or electronic device 122. As one example, transmitters 102 receive orientation information from receiver sensor 128 and the transmitters 102 (or a component thereof, such as the processor 104) use the received orientation information to determine whether electronic device 122 is flat on a table, in motion, and/or in use (e.g., next to a user's head).

In some embodiments, receiver sensor 128 is a sensor of electronic device 122 (e.g., an electronic device 122 that is remote from receiver 102). In some embodiments, receiver 120 and/or electronic device 122 includes a communication system for transmitting signals (e.g., sensor signals output by receiver sensor 128) to transmitter 102.

Non-limiting examples of transmitter sensor 114 and/or receiver sensor 128 include, e.g., infrared, pyroelectric, ultrasonic, laser, optical, Doppler, gyro, accelerometer, microwave, millimeter, RF standing-wave sensors, resonant LC sensors, capacitive sensors, and/or inductive sensors. In some embodiments, technologies for transmitter sensor 114 and/or receiver sensor 128 include binary sensors that acquire stereoscopic sensor data, such as the location of a human or other sensitive object.

In some embodiments, transmitter sensor 114 and/or receiver sensor 128 is configured for human recognition (e.g., capable of distinguishing between a person and other objects, such as furniture). Examples of sensor data output by human recognition-enabled sensors include: body temperature data, infrared range-finder data, motion data, activity recognition data, silhouette detection and recognition data, gesture data, heart rate data, portable devices data, and wearable device data (e.g., biometric readings and output, accelerometer data).

In some embodiments, transmitters 102 adjust one or more characteristics used to transmit the power waves 116 to ensure compliance with electromagnetic field (EMF) exposure protection standards for human subjects. Maximum exposure limits are defined by US and European standards in terms of power density limits and electric field limits (as well as magnetic field limits). These include, for example, limits established by the Federal Communications Commission (FCC) for maximum permissible exposure (MPE), and limits established by European regulators for radiation exposure. Limits established by the FCC for MPE are codified at 47 C.F.R. § 1.1310. For electromagnetic field (EMF) frequencies in the microwave range, power density can be used to express an intensity of exposure. Power density is defined as power per unit area. For example, power density can be commonly expressed in terms of watts per square meter ($W/m^2$), milliwatts per square centimeter ($mW/cm^2$), or microwatts per square centimeter ($\mu W/cm^2$). In some embodiments, output from transmitter sensor 114 and/or receiver sensor 128 is used by transmitter 102 to detect whether a person or other sensitive object enters a power transmission region (e.g., a location within a predetermined distance of a transmitter 102, power waves generated by transmitter 102, and/or a pocket of energy). In some embodiments, in response to detecting that a person or other sensitive object has entered the power transmission region, the transmitter 102 adjusts one or more power waves 116 (e.g., by ceasing power wave transmission, reducing power wave transmission, and/or adjusting the one or more characteristics of the power waves). In some embodiments, in response to detecting that a person or other sensitive object has entered the power transmission region, the transmitter 102 activates an alarm (e.g., by transmitting a signal to a loudspeaker that is a component of transmitter 102 or to an alarm device that is remote from transmitter 102). In some embodiments, in response to detecting that a person or other sensitive object has entered a power transmission region, the transmitter 102 transmits a digital message to a system log or administrative computing device. These techniques for ensuring compliance with EMF exposure standards.

In some embodiments, antenna array 110 includes multiple antenna elements (e.g., configurable "tiles") collectively forming an antenna array. Antenna array 110 generates power transmission signals, e.g., RF power waves, ultrasonic power waves, infrared power waves, and/or magnetic resonance power waves. In some embodiments, the antennas of an antenna array 110 (e.g., of a single transmitter, such as transmitter 102*a*, and/or of multiple transmitters, such as transmitters 102*a*, 102*b*, . . . , 102*n*) transmit two or more power waves that intersect at a defined location (e.g., a location corresponding to a detected location of a receiver 120), thereby forming a pocket of energy (e.g., a concentration of energy) at the defined location.

In some embodiments, transmitter 102 assigns a first task to a first subset of antenna elements of antenna array 110, a second task to a second subset of antenna elements of antenna array 110, and so on, such that the constituent antennas of antenna array 110 perform different tasks (e.g., determining locations of previously undetected receivers 120 and/or transmitting power waves 116 to one or more receivers 120). As one example, in an antenna array 110 with ten antennas, nine antennas transmit power waves 116 that form a pocket of energy and the tenth antenna operates in conjunction with communications component 112 to identify new receivers in the transmission field. In another example, an antenna array 110 having ten antenna elements is split into two groups of five antenna elements, each of which transmits power waves 116 to two different receivers 120 in the transmission field.

Figure 4A:
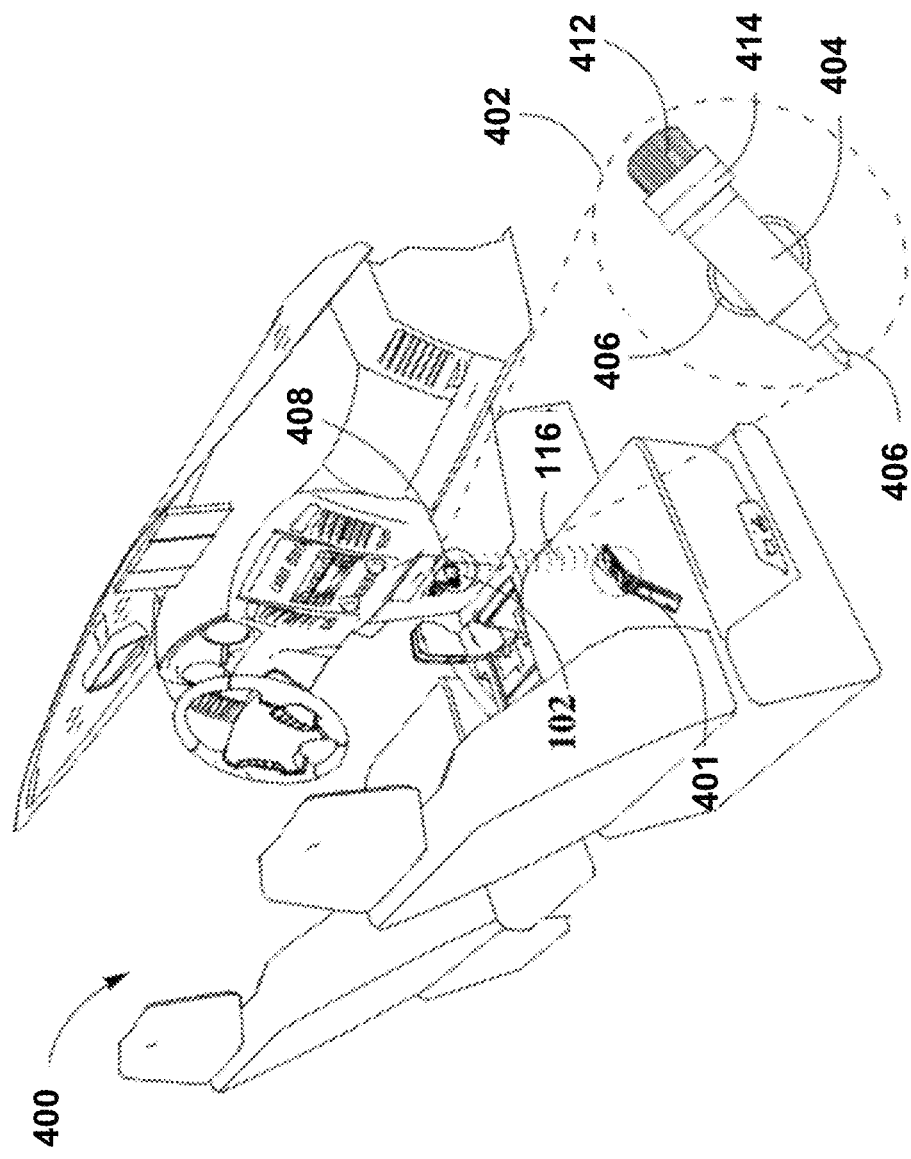
FIG. 4A illustrates a wireless power transmission system used for charging or powering one or more electronic devices inside a vehicle, in accordance with some embodiments.
Figure 4B:
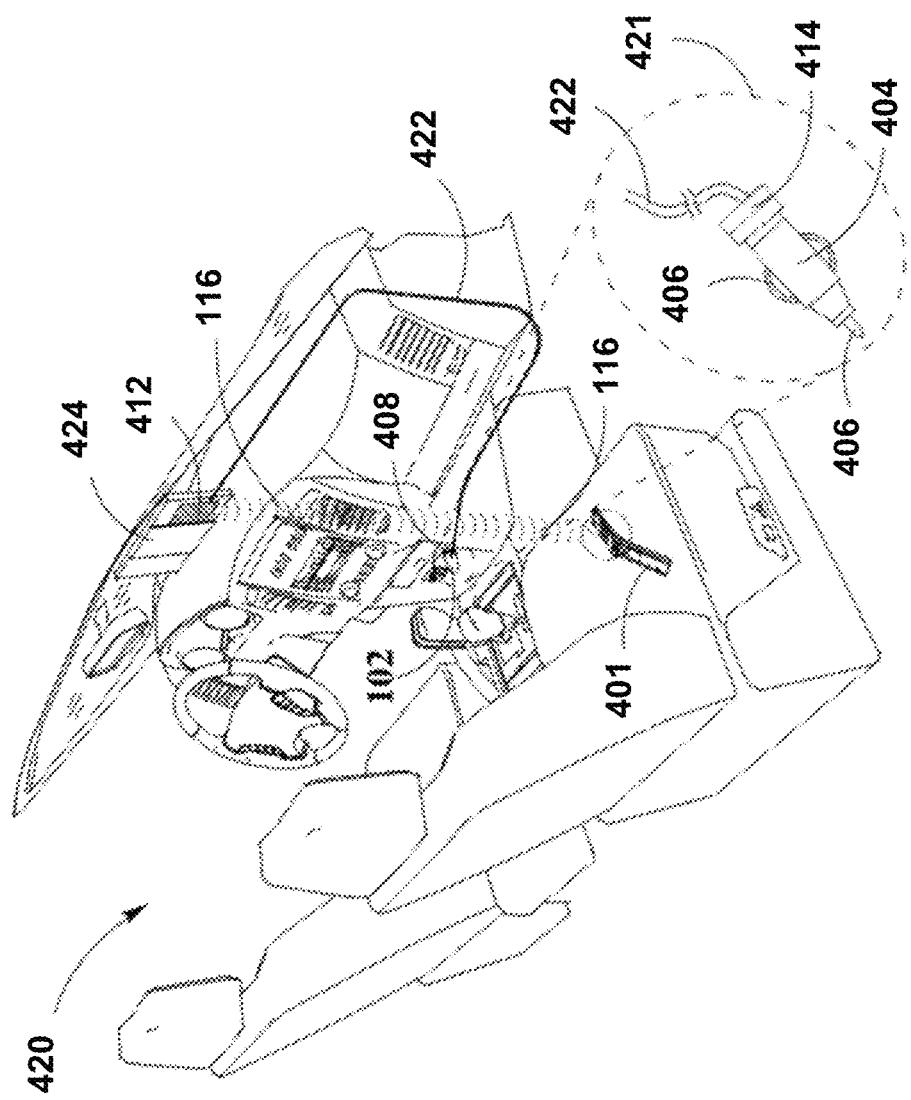
FIG. 4B illustrates a wireless power transmission system used for charging or powering one or more electronic devices inside a vehicle, in accordance with some embodiments.
Figure 4C:
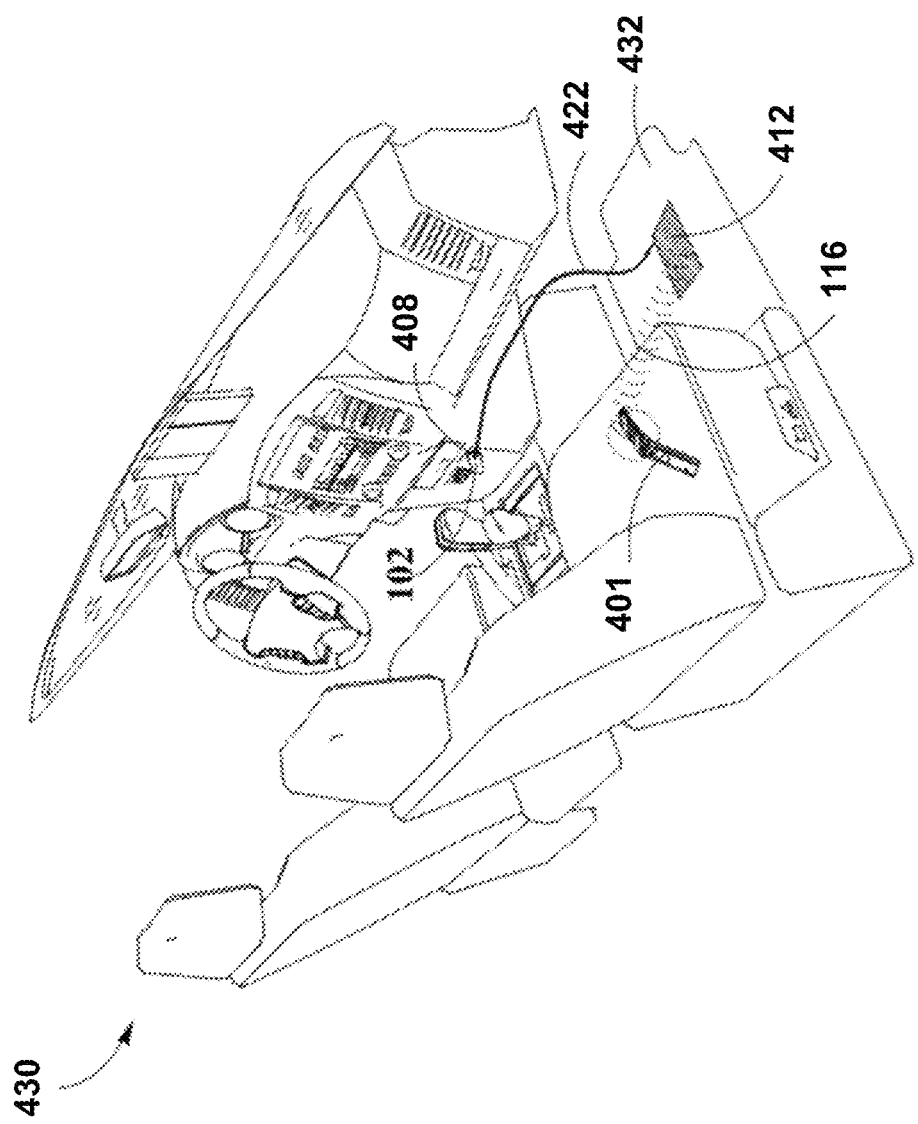
FIG. 4C illustrates a wireless power transmission system used for charging or powering one or more electronic devices inside a vehicle, in accordance with some embodiments.
Figure 6A:
FIGS. 6A-6C illustrate wireless power transmission systems, including a toolbox with an embedded transmitter, used for providing power to cordless power tools, in accordance with some embodiments.
Figure 6B:
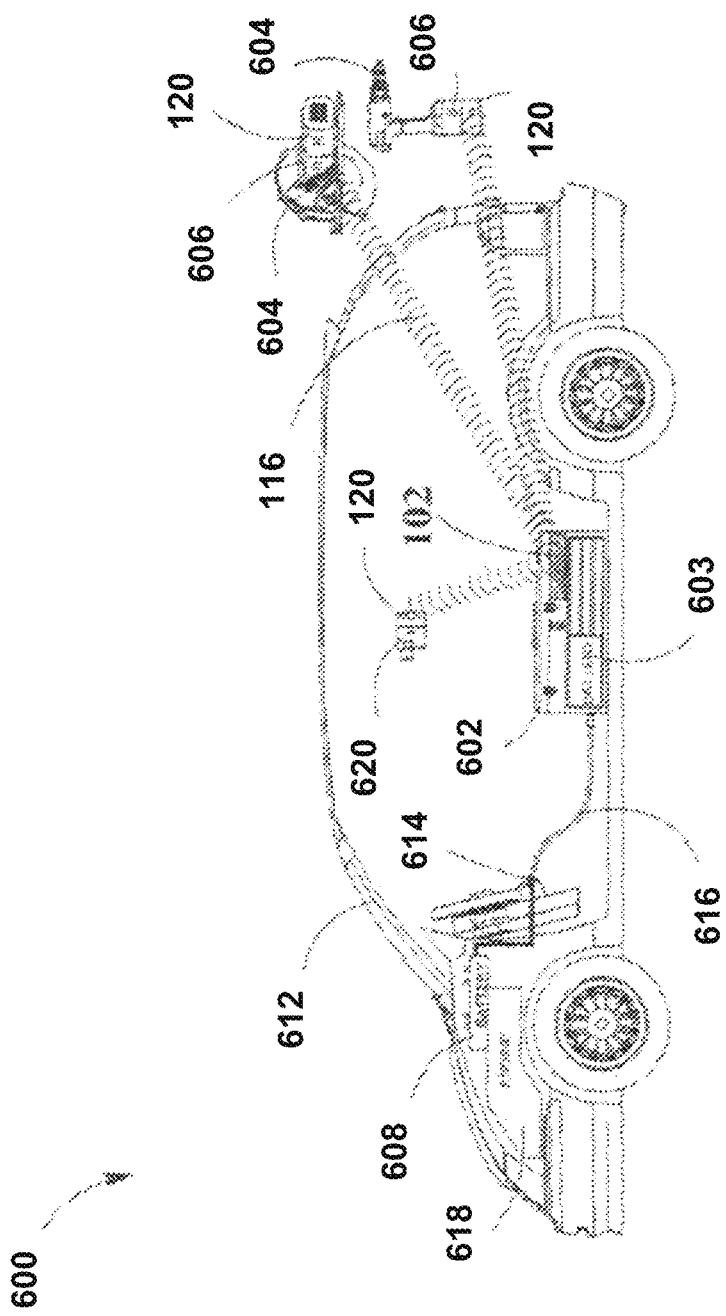

Various embodiments of the transmitter 102 are illustrated and described herein. For example, an embodiment of the transmitter 102 is connected to a power source inside a vehicle (e.g., as shown in FIGS. 4A-4C and described below), another embodiment of the transmitter 102 is embedded in a toolbox (e.g., as shown in FIGS. 6A-6B and described below), and another embodiment of the transmitter 102 is placed on a police vehicle (e.g., as shown in FIGS. 11B-11D and described below). Various other examples are provided below.

Figure 6C:
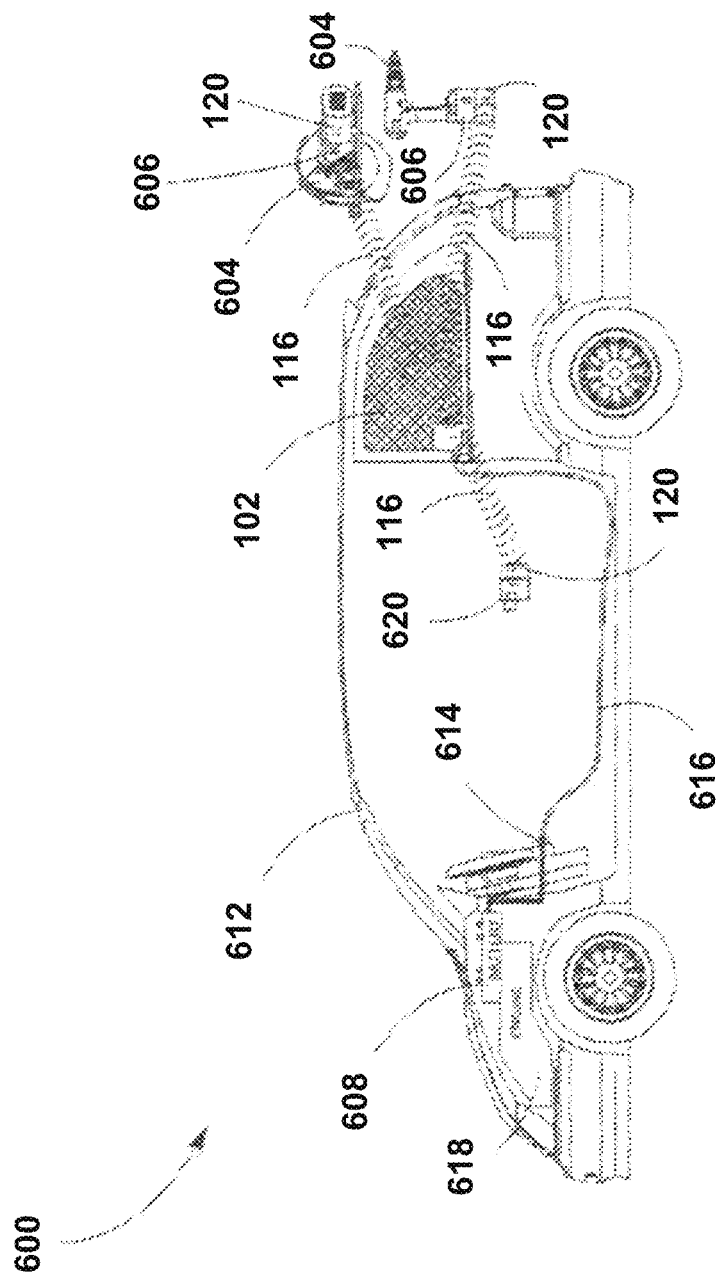
Figure 10A:
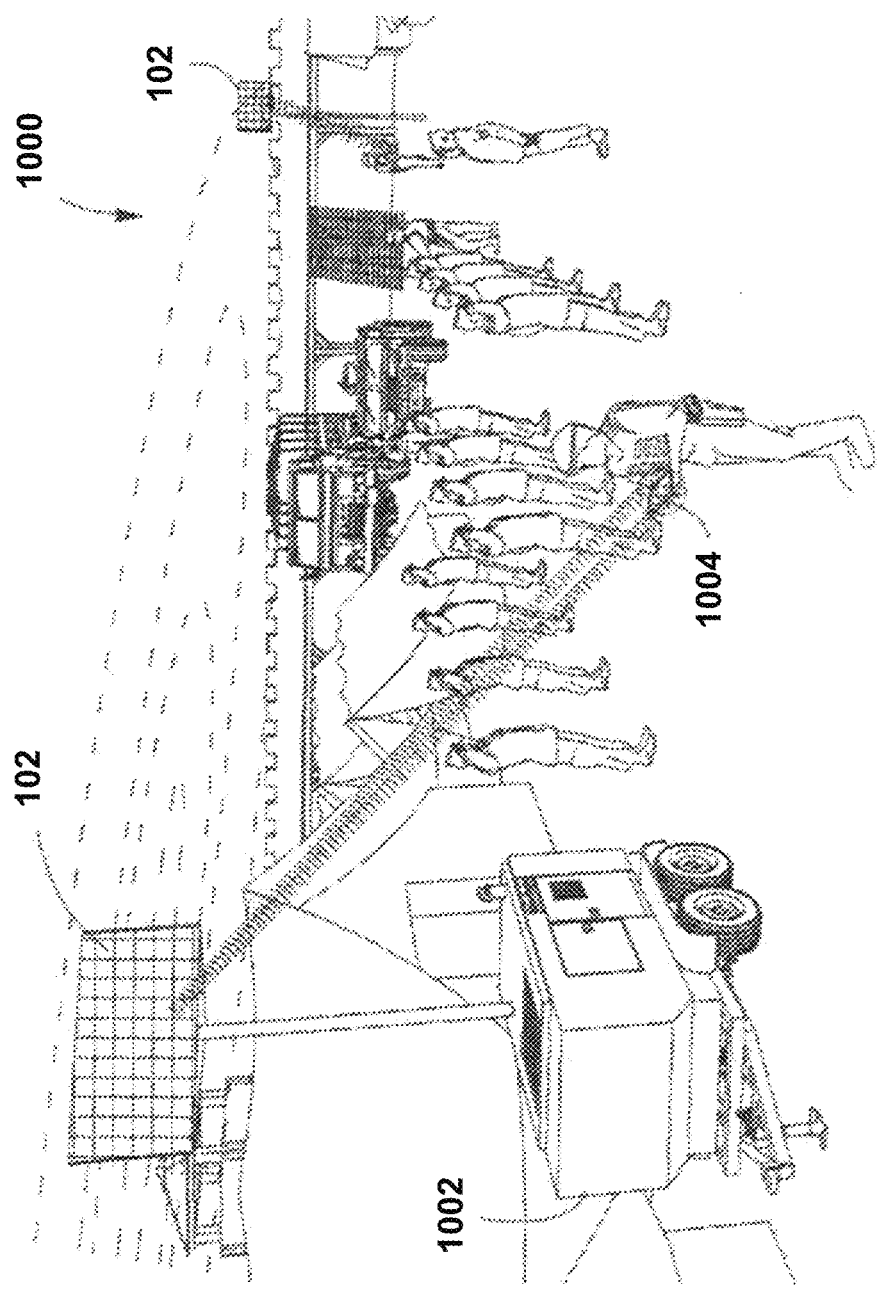
FIGS. 10A-10C illustrate wireless power transmission systems used in military applications, in accordance with some embodiments.
Figure 10B:
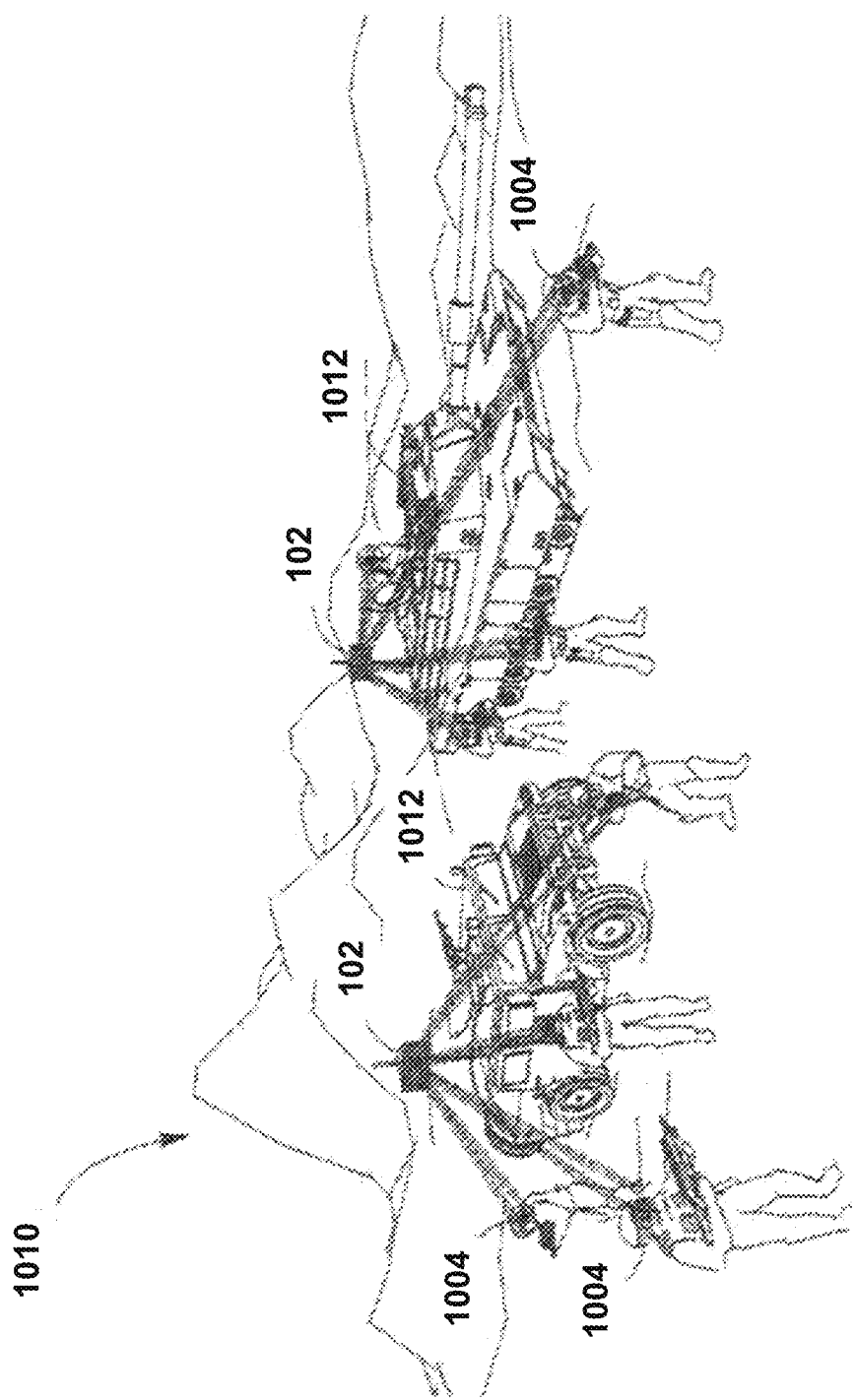
Figure 18C:
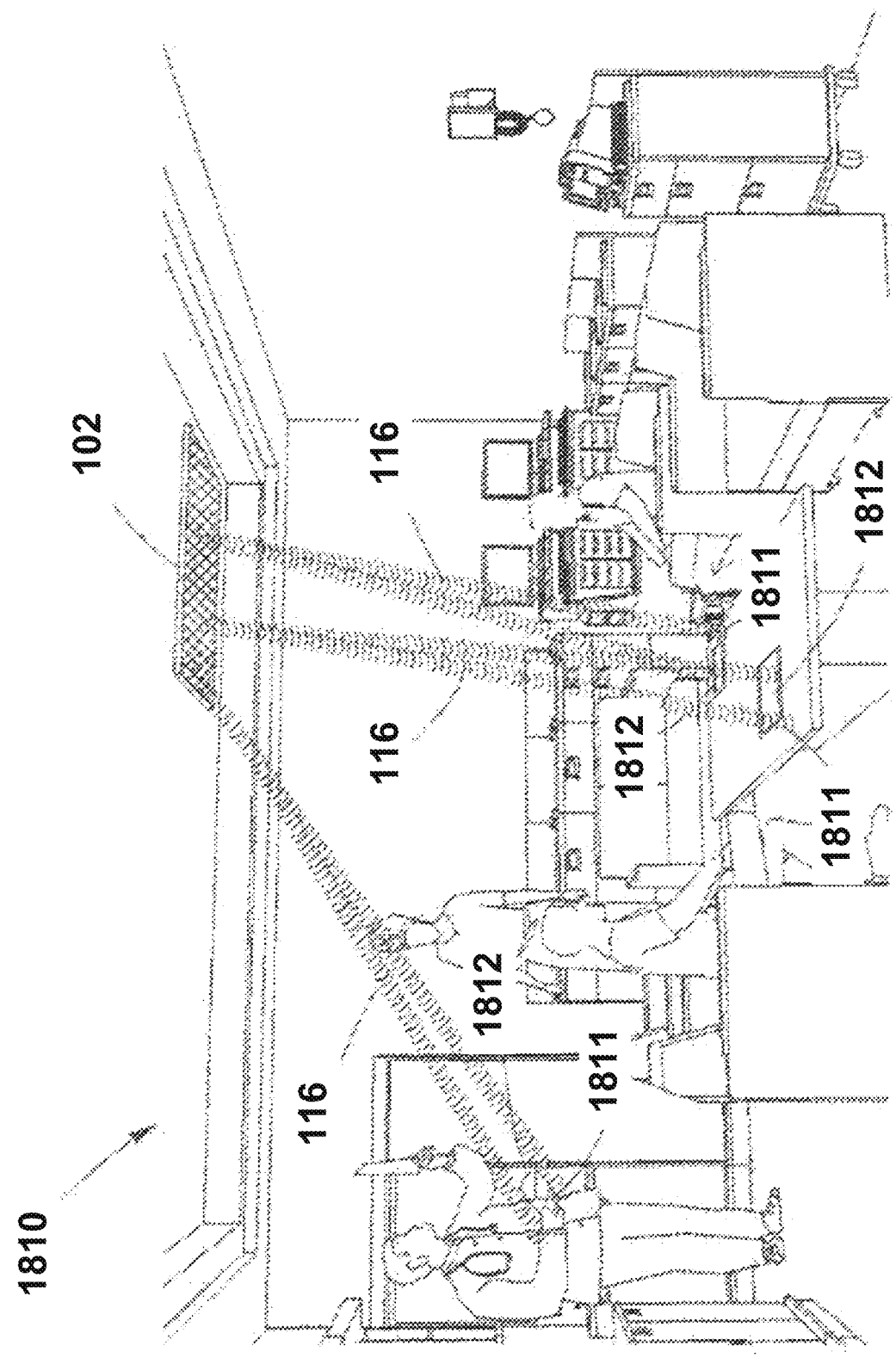
FIGS. 18C-18E are illustrations of wireless power transmission systems for wirelessly delivering power to medical devices, in accordance with some embodiments.

Various embodiments of the receiver 120 are also illustrated and described herein. For example, an embodiment of the receiver 120 is connected to a wireless power tool (e.g., as shown in FIGS. 6A-6C and described below), another embodiment of the receiver 120 is embedded in a military uniform (e.g., as shown in FIGS. 10A-10B and described below), and yet another embodiment of the receiver 120 is embedded in medical devices (e.g., as shown in FIGS. 18A-18C and described below). Various other examples are provided below.

Figure 2:
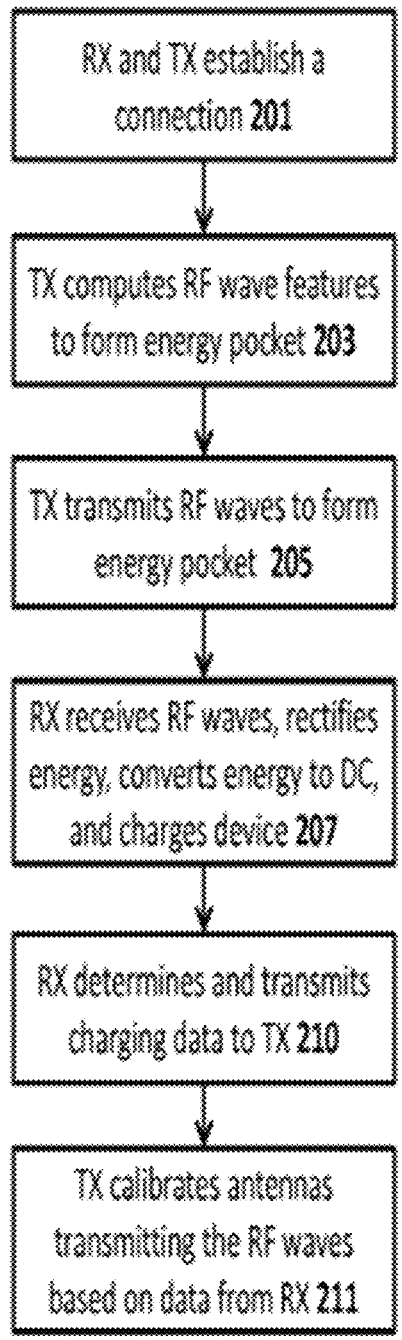
FIG. 2 illustrates steps of wireless power transmission, in accordance with some embodiments.

FIG. 2 provides an example flowchart of a process for wireless power transmission, in accordance with some embodiments.

In a first step 201, a transmitter 102 (TX) establishes a connection or otherwise associates with a receiver 120 (RX). That is, in some embodiments, transmitters and receivers may communicate with one another over a wireless communication protocol capable of transmitting information between two processors of electrical devices (e.g., BLUETOOTH, BLUETOOTH Low Energy (BLE), WI-FI, NFC, ZIGBEE). For example, in embodiments implementing BLUETOOTH or BLUETOOTH variants, the transmitter may scan for receivers broadcasting advertisement signals or a receiver may transmit an advertisement signal to the transmitter. The advertisement signal may announce the receiver's presence to the transmitter, and may trigger an association between the transmitter and the receiver. As described herein, in some embodiments, the advertisement signal may communicate information that may be used by various devices (e.g., transmitters, client devices, server computers, other receivers) to execute and manage pocket-forming procedures. Information contained within the advertisement signal may include a device identifier (e.g., MAC address, IP address, UUID), the voltage of electrical energy received, client device power consumption, and other types of data related to power transmission. The transmitter may use the advertisement signal transmitted to identify the receiver and, in some cases, locate the receiver in a two-dimensional space or in a three-dimensional space. Once the transmitter identifies the receiver, the transmitter may establish the connection associated in the transmitter with the receiver, allowing the transmitter and receiver to communicate control signals over a second channel. The advertising signal is an example of the communication signal 118 (FIG. 1).

In a next step 203, the transmitter may use the advertisement signal to determine waveform characteristics (discussed above) for transmitting the power transmission signals, to then establish the pockets of energy. The transmitter may use information contained in the receiver's advertisement signal, or in subsequent control/feedback signals received from the receiver, to determine how to produce and transmit the power transmission signals so that the receiver may receive the power transmission signals. In some cases, the transmitter may transmit power transmission signals in a way that establishes a pocket of energy, from which the receiver may harvest electrical energy. In some embodiments, the transmitter may include a processor 104 executing software modules capable of automatically identifying the power transmission signal features needed to establish a pocket of energy based on information received from the receiver, such as the voltage of the electrical energy harvested by the receiver from the power transmission signals. It should be appreciated that in some embodiments, the functions of the processor and/or the software modules may be implemented in an Application Specific Integrated Circuit (ASIC).

Additionally or alternatively, in some embodiments, the advertisement signal or a subsequent signal transmitted by the receiver over a second communications channel may indicate one or more waveform characteristics (also referred to herein as power transmission signals features), which the transmitter may then use to produce and transmit power transmission signals to establish a pocket of energy. For example, in some cases the transmitter may automatically identify the phase and gain necessary for transmitting the power transmission signals based on the location of the device and the type of device or receiver; and, in some cases, the receiver may inform the transmitter of the phase and gain for effectively transmitting the power transmission signals.

In a next step 205, after the transmitter determines the appropriate waveform characteristics to use when transmitting the power transmission signals, the transmitter may begin transmitting power transmission signals, over a separate channel from the signals (e.g., power waves 116 are distinct from the communication signals 118, FIG. 1). Power transmission signals may be transmitted to establish a pocket of energy. The transmitter's antenna elements may transmit the power transmission signals such that the power transmission signals converge in a two-dimensional or three-dimensional space around the receiver. The resulting field around the receiver forms a pocket of energy from which the receiver may harvest electrical energy. One antenna element may be used to transmit power transmission signals to establish two-dimensional energy transmissions; and in some cases, a second or additional antenna element may be used to transmit power transmission signals in order to establish a three-dimensional pocket of energy. In some cases, a plurality of antenna elements may be used to transmit power transmission signals in order to establish the pocket of energy. Moreover, in some cases, the plurality of antennas may include all of the antennas in the transmitter; and, in some cases, the plurality of antennas may include a number of the antennas in the transmitter, but fewer than all of the antennas of the transmitter. Various techniques for transmitting power transmission signals are discussed in further detail above with reference to FIG. 1.

As previously mentioned, the transmitter 102 may produce and transmit power transmission signals, according to a determined set of power transmission signal features. In some embodiments, the power transmission signals are produced and transmitted using an external power source and a local oscillator chip comprising a piezoelectric material. The transmitter may include a controller circuit (e.g., an RFIC) that controls production and transmission of the power transmission signals based on information related to power transmission and pocket-forming received from the receiver. This control data may be communicated over a different channel from the power transmission signals, using wireless communications protocols, such as BLE, NFC, or ZIGBEE®. The RFIC of the transmitter may automatically adjust the phase and/or relative magnitudes of the power transmission signals as needed. Pocket-forming is accomplished by the transmitter transmitting the power transmission signals in a manner that forms constructive interference patterns.

In a next step 207, the receiver may harvest or otherwise receive electrical energy from the power transmission signals of a single beam or a pocket of energy. The receiver may include a rectifier and AC/DC converter (e.g., power converters 126, FIG. 1), which may convert the electrical energy from AC current to DC current, and the rectifier of the receiver may then rectify the electrical energy, resulting in useable electrical energy for a client device associated with the receiver, such as a laptop computer, smartphone, battery, toy, or other electrical device. The receiver may utilize the pocket of energy produced by the transmitter during pocket-forming to charge or otherwise power the electronic device. Receiving the power transmission signals is discussed in further detail above with reference to FIG. 1.

In next step 210, the receiver may generate data containing information indicating the effectiveness of the single beam or energy pockets providing the receiver power transmission signals. The receiver may then transmit control/feedback signals containing the data to the transmitter. The control/feedback signal is an example of the communication signals 118. The control signals may be transmitted intermittently, depending on whether the transmitter and receiver are communicating synchronously (i.e., the transmitter is expecting to receive control data from the receiver). Additionally, the transmitter may continuously transmit the power transmission signals to the receiver, irrespective of whether the transmitter and receiver are communicating control signals. The data may contain information related to transmitting power transmission signals and/or establishing effective pockets of energy. Some of the information in the control data may inform the transmitter how to effectively produce and transmit, and in some cases adjust, the features of the power transmission signals. The control signals may be transmitted and received over a second channel, independent from the power transmission signals, using a wireless protocol capable of transmitting control data related to power transmission signals and/or pocket-forming, such as BLE, NFC, WI-FI, or the like.

As mentioned, the data may contain information indicating the effectiveness of the power transmission signals of the single beam or establishing the pocket of energy. The data may be generated by a processor of the receiver monitoring various aspects of the receiver and/or the client device associated with the receiver. The data may be based on various types of information, such as the voltage of electrical energy received from the power transmission signals, the quality of the power transmission signals reception, the quality of the battery charge or quality of the power reception, and location or motion of the receiver, among other types of information useful for adjusting the power transmission signals and/or pocket-forming.

In some embodiments, a receiver may determine the amount of power being received from power transmission signals transmitted from the transmitter and may then indicate that the transmitter should "split" or segment the power transmission signals into less-powerful power transmission signals. The less-powerful power transmission signals may be bounced off objects or walls nearby the device, thereby reducing the amount of power being transmitted directly from the transmitter to the receiver.

In a next step 211, the transmitter may calibrate the antennas transmitting the power transmission signals, so that the antennas transmit power transmission signals having a more effective set of features (e.g., direction, phase, gain, amplitude). In some embodiments, a processor of the transmitter may automatically determine more effective features for producing and transmitting the power transmission signals based on the signal(s) received from the receiver. The transmitter may then automatically reconfigure the antennas to transmit recalibrated power transmission signals according to the newly determined more-effective features. For example, the processor of the transmitter may adjust gain and/or phase of the power transmission signals, among other features of power transmission feature, to adjust for a change in location of the receiver, after a user moved the receiver outside of the three-dimensional space where the pocket of energy is established.

Figure 3:
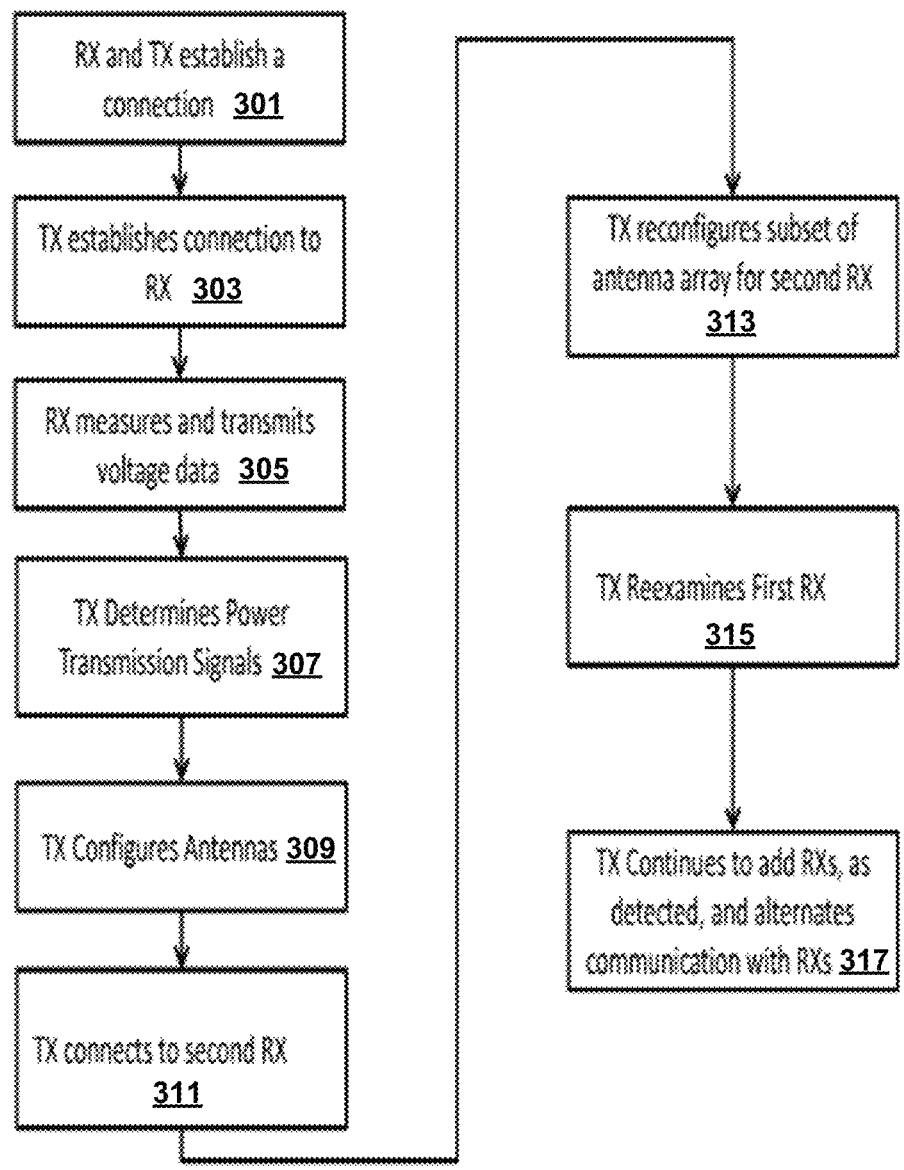
FIG. 3 illustrates steps of powering a plurality of receiver devices, in accordance with some embodiments.

FIG. 3 provides an example flowchart of a process for wirelessly powering a plurality of receivers, in accordance with some embodiments. For the sake of brevity, features already described above with reference to FIGS. 1 and 2 are not repeated here.

In a first step 301, a transmitter 102 (TX) establishes a connection or otherwise associates with a receiver 120 (RX), as discussed above. The transmitter may scan for receivers broadcasting advertisement signals or a receiver may transmit an advertisement signal to the transmitter. The advertisement signal may announce the receiver's presence to the transmitter, and may trigger an association between the transmitter and the receiver.

Next, in step 303, when the transmitter detects the advertisement signal, the transmitter may automatically form a communication connection with that receiver, which may allow the transmitter and receiver to communicate control signals and power transmission signals. The transmitter may then command that receiver to begin transmitting real-time sample data or other data. The transmitter may also begin transmitting power transmission signals from antennas of the transmitter's antenna array.

In a next step 305, the receiver may then measure the voltage, among other metrics related to effectiveness of the power transmission signals, based on the electrical energy received by the receiver's antennas. The receiver may generate data containing the measured information, and then transmit control signals (e.g., communication signals 118, FIG. 1) containing the data to the transmitter. For example, the receiver may sample the voltage measurements of received electrical energy, for example, at a rate of 100 times per second. The receiver may transmit the voltage sample measurement back to the transmitter, 100 times a second, in the form of control signals.

In a next step 307, the transmitter may execute one or more software modules monitoring the metrics, such as voltage measurements, received from the receiver. Algorithms may vary production and transmission of power transmission signals by the transmitter's antennas, to maximize the effectiveness of the pockets of energy around the receiver. For example, the transmitter may adjust the phase at which the transmitter's antennas transmit the power transmission signals, until that power received by the receiver indicates establishment of a pocket of energy around the receiver. When an optimal configuration for the antennas is identified, memory 106 of the transmitter may store the configurations to keep the transmitter broadcasting at that highest level.

In a next step 309, algorithms of the transmitter may determine when it is necessary to adjust the power transmission signals and may also vary the configuration of the transmit antennas, in response to determining such adjustments are necessary. For example, the transmitter may determine the power received at a receiver is less than maximal, based on the data received from the receiver. The transmitter may then automatically adjust the phase of the power transmission signals, but may also simultaneously continue to receive and monitor the voltage being reported back from receiver.

In a next step 311, after a determined period of time for communicating with a particular receiver, the transmitter may scan and/or automatically detect advertisements from other receivers that may be in range of the transmitter. The transmitter may establish a connection to the second receiver responsive to, e.g., BLUETOOTH advertisements, from a second receiver.

In a next step 313, after establishing a second communication connection with the second receiver, the transmitter may proceed to adjust one or more antennas in the transmitter's antenna array. In some embodiments, the transmitter may identify a subset of antennas to service the second receiver, thereby parsing the array into subsets of arrays that are associated with a respective receiver. In some embodiments, the entire antenna array may service a first receiver for a given period of time, and then the entire array may service the second receiver for that period of time.

Manual or automated processes performed by the transmitter may select a subset of arrays to service the second receiver. In this example, the transmitter's array may be split in half, forming two subsets. As a result, half of the antennas may be configured to transmit power transmission signals to the first receiver, and half of the antennas may be configured for the second receiver. In the current step 313, the transmitter may apply similar techniques discussed above to configure or optimize the subset of antennas for the second receiver. While selecting a subset of an array for transmitting power transmission signals, the transmitter and second receiver may be transmitting and receiving data. As a result, by the time that the transmitter alternates back to communicating with the first receiver and/or scan for new receivers, the transmitter has already received a sufficient amount of sample data to adjust the phases of the waves transmitted by the second subset of the transmitter's antenna array to transmit power transmission waves to the second receiver effectively.

In a next step 315, after adjusting the second subset to transmit power transmission signals to the second receiver, the transmitter may alternate back to communicating data with the first receiver, or scanning for additional receivers. The transmitter may reconfigure the antennas of the first subset, and then alternate between the first and second receivers at a predetermined interval.

In a next step 317, the transmitter may continue to alternate between receivers and scanning for new receivers, at a predetermined interval. As each new receiver is detected, the transmitter may establish a connection and begin transmitting power transmission signals, accordingly.

In one example embodiment, the receiver may be electrically connected to a device like a smart phone. The transmitter's processor would scan for any BLUETOOTH devices. The receiver may begin advertising that it's a BLUETOOTH device through the BLUETOOTH chip (e.g., broadcasting advertising signals). The advertising signal may include unique identifiers so that the transmitter, when it scanned that advertisement, could distinguish that advertisement and ultimately that receiver from all the other BLUETOOTH devices nearby within range. When the transmitter detects that advertisement and notices it is a receiver, then the transmitter may immediately form a communication connection with that receiver and command that receiver to begin sending real time sample data.

The receiver would then measure the voltage at its receiving antennas, and send that voltage sample measurement back to the transmitter (e.g., 100 times a second). The transmitter may start to vary the configuration of the transmit antennas by adjusting the phase. As the transmitter adjusts the phase, the transmitter monitors the voltage being sent back from the receiver. In some implementations, the higher the voltage, the more energy may be in the pocket. The antenna phases may be altered until the voltage is at the highest level and there is a maximum pocket of energy around the receiver. The transmitter may keep the antennas at the particular phase so the voltage is at the highest level.

The transmitter may vary each individual antenna, one at a time. For example, if there are 32 antennas in the transmitter, and each antenna has 8 phases, the transmitter may begin with the first antenna and would step the first antenna through all 8 phases. The receiver may then send back the power level for each of the 8 phases of the first antenna. The transmitter may then store the highest phase for the first antenna. The transmitter may repeat this process for the second antenna, and step it through 8 phases. The receiver may again send back the power levels from each phase, and the transmitter may store the highest level. Next the transmitter may repeat the process for the third antenna and continue to repeat the process until all 32 antennas have stepped through the 8 phases. At the end of the process, the transmitter may transmit the maximum voltage in the most efficient manner to the receiver.

In another example embodiment, the transmitter may detect a second receiver's advertisement and form a communication connection with the second receiver. When the transmitter forms the communication with the second receiver, the transmitter may aim the original 32 antennas towards the second receiver and repeat the phase process for each of the 32 antennas aimed at the second receiver. Once the process is completed, the second receiver may receive as much power as possible from the transmitter. The transmitter may communicate with the second receiver for a period of time (e.g., a second), and then alternate back to the first receiver for a period of time (e.g., a second), and the transmitter may continue to alternate back and forth between the first receiver and the second receiver at the time period intervals.

In yet another implementation, the transmitter may detect a second receiver's advertisement and form a communication connection with the second receiver. First, the transmitter may communicate with the first receiver and re-assign half of the example 32 the antennas aimed at the first receiver, dedicating only 16 towards the first receiver. The transmitter may then assign the second half of the antennas to the second receiver, dedicating 16 antennas to the second receiver. The transmitter may adjust the phases for the second half of the antennas. Once the 16 antennas have gone through each of the 8 phases, the second receiver may be receiving the maximum voltage in the most efficient manner.

FIGS. 4A-4D illustrate in-vehicle wireless power transmission systems, in accordance with some embodiments.

Referring to FIG. 4A, a wireless power transmitter system 400 can be implemented in order to charge or power one or more electronic devices 401 (e.g., an embodiment of the electronic device 122, FIG. 1) inside a vehicle. According to some aspects of this embodiment, transmitter 102 can be configured within a cylindrical shape, exhibiting a longitude between about 2 and 3 inches, and a diameter ranging from about 0.5 inch to about 1 inch. As illustrated in close-up view 402, transmitter 102 can include a suitable connector 404 with pins 406 that can be inserted into car lighter socket 408 for powering transmitter 102. Transmitter 102 can function as a standalone, self-contained device that can integrate circuitry module 414 and antenna array 412 (e.g., an embodiment of the antenna array 110, FIG. 1), along with connector 404 and pins 406.

Car lighter socket 408 can supply 12 or 24 DC volts for powering transmitter 102, which may be sufficient power for most portable electronic devices 401 such as smartphones, DVD players, portable gaming systems, tablets, laptops computers, and the like. In some embodiments, circuitry module 414 of transmitter 102 can include a DC-to-DC converter or a DC-to-AC converter, depending on the electrical charging requirements of electronic device 401. Yet in other embodiments, circuitry module 414 can include a switchable power converter that can be configured according to the charging requirements of electronic device 401.

Operation of transmitter 102 in FIG. 4A can be driven by a power source, in this case, car lighter socket 308. Transmitter 102 can use communication component 112 (not shown in FIG. 4A) in circuitry module 414 to locate a receiver 120 (not shown in FIG. 4A) embedded in electronic device 401. Processor(s) 104 (not shown in FIG. 4A) which may be included in circuitry module 414 of the transmitter 102 may determine the optimum path for the generation of pocket-forming, according to the location of electronic device 401 within the vehicle. As depicted in FIG. 4A, electronic device 401 can be located in the passenger seat, right beside the driver seat. Processors 104 may communicate with a radio frequency integrated circuit in circuitry module 414 so as to control the generation and transmission of RF waves 116 through antenna array 412 which may include two or more antenna elements. Transmission of RF waves 116 can be aimed at electronic device 401 in the passenger seat for the generation of pocket-forming suitable for charging or powering electronic device 401.

The wireless power transmission system 400 can also be used for powering or charging an electronic device 401 located in the backseats of the vehicle, or any other locations inside vehicle. In this case, transmitter 102 can use any suitable reflecting surface of the vehicle, preferably metallic, in order to transmit RF waves 116 and redirect the formation of pockets of energy towards electronic device 401, with minimal or no power loss. For example, transmitter 102 can use the vehicle ceiling to bounce off transmitted RF waves 116 towards electronic device 401 for the generation of pockets of energy capable of providing suitable charging or powering to electronic device 401.

In some embodiments, the wireless power transmission 400 powers or charges two or more electronic devices 401 inside vehicle, where transmitter 102 can be capable of producing multiple pocket forming. In such case, transmitter 102 can generate multiple RF waves 116 directly aimed at or reflected towards electronic devices 401 through the use of suitable reflecting surfaces of the vehicle, thereby powering or charging one or more electronic devices 401 at the same time.

FIG. 4B illustrates a wireless power transmission system 420 where transmitter 102 includes a cable 422 for positioning antenna array 412 in different areas inside a vehicle. As seen in close-up view 421, transmitter 102, through the use of connector 404 and pins 406, can be connected to car lighter socket 408 to receive power necessary for operation. According to some aspects of this embodiment, circuitry module 414 of transmitter 102 can be operatively coupled with car lighter socket 408, while antenna array 412 can be operatively connected with circuitry module 414 through cable 422, thereby allowing antenna array 412 to be separately positioned across vehicle, as required by the application or according to the relative position of one or more electronic devices 401. For example, as shown in FIG. 4B, cable 422 can be run from circuitry module 414 to antenna array 412 which can be slipped in one of the vehicle's sun visor 424. In this way, antenna array 412 can emit RF waves 116 from a high-up position down to one or more electronic devices 401 for the generation of pockets of energy that may provide suitable charging or powering. This configuration may be particularly beneficial for charging or powering electronic devices 401 in the vehicle's backseats.

Antenna array 412 in FIG. 4B can exhibit a flat rectangular shape, with dimensions between about 4×2 inches to about 8×4 inches, depending on the number and configuration of antenna elements 412. Cable 422 can include a suitable conductor covered by an insulating material, it may be flexible and may exhibit a suitable length as required by the application. Preferably, cable 422 can be positioned between circuitry module 414 of transmitter 102 and antenna array 412 in such a way as to not obstruct the visibility of the windshield, as illustrated in FIG. 4B.

Referring now to FIG. 4C, a wireless power transmission system 430 includes a transmitter 102 with its circuitry module 414 connected to car lighter socket 408, while its antenna array 412 can be positioned on the vehicle's floor 432. Similarly as in FIG. 4B, antenna array 412 may exhibit a flat rectangular shape with dimensions between about 4×2 inches to about 8×4 inches, depending on the number and configuration of antenna elements. According to some aspects of this embodiment, antenna array 412 can be covered by the vehicle floor mats (not shown in FIG. 4C), where this antenna array 412 can emit RF waves 116 from the bottom of the vehicle floor 432 upwards to one or more electronic devices 401 that may be positioned in the passenger seat, as illustrated in FIG. 4C, or in any another suitable location within the vehicle.

Similarly as in FIG. 4B, cable 422 can operatively connect circuitry module 414 (not shown in FIG. 4C) to antenna array 412 for the transmission of RF waves 116 that may produce pockets of energy suitable for charging or powering one or more electronic devices 401 inside the vehicle. In this particular embodiment, antenna array 412 may include a suitable combination of flexible and conducting materials that may allow transmission of RF waves 116, while avoiding fractures or breakdown when a passenger steps on antenna array 412 placed underneath the vehicle's floor 432 mats.

Although these example embodiments of wireless power transmission may describe transmitter 102 as a standalone device that may be connected to a car lighter socket 408, including the different configurations and positions for its antenna array 412, other transmitter 102 configurations and features may be contemplated as well. For example, antenna array 412 of transmitter 102 may be positioned in any suitable areas inside the vehicle such as passenger seats and backseats, storage compartments, and center console among others. In other embodiments, transmitter 102 may be configured as a built-in device that may be factory-integrated in suitable areas or parts of the vehicle such as sun-visors, sunroofs, sound speakers, dashboards, and the like.

Figure 4D:
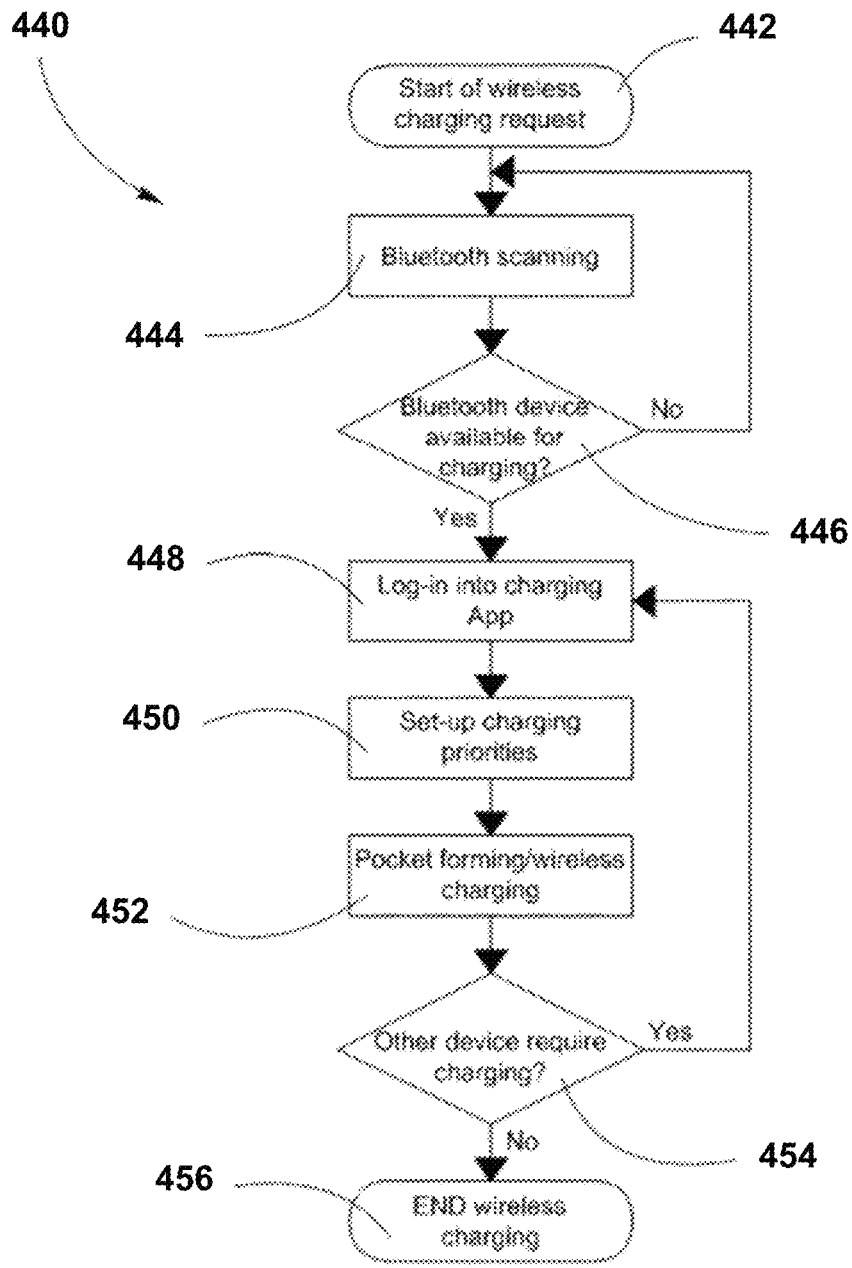
FIG. 4D is a flow diagram of wirelessly charging or powering one or more electronic devices inside a vehicle, in accordance with some embodiments.

FIG. 4D shows a simplified flowchart of a wireless power transmission process 440 that may be implemented for charging one or more electronic devices 401 inside a vehicle. This process may be applicable in the embodiments of the wireless power transmission systems 400, 420, and 430.

The wireless power transmission process 440 may begin with a wireless charging request, at block 442. Subsequently, transmitter 102 may perform a BLUETOOTH scanning for identifying any suitable electronic device 401 that may require wireless charging or powering, at block 444. Specifically, this BLUETOOTH scanning may be carried out by a communication component integrated in circuitry module 414 of transmitter 102.

Using BLUETOOTH scanning, transmitter 102 may determine if there are one or more electronic devices 401 available for charging or powering, at block 446. Basically, any suitable electronic device 401 operatively coupled with a receiver 120 and capable of BLUETOOTH communication may be considered "available" for wireless charging or powering. If there are no available electronic devices 401 for wireless charging or powering, then BLUETOOTH scanning can be repeated until there is at least one electronic device 401 available. If one or more electronic devices 401 are available, then wireless power transmission process 440 may continue at block 448, where one or more electronic devices 401 may log into a charging application developed in any suitable operating systems such as iOS, ANDROID, and WINDOWS, among others. This charging application may establish a suitable communication channel between transmitter 102 and electronic device 401, where configuration of transmitter 102 can be accessed and reprogrammed according to the charging or powering requirements of electronic devices 401.

One or more electronic devices 401 may access the charging application in order to modify the configuration of transmitter 102. Specifically, one or more electronic devices 401 can communicate with transmitter 102 via BLUETOOTH and log into the charging application to set up charging or powering priorities as necessary, at block 450. For example, in a long family trip, charging or powering priorities can be established to first charge or power-up electronic devices 401 for kids' entertainment such as portable gaming consoles and tablets, followed by the charging or powering of parents' electronic devices 401 such as smartphones and laptops. Other transmitter 102 parameters such as power intensity and pocket-forming focus/timing can also be modified through the use of this charging application. However, authorization access to transmitter 102 configuration may be restricted to certain users who may be required to provide corresponding user-credentials and passwords.

After charging priorities in transmitter 102 are set, transmission of RF waves 116 towards the designated electronic devices 401 can begin, at block 452, where these RF waves 116 may generate pockets of energy at receivers 120 for powering or charging one or more electronic devices 401 sequentially or simultaneously. In other embodiments, different charging or powering thresholds may be established for maintaining suitable operation. For example, minimum and maximum charging thresholds may be established at about 20% and 95% of total charge respectively, where charging or powering of electronic devices 401 may be stopped when reaching 95% of total charge, and may resume when total charge of electronic devices 401 falls below 20%.

BLUETOOTH scanning may continue throughout the process in order to identify additional electronic devices 401 that may require wireless charging or powering, at block 454. If new or additional electronic devices 401 are identified, then transmitter 102 may be accessed through the charging application to set charging or powering priorities for these additional electronic devices 401. If no further electronic devices 401 are recognized by BLUETOOTH scanning, then wireless power transmission process 440 may end, at block 456.

FIGS. 4A-4D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 4A-4D.

Presented below are example methods of wirelessly delivering power to receivers in a vehicle.

In some embodiments, an example method includes defining, by a transmitter, a pocket of energy positioned within a vehicle, and the vehicle includes the transmitter and a power source powering the transmitter. The method further includes charging, by the transmitter, an electronic device positioned within the vehicle, and the electronic device includes a receiver that interfaces with the pocket of energy in the vehicle.

In some embodiments, the power source includes at least one of a vehicle lighter socket and a direct connection to a power wire within the vehicle.

In some embodiments, the electronic device is a first electronic device and the transmitter charges a second electronic device positioned within the vehicle based on the second device interfacing with the pocket of energy in the vehicle.

In some embodiments, another example method includes scanning, using a wireless communication component of a transmitter, for available receivers within a vehicle that are authorized to receive wirelessly delivered power from the transmitter and detecting, by the transmitter, a first receiver and a second receiver of the available receivers within the vehicle based on the scanning. The method further includes, while continuing to scan for available receivers within the vehicle: (i) receiving, by a connector of the transmitter, where the connector is coupled to a power source of the vehicle, electrical current from the power source that is used by the transmitter to generate a plurality of power waves, (ii) receiving, by the wireless communication component of the transmitter, a charging request from the second receiver within the vehicle, (iii) adjusting, by a controller of the transmitter, respective gains and phases of at least a second set of the plurality of power waves, and (iv) transmitting the second set of the plurality of power waves such that the second set of the plurality of power waves converge to form a second constructive interference pattern, distinct from the first constructive interference pattern, in proximity to a location of the second receiver within the vehicle.

In some embodiments, the charging request (i) corresponds to a request for wirelessly delivered power from the transmitter, and (ii) is sent by the second receiver when a charge level of the second receiver is less than a minimum level of charge.

FIGS. 5A-5D illustrate additional embodiments of wireless power transmission systems associated with vehicles, in accordance with some embodiments.

Figure 5A:
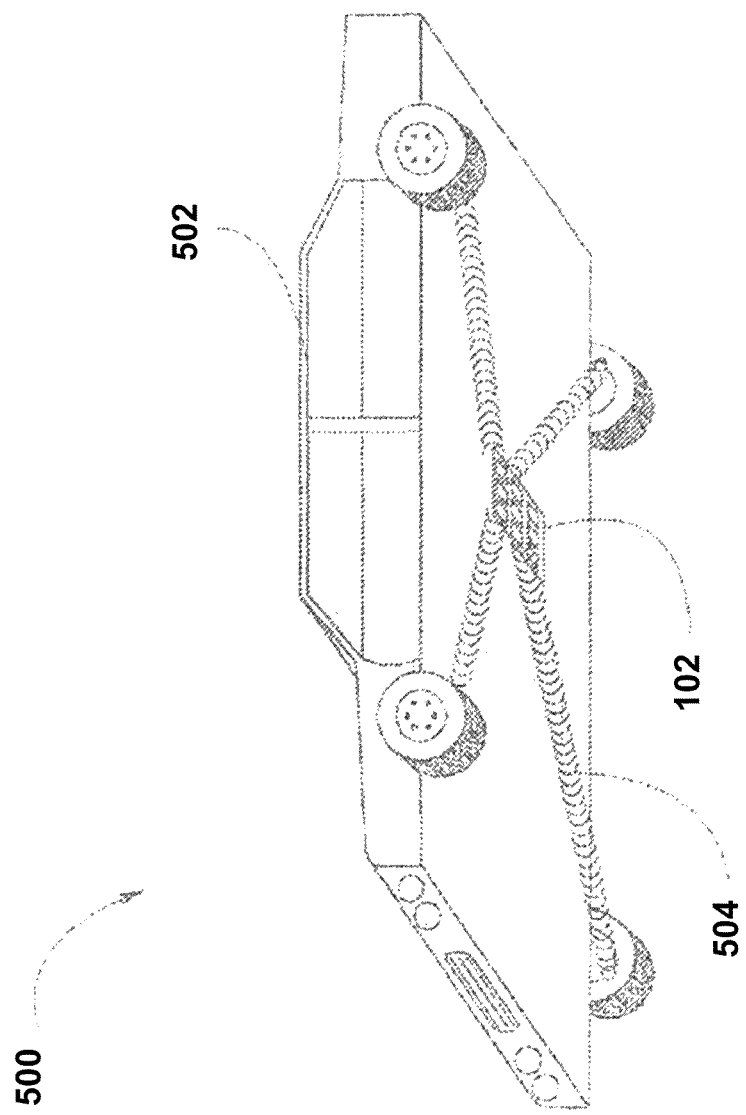
FIG. 5A illustrates a wireless power transmission system used for providing power to sensors on a bottom portion of a vehicle, in accordance with some embodiments.

FIG. 5A illustrates a wireless power transmission system 500 where a transmitter 102 may provide wireless power, through pocket-forming, to sensors in the bottom part of a car 502. Transmitter 102 can be placed in the bottom of car 502, and may power, for example, tire pressure gauges, brake sensors and the like. The foregoing gauges and sensors may include embedded or otherwise operatively coupled receivers (not shown) (e.g., an embodiment of the receiver 120, FIG. 1) for converting pockets of energy into usable energy. Even though the paths of RF waves 504 appear to be in straight lines, transmitter 102 can bounce RF waves 504 off of suitable reflecting areas of car 502 to improve power delivery efficiency. One of the main advantages of the foregoing disclosed configuration of the wireless power transmission system 500 may be the cost-effective solution of eliminating the wires required for powering the aforementioned sensors in the bottom of car 502.

Figure 5B:
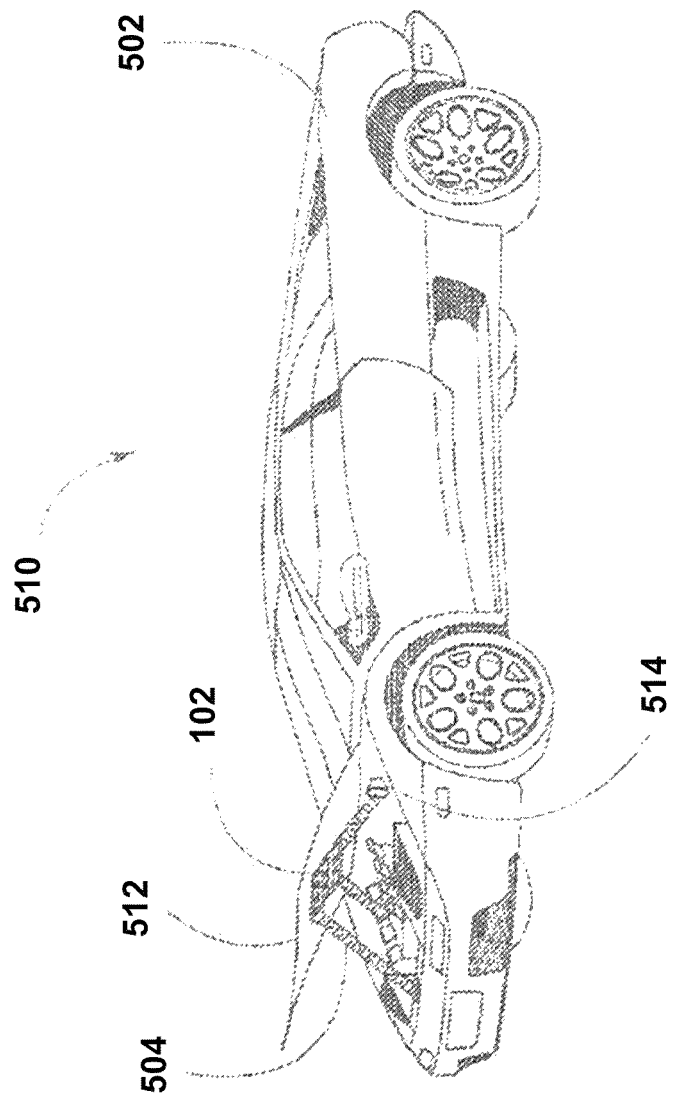
FIG. 5B illustrates a wireless power transmission system used for providing power to sensors located in an engine compartment of a vehicle, in accordance with some embodiments.

FIG. 5B illustrates a wireless power transmission system 510 where a transmitter 102 may provide wireless power, through pocket-forming, to sensors in the engine compartment of a car 502. Transmitter 102 can be placed in the bottom internal surface of a hood 512 (or other suitable locations) of car 502 in order to power engine sensors such as throttle position sensors, engine coolant temperature sensors, barometric sensors and the like. The transmitter 102 can use reflecting areas from the engine compartment of car 502 to bounce off RF waves 504 (e.g., power waves 116, FIG. 1) to improve power delivery efficiency. In some embodiments, transmitter 102 can be used to power the sensors present in typical alarm systems, for example, door sensors, pressure sensors (for the interior of car 502), shock sensors and the like. In other embodiments, transmitter 102 can function as an alternate or main power supply for alarm speakers 514.

Figure 5C:
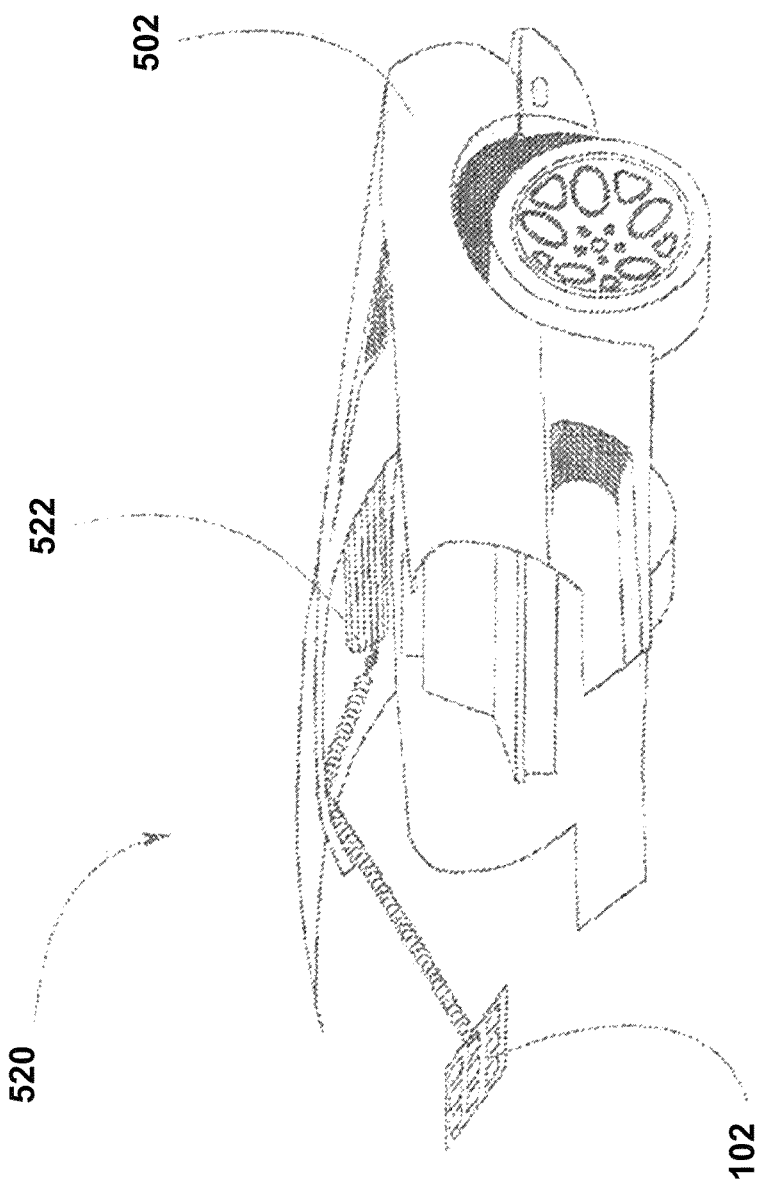
FIG. 5C illustrates a wireless power transmission system used for providing power to sensors located in a passenger compartment of a vehicle, in accordance with some embodiments.

FIG. 5C illustrates a wireless power transmission system 520 where a transmitter 102 may provide wireless power, through pocket-forming, to sensors, gauges or small miscellaneous devices in the interior of a car 502. In some embodiments, transmitter 102 can be placed in the instrument panel (not shown) of car 502. In this particular embodiment, transmitter 102 is shown to be powering a rear window defroster 522 of car 504, and thus diminishing the need for wires. In some embodiments, transmitter 102 can provide power to the actuators in the car windows, and even to the interior lighting system.

Figure 5D:
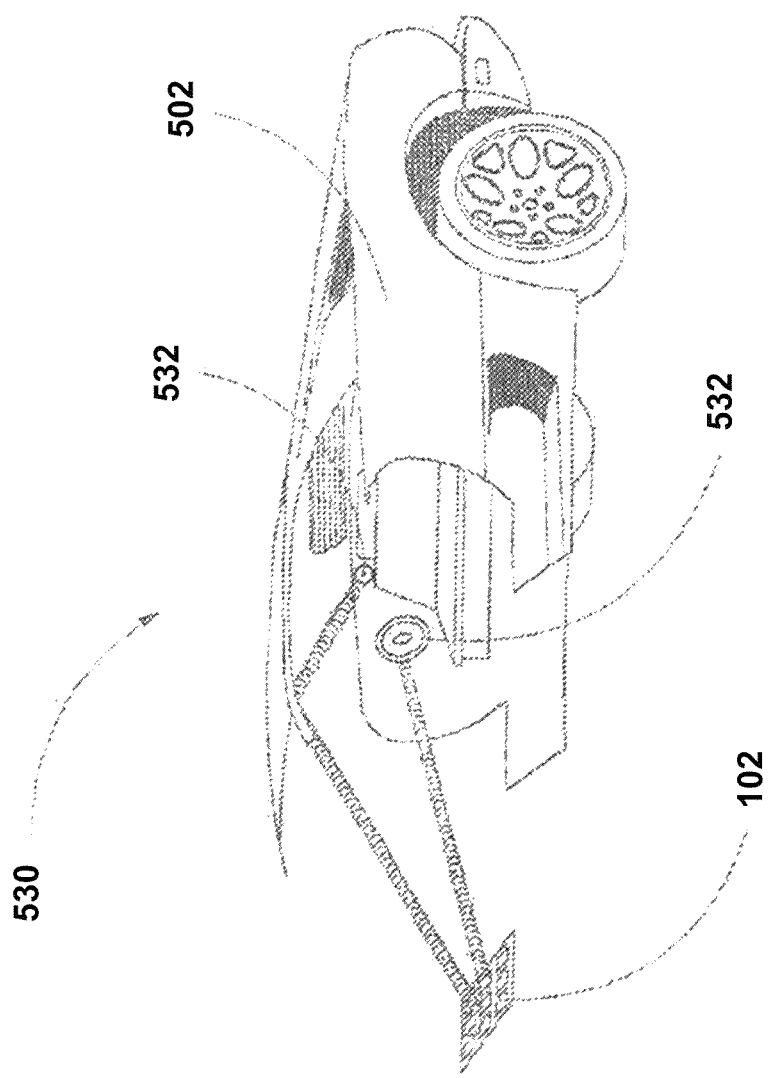
FIG. 5D illustrates a wireless power transmission system used for providing power to devices located in a passenger compartment of a vehicle, in accordance with some embodiments.

FIG. 5D illustrates a wireless power transmission system 530 where a transmitter 102 may provide wireless power, through pocket-forming, to devices in the interior of car 502. In this embodiment, transmitter 102 can provide wireless power to speakers 532 while eliminating the use of wires.

FIGS. 5A-5D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 5A-5D.

Presented below are example systems and methods of wirelessly delivering power to receivers on or within a vehicle.

In some embodiments, an example method includes defining, by a transmitter, a pocket of energy within a vehicle via a plurality of wireless power transmission waves emitted by the transmitter, the vehicle including the transmitter, a receiver, and a vehicle sensor coupled to the receiver. The method further includes interfacing, by the receiver, with the pocket of energy within the vehicle, and providing, by the receiver, power to the vehicle sensor based on the interfacing.

In some embodiments, the vehicle includes a bottom portion, and the transmitter is located in the bottom portion. The sensor is at least one of a tire pressure sensor and a brake sensor.

Alternatively or in addition, in some embodiments, the vehicle includes an engine compartment and the transmitter is located in the engine compartment. In such embodiments, the sensor is an engine sensor.

In some embodiments, an example system includes a vehicle, one or more sensors coupled to the vehicle, and a transmitter coupled to the vehicle (e.g., an exterior of the vehicle). The vehicle is configured to power the transmitter and the transmitter is configured to define a pocket of energy within the vehicle via a plurality of wireless power transmission waves emitted by the transmitter. The system further includes a receiver coupled to the vehicle. The sensor is coupled to the receiver and the receiver is configured to power the sensor by interfacing with the pocket of energy.

FIGS. 6A-6D provide examples of wireless power transmission for wirelessly delivering power to cordless power tools, in accordance with some embodiments.

Referring to FIG. 6A, a wireless power transmission system 600 may include a transmitter 102 embedded in a toolbox 602 to wirelessly charge or power one or more cordless power tools 604, according to an embodiment. Toolbox 602 may be capable of storing and transporting a plurality of cordless power tools 604 and other related tools or components. Transmitter 102 may be embedded in a region or area of toolbox 602 suitable for transmitting RF waves 116 towards receiver 120 which may be attached or operatively coupled to the battery 606 of cordless power tool 604. For example, transmitter 102 may be positioned at the top right corner of toolbox 602 housing to direct RF waves 116 towards receiver 120 for the generation of pockets of energy capable of wirelessly charging the battery 606 of cordless power tool 604. The cordless power tool 604 may be an example of the electronic device 122.

Toolbox 602 may also include a battery 603 which may be operatively coupled with transmitter 102 through a cable (not shown) for allowing the generation and transmission of RF waves 116 as required by the application. Simply put, battery 603 may function as a power source for transmitter 102. In some embodiments, toolbox 602 may be connected to an external power source 608 to charge battery 603 through a suitable cable 610, while simultaneously powering transmitter 102 for the generation and transmission of RF waves 116 directed towards receiver 120, which can be embedded or attached to cordless power tool 604. External power source 608 source may include a 120/220 AC volt outlet, in which case toolbox 602 may include a suitable AC/DC converter (not shown) for converting AC voltage and supplying DC voltage to battery 603 for charging.

In another embodiment, when battery 603 is charged to a suitable level, toolbox 602 may be disconnected from external power source 608, and subsequently carried and positioned in a desired working area where cordless power tool 604 may be used. In this case, transmitter 102 may receive power for the generation and transmission of RF waves 116 solely and directly from battery 603. Charged battery 603 in toolbox 602 may provide enough charge to transmitter 102 for the generation of pockets of energy within a power range of about 1 watt to about 5 watts, and within a working distance of about 5 ft. to about 20 ft. These power levels of pocket of energy may be suitable for charging the battery 606 of cordless power tool 604 while in use, or at least extending the life of battery 606 during operation. In general, the power and range of the generated RF waves 116 may vary according to the number of antenna elements, distribution, and size of transmitter 102. A cordless power tool 604 not in use or in standby can also be charged by a transmitter 102 embedded in toolbox 602.

FIG. 6B shows another configuration of the wireless power transmission system 600. In this configuration, the portable toolbox 602 may be located on or within a vehicle 612, according to an embodiment. Vehicle 612 may be a private car or a service van commonly used by technicians having to perform field work or related activities. Similarly as in FIG. 6A, toolbox 602 may be connected to external power source 608 for charging battery 603 and powering transmitter 102. External power source 608, in this case, may be the battery of vehicle 612. Toolbox 602 may be operatively coupled to external power source 608 through a suitable connection that includes a car lighter socket 614 and cable 616. In order to avoid draining the battery of vehicle 612, engine 618 may be on or running when charging battery 603 or powering transmitter 102 in toolbox 602. In some embodiments, transmitter 102 may generate and direct RF waves 116 towards the receivers 120 embedded or attached to one or more cordless power tools 604 for the wireless charging of batteries 112. Transmitter 102 in toolbox 602 may wirelessly charge or power two or more cordless power tools 604 simultaneously or sequentially according to the power or application requirements. Transmitter 102 in toolbox 602 may also charge a spare battery 620 having a suitable receiver 120 attached.

In some embodiments, when battery 603 in toolbox 602 is charged to a suitable level, toolbox 602 can be disconnected from the car lighter socket 614 and placed at a location outside vehicle 612. Transmitter 102 in toolbox 602 may subsequently generate RF waves 116 which may wirelessly charge or at least extend the life of batteries 606 during the operation of cordless power tools 604, in this case, transmitter 102 may be energized directly from the charged battery 603 in toolbox 602. In some embodiments, a surface area of the antenna array 110 (FIG. 1) of the transmitter 102 embedded in toolbox 602 may range from approximately 2 in$^2$ to about 12 in$^2$ depending on the dimensions of toolbox 602.

FIG. 6C illustrates an additional configuration of wireless power transmission system 600. In this configuration, transmitter 102 may be configured in the doors or windows of vehicle 612, according to an embodiment. Specifically, the antenna array of transmitter 102 may be configured to fit one window of vehicle 612. In such a case, the antenna array may include between about 300 and about 600 antenna elements distributed within a surface area that may vary between about 90 in$^2$ and about 160 in$^2$. This increased number of antenna elements and footprint of transmitter 102 may allow for a higher level of power distribution and reach of the emitted RF waves 116 as compared to the embodiment shown in FIG. 6B. For example, transmitter 102 within the specified dimensions and number of antenna elements may emit RF waves 116 capable of generating a pocket of energy between about 1 Watt and 10 Watts of power, and within a distance of about 30 ft and about 50 ft.

In FIG. 6C, transmitter 102 may be constantly and directly connected to an external power source 608 such as vehicle 612 battery via car lighter socket 614 and cable 616. Engine 618 may be on or running when transmitter 102 is in operation in order to prevent draining of the vehicle's 612 battery. Transmitter 102 may generate and direct RF waves 116 towards the receivers 120 embedded or attached to one or more cordless power tools 604 for the charging of batteries 606. Transmitter 102 may wirelessly charge or power two or more cordless power tools 604 simultaneously or sequentially according to the power or application requirements. Transmitter 102 may also wirelessly charge a spare battery 620 having a suitable receiver 120 attached.

Figure 6D:
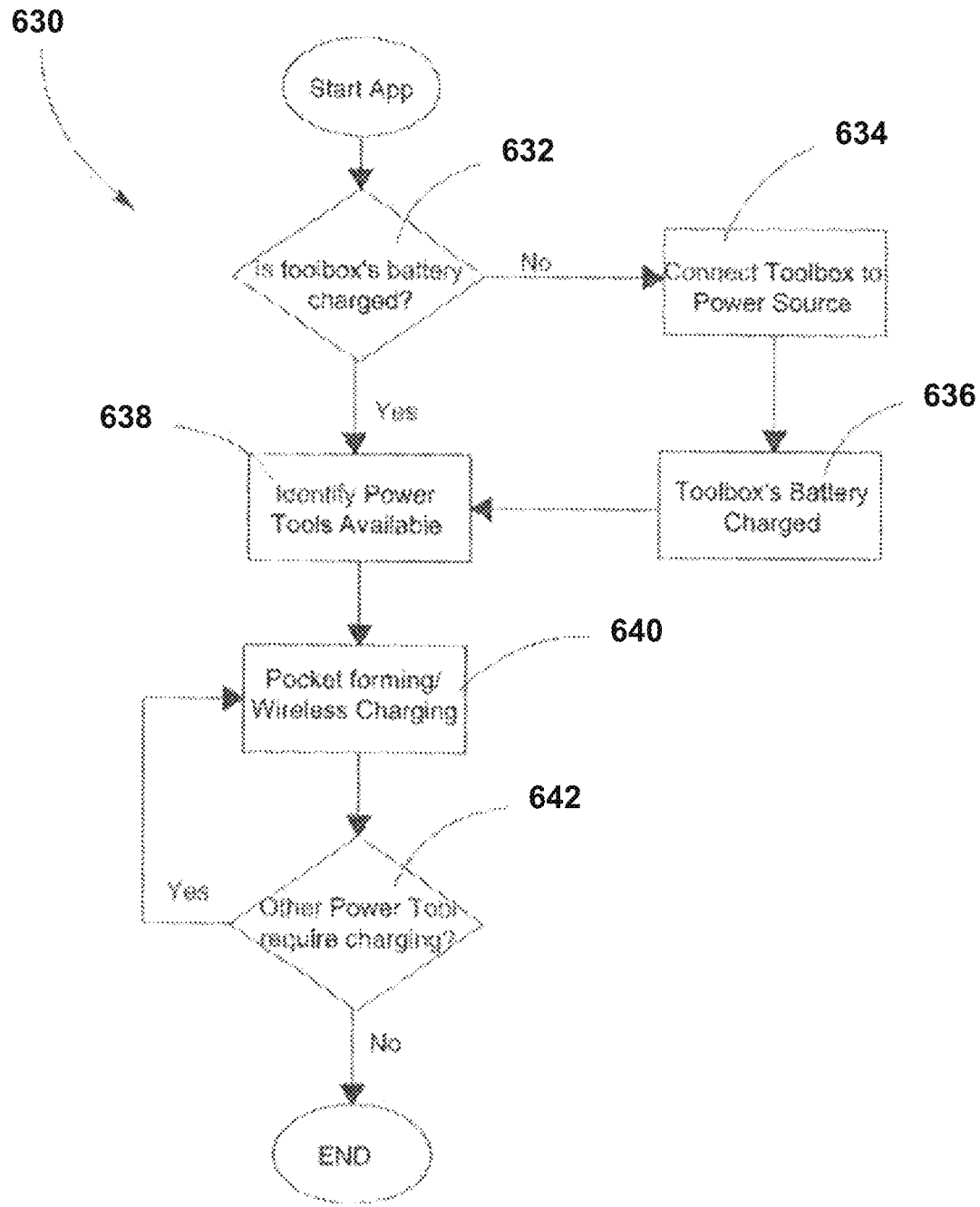
FIG. 6D is a flow diagram of wirelessly charging or powering one or more cordless power tools, in accordance with some embodiments.

FIG. 6D shows a flowchart of a wireless power transmission process 630 that may be implemented for charging one or more cordless power tools 604 using toolbox 602 as a portable device. This process may be applicable to the embodiments of wireless power transmission systems 600 shown in FIGS. 6A-6C.

Wireless power transmission process 630 may begin by checking the charge levels of battery 603 embedded in toolbox 602, at block 632. This charge check may be performed by a control module included in toolbox 602 (not shown in FIGS. 6A-6B) or by micro-controller (e.g., processor 104, FIG. 1) in transmitter 102, which may be operatively connected to battery 603. Different charging levels for battery 603 may be established for maintaining suitable operation. For example, minimum and maximum charging thresholds may be established at about 25% and 99% of total charge respectively. At block 634, if battery 603 charge is below the minimum threshold or 25%, then toolbox 602 can be connected to external power source 608 using cable 610, where external power source 608 may include vehicle 612 battery or a standard 120/220 AC volts outlet as explained in FIGS. 6A-6B. When battery 603 charge is at 99% or at least above 25%, toolbox 602 can be disconnected from external power source 608, at block 436.

If battery 603 is charged to a suitable level, specifically between about 25% and about 99%, then wireless power transmission process 630 may continue at block 638, where communications component 112 in transmitter 102 may identify one or more cordless power tools 604 that may require wireless charging. Charging or powering priorities and other parameters such as power intensity and pocket-forming focus/timing may be established using a control module included in toolbox 602 or micro-controller in transmitter 102. For example, based on charging or powering priorities, transmitter 102 may be configured to first provide wireless charging to cordless power tools 604 in use, followed by cordless power tools 604 in standby, and lastly to spare batteries 620.

After cordless power tools 604 are identified and charging priorities/parameters in transmitter 102 are set, transmission of RF waves 116 towards the designated cordless power tools 604 or spare batteries 620 can begin, at block 640, where these RF waves 116 may generate pockets of energy at receivers 120 for powering or charging one or more cordless power tools 604 and spare batteries 620 sequentially or simultaneously.

Using communications component 112, transmitter 102 in toolbox 602 may continuously check if there are other cordless power tools 604 or spare batteries 620 that may require wireless charging or powering, at block 642. If new or additional cordless power tools 604 or spare batteries 620 are identified, then transmitter 102 in toolbox 602 may wirelessly charge the identified cordless power tools 604 and spare batteries 620 according to the established charging priorities and parameters. If no further cordless power tools 604 are recognized by communications component 112 in transmitter 102, then wireless power transmission process 630 may end.

FIGS. 6A-6D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 6A-6D.

Presented below are example methods of wirelessly delivering power to cordless power tools.

In some embodiments, an example method includes establishing, by a transmitter, a connection with a power source; generating, by the transmitter, a plurality of power transmission waves to form a pocket of energy; receiving, by the transmitter, a transmission of a power requirement of a cordless power tool and a receiver location; and transmitting, by the transmitter, the power transmission waves through at least two antennas coupled to the transmitter in response to the received transmission.

In some embodiments, the transmitter establishes communication with the receiver when the cordless power to the cordless power tool is within a predetermined distance (e.g., a distance of 10 feet or less) from the transmitter.

In some embodiments, another example method includes establishing, by a transmitter that is coupled to at least two antennas for transmitting power transmission waves to a plurality of cordless power tools, a connection with a power source that is used to charge a battery of the transmitter and determining, by the transmitter, whether the battery has a charge level that is above a threshold charge level. The method further includes, in accordance with determining that the battery has the charge level that is above the threshold charge level, identifying, by a communication component of the transmitter that is distinct from the at least two antennas of the transmitter, a cordless power tool of the plurality of cordless power tools that requires wireless charging. The method further includes receiving, by the communication component of the transmitter, information that identifies a power requirement of the cordless power tool and a location of a receiver that is coupled to the cordless power tool and transmitting, by the transmitter, a plurality of power transmission waves through the at least two antennas in response to the received information, and the plurality of power transmission waves are transmitted so that the plurality of power transmission waves converges to form a pocket of energy in proximity to the location of the receiver.

Figure 7A:
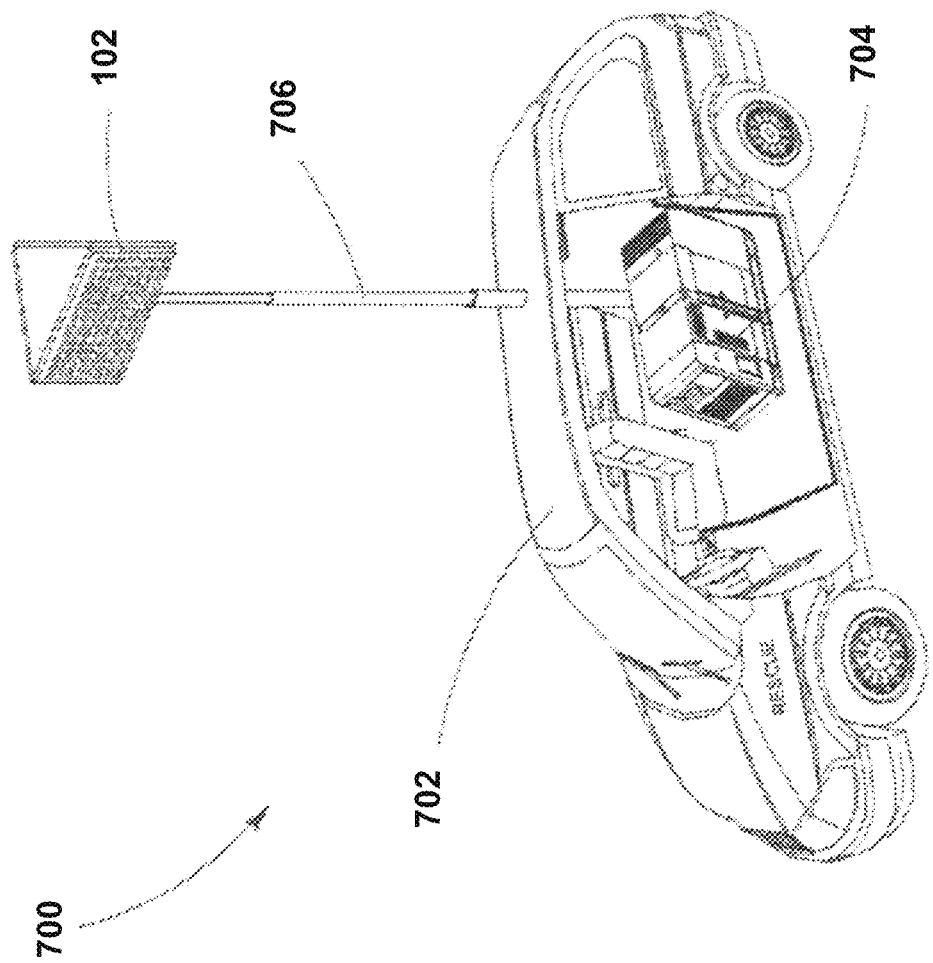
FIG. 7A illustrates a wireless power transmission system having a transmitter attached to a mast of a rescue vehicle, in accordance with some embodiments.
Figure 7B:
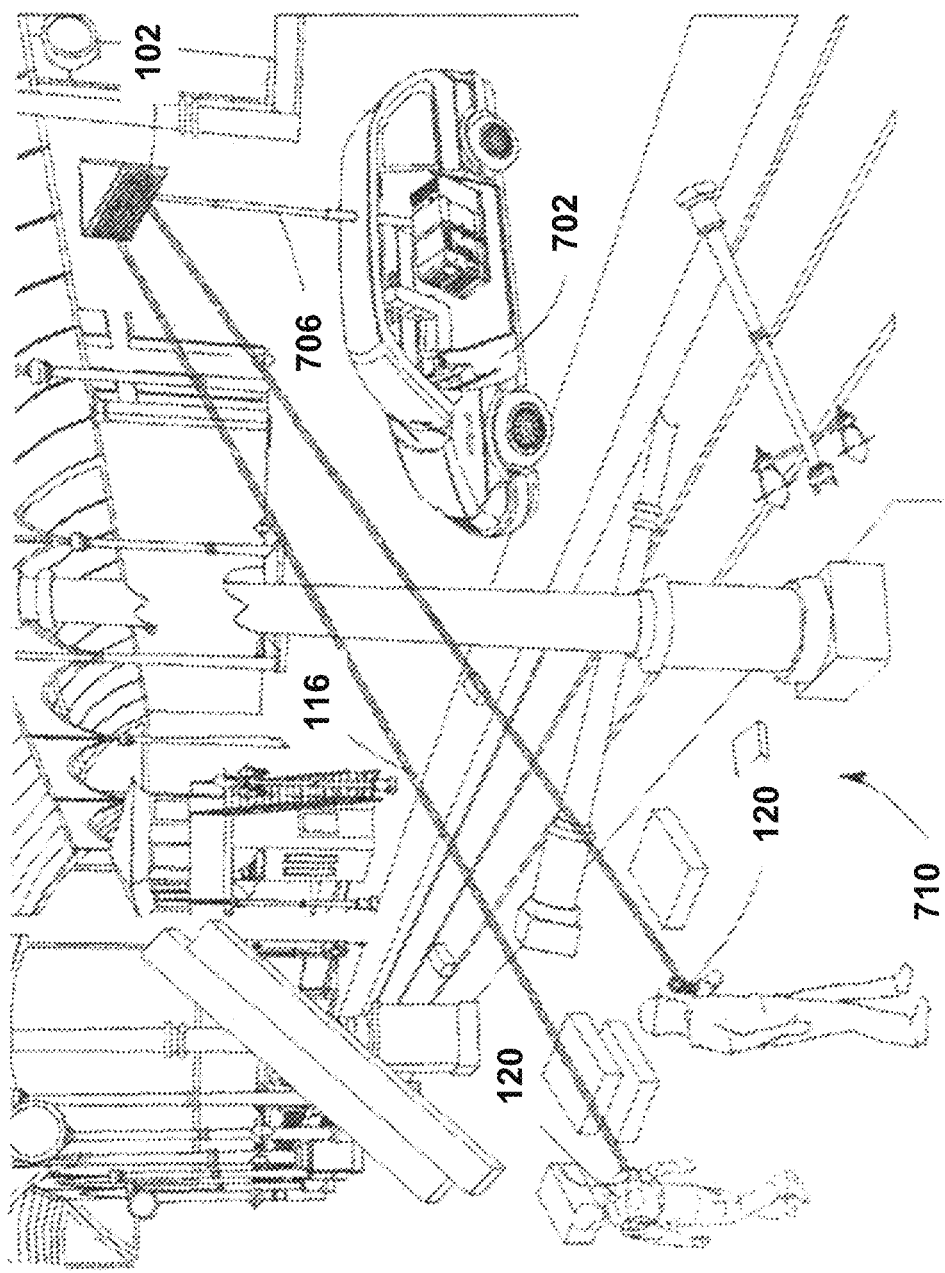
FIG. 7B illustrates a rescue vehicle with a transmitter operating in a disaster zone, in accordance with some embodiments.

FIGS. 7A-7B illustrate wireless power transmission systems used in rescue situations, in accordance with some embodiments.

FIG. 7A shows a configuration of wireless power transmission system 700 where a transmitter 102 may be located on or within a vehicle 702, according to some embodiments. Vehicle 702 may be a rescue car, fire truck, ambulance and the like. Transmitter 102 may use a diesel generator 704 as power source 210. However, other power sources may be employed too. Transmitter 102 may generate and direct RF waves 116 towards receivers 120 embedded or attached to rescue devices such as lamps, GPS, radios, cellphones, lights, among others. In addition, transmitter 102 in vehicle 702 may wirelessly extend the life of batteries in the previously mentioned devices during the operation.

Transmitter 102 may be located in a telescopic mast 706, which may be lifted up for increased range of wireless powering. Furthermore, other transmitter 102 configurations may be used in dependency of the region and requirements, such requirements may include low profile transmitters for a higher stability of vehicle 702 during gales or winds with high speed.

FIG. 7B illustrates a disaster zone 710, where a rescue vehicle 702 provides power and charge to a variety of rescue devices of a rescue team. Vehicle 702 may include a transmitter 102 located at the top of a telescopic mast 706. RF waves 116 may be transmitted through obstacles and may be reflected on objects for reaching receivers 120.

Receivers 120 may allow tracking of vehicle 702, such a feature may allow the capacity to operate beyond the range of transmitter 102 through the charge on the batteries. When batteries have low charge, receivers 120 may guide its user to vehicle 702 in order to obtain charge.

Vehicle 702 may operate and reach sharper areas than vehicles with a wired power source, such capability is enabled through the wireless power transmission, which allows a higher mobility than cabled power sources.

FIGS. 7A-7B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 7A-7B.

Presented below are example methods of wirelessly delivering power to rescue devices.

In some embodiments, an example method includes generating power RF signals from a RF circuit connected to the transmitter controlling the generated RF signals with a controller to provide a power RF signal and short RF communication signals; transmitting the power RF and short RF communication signals, through antenna elements connected to the transmitter, capturing power RF signals in a receiver with an antenna connected to the rescue electronic device to convert the pockets of energy into a DC voltage for charging or powering the rescue electronic device; and communicating power requirements of the rescue electronic device and the receiver location information between the pocket-forming transmitter and receiver with the short RF signals.

In some embodiments, the power source is a mobile diesel generator, a mobile gasoline generator or a vehicle generator or battery.

In some embodiments, the transmitter includes a housing suitable for field use, at least two antenna elements, at least one RF integrated circuit, at least one digital signal processor (DSP), and a communication component for generating the power RF and short RF signals.

In some embodiments, a telescopic mast connected to the transmitter is used to elevate the transmitter above the clutter at a rescue site.

In some embodiments, the method further includes extending the transmission distance of the pocket-forming transmitter by mounting the pocket-forming transmitter a predetermined height with the telescopic mast connected to a top surface of a vehicle including a fire truck, ambulance, rescue truck or other rescue vehicle.

In some embodiments, another example method includes, at a wireless power transmitter that includes a receiver antenna element, a radio frequency (RF) circuit, and a plurality of transmitter antenna elements, and the wireless power transmitter is connected to a power source and a telescoping mast of a mobile vehicle, the telescoping mast extending in a vertical direction above the mobile vehicle, receiving, via the receiver antenna element, a communication signal from a receiver device positioned at a location within a transmission range of the wireless power transmitter and controlling, via the RF circuit, operation of the plurality of transmitter antenna elements to generate wireless power transmission RF signals having predetermined phases and amplitudes using power from the power source. The method further includes transmitting and steering, via the RF circuit, the wireless power transmission RF signals via the plurality of transmitter antenna elements so that the wireless power transmission RF signals constructively interfere at the location.

Figure 8A:
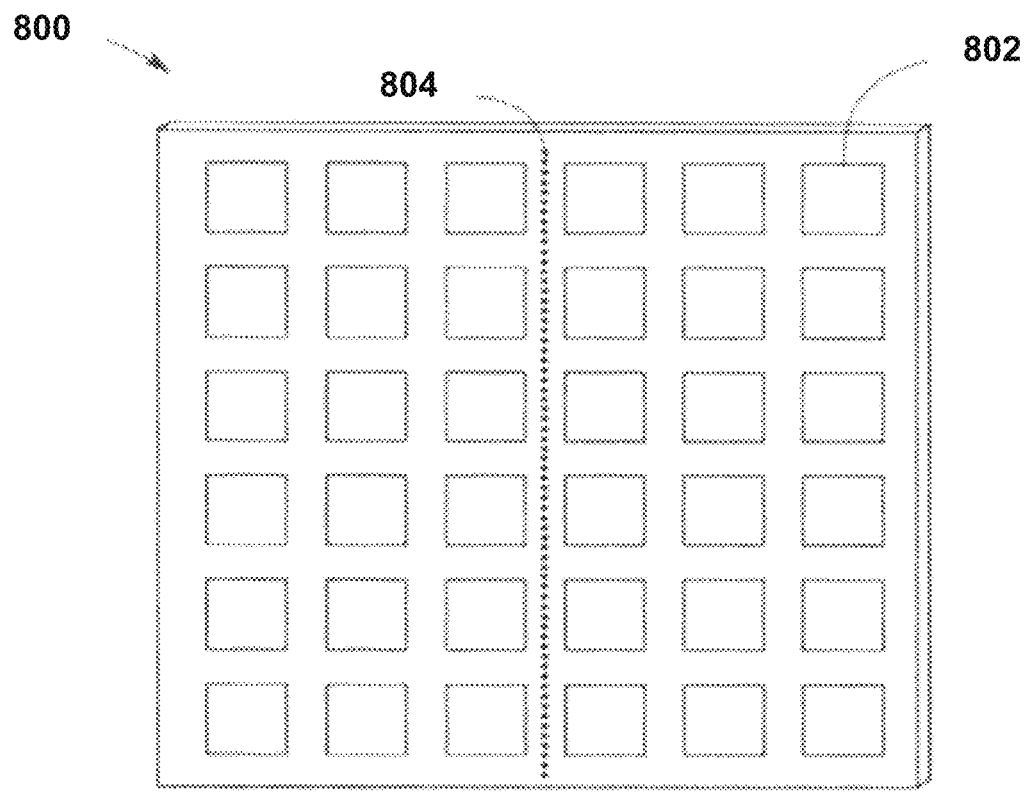
FIG. 8A illustrates an example multi-mode transmitter, in accordance with some embodiments.

FIG. 8A illustrates an example embodiment of a multimode transmitter. Some elements of this figure are described above.

A multimode transmitter 800, such as transmitter 102, is configured to operate as or includes a wireless power router and/or a communication network router, whether in a serial manner, such as one at a time, or a parallel manner, such as concurrently. More particularly, transmitter 800 is configured to define a pocket of energy via a plurality of wireless power waves so that a first receiver is able to interface with the pocket of energy, as described herein. Transmitter 800 is configured to emit the wireless power waves, as described herein. For example, at least one of the wireless power waves can be based on a radio frequency.

Transmitter 800 is also configured to provide a network communication signal to a second receiver so that the second receiver is able to interface with the network signal (i.e., is able to access the Internet using the network signal). Such provision can be performed in a wired manner, such as via a cable, a wire-line, or others. Such provision can also be performed in a wireless manner, such as optical, radio, laser, sound, infrared, or others. Such provision can based at least in part on the transmitter receiving a unique identifier from the second receiver, such as a media access control (MAC) address. For example, the network signal includes at least one of an Ethernet signal, a WI-FI signal, an optical signal, a radio signal, an infrared signal, a laser signal, or another type of signal, whether via a short range communication protocol, such as BLUETOOTH, or via a long range communication protocol, such as a satellite signal or a cellular signal, such as a cell site. The network signal is based at least in part on a network, and the network is or includes at least one of a local area network (LAN), a wide area network (WAN), a storage area network (SAN), a backbone network, a metropolitan area network, a campus network, a virtual private network, a global area network, a personal area network (PAN), or others, whether for an intranet, an extranet, an internetwork, or darknet.

Transmitter 800 includes a plurality of antenna elements 802, as described herein, and a radio frequency integrated circuit (RFIC). Antenna elements 802 and RFIC are arranged in a flat array arrangement, which reduces losses due a shorter distance between components. However, other types of arrangements are possible, such as non-flat, for instance, hemispherical. Transmitter 800 is configured to regulate a phase and an amplitude of pocket-forming operations in antenna elements 802, as described herein. For example, such regulation can be via corresponding RFIC in order to generate a desired pocket-forming output and null-space steering. Furthermore, transmitter 800 can be configured so that multiple pocket-forming outputs may charge a higher number of receivers and allow a better wave trajectory to such receivers. Transmitter 800 can include an omnidirectional antenna.

In some embodiments, transmitter 800 includes or is coupled to a plurality of arrays comprising antenna elements 802. Such coupling can be direct or indirect, wired or wireless, and/or local or remote. For example, such coupling can be via a wire spanning between transmitter 800 and at least one of such arrays. Note that such arrays can be embodied as one unit or a plurality of inter-coupled units or intra-coupled units. Such coupling can be direct or indirect, wired or wireless, and/or local or remote. For example, such coupling can be via a wire spanning between at least two of such arrays. Also, note that at least two of such arrays can be identical to each other or different from each based on at least one of structure, function, shape, size, coupling characteristics, or material properties. A presence of such arrays may increase or decrease a number of antenna elements 802 operating for each application, such as either for a wireless power transmission or a communication network signal transmission. In some embodiments, transmitter 800 lacks distinct array division, such as visual, such as into the first portion and the second portion. Resultantly, at least one of such arrays comprising antenna elements 802 operates for the communication network signal transmission only, and the switch, as described herein, changes an operational mode to enable the power router functionality. For example, transmitter 800 is configured to operate such that a first portion of an array, as described herein, such as a half, transmits the network signal, such as a WI-FI signal, and a second portion of the array, such as the other half, defines the pocket of energy, such as described herein. Line 804 represents a division in the array arrangement. Note that although the first portion and the second portion are symmetrical, the first portion and the second portion can be asymmetrical. Also, note that the first portion and the second portion can differ from each other or be identical to each other in at least one of a shape, a size, and a number of antenna elements 802.

In some embodiments, transmitter 800 includes an antenna, as described herein. Therefore, transmitter 800 defines the pocket and provides the network signal via the antenna. Transmitter 800 can define the pocket and provide the signal simultaneously. Alternatively or additionally, transmitter 800 is configured to switch between a first operational mode and a second operational mode. Resultantly, transmitter 800 includes a switch configured to switch between the first mode and the second mode. The switch can be hardware based, such as an A/B switch, a knob, or a lever. The switch can also be software based, such as via a set of processor-executable instructions, for instance. via machine code. Such switch can switch manually, such as via a user input, for instance, via a button. Such switch can also switch automatically, such as via a set of processor-executable instructions, for instance via machine code. In the first mode, transmitter 800 defines the pocket only. In the second mode, transmitter 800 provides the network signal only. For example, such switch can be an A/B switch, whether manually switchable or automatically switchable, based on at least one input criterion, which can be remotely updateable. Note that transmitter 800 can be configured so that the communication network router functionality and the wireless power functionality are simultaneously operating, such as parallel operation, whether dependent or independent on each other, or only the communication network router functionality or the wireless power functionality operates at one time, such as serial operation, whether dependent or independent on each other.

In some embodiments, transmitter 800 includes a first antenna, as described herein, and a second antenna, as described herein. Therefore, transmitter 800 defines the pocket via the first antenna and provides the network signal via the second antenna. The first antenna and the second antenna can be controlled via a controller, whether or not transmitter 800 includes such controller, whether or not such controller is local or remote to transmitter 800, whether or not such controller is directly or indirectly coupled to at least one of the first antenna and the second antenna. Note that the first antenna and the second antenna can be part of a larger antenna, such as an array. Also, note that the first antenna and the second antenna can be coupled to each other. Further, the first antenna and the second antenna can be not coupled to each other. Transmitter 800 is configured to that the first antenna defines the pocket of energy and the second antenna provides the network signal simultaneously. Alternatively or additionally, transmitter 800 is configured to switch between a first operational mode and a second operational mode. Resultantly, transmitter 800 includes a switch configured to switch between the first mode and the second mode. The switch can be hardware based, such as an A/B switch, a knob, or a lever. The switch can also be software based, such as via a set of processor-executable instructions, for instance via machine code. Such switch can switch manually, such as via a user input, for instance, via a button. Such switch can also switch automatically, such as via a set of processor-executable instructions, for instance via machine code. In the first mode, transmitter 800, via the first antenna defines the pocket only. In the second mode, transmitter 800, via the second antenna, provides the network signal only. However, in some embodiments, the transmitter 800 includes a plurality of antennas, as described herein, such as at least two, defining the pocket of energy. In some embodiments, the plurality of antennas further provides the network signal. For example, such switch can be an A/B switch, whether manually switchable or automatically switchable, based on at least one input criteria, which can be remotely updateable. Note that transmitter 800 can be configured so that the communication network router functionality and the wireless power functionality are simultaneously operating, such as parallel operation, whether dependent or independent on each other, or only the communication network router functionality or the wireless power functionality operates at one time, such as serial operation, whether dependent or independent on each other.

In some embodiments, a device includes the first receiver and the second receiver. For example, an electronic device, such as a smartphone, includes the first receiver, embodied as a first hardware unit, as described herein, and the second receiver, embodied as a second hardware unit, such as a WI-FI card. Note that the first receiver is physically distinct from the second receiver, whether or not the first receiver is operably coupled to the second receiver. However, in other embodiments, a first device, such as a smartphone, includes the first receiver and a second device, such as a tablet computer, includes a second receiver. Yet, in other embodiments, the first receiver and the second receiver are one receiver, such as described herein.

In some embodiments, transmitter 800 includes a network communication unit, which can include the communication network router or be coupled to the communication network router, such as via wiring. Such unit can facilitate transmitter 800 in providing the network signal. Such unit can be implemented via hardware, such as a chip or an appliance, and/or software, such as a module or a software application, in any combination. Such unit can communicate in at least one of a wired manner and a wireless manner. Such unit includes at least one of a router, a network bridge, a firewall, a modem, a network switch, a printer server, or a network repeater. At least two of such components can be structurally distinct from each other or embodied as one unit. At least two of such components can be functionally distinct from each other or function as one unit.

The network bridge enables a connection, whether direct or indirect, such as a link, a path, a network, or a channel, between a plurality of communication networks for intercommunication there between. For example, a first network can be a wired network and a second network can be a wireless network, where the network bridge bridges the first network and the second network so that members of each of the first network and the second network can communicate with each other through the network bridge. Note that the first network and the second network can be of one type, such as based on a common protocol, such as Ethernet, or of different types, such as where the bridge translates a plurality of protocols. Also, note that the plurality of networks can be local to each other or remote from each other in any manner.

The firewall enables control, whether direct or indirect, of at least one of incoming network traffic and outgoing network traffic based on a set of rules applied thereon. For example, the firewall can operate as a barrier between a first network and a second network. The firewall can be network-layer based or a packet-filter based. The firewall can also be application-layer based. The firewall can also be proxy-server based. The firewall can also be network address translation based.

The modem enables signal modulation and signal demodulation. The modem can be a networking modem, such as a broadband modem, or a voice modem.

The network switch enables a connection, whether direct or indirect, of a plurality of devices together on a communication network via packet switching, such as based on a unique network address, for instance MAC address. The switch operates at least one level of an Open Systems Interconnection model (OSI) model, including at least one of a data link layer and a network layer. The network switch can be a multilayer switch. The network switch can be managed or unmanaged.

The print server enables a connection, whether direct or indirect, of a printer to a computer, such as a desktop computer or a laptop computer, over a network. The printer server can receive a print job from the computer, manage the job with other, if any, and send the job to the printer. In some embodiments, the print server is a networked computer. In some embodiments, the print server is a dedicated network device. In some embodiments, the print server is a software application.

The network repeater enables a regeneration or a retransmission of a signal at a higher level or a higher power than when received, such as due to a transmission loss. The network repeater can communicate such signal over an obstruction or extend a range of the signal. The network repeater can translate the signal from a first communication protocol to a second communication protocol. In some embodiments, transmitter 800 is configured for tethering, such as connecting one device to another. For example, transmitter 800 allows sharing of a network connection with another device, such as a tablet or a smartphone. Such tethering can be done over any type of network described herein. The tethering can be in a wired manner or a wireless manner.

In some embodiments, the network signal is encrypted, whether onboard or via another device. Such encryption can be performed via a symmetric key architecture, where an encryption key is identical to a decryption key. For example, the key can include alphanumeric or biometric information. However, the network communication signal is encrypted via a public key encryption architecture, such as comprising a public key and a private key, for instance a Pretty Good Privacy (PGP) method. The network signal can be encrypted automatically, such as via an algorithm, for instance a set of processor-executable instructions. However, the network signal can also be encrypted manually, such as via a user input. The network signal can be decrypted in a manner, as described herein. Also, transmitter 800 can include at least one of an encryption chip and a decryption chip to facilitate the provision of the encryption signal. Note that the encryption chip and the decryption chip can be embodied as at least one of a functional unit and a structural unit.

In some embodiments, transmitter 800 is configured to define the pocket via a signal path to the first receiver. The signal path is defined via transmitter 800 based at least in part on at least one of a gain information obtained from the second receiver and a phase information obtained from the second receiver. At least one of the gain information and the phase information can be obtained based on transmitter 800 providing the network signal, such as based at least in part on receiving a response from the second receiver.

In some embodiments, transmitter 800 defines the pocket of energy adaptively, as described herein, based on providing the network signal. Such adaption can be based at least in part on at least partially avoiding at least a wireless power wave obstacle portion, such as a chair, positioned between transmitter 800 and the first receiver. For example, transmitter 800 can define the pocket of energy via a signal path to the first receiver. The signal path is defined via transmitter 800 based at least in part on at least one of a gain information obtained from the second receiver and a phase information obtained from the second receiver, such as based at least in part on receiving a response from the second receiver. The at least partially avoiding is based at least in part on the signal path, as previously established.

In some embodiments, transmitter 800 defines the pocket of energy indoors, such as within a structure, for instance, a building, a tunnel, a vehicle, a hangar, a warehouse, a tent, an arena, or others. Such defining can be based at least in part on bouncing at least one of the wireless power waves from at least one of a floor, a wall extending from the floor, and a ceiling extending from the wall. For example, transmitter 800 can define the pocket of energy via a signal path to the first receiver. The signal path is defined via transmitter 800 based at least in part on at least one of a gain information obtained from the second receiver and a phase information obtained from the second receiver, such as based at least in part on receiving a response from the second receiver. The bouncing is at least until the signal path is defined. However, in other embodiments, transmitter 800 defines the pocket of energy outdoors, such as at a camp site, an air field, a vehicle, a stadium, a street, a yard, a park, a field, or others.

In some embodiments, transmitter 800 is configured to determine a position of the first receiver based at least in part on a signal triangulation of the second receiver, such as a cellular signal. Transmitter 800 defines the pocket of energy based at least in part on the position.

Figure 8B:
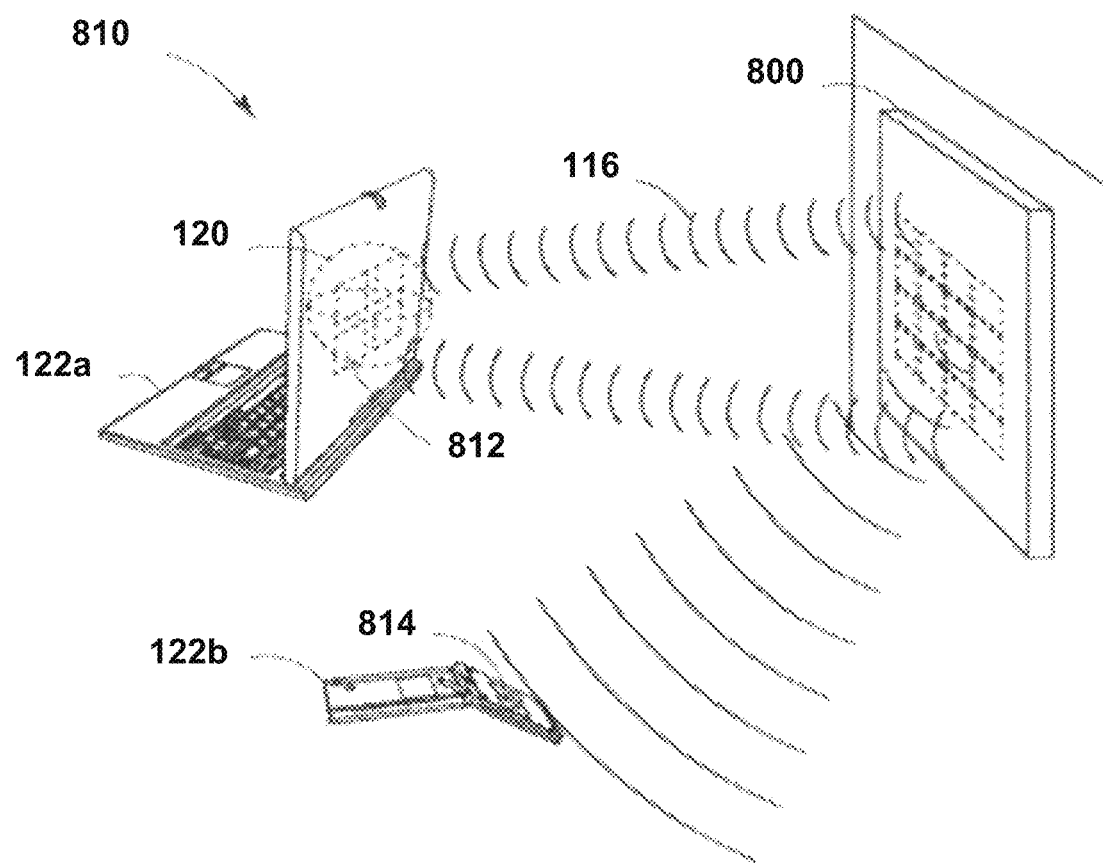
FIG. 8B illustrates a multi-mode transmitter defining a pocket of energy and providing a network signal, in accordance with some embodiments.

FIG. 8B illustrates an example embodiment 810 of a multimode transmitter defining a pocket of energy and providing a network signal.

Transmitter 800 outputs power waves 116 to define pocket of energy 812. Receiver 120 interfaces with pocket energy 812 to charge laptop computer 122a. Transmitter 800 also provides a network signal to phone 122b, which includes a network receiver 814 to interface with the network signal. Transmitter 800 determines which signal to output (network or power) through micro-controller (e.g., processor 104, FIG. 1), which, for example, receives a unique identifier, such as a MAC address of laptop computer 122a or phone 122b.

For example, once transmitter 800 identifies and locates receiver 120, a channel or path can be established by knowing the gain or the phases coming from receiver 120, as described herein. Transmitter 800 starts to transmit controlled power waves 116, via antenna elements 802 (FIG. 8B), which converge in 3-dimensional space. Power waves 116 are produced using power source (not shown) and a local oscillator chip using a suitable piezoelectric material. Power waves 116 are controlled by RFIC, which includes a chip for adjusting phase and/or relative magnitudes of RF signals, which serve as inputs for antenna elements 802 to form constructive and destructive interference patterns (pocket-forming). Pocket-forming may take advantage of interference to change the directionality of the antenna elements 802 where constructive interference generates pocket of energy 812 and destructive interference generates a null space. Receiver 120 utilizes pocket of energy 812 produced by the pocket-forming for charging or powering an electronic device, for example laptop computer 122a and thus effectively providing wireless power transmission using pocket-forming.

Transmitter 800 also identifies and locates receiver 814 from smartphone 122b. Smartphone 122b may request the network signal, such as a WI-FI signal. Therefore, transmitter 800 may send the requested network signal in parallel with the power waves 116 for powering laptop computer 122a.

In some embodiments, a network router, such as a WI-FI router, includes a housing, which houses transmitter 800 that outputs power waves 116 to define pocket of energy 812, as described herein, and a network signal, such as a WI-FI signal, as described herein. Such output can be concurrent or non-concurrent. The router can also be configured to provide a wired network connection, whether for a same network or a different network. The router can be used to wirelessly charge a first electronic device and to wirelessly provide network access to a second electronic device. Note that the first device and the second device can be one device or different devices. For example, the router can wirelessly charge a cellular phone, as described herein, and simultaneously provide an internet connection to the cellular phone, as described herein. Alternatively, transmitter 800 includes a WI-FI router or WI-FI circuitry which is configured to power a tablet computer and provide an internet connection to that tablet computer.

FIG. 8C illustrates a schematic diagram of an example embodiment of a multimode receiver. Thus, same reference characters identify identical and/or like components described above and any repetitive detailed description thereof will hereinafter be omitted or simplified in order to avoid complication.

Transmitter 800 includes power source 820, a network unit 822, and a security unit 824 operably interconnected with each other in any operational manner, whether directly or indirectly. Note that network unit 822 and security unit 824 can also be one unit. Network unit 822 includes the network communication unit, as described herein. Security unit 824 enables security operations, such as encryption or decryption, as described herein. For example, security unit 824 includes at least one of the encryption chip, the decryption chip, and the encryption-decryption chip. Power source 820 can operate as described herein. However, in other embodiments, power source 820 can also receive power, include, or be at least one of a mains electricity outlet, a wireless power receiver, as described herein, or an energy storage device, such as a battery. In some embodiments, transmitter 800 receives power, includes, or is a renewable energy source, such as a wind turbine, a liquid turbine, a photovoltaic cell, a geothermal turbine, or others. For example, transmitter 800 includes the renewable energy source or is coupled to the renewable energy source, whether directly or indirectly, whether locally or remotely. For example, the wind turbine can be at least one of a vertical axis turbine and a horizontal axis turbine, or others. The liquid turbine can be at least one of a reaction turbine or an impulse turbine, or others. The photovoltaic cell can be at least one of a silicon cell and a thin film cell, or others. The geothermal turbine can be steam-based or others.

FIGS. 8A-8C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 8A-8C.

Presented below an example of a multi-mode transmitter.

In some embodiments, a multi-mode transmitter includes a first antenna element and a second antenna element. Further, the transmitter is configured to emit a first signal by the first antenna element and a second signal by the second antenna element, where the first signal includes a plurality of wireless power waves establishing a pocket of energy. Moreover, the second signal is different from the first signal and the second signal provides WI-FI access.

In some embodiments, the transmitter includes an antenna array, and the antenna array includes the first antenna element and the second antenna element.

In some embodiments, the antenna array is defined via a first portion and a second portion, and the transmitter is configured to emit the first signal via the first portion, and the transmitter is configured to emit the second signal via the second portion.

In some embodiments, the first portion and the second portion are symmetrical geometrically.

In some embodiments, the first portion and the second portion are asymmetrical geometrically.

In some embodiments, the first portion includes a first plurality of antenna elements and the second portion includes a second plurality of antenna elements. Moreover, in some embodiments, the first plurality of antenna elements is numerically different from the second plurality of antenna elements. Alternatively, in some embodiments, the first plurality of antenna elements is numerically identical to the second plurality of antenna elements.

In some embodiments, the transmitter is configured to switch between a first mode and a second mode, and the transmitter is configured to emit the first signal during the first mode only and the second signal during the second mode only.

In some embodiments, the transmitter is configured to emit the first signal to a first receiver and the second signal to a second receiver, and a device includes the first receiver and the second receiver.

In some embodiments, the transmitter is configured to emit the first signal to a first receiver coupled to a first device and the second signal to a second receiver coupled to a second device different from the first device.

In some embodiments, the transmitter is configured to emit the first signal to a first receiver and the second signal to a second receiver, and the first receiver and the second receiver are one receiver.

In some embodiments, the transmitter includes a third antenna element, and the transmitter is configured to emit the first signal concurrently by the first antenna element and the third antenna element.

In some embodiments, the second signal provides WI-FI access by providing a device that receives the second signal with an internet connection.

Figure 9A:
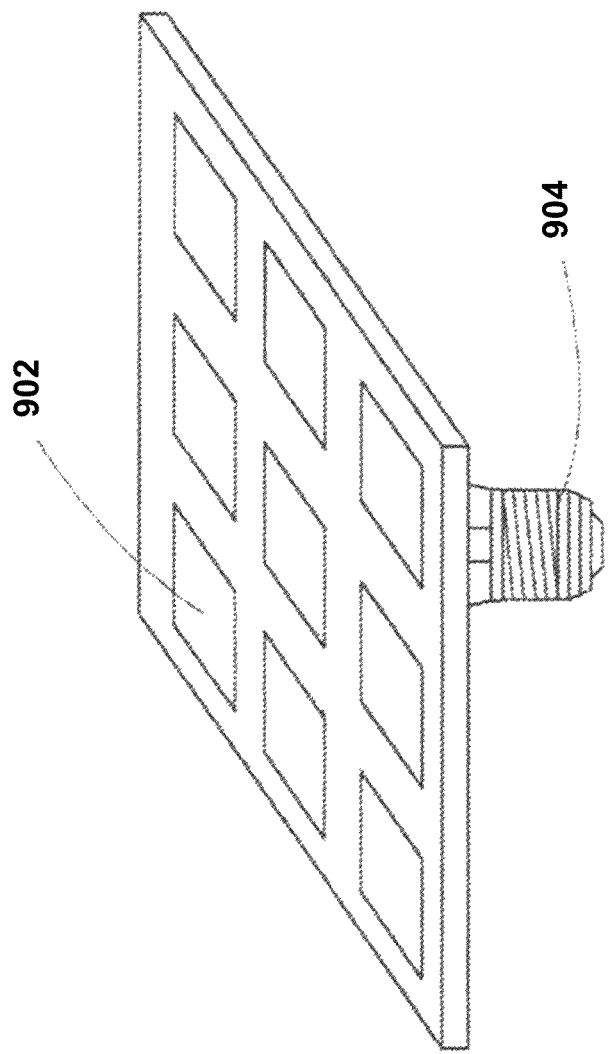
FIG. 9A illustrates a transmitter having a screw cap for power coupling, in accordance with some embodiments.
Figure 9B:
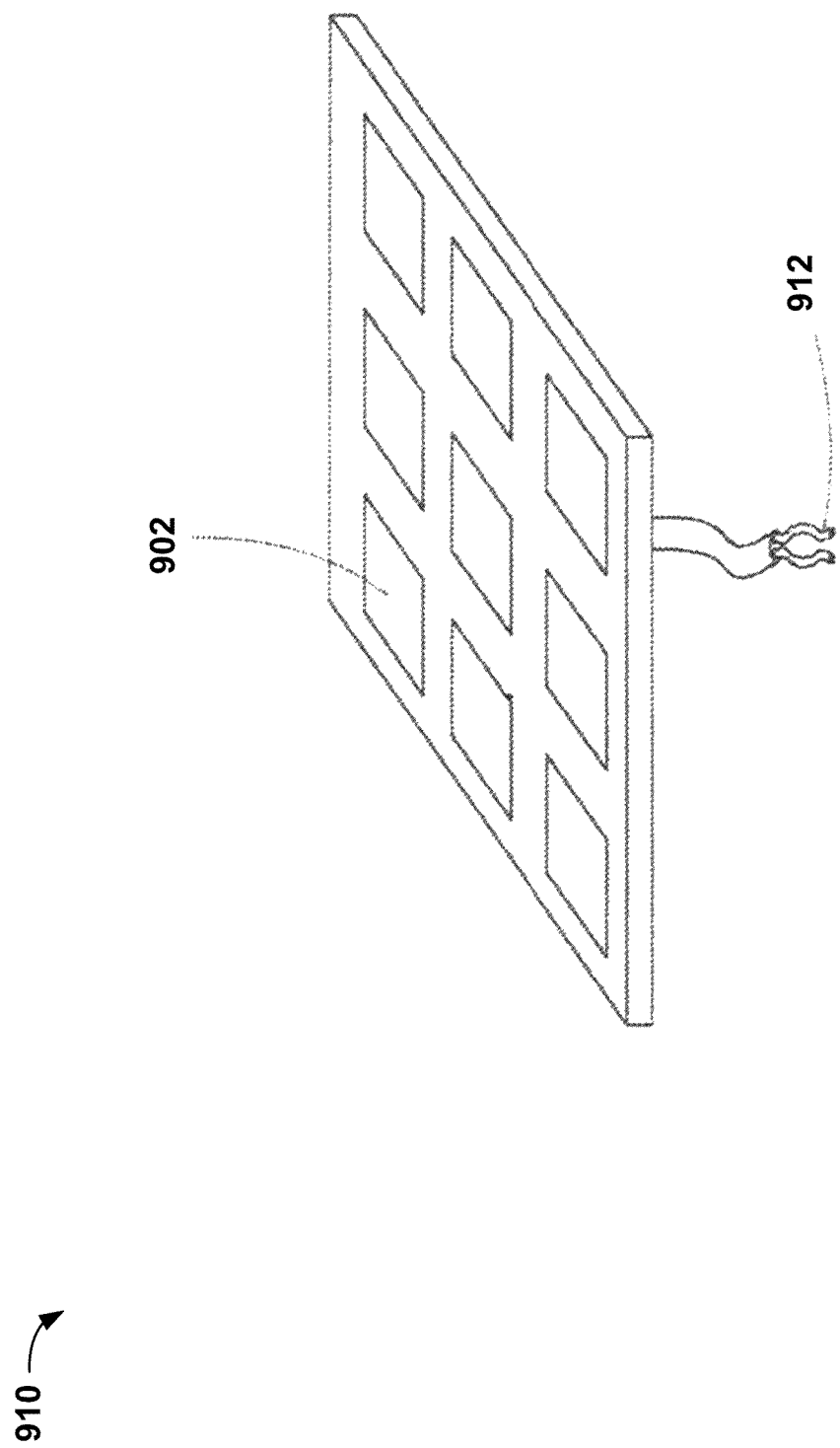
FIG. 9B illustrates a transmitter having bare wires for power coupling, in accordance with some embodiments.
Figure 9C:
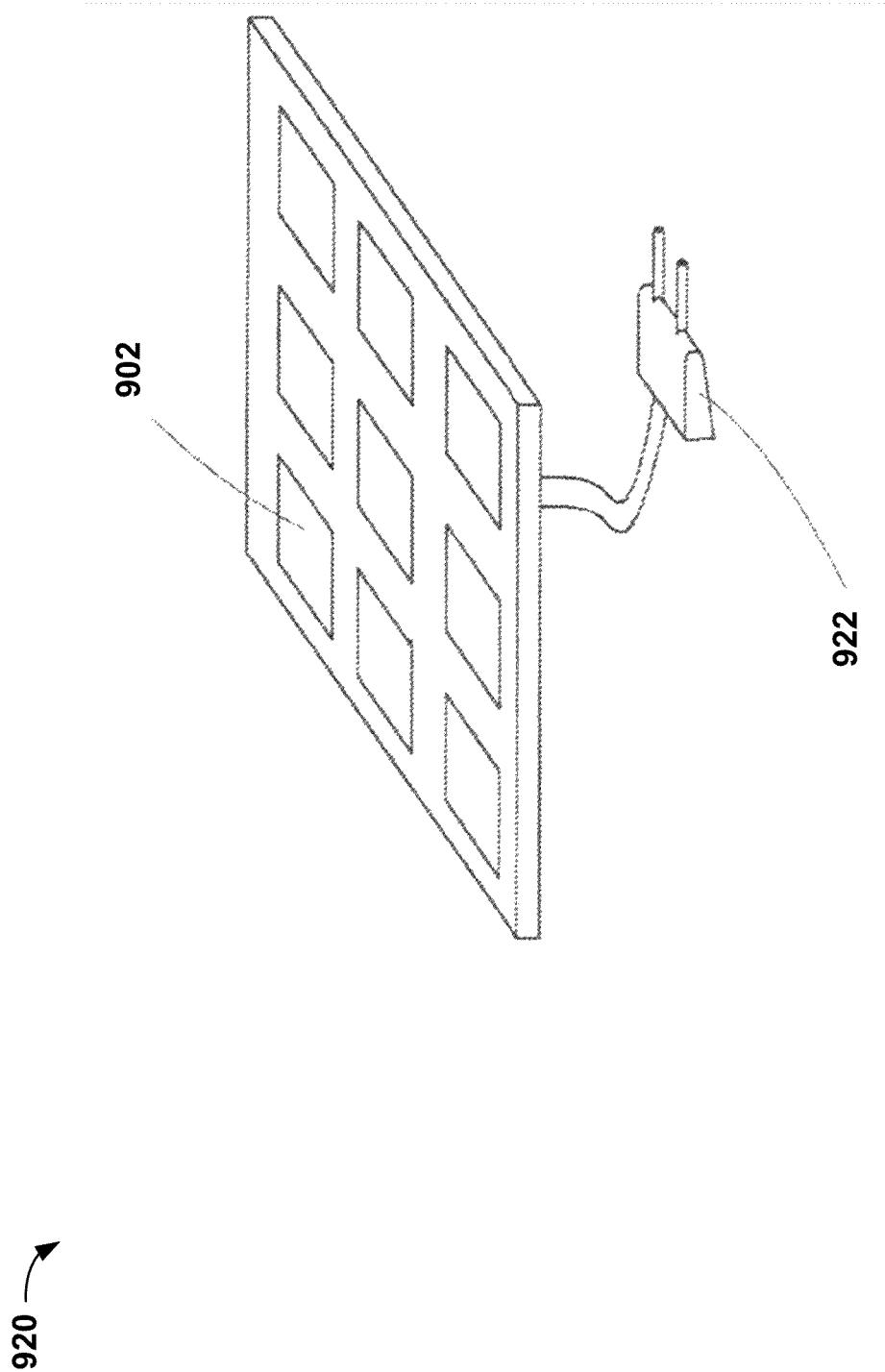
FIG. 9C illustrates a transmitter having a power plug for power coupling, in accordance with some embodiments.

FIGS. 9A-9C illustrate various power couplings for transmitters used in wireless power transmission systems, in accordance with some embodiments.

FIG. 9A depicts a flat transmitter 900 (e.g., an embodiment of the transmitter 102, FIG. 1) of a predetermined size to fit into a number of spaces, which includes antenna elements 902. Transmitter 900 includes a screw cap 904. Screw cap 904 connects the transmitter 900 to a light socket, wherein the light socket operates as a power source for the transmitter 900.

Screw cap 904 may include a variety of electronics devices, such as, capacitors, inductors, power converters and the like. Such electronic devices may be intended for managing the power source, which feeds transmitter 900.

Furthermore, transmitter 900 including screw cap 904 as power connection may increase versatility of transmitter 900, because transmitter 900 is able to be located in every place where a screw cap 905 is received by a light socket.

Transmitter 900 includes several shapes which may vary in dependence with final application and user preferences.

FIG. 9B depicts a flat transmitter 910 (e.g., an embodiment of the transmitter 102, FIG. 1), which includes antenna elements 904. Transmitter 910 includes a cable 912 with a pair of wires for connection to the power source. Power source includes an electrical service in a building or mobile vehicle and the like.

Cables 912 include labels of positive and negative cables in case of connecting to a DC current power source and/or ILA and L2 cables in case of AC current power source. Furthermore, more cables may be included, and such cables may be for three-phase power source and a ground cable connection.

Transmitter 910 includes a variety of electronics devices, such as, capacitors, inductors, power converters and the like. Such electronic devices may be intended for managing the power source which may feed transmitter 910.

Transmitter 910 is located in several places due to the cables 912, which may be connected to any power source, and such power source may be AC or DC in dependence with final application and user preferences.

Transmitter 910 includes several shapes which may vary in dependence with final application and user preferences.

FIG. 9C depicts a transmitter 920 (e.g., an embodiment of the transmitter 102, FIG. 1) which includes antenna elements 902 in a flat arrangement. Transmitter 920 is connected to a power source through one or more power plug 922. Such power plug 922 complies with the standard of each country and/or region. Power plug 922 is intended to connect transmitter 920 to one or more power outlet on the walls, floors, ceilings and/or electric adapters.

Transmitter 920 includes a variety of electronics devices, such as capacitors, inductors, power converters and the like. Such electronic devices are intended for managing the power source which feeds transmitter 920.

Transmitter 920 includes several shapes which may vary in dependence with final application and user preferences.

FIGS. 9A-9C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 9A-9C.

Presented below is an example method of coupling a transmitter to a power source.

In some embodiments, an example method includes receiving, by an antenna of a receiver coupled to the electronic device, pockets of energy generated in response to RF waves emitted by a pocket-forming transmitter coupled to a power source through a power coupling and converting, by a rectifying circuit of the receiver, the received pockets of energy into electricity to charge the electronic device.

In some embodiments, the power coupling of the transmitter includes an Edison screw cap for insertion into a light socket connected to the power source, and the power source is an electrical service available to a user of the electronic device.

In some embodiments, the power coupling of the transmitter includes a cable with a pair of wires for connection to the power source, and the power source is an electrical service available to a user of the electronic device.

In some embodiments, the power coupling of the transmitter includes an electrical plug for insertion into a socket connected to the power source, and the power source is an electrical service available to a user of the electronic device.

Figure 10C:
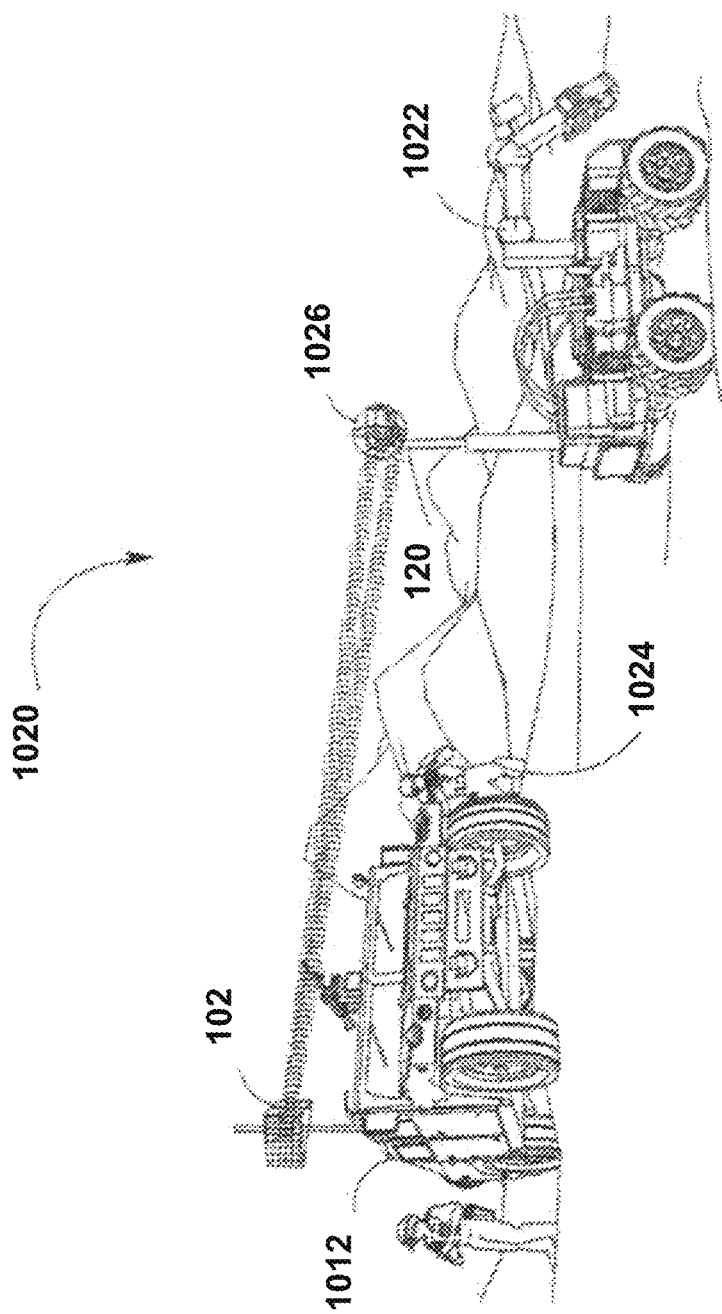

FIGS. 10A-10C illustrate wireless power transmission systems used in military applications, in accordance with some embodiments.

FIG. 10A is an example embodiment of a power distribution system 1000 in a military camp where troops may be settled in remote locations. Power distribution system 1000 may include a mobile power generator 1002, which may serve to power electrical equipment. Mobile power generator 1002 may be a mobile diesel generator or other sources such as solar photovoltaic arrays, wind turbines or any reliable power source or combination thereof coupled with mobile power generator 1002. The power generator 1002 is configured to power a transmitter 102, which may enable wireless power transmission. Transmitter 102 may use mobile power generator 1002 as a power source to form pockets of energy. Pockets of energy may form at constructive interference patterns and can be 3-dimensional in shape whereas null-spaces may be generated at destructive interference patterns. Electrical devices 1004 such as radios, laptops or any devices requiring a power input may be coupled with a receiver 120 (not shown). Receiver 120 may then utilize pockets of energy produced by pocket-forming for charging or powering electrical devices 1004.

Transmitter 102 may form pockets of energy covering a range from about a few feet to hundreds of feet depending on the size of the antenna array. For the foregoing application, about 30 to about 60 feet may suffice. Additional transmitters 102 may be used to extend the distance in a power distribution system. A central transmitter 102 coupled with mobile power generator 1002 may serve as a central distribution center while additional transmitters 102 may be placed at a distance and retransmit energy received from the central transmitter to reach greater distances. Each transmitter 102 size may be relative to the desired transmission distance.

FIG. 10B is another example embodiment of a power distribution system 1010. A transmitter 102 coupled with a mobile power generator 1002 may be mounted over a military vehicle 1012 in order to add mobility. Military vehicle 1012 may be any vehicle with enough robustness and ruggedness for battlefield applications such as a high mobility multi-purpose wheeled vehicle (HMMWV/Humvee) armored trucks, tanks or any vehicle capable of carrying transmitter 102 coupled with mobile power generator 1004. Military vehicle 1012 may accompany soldiers into the battlefield and serve as a power source for electrical devices 1004 carried by soldiers. Electrical devices 1004 carried by soldiers may be coupled with receivers 120 (not shown in FIG. 10B) in order to receive energy from transmitter 102.

FIG. 10C is another embodiment of power distribution system 1020 where remote controlled vehicles 1022 designed for espionage, detecting mines or disabling bombs may be powered wirelessly. In this embodiment, remote control and power may be critical factors to prevent exposure or harm to human soldiers 1024. Remote controlled vehicle 1022 may be coupled with a receiver 120. A transmitter 102 coupled with a mobile power generator 1004 may form pockets of energy 1026 at constructive interference patterns that may be 3-dimensional in shape whereas null-spaces may be generated at destructive interference patterns. A receiver 120 may then utilize pockets of energy 1026 produced by pocket-forming for charging or powering remote controlled vehicle 1022.

FIGS. 10A-10C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 10A-10C.

Presented below are example systems and methods of wireless power transmission in military applications.

In some embodiments, an example method includes: (i) communicating, by a receiver associated with a mobile electronic device, a security code to a transmitter coupled to a power source, the transmitter configured to recognize the security code; (ii) receiving, by an antenna of the receiver associated with the mobile electronic device, a pocket of energy generated in response to transmission signal waves emitted by the transmitter, the transmission signal waves being emitted upon recognition of the security code by the transmitter; and (iii) charging, by the receiver, the mobile electronic device, the receiver including a rectifying circuit to convert the received pocket of energy into electricity.

In some embodiments, the power source is one or more of a mobile diesel generator, a mobile gasoline generator, solar panels, and wind turbines.

In some embodiments, the method further includes charging, by the receiver, the mobile electronic device by establishing a path for the pocket of energy to converge in 3-dimensional space upon an antenna of the receiver. The antenna of the receiver is in communication with an antenna of the transmitter and the antenna of the transmitter is broadcasting the transmission signal waves.

In some embodiments, the transmitter includes a plurality of antennas, a radio frequency integrated circuit, and a processor configured to implement security logic and a communications component.

In some embodiments, the method further includes receiving, by the receiver associated with the mobile electronic device, the pocket of energy generated in response to transmission signal waves emitted by a secondary transmitter, the transmission signal waves being emitted by a secondary transmitter in response to the transmission signal waves emitted by the transmitter.

In some embodiments, the receiver receives the pocket of energy from the transmitter and is switched to the secondary transmitter to continue charging the mobile electronic device.

In some embodiments, the pocket of energy is regulated by utilizing adaptive pocket-forming.

In some embodiments, the power source is a mobile generator mechanically coupled to the transmitter and configured to extend reach of the transmission signal waves emitted by transmitter.

In some embodiments, the receiver is in a remote controlled vehicle.

In some embodiments, another example method includes, at a receiver having a communications component, at least one antenna element, and a rectifying circuit: (i) communicating, by the communications component of the receiver, a communications signal, which includes a security code, to a transmitter coupled to a power source, and the transmitter is configured to recognize the security code; (ii) receiving, by the at least one antenna element of the receiver, energy from a plurality of power transmission waves that forms a constructive interference pattern proximate to a location of the receiver, and the transmitter transmits the plurality of power transmission waves in response to recognizing the security code communicated to the transmitter by the receiver; and (iii) charging, using electricity generated by the rectifying circuit using the energy from the plurality of power transmission waves received by the at least one antenna element of the receiver, an electronic device that is coupled with the receiver.

In some embodiments, the transmitter includes a plurality of antennas, a radio frequency integrated circuit, a processor configured to implement a security logic used to recognize the security code, and a communications component.

In some embodiments, the transmitter, in response to recognizing the security code communicated to the transmitter by the receiver: (i) transmits the plurality of power transmission waves to form the constructive interference pattern in proximity to the receiver in response to determining that the receiver is within range of the transmitter; and (ii) transmits the plurality of power transmission waves to a secondary transmitter, that is distinct and separate from the transmitter, in response to determining that the receiver is outside the range of the transmitter, and the secondary transmitter re-transmits the plurality of power transmission waves that forms the constructive interference pattern proximate to the location of the receiver.

In some embodiments, an example system for secured wireless charging of a mobile electronic device includes: (i) a mobile electronic device coupled to a receiver; (ii) the receiver configured to communicate a security code to a transmitter; and (iii) the transmitter configured to: receive the security code from the receiver; recognize, using security logic of the transmitter, the security code; and in response to recognizing the security code, transmit a plurality of power transmission waves that forms a constructive interference pattern proximate to a location of the receiver. The receiver is further configured to: receive, via an antenna element of the receiver, energy from the plurality of power transmission waves; and charge, using electricity generated using the energy from the plurality of power transmission waves received by the antenna element of the receiver, the mobile electronic device.

In some embodiments, the system further includes a secondary transmitter distinct and separate from the transmitter. The transmitter is further configured to, in response to determining that the receiver is outside a range of the transmitter, transmit the plurality of power transmission waves to the secondary transmitter; and the secondary transmitter is configured to re-transmit the plurality of power transmission waves that form a constructive interference pattern proximate to the location of the receiver.

In some embodiments, another example method includes, at a transmitter having a communications component, at least one processor, and a plurality of antenna elements: (i) receiving, by the communications component, a communication signal from a receiver that includes a security code; (ii) analyzing via the at least one processor, using security logic of the transmitter, the security code received from the receiver; and (iii) in response to recognizing the security code, transmitting, by at least some of the plurality of antenna elements, a plurality of power transmission waves that forms a constructive interference pattern proximate to a location of the receiver. In some embodiments, at least one antenna element of the receiver receives energy from the plurality of power transmission waves transmitted by the transmitter; and the receiver, using electricity generated from the plurality of power transmission waves received from the transmitter, charges or powers an electronic device that is coupled with the receiver.

In some embodiments, the plurality of power transmission waves is a plurality of RF power transmission waves.

In some embodiments, the transmitter is a far-field transmitter.

Figure 11A:
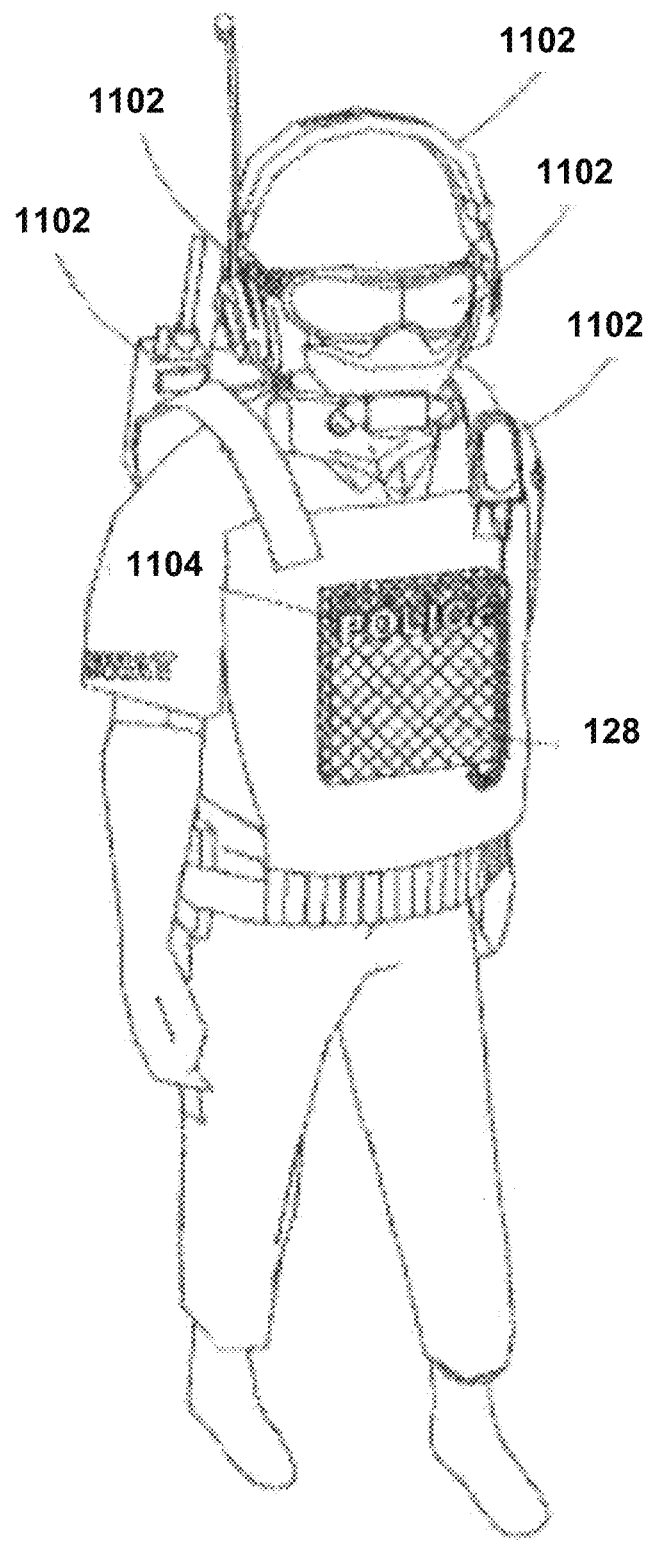
FIG. 11A illustrates a law enforcement officer wearing a uniform with an integrated wireless power receiver, in accordance with some embodiments.
Figure 11B:
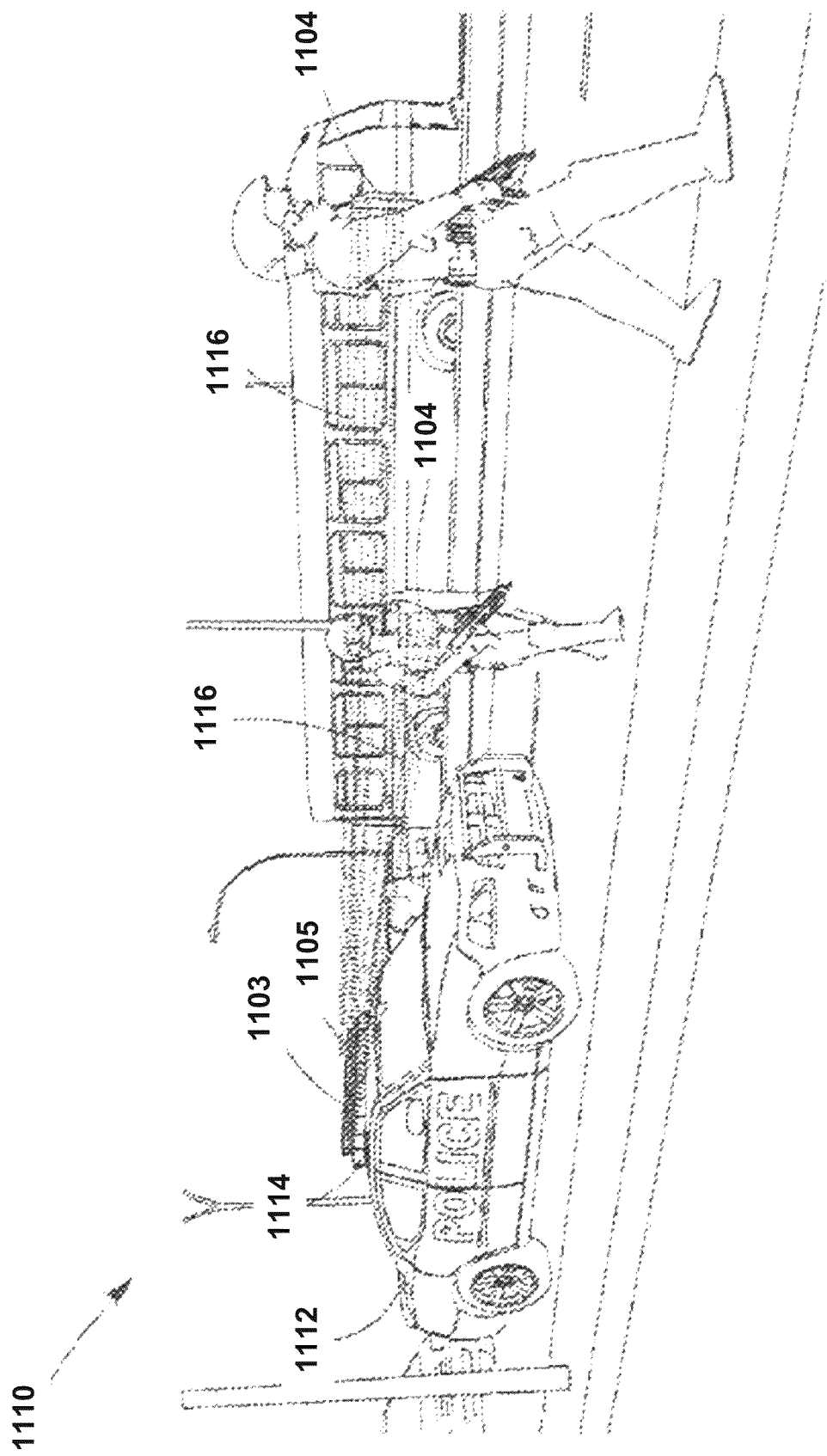
FIGS. 11B-11D illustrate wireless power transmitters integrated with various types of mobile law enforcement equipment (e.g., a police squad car and a SWAT team vehicle) for use in conjunction with law enforcement operations, in accordance with some embodiments.
Figure 11C:
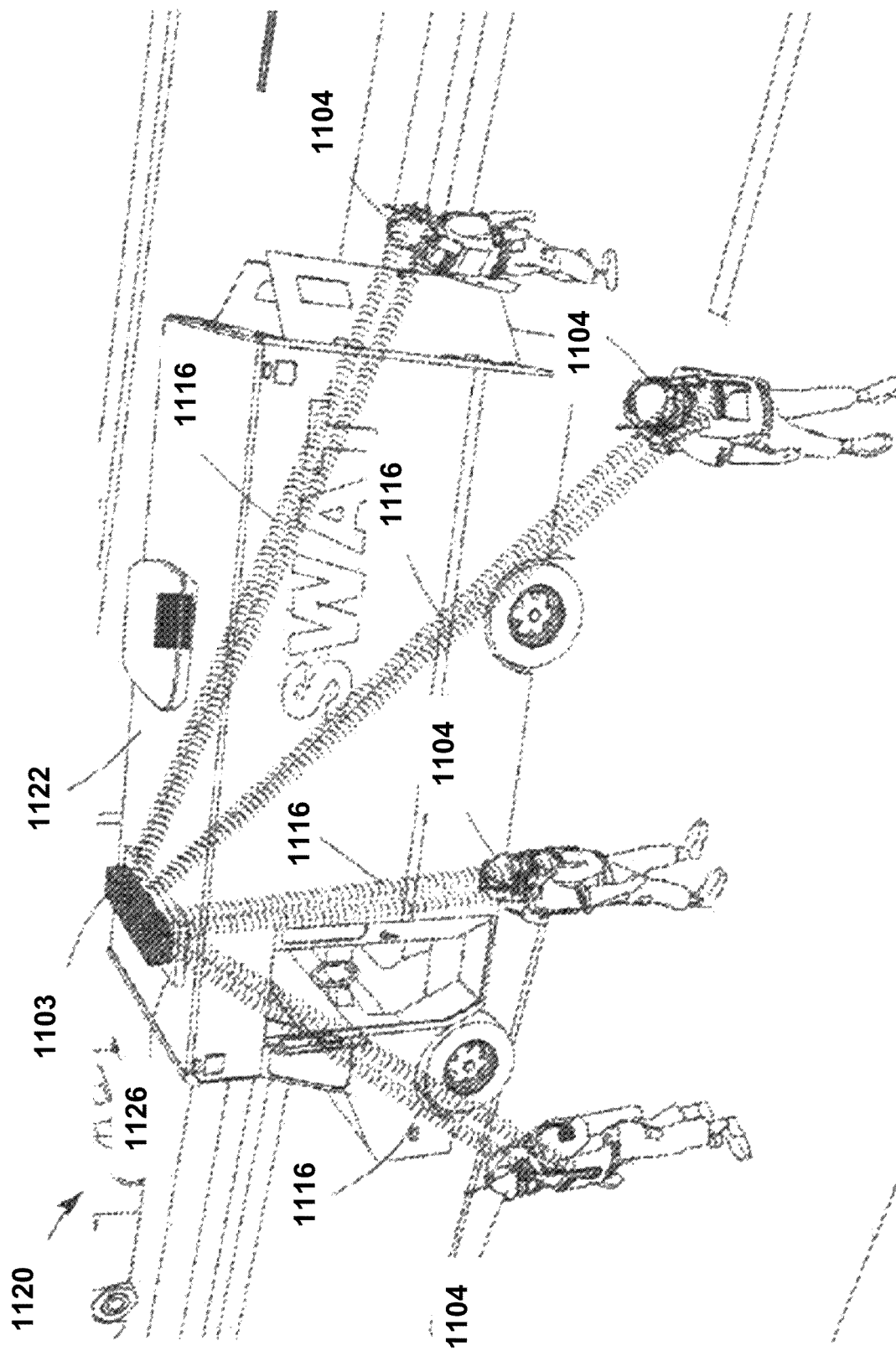
Figure 11D:
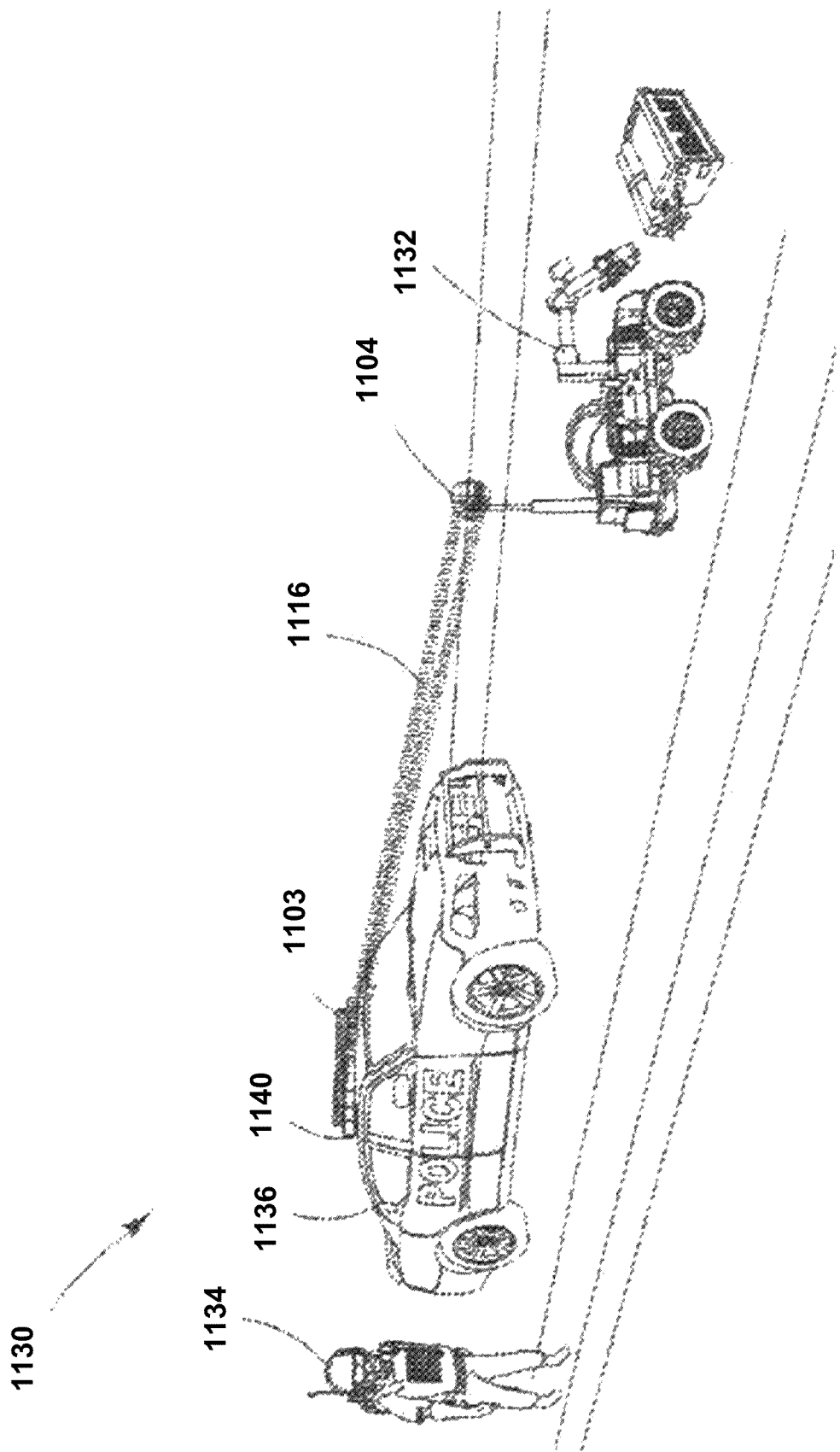

FIG. 11A illustrates a law enforcement officer wearing a uniform with an integrated wireless power receiver, in accordance with some embodiments.

In FIG. 11A, a law enforcement officer is wearing a uniform with an integrated receiver 1104. Uniform with an integrated receiver 1104 (e.g., an embodiment of the receiver 120, FIG. 1) may include electrical devices 1102 such as radios, night vision goggles, and wearable cameras among others. Electrical devices 1102 may be coupled to receiver 1104 through wires strategically distributed in the uniform. Receiver 1104 may then have an array of sensor elements 128 distributed thereon.

FIGS. 11B-11D illustrate wireless power transmitters integrated with various types of mobile law enforcement equipment (e.g., a police squad car and a SWAT team vehicle) for use in conjunction with law enforcement operations, in accordance with some embodiments.

FIG. 11B illustrates a mobile power source 1110 for police officers wearing uniforms with an integrated receiver 1104. Mobile power source 1100 may also serve electrical devices 1102 coupled with receivers 1104 independently. In some embodiments, a police car 1112 may include a transmitter 1103 (e.g., an embodiment of the transmitter 102, FIG. 1) which may be placed on top of siren 1114. Transmitter 1103 may be coupled to any suitable battery management system in police car 1112 to get the power necessary to enable wireless power transmission. Transmitter 1103 may include an array of transducer elements 1105 which may be distributed along the edge of the structure located on top of siren 1114. Transmitter 1103 may then transmit controlled RF waves 1116 which may converge in 3-dimensional space. These RF waves 1116 may be controlled through phase and/or relative amplitude adjustments to form constructive and destructive interference patterns (pocket-forming). Uniforms with an integrated receiver 1104 may then utilize pockets of energy produced by pocket-forming for charging or powering electrical devices 1102.

FIG. 11C illustrates a mobile power source 1120 for specialized police officers wearing uniforms with an integrated receiver 1104. Mobile power source 1120 may also serve electrical devices 1102 coupled with receivers 1104 independently. In FIG. 11C, a SWAT Mobile Command Truck 1122 may include a transmitter 1103 which may be placed on top of siren 1126. Transmitter 1103 may be coupled to any suitable battery management system in SWAT Mobile Command Truck 1122 to get the power necessary to enable wireless power transmission. Transmitter 1103 may include an array of transducer elements 204 which may be distributed along the edge of the structure located on top of siren 1126. Transmitter 1103 may then transmit controlled RF waves 1116 which may converge in 3-dimensional space. These RF 1116 may be controlled through phase and/or relative amplitude adjustments to form constructive and destructive interference patterns (pocket-forming). Uniforms with an integrated receiver 1104 may then utilize pockets of energy produced by pocket-forming for charging or powering electrical devices 1102.

FIG. 11D illustrates a mobile power source 1130 for remote controlled vehicles 1132 designed for espionage, detecting mines or disabling bombs that may be powered wirelessly. In this embodiment, remote control and power may be critical factors to prevent exposure or harm to police officers 1134. In some embodiments, a police car 1136 may include a transmitter 1103, which may be placed on top of siren 1140. Transmitter 1103 may be coupled to any suitable battery management system in police car 1136 to get the power necessary to enable wireless power transmission. Transmitter 1103 may include an array of transducer elements 1105, which may be distributed along the edge of the structure located on top of siren 1140. Transmitter 1103 may then transmit controlled RF waves 116, which may converge in 3-dimensional space. These RF waves 1116 may be controlled through phase and/or relative amplitude adjustments to form constructive and destructive interference patterns (pocket-forming). Remote controlled vehicle 1132 may be coupled with the receiver 1104. The receiver 1104 may then utilize pockets of energy produced by pocket-forming for charging or powering remote controlled vehicle 1132.

In summary, law enforcement officers may be required to carry a great deal of equipment which in most cases are electrical devices, the wireless power distribution system disclosed here may charge or power the electrical devices wirelessly. In some embodiments, the wireless power distribution system may include at least one transmitter coupled with any suitable battery management system in a Law Enforcement vehicle, in other embodiments, a Law Enforcement uniform may be coupled with wireless receiver components that may use the pockets of energy to charge or power the electrical devices.

FIGS. 11A-11D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 11A-11D.

Presented below are example systems and methods of wireless power transmission in law enforcement applications.

In some embodiments, an example method for wireless power transmission for electrical devices used by law enforcement equipment is provided. The method includes: emitting RF waves from a pocket-forming transmitter each having an RF wave; integrated circuit, transducer elements, and communication circuitry; generating pockets of energy from the transmitter to converge in 3-dimensional space at predetermined locations within a predefined range; incorporating a receiver within a law enforcement uniform; attaching the electrical devices to the receiver; and convening the pockets of energy in 3-dimensional space from the transmitter to the receiver located within the law enforcement uniform to charge or power the electrical devices. In some embodiments, the electrical devices are radios, night vision goggles, wearable cameras, flashlights, sensors and other portable law enforcement electrical devices for use in law enforcement. In some embodiments, the electrical devices are coupled to the receiver through wires strategically distributed in the uniform. In some embodiments, the transmitter and receiver include transducer and sensor elements, respectively.

In some embodiments, an example apparatus for wireless power receipt by a law enforcement equipment device includes: a receiver configured to be removably coupled to an article of clothing and configured to communicate a security code to a transmitter, the receiver comprising: an antenna configured to receive a pocket of energy, the pocket of energy being generated in response to power transmission waves from the transmitter, the power transmission waves being transmitted upon recognition of the security code by the transmitter; and a rectifying circuit configured to convert the received pocket of energy into electricity to charge a law enforcement equipment removably coupled to the article of clothing.

In some embodiments, the receiver further communicates to the transmitter information including an identification, a location, and an indication of the power level of the law enforcement equipment.

In some embodiments, the antennas of the receiver are arranged as an array integrated into the article of clothing.

It should be noted that the embodiments described above in FIGS. 10A-10C equally apply to the embodiments shown in FIGS. 11A-11D.

FIGS. 12A-12D illustrate tracking systems that upload data to a cloud-based service for use in conjunction with wireless power transmission systems, in accordance with some embodiments.

Figure 12A:
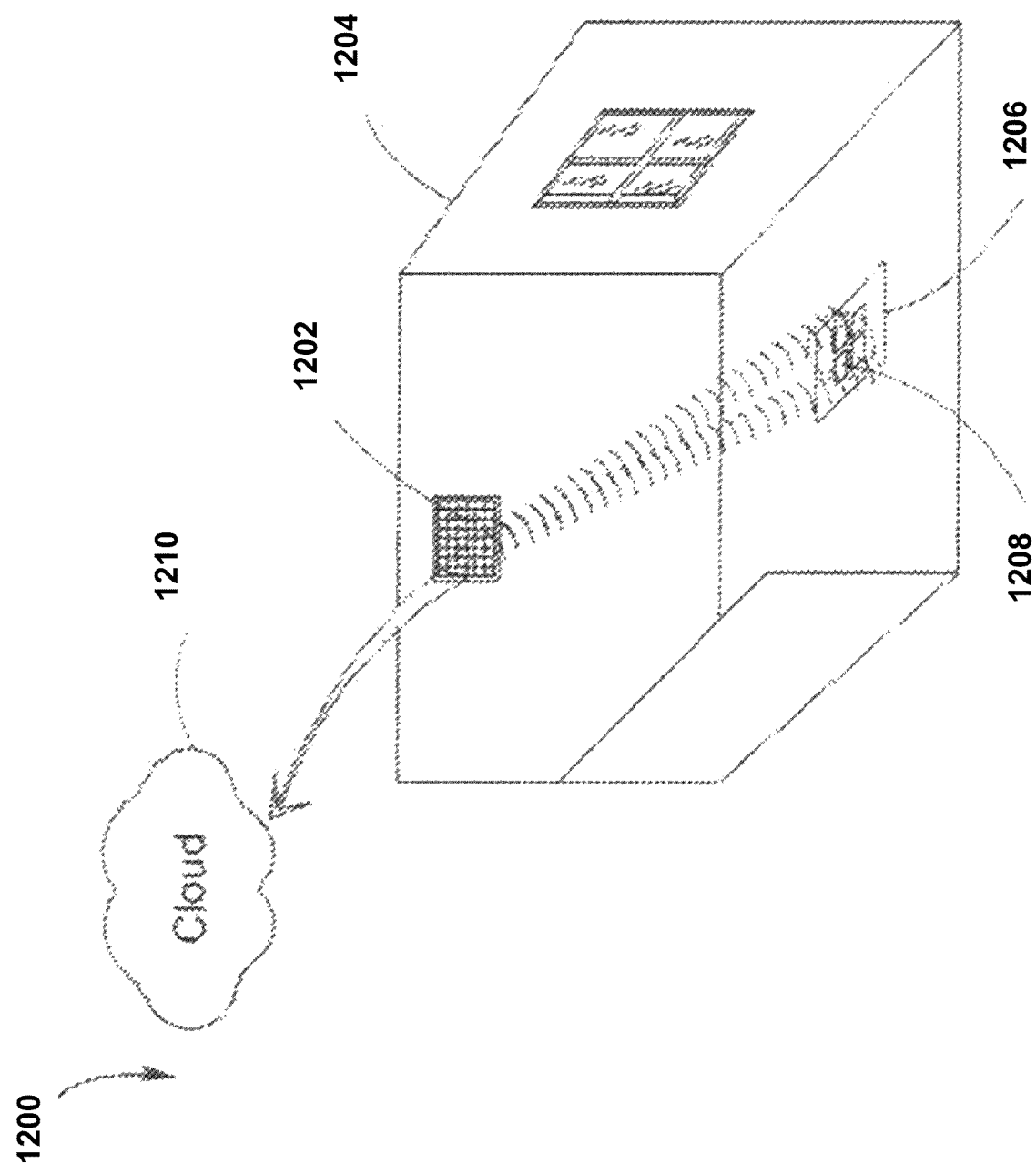
FIGS. 12A-12D illustrate tracking systems that upload to a cloud-based service for use in conjunction with wireless power transmission systems, in accordance with some embodiments.

FIG. 12A shows a wireless tracking system 1200 for determining the location of objects or living beings. In some embodiments, wireless tracking system 1200 may be applied in a wireless power transmission system using pocket-forming techniques. Transmitter 1202 (e.g., an embodiment of the transmitter 102, FIG. 1) may be in house 1204 placed on a suitable location, such as on a wall, for an effective wireless power transmission to electronic device 1206. Objects or living beings may use an electronic device 1206 with embedded or adapted receiver 1208. Receiver 1208 (e.g., an embodiment of the receiver 120, FIG. 1) may include components described in FIG. 1 and transmitter 1202 may also include components described in FIG. 1.

While transmitter 1202 may charge or power receiver 1208, micro-controller 208 (from transmitter 1202) may be able to process information provided by communications component from receiver 1208, as described above. This information may be repeatedly uploaded to a cloud-based service 1210 to be stored in a database in determined intervals of time. Through data stored in database, the information may be read through a suitable interface such as computer software from any suitable computing device and from any suitable location. Transmitter 1202 may use a unique identifier of receiver 1208 for identifying and tracking electronic device 1206 from other devices. The unique identifier of receiver 1208 may be according to the type of communications component that may be used in receiver 1208; for example, if a protocol is used, the MAC address may be the unique identifier. This unique identifier may allow the information of electronic device 1206 with receiver 1208 to be mapped and stored in the database stored in cloud-based service 1210. Other unique identifiers may include International Mobile Equipment Identity (IMEI) numbers, which usually include a 15-digit unique identifier associated with all GSM, UNITS and LTE network mobile users; Unique Device ID (UDID) from iPhones, iPads and Mods, comprising a combination of 40 numbers and letters set by Apple; Android ID, which is set by Google and created when a user first boots up the device; or International Mobile Subscriber Identity (IMSI), which is a unique identification associated with the subscriber identity module (SIM). Furthermore, a user may be able to obtain user credentials to access the database stored in a private or public cloud-based service 1210 to obtain the information of receiver 1208. In some embodiments, cloud-based service 1210 may be public when the service, provided by the same transmitter 1202 or wireless manufacturer, is utilized in the public network by using only the user credentials for obtaining the desired information. And, cloud-based service 1210 may be private when transmitter 1202 may be adapted to a private network that has more restrictions besides user credentials.

In some embodiments, in order to track the location of a determined living being or object, a cloud-based service 1210 may be suitable for finding the location of receiver 1208. For example, when receiver 1208 may not be in house 1204, a user may be able to access with user credentials a suitable interface such as an Internet explorer, to visually depict the places where receiver 1208 was located, using information uploaded in database from the cloud-based service 1210. Also, if receiver 1208 may reach power or charge from another transmitter 1202 located in public establishments such as stores, coffee shops, and libraries, among others, the information may be uploaded to cloud-based service 1210, where the user may also be able to depict the information stored in the cloud-based service 1210.

In some embodiments, wireless tracking system 1200 may be programmed to send notifications when living beings or objects are not in the place where it/she/he has to be. For example, if a cat is not at owner's home, a notification such as an interactive message may be sent to a cellphone notifying that the cat is not at home. This interactive message service may be adapted to cloud-based service 1210 as an extra service. The interactive message may be optionally sent to an e-mail or to computer software as it may be desired. Furthermore, additional information may be included in the interactive message such as current location, time, battery level of receiver 1208, among other types of data.

In some embodiments, wireless tracking system 1200, may operate when receiver 1208 includes at least one audio component, such as a speaker or microphone, which may enable location determination via sonic triangulation or other such methods.

In some embodiments, transmitter 1202 may be connected to an alarm system which may be activated when receiver 1208 is not located in the place where it has to be.

Figure 12B:
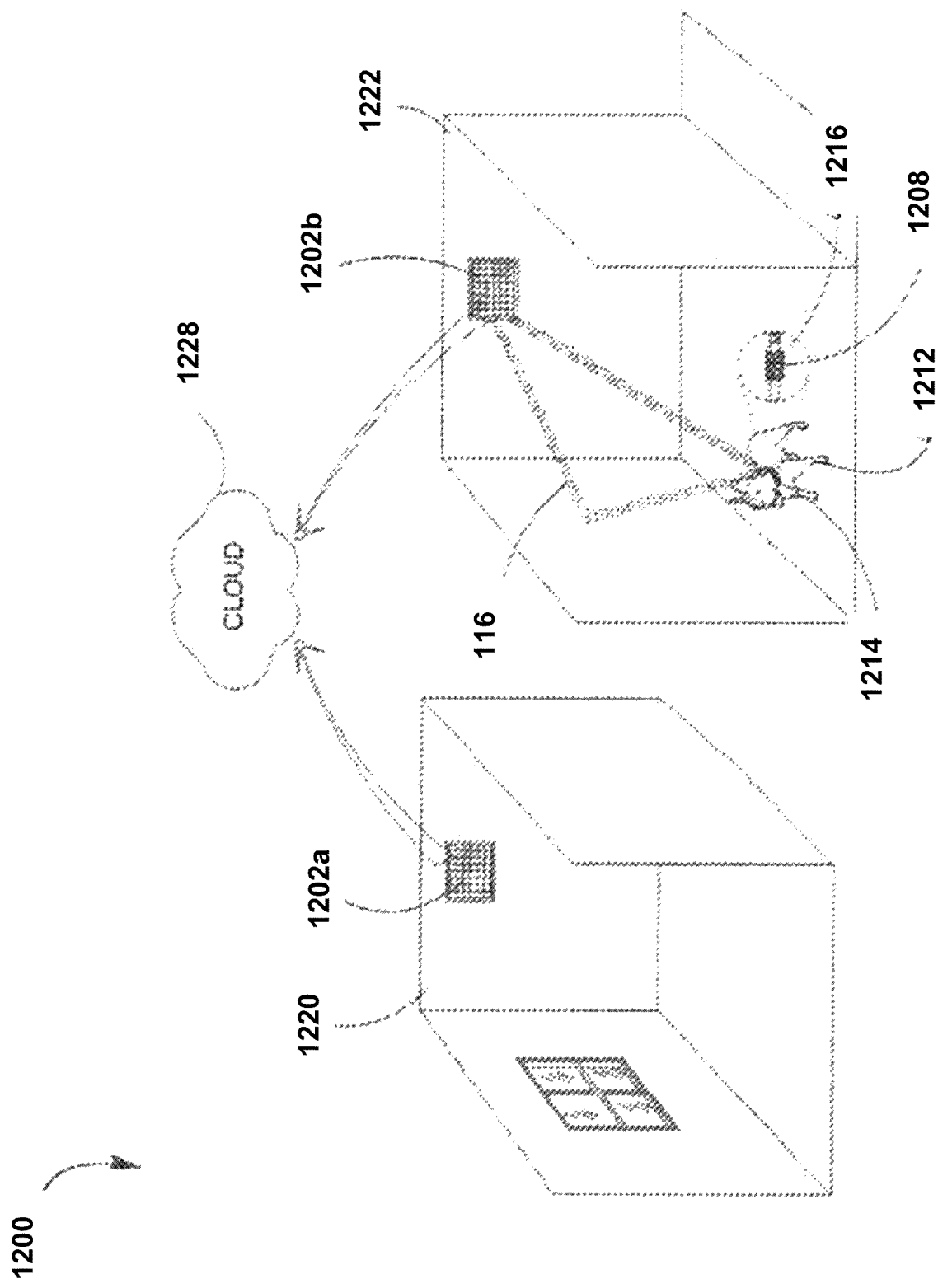

In one example, FIG. 12B shows a wireless tracking system 1200 for tracking the location of a dog 1212. In some embodiments, dog 1212 is wearing a necklace collar 1214 that may include an integrated chip 1216 with an embedded receiver 1208. Dog 1212 may be outside first room 1220 and inside second room 1222. First room 1220 may be the place where dog 1212 lives; however dog 1212 escaped and arrived at second room 1222 (e.g., a coffee shop). In first room 1220, a first transmitter 1202*a* (e.g., an embodiment of the transmitter 102, FIG. 1) is hanging on a wall, and in second room 1222, a second transmitter 1202*b* (e.g., an embodiment of the transmitter 102, FIG. 1) is hanging on a wall. First transmitter 1202*a* detects that dog 1212 is not at home, here the interruption of RF waves 116 transmission to receiver 1208 from necklace collar 1214 allows first transmitter 1202*a* to detect the absence of dog 1212 in first room 1220. In some embodiments, the type of communication component to communicate first transmitter 1202*a* or second transmitter 1202*b* with receiver 1208, is a WI-FI protocol.

Subsequently, the owner of dog 1212 receives a message notification informing him/her that his/her dog 1212 is outside first room 1220. When dog 1212 arrived at second room 1222, receiver 1208 received RF waves 116 from second transmitter 1202*b*, while this second transmitter 1202*b* detects the presence of a new receiver 1208 and uploads the location and time to database stored in the public cloud-based service 1228. Afterwards, the owner of dog 1212 accesses public cloud-based service 1228 through a smartphone application for tracking the location of dog 1212. The owner may have his/her credentials to access cloud-based service 1228, where the user account is mapped with MAC address of first transmitter 1202*a* and receiver 1208. In the cloud-based service 1228, a display is provided with the locations with determined times where dog 1212 has been during its absence from first room 1220, using the MAC address of receiver 1208. Finally, the owner is now able to rescue his/her dog 1212 by knowing the current location where dog 1212 is.

Figure 12C:
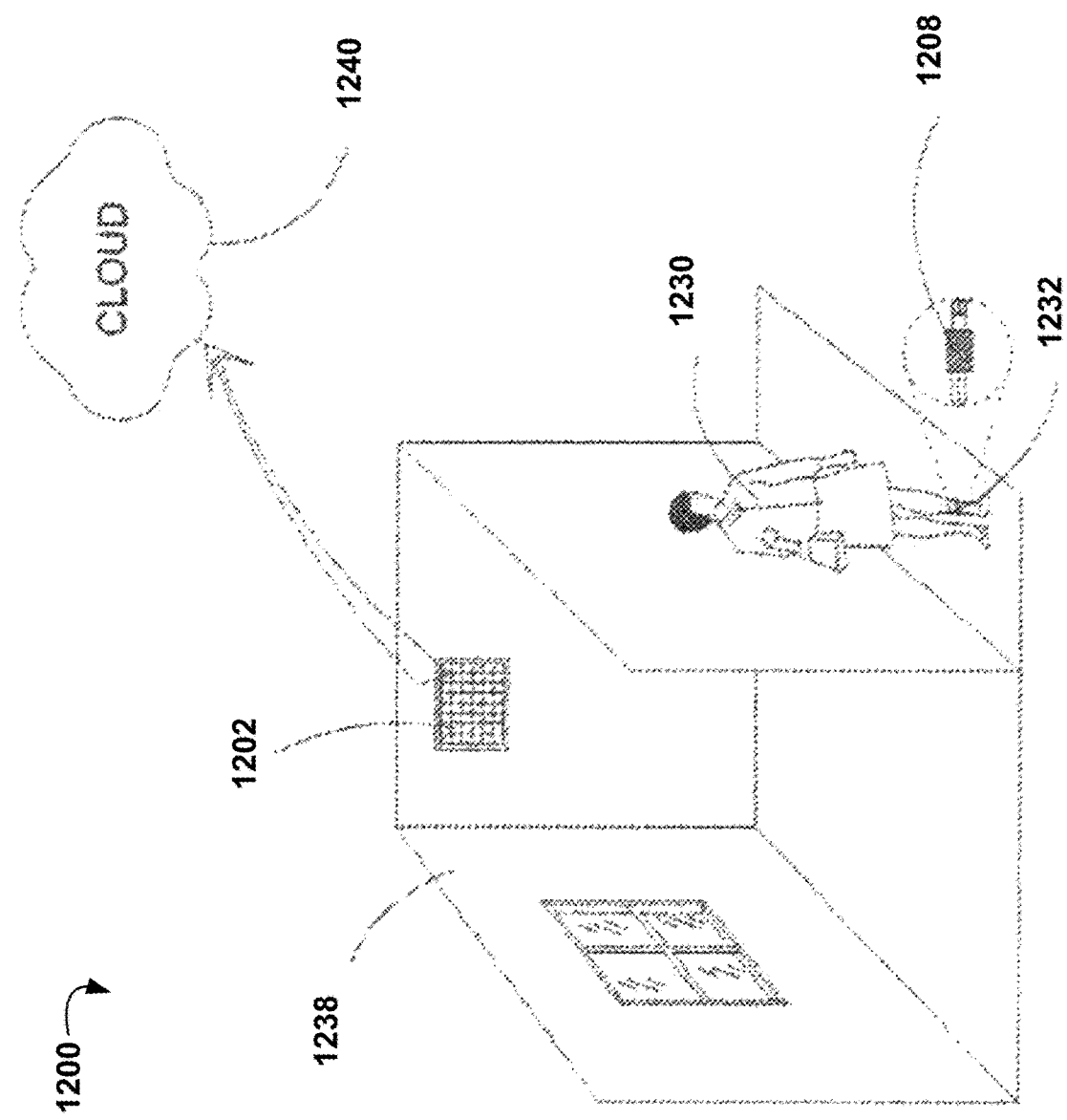

In another example, FIG. 12C shows a wireless tracking system 1200 for tracking and controlling the location of a woman 1230 that has conditional liberty in her house 1238, in this example, woman 1230 is wearing an ankle monitor 1232 that may include a GPS chip 1216 with an adapted receiver 1208 to charge its battery. Ankle monitor 1232 receives RF waves 116 from transmitter 1202 that is hanging on a wall from house 1238. Receiver 1208 communicates with transmitter 1202 through a ZIGBEE protocol. In this case, the unique identifier which is used to identify receiver 1208 is Personal Area Network Identifier (PAN ID). Receiver 1208 sends information to transmitter 1202 about the battery status, how many times battery has been charged, battery age indicator, and cycle efficiency. This information may be uploaded to a private cloud-based service 1240 which, is monitored by a police station that supervises woman 1230. Further, transmitter 1202 may include an alarm system which may be activated when receiver 1208 is not receiving RF waves 116 or/and woman 1230 is not in house 1238. This alarm system provides an audio RF alert, while transmitter 1202 sends a notification to computer software of police office.

As shown in FIG. 12C, woman 1230 escaped house 1238; therefore the alarm system is activated providing audio sound alert and a police office receives a message notification informing it that woman 1230 is outside house 1238. Then, a police officer detects the location of woman 1230 in a map using the GPS chip 1216 from ankle monitor 1232. Further, the police officer accesses the private cloud-based network to monitor the battery life and the last time when receiver 1208 received RF waves 116. The police officer may also have his/her credentials to access the private cloud-based service 1240, where the user account is mapped with PAN ID of transmitter 1202. In addition, if the woman 1230 arrived to a public place such as coffee shop, receiver 1208 may upload information and location of the woman 1230 to public cloud-based service 1240 which may be transferred to private cloud-based service 1240; this operation is used as a back-up tracking system in case GPS does not work appropriately. Finally, the woman 1230 may be found and handcuffed by police officer due to location was provided by GPS and/or private-cloud based service.

Figure 12D:
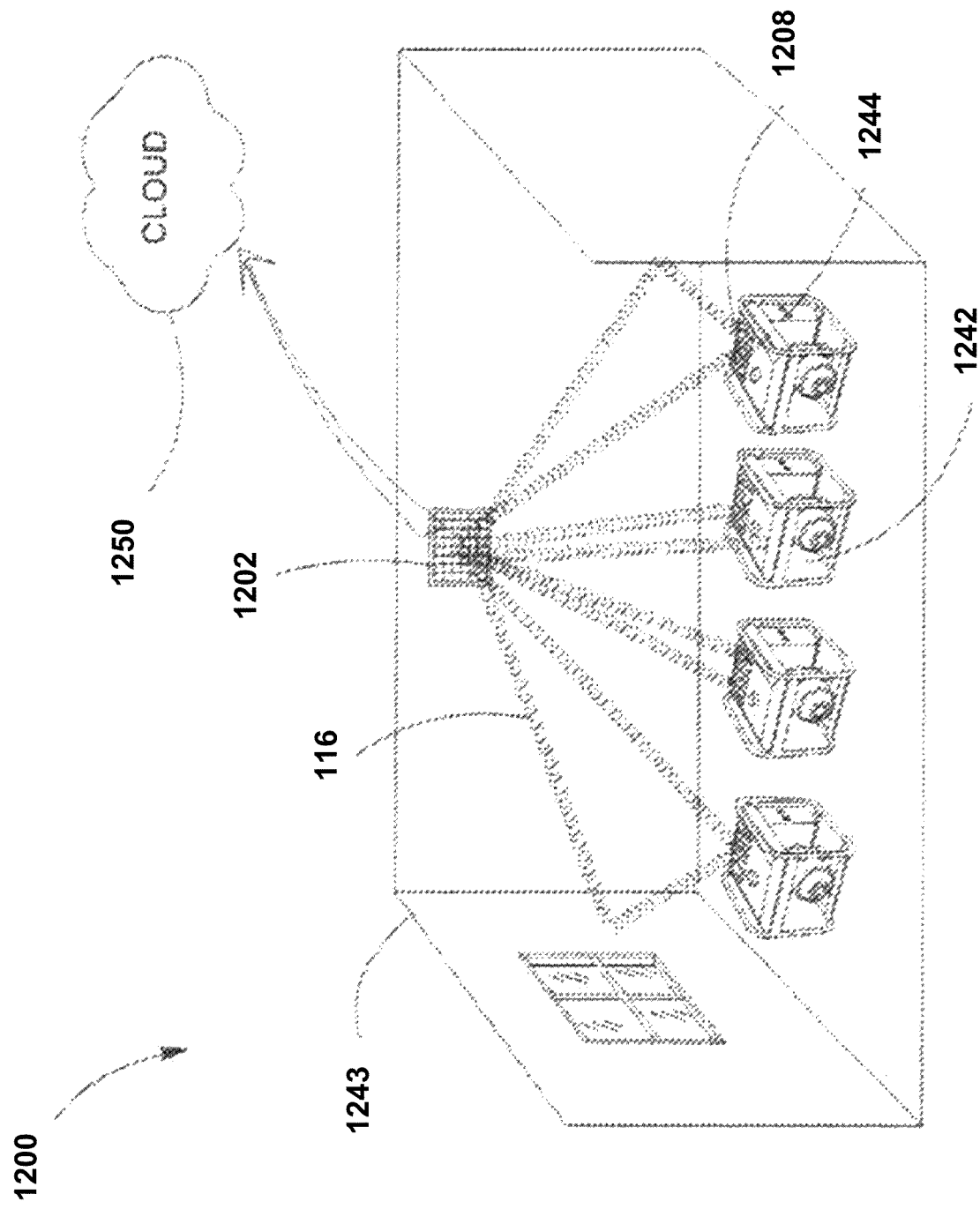

In one more example, FIG. 12D shows a wireless tracking system 1200 for tracking and controlling commodities of generators 1242 stored inside a warehouse 1243. Here, one transmitter 1202 is used, which is hanging on a wall of warehouse 1243. Each generator 1242 has an electronic tag 1244 with an adapted receiver 1208. Transmitter 1202 may transfer RF waves 116 to each receiver 1208 for powering and tracking each electronic tag 1244. The communication component used in these receivers 1208 is a BLUETOOTH protocol. In this embodiment, the unique identifier is U LIII for the BLUETOOTH protocol. If one or more generators are illegally removed from warehouse 1243, transmitter 1202 activates an alarm and notifies a security guard through an interactive message informing him/her that one or more generators 1242 are being stolen. The security guard accesses a cloud-based service 1250 through an application and identifies generators 1242 that were stolen through UUID of each electronic tag 1244. The security guard receives another interactive message informing the current location of the stolen generators 1242, in which this information was obtained when receivers 1208 from electronic tags 1244 receive RF waves 116 from other transmitter 1202. This other transmitter 1202 may upload the information of the current location of the stolen generators, allowing the guard to find these generators 1242.

FIGS. 12A-12D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 12A-12D.

Presented below are example methods of wireless power transmission in tracking systems.

In some embodiments, an example method includes: (i) transmitting, by a transmitter, a plurality of wireless power transmission waves; (ii) defining, by the transmitter, a pocket of energy via the waves whereby a receiver is configured to interface with the pocket of energy to charge an electronic device coupled to the receiver; (iii) receiving, by the transmitter, a signal from the receiver based on the receiver interfacing with the pocket of energy; and (iv) tracking, by the transmitter, the electronic device based on the signal from the receiver, and the electronic device is associated with a living being or object.

In some embodiments, the signal includes a unique identifier associated with the electronic device.

In some embodiments, the unique identifier includes at least one of a media access control (MAC) address, an International Mobile Equipment identity number, a 15-digit unique identifier for at least one of a Global System for Mobile Communications (GSM) network, a Universal Mobile Telecommunications System (UMTS) network, and a Long Term Evolution (LTE) network, a Unique Device ID for at least one of a smartphone and a portable music player, an Android advertising ID, and an International Mobile Subscriber identity for a SIM card.

In some embodiments, the transmitter includes a controller and a communication device coupled to the controller, and the communication device is configured to communicate with the receiver in order to control the tracking.

In some embodiments, the signal includes information corresponding to at least one of a battery level of the electronic device, a geographical location of the electronic device, and a unique identifier associated with the electronic device.

In some embodiments, the method further includes uploading, by the transmitter, the information to a cloud based service.

In some embodiments, the electronic device is at least one of a bracelet, a necklace, a belt, a ring, an ear chip, and a watch.

In some embodiments, the receiver is coupled to at least one of a global positioning system (GPS) chip and a real-time location system chip.

In some embodiments, the method further includes decoding, by the transmitter, a short RF signal to identify at least one of a gain and a phase of the receiver, and the decoding facilitates a determination of a geographical location of the receiver; and tracking, by the transmitter, the device based on the decoding.

In some embodiments, another example method includes: (i) transmitting, by a set of a plurality of antennas of a transmitter, a plurality of power waves, such that at least a portion of the plurality of power waves are phase shifted by the transmitter to converge to form a first constructive interference pattern at a first location of a receiver that is coupled with an electronic device; (ii) receiving, by a communications device of the transmitter, a signal from the receiver, the signal indicating a geographical location of the electronic device coupled to the receiver, a power level of a battery of the electronic device, and a unique identifier associated with the electronic device; (iii) storing, by the transmitter, into a database configured to store device data associated with one or more electronic devices, the geographical location and the unique identifier; and (iv) transmitting, by the set of the plurality of antennas of the transmitter, the plurality of power waves while receiving the signal from the receiver, such that at least a portion of the plurality of power waves are phase shifted by the transmitter to converge to form a second constructive interference pattern, distinct from the first constructive interference pattern, at the second location of the receiver, and the second location is based on at least one of the geographical location of the electronic device, the power level of the battery of the electronic device, and the unique identifier associated with the electronic device, and the receiver is configured to harvest energy from the first and second constructive interference patterns to at least partially power the electronic device.

In some embodiments, the method further includes: (i) identifying, by the transmitter, a new geographical location of the receiver based upon the signal received from the receiver; and (ii) updating, by the transmitter, the device data of the electronic device stored in one or more storage media according to at least one geographical location received from the signal, in response to identifying the new geographical location based on the signal.

In some embodiments, storing the geographical location into the database further includes: uploading, by the transmitter, the geographical location of the electronic device to the database of a cloud-based service.

In some embodiments, the method further includes: (i) determining whether the second location (e.g., the new geographic location) of the receiver indicates that the electronic device is located within a predetermined location; and (ii) in accordance with a determination that the second location of the receiver indicates that the electronic device is not located within the predetermined location, sending a notification to a user other than a user associated with the electronic device.

In some embodiments, the method further includes: (i) determining whether the second location (e.g., the new geographic location) of the receiver indicates that the electronic device is located within a predetermined location; and (ii) in accordance with a determination that the second location of the receiver indicates that the electronic device is not located within the predetermined location, activating an alarm system that is connected to the transmitter.

FIGS. 13A-13D illustrate wireless power transmission systems powered with alternative energy sources, in accordance with some embodiments.

Figure 13A:
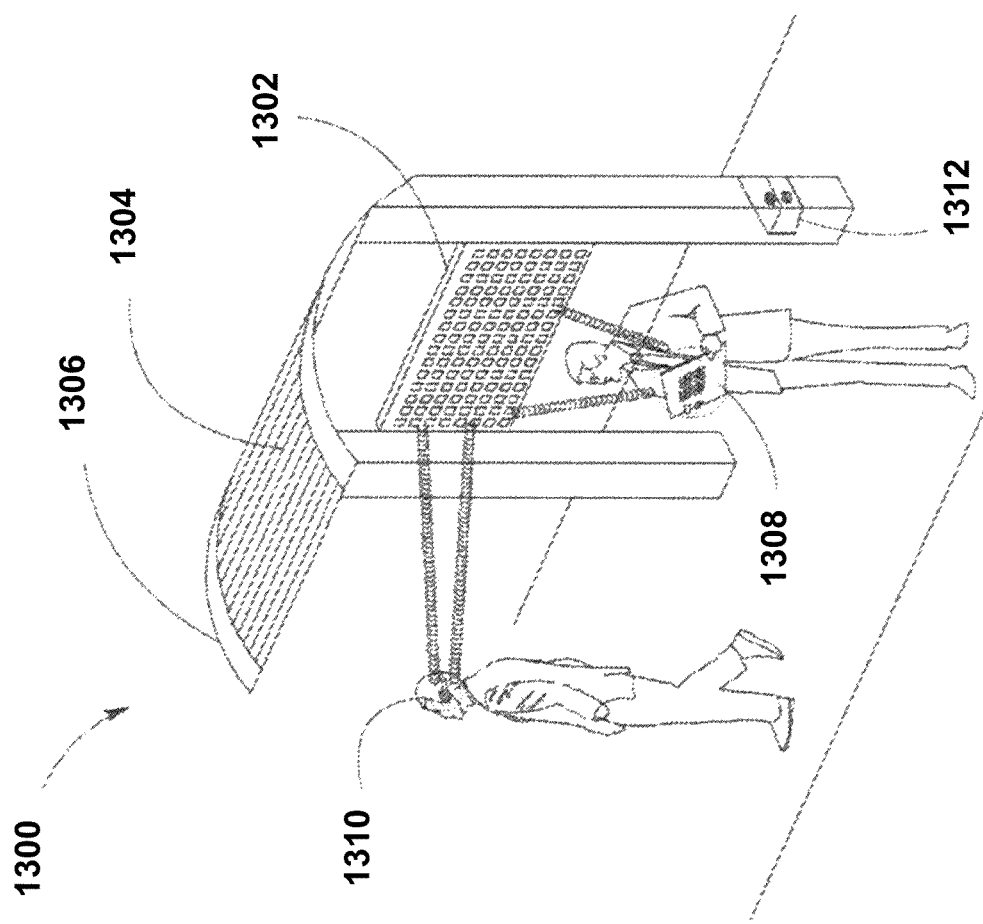
FIGS. 13A-13D illustrate various renewable energy sources for use in conjunction with wireless power transmission systems, in accordance with some embodiments.

FIG. 13A illustrates a wireless power transmission system (WPT) 1300 where a transmitter 1302, similar to transmitter 102 described in FIG. 1 above, utilizes at least one solar panel 1304 as power supply for providing wireless power, through pocket-forming, to users wanting to charge their electronic devices. In this embodiment, a bus stop station may include solar panel 1304 in its roof 1306 for providing solar power to transmitter 1302. Users at such a bus stop station may power their electronic devices, wirelessly through pocket forming, while waiting for transportation. In this embodiment, one user may charge a tablet 1308 while another user may power a BLUETOOTH headset 1310. Both electronic devices, i.e., tablet 1308 and/or headset 1310 may include receivers suitable for pocket forming (e.g., an embodiment of the receiver 120, FIG. 1). Moreover, the aforementioned bus stop station may include an energy storing unit 1312 for saving surplus solar energy. Such energy storing unit 1312 may function as battery component for transmitter 1302. WPT 1300 may be beneficial because users can power devices using alternative sources of energy different from coal or fuel oils. Moreover, electronic devices can be charged while traveling without requiring any wired connections and without the inconveniences typically associated with carrying chargers. The disclosed arrangement could also be employed in train stations, airports and other such places. Furthermore, energy storing unit 1312 can be used to provide power at such locations during the night, or during poor solar conditions.

Figure 13B:
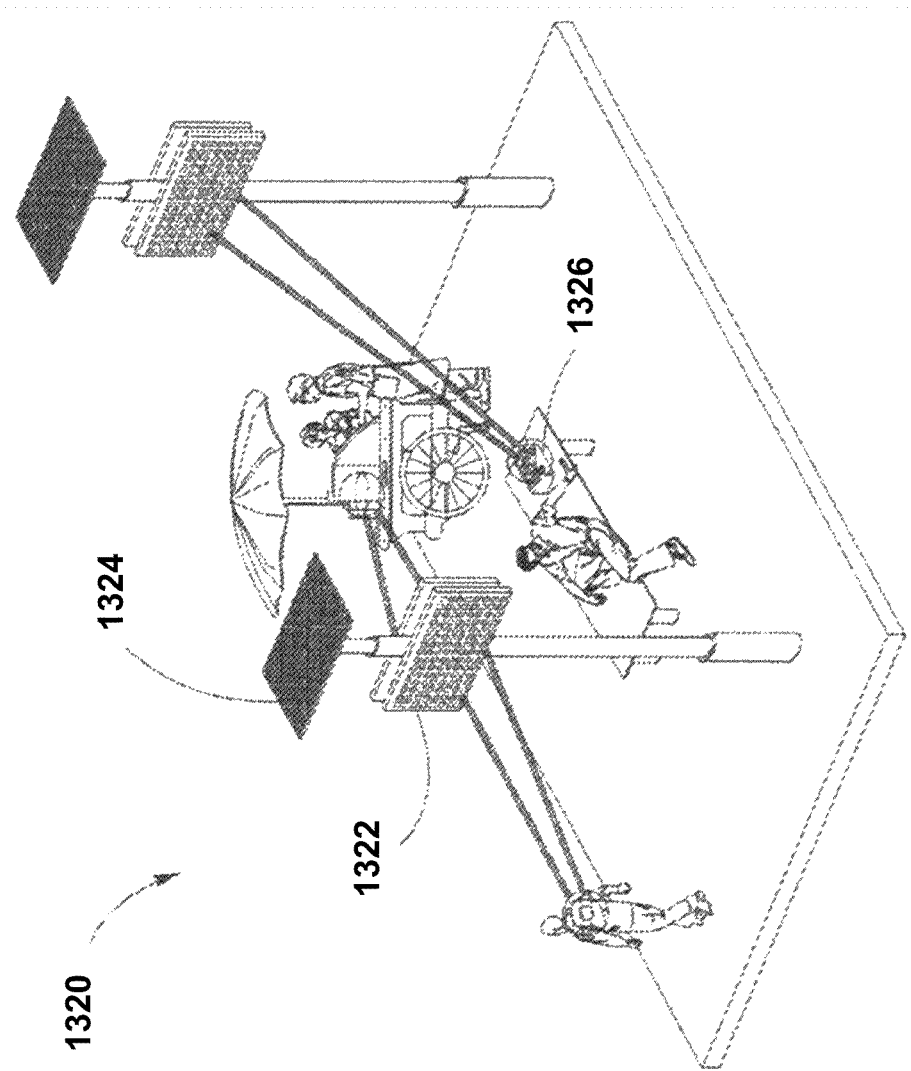

FIG. 13B illustrates a wireless power transmission system (WPT) 1320 where either one or a plurality of transmitters 1322 can be used to provide wireless power, through pocket-forming, to pedestrians wanting to charge electronic devices. As in the previous embodiment from FIG. 13A, transmitter 1322 can utilize solar panels 1324 as power supply. In addition, transmitter 1322 and solar panel 1324 can be placed in lamp pole structures and can be seen as mainstream infrastructure. Solar panels 1324 for this application can be from about 10 feet to about 30 feet in size. In this embodiment, pedestrians may charge their electronic devices, which may operatively be coupled to, attached to, or otherwise include receivers suitable for pocket-forming, while walking on the street on their way to work or while enjoying foods or beverages in food carts and the like. In some embodiments, WPT 1320 can be used wherever a lamp pole structure can be placed, for example, in parks, bridges and the like. In other variations of WPT 1320, pedestrians may charge portable rechargeable batteries 1326 which upon charging may be utilized at their homes or work sites. This foregoing embodiment may be beneficial for regions where electricity may be scarce, for example, in villages or in third world contexts. Moreover, electric companies can set up dedicated stations for powering such batteries 1326 and may charge a fee based on the amount of power requested. WPT 1320 may lead to spreading green infrastructures for power handling and distribution. Such an example can be seen in FIG. 13C below.

Figure 13C:
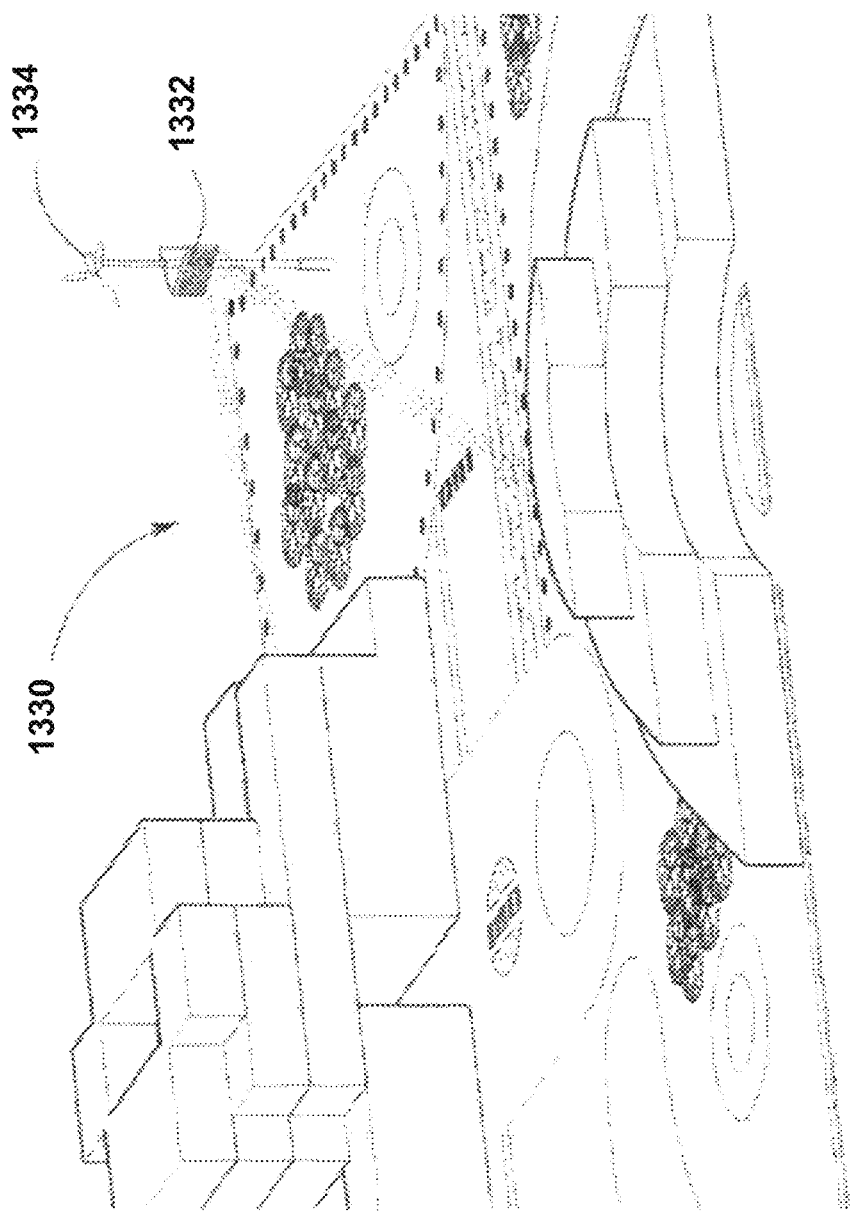

FIG. 13C illustrates a wireless power transmission system (WPT) 1330 where a transmitter 1332 may utilize a typical wind turbine 1334 as power supply. By using the power of the wind and the components typically associated with wind turbine 1334, power can be delivered wirelessly, through transmitter 1332 and pocket-forming, to houses or dedicated regions without utilizing wires, thereby reducing the cost associated with the distribution of energy. In addition, wireless power can be used by any user in the region utilizing a pocket-forming enabled device, i.e., utilizing devices which may operatively be coupled to, attached to or otherwise include receivers suitable for pocket-forming.

Figure 13D:
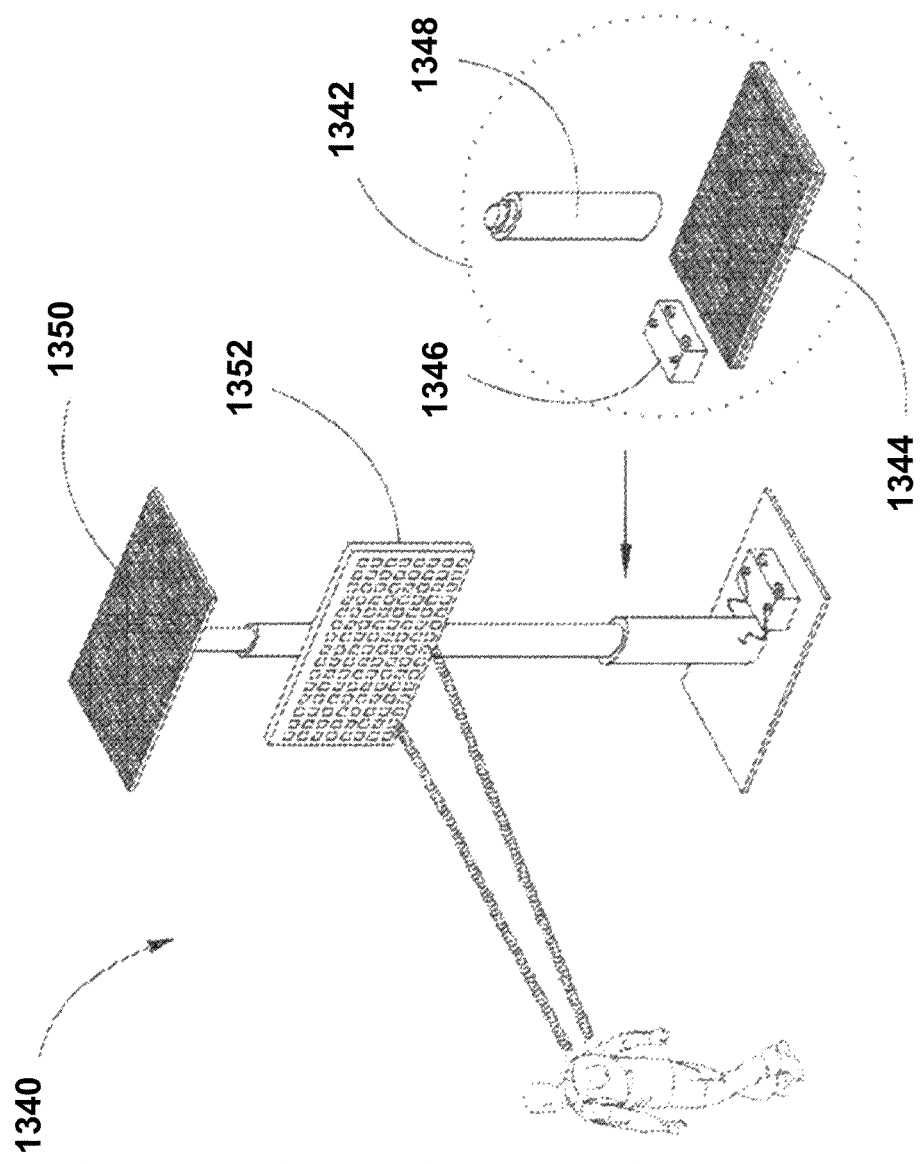

FIG. 13D illustrates a wireless power transmission system (WPT) 1340 where a portable assembly 1342 for delivering power wirelessly may be utilized. Assembly 1342 may include a power module 1344 which may further include a power source and a transmitter (not shown), a battery component 1346 for storing surplus energy, and a collapsible pole structure 1348 for mounting the aforementioned components. Pole structure 1348 can be made of a suitable material, for example aluminum, which provides high strength, durability, and low weight. Pole structure 1348 when extended can be about 10 to 30 feet in height. In its top part, a power source, such as a solar panel 1350 (included in module 1344) may be placed. Then, a transmitter 1350 (also from module 1344) may be attached to pole structure 1348 by suitable mechanical means such as brackets, fasteners, and the like. Moreover, transmitter 1352 may electrically be connected to solar panel 1350 to utilize solar energy for providing wireless power. Lastly, battery component 1346 may also be connected to store surplus energy which can be used to provide power during the night, or during poor solar conditions. Finished Assembly 1342 can be seen centered in FIG. 13D. This configuration for WPT 1340 can be beneficial when users requiring power find themselves in areas where electricity may be scarce, for example, in villages in the third world, in jungles, deserts, while navigating in the ocean, or any other situation or location where power may not be accessible.

FIGS. 13A-13D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 13A-13D.

Presented below are example methods of wirelessly delivering power to receivers using renewable energy source.

In some embodiments, an example method includes transmitting controlled RF waves from a transmitter that converge to form pockets of energy in 3-dimensional space for powering a portable electronic device, connecting an alternate energy source to the transmitter to provide power to the transmitter, and capturing the pockets of energy by a receiver to charge or power the electronic device connected to the receiver.

In some embodiments, another example method includes: (i) receiving, by an antenna of a receiver associated with the mobile electronic device, a pocket of energy generated in response to transmission signal waves emitted by a pocket-forming transmitter coupled to a power source, the power source configured to use alternative energy; and (ii) converting, by a rectifying circuit of the receiver, the received pocket of energy into electricity to charge the electronic device.

In some embodiments, the power source is configured to use alternative energy includes a solar panel. In some embodiments, the solar panel is of a predetermined size and mounted on a pole configured to extend reach of the transmission signal waves emitted by the pocket-forming transmitter.

In some embodiments, the power source is configured to use alternative energy includes a wind turbine.

Figure 14A:
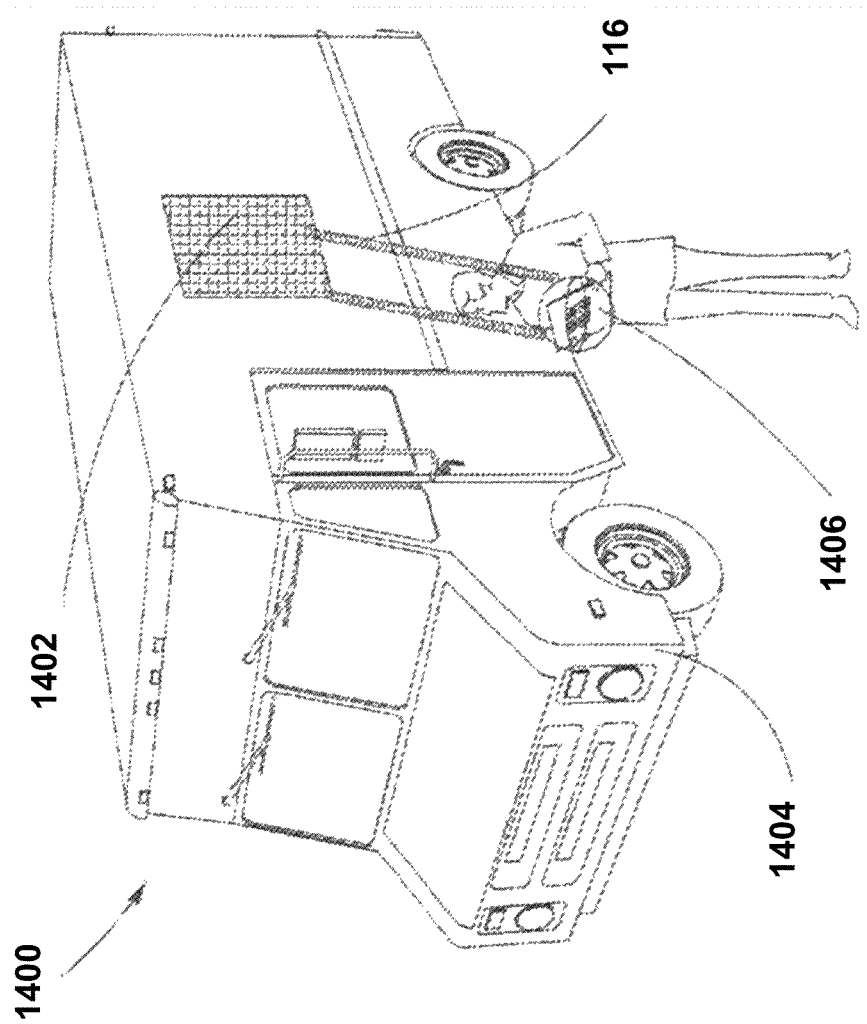
FIGS. 14A-14B illustrate wireless power transmission systems used in logistic services, in accordance with some embodiments.
Figure 14B:
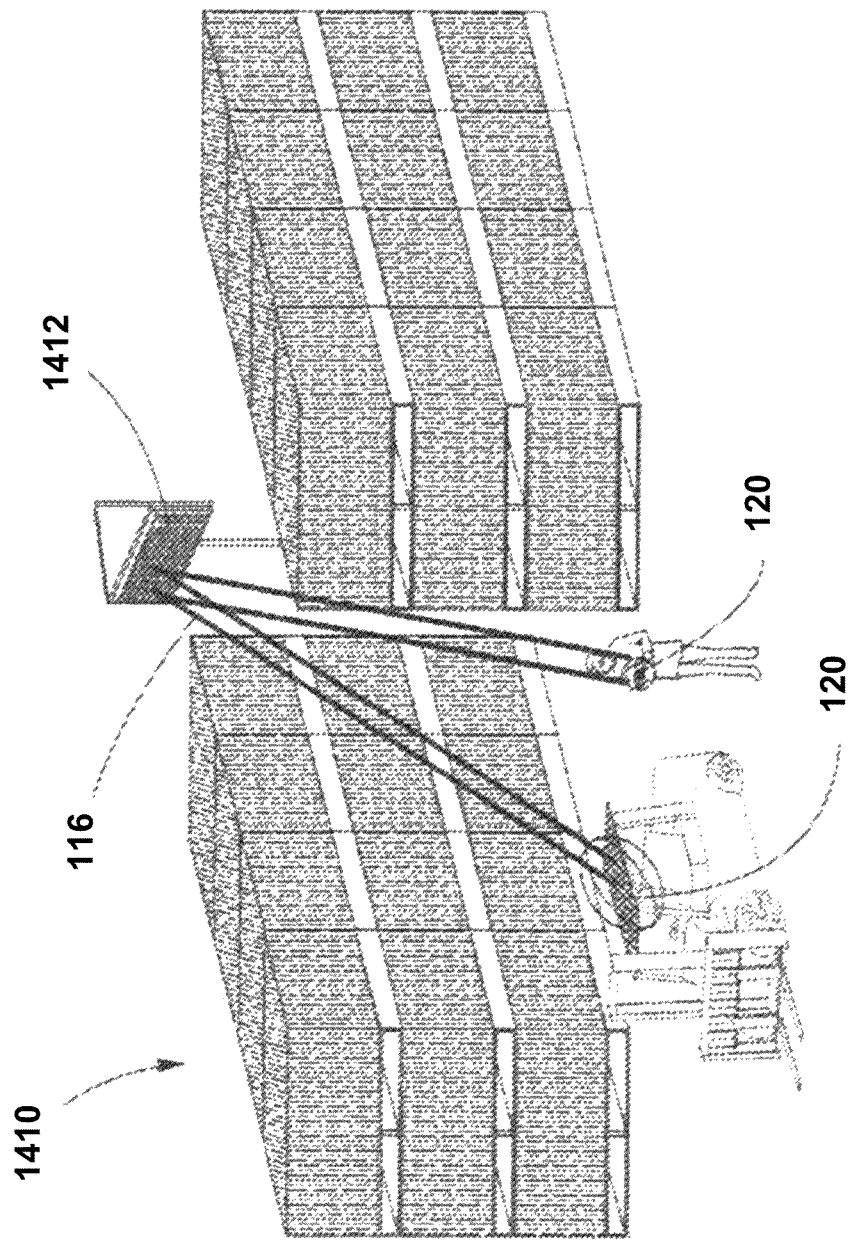

FIGS. 14A-14B illustrate wireless power transmission systems for logistic services, in accordance with some embodiments.

FIG. 14A shows a wireless power transmission system 1400 where a transmitter 1402 (e.g., an embodiment of the transmitter 102, FIG. 1) may be located on or within a delivery vehicle 1404, according to an embodiment. Delivery vehicle 1404 may be a postal truck, a pizza truck, armored truck for bank services and the like. Transmitter 1402 may use a diesel generator as power source, however, other power sources such as, an alternator of vehicle 1404, photovoltaic cells, and the like may be employed too. Transmitter 1402 may generate and direct RF waves 116 (FIG. 1) towards the receivers embedded or attached to electronic devices such as laptops, GPS, radios, cellphones, and tablets, among others. In addition, transmitter 1402 in delivery vehicle 1404 may wirelessly extend the life of batteries in the previously mentioned devices during the operation.

Transmitter 1402 may be in a door, wall, top of the delivery vehicle 1404 and the like. Furthermore, other transmitter 1402 configurations may be used in dependency of the region and requirement, such requirement may include transmitter 1402 on telescopic mast for increasing range.

FIG. 14B shows warehouse 1410 where one or more transmitters 1412 may be located in walls or ceiling for powering and charging electronic devices, such electronic devices may include tablets, laptops, cellphones, radios, lifters, hoists and the like. Transmitter 1412 may be connected to an electrical grid which may operate as power source, other power sources may be employed too. Transmitter 1412 may generate and direct RF waves 116 towards the receivers 120 embedded or attached to electronic devices such as laptops, GPS, radios, cellphones, hoists, and tablets, among others. In addition, transmitter 1412 may wirelessly extend the life of batteries in the previously mentioned devices during the operation.

Transmitter 1412 may be in/on the wall of the warehouse 1410, ceiling of the warehouse 1410, and the like. Furthermore, other transmitter 1412 configurations may be used in dependency of the region and requirement, such requirement may include transmitter 1412 on a telescopic mast for increasing range.

FIGS. 14A-14B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 14A-14B.

Presented below is an example method of wirelessly delivering power to receivers used in logistic services.

In some embodiments, an example method includes: (i) communicating, by a receiver associated with the electronic logistics device, a power requirement for the electronic logistics device to a transmitter, (ii) receiving, by an antenna of the receiver, a pocket of energy generated in response to power transmission waves emitted by the transmitter, and (iii) converting, by a rectifying circuit of the receiver, the received pocket of energy into electricity to charge the electronic logistics device.

In some embodiments, the receiver includes a power converter and a communication component to establish communication with the transmitter when the electronic logistics device is within a predetermined distance from the pocket-forming transmitter.

In some embodiments, the communication component communicates with the transmitter through a transmission signal using a protocol selected from the group consisting of: BLUETOOTH®, WI-FI®, ZIGBEE®, or FM radio.

Figure 15A:
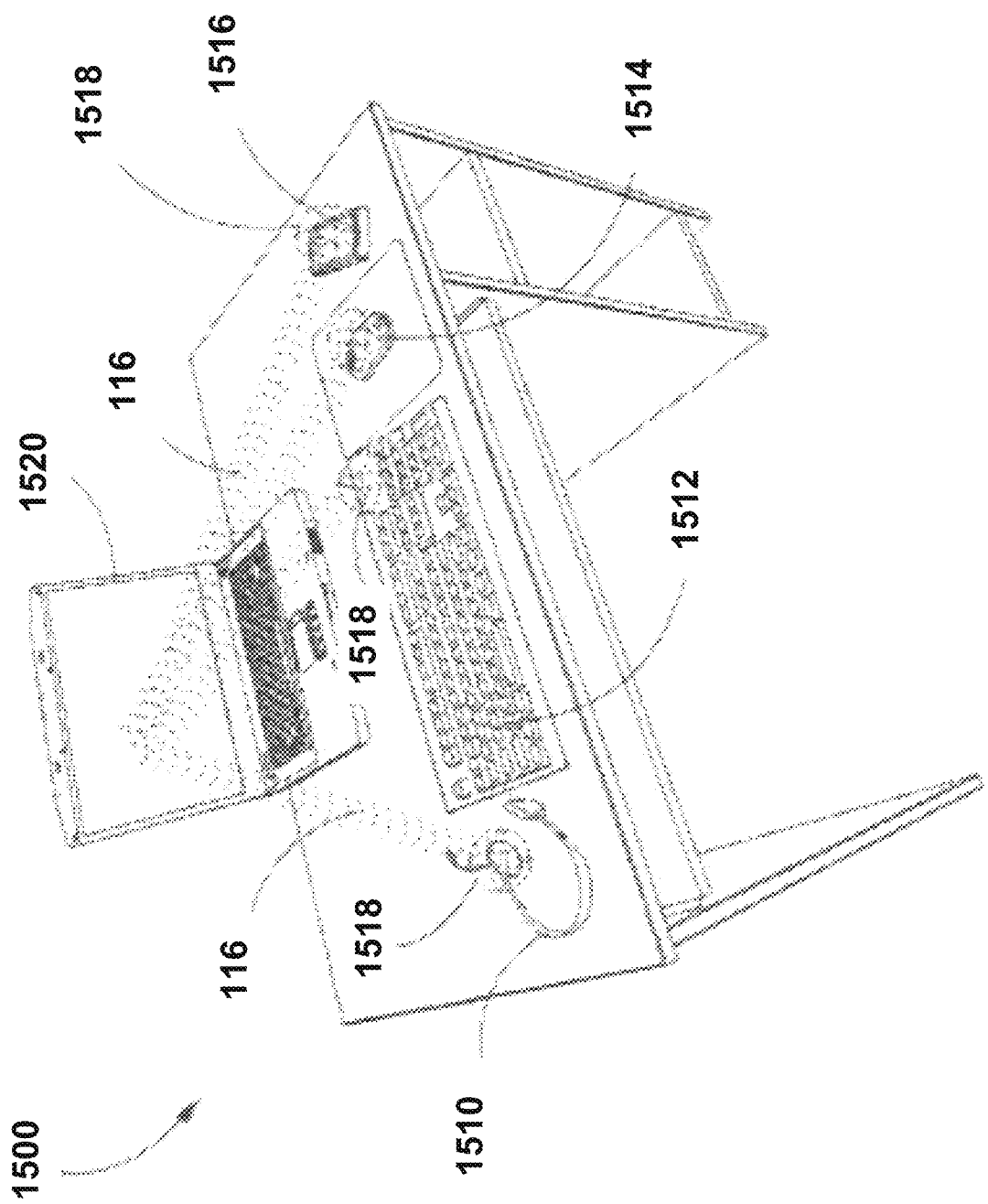
FIG. 15A illustrates a wireless power transmission system used for charging one or more peripheral devices via a transmitter associated with a laptop computer, in accordance with some embodiments.

FIG. 15A is an illustration showing a wireless power transmission system 1500 used for charging one or more peripheral devices via a transmitter (e.g., an embodiment of the transmitter 102, FIG. 1) associated with a laptop computer (e.g., a laptop with an embedded transmitter and which may also include an embedded receiver 120, FIG. 1), in accordance with some embodiments. The peripheral devices may include a headset 1510, a keyboard 1512, a mouse 1514, and a smartphone 1516, among others. In some embodiments, these peripheral devices may operate wirelessly with laptop computer through BLUETOOTH communication, and may include rechargeable batteries that are charged using wirelessly delivered power, as described below.

A transmitter (which may be embedded within the laptop 1520) may transmit controlled RF waves 116 which may converge in 3-dimensional space to form a pocket of energy near one or more of the peripheral devices. These RF waves 116 may be controlled through phase and/or relative amplitude adjustments to form constructive and destructive interference patterns (pocket-forming). Pockets of energy 1518 may be formed as constructive interference patterns and may be 3-dimensional in shape, while null-spaces may be generated using destructive interference of RF waves. As explained above, respective receivers 120 embedded in the peripheral devices convert energy from the RF waves that have accumulated in the pockets of energy 1518 to usable power for charging or powering batteries in the peripheral devices.

In some embodiments, the laptop computer 1520 may be connected to a conventional wall outlet for charging its battery to suitable levels, while providing wireless power transmission to the peripheral devices.

Figure 15B:
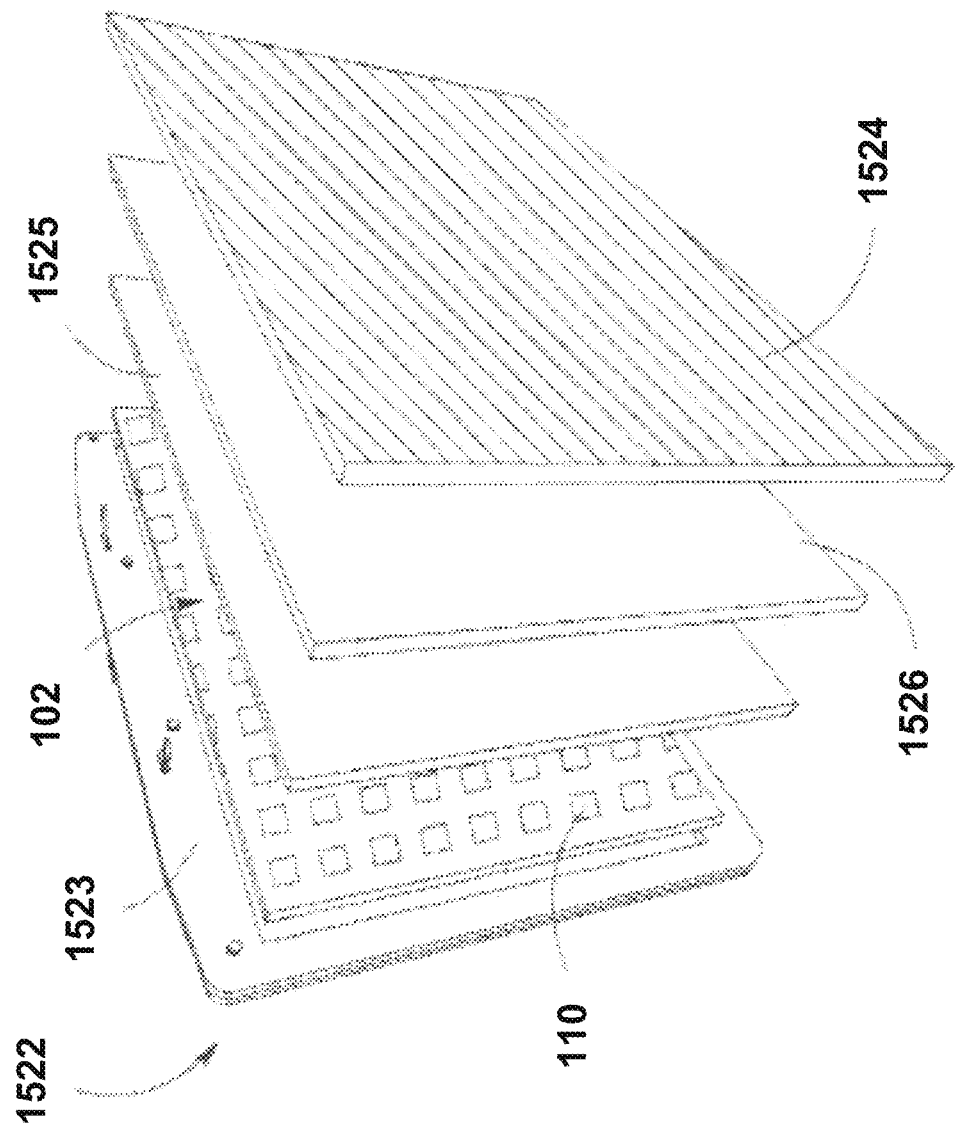
FIG. 15B is an exploded view of a laptop screen, showing components including an embedded wireless power transmitter, in accordance with some embodiments.

FIG. 15B is an exploded view of a laptop screen 1522, showing components including an embedded wireless power transmitter 102 with transducer elements 110 (FIG. 1), in accordance with some embodiments. In some embodiments, the laptop screen 1522 may be formed of different layers, including a front transparent screen layer 1524, a polarized film layer 1526, a LED/LCD back-light layer 1525, and a frame 1523. In some embodiments, transmitter 102 may be integrated in the screen, specifically between LED/LCD back-light layer 1525 and frame 1523. As shown in FIG. 15B, the transmitter 102 may include a plurality of transducer elements 110 facing out of the screen. This configuration of transducer elements 110 may allow suitable transmission of RF waves towards the peripheral devices discussed above in reference to FIG. 15A. In other embodiments, the transmitter 102 may be embedded in circuitry elements or metal mesh (touchscreen versions) of the screen.

Figure 15C:
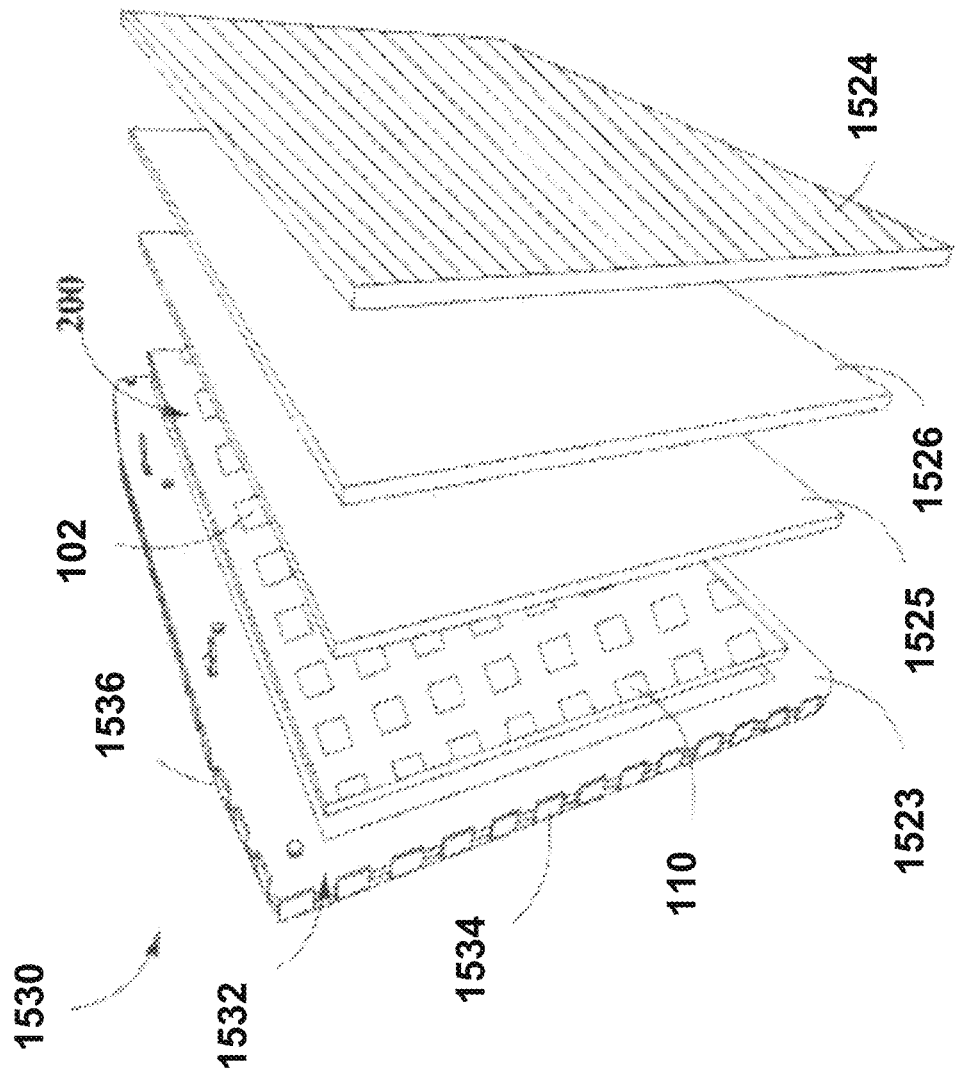
FIG. 15C is an exploded view of a laptop screen, showing components including an embedded wireless power transmitter and an embedded wireless power receiver, in accordance with some embodiments.

FIG. 15C is an exploded view of a laptop screen 1530, showing components including an embedded wireless power transmitter 102 with transducer elements 110 and an embedded wireless power receiver 1532 (e.g., an embodiment of receiver 120, FIG. 1), in accordance with some embodiments. The laptop screen 1530 may be formed of different layers, as described above in reference to FIG. 15B. In some embodiments, the transmitter 102 may be integrated between LED/LCD back-light layer 1525 and frame 1523, while receiver 1532 may be integrated along frame 1523. As shown in FIG. 15C, in some embodiments, transducer elements 110 of transmitter 102 may point out of the screen 1530, while sensor elements 1534 of receiver 1532 may be embedded around the edges of frame 1523 for allowing reception of RF waves from sources or transmitters at different locations.

The location and configuration of transmitter 102 and receiver 1532 in laptop computer screen 1530 may vary according to the application. In some embodiments, the receiver 1532 may be configured in the middle of the back of frame 1523 and may include high directional sensor elements 1536 that can be oriented towards a transmitter in proximity to the laptop computer 1520 for receiving suitable wireless power transmissions that may be used to power the laptop 1520. In other embodiments, laptop computer screen 1530 may include a single transmitter 102 that may also operate as a receiver 120, in which case the transmitter 102 may use same transducer elements 110 for transmitting and receiving RF waves. That is, the transmitter embedded in laptop computer screen 1530 may switch between those transducer elements 110 receiving RF waves for charging a battery of the laptop or transmitting RF waves for charging batteries in peripheral devices. An algorithm executed by a microcontroller of the laptop may be used to control the switching between transmitting and receiving RF waves.

Figure 15D:
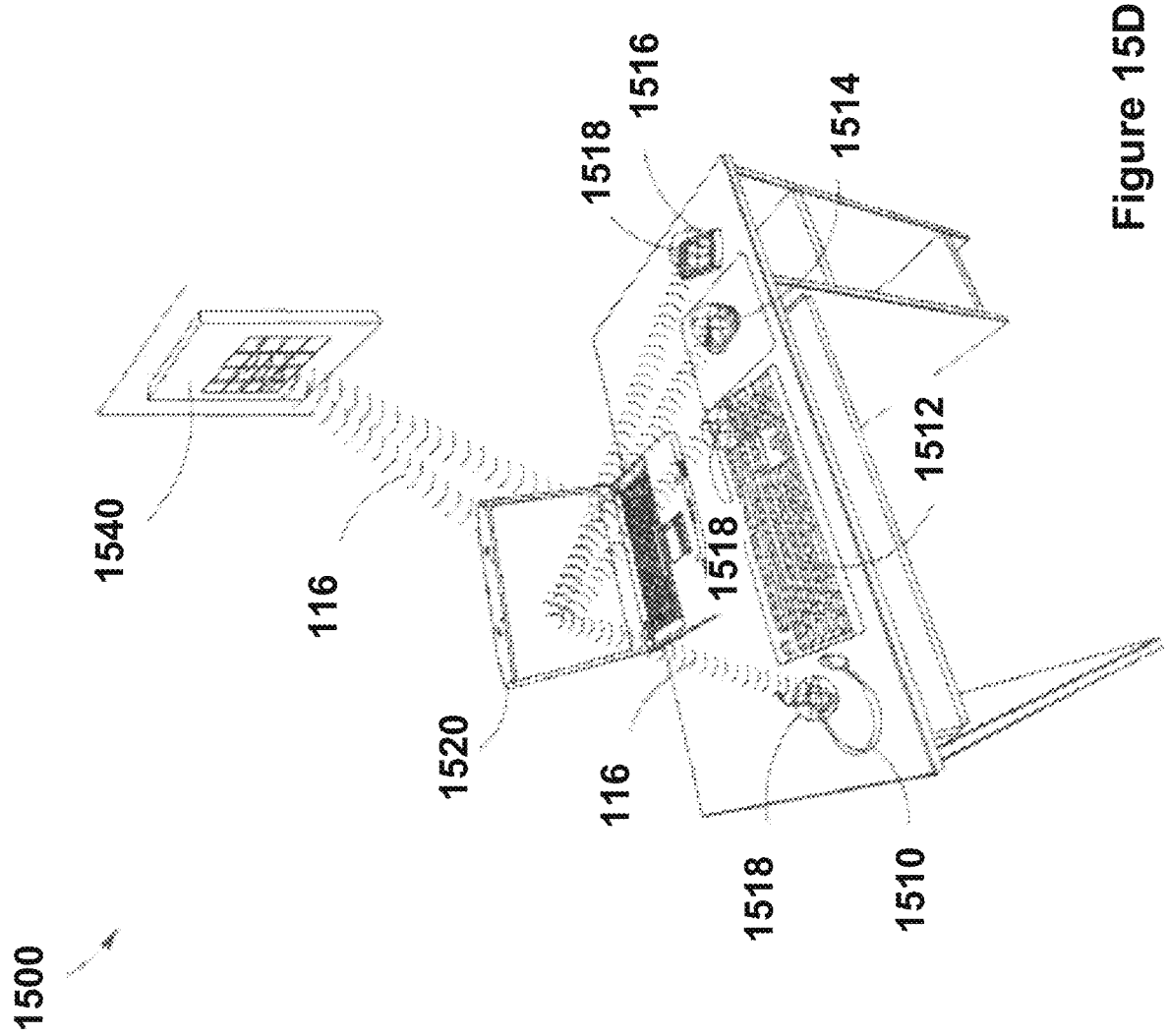
FIG. 15D illustrates a wireless power transmission system in which a laptop computer may receive and transmit radio frequency waves in a substantially simultaneous fashion, in accordance with some embodiments.

FIG. 15D is an illustration showing the wireless power transmission system 1500 of FIG. 15A, in which the laptop computer 1520 is also configured with an embedded receiver 120, so that the laptop 1520 may receive and transmit RF waves in a substantially simultaneous fashion, in accordance with some embodiments. In some embodiments, one or more separate transmitters 1540 may direct RF waves 116 towards edges of the laptop computer's screen where sensor elements of the embedded receiver may be integrated (not shown). In this way, pockets of energy may be captured by the sensor elements and utilized by the embedded receiver to charge a battery of the laptop 1520. Simultaneously, an embedded transmitter 102 (not shown), may direct RF waves towards one or more peripheral devices.

In some embodiments, transmitter 1540 may include a higher amperage power source such as a standard 120/220 volts AC house connection compared to transmitter 102 embedded in the laptop, which may obtain power only from a battery of the laptop. This may allow the transmitter 1540 to have a wider wireless charging range as compared to the embedded transmitter of the laptop. In some embodiments, the various peripheral devices 1510, 1512, 1514, and 1516 may receive wirelessly delivered power from either or both of the transmitter 1540 and the embedded transmitter of the laptop. In some embodiments, an algorithm processed by a microcontroller of the laptop and/or the transmitter 1540 may coordinate wireless power delivery operations between the transmitters. For example, this algorithm may decide which transmitter should send RF waves to wirelessly charge peripheral devices, depending on proximity and/or energy levels of a battery in the laptop computer.

Figure 15E:
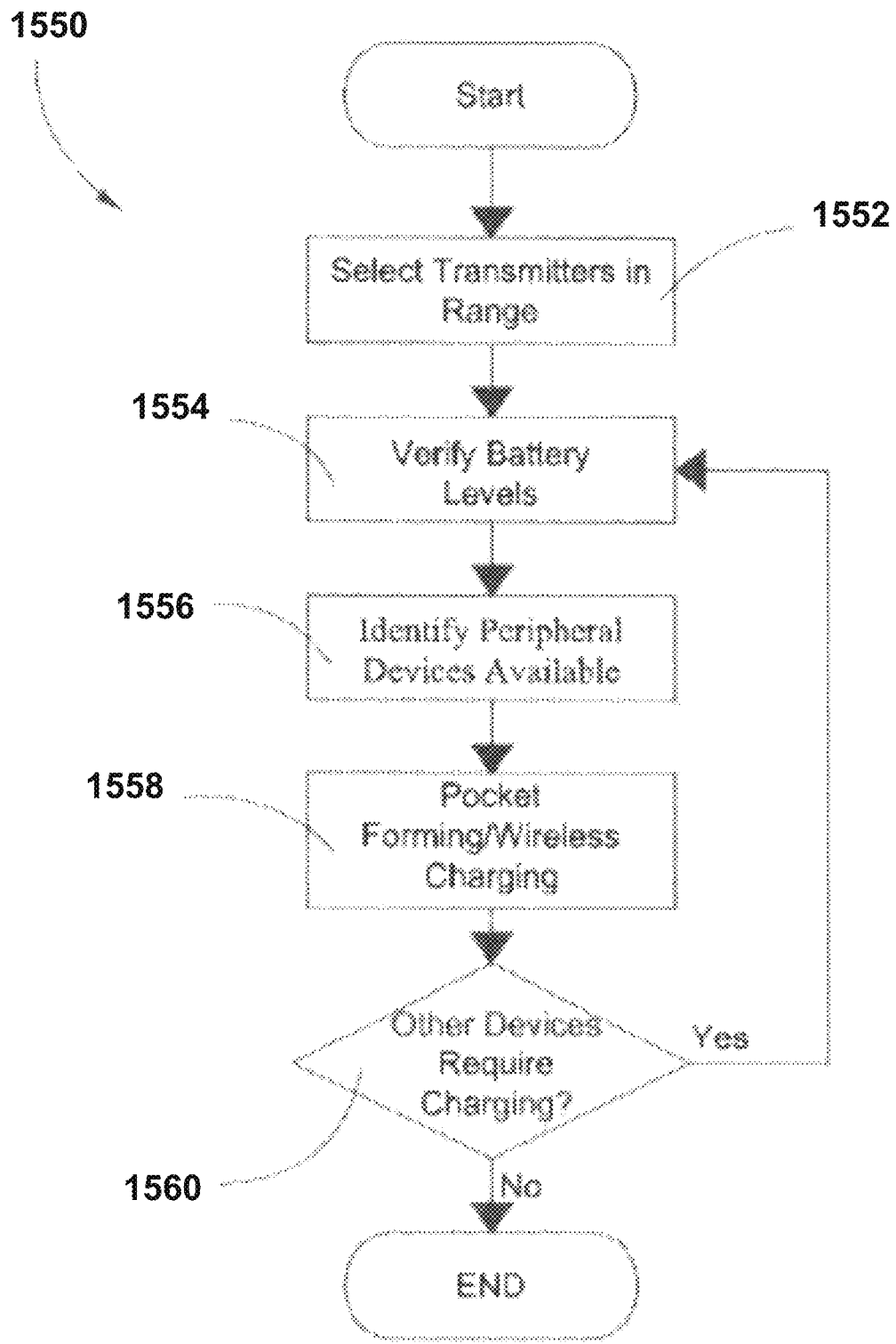
FIG. 15E is a flow diagram of a wireless power transmission process that may be implemented for charging one or more peripheral devices using a laptop computer, in accordance with some embodiments.

FIG. 15E is a flow diagram of a method of wireless power transmission that may be implemented for charging one or more peripheral devices using a laptop computer (e.g., the laptop discussed above in reference to FIGS. 15A-15D), in accordance with some embodiments.

Wireless power transmission process 1550 may begin by selecting one or more transmitters in range, at block 1552. One or more peripheral devices may require wireless charging, in which case, one or more transmitters in a room, or an embedded transmitter 102 of the laptop may be selected if they are within a suitable range. For example, if a smartphone is not within a suitable charging distance from the laptop (e.g., not on the table, or within 3-4 feet of the laptop), then a higher power transmitter 1540 may be selected for delivering wireless power. In some embodiments, a wireless charging distance for the embedded transmitter of the laptop may be within a range of about 1 to 3 meters, and if peripheral devices are outside this range, then they instead will be wirelessly charged by transmitter 1540.

The laptop may also include a software application that may provide information about distance, charging levels, efficiency, location, and optimum positioning of the laptop computer with respect to peripheral devices and transmitter 1540.

After selecting the transmitter within the optimal charging range, wireless power transmission process 1550 may continue by checking charge levels of the battery in the laptop, at block 1554. This check may be performed by a control module included in the laptop (not shown) or by a microcontroller included with the transmitted embedded in the laptop. In some embodiments, a charge level of the laptop must be above a certain threshold to allow the laptop to transmit wireless power. For example, minimum and maximum charging thresholds may be established at about 25% and 99% of total charge, respectively. That is, if battery charge is below the minimum threshold or 25%, then the laptop must be connected to a power outlet or it may receive wireless charging from transmitter 1540. When battery charge is at 99% or at least above 25%, the laptop 1520 may transmit RF waves for charging peripheral devices that are within range.

Wireless power transmission process 1550 may continue at block 1556, where a communications component of the embedded transmitter or transmitter 1540 may identify one or more peripheral devices that may require wireless charging. In some embodiments, priority charging orders are established and utilized to ensure that the one or more peripheral devices are charged in a particular order.

After the one or more peripheral devices are identified and charging priorities/parameters in the embedded transmitter or transmitter 1540 are set, transmission of RF waves towards designated peripheral devices can begin, at block 1558, where these RF waves may constructively interfere to generate pockets of energy proximate to the peripheral devices, which pockets of energy may be converted by respective embedded receivers to usable power for powering or charging the one or more peripheral devices, sequentially or simultaneously.

Using a communications component, the embedded transmitter of the laptop or transmitter 1540 on the wall may continuously check if there are other peripheral devices that may require wireless charging or powering, at block 1560. If new or additional peripheral devices are identified, then either transmitter may wirelessly charge the newly identified peripheral devices according to the established charging priorities, optimum ranges, battery levels and/or other parameters. If no further peripheral devices are recognized or need wireless charging, then wireless power transmission process 1550 may end.

FIGS. 15A-15E illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 15A-15E.

Presented below are example systems and methods of wirelessly delivering power to receivers using a transmitter coupled to an electronic device (e.g., a laptop).

In some embodiments, an example method includes, embedding a pocket-forming transmitter in a screen display of the computer system; transmitting power RF waves from the pocket-forming transmitter having a radio frequency integrated circuit, antenna elements, a microprocessor and communication circuitry; generating pockets of energy from the transmitter to converge in 3-dimensional space at predetermined locations; integrating a receiver having antenna elements and communication circuitry within the electronic device; and converting the pockets of energy from the transmitter to the integrated receiver to power the electronic device.

In some embodiments, the computer system is a laptop, notebook or nano-notebook. In some embodiments, computer system is a desktop computer, a tablet, iPad, iPhone, smartphone or other peripheral portable electronic devices.

In some embodiments, the computer system includes an embedded receiver whereby a separate transmitter in proximity to the computer system powers the computer system while the transmitter of the computer system wirelessly charges the electronic device.

In some embodiments, another example method includes, receiving, at a computer system that is coupled (e.g., directly, mechanically coupled) to a first transmitter, information identifying a location of a receiver device that requires charging, and the location is within a predetermined range of the computer system; in accordance with a determination that a charge level of the computer system is sufficient to allow the computer system to provide wireless power to the receiver device, transmitting a first set of power waves, via a plurality of antennas of the first wireless power transmitter, that converge proximate to the location of the receiver device to form a pocket of energy at the location; and while transmitting the first set of power waves that converge proximate to the location of the receiver device to form the pocket of energy at the location: (i) receiving, at the computer system, a second set of power waves from a second wireless power transmitter, distinct and separate from the first wireless power transmitter, and (ii) charging the computer system by converting energy from the second set of power waves into usable electricity.

In some embodiments, the first transmitter is integrated between a back-light layer and a frame of a screen display of the computer system.

In some embodiments, the first transmitter is embedded in a screen of the computer system.

FIGS. 16A-16B are illustrations of game controllers that are coupled with wireless power receivers, in accordance with some embodiments. As shown in FIG. 16A, a receiver 120 may be integrated on a front side of the game controller 1602, and the receiver 120 may include an array of sensor elements strategically distributed to match the game controller's design.

In FIG. 16B, another game controller 1604 is shown and that controller includes a receiver 120 that is integrated with an additional case 1606 to provide wireless power receiver capabilities to the game controller 1604. Case 1606 may be made out of plastic rubber or any other suitable material for cases, and it may include an array of sensor elements located on the back side of the case, which number and type may be calculated according to the game controller design. Case 1606 may also be connected to game controller 1604 through a cable 1608, or in other embodiments, the case 1606 may be attached to a surface of the game controller 1604.

FIGS. 16C-16G illustrate various wireless power transmission systems in which power is wirelessly delivered to electronic devices using RF waves, in accordance with some embodiments.

Figure 16C:
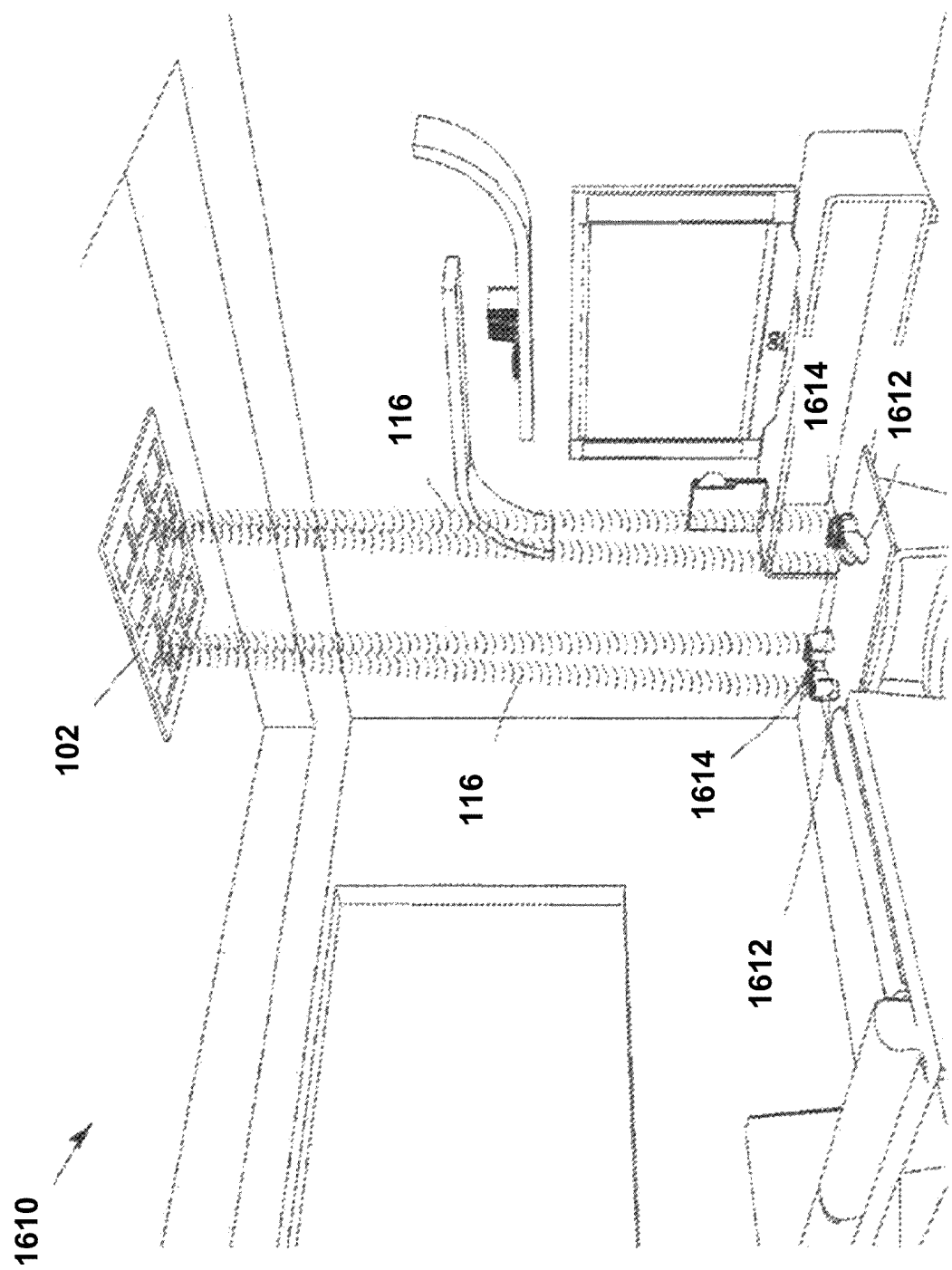

FIG. 16C illustrates a wireless power delivery system 1610 that wirelessly transmits power to game controllers 1612, using pocket-forming. In some embodiments, transmitter 102 may be located at the ceiling of a living room pointing downwards, and may transmit controlled RF waves 116 which may converge in 3-dimensional space. The amplitude of the RF waves 116 may be controlled through phase and/or relative amplitude adjustments to form constructive and destructive interference patterns (pocket-forming), and produce controlled pockets of energy 1614. Receiver 120, embedded or attached to game controllers 1612, may then utilize energy from the pockets of energy for charging or powering an electronic device.

Figure 16D:
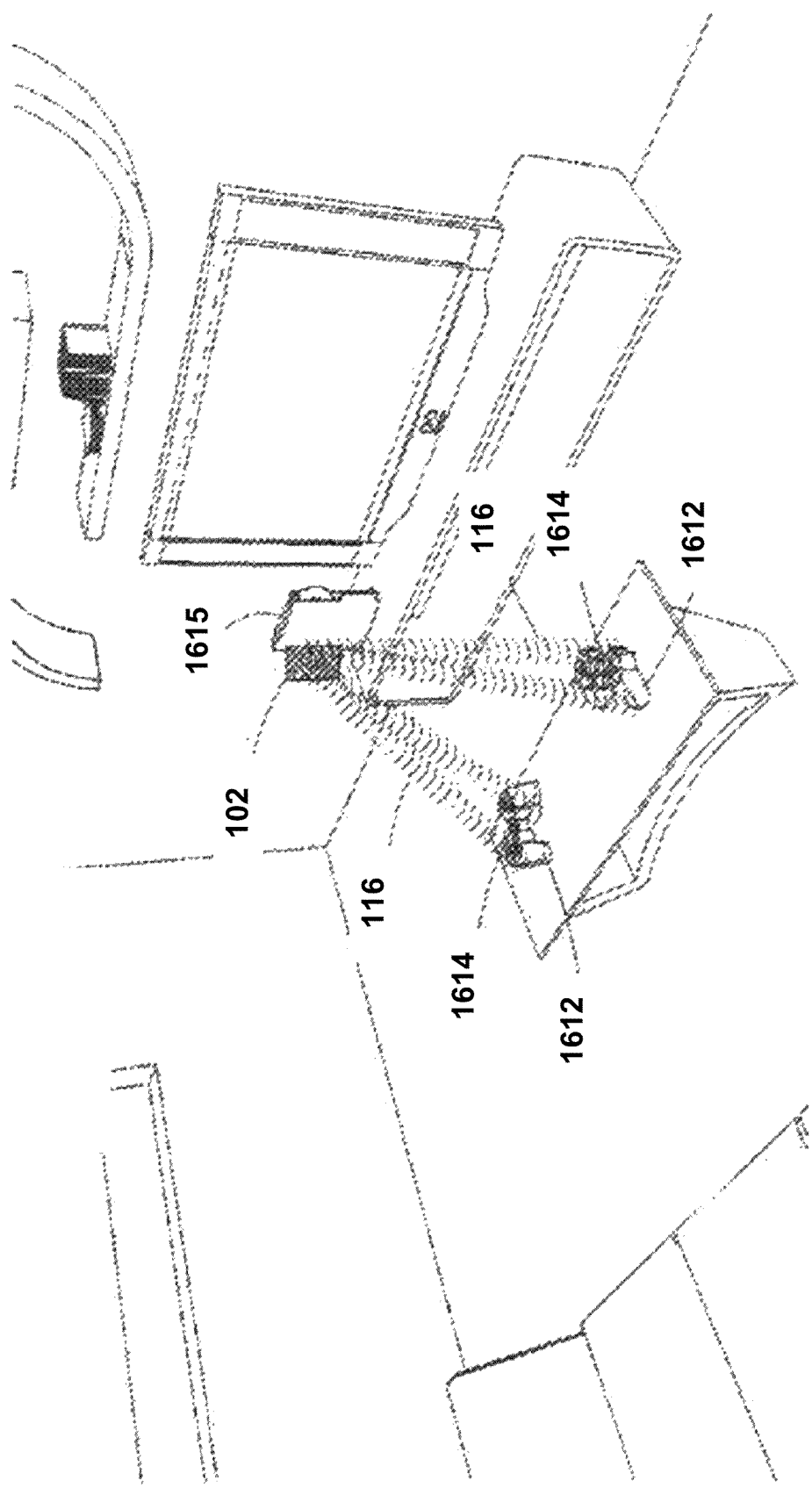

In FIG. 16D, the transmitter 102 is coupled with a game console 1615, and the receivers embedded within respective game controllers 1612 wirelessly receive RF waves from the transmitter 102 and then convert energy from the RF waves that has accumulated in pockets of energy 1614 into usable power.

Figure 16E:
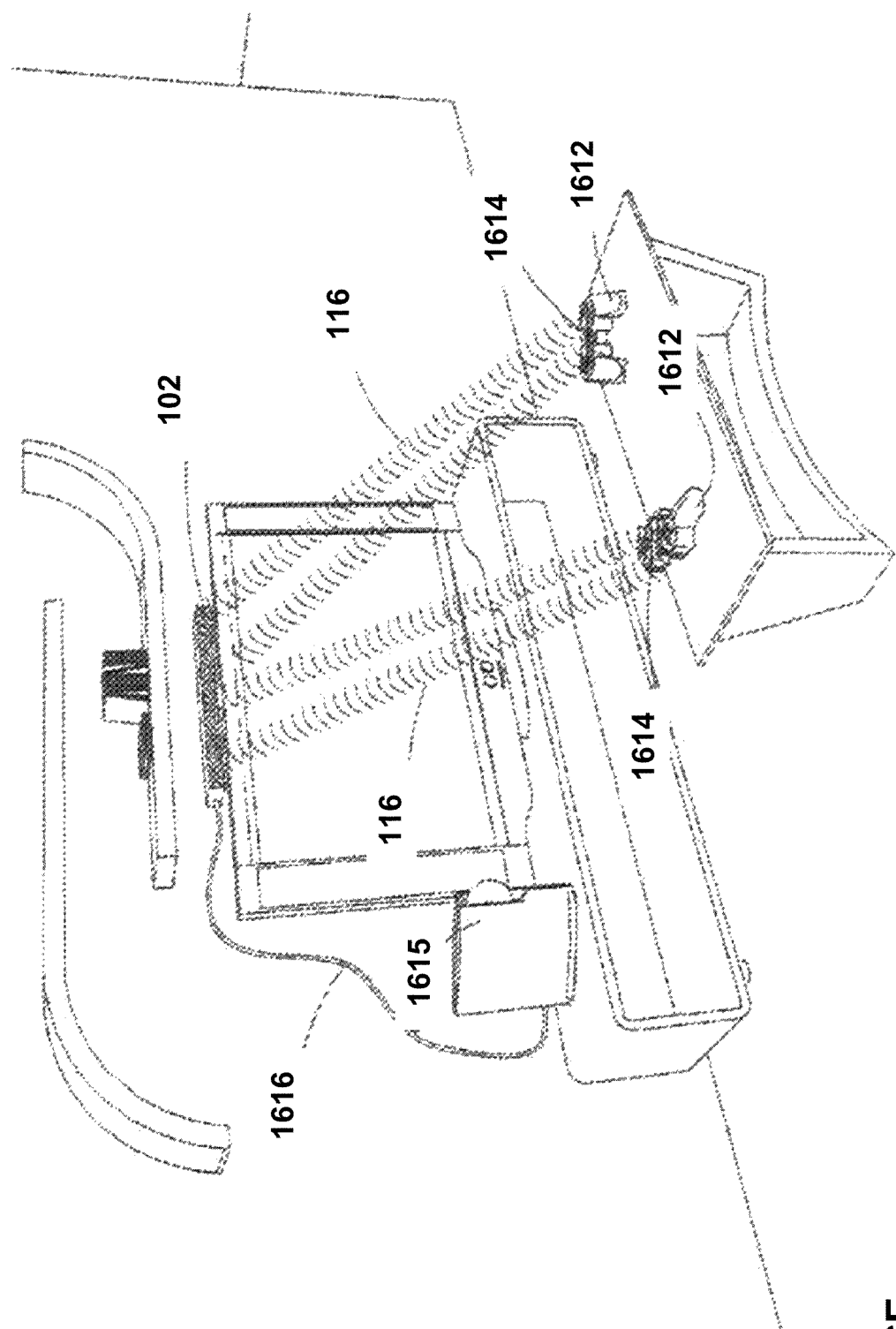

In FIG. 16E, the transmitter 102 is coupled with a game console 1615 via a cable 1616 (such as a USB cable), and the receivers embedded within respective game controllers 1612 wirelessly receive RF waves from the transmitter 102 and then convert energy from the RF waves that has accumulated in pockets of energy 1614 into usable power. In some embodiments, the game console 1615 produces power along the cable 1616, and the transmitter uses that power to generate RF waves that are then transmitted to the game controllers 1612 for charging and powering purposes, as described above.

Figure 16F:
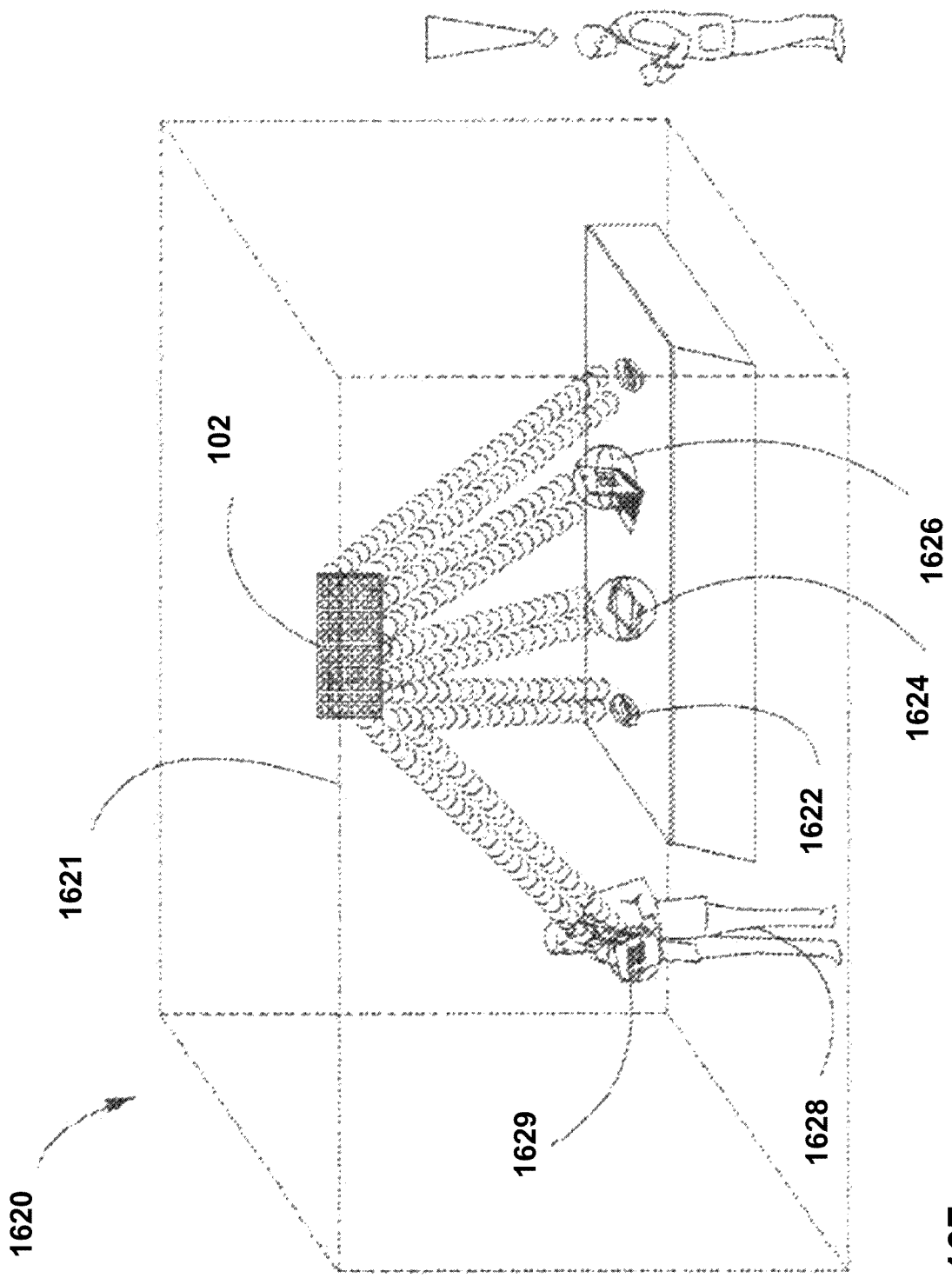

FIG. 16F illustrates a wireless power delivery system 1620 where various electronic devices, for example a smartphone 1622, a tablet 1624, and a laptop 1626 may receive power, through pocket-forming techniques (as described throughout this detailed description), utilizing a transmitter 102 at a predefined range 1621. In some embodiments, these devices may include embedded receivers 120 (or be otherwise operatively coupled to receivers) and capacitors for obtaining necessary power for performing their intended functions. In some embodiments, the system 1620 may be utilized in retail stores where interaction between electronic devices (used for showcase) and potential buyers may be limited due to the presence of wired connections. A potential buyer 1628 may be interested in acquiring a tablet 1629 and, because the system 1620 has been implemented, the buyer 1628 may interact freely with the tablet 1629 before purchasing, but subject to certain restrictions. For example, were buyer 1628 to step out of the range at which transmitter 102 wirelessly delivers power, tablet 1629 may no longer operate (as can be seen in the rightmost part of FIG. 16F for another buyer). In some embodiments, the transmitter 102 may also detect when a tablet or other device travels outside of its range, and may then issue an alarm.

The wireless power delivery system of FIG. 16F may be applied to other settings, such as educational environments 1630, as shown in FIG. 16G. For example, in educational programs for developing or unprivileged cities, regions and countries, teachers and students may be provided with tablets, electronic readers, laptops or even virtual glasses for imparting and taking notes during lectures. However, such equipment may be expensive. Therefore, measures for preventing unauthorized usage of such devices may be employed. For example, devices may be wired to school chairs so that they may not be taken outside classrooms. However, utilizing electronic devices with embedded wireless power receivers may improve the foregoing situation. In some embodiments, a transmitter 102 inside a classroom may provide wireless power, through pocket-forming techniques, to various electronic devices with embedded receivers and capacitors (not shown), for example an e-reader 1632, a laptop 1634, and virtual glasses 1636 which may be used by different users in the educational setting. The foregoing electronic devices may become inoperable outside the range of transmitter 102, as can be seen in the rightmost part of FIG. 16G.

Figure 16H:
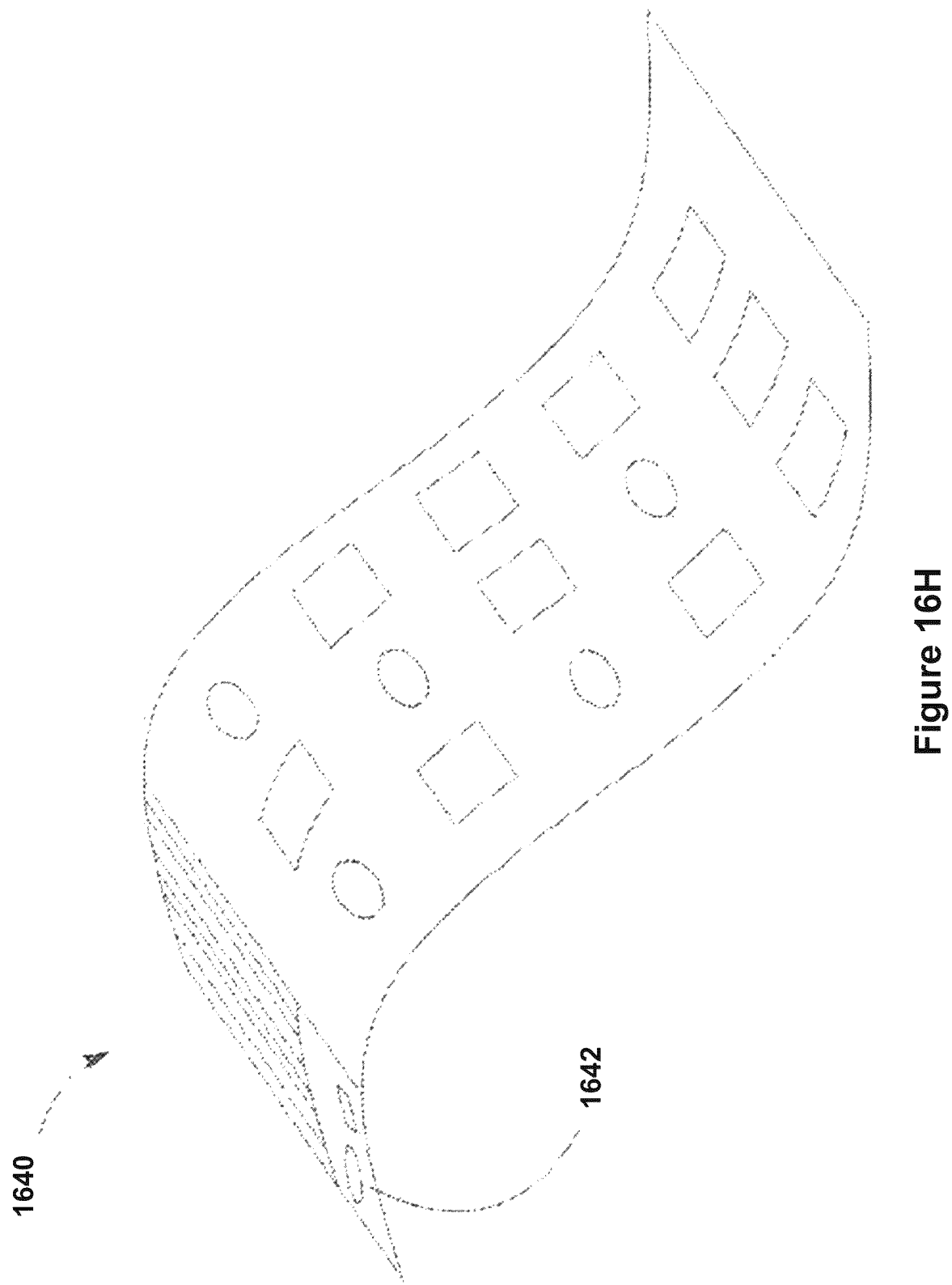
FIG. 16H illustrates an improved roll-able electronic paper display used to explain certain advantages of wireless power transmission systems, in accordance with some embodiments.

FIG. 16H illustrates an improved rollable electronic paper display 1640 used to explain certain advantages of wireless power transmission systems, in accordance with some embodiments. In some embodiments, the display 1640 is produced using flexible organic light emitting diodes (FOLED). In some embodiments, the display 1640 may include at least one embedded receiver 1642 (e.g., an embodiment of the receiver 120 described herein) with a capacitor in one of its corners. Thus, the circuitry for providing power to rollable electronic paper display 1640 may be confined to only a fraction of its surface area, This may improve transparency of the rollable electronic paper display 1640. In other embodiments, an e-reader including the aforementioned receivers and capacitors, may diminish its weight considerably, as well as improve its display brightness. Currently, the weight of e-readers may be driven by their batteries, e.g., up to about 60% to about 80% of the total weight. However, by utilizing the structure described herein, batteries may not be required to be as powerful, thereby reducing overall size and weight of the batteries, and in turn diminishing weight of e-readers. Moreover, by diminishing such weight considerably, e-readers can be made thinner. In some embodiments, previous volume used up for battery allocation, can be distributed to increase display capacity.

FIGS. 16A-16H illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 16A-16H.

Presented below are example methods of wirelessly delivering power to receivers in controllers and other devices.

In some embodiments, an example method of wirelessly supplying power to a game controller includes: (i) receiving, by a transmitter, a communication signal indicating a power requirement from a game controller; (ii) generating, by the transmitter, one or more power transmission waves in response to the communication signal from the game controller; (iii) controlling, by the transmitter, the generated power transmission waves, and the transmitter shifts a phase and a gain of a power transmission wave with respect to other power transmission waves based on the communication signal; and (iv) transmitting, by the transmitter, the one or more power transmission waves through at least two antennas coupled to the transmitter.

In some embodiments, the method further includes receiving, by the transmitter, an indication of power remaining in a battery coupled to the game controller and a location of the game controller.

In some embodiments, the game controller is coupled to a receiver, the receiver configured to receive a pocket of energy from the transmitter.

In some embodiments, the receiver includes a plurality of antennas adapted to be a part of an external cover of the game controller.

In some embodiments, another example method includes: (i) receiving, by a transmitter and from a receiver coupled with a game controller, a communication signal indicating a power requirement of the game controller; (ii) in response to receiving the communication signal from the receiver: determining a location of the game controller based on the communication signal; and generating, by the transmitter, a plurality of radio frequency (RF) power transmission waves; and (iii) controlling, by the transmitter, transmission of the generated plurality of RF power transmission waves through at least two antenna elements coupled to the transmitter, and the transmitter shifts a phase and a gain of a respective RF power transmission wave with respect to other respective RF power transmission waves so that the plurality of RF power transmission waves converges to form a constructive interference pattern in proximity to the determined location of the game controller.

In some embodiments, the receiver is coupled with the game controller via an external cover of the game controller, and the receiver includes a plurality of antennas adapted to be a part of the external cover of the game controller.

In some embodiments, the transmitter is a far-field transmitter.

In some embodiments, the method further includes, in response to receiving an additional communication signal from an additional receiver coupled to an additional game controller, and the additional receiver is distinct from the receiver and the additional game controller is distinct from the game controller: controlling, by the transmitter, transmission of an additional plurality of RF power transmission waves so that the additional plurality of RF power transmission waves converges to form an additional constructive interference pattern in proximity to a location of the additional game controller, and the location of the additional game controller is determined by the transmitter based on the additional communication signal.

In some embodiments, the transmitter is coupled with a game console, and generating the plurality of RF power transmission waves includes generating the plurality of RF power transmission waves using power received from the game console.

In some embodiments, an example method includes: (i) connecting a pocket-forming transmitter to a power source; (ii) generating RF waves from a RF circuit embedded within the transmitter; (iii) controlling the generated RF waves with a digital signal processor m the transmitter; (iv) transmitting the RF waves through antenna elements connected to the transmitter within a predefined range; and (v) capturing the RF waves forming pockets of energy converging in 3-dimensional space at a receiver with antenna elements connected to the electronic device within the predefined range to convert the pockets of energy into a DC voltage for charging or powering the electronic device.

In some embodiments, the transmitter identifies each electronic device within the predefined range and delivers power to each approved electronic device through pocket-forming but disables, locks out and removes power from each electronic device when the approved electronic device is moved out of the range of the transmitter for security reasons.

In some embodiments, the transmitter identifies each receiver requesting power and then only powers approved electronic devices within the predefined range of the transmitter.

In some embodiments, the method further includes generating multiple pockets of energy from the pocket-forming transmitter to power or charge multiple, approved electronic devices in an educational setting within the predefined range of the transmitter. In some embodiments, the electronic devices in the educational setting are tablets, electronic readers, laptops, virtual glasses or smartphones provided wireless power through pocket-forming whenever in range of the transmitter but disabled whenever outside of the predefined range of the transmitter.

In some embodiments, another example method includes, transmitting, by a plurality of antennas of a transmitter, a plurality of power waves forming a constructive interference pattern at a location of a receiver, and the receiver is configured to receive power waves only from the transmitter when the receiver is within a predefined distance threshold from the transmitter; and detecting, based on communications signals received from the receiver, that the receiver has moved to a new location. In response to detecting that the receiver has moved to the new location, determining, by a controller of the transmitter, whether the new location of the receiver is within the predefined distance threshold; in response to determining by the controller of the transmitter that the new location is within the predefined distance threshold, adjusting, by the controller of the transmitter, the plurality of antennas such that transmission of the plurality of power waves forms a new constructive interference pattern at the new location of the receiver. The method further includes, in response to determining that the new location is not within the predefined distance threshold, providing, by the transmitter, an indication that the receiver is not within the predefined distance threshold, and the receiver is configured to be inoperable upon exceeding the predefined distance threshold from the transmitter.

In some embodiments, the transmitter: (i) identifies a plurality of receivers, including the receiver, as being within the predefined distance threshold; (ii) delivers power to each approved receiver of the plurality of receivers through one or more constructive interference patterns formed by convergence of power waves in proximity to each approved receiver; and (iii) ceases delivering power to a respective approved receiver when the respective approved receiver is moved out of the predefined distance threshold from the transmitter.

In some embodiments, providing the indication includes issuing an alarm.

In some embodiments, the method further includes, in response to determining by the controller of the transmitter that the new location is within the predefined distance threshold, determining, based on the communications signals received from the receiver, an optimum time and location for forming the new constructive interference pattern at the new location of the receiver.

FIGS. 17A-17G illustrate various articles (e.g., heating blanket, heating sock, heating glove, warming jacket, shirt, cap, and cooling shirt) with embedded wireless power receivers, in accordance with some embodiments.

Figure 17A:
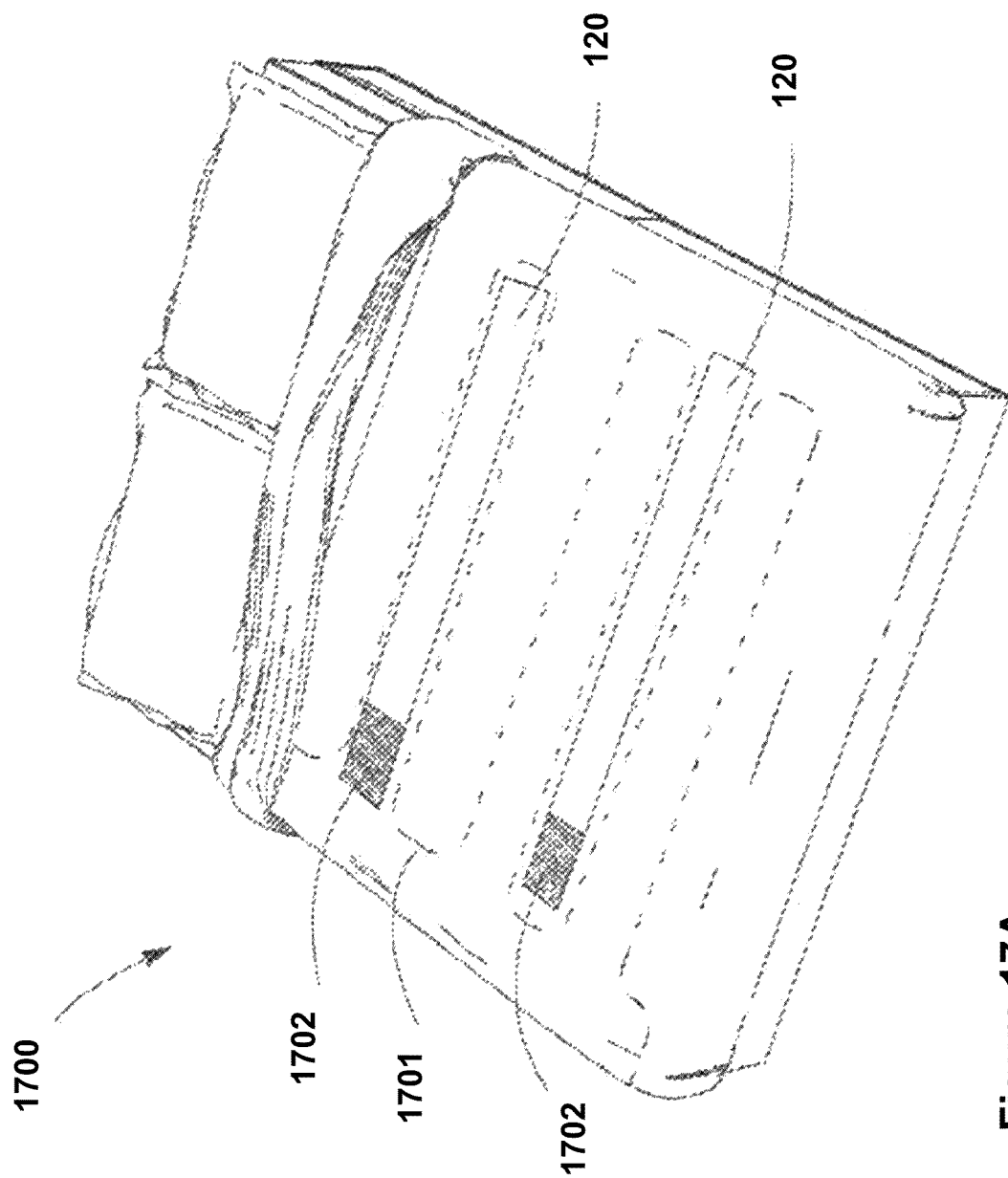
FIGS. 17A-17G illustrate various articles (e.g., heating blanket, heating sock, heating glove, warming jacket, shirt, cap, and cooling shirt) with embedded wireless power receivers, in accordance with some embodiments.
Figure 17B:
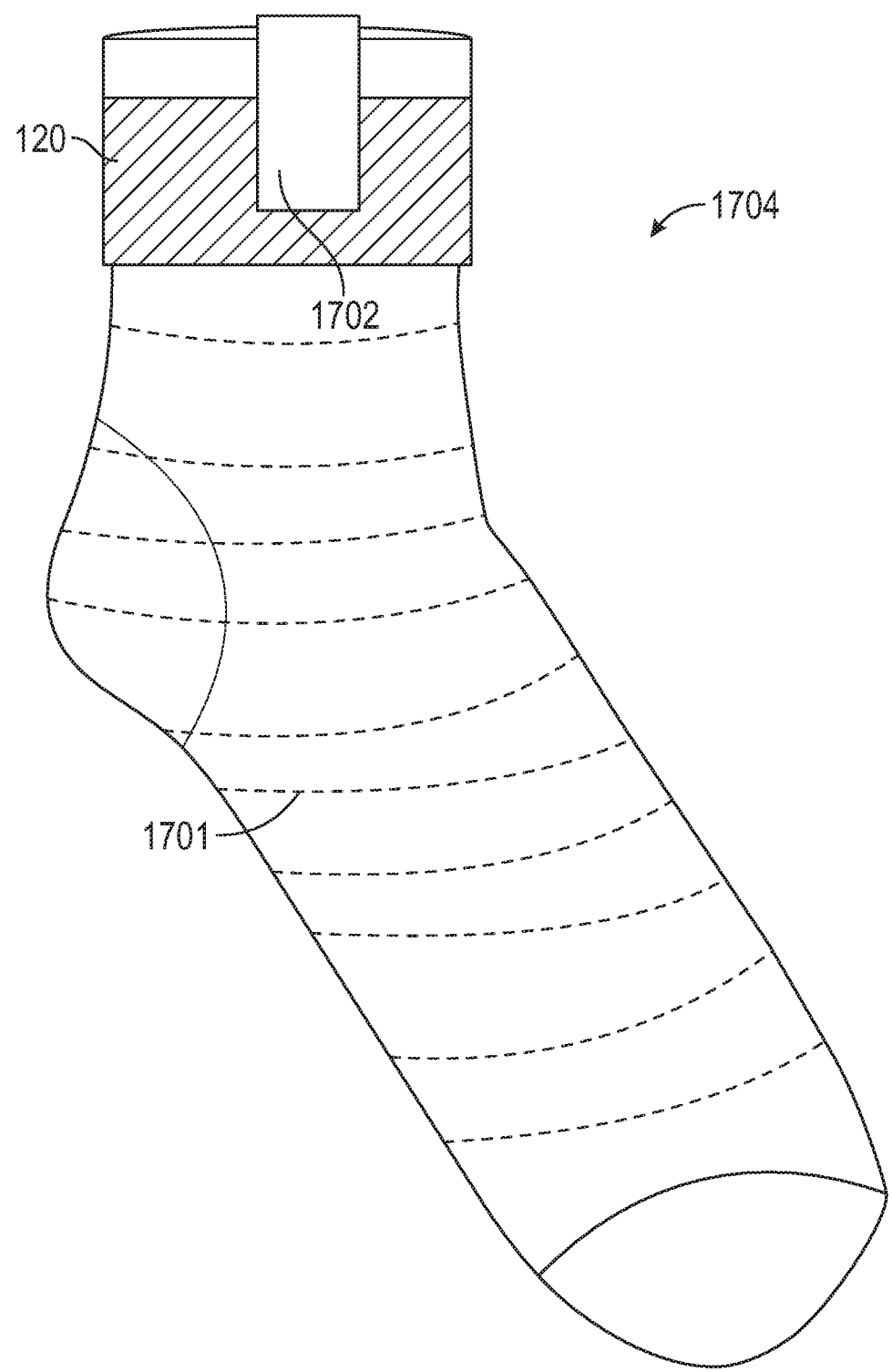
Figure 17C:
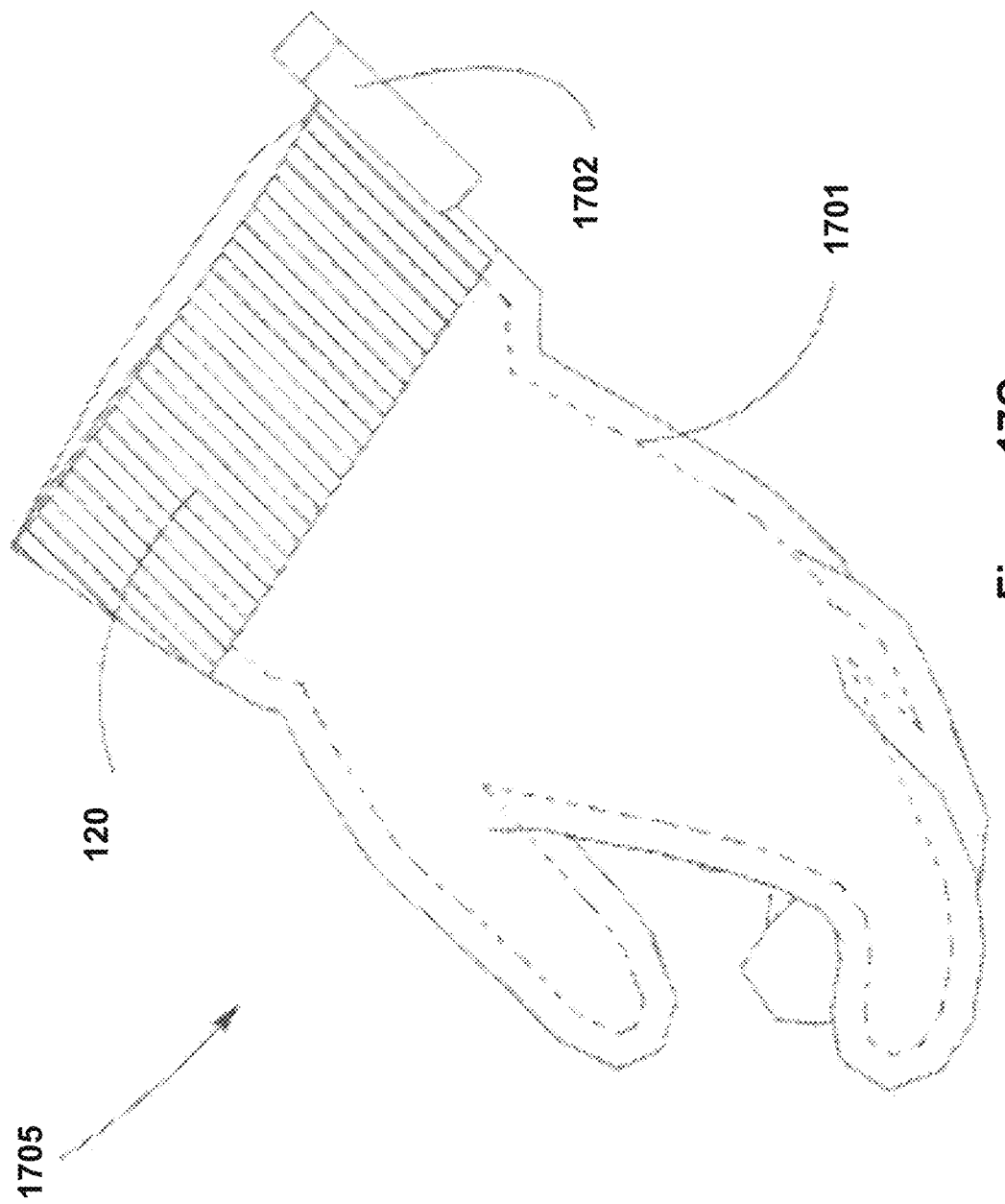
Figure 17D:
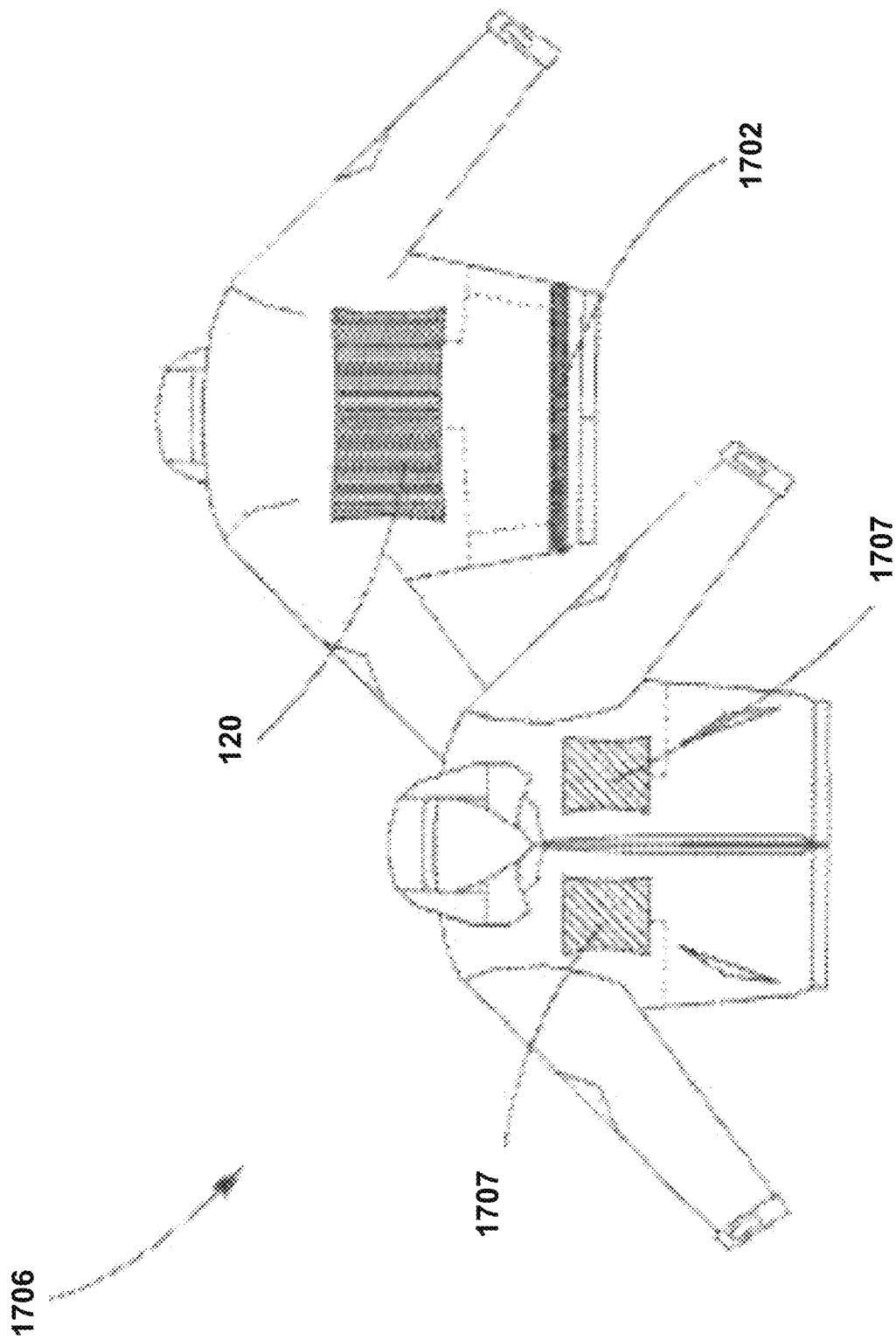
Figure 17E:
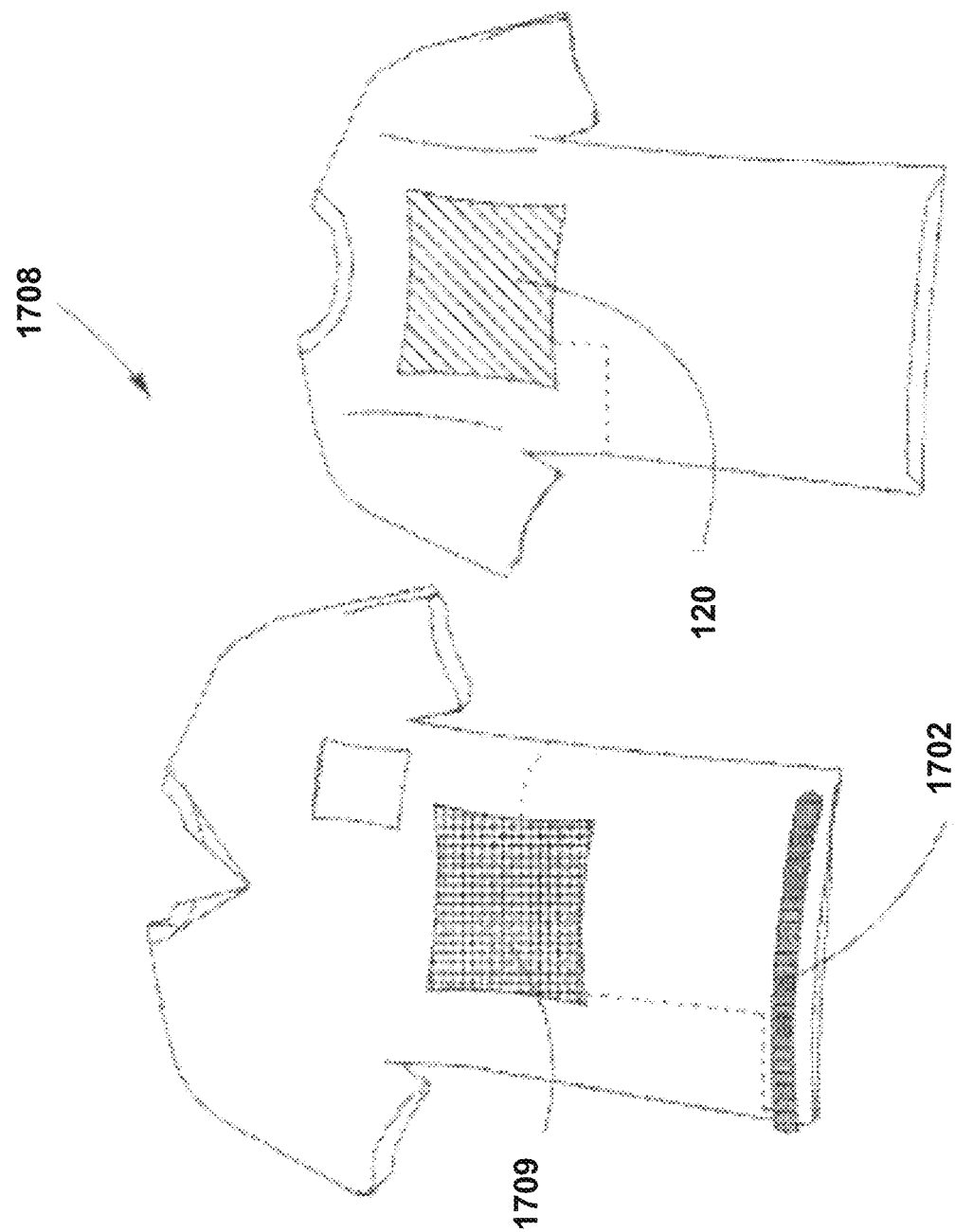
Figure 17F:
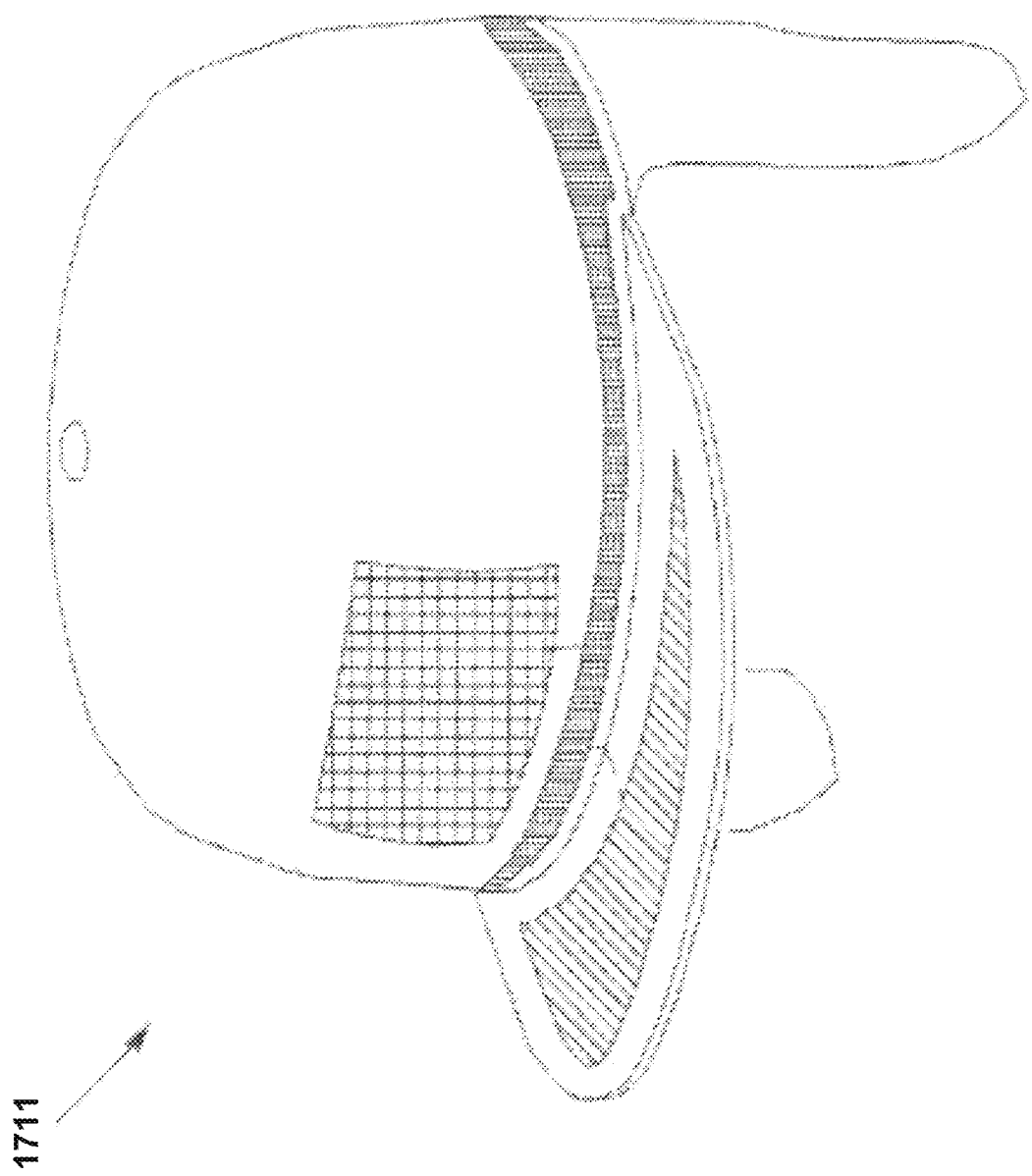
Figure 17G:
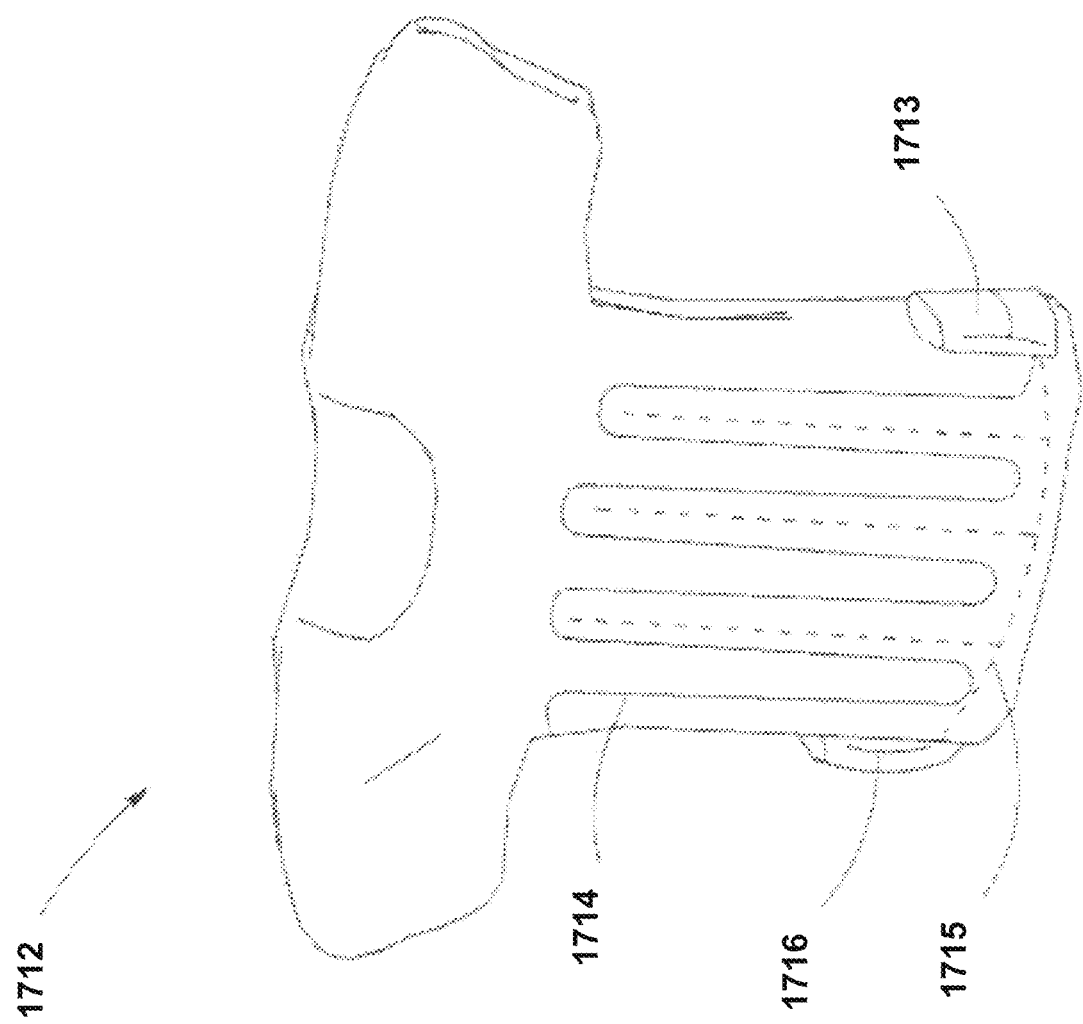

In particular, FIG. 17A shows a heating blanket 1700, according to an embodiment, which includes a heating circuit 1701, receivers 120, and flexible batteries 1702; FIG. 17B illustrates a heating sock 1704 with a heating circuit 1701, a receiver 120 and flexible rechargeable batteries 1702; FIG. 17C shows a heating glove 1705 with a heating circuit 1701, a receiver 120 and batteries 1702; FIG. 17D illustrates a heating jacket 1706 that includes heating patches 1707, a receiver 120 and flexible batteries 1702; FIG. 17E shows a shirt 1708 with a display 1709, a receiver 120, and flexible batteries 1702; FIG. 17F illustrates a cap 1711 with a display, a receiver, and flexible batteries; and FIG. 17G shows a cooling shirt 1712 with a cooling liquid reservoir 1713, cooling tubes 1714, sensor wiring 1715, and case 1716 (in some embodiments, case 1716 may include a battery, a receiver and a pump for controlling the flow of cooling liquid through cooling tubes 1714).

In some embodiments, the articles of clothing with embedded receivers may operate at 7.4V and may be powered or charged wirelessly (as described herein).

In example #1, a portable electronic heating jacket that may operate at 7.4V may be powered or charged. In this example, a transmitter 102 may be used to deliver pockets of energy onto heating jacket, in a process similar to the one depicted in FIG. 1. Transmitter 102 may have a single array of 8×8 flat panel antennas where all the antenna elements may operate in the same frequency band. Flat antennas may occupy less volume than other antennas, hence allowing a transmitter 102 to be located in small and thin spaces, such as, walls, mirrors, doors, ceilings and the like. In addition, flat panel antennas may be optimized for operating at long distances into narrow hall of wireless power transmission, such feature may allow operation of portable devices in long areas such as, train stations, bus stations, airports and the like. Furthermore, flat panel antennas of 8×8 may generate smaller pockets of energy than other antennas since its smaller volume, this may reduce losses and may allow more accurate generation of pockets of energy. In this way, heating jacket may be charged without being plugged and even during use. Heating jacket may include a receiver (e.g., an embodiment of receiver 120, FIG. 1) coupled to antenna elements; the optimal amount of antenna elements that may be used with receivers for heating jacket may vary from about 10° F. to about 200° F., being most suitable at about 50° F.; however, the amount of antennas within receivers may vary according to the design and size of the heating jacket. Antenna elements may be made of different conductive materials such as cooper, gold, and silver, among others. Furthermore, antenna elements may be printed, etched, or laminated onto any suitable non-conductive flexible substrate and embedded in the heating jacket.

In example #2, a portable electronic heating socks, that may operate at 7.4V may be powered or charged. In this example, a transmitter 102 may be used to deliver pockets of energy onto receivers 120 embedded on the heating socks following a process similar to the one depicted in FIG. 1.

FIGS. 17A-17G illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 17A-17G.

Presented below are example methods of wirelessly delivering power to receivers in clothing.

In some embodiments, an example method includes: (i) receiving, by a transmitter, a communication of a power requirement of a temperature regulating component coupled to an article of clothing; (ii) generating, by the transmitter, a plurality of power transmission waves to form a pocket of energy in response to the power requirement; (iii) controlling, by the transmitter, generated power transmission waves to provide phase shifting and gain shifting with respect to other power transmission waves; and (iv) transmitting, by the transmitter, the power transmission waves through at least two antennas coupled to the transmitter.

In some embodiments, the pocket of energy is received by a receiver associated with the temperature regulating component, the receiver being configured to be coupled to the article of clothing.

In some embodiments, the temperature regulating component includes an electrical resistance heater configured to dissipate the electrical energy as heat within the article of clothing.

In some embodiments, the temperature regulating component includes a sensor coupled to the article of clothing, the sensor configured to determine the temperature of the article of clothing.

In some embodiments, the receiver includes a plurality of antennas, a power converter, and a communications component configured to communicate with the transmitter.

In some embodiments, the receiver communicates to the transmitter information including a temperature of the article of clothing and an indication of the power level of the temperature regulating component.

In some embodiments, an example receiver includes: (i) an antenna configured to receive a pocket of energy formed by a convergence of power transmission waves from a transmitter; and (ii) a rectifying circuit configured to convert the received pocket of energy into electricity to charge a temperature regulating component associated with the article of clothing, the temperature regulating component being configured to alter temperature of the article of clothing to a desired temperature.

In some embodiments, the temperature regulating component includes an electrical resistance heater configured to dissipate the electrical energy as heat within the article of clothing.

In some embodiments, the temperature regulating component includes a sensor coupled to the article of clothing, the sensor configured to determine the temperature of the article of clothing.

In some embodiments, another example wireless power receiver embedded in an article of clothing includes: (i) a flexible antenna forming a pattern in the article of clothing, the flexible antenna being configured to receive radio frequency (RF) wireless power waves from a far-field wireless power transmitter, and some of the RF wireless power waves constructively interfere at the flexible antenna and some RF wireless power waves destructively interfere near the flexible antenna; (ii) a rectifying circuit coupled to the flexible antenna, the rectifying circuit being configured to rectify the received RF wireless power waves into a direct current; (iii) a temperature regulating component coupled to the rectifying circuit, the temperature regulating component being configured to alter a temperature of the article of clothing to a desired temperature using the direct current, and the temperature regulating component includes a sensor coupled to the article of clothing, the sensor configured to determine the temperature of the article of clothing; and (iv) a communications component in communication with the far-field wireless power transmitter, the communications component being configured to communicate information to the far-field wireless power transmitter, including the temperature of the article of clothing determined by the sensor.

In some embodiments, the temperature regulating component further includes an electrical resistance heater configured to dissipate the direct current as heat within the article of clothing.

FIGS. 18A-18B are illustrations of medical devices with wireless power receivers coupled thereto, in accordance with some embodiments.

FIGS. 18A-18B are illustrations of medical devices with wireless power receivers coupled thereto, in accordance with some embodiments. For example, FIG. 18A shows a blood glucose meter 1801 that includes a receiver 120. FIG. 18B shows a portable medical electronic device such as a portable ultrasound machine 1802 that includes multiple receivers 120, coupled to both a front and side portion of the device 1802.

The above described may not be limited to portable electronic medical devices shown in FIGS. 18A-18B. Receiver 120 may also be included in a plurality of medical electronic devices such as infrared electronic thermometer, electronic pads like tablets, blood pressure monitor, blood glucose meter, pulse oximeter, and ECG among others. The number and type of sensor elements are calculated according the medical electronic device's design.

Figure 18D:
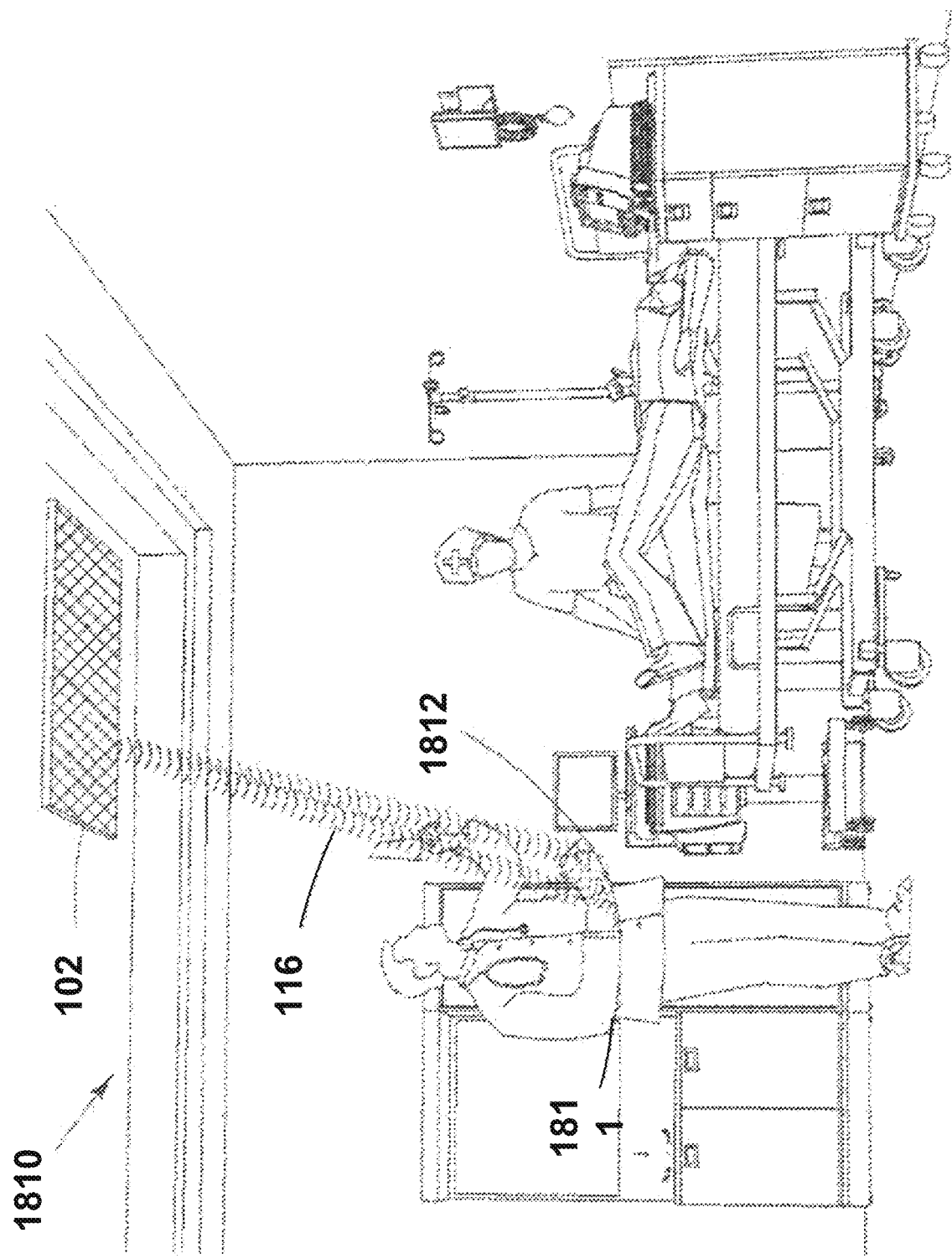
Figure 18E:
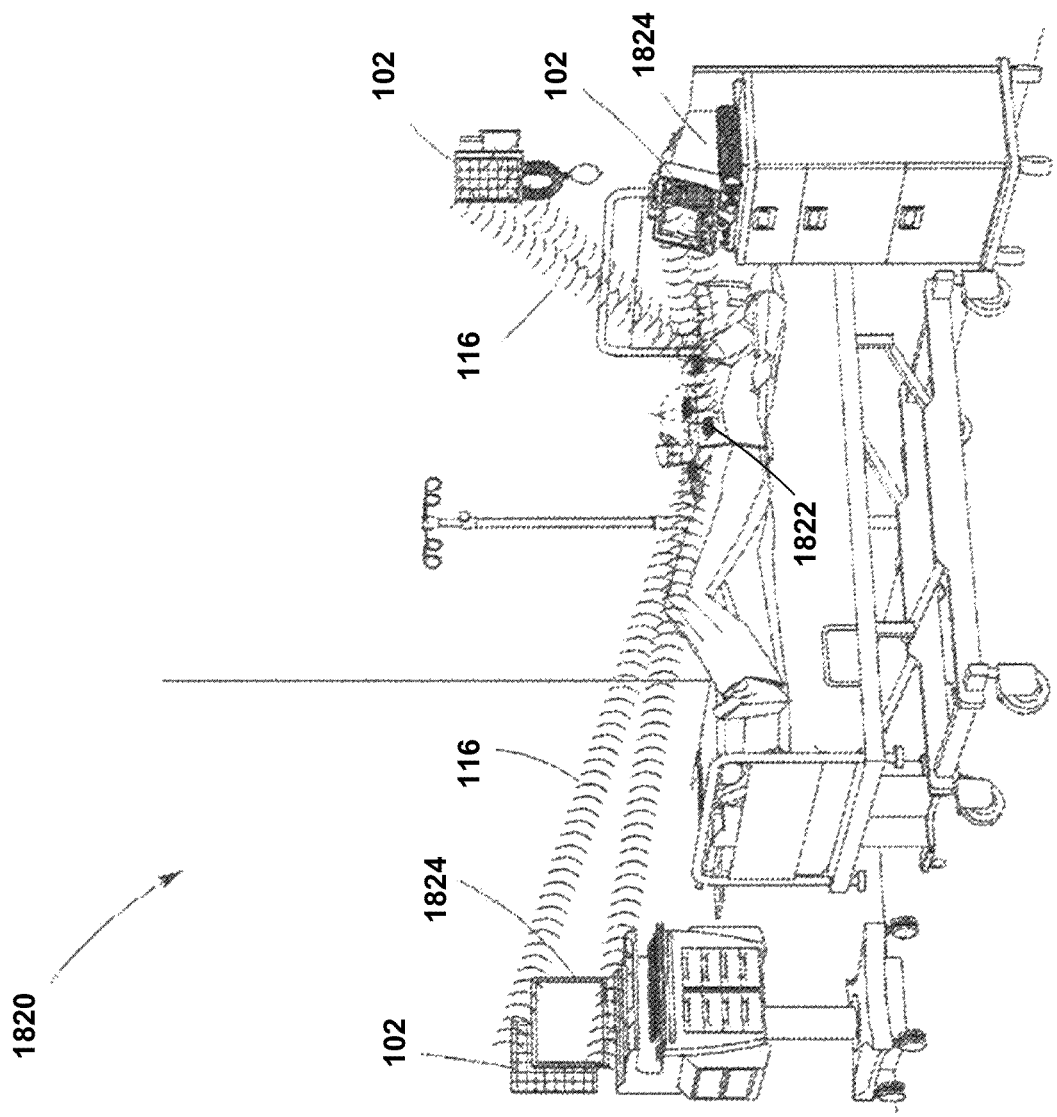

FIGS. 18C-18E are illustrations of wireless power transmission systems for wirelessly delivering power to medical devices, in accordance with some embodiments.

FIGS. 18C-18D show wireless power delivery system 1810, in accordance with some embodiments. Transmitter 102 may be located at the ceiling of a room pointing downwards, and may transmit controlled RF waves 116 which may converge in 3-dimensional space to form pockets of energy. A receiver 120, embedded or attached to portable electronic medical device 1812, may then convert energy that has accumulated by constructively interfering RF waves at pockets of energy 1811 for charging or powering these devices.

FIG. 18E illustrates a wireless power delivery system 1820 for wirelessly providing power to wireless sensors 1822, which may be used for measuring physiological parameters of a patient. In some embodiments, multiple transmitters 102 attached to or embedded in medical devices 1824 may provide controlled RF waves 116 to wireless sensors 1822.

In some embodiments, the wireless power delivery techniques for health care environments may even be utilized in rooms in which a patient has a pacemaker, as the RF waves will not interfere with or damage functioning of those types of devices because electromagnetic fields are not generated when using RF waves to wirelessly deliver power.

FIGS. 18A-18E illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 18A-18E.

Presented below are example methods of wirelessly delivering power to receivers in medical devices.

In some embodiments, an example method of wireless power receipt by an electronic medical device includes: (i) communicating, by a receiver associated with the electronic medical device, a power requirement and an identifier for the electronic medical device to a transmitter, the identifier being data uniquely associated with the electronic medical device; (ii) receiving, by an antenna of the receiver, a pocket of energy formed by converging power transmission waves; and (iii) converting, by a rectifying circuit of the receiver, the received pocket of energy into electricity to charge the electronic medical device.

In some embodiments, the electronic medical device is a sensor configured to record medical information from a patient. In some embodiments, the electronic medical device is configured to record a blood glucose level from a patient. In some embodiments, the electronic medical device is configured to communicate an electronic medical record with a medical professional.

In some embodiments, the receiver is configured to transmit information to a medical professional located remotely from the electronic medical device.

In some embodiments, the receiver communicates information (e.g., instructions) to a transmitter of the power transmission waves to determine an optimum time and location for receiving a pocket of energy from the transmitter.

In some embodiments, an example method of wireless transmission of power to an electronic medical device or a sensor includes: (i) generating pocket forming power radio frequency (RF) signals from a RF circuit embedded within a transmitter connected to a power source; (ii) generating communication signals from a communication circuit embedded within the transmitter, and the transmitter includes a communication antenna configured to transmit and receive communications signals to and from a receiver coupled to an electronic device, and the electronic device is a medical device or a sensor; (iii) controlling the generated power RF signals and the communication signals with a digital signal processor coupled to the transmitter; and (iv) transmitting the power RF signals by at least two antennas electrically connected to the RF circuit within the transmitter. An antenna of the receiver is configured to capture energy from the pocket of energy produced by the pocket-forming power RF signals in converging in 3-dimensional space, and the receiver is configured to convert the energy into a DC voltage for charging or powering the medical device or the sensor coupled to the receiver. The method further includes: (v) transmitting, by the communication circuit of the transmitter, instructions in the communication signals to the receiver to generate location data, power requirements, and timing data; and (vi) receiving, by the communication circuit, the communications signals from the receiver, and the communication signals received from the receiver provide an optimum time and location data indicating the location associated with the electronic device coupled to the receiver for converging the power RF signals to form the pocket of energy in 3-dimensional space at the location.

In some embodiments, the pocket-forming transmitter is centrally located in a recovery room, operating room, patient room, emergency room or common area of a hospital for charging the electronic medical device or the sensor.

In some embodiments, the at least two antennas of the transmitter are located on a ceiling in a room, for charging the electronic device.

Figure 19A:
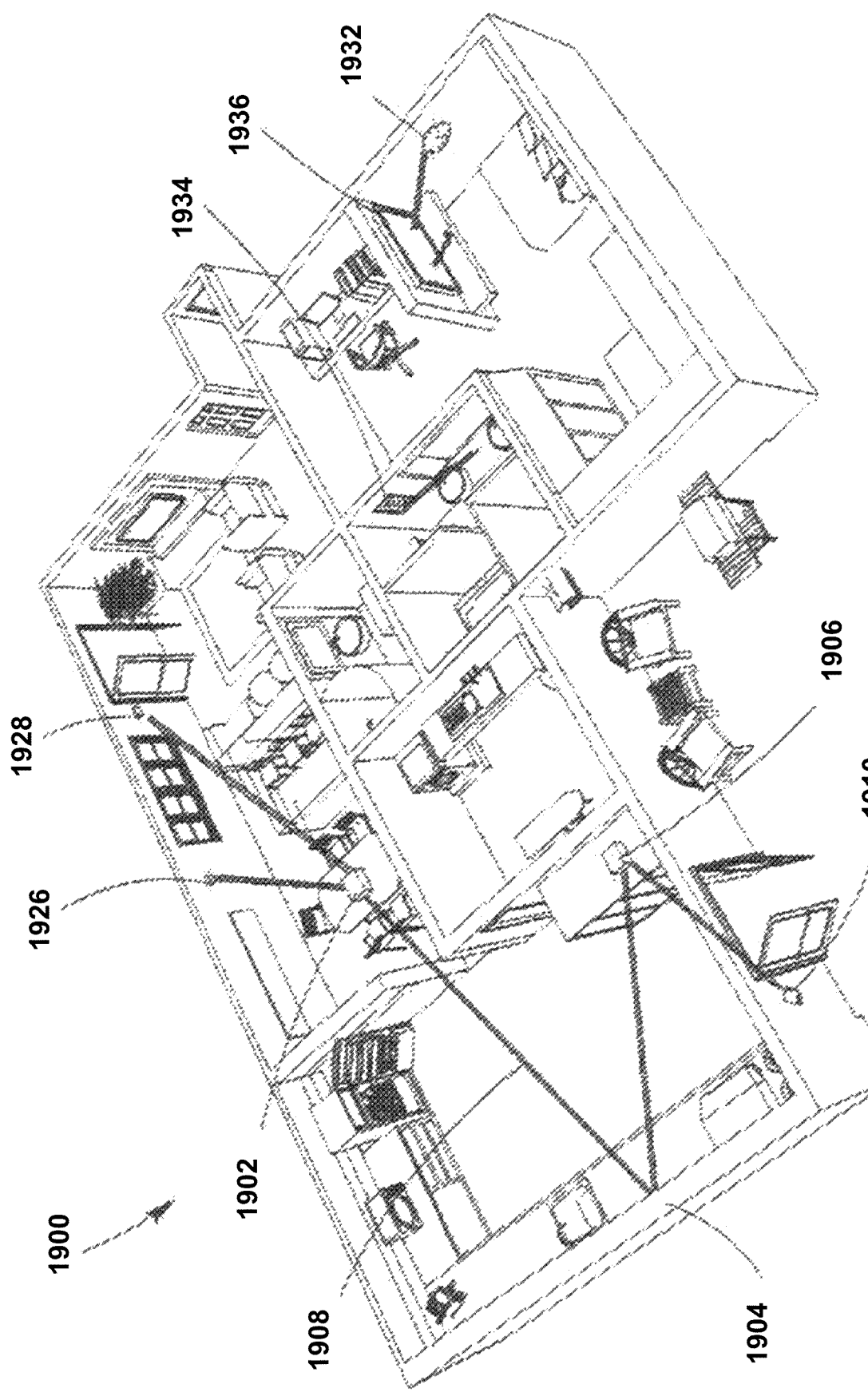
FIG. 19A is an illustration of a house configured with a number of wireless power transmitters and receivers, in accordance with some embodiments.

FIG. 19A is an illustration of a house configured with a number of wireless power transmitters and receivers, in accordance with some embodiments.

FIG. 19A depicts a wireless powered house 1900, which may include a plurality of transmitters 102 (e.g., instances of the transmitter 102, FIG. 1) connected to a single base station 1902, which may also include a main transmitter. In some embodiments, base station 1902 manages wireless power delivery to mobile and non-mobile devices in wireless powered house 1900 (additional details regarding base stations are provided above). Additionally, transmitters 102 may be embedded into a plurality of electronic devices and objects in wireless powered house 1900.

Base station 1902 may enable communication between every transmitter 102 and receivers 120 in wireless powered house 1900. Furthermore, wireless powered house 1900 may include a variety of range enhancers, which may increase range of wireless power transmission, such range enhancers may include: reflectors 1904 and wireless repeaters 1906, Reflectors 1904 may be included in several places in the wireless powered house 1900, such as curtains, walls, floor, and ceiling among others. Wireless repeaters 1906 may include a receiver 120 and a transmitter 102 for re-transmitting power. FIG. 19A illustrates an example for using reflectors 1904 and wireless repeaters 1906, where a CCTV camera 1910 requires charge, but it is too far for receiving power at an optimal efficiency. However, base station 1902 may trace a trajectory for RF waves 1908, which may imply less losses and includes the use of reflectors 1904 that may be embedded in the walls and a wireless repeater 1906, which may receive the reflected RF waves 1908 and re-transmits these to the CCTV camera 1910 with higher power than the received.

In some embodiments, base station 1902 may send RF waves 1908 to any device in wireless powered house 1900, these devices may include static devices such as: smoke detectors 1926, digital door locks 1928, CCTV cameras 1910, wall clocks 1932 among others devices that require wired powered connections. The lack of cables for powering such devices may reduce work time for installing and maintaining those devices. Furthermore, walls, ceilings, and floors need not be drilled for installing cables.

Device locations may be updated automatically by base station 1902, which may set a communication channel between each device, regardless if it is a mobile or non-mobile device. Some devices such as mirrors 1934 may allow a transmitter 102 to be embedded therein in order to charge small devices and disposable devices in the bathroom and/or in the bedroom. Such devices may include: electric razors, electric toothbrushes, lamps, massagers, UV-sterilizers among others. Therefore, mirror 1934 may significantly reduce wired chargers for each electric device in bathrooms and bedrooms.

Similar to mirror 1934, televisions 1936 may include transmitters 102 for powering and charging mobile and non-mobile devices.

Base station 1902 may establish areas where wireless power transmission may have specialized protocols, these areas may include an infirmary, children's rooms, rooms for pregnant women, and other regions where devices may be sensitive to radio frequency waves but not to RF waves 1908. Some areas may represent a permanent null space, where no pockets of energy are generated. Furthermore, some receivers 120 may possess the same specialized protocols regardless their location in wireless powered house 1900. Such devices may include electric knives, drills, and lighters among others. Therefore, each device may be restricted to a specific area and to a specific user, thus, safety in wireless powered house 1900 may be higher. Hence, children may not be exposed or in proximity to harmful hardware and thieves may not be able to use stolen equipment outside the wireless powered house 1900.

Figure 19B:
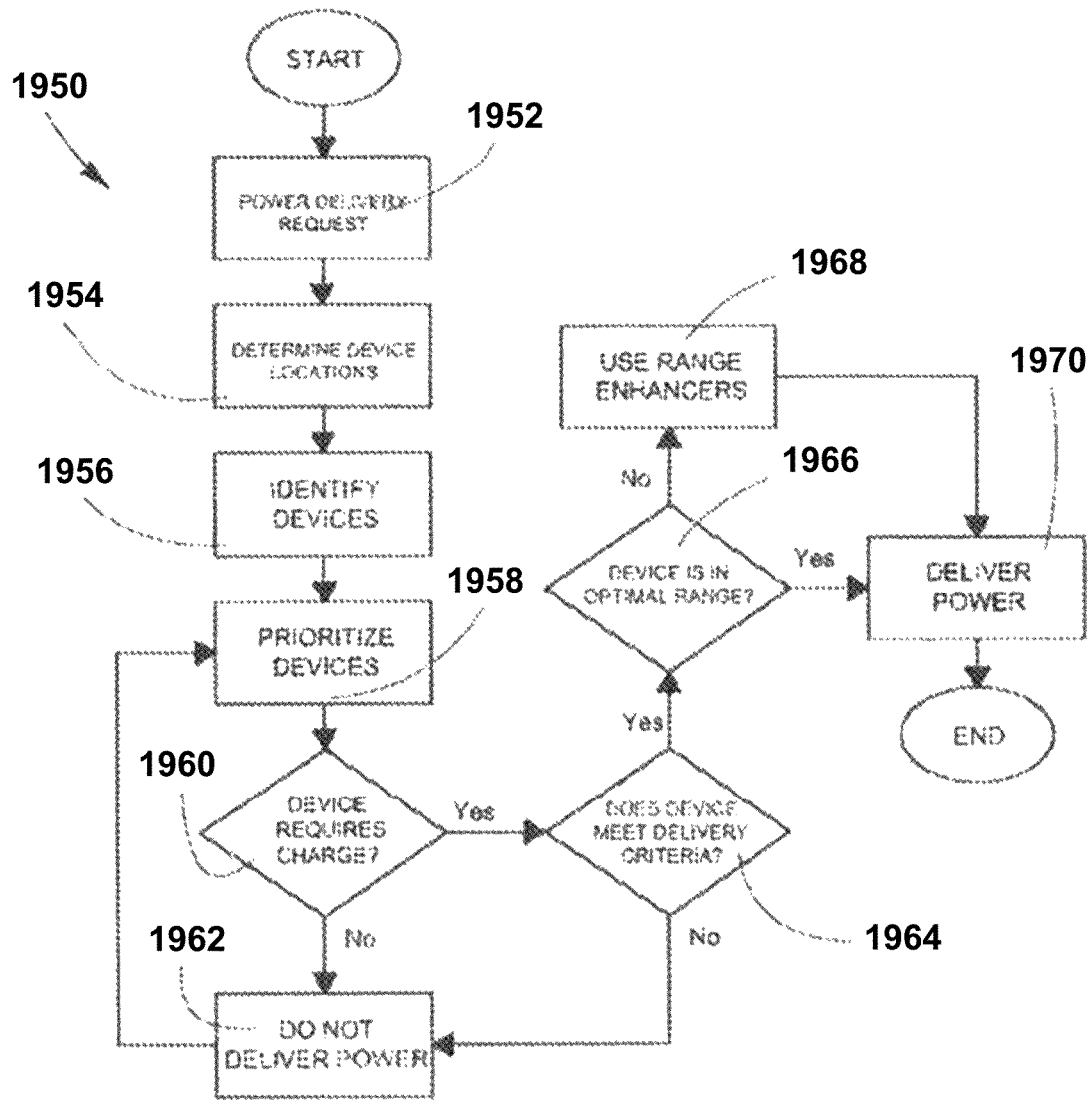
FIG. 19B is a flow diagram of a wireless power transmission process that may be implemented for charging one or more devices located within a house configured with a number of wireless power transmitters and receivers, in accordance with some embodiments.

FIG. 19B is a flow diagram of an example routine that may be utilized by a microcontroller of a base station in a wireless powered house to control wireless power transmission, in accordance with some embodiments.

Routine 1950 may begin when any transmitter 102 in wireless powered house 1900 receives a power delivery request Step 1952 from receiver 120. Subsequently, at determine device locations Step 1954, a receiver 120 may send a signal via BLUETOOTH, RF waves, or infrared, among others to the closest transmitter 102. Then, transmitter 102 may determine a location of receiver 120 in wireless powered house 1900. After this procedure, at identify devices Step 1956 receiver 120 may send a signature signal to the closest transmitter 102, such signal may be coded using suitable techniques such as delay encoding, orthogonal frequency-division multiplexing (OFDM), code division multiplexing (CDM) or other suitable binary coding for identifying a given electronic device including receiver 120. At this step, micro-controller may obtain information from receiver 120 such as type of device, manufacturer, serial number, and total power required. Then, the micro-controller in base station 1902 may proceed to authenticate where it may evaluate the signature signal sent by receiver 120. The micro-controller may proceed to a decision. If receiver 120 is not authorized to receive power, micro-controller may decide to block it. If receiver 120 is authorized, it may receive charge based on its assigned priority, such value is determined at prioritize devices Step 1558, such value may be set by the user preferences and charge level of the equipment, such charge level may be determined in device requires charge Step 1560. If the device does not requires charge, transmitter 102 may not charge it at do not deliver power Step 1562. Furthermore, such device may be listed as low priority to charge during prioritize devices Step 1558.

In addition, if multiple receivers 120 are requiring power, the micro-controller may deliver power equally to all receivers 120 or may utilize a priority status for each receiver 120. In some embodiments, the user may choose to deliver more power to its smartphone, than to its gaming device. In other cases, the user may decide to first power its smartphone and then its gaming device. Furthermore, smoke detectors 1926, digital door locks 1928, CCTV cameras 1910 among others similar devices, may have the highest priority.

When the receiver 120 is authorized to receive charge, it has to meet some criteria at does device meet delivery criteria Step 1964. The foregoing powering criteria may depend on the electronic device requiring power and/or based in user preferences. For example, smartphones may only receive power if they are not being used, or maybe during usage but only if the user is not talking through it, or maybe during usage as long as WI-FI is not compromised among other such criteria. In the case of a user custom profile, the user may specify the minimum battery level its equipment can have before delivering power, or the user may specify the criteria for powering his or her device among other such options. In addition, in wireless powered house 1900, some devices may possess some special criteria, as described in FIG. 19A; such devices may be required to operate in specific rooms. Such devices may include drillers, electric knives, lighters, electric screwdrivers, saws, among others. Furthermore, some devices may require some user authentication, which may be achieved through password verification or biometric authentication. These two criteria may be used in combination for a maximum level of safety. Such combination may generate a single criterion related to parental control protocol, which may also include managing power intensity for toys and operation areas for them.

Alternatively, the micro-controller may also record data on a processor on transmitter 102. Such data may include powering statistics related to how often a device requires power, at what times the device is requesting power, how long it takes to power the device, how much power was delivered to such device, the priority status of devices, where the device is mostly being powered (for example, at home or in the workplace). In addition, such statistics could be uploaded to a cloud based server so that the user can look at all such statistics. Thus, the aforementioned statistics can help the micro-controller decide when to stop delivering power to such a user.

Continuing, does device meet delivery criteria? Step 1964, micro-controller in base station 1902 may determine if receiver 120 is within the optimal range from the closest transmitter 102, such analysis may be carried out at device is in optimal range? Step 1966. If receiver 120 is within the optimal range, then transmitter 102 may deliver power at deliver power Step 1970, if receiver 120 is out of the optimal range, then micro-controller may use reflectors 1904 and wireless repeaters 1906 for increasing the optimal range, such operation may be performed at use range enhancers Step 1968. Subsequently, receiver 120 may receive charge at deliver power Step 1970.

FIGS. 19A-19B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 19A-19B.

Presented below are example systems and methods of wirelessly delivering power to receivers in a wirelessly powered house.

An example method includes receiving, by a base station, a communication of a power requirement for an electronic device coupled to a receiver, and the base station is coupled to a plurality of transmitters, and activating, by the base station, a transmission of a plurality of power transmission waves from at least one of the plurality of transmitters to form a pocket of energy converging proximate to at least one receiver to charge the electronic device.

In some embodiments, the method further includes controlling, by the base station, each of the plurality of transmitters to deliver a pocket of energy at a determined time and location to charge of the electronic device through the at least one receiver.

In some embodiments, the method further includes determining, by the base station, priority among a plurality of electronic devices to receive, through the at least one receiver, the pocket of energy from at least one of the plurality of transmitters.

In some embodiments, the method further includes communicating, by the base station, with the at least one receiver and the plurality of transmitters through a communication signal using a protocol selected from the group consisting of: BLUETOOTH®, WI-FI, ZIGBEE®, or FM radio.

In some embodiments, the pocket of energy is regulated by utilizing adaptive pocket-forming.

In some embodiments, an example charging apparatus includes a base station coupled to a power source; and a first communication component coupled to the base station and configured to transmit information to a plurality of transmitters and a plurality of receivers, each of the plurality of transmitters comprising: (i) an antenna configured to transmit power transmission waves that converge to become a pocket of energy; and (ii) a second communication component configured to communicate with the base station and at least one of the plurality of receivers.

In some embodiments, the base station is configured to receive information from at least one of the plurality of receivers, the information including an identification, a location, and an indication of the power level of at least one of the plurality of electronic devices associated with the at least one of the plurality of receivers.

Figure 20A:
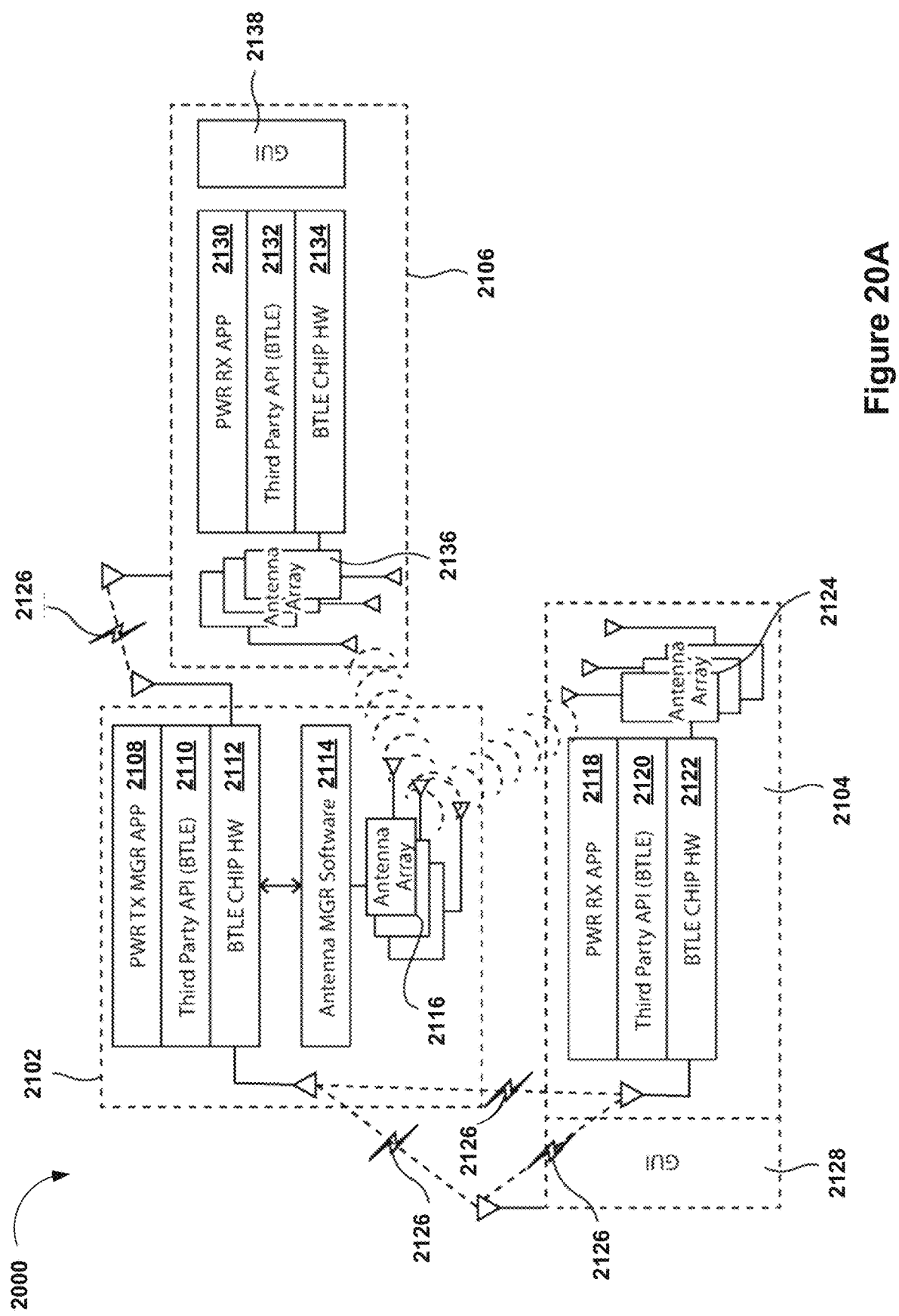
FIG. 20A illustrates a system architecture for a wireless power network, in accordance with some embodiments.

FIG. 20A shows a system architecture 2000 for a wireless power network, according to an embodiment. System architecture 2000 may enable the registration and communication controls between wireless power transmitter 2102 and one or more wireless power receivers (e.g., an embodiment of the receiver 120, FIG. 1) within a wireless power network. Wireless power receivers may include covers 2104 and customer pocket-forming enabled devices 2106.

In one embodiment, wireless power transmitter 2102 (e.g., an embodiment of the transmitter 102, FIG. 1) may include a microprocessor that integrates a power transmitter manager app 2108 (PWR TX MGR APP), and a third party application programming interface 2110 (Third Party API) for a BLUETOOTH Low Energy chip 2112 (BTLE CHIP HW). Wireless power transmitter 102 may also include an antenna manager software 2114 (Antenna MGR Software) to control an RF antenna array 2116 that may be used to transmit controlled Radio Frequency (RF) waves which may converge in 3-dimensional space. These RF waves may be controlled through phase and/or relative amplitude adjustments to form constructive and destructive interference patterns (pocket-forming). Pockets of energy may form at constructive interference patterns that may be 3-dimensional in shape whereas null-spaces may be generated at destructive interference patterns. Pockets of energy may be formed on wireless power receivers (covers and customer pocket-forming enabled devices 2106). In some embodiment, BLUETOOTH Low Energy chip 2112 may be another type of wireless protocol such as WiFi or the like.

Power transmitter manager app 2108 may include a database (not shown), which may store system status, configuration, or relevant information from wireless power receivers such as, identifiers, voltage ranges, location, signal strength and/or any relevant information from a wireless power receivers.

Power transmitter manager app 2108 may call third party application programming interface 2110 for running a plurality of functions such as start a connection, end a connection, and send data among others. Third party application programming interface 2110 may command BLUETOOTH Low Energy chip 2112 according to the functions called by power transmitter manager app 2108.

Third party application programming interface 2110 at the same time may call power transmitter manager app 2108 through a callback function which may be registered in the power transmitter manager app 2108 at boot time. Third party application programming interface 2110 may have a timer callback that may go for ten times a second, and may send callbacks every time a connection begins, a connection ends, a connection is attempted, or a message is received.

Covers 2104 may include a power receiver app 2118 (PWR RX APP), a third party application programming interface 2120 (Third party API) for a BLUETOOTH Low Energy chip 2122 (BTLE CHIP HW), and a RF antenna array 2124 which may be used to receive and utilize the pockets of energy sent from wireless power transmitter 2102.

Power receiver app 2118 may call third party application programming interface 120 for running a plurality of functions such as start a connection, end the connection, and send data among others. Third party application programming interface 2120 may have a timer callback that may go for ten times a second, and may send callbacks every time a connection begins, a connection ends, a connection is attempted, or message is received.

Covers 2104 may be paired to a wireless device such as a smartphone, or tablet among others via a BTLE connection 2126 by using a graphical user interface (GUI 2128) that may be downloaded from any suitable application store and may run on any suitable operating system such as iOS and Android, among others. Covers 2104 may also communicate with wireless power transmitter 2102 via a BTLE connection 2126 to send important data such as an identifier for the device as well as battery level or charge status information, antenna voltage, any other hardware status, software status, geographic location data, or other information that may be of use for the wireless power transmitter 2102.

In other embodiments, GUI 2128 may also be installed on a wireless device (smartphones or tablets) that may not have the cover 2104. GUI 2128 may perform operations to communicate with power transmitter manager app 2108 via BTLE connection 2126 or any other wireless communication protocols such as Wi-Fi, and LAN among others. In this embodiment, GUI management app still performs the same function as previously described, to manage or monitor the wireless power transmission system.

Customer pocket-forming enabled devices 2106 may refer to a wireless device such as smartphones, tablets, or any of the like that may include an integrated wireless power receiver circuit for wireless power charging (e.g., receiver 120, FIG. 1). Customer pocket-forming enabled devices 2106 may include a power receiver app 2130 (PWR RX APP), and a third party application programming interface 2132 (Third Party API) for a BLUETOOTH Low Energy chip 2134 (BTLE CHIP HW). Customer pocket-forming enabled devices 2106 may also include an RF antenna array 2136 which may receive and utilize pockets of energy sent from wireless power transmitter 2102. GUI 2138 may be downloaded from any suitable application store and may run on any suitable operating system such as iOS and Android, among others.

Power receiver app 2130 may call third party application programming interface 2132 for running a plurality of functions such as start a connection, end the connection, and send data among others. Third party application programming interface 2132 may have a timer callback that may go for ten times a second, and may send callbacks every time a connection begins, a connection ends, a connection is attempted, or message is received.

Customer pocket-forming enabled devices 2106 may also communicate with wireless power transmitter 2102 via a BTLE connection 2126 to send important data such as an identifier for the device as well as battery level information, antenna voltage, geographic location data, or other information that may be of use for the wireless power transmitter 2102.

Figure 20B:
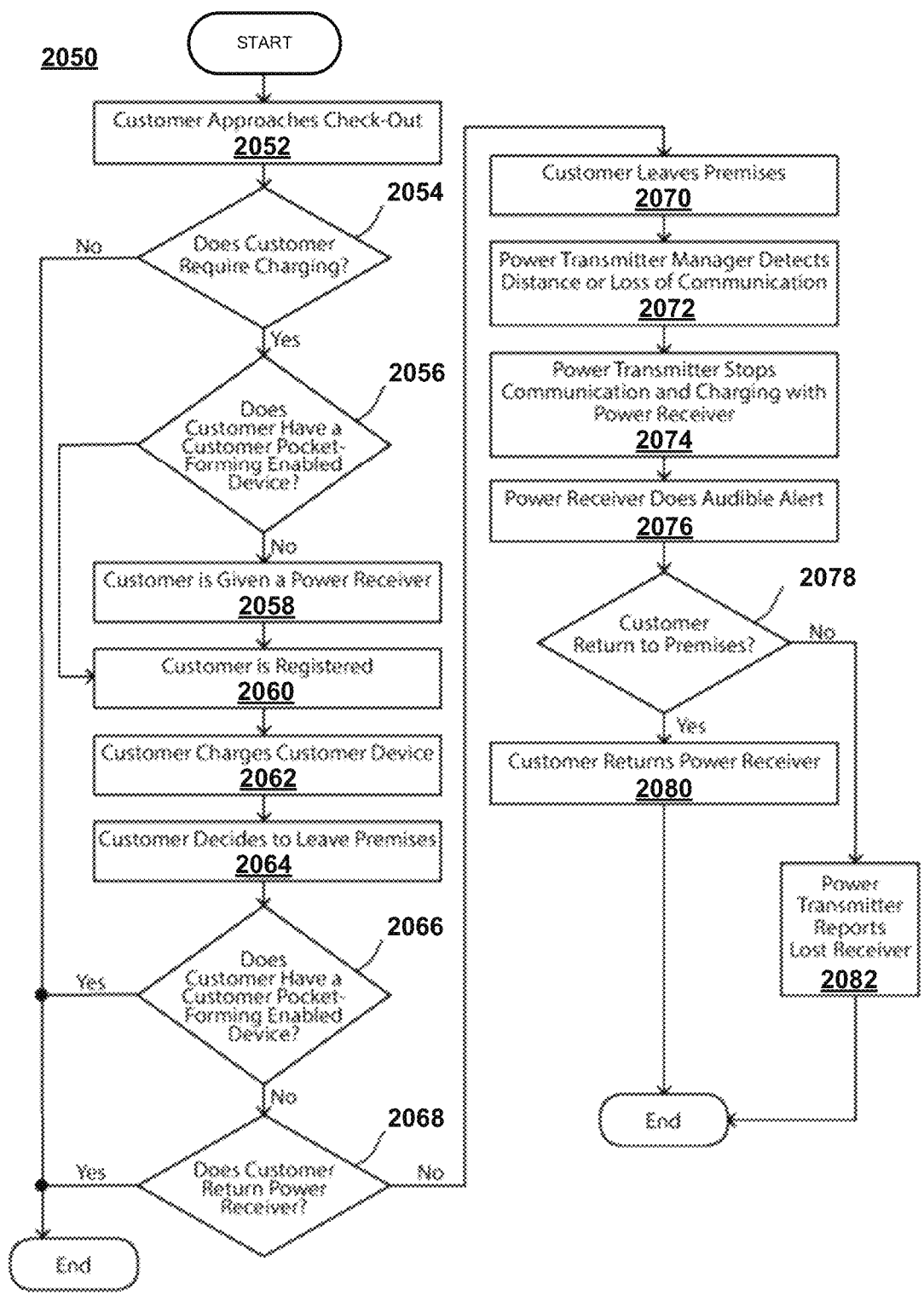
FIG. 20B is a flow diagram for an off-premises alert method for wireless power receivers in a wireless power network, in accordance with some embodiments.

FIG. 20B shows a flowchart for an off-premises alert method 2500 for wireless power receivers in a wireless power network.

The wireless power network may include one or more wireless power transmitter and multiple wireless power receivers that may be either a cover or a customer pocket-forming enabled devices.

Method 2050 may include automated software embedded on a wireless power receiver that may be triggered every time a wireless power receiver is turned on.

In one embodiment, method 2050 may start at step 2052 when a customer goes into a shop and approaches the check-out. Then, at step 2054, an employee of the shop that may be at the counter may ask the customer if he or she requires charging for the customer's device. If the customer does not require charging for his or her device, then the process ends. If the customer does require charging, the employee may ask the customer if his or her device has a customer pocket-forming enabled device, at step 2056. If the customer's device is not a pocket forming enabled device, then at step 2058, the customer is given a power receiver device, also referred as a cover, and the employee may use a GUI to register the given cover at step 2060. Likewise, if the customer does have a pocket-forming enabled device, the employee may use a GUI to register the customer pocket-forming enabled device at step 2060. Then, at step 2062, customer may charge his or her device for the time they need charge. Next, at step 2064, the customer may decide to leave the premises. Then, at step 2066, if the customer has a customer pocket-forming enabled device, the customer may just leave the premises and the process ends. However, if the customer has a power receiver or cover, then the customer may return the cover and leave the premises or he or she may forget to return the cover, at step 2068.

If customer forgets to return the cover, he or she may leave the premises at step 2070. Subsequently, at step 2072, when the customer is at a certain distance away from the store, the power transmitter manager at the store may detect the distance or loss of communication with the power receiver or cover lent to the customer. In other embodiments, the power receiver detects no communication with the power transmitter manager for a minimum amount of time. Then, at step 2074, the power transmitter manager may stop communication with and charging the power receiver. The power receiver, then at step 2076, may generate an audible alert that the customer may hear as he or she goes further from the store. Subsequently, at step 2078, the customer may decide to whether return to premises or not. If customer returns to premises, then at step 2080, customer may return the power receiver. If customer decides to not return to premises, then at step 2082, power transmitter reports details of the lost receiver such as when, where, and receiver's ID among others, to the system management server or the remote information service that are both part of the wireless power transmission system's network.

EXAMPLES

In example #1 a customer enters a coffee shop and buys a cup of coffee. At checkout, the costumer asks for power to charge a smartphone. The customer's smartphone includes a suitable GUI for interacting with a wireless power network. A power receiver or cover with an embedded power receiver is associated with the customer, by an employee using a GUI device, and the cover is given to the customer. Then, the smartphone is paired with a power receiver or cover. The smartphone starts receiving power from the power transmitter as long as the customer stays in the coffee shop. After some time, the smartphone reaches a desired level of charge and the customer leaves the coffee shop. Subsequently, when the customer is at a certain distance away from the coffee shop, the power transmitter manager may detect the distance or loss of communication with the power receiver or cover lent to the customer, and then stop charging and communication with the power receiver. Then, the power receiver or cover may generate an audible alert that may increase in volume as the customer gets further from the coffee shop. The customer then hears the alert and returns to the coffee shop to return the power receiver or cover.

FIGS. 20A-20B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 20A-20B.

Presented below are example systems and methods of wirelessly delivering power to receivers in off-premises alert systems.

In some embodiments, an apparatus includes an antenna array, configured to receive pocket-forming energy in three-dimensional space from a transmitter (e.g., transmitter 102, FIG. 1), a power receiver (e.g., a receiver 120, FIG. 1) operatively coupled to the antenna array, the power received further being configured to be coupled to a device. and communications for wirelessly communicating data to the transmitter and the device. In some embodiments, the power receiver is configured to detect an absence of least one of (i) pocket-forming energy and (ii) data communication from the transmitter, and the power receiver is configured to generate an alarm based on the detected absence.

In some embodiments, the data includes registration data indicating an identity of at least one of (i) the device and (ii) a user associated with the device.

In some embodiments, the communications is configured to transmit registration data to the transmitter prior to the receipt of pocket forming energy in the antenna array.

In some embodiments, the power receiver is configured to generate the alarm after a predetermined time period after the detected absence.

In some embodiments, the alarm is an audible alarm, and the power receiver is configured to increase the volume of the audible alarm over a time period.

In some embodiments, the communicated data includes at least one of identification data for the device, device battery level data, device charge status data, antenna voltage data, device hardware status data, device software status data and geographic location data.

In some embodiments, the power receiver is configured to modify the generated alarm based on the geographic location data.

In some embodiments, a method includes (i) configuring a device to receive pocket-forming energy in three dimensional space in an antenna array from a transmitter via a power receiver configured to be coupled o the device, (ii) wirelessly communicating data from communications coupled to the power receiver to the transmitter and the device, (iii) detecting, via the power receiver, an absence of least one of (a) pocket-forming energy and (b) data communication from the transmitter, and (iv) generating an alarm via the power receiver for the device based on the detected absence.

In some embodiments, the data includes registration data indicating an identity of at least one of (i) the device and (ii) a user associated with the device.

In some embodiments, the registration data is communicated to the transmitter prior to the receipt of pocket forming energy in the antenna array.

In some embodiments, the alarm is generated after a predetermined time period after the detected absence.

In some embodiments, the alarm is an audible alarm, and the alarm is modified to increase the volume of the audible alarm over a time period.

In some embodiments, the communicated data includes at least one of identification data for the device, device battery level data, device charge status data, antenna voltage data, device hardware status data, device software status data and geographic location data.

In some embodiments, the generated alarm is modified based on the geographic location data.

Figure 21A:
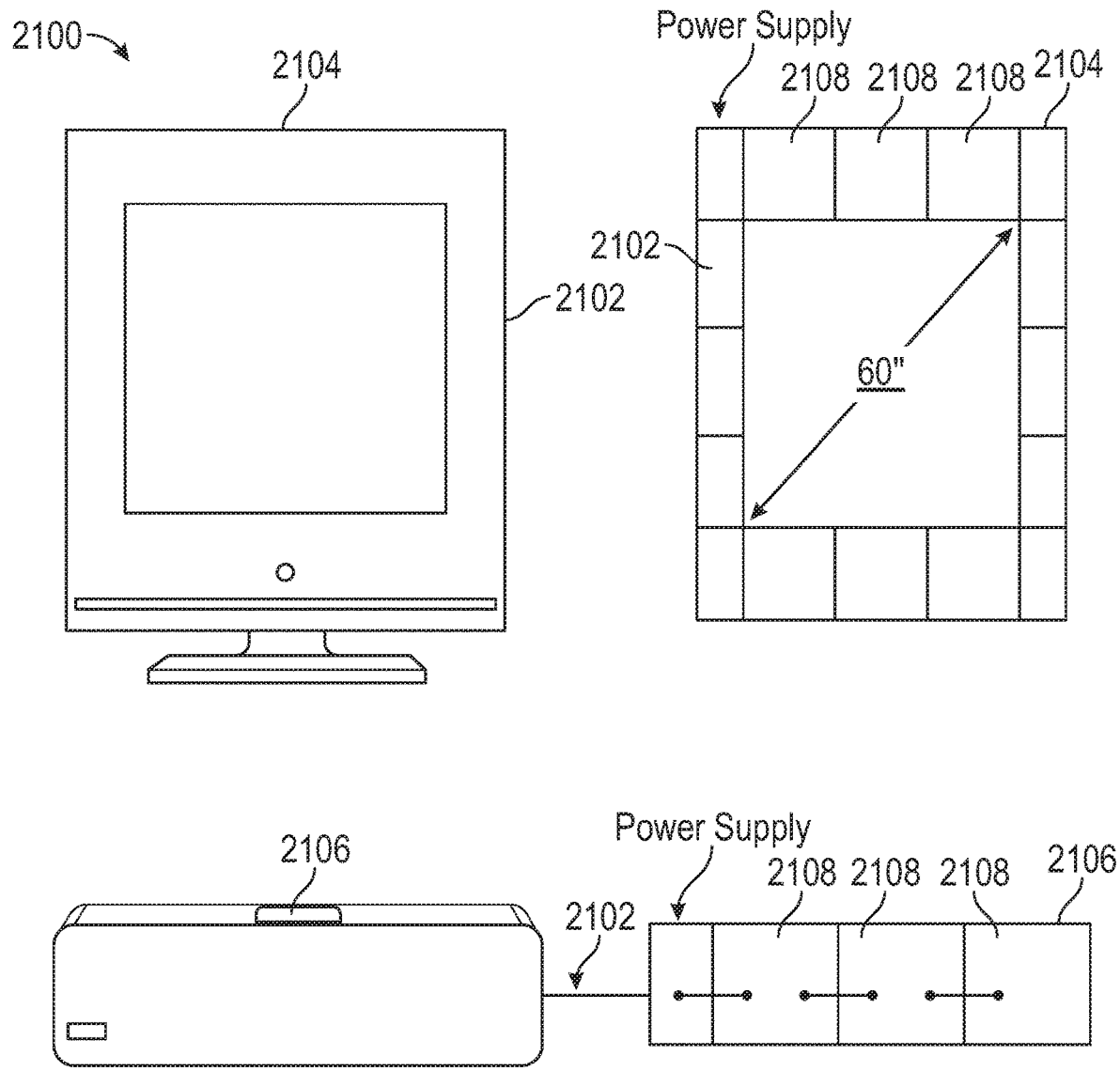
FIG. 21A illustrates a diagram of architecture for incorporating a transmitter into different devices, in accordance with some embodiments.

FIG. 21A depicts a diagram of architecture 2100 for incorporating transmitter 2102 (e.g., an embodiment of the transmitter 102, FIG. 1) into different devices. For example, the flat transmitter 2102 may be applied to the frame of a television 2104 or across the frame of a sound bar 2106. Transmitter 2102 may include multiple tiles 2108 with antenna elements and RFICs in a flat arrangement. The RFIC may be directly embedded behind each antenna elements; such integration may reduce losses due the shorter distance between components.

Tiles 2108 can be coupled to any surface of any object. Such coupling can be via any manner, such as fastening, mating, interlocking, adhering, soldering or others. Such surface can be smooth or rough. Such surface can be of any shape. Such object can be a stationary object, such as a building portion or an appliance, or a movable object, whether self-propelled, such as a vehicle, or via another object, such as handheld. Tiles 2108 can be used modularly. For example, tiles 2108 can be arranged to form any 2-dimensional or 3-dimensional shape, whether open or closed, symmetrical or asymmetrical. In some embodiments, tiles 2108 can be arranged in a figure shape, or a device/structure shape, such as a tower. Tiles 2108 can be configured to couple to each other, such as via interlocking, mating, fastening, adhering, soldering, or others. Tiles 2108 can be configured to operate independently of each other or dependently on each other, whether synchronously or asynchronously. In some embodiments, tiles 2108 are configured to be fed serially or in parallel, whether individually or as a group. Tiles 2108 can be configured to output from at least one side, such as top, lateral, or bottom. Tiles 2108 can be rigid, flexible, or elastic. In some embodiments, at least one other component, whether digital, analog, mechanical, electrical or non-electrical, can be positioned between at least two of tiles 2108. In some embodiments, at least one of tiles 1650 can be run via a hardware processor coupled to a memory.

Tiles 2108 can be used for heat map technology, as described herein. For example, transmitter 2102 includes multiple tiles 2108 with antenna elements and RFICs in a flat arrangement, where transmitter 2102 can facilitate heat map creation for a group of tiles 2108, such as for a particular receiver (e.g., an embodiment of the receiver 120, FIG. 1), such as when tiles 2108 send BLE identifiers for heat map generation. In some embodiments, the group of tiles 2108 is defined via tiles 2108 positioned within a specified distance, such as how many tiles 2108 positioned within a specified distance are sending out signals, scanning an area, and receiving receiver input, such as locational input. Note that such performance can occur simultaneously under different communication protocols as well, such BLE® and ZIGBEE®. In some embodiments, at least two groups of tiles 2108 perform different tasks. In some embodiments, a group of tiles 2108 includes two tiles, such as when the two tiles are each eight inches long by two inches wide. In some embodiments, an entire array can run along a perimeter of television 2104, where the array includes via a plurality of tiles 2108 arranged in or functioning as a plurality of groups of tiles 2108 as each of such groups might obtain a different heat map, as described herein, which can be subsequently analyzed together to obtain a better grand scale heat map understanding. Accordingly, a plurality of heat map sets can exists without being reconciled with each other as each of the heat map sets can include different information. For example, a first heat map can be associated with a first device and a second heat map associate with a second device, different from the first device.

For example, a television 2104 may have a bezel around a television 2104, comprising multiple tiles 2108, each tile comprising of a certain number of antenna elements. For example, if there are 20 tiles 2108 around the bezel of the television 2104, each tile 2108 may have 24 antenna elements and/or any number of antenna elements.

Note that tiles 2108 are positioned or configured to avoid signal interference with television 2104 or wiring coupled to television 2104. Alternatively or additionally, television 2104 can be shielded against such signal interference. Similar configurations can be applied to sound bar 2106 or any other type of speaker, whether a standalone speaker or a component of a larger system. However, also note that such tiles 2108 can be arranged on any device, whether a standalone device or a component of a larger system, whether electronic or non-electronic.

In tile 2108, the phase and the amplitude of each pocket-forming in each antenna element may be regulated by the corresponding RFIC in order to generate the desired pocket-forming and transmission null steering. RFIC singled coupled to each antenna element may reduce processing requirement and may increase control over pocket-forming, allowing multiple pocket-forming and a higher granular pocket-forming with less load over microcontroller, thus, a higher response of higher number of multiple pocket-forming may be allowed. Furthermore, multiple pocket-forming may charge a higher number of receivers and may allow a better trajectory to such receivers.

RFIC may be coupled to one or more microcontrollers, and the microcontrollers may be included into an independent base station or into the tiles 2108 in the transmitter 2102. A row or column of antenna elements may be connected to a single microcontroller. In some implementations, the lower number of RFICs present in the transmitters 2102 may correspond to desired features such as: lower control of multiple pocket-forming, lower levels of granularity and a less expensive embodiment. RFICs connected to each row or column may allow reduce costs by having fewer components because fewer RFICs are required to control each of the transmitters 2104. The RFICs may produce pocket-forming power transmission waves by changing phase and gain, between rows or columns.

In some implementations, the transmitter 2102 may use a cascade arrangement of tiles 2108 comprising RFICs that may provide greater control over pocket-forming and may increase response for targeting receivers. Furthermore, a higher reliability and accuracy may be achieved from multiple redundancies of RFICs.

In one embodiment, a plurality of PCB layers, including antenna elements, may provide greater control over pocket-forming and may increase response for targeting receivers. Multiple PCB layers may increase the range and the amount of power that could be transferred by transmitter 2102. PCB layers may be connected to a single microcontroller or to dedicated microcontrollers. Similarly, RFIC may be connected to antenna elements.

A box transmitter 2102 may include a plurality of PCB layers inside it, which may include antenna elements for providing greater control over pocket-forming and may increase response for targeting receivers. Furthermore, range of wireless power transmission may be increased by the box transmitter 2102. Multiple PCB layers may increase the range and the amount of RF power waves that could be transferred or broadcasted wirelessly by transmitter 2102 due the higher density of antenna elements. PCB layers may be connected to a single microcontroller or to dedicated microcontrollers for each antenna element. Similarly, RFIC may control antenna elements. The box shape of transmitter 2102 may increase action ratio of wireless power transmission. Thus, box transmitter 2102 may be located on a plurality of surfaces such as, desks, tables, floors, and the like. In addition, box transmitter may include several arrangements of PCB layers, which may be oriented in X, Y, and Z axis, or any combination these.

In some embodiments, sound bar 2106 is elongated, such as by being four feet long and two inches high. Such shaping provides a provision of tiles 2108 along a longitudinal axis of sound bar 2106 such that at least some of tiles 2108 are able to send or receive signals, as described herein, in a surrounding manner.

Figure 21B:
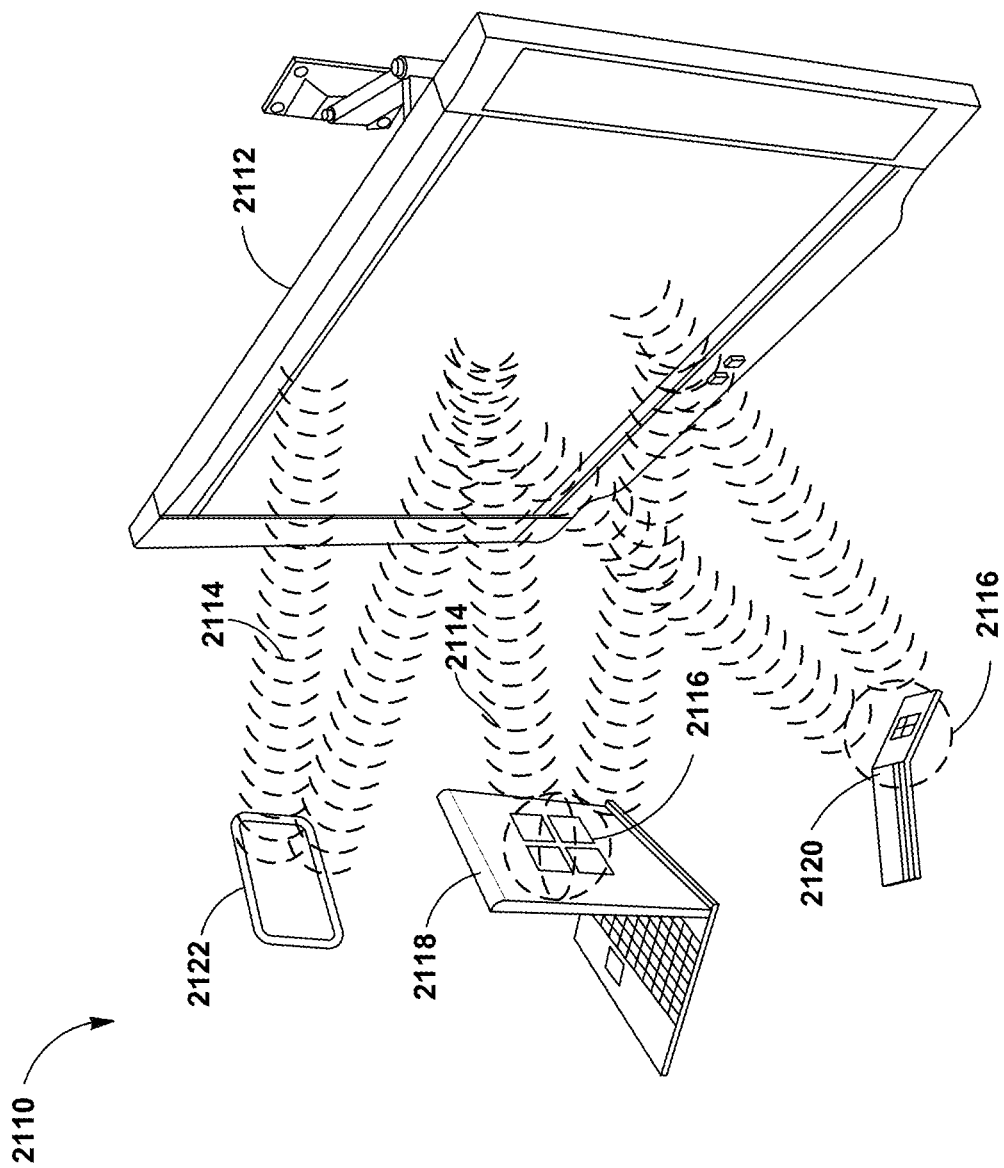
FIG. 21B illustrates an example embodiment of a television (TV) system outputting wireless power, in accordance with some embodiments.

FIG. 21B illustrates an example embodiment of a television (TV) system outputting wireless power. Some elements of this figure are described above. Thus, same reference characters identify identical and/or like components described above and any repetitive detailed description thereof will hereinafter be omitted or simplified in order to avoid complication.

A wireless power transmission 2100 that includes pocket-forming is described. The transmission 2110 entails a TV system 2112 transmitting a plurality of controlled wireless power waves 2114 converging in multidimensional space. The TV system 2112 uses a transmitter, as described herein, such as transmitter 102, to output waves 2114, such as in any direction, such as frontal or lateral or backward or upward or downward. The transmitter can be powered via the TV system 2112 or another power source, such as a battery, whether coupled to or not to the TV system 2112. Alternatively or additionally, the transmitter can power the TV system 2112 or the transmitter and TV system 2112 are powered independently of each other, such as from two different power sources, such as a battery and mains electricity. Waves 2114 are controlled through phase and/or relative amplitude adjustments to form constructive and destructive interference patterns, such as pocket-forming. Pockets of energy 2116 are formed at constructive interference patterns of waves 2114 and are 3-dimensional in shape, whereas null-spaces are generated at destructive interference patterns of waves 2114. A receiver, as described herein, such as receiver 120, utilizes pockets of energy 2116 produced by pocket-forming for charging or powering an electronic device, for example a laptop computer 2118, a mobile phone 2120, a tablet computer 2122 or any electrical devices at least within reach or a defined range from TV system 2112, such as about 20 feet in a specific direction, an arc comprising a peak height distance of about 20 feet, or a radius of 20 feet, and thus effectively providing wireless power transmission 2110. In some embodiments, adaptive pocket-forming may be used to regulate power on electronic devices. In some embodiments, TV system 2112 includes a speaker or a sound bar, whether as described herein, or of another type. In some embodiments, TV system 2112 includes a remote control unit, which can include a receiver, as described herein, configured to receive wireless power from TV system 2112, as described herein.

Figure 21C:
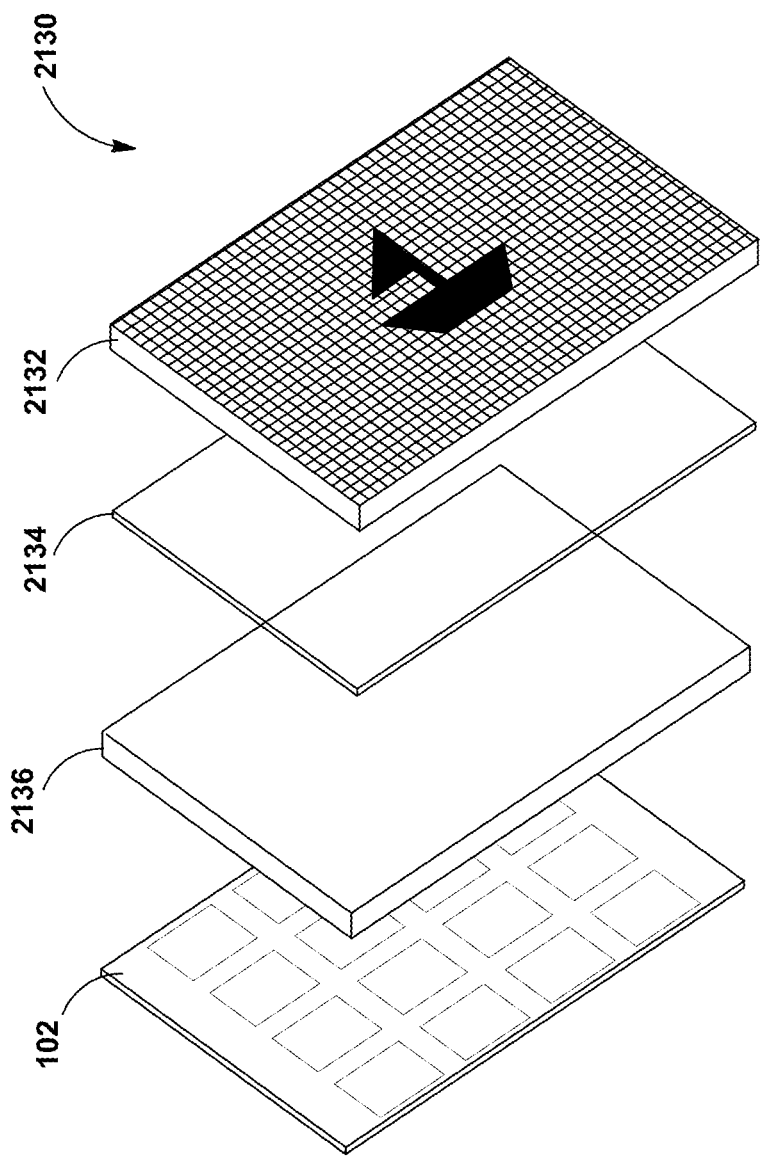
FIG. 21C illustrates an example embodiment of an internal structure of a TV system, in accordance with some embodiments.

FIG. 21C illustrates an example embodiment of an internal structure of a TV system. Some elements of this figure are described above. Thus, same reference characters identify identical and/or like components described above and any repetitive detailed description thereof will hereinafter be omitted or simplified in order to avoid complication.

An internal structure view 2130 depicts TV system 2112 with a transmitter, as described herein. TV system 2112 includes a plurality of components. TV system 2112 includes a front transparent screen layer 2132, a polarized film layer 2134, and an LED/LCD backlight layer 2136. TV system 2112 additionally include transmitter 102, as described herein. In another embodiment, transmitter 102 may be integrated within at least one of layers 2132, 2134, 2136 instead of as a separate layer.

In other embodiments, most of the circuitry of transmitter 102 is placed inside TV system 2112, with antenna elements 1106 placed around the edges of TV system 3002. In other embodiments, antenna elements are placed on the outside surface of a back portion of TV system 2112. In yet further embodiments, antenna elements can be printed micro-antennas which can be built-in on TV system 2112 display area. Such printed-antennas can be produced with well-known in the art photolithographic or screen printing techniques. Such antennas can be beneficial because they can be printed at tinny scales which render them invisible to the human eye. Note that TV system can be of any type, such as a liquid crystal display (LCD), a plasma, a cathode ray, or others.

FIG. 21D illustrates an example embodiment of a tile architecture. Some elements of this figure are described above. Thus, same reference characters identify identical and/or like components described above and any repetitive detailed description thereof will hereinafter be omitted or simplified in order to avoid complication.

A tile 2108 (FIG. 21A) includes an antenna 2152 and an RFIC 2154 coupled to antenna 2152, as described herein. Tile 2108 can be structure in any way as described herein. Tile 2108 operates are described herein. Although tile 2108 is shaped in a rectangular shape, in other embodiments, tile 2108 can be shaped differently, whether in an open shape or a closed shape. For example, tile 2108 can be shaped as a star, a triangle, a polygon, or others.

FIGS. 21A-21D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 21A-21D.

Presented below are example systems for wirelessly delivering power to receivers using transmitters in various devices.

In some embodiments, an example system for wireless power transmission includes: (i) a sound bar frame; and (ii) a plurality of tiles positioned along the sound bar frame. At least one of the tiles includes an antenna and a radio frequency integrated circuit (RFIC) coupled to the antenna and the RFIC is configured to engage the antenna such that the antenna emits a plurality of wireless power waves defining a pocket of energy.

In some embodiments, an example system for wireless power transmission includes: (i) a display frame; and (ii) a plurality of tiles positioned along the sound bar frame. At least one of the tiles includes an antenna and a radio frequency integrated circuit (RFIC) coupled to the antenna and the RFIC is configured to engage the antenna such that the antenna emits a plurality of wireless power waves defining a pocket of energy.

In some embodiments, an example system for wireless power transmission includes: (i) a speaker enclosure; and (ii) a plurality of tiles positioned along the sound bar frame. At least one of the tiles includes an antenna and a radio frequency integrated circuit (RFIC) coupled to the antenna and the RFIC is configured to engage the antenna such that the antenna emits a plurality of wireless power waves defining a pocket of energy.

In some embodiments, the tiles are configured to operate dependent on each other.

In some embodiments, the tiles are configured to operate independent of each other.

In some embodiments, the sound bar frame includes an external face, and the tiles are coupled to the external face. In some embodiments, the display frame includes an external face, and the tiles are coupled to the external face. In some embodiments, the speaker enclosure includes an external face, and the tiles are coupled to the external face.

In some embodiments, the sound bar frame includes an internal face, and the tiles are coupled to the internal face. In some embodiments, the display frame includes an internal face, and the tiles are coupled to the internal face. In some embodiments, the speaker enclosure includes an internal face, and the tiles are coupled to the internal face.

In some embodiments, the sound bar frame includes the tiles. In some embodiments, the display frame includes the tiles. In some embodiments, the speaker enclosure includes the tiles.

In some embodiments, the system further includes a display, and the display frame frames the display, and the tiles define a closed shape, and the closed shape encloses the display. Moreover, in some embodiments, the display is configured to receive power from a first power source, and the at least one of the tiles is configured to receive power from a second power source, and the first power source and the second power source are one power source.

In some embodiments, the system further includes a speaker, where the sound bar frame encloses the speaker, the tiles define a closed shape, and the closed shape encloses the speaker. In some embodiments, the speaker is configured to receive power from a first power source, where the at least one of the tiles is configured to receive power from a second power source. The first power source and the second power source are one power source.

In some embodiments, the system further includes a speaker, and the speaker enclosure encloses the speaker, and the tiles define a closed shape, and the closed shaped encloses the speaker. Moreover, in some embodiments, the speaker is configured to receive power from a first power source, and the at least one of the tiles is configured to receive power from a second power source, and the first power source and the second power source are one power source.

In some embodiments, the system further includes a controller coupled to the RFIC in the at least one of the tiles, where the controller is positioned off the tiles.

In some embodiments, the tiles are in contact with each other. In addition, in some embodiments, the tiles are coupled to each other. Alternatively, in some embodiments, the tiles avoid contact with each other.

In some embodiments, the tiles define a row. Alternatively or in addition, in some embodiments, the tiles define a column.

In some embodiments, the tiles are powered serially. In some embodiments, the tiles are powered in parallel.

In some embodiments, tiles identify a path via which the pocket of energy is defined.

In some embodiments, the tiles are part of an antenna array.

In some embodiments, the tiles define the pocket of energy.

In some embodiments, the at least one of the tiles includes a controller coupled to the RFIC, and the controller is configured to control the RFIC.

Figure 22:
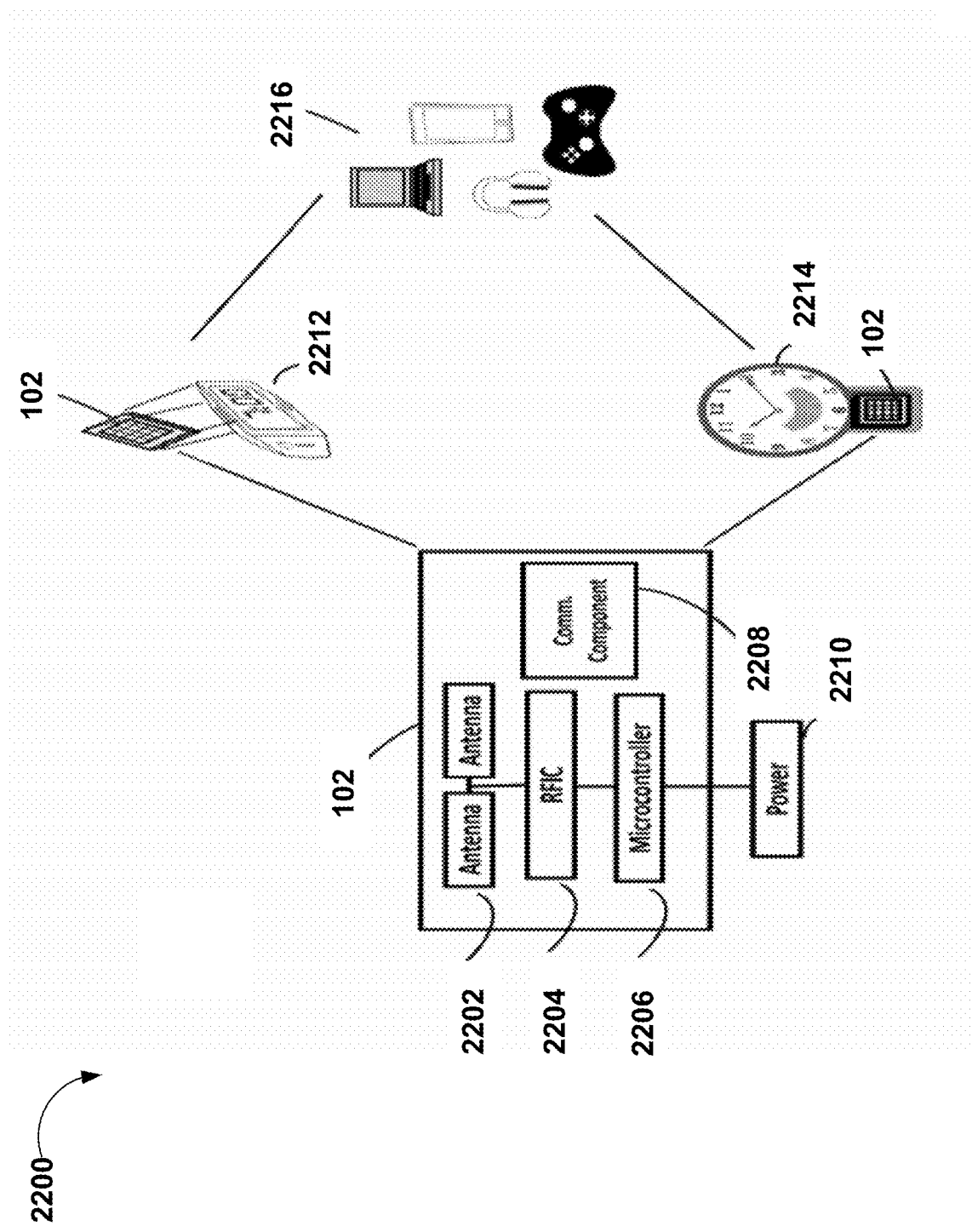
FIGS. 22-24 illustrate transmitters integrated with various devices, in accordance with some embodiments.

FIG. 22 illustrates a transmitter integrated with a timing device. In some embodiments, a timing device capable of wireless power transmission includes a housing comprising: a transmitter 102 configured to generate a plurality of wireless power transmission waves, the transmitter 102 comprising: a plurality of antennas 2202 (e.g., an embodiment of antennas 110, FIG. 1) configured to transmit the wireless power transmission waves in response to a communication signal indicating a power requirement of an electronic device; a digital signal processor 2204 configured to control the plurality of wireless power transmission waves in order to form a pocket of energy in a plurality of predetermined regions in a space; and a communication component 2208 configured to communicate with a receiver (e.g., receiver 120, FIG. 1) coupled to the electronic device; a time display 2212 on a surface of the housing; and a power source 2210 coupled to the transmitter 102 and the time display 2212. The time display 2212 can be from a digital clock, or an analog clock 2214, or couple to a transmission of time from a component associated with the transmitter 102.

In some embodiments, a method for wireless transmission of power to an electronic device from a timing device includes establishing, by a transmitter associated with the timing device, a connection with a power source, the timing device being configured to house the transmitter and a time display; receiving, by the timing device, a reference time obtained from an atomic clock; presenting, by the timing device, the reference time on a time display of the timing device; providing, by the timing device, the reference time to a processor of the transmitter; generating, by the transmitter associated with the timing device, a plurality of wireless power transmission waves to form a pocket of energy; receiving, by the transmitter associated with the timing device, a transmission of a power requirement and location of an electronic device through a receiver associated with the electronic device; and transmitting, by the transmitter associated with the timing device, the plurality of wireless power transmission waves using a plurality of antennas in order to form a pocket of energy in a plurality of predetermined regions at the receiver in response to the received transmission.

FIG. 22 illustrates examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIG. 22.

Figure 23:
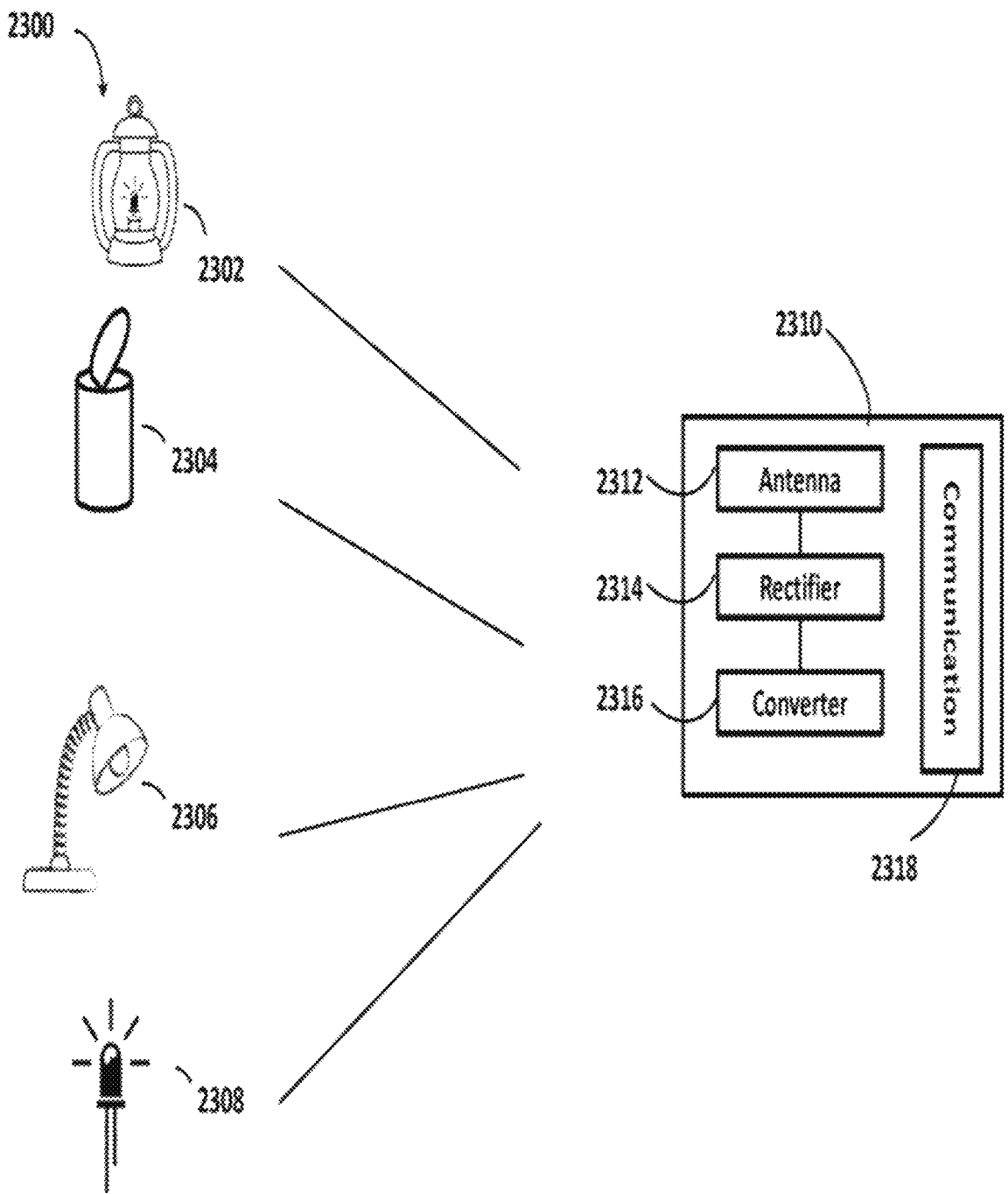

FIG. 23 illustrates an example embodiment of lighting devices, such as a lantern 2302, a flameless candle 2304, a desk lamp 2306, or a LED lighting device 2308, coupled to a receiver (e.g., an embodiment of the receiver 120, FIG. 1), where the receiver 2302 may be used for receiving wireless power transmission from a transmitter (e.g., an embodiment of the transmitter 102, FIG. 1). Each lighting device may include a light generating component (e.g., LED bulb, halogen bulb, or other bulb, diode, or capacitor) coupled to a battery or other power source. Receiver 2310 may be embedded in these devices or otherwise coupled to the lighting devices. In some implementations, the receiver 2310 may include one or more antenna elements 2312. The number, spacing and type of antenna elements 2312 may be calculated according to the design, size and/or type of external battery. The receiver 2310 also includes other components such as a rectifier 2314, an electric current converter 2316, and a communications component 2318 that includes a communication circuit associated with a communication antenna. In some implementations, terminating the transmission of power from the transmitter will result in turning off all the lighting devices that were powered by the wireless power from the transmitter. In some implementations, the receipt of power at the receiver may be terminated. In some implementations, a string of lighting devices may be connected through a single receiver system.

Figure 24:
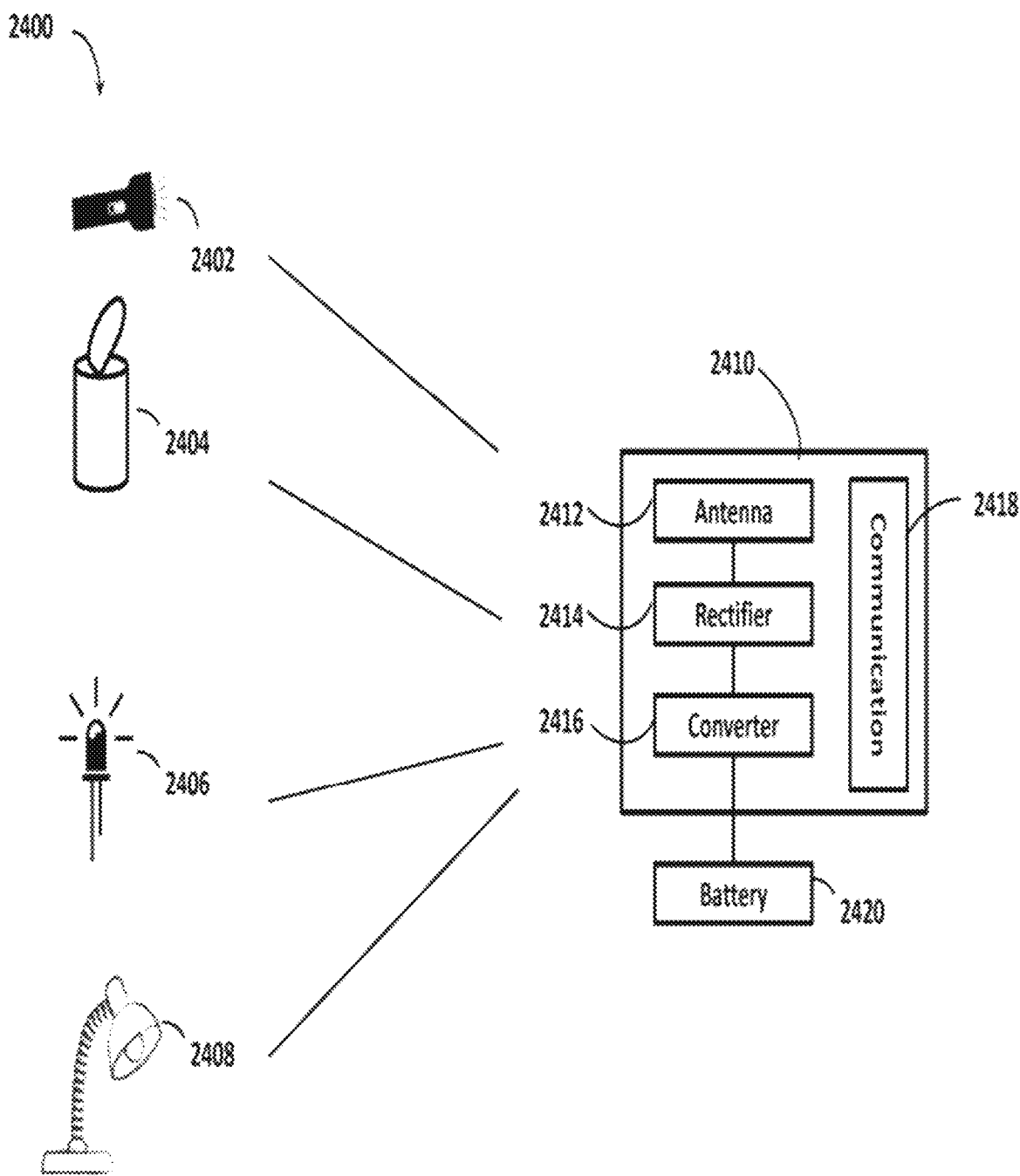

FIG. 24 illustrates an example embodiment of lighting devices, such as a flashlight 2402, a flameless candle 2404, a LED lighting device 2406, or a desk lamp 2408, coupled to a receiver 2410 (e.g., an embodiment of the receiver 120, FIG. 1), where the receiver 2410 may be used for receiving wireless power transmission from a transmitter (e.g., an embodiment of the transmitter 102, FIG. 1). Receiver 2410 may be coupled to a battery 2420 that is associated with the lighting devices, either as an embedded or built-in battery or an external one. In some implementations, the receiver 2410 may include one or more antenna elements 2412. The number, spacing and type of antenna elements 2412 may be calculated according to the design, size and/or type of external battery. The receiver 2410 also includes other components such as a rectifier 2414, an electric current converter 2416, and a communications component 2418 including a communication circuit associated with a communication antenna.

FIGS. 23 and 24 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 23 and 24

Presented below are example devices for and methods of wirelessly delivering power to receivers using transmitters in various lighting devices.

In some embodiments, a lighting device with a wireless power transmission receiver includes a receiver coupled to the lighting device, the receiver comprising: (i) an antenna element configured to receive one or more power transmission waves converging to form a pocket of energy and generate an electrical current by harvesting energy from the one or more power transmission waves, and the electrical current is in an alternating current form of electricity; (ii) a rectifier coupled to the antenna element and configured to rectify the alternating current form of electricity into a direct current form of electricity; and (iii) a power converter coupled to the rectifier and configured to generate a constant voltage output of electrical current in the form of direct current, and the power converter is communicatively coupled to the lighting device, and the receiver provides the direct current to the lighting device.

In some embodiments, the receiver is integrated into the lighting device.

In some embodiments, the lighting device is portable.

In some embodiments, the lighting device is selected from the group consisting of: a lantern, a lamp, a flameless candle, and a LED device.

In some embodiments, the receiver further includes one or more communications components configured to transmit a communication signal to a transmitter, and the communication signal identifies the receiver to the transmitter and indicates the location of the receiver relative to the transmitter.

In some embodiments, the lighting device further includes a battery coupled to the lighting device. Furthermore, in some embodiments, the battery is configured to function as a sole source of power for the lighting device. Alternatively, in some embodiments, the battery is configured to be a back-up source of power for the lightening device. In some embodiments, the battery is removably coupled to the lighting device. The battery may be integrated into the lighting device.

In some embodiments, an example method of providing wireless power to a lighting device includes interfacing, by an antenna element of a receiver associated with a lighting device, with a pocket of energy defined via a plurality of wireless power transmission waves; producing, by the antenna element of the receiver, electrical energy having an alternating current form based on the pocket of energy; and rectifying, by a rectifier of the receiver, the alternating current form of electricity into a direct current form of electricity, and the rectifier is coupled to the antenna element. The method further includes converting, by a power converter of the receiver, the direct current form of electricity to a constant voltage output of electrical current, and the power converter is coupled to the rectifier; and providing, by the power converter of the receiver, the electrical energy to power the lighting device.

Figure 26:
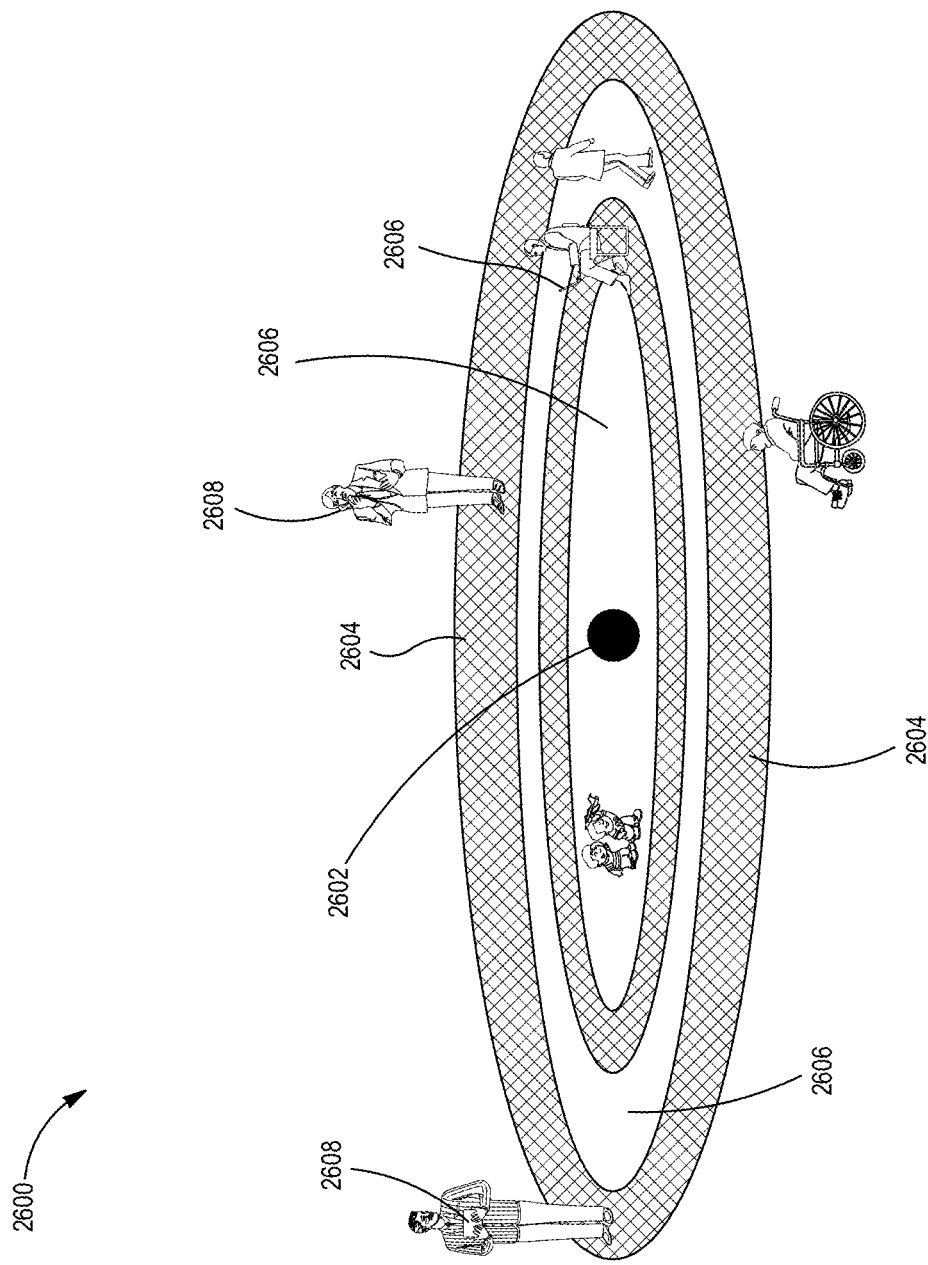
FIGS. 26 and 27 illustrate wireless power transmission with selective range, where a plurality of pockets of energy may be generated along various radii from transmitter, in accordance with some embodiments.
Figure 27:
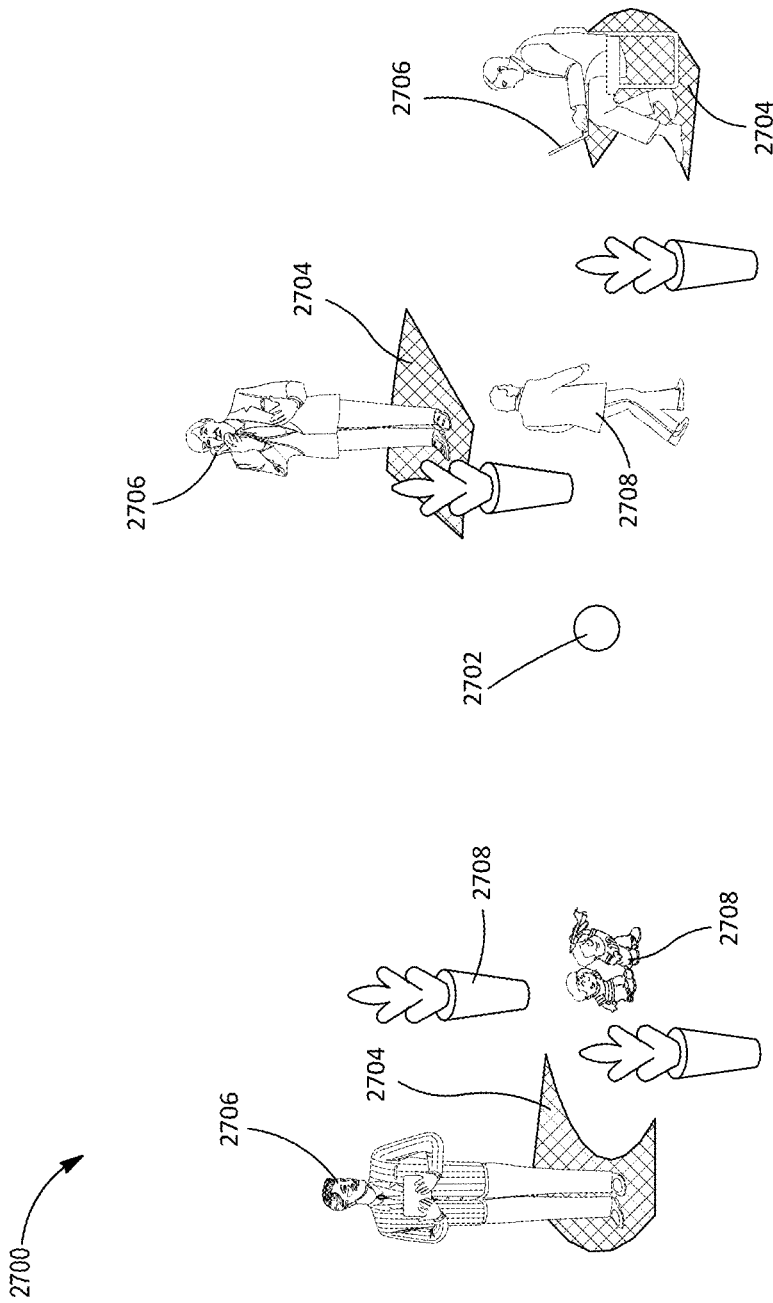

FIGS. 25-27 illustrate wireless power transmission with selective range in accordance with some embodiments.

FIGS. 25A and 25B depict a wireless power transmission principle 2500, where two waveforms, for example waveform 2502 and waveform 2504, as depicted in FIG. 25A may result in a unified waveform 2506 as depicted in FIG. 25B. Such unified waveform 2506 may be generated by constructive and destructive interference patterns between waveform 2502 and waveform 2504.

As depicted in FIG. 25A, at least two waveforms with slightly different frequencies such as waveform 2502 and waveform 2504 may be generated at 5.7 Gigahertz (GHz) and 5.8 GHz respectively. By changing the phase on one or both frequencies using suitable techniques such as pocket-forming, constructive and destructive interferences patterns may result in unified waveform 2506. Unified waveform 2506 may describe pockets of energy and null-spaces along pocket-forming, such pockets of energy 108 may be available in certain areas where a constructive interference exists; such areas may include one or more spots which may move along pocket-forming trajectory and may be contained into wireless power range 2508 X2. Wireless power range 2508 X2 may include a minimum range and a maximum range of wireless power transmission 100, which may range from a few centimeters to over hundreds of meters. In addition, unified waveforms 2506 may include several null-spaces, which may be available in certain areas where a destructive interference exists, such areas may include one or more null-spaces which may move along pocket-forming trajectory and may be contained into wireless power range 2510 X 1. Wireless power range 2510 X 1 may include a minimum range and a maximum range of wireless power transmission 100, which may range from a few centimeters to over hundreds of meters.

FIG. 26 depicts wireless power transmission with selective range 2600, where a transmitter 2602 may produce pocket-forming for a plurality of receivers 2608. Transmitter 2602 may generate pocket-forming through wireless power transmission with selective range 2600, which may include one or more wireless charging radii 2604 and one or more radii of null-space 2606. A plurality of electronic devices may be charged or powered in wireless charging radii 2604. Thus, several spots of energy may be created, such spots may be employed for enabling restrictions for powering and charging electronic devices, such restrictions may include: Operation of specific electronics in a specific or limited spot contained in wireless charging radii 2604. Furthermore, safety restrictions may be implemented by the use of wireless power transmission with selective range 2600, such safety restrictions may avoid pockets of energy 108 over areas or zones where energy needs to be avoided, such areas may include areas including sensitive equipment to pockets of energy 108 and/or people who do not want pockets of energy 108 over and/or near them.

FIG. 27 depicts wireless power transmission with selective range 2700, where a transmitter 2702 may produce pocket-forming for a plurality of receivers 2706. Transmitter 2702 may generate pocket-forming through wireless power transmission with selective range 2700, which may include one or more wireless charging spots 2704. A plurality of electronic devices may be charged or powered in wireless charging spots 2704. Pockets of energy may be generated over a plurality of receivers 2706 regardless of the obstacles 2708 surrounding them, such effect may be produced because destructive interference may be generated in zones or areas where obstacles 2708 are present. Therefore, pockets of energy 108 may be generated through constructive interference in wireless charging spots 2704. Location of pockets of energy may be performed by tracking receivers 2706 and by enabling a plurality of communication protocols by a variety of communication systems such as, Bluetooth technology, infrared communication, WI-FI, FM radio among others.

FIGS. 25-27 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 25-27.

Presented below are example systems and methods for wireless power transmission with selective range to power a portable electronic device.

A system for wireless power transmission with selective range to power a portable electronic device may include: (i) a transmitter for generating at least two pocket-forming RF waves through an antenna connected to the transmitter, (ii) a micro-controller within the transmitter for controlling the at least two pocket-forming RF waves to accumulate pockets of energy in regions of space in the form of constructive interference patterns of the generated RF waves, and (iii) a selective range for charging or powering the electronic device in a predetermined variety of spots in regions of space with the accumulated pockets of energy surrounded by null-spaces without accumulated pockets of energy.

In some embodiments, the micro-controller changes a phase on one or more RF waves in pocket-forming with constructive and destructive interference patterns resulting in a unified waveform in the predetermined variety of spots for charging the electronic device. Furthermore, in some embodiments, the unified waveform defines pockets of energy and null-spaces along pocket-forming whereby the pockets of energy are available in certain predetermined regions of space where constructive interference exists defining one or more hot spots for charging the electronic devices over a minimum or maximum selected range responsive to a program within the micro-controller. Furthermore, in some embodiments, the unified waveform is comprised of at least two RF waves with slightly different frequencies with phase shifting on one or both frequencies to form a wireless power range from a few centimeters to over hundreds of meters.

In some embodiments, the transmitter provides pocket-forming for a plurality of receivers including one or more wireless charging radii surrounded by one or more radii of null-space to create spots enabling restrictions for powering and charging electronic devices.

In another system for wireless power transmission with selective range to power a portable electronic device, the system may include: (i) a transmitter for generating at least two RF waves and short RF control signals having at least two RF antennas to transmit at least two RF waves through the antennas converging in 3-dimensional space to accumulate as pockets of energy in the form of constructive interference patterns of RF waves, (ii) a micro-controller within the transmitter for controlling constructive interference patterns of the RF waves to accumulate pockets of energy in predetermined areas or regions in 3-dimensional space and for controlling the destructive interference patterns of the RF waves to form null-spaces surrounding the pockets of energy, where the constructive interference patterns of RF waves form charging hot spots of a predetermined selected range for charging portable electronic devices and where the destructive interference patterns of RF waves form null spots of a predetermined selected range surrounding the charging spots without charging energy therein.

In some embodiments, the hot spots include one or more wireless charging radii and one or more null-space radii whereby the hot spots are created for enabling restrictions for powering and charging the electronic device.

In some embodiments, the predetermined selected range of charging spots provide safety restrictions to eliminate pockets of energy over areas or zones where energy is avoided to protect sensitive equipment or people within predetermined designated regions in 3-dimensional space.

In some embodiments, the system further includes a receiver connected to the portable electronic device having a micro-controller to communicate with the transmitter micro-controller to generate wireless charging spots over a plurality of receivers regardless of the obstacles surrounding the receivers for the predetermined selected range from the transmitter. Furthermore, in some embodiments, the micro-controllers for the transmitter and receiver locate, track or direct the pockets of energy over preselected range of hot spots by enabling a plurality of standard wireless communication protocols of Bluetooth, Wi-Fi, FM, or Zigbee. Furthermore, in some embodiments, the micro-controllers of the transmitter and receiver dynamically adjust pocket-forming over preselected ranges to regulate power on one or more targeted receivers. Furthermore, in some embodiments, the receiver and transmitter micro-controllers communicate to change frequencies and phase on one or more RF waves to form a unified waveform that describes pockets of energy and null-spaces along pocket-forming, where pockets of energy are available in certain predetermined areas where a constructive interference of the waves exist and such areas include one or more spots which move along pocket-forming trajectory and are contained within the wireless power range that include either a minimum or maximum range of wireless power transmission.

In some embodiments, the antennas operate in predetermined frequencies at generally 900 MHz, 2.4 GHz, and 5.7

GHz to transmit at least two RF waveforms to create a unified waveform for a preselected range for charging hot spots and null-space spots.

In some embodiments, the antennas operate in frequency bands of generally 900 MHz, 2.4 GHz, or 5.7 GHz bands.

In some embodiments, the electronic devices are various electronic equipment, smartphones, tablets, music players, computers, toys and others powered at the same time over selected ranges and restricted locations for each electronic device.

A method for wireless power transmission with selective range to power a portable electronic device may include: (i) generating pocket-forming RI waves from a transmitter through an antenna connected to the transmitter, (ii) accumulating pockets of energy in regions of space in the form of constructive interference patterns of the generated RF waves, and (iii) employing a selective range for charging or powering the electronic device in a predetermined variety of spots with the accumulated pockets of energy surrounded by null-spaces without accumulated pockets of energy.

In some embodiments, the method comprises intercepting the accumulated pockets of energy in regions of space by a receiver with an RF antenna connected to the portable electronic device.

In some embodiments, the method comprises implementing an adaptive power focusing to avoid obstacles interfering with the RF signals between the receiver and the transmitter for regulating two or more receivers providing charging or powering of the portable electronic device.

In some embodiments, the null-spaces are generated in the form of destructive interference patterns of the generated RF waves and the null-spaces are distributed in predetermined selective zones around the variety of spots.

In some embodiments, the employing the selective range increases control over electronic devices to receive charging by limiting the operation area of certain portable electronic devices to eliminate pockets of energy in sensitive areas including people or other equipment affected by pockets of energy.

In another system for wireless power transmission with selective range to power a portable electronic device, the system may include: (i) a transmitter comprising an antenna configured to transmit one or more power transmission waves and (ii) a micro-controller within the transmitter configured to control transmission of the power transmission waves. In some embodiments, the micro-controller: (i) generates a pocket of energy at a location relative to a receiver by transmitting the one or more power transmission waves to accumulate at the location relative to the receiver resulting from constructive interference patterns associated with accumulation of the one or more power transmission waves at the location and (ii) selects the location to generate the pocket of energy from a selective range of one or more predetermined locations for charging or powering the electronic device characterized by the accumulation of power transmissions signals resulting in one or more pockets of energy surrounded by a corresponding null-space.

In some embodiments, the null-spaces are generated in the form of destructive interference patterns of the generated power transmission waves and are distributed in one or more zones substantially adjacent to at least one pocket of energy from the one or more pockets of energy.

In some embodiments, each selected range of charging hot spots is surrounded by one or more null-spaces resulting from destructive interference patterns corresponding to the constructive interference patterns forming the pocket of energy at the hot spot and the one or more null-spaces inhibit formation of pockets of energy over and/or at one or more sensitive locations having people or sensitive equipment.

In some embodiments, the antennas operate in predetermined frequencies at ranges of about 900 MHz to about 5.7 GHz to transmit at least two power transmission waveforms to create a unified waveform for a preselected range for charging hot spots.

In another method for wireless power transmission with selective range to power a portable electronic device, the method may include: (i) transmitting, by a transmitter, the power transmission waves to converge at a predetermined location relative to a receiver, (ii) accumulating, by the transmitter, the power transmission waves at the location, thereby forming a constructive interference pattern at the location, where the constructive interference pattern establishes a pocket of energy, and (iii) establishing, by the transmitter, a selective range of one or more intervals of distance from the transmitter for one or more predetermined locations, where the transmitter establishes a pocket of energy at each respective predetermined location.

In some embodiments, the method comprises establishing, by the transmitter, the one or more pockets of energy in particular regions of space such that the pockets of energy are capable of being intercepted by a receiver with one or more antennas.

In some embodiments, the method comprises: (i) receiving, by the transmitter, from the receiver one or more communications signals containing data indicating the relative location of the receiver, one or more obstacles situated between the transmitter and the receiver, and indicating an amount of power received the receiver and (ii) responsive to receiving the one or more communications signals, automatically adjusting, by the transmitter, the power transmission waves to avoid the one or more obstacles situated between the receiver and the transmitter in accordance with the data of the one or more communications signals.

In some embodiments, the method comprises selecting, by the transmitter, a safer range at an interval of distance corresponding to a next predetermined location in the one or more predetermined locations to establish a respective pocket of energy, in response to receiving an instruction to avoid establishing one or more pockets of energy at least one of the predetermined locations identified in the instruction as coinciding with one or more sensitive locations associated with people or sensitive equipment.

FIGS. 28-31 illustrate examples of wireless power transmission using a button to designate locations, in accordance with some embodiments.

Figure 28:
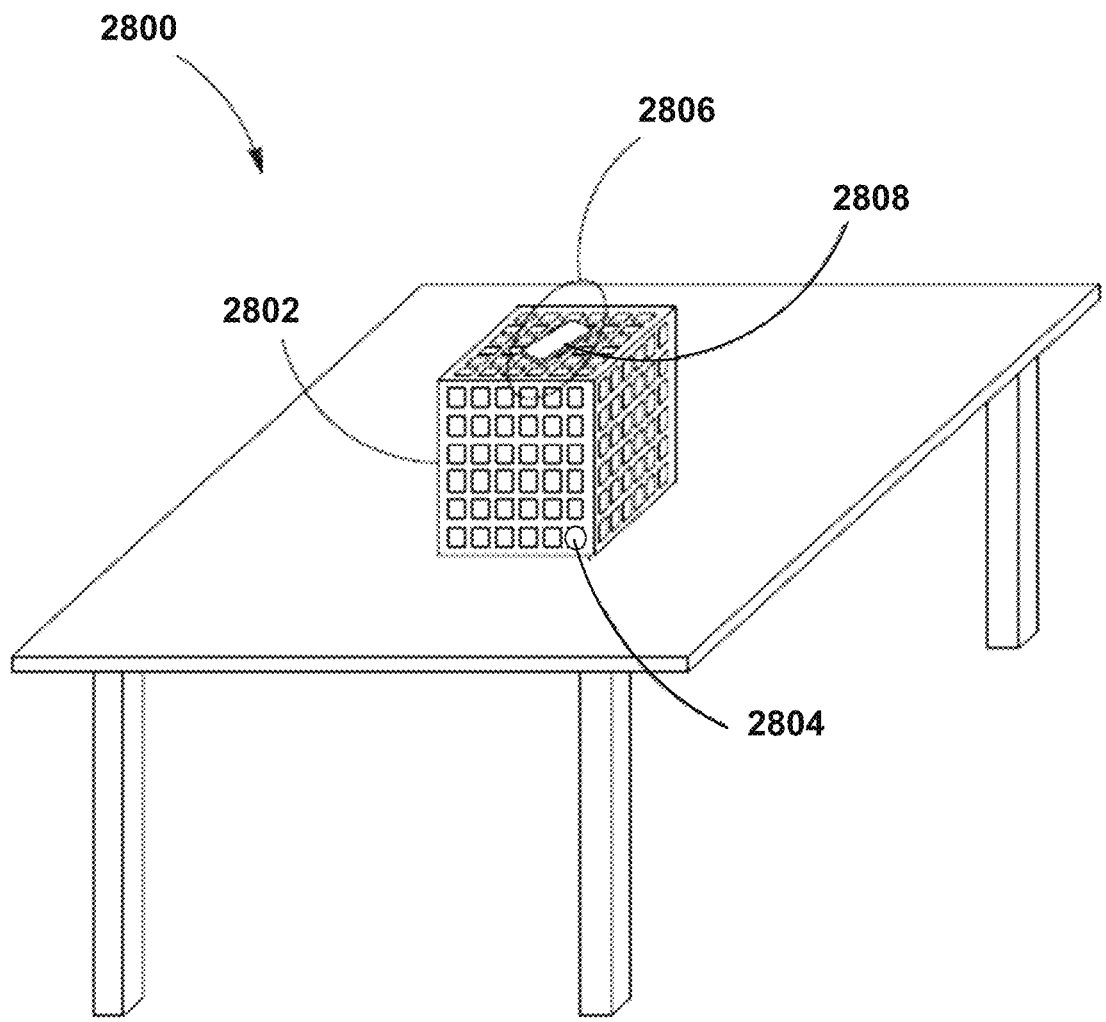
FIGS. 28 and 29 illustrate transmitters having buttons to create pockets of energy, in accordance with some embodiments.

FIG. 28 illustrates a wireless power transmission 2800 where a transmitter 2802 (e.g., transmitter 102, FIG. 1) may include a button 2804 which upon activation may create at least one pocket of energy 2806 in its top surface. A smartphone 2808 operatively coupled to a receiver (not shown), upon being placed atop such surface, may receive power wirelessly by utilizing the aforementioned pocket of energy 2806. This configuration for wireless power transmission 2800 can be beneficial whenever smartphone 2808 cannot communicate its location by to transmitter 2802, for example whenever smartphone 2808 runs out of power completely. In addition, smartphone 2808 may charge faster because of its proximity to transmitter 2802. An even further advantage of this configuration is that if the user decides to remove smartphone 2808 (after smartphone 2808 has built the minimum charge for establishing communication with transmitter 2802) form the surface of transmitter 2802, smartphone 2808 may still receive power wirelessly through (e.g., pocket-forming. Thus, the mobility of smartphone 2808 may not be compromised.

Figure 29:
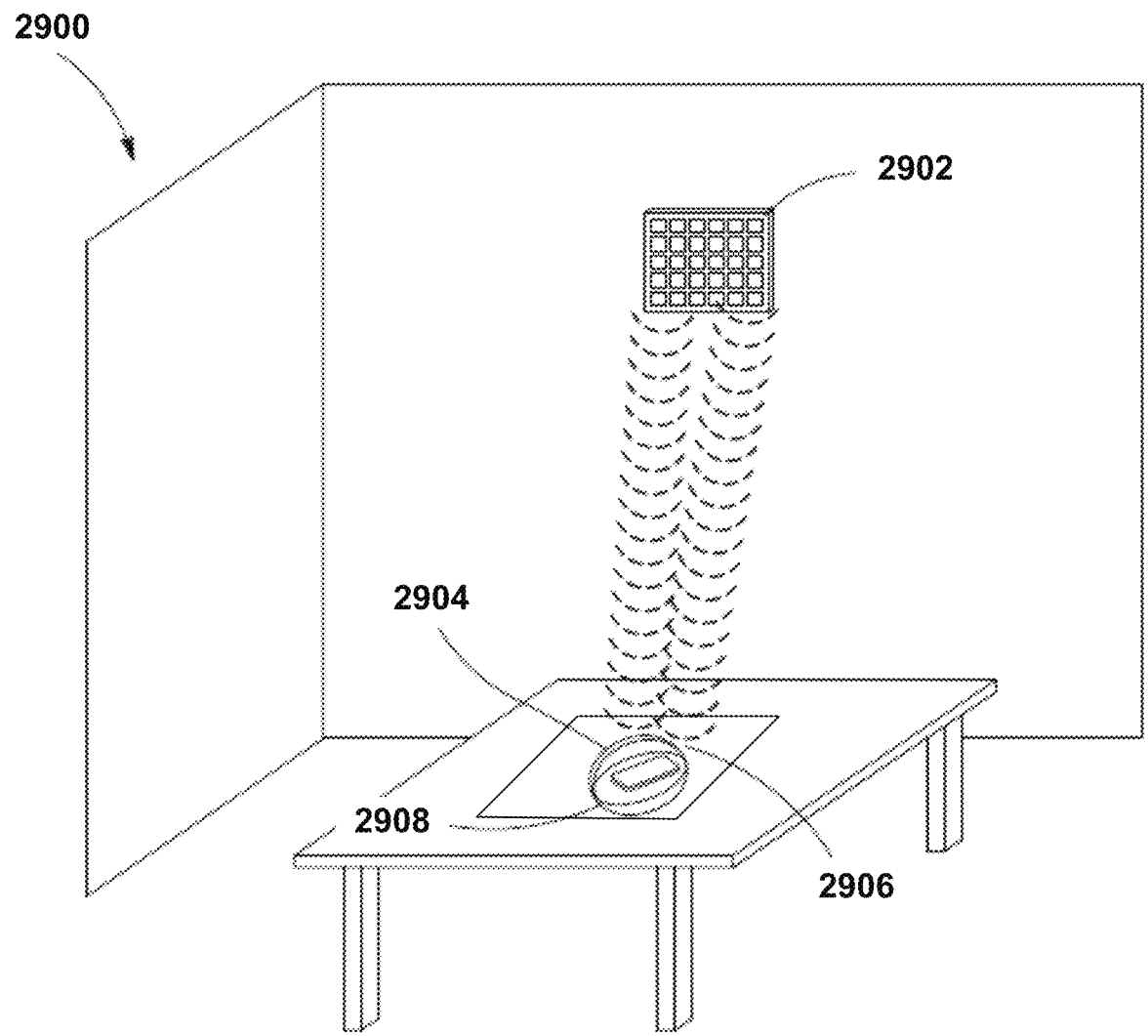

FIG. 29 illustrates an alternative configuration to wireless power transmission in the form of a wireless power transmission (WPT) 2900 where a transmitter 2902 (e.g., transmitter 102, FIG. 1) may create at least one pocket of energy 2904 on a portable mat 2906. Mat 2906 may include at least one receiver and at least one transmitter (not shown) for receiving wireless power from transmitter 2902 and re-transmitting such power, through pocket-forming, to a device, for example a smartphone 2908 operatively coupled to a receiver (not shown). In some embodiments, mat 2906 may communicate to transmitter 2902 through short RF signals sent through its antenna elements or via standard communications protocol. The foregoing may allow transmitter 2902 to easily locate mat 2906. The disclosed configuration may be beneficial whenever smartphone 2908 may not be able to communicate directly to transmitter 2902. This configuration may also be beneficial because mat 2906 can be placed virtually in any desirable and easy to reach location. Lastly, transmitter 2902 may include a button (not shown) similar to that of transmitter 2802 which upon activation may produce pocket of energy 2904 upon mat 2906. The duration of pocket of energy 2904 upon mat 2906 can be custom defined to suit the needs of various users. An even further advantage of WPT can be that other devices may be placed in the vicinity of mat 2906 and can too receive power wirelessly, i.e. electronic devices requiring charge may not even be required to be placed upon mat 2906.

Figure 30B:
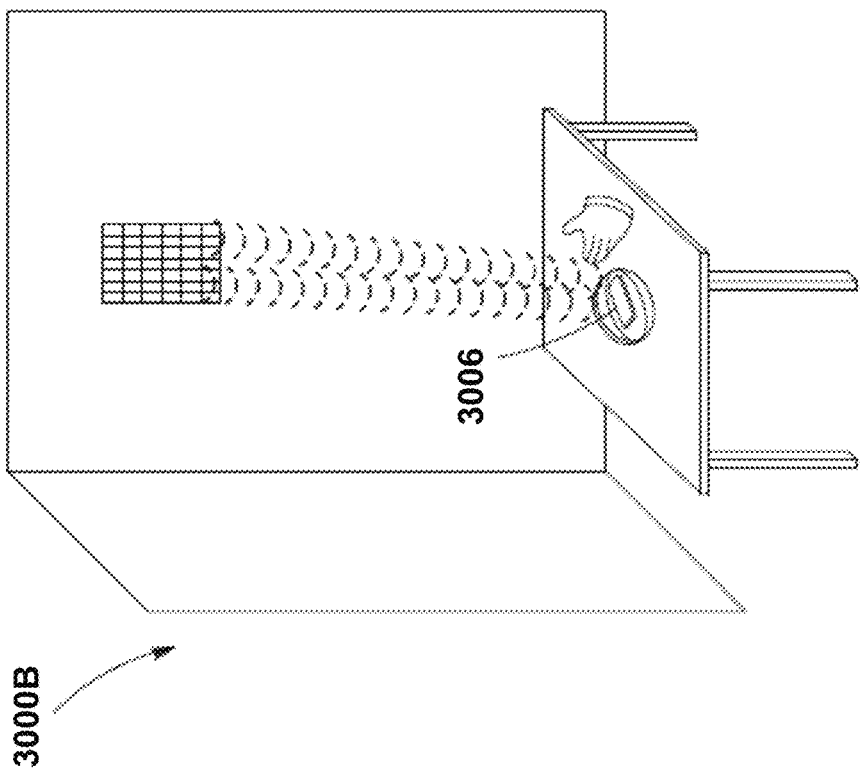
FIGS. 30A, 30B, and 31 illustrate a tracer used for establishing locations of pockets of energy, in accordance with some embodiments.
Figure 30A:
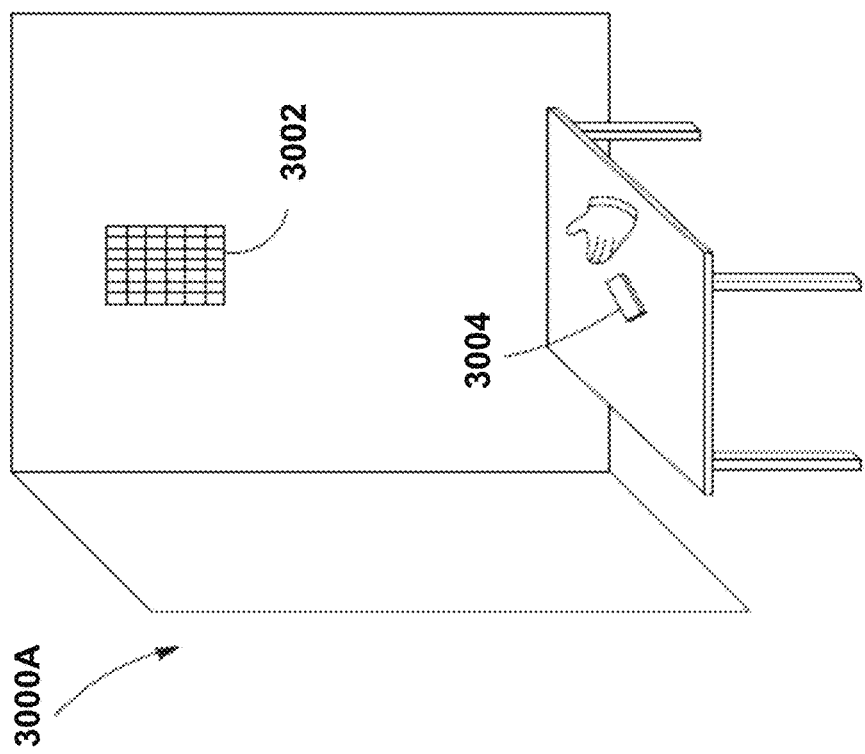

FIG. 30A depicts a wireless power transmission 3000A. Referring first to FIG. 30A, a smartphone 3004 operatively coupled to a receiver (not shown) may be out of usable power and may not be able to communicate with a transmitter 3002 (e.g., transmitter 102, FIG. 1). In this embodiment, a tracer can be used to communicate to transmitter 3002 the locations at which power should be delivered. Tracer can include a communications component within it (not shown), as those described above for transmitters and receivers, for communicating the foregoing locations to the transmitter 3002. Such communications component may become active at the user's request. For example, tracer can include an activation button (not shown) which after being pressed may activate the aforementioned communications component.

FIG. 30B illustrates a wireless power transmission including a tracer which may serve for establishing desired locations for the generation of pockets of energy over at least one receiving device, according to an exemplary embodiment.

Following this activation, communications component may send a request to transmitter 3002 for creating a pocket of energy 3006 at the location of tracer. In order to charge smartphone 3004, users may activate tracer at the same or approximate location of smartphone 3004. Upon building the necessary charge, smartphone 3004 may optionally communicate its location to transmitter 3002 (by its own means) to continue the wireless delivery of power. In other embodiments, pockets of energy 3006 can be created at areas or regions of space which may be beneficial or easy to reach for users but where no electronic devices may be present. In this case, electronic devices requiring charge such as smartphone 3004 can be moved to the foregoing locations for utilizing pockets of energy 3006. The duration of pockets of energy 3006, at the absence of electronic devices requiring charge, may be custom defined by users. In some other embodiments, the duration of pockets of energy 3006 can be given by the operation of tracer, for example, at least one pocket of energy 3006 can be generated upon activating tracer. Such pocket of energy 3006 may remain active until a second press of the activation button of tracer.

In the foregoing configuration of wireless power transmission, electronic devices such as smartphone 3004 can utilize smaller and cheaper receivers. The foregoing can be accomplished because receivers may not require a communications component on their own for communicating locations to transmitter 3002. Rather, tracer can be used to perform such function. In some other embodiments, tracer can take the form of accessories which may connect to electronic via connections such as Universal Serial Bus (USB). In this case, tracer may become active upon being connected to a device, and may control the totality of the wireless delivery of power. In some embodiments, users may create as many pockets of energy 3006 as devices requiring charge.

Figure 31:
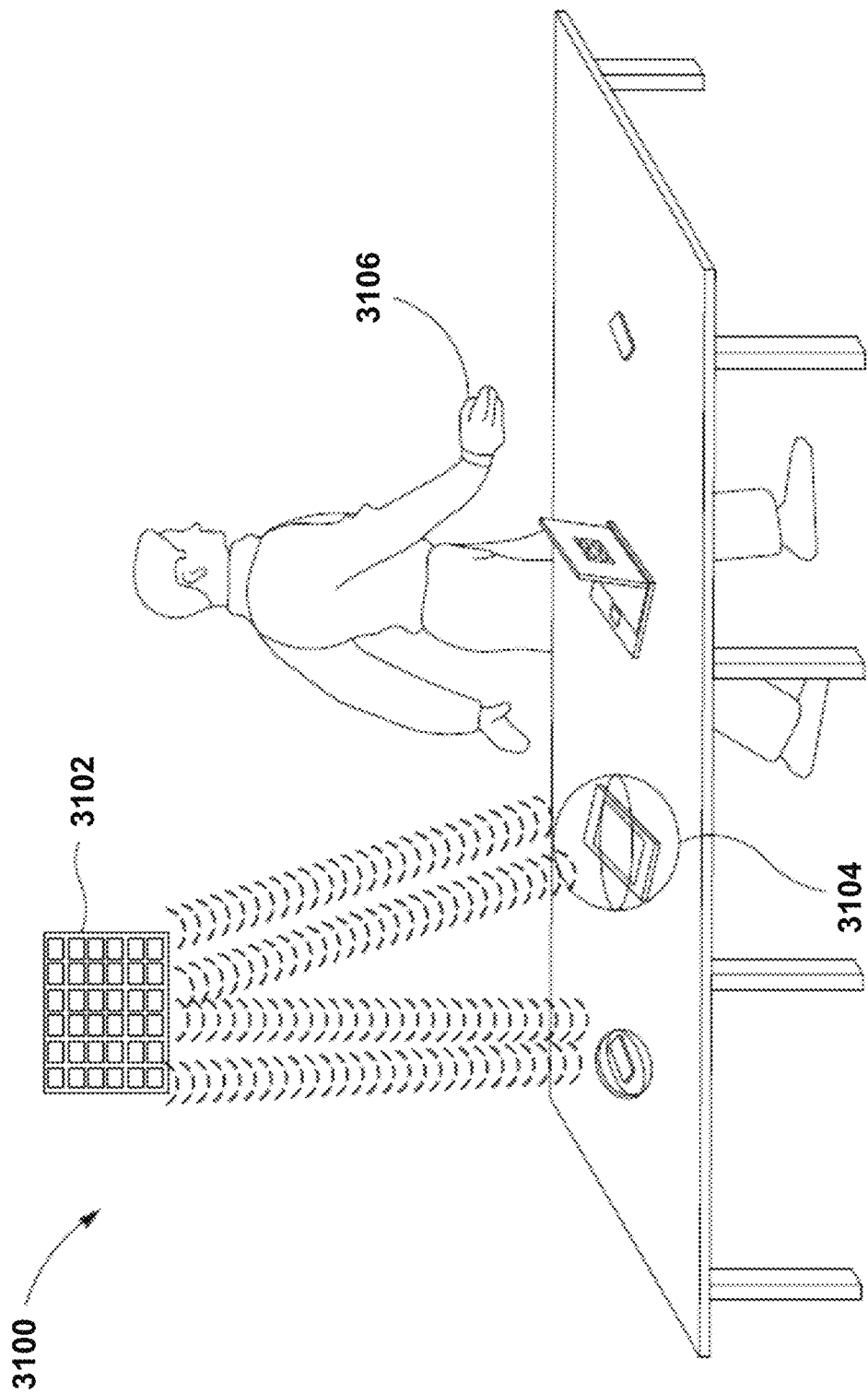

FIG. 31 illustrates a wireless power transmission 3100 where a user carrying a tracer 3106 may create various pockets of energy 3104 in different locations for powering various electronic devices which may include receivers for pocket-forming. Pockets of energy 3104 may be formed by a transmitter 3102, at the request and locations the user specifies. In addition, once devices build up charge they may optionally communicate their location to transmitter 3102 (by their own means) to continue the wireless delivery of power.

FIGS. 28-31 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 28-31.

Presented below are example apparatuses and methods for wireless powering of an electronic device using a button to designate locations.

An apparatus for wireless powering of an electronic device may include: (i) a pocket-forming transmitter for transmitting controlled power RF waves to form pockets of energy in 3-dimensional space to charge the electronic device and (ii) a receiver connected to the electronic device or in close proximity to the electronic device for capturing the pockets of energy to charge or power the electronic device when the electronic device is unable to communicate with the transmitter due to a low battery power level.

In some embodiments, the apparatus comprises a tracer used to communicate with the transmitter to send pockets of energy near the tracer location to charge the electronic device in close proximity to the tracer location when activated. Furthermore, in some embodiments, the tracer when activated directs a predetermined number of pockets of energy to several locations in the vicinity of the tracer to charge multiple electronic devices at the same time for a predetermined time related to the activation of the tracer. Furthermore, in some embodiments, the tracer comprises an activation switch to begin communication with the transmitter to continue sending pockets of energy to the location of the tracer for a predetermined amount of time or until the switch is activated again causing the pockets of energy from the transmitter to cease. Furthermore, in some embodiments, the activation of the tracer provides signals to the transmitter to send a predetermined number of pockets of energy to different locations for powering multiple electronic devices or receivers configured for pocket-forming to power other electronic devices in proximity to the receivers.

In some embodiments, the apparatus comprises a portable mat having both a transmitter and receiver for communicating with the transmitter to receive pockets of energy for re-transmitting power to the electronic device placed on the mat or in close proximity thereto until the electronic device reaches a predetermined power level to communicate directly with the transmitter to continue receiving power even after moving away from the mat. Furthermore, in some embodiments, the mat communicates to the transmitter through short RF signals sent through antenna elements within the mat. Furthermore, in some embodiments, the apparatus utilizes adaptive pocket-forming to regulate the pockets of energy to power the mat for re-transmitting power to electronic devices on or in proximity to the mat that are low on power and unable to communicate directly with the transmitter to receive a charge.

In some embodiments, the receiver captures the pockets of energy to charge or power the electronic device connected to the receiver or in the immediate vicinity of the receiver.

In some embodiments, the transmitter is a portable block configuration that comprises an activation button to create at least one pocket of energy on a top surface of the transmitter to power the electronic device placed on the top surface or in proximity to the transmitter when the electronic device is too low on battery power to communicate directly with the transmitter.

In some embodiments, the electronic device is charged to a predetermined level to establish communication with the transmitter for continuing to receive power from the transmitter through pocket-forming when moved away from the proximity of the transmitter.

A method for wireless powering of an electronic device may include: (i) transmitting controlled radio frequency waves from a pocket-forming transmitter to converge pockets of energy in 3-dimensional space and (ii) capturing the pockets of energy in a receiver to charge or power the electronic device connected to the receiver or in the immediate vicinity of the receiver.

In some embodiments, the method comprises coupling a receiver of the electronic device out of usable power to communicate with the transmitter through use of a tracer communicating with the transmitter to send pockets of energy to the location of the tracer whereupon the electronic device near the location of the tracer is charged until a predetermined power level is reached allowing direct communication between the electronic device and the transmitter to continue the charging.

Figure 32:
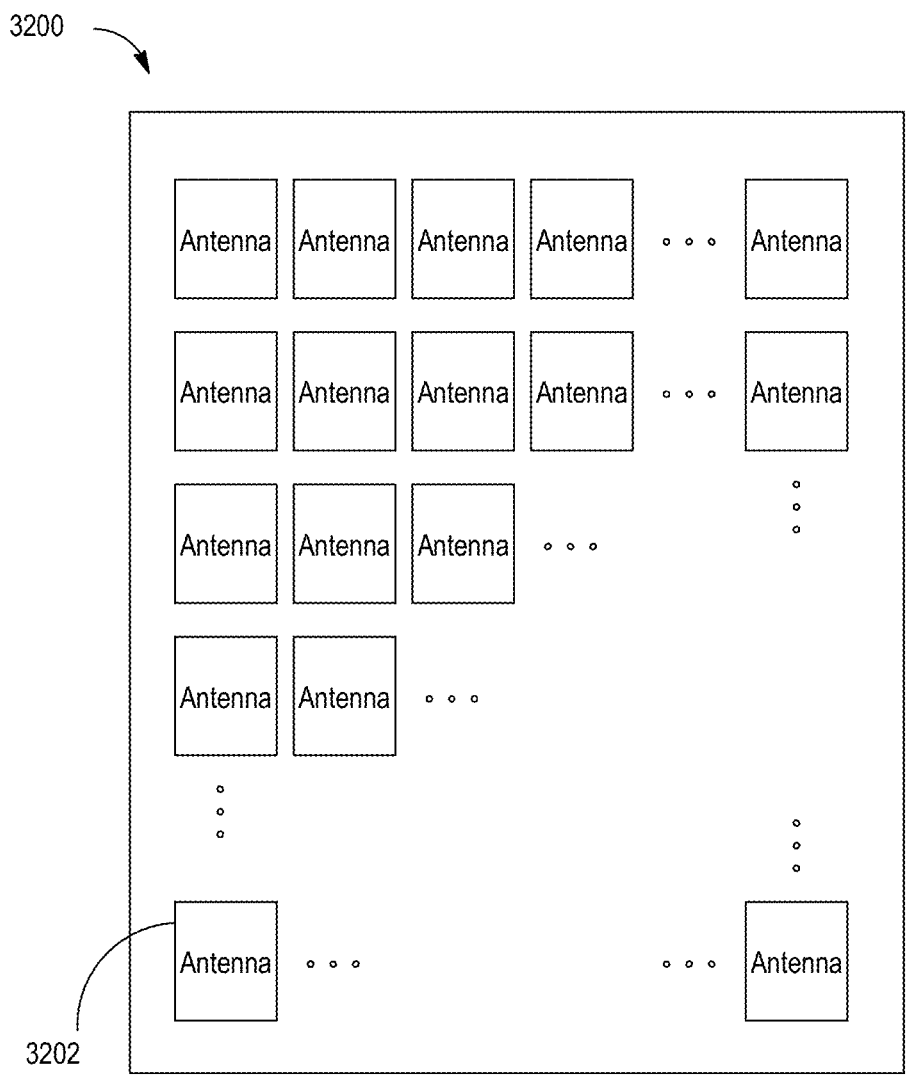
FIG. 32 is an exemplary illustration of a flat panel antenna array that may be used in a transmitter, in accordance with some embodiments.

FIGS. 32 and 33 illustrate examples of wireless power transmission antenna arrays, in accordance with some embodiments.

FIG. 32 is an exemplary illustration of a flat panel antenna array 3200 that may be used in transmitter 102, described in FIG. 1. Flat panel antenna array 3200 may then include an N number of antenna elements 3202 where gain requirements for power transmitting may be from 64 to 256 antenna elements 3202 which may be distributed in an equally spaced grid. In one embodiment, flat panel antenna array 3200 may have an 8×8 grid to have a total of 64 antenna elements 3202. In another embodiment, flat panel antenna array 3200 may have a 16×16 grid to have a total of 256 antenna elements 3200. However, the number of antenna elements 3200 may vary in relation with the desired range and power transmission capability on transmitter 102, the more antenna elements 3202, the wider range and higher power transmission capability. Alternate configurations may also be possible including circular patterns or polygon arrangements.

Flat panel antenna array 3200 may also be broken into numerous pieces and distributed across multiple surfaces (multi-faceted).

Antenna elements 3202 may include flat antenna elements 3202, patch antenna elements 3202, dipole antenna elements 3202 and any suitable antenna for wireless power transmission. Suitable antenna types may include, for example, patch antennas with heights from about ½ inch to about 6 inches and widths from about ½ inch to about 6 inches. Shape and orientation of antenna elements 3202 may vary in dependency of the desired features of transmitter 102 orientation may be flat in X, Y, and Z axis, as well as various orientation types and combinations in three dimensional arrangements. Antenna elements 3202 materials may include any suitable material that may allow radio signal transmission with high efficiency, good heat dissipation and the like.

Antenna elements 3202 may include suitable antenna types for operating in frequency bands such as 900 MHz, 2.5 GHz or 5.8 GHz as these frequency bands conform to Federal Communications Commission (FCC) regulations part 18 (Industrial, Scientific and Medical equipment). Antenna elements 202 may operate in independent frequencies, allowing a multichannel operation of pocket-forming.

In addition, antenna elements 3202 may have at least one polarization or a selection of polarizations. Such polarization may include vertical pole, horizontal pole, circularly polarized, left hand polarized, right hand polarized, or a combination of polarizations. The selection of polarizations may vary in dependency of transmitter 102 characteristics. In addition, antenna elements 3202 may be located in various surfaces of transmitter 200.

Antenna elements 3202 may operate in single array, pair array, quad array and any other suitable arrangement, which may be designed in accordance with the desired application.

Figure 33C:
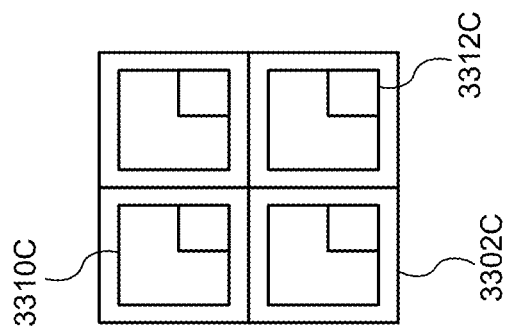
FIGS. 33A-33C show various antenna arrays, in accordance with some embodiments.
Figure 33B:
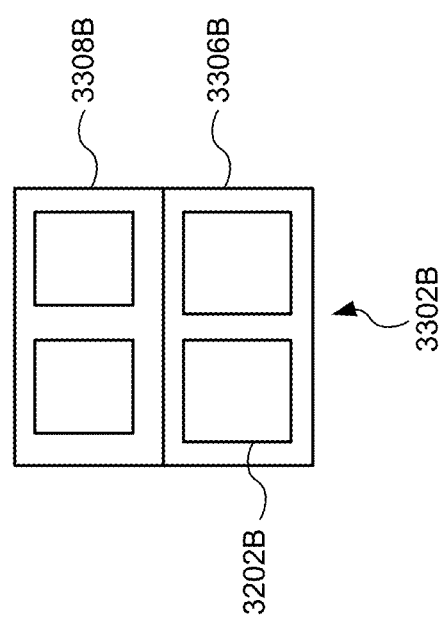
Figure 33A:
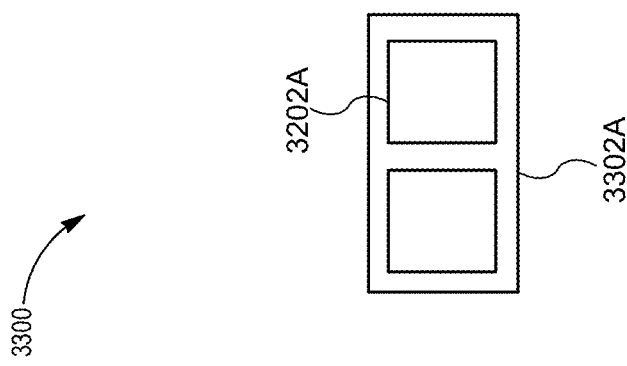

FIGS. 33A-33C shows antenna arrays 3300 according to various embodiments. Antenna arrays 3300 may include suitable antenna types for operating in frequency bands such as 900 MHz, 2.5 GHz, and 5.8 GHz, as these frequency bands may comply with the FCC regulations, part 18.

FIG. 33A shows a single array 3302A where all antenna elements 3302 may operate at 5.8 GHz. Thus single array 3302A may be used for charging or powering a single device, similar to the embodiment described in FIG. 1. FIG. 33B shows pair array 3302B, where the top half 3308B of antenna elements 3202B may operate at 5.8 GHz and the bottom half 3306B may operate at 2.4 GHz. Pair array 3302B may then be used to charge or power, at the same time, two receivers that may operate at different frequency bands such as the ones described above. As seen in FIG. 33B, antenna elements 3202B may vary in size according to the antenna type.

FIG. 33C shows a quad array 3302C where each antenna element 3202 may be virtually divided to avoid power losses during wireless power transmission. In this embodiment, each antenna element 3202 may be virtually divided in two antenna elements 3202, antenna element 3310C and antenna element 3312C. Antenna element 3310C may be used for transmitting in 5.8 GHz frequency band and antenna element 3312C may be used for transmitting in 2.4 GHz frequency band. Quad array 3302C may then be used in situations where multiple receivers 106 operating at different frequency bands require to be charged or powered.

In example #1 a portable electronic device that may operate at 2.4 GHz may be powered or charged. In this example, a transmitter 102, may be used to deliver pockets of energy onto one electronic device, as in FIG. 1. This transmitter may have a single array of 8×8 of flat panel antennas where all the antenna elements may operate in the frequency band of 2.4 GHz. Flat antennas may occupy less volume than other antennas, hence allowing a transmitter to be located at small and thin spaces, such as, walls, mirrors, doors, ceilings and the like. In addition, flat panel antennas may be optimized for operating to long distances into narrow hall of wireless power transmission, such feature may allow operation of portable devices in long areas such as, train stations, bus stations, airports and the like. Furthermore, flat panel antennas of 8 λ8 may generate smaller pockets of energy than other antennas since its smaller volume, this may reduce losses and may allow more accurate generation of pockets of energy, such accuracy may be employed for charging/powering a variety of portable electronic devices near areas and/or objects which do not require pockets of energy near or over them.

In example #2 two electronic devices that may operate at two different frequency bands may be powered or charged at the same time. In this example, the transmitter 102, may be used to deliver pockets of energy onto two electronic devices. In this example, the transmitter may have a pair array with different type of antennas, flat panel antennas and dipole antennas, where ½ of the array may be formed by flat panel antennas and the other half by dipole antennas, as shown in FIG. 33B. As described in example #1, flat panel antennas may be optimized to radiate power within narrow halls at considerable distances. On the other hand, dipole antennas may be employed for radiating power at nearer distances but covering more area because of their radiation pattern. Furthermore, dipole antennas may be manually adjusted, this feature may be beneficial when the transmitter is located at crowded spaces and transmission needs to be optimized.

FIGS. 32 and 33 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 32 and 33.

Presented below are example systems and methods for transmitting wireless power using antenna arrays.

A system for transmitting wireless power may include: (i) a transmitter for generating two or more RF waves having at least two RF transmit antennas to form controlled constructive interference patterns from the generated RF waves, (ii) a micro-controller within the transmitter controlling the constructive interference patterns of generated RF waves for pocket-forming to accumulate pockets of energy in predetermined areas or regions in space, (iii) a receiver with at least one antenna to receive the accumulated pockets of energy converging in 3-dimensional space to a targeted electronic device, and (iv) a communication network connected to the transmitter and receiver for determining the areas or regions in space to receive the pockets of energy from the transmitter through an array of antennas for charging or operating the targeted electronic device.

In some embodiments, the transmitter generates RF waves to form controlled destructive interference patterns that form null-spaces without pockets of energy and the array of antennas is an 8×8 grid having a total of 64 antenna elements distributed in an equally spaced grid.

In some embodiments, the array of antennas is a 16×16 having a total of 256 antenna elements distributed in an equally spaced grid.

In some embodiments, the number of antennas varies depending upon the predetermined range and power transmission.

In some embodiments, an antenna arrangement includes circular patterns or polygon configurations for charging or operating a plurality of electronic devices.

In some embodiments, the antennas operate in a frequency band of at least one of about 900 MHz, about 2.5 GHz, and about 5.8 GHz.

In some embodiments, the antennas have at least one polarization or a polarization including a vertical pole, horizontal pole, a circularly polarized, left hand polarized, right hand polarized or a combination of polarizations.

In some embodiments, the antennas operate in at least one of a single array, pair array, quad array or any other suitable array arrangement for transmission of pockets of energy.

In some embodiments, the antennas are arranged in a pair array where the top half of the antennas operates at 5.8 GHz and the bottom half of the array operates at 2.4 GHz and at least one of such operation is driven by the transmitter and controlled by the micro-controller.

In some embodiments, the micro-controller dynamically adjusts the pocket-forming through a predetermined antenna array to regulate power on one or more targeted electronic devices.

In another system for transmitting wireless power, the system may include: (i) a transmitter having two RF antennas in an array for generating pockets of energy, (ii) a receiver electrically connected to at least one electronic device for receiving the pockets of energy, and (iii) a micro-controller connected to a power source for controlling the generated pockets of energy delivered to the electronic device from a predetermined array of antennas.

In some embodiments, the generated pockets of energy are received by a plurality of electronic devices at a higher efficiency due to antenna array orientation on the transmitter and receiver directed by the microcontroller in response to a communication signal from the receiver.

In some embodiments, the system further includes a radio frequency integrated circuit driven by a predetermined program in the micro-controller for pocket-forming to charge or operate the electronic device through an antenna array including an N number of antenna elements in the range of 64 to 256 antenna elements distributed in an equally spaced grid on the transmitter.

A method for transmitting wireless power may include: (i) generating two or more RF waves from a transmitter with at least two RF transmit antennas, (ii) forming controlled constructive and destructive interference patterns from the generated RF waves by a radio frequency integrated circuit controlled by a microcontroller, (iii) accumulating energy or power in the form of constructive interference patterns from the RF waves to form pockets of energy, (iv) converging the pockets of energy in 3-dimensional space to a targeted electronic device, and (v) arranging the antennas in an array optimal for charging or operating the targeted electronic device with the pockets of energy.

In some embodiments, the number and type of antennas varies in relationship to a predetermined desired range and power transmission capability of the transmitter whereby the greater the number of antennas results in a wider range and a higher power delivery of pockets of energy to the targeted electronic device.

In some embodiments, the antennas are flat antennas, patch antennas, dipole antennas or any other antennas configured for transmission of pockets of energy.

In another system for transmitting wireless power, the system may include: (i) a first device comprising a controller, a transmitter coupled to the controller, and a plurality of antennas coupled to the transmitter, where the antennas output a plurality of RF waves so a controlled constructive interference pattern is formed based on the waves, and where the controller controls the pattern so a pocket of energy is formed in a first defined area, (ii) a second device comprising a receiver and an antenna coupled to the receiver, where the second device is charged via the antenna engaging the pocket based on the second device being positioned in the area, and (iii) a computer communicating with the first device and the second device so the computer is able to determine the area.

In some embodiments, an orientation of the array is optimized for maximum efficiency and the controller controls the second device in response to receiving a signal from the second device. Furthermore, in some embodiments, the first device comprises a flat panel antenna array comprising a number of antennas where a gain requirement for power transmission ranges from 64 to 256 antennas distributed in an equally spaced grid for enhancing reception of the pocket of energy by the second device.

In some embodiments, a number of the antennas are optimized for at least one of a transmission range and a transmission power.

In some embodiments, at least one of a number and a type of antennas in the array corresponds to at least one of a predetermined desired range and a power transmission capability of the first device so an increase in a value of the number corresponds to at least one of a wider range and a higher power delivery associated with the pocket.

In another system for transmitting wireless power, the system may include a first device comprising a controller, a transmitter coupled to the controller, and a plurality of RF antennas coupled to the transmitter, where the antennas are arranged in an array, and where the controller controls the transmitter so the antennas generate a pocket of energy so a second device is able to be charged via the pocket based on the second device being positioned in proximity of the pocket.

In another method for transmitting wireless power, the method may include: (i) forming, by a first device, a constructive interference pattern based on a plurality of RF waves output via the first device, where the first device comprises a transmitter and an antenna coupled to the transmitter and (ii) defining, by the first device, a pocket of energy based on the constructive pattern so a second device is able to be charged via the pocket based on the second device being positioned in proximity of the pocket.

Figure 34:
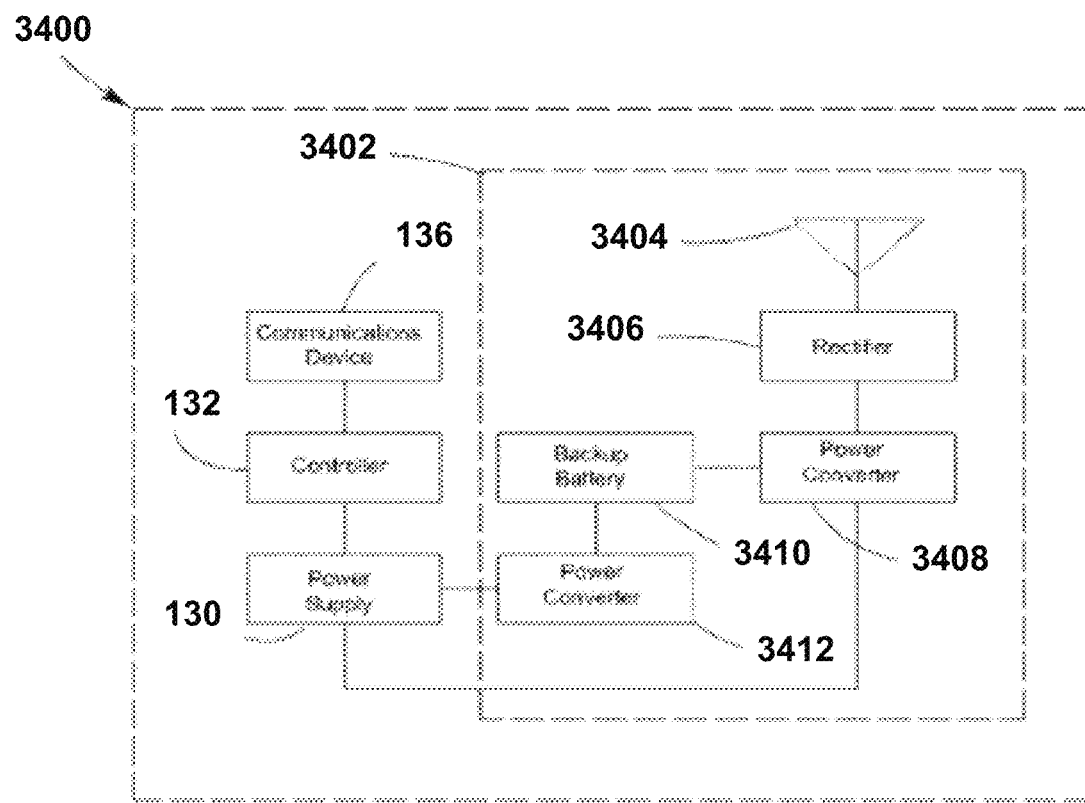
FIG. 34 illustrates an electronic device including at least one embedded receiver that contains a backup battery, in accordance with some embodiments.

FIGS. 34 and 35 illustrate systems for wireless transmission of power to a portable electronic device having a backup battery, in accordance with some embodiments.

FIG. 34 illustrates an electronic device 3400, similar to electronic device 122 described in FIG. 1. Electronic device 3400 may include at least one embedded receiver 3402, that may have a backup battery 3410 as an additional feature compared to the receiver 120 described in FIG. 1. Embedded receiver 3402, may also include a subset of antenna elements 3404 for converting pockets of energy, produced through pocket-forming, into AC voltage, at least one rectifier 3406 where AC voltage may be converted to direct current (DC) voltage, and at least one power converter 3408 for providing constant DC voltage output to either a backup battery 3410 or to power supply 130.

In this embodiment, backup battery 3410 may be an additional source of energy for electronic device 3400 and may be any suitable battery that provides enough voltage to power or charge electronic device 3400. Backup battery 3410 may also require a power converter 3412 to deliver DC voltage to power supply 130. Backup battery 3410 may be charged while embedded receiver 3402 is capturing pockets of energy from the transmitter to which is connected. In other embodiments, power converter 3408 may pass DC voltage directly to power supply 130 without charging backup battery 3410. In yet another embodiment power converter 3408 may pass DC voltage to both power supply 130 and backup battery 3410 at the same time. Power supply 130 may constantly provide DC voltage to micro-controller 132 and communications device 136 as long as it does not run out of charge or power from embedded receiver 3402.

Figure 35A:
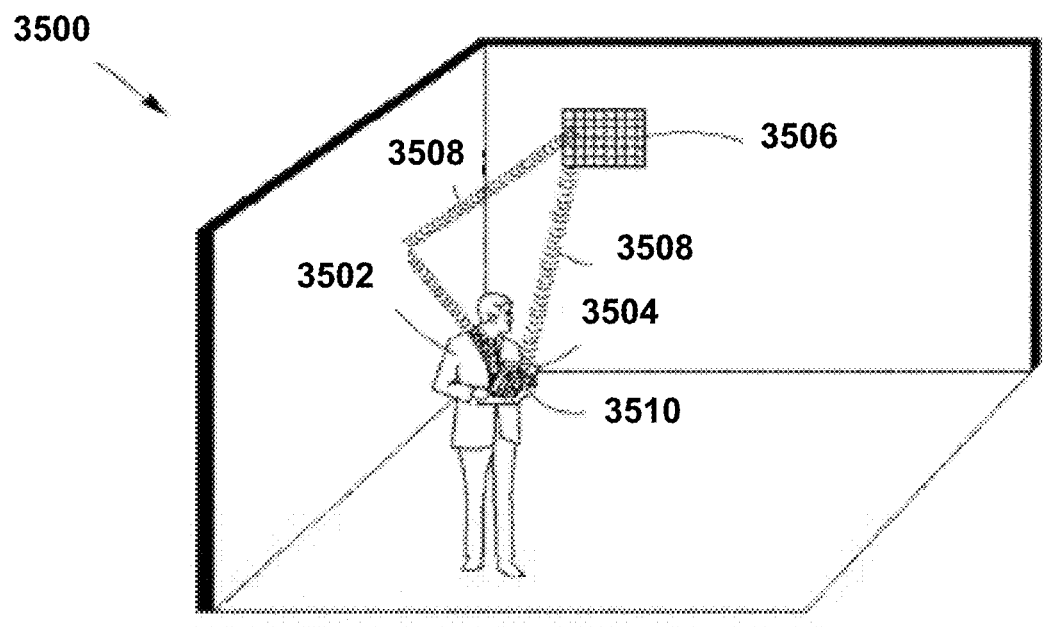
FIGS. 35A and 35B show examples where wireless power transmission may or may not occur, in accordance with some embodiments.
Figure 35B:
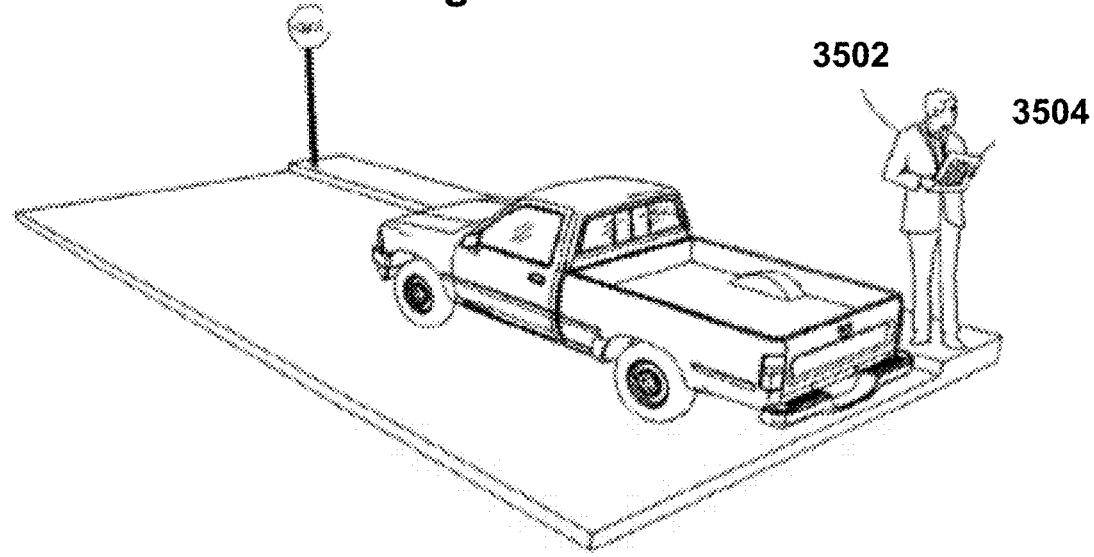

FIGS. 35A and 35B illustrate two embodiments where wireless power transmission 3500 may or may not occur. In FIG. 35A, a user 3502 may be inside a room and may hold on his hands an electronic device, which in this case, may be a tablet 3504. Tablet 3504 may include a receiver (not shown) either embedded to it or as a separate adapter connected to tablet 3504. The receiver embedded or connected to tablet 3504 may be as the one described in FIG. 34, hence including an additional feature such as a backup battery (not shown). The backup battery included in the receiver may be fully or partially charged while wireless power transmission takes place. FIG. 35A also shows a transmitter 3506, as the one described in FIG. 1. Transmitter 3506 may transmit controlled RF waves 3508 which may converge in 3-dimensional space and deliver pockets of energy 3510 to the receiver. In this embodiment, the receiver may either power tablet 3504 directly or charge backup battery first and then power tablet 3504.

FIG. 35B shows an example where wireless power transmission may not occur. In this embodiment, user 3502 may be found outdoors walking down the sidewalk where transmitter 3506 may not be available, and hence no wireless power transmission may occur. However, tablet 3504 may still have an extra source of power (backup battery 3410) included as an internal part of the receiver. As described in FIG. 35A, backup battery 3410 may have been charged while transmitter 3506 was available. Tablet 3504 may then use the available power from the backup battery 3410 in the receiver when power supply 130 (tablet 3504's battery) runs out. Thus, power supply 130 life can be greatly increased.

FIGS. 34 and 35 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 34 and 35.

Presented below are example hybrid receivers and hybrid charging methods for wireless transmission of power to a portable electronic device having a backup battery.

A hybrid receiver for wireless transmission of power to a portable electronic device may include: (i) an antenna for receiving pockets of energy formed from constructive interference patterns of RF waves from a transmitter and for transforming the pockets of energy into AC voltage, (ii) a rectifier connected to the antenna for converting the AC voltage into DC voltage, (iii) a power converter for changing the DC voltage into a constant DC voltage, (iv) a power source within the portable electronic device connected to the power converter for receiving the constant DC voltage to power or charge the power source, and (v) a backup battery connected to the power converter for receiving the constant DC voltage to power or charge the backup battery.

In some embodiments, the hybrid receiver communicates with the transmitter through short RF waves or pilot signals sent through the antenna.

In some embodiments, the power source is a rechargeable or disposable lithium-ion battery.

In some embodiments, the hybrid receiver is embedded in the portable electronic device.

In some embodiments, the power converter powers the electronic device directly or charges the backup battery first and then powers the electronic device.

In some embodiments, the hybrid receiver and transmitter each comprises a controller connected to a communication device for communications between the hybrid receiver and the transmitter to control the power received by the backup battery or the power source. Furthermore, in some embodiments, the hybrid receiver and transmitter controllers are a digital signal processor, a microprocessor, or an ASIC.

In some embodiments, backup battery and power source status information control the power delivered to the backup battery or the power source.

In some embodiments, the power converter is directly connected between the backup battery and the power source of the hybrid receiver.

In some embodiments, the backup battery is connected to the power source of the receiver.

In some embodiments, the hybrid receiver implements externally the connection of the hybrid receiver to the portable electronic device in the configuration of a case. Furthermore, in some embodiments, the hybrid receiver connects the case to the electronic device through a universal serial bus or electrical plug.

In some embodiments, the power converter of the hybrid receiver is connected to the power source and to the backup battery for maintaining the power levels for charging the power source and backup battery for continuous use without total loss of power during continuous operation of the electronic device.

In some embodiments, the power converter of the hybrid receiver comprises two power converters, one connected to the backup battery and the power source and the other connected between the backup battery and the power source to regulate the constant direct current voltage to operate the portable electronic device.

In some embodiments, the power converter powers simultaneously the backup battery and the power source.

In some embodiments, the hybrid receiver communicates power status of the backup battery and power source to the transmitter and a transmitter DSP through a RF integrated circuit that controls the phases and amplitudes of the power RF signals in each transmitter antenna in order to generate the desired pocket-forming to power the backup battery and power source.

A hybrid charging method for wireless transmission of power to a portable electronic device may include: (i) connecting a hybrid receiver to an internal power source and a backup battery, (ii) receiving pockets of energy comprised of power RF signals at receiver antenna elements to produce an AC voltage from a RF circuit connected to a transmitter, (iii) rectifying the AC voltage to a direct current voltage, (iv) converting the direct current voltage to a constant direct current voltage output, and (v) providing the constant direct current voltage output to power either or both the backup battery and the internal power source of the hybrid receiver.

In some embodiments, the method comprises transmitting simultaneously both Wi-Fi signals and power RF signals from the transmitter to the receiver.

In another hybrid charging method for wireless transmission of power to a portable electronic device, the method may include: (i) supplying RF power signals to a hybrid receiver comprising antenna elements, a DSP, a rectifier, a power converter, a backup battery, a power supply and a communications device, (ii) generating the RF power signals through a RF integrated chip controlled by a DSP in a transmitter with a communication device controlled by the DSP, (iii) communicating the power status of the backup battery and power supply of the receiver to the transmitter through the transmitter and receiver communication devices on short RF signals with standard wireless communication protocols, and (iv) transmitting the power RF signals to the antenna elements of the hybrid receiver for rectifying the AC voltage at the antenna elements into a direct current voltage and converting the direct current voltage into a constant direct current voltage for powering the backup battery and the power source of the receiver.

In some embodiments, the method comprises: (i) decoding the short RF signals to identify the gain and phase of the receiver to determine the direction of the receiver, (ii) transmitting pockets of energy consisting of power RF signals from the transmitter through at least two RF antennas in the transmitter to the antenna elements of the receiver, and (iii) running continuously the portable electronic device with either the power source or the backup battery while charging either the backup battery or the power source to provide an inexhaustible source of operating power for the electronic device.

FIGS. 36-41 illustrate wireless power transmission environments utilizing reflectors, in accordance with some embodiments.

Figure 36:
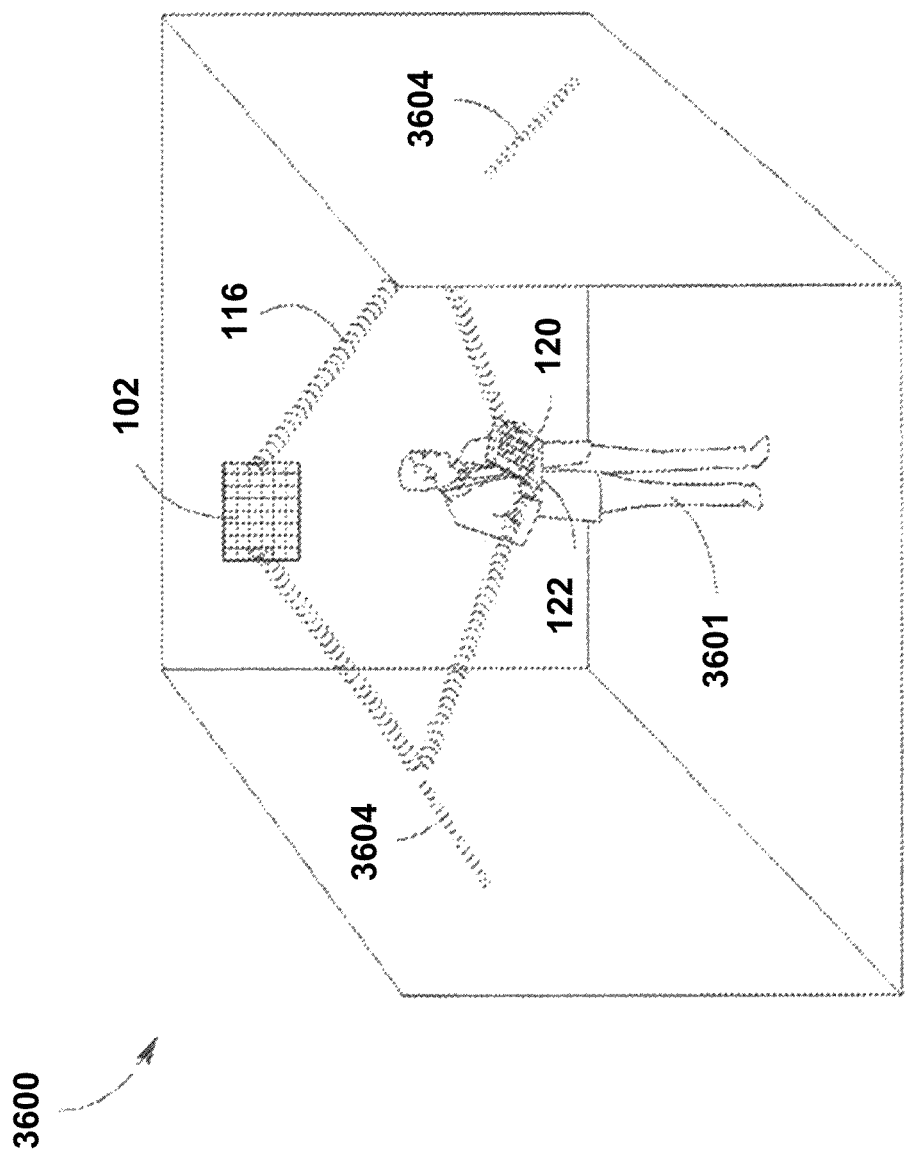
FIG. 36 illustrates a wireless power transmission using adaptive pocket-forming using reflected RF waves, in accordance with some embodiments.

Referring now to FIG. 36, an exemplary illustration of a wireless power transmission 3600 using adaptive pocket-forming can include a user 3601 inside a room holding an electronic device 122 which may include a receiver 120 either embedded or as a separate adapter. A transmitter 102 may be hanging on one of the walls of the room behind user 3601, as shown in FIG. 36. As user 3601 may seem to be obstructing the path between receiver 120 and transmitter 102, RF waves 116 may not be easily aimed to receiver 120 in a linear direction.

Given that the signals generated from receiver 120 may be omnidirectional (according to the type of antenna elements used), these signals may bounce over the walls, floor, and/or ceiling until they find transmitter 102. Almost instantly, a micro-controller (not shown in FIG. 36) which may reside in transmitter 102, may recalibrate the signals sent by receiver 120 by adjusting gain and phases, forming conjugates taking into account the built-in phases of antenna elements. Once calibration is performed, transmitter 102 may focus RF waves 116 in one or more channels following one or more paths as described in FIG. 36. Subsequently, a pocket of energy may be generated on electronic device 122 while avoiding obstacles such as user 3601 or any room furniture such as chairs, tables, and sofas (not shown in FIG. 36).

While wireless power transmission 3600 is illustrated as using the room walls to reflect the transmitted RF waves 116 towards receiver 120, other room structures such as ceiling or floor may also be used for this purpose. However, depending on the thickness and materials used in the room walls, ceiling or floor, the reflected RF waves 116 can lose significant signal power as they can go through or be absorbed by these structures. For example, as shown in FIG.

36, if a portion 3604 of RF waves 116 goes through room walls made of wood, cement or plaster; the signal power of RF waves 116 reaching receiver 120 can be decreased to up to about 50%, thereby negatively affecting charging efficiency.

Figure 37:
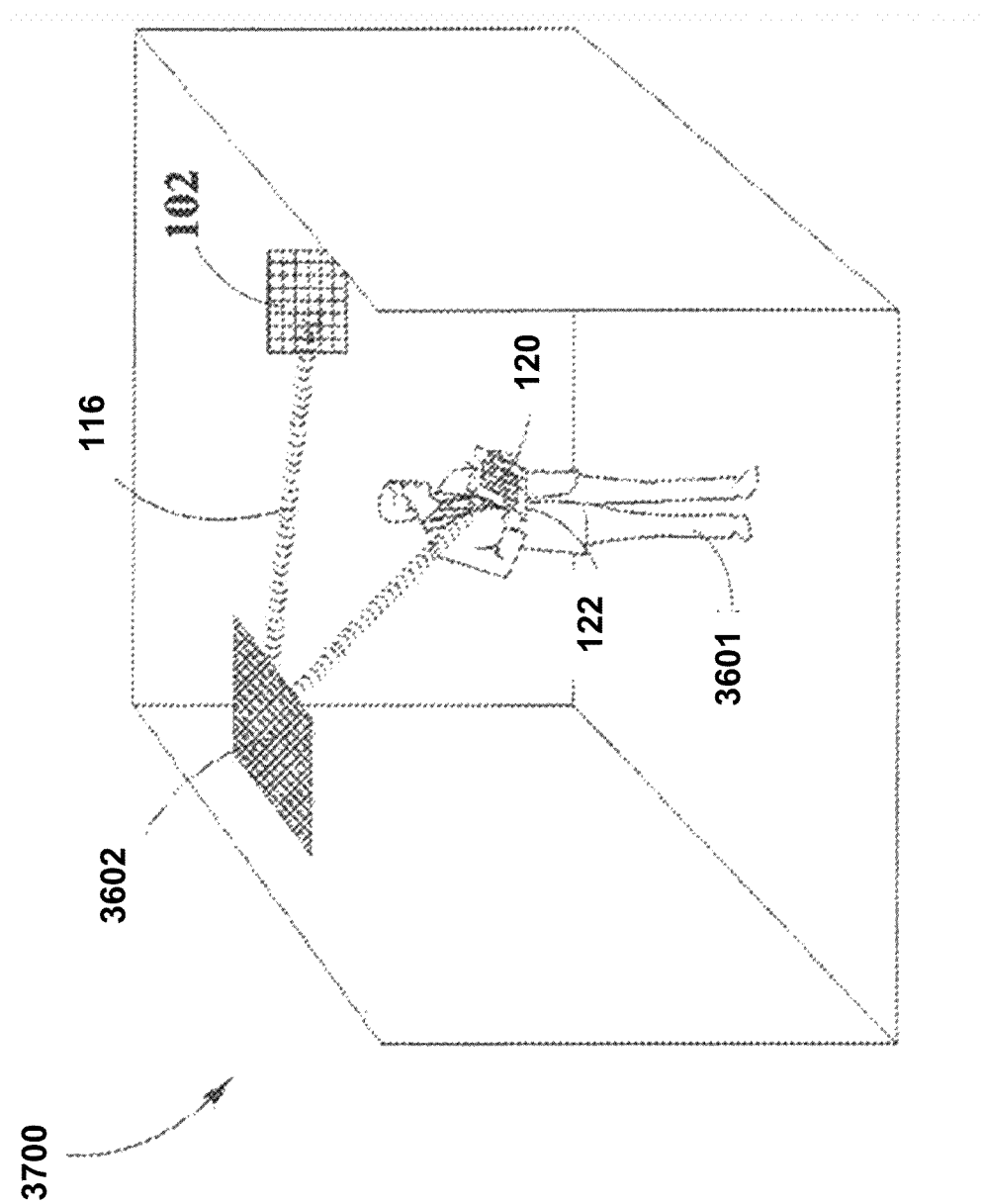
FIGS. 37 and 38 illustrate wireless power transmissions using a reflector for improving power transmission and charging efficiency, in accordance with some embodiments.

FIG. 37 illustrates a wireless power transmission 3700 using pocket forming and a reflector 302, according to an embodiment. Transmitter 102 can be purposely aimed at reflector 3602, so that the generated RF waves 116 can be accurately and efficiently reflected towards the location of electronic device 122, which can be under user 3601 operation or it can be just resting over any room furniture (not shown in FIG. 36). According to an embodiment, reflector 3602 can be made of metallic materials such as steel, aluminum, copper, and the like, in order to reflect close to 100% of the RF waves 116 power directly towards receiver 120 in electronic device 122 for the generation of pockets of energy that provide suitable charge or power. In another embodiment, reflector 3602 can be capable of increasing the power of reflected RF waves 116 by a factor between about 2 and 3, thereby enhancing the charging efficiency of electronic device 122 and improving the spatial 3-dimensional pocket formation.

Reflector 3602 can be a sheet of metal exhibiting a rectangular shape within suitable dimensions, preferably between 1 and 2 ft. Surface area of reflector 3602 may vary according to the dimensions of RF waves 116 which typically may be less than 1 foot wide. In another embodiment, reflector 3602 can include a printed circuit board (PCB) with a metal layer that can bounce off RF waves 116 generated by transmitter 102.

Reflector 3602 can be positioned in the room ceiling in order to avoid as many obstacles as possible when reflecting RF waves 116 towards electronic device 122. However, other locations or structures across the room can also be considered. For example, reflector 3602 may be positioned in the walls or floor, relative to the location of electronic device 122 and transmitter 102. Reflector 3602 can also be slightly tilted according to a desired reflection path relative to the location of electronic device 122. In addition, reflector 3602 may be painted or covered according to the color, texture or decoration of room walls, ceiling, or floor.

Mounting methods of reflector 3602 in room ceiling, walls, or floor can include four screws at each corner of reflector 3602, in addition to suitable adhesives or glues that may securely install reflector 3602 relative to transmitter 102 and electronic device 122.

Figure 38:
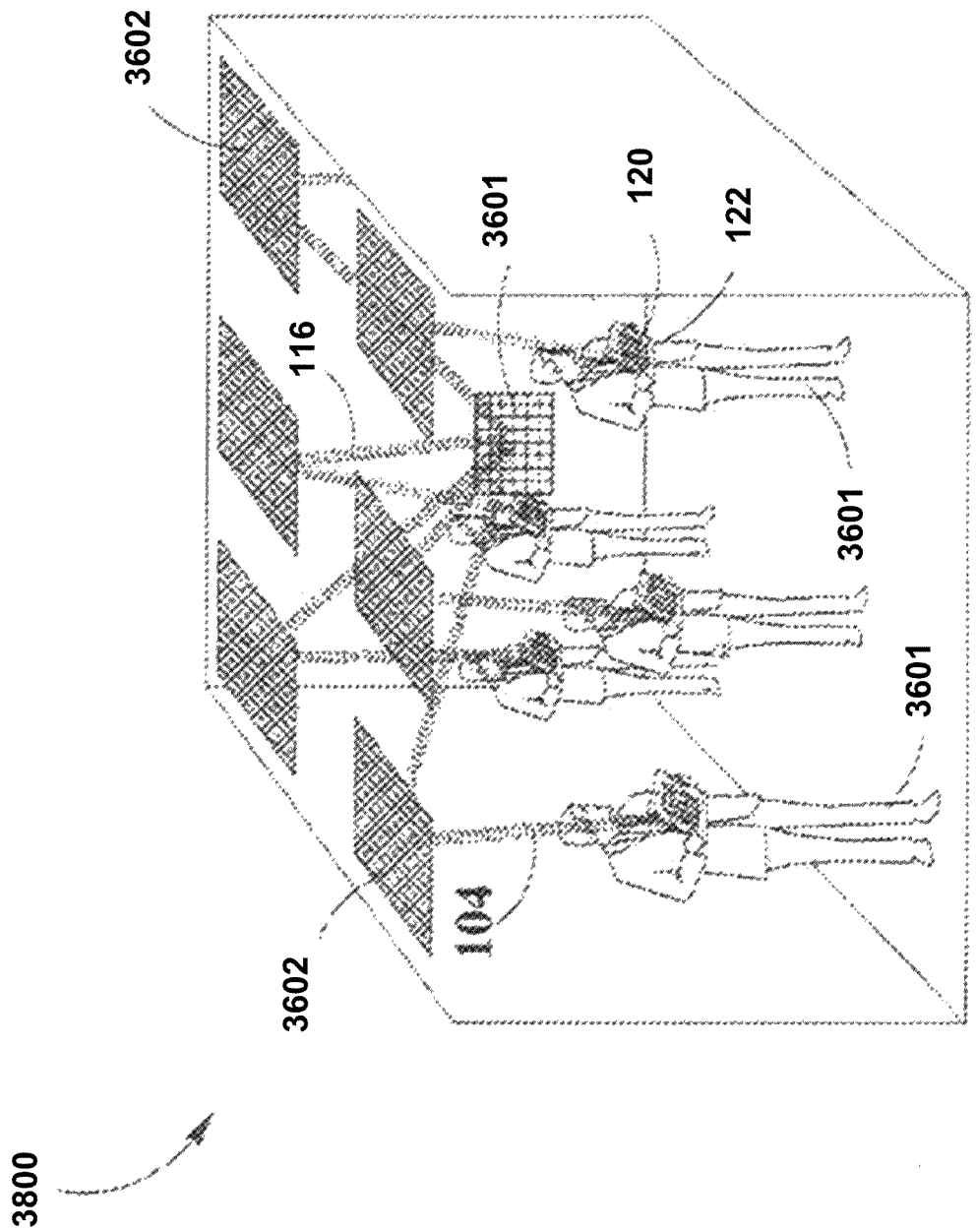

Referring now to FIG. 38, a wireless power transmission 3800 may utilize pocket forming in combination with a plurality of reflectors 3602, according to an embodiment. Two or more reflectors 3602 can be positioned in the room ceiling in order to reflect transmitted RF waves 116 into different areas across the room. According to some aspects of this embodiment, transmitter 102 can be purposely aimed at any of the six reflectors 3602, as shown in FIG. 37, for allowing the reflection of RF waves 116 towards one or more locations in the room where electronic device 122 or a user 3601 holding said electronic device 122 may be positioned. As previously explained, receiver 120 incorporated into electronic device 122 can receive reflected RF waves 116 for the generation of pockets of energy that can suitability charge electronic device 122.

In another embodiment, a plurality of transmitters 102 can be installed in the room so as to match the number of reflectors 3602 installed in the ceiling. In such case, one transmitter 102 may correspond to one reflector 3602, where all transmitters 102 can simultaneously generate RF waves 116 aimed at corresponding reflectors 3602, which can then redirect these RF waves 116 across the room for providing pockets of energy to a plurality of electronic devices 122 at the same time. This can also allow continuous charging for a user 3601 who may be utilizing electronic device 122, while being in constant movement across the room.

In FIG. 38, a plurality of reflectors 3602 can also be combined with a single transmitter 102 capable of producing multi-pocket forming. In such case, transmitter 102 can generate multiple RF waves 116 aimed at reflectors 3602, which can then redirect these RF waves 116 across the room, thereby powering one or more electronic devices 122 at the same time.

Figure 39:
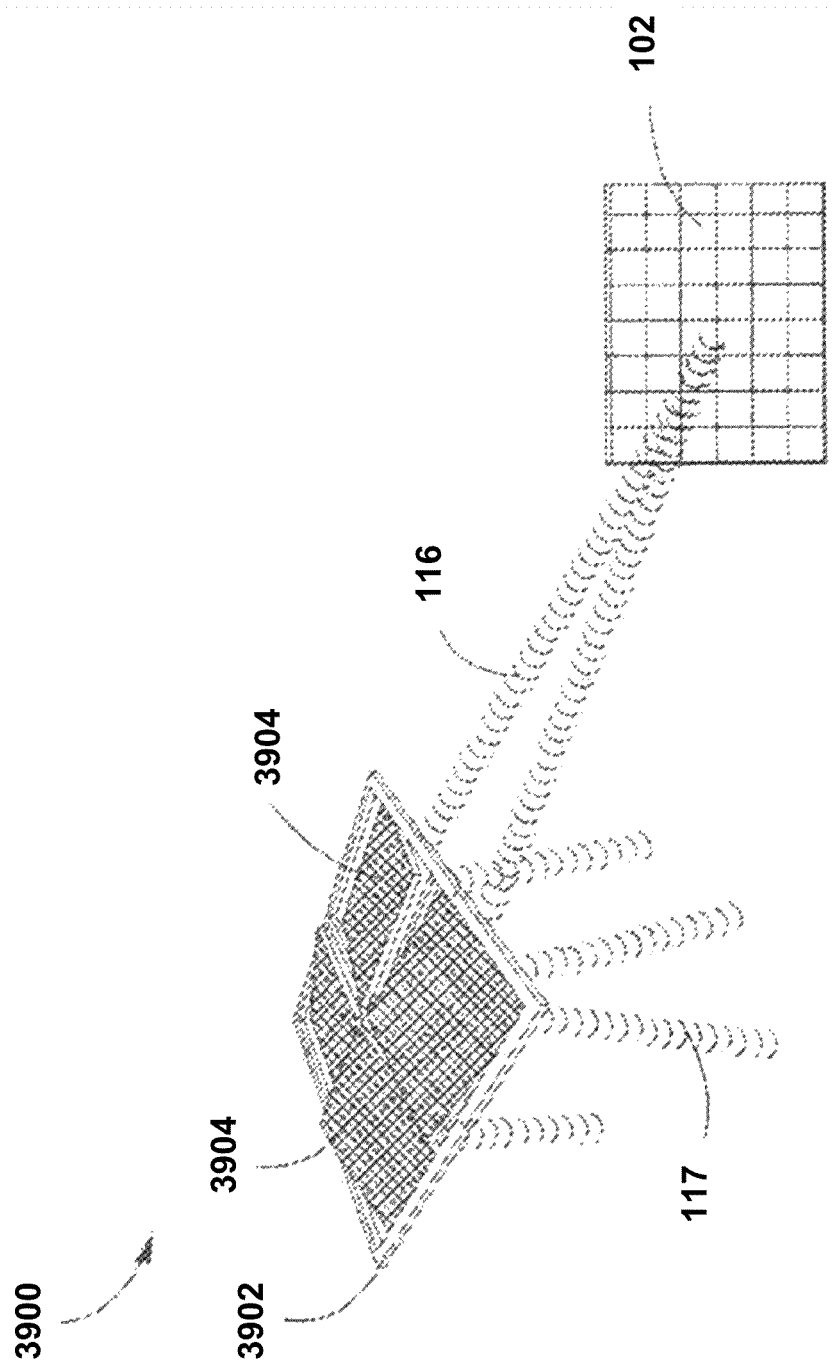
FIG. 39 illustrates a reflector structure that can include one or more reflector pieces which can be independently aligned for reflecting RF waves in different directions during wireless power transmission, in accordance with some embodiments.

FIG. 39 shows a reflector structure 3900 that can be used in wireless power transmission, according to an embodiment. Similar to reflector 3602 in FIG. 37, reflector structure 3900 can be installed in the room ceiling in order to redirect the formation of pockets of energy according the position of electronic device 122. This reflector structure 3900 may include a frame 3902 enclosing individual two or more reflector pieces 3904 which can be angled or tilted depending on the desired direction of the reflected RF wave 117. For example, each of these reflector pieces 3904 can be differently angled relative to transmitter 102 to cover each of the four quadrants of the room. Depending on which reflector piece 3904 the transmitted waves 116 hit, reflected waves 117 can he scattered in four different quadrants according to the configuration of each reflector piece 3904 in reflector structure 3900.

According to some aspects of this embodiment, reflector structure 3900 can exhibit a suitable dimension of about 2 ft×2 ft, which can translate into a 1 square foot surface area for each reflector piece 3904. Similar to reflector 3602, these reflector pieces 3904 can be made of suitable metal materials such as copper, steel and aluminum capable of reflecting most of the signal power of RF waves 116 towards receiver 120 in electronic device 122, in this manner achieving a more efficient power generation and battery charging.

Although reflectors 3902 and reflector pieces 3904 are shown within respective shapes, features and geometric relationships, other geometric relationships, features and shapes may be contemplated.

Figure 40A:
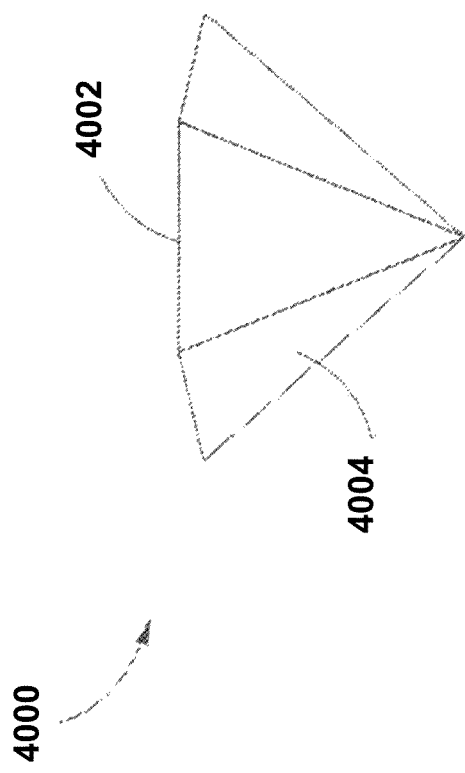
FIGS. 40A and 40B illustrates reflector configurations that can be used during a wireless power transmission, in accordance with some embodiments.

FIG. 40 shows reflector configurations 4000 that can be applied in reflectors 3602 and reflector pieces 3904, according to an embodiment. FIG. 40A shows a pyramid configuration 602 with three or more faces 604. Compared to pyramid configuration 4002, reflectors 3602 and reflector pieces 3904 in wireless power transmission 3700, 3800 can typically exhibit a flat surface which can provide only one dedicated or specific angle of reflection. Reflectors 3602 and reflector pieces 3904 incorporating pyramid configuration 4002 can offer more than one angle of reflection depending on which face 4004 the transmitted RF waves 116 hit. In this way, RF waves 116 can be reflected in more than one direction, without requiring moving or tilting reflector 3602 and reflector pieces 3904.

Figure 40B:
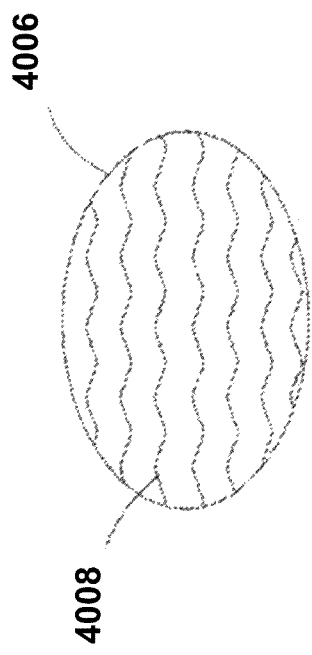

FIG. 40B shows an oval-shape configuration 4006 that can also be applied to reflector 3602 and reflector pieces 3904 in order to reflect RF waves 116 in more than one direction, without requiring any change their position or orientation. This uneven oval-shape configuration 4006 can include a plurality of curves 4008 which may form an uneven surface texture compared to the typically smooth surface of reflector 3602 and reflector pieces 3904 used in wireless power transmission 3700, 3800. When transmitted RF waves 116 strike a reflector 3602 or reflector piece 3904 using oval-shape configuration 4006, the uneven surface texture can scatter the reflected RF waves 116 in different directions that may correspond the location of electronic device 122.

Figure 41:
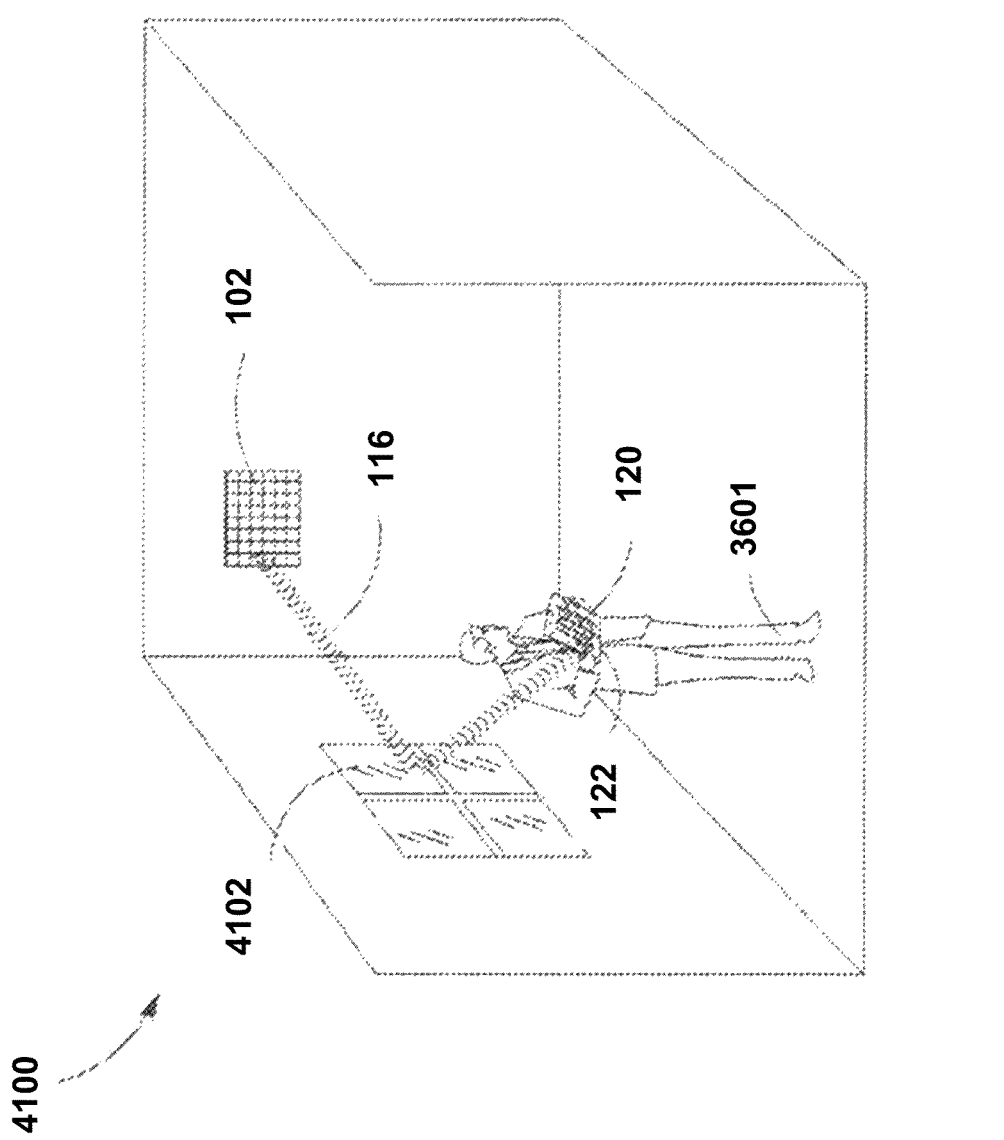
FIG. 41 illustrates a wireless power transmission that may include a window reflector for improving power transmission and charging efficiency, in accordance with some embodiments.

Referring now to FIG. 41, a wireless power transmission 4100 can employ pocket forming in conjunction with a window reflector 4102 for powering electronic device 112, according to an embodiment. Window reflector 4102 can be formed when a commercially available insulating film is installed in a room window, where this insulating film can include a flexible and transparent metallic layer capable of reflecting RF waves 116. According to some aspects of this embodiment, transmitter 102 can be purposely aligned towards window reflector 4102, which can then redirect RF waves 116 to receiver 120 in electronic device 122 for the generation of pockets of energy capable of charging electronic device 122. In another embodiment, the metallic layer included in window reflector 4102 can be configured for allowing certain wavelengths of communication signals, such as satellite or cellphone, to pass through window reflector 4102, while reflecting nearly 100% of RF waves 116 from transmitter 102 towards electronic device 122 for charging.

In other embodiments, metallic paint can also be applied to different structures in the room to act as reflectors of RF waves 116, where the reflection efficiency may vary according to the metallic concentration in the paint composition.

FIGS. 36-41 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 36-41.

Presented below are example systems and methods for transmitting wireless power utilizing reflectors.

A system for transmitting wireless power may include: (i) a transmitter for generating two or more RF waves having at least two RF transmit antennas in an array to form controlled constructive interference patterns from the generated RF waves for generating pockets of energy, (ii) a micro-controller within the transmitter controlling the constructive interference patterns of generated RF waves for pocket-forming to accumulate pockets of energy in predetermined areas or regions in space, (iii) a receiver mounted within a targeted electronic device with at least one antenna to receive the accumulated pockets of energy converging in 3-dimensional space to the targeted electronic device, (iv) a communication network connected to the transmitter and receiver for determining the areas or regions in space to receive the pockets of energy from the transmitter through an array of antennas for charging or operating the targeted electronic device, and (v) a reflector having one or more angles of reflection for directing pockets of energy to the targeted electronic device within a space.

In some embodiments, the reflector is made of metallic materials comprising steel, aluminum, copper, or similar materials to reflect approximately 100% of the pockets to predetermined locations within the 3-dimensional space.

In some embodiments, the reflector has a predetermined square footage of between 1 and 2 feet squared to reflect the transmitter-generated RF waves forming the constructive interference patterns creating the pockets of energy in the direction of the receiver to charge or power the electronic device.

In some embodiments, the reflector is generally configured in a flat panel mounted on a wall, ceiling, or floor and is capable of being painted or covered according to a color, texture, or decoration of the room walls, ceiling, or floor.

In some embodiments, the reflector is a plurality of reflectors positioned within a room ceiling in order to reflect transmitted RF waves into different areas across the room.

In some embodiments, the transmitters are a plurality of transmitters and the number of reflectors installed within a space are a plurality of reflectors matching the number of transmitters where all of the transmitters simultaneously generate RF waves that are aimed at corresponding reflectors to redirect RF waves across the space for providing pockets of energy to electronic devices equal to the number of reflectors.

In some embodiments, the antennas operate in frequency bands of 900 MHz, 2.5 GHz, or 5.8 GHz bands.

In some embodiments, the reflector is a plurality of reflectors combined with a single transmitter to generate multiple RF waves aimed at the plurality of reflectors that redirect the multiple RF waves across the space to power one or more electronic devices.

In some embodiments, the reflector or reflector components are configured in a number of different geometric relationships or shapes capable of transmitting RF waves to the targeted electronic devices.

In some embodiments, the reflector is an oval-shape configuration in order to reflect RF waves in more than one direction without requiring any change in the position or orientation of the reflector and the reflector comprises a plurality of curves to form an uneven surface compared to a smooth surface to scatter reflected RF waves in different directions that may correspond to the locations of electronic devices.

In some embodiments, the reflector is incorporated into the insulating film installed within a room window comprised of a transparent metallic layer capable of reflecting RF waves to redirect RF waves to the receiver in the electronic device or the reflector is a metallic concentration within a paint composition to reflect and redirect RF waves to the receiver.

In some embodiments, the reflector comprises a frame enclosing individual reflector components configured to be angled or tilted depending on a predetermined direction relative to the transmitted pockets of energy in 3-dimensional spaces for charging or operating the electronic device. Furthermore, in some embodiments, the reflector components are angled relative to the transmitter to cover each of four quadrants of a room. Furthermore, in some embodiments, the reflector is a pyramid configuration with at least three faces offering more than one angle of reflection depending on the face transmitting the RF waves in one or more predetermined directions without requiring moving or tilting the reflector or reflector components.

In some embodiments, the reflector increases the power of the reflected RF waves forming the pockets of energy a factor of approximately 2 and 3 times and further enhances the charging efficiency of the targeted electronic device and improves the spatial 3-dimensional pocket of energy formation.

A method for transmitting wireless power may include: (i) generating two or more RF waves from a transmitter with at least two RF transmit antennas, (ii) forming controlled constructive interference patterns from the generated RF waves, (iii) accumulating energy or power in the form of constructive interference patterns from the RF waves to form pockets of energy, (iv) converging the pockets of energy in 3-dimensional space to a targeted electronic device, and (v) redirecting the transmitted RF waves to the targeted electronic device by a reflector for charging or operating the targeted electronic device with the pockets of energy.

FIGS. 42-45 illustrate examples of wireless power transmission using a transceiver pad, in accordance with some embodiments.

Figure 42:
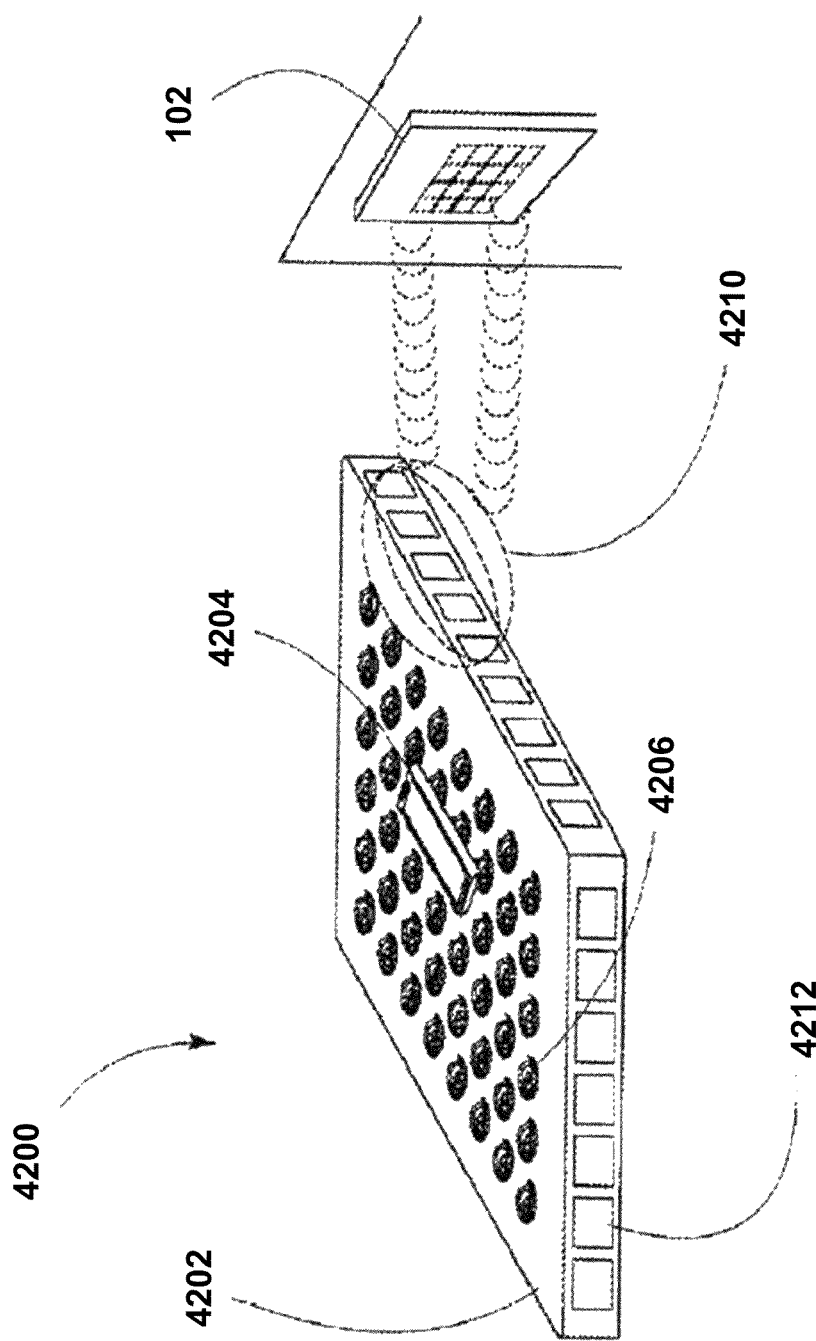
FIGS. 42 and 43 illustrate wireless power transmission where a pad, with improved portability, provides wireless power to an electronic device, in accordance with some embodiments.

FIG. 42 illustrates a wireless power transmission 4200 where a pad 4202, with improved portability, may provide wireless power to a smartphone 4204. In the prior art, pad 4202 may include a power chord which may connect to a wall outlet running on alternating current (AC) power. Such AC power may then be transmitted wirelessly to smartphone 4204, through magnetic induction or electrodynamics induction, via a plurality of inductive elements 4206. Inductive elements 4206 may include, for example, coils or inductors. As is known in the prior art, smartphone 4204 may also incorporate external hardware, such as cases, which may include a plurality of inductive elements 4206 (not shown) for receiving the power sent by pad 4202. The foregoing configuration may not really be wireless because a power chord may still be required. In addition, the location of pad 4202, and therefore of smartphone 4204 may negatively be affected by the location of an available power outlet, i.e. if the wall outlet is in hard-to-reach locations such as behind a sofa or TV screen, so will be pad 4202 and smartphone 4204. The foregoing situation can easily be solved by eliminating the power chord used in the prior art. In an embodiment, wireless power transmission 4200 may be carried out using a transmitter 102 and embedding at least one receiver (not shown) within pad 4202. Transmitter 102 may provide pockets of energy 4210 to embedded receivers which may provide power to inductive elements 4206 from pad 4202 for powering smartphone 4204 wirelessly. Antenna elements 4212 (as described with reference to FIG. 1), from the foregoing embedded receivers, may be placed outside the edges of pad 4202 for improved power reception independent of the location of transmitter 102. The foregoing configuration may be beneficial because pad 4202 may no longer be constrained by the location of a suitable wall outlet. In addition, pad 4202 can be put in easy-to-reach locations such as tables, counters and the like that are inside the range of transmitter 102. In some embodiments, the range of transmitter 102 can be up to about 15 feet. The foregoing can be achieved by placing about 256 antennas in transmitter 102, and an embedded receiver with about 80 antennas. The power transmitted can be up to one watt.

Figure 43:
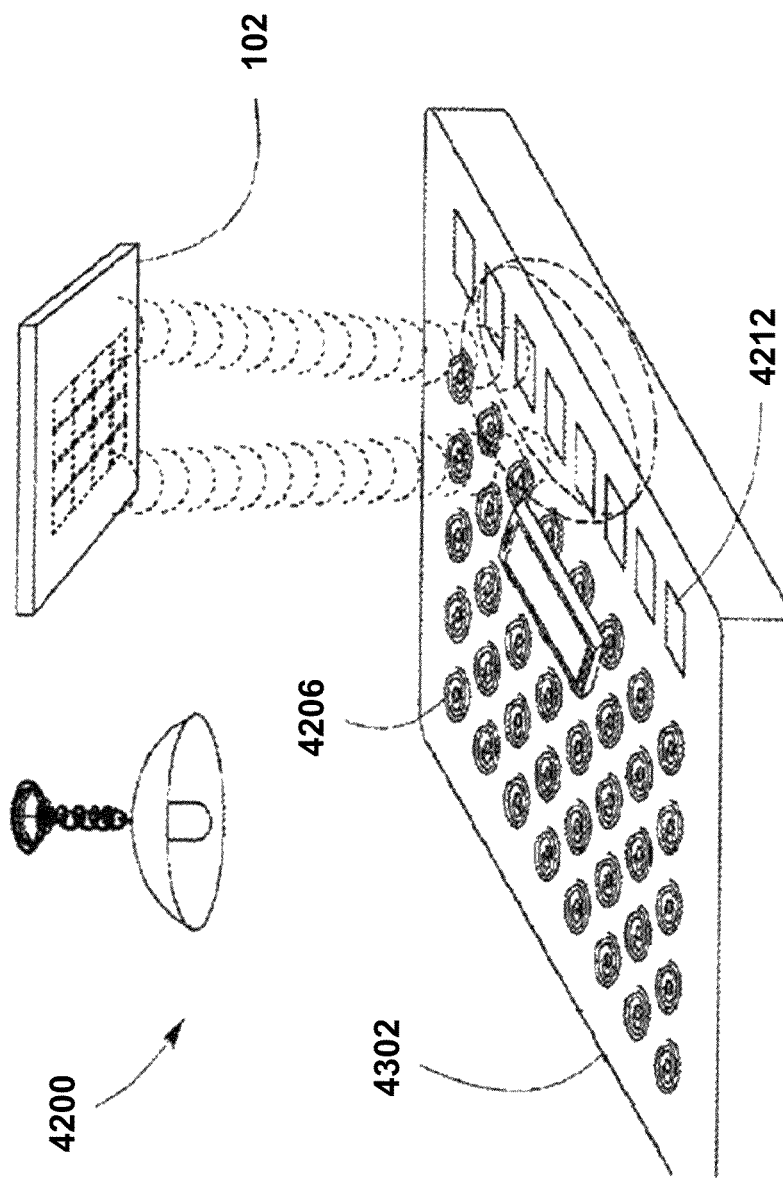

FIG. 43 illustrates another embodiment of wireless power transmission 4200 where a pad 4302 (similar to pad 4202 from FIG. 42 above) may include a plurality of inductive elements 4206 and at least one embedded receiver (not shown). Embedded receivers may include antenna elements 4212 located on the top surface of pad 4302. This configuration may be beneficial when using a transmitter 102 located above pad 4302, for example in ceilings. In other embodiments, the foregoing pads, as described through FIG. 42 and FIG. 43, may not use inductive elements 4206, but in contrast may utilize pocket-forming for transmitting power wirelessly. For example, transmitter 102 may provide power to either pad 4202 or pad 4302 through pocket-forming. Then, a second transmitter within either pad 4202 or pad 4302 may re-transmit the power sent by transmitter 102 to electronic devices nearby the aforementioned pads. Lastly, electronic devices requiring power may incorporate external hardware, for example cases, similar to those utilized in the prior art for magnetic induction or electrodynamics induction. Such external hardware may incorporate receivers suited for pocket-forming instead of inductive elements 4206. The aforementioned configuration may further expand the range wireless power transmission 4200 because electronic devices such as smartphone 4204 may not even be required to be placed on the pads, but only near the pads (up to 15 feet away for example). Thus, pad 4202 or pad 4302 may need only to be from about 2 inches×4 inches in surface area.

Figure 44:
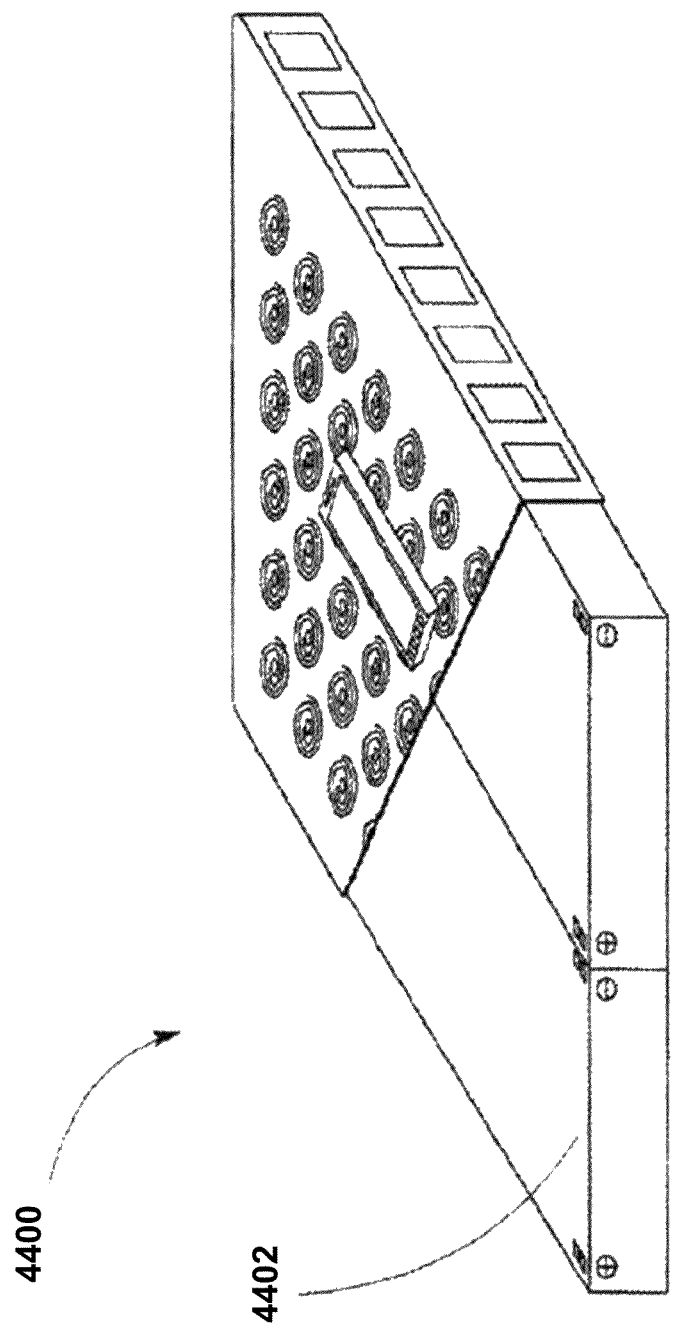
FIG. 44 illustrates a portable pad that includes a module for storing charge, in accordance with some embodiments.

FIG. 44 illustrates a pad 4400 which in this embodiment may include a plurality of inductive elements 4206, at least one embedded receiver (not shown) for powering smartphone 4204. As described above, with reference to at least one of FIG. 42 and FIG. 43, pad 4400 may receive power wireless through pocket-forming and may not require a power chord for connecting to a power supply such as a wall outlet. In some embodiments, pad 4400 may also include at least one module 4402 for storing charge, for example a lithium ion battery. Module 4402 may store charge while charging or not smartphone 404. In some embodiments, pad 4400 may utilize magnetic induction, electrodynamics induction of pocket-forming for powering smartphone 404 as described through FIG. 4 and FIG. 43. Once pad 4400 is charged, it may be placed at any location, or even carried around for powering electronic devices as described in FIG. 7 below.

Figure 45:
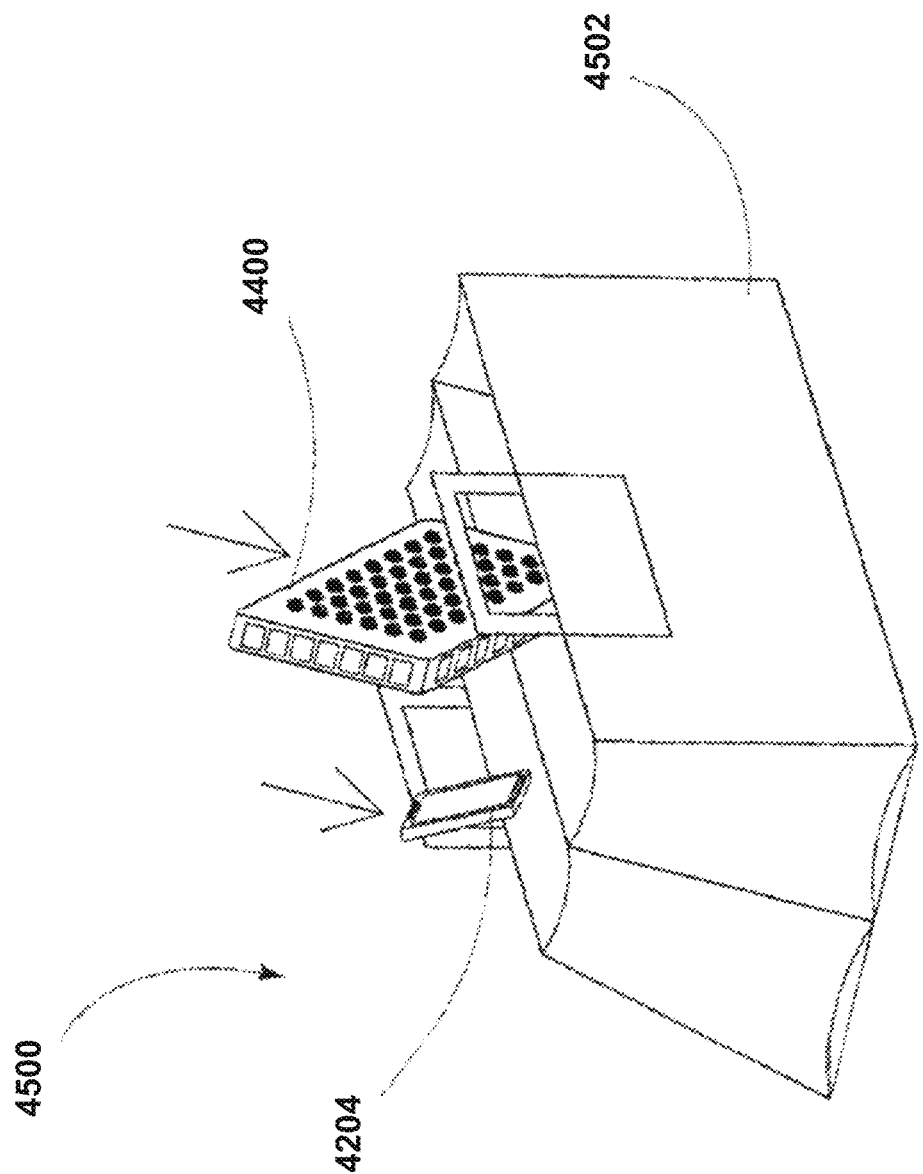
FIG. 45 illustrates an example situation where pad from FIG. 44 can be used, in accordance with some embodiments.

FIG. 45 illustrates an example situation 4500 where pad 4400 may be carried around in a briefcase 4502 for powering smartphone 404. Pad 4400 can be carried in backpacks, women purses and the like. In some embodiments, pad 4400 may be embedded within the foregoing items and sold as one charging unit. Furthermore, such a charging unit can be powered wirelessly through pocket-forming or may incorporate a power chord for plugging into a wall outlet. Devices inside a bag, purse or the like are by default not in use, and can therefore sacrifice mobility while powering using the former option.

FIGS. 42-45 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 42-45.

Presented below are example portable wireless charging transceiver pads and methods for a portable wireless charging transceiver pad.

A portable wireless charging pad may include: (i) a pad receiver embedded within the charging pad connected to antenna elements on a surface of the pad for receiving pockets of energy from a pocket-forming power transmitter to charge a pad battery and (ii) a pad pocket-forming transmitter powered by the pad battery comprising a RF chip connected to antenna elements for generating pockets of energy to charge or power a portable electronic device having a receiver connected to a battery to capture the pockets of energy from the pad transmitter when in the proximity of the charging pad.

In some embodiments, the electronic device receiver communicates power requests to the pad transmitter through short RF waves or pilot signals sent between the electronic device receiver and the pad transmitter, respectively.

In some embodiments, the pad comprises inductive elements for charging the electronic device in close proximity to the inductive elements.

In some embodiments, the pockets of energy generated from the pad transmitter have a range of approximately 15 feet to the electronic device.

In some embodiments, the pad comprises a power cord and the pad battery is a lithium ion battery module connected to the pad transmitter and the lithium battery is charged either through the power cord or the pad receiver.

In some embodiments, the pad receiver and the pad transmitter each comprises a circuitry for a RF integrated circuit, an antenna array, a microcontroller, and a communication component circuit for communications between the pad receiver and the pad transmitter to control the powering and charging of the portable electronic device.

In some embodiments, the pad transmitter generates single or multiple pocket-forming for charging or powering one or more electronic devices located in proximity to the pad.

In some embodiments, the pad transmitter comprises integrated RF circuitry connected to an antenna array configured around a perimeter or on a surface of the pad.

In some embodiments, the pad comprises circuitry to accommodate both a power cord and a battery as a power source for the pad transmitter.

In some embodiments, the pad is configured in a generally flat rectangular shape of approximately 2 inches by 4 inches and is capable of being placed into a brief case, bag, or purse along with the electronic device to be charged or powered.

In some embodiments, the antenna elements of the pad receiver are in a generally flat configuration and located on a surface of the pad to receive the pockets of energy within a 15-foot range from the power transmitter.

In some embodiments, the pad transmitter is configured in the shape of a generally flat rectangular box having antenna elements around the circumference of the box for receiving the pockets of energy for the pad receiver.

A method for a portable wireless charging pad may include: (i) embedding at least one receiver within the pad, (ii) receiving pockets of energy from a pocket-forming transmitter at the receiver, and (iii) charging wirelessly a portable electronic device in proximity to the pad.

In some embodiments, the method comprises authenticating the electronic device in proximity to the pad for charging through Wi-Fi communication to a cloud based service for confirming the electronic device access for charging from the pad.

In some embodiments, the method comprises scanning for Bluetooth electronic devices available for wireless pad charging and prioritizing the charging or powering of the available electronic devices whereby the pad transmitter directs pocket-forming towards predetermined electronic devices in a predetermined priority order.

In some embodiments, the method comprises authenticating and selecting the electronic device receiver for the pad transmitter to charge by communicating requests for power over Bluetooth, infrared, Wi-Fi, and FM radio signals between the pad transmitter and the electronic device receiver.

In some embodiments, the method comprises transmitting simultaneously both Wi-Fi signals and pocket-forming RF waves from the pad transmitter to the portable electronic device receiver in proximity to the pad.

In another method for a portable wireless charging pad, the method may include: (i) supplying pockets of energy to a pad receiver comprising circuitry of an antenna element, a DSP, a rectifier, a power converter, and a communications device connected to a pad battery, (ii) pocket-forming in a pad transmitter comprising circuitry of antenna elements, a RF integrated chip controlled by a DSP for pocket-forming to develop pockets of energy for charging and powering a battery in an electronic device in proximity to the pad and a communication device controlled by the DSP, (iii) pocket-forming in a power transmitter supplying pockets of energy to the pad receiver, and (iv) communicating the power level of the pad battery from the pad receiver to the power transmitter through short RF signals between the pad receiver and power transmitter communication devices, respectively, over conventional wireless communication protocols.

In some embodiments, the method comprises: (i) decoding short RF signals from a portable electronic device receiver having communication circuitry to identify the gain and phase of the electronic device receiver to determine the proximity of the electronic device receiver to the pad, (ii) controlling the charging and powering of the electronic device by the decoded short RF signals, and (iii) charging the battery of the electronic device when in the proximity of the pad transmitter to provide an inexhaustible source of operating power for the electronic device.

In some embodiments, the method comprises uploading battery information and uploading the proximity information of the electronic device to the charging pad.

In another method for a portable wireless charging pad, the method may include: (i) searching for a wireless charging request from a portable electronic device within a predetermined range from the charging pad, (ii) scanning for a standard communication protocol signal representing the charging request from the portable electronic device, (iii) pocket-forming from a pad transmitter for supplying pockets of energy to an electronic device receiver requiring the charging, and (iv) ending wireless power transmission to the electronic device when a predetermined charging has occurred or when the electronic device is out of range from the charging pad.

Figure 46:
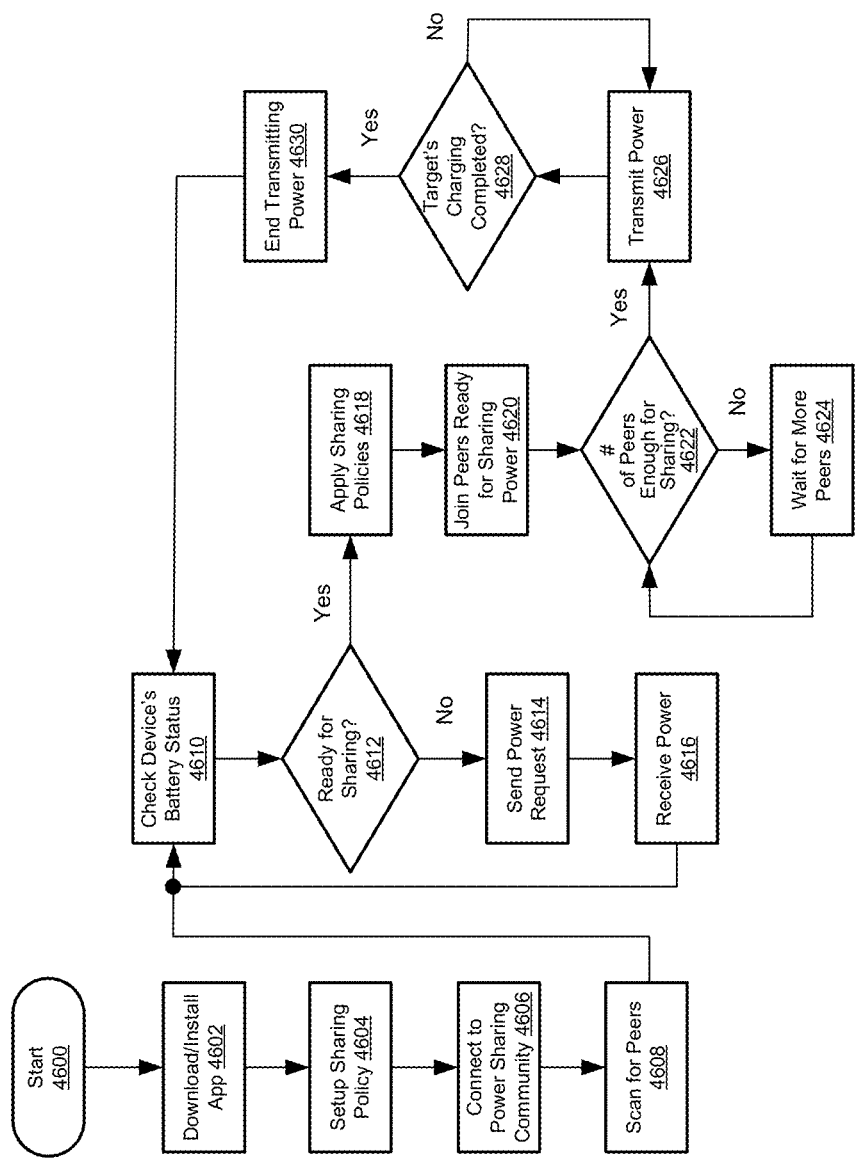
FIG. 46 illustrates a flowchart describing a method for social power sharing, in accordance with some embodiments.
Figure 47:
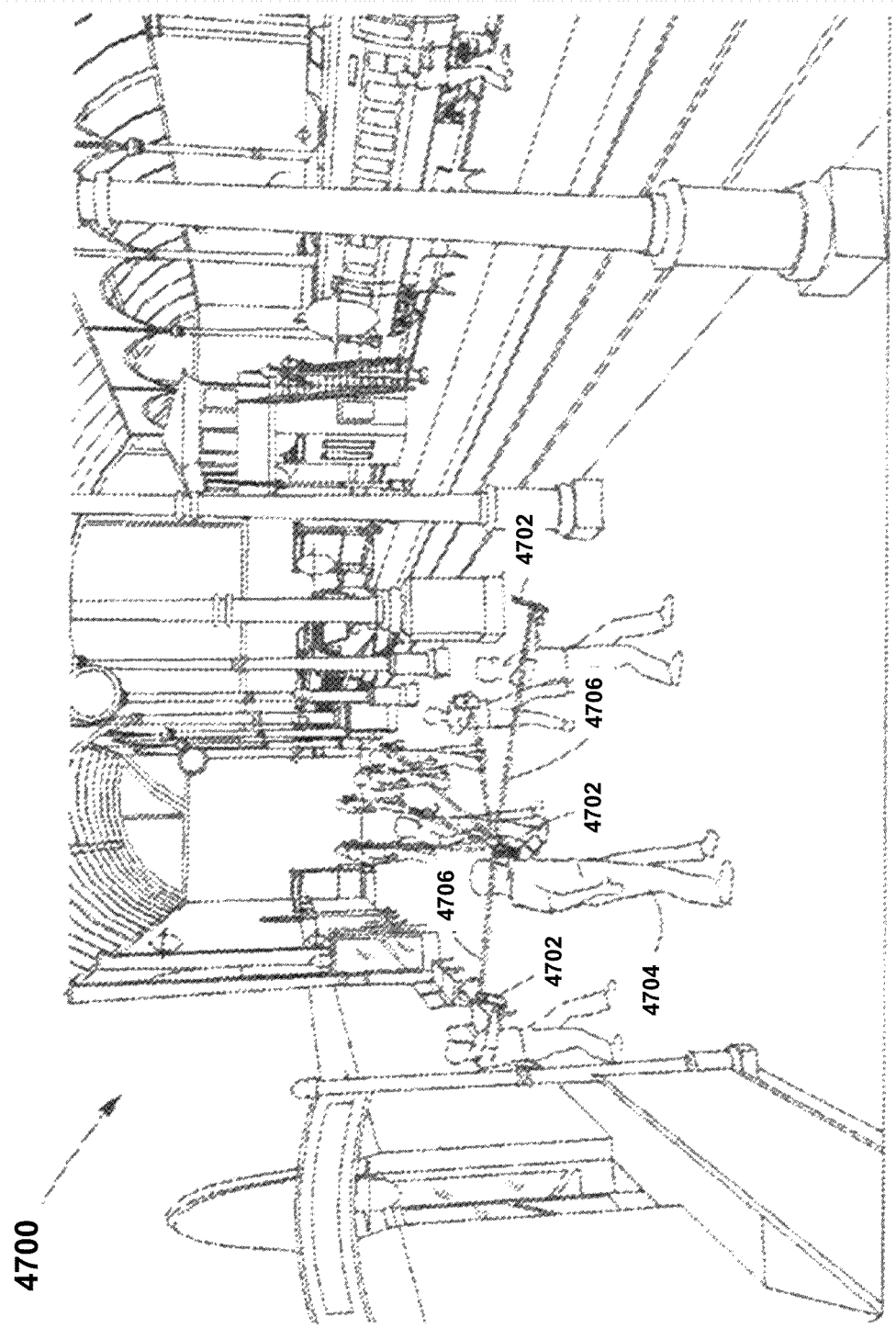
FIG. 47 illustrates an example situation where social power sharing may be applied, in accordance with some embodiments.

FIGS. 46 and 47 illustrate wirelessly sharing power between mobile electronic devices in public or other spaces, in accordance with some embodiments.

FIG. 46 illustrates a flowchart describing a method for social power sharing 4600, based on the concept explained in FIG. 1. Social power sharing 4600 may work with any mobile device that has Wi-Fi, Bluetooth or both as a built-in hardware, and may also include the receiver 120 described in FIG. 1.

The method for social power sharing 4600 may start by downloading and installing an App 4602 in the mobile device that is desired to either share or receive power. App 4602 may be developed to be compatible with any operating system for mobile devices available in the market. After installing App 4602, the user of the mobile device may need to setup a group of sharing policies 4604 in which a set of constrains may be defined. Within the set of constrains, the user may first need to grant permission to app 4602 by digital signing an agreement where the user allows full control of the built-in hardware of the mobile device needed for social power sharing 4600. After grating full control of the hardware needed, the user may also need to establish the working parameters for sharing its mobile device's power. The working parameters may include, but is not limited to, the minimum charge needed to start sharing, for example the user may define a. minimum charge of 80% of its battery to start sharing power. Another parameter may be the amount of charge that the user desires to share, for example the user may only wish to share 5% of its battery with others. Furthermore, the user may also define the timing for sharing, for example the user may define that the mobile device may only share power if the mobile device is idle.

After setting up the sharing policies 4604, app 4602 may connect to a power sharing community 4606. The connection may be established through any suitable network by either using Wi-Fi or Bluetooth. In one embodiment, App 4602 may need to be connected to the internet to download additional information from other users. In other embodiments, an internet connection may not be required. Once the mobile device is connected to the power sharing community 4606, app 4602 may start scanning for peers 4608 within the area. Peers 4608 may be all users that may have already connected their mobile devices to power sharing community 4606, and that may also be waiting to share or receive power. When scanning for peers 4608 is finished, app 4602 may proceed to check the device's battery status 4610 to determine if the mobile device is ready for sharing 4612 or not. App 4602 may then compare the actual battery status 4610 with the constrain previously defined. For example, if the actual battery status 4610 is 80% and the constrain was defined to allow power sharing only if the battery status is equal or greater than 80%, then app 4602 will subsequently enable the mobile device to start sharing power, however another set of policies 4616, previously defined, may be applied. If the battery status 4610 is below 80%, then app 4602 may be configured to send a power request message 4614 to power sharing community 4606. The mobile device may then receive power 4616, recharge and then go back to check battery status 4610.

Following the process, once all the sharing policies 4618 are applied, app 4602 may join other peers ready for sharing power 4620. Social power sharing 4600 may employ a great number of mobile devices connected and synced together so as to send pockets of energy 108 to a single mobile device. Since the transmission may be for low power, app 4602 may utilize at least a hundred mobile devices coordinated and aligned so as to focus all RF waves on a single device to create a pocket of energy with enough power to charge it. If the number of peers connected to power sharing community 4606 is enough for sharing 4622, then the mobile device may start to transmit power 4626 to a targeted mobile device. If the number of peers is not enough, then app 4602 may set the mobile device in a standby mode in order to wait for more peers 4624 until the number of peers is enough to start transmitting power. In some embodiments, app 4602 can decide to provide power even though the number of peers may not be sufficient for a fast charge, and may therefore issue a warning to the user requesting power.

App 4602 may constantly check within all peers how much power is being transmitted. When target's charging is completed 4628, app 4602 may end power transmission 4630 and return to check device's battery status 4610. If the target is not yet completed, app 4602 may continue transmitting power to the targeted mobile device. As long as app 4602 is running in the background, the process may run indefinitely or until the mobile device goes out of range.

FIG. 47 shows an example situation where social power sharing 4600 may be applied. In this embodiment, a crowded train station 4700 is disclosed. Train station 4700 may be a place where many people, having multiple mobile devices, may be found, People may spend a great deal of time waiting for the train that will take them to their destination, and in many occasions people may need to use their mobile devices to do multiple tasks such as check emails, make phone calls, browse the internet, or anything their mobile device may be able to do. The latter may be a reason for applying social power sharing 46400.

In FIG. 47, a group of people is shown, each person may have a mobile device 4702 which may already include a built-in Wi-Fi or Bluetooth module which could be used as a transmitter, similar to transmitter 102 described in FIG. 1. Also, each mobile device 4702 may also include a receiver 120, either attached or embedded to it. Furthermore, each mobile device 4702 may also have installed and configured app 4600 in its operating system, as the one described in FIG. 46.

In this embodiment, FIG. 47 shows a user 4704 receiving power from all the people that have accepted a request for sharing their power. Also FIG. 47 shows controlled RF waves 4706 being transmitted from each mobile device 4702 and aimed to user 4704. In this embodiment, all the people having mobile device 4702 may have already accepted to share at least 5% of their battery charge in order to help user 4703 to charge its mobile device 4702 faster. App 4602, as described in FIG. 46, may be responsible for controlling and coordinating social power sharing 200 within all users, including pocket-forming.

EXAMPLES

In example #1 a user may be found at a crowded bus station where he or she may have a smartphone which battery is almost empty, At the bus station, the user may then follow the method social power sharing 4600, described in FIG. 46, to request power from other users or peers within the area. The user may then connect his or her smartphone to power sharing community 4600, using app 4602, and send a power request. If the number of users connected to power sharing community in app 4602 is at least 100, then the user may start receiving power for a certain amount of time to charge his or her phone up to a point that allows the smartphone to have power few more hours.

In example #2 a user may be found at a crowded airport where he or she may have a tablet which battery is full of charge. At the airport, other users, having multiple mobile devices, may also be found. The user may then decide to share his or her tablet's battery charge with others by following the method social power sharing 4600, described in FIG. 46. The user may then connect his or her tablet to power sharing community 4606, using app 4602, and join other users or peers ready for sharing power. If the number of users connected to power sharing community 4606 is at least 100, then the user may start transmitting power for a certain amount of time to charge the user's mobile device that may have request for power and allow the mobile device to have power few more hours.

In example #3 users may configure app 4602 in their mobile devices to charge money for their power. In other words, a user may join a network where you can purchase or sell a certain amount of power to others. This latter modality may work for users that usually carry extra batteries and want to find a way to make some extra money.

FIGS. 46 and 47 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 46 and 47.

Presented below are example apparatuses and methods for wirelessly sharing power between mobile electronic devices in public or other spaces.

An apparatus for wirelessly sharing power between mobile electronic devices in public or other spaces may include: (i) an application software configuring each mobile device to have a pocket-forming transmitter for generating power RF waves to form pockets of energy for wirelessly transmitting power in the form of pockets of energy and (ii) a power sharing community network defined by a mobile device having the application software installed thereon for directing the pockets of energy from transmitters associated with mobile devices having batteries charged to a predetermined limit to share power with mobile devices having low charged batteries.

In some embodiments, the communicating mobile devices on the power sharing network employ a predetermined number of mobile devices connected and synced together to send pockets of energy to a single or targeted mobile device.

In some embodiments, the mobile devices on the power sharing network scan for peer mobile devices to join together and to constantly check how much power is being transmitted to a low battery mobile device.

In some embodiments, the mobile electronic devices comprise built-in hardware that runs either or both Wi-Fi and Bluetooth wireless power sharing.

In some embodiments, the application software sets predetermined parameters for sharing or receiving power with or from other mobile devices on the network. Furthermore, in some embodiments, the predetermined parameters comprise a minimum battery charge on each mobile device to start sharing power on the network and comprises a limit on the battery charge from each mobile device shared with another mobile device on the network.

In some embodiments, the application software is configured to be compatible with any operating system for mobile devices.

In some embodiments, the pocket-forming transmitter of the powering mobile devices on the community network comprises a battery connected to a microcontroller with the application software for controlling a radio frequency integrated chip for driving at least two antennas for pocket-forming and for adjusting the transmitter antennas to form the pockets of energy used by a receiver on a targeted mobile device for powering or charging the same.

In some embodiments, the mobile devices receive recharge power from other mobile devices on the community network and then go back to a check battery status when fully charged and becomes a power sharing mobile device on the network.

In some embodiments, the mobile devices each comprise a receiver communicating on the community network for capturing the pockets of energy converging in 3-dimensional space through antennas to charge or power a battery when below a minimum battery charge.

In another apparatus for wireless sharing of power between mobile electronic devices in public or other spaces, the apparatus may include: (i) an application software for downloading to mobile electronic devices to configure the mobile devices to transmit pocket-forming controlled RF power waves to form pockets of energy that converge in 3-dimensional space and (ii) communication circuitry on each mobile device driven by the application software with predetermined parameters for networking each mobile device with the application software to either power share or power receive from a power sharing community network comprising the mobile electronic devices.

A method for wirelessly sharing power between mobile electronic devices in public or other spaces may include: (i) downloading application software to mobile electronic devices, (ii) networking mobile electronic devices with the application software together into a power sharing community network between mobile electronic devices, (iii) transforming each mobile electronic device with the application software into a pocket-forming transmitter on the power sharing community network, and (iv) emitting controlled RF power waves from the mobile electronic devices on the network to power other networked mobile devices through pockets of energy.

In some embodiments, the method comprises broadcasting short RF signals through antenna elements in the transmitter and a receiver on each mobile device with the application software for communicating between the transmitter and the receiver on one mobile device to at least one other mobile device on the power sharing community network to establish a path or channel for the pockets of energy from each mobile device to converge in 3-dimensional space upon antennas of the receiver of a targeted mobile electronic device for charging or powering the same.

In some embodiments, the method comprises utilizing adaptive pocket-forming to regulate the pockets of energy to power the mobile electronic devices on the community network.

In some embodiments, the method comprises scanning for peer mobile electronic devices on the community network to check battery status of each peer mobile device on the network to determine if each mobile device on the network is in a power mode for sharing power on the community network or in a low power mode requiring charging from the community network.

Figure 48A:
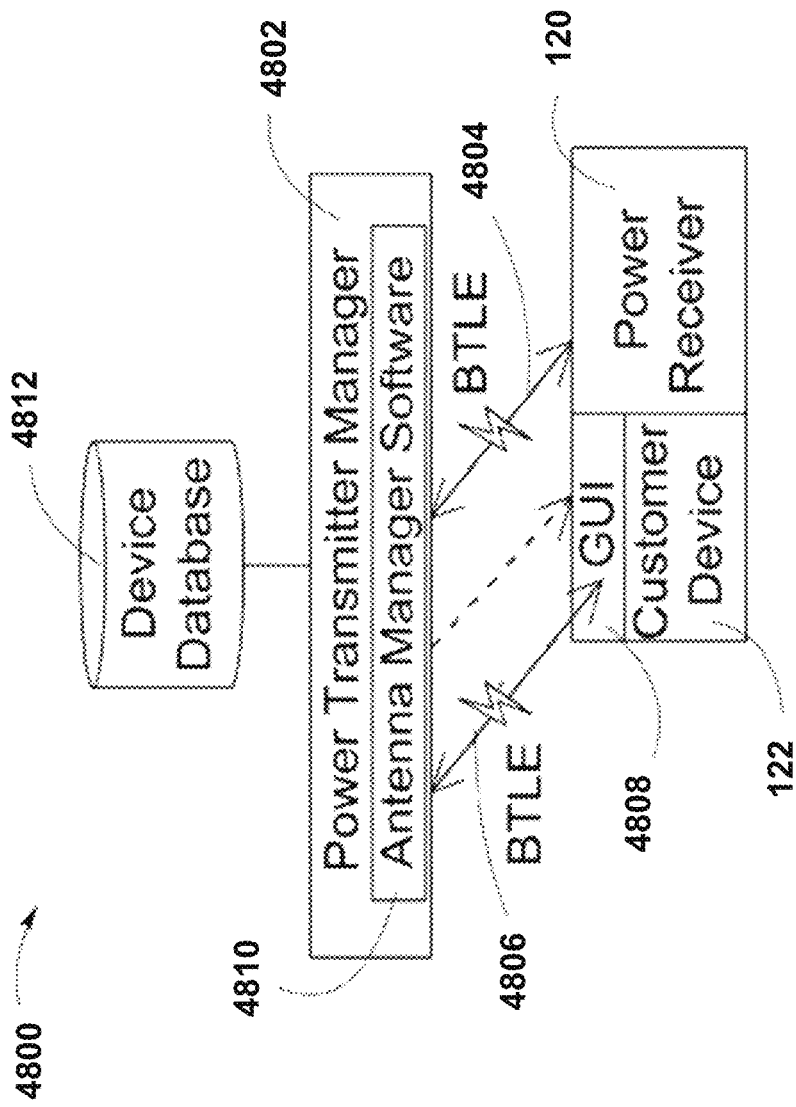
FIG. 48A illustrates a wireless power transmission system using a wireless power transmitter manager, in accordance with some embodiments.
Figure 48B:
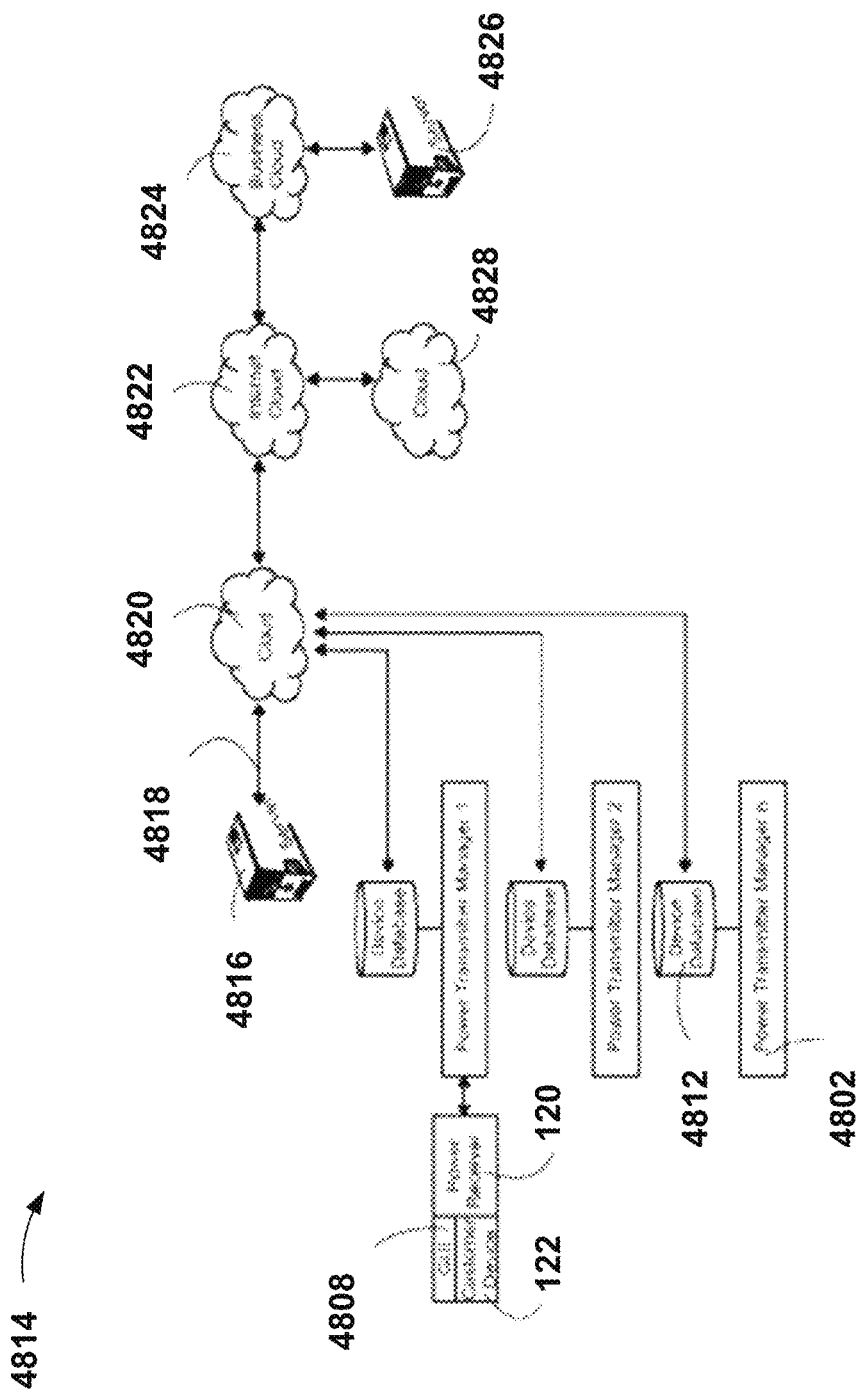
FIG. 48B illustrates a wireless power transmission network, in accordance with some embodiments.
Figure 48C:
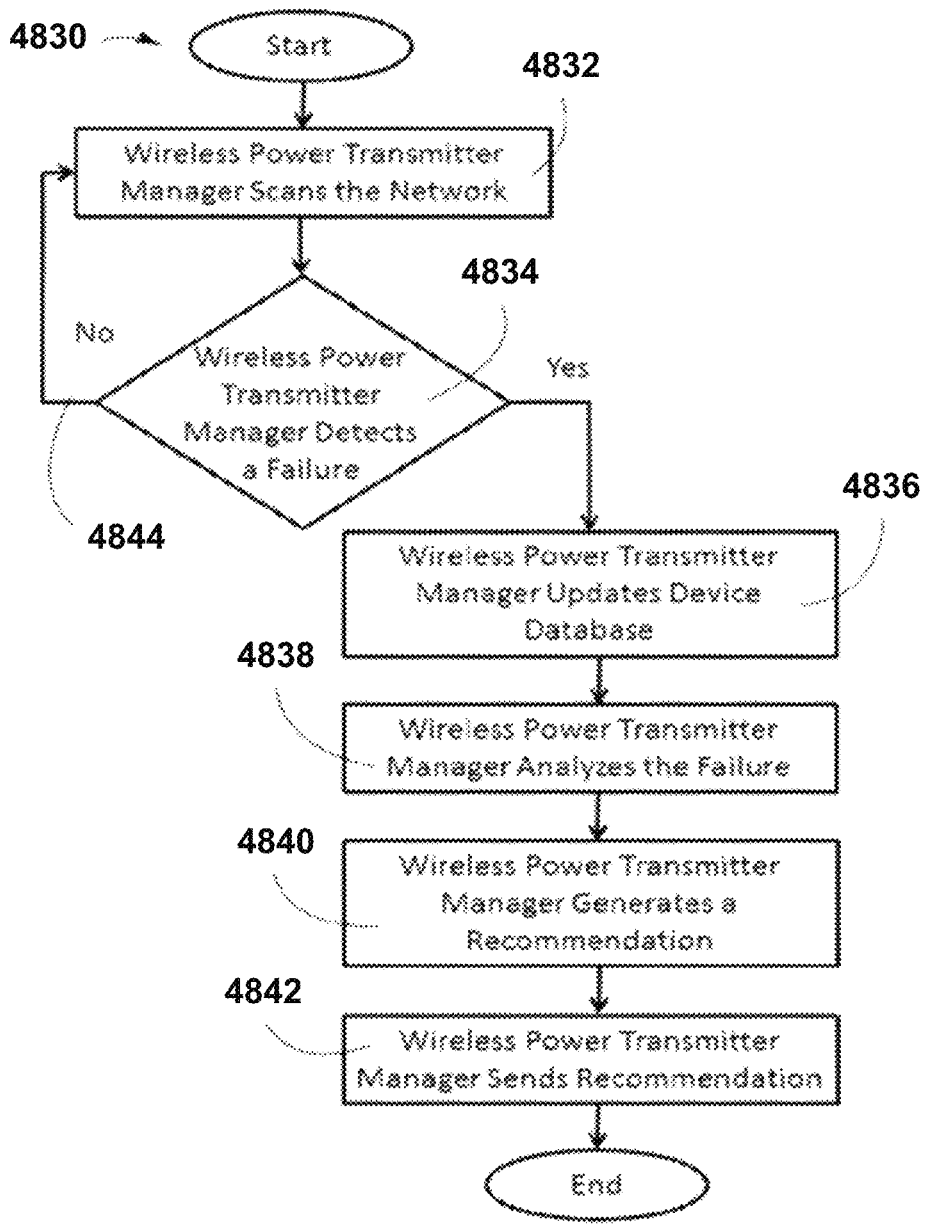
FIG. 48C is a flowchart of a method for self-system analysis in a wireless power transmission network, in accordance with some embodiments.

FIGS. 48A-48C illustrate wireless power transmission systems, networks, and methods, in accordance with some embodiments.

FIG. 48A shows a wireless power transmission system 4800 using a wireless power transmitter manager 4802, according to an embodiment. Wireless power transmitter manager 4802 may include a processor with computer-readable medium, such as a random access memory (RAM) (not shown) coupled to the processor. Examples of processor may include a microprocessor, an application specific integrated circuit (ASIC), and field programmable object array (FPOA), among others.

Wireless power transmitter manager 4802 may transmit controlled radio RF waves which may converge in 3-dimensional space to a wireless power receiver 120 (FIG. 1) for charging or powering a customer device 122 (FIG. 1). These RF waves may be controlled through phase and/or relative amplitude adjustments to form constructive and destructive interference patterns (pocket-forming). Pockets of energy may form at constructive interference patterns and can be 3-dimensional in shape whereas null-spaces may be generated at destructive interference patterns.

Wireless power receiver 120 may be paired with customer device 122 or may be built into customer device 122. Examples of customer devices 122 may include laptop computer, smartphones, tablets, music players, and toys, among other. Customer device 122 may include a graphical user interface (GUI) 4808. Wireless power transmitter manager 4802 may receive customer device's signal strength from advertisement emitted by wireless power receiver 120 and GUI 4808 for detecting if wireless power receiver 120 is paired with GUI 4808 and also for the purpose of detecting if wireless power receiver 120 is nearer to wireless power transmitter manager 4802 than to any other wireless power transmitter manager 4802 in the wireless power transmission system 4800. Wireless power receiver 120 may be defined as assigned to wireless power transmitter manager 4802, which may have exclusive control and authority to change the wireless power receiver's record in device database 4812 until wireless power receiver 120 moves to a new location closer to another wireless power transmitter manager 4802. An individual copy of wireless power receiver's record may be stored in device database 4812 of each wireless power transmitter manager 4802 and also in each server of wireless power transmission system 4800, through a cloud (not shown in FIG. 48A).

According to some aspects of this embodiment, one or more servers (not shown in FIG. 48A) may be a backup of device database 4812 shared by every wireless power transmitter manager 4802 in wireless power transmission system 4800.

Wireless power transmitter manager 4802 may transfer power in a range up to 30 feet.

Wireless power transmitter manager 4802 may use, but is not limited to, Bluetooth low energy (BTLE) to establish a communication link 4804 with wireless power receiver 120 and a control link 4806 with customer device's GUI. Wireless power transmitter manager 4802 may use control link 4806 to receive commands from and receive pairing information from customer device's GUI.

Wireless power transmitter manager 4802 may include antenna manager software 4810 to track customer device 122. Antenna manager software 4810 may use real time telemetry to read the state of the power received by customer device 122.

According to some aspects of this embodiment, wireless power transmitter manager 4802 may include a device database 4812, where device database 4812 may store three sub-dimensions of data: past, present, and future. The future data may include customer device's 122 power schedules. The present data may include the locations and/or movements in the system, configuration, pairing, errors, faults, alarms, problems, messages sent between the wireless power devices, and tracking information, among others. The past data may include details such as the amount of power customer device 122 used, the amount of energy that was transferred to customer device's battery, and thus sold to the customer who has or owns the device, the amount of time customer device 122 has been assigned to a given wireless power transmitter manager, when did customer device 122 start pairing with GUI 4808, activities in the system, any action or event of any wireless power device in the system, errors, faults, and design problems, among others, for each customer device 122 in wireless power transmission system 4800. Device database 4812 may also store customer device's power schedule, customer device's status, names, customer sign-in names, authorization and authentication credentials, encrypted information, areas, details running the system, and information about all wireless power devices such as wireless power transmitter managers, wireless power receivers, end user hand-held devices, and servers, among others.

In other situations, there can be multiple wireless power transmitter managers 4802 and/or multiple wireless power receivers 120 for powering various customer devices 122.

FIG. 48B illustrates a wireless power transmission network 4801, according to an embodiment.

In a wireless power transmission network 4801, multiple wireless power transmitter managers and/or multiple wireless power receivers may be used for powering various customer devices 122 (FIG. 1). A wireless power receiver 120 (FIG. 1) may be paired with customer device 122 or may be built in customer device 122. Examples of customer devices 122 may include smartphones, tablets, music players, toys and others at the same time. Customer device 122 may include a graphical user interface (GUI) 4808.

Each wireless power transmitter manager 4802 in wireless power transmission network 4801 may receive customer device's signal strength from advertisement emitted by wireless power receiver 120 and GUI 4808 for the purpose of detecting if wireless power receiver 120 is paired with GUI 208 and also for detecting if wireless power receiver 120 is nearer to wireless power transmitter manager 4802 than to any other wireless power transmitter manager 4802 in the wireless power transmission network 4801. Wireless power receiver 120 may be defined as assigned to wireless power transmitter manager 4802, which may have exclusive control and authority to change the wireless power receiver's record in device database 4812 until wireless power receiver 120 moves to a new location closer to another wireless power transmitter manager 4802. An individual copy of wireless power receiver's record may be stored in device database 4812 of each wireless power transmitter manager 4802 and also in each server 4816 of wireless power transmission network 4814, through a cloud 4818.

According to some aspects of this embodiment, one or more servers 4816 may function as a backup of device database 4812 in the wireless power transmission network 4814. Server 4816 may search devices in wireless power transmission network 4814. Server 4816 may locate device database 4812 through user datagram protocol (UDP) packets that are broadcast when a given wireless power transmitter manager 4802 boots up. The UDP packet may include the universally unique identifier (UUID) of wireless power transmitter manager 4802 and also its location. To back up a specific device database 4812, server 4816 may request access to a given wireless power transmitter manager 4802 in the network 4814. Server 4816 may establish a connection with wireless power transmitter managers 4802 and wireless power transmitter manager 4802 may accept the connection and wait for the first amount of data from server 4816. The first amount of data may be 128 bits UUID and once wireless power transmitter manager 4802 verifies the data, it may allow server 4816 to read a device database 4812. Server 4816 may backup device database 4812. Also wireless power transmitter manager 4802 may be able to reestablish its own device database 4812 from the information stored in server 4816. For example, if a given wireless power transmitter manager 4802 experiences a power interruption, resulting in a software restart or system boot up, it may broadcast a UDP packet to search any server 4816 in the network 4814. Once wireless power transmitter manager 4802 finds server 4816, it may establish a TCP connection to restore its own device database 4812.

Each wireless power transmitter manager in wireless power transmission network 4814 may include device database 4812. When a record change in a given device database 4812, this change may be distributed to all device databases 4812 in wireless power transmission network 4814.

Device database 4812 may store three sub-dimensions of data: past, present, and future. The future data may include customer device's 122 power schedules. The present data may include the locations and/or movements in the system, configuration, pairing, errors, faults, alarms, problems, messages sent between the wireless power devices, and tracking information, among others. The past data may include details such as the amount of power customer device 122 used, the amount of energy that was transferred to customer device's battery, and thus sold to the customer who has or owns the device, the amount of time customer device 122 has been assigned to a given wireless power transmitter manager 4802, when did customer device 122 start pairing with GUI 4808, activities in the system, any action or event of any wireless power device in the system, errors, faults, and design problems, among others, for each customer device 122 in wireless power transmission network. Device database 4812 may also store customer device's power schedule, customer device's status, names, customer sign-in names, authorization and authentication credentials, encrypted information, areas, details running the system, and information about all wireless power devices such as wireless power transmitter managers, wireless power receivers, end user hand-held devices, and servers, among others.

Each wireless power device in wireless power transmission network 4814 may include a UUID. When a given wireless power transmitter manager 4802 boots up, and periodically thereafter, it may broadcast a UDP packet that contains its unique UUID, and status to all devices in wireless power transmission network 4814. The UDP packet is only distributed through the local network. Each wireless power transmitter manager 4802 and server 4816 in wireless power transmission network may establish, but is not limited to, a WiFi connection 4818 to share updated device database's records between other wireless power devices in the system, including such device database information as: quality control information, wireless power device's status, wireless power device's configuration, control, logs, schedules, statistics, and problem reports, among others.

In another aspect of this embodiment, any wireless power transmitter manager, besides using UDP packets to send information through wireless power transmission network 4814, may also use transmission control protocol (TCP) to exchange information outside the local network.

In another aspect of this embodiment, server 4816 and wireless power transmitter managers 4802 may be connected to a cloud 4818. Cloud 4818 may be used to share between wireless power devices any device database information, among others.

According to some aspects of this embodiment, each wireless power transmitter manager 4802 and server 4816 in the network may be connected to a business cloud 4824 through an internet cloud 4822. Business cloud 4824 may belong to a given business using a service provider to offer wireless power transfer to their users. Business cloud 4824 may be connected to a business service provider server 4826. Business service provider server 4826 may store marketing information, customer billing, customer configuration, customer authentication, and customer support information, among others.

Internet cloud 4822 may be also connected to a service provider cloud 4828. Service provider cloud 4828 may store marketing and engineering information, such as less popular features, errors in the system, problems report, statistics, and quality control, among others.

Each wireless power transmitter manager 4802 may periodically establish a TCP connection with business cloud 4824 and service provider cloud 4828 to send its respective device database 4812.

In a different aspect of this embodiment, each wireless power transmitter manager 4802 in wireless power transmission network 4814 may be able to detect failures in the network. Examples of failure in the network may include overheating in any wireless power transmitter manager 4802, malfunction, and overload, among others. If a failure is detected by any of wireless power transmitter manager 4802 in the system, then the failure may be analyzed by any wireless power transmitter manager 4802 in the system. After the analysis is completed, a recommendation may be generated to enhance or correct the system. The recommendation may be sent through cloud 4820 to business service provider server 4826 and also to service provider cloud 4828. Service provider cloud 4828 may use the recommendation as quality control, engineering control, and to generated statistics, among others. Also, the recommendation may be communicated to the person in charge of managing wireless power transmission network 4814 by text messages or email. Also, any device in the network with a copy of device database 4812 may be able to perform an analysis and generate a recommendation to enhance or correct the system.

In another aspect of this embodiment, each wireless power transmitter manager 4802 may send an alert message for different conditions, where wireless power transmitter manager 4802 may include an LED, which blinks for indicating under which conditions wireless power transmitter manager 4802 may be working.

In another aspect of this embodiment, wireless power transmitter manager 206 may be able to detect failures on its own performance. If wireless power transmitter manager 4802 detects a failure, the analysis may be performed locally by wireless power transmitter manager 4802. After the analysis is completed, a recommendation may be generated to enhance or correct the system. Then wireless power transmitter manager 4802 may send the information through cloud 4820 to business service provider server 4826 and service provider cloud 4828. Also the recommendation may be communicated to the person in charge of managing wireless power transmission network 4814 by text messages or email.

FIG. 48C is a flowchart 4830 of a method for self-system analysis in a wireless power transmission network, according to an embodiment.

In a wireless power transmission network, multiple wireless power transmitter managers and/or multiple wireless power receivers may be used for powering various customer devices.

Each wireless power transmitter manager in the system may scan the wireless power transmission network, at step 4832. Each wireless power transmitter manager in wireless power transmission network may receive customer device's signal strength from advertisement emitted by a wireless power receiver and a graphical user interface (GUI) for the purpose of detecting if a wireless power receiver is paired with GUI and also for detecting if wireless power receiver is nearer to wireless power transmitter manager than to any other wireless power transmitter manager in the wireless power transmission network. Wireless power receiver may be defined as assigned to wireless power transmitter manager, which may have exclusive control and authority to change the wireless power receiver's record in device database until wireless power receiver moves to a new location closer to another wireless power transmitter manager. An individual copy of wireless power receiver's record may be stored in device database of each wireless power transmitter manager and also in each server of wireless power transmission network, through a cloud.

According to some aspects of this embodiment, one or more servers may function as a backup of the device database in the wireless power transmission network. The servers and wireless power transmitter managers in the wireless power transmission network may be connected to the cloud. The cloud may be used to share between system devices: quality control information, statistics, and problem reports, among others.

Wireless power transmitter manager may search for wireless power receivers to communicate with and send power. A wireless power receiver may be paired with customer device or may be built in customer device. Examples of customer devices may include smartphones, tablets, music players, toys and others at the same time. Customer device may include a GUI.

Wireless power transmitter manager may be able to detect failures in the wireless power transmission network, at step 4834. Examples of failure may include loss of power, failure in the hardware or software of the wireless power transmitter manager, malfunction in a wireless power transmitter manager, and overload of the wireless power transmitter manager, and malfunction in a wireless power receiver, overheating or other environmental problems, and intrusion, among others.

If wireless power transmitter manager detects a failure in the wireless power transmission network, it may update its device database to register the failure, at step 4836. Each wireless power transmitter manager in wireless power transmission network may include a device database, where device database may store three sub-dimensions of data: past, present, and future. The future data may include customer devices power schedules. The present data may include the locations and/or movements in the system, configuration, pairing, errors, faults, alarms, problems, messages sent between the wireless power devices, and tracking information, among others. The past data may include details such as the amount of power customer device used, the amount of energy that was transferred to customer device's battery, and thus sold to the customer who has or owns the device, the amount of time customer device has been assigned to a given wireless power transmitter manager, when did customer device start pairing with the graphical user interface (GUI), activities in the system, any action or event of any wireless power device in the system, errors, faults, and design problems, among others, for each customer device in wireless power transmission network. Device database may also store customer device's power schedule, customer device's status, names, customer sign-in names, authorization and authentication credentials, encrypted information, areas, details running the system, and information about all wireless power devices such as wireless power transmitter managers, wireless power receivers, end user hand-held devices, and servers, among others.

When a record changes in a given device database, this change may be distributed to all device databases in wireless power transmission network.

Subsequently, wireless power transmitter manager may analyze the failure in the wireless power transmission network, at step 4838. In another aspect of this embodiment the failure may be analyzed by any device in the wireless power transmission network with a copy of device database.

After the analysis is completed, a recommendation may be generated to enhance or correct the system, at step 4840.

Wireless power transmitter manager may send the recommendation to a business service provider server and also to service provider cloud, at step 4842. Service provider cloud may use the recommendation as quality control, engineering control, and to generated statistics, among others. Also, the recommendation may be communicated to the person in charge of managing wireless power transmission network by text messages or email.

Else wireless power transmitter manager may continue scanning the wireless power transmission network, at step 4844.

EXAMPLE

An example is a wireless power transmission network with components similar to those described in FIG. 48B. The wireless power transmission network may be working in a school, where students may charge their electronic devices wirelessly. A student may be charging his cellphone in the science classroom. The student starts moving because he needs to take another class in a different classroom. The student arrives to the computer classroom, but he is unable to continue charging his cellphone. At the same time that the student arrives to the computer classroom, the wireless power transmitter manager near the computer classroom exceeds the amount of electronic devices to be powered. Wireless power transmitter manager may detect a failure in its performance and may start analyzing the reason performance was affected. Wireless power transmitter manager may find that an overload was the reason of its performance being affected. After the analysis is completed, a recommendation may be generated to enhance the system by installation of another wireless power transmitter manager. This recommendation may be sent to the manager of the wireless power transmission network by text messages or email. Also, the recommendation may be sent to the school service provider server and to the service provider cloud.

FIGS. 48A-48C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 48A-48C.

Presented below are example systems and methods for wirelessly providing power and detecting faults.

A system for wirelessly providing power may include: (i) a plurality of power sources, each comprising a wireless power transmitter and a wireless power transmitter manager, operatively coupled to the wireless power transmitter, where the wireless power transmitter manager is configured to control RF waves to form three-dimensional pockets of energy for providing power from the wireless power transmitter to a respective receiver, and where each of the wireless power transmitters are configured to detect a fault in at least one of the wireless power transmitter and the respective receiver, (ii) a communication apparatus for communicating with a network, and (iii) a server, communicatively coupled to each of the plurality of power sources via the network, the server being configured to receive any of the detected faults transmitted from the power sources, process the received faults and provide a recommendation for correcting the received fault.

In some embodiments, each of the plurality of power sources further comprises a storage device operatively coupled to the wireless power transmission manager, the storage device being configured to store information for a device associated with the receiver that is registered with each power source, and communicate the information to a cloud. Furthermore, in some embodiments, each of the wireless power transmitter managers are configured to update the stored information for the device in response to the detected fault. Furthermore, in some embodiments, the device information comprises at least one of (1) a power schedule for the device, (2) location of the device, (3) movement of the device, (4) configuration of the device, (5) amount of power used by the device, (6) amount of power transmitted to the device from the wireless power transmitter, (7) pairing of the device with the system, and (8) other wireless power devices registered with the device. Furthermore, in some embodiments, the server is configured to receive the stored information for each device associated with the respective receiver that is registered with each power source. Furthermore, in some embodiments, the wireless power transmission manager is configured to process the information for the device to determine at least one of quality control information, device status, wireless power transmitter configuration, control, statistics and problem reports.

In some embodiments, the communication apparatus is configured to receive the recommendation from the server in response to the transmission of the detected fault.

In some embodiments, the server is further configured to receive information regarding at least one receiver's location to its respective power source and to other power sources in the system.

In some embodiments, the communication apparatus is configured to communicate to a business cloud within the cloud.

In some embodiments, the wireless power transmitter is configured to transmit the detected fault to the network via the communication apparatus.

A method for wirelessly providing power may include: (i) controlling RF waves in a wireless power transmitter via a wireless transmitter manager, to form three-dimensional pockets of energy for providing power from the wireless power transmitter to a receiver, (ii) detecting, via the wireless power transmitter, a fault in at least one of the wireless power transmitter and the receiver, and (iii) transmitting the detected fault to a network via a communication apparatus.

FIGS. 49-56 illustrate enhanced receivers, transmitters, and methods for performing maximum power point transfer (MPPT), in accordance with some embodiments.

Figure 49A:
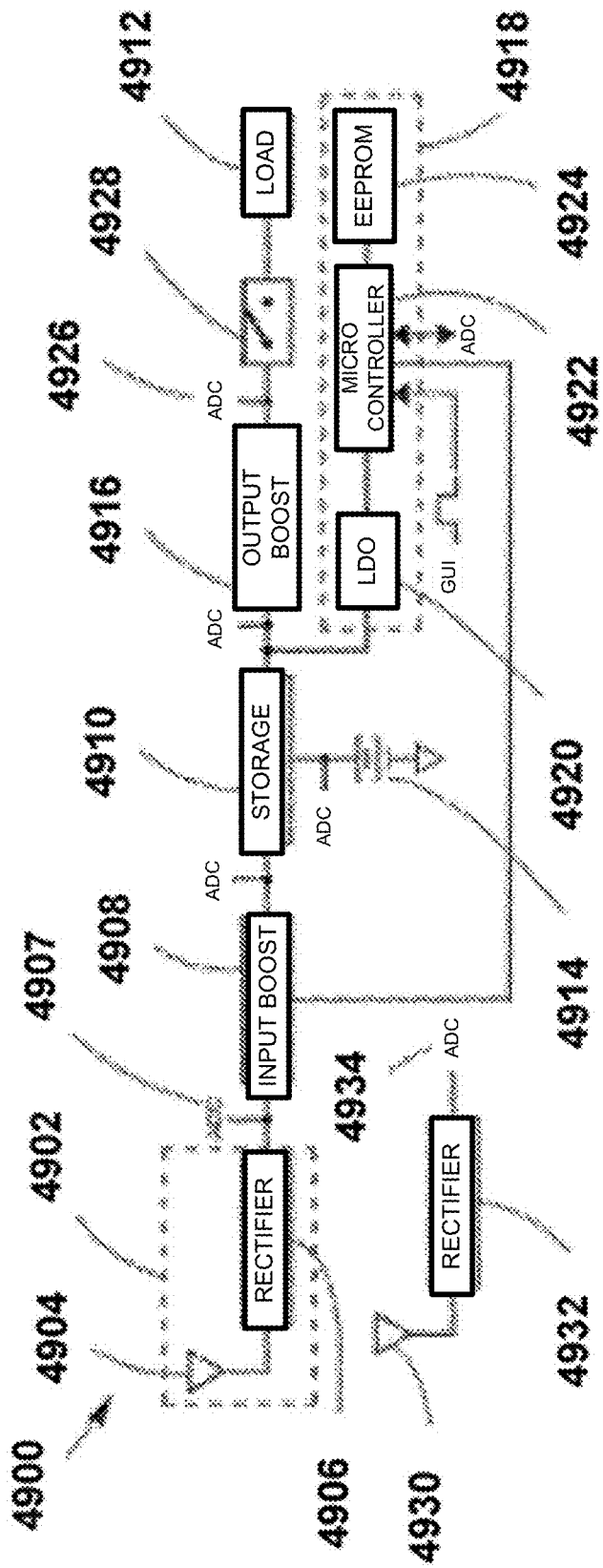
FIG. 49A illustrates a block diagram of an enhanced receiver that may be used for extracting and converting power from power transmission waves, in accordance with some embodiments.

FIG. 49A shows a block diagram of receiver configuration 4900 which can be used for wireless powering or charging one or more electronic devices 122 as exemplified in wireless power transmission 100 (FIG. 1). According to some aspects of this embodiment, receiver 120 may operate with the variable power source generated from transmitted RF waves 116 to deliver constant and stable power or energy to electronic device 122. In addition, receiver 120 may use the variable power source generated from RF waves 116 to power up electronic components within receiver 120 for proper operation.

Receiver 120 may be integrated in electronic device 122 and may include a that can be made of any suitable material to allow for signal or wave transmission and/or reception, for example plastic or hard rubber. This housing may be an external hardware that may be added to different electronic equipment, for example in the form of cases, or can be embedded within electronic equipment as well.

Receiver 120 may include an antenna array 4902 which may convert RF waves 116 or pockets of energy into electrical power. Antenna array 4902 may include one or more antenna elements 4904 coupled with one or more rectifiers 4906. RF waves 116 may exhibit a sinusoidal shape within a voltage amplitude and power range that may depend on characteristics of transmitter 102 and the environment of transmission. The environment of transmission may be affected by changes to or movement of objects within the physical boundaries, or movement of the boundaries themselves. It is also affected by changes to the medium of transmission; for example, changes to air temperature or humidity. As a result, the voltage or power generated by antenna array 4902 at the receiver 120 may be variable. As an illustrative embodiment, and not by way of limitation, the alternating current (AC) voltage or power generated by antenna element 4904 from RF waves 116 or pocket of energy may vary from about 0 volts at 0 watts to about 5 volts at 3 watts.

Antenna element 4904 may include suitable antenna types for operating in frequency bands similar to the bands described for transmitter 102 from FIG. 1. Antenna element 4904 may include vertical or horizontal polarization, right hand or left hand polarization, elliptical polarization, or other suitable polarizations as well as suitable polarization combinations. Using multiple polarizations can be beneficial in devices where there may not be a preferred orientation during usage or whose orientation may vary continuously through time, for example electronic device 122. On the contrary, for devices with well-defined orientations, for example a two-handed video game controller, there might be a preferred polarization for antennas which may dictate a ratio for the number of antennas of a given polarization. Suitable antenna types may include patch antennas with heights from about ⅛ inch to about 6 inches and widths from about ⅛ inch to about 6 inches. Patch antennas may have the advantage that polarization may depend on connectivity, i.e. depending on which side the patch is fed, the polarization may change. This may further prove advantageous as receiver 120 may dynamically modify its antenna polarization to optimize wireless power transmission.

Rectifier 4906 may include diodes or resistors, inductors or capacitors to rectify the AC voltage generated by antenna element 4904 to direct current (DC) voltage. Rectifier 4906 may be placed as close as is technically possible to antenna element 4904 to minimize losses. In one embodiment, rectifier 4906 may operate in synchronous mode, in which case rectifier 4906 may include switching elements that may improve the efficiency of rectification. As an illustrative embodiment and not by way of limitation, input boost converter 4908 may operate with input voltages of at least 0.6 volts to about 5 volts to produce an output voltage of about 5 volts. In addition, input boost converter 4908 may reduce or eliminate rail-to-rail deviations and may operate as a step-up DC-to-DC converter to increase the voltage from rectifier 4906 to a voltage level suitable for proper operation of receiver 120. In one embodiment, intelligent input boost converter 4908 may exhibit a synchronous topology to increase power conversion efficiency.

As the voltage or power generated from RF waves 116 may be zero at some instants of wireless power transmission, receiver 120 can include a storage element 4910 to store energy or electric charge from the output voltage produced by input boost converter 4908. In this way, storage element 4910 may deliver a constant voltage or power to a load 4912 which may represent the battery or internal circuitry of electronic device 122 requiring continuous powering or charging. For example, load 4912 may be the battery of a mobile phone requiring constant delivery of 5 volts at 2.5 watts.

Storage element 4910 may include a battery 4914 to store power or electric charge from the voltage received from input boost converter 4908. Battery 4914 may be of different types, including but not limited to, alkaline, nickel-cadmium (NiCd), nickel-metal hydride (NiHM), and lithium-ion, among others. Battery 4914 may exhibit shapes and dimensions suitable for fitting receiver 120, while charging capacity and cell design of battery 4914 may depend on load 4912 requirements. For example, for charging or powering a mobile phone, battery 4914 may deliver a voltage from about 3 volts to about 4.2 volts.

In another embodiment, storage element 4910 may include a capacitor (not shown in FIG. 49A) instead of battery 4914 for storing and delivering electrical charge or power to load 4912. As a way of example, in the case of charging or power a mobile phone, receiver may include a capacitor with operational parameters matching the load device's power requirements.

Receiver 120 may also include an output boost converter 4916 operatively coupled with storage element 4910 and input boost converter 4908, where this output boost converter 4916 may be used for matching impedance and power requirements of load 4912. As an illustrative embodiment, and not by way of limitation, output boost converter 4916 may increase the output voltage of battery 4914 from about 3 or 4.2 volts to about 5 volts which may be the voltage required by the battery 4914 or internal circuitry of a mobile phone. Similar to input boost converter 4908, output boost converter 4916 may be based on a synchronous topology for enhancing power conversion efficiency.

Storage element 4910 may provide power or voltage to a communication subsystem 4918 which may include a low-dropout regulator (LDO 4920), a main system micro-controller 4922, and an electrically erasable programmable read-only memory (EEPROM 4924). LDO 4920 may function as a DC linear voltage regulator to provide a steady voltage suitable for low energy applications as in main system micro-controller 4922. Main system micro-controller 4922 may be operatively coupled with EEPROM 4924 to store data pertaining to the operation and monitoring of receiver 120. Main system micro-controller 4922 may also include a clock (CLK) input and general purpose inputs/outputs (GPIOs).

In one embodiment, intelligent input boost converter 4908 may include a built-in micro-controller (not shown in FIG. 49A) operatively coupled with a main system micro-controller 4922. The main system micro-controller 4922 may actively monitor the overall operation of receiver 120 by taking one or more power measurements 4926 (ADC) at different nodes or sections as shown in FIG. 49A. For example, main system micro-controller 4922 may measure how much voltage or power is being delivered at rectifier 4906, input boost converter 4908, battery 4914, output boost converter 4916, communication subsystem 4918, and/or load 4912. Main system micro-controller 4922 may communicate these power measurements 4926 to load 4912 so that electronic device 122 may know how much power it can pull from receiver 120. In another embodiment, main system micro-controller 4922, based on power measurements 4926, may control the power or voltage delivered at load 4912 by adjusting the load current limits at output boost converter 4916.

Main system micro-controller 4922 may monitor the voltage levels at the output of the main antenna array 4902 using ADC node point 4907.

In another embodiment, main system micro-controller 4922 may regulate how power or energy can be drained from storage element 4910 based on the monitoring of power measurements 4926. For example, if the power or voltage at input boost converter 4908 runs too low, then main system micro-controller 4922 may direct output boost converter 4916 to drain battery 4914 for powering load 4912.

Yet in another embodiment, receiver 120 may have a dedicated antenna element 4930 operatively coupled with a corresponding rectifier 4932, where these dedicated antenna element 4930 and rectifier 4932 may be used for continuously monitoring the surrounding pocket of energy. This dedicated antenna element 4930 may be separate from the main antenna array 4902. More specifically, the main system micro-controller 4922 may measure power level at ADC node point 4934 to compare against actual DC power levels extracted from the receiver 120 system.

Receiver 120 may include a switch 4928 for resuming or interrupting power being delivered at load 4912. In one embodiment, main system micro-controller 4922 may control the operation of switch 4928 according to terms of services contracted by one or more users of wireless power transmission 100 or according to administrator policies.

Figure 49B:
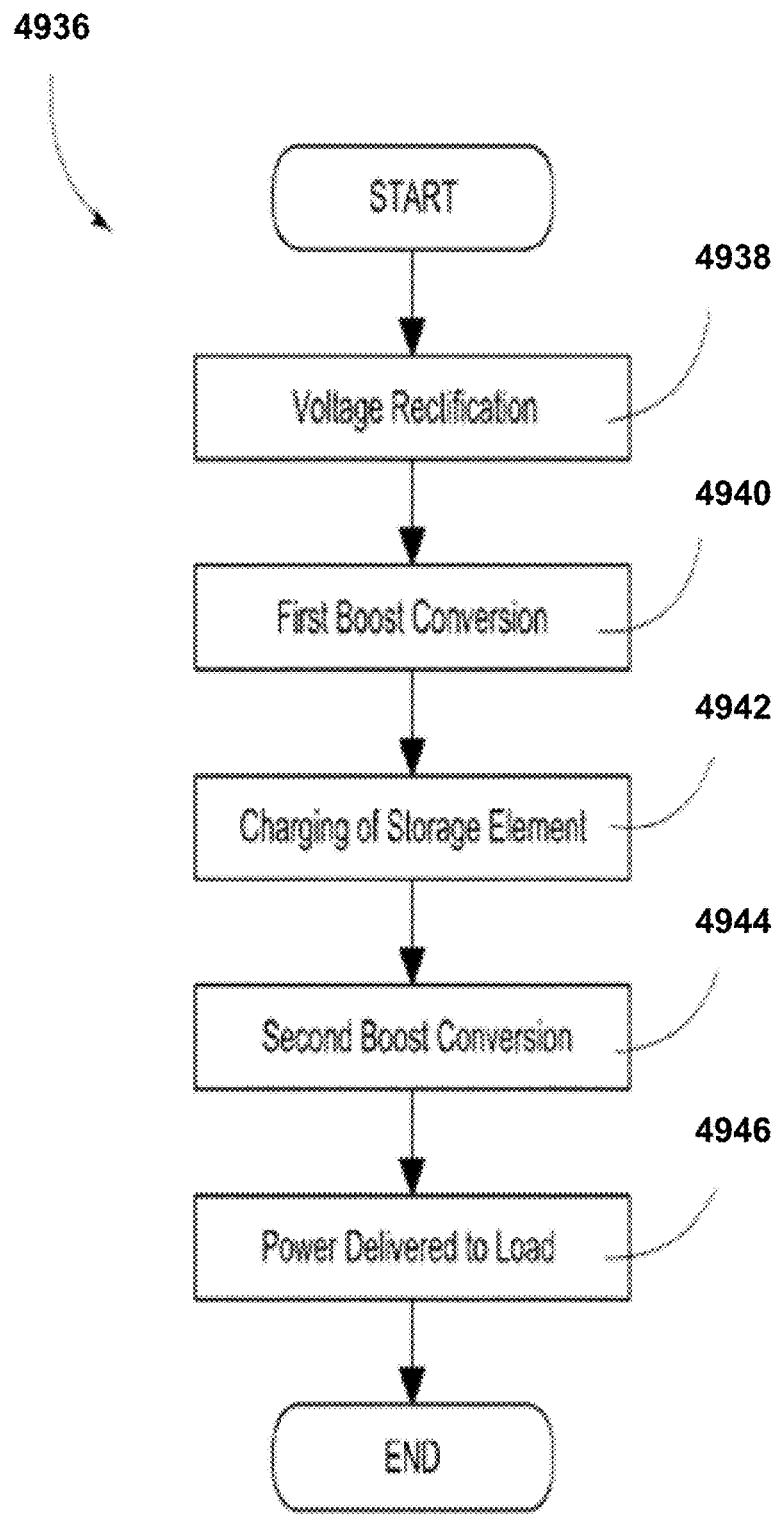
FIG. 49B illustrates a flowchart of a wireless power transmission process that may be implemented by an enhanced receiver during wireless power transmission, in accordance with some embodiments.

FIG. 49B shows an exemplary power conversion process 4936 that may be implemented in a receiver during wireless power transmission. According to some aspects of this embodiment, power conversion process 4936 may allow energy harvesting from power transmission waves from pockets of energy, which may provide voltage or power to internal components of a receiver, which may be embedded in an electronic device.

Power conversion process 4936 may start when antenna element may convert power transmission waves and/or pockets of energy into AC voltage or power. At step 4938, rectifier may rectify this AC voltage or power into DC voltage or power. The DC voltage or power generated at rectifier may be variable depending on conditions for extracting power from power transmission waves in a pocket of energy.

Subsequently at step 4940, input boost converter may step up the DC voltage or power obtained from rectifier to a voltage or power level that may be used by storage element or other internal components of receiver. In one embodiment, input boost converter may receive an input, which may be based on a maximum power point transfer (MPPT) algorithm, from micro-controller for adjusting and optimizing the amount of power that can be pulled from antenna array. The stabilized and increased voltage at input boost converter may be directly utilized by load, but it may not be continuous at all times given the inherently characteristics of power transmission waves.

The stabilized DC voltage produced by input boost converter may be used to charge storage element, where storage element may be in the form of a battery or a capacitor, at step 4942. Storage element may maintain suitable charging levels at all times for delivering continuous power to load. In addition, storage element may provide suitable power or voltage to communication subsystem.

The voltage or power generated by storage element can be step up by output boost converter to match impedance and power requirements of load, at step 4944. In one embodiment, micro-controller may set up current limits at output boost converter to adjust the amount of power being delivered at load according to the application.

After a second boost conversion, output boost converter may now supply stable and continuous power or voltage to load within suitable electrical specifications for charging or powering electronic device, which may be operatively coupled with receiver, at step 4946.

In some embodiments, a micro-controller may control switch to interrupt or resume the delivery of power or voltage at load, according to terms of services contracted by users of wireless power transmission service. For example, if wireless power transmission is a service provided to a user of receiver, then micro-controller, through the use of switch, can interrupt or resume the powering or charging of electronic device according to the status of user's contract. Furthermore, micro-controller may regulate the operation of switch based on charging or powering priorities established for one or more electronic devices. For example, micro-controller may open switch if the electronic device coupled with receiver has a lower powering or charging priority compared to another electronic device coupled with a suitable receiver that may require charging and that may have a higher priority for charging. In this case, transmitter may direct power transmission waves towards the receiver coupled with the electronic device, with higher charging and powering priority.

Figure 49C:
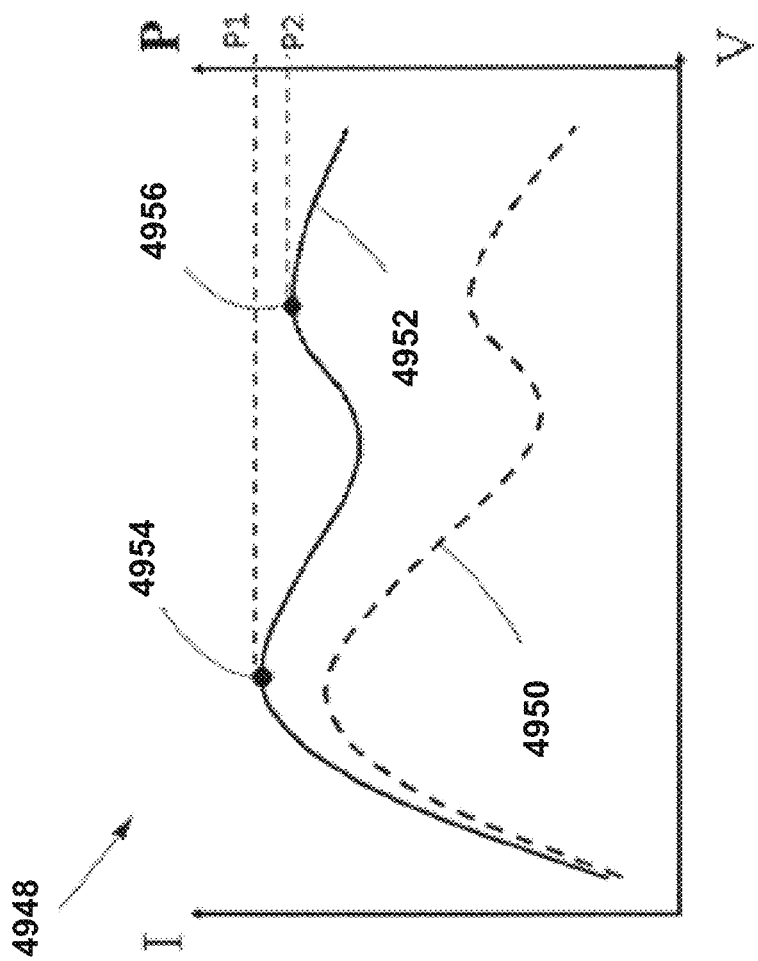
FIG. 49C illustrates the maximum power point transfer (MPPT) of characteristic curves, in accordance with some embodiments.

FIG. 49C illustrates a graph 4948, depicting (I) the intensity of current available from main antenna array, (P) the power available from main antenna array, and (V) the voltage from main antenna array. FIG. 49C shows a current-to-voltage curve 4950 that may be obtained from receiver 120 (FIG. 1) operation and which may vary according to the characteristics of receiver 120. FIG. 49C also shows a corresponding power curve 4952 which may represent the power available (current x voltage) from the main antenna array 4902.

In one embodiment, voltage levels measured at ADC node point 4907 may not necessarily exhibit a linear relationship with the available current from the main antenna array 4902. Thus, power curve 4952 may have multiple local peaks, including a global power maximum 4954 at P1, and a local power maximum 4956 at P2.

The MPPT algorithm running in the input boost converter 4908 may continuously track for a global power maximum 4954 in graph 4948, so that input boost converter 4908 may be able to extract the maximum amount of power from antenna array 4902. However, in some circumstances, the MPPT algorithm may be stuck at a local power maximum 4956 which may not correspond to the global power maximum 4954 in graph 4948. When operating at a local power maximum 4956, intelligent input boost converter 4908 may not be able to maximize the amount of power that can be extracted from antenna array 4902.

It may be an object of embodiments described herein to adjust the MPPT algorithm to control the operation of intelligent input boost converter 4908 so that it can continuously operate at global power maximum 4954 to make the best use of the power that can be extracted from antenna array 4902 in receiver 120 system.

Figure 49D:
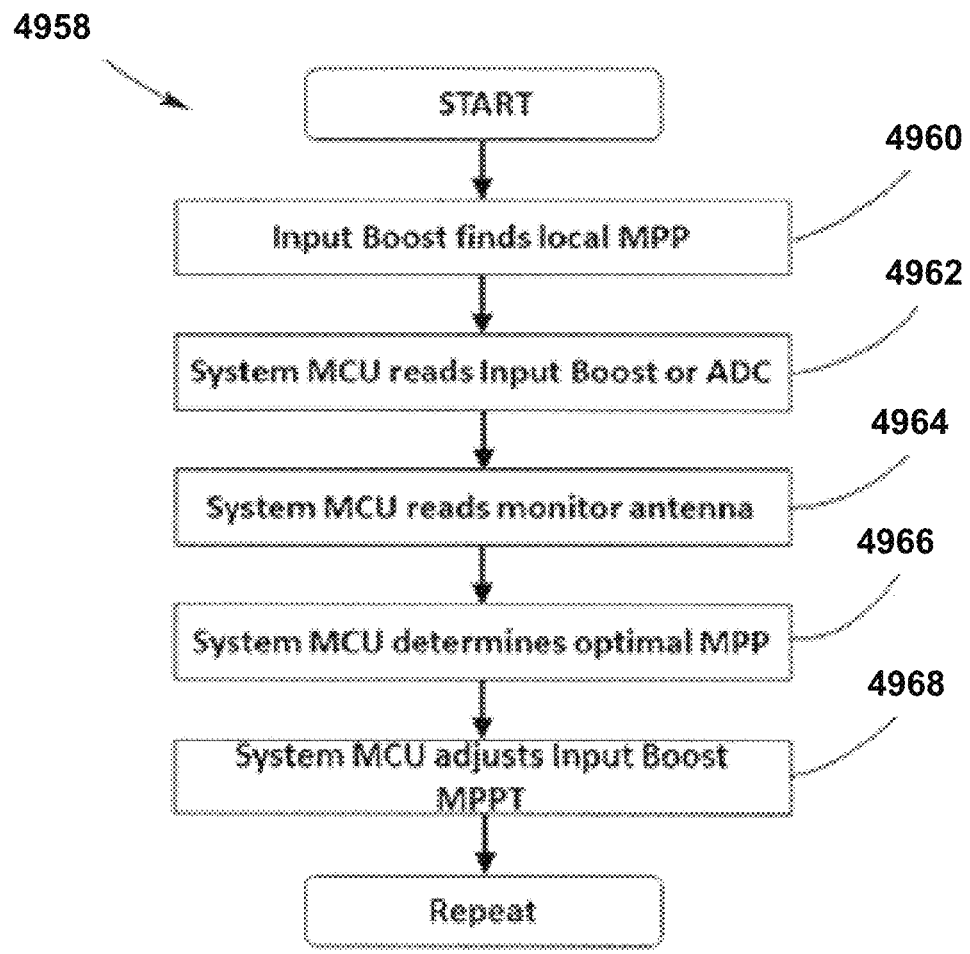
FIG. 49D illustrates a flowchart for the method enabled by the proprietary MPPT algorithm controlling maximum power point transfer and operation of the input boost converter, in accordance with some embodiments.

FIG. 49D shows a MPPT management method 4958 that may be used for maximizing the amount of power that can be extracted from antenna array 4902 to deliver continuous and suitable power to receiver 120 (FIG. 1).

At monitoring step 4960, the built-in micro-controller in the intelligent input boost converter 4908 may monitor voltage from antenna array 4902 and search for a global power maximum 4954 or local power maximum 4956.

At step 4962, the main system micro-controller 4922 may read the result from the input boost converter 4908 or use ADC node point 4907 to establish the input boost converter 4908 current operational MPPT. Subsequently, at step 4964, the main system micro-controller 4922 may read the voltage of dedicated antenna element 4930 at ADC node point 4934. At step 4966, the combination of the input boost converter 4908 MPP and the output value of dedicated antenna element 4904 may be used to either index a predefined look-up table or be used in an algorithm. This result may or may not require an adjustment of the operational input parameters of the input boost converter 308 MPPT algorithm. Once action is determined, the main system micro-controller 4922 may adjust the MPPT algorithm executed by input boost converter 4908, thus moving the operation of input boost converter 4908 from local power maximum 4956 P2 to global power maximum 4954 P1, at step 4968.

The predefined MPPT tables may include a characterization of a plurality of receivers 120 in terms of ability to extract power from a particular field. For example, the capability of receiver 120 for extracting power from RF waves 116 may vary according to the configuration of antenna array 4902. In one embodiment, these MPPT tables may be determined by laboratory measurements of different receivers 120 in a way that a particular receiver 120 may be mapped to an optimal MPPT.

In one embodiment, main system micro-controller 4922 may use the information contained in MPPT tables to provide initial conditions for running an optimal MPPT at intelligent input boost converter 4908 according to the specific characteristics or configuration of receiver 120.

Figure 50A:
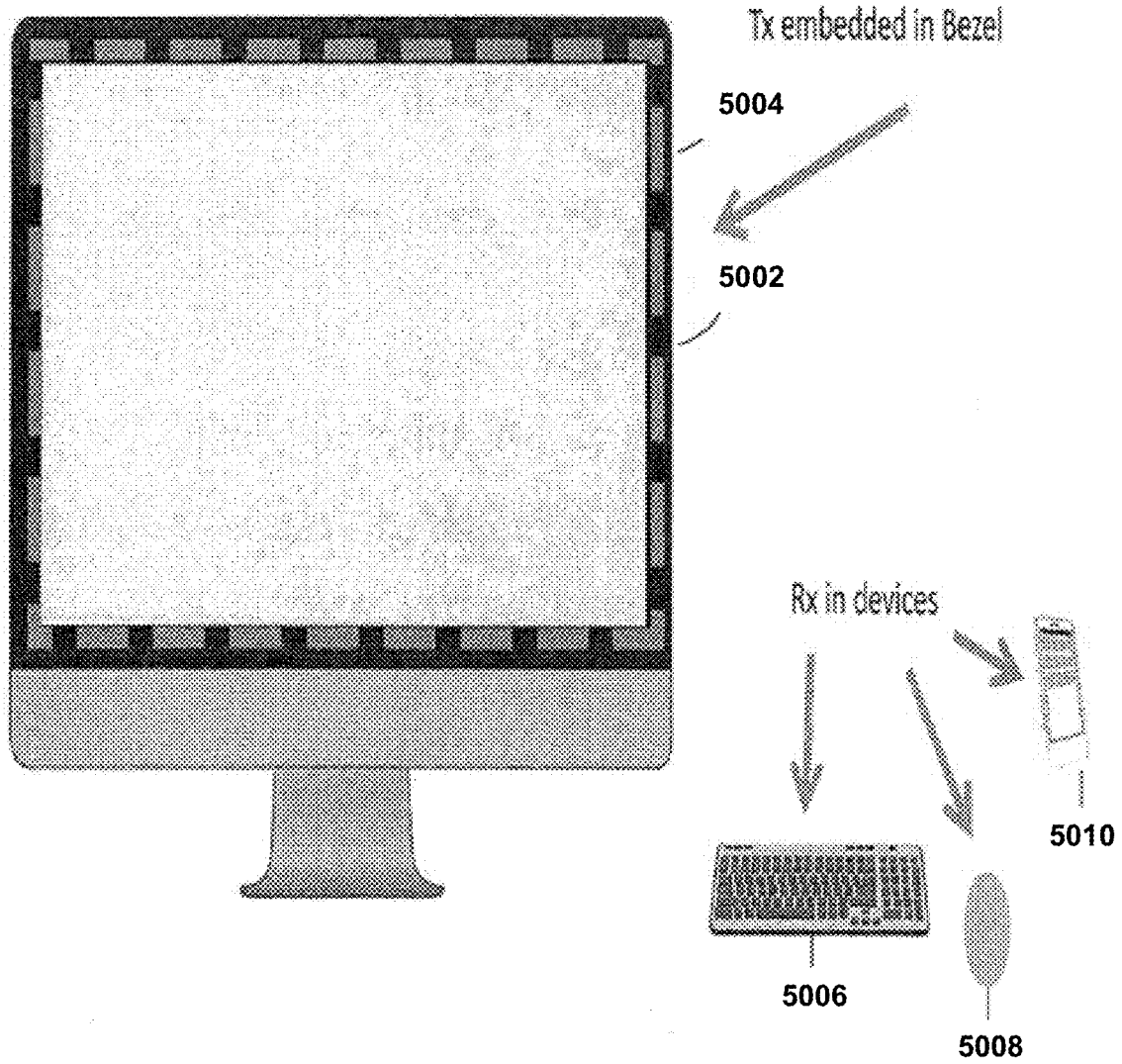
FIG. 50A illustrates a plurality of transmitter antennas positioned in a bezel of a computer display, in accordance with some embodiments.

FIG. 50 shows a plurality of transmitter antennas positioned in a bezel of a computer display in a segmented closed shape to wirelessly transmit energy to a plurality of receiver antennas of electronic devices, according to an embodiment. As illustrated, a computer display 5002 includes a bezel with a plurality of transmitter antennas 5004 positioned in a segmented closed shape along the bezel. Note that the transmitter antennas 5004 can be coupled to or included with the computer display 5002. Such coupling can include retrofitting. For example, the transmitter antennas 5004, such as the antenna elements 2202 (FIG. 22) described above, can number at least two hundred, but a lower amount of the transmitter antennas 5004 is possible as well, such as at least two. Also, for example, the transmitter antennas 5004 can be positioned in a continuous closed shape along the bezel. Moreover, for example, the transmitter antennas 5004 can be positioned in an open shape along the bezel, whether continuous or segmented. In other embodiments, at least one of the transmitter antennas 5004 is positioned in another area or areas of the computer display 5002 in any shape, whether open or closed, or in any manner, whether continuous or segmented, such as a rear face, a sidewall, a floor, a ceiling, a stand, a leg, or a surface mount, or positioned within the computer display 5002.

The computer display 5002 is a desktop display or an all-in-one computer display. The computer display 5002 is rectangular shaped, but other shapes are possible, such as a square, a triangle, a pentagon, a trapezoid, a star, a sphere, a pyramid, or others. The computer display 5002 is of liquid crystal display (LCD) type, but other display types are possible, such as a light emitting diode (LED) type, a plasma type, a cathode ray tube (CRT) type, an electrophoretic type, a laser type, a surface-conduction electron-emitter display (SED) type, a field emission display (FED) type, a mechanical type, or others. The computer display 5002 is supported on a stand or a leg. However, in other embodiments, the computer display 5002 can be any type of a display, whether stationary, portable, mobile, billboard, vehicular, or wearable, whether battery powered, mains electricity powered, movement powered, or renewable energy powered, such as a photovoltaic cell or a fluid turbine, whether with a stand or one or more legs or without a stand or one or more legs or whether coupled to a surface, such as a sidewall, a ceiling, or a floor, whether touch enabled or not, whether haptic enabled or not. In other embodiments, the computer display 5002 is a television display. Note that the computer display 5002 can include or be coupled to a speaker or a sound bar.

The transmitter antennas 5004 can be positioned on the bezel, within the bezel, or underneath the bezel. For example, the transmitter antennas 5004 can be embedded in the bezel. As described above, the transmitter antennas 5004 are operably coupled to the RFIC 2204 (FIG. 22) to enable wireless transmission of energy, as described herein. Accordingly, the computer display 5002 operates as the transmitter 102 (FIG. 1), as described herein. However, in other embodiments, the computer display 5002 operates as the receiver 120 (FIG. 1), as described herein.

The transmitter antennas 5004 wirelessly transmit energy to a keyboard 5006, a mouse 5008, and a mobile phone 5010. Each of the keyboard 5006, the mouse 5008, and the mobile phone 5010 includes a storage device, such as a battery or a capacitor. Each of such storage devices provides stored energy for operation of each of the keyboard 5006, the mouse 5008, and the mobile phone 5010. Each of the keyboard 5006, the mouse 5008, and the mobile phone 5010 also includes or is coupled to the receiver 120, as described herein. The receiver 120 includes at least one antenna element 4904 (FIG. 49A). The receiver 120 is coupled to the storage device and configured to interface with the wirelessly transmitted energy, as described herein, such that each storage device of the keyboard 5006, the mouse 5008, and the mobile phone 5010 is at least partially charged thereby. Note that although the keyboard 5006, the mouse 5008, and the mobile phone 5010 are shown, such depiction is an example and other devices of any type can be used, where such devices include or are coupled to the receiver 120, as described herein. For example, such devices can comprise any type of medical equipment.

Figure 50B:
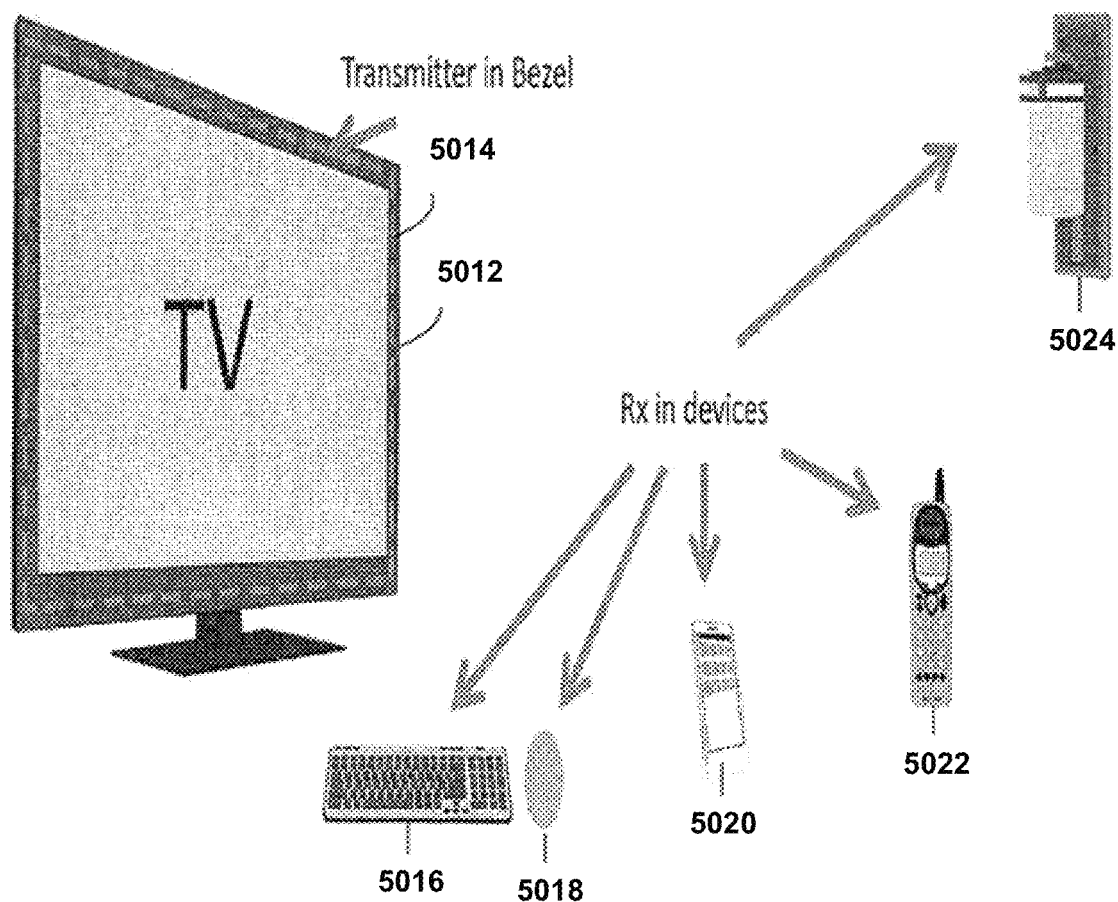
FIG. 50B illustrates a plurality of transmitter antennas positioned in a bezel of a television display, in accordance with some embodiments.

FIG. 50B shows a plurality of transmitter antennas positioned in a bezel of a television display in a segmented closed shape to wirelessly transmit energy to a plurality of receiver antennas of electronic devices, according to an embodiment. As illustrated, a television display 5012 includes a bezel with a plurality of transmitter antennas 5014 positioned in a segmented closed shape along the bezel. Note that the transmitter antennas 5014 can be coupled to or included with the television display 5012. Such coupling can include retrofitting. For example, the transmitter antennas 5014, such as the antenna elements 2202 (FIG. 22) described above, can number at least two hundred, but a lower amount of the transmitter antennas 5014 is possible as well, such as at least two. Also, for example, the transmitter antennas 5014 can be positioned in a continuous closed shape along the bezel. Moreover, for example, the transmitter antennas 5014 can be positioned in an open shape along the bezel, whether continuous or segmented. In other embodiments, at least one of the transmitter antennas 5014 is positioned in another area or areas of the television display 5012 in any shape, whether open or closed, or in any manner, whether continuous or segmented, such as a rear face, a sidewall, a floor, a ceiling, a stand, a leg, or a surface mount, or positioned within the television display 5012.

The television display 5012 is rectangular shaped, but other shapes are possible, such as a square, a triangle, a pentagon, a trapezoid, a star, a sphere, a pyramid, or others. The television display 5012 is of LCD type, but other display types are possible, such as an LED type, a plasma type, a CRT type, an electrophoretic type, a laser type, a SED type, a FED type, a mechanical type, or others. The television display 5012 is supported on a stand or a leg. However, in other embodiments, the television display 5012 can be any type of a display, whether stationary, portable, mobile, billboard, vehicular, or wearable, whether battery powered, mains electricity powered, movement powered, or renewable energy powered, such as a photovoltaic cell or a fluid turbine, whether with a stand or one or more legs or without a stand or one or more legs or whether coupled to a surface, such as a sidewall, a ceiling, or a floor, whether touch enabled or not, whether haptic enabled or not. In other embodiments, the television display 5012 is a computer display. Note that the television display 5012 can include or be coupled to a speaker or a sound bar.

The transmitter antennas 5014 can be positioned on the bezel, within the bezel, or underneath the bezel. For example, the transmitter antennas 5014 can be embedded in the bezel. As described above, the transmitter antennas 5014 are operably coupled to the RFIC 2204 (FIG. 22) to enable wireless transmission of energy, as described herein. Accordingly, the television display 5012 operates as the transmitter 102 (FIG. 1), as described herein. However, in other embodiments, the television display 5012 operates as the receiver 120 (FIG. 1), as described herein.

The transmitter antennas 5014 wirelessly transmit energy to a keyboard 5016, a mouse 5018, a cellular phone 5020, a cordless phone 5022, and a lamp 5024. Each of the keyboard 5016, the mouse 5018, the cellular phone 5020, the cordless phone 5022, and the lamp 5024 includes a storage device, such as a battery or a capacitor. Each of such storage devices provides stored energy for operation of each of the keyboard 5016, the mouse 5018, the cellular phone 5020, the cordless phone 5022, and the lamp 5024. Each of the keyboard 5016, the mouse 5018, the cellular phone 5020, the cordless phone 5022, and the lamp 5024 also includes or is coupled to the receiver 120, as described herein. The receiver 120 includes at least one antenna element 4904 (FIG. 49A). The receiver 120 is coupled to the storage device and configured to interface with the wirelessly transmitted energy, as described herein, such that each storage device of the keyboard 5016, the mouse 5018, the cellular phone 5020, the cordless phone 5022, and the lamp 5024 is at least partially charged thereby. Note that although the keyboard 5016, the mouse 5018, the cellular phone 5020, the cordless phone 5022, and the lamp 5024 are shown, such depiction is an example and other devices of any type can be used, where such devices include or are coupled to the receiver 120, as described herein. For example, such devices can comprise any type of medical equipment.

Figure 50C:
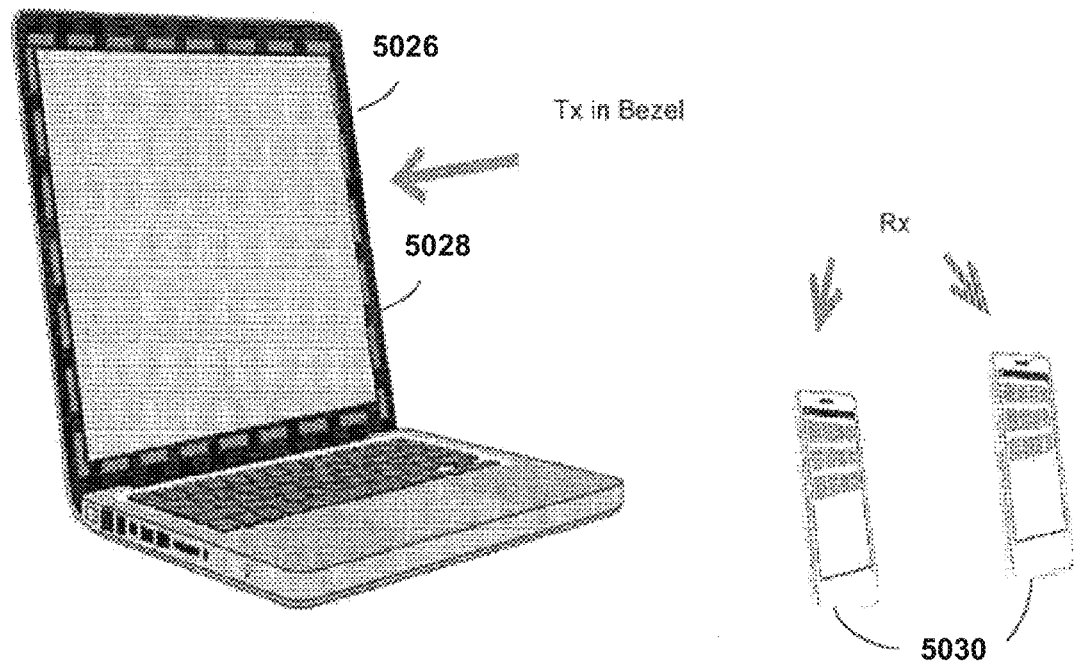
FIG. 50C illustrates a plurality of transmitter antennas positioned in a bezel of a laptop display, in accordance with some embodiments.
Figure 51A:
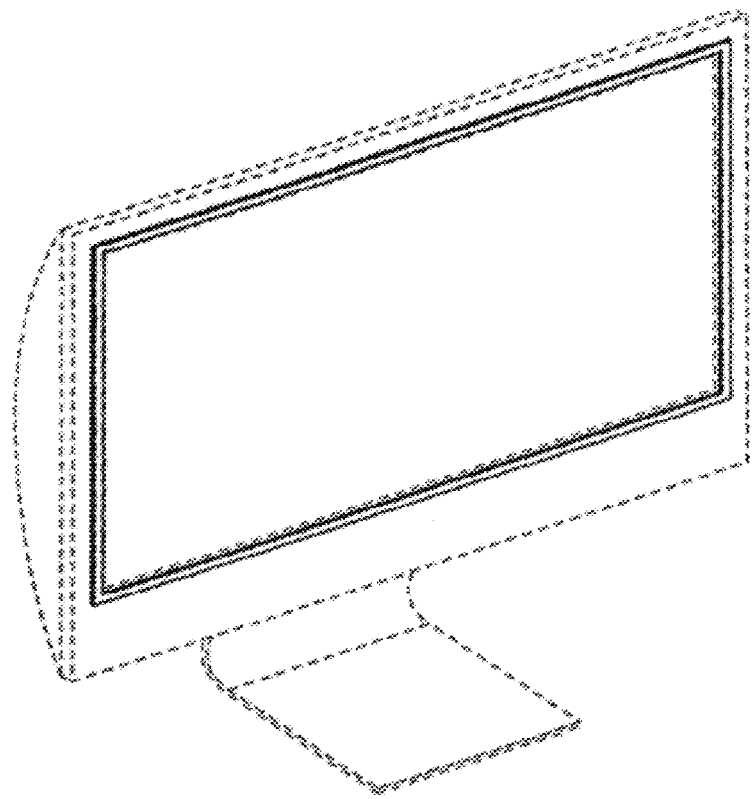
FIGS. 51A-51E illustrate various views of a display with a transmitter antenna having a continuous closed shape on a frontal face of the display, in accordance with some embodiments.
Figure 51B:
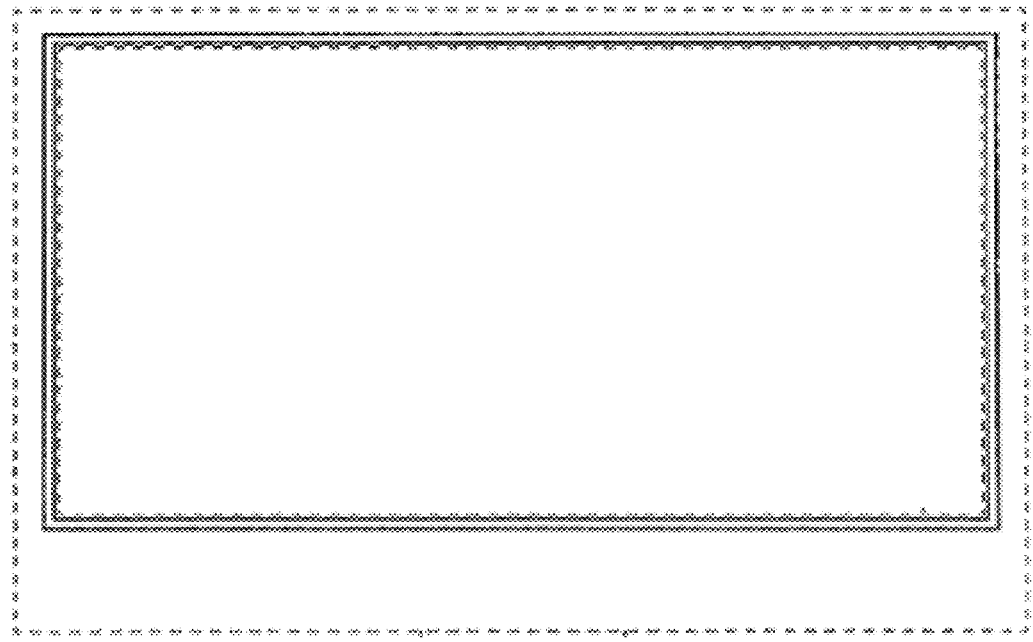
Figure 51C:
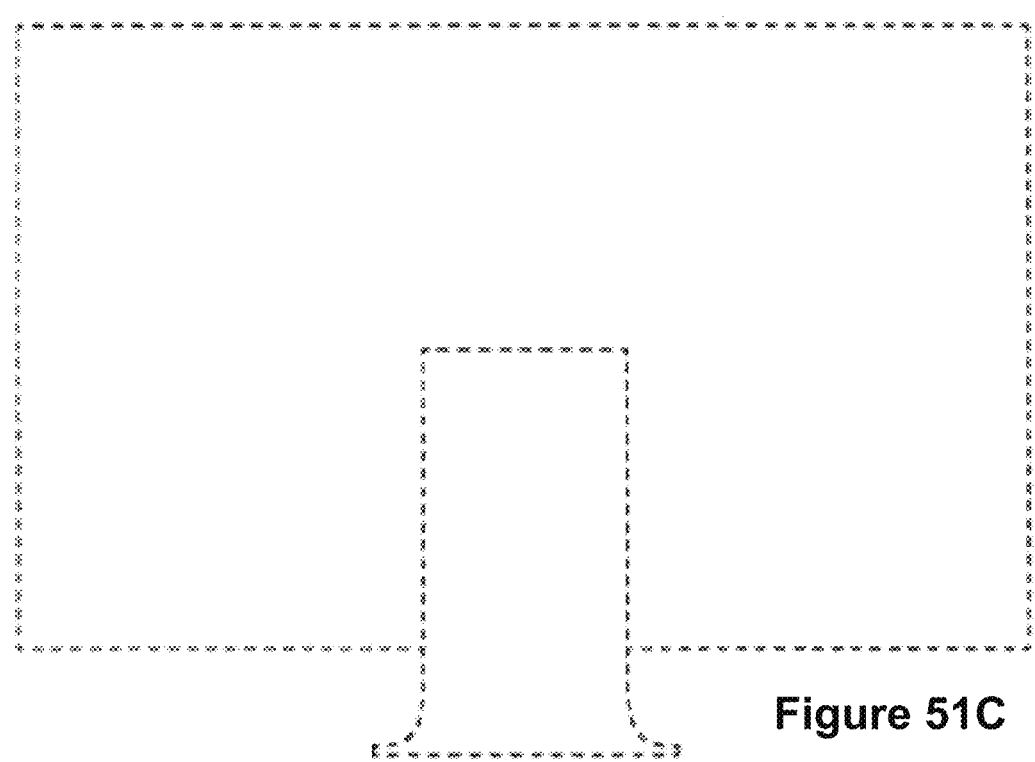
Figure 51D:
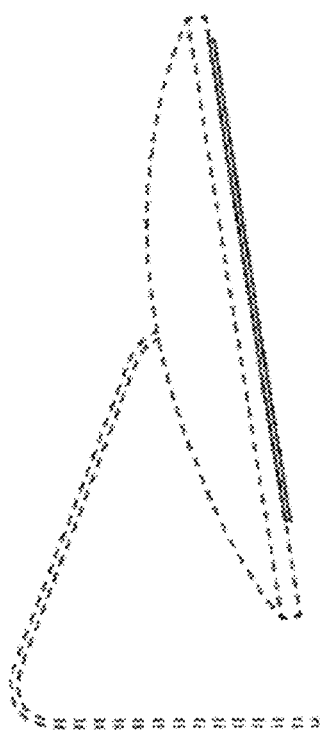
Figure 51E:
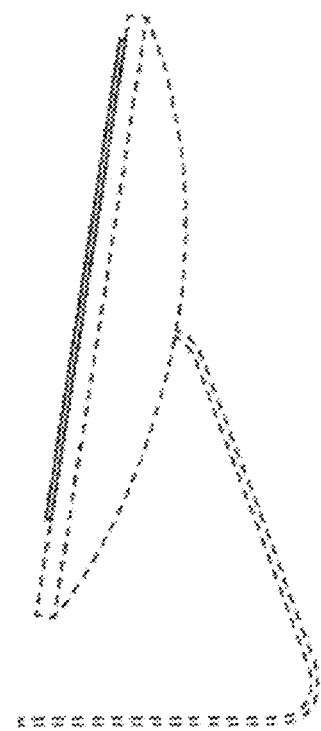
Figure 52A:
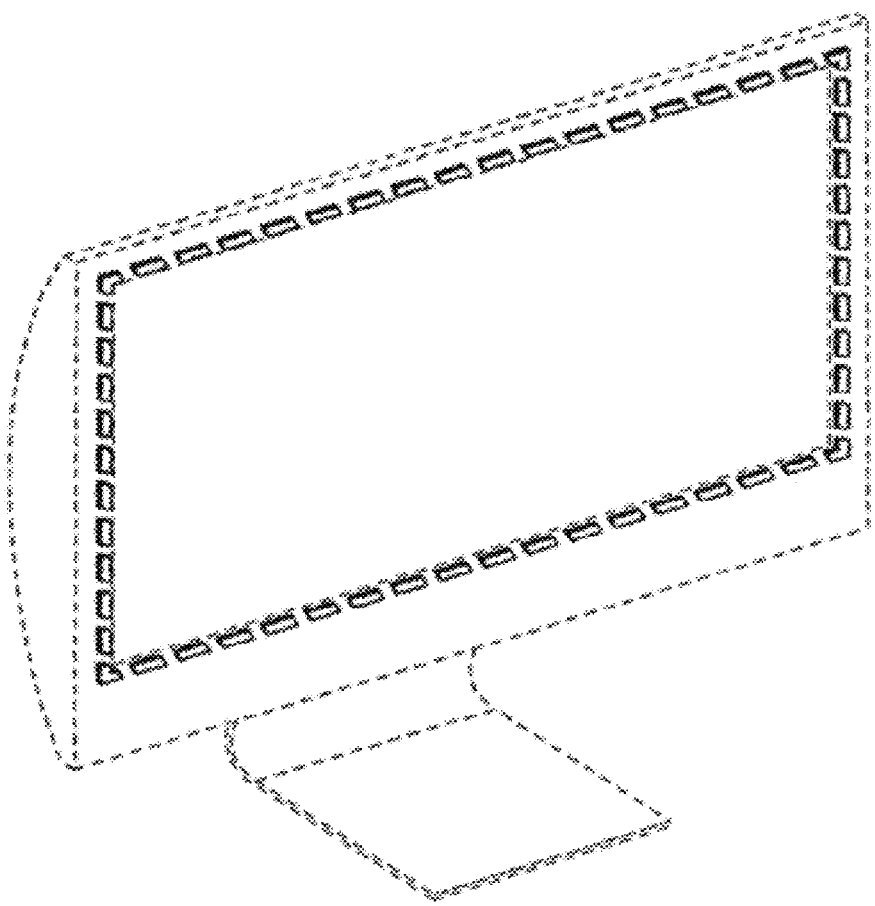
FIGS. 52A-52E illustrate various views of a display with a plurality of transmitter antennas positioned in a segmented closed shape on a frontal face of the display, in accordance with some embodiments.
Figure 52B:
Figure 52C:
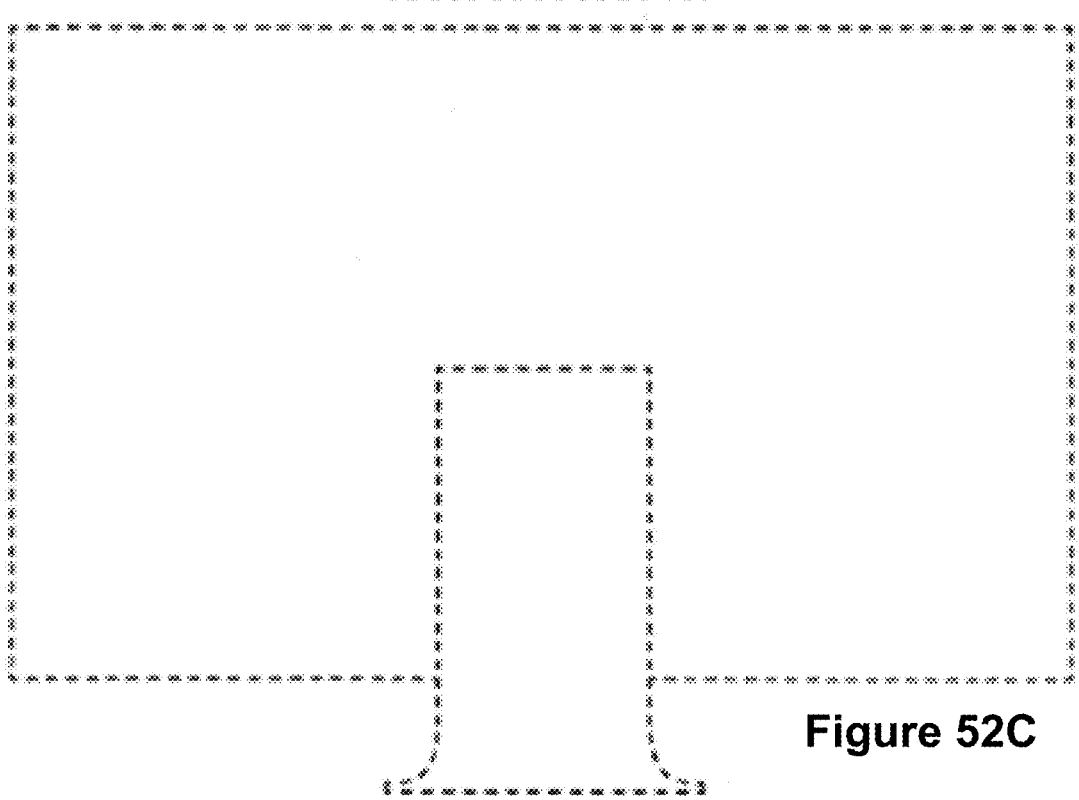
Figure 52D:
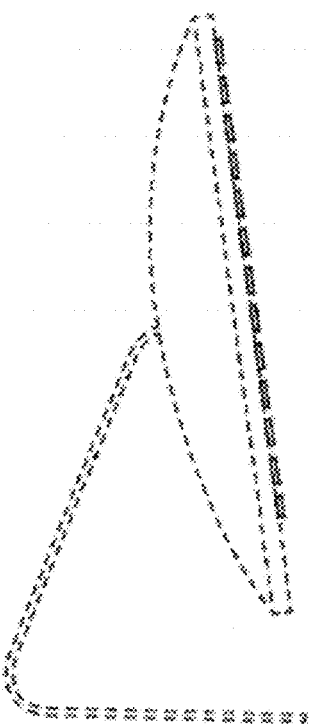
Figure 52E:
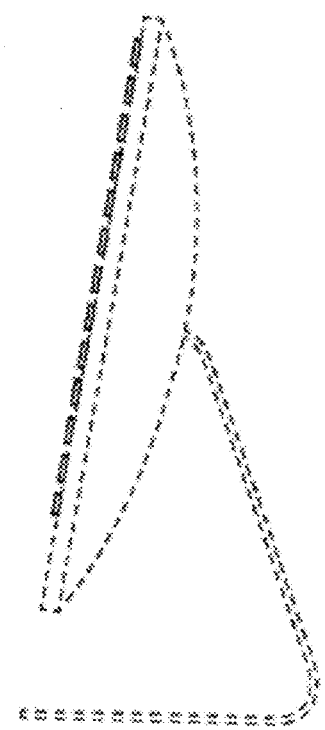
Figure 53A:
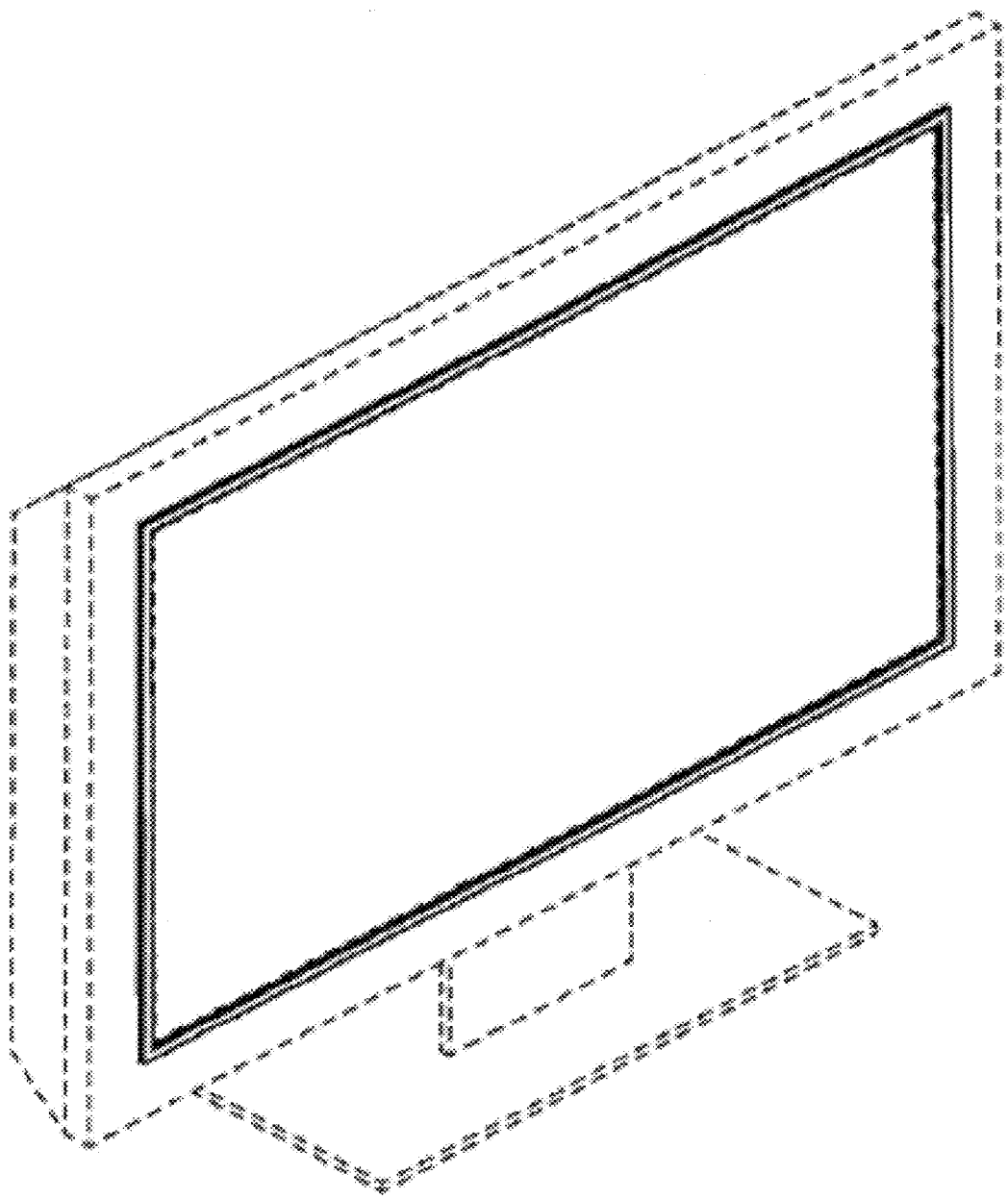
FIGS. 53A-53E illustrate various views of a display with a transmitter antenna having a continuous closed shape on a frontal face of the display, in accordance with some embodiments.
Figure 53B:
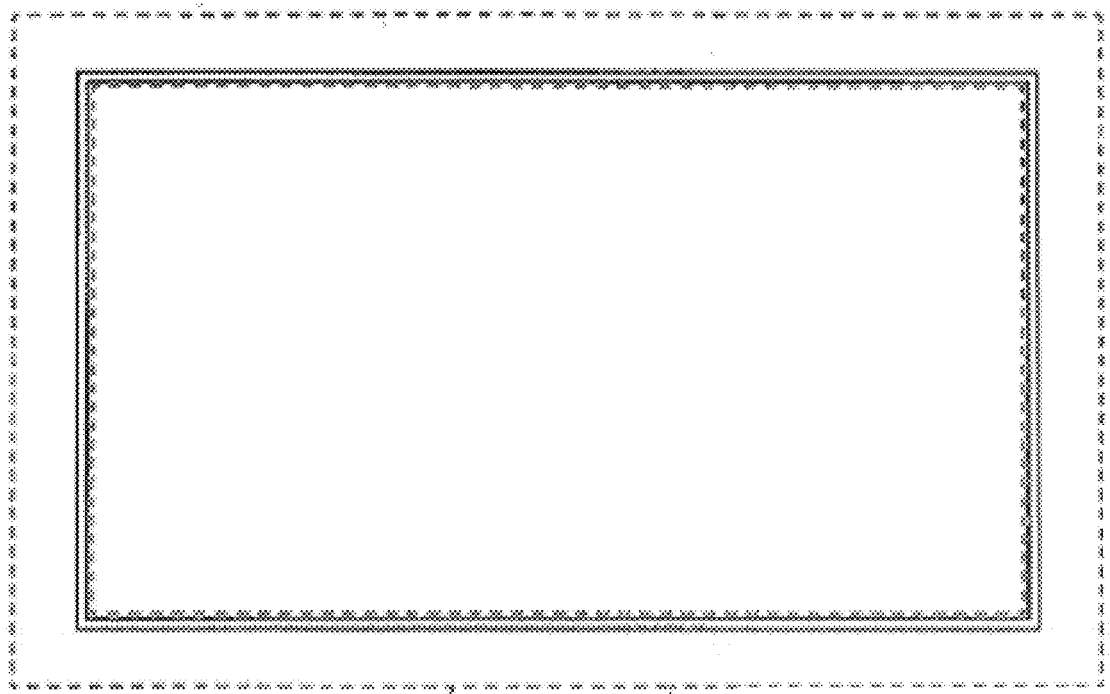
Figure 53C:
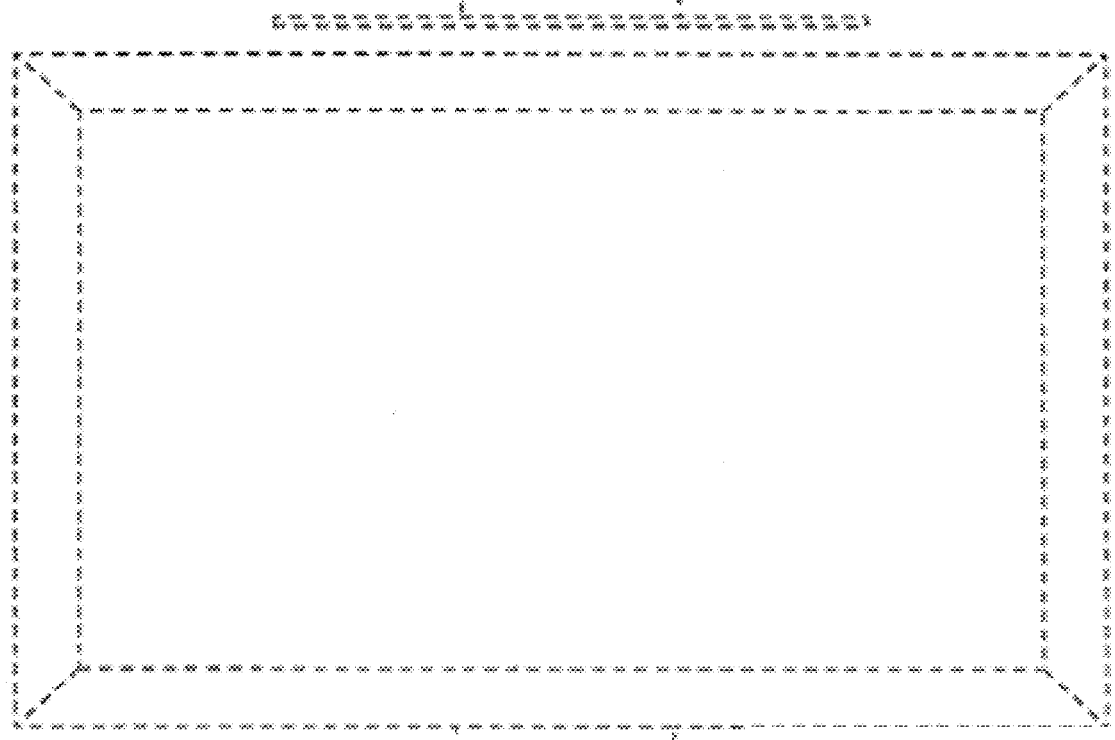
Figure 53D:
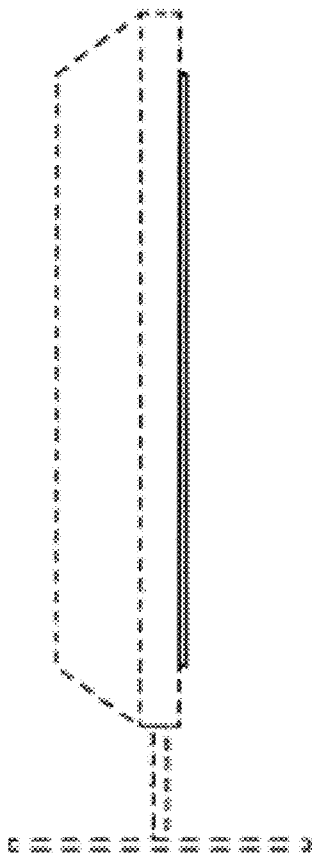
Figure 53E:
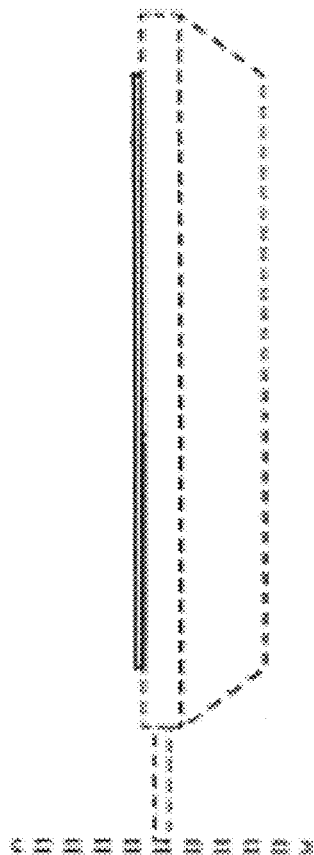
Figure 54A:
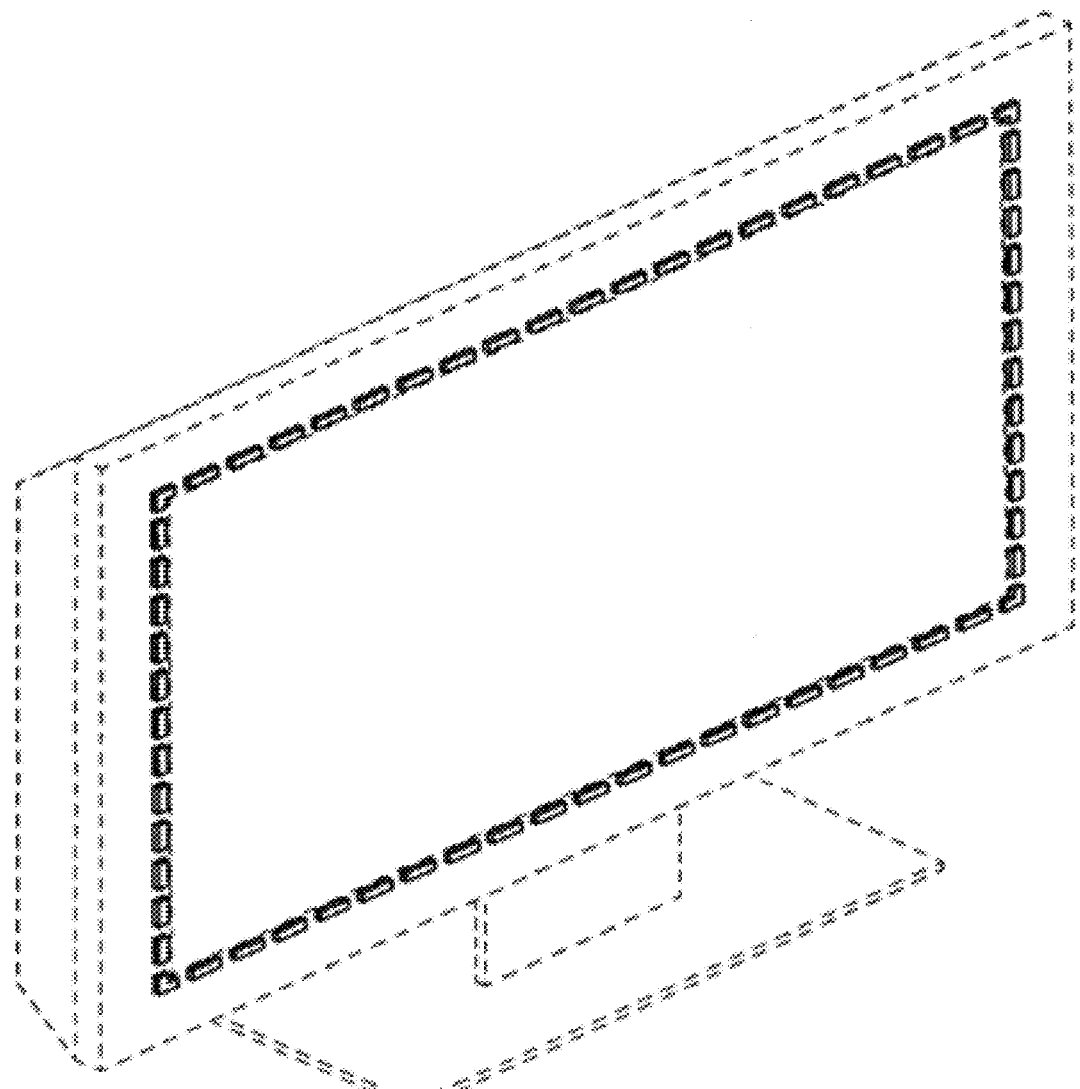
FIGS. 54A-54E illustrate various views of a display with a plurality of transmitter antennas positioned in a segmented closed shape on a frontal face of the display, in accordance with some embodiments.
Figure 54B:
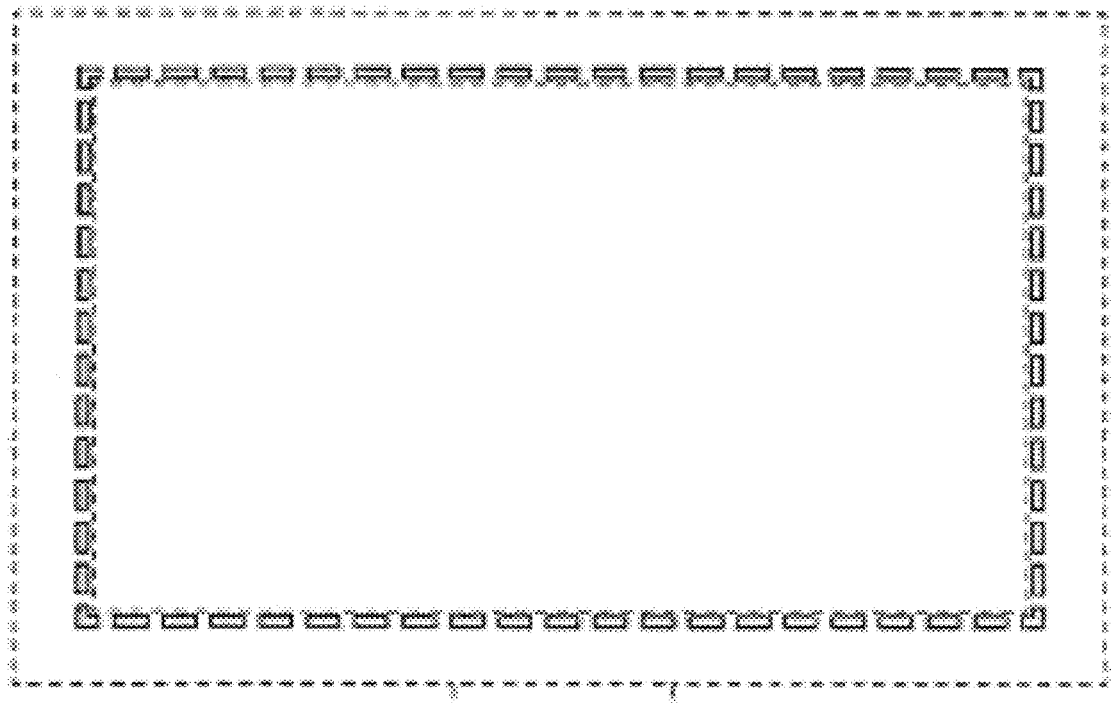
Figure 54C:
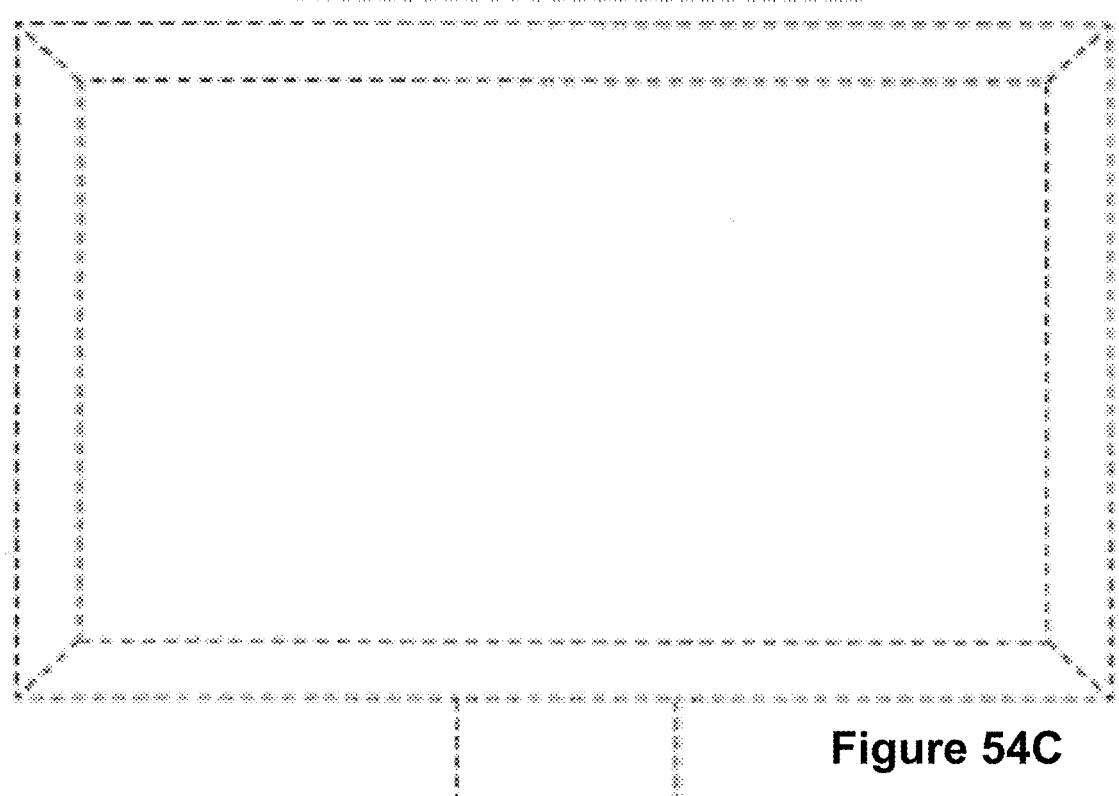
Figure 54D:
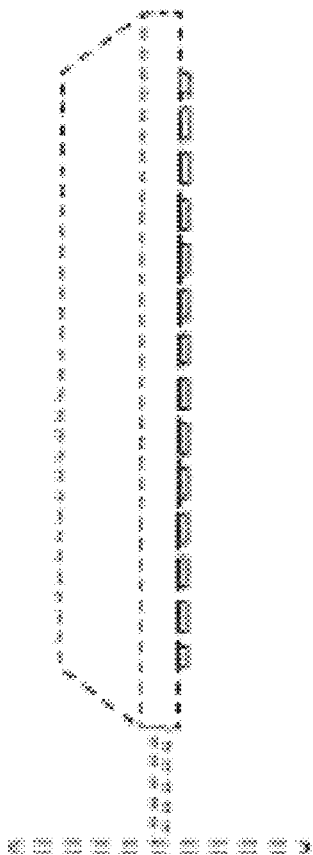
Figure 54E:
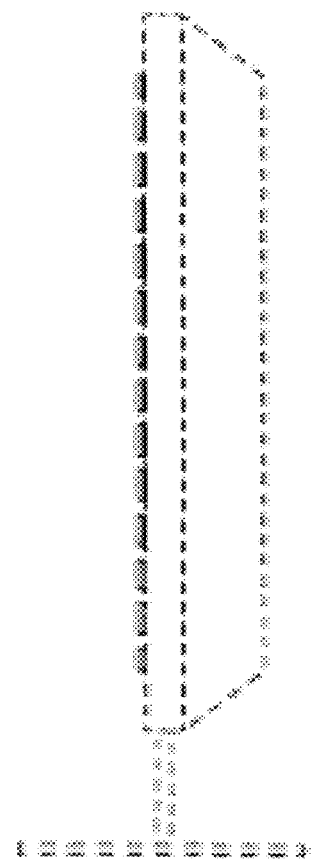
Figure 55A:
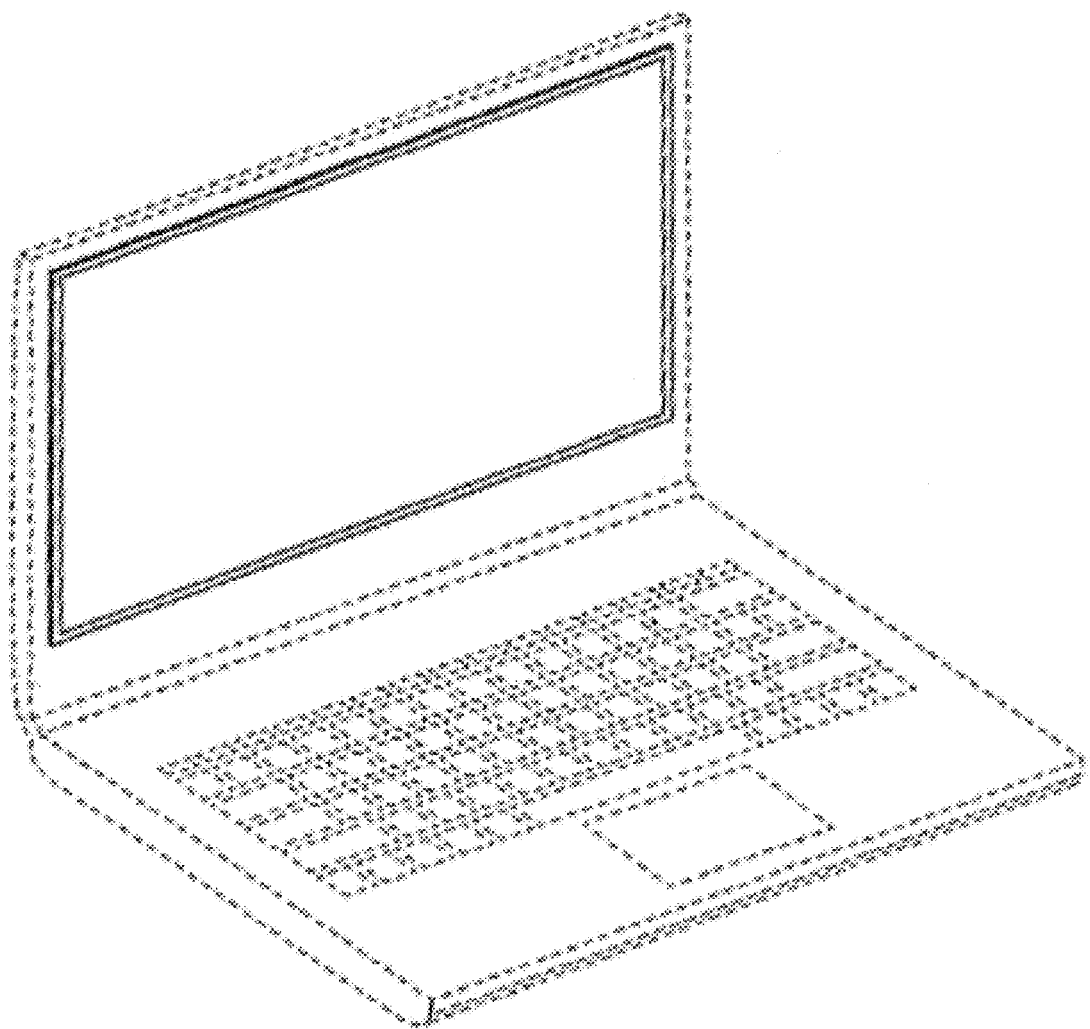
FIGS. 55A-55E illustrate various views of a laptop display with a transmitter antenna having a continuous closed shape on a frontal face of the laptop display, in accordance with some embodiments.
Figures 55B, 55C:
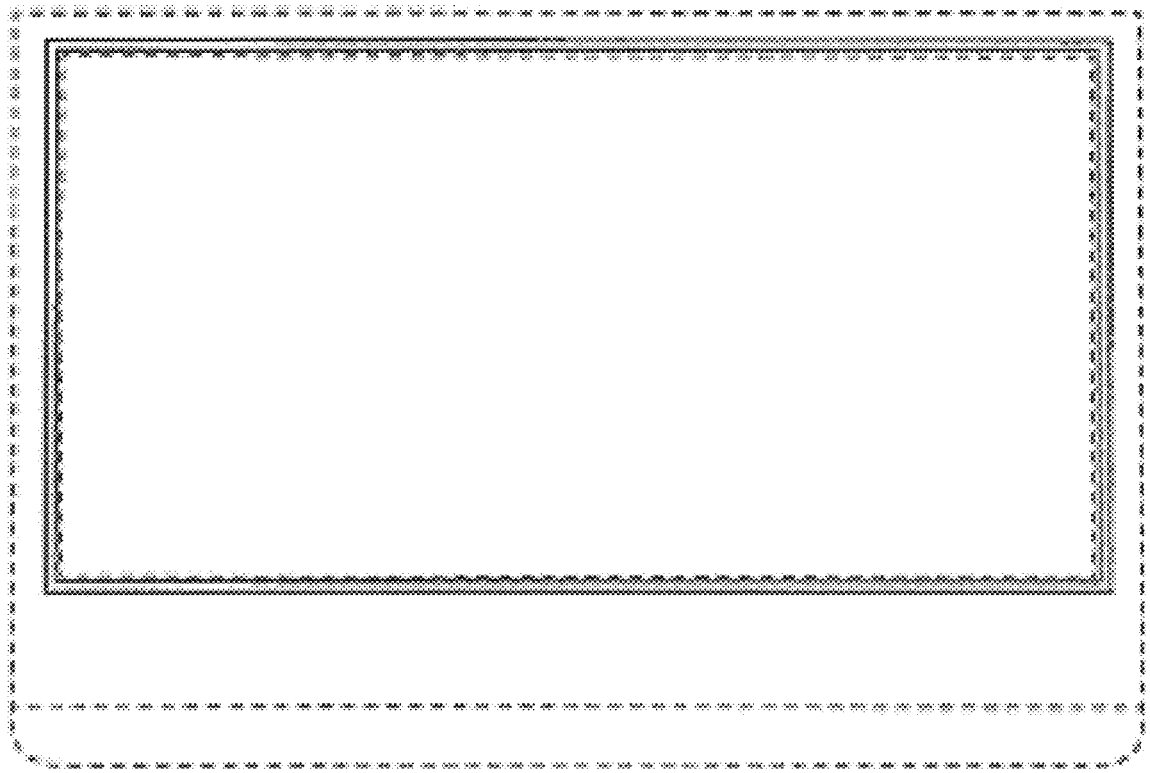
Figure 55D:
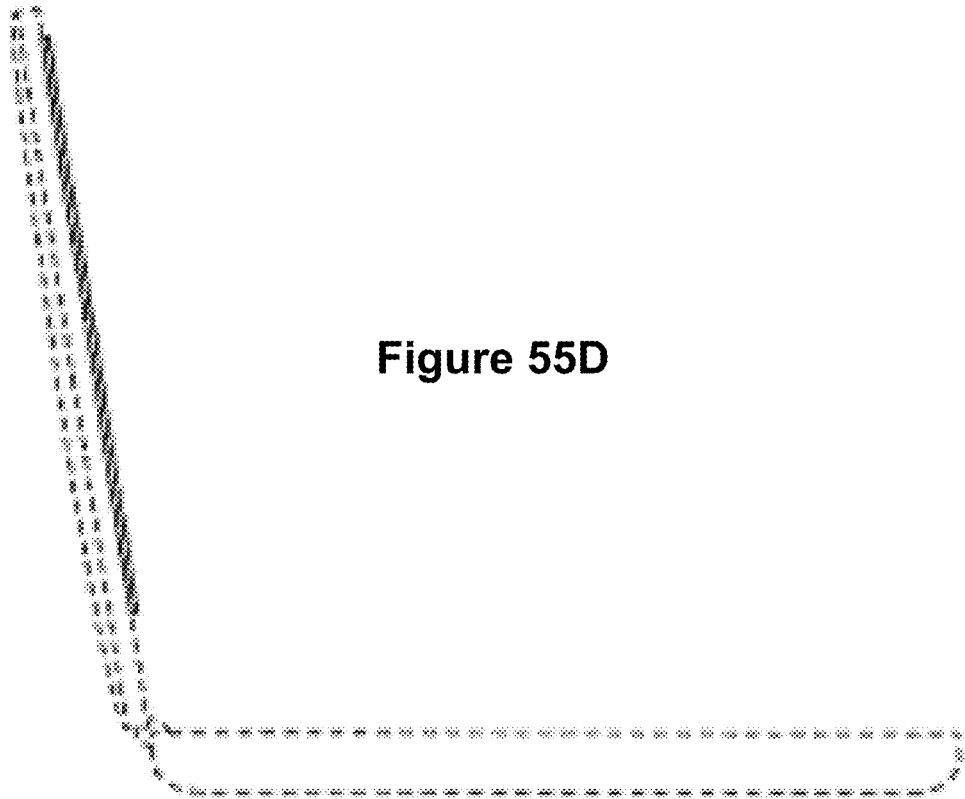
Figure 55E:
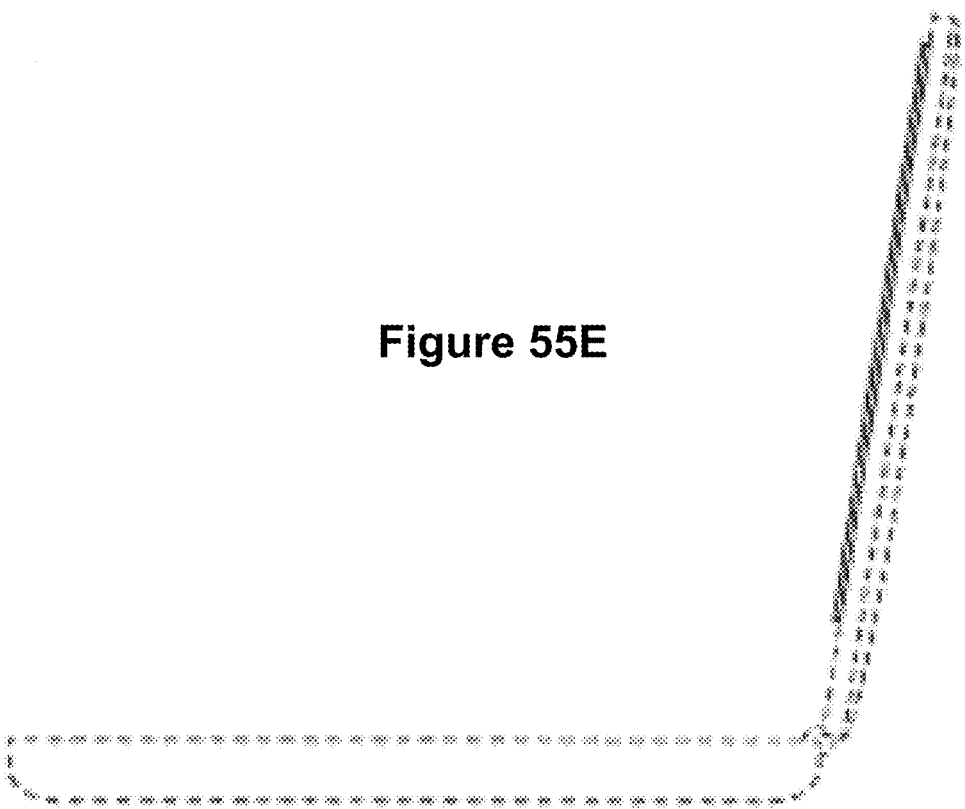
Figure 56A:
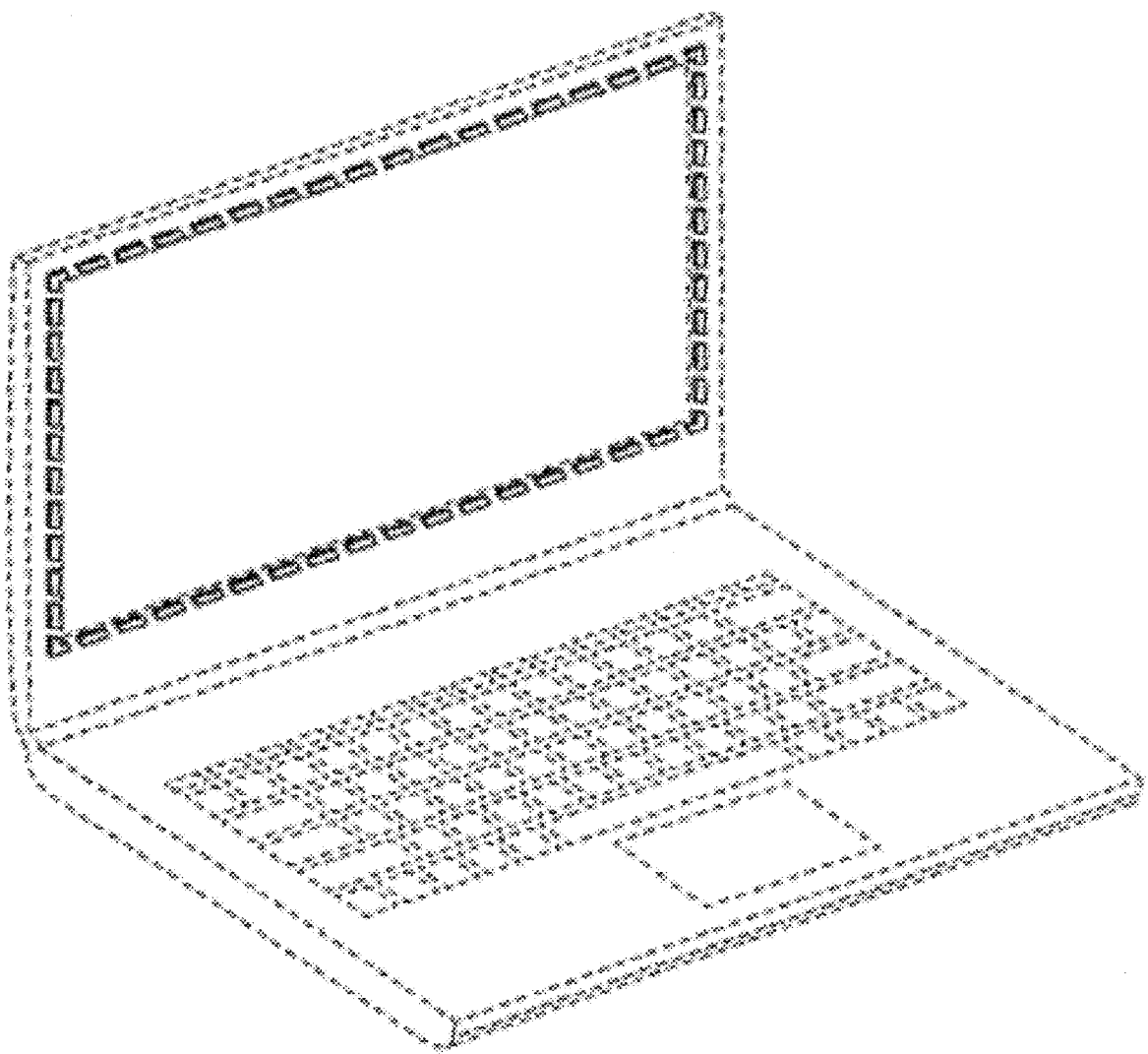
FIGS. 56A-56E illustrate various views of a laptop display with a plurality of transmitter antennas positioned in a segmented closed shape on a frontal face of the laptop display, in accordance with some embodiments.
Figures 56B, 56C:
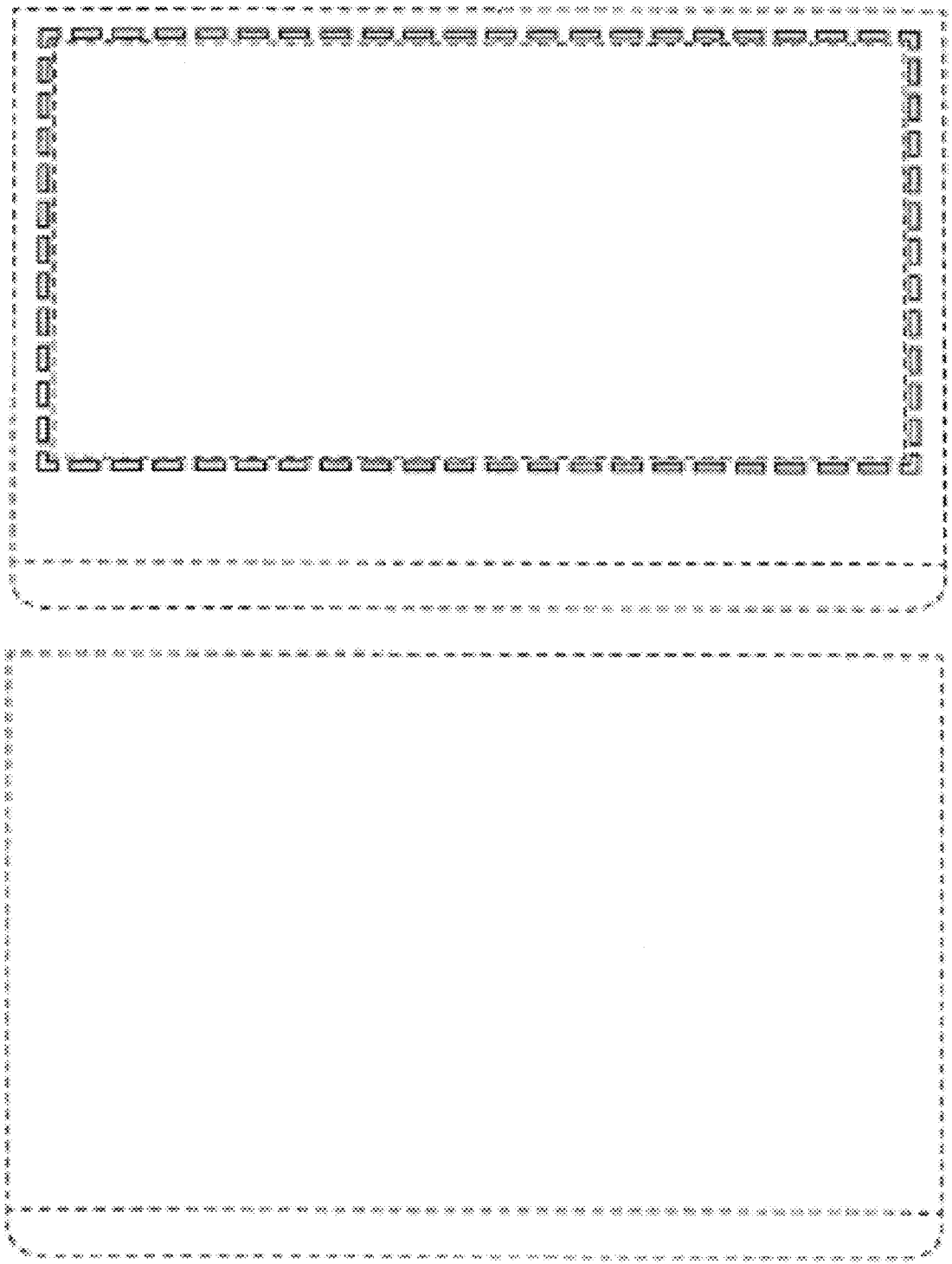
Figure 56D:
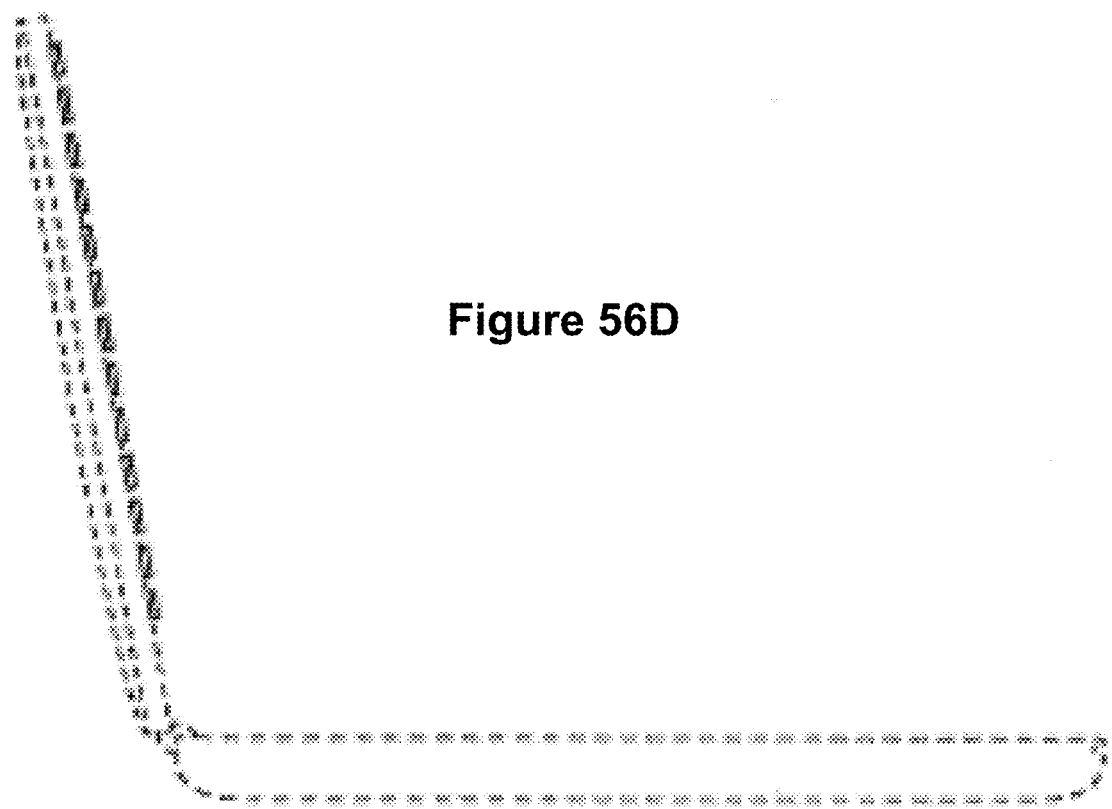
Figure 56E:
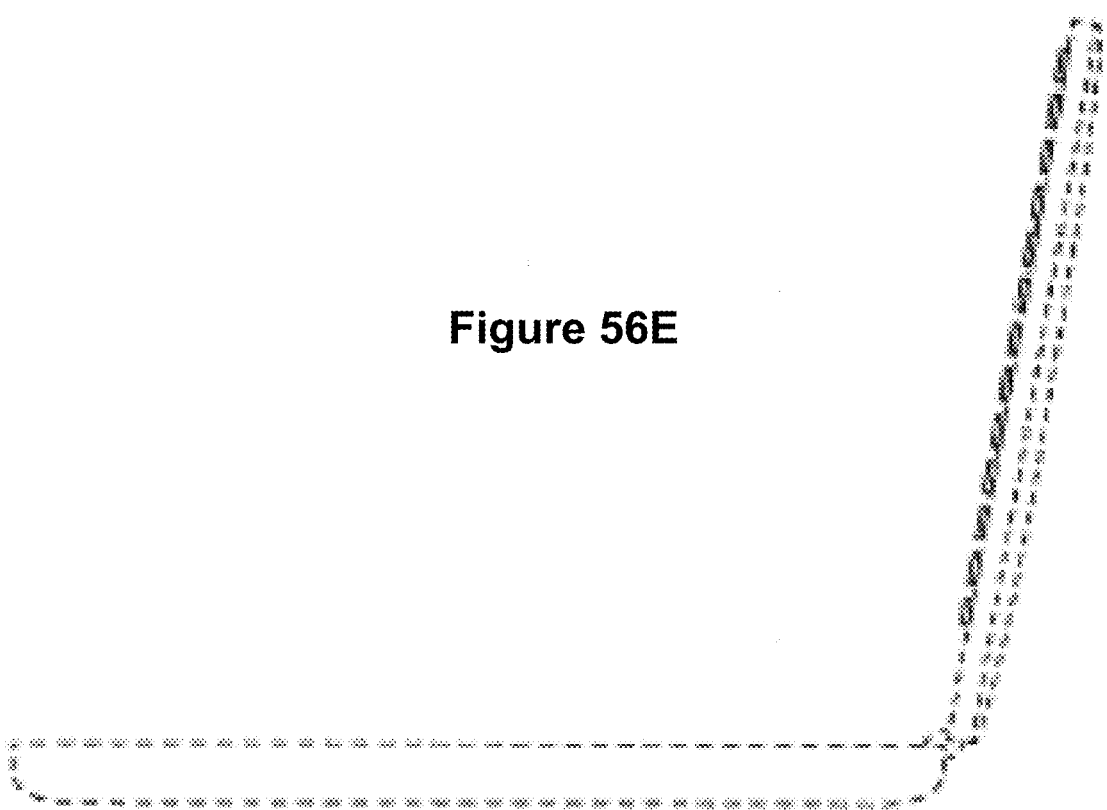

FIG. 50C shows a plurality of transmitter antennas positioned in a bezel of a laptop display in a segmented closed shape to wirelessly transmit energy to a plurality of receiver antennas of electronic devices, according to an embodiment. As illustrated, a laptop display 5026 includes a bezel with a plurality of transmitter antennas 5028 positioned in a segmented closed shape along the bezel. Note that the transmitter antennas 5028 can be coupled to or included with the laptop display 5026. Such coupling can include retrofitting. For example, the transmitter antennas 5028, such as the antenna elements 2202 (FIG. 22) described above, can number at least two hundred, but a lower amount of the transmitter antennas 5028 is possible as well, such as at least two. Also, for example, the transmitter antennas 5028 can be positioned in a continuous closed shape along the bezel. Moreover, for example, the transmitter antennas 5028 can be positioned in an open shape along the bezel, whether continuous or segmented. In other embodiments, at least one of the transmitter antennas 5028 is positioned in another area or areas of the laptop display 5026 in any shape, whether open or closed, or in any manner, whether continuous or segmented, such as a rear face, a sidewall, a floor, or a ceiling, or positioned within the laptop display 5026 or another area or areas of the laptop, such as a keyboard portion.

The laptop display 5026 is rectangular shaped, but other shapes are possible, such as a square, a triangle, a pentagon, a trapezoid, a star, a sphere, a pyramid, or others. The laptop display 5026 is of LCD type, but other display types are possible, such as an LED type, a plasma type, a CRT type, an electrophoretic type, a laser type, a SED type, a FED type, a mechanical type, or others. The laptop display 5026 is coupled to the keyboard portion of the laptop. However, in other embodiments, the laptop display 5026 can be any type of a display, whether battery powered, mains electricity powered, movement powered, or renewable energy powered, such as a photovoltaic cell or a fluid turbine, whether touch enabled or not, whether haptic enabled or not. In other embodiments, laptop display 5026 is a computer display or a television display. Note that the laptop display 5026 can include or be coupled to a speaker or a sound bar.

The transmitter antennas 5028 can be positioned on the bezel, within the bezel, or underneath the bezel. For example, the transmitter antennas 5028 can be embedded in the bezel. As described above, the transmitter antennas 5028 are operably coupled to the RFIC 2204 (FIG. 22) to enable wireless transmission of energy, as described herein. Accordingly, the laptop display 5026 operates as the transmitter 102 (FIG. 1), as described herein. However, in other embodiments, the laptop display 5026 operates as the receiver 120 (FIG. 1), as described herein.

The transmitter antennas 5028 wirelessly transmit energy to a plurality of cellular phones 5030. Each of the cellular phones 5030 includes a storage device, such as a battery or a capacitor. Each of such storage devices provides stored energy for operation of each of the cellular phones 5030. Each of the cellular phones 5030 also includes or is coupled to the receiver 120, as described herein. The receiver 120 includes at least one antenna element 4904 (FIG. 49A). The receiver 120 is coupled to the storage device and configured to interface with the wirelessly transmitted energy, as described herein, such that each storage device of the cellular phones 5030 is at least partially charged thereby. Note that although the cellular phones 5030 are shown, such depiction is an example and other devices of any type can be used, where such devices include or are coupled to the receiver 120, as described herein. For example, such devices can comprise any type of medical equipment.

FIGS. 51A-51E show various views of a display with a transmitter antenna having a continuous closed shape on a frontal face of the display, according to an embodiment. Note that the transmitter antenna is not flush with the display. However, in other embodiments, the transmitter antenna is at least partially flush with the display. In yet other embodiments, the transmitter antenna is at least partially recessed into the display. Note that any permutations or combinations of flush or recessed transmitter antenna configurations are possible, in whole or in part. Also, such display can be a computer display or a television display, as described herein.

FIGS. 52A-52E show various views of a display with a plurality of transmitter antennas positioned in a segmented closed shape on a frontal face of the display, according to an embodiment. Note that the transmitter antennas are not flush with the display. However, in other embodiments, at least one of the transmitter antennas is at least partially flush with the display. In yet other embodiments, at least one of the transmitter antennas is at least partially recessed into the display. Note that any permutations or combinations of flush or recessed transmitter antenna configurations are possible, in whole or in part for at least one transmitter antenna. Also, such display can be a computer display or a television display, as described herein.

FIGS. 53A-53E show various views of a display with a transmitter antenna having a continuous closed shape on a frontal face of the display, according to an embodiment. Note that the transmitter antenna is not flush with the display. However, in other embodiments, the transmitter antenna is at least partially flush with the display. In yet other embodiments, the transmitter antenna is at least partially recessed into the display. Note that any permutations or combinations of flush or recessed transmitter antenna configurations are possible, in whole or in part. Also, such display can be a computer display or a television display, as described herein.

FIGS. 54A-54E show various views of a display with a plurality of transmitter antennas positioned in a segmented closed shape on a frontal face of the display, according to an embodiment. Note that the transmitter antennas are not flush with the display. However, in other embodiments, at least one of the transmitter antennas is at least partially flush with the display. In yet other embodiments, at least one of the transmitter antennas is at least partially recessed into the display. Note that any permutations or combinations of flush or recessed transmitter antenna configurations are possible, in whole or in part for at least one transmitter antenna. Also, such display can be a computer display or a television display, as described herein.

FIGS. 55A-55E show various views of a laptop display with a transmitter antenna having a continuous closed shape on a frontal face of the laptop display, according to an embodiment. Note that the transmitter antenna is not flush with the laptop display. However, in other embodiments, the transmitter antenna is at least partially flush with the laptop display. In yet other embodiments, the transmitter antenna is at least partially recessed into the laptop display. Note that any permutations or combinations of flush or recessed transmitter antenna configurations are possible, in whole or in part.

FIGS. 56A-56E show various views of a laptop display with a plurality of transmitter antennas positioned in a segmented closed shape on a frontal face of the laptop display, according to an embodiment. Note that the transmitter antennas are not flush with the laptop display. However, in other embodiments, at least one of the transmitter antennas is at least partially flush with the laptop display. In yet other embodiments, at least one of the transmitter antennas is at least partially recessed into the laptop display. Note that any permutations or combinations of flush or recessed transmitter antenna configurations are possible, in whole or in part for at least one transmitter antenna.

FIGS. 49-56 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 49-56.

Presented below are example receivers and methods for maximum power point transfer.

A receiver may include: (i) a plurality of antenna elements configured to receive a wireless signal comprising energy resulting from a constructive interference pattern of a plurality of wireless power transmission signal waves emitted from a visual output device, (ii) a plurality of rectifiers corresponding to the antenna elements and configured to rectify the energy received by the antenna elements, where the rectifiers comprise a first rectifier and a second rectifier, (iii) an input boost converter coupled to the first rectifier, configured to step up the energy rectified by the first rectifier, and configured to determine at least one of a global power maximum and a local power maximum produced in the first rectifier, and (iv) a controller coupled to the input boost converter and the second rectifier, configured to determine an available energy at the second rectifier, configured to determine a maximum power point (MPP) value from the first rectifier via the input boost converter, and configured to transmit an operational instruction to the input boost converter to further step up the energy rectified by the first rectifier.

In some embodiments, the input boost converter comprises a second controller coupled to the controller.

In some embodiments, the operational instruction comprises data to configure the input boost converter to further step up the energy rectified by the first rectifier to the global power maximum.

In some embodiments, the controller is configured to index the available energy and the MPP value in a look-up table.

In some embodiments, the controller is configured to compare the available energy to the MPP value and determine the operational instruction thereby.

In some embodiments, the receiver comprises an output boost converter, the controller is configured to determine a load requirement for the receiver, and the controller is configured to control an operation of at least one of the input boost converter and the output boost converter based on the load requirement.

In some embodiments, the receiver comprises a storage element coupled to the input boost converter and configured to store at least a portion of the first energy as rectified by the first rectifier, input into the input boost converter, and output from the input boost converter.

In some embodiments, the receiver comprises a communication component, an output boost converter, and a storage element coupled to the output boost converter, the controller is configured to obtain a measurement of a voltage from at least one of the first rectifier, the input boost converter, the storage element, and the output boost converter, and the controller is configured to communicate the measurement to a load via the communication component.

In some embodiments, the controller is configured to control an operation of the output boost converter by adjusting a load current limit at the output boost converter.

In another receiver, the receiver may include: (i) a first antenna element configured to receive a first wireless signal comprising a first energy resulting from a first constructive interference pattern of a first plurality of wireless power transmission waves emitted from a visual output device, (ii) a first rectifier coupled to the first antenna element and configured to rectify the first energy received by the first antenna element, (iii) a second antenna element configured to receive a second wireless signal comprising a second energy resulting from a second constructive interference pattern of a second plurality of wireless power transmission signal waves emitted from the visual output device, (iv) a second rectifier coupled to the second antenna element and configured to rectify the second energy received by the second antenna element, (v) an input boost converter coupled to the first rectifier, configured to step up the first energy rectified by the first rectifier, and configured to determine at least one of a global power maximum and a local power maximum produced in the first rectifier, and (vi) a controller coupled to the input boost converter and the second rectifier, configured to determine an available energy at the second rectifier based on the second energy, configured to determine a MPP value from the first rectifier via the input boost converter, and configured to transmit an operational instruction to the input boost converter to further step up the first energy rectified by the first rectifier.

A method may include: (i) receiving, by a first antenna element of a receiver, a first wireless signal comprising a first energy resulting from a first constructive interference pattern of a first plurality of wireless power transmission waves emitted from a visual output device, (ii) rectifying, by a first rectifier of the receiver, the first energy received by the first antenna element, (iii) receiving, by a second antenna element of the receiver, a second wireless signal comprising a second energy resulting from a second constructive interference pattern of a second plurality of wireless power transmission signal waves emitted from the visual output device, (iv) rectifying, by a second rectifier of the receiver, the second energy received by the second antenna element, (v) stepping up, by an input boost converter of the receiver, the first energy rectified by the first rectifier, (vi) determining, by the input boost converter of the receiver, at least one of a global power maximum and a local power maximum produced in the first rectifier, (vii) determining, by a controller of the receiver, an available energy at the second rectifier based on the second energy, (viii) determining, by the controller of the receiver, a MPP value from the first rectifier via the input boost converter, and (ix) transmitting, by the controller of the receiver, an operational instruction to the input boost converter to further step up the first energy rectified by the first rectifier.

FIGS. 57-62 illustrate systems and methods for wireless power transmission with selective range and multiple adaptive pocket-forming, in accordance with some embodiments.

Figure 57:
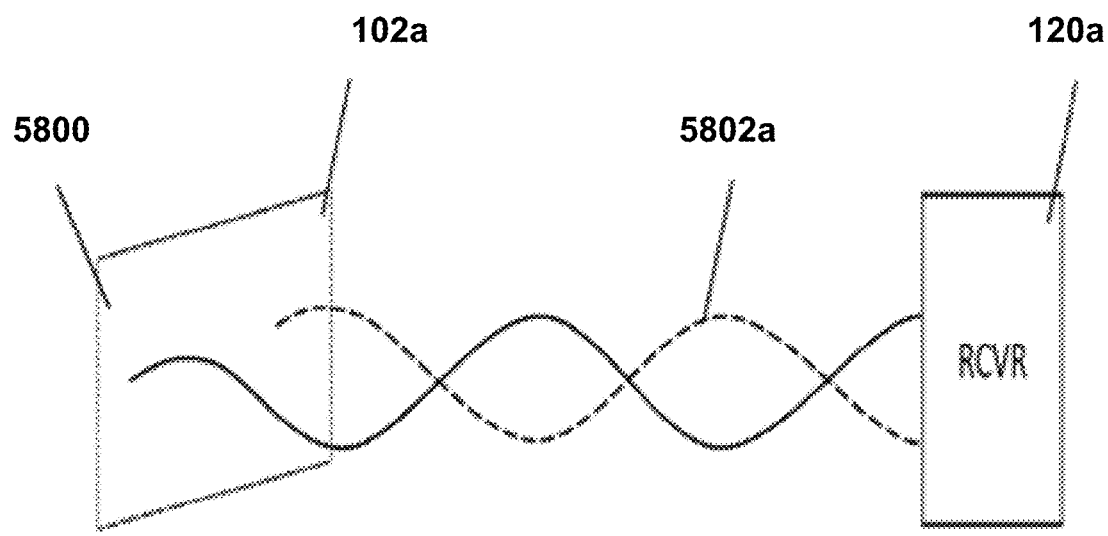
FIGS. 57 and 58 illustrate waveforms for wireless power transmission with selective range, which may get unified in a single waveform, in accordance with some embodiments.
Figure 58:
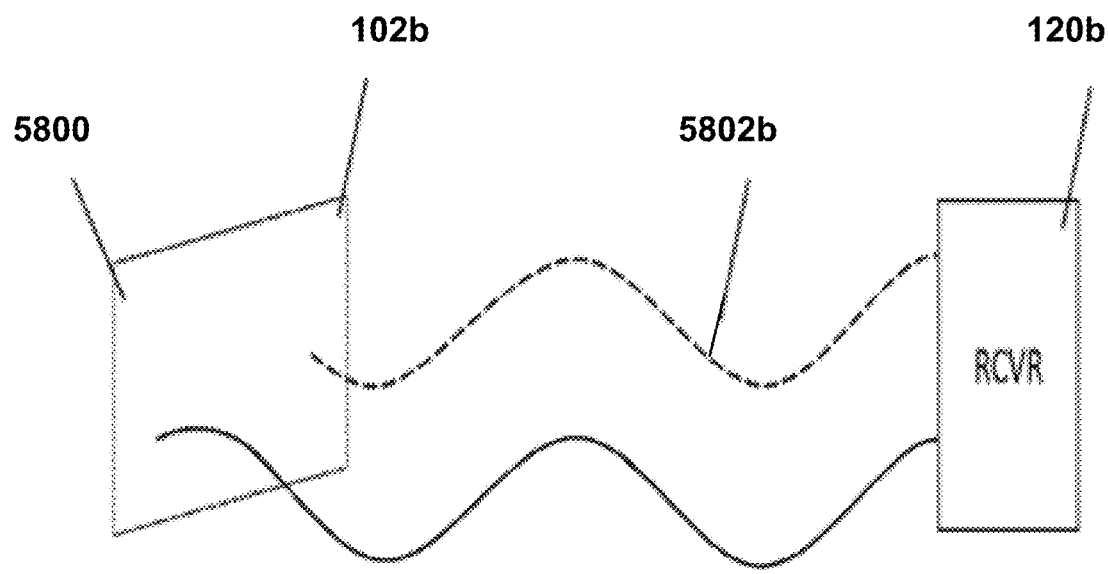

FIGS. 57 and 58 show an exemplary system 5800 implementing wireless power transmission principles that may be implemented during exemplary pocket-forming processes. A transmitter 102 (FIG. 1) comprising a plurality of antennas in an antenna array, may adjust the phase and amplitude, among other possible attributes, of power transmission waves 5802, being transmitted from antennas of the transmitter 102. As shown in FIG. 57, in the absence of any phase or amplitude adjustment, power transmission waves 5802*a* may be transmitted from each of the antennas and will arrive at different locations and have different phases. These differences are often due to the different distances from each antenna element of the transmitter 102*a* to a receiver 120*a* or receivers 120*a*, located at the respective locations.

Continuing with FIG. 57, a receiver 120*a* may receive multiple power transmission signals, each comprising power transmission waves 5802*a*, from multiple antenna elements of a transmitter 102*a*; the composite of these power transmission signals may be essentially zero, because in this example, the power transmission waves add together destructively. That is, antenna elements of the transmitter 102*a* may transmit the exact same power transmission signal (i.e., comprising power transmission waves 5802*a* having the same features, such as phase and amplitude), and as such, when the power transmission waves 5802*a* of the respective power transmission signals arrive at the receiver 120*a*, they are offset from each other by 180 degrees. Consequently, the power transmission waves 5802*a* of these power transmission signals "cancel" one another. Generally, signals offsetting one another in this way may be referred to as "destructive," and thus result in "destructive interference."

In contrast, as shown in FIG. 58, for so-called "constructive interference," signals comprising power transmission waves 5802*b* that arrive at the receiver exactly "in phase" with one another, combine to increase the amplitude of each signal, resulting in a composite that is stronger than each of the constituent signals. In the illustrative example in FIG. 58, note that the phase of the power transmission waves 5802*a* in the transmit signals are the same at the location of transmission, and then eventually add up destructively at the location of the receiver 120*a*. In contrast, in FIG. 58, the phase of the power transmission waves 5802*b* of the transmit signals are adjusted at the location of transmission, such that they arrive at the receiver 120b in phase alignment, and consequently they add constructively. In this illustrative example, there will be a resulting pocket of energy located around the receiver 120b in FIG. 58; and there will be a transmission null located around receiver in FIG. 57.

Figure 59:
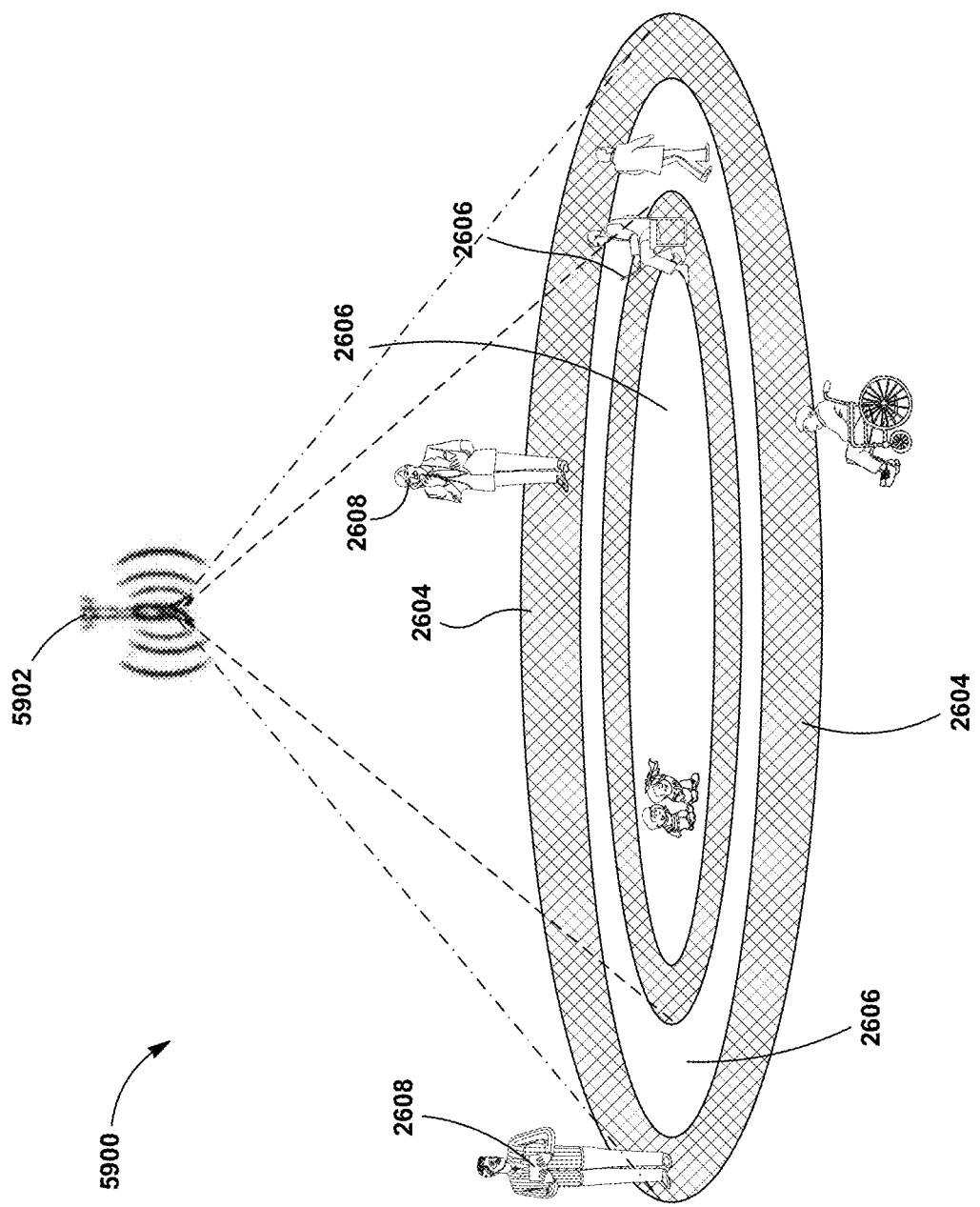
FIG. 59 illustrates wireless power transmission with selective range, where a plurality of pockets of energy may be generated along various radii from transmitter, in accordance with some embodiments.

FIG. 59 depicts wireless power transmission with selective range 5900, where a transmitter 5902 may produce pocket-forming for a plurality of receivers associated with electrical devices 2608 (FIG. 26). Transmitter 5902 may generate pocket-forming through wireless power transmission with selective range 5900, which may include one or more wireless charging radii 2604 (FIG. 26) and one or more radii of a transmission null at a particular physical location 2606. A plurality of electronic devices 2608 may be charged or powered in wireless charging radii 2604. Thus, several spots of energy may be created, such spots may be employed for enabling restrictions for powering and charging electronic devices 2608. As an example, the restrictions may include operating specific electronics in a specific or limited spot, contained within wireless charging radii 2604. Furthermore, safety restrictions may be implemented by the use of wireless power transmission with selective range 5900, such safety restrictions may avoid pockets of energy over areas or zones where energy needs to be avoided, such areas may include areas including sensitive equipment to pockets of energy and/or people which do not want pockets of energy over and/or near them. In embodiments such as the one shown in FIG. 59, the transmitter 5902 may comprise antenna elements found on a different plane than the receivers associated with electrical devices 2608 in the served area. For example, the receivers of electrical devices 2608 may be in a room where a transmitter 5902 may be mounted on the ceiling. Selective ranges for establishing pockets of energy using power transmission waves, which may be represented as concentric circles by placing an antenna array of the transmitter 5902 on the ceiling or other elevated location, and the transmitter 5902 may emit power transmission waves that will generate 'cones' of energy pockets. In some embodiments, the transmitter 5902 may control the radius of each charging radii 2604, thereby establishing intervals for service area to create pockets of energy that are pointed down to an area at a lower plane, which may adjust the width of the cone through appropriate selection of antenna phase and amplitudes.

Figure 60A:
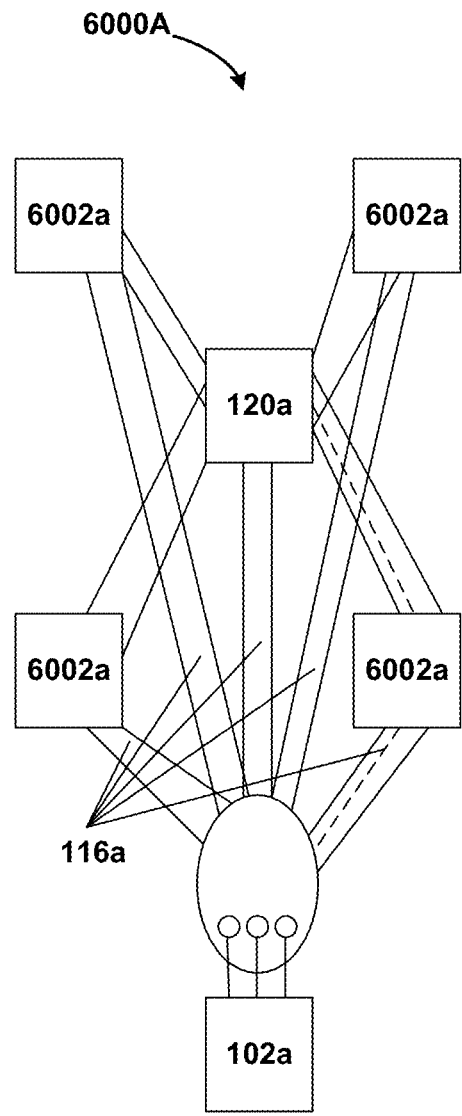
FIGS. 60A and 60B illustrate diagrams of architecture for wirelessly charging client computing platform, in accordance with some embodiments.
Figure 60B:
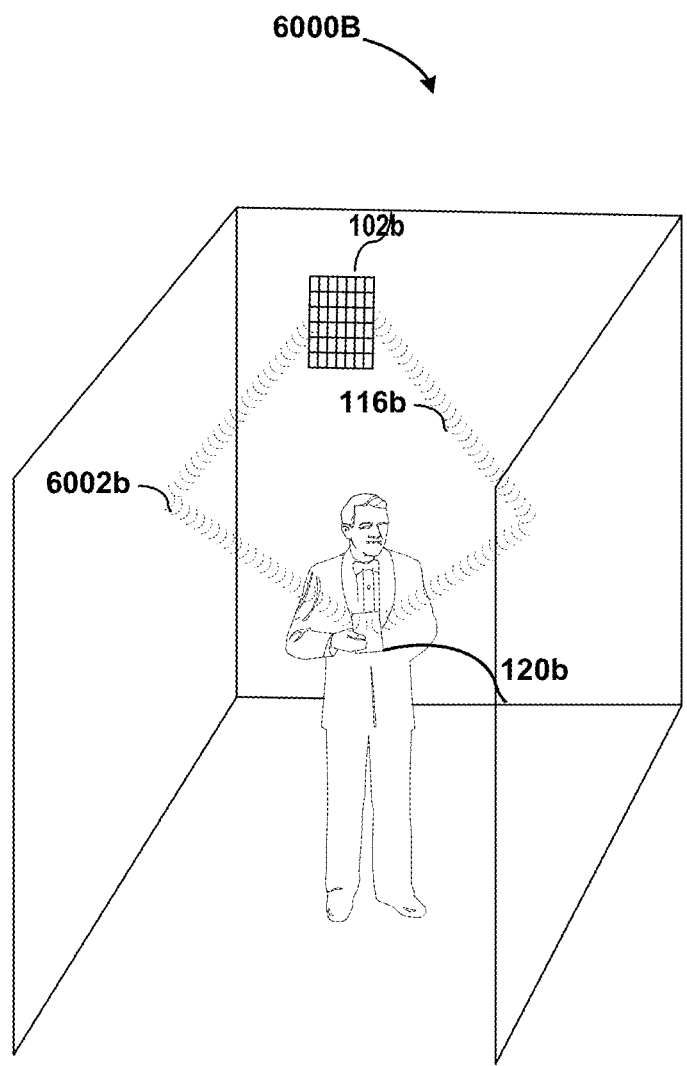

FIGS. 60A and 60B illustrate a diagram of architecture 6000A and 6000B for a wirelessly charging client computing platform, according to an exemplary embodiment. In some implementations, a user may be inside a room and may hold on his hands an electronic device (e.g., a smartphone, tablet). In some implementations, electronic device may be on furniture inside the room. The electronic device may include a receiver 120a, 120b (FIG. 1) either embedded to the electronic device or as a separate adapter connected to electronic device. Receivers 120a and 120b may include all the components described in FIG. 1. A transmitter 102a, 102b may be hanging on one of the walls of the room right behind user. Transmitters 102a and 102b may also include all the components described in FIG. 1.

As user may seem to be obstructing the path between receivers 120a, 120b and transmitters 102a, 102b, RF waves may not be easily aimed to the receivers 120a, 120b in a linear direction. However, since the short signals generated from receivers 120a, 120b may be omni-directional for the type of antenna element used, these signals may bounce over the walls 6002a, 6002b until they reach transmitters 102a, 102b. A hot spot 6002a, 6002b may be any item in the room which will reflect the RF waves. For example, a large metal clock on the wall may be used to reflect the RF waves to a user's cell phone.

A micro controller in the transmitter adjusts the transmitted signal from each antenna based on the signal received from the receiver. Adjustment may include forming conjugates of the signal phases received from the receivers and further adjustment of transmit antenna phases taking into account the built-in phase of antenna elements. The antenna element may be controlled simultaneously to steer energy in a given direction. The transmitters 102a, 102b may scan the room and look for hot spots 6002a, 6002b. Once calibration is performed, transmitters 102a, 102b may focus RF waves in a channel following a path that may be the most efficient paths. Subsequently, RF signals 116a, 116b (FIG. 1) may form a pocket of energy on a first electronic device and another pocket of energy in a second electronic device while avoiding obstacles such as user and furniture.

When scanning the service area, the room in FIGS. 60A and 60B, the transmitters 102a, 102b may employ different methods. As an illustrative example, but without limiting the possible methods that can be used, the transmitters 102a, 102b may detect the phases and magnitudes of the signal coming from the receiver and use those to form the set of transmit phases and magnitudes, for example by calculating conjugates of them and applying them at transmit. As another illustrative example, the transmitter may apply all possible phases of transmit antennas in subsequent transmissions, one at a time, and detect the strength of the pocket of energy formed by each combination by observing information related to the signal from the receivers 120a, 120b. Then the transmitters 102a, 102b repeat this calibration periodically. In some implementations, the transmitters 102a, 102b do not have to search through all possible phases, and can search through a set of phases that are more likely to result in strong pockets of energy based on prior calibration values. In yet another illustrative example, the transmitters 102a, 102b may use preset values of transmit phases for the antennas to form pockets of energy directed to different locations in the room. The transmitter may for example scan the physical space in the room from top to bottom and left to right by using preset phase values for antennas in subsequent transmissions. The transmitters 102a, 102b then detect the phase values that result in the strongest pocket of energy around the receivers 120a, 120b by observing the signal from the receivers 120a, 120b. It should be appreciated that there are other possible methods for scanning a service area for heat mapping that may be employed, without deviating from the scope or spirit of the embodiments described herein. The result of a scan, whichever method is used, is a heat-map of the service area (e.g., room, store) from which the transmitters 102a, 102b may identify the hot spots that indicate the best phase and magnitude values to use for transmit antennas in order to maximize the pocket of energy around the receiver.

The transmitters 102a, 102b may use the Bluetooth connection to determine the location of the receivers 120a, 120b, and may use different non-overlapping parts of the RF band to channel the RF waves to different receivers 120a, 120b. In some implementations, the transmitters 102a, 102b may conduct a scan of the room to determine the location of the receivers 120a, 120b and form pockets of energy that are orthogonal to each other, by virtue of non-overlapping RF transmission bands. Using multiple pockets of energy to direct energy to receivers may inherently be safer than some alternative power transmission methods since no single transmission is very strong, while the aggregate power transmission signal received at the receiver is strong.

Figure 60C:
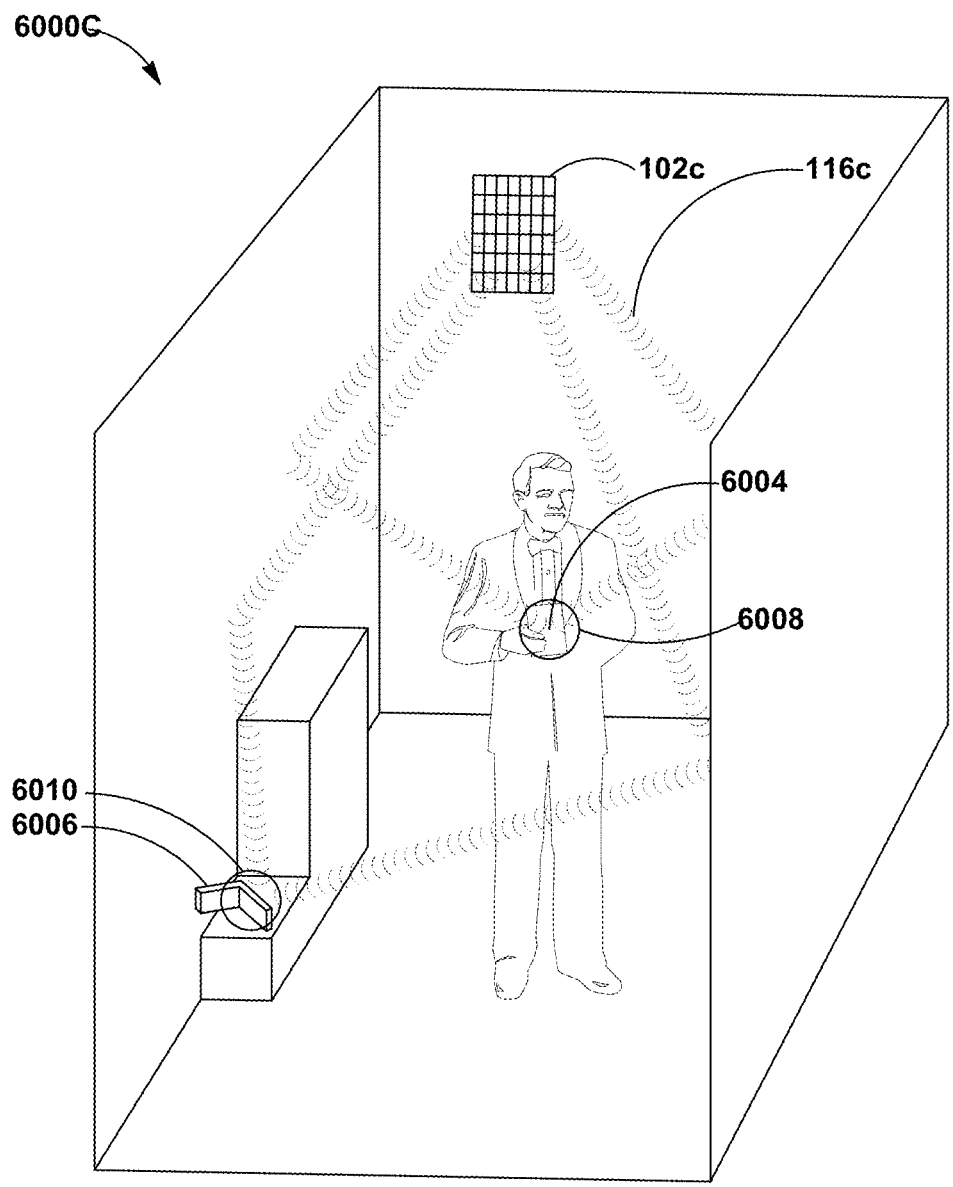
FIG. 60C illustrates multiple adaptive pocket-forming, in accordance with some embodiments.

FIG. 60C is an exemplary illustration of multiple adaptive pocket-forming 6000C. In this embodiment, a user may be inside a room and may hold on his hands an electronic device, which in this case may be a tablet 6004. In addition, smartphone 6006 may be on furniture inside the room. Tablet 6004 and smartphone 6006 may each include a receiver either embedded to each electronic device or as a separate adapter connected to tablet 6004 and smartphone 6006. Receiver may include all the components described in FIG. 1. A transmitter 102c (FIG. 1) may be hanging on one of the walls of the room right behind user. Transmitter 102c may also include all the components described in FIG. 1. As user may seem to be obstructing the path between receiver and transmitter 102c, RF waves 116c (FIG. 1) may not be easily aimed to each receiver in a line of sight fashion. However, since the short signals generated from receivers may be omni-directional for the type of antenna elements used, these signals may bounce over the walls until they find transmitter 102c. Almost instantly, a microcontroller which may reside in transmitter 102c, may recalibrate the transmitted signals, based on the received signals sent by each receiver, by adjusting gain and phases and forming a convergence of the power transmission waves such that they add together and strengthen the energy concentrated at that location—in contrast to adding together in a way to subtract from each other and diminish the energy concentrated at that location, which is called "destructive interference" and conjugates of the signal phases received from the receivers and further adjustment of transmit antenna phases taking into account the built-in phase of antenna elements. Once calibration is performed, transmitter 102c may focus RF waves following the most efficient paths. Subsequently, a pocket of energy 6008 may form on tablet 6004 and another pocket of energy 6010 in smartphone 6006 while taking into account obstacles such as user and furniture. The foregoing property may be beneficial in that wireless power transmission using multiple pocket-forming 6000C may inherently be safe as transmission along each pocket of energy is not very strong, and that RF transmissions generally reflect from living tissue and do not penetrate.

Once transmitter 102c identities and locates receiver, a channel or path can be established by knowing the gain and phases coming from receiver. Transmitter 102c may start to transmit controlled RF waves 116c that may converge in 3-dimensional space by using a minimum of two antenna elements. These RF waves 116c may be produced using an external power source and a local oscillator chip using a suitable piezoelectric material. RF waves 116c may be controlled by RFIC that may include a proprietary chip for adjusting phase and/or relative magnitudes of RF signals, which may serve as inputs for antenna elements to form constructive and destructive interference patterns (pocket-forming). Pocket-forming may take advantage of interference to change the directionality of the antenna elements where constructive interference generates a pocket of energy and deconstructive interference generates a null in a particular physical location. Receiver may then utilize pocket of energy produced by pocket-forming for charging or powering an electronic device, for example a laptop computer and a smartphone and thus effectively providing wireless power transmission.

Multiple pocket-forming 6000C may be achieved by computing the phase and gain from each antenna of transmitter to each receiver. The computation may be calculated independently because multiple paths may be generated by antenna elements from transmitter to antenna elements from receiver.

An example of the computation for at least two antenna elements may include determining the phase of the signal from the receiver and applying the conjugate of the receive parameters to the antenna elements for transmission.

In some embodiments, two or more receivers may operate at different frequencies to avoid power losses during wireless power transmission. This may be achieved by including an array of multiple embedded antenna elements in transmitter 102c. In one embodiment, a single frequency may be transmitted by each antenna in the array. In other embodiments, some of the antennas in the array may be used to transmit at a different frequency. For example, ½ of the antennas in the array may operate at 2.4 GHz while the other ½ may operate at 5.8 GHz. In another example, ⅓ of the antennas in the array may operate at 900 MHz, another ⅓ may operate at 2.4 GHz, and the remaining antennas in the array may operate at 5.8 GHz.

In another embodiment, each array of antenna elements may be virtually divided into one or more antenna elements during wireless power transmission, where each set of antenna elements in the array can transmit at a different frequency. For example, an antenna element of the transmitter may transmit power transmission signals at 2.4 GHz, but a corresponding antenna element of a receiver may be configured to receive power transmission signals at 5.8 GHz. In this example, a processor of the transmitter may adjust the antenna element of the transmitter to virtually or logically divide the antenna elements in the array into a plurality patches that may be fed independently. As a result, ¼ of the array of antenna elements may be able to transmit the 5.8 GHz needed for the receiver, while another set of antenna elements may transmit at 2.4 GHz. Therefore, by virtually dividing an array of antenna elements, electronic devices coupled to receivers can continue to receive wireless power transmission. The foregoing may be beneficial because, for example, one set of antenna elements may transmit at about 2.4 GHz and other antenna elements may transmit at 5.8 GHz, and thus, adjusting a number of antenna elements in a given array when working with receivers operating at different frequencies. In this example, the array is divided into equal sets of antenna elements (e.g., four antenna elements), but the array may be divided into sets of different amounts of antenna elements. In an alternative embodiment, each antenna element may alternate between select frequencies.

The efficiency of wireless power transmission as well as the amount of power that can be delivered (using pocket-forming) may be a function of the total number of antenna elements used in a given receivers and transmitters system. For example, for delivering about one watt at about 15 feet, a receiver may include about 80 antenna elements while a transmitter may include about 256 antenna elements. Another identical wireless power transmission system (about 1 watt at about 15 feet) may include a receiver with about 40 antenna elements, and a transmitter with about 512 antenna elements. Reducing in half the number of antenna elements in a receiver may require doubling the number of antenna elements in a transmitter. In some embodiments, it may be beneficial to put a greater number of antenna elements in transmitters than in receivers because of cost, because there will be much fewer transmitters than receivers in a system-wide deployment. However, the opposite can be achieved, e.g., by placing more antenna elements on a receiver than on a transmitter as long as there are at least two antenna elements in a transmitter 102c.

Figure 61:
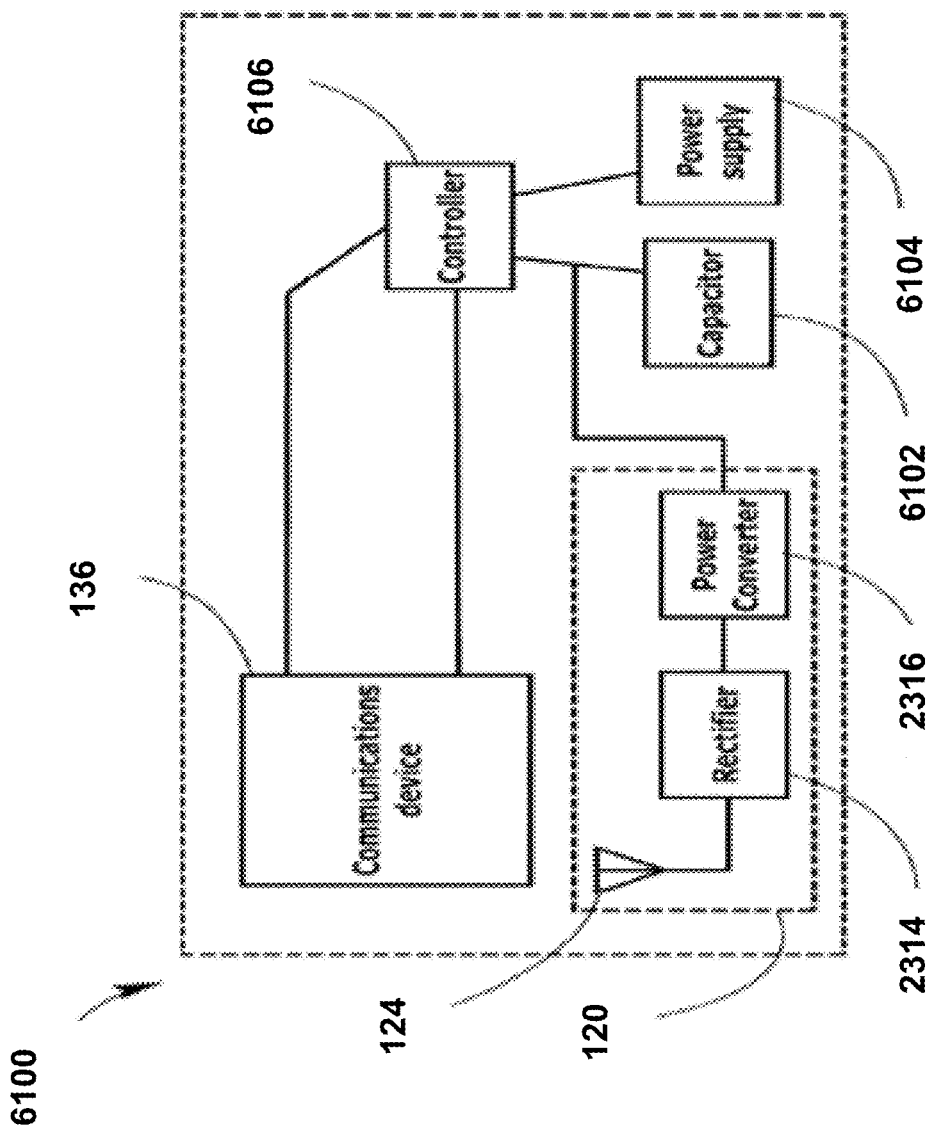
FIG. 61 illustrates an electronic device including at least one embedded receiver and at least one auxiliary power supply for improving a portable electronic device's main power supply life, in accordance with some embodiments.

FIG. 61 illustrates an electronic device 6100 comprising an embedded receiver 120 (FIG. 1), which may be integrated into the electronic device 6100 or otherwise detachably coupled within the electronic device 6100, as discussed above with reference to FIG. 1. The electronic device 6100 may further comprise a capacitor that may store electrical energy and serve the function of an auxiliary power supply 6102, which may improve the period of time the electronic device 6100 may be used, particularly after a power supply 6104 is depleted.

An embedded receiver 120 may comprise one or more antenna elements 124 capable of receiving power transmission waves from a pocket of energy and converting energy caused by the power transmission waves into AC voltage, as discussed above with reference to FIG. 1. The embedded receiver 120 may further comprise a rectifier circuit 2314 (FIG. 23) configured to convert the AC voltage into direct current (DC) voltage, and a power converter 2316 (FIG. 23) configured to provide a constant DC voltage output to the capacitor serving as the auxiliary power supply 6102. Although in the exemplary system 6100 embodiment, the auxiliary power supply 6102 may be a capacitor, it should be appreciated that the auxiliary power supply 6102 may be any combination of one or more electrical circuits capable of receiving, storing, and supplying a charge on behalf of the electronic device 6100; for example, the auxiliary power supply 6102 may be a battery. Capacitors, however, may be easily and cheaply be manufactured in small sizes, which may be beneficial for many wearable devices. The auxiliary power supply 6102 may fully or partially power the electronic device 6100, and thus the auxiliary power supply 6102 may fully or partially decrease the power demands placed on a power supply 6102 by the electronic device 6100.

In some embodiments, an embedded receiver 120 in the electronic device 6100 may use a communications device 136 (FIG. 1) also embedded within the electronic device 6100 to communicate with a transmitter and/or other electronic devices. In some embodiments, the electronic device 6100 may not include a communications device 136, and thus the embedded receiver 120 may comprise a communications component (not shown). In some embodiments, the electronic device 6100 may comprise a micro-controller 6106 circuit that not only control the intended functions of the electronic device 6100, but the micro-controller may also manage power loads on auxiliary power supply 6102 and/or power supply 6104. In other embodiments, the micro-controller 6106 may be embedded within the embedded receiver 120. The foregoing configuration may be beneficial when implementing receivers on electronic devices that may not include a micro-controller 6106, for example, an ordinary analog wristwatch.

Figure 62A:
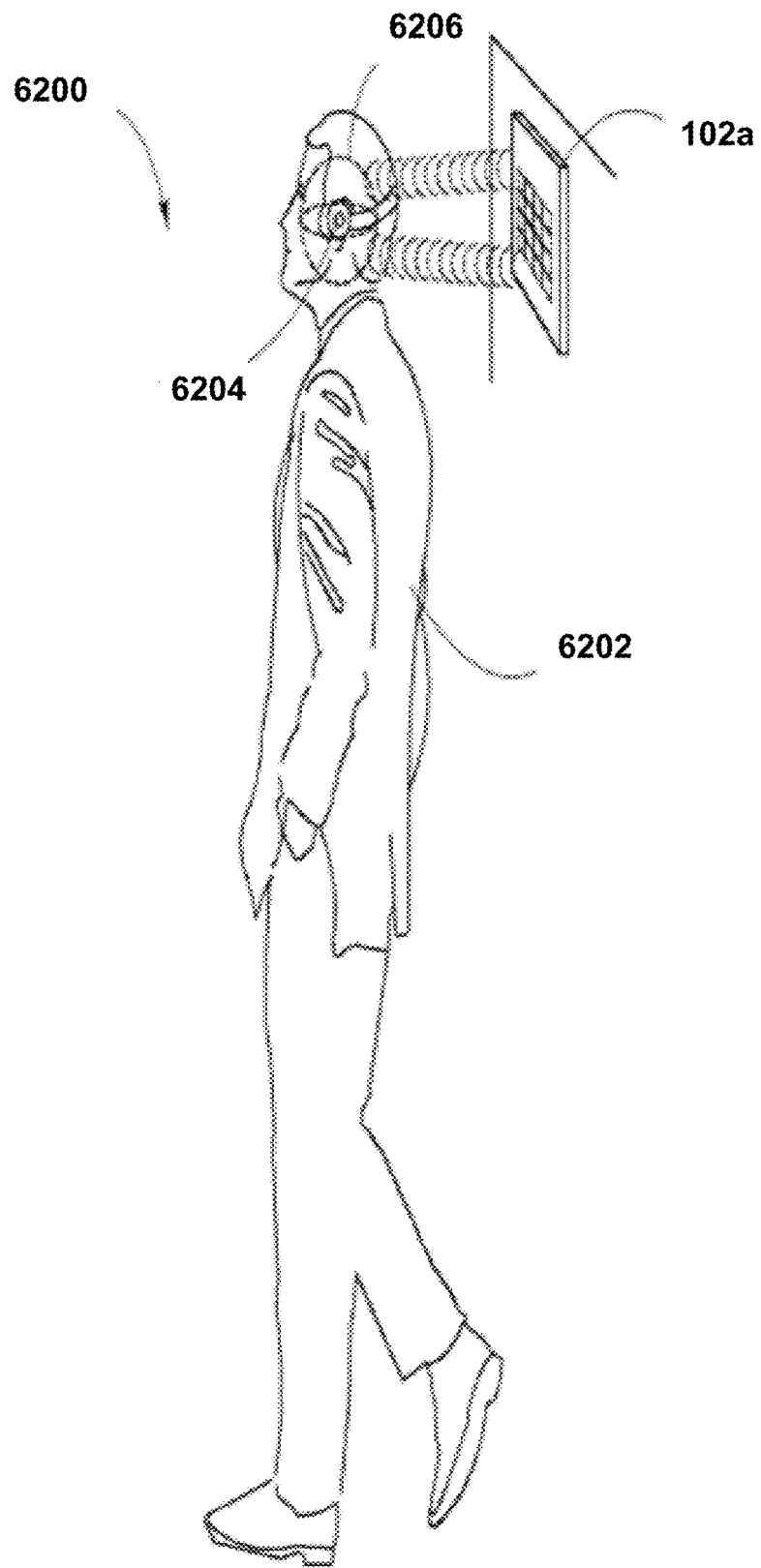
FIG. 62A illustrates an electronic wearable device in the form of a Bluetooth headset including at least one embedded receiver for providing wireless power transmission, in accordance with some embodiments.

FIG. 62A illustrates implementation of a wireless power transmission system 6200 in which an individual user 6202 may be wearing a Bluetooth-enabled headset 6204, and wireless power transmissions may be powering the headset 6204, through pocket-forming established by transmitter 102a (FIG. 1). The headset 6204 may include an embedded receiver (not shown) for utilizing pockets of energy 6206 to power a capacitor (not shown) embedded within the headset 6204. In some embodiments, such as the exemplary system 6200, the embedded receiver may utilize a native Bluetooth chip (not shown) of the headset 6204 for communicating wirelessly with the transmitter 102a. The headset 6204 may use a native, embedded micro-controller to manage power loads being generated between the capacitor and the native power supply of the headset 6204. In some implementations, the transmitter 102a may be located within a house or on other such buildings where the individual 6202 may be frequently located, thereby providing convenient charging to the headset 6204. In other embodiments, the transmitter 102a may be placed inside a car belonging to the individual 6202 to power the headset 6204 while driving.

Figure 62B:
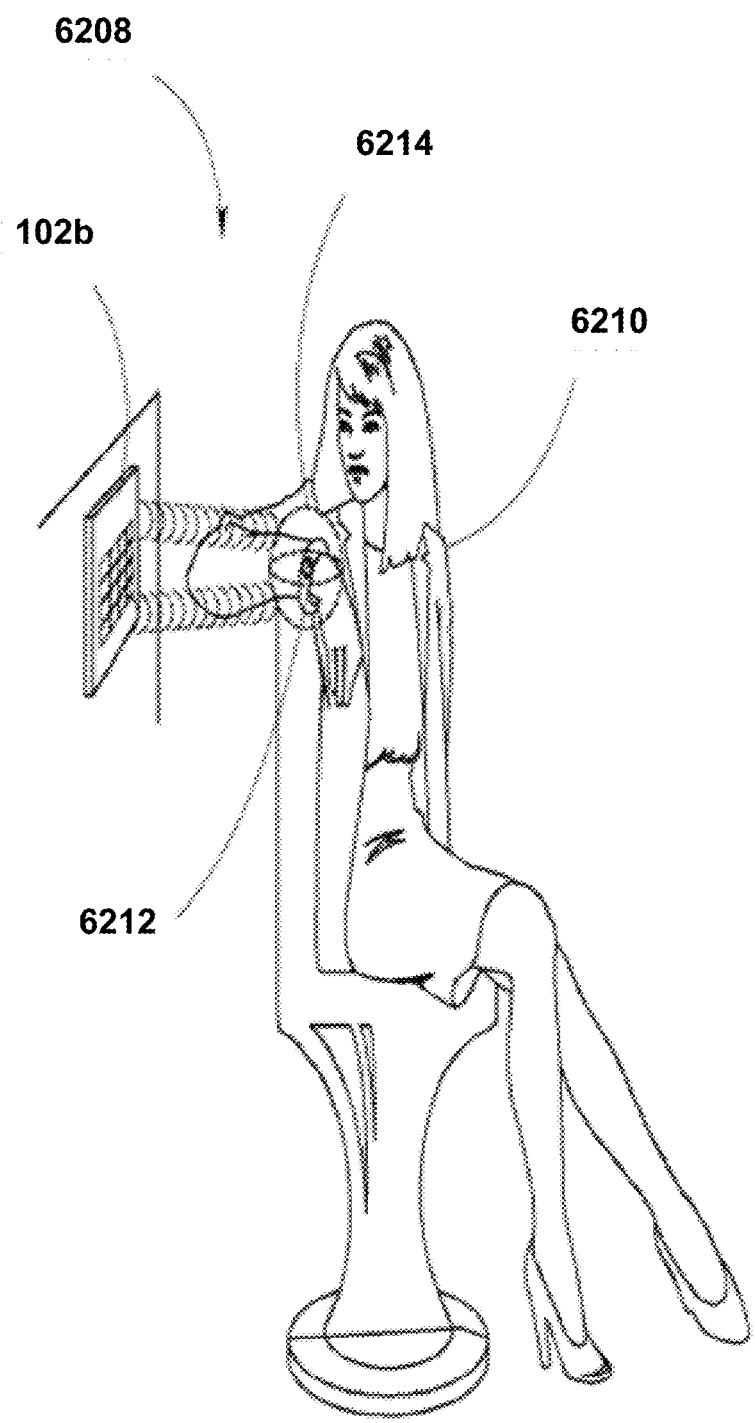
FIG. 62B illustrates an electronic wearable device in the form of a wristwatch including at least one embedded receiver, for providing wireless power transmission, in accordance with some embodiments.

FIG. 62B illustrates wireless power transmission 6208 where an individual user 6210 may be wearing a typical digital wristwatch 6210, which may be powered by power transmission waves from pockets of energy established by a transmitter 102b (FIG. 1). The wristwatch 6212 may include an embedded receiver (not shown) for utilizing pockets of energy 6214 to provide power (i.e., electrical charge) to a capacitor (not shown) embedded within the wristwatch 6212. However, typical wristwatches, such as wristwatch 6212, may not include a Bluetooth chip or a micro-controller, in which case, the embedded receiver may include an optional communications device and an embedded micro-controller. In this embodiment, communications device can be a Bluetooth chip.

Figure 62C:
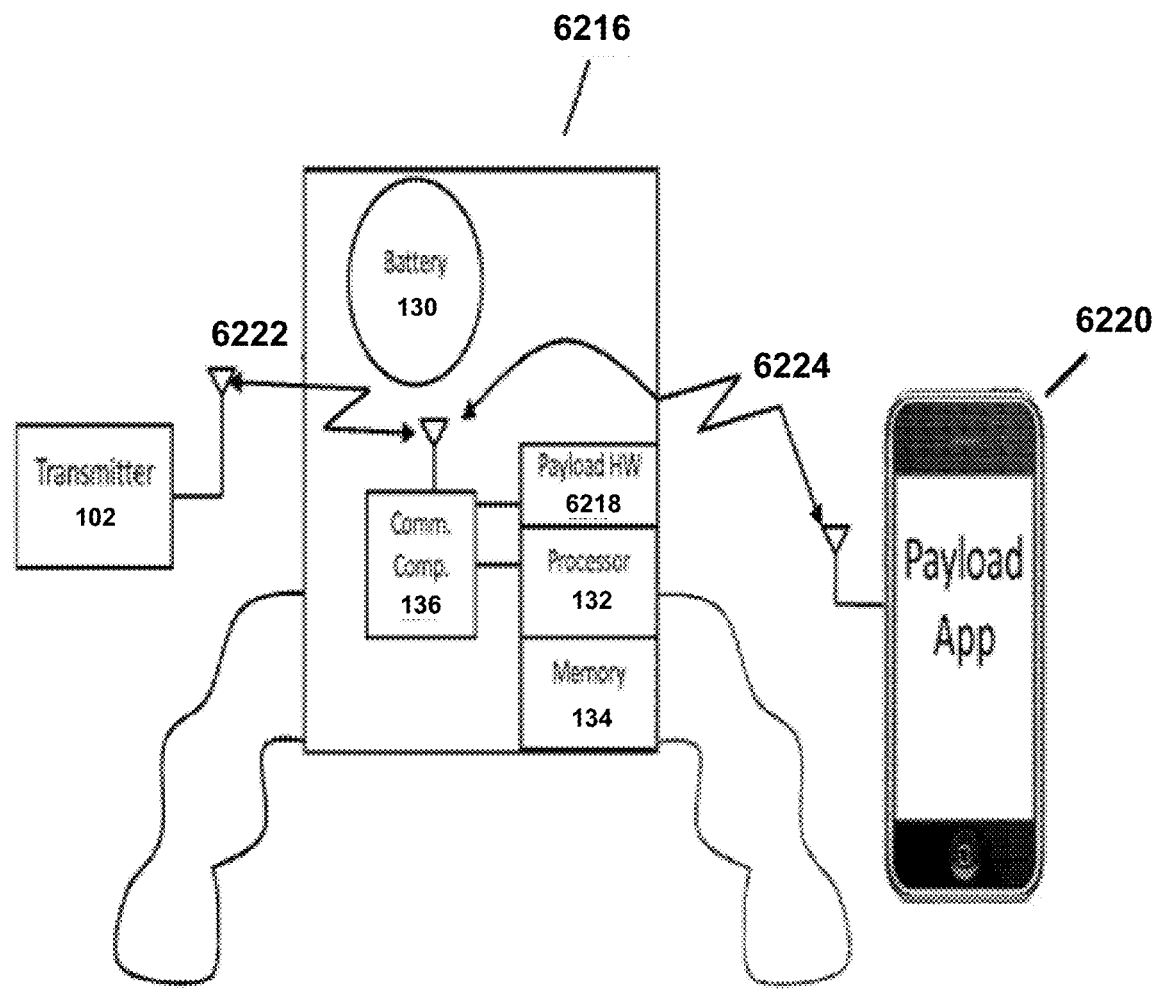
FIG. 62C illustrates a schematic representation of a wearable device, in accordance with some embodiments.

FIG. 62C shows a schematic representation of a wearable device 6216, which may be a type of computing device comprising a receiver, as described above. A wearable 6216 may be an article of clothing (e.g., shirt, hat, pants, shoes) or other personal accessory (e.g., jewelry, belt, book bag, wristband, watch, anklet) of a user, and may comprise a computing processor 132 (FIG. 1), payload hardware 6218, a battery 130 (FIG. 1), and a communication component 136 (FIG. 1), which in FIG. 62C is a Bluetooth® low-energy antenna and processor (BLE). The wearable 6216 may further comprise memory 134 (FIG. 1) for storing the computer's programming and payload application data.

A computing processor 132 of the wearable 6216 may be integrated circuitry capable of performing power and payload functionality for the wearable 6216. The wearable 6216 may communicate payload application data with a smart device 6220 to provide the user with the desired functionality, for which the wearable 6216 was designed. For example, if the wearable 6216 is a heart rate monitor, then the payload application executed by the smart device 6220 may be a software application that provides features such as heart rate tracking, dietary data, exercise data, among other heart health information and features. In this example, the payload application data may be heart rate measurements observed by the wearable 6216. The smart device 6220 may be any computing device comprising a processor capable of executing the payload application and that is capable of communicating payload application instructions and data over a wireless protocol, such as Bluetooth®, NFC, BLE, RFID, Wi-Fi, and the like. Non-limiting examples of the smart device 6220 may include a smartphone, laptop, or other computing device.

Payload hardware 6218 may be circuitry of the wearable 6216 capable of executing various processes and tasks in accordance with the features of the payload application and functional purpose of the wearable 6216. Returning to the example in which the wearable 6216 is a heart rate monitor, which may be worn on a user's wrist: in this example, the payload hardware 6218 may comprise components capable of measuring the user's heart rate and blood pressure. The processor 132 of the wearable 6216 may receive the measurements from the payload hardware 6218 and then produce payload application data from the measurements. Although the examples of a wearable 6216 describe a heart rate monitor, it should be appreciated that the wearable 6216 may be any device that is worn by the user and provides various computing features (e.g., smart watches, smart glasses). As such, a wearable 6216 may comprise payload hardware 6218 rendering the wearable 6216 capable of the intended functionality.

In some embodiments, the wearable 6216 may comprise a battery 130 capable of holding an electrical charge. The battery 130 may power the computing processor 132 and the payload hardware 6218. In some embodiments, the battery 130 of the wearable 6216 may receive the electrical charge from the communications component 136, which may comprise a receiver configured to harvest energy from pockets of energy produced by transmitters 102 (FIG. 1). In some embodiments, the wearable 6216 may forego a battery 130 and may be powered entirely by electrical energy harvested by a receiver of the communications component 136.

A communications component 136 may be circuitry of the wearable 6216 that may communicate control signals 6222 with a transmitter 102 data using one or more wireless communications protocols (e.g., Bluetooth, BLE, Wi-Fi, NFC, RFID). The communications component 136 may communicate payload application data over a second communication channel 6224 with a smart device 6220 executing a payload application associated with the functionality of the wearable 6216. The wearable 6216 may communicate control signals 6222 with a transmitter 102 concurrently to communicating the payload application data to the smart device 6220 over the second communication channel 6224. In some embodiments, the wearable 6216 may communicate simultaneously with both the transmitter 102 and the smart device 6220. In such embodiments, the communications component 136 and the processor 132 may be capable of receiving and processing the respective communications signals simultaneously. In some embodiments, the wearable 6216 may alternate communications between the transmitter 102 and the smart device 6220. In such embodiments, the processor 132 and communications component 136 may communicate with each device for a predetermined period of time.

Control signals 6222 may contain control data produced by the processor 132 and communications component 136 of the wearable 6216, which the transmitter 102 may use to adjust power transmission waves that the transmitter 102 emits to generate pockets of energy. The control data of the control signals 6222 may contain, for example, data indicating the location of the wearable relative to the transmitter 102, and data indicating the amount of power that the wearable 6216 has effectively harvested from a pocket of energy generated by the transmitter 102. In some cases, the control signals 6222 may include an advertisement signal for establishing a first communication between the transmitter 102 and the communications component 136 of the wearable 6216.

Payload application data collected by the payload hardware 6218 may be transmitted to the smart device 6220, over a second communication channel 6224. The second communication channel 6224 hosting the payload application data may implement any wireless communication protocol capable of transmitting the payload application data from the wearable to the smart device 6220. In some embodiments, the communications component 136 may transmit the payload application data at a given interval. In some embodiments, the payload application data may be transmitted at the moment the wearable 6216 and the smart device 6220 are brought into communicative proximity; in such embodiments, the second communication channel 6224 may be automatically established, and the smart device 6220 and wearable 6216 may then automatically exchange payload application data collected by the payload hardware 6218 of the wearable 6216.

In some embodiments, the wearable 6216 may comprise memory 134, which may be a non-transitory machine-readable storage media that is capable of storing binary data. In some cases, the memory 134 may store programming associated with the payload application that may be executed by the processor 132 and/or the payload hardware 6218. When the processor 132 executes the programming stored in the memory 134, the payload hardware 6218 may collect measurements and perform various tasks intended to provide the intended functionality of the wearable 6216 and the associated payload application. In some cases, the memory 134 may store control data that may inform transmitters 102 of an optimal waveform and direction for transmitting power transmission waves to establish pockets of energy. In such cases, the wearable 6216 may transmit the control data for the transmitters 102 to determine how the power transmission waves should be produced and transmitted. The processor 132 may continuously update the memory 134 with control data representing more effective ways for the transmitters 102 to produce and transmit power control waves.

A smart device 6220 may be any computing device comprising a processor that executes a payload application associated with the wearable 6216, a communication component that communicates payload application data and instructions with the wearable 6216 over a second communications channel 6224. In some embodiments, communication between wearable and smart device 6220 may be through Bluetooth Low Energy (BLE), Wi-Fi, or other wireless communication protocol. Application payload data may include wearable 6216 status or usage reports, or payload application data generated by the wearable 6216. As an example, for embodiments in which the wearable 6216 is a heart rate monitor, the payload application data may include heart rate measurements or physical exertion data.

A transmitter 102 may be any device that emits power transmission waves that establish a pocket of energy, which may be harvested by receivers and converted to electric energy. The transmitter 102 may transmit power transmission waves to a wireless power receiver, which may be a component of the communications component 136 of the wearable 6216 shown in FIG. 62C. In some embodiments, the wearable 6216 may communicate an advertisement signal to establish a first communication channel, which hosts control data 6222. After establishing the first communication channel hosting control data 6222, the transmitter 102 may then begin communicating control data 6222 with the wearable 6216, to manage delivery of electrical energy to the battery 130 of the wearable 6216. In some embodiments, the wearable 6216 may use the same or a different communication channel to upload application payload data to the transmitter 102, which the transmitter 102 may upload to a server of a computing service associated with the transmitter 102. Control data may include wearable 6216 device status and usage reports.

Figure 62D:
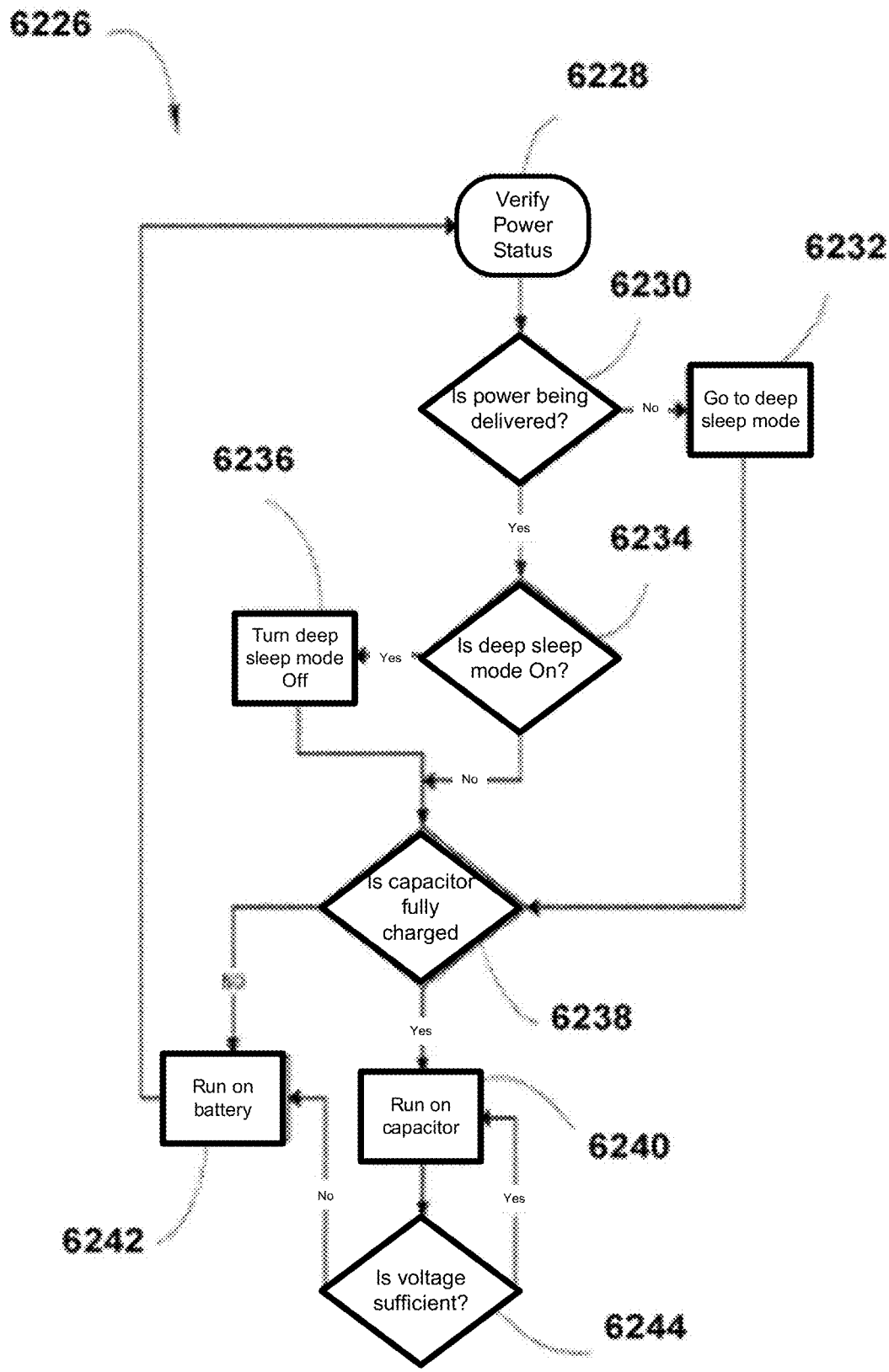
FIG. 62D illustrates an algorithm for managing power loads on an electronic device, in accordance with some embodiments.

FIG. 62D illustrates a logical execution of method 6226 implemented by a controller of a receiver or electronic device. The exemplary method 6226 may be used for managing power loads on auxiliary power supply, which may be in the form of a capacitor and/or a power supply in the form of battery. The method 6226 may begin at a verify power step 6228 where a micro-controller may determine whether power is being delivered to an embedded receiver of the electronic device.

After verifying power step 6228, the micro-controller may continue to a power decision step 6230 where the micro-controller may determine whether to proceed to a deep sleep mode step 6232 or to proceed to a deep sleep mode decision step 6234; the determination may be based on a power delivery status. That is, if power is not being delivered, the micro-controller may proceed to deep sleep mode step 6232 where power saving may be prioritized. On the other hand, if the power is being delivered, the micro-controller may proceed to a deep sleep mode decision step 6234, where the micro-controller may determine whether the electronic device is in deep sleep mode. If the electronic device is in deep sleep mode, then the micro-controller may proceed to a turn deep sleep mode off step 6236, where deep sleep mode may be turned off. After determining a determination of sleep mode status, the micro-controller may proceed to a capacitor charge decision step 6238. However, if the electronic device is not in deep sleep mode, the micro-controller may proceed directly to capacitor charge decision step 6238.

At capacitor charge decision step 6238, the micro-controller determine whether to proceed to an operate on capacitor step 6240, or proceed to an operate on battery step 6242. If auxiliary power supply, in the form of a capacitor, is fully charged, then the micro-controller may proceed to operate on capacitor step 6240 in which a capacitor may provide power to the electronic device. On the other hand, if the auxiliary power supply, in the form of a capacitor, is not fully charged, then the micro-controller may proceed to operate on battery step 6242 where the power supply, in the form of a battery, may provide power to the electronic device.

Referring back to the operate on capacitor step 6240, in some cases a sub-routine may be added where the micro-controller may ordinarily proceed to a voltage verification step 6244. In voltage verification step 6244, the micro-controller may continuously or on predefined time intervals, verify the voltage across the auxiliary power supply to detect and prevent the electronic device from turning off. If the voltage level across the auxiliary power supply is not sufficient for powering the electronic device, the micro-controller may proceed to operate on battery step 6242. Otherwise, the micro-controller may remain at the operate on capacitor step 6240. In many circumstances, where micro-controller reaches an operate on battery step 6242, the method 6226 may begin, again, to verify power delivery status and minimize the power load on the power supply. In addition, when on deep sleep mode step 6232, the micro-controller may proceed to a capacitor charge decision step 6238, in which the micro-controller may decide whether to operate on deep sleep mode and whether to draw energy from power supply or auxiliary power supply.

In other embodiments of the method 6226, the micro-controller may decide to power the electronic device using the power supply and auxiliary power supply simultaneously. This option may be beneficial when the power load on the electronic device is too large for a capacitor to handle alone. However, such a configuration may still diminish the power load on the power supply. In other embodiments, a plurality of capacitors can be used as an auxiliary power supply to compensate for power surges or high power demands.

FIGS. 57-62 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 57-62.

Presented below are example wearable devices and wireless power charging systems.

A wearable device may include: (i) one or more antenna elements configured to extract energy from one or more power transmission waves establishing a pocket of energy and further configured to convert the energy of the power transmission waves to an electrical current, (ii) a communication component configured to transmit to a transmitter one or more control signals indicating a location of the wearable device relative to the transmitter, (iii) a rectifier configured to convert the electrical current produced from the antenna elements from an alternating current (AC) to a direct current (DC), and (iv) a battery configured to store energy from the electrical current.

In some embodiments, the wearable device comprises an auxiliary power supply configured to store energy from the electrical current. Furthermore, in some embodiments, the auxiliary power supply is a capacitor circuit. Furthermore, in some embodiments, the auxiliary power supply is a second battery. Furthermore, in some embodiments, the wearable device is powered by the auxiliary power supply upon the battery of the wearable device being depleted.

In some embodiments, the wearable device comprises a processor configured to monitor a power level of the battery of the device. Furthermore, in some embodiments, the processor is further configured to switch an auxiliary power supply upon determining the battery level is depleted. Furthermore, in some embodiments, the processor is further configured to execute one or more payload application instructions received from a smart device associated with the wearable device.

In some embodiments, the communication component is further configured to broadcast an advertisement signal to a transmitter in response to determining the battery level requires a recharge threshold.

In another wearable device, the wearable device may include: (i) payload hardware configured to capture one or more measurements in accordance with a payload application associated with the wearable device, (ii) a processor configured to execute the payload application according to one or more instructions received from a smart device, and (iii) a communications component configured to communicate payload application data and payload application instructions with the smart device, and (iv) a power supply detachably coupled to a receiver, where the power supply is configured to receive electrical current from the receiver.

In some embodiments, the power supply of the wearable device is a battery configured to store the electrical current.

In some embodiments, the wearable device further comprises a processor configured to determine an amount of energy received from the receiver. Furthermore, in some embodiments, the processor is further configured to charge a battery of the wearable device in response to determining the amount of energy received from the receiver exceeds a threshold amount.

In some embodiments, the wearable device is further configured to receive electrical current stored in a second battery of the receiver.

A wireless power charging system may include: a wearable device comprising: (i) payload hardware configured to capture one or more measurements in accordance with a payload application associated with the wearable device, (ii) a processor configured to execute the payload application according to one or more instructions received from a smart device, and (iii) a communications component configured to communicate payload application data and payload application instructions with the smart device, where the wearable device is detachably coupled to a receiver. In some embodiments, the receiver comprises: (i) one or more antenna elements configured to extract energy from one or more power transmission waves in a pocket of energy and convert the energy of the power transmission wave to an electrical current and (ii) a rectifier configured to convert the electrical current produced from the antenna elements from an AC to a DC, where the DC current is provided to the wearable device.

In some embodiments, the receiver further comprises a second communications component configured to transmit to a transmitter one or more control signals indicating a location of the wearable device relative to the transmitter.

In some embodiments, the wearable device further comprises a battery storing energy from the electrical current output from the receiver.

In some embodiments, the receiver further comprises a DC-to-DC converter circuit configured to generate a consistent output of DC current from the DC current produced by the rectifier.

In some embodiments, the receiver further comprises a battery configured to store the energy from DC current produced by the rectifier.

FIGS. 63A-63H show exemplary graphical user interface (GUI) embodiments for status and usage reporting (graphical user interface demo). Primary display options (as seen at the left side of various display views, for example the screen shot of FIG. 63A) include dashboard, devices, locations, transmitters, accounts, and settings.

Figure 63A:
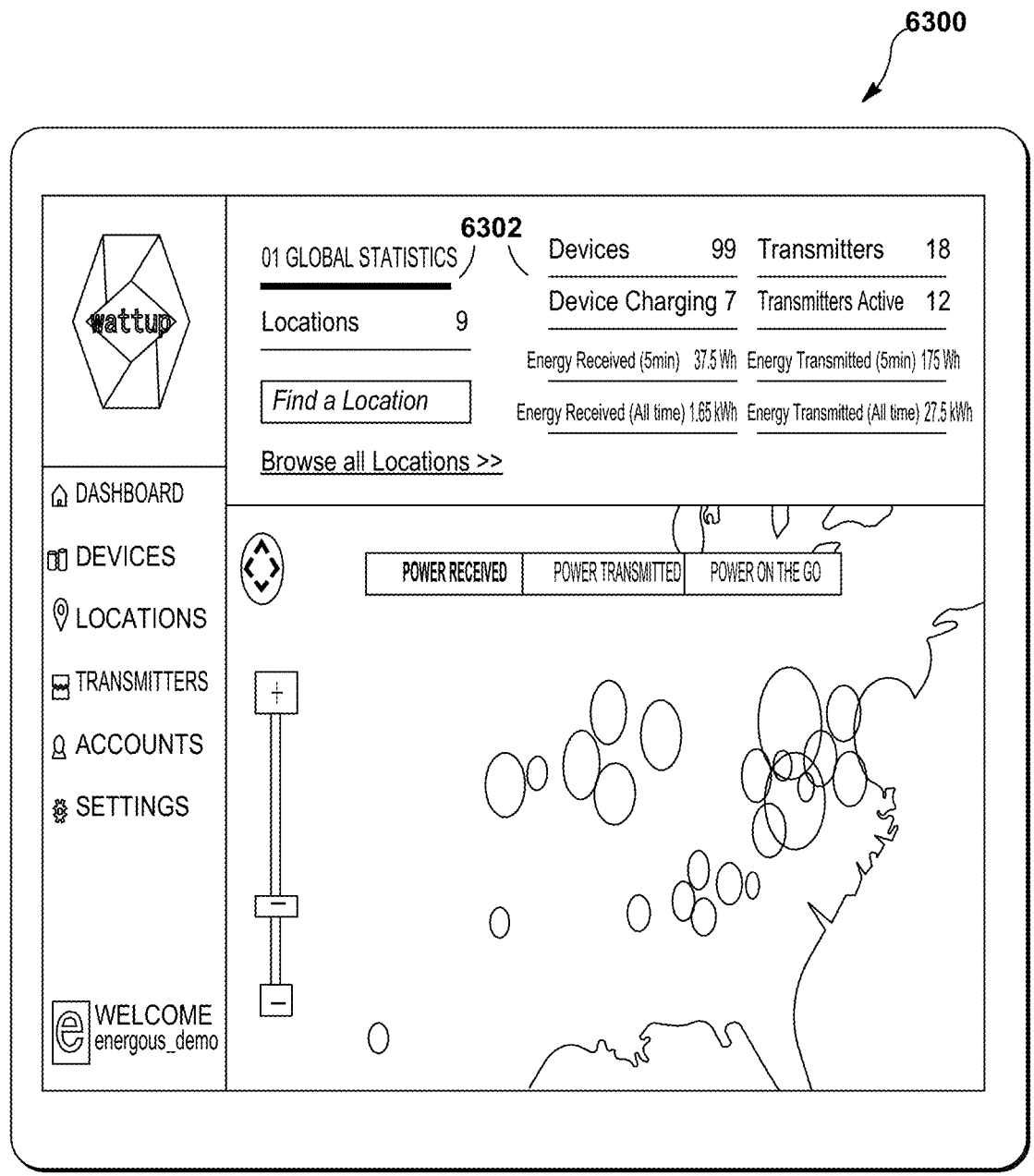

FIG. 63A shows an exemplary graphical user interface (GUI) 6300 for users to administer their account for a wireless power management system. The GUI 6300 exemplifies the scalable nature of the wireless power management system, as applied to display 6302 of statistics. Local, regional, national, or international organizations can view data and graphical depictions (e.g. the bubble charts seen here) of power transfer statistics, such as number of power transmitters, number of power receivers, volume of power transmitted, number of devices recognized, and number of devices currently charging.

Figure 63B:
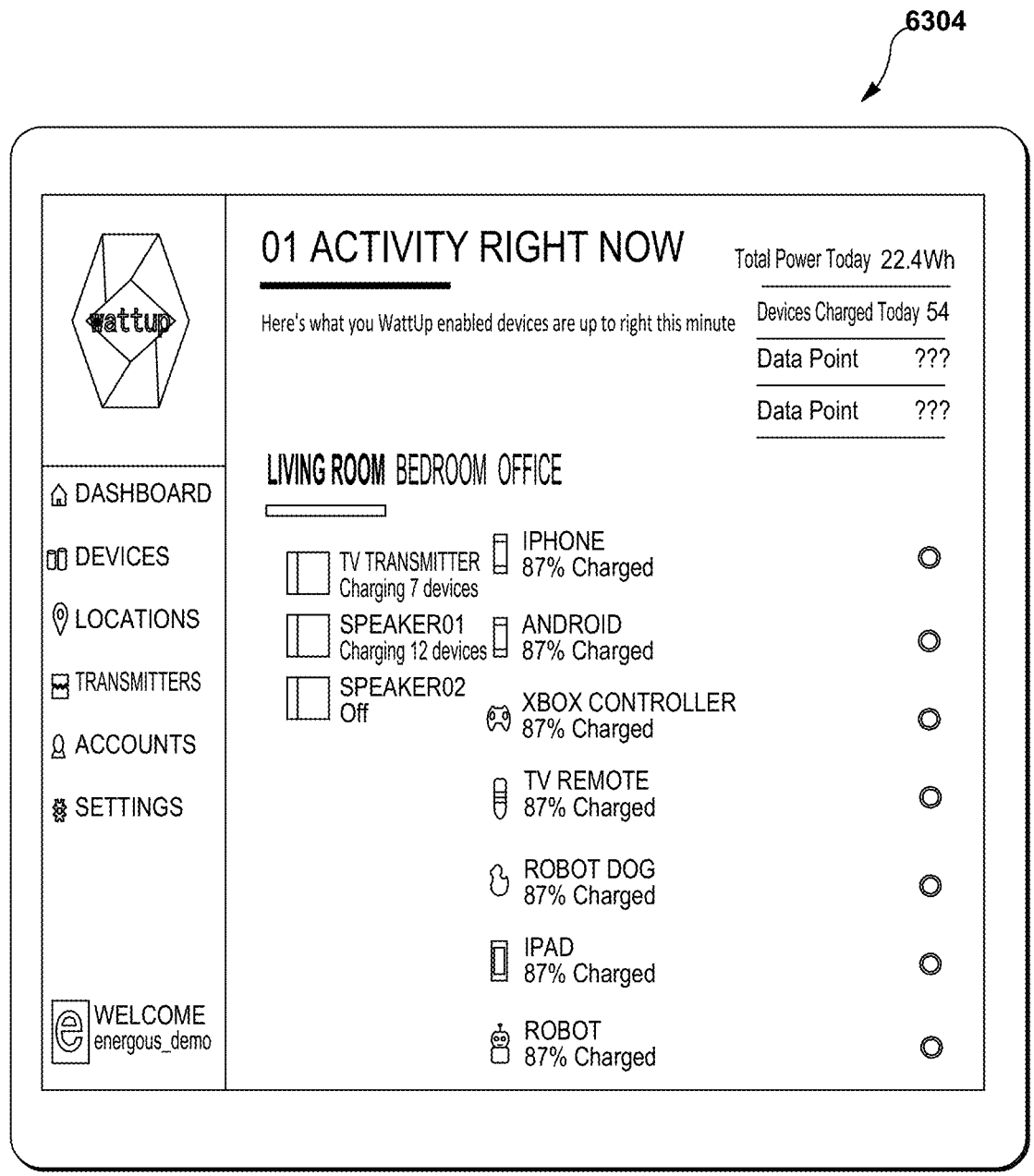

FIG. 63B shows an exemplary GUI 6304 of the system displaying location and tracking within a home, office, or other facility. The user can select a room or other area within the facility, such as living room, and view status and usage metrics for transmitters (e.g. how many devices are currently being charged) and devices (charging status for each device). Data on the cloud-based management system can be viewed, as seen here, using a web portal.

FIG. 63C shows an exemplary GUI 6306 of the system displaying various types of status and usage data that is compiled by the management system, and made available to users, through the GUI 6306, to help them analyze and manage their use of the wireless power service. The GUI 6306 shows a bar chart 6308 of power received by a user's devices in each of the last five days. FIG. 63D shows an exemplary GUI 6310 of the system displaying recent usage history, i.e. a record of where and when each of a user's devices has received power, total power received and duration of power transfer.

Figure 63E:
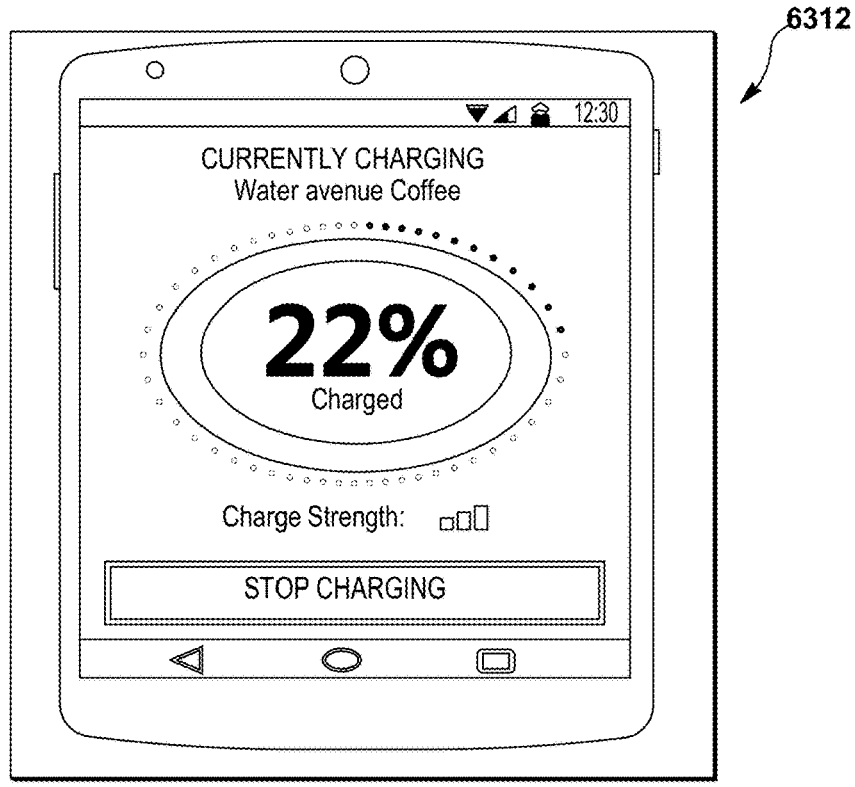
Figure 63F:
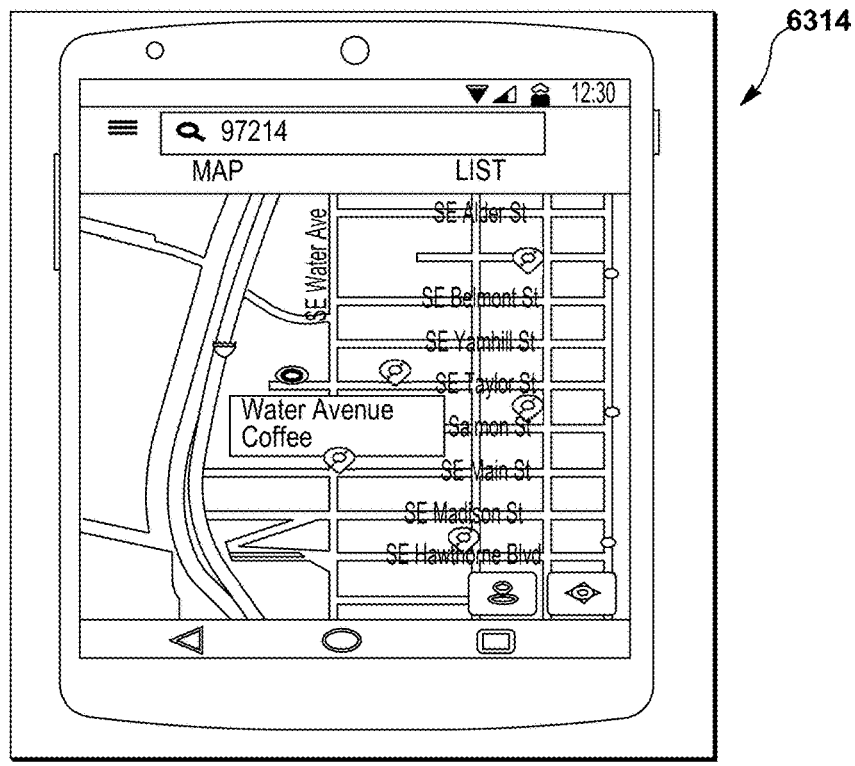

Another format of status and usage reporting uses the form factor for PDAs and other mobile devices. FIGS. 63E and 63F show two views of a mobile phone app. These status and usage data represent a subset of the data available on using a web browser on a workstation, but are tailored to the most important status and usage categories for mobile device users. The mobile app GUI 6312 of FIG. 63E shows the charging status and charge strength of a mobile phone. The mobile app GUI 6314 of FIG. 63F provides another example of location information, a map of a neighborhood with names and locations of businesses providing the wireless charging service.

Figure 63G:
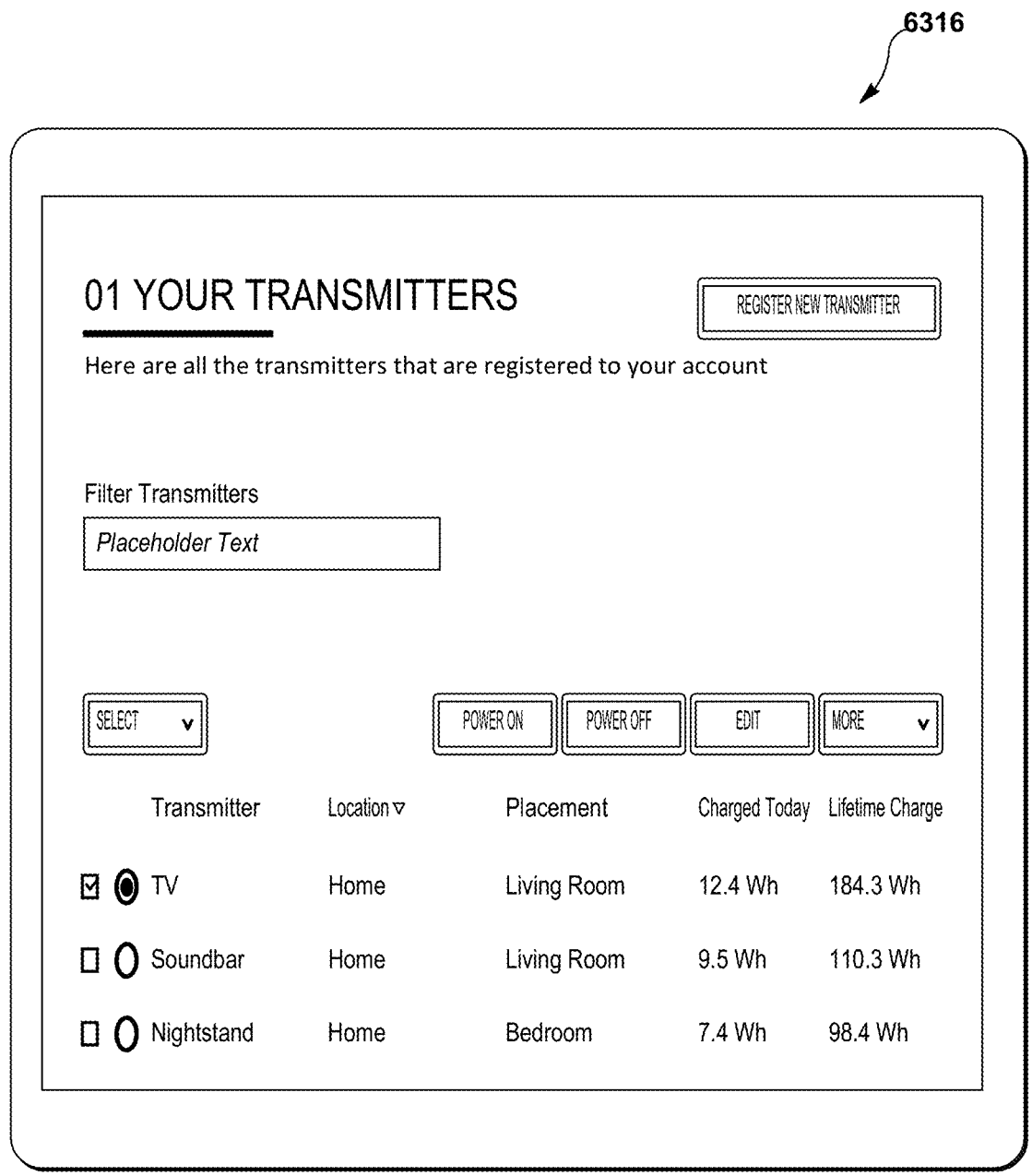

FIG. 63G shows an example of an Accounts GUI 6316, showing status and usage information for all transmitters that are registered to the account. This accounts screen permits an authorized user to register a new transmitter to the account. Other accounts screens permit users to register receivers and devices newly included in the management system, and to view status and usage data for such receivers and devices.

Figure 63H:
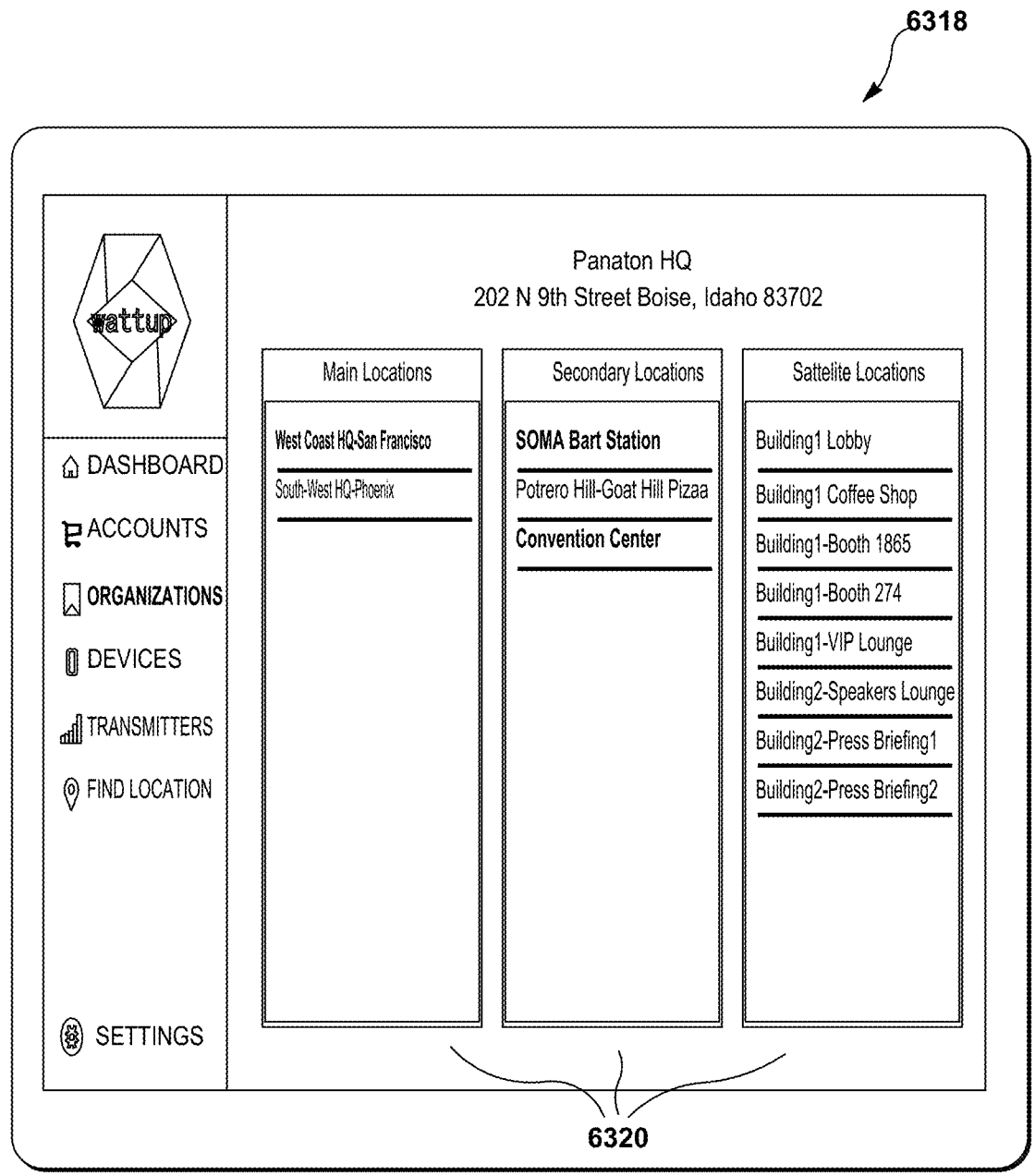

FIG. 63H, with Organizations GUI 6318, illustrates how organizations can remotely monitor their power transfer activities at other geographic locations. Here an organization has a headquarters in Boise ID with primary, secondary, and satellite locations in other parts of the U.S., as displayed at 6320. A representative of the organization can select any of these locations using this screen, and monitor wireless power status and usage analytics at the selected location.

FIGS. 63A-63H illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 63A-63H.

Presented below are example processor-based systems and methods for managing a wireless power transmission system.

A processor-based system for managing a wireless power transmission system comprising at least one power transmitter, configured to generate pocket-forming energy in 3-dimensional space to at least one power receiver may include: (i) a processor, (ii) a database operatively coupled to the processor, and (iii) communications, operatively coupled to the processor, where the communications is operable to communicate with a network, where the processor is configured to receive system operation data from the at least one power transmitter via the network and to communicate the system operation data to a cloud, and where the system operation data comprises at least one of power transmitter status, power transmitter usage, power receiver status, and power receiver usage.

In some embodiments, the processor is configured to generate a record of the received system operation data.

In some embodiments, the processor is configured to generate an analysis of the received system operation data.

In some embodiments, the processor is configured to communicate the received system operation data to a client device for display using a graphical user interface (GUI). Furthermore, in some embodiments, the client device is operable to manage the wireless power transmission system using the GUI. Furthermore, in some embodiments, the client device is associated with the receiver for charging the client device with the pocket-forming energy generated by the at least one power transmitter. Furthermore, in some embodiments, the client device is a workstation that is not charged with the pocket-forming energy generated by the at least one power transmitter. Furthermore, in some embodiments, the client device is configured to download the GUI from an application store to communicate with the processor.

In some embodiments, the system operation data comprises at least one of errors, faults, trouble reports, logs of operational events, a command issued by the at least one power receiver, power receiver and power transmitter hardware configurations, amount of power transmitted per power transmitter and per power receiver, metrics of software and hardware activity, metrics of automatic operation performed by system software, location of the at least one power receiver, a transmitter communications transition, and power receiver charge scheduling configuration.

In some embodiments, the system operation data comprises at least one of client device battery level information, receiver antenna voltage, client device geographic location data, client device hardware configurations, metrics of client device charging activity, and client device charge scheduling.

In some embodiments, the processor is configured to receive the system operation data by one of XML and SMTP.

In some embodiments, the network comprises one of a local area network (LAN), virtual private network (VPN) and a wireless area network (WAN).

In some embodiments, the processor is configured to communicate the system operation data to a business cloud within the cloud.

A processor-based method for managing a wireless power transmission system comprising at least one power transmitter, configured to generate pocket-forming energy in 3-dimensional space to at least one power receiver for charging may include: (i) configuring, by a processor, communications operatively coupled to the processor and a database, to communicate with a network, (ii) receiving, by the processor, system operation data from the at least one power transmitter via the communications, where the system operation data comprises at least one of power transmitter status, power transmitter usage, power receiver status, and power receiver usage, and (iii) communicating, by the processor, the received system operation data to a client device for display using a graphical user interface (GUI).

Figure 64A:
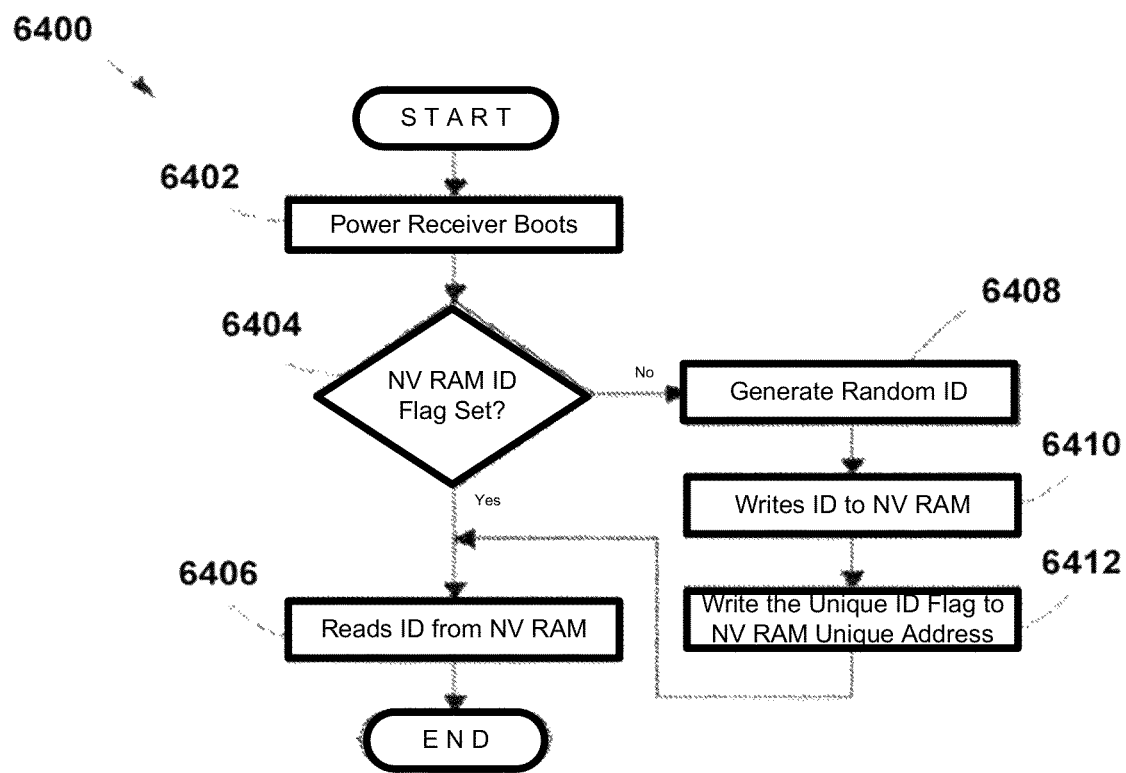
FIG. 64A shows a flowchart of a method that may be used to generate a unique identifier for a wireless power receiver device within a wireless power network, in accordance with some embodiments.
Figure 64B:
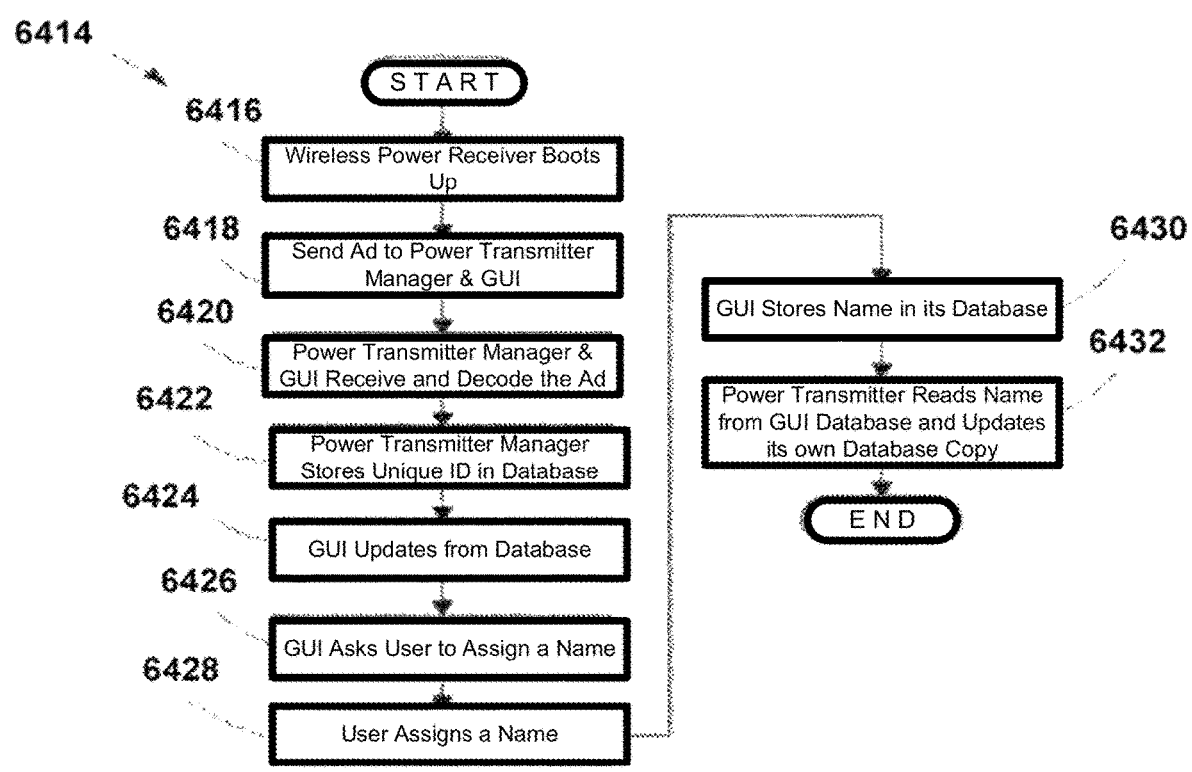
FIG. 64B shows a flowchart of a method for registering and associating a wireless power receiver to a wireless power network, in accordance with some embodiments.

FIGS. 64A and 64B show flowcharts of methods that may be used to generate a unique identifier for a wireless power receiver device within a wireless power network and to register and associate a wireless power receiver to a wireless power network.

FIG. 64A shows a flowchart of a method 6400 that may be used to generate a unique identifier for one or more wireless power receiver within a wireless power network.

Method 6400 may include automated software embedded on a wireless power receiver chip that may be triggered the first time a wireless power receiver is turned on.

In one embodiment, method 6400 may start at step 6402 when a wireless power receiver, either a cover or a customer pocket-forming enable device, boots up the first time within a wireless power network. Then, at step 6404, method 6400 may check if the ID flag at a unique address is in non-volatile (NV) RAM is set in the wireless power receiver. If ID flag is set, at step 6406, the method 6400 reads from its unique address in NVRAM in the wireless power receiver and it continues normal operation. If ID flag is not set, then at step 6408, the method 6400 triggers a suitable random number generator method to generate a random ID which may be 32-bits or greater. Once the ID is generated, at step 6410, the method 6400 writes the ID to its unique address in NV RAM. Finally, at step 6412, method 6400 may write the unique 32-bits (or greater) ID flag to unique address in NV RAM, read ID from NV RAM and continue normal operation.

In another embodiment, method 6400 may also be used to not only generate unique IDs for wireless power receivers, but also to generate unique IDs for wireless power transmitters and GUIs. By generating unique IDs for each of the components in a wireless power network, the components may be more easily associated to users and have friendly names. For example, a user may have in his or her home more than one wireless power transmitter located at different places such as the living room, bedrooms, and kitchen among others. Then the power transmitter's unique ID may be associated with a custom label for each of the wireless power transmitters at different locations.

FIG. 64B shows a flowchart of a method 6414 for registering and associating one or more wireless power receivers to a wireless power network.

In one aspect of the present disclosure, method 6414 may include automated software embedded on a wireless power receiver chip that may be triggered when a wireless power receiver boots up. Therefore, method 6414 may start at step 6416, when a wireless power receiver boots up when turned on by the user. Then, at step 6418, the wireless power receiver broadcasts advertisement, which may include a unique ID number, to any power transmitter manager and GUI that is within its range. Next, at step 6420, power transmitter manager and GUI, that are within the radio of the wireless power receiver broadcast, receive and decode the advertisement. Then, power transmitter manager, at step 6422, may store the unique ID number of said wireless power receiver in a database. This database may serve to store relevant information from wireless power receivers such as, identifiers, voltage ranges, location, signal strength and/or any relevant information. Following method 6414, at step 6424, GUI may update and sync all relevant information from said transmitter's database for better control of the wireless power devices. At step 6426, GUI may ask the user to assign a name for the wireless power receiver that may have joined the wireless power network. Next, at step 6428, the user assigns a name of its preference. Then, at step 6430, GUI syncs that name and stores it in its database. Finally, at step 6432, power transmitter manager reads name from GUI database and updates its own database copy. The system database in power transmitter devices and GUI devices may be identical between every device, when up to date. All system devices may operate and communicate so as to keep each one's database up to date.

FIGS. 64A and 64B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 64A and 64B.

Presented below are example apparatuses and methods for wirelessly receiving power and an example apparatus for wirelessly transmitting power.

An apparatus for wirelessly receiving power may include: (i) a processor, (ii) communication links, operatively coupled to the processor, (iii) a memory, operatively coupled to the processor, and (iv) a receiver operatively coupled to the processor, where the receiver is configured to wirelessly extract power from three-dimensional pockets of energy present in RF waves. In some embodiments, the processor is configured to determine if an identification value for the apparatus is stored in the memory, and, if no identification value is stored, generate an identification value for the apparatus. Furthermore, in some embodiments, the processor is configured to transmit to the communication links one of (i) the stored identification value and (ii) the generated identification value. Furthermore, in some embodiments, the receiver is configured to begin wirelessly extracting power after the processor has transmitted the stored or generated identification value to the communication links.

In some embodiments, the memory is a non-volatile random access memory (NVRAM). Furthermore, in some embodiments, the processor is configured to determine if the identification value for the apparatus is stored in the memory from a unique address in the NVRAM memory.

In some embodiments, the processor is configured to generate the identification value for the apparatus using a random number generator.

In some embodiments, the processor is configured to determine if the identification value for the apparatus is stored in the memory during a boot-up process.

In some embodiments, the processor is configured to store information regarding one or more transmitters responding to the transmitted stored or generated identification value.

In some embodiments, the apparatus further comprises at least one of a power receiver app, an application programming interface and a graphical user interface.

In some embodiments, the processor is configured to receive or generate one or more other identification values for at least one of a wireless power transmitter and graphical user interface.

A method for wirelessly receiving power may include: (i) determining, via a processor, if an identification value for the apparatus is stored in a memory, (ii) generating, via the processor, an identification value for the apparatus if the determining step determines that no identification value is stored, (iii) transmitting one of: the stored identification value and the generated identification value, and (iv) extracting power from three-dimensional pockets of energy present in RF waves via a receiver in the apparatus after the stored or generated identification value is transmitted.

In another apparatus for wirelessly transmitting power, the apparatus may include: (i) a processor, communications links, operatively coupled to the processor, (ii) a memory, operatively coupled to the processor, and (iii) a transmitter operatively coupled to the processor, where the transmitter is configured to wirelessly transmit power by three-dimensional pockets of energy present in RF waves. In some embodiments, the processor is configured to determine if an identification value for the apparatus is stored in the memory, and, if no identification value is stored, generate an identification value for the apparatus. Furthermore, in some embodiments, the processor is configured to transmit to the communication links one of (i) the stored identification value and (ii) the generated identification value. Furthermore, in some embodiments, the transmitter is configured to begin wirelessly transmitting power after the processor has transmitted the stored or generated identification value to the communications.

FIG. 65A-65D illustrate systems and processor-based methods for selectively charging one or more devices in a wireless power network, in accordance with some embodiments.

Figure 65A:
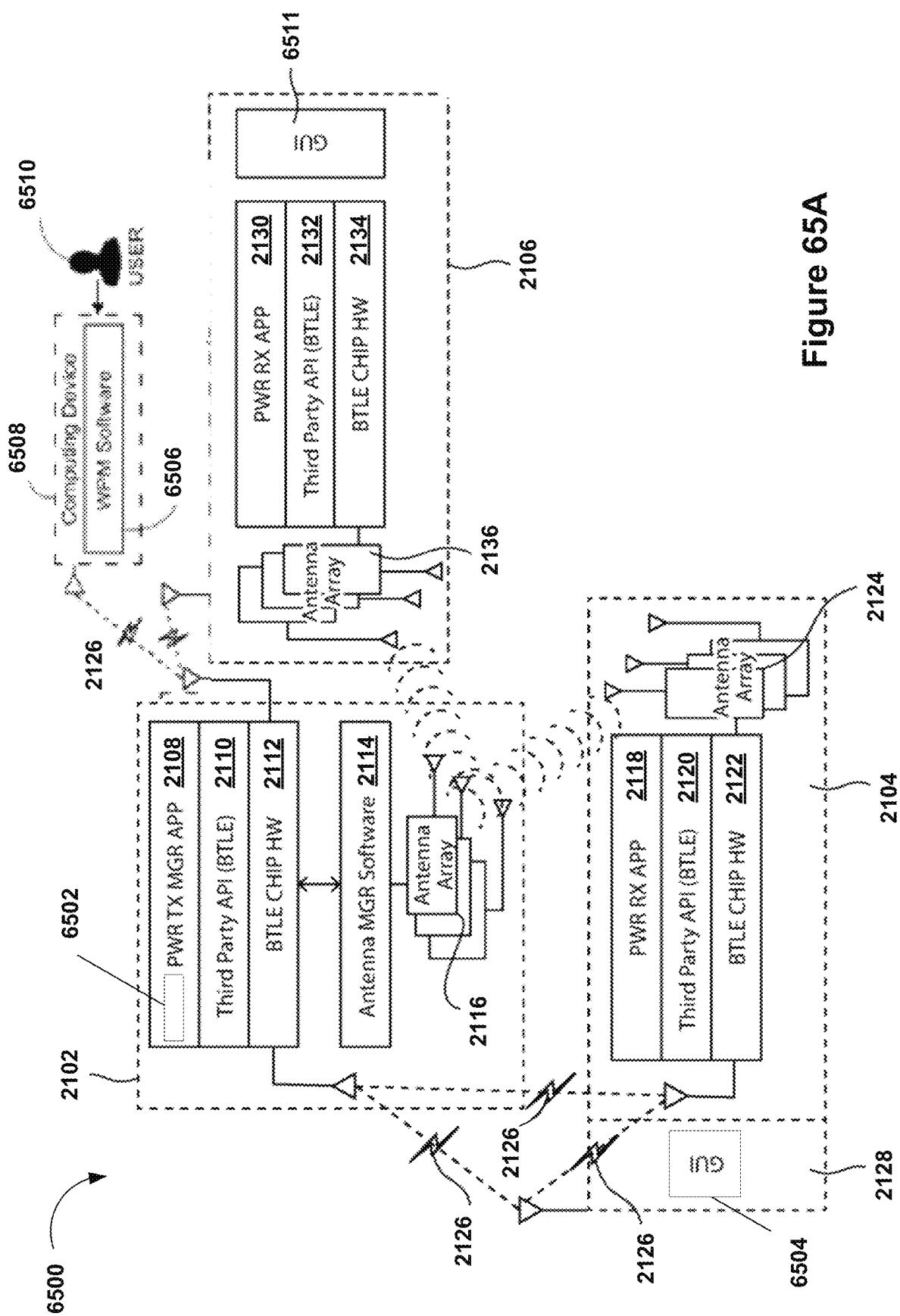
FIG. 65A illustrates an exemplary embodiment of a wireless power network including a transmitter and wireless receivers, in accordance with some embodiments.

FIG. 65A shows an exemplary embodiment of a wireless power transmission system 6500 in which one or more embodiments of the present disclosure may operate. Wireless power transmission system 6500 may include communication between wireless power transmitter 2102 (FIG. 20A) and one or more wireless powered receivers 2104 (FIG. 20A) and with client device 2128 (FIG. 20A). Client device 2128 may be paired with an adaptable paired receiver 2104 that may enable wireless power transmission to the client device 2128. In another embodiment, a client device 2106 (FIG. 20A) may include a wireless power receiver built in as part of the hardware of the device. Client device 2128 or 2106 may be any device which uses an energy power source, such as, laptop computers, stationary computers, mobile phones, tablets, mobile gaming devices, televisions, radios and/or any set of appliances that may require or benefit from an electrical power source.

In one embodiment, wireless power transmitters 2102 may include a microprocessor that integrates a power transmitter manager app 2108 (PWR TX MGR APP) (FIG. 20A) as embedded software, and a third party application programming interface 2110 (Third Party API) (FIG. 20A) for a Bluetooth Low Energy chip 2112 (BTLE CHIP HW) (FIG. 20A). Bluetooth Low Energy chip 2112 may enable communication between wireless power transmitter 2102 and wireless power receiver 2104 client devices 2128 and 2106, and others. Wireless power transmitter 2102 may also include an antenna manager software 2114 (Antenna MGR Software) (FIG. 20A) to control an RF antenna array 2116 (FIG. 20A) that may be used to form controlled RF waves which may converge in 3-dimensional space and create pockets of energy around wireless powered receivers. In some embodiments, Bluetooth Low Energy chips 2112 may utilize other wireless communication protocols, including Wi-Fi, Bluetooth, LTE direct, or the like.

Power transmitter manager app 2108 may call third party application programming interface 2110 for running a plurality of functions, including the establishing of a connection, ending a connection, and sending data, among others. Third party application programming interface 2110 may command Bluetooth Low Energy chip 2112 according to the functions called by power transmitter manager app 2108.

Power transmitter manager app 2108 may also include a distributed system database 6502, which may store relevant information associated with client devices 2128 or 2106, such as their identifiers for a client device 2128 or 2106, voltage ranges for power receiver 2104, location of a client device 2128 or 2106, signal strength and/or any other relevant information associated with a client device 2128 or 2106. Database 6502 may also store information relevant to the wireless power network, including receiver ID's, transmitter ID's, end-user handheld devices, system management servers, charging schedules, charging priorities and/or any other data relevant to a wireless power network.

Third party application programming interface 2110 at the same time may call power transmitter manager app 2108 through a callback function which may be registered in the power transmitter manager app 2108 at boot time. Third party application programming interface 2110 may have a timer callback that may go for ten times a second, and may send callbacks every time a connection begins, a connection ends, a connection is attempted, or a message is received.

Client device 2128 may include a power receiver app 2118 (PWR RX APP) (FIG. 20A), a third party application programming interface 2120 (Third party API) (FIG. 20A) for a Bluetooth Low Energy chip 2122 (BTLE CHIP HW) (FIG. 20A), and a RF antenna array 2124 (FIG. 20A) which may be used to receive and utilize the pockets of energy sent from wireless power transmitter 2102.

Power receiver app 2118 may call third party application programming interface 2120 for running a plurality of functions including establishing a connection, ending a connection, and sending data, among others. Third party application programming interface 2120 may have a timer callback that may go for ten times a second and may send callbacks every time a connection begins, a connection ends, a connection is attempted, or message is received.

Client device 2128 may be paired to an adaptable paired receiver 2104 via a BTLE connection 2126 (FIG. 20A). A graphical user interface (GUI) 6504 may be used to manage the wireless power network from a client device 2128. GUI 6504 may be a software module that may be downloaded from any suitable application store and may run on any suitable operating system such as iOS and Android, amongst others. Client device 2128 may also communicate with wireless power transmitter 2102 via a BTLE connection 2126 to send important data, such as an identifier for the device, battery level information, geographic location data, or any other information that may be of use for wireless power transmitter 2102.

A wireless power manager 6506 software may be used in order to manage wireless power transmission system 6500. Wireless power manager 6506 may be a software module hosted in memory and executed by a processor inside a computing device 6508. The wireless power manager 6506 may include a local application GUI or host a web page GUI, from where a user 6510 may see options and statuses, as well as execute commands to manage the wireless power transmission system 6500. The computing device 6508, which may be cloud-based, may be connected to the wireless power transmitter 2102 through standard communication protocols, including Bluetooth, Bluetooth Low Energy, Wi-Fi, or ZigBee, amongst others. Power transmitter manager app 2108 may exchange information with wireless power manager 6506 in order to control access by and power transmission to client devices 2128. Functions controlled by wireless power manager 6506 may include scheduling power transmission for individual devices, prioritizing between different client devices, accessing credentials for each client, tracking physical locations of power receivers relative to power transmitter areas, broadcasting messages, and/or any functions required to manage the wireless power transmission system 6500.

Multiple wireless power transmitter 2102 units may be placed together in the same area to deliver more power to individual power receivers or to power more receivers at the same time, said power receivers being within power reception range of all said power transmitters 2102.

Figure 65B:
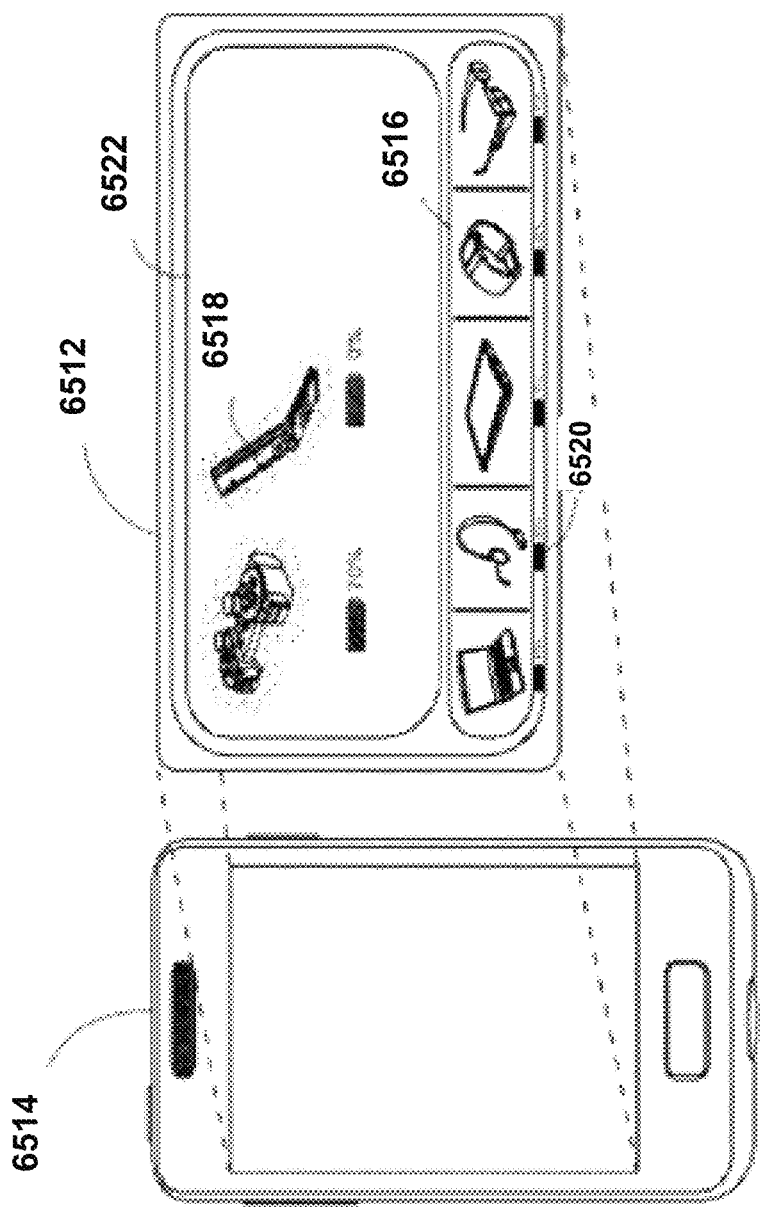
FIG. 65B is an exemplary embodiment of a Wireless Power Manager Graphic User Interface (GUI), in accordance with some embodiments.

FIG. 65B is an exemplary embodiment of a wireless power charging user interface (UI) 6512. Wireless power charging UI 6512 may be a software module hosted in memory and executed by a processor in a computing device 6514. Wireless power charging UI 6512 may be included as part of a wireless power manager application in order to select and deselect one or more wireless power devices to charge or power in a wireless power network.

Wireless power charging UI 6512 may include a charge off area 6516 which may display device icons that represent the different client devices 6518 that are not to have power transmitted to them in a wireless power network. If the device, represented by a given icon, contains a battery then its icon, or a sub-icon near the device icon may also additionally include a charge level 6520 icon which may serve as an indication of battery present charge or state and/or how much energy charge the client devices 6518 battery, if any, possess at the moment.

Wireless power charging UI 6512 may also include a charging area 6522 which may display icons that represent the different client devices 6518 that are receiving power from a wireless power transmitter in a wireless power network. Each icon may also include a charge level 6520 icon which may serve as an indication of battery present charge state and/or how much energy charge the client device's 6518 battery, if any, possess at the moment. A client device 6518 in the charging area 6522 may also include additional indicators to show a device is charging. For example, and without limitation, a client device 6518 icon may be surrounded by a flashing or pulsating halo when the device is receiving power; in another example the charge level 6520 icon may be flashing. In yet another example, the client device 6518 may include transparent overlapped text such as a message reading "Charging."

User may drag and drop a client device 6518 from the charge off area 6516 into the charging area 6522 in order to begin charging a device. A user may also select a client device 6518 from the charging area 6522 and drag and drop it into the charge off area 6516 in order to stop charging the device. The user may perform these actions using known in the art UI navigation tools such as, a mouse click or touch screen for example.

Figure 65C:
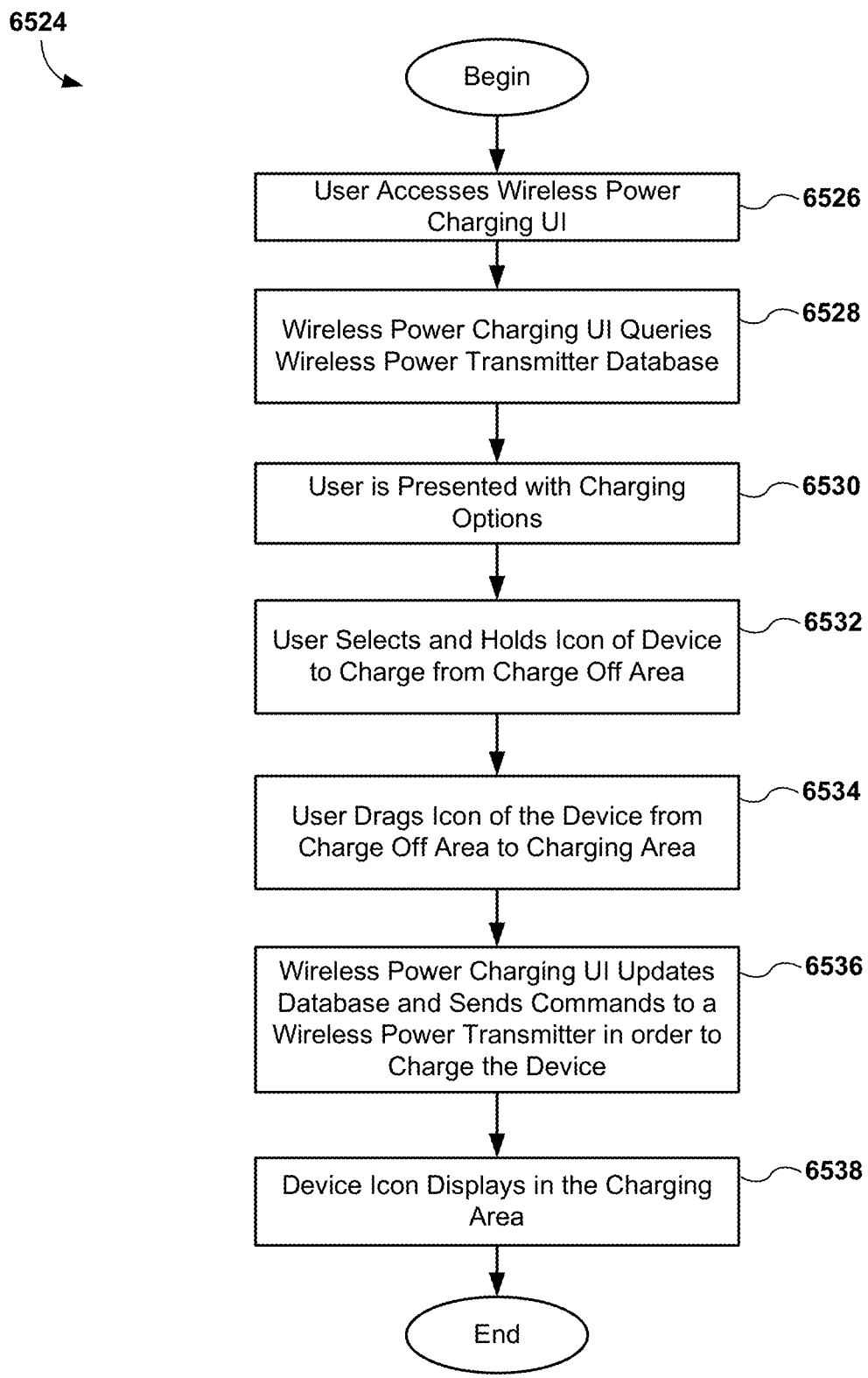
FIG. 65C is a flowchart of a process to manually enable power charging of a device in a wireless power network, in accordance with some embodiments.

FIG. 65C is a flowchart describing a process 6524 by which a user may charge a device in a wireless power network. The process may begin when a user accesses, logs on to, or begins to use the wireless power charging UI (block 6526). The wireless power charging UI may be a software module hosted in memory and executed by a processor in a suitable computing device, such as, a laptop computer, smartphone and the like. The wireless power charging UI may be a software module implemented as part of the wireless power manager application (described in FIG. 65A) used to manage a wireless power network. The wireless power charging software may then query (block 6528) a database stored in a wireless power transmitter in order to extract records of all wireless power receivers in the wireless power network. The wireless power charging UI may also create a local copy of the database in the memory of the computing device hosting the wireless power charging UI. A copy of the database may be re-created and mirrored into each computing device in the wireless power network in order to create a distributed database environment and enable sharing all the information across all computing devices in the wireless power network. Extracted information may include for example records indicating status of each wireless power receiver in the wireless power network, their associated client devices, battery level and charge status, owner, and/or any associated information from the components in a wireless power network. The extracted information may then be presented (block 6530) and shown to the user in a wireless power charging UI such as the one described in FIG. 65B. From the wireless power charging UI the user may select and hold the icon for the device he may desire to charge from the charge off screen area of the wireless power charging UI (block 6532). At this point the icon for the device may change or become highlighted in order to indicate that the device has been selected, for example the image of the icon may become larger when a user selects the device from the charge off area. The user may then drag the icon device from the charge off area to the charging area (block 6534). The wireless power charging UI may then update the database and send commands to the wireless power transmitter (block 6536) in order to begin charging the device. The database in the wireless power transmitter may then be updated with any necessary information. The charging area of the wireless power charging UI may then display an icon indicating that the selected device is charging (block 6538). The icon from the corresponding device may then be removed from the charge off area of the wireless power charging UI.

Figure 65D:
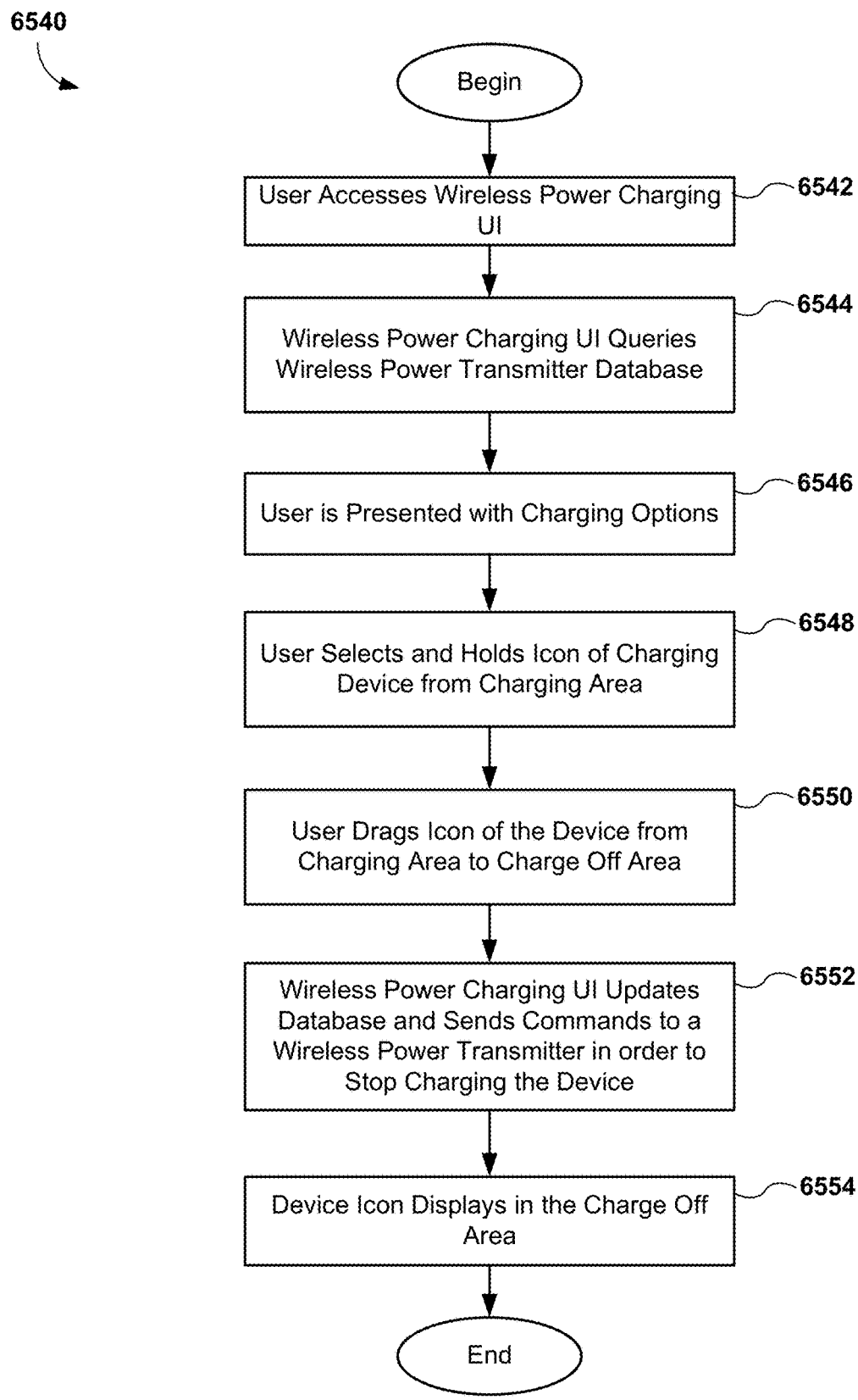
FIG. 65D is a flowchart of a process for disabling a device from charging in a wireless power network, in accordance with some embodiments.

FIG. 65D is a flowchart describing a process 6540 by which a user may disable a device from charging in a wireless power network. The process may begin when a user accesses the wireless power charging UI (block 6542). The wireless power charging UI may be a software module hosted in memory and executed by a processor in a suitable computing device, such as, a laptop computer, smartphone and the like. The wireless power charging UI may be a software module implemented as part of the wireless power manager application (described in FIG. 65A) used to manage a wireless power network. The wireless power charging software may then query (block 6544) a database stored in a wireless power transmitter in order to extract records of all wireless power receivers in the wireless power network. Extracted information may include for example records indicating status of each wireless power receiver in the wireless power network, their associated devices, battery level and charge status, owner, and/or any associated information from the components in a wireless power network. The extracted information may then be presented (block 6546) and shown to the user in a wireless power charging UI such as the one described in FIG. 65B. From the wireless power charging UI the user may select and hold the icon for the device he may desire to charge off, from within the charging area of the wireless power charging UI (block 6548). At this point the icon for the device may change or be highlighted in order to indicate that the device has been selected, for example the image of the icon may become larger when a user selects the device from the charging area. The user may then drag and drop the icon device from the charging area to the charge off area (block 6550). The wireless power charging UI may then update the database and send commands to the wireless power transmitter (block 6552) to disable charging the device. The database in the wireless power transmitter may then be updated with any necessary information. The charge off area of the wireless power charging UI may then display an icon of the device indicating that the selected device is no longer being charged (block 6554). The icon of the corresponding device may then be removed from the charging area of the wireless power charging UI.

FIGS. 65A-65D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 65A-65D.

Presented below are example apparatuses and methods for selectively charging one or more devices in a wireless power network.

An apparatus for selectively charging one or more devices in a wireless power network may include: (i) a processor, (ii) a display, operatively coupled to the processor, (iii) communications for communicating with at least one transmitter configured to generate pocket-forming energy in 3-dimensional space within the wireless power network, where the processor is configured to determine the presence of one or more receivers configured to receive pocket-forming energy within the wireless power network, where the communications is configured to receive receiver data relating to each of the one or more receivers within the wireless power network, and an input for selecting an operational configuration for at least one of the one or more receivers for receiving pocket-forming energy.

In some embodiments, the receiver data comprises at least one of receiver status in the wireless power network, associated device data for each receiver, receiver battery level data and receiver charge status data.

In some embodiments, the display is configured to display the receiver data.

In some embodiments, the communications are configured to transmit the operational configuration to the at least one transmitter.

In some embodiments, the display is configured to display each receiver with a selected operational configuration.

In some embodiments, the operational configuration is selected via the input comprising a graphical user interface.

In some embodiments, the operational configuration comprises one of an enable and disable charging configuration.

A processor-based method for selectively charging one or more devices in a wireless power may include: (i) communicating with at least one transmitter configured to generate pocket-forming energy in 3-dimensional space within the wireless power network, (ii) determining and displaying the presence of one or more receivers configured to receive pocket-forming energy within the wireless power network, (iii) receiving receiver data relating to each of the one or more receivers within the wireless power network, and (iv) selecting an operational configuration for at least one of the one or more receivers for receiving pocket-forming energy.

In another processor-based method for selectively charging one or more devices in a wireless power network, the method may include: (i) registering with at least one transmitter configured to generate pocket-forming energy in 3-dimensional space within the wireless power network, (ii) determining and displaying the presence of one or more receivers configured to receive pocket-forming energy within the wireless power network, (iii) receiving receiver data relating to each of the one or more receivers within the wireless power network, and (iv) selecting one or more charging options for at least one of the one or more receivers for receiving pocket-forming energy within the wireless power network.

In some embodiments, the method includes transmitting the charging options to the at least one transmitter.

In some embodiments, the method includes displaying each receiver with a selected charging option.

In some embodiments, the charging option is selected via a graphical user interface.

Figure 66A:
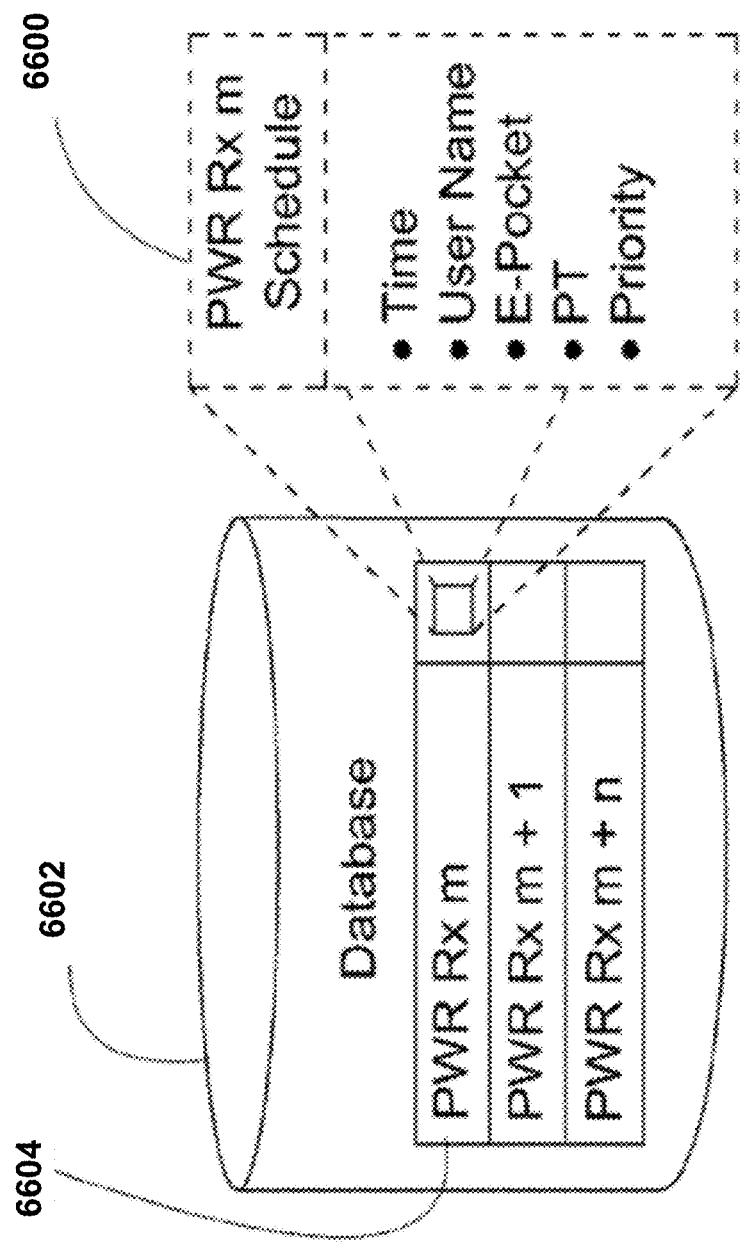
FIG. 66A is an exemplary embodiment of scheduling records stored in a database, in accordance with some embodiments.
Figure 66B:
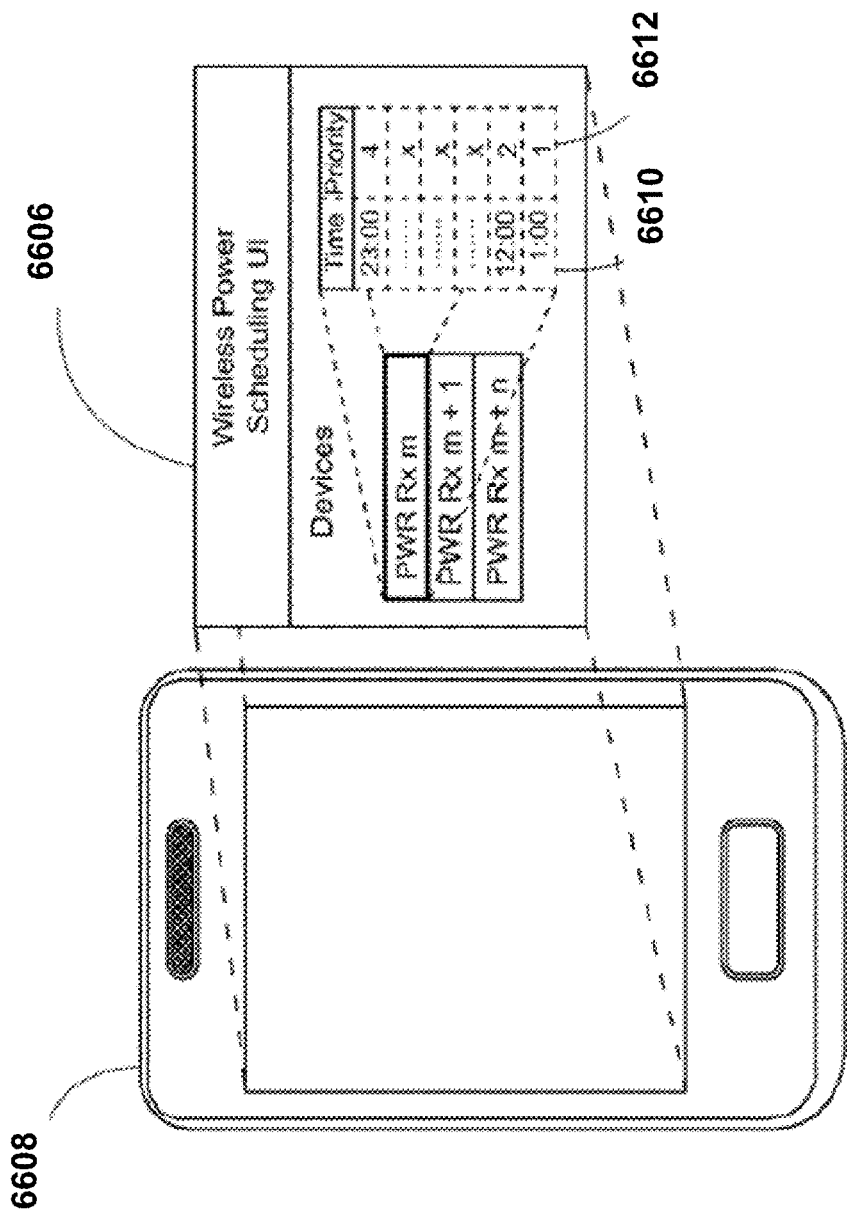
FIG. 66B is an exemplary embodiment of a wireless power scheduling UI, in accordance with some embodiments.
Figure 66C:
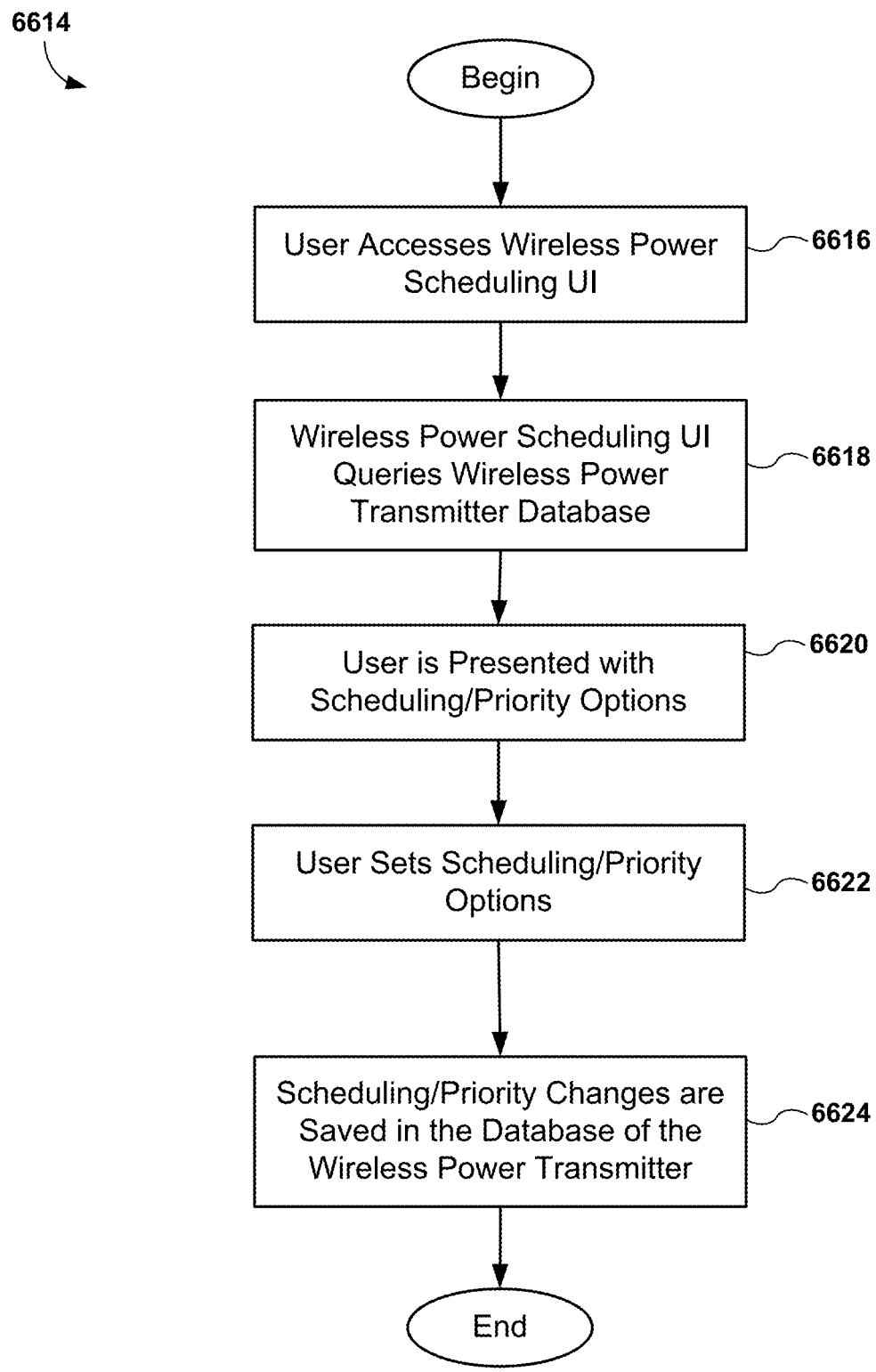
FIG. 66C is a flowchart of a process for managing charging schedules or priorities, in accordance with some embodiments.

FIGS. 66A-66C illustrate diagrams, interfaces, and methods of setting charging schedules, in accordance with some embodiments.

FIG. 66A is an exemplary embodiment of how scheduling records 6600 may be stored in the database 6602 in a wireless power network. The database 6602 may contain a power receiver record 6604 for each power receiver found in the wireless power network. Power receiver records 6604 may include scheduling records 6600 associated with each power receiver record 6604, and also a record for every other type of device in the wireless power network, such as power transmitter records, management server records, and client device records, all of which store such information as, but not limited to, status, control, command, and configuration. Power receiver records 6604 may include scheduling records 6600 associated with each power receiver record 6604. Scheduling records may include information such as time, user name, e-pocket, 3d or angular location, power transmitter manager, priority or/and any set of information used for automatic or manually scheduling power transmission to one or more power receiving devices. For example, time may serve to store times of the day at which device may be charged. Priority may serve to indicate the priority of charging the device over other devices, at a specific time. User name may serve to differentiate device users from each other and assign priorities depending on that. E-pocket may serve to store the physical location at which any wireless power receiver shall be immediately charged.

FIG. 66B is an exemplary embodiment of a wireless power scheduling UI 6606. Wireless power scheduling UI 6606 may be a software module hosted in memory and executed by a processor in a computing device 6608. Wireless power scheduling UI 6606 may also be included as part of a wireless power manager application in order to manage wireless power schedules in a wireless power network.

Wireless power scheduling UI 6606 may query scheduling records from a database in a wireless power transmitter and present them to a user in the display of a computing device 6608 such as, a smartphone or laptop, or web page. The user may select a power receiver and set scheduling options for that power receiver or execute any user interface function of the wireless power network using known in the art UI navigation tools such as, a mouse click or touch screen for example or by text message (SMS) or by email or by voice recognition or by motion gesture of handheld device, for example. In the exemplary embodiment the wireless power scheduling UI 6606 may allow the user to select time 6610 periods and assign a priority level 6612 for charging the device during that time period.

In another embodiment, a user may set priorities based on the user of a device. For example, the UI may present a user with the user names associated with each power receiver record. The user may then assign different priority levels 6612 for each user.

In another embodiment, priorities may be set depending on a place or location. For example, the UI may present a user with the pockets of energy (e-pockets) and a user may assign a priority level 6612 to the specific pocket of energy which in turn may be a fixed location.

Changes or configurations done by a user in wireless power scheduling UI 6606 may then be saved to the database in a wireless power transmitter. The wireless power transmitter may then refer to the scheduling records stored in the database in order to perform any time scheduled power transmission or identify transmission priorities.

FIG. 66C is a flowchart describing a process 6614 by which a user may set up charging schedules or priorities. The process may begin when a user accesses a wireless power scheduling UI (block 6616). The wireless power scheduling UI may be a software module hosted in memory and executed by a processor in a suitable computing device, such as, a laptop computer, smartphone and the like. The wireless power scheduling software may then query (block 6618) a database stored in a wireless power transmitter in order to extract scheduling records and priorities for all wireless power receivers in the wireless power network. The extracted information may then be presented (block 6620) to the user in a wireless power scheduling UI such as the one described in FIG. 66B. The user may then manage schedules and priorities (block 6622) for all the devices through the wireless power scheduling UI using any navigation tools provided by the computing device such as, for example, touchscreens, keyboards and mouse. Schedules and priorities set or changed by the user may then be saved to the database stored in a wireless power transmitter (block 6624).

A wireless power transmitter may continually query scheduling records and perform actions accordingly to automatically control the present state of charging for one or more power receivers.

FIGS. 66A-66C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 66A-66C.

Presented below are example apparatuses and methods for controlling wireless power delivery.

An apparatus for controlling wireless power delivery, may include: (i) a transmitter comprising two or more antenna elements, (ii) a RF circuit, operatively coupled to the transmitter, (iii) a processor, operatively coupled to the RF circuit, where the processor is configured to generate pocket-forming energy in 3-dimensional space to one or more receivers via the transmitter and RF circuit, and (iv) a storage, operatively coupled to the processor, the storage being configured to store receiver data for each of the one or more receivers, where the processor is configured to process the receiver data to control the generation of pocket-forming energy.

In some embodiments, the receiver data comprises schedule data.

In some embodiments, the schedule data comprises one or more of time data, receiver user name data, energy pocket data, 3-dimensional data, angular location data, and receiver priority data.

In some embodiments, the processor is configured to receive and process modified receiver data to perform a modified control of generation of pocket-forming energy.

In some embodiments, the receiver data comprises feedback data comprising a measurement of pocket-forming energy being received at each receiver. Furthermore, in some embodiments, the processor is configured to perform a modified control of generation of pocket-forming energy based on the feedback data.

In some embodiments, the storage is configured to store transmitter data for one or more other apparatuses providing wireless power delivery.

A method for controlling wireless power delivery may include: (i) generating pocket-forming energy in 3-dimensional space, via a transmitter comprising two or more antenna elements, for transmission to one or more receivers, (ii) receiving receiver data for each of the one or more receivers, (iii) processing the receiver data, and (iv) controlling the generation of pocket-forming energy based on the processed receiver data.

In another method for controlling wireless power delivery, the method may include: (i) generating pocket-forming energy in 3-dimensional space, via a processor-controlled RF circuit operatively coupled to a transmitter comprising two or more antenna elements, (ii) receiving receiver data for each of the one or more receivers, (iii) processing the receiver data, and (iv) controlling at least one of a time, direction and power of generation of pocket-forming energy based on the processed receiver data.

FIGS. 67A-67E illustrate a wireless power transmission network diagram and methods of transmitter self-test, in accordance with some embodiments.

Figure 67A:
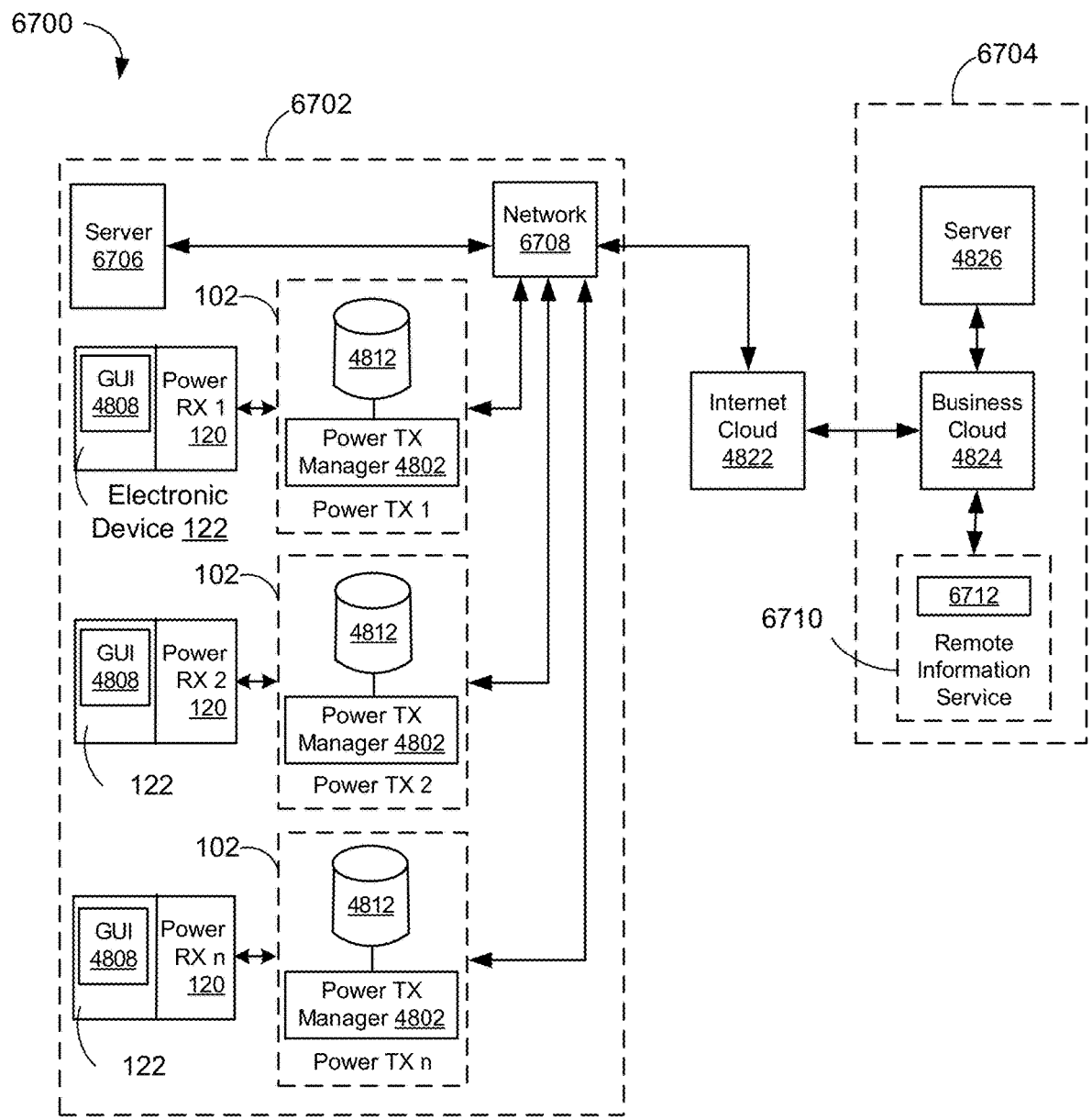
FIG. 67A shows a wireless power transmission network diagram, in accordance with some embodiments.

FIG. 67A illustrates a wireless power transmission system network 6700, according to an exemplary embodiment.

According to some embodiments, wireless power transmission system network 6700 may include multiple wireless power transmission systems 6702 capable of communicating with a remote information service 6704 through internet cloud 4822 (FIG. 48B).

In some embodiments, wireless power transmission system 6702 may include one or more wireless power transmitters 102 (FIG. 1), one or more power receivers 120 (FIG. 1), one or more optional back-up servers 6706 and a local network 6708.

According to some embodiments, each power transmitter 102 may include wireless power transmitter manager 4802 (FIG. 48A) software and a distributed wireless power transmission system database 4812 (FIG. 48A). Each power transmitter 102 may be capable of managing and transmitting power to one or more power receivers 120, where each power receiver 120 may be capable of charging or providing power to one or more electronic devices 122 (FIG. 1).

Power transmitter managers 4802 may control the behavior of power transmitters 102, monitor the state of charge of electronic devices 122, and control power receivers 120, keep track of the location of power receivers 120, execute power schedules, run system check-ups, and keep track of the energy provided to each of the different electronic devices 122, amongst others.

According to some embodiments, database 4812 may store relevant information from electronic devices 122 such as, identifiers for electronic devices 122, voltage ranges for measurements from power receivers 122, location, signal strength and/or any relevant information from electronic devices 122. Database 4812 may also store information relevant to the wireless power transmission system 6702 such as, receiver ID's, transmitter ID's, end-user handheld device names or ID's, system management server ID's, charging schedules, charging priorities and/or any data relevant to a power transmission system network 6700.

Additionally, in some embodiments, database 4812 may store data of past and present system status.

The past system status data may include details such as the amount of power delivered to an electronic device 122, the amount of energy that was transferred to a group of electronic devices 122 associated with a user, the amount of time an electronic device 122 has been associated to a wireless power transmitter 102, pairing records, activities within the system, any action or event of any wireless power device in the system, errors, faults, and configuration problems, among others. Past system status data may also include power schedules, names, customer sign-in names, authorization and authentication credentials, encrypted information, physical areas of system operation, details for running the system, and any other suitable system or user-related information.

Present system status data stored in database 4812 may include the locations and/or movements in the system, configuration, pairing, errors, faults, alarms, problems, messages sent between the wireless power devices, and tracking information, among others.

According to some exemplary embodiments, databases 4812 within power transmitters 102 may further store future system status information, where the future status of the system may be forecasted or evaluated according to historical data from past system status data and present system status data.

In some embodiments, records from all device databases 4812 in a wireless power transmission system 6702 may also be stored and periodically updated in server 6706. In some embodiments, wireless power transmission system network 6700 may include two or more servers 6706. In other embodiments, wireless power transmission system network 6700 may not include any servers 6706.

In another exemplary embodiment, wireless power transmitters 102 may further be capable of detecting failures in the wireless power transmission system 6702. Examples of failures in power transmission system 6702 may include overheating of any component, malfunction, and overload, among others. If a failure is detected by any of wireless power transmitters 102 within the system, then the failure may be analyzed by any wireless power transmitter manager 4802 in the system. After the analysis is completed, a recommendation or an alert may be generated and reported to owner of the power transmission system or to a remote cloud-based information service, for distribution to system owner or manufacturer or supplier.

In some embodiments, power transmitters 102 may use network 6708 to send and receive information. Network 6708 may be a local area network, or any suitable communication system between the components of the wireless power transmission system 6702. Network 6708 may enable communication between power transmitters, system management servers 6706 (if any), and other power transmission systems 6702 (if any), amongst others.

According to some embodiments, network 6708 may facilitate data communication between power transmission system 6702 and remote information service 6704 through internet cloud 4822.

Remote information service 6704 may be operated by the owner of the system, the manufacturer or supplier of the system, or a service provider. Remote management system may include business cloud 4824 (FIG. 48B), remote manager software 6710, and one or more backend servers 4826 (FIG. 48B), where the remote manager software 6710 may further include a general database 6712. Remote manager software 6710 may run on a backend server 4826, which may be a one or more physical or virtual servers.

General database 6712 may store additional backups of the information stored in the device databases 4812. Additionally, general database 4826 may store marketing information, customer billing, customer configuration, customer authentication, and customer support information, among others. In some embodiments, general database 6712 may also store information, such as less popular features, errors in the system, problems report, statistics, and quality control, among others.

Each wireless power transmitter 102 may periodically establish a TCP communication connection with remote manager software 6710 for authentication, problem report purposes or reporting of status or usage details, among others.

Figure 67B:
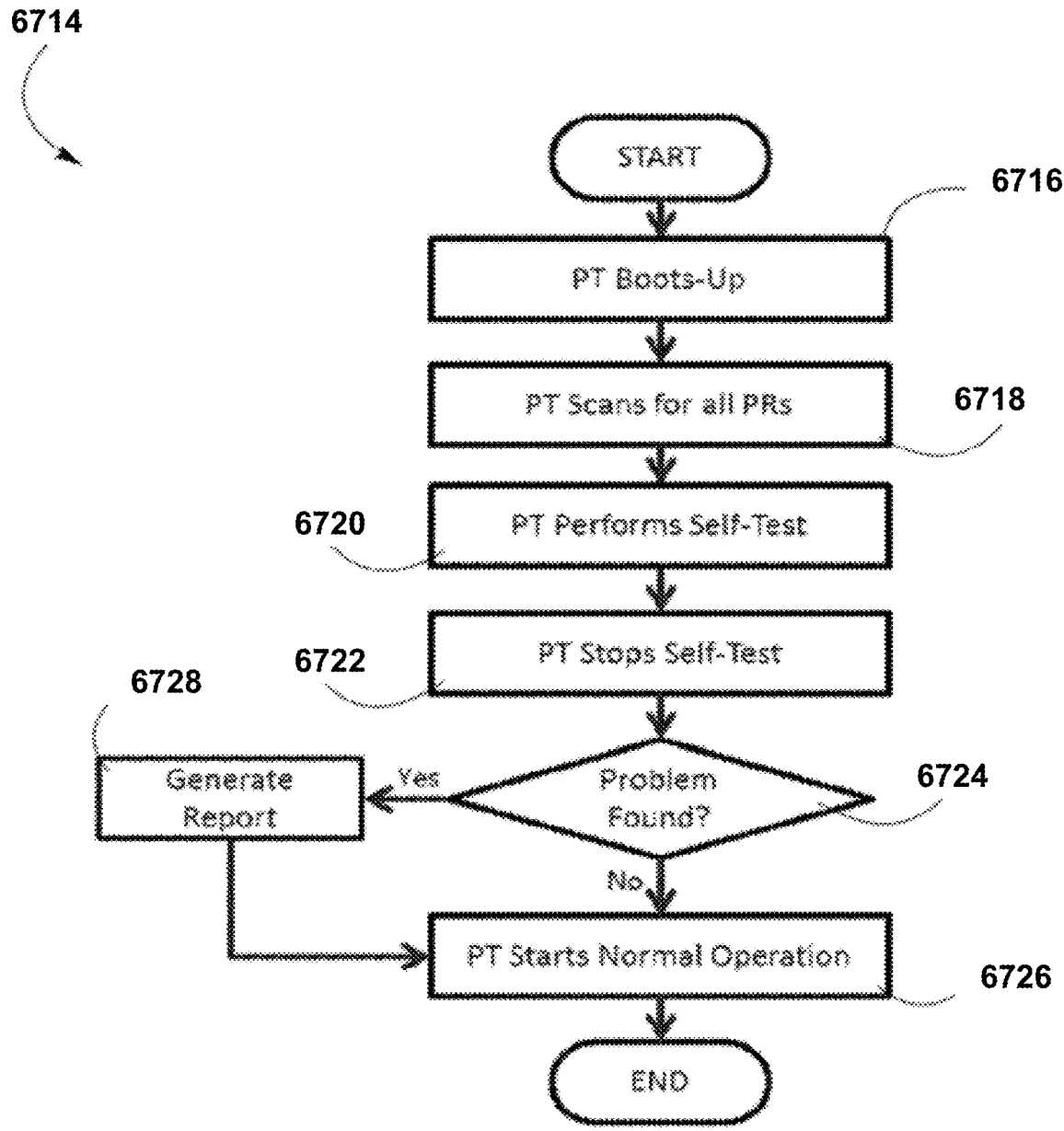
FIG. 67B is a flowchart showing a method for automatic initiation of a self-test of a power transmitter software at boot, in accordance with some embodiments.

FIG. 67B is a flowchart showing a method for automatic initiation at boot 6714 of a power transmitter self-test, according to an exemplary embodiment.

The method for automatic initiation at boot 6714 of a power transmitter (PT) self-test may start when a PT manager boots-up 6716 a PT. Subsequently, PT may scan 6718 for all power receivers (PR) within communications range. For each PR found, wireless power transmission system may command PT to perform 6720 a communication self-test for a finite period of time, and then PT stops 6722 the communication self-test. If the PT finds a problem 6724 during the self-test, PT manager may generate 6728 a report to inform a user, at a computing device, of the problem. Afterwards, PT may start its normal operation 6726.

Figure 67C:
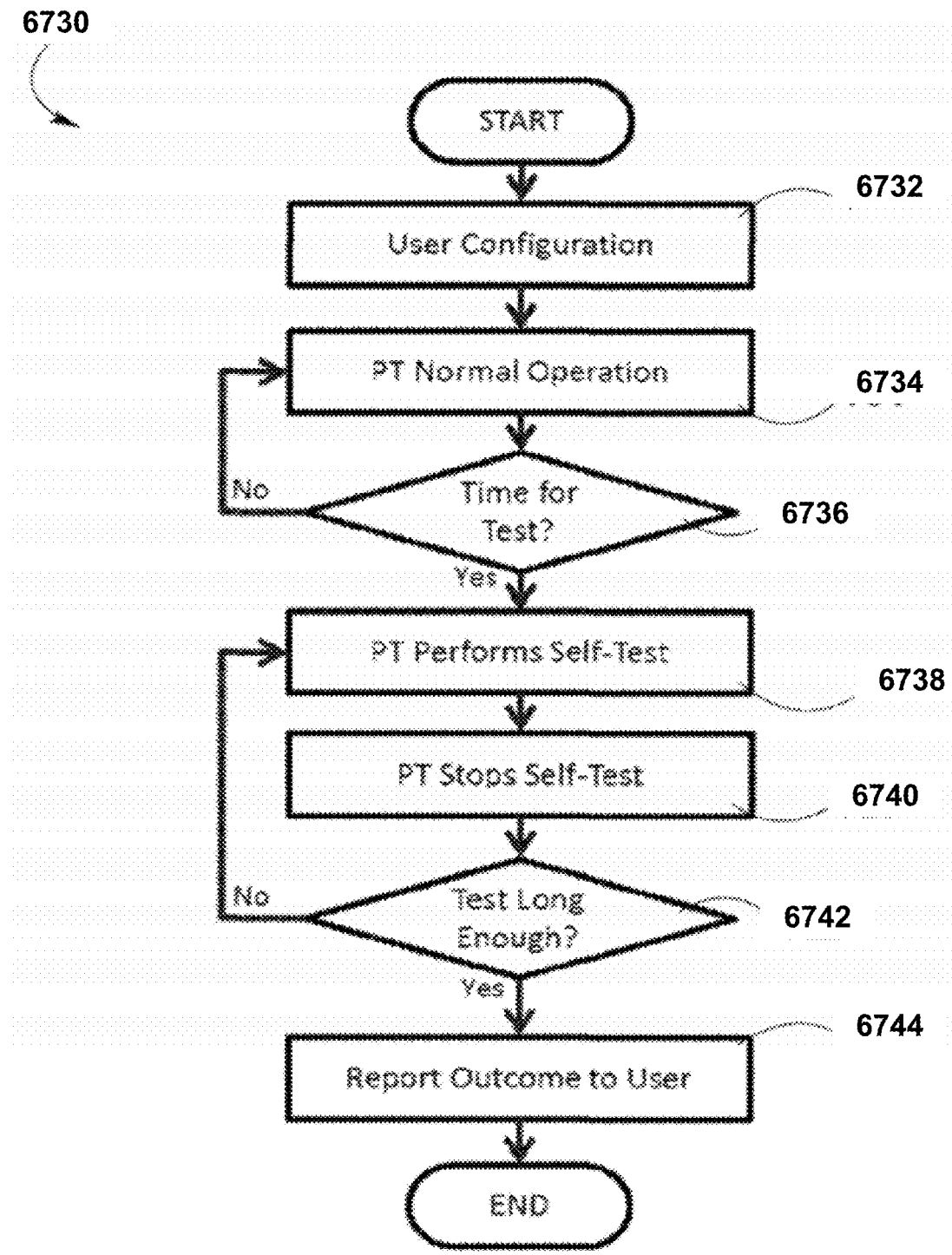
FIG. 67C is a flowchart showing a method for automatic initiation of a self-test during a normal operation of a power transmitter, in accordance with some embodiments.

FIG. 67C is a flowchart showing a method for automatic initiation during normal operation 6730 of a PT self-test, according to an exemplary embodiment.

Periodically, a wireless power transmission system may automatically initiate an automatic self-test and report outcome to system user. The wireless power transmission system may automatically initiate test of an individual system unit or end-to-end test of complete system. Control of automatic initiation of test for one or more PTs by system may be configured by user. Control of automatic initiation may include when to start automatically initiated test, what to test, and how long to run the automatic test, among other parameters.

The method for automatic initiation during normal operation 6730 of a PT self-test may start when a wireless power transmission system receives a user configuration 6732 from a user computing device. User configuration 6732 may be through a system management GUI web site hosted by the system management service that is cloud based or on a local server, or through a system management GUI app running on the user's mobile computing device.

Following user configuration 6732, PT may start its normal operation 6734, during which PT manager may employ the user configuration 6732 to check 6736 if it's time to perform the self-test. If current time does not correspond with the user configuration 6732, PT may continue with its normal operation 6734. If current time does correspond with the user configuration 6732, wireless power transmission system may command each configured PT to perform 6738 a communication self-test. Subsequently, after the period of time has been completed, according to user configuration 6732, wireless power transmission system may command the PTs whose period has been completed to stop 6740 self-test. Wireless power transmission system may then check 6742 if testing has been performed long enough. If self-test has not been performed long enough, wireless power transmission system may command each configured PT to again perform 6748 communication self-test. If self-test has been performed long enough PT manager application may send a report 6744 of the outcome to the user computing device and inform the user that the automatic self-test has been performed.

Figure 67D:
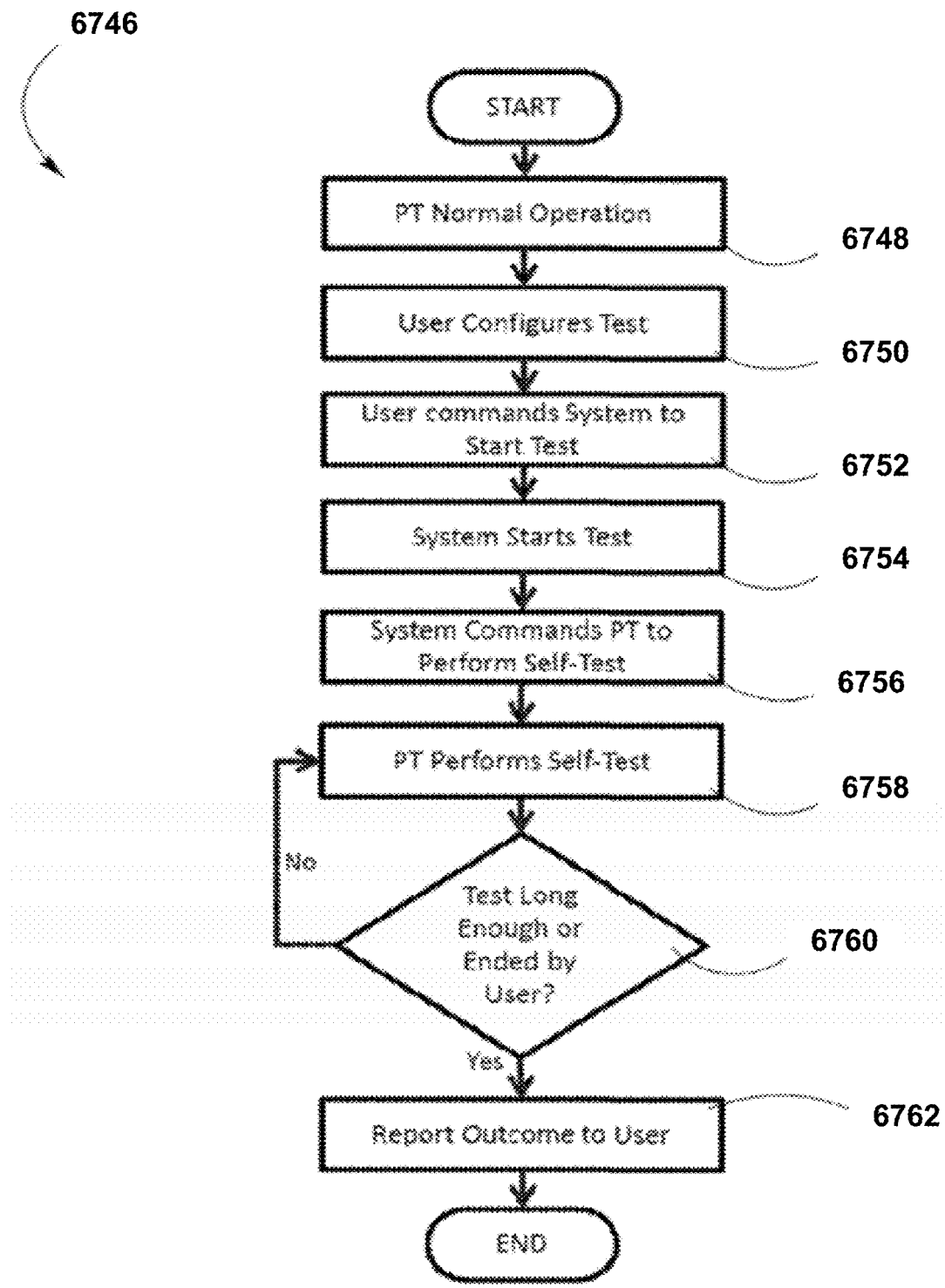
FIG. 67D is a flowchart showing a method for manually initiated power transmitter self-test, in accordance with some embodiments.

FIG. 67D is a flowchart showing a method for manual initiation 6746 of a PT self-test, according to an exemplary embodiment.

A user may employ a computing device and manually start a self-test of a single PT, specific set of PTs, or all system PTs. Manual initiation 6746 of self-test may be commanded by a user computer device operating the system management GUI, either an app running on a user computing device, or a web site hosted by a system management server.

The method for manual initiation 6746 of a PT self-test may start during PT normal operation 6748. A user employs a computing device to configure 6750 the test and subsequently command 6752 a wireless power transmission system to start the test. The wireless power transmission system may then start 6754 the test commanding 6756 each configured PT to perform 6758 the self-test. The algorithm employed by the wireless power transmission system to command the start of the test may be performed by a PT manager application in a wireless power transmission system cloud or a PT application running on the user computing device. The user, by means of a computing device, may specify the duration of test at start.

Wireless power transmission system may then check 6760 if testing has been performed long enough. If self-test has not been performed long enough, wireless power transmission system may command the next configured PT to perform 6758 a communication self-test. PT self-test may run indefinitely until self-test has been performed long enough or test is ended by a user by means of a computing device.

If self-test has been performed long enough or test is ended by a user computing device, then PT manager application may send a report 6762 of the outcome to the user at the system management GUI and inform the user that the automatic self-test has been performed.

Figure 67E:
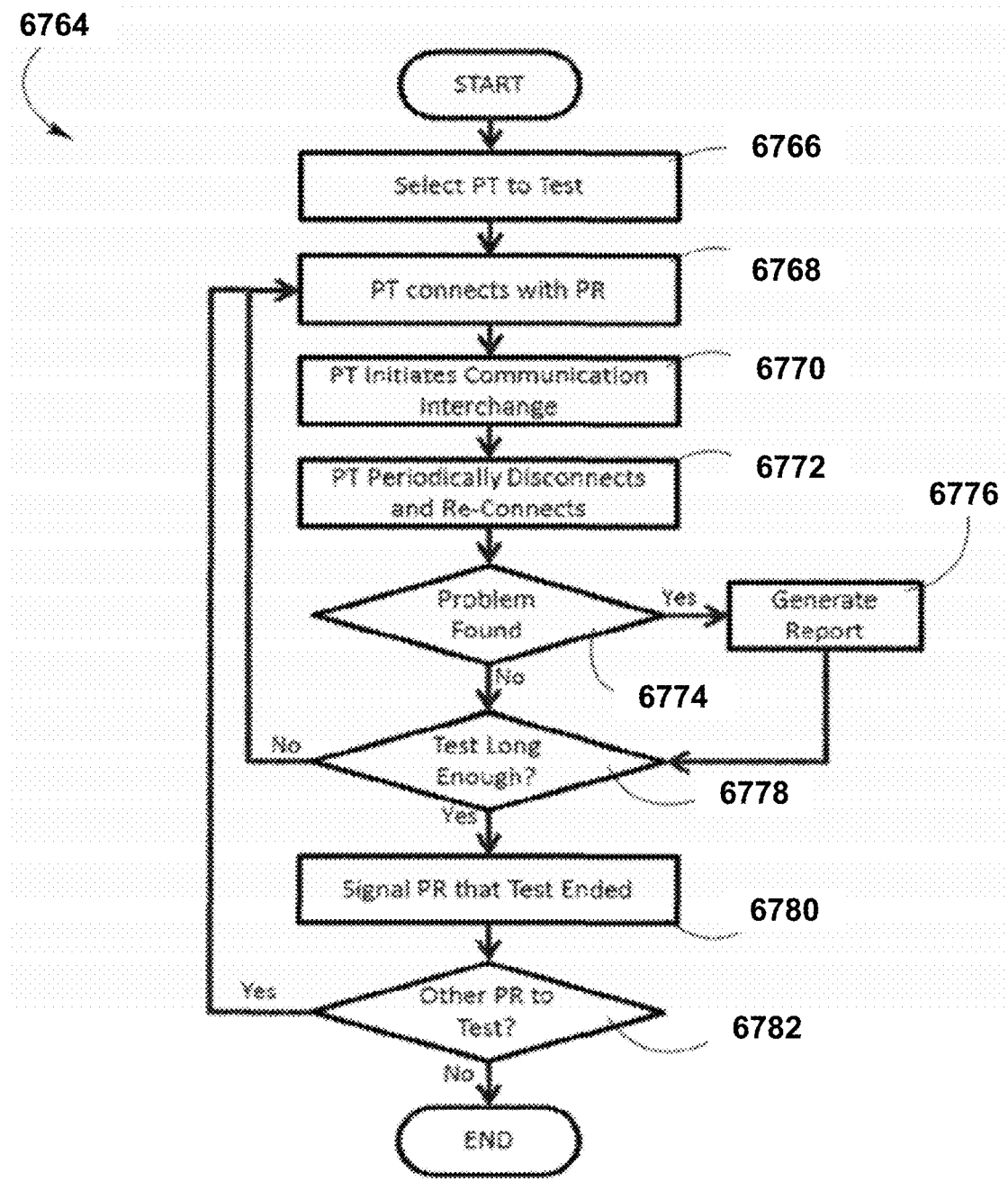
FIG. 67E is a flowchart showing a method for performing a self-test of a power transmitter, in accordance with some embodiments.

FIG. 67E is a flowchart showing a method for performing a PT communication self-test 6764, according to an exemplary embodiment.

In one embodiment, when a PT boots-up, PT may scan for all PRs within the communication range. For each PR found, PT may perform an automatic communication self-test for a finite period of time, and then PT may stop self-test and may start normal operation. Once boot-time communication self-test has passed, PT may periodically check if a command to run self-test has been communicated to it from system management software that is external to the PT.

In other embodiments, wireless power transmission system may periodically automatically initiate the automatic communication self-test and report outcome to system user. The system may automatically initiate the communication self-test of an individual system unit or an end-to-end test of the complete system. Control of automatic initiation of test by system may be configured by a user.

In another embodiment, a user may manually start self-test of a single transmitter, specific set of transmitters, or all system transmitters. Communication self-test may run indefinitely until stopped by user, or user may specify duration of test at start.

In some embodiments, a wireless power transmission system management software may communicate the self-test command to a PT in response to a user command entered at a client device that is running a system mobile management app, or at the system web page that is hosted by the system management server.

In some embodiments, a wireless power transmission system management software may communicate the self-test command to a PT automatically in response to some trigger event, such as the passage of a finite amount of time, or other. The command may indicate that the PT should run the test until commanded to stop, or run the test for a specific duration.

Method for performing a PT communication self-test 6764 may start when a wireless power transmission system's management application software, running on a system management server, selects 6766 a PT to test. Subsequently, the selected PT may scan for all PRs within communication range. For each PR found, the PT may connect 6768 and then initiate communication interchange 6770 with PR. Communication interchange 6770 may be in real-time. Once communication is established, the PT may perform any suitable type of system message exchange, employing any suitable type of system message between the PT and the PR. Then, PT may periodically disconnect and re-connect 6772 from PR, in order to test re-connection. PT may update metrics counters with software actions and operations.

Afterwards, wireless power transmission manager app may check 6774 if there is a problem of communication between PT and PR. If a problem is found, PT manager application may generate 6776 a report to send to the wireless power transmission manager app on the system management server any unexpected patterns of metrics counters or, unexpected operation, or any test failure. If a problem is not found, PT may report that self-test passed to the wireless power transmission manager application.

The wireless power transmission manager app may then check 6778 if testing has been performed long enough. If self-test has not been performed long enough, PT may connect 6768 to the next PR, and then initiate communication interchange 6770 with PR. If self-test has been performed long enough PT manager application may signal 6780 the PR that the self-test has ended, and then end communication with PR.

PT may check 6782 if there are other PRs to be tested and subsequently connect 904 with a PR to test and begin the process of method for performing a PT communication self-test 6764. If there are no other PRs to be tested, the process may end and tested PT may begin normal operation.

If transmitter started the test at boot, then test may end after a finite duration that may be set or hard-coded in the system software.

If test was started by external management software to run for a finite duration, then test may end when transmitter determines that duration has elapsed.

If test was started by external management software to run indefinitely, then test may only end when external management software communicates a command to transmitter to end the test.

After the communication self-test ends, each PT performing the self-test may end communication connection with latest PR being tested. PRs may begin normal operation.

The counts of all actions and operations, performed by the wireless power transmission system while testing connections and communication may be stored in metrics counters within a database. When the PT communication self-test 6764 is complete, said metrics counters may be compared with expected values. If said metrics counters match the expected values, then test passed, otherwise test failed. The wireless power transmission system may report to the user computing device the outcome of the test.

EXAMPLE

Example #1 is an embodiment of the application of method for performing a PT communication self-test 6764, where a wireless power transmission system is being used in an office environment. The office environment includes a first and second wireless power transmitter, the two of which are in communication with a wireless power management service running on a server in the IT department. In example #1, the wireless power transmission system receives a command from a user computing device stating that the computing device is to be charged, and the wireless power transmission manager proceeds to command the PT within the communication range of the user computing device to perform PT communication self-test 6764 as described in FIG. 67E. The PT looks up in its copy of the system database the PR that powers said computing device. When checking the communication between the PT and the PR, unexpected patterns of metrics counters are identified and the self-test fails. The power transmitter manager software within the tested PT then generates a report including the information of the outcome of the self-test and communicates the generated report to the computing device, which is running the system management GUI, which notifies user computing device of test result.

FIGS. 67A-67E illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 67A-67E.

Presented below are example power systems and methods of operating a power system.

A power system may include: (i) a plurality of antenna elements, (ii) a RF circuit, operatively coupled to the plurality of antenna elements, (iii) a processing apparatus, operatively coupled to the RF circuit, where the processing apparatus is configured to cause the RF circuit and plurality of antenna elements to generate pocket-forming energy in 3-dimensional space, and (iv) communications for communicating with a receiver, configured to receive the pocket-forming energy in three dimensional space, where the processing apparatus is configured to perform a self-test of the power system upon the occurrence of a predetermined event.

In some embodiments, the predetermined event comprises one of a boot-up, passage of a predetermined period of time, a self-test command received in the communications from the receiver, and a self-test command received in the communications from a server.

In some embodiments, the processing apparatus is configured to transmit a result of the self-test via the communications.

In some embodiments, the result of the self-test comprises a comparison of the power systems functions to at least one metrics counter.

In some embodiments, the comparison comprises determining if patterns of metrics counters are present.

In some embodiments, the processing apparatus comprises at least one of a digital signal processor and a microcontroller.

In another power system, the system may include: (i) a plurality of antenna elements, (ii) a RF circuit, operatively coupled to the plurality of antenna elements the RF circuit being configured to adjust at least one of phase and magnitude of RF signals provided to the plurality of antenna elements, (iii) a processing apparatus comprising at least one of a microcontroller and a digital signal processor (DSP), operatively coupled to the RF circuit, where the processing apparatus is configured to cause the RF circuit and plurality of antenna elements to generate pocket-forming energy in 3-dimensional space, and (iv) communications for communicating with a receiver, configured to receive the pocket-forming energy in 3-dimensional space, where the processing apparatus is configured to perform a self-test of the power system upon the occurrence of a predetermined event.

A method of operating a power system may include: (i) configuring a processing apparatus to activate a RF circuit operatively coupled to a plurality of antenna elements to generate pocket-forming energy in three dimensional space, (ii) configuring communications to communicate with a receiver configured to receive the pocket-forming energy in 3-dimensional space, and (iii) performing, via the processing apparatus a self-test of the power system upon the occurrence of a predetermined event.

Figure 68A:
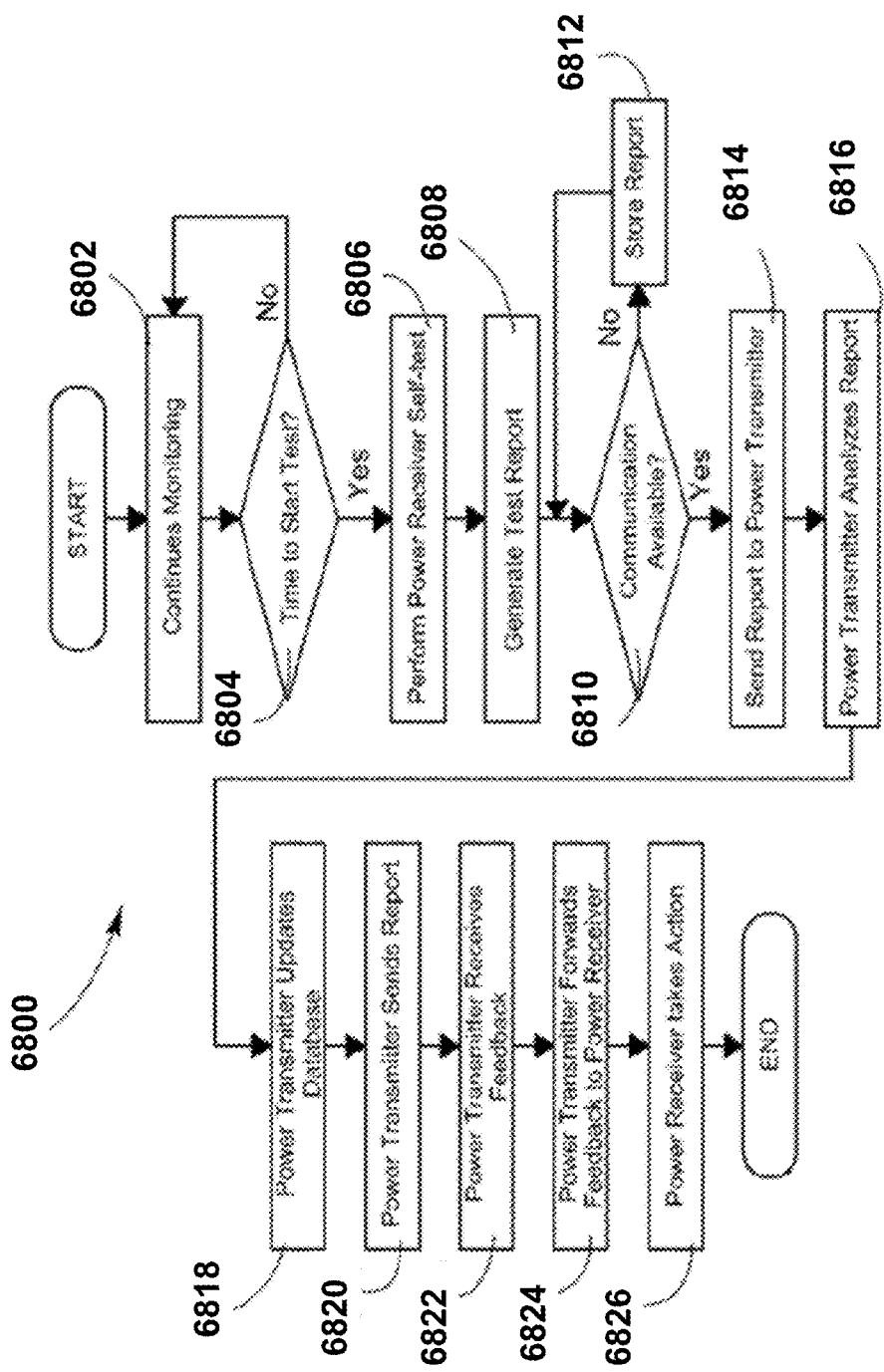
FIG. 68A is a flowchart of a method for automatically testing the operational status of a wireless power receiver, in accordance with some embodiments.
Figure 68B:
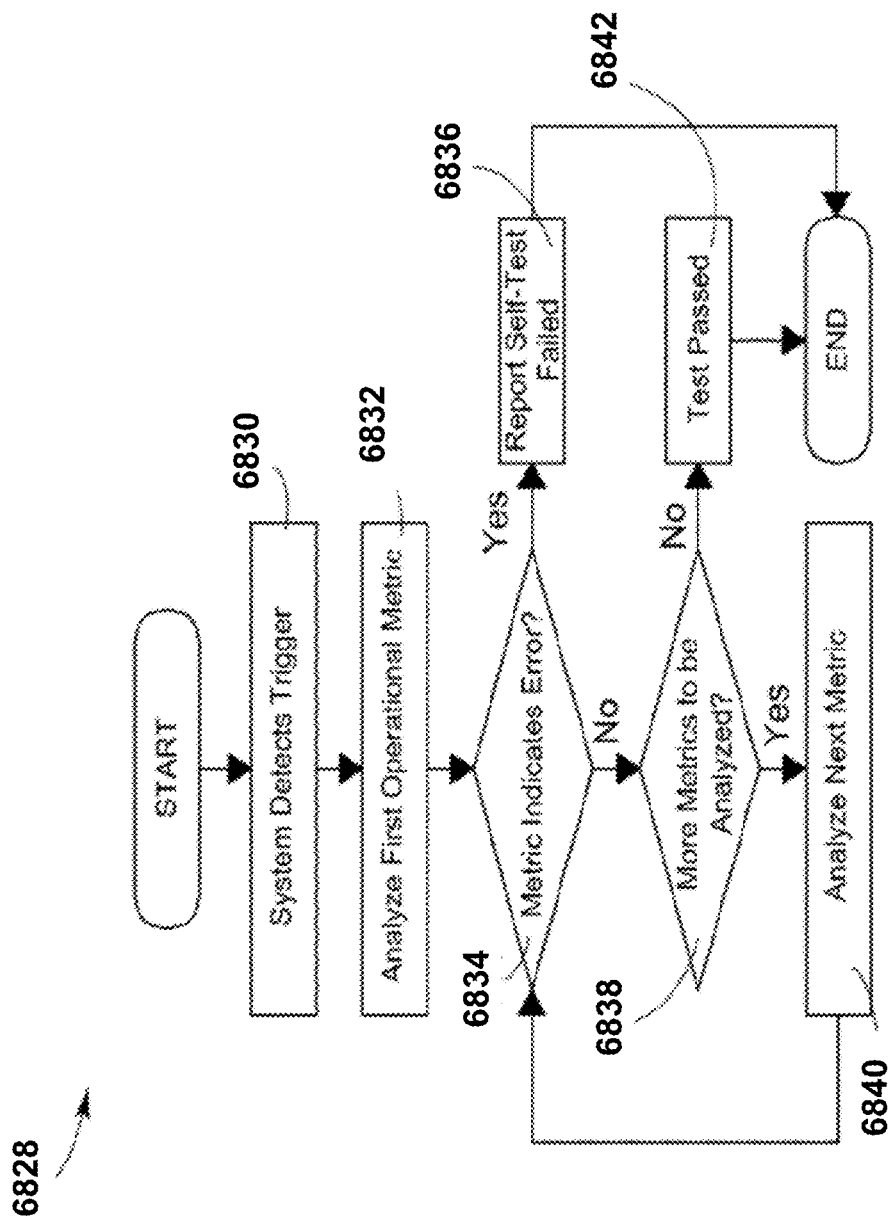
FIG. 68B is a flowchart of a method for performing a power receiver self-test, in accordance with some embodiments.

FIGS. 68A and 68B illustrate flowcharts of methods for wireless power receiver testing, in accordance with some embodiments.

FIG. 68A shows a flowchart of a method 6800 for automatically testing the operational status of a wireless power receiver unit in a wireless power transmission system, according to an embodiment.

In some embodiments, power receiver self-test software may be included in Power Receiver App, which performs communication with wireless power transmitters and manages the functionality of the power receiver for receiving power and transmitting it to its client device.

Method 6800 may start when a power receiver boots up and starts continuous monitoring 6802 of power receiver operational metrics. According to an embodiment, values of operational metrics counters may be stored in power receiver's memory. The counters may be updated whenever the power receiver's software detects any kind of event, status, or change in status, of receiver's software, hardware, operation, communication, or performance. According to some embodiments, power receiver memory for storage of system operational metrics may be volatile or non-volatile.

According to some embodiments, wireless power receiver software may include a timer callback from the underlying application programming interface (API) to the CPU. The timer callback may periodically trigger the software that self-tests the wireless power receiver, when time to start 6804 self-test is reached. In some embodiments, the self-test may also be run in response to a command received from a wireless power transmitter. In further embodiments, the self-test may also be initiated by boot-up or restart or reset of power receiver's software.

Then, wireless power receiver's software may perform self-test 6806. During self-test 6806, the wireless power receiver may analyze the present or past status of the receiver's software, hardware, operation, communication, or performance by analyzing the values of the receiver's operational metrics. According to some embodiments, power receiver's software may be capable of detecting indicators of past, present, or possible future errors based on the analysis of the system operational metrics. According to some embodiments, unexpected patterns in metrics may also be interpreted as errors. Self-test 6806 may test for any number of software, hardware, operation, communication, or performance errors.

According to some embodiments, self-test 6806 may check for and report errors for any kind of unexpected performance operational metrics such as low power transmitted to client device compared with power received at antennas, or such as power at receiver antenna unexpectedly too low for too much time, or such as unexpected low level of power efficiency from received RF power to transmitted electrical power to client device.

In some embodiments, self-test 6806 may check for and report errors for any kind of unexpected software operational metrics such as software stack overflow or underflow, or unexpected number or rate of software restarts or watchdog reboots, or metrics of power generated is impossibly high, or the like.

In some embodiments, self-test 6806 may check for and report errors for any kind of unexpected hardware operational metrics such as analog-to-digital values below or above expected limits, or errors with relay connection switch to client device in unexpected state, such as open when wireless power receiver is receiving power from a wireless power transmitter, or closed when the wireless power receiver is not receiving power from a wireless power transmitter; or errors for unexpected voltage measured before and after conditioning of voltage from wireless power receiver antenna rectifiers, or conditioning errors, or errors reported by any hardware device, or other erroneous hardware conditions.

In further embodiments, self-test 6806 may also check for and report errors for any kind of unexpected communication operational metrics such as count or rate of unexpected disconnections with wireless power transmitter, or count or rate of invalid received communications.

According to an exemplary embodiment, detection of errors may take place by analyzing only the system operational metrics, which may simplify the analysis procedure or may save software development time.

After self-test 6806, power receiver's software may generate a test report 6808, including system operational metrics and error reports, if found.

Afterwards, the power receiver App may check 6810 if there is an available communication connection with a power transmitter. If there is no communication connection established with a wireless power transmitter, the wireless power receiver may store 6812 the self-test 6806 results or details in its memory, where the memory may be volatile or non-volatile.

If there is an available communication connection with a wireless power transmitter, the wireless power receiver may send 6814 the self-test 6806 results to the power transmitter. The wireless power transmitter may then analyze 6816 operational metrics from the wireless power receiver and compare with operational metrics or other status at the wireless power transmitter to detect other errors.

In some exemplary embodiments, the wireless power receiver may report the results of the self-test 6806 that was performed just before establishment of communication connection. This may be reported immediately upon establishment of communication connection with a wireless power transmitter.

Furthermore, in some embodiments, a wireless power receiver may also perform its self-test 6806 immediately upon establishment of communication with a wireless power transmitter, and not wait until the next scheduled periodic time.

Then, wireless power transmitter may update 6818 its database and store the results of the analysis. Afterwards, wireless power transmitter may send 6820 the results to the user by a management mobile device GUI or system server hosted web page, by displayed graph, or line by line report or log of each error, and may include time stamp, ID of wireless power receiver, ID of wireless power transmitter, error code or label or description or other. In some embodiments, a wireless power receiver may be capable of reporting results or details of self-test 6806 by blinking or colored LED's, or system management server may report said results by SMS text message, email, or voice synthesis telephone or VOIP call, or other computer-to-human or computer-to-computer means.

According to some embodiments, the wireless power transmitter may communicate any of receiver's automatic self-test result information to any mobile system management GUI client device, or any system management server, or a remote wireless power transmission system information distribution service.

In some embodiments, the wireless power transmitter may distribute the self-test results through a distributed wireless power transmission database to each server, transmitter, and mobile device of said wireless power transmission system.

According to some embodiments, the wireless power transmitter may receive feedback 6822 from the user or a remote management system. In some embodiments, a user may issue one or more commands through a system management device including wireless power management software. Then, system management device that receives the command from the user may forward the command to all wireless power transmitters within the system.

Subsequently, the present or next wireless power transmitter in communication with the target wireless power receiver may forward 6824 the command to the wireless power receiver. The wireless power receiver may then receive the feedback 6822 and take a suitable action 6826 in response to the received feedback, such as, but not limited to, rebooting or restarting the power receiver's software.

In some embodiments, user feedback 6822 may include manual commands to reset the operational metrics of any wireless power receiver, which effectively erases all past error detections.

FIG. 68B is a flowchart of a method for performing a power receiver self-test 6828, according to an embodiment. Method for performing a wireless power receiver self-test 6828 may start when wireless power transmitter app detects a suitable trigger 6830. Then, self-test software may analyze 6832 first system operational metric and determine 6834 if the analyzed metric indicates an error. If self-test software determines that the metric indicates an error, self-test software may generate a self-test failed 6836 report and the process may end. If self-test software determines that the metric does not indicate an error, self-test software may check 6838 if there are more system operational metrics to be analyzed. If there are, the self-test software may continue to analyze the next system operational metric 6840 until all system operational metrics have been analyzed or an error has been detected. If there are no more system operational metrics to be analyzed and no errors have been detected, self-test software may generate a self-test passed 6842 report and the process may end.

EXAMPLES

In example #1 a wireless power receiver performs a pre-scheduled self-test. To perform the test, the wireless power receiver self-test software analyzes receiver's operational metrics related to software, hardware and communication. In example #1 the self-test software doesn't identify any error and generates self-test report that indicates the test passed. Then, the wireless power receiver sends the report along with the receiver's operational metrics to the wireless power transmitter in communication with the receiver. The wireless power transmitter analyzes report and its included operational metrics, and may compare with its transmitter operational metrics or status, and finds no indicator of possible error. Afterwards, the wireless power transmitter sends the report to a system management server or service.

In example #2 a wireless power receiver performs an automatic self-test. To perform the test, the wireless power receiver self-test software analyzes receiver operational metrics related to software, hardware and communication. In example #2 the self-test software doesn't identify any error and generates the test report. Then, the wireless power receiver sends the report to a wireless power transmitter. The wireless power transmitter analyzes the report and finds an indicator of a possible error. Afterwards, the wireless power transmitter sends the report to a remote management system. The report is analyzed by the remote management system and the operator of the wireless power transmission system is notified of the possible error, and suggestions to prevent the error are delivered to the operator. Then, the operator, through a system management device, changes certain configuration parameters in the system to prevent the error.

FIGS. 68A and 68B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 68A and 68B.

Presented below are example power system receivers and methods of operating a power system receiver.

A power system receiver may include: (i) a plurality of antenna elements, (ii) a rectifier, operatively coupled to the plurality of antenna elements, (iii) a power converter, operatively coupled to the rectifier, where the power converter and rectifier are configured to receive pocket-forming energy in 3-dimensional space for use in charging a battery, and (iv) a processing apparatus, configured to perform a self-test of the power system receiver upon the occurrence of a predetermined event.

In some embodiments, the power system receiver may include communications configured to send and receive data to the power system receiver.

In some embodiments, the predetermined event comprises one of a boot-up, restart, reset, and passage of a predetermined period of time, a self-test command received in the communications from a transmitter, and a self-test command received in the communications from a server.

In another power system receiver, the power system receiver may include: (i) a plurality of antenna elements, (ii) a rectifier, operatively coupled to the plurality of antenna elements, (iii) a power converter, operatively coupled to the rectifier, where the power converter and rectifier are configured to receive pocket-forming energy in 3-dimensional space for use in charging a battery, (iv) communications configured to send and receive data to the power system receiver, and (v) a processing apparatus, configured to perform a self-test of at least one of (i) the power system receiver and (ii) the communications upon the occurrence of a predetermined event.

A method of operating a power system receiver may include: (i) configuring a plurality of antenna elements, a rectifier, operatively coupled to the plurality of antenna elements and a power converter, operatively coupled to the rectifier, to receive pocket-forming energy in 3-dimensional space in the power system receiver for use in charging a battery and (ii) performing, via a processing apparatus in the power system receiver, a self-test of the power system upon the occurrence of a predetermined event.

In some embodiments, the method includes configuring communications to communicate with a transmitter configured to transmit the pocket-forming energy in 3-dimensional space.

Figure 69A:
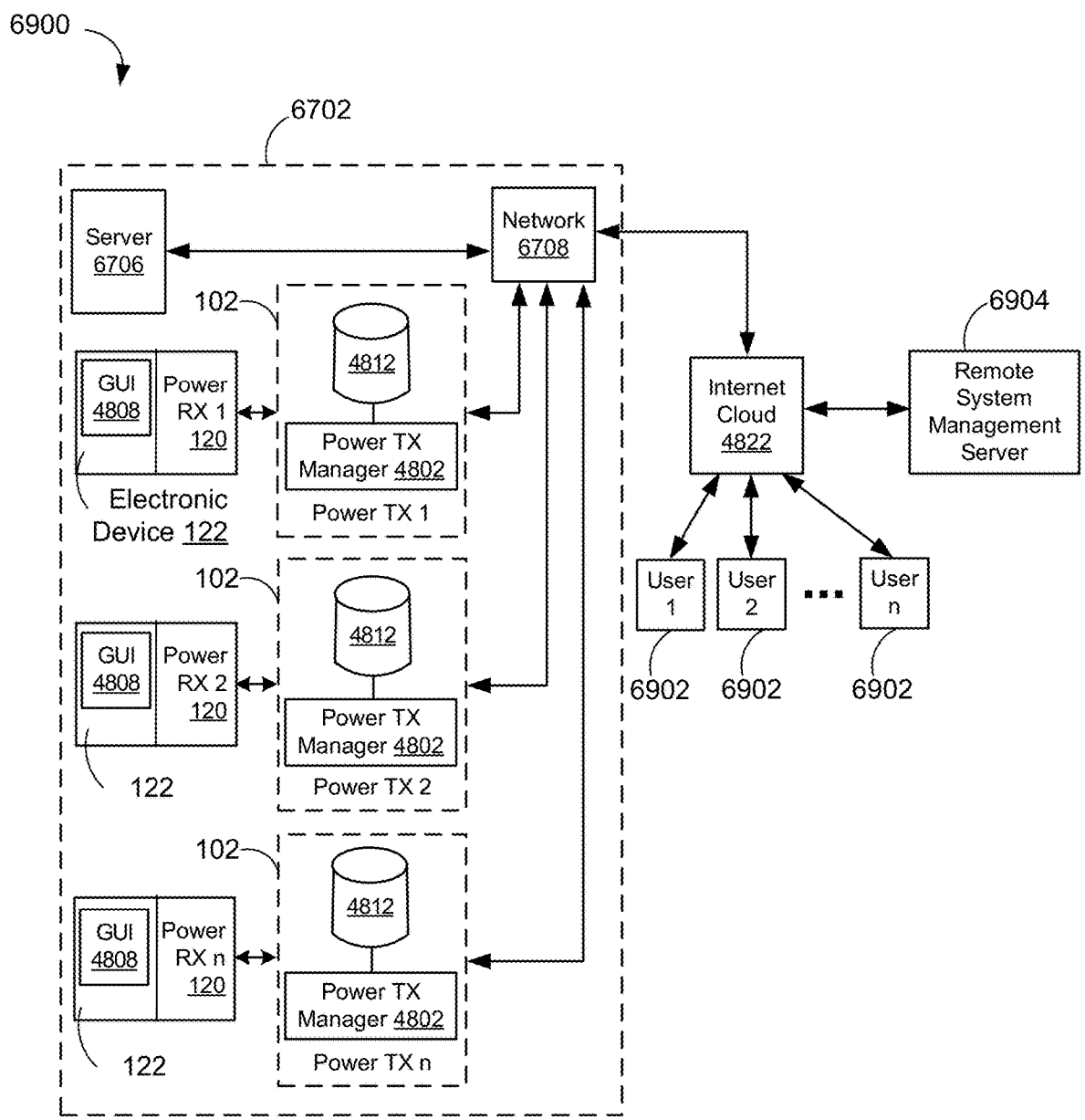
FIG. 69A illustrates a system architecture for wireless power transmission system, in accordance with some embodiments.
Figure 69B:
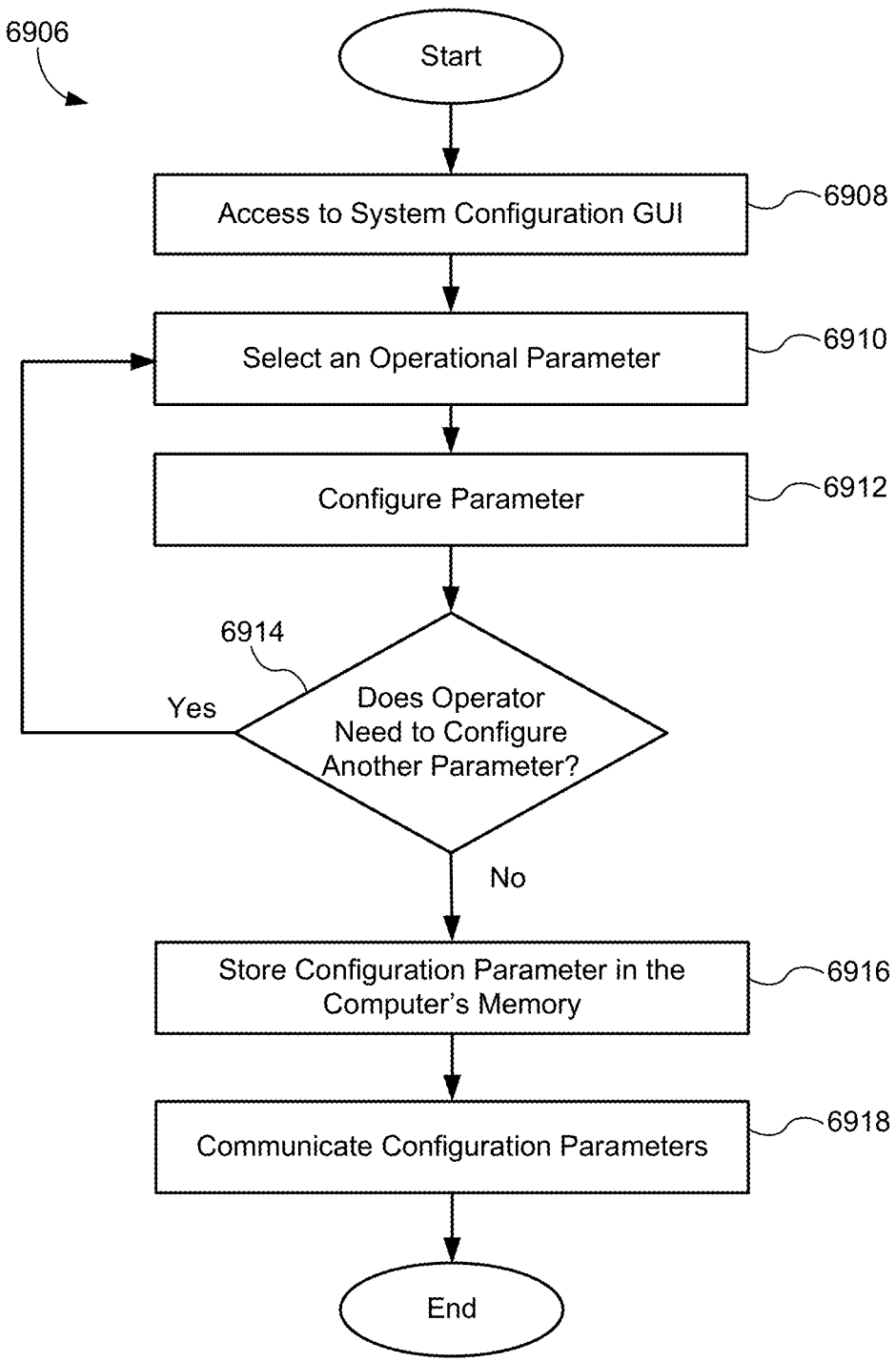
FIG. 69B is a flowchart of a method to control a wireless power transmission system by configuration of wireless power transmission control parameters, in accordance with some embodiments.

FIGS. 69A and 69B illustrate a system architecture and a flowchart to control a wireless power transmission system by configuration of wireless power transmission control parameters, in accordance with some embodiments.

FIG. 69A illustrates a system architecture 6900 for a wireless power transmission system 6702 (FIG. 67A), according to another embodiment.

A wireless power transmission system 6702 may include one or more wireless power transmitters 102 (FIG. 1), one or more wireless power receivers 120 (FIG. 1), one or more optional system management servers 6706 (FIG. 67A), and one or more optional mobile or hand-held computers or smart phones, or the like.

Wireless power transmission system 6702 may include communication between one or more wireless power transmitters 102 and one or more wireless power receivers 120. Client device 122 (FIG. 1) may be coupled to an adaptable wireless power receiver 120 that may enable wireless power transmission to client device 122. In another embodiment, a client device 122 may include a wireless power receiver 120 built in as part of the hardware of the device. Client device 122 may be any device which uses an energy power source, such as, laptop computers, stationary computers, mobile phones, tablets, mobile gaming devices, televisions, radios and/or any set of appliances that may require or benefit from an electrical power source.

In one embodiment, one or more wireless power transmitters 102 may include a microprocessor that integrates a power transmitter manager 4802 (FIG. 48A) application (PWR TX MGR APP) as embedded software. Power transmitter manager 4802 application (PWR TX MGR APP) may also include a distributed system database 4812 (FIG. 48A), which may store relevant information associated with client device 122, such as their identifiers for a client device 122, voltage ranges for wireless power receiver 120, location of a client device 122, signal strength and/or any other relevant information associated with a client device 122. Database 4812 may also store information relevant to the wireless power transmission system, including wireless power receiver ID's, wireless power transmitter ID's, end-user handheld devices, system management servers, charging schedules, charging priorities and/or any other data relevant to a wireless power network.

Communication between wireless power transmitters and wireless power receivers may be achieved using standard network communication protocols such as, Bluetooth Low Energy, WiFi, or the like.

A graphical user interface (GUI) 4808 (FIG. 48A) may be used to manage the wireless power transmission system from a client device 122. GUI 4808 may be a software module that may be downloaded from any suitable application store and may run on any suitable operating system, including iOS and Android, among others.

In some embodiments, wireless power transmitters 102 may use network 6708 (FIG. 67A) to send and receive information. Network 6708 may be a local area network, or any suitable communication system between the components of the wireless power transmission system 6702. Network 6708 may enable communication between two or more wireless power transmitters 102, the communication of wireless power transmitters 102 with system management server 6706, and may facilitate the communication between wireless power transmission system 6702 and remote (cloud) system Internet cloud 4822 (FIG. 48B), among others.

The configuration of the wireless power transmission system may be performed by a user or an operator using a standard web browser on a computing device 6902 such as mobile, desktop, laptop, or other computer device. The web browser may access to the system configuration graphical user interface (GUI). The system configuration GUI may be hosted by a remote (cloud) system management server 6904 connected to an Internet cloud 4822. The system configuration GUI (not shown in FIG. 69A) presented at the browser to the operator may be functionally identical regardless of the computing device 6902 running the browser.

In a different embodiment system configuration GUI may be hosted by any wireless power transmitter 102 of the system. In another embodiment system configuration GUI may be hosted by the system's management service that may be hosted by a system management server 6706, where system's management service may be a software application to manage wireless power transmission system 6702. System management server and remote (cloud) system management server 6904 may be cloud-based backend servers and may be implemented through known in the art database management systems (DBMS) such as, for example, MySQL, PostgreSQL, SQLite, Microsoft SQL Server, Microsoft Access, Oracle, SAP, dBASE, FoxPro, IBM DB2, LibreOffice Base, FileMaker Pro and/or any other type of database that may organize collections of data.

The configuration of the wireless power transmission system may also be performed using GUI software application (not shown in FIG. 69A) on a mobile computer or computing device 6902, such as smartphones, tablets, desktop, and laptop, among others.

In a different embodiment, the system configuration may be performed using Short Message Service (SMS) text message or Simple Mail Transfer Protocol (SMTP) email to access to the system or any other method to communicate with the system.

The system configuration GUI may be connected to the system through the system configuration application programming interface (API). The system configuration API may run on system management server 6706, in a remote (cloud) system management server 6904, or on a mobile system device. The web browser may access to system configuration API on the computer system hosting the system configuration GUI such as remote (cloud) system management server 6904 or system management server 6706.

The system configuration API may be used in response to each operation action performed at system configuration GUI. The system configuration API may then store configuration parameters in the computer's memory. These configuration parameters are then communicated to other system computers, so that each computer of the system, such as wireless power transmitter 102, system management server 6706 or remote (cloud) system management server 6904 always has the same system configuration. The system configuration API may also be used to read the system configuration for the system configuration GUI to present it to the user or operator.

The system configuration API at each system computer may have a built-it or hard-coded communication format version that is presented and verified during communication with other system computers to prevent configuration problems due to operation of system computers with incompatible software versions. Although system configuration may take the form of a web page, a mobile or computer device software application, text message, and email, among others method, the configuration functionality of each method is the same, and each method employs the system configuration API with the exact same compatibility with the system.

The system configuration controls the operational parameters of the entire system, the operational parameters of each system device, and controls password access to system configuration, among others.

According to some aspects of this embodiment, the operator using system configuration GUI may select a parameter that configures a specific wireless power transmitter 102 to always transmit power to any wireless power receiver 120 within range. Also the user or operator may select a parameter to configure wireless power transmitter 102 to only power wireless power receivers 120 that are specified by the operator. Then operator may enter the identification of each of these wireless power receivers 120, or if wireless power receiver 120 has been in communication with wireless power transmitter 102 operator may be able to select the identification of the wireless power receivers 120 from a list on the web page, because wireless power receiver's unique identification may be store into wireless power transmitter's database 4812.

In a different aspect of this embodiment, the operator may use system configuration GUI to specify that wireless power transmission always take place at a set of hours of the day for a specific wireless power receiver. If multiple wireless power receivers are restricted to the same hour, wireless power receiver 120 may be configured to have a priority, so the wireless power receiver 120 with the highest priority is charged and wireless power receivers with lower priority are not charged, and wireless power receivers of equal priority are charged at the same time.

In another embodiment, the operator may use system configuration GUI to select situations in which wireless power transmitter 102 may not transmit power to a wireless power receiver 120. For example, if a client device 122 receiving power from wireless power receiver 120 is not lying flat or is in movement or other situations that are detected by the system application running on the device the wireless power transmitter 102 may not transmit power to the client device 122. This system application may communicate by Wi-Fi or other means to the wireless power transmitter 102 so wireless power transmitter 102 can decide whether or not to transmit power to client device 122, based on situational settings. Wireless power transmitter 102 may also communicate present situations of devices to other system computers. These situational configurations may be used to enable or disable wireless power transmission in situations where the health of the user of the client device is believed to be at risk or any other situations where wireless power transmission may not be desired.

In a further embodiment each system computer with the system configuration API may also support automatic configuration by an external computer. The external computer would have the capability to read from one of the system computers the present configuration of the system, and then send back changes to the configuration. The external computer, local or in the Internet cloud may communicate with the system computer through its web service, or by any other method of communication such as TCP/IP socket connection, XML messages, simple mail transport protocol (SMTP), and SMS text message, among others.

In a different embodiment the operator may use system configuration GUI to assign names of the wireless system users, so that a specific user may be associated with a specific client device 122 or wireless power receiver 120. Operator may also configure other details about users, such as contact info, employee number, customer number, billing information, and password level, among others. The operator may need to use system configuration service to assign friendly device names to client devices, wireless power receivers, wireless power transmitters, or system management servers, so that a specific device may be conveniently referred to by its friendly name during system configuration.

The operator may need to use system configuration GUI to define the various physical wireless power transmission areas, locations, buildings or rooms of service, among others. The operator may also need to assign which wireless power transmitters belong to an area. The operator may assign a friendly name to the area, and then this name may be used to configure system operational parameters for that area.

Also the operator may use system configuration GUI to specify users that may be automatically contacted in the occurrence of a significant system event, such as malfunctioning of wireless power transmitter, the need to add more wireless power transmitters to an overly busy area, or the like.

The operator may use system configuration GUI to setup system account and password control for specific users, to control system usage, operation, or to perform billing for power consumption, among others.

For specific system operational requirements, certain users may be allowed access to subsets of system configuration, depending on user's password authorization level or role. For example, a clerk at a Starbucks or restaurant may be authorized to only configure the local wireless power transmission system to add a new supply of wireless power receivers to the list that may receive power.

In a different embodiment, the storage of configuration within each system computer may be encrypted. The encryption keys may be controlled by the configuration API, to prevent malicious examination of the system configuration details within a system computer's non-volatile memory.

FIG. 69B is a flowchart 6906 of a method to control a wireless power transmission system by configuration of wireless power transmission control parameters, according to an embodiment.

A wireless power transmission system may include one or more wireless power transmitters, one or more wireless power receivers, one or more optional system management servers, and one or more optional mobile, hand-held computers, smart phones, or the like.

The method may start at step 6908 when an operator accesses the system configuration GUI. The operator may use a standard web browser on a computing device such as mobile, desktop, laptop, or other computer device. The system configuration GUI may be hosted by a remote (cloud) management server connected to the Internet cloud. The system configuration GUI presented at the browser to the operator may be functionally identical regardless of the computing device running the browser.

In a different embodiment, the system configuration GUI may be hosted by any wireless power transmitter of the system. In another embodiment, system configuration GUI may be hosted by the system's management service that may be hosted by a system management server, where system's management service may be a software application to manage wireless power transmission system. System management server and remote (cloud) system management server may be cloud-based back-end servers and may be implemented through known in the art database management systems (DBMS) such as, for example, MySQL, PostgreSQL, SQLite, Microsoft SQL Server, Microsoft Access, Oracle, SAP, dBASE, FoxPro, IBM DB2, LibreOffice Base, FileMaker Pro and/or any other type of database that may organize collections of data.

The configuration of the wireless power transmission system may also be performed using a GUI software application on a mobile computer or computing device, such as smartphones, tablets, desktop, and laptop, among others.

In a different embodiment, the system configuration may be performed using Short Message Service (SMS) text message or Simple Mail Transfer Protocol (SMTP) email to access to the system or any other method to communicate with the system.

Once the operator accesses system configuration GUI, system configuration GUI may show various operational parameters to set up the system, such as wireless power transmission operation, automatic charging, situational configuration, configuration by external computer, user names and info, devices names, area definition, contact info for alerts, credential authentication, subset configurations, and encryption among others.

The operator may then select an operational parameter to configure the system, at step 6910.

Subsequently, the system configuration GUI may display another page with the information regarding the operational parameter previously selected, at step 6912.

Operator may be able to configure a parameter that enables a specific wireless power transmitter to always transmit power to any wireless power receiver within range. Also the operator may be able to select a parameter to configure wireless power transmitter to only power wireless power receivers that are specified by the operator.

According to some aspect of this embodiment, if operator selects to configure automatic charging, the operator may be able to set up a set of hours of the day in which the wireless power transmission takes place for a specific wireless power receiver. Also operator may be able to assign priorities to the wireless power receivers in the case multiple wireless power receivers are restricted to the same hour, so that at that hour the wireless power receiver with the highest priority is charged and wireless power receivers with lower priority are not charged, and wireless power receivers of equal priority are charged at the same time.

For situational configuration, the operator may configure situations in which wireless power transmitter may not transmit power to a wireless power receiver. For example, if a client device receiving power from wireless power receiver is not lying flat or is in movement or other situations that are detected by the system application running on the device the wireless power transmitter may not transmit power to the client device.

According to some aspects of this embodiment, operator may use system configuration GUI to assign names of the wireless system users, so that a specific user may be associated with a specific client device or wireless power receiver. Operator may also able to configure other details about users, such as contact info, employee number, customer number, billing information, and password level, among others.

The operator may be able to configure physical wireless power transmission areas of service. The operator may also be able to assign wireless power transmitters to an area.

If operator selects to configure contact info for alert, operator may be able to specify users to be automatically contacted in the occurrence of a significant system event, such as malfunctioning transmitter, the need to add more transmitter to a busy area, or the like.

In case the operator may select to configure credential authentication, the operator may have the option to set up the system account and password control for specific users, control system usage, operation, or to perform billing for power consumption, among others.

For specific system operational requirements, certain users may be allowed access to subsets of system configuration, depending on user's password authorization level or role. For example, a clerk at a Starbucks or restaurant may be authorized to only configure the local wireless power transmission system to add a new supply of wireless power receivers to the list that may receive power.

The operator may have the option to continue configuring the rest of the operational parameters after finished configuring the operational parameter previously selected, at step 6914.

If operator have finished configuring the operational parameter previously selected and does not need to configure another parameter, then a system configuration application programming interface (API) information may store configuration parameters in the computer's memory, at step 6916.

The system configuration API may run on a system management server, in a remote (cloud) system management server, or on a mobile system device. The system configuration API may connect the system with the system configuration GUI, and may be used in response to each operation action performed at system configuration GUI. The system configuration API may also be used to read the system configuration for the system configuration GUI to present to the user or operator.

According to some aspects of this embodiment, each system computer with the system configuration API may also support automatic configuration by an external computer. The external computer may have the capability to read from one of the system computers the present configuration of the system, and then send back changes to the configuration. The external computer, local or in the Internet cloud may communicate with the system computer through its web service, or by any other method of communication such as TCP/IP socket connection, XML messages, simple mail transport protocol (SMTP), and SMS text message, among others.

Configuration parameters are then communicated to other system computers, so that each computer of the system, such as wireless power transmitter or management server, always has the same system configuration, at step 6918.

The system configuration API at each system computer may have a built-it or hard-coded communication format version that is presented and verified during communication with other system computers to prevent configuration problems due to operation of system computers with incompatible software versions. Although system configuration GUI may take the form of a web page, a mobile or computer device software application, text message, and email, among others method, the configuration functionality of each method is the same, and each method employs the system configuration API with the exact same compatibility with the system.

According to some aspects of this embodiment, the storage of configuration parameters within each system computer may be encrypted. The encryption keys may be controlled by the system configuration API, to prevent malicious examination of the system configuration details within a system computer's non-volatile memory.

EXAMPLES

Example #1 is a wireless power transmission system with components similar to those described in FIG. 69A. An operator may need to set up authorization levels in the system, to assign permission to certain users to change some configurations. For example, in a wireless power transmission system that belongs to a particular house, the operator may assign permission to some members of the house to allow the charging of a game controller brought over by a visiting friend. The operator may access a system configuration GUI, where the operator may select the operational parameter he or she wants to configure, then another GUI page will allow configuration of authorizations level. Once the operator finishes with the configuring process, the configuration may be stored in the computer memory and subsequently the information may be communicated to others system computers.

Example #2 is a wireless power transmission system with components similar to those described in FIG. 69A. An operator may need to configure situational configurations in the system such as, if a client device receiving power from wireless power receiver is a smart phone and is being used for a telephone call the wireless power transmitter may not transmit power to the client device. The operator may access to the system configuration GUI, where the operator may select the operational parameter he wants to configure, then another GUI page will display to configure the situational configuration. Once the operator finishes with the configuring process, the configuration may be stored in the computer memory and subsequently the information may be communicated to others system computers. Once configured, the system software application running on the client device will communicate to the rest of the system whether or not the device is presently placing a telephone call. Then, if the wireless power transmission system decides to begin sending wireless power to the device, the wireless power transmitter that is within range of the client device will not attempt to transmit wireless power to the device if the device is presently placing a telephone call. If the device is not presently placing a telephone call, then the wireless power transmitter will start transmitting wireless power to the device. If while the device is receiving wireless power the device begins to make a telephone call, then the system software application running on the device will communicate this new situation to the system, and the wireless power transmitter will stop transmitting power to the device.

FIGS. 69A and 69B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 69A and 69B.

Presented below are example systems and methods of wireless charging a receiver based on operational parameters.

A processor-based system for managing a power system comprising a plurality of power transmitters, configured to generate pocket-forming energy in 3-dimensional space to at least one receiver for charging may include: (i) a processor, (ii) a database operatively coupled to the processor, and (iii) communications, operatively coupled to the processor, where the communications is operable to communicate with a network, that is further communicatively coupled to the plurality of power transmitters, where the processor is configured to receive an operational parameter via the communications for the at least some of the plurality of power transmitters and utilize the operational parameter for controlling system configuration for each of the plurality of power transmitters.

In some embodiments, the operational parameter comprises at least one of (i) authorization for the at least one receiver for charging, (ii) a priority for the at least one receiver for charging, (iii) one or more times or conditions for generating pocket-forming energy in 3-dimensional space, and (iv) one or more times or conditions for stopping the generating of pocket-forming energy in 3-dimensional space.

In some embodiments, the network comprises one of a local area network (LAN), virtual private network (VPN) and a wireless area network (WAN).

In some embodiments, the processor is configured to transmit the operational parameter via the communications to a remote system computer. Furthermore, in some embodiments, the processor is configured to receive a further operational parameter via the communications from the remote system computer and utilize the further operational parameter for further system configuration.

In some embodiments, the processor is configured to receive a system event via the communications and modify the system configuration in response thereto.

In some embodiments, the processor is configured to authorize the received operational parameter.

A processor-based system for configuring a power system comprising at least one power transmitter, configured to generate pocket-forming energy in 3-dimensional space to at least one receiver for charging may include: (i) a processor, (ii) a database operatively coupled to the processor, and (iii) communications, operatively coupled to the processor, where the communications is operable to communicate with a network, where the processor is configured to receive an operational parameter via the communications for the at least one power transmitter and utilize the operational parameter for controlling system configuration.

A processor-based method for configuring a power system comprising at least one power transmitter, configured to generate pocket-forming energy in 3-dimensional space to at least one receiver for charging may include: (i) configuring communications, operatively coupled to a processor and a database to communicate with a network, (ii) receiving an operational parameter via the communications for the at least one power transmitter, and (iii) utilizing the operational parameter for controlling system configuration.

Figure 70:
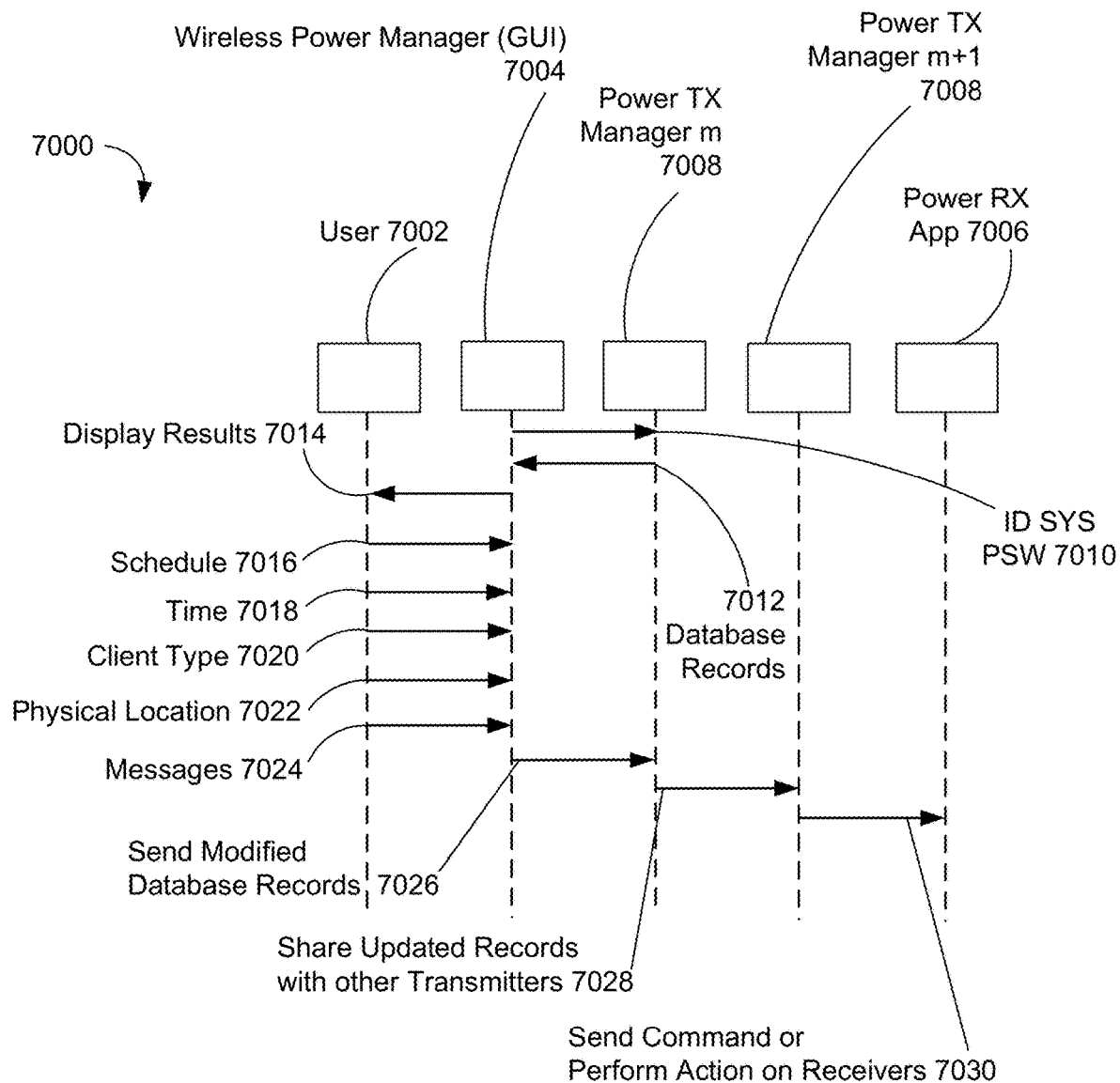
FIG. 70 illustrates a sequence diagram of real time communication between wireless power transmitters, wireless power receivers, a wireless power manager UI, and a user, in accordance with some embodiments.

FIG. 70 shows a sequence diagram 7000 for a real time communication between wireless powered transmitters and wireless powered receivers, according to an embodiment.

Sequence diagram 7000 illustrates the interactions between objects or roles in a wireless powered network. The objects or roles described here may include, but is not limited to, a user 7002 which manages the wireless power network, a wireless power manager 7004 which serves as a front end application for managing the wireless power network, power receiver devices with corresponding power receiver apps 7006 and transmitters with corresponding power transmitter manager apps 7008.

The process may begin when wireless power manager 7004 requests 7010 information from a power transmitter manager app 7008 hosted in a wireless transmitter. Request 7010 may include authentication security such as user name and password. Power transmitter manager apps 7008 may then verify the request 7010 and grant access to the wireless power manager 7004.

Wireless power manager 7004 may continuously request 7010 information for different time periods in order to continue updating itself. Power transmitter manager app 7008 may then send database records 7012 to the wireless power manager 7004. Wireless power manager 7004 may then display 7014 these records with options in a suitable GUI to a user 7002. User 7002 may then perform different actions in order to manage the wireless power network. For example and without limitation, a user 7002 may configure powering schedules 7016 for different devices, the user 7002 may also establish priorities depending on time 7018, type of client 7020, physical location 7022 or may even choose to broadcast a message 7024 to client devices. The wireless power manager 7004 may then send 7026 the updated database records back to the power transmitter manager apps 7008.

In a wireless network power grid more than one transmitter may be used. Power transmitter manager apps 7008 hosted on each transmitter may share updates 7028 to the device database. Power transmitter manager apps 7008 may then perform an action 7030 depending on the command and updates made by the user 7002 such as, charge a wireless device, send a message to the wireless devices, set a schedule to charge different devices, set power priority to specific devices, etc.

Figure 71:
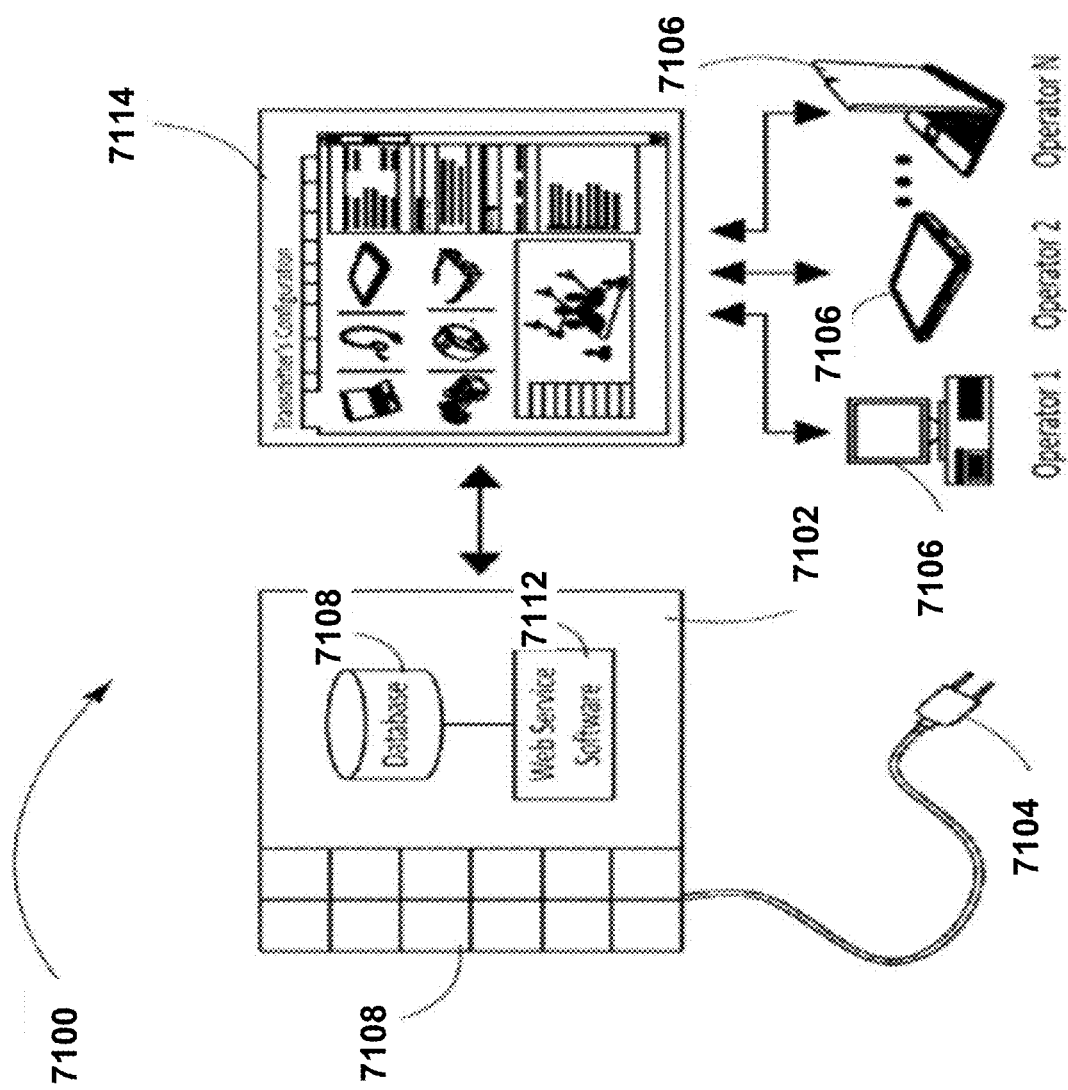
FIG. 71 illustrates a wireless power transmitter configuration network, in accordance with some embodiments.

FIG. 71 illustrates a wireless power transmitter configuration network 7100, according to another embodiment. Wireless power transmitter configuration network 7100 may include at least one wireless power transmitter 7102 connected to an energy power source 7104 and at least one computer device 7106, which may communicate with each other through an ad hoc network connection of wireless power transmitter 7102, that may be wireless or wired. Network connections may refer to Wi-Fi service, Bluetooth, LTE direct, or the like.

Each wireless power transmitter 7102 may be capable of managing and transmitting power to one or more wireless power receivers within a wireless power transmission system, where each wireless power receiver may be capable of providing power to one or more electronic devices such as laptop computers, stationary computers, mobile phones, tablets, mobile gaming devices, televisions, radios and/or any appliance which may require and/or benefit from an electrical power source. The wireless power transmission may be performed through an RF antenna array 7108 that may be used to form controlled RF waves that act as power transmission signals that may converge in 3-d space and create pockets of energy on wireless power receivers. Although the exemplary embodiment recites the use of RF waves as power transmission signals, the power transmission signals may include any number of alternative or additional techniques for transmitting energy to a wireless power receiver converting the transmitted energy to electrical power.

According to some embodiments in the present disclosure, each wireless power transmitter 7102 within the wireless power transmission system may include at least one distributed system database 7110 coupled to a web service software 7112, among others. Wireless power transmitter 7102 may contain a computer for running the wireless power transmitter's ad hoc network connection which may provide access to the wireless power transmitter's configuration GUI web pages 7114. Distributed system database 7110 may store relevant information from wireless power receivers of electronic devices and wireless power transmitters 7102 among others. This information may include, but is not limited to, voltage ranges for electronic device, location and signal strength of electronic device, ID of wireless power receiver, ID of wireless power transmitter 7102, ID of electronic device, charging schedules, charging priorities, and/or any other data which may be relevant to wireless power transmitter configuration network 7100. Distributed system database 7110 may be implemented through known in the art database management systems (DBMS) such as, for example, MySQL, PostgreSQL, SQLite, Microsoft SQL Server, Microsoft Access, Oracle, SAP, dBASE, FoxPro, IBM DB2, LibreOffice Base, FileMaker Pro and/or any other type of database that may organize collections of data. In exemplary embodiments, wireless power transmitter 7102 may distribute a replication of its distributed system database 7110 to other system devices or other wireless power transmitters if LAN becomes available, or to remote or cloud based system management service if internet access becomes available.

The configuration of wireless power transmitter 7102 may be performed by an operator/user accessing a standard web browser on a computer device 7106, such as a smartphone, a desktop computer, a laptop computer, a tablet, a PDA, and/or another type of processor-controlled device that may receive, process, and/or transmit digital data. The operator/user may browse the specific URL or IP address associated to configuration GUI web pages 7114 provided by web service software 7112 operating within wireless power transmitter 7102, and may then access configuration GUI web pages 7114 in order to specify the wireless power transmitter's configuration information. Web service software 7112 may use JavaScript or other suitable method for serving web pages, through embedded web, Apache, Internet Information Services (IIS), or any other suitable web server application.

The operator/user may get the specific URL or IP address associated to wireless power transmitter 7102, which may be printed on a "quickstart" instruction card that may come within the box of a newly purchased wireless power transmitter 7102, may be printed on the unit itself, and/or may be acquired from some other suitable source. The operator/user may use computer device 7106 with a suitable operating system such as Microsoft Windows, Apple iOS, Android or Linux, among others, to browse configuration GUI web pages 7114 using a standard web browser such as Chrome, Firefox, Internet Explorer, or Safari, among others, via an input device such as a touch screen, a mouse, a keyboard, a keypad, and others.

Web service software 7112 within wireless power transmitter 7102 may be capable of detecting and analyzing pending configuration settings of wireless power transmission system, and may also be capable of generating a recommendation or an alert which may be reported to the operator/user of the wireless power transmission system via configuration GUI web pages 7114 of wireless power transmitter 7102. Pending configuration settings of wireless power transmission system which may be reported to the operator/user, may include the detection of devices which may have not been configured, the need to add more wireless power transmitters 7102 to an overly busy area, and others. Web service software 7112 within wireless power transmitter 7102 may be configured to authorize received operational parameters.

In exemplary embodiments, wireless power transmitter 7102 may also support automatic configuration by an external or remote computer device 7106 running automated software through any suitable method of communication with wireless power transmitter 7102 such as TCP/IP socket connection, and others. In addition, the configuration of wireless power transmitter 7102 may also be performed through an XML message, or Simple Mail Transfer Protocol (SMTP), among others.

Figure 72:
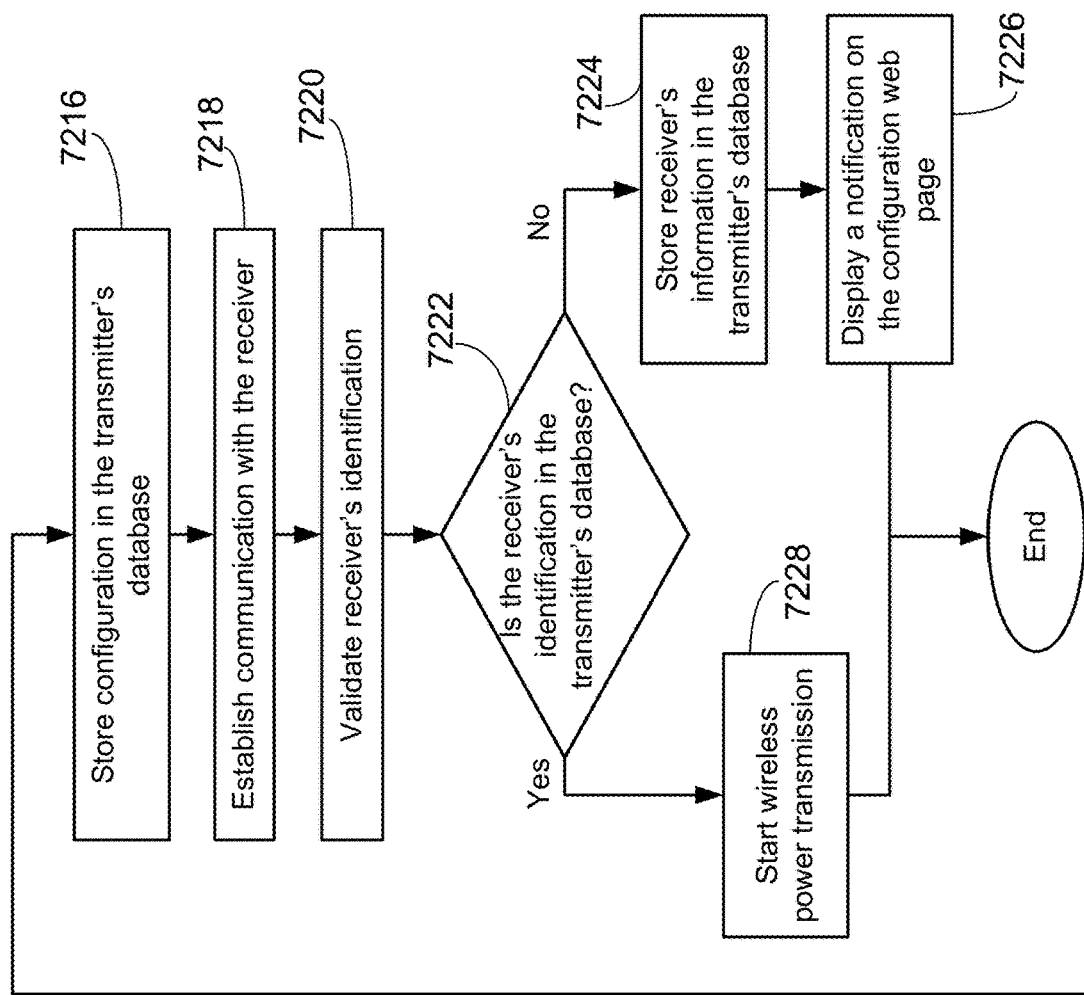
FIG. 72 is a flowchart of a process for installation and configuration of a wireless power transmitter through a configuration web service, in accordance with some embodiments.
Figure 72:
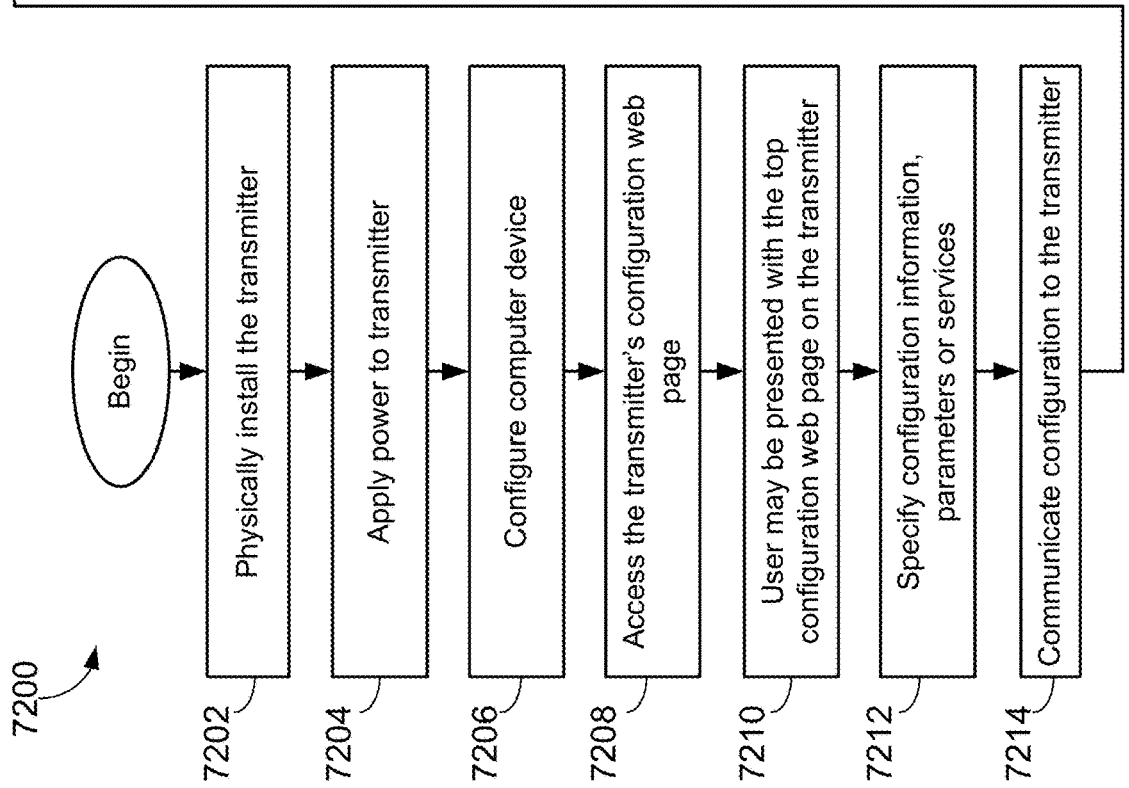

FIG. 72 is a flowchart of a process 7200 for installation and configuration of a wireless power transmitter through a configuration web service, according to a further embodiment.

Process 7200 may begin when an operator/user removes a newly purchased wireless power transmitter from its box, and physically installs (block 7202) the wireless power transmitter at a location where it may be in power transmission range of each wireless power receiver that the wireless power transmitter may power. The operator/user may then apply power (Block 7204) to the wireless power transmitter, which may start the wireless power transmitter's web service software and may initiate the hardware within the wireless power transmitter that may support Wi-Fi service, or wireless or wired network, among other suitable network connections. Web service software may then start an ad hoc or other network which may provide access to the configuration GUI web pages hosted by the wireless power transmitter. This ad hoc network may be wireless or wired.

Subsequently, the operator/user may perform the configuration (block 7206) at a computer device with Wi-Fi capabilities, such as a smartphone, a desktop computer, a laptop computer, a tablet, a PDA, and/or another type of processor-controlled device that may receive, process, and/or transmit digital data, and which may be within Wi-Fi communication range of the wireless power transmitter, in order to connect to the wireless power transmitter's Wi-Fi service. Then, the operator/user may browse (block 7208) on the computer device, the specific URL or IP address of the configuration web page provided by or hosted by the web service software operating within the wireless power transmitter, and may then access the configuration GUI web pages of the wireless power transmitter. The web service software may be programmed to respond to the specific URL or IP address by sending configuration web pages back to the browser. The wireless power transmitter's specific URL or IP address may be printed on a "quickstart" instruction card which may come within the box of a newly purchased wireless power transmitter, may be printed on the wireless power transmitter's unit itself, and/or may be acquired from some other suitable source. The operator/user may use a computer device with a suitable operating system such as Microsoft Windows, Apple iOS, Android or Linux among others, to browse the configuration GUI web pages using a standard web browser such as Chrome, Firefox, Internet Explorer, Safari and others, via an input device such as a touch screen, a mouse, a keyboard, a keypad, and others. Wireless power transmitter may use JavaScript or other suitable method for serving web pages, through embedded web, Apache, Internet Information Services (IIS), or any other suitable web service application.

The operator/user may be presented (block 7210) with the top configuration GUI web pages which the wireless power transmitter may host and render. The operator/user may then specify via an input device (block 7212), the desired configuration information, parameters, and/or services, among others, presented by one or more configuration GUI web pages hosted by the wireless power transmitter. Configuration information that the operator/user may specify through the configuration web pages GUI may include, but is not limited to, a list of the wireless power receivers which may receive power from one or more wireless power transmitters within the wireless power transmission system, charging schedules, charging priorities, the selection of situations in which one or more wireless power transmitters may not transmit power to one or more wireless power receivers, user names, user contact information, or any other user information, employee number, customer number, billing information, password level, physical wireless power transmission areas of service, contact information of users which may be automatically contacted when a significant system event may occur, account setups, password control, and friendly device names for electronic devices, wireless power receivers, and wireless power transmitters, among other types of configuration information. In addition, the operator/user may also use the configuration GUI web pages to manually override the automatic power control of the wireless power transmission and immediately start or stop charging or powering one or more electronic devices; or end manual power control of the wireless power transmission and restore the automatic power control.

The specified configuration information collected through the configuration GUI web pages may be communicated (block 7214) by the web browser to the wireless power transmitter's web service software through suitable network connections. Web service software may then store (block 7216) the configuration information specified by the operator/user, into the wireless power transmitter's memory or local memory copy of a distributed system database. This configuration information may be stored in the wireless power transmitter's memory or distributed system database until the operator/user modifies the configuration features and parameters. In exemplary embodiments, wireless power transmitter may distribute a replication of its distributed system database to other system devices if LAN becomes available, or to remote or cloud based system management service if internet access becomes available.

The wireless power transmitter may automatically establish communication (block 7218) with one or more wireless power receivers and may read and validate (block 7220) the wireless power receiver's identification. If the wireless power receiver's identification is not stored in the wireless power transmitter's memory or distributed system database (decision 7222), then the wireless power transmitter may store (block 7224) the wireless power receiver's information in the wireless power transmitter's memory or distributed system database, and may display a notification (block 7226) to the operator/user, the next time the operator/user accesses the configuration GUI web pages. This may indicate to the operator/user that a new receiver needs to be configured. However, if the wireless power receiver's identification is already stored in the wireless power transmitter's memory or distributed system database, then the wireless power transmitter may immediately start the normal operation (block 7228) of the wireless power transmission based on the configuration parameters and features specified by the operator/user through the wireless power transmitter's configuration web pages.

In exemplary embodiments, wireless power transmitter may also support automatic configuration by an external computer device through any suitable method of communication with wireless power transmitter such as TCP/IP socket connection, and others. In addition, the configuration of wireless power transmitter may also be performed through an XML message, or Simple Mail Transfer Protocol (SMTP), among others.

Figure 73:
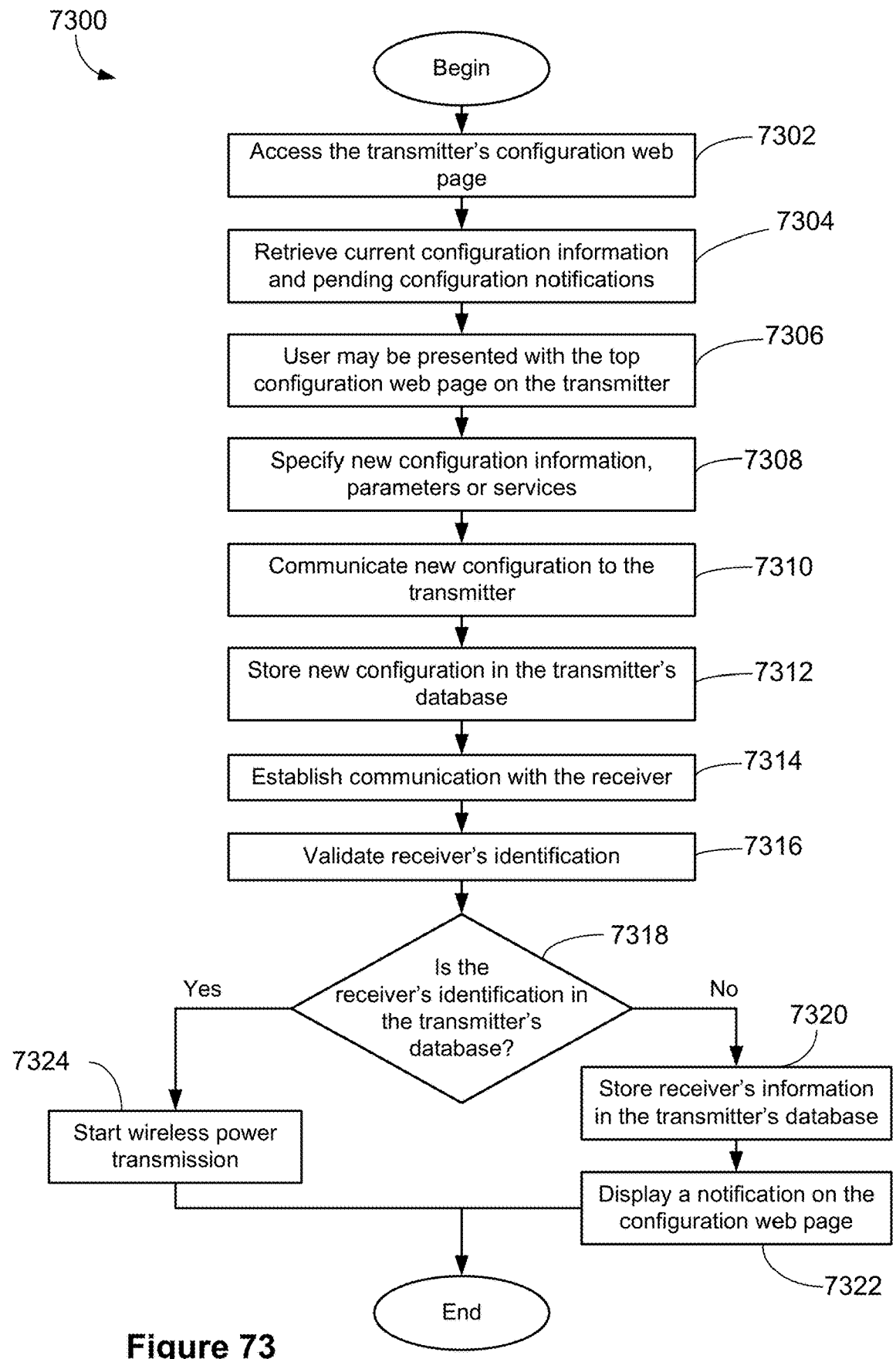
FIG. 73 is a flowchart of a process for re-configuring a wireless power transmitter through a configuration web service, in accordance with some embodiments.

FIG. 73 is a flowchart of a process 7300 for re-configuring a wireless power transmitter through a configuration web service, according to yet a further embodiment.

Process 7300 may begin when an operator/user accesses (block 7302) the wireless power transmitter's top configuration GUI web pages by browsing on a computer device, which may be within Wi-Fi communication range of the wireless power transmitter, the specific URL or IP address of the configuration web page provided by the web service software operating within the wireless power transmitter. Examples of computer devices may include a smartphone, a desktop computer, a laptop computer, a tablet, a PDA, and/or another type of processor-controlled device that may receive, process, and/or transmit digital data. The wireless power transmitter's specific URL or IP address may be printed on a "quickstart" instruction card which may come within the box of a newly purchased wireless power transmitter, may be printed on the wireless power transmitter's unit itself, and/or may be acquired from some other suitable source. The operator/user may use a computer device with a suitable operating system such as Microsoft Windows, Apple iOS, Android or Linux among others, to browse the configuration GUI web pages using a standard web browser such as Chrome, Firefox, Internet Explorer, Safari and others, via an input device such as a touch screen, a mouse, a keyboard, a keypad, and others. Wireless power transmitter may use JavaScript or other suitable method for serving web page through embedded web, Apache, Internet Information Services (IIS), or any other suitable web server application.

The web service software may be programmed to respond to the specific URL or IP address by sending configuration web pages back to the browser. The web service software may then retrieve the current configuration information (block 7304) of the wireless power transmission system from its local memory copy of a distributed system database. The web service software may also retrieve any information concerning pending configuration settings which may need to be notified to the operator/user of the wireless power transmission system such as pending configurations for newly discovered wireless power receivers or wireless power transmitters among others. The operator/user may be presented (block 7306) with the top configuration GUI web pages which the wireless power transmitter may host and render. These top configuration GUI web pages may display one or more configuration options, the current configuration features and parameters for the devices within the wireless power transmission system, and any notification of new devices detected within the wireless power transmission system, among others.

The operator/user may specify (block 7308) the new configuration features, parameters, and/or services through one or more configuration GUI web pages hosted by the wireless power transmitter, via an input device such as a touch screen, a mouse, a keyboard, a keypad, and others. New configuration information that the operator/user may specify through the configuration GUI web pages may include, but is not limited to, the wireless power receivers which may receive power from one or more wireless power transmitters within the wireless power transmission system, charging schedules, charging priorities, situations in which one or more wireless power transmitters may not transmit power to one or more wireless power receivers, user names, user contact info, employee number, customer number, billing information, password level, physical wireless power transmission areas of service, users which may be automatically contacted when a significant system event may occur, account setups, password control, and friendly device names for electronic devices, wireless power receivers, and wireless power transmitters, among other types of configuration information. In addition, the operator/user may also use the configuration GUI web pages to manually override the automatic power control of the wireless power transmission and immediately start or stop charging or powering one or more electronic devices; or end manual power control of the wireless power transmission and restore the automatic power control.

The new configuration information collected through the configuration GUI web pages may be communicated (block 7310) by the web browser to the wireless power transmitter's web service software through suitable network connections. Web service software may then store (block 7312) the new configuration information specified by the operator/user, into the wireless power transmitter's memory or local memory copy of a distributed system database. This new configuration information may be stored in the wireless power transmitter's memory or distributed system database until the operator/user performs additional modifications to the new configuration features and parameters. In exemplary embodiments, wireless power transmitter may distribute a replication of its distributed system database to other system devices if LAN becomes available, or to remote or cloud based system management service if internet access becomes available.

The wireless power transmitter may automatically establish communication (block 7314) with one or more wireless power receivers and may read and validate (block 7316) the wireless power receiver's identification. If the wireless power transmitter has no record of the wireless power receiver, or the wireless power receiver's identification is not stored in the wireless power transmitter's memory or distributed system database (decision 7318), then the wireless power transmitter may store (block 7320) the wireless power receiver's information in the wireless power transmitter's memory or distributed system database and may display a notification (block 7322) to the operator/user, the next time the operator/user accesses the configuration GUI web pages. However, if the wireless power receiver's identification is stored in the wireless power transmitter's memory or distributed system database, then the wireless power transmitter may immediately start the normal operation (block 7324) of wireless power transmission, based on the configuration parameters and features specified by the operator/user through the wireless power transmitter's configuration web pages.

In exemplary embodiments, wireless power transmitter may also support automatic configuration by an external or remote computer device through any suitable method of communication with wireless power transmitter such as TCP/IP socket connection, and others. In addition, the configuration of wireless power transmitter may also be performed through an XML message, or Simple Mail Transfer Protocol (SMTP), among others.

EXAMPLES

Example #1 refers to a user configuring a wireless power transmitter through a configuration web service, employing the method described in FIG. 14. An individual may buy a new wireless power transmitter and may begin the installation process. The individual may remove the newly purchased transmitter from the box, may physically install the unit mounted on the living room wall, and may apply power to the unit which may start the wireless network in the wireless power transmitter. The individual may configure a laptop which may be within Wi-Fi communication range of the wireless power transmitter in order to connect to the wireless power transmitter's Wi-Fi service. The individual may then, browse the wireless power transmitter's specific IP address provided by the wireless power transmitter's web service software, where this specific IP address may be found printed on the wireless power transmitter's quickstart instruction card. Then, the individual may select the desired configuration parameter, feature, and services for wireless power transmission. This configuration information may be communicated to the wireless power transmitter's web service software through the browser, and may then be stored in the wireless power transmitter's memory or distributed system database. The wireless power transmitter may then start the wireless power transmission according to the individual's configured parameters, features, and services.

Example #2 refers to a user re-configuring a wireless power transmitter through a configuration web service, employing the method described in FIG. 73. If during the wireless power transmitter's normal operation, a new receiver is within power and communication range of the wireless power transmitter, and the individual, who may be the operator/user of the wireless power transmission system, is browsing the wireless power transmitter's configuration web page, then the wireless power transmitter may automatically establish communication with the new receiver, may read its identification, may store this information in the wireless power transmitter's memory or distributed system database, and may display a notification to the individual on the configuration GUI web pages that a new receiver is available for configuration. The individual may then use the wireless power transmitter's configuration web service to provide configuration for the new wireless power receiver, including the wireless power receiver's power schedule, among others. This new configuration information may be communicated to the wireless power transmitter's web service software through the browser, and may then be stored in the wireless power transmitter's memory or distributed system database. The wireless power transmitter may then start the wireless power transmission according to the new configured parameters, features, and services provided by the individual.

FIGS. 70-73 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 70-73.

Presented below are example systems and methods of a configuration web service to provide configuration of a wireless power transmitter in accordance with some embodiments.

A processor-based system for configuring a wireless power transmission system comprising at least one power transmitter, configured to generate pocket-forming energy in three dimensional space to at least one receiver for charging, the processor-based system comprising; (i) a processor, (ii) a database operatively coupled to the processor, and (iii) communications, operatively coupled to the processor, where the communications is operable to communicate with a network. The processor is configured to receive an operational parameter via the communications for the at least one power transmitter and to utilize the operational parameter for controlling system configuration.

In some embodiments, the operational parameter comprises at least one of (i) authorization for the at least one receiver for charging, (ii) a priority for the at least one receiver for charging, (iii) one or more times or conditions for generating pocket-forming energy in three dimensional space, and (iv) one or more times or conditions for stopping the generating of pocket-forming energy in three dimensional space.

In some embodiments, the network comprises one of a local area network (LAN), virtual private network (VPN) and a wireless area network (WAN).

In some embodiments, the processor is configured to transmit the operational parameter via the communications to a remote system computer.

In some embodiments, the processor is configured to receive a further operational parameter via the communications from the remote system computer and utilize the further operational parameter for further system configuration.

In some embodiments, the processor is configured to receive a system event via the communications and modify the system configuration in response thereto.

In some embodiments, the processor is configured to authorize the received operational parameter.

An exemplary method of configuring a wireless power transmission system comprising at least one power transmitter, configured to generate pocket-forming energy in three dimensional space to at least one receiver for charging, the method includes (i) configuring, by a processor, communications operatively coupled to the processor and to a database to communicate with a network, (ii) receiving, by the processor, an operational parameter via the communications for the at least one power transmitter, and (iii) utilizing, by the processor, the operational parameter for controlling system configuration.

Another exemplary method of configuring a wireless power transmission system includes: (i) receiving, by a wireless power transmitter that is hosting a web service for configuring the wireless power transmitter, a user-configured operational parameter that includes information identifying a plurality of electronic devices authorized to receive power transmission signals from the wireless power transmitter, wherein the user-configured operational parameter is received via a configuration webpage provided by the web service, (ii) detecting, by a short-range communication radio of the wireless power transmitter, an electronic device within wireless power transmission range of the wireless power transmitter, (iii) in response to detecting the electronic device within the wireless power transmission range of the wireless power transmitter, determining whether the electronic device is one of the plurality of electronic devices authorized to receive power transmission signals from the wireless power transmitter, and (iv) in accordance with a determination that the electronic device is one of the plurality of electronic devices authorized to receive power transmission signals from the wireless power transmitter, transmitting, by two or more antennas of the wireless power transmitter, power transmission signals comprising radio frequency (RF) signals that constructively interfere proximate to the electronic device.

In some embodiments, the user-configured operational parameter is a first user-configured operational parameter, and the method further comprises receiving, by the wireless power transmitter, a second user-configured operational parameter defining a charging schedule for transmitting power transmission signals to one or more of the plurality of electronic devices, where the second user-configured operational parameter is received via the configuration webpage provided by the web service. In addition, transmitting the power transmission signals comprises transmitting the power transmission signals to the electronic device in accordance with the charging schedule.

In some embodiments, the user-configured operational parameter is a first user-configured operational parameter, and the method further comprises receiving, by the wireless power transmitter, a second user-configured operational parameter a prioritized order used by the wireless power transmitter to provide power to the plurality of electronic devices, where the second user-configured operational parameter is received via the configuration webpage provided by the web service. In addition, transmitting the power transmission signals comprises transmitting the power transmission signals to the electronic device in accordance with the prioritized order.

Figure 74A:
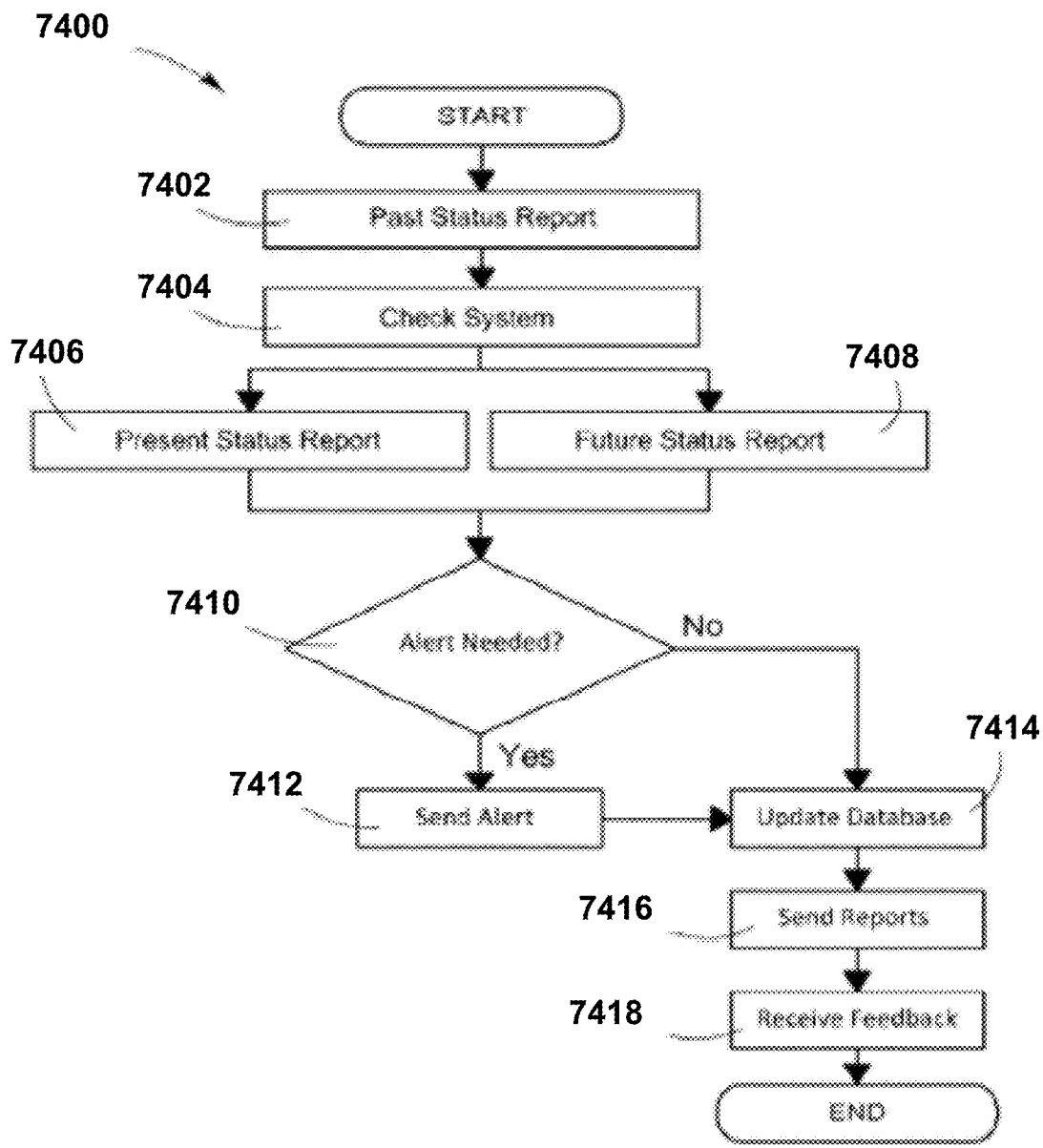
FIG. 74A is a flowchart of a general status report generation, in accordance with some embodiments.
Figure 74B:
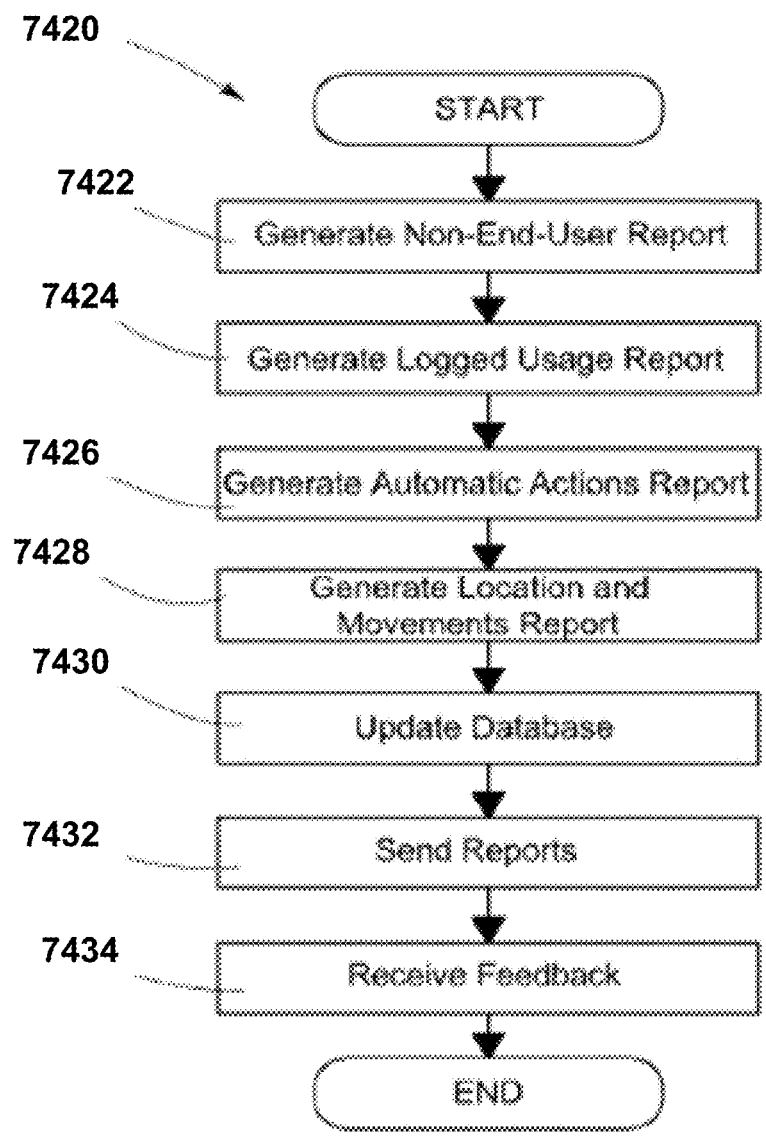
FIG. 74B is a flowchart of a past status report generation, in accordance with some embodiments.

FIGS. 74A-74B illustrate a system architecture and a flowchart to control a wireless power transmission system by configuration of wireless power transmission control parameters, in accordance with some embodiments.

FIG. 74A shows a flowchart of a general system status 7400 report generation process, according to an exemplary embodiment. Wireless power transmission systems may periodically send status reports to a remote management system, similar to the management systems previously described. General system status 7400 report generation process may start with past status report generation 7402, in this step any server within a wireless power transmission system may gather information that may include details such as the amount of power delivered to each of the electronic devices in the system during a certain time period, the amount of energy that was transferred to a group of electronic devices associated with a user, the amount of time an electronic device has been associated to a wireless power transmitter, pairing records, activities within the system, any action or event of any wireless power device in the system, errors, faults, and configuration problems, among others. Past system status data may also include power schedules, names, customer sign-in names, authorization and authentication credentials, encrypted information, areas, details for running the system, and any other suitable system or user-related information.

Then, the server within the wireless power transmission system may run a system check-up 7404. In this step, the server within the wireless power transmission system may check for any present failure, error or abnormal function of any system or subsystem components. Additionally, the server within the wireless power transmission system may check and perform an evaluation of the current system configuration.

Afterwards, the system may generate present status report 7406 and future status report 7408. Present status report may include any present failure, error or abnormal function of any system or subsystem components; a list of presently online end-users and devices, current system configuration and power schedules, amongst others.

Future status report 7408 may include forecasts based on the extrapolation or evaluation of past and present system status reports. For example, the system may be able to extrapolate possible impending sub-system component failure based on logged past behavior of sub-system components. The system may also be able to evaluate the power schedules and determine is any device will be out of energy according to historical power consumption and current power schedule.

In some embodiments, the system may further evaluate the system configuration to check if any configuration set by an operator or end-user may cause an unwanted system behavior. Such will be reported using the same techniques described above.

Then, the wireless power transmitters may evaluate 7410 if an alert is needed. If an alert is needed, the alert may be immediately generated and sent 7412. Depending of the type of problem detected, the alerts may be sent to the end-users, the system's owner, the service provider or any suitable combination, or to a remote system manager which can distribute a description of this urgent situation to customer service or other personnel via email, text message, or synthesized voice telephone call, according to alert configuration records stored within general database.

After the alert has been sent or if there is no alert needed, the server within the wireless power transmission system executing the report generation algorithm described in FIG. 74 may update 7414 its database with the reports and optionally back them up in a suitable server. If there are multiple servers, then only one at a time will be active for the generation of reports, while the others remain in stand-by mode, to take over if the active server goes offline. A hierarchy of priority will determine which online server is the present active (master) server.

Then, using a suitable TCP/IP connection the reports may be sent 7416 to a remote system manager for further evaluation. In some embodiments, the system may receive 7418 feedback from the remote system manager to indicate verification and storage of any received information.

FIG. 74B is a flowchart of a past status report 7420 generation process, according to an exemplary embodiment. The process for generation of a past status report 7420 may start with the generation 7422 of a non-end-user report, where no-end-user report may include logged activity, commands and configuration inputs of any non-end-user system operator.

Then, the system may generate 7424 a logged usage report which may include logged usage details and wireless energy consumption details. The wireless energy consumption details may include the amount of power delivered to each device and total amount of power delivered to the devices associated with each end user.

In some embodiments, the logged usage report may be used to compute power bills to charge end-users for the amount of wireless power received during a given time period.

Then, the system may generate 7426 an automatic actions report which may include automatic actions performed by or over any of the system components, including all power transmitters, power receivers, and any system management GUI.

Subsequently, the system may generate 7428 a location and movement report, which may include the location and movement tracking details of power receivers relative to power transmitters in the system.

After the reports have been generated the system may assemble past status report 7420 and update 7430 the database.

Then, using a suitable TCP/IP connection the reports may be sent 7432 to a remote system manager for further evaluation. In some embodiments, the system may receive 7434 feedback from the remote system manager to indicate verification and storage of any received information.

Figure 74C:
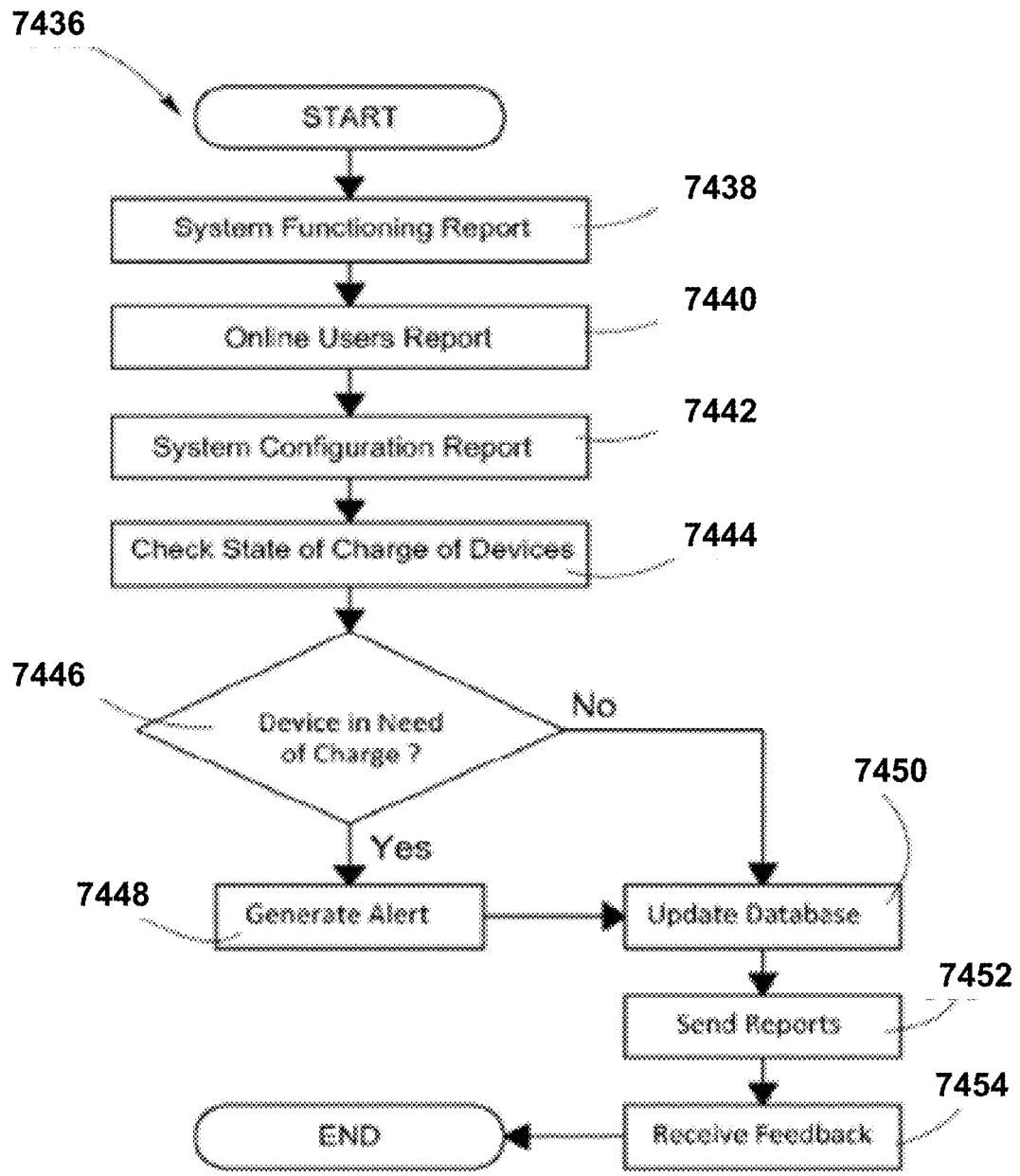
FIG. 74C is a flowchart of a present status report generation, in accordance with some embodiments.

FIG. 74C is a flowchart of a present status report 7436 generation process, according to an exemplary embodiment. The process of generation of present status reports 7436 may start with the generation 7438 of a system functioning report, in which the system may evaluate the performance of each of the systems components to detect any failure, error or abnormal function of any system or subsystem component. Then the system may generate 7440 a list of all online users and devices. Afterwards, the system may generate 7442 a report of the current system configuration.

Additionally, the system may check 7444 the state of charge all the electronic devices within the system. If any electronic device within the system is in urgent need 7446 of charge the system may generate and send 7448 an alert. The alert may be sent to the users in form of text messages, emails, voice synthesis telephone communication or any other suitable means.

In some embodiments, whenever an electronic device has a minimum amount of energy left the system may be capable of contacting the end-user to make the end user aware of the current state of charge of the electronic device.

After the reports have been generated the system may assemble present status report 7436 and update 7450 the database.

Then, using a suitable TCP/IP connection the reports may be sent 7452 to a remote system manager for further evaluation. In some embodiments, the system may receive 7454 feedback from the remote system manager to indicate verification and storage of any received information.

Figure 74D:
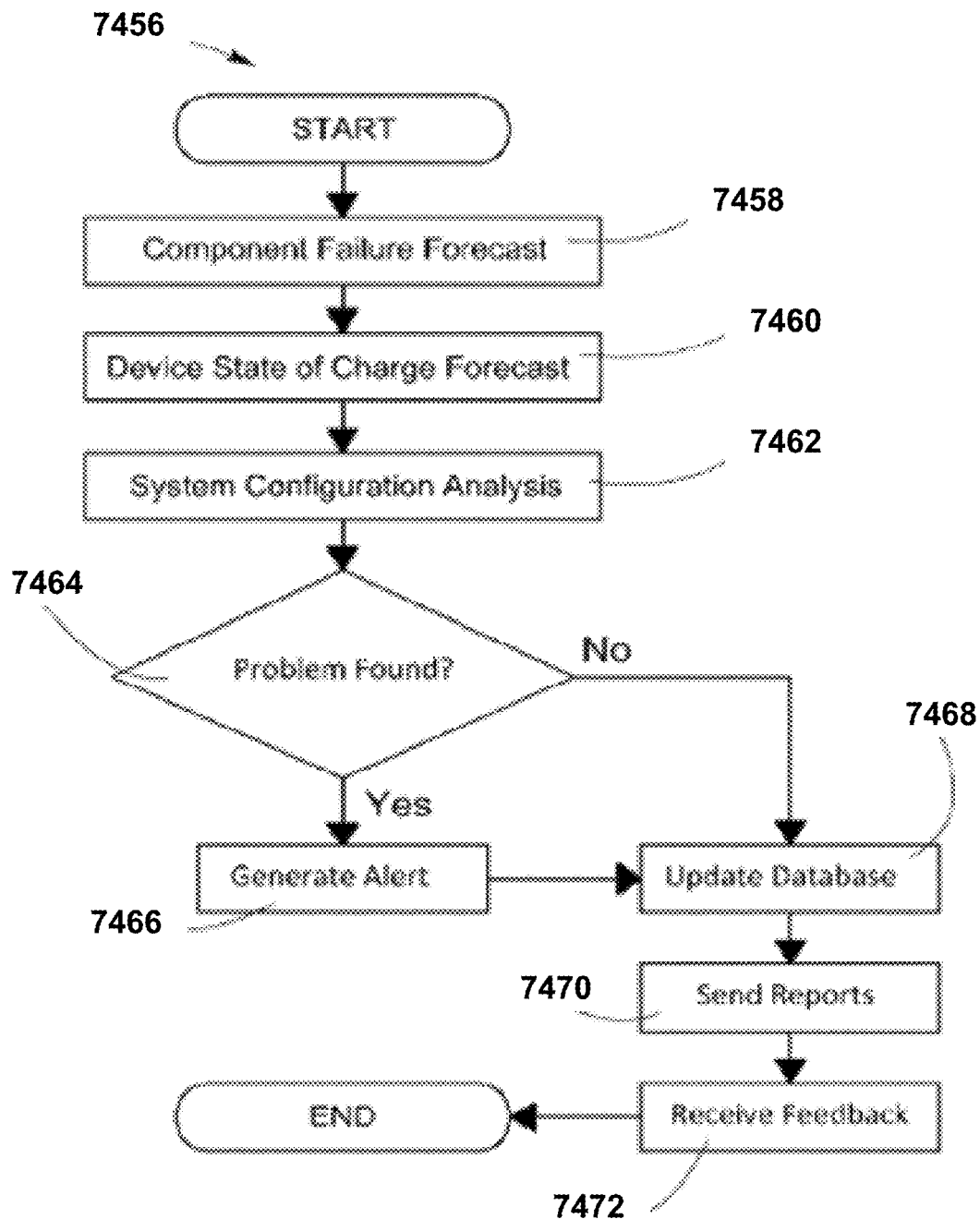
FIG. 74D is a flowchart of a future status report generation, in accordance with some embodiments

FIG. 74D is a flowchart of a future status report 7456 generation process, according to an exemplary embodiment. The process of generation of future status report 7456 may start with the generation 7458 of a component failure forecast in which impending sub-system component failure may be extrapolated from logged past behavior of sub-system components. Then the system may generate 7460 a device state of charge forecast, based on present rate of energy consumption of the devices, configured charging schedule, logged usage and any other suitable parameter. In this step the system may determine if any device will reach an unexpected critically low level of charge at some point in the future.

Afterwards, the system may perform 7462 a system configuration analysis, in which the system may evaluate any configuration set by the system operator or end-user to determine if it may cause any unwanted system behavior.

Then, if a problem was found 7464 in any of the first 3 steps, the system may generate a suitable alert 7466. If an alert is sent to an end-user or system operator it may be in the form of text messages, emails, voice synthesis telephone communication or any other suitable means. In some embodiments, the system provider may be contacted by similar means.

Afterwards, the system may assemble future status report 7456 and update 7468 the database.

Subsequently, using a suitable TCP/IP connection the reports may be sent 7470 to a remote system manager for further evaluation. In some embodiments, the system may receive 7472 feedback from the remote system manager to indicate verification and storage of any received information.

EXAMPLES

In example #1 a wireless power transmission system generates a general status report as described in FIG. 74A. When checking the state of charge of the electronic devices within the system, an electronic device with critically low level of charge and no scheduled charge time is identified. In this example, the wireless power system is able to contact the owner of the electronic device via SMS message. The user schedules a charging period for the device and the device is charged before it runs out of energy.

In example #2 a wireless power transmission system generates a general status report as described in FIG. 74A. When checking the system configuration, a possible unwanted behavior is identified. A device is scheduled to charge for too long without usage, which may cause overheating of some components. In this example, the power transmitter send a report to the remote management system and the remote management system sends an alert via email to the user.

In example #3 a wireless power service provider utilizes the past status reports generated by wireless power delivery system over the past 30 days to compute bills and charge end-users for their wireless power consumption.

In example #4 an end-user's electronic device requests wireless power. The wireless power transmitter utilizes a suitable TCP/IP connection to communicate with a remote system manager and authenticate the end-user's credentials. The credentials of the end-user are authenticated and the electronic device is charged.

FIGS. 74A-74D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 74A-74D.

Presented below are example systems and methods for monitoring wireless power charging.

A system for monitoring the distribution of pocket-forming energy in three-dimensional space may include: at least one transmitter and a remote system manager. In some embodiments, the at least one transmitter each comprises: (i) an antenna array, the transmitter configured to provide the pocket-forming energy in three-dimensional space via the antenna array to at least one of a plurality of devices, (ii) an antenna manager configured to control power and a direction angle of the antenna array, (iii) a storage configured to receive and store data comprising at least one of transmitter data and device data, and (iv) communications configured to communicate the data to a network. Furthermore, in some embodiments, the remote system manager is operatively coupled to the network and is configured to receive and process communicated data to determine a status of the system and perform an action in response to the determined status.

In some embodiments, the status comprises at least one of a past system status, a present system status, a future system status, a device failure status, and a transmitter failure status. Furthermore, in some embodiments: (i) the past system status comprises at least one of a non-end-user report, a logged usage report, an automatic actions report and a location and movement report, (ii) the present system status comprises at least one of a system functioning report, an online users report, a system configuration report and a state of charge report, and (iii) the future system status comprises at least one of component failure forecast data, device state of change forecast data and system configuration analysis data.

In some embodiments, the device data comprises at least one of device identification data, device voltage range data, device location data, and device signal strength data.

In some embodiments, the transmitter data comprises at least one of transmitter identification data, receiver identification data, end-user device name data, system management server identification data, charging schedule data and charging priority data.

In some embodiments, the action comprises generating one or more alerts in response to a determined status of the system.

In another system, the system may include: (i) at least one transmitter comprising an antenna array, the transmitter being configured to provide pocket-forming energy in three-dimensional space via the antenna array to at least one of a plurality of devices, where the transmitter is further configured to communicate data to a network, and where the data comprises at least one of transmitter data and device data and (ii) a remote system manager, operatively coupled to the network, where the remote system manager is configured to process communicated data to determine a status of the system.

A method may include: (i) providing pocket-forming energy in three-dimensional space to at least one of a plurality of devices via at least one transmitter coupled to a respective antenna array, (ii) communicating data from the transmitter to a network, the data comprising at least one of transmitter data and device data, and (iii) processing the communicated data in a remote system manager, operatively coupled to the network, to determine a status of the wireless power system.

FIGS. 75A-75F illustrate examples of synchronous rectifier designs for wireless power receivers, in accordance with some embodiments. "Synchronous rectifier" refers to a power transmission circuit including active rectifiers controlled by switches such as transistors for improving the efficiency of rectification. The control circuitry for active rectification usually uses sensors for the voltage of the input AC to open the transistors at the correct times to allow current to flow in the correct direction.

Figure 75A:
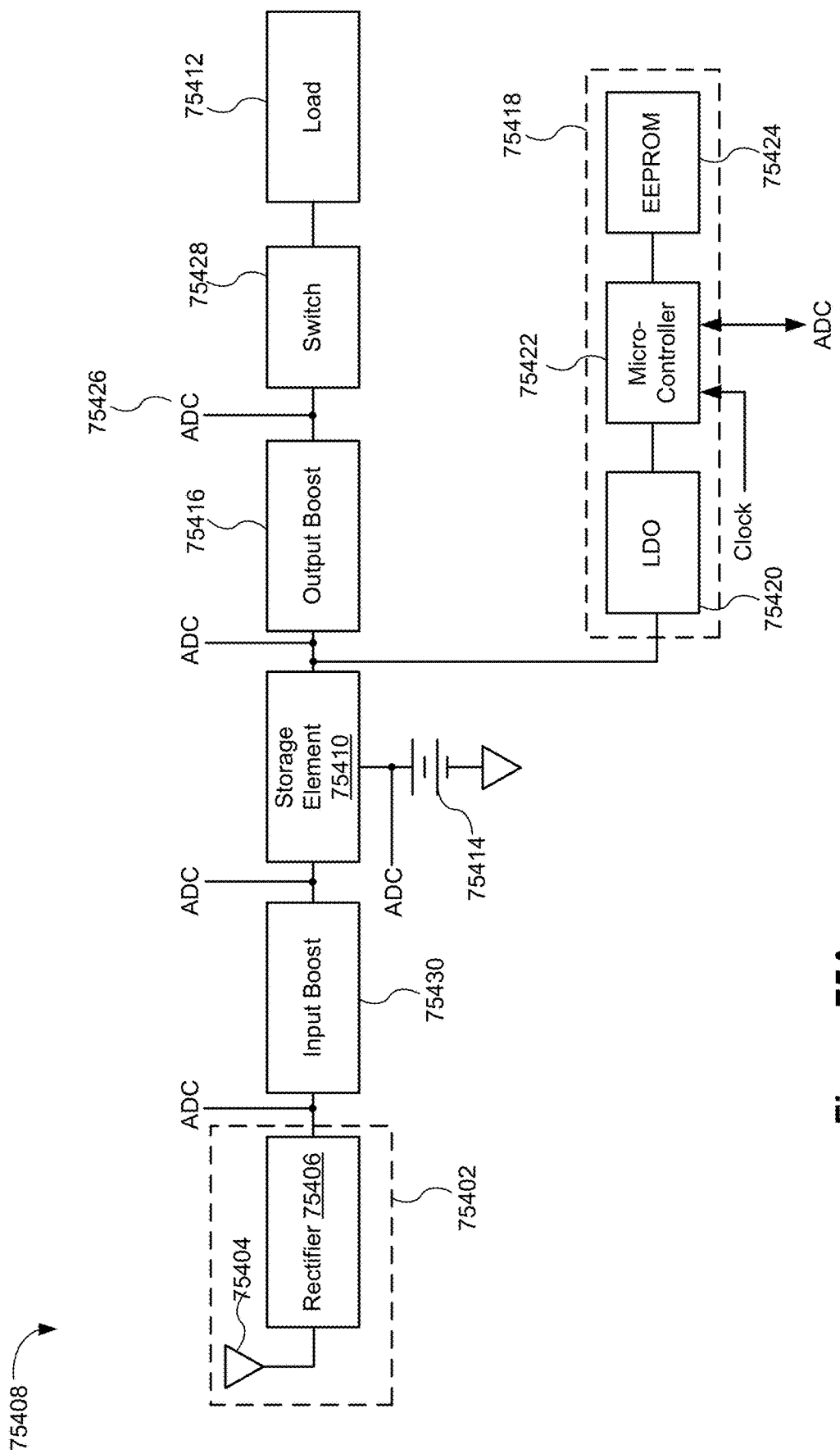
FIGS. 75A-75F illustrate examples of synchronous rectifier designs for wireless power receivers, in accordance with some embodiments.

FIG. 75A shows a block diagram of receiver 75408 (e.g., receiver 120, FIG. 1) which can be used for wireless powering or charging one or more electronic devices 122 as exemplified in wireless power transmission 100. According to some aspects of this embodiment, receiver 75408 may operate with the variable power source generated from transmitted RF waves 116 to deliver constant and stable power or energy to electronic device 122. In addition, receiver 75408 may use the variable power source generated from RF waves 116 to power up electronic components within receiver 75408 for proper operation.

Receiver 75408 may be integrated in electronic device 122 and may include a housing (not shown in FIG. 75A) that can be made of any suitable material to allow for signal or wave transmission and/or reception, for example plastic or hard rubber. This housing may be an external hardware that may be added to different electronic equipment, for example in the form of cases, or can be embedded within electronic equipment as well.

Receiver 75408 may include an antenna array 75402 which may convert RF waves 116 or pockets of energy into electrical power. Antenna array 75402 may include one or more antenna elements 75404 operatively coupled with one or more rectifiers 75406. RF waves 116 may exhibit a sinusoidal shape within a voltage amplitude and power range that may depend on characteristics of transmitter 102 and the environment of transmission. The environment of transmission may be affected by changes to or movement of objects within the physical boundaries, or movement of the boundaries themselves. It is also affected by changes to the medium of transmission; for example, changes to air temperature or humidity. As a result, the voltage or power generated by antenna array 75402 may be variable. As an illustrative embodiment, and not by way of limitation, the alternating current (AC) voltage or power generated by antenna element 75404 from transmitted RF waves 116 or pocket of energy may vary from about 0 volts or 0 watt to about 5 volts at 3 watts.

Antenna element 75404 may include suitable antenna types for operating in frequency bands similar to the bands described for transmitter 102 from FIG. 1. Antenna element 75404 may include vertical or horizontal polarization, right hand or left hand polarization, elliptical polarization, or other suitable polarizations as well as suitable polarization combinations. Using multiple polarizations can be beneficial in devices where there may not be a preferred orientation during usage or whose orientation may vary continuously through time, for example electronic device 122. On the contrary, for devices with well-defined orientations, for example a two-handed video game controller, there might be a preferred polarization for antennas which may dictate a ratio for the number of antennas of a given polarization. Suitable antenna types may include patch antennas with heights from about ⅛ inches to about 6 inches and widths from about ⅛ inches to about 6 inches. Patch antennas may have the advantage that polarization may depend on connectivity, i.e. depending on which side the patch is fed, the polarization may change. This may further prove advantageous as receiver 75408 may dynamically modify its antenna polarization to optimize wireless power transmission.

Rectifier 75406 may include diodes or resistors, inductors or capacitors to rectify the AC voltage generated by antenna element 75404 to direct current (DC) voltage. Rectifier 75406 may be placed as close as is technically possible to antenna element 75404 to minimize losses. In one embodiment, rectifier 75406 may operate in synchronous mode, in which case rectifier 75406 may include switching elements that may improve the efficiency of rectification. As an illustrative embodiment, and not by way of limitation, output of rectifier 75406 may vary from about 0 volts to about 5 volts.

An input boost converter 75430 can be included in receiver 75408 to convert the variable DC output voltage of rectifier 75406 into a more stable DC voltage that can be used by components of receiver 75408 and/or electronic device 122. Input boost converter 75430 may operate as a step-up DC-to-DC converter to increase the voltage from rectifier 75406 to a voltage level suitable for proper operation of receiver 75408. As an illustrative embodiment, and not by way of limitation, input boost converter 75430 may operate with input voltages of at least 0.4 volts to about 5 volts to produce an output voltage of about 5 volts. In addition, input boost converter 75430 may reduce or eliminate rail-to-rail deviations. In one embodiment, input boost converter 75430 may exhibit a synchronous topology to increase power conversion efficiency.

As the voltage or power generated from RF waves 116 may be zero at some instants of wireless power transmission, receiver 75408 can include a storage element 75410 to store energy or electric charge from the output voltage produced by input boost converter 75430. In this way, storage element 75410, through an output boost converter 75416, may deliver continuous voltage or power to a load 75412, where this load 75412 may represent the battery or internal circuitry of electronic device 122 requiring continuous powering or charging. For example, load 75412 may be the battery of a mobile phone requiring constant delivery of 5 volts at 2.5 watts.

Storage element 75410 may include a battery 75414 to store power or electric charge from the voltage received from input boost converter 75430. Battery 75414 may be of different types, including but not limited to, alkaline, nickel-cadmium (NiCd), nickel-metal hydride (NiHM), and lithium-ion, among others. Battery 75414 may exhibit shapes and dimensions suitable for fitting receiver 75408, while charging capacity and cell design of battery 75414 may depend on load 75412 requirements. For example, for charging or powering a mobile phone, battery 75414 may deliver a voltage from about 3 volts to about 4.2 volts.

In another embodiment, storage element 75410 may include a capacitor (not shown in FIG. 75A) instead of battery 75414 for storing and delivering electrical charge as required by the receiver. As a way of example, in the case of charging or powering a mobile phone, receiver 75408 may include a capacitor with operational parameters matching the load device's power requirements.

Receiver 75408 may also include output boost converter 75416 operatively coupled with storage element 75410 and input boost converter 75430, where this output boost converter 75416 may be used for matching impedance and power requirements of load 75412. As an illustrative embodiment, and not by way of limitation, output boost converter 75416 may increase the output voltage of battery 75414 from about 3 or 4.2 volts to about 5 volts which may be the voltage required by the battery or internal circuitry of electronic device 122. Similarly to input boost converter 75430, output boost converter 75416 may be based on a synchronous topology for enhancing power conversion efficiency.

Storage element 75410 may provide power or voltage to a communication subsystem 75418 which may include a low-dropout regulator (LDO 75420), a main system micro-controller 75422, and an electrically erasable programmable read-only memory (EEPROM 75424). LDO 75420 may function as a DC linear voltage regulator to provide a steady voltage suitable for low energy applications as in main system micro-controller 75422. Main system micro-controller 75422 may be operatively coupled with EEPROM 75424 to store data for the operation and monitoring of receiver 75408. Main system micro-controller 75422 may also include a clock (CLK) input and general purpose inputs/outputs (GPIOs).

In one embodiment, main system micro-controller 75422 in conjunction with EEPROM 324 may run an algorithm for controlling the operation of input boost converter 75430 and output boost converter 75416 according to load 75412 requirements. Main system micro-controller 75422 may actively monitor the overall operation of receiver 75408 by taking one or more power measurements 75426 (ADC) at different nodes or sections as shown in FIG. 75A. For example, micro-controller 75422 may measure how much voltage or power is being delivered at rectifier 75406, input boost converter 75430, battery 75414, output boost converter 75416, communication subsystem 75418, and/or load 75412. Main system micro-controller 75422 may communicate these power measurements 75426 to load 75412 so that electronic device 122 may know how much power it can pull from receiver 75408. In another embodiment, main system micro-controller 75422, based on power measurements 75426, may control the power or voltage delivered at load 75412 by adjusting the load current limits at output boost converter 75416. Yet in another embodiment, a maximum power point tracking (MPPT) algorithm may be executed by main system micro-controller 75422 to control and optimize the amount of power that input boost converter 75430 can pull from antenna array 75402.

In another embodiment, main system micro-controller 75422 may regulate how power or energy can be drained from storage element 75410 based on the monitoring of power measurements 75426. For example, if the power or voltage at input boost converter 75430 runs too low, then micro-controller 75422 may direct output boost converter 75416 to drain battery 75414 for powering load 75412.

Receiver 75408 may include a switch 75428 for resuming or interrupting power being delivered at load 75412. In one embodiment, micro-controller 75422 may control the operation of switch 75428 according to terms of services contracted by one or more users of wireless power transmission or according to administrator policies.

Figure 75B:
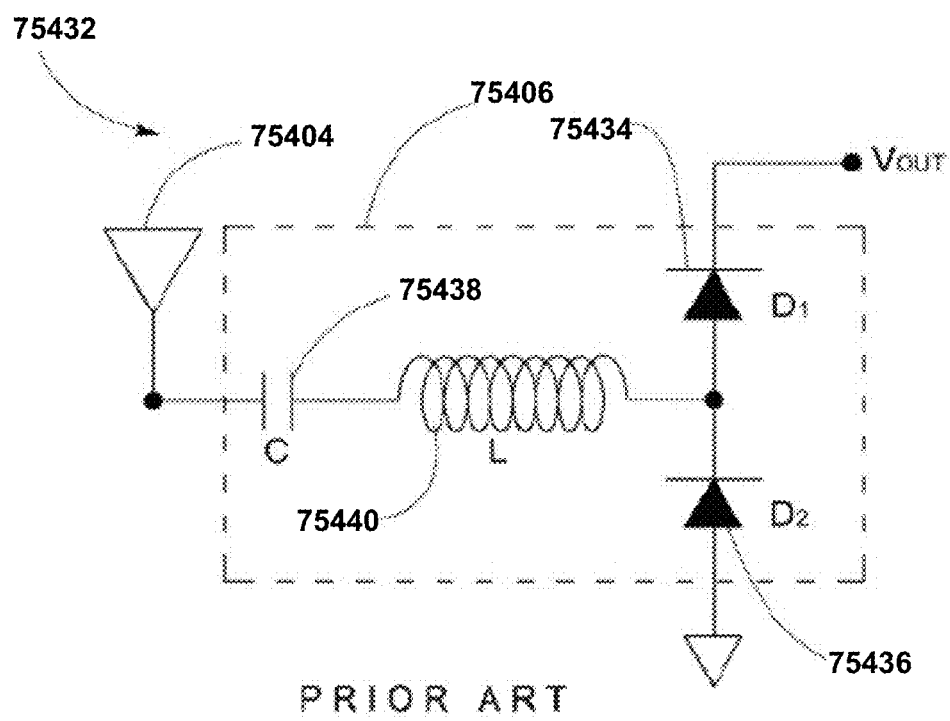

FIG. 75B represents a circuit diagram 75432 of a half-bridge diode rectifier 75406 of the prior art, according to embodiment shown in FIG. 75A as antenna array 75402, including antenna element 75404.

When an alternating RF signal is received from wireless transmitter 102, a direct voltage output $V_{OUT}$ may be drawn from the output terminals of the half-bridge diode rectifier 75406.

Two diodes, $D_1$ and $D_2$, respectively identified as diode 75434 and diode 75436 are wired in series upstream and connected to output terminal. Antenna element 75404 is connected in series to capacitor 75438, which is connected in series to inductor 75440, both acting as the resonant filter for the power signal being transferred from wireless transmitter 102 and received by antenna element 75404 of wireless power receiver 75408.

When the polarity of the alternating RF signal received may be positive, current flows through the first upstream diode $D_1$ and when the polarity of the alternating RF signal received is negative, current flows through second upstream diode $D_2$.

Half-bridge diode rectifiers, such as that shown in FIG. 75B, may be used to produce an output with a fixed polarity that is independent of the polarity of the input. Half-bridge diode rectifiers may be used in AC-to-DC power converters, for example. Optionally, the output may be smoothed by a smoothing capacitor (not shown).

It may be noticed that as output voltages drop, the diode's forward voltage is more significant and may reduce conversion efficiency. Physical limitations prevent the forward voltage drop of diodes 75434, 75436 from being reduced to a level of voltage drop that may be less than about 0.3 V. Additionally, power is lost from each diode 75434, 75436 with each reversal of polarity. In high frequency power converters, where the polarity of the input signal may oscillate at frequencies of 100 kHz or more, such power losses may result in significant heating of the rectifier circuit and other components surrounding the rectifier. This situation may result in reduced reliability or failure of the rectifier circuit.

Control-Driven Synchronous Rectifier Circuit Topology

Figure 75C:
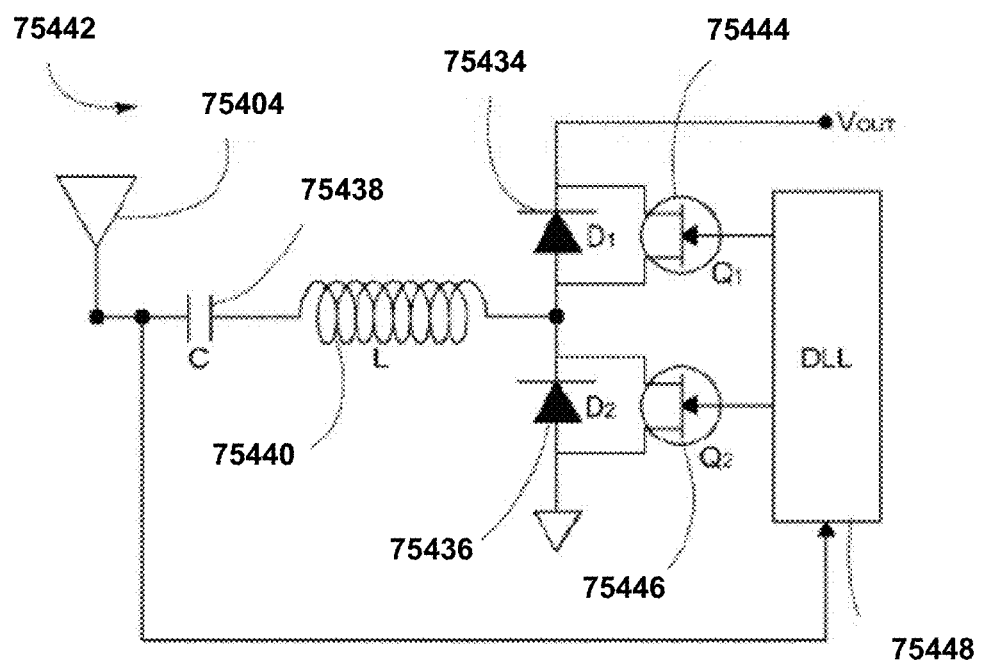

FIG. 75C illustrates a circuit diagram 75442 of synchronous rectifier 75406 for wireless power receiver 75408, connected to antenna element 75404 and resonant filter including capacitor 75438 and inductor 75440, according to an embodiment. In this circuit, synchronous rectification may be enabled by a half-bridge rectifier configuration using diode 75434 coupled to FET transistor 75444 (Q1) and diode 75436 coupled to FET transistor 75446. This half-bridge rectifier configuration using synchronous rectification with coupled diode 75434 and FET transistor 75444, and coupled diode 75436 and FET transistor 75446 may be used to improve the efficiency limit which may result from using a half-bridge diode rectifier of prior art. As power conversion efficiency is primarily a function of the output voltage, output current, and the on-resistance and forward voltage drop of diodes 75434, 75436, adding FET transistors 75444, 75446 may provide significant improvement in power transfer from wireless transmitter 102 to wireless power receiver 75408. Replacing a half-bridge diode rectifier of prior art with a synchronous rectifier 75406 depicted in circuit diagram 75442 may introduce a synchronous rectifier possessing almost linear resistance characteristics and a lower forward-voltage drop. Consequently, the rectifier conduction loss may be reduced.

In this synchronous rectifier circuit topology, FET transistors 75444, 75446 may be driven by gate-drive signals derived from delayed-lock loop (DLL) clock 75448 for conduction control of synchronous rectification of a plurality of high-frequency signals received from wireless transmitter 102. In present embodiment, the level of high-frequency signals may be within the 900 MHz, 2.4 GHz, and 5.7 GHz unlicensed bands.

Conduction times which may result by driving the half-bridge synchronous rectifiers from DLL clock 75448 may reach a maximum conduction time of FET transistor 75444 because it has no effect of the conduction time of current through diode 75436 during dead time given that during dead time FET transistor 75446 is in off state.

DLL clock 75448 may be used to change the phase of the clock signal controlling FET transistors 75444, 75446 with a delay chain of delay gate signals which may be phase-locked depending on the frequency of the signal received by antenna element 75404.

The precise gate-drive timing provided by DLL clock 75448 may allow that when conduction through diode 75434 may be applied or terminated, at the same instant conduction through diode 75436 may be terminated or applied.

Circuit diagram 75442 may be modified using a separate antenna element (not shown in FIG. 75C) which is not included in antenna array 75402. A modified synchronous rectifier circuit topology may be implemented by having DLL clock 75448 directly connected to this second antenna element rather than deriving the control signal from the first antenna element 75404 as shown in FIG. 75C. The use of a separate antenna element connected to DLL clock 75448 may prevent increasing the input impedance from antenna element 75404 thus causing a reduction in the efficiency of the synchronous rectifier 75406.

Switching Control Scheme

Figure 75D:
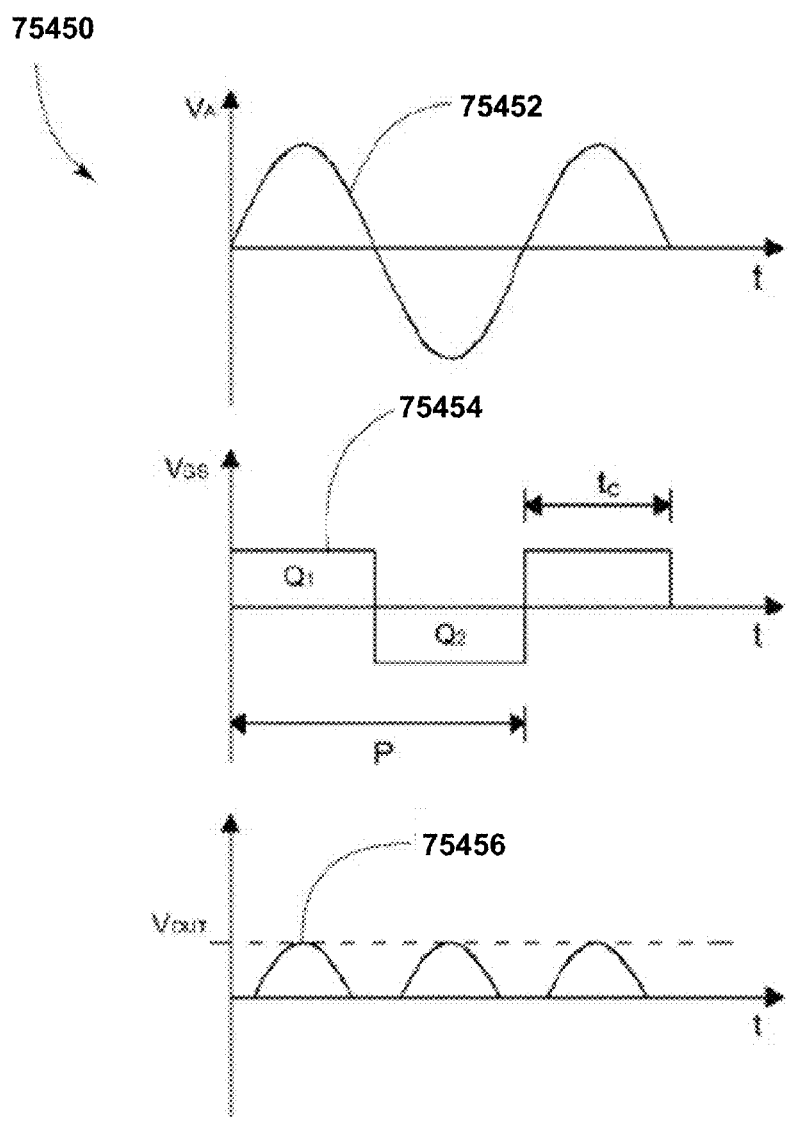

FIG. 75D corresponds to a graph of waveforms 75450 depicting voltage received and conduction times of synchronous rectifier 75406, for wireless power receiver 75408 described in FIG. 75A.

In FIG. 75D, waveform 75452 may represent the input voltage ($V_A$) received by antenna element 75404; waveform 75454 may illustrate the voltage of gate signals ($V_{GS}$) respectively applied to FET transistor 75444, 75446 to control conduction; and waveform 75456 may show the output voltage ($V_{OUT}$) at the terminals of synchronous rectifier 75406.

The gate-drive timing of SRs may not allow conduction of diodes 75434, 75436 of synchronous rectifier 75406 except for the unavoidable conduction of diode 75436 during the dead time. This may only be possible with a very precise gate-drive timing where the gate-drive for FET transistor 75444 may be applied or terminated at the same instant the gate-drive of FET transistor 75446 may be terminated or applied. In practical applications, any accidental, brief overlapping of the gate-drive signals that turn on both SRs simultaneously may cause a short-circuit which may lower efficiency or, in severe cases, may cause the synchronous rectifier failure. To avoid simultaneous conduction of SRs in practical applications, a delay between the gate-drive signals may be introduced. Since during the delay period no gate-drive signal is applied to the SRs, the diodes 75434, 75436 of the SRs are conducting. This not only increases conduction loss but also introduces reverse-recovery loss. Therefore, the performance of control-driven SRs is strongly dependent on the timing of the gate drive that may be enabled using DLL clock 75448 as seen in circuit diagram 75442. This may be seen in waveform 75454 for which a positive gate signal (+$V_{GS}$) may be applied from DLL clock 75448 to FET transistor 75444 for a conduction time, $t_C$, during which FET transistor 75446 is on off state. During FET transistor 75444 conduction time, losses due to voltage drop may be practically the voltage drop losses of FET transistor 75444, which are much lower than the voltage drop losses of diode 75434, thus allowing only current to flow through diode 75434 during the high conduction time. Similarly, since input voltage $V_A$ is from a monotonic power source, DLL clock 75448 have to phase shift current to turn on FET transistor 75446 at appropriate time once there is no current through diode 75434, then allowing current to flow through diode 75436 with a minimum level of voltage drop losses, which are mainly related to the voltage drop losses of FET transistor 75446, during the high conduction time during the negative voltage of gate signal (-$V_{GS}$).

As seen in waveform 75456, the switching control that may be provided by DLL clock 75448 may result in a more significant level of power transfer to the other components in wireless power receiver 75408. Waveform 75456, when DLL clock 75448 is operating, has a focus on high conduction time.

As seen, both SR gate drives may be regulated and, therefore, independent of input voltage variations or incoming power variations, so switching transitions remain constant over line and load. Since the output is controlled by the DLL clock 75448, decisions may be made regarding when to turn off the SRs based on load current or output voltage. Optimizing proper SR gate drive timing in implementing control-driven SR often may require more accurate timing adjustment algorithms that can be designed discretely, but are much simpler when integrated into an integrated circuit solution, such as a DLL clock 75448.

Synchronous Rectifier Circuit Topology Including Phase Shifters

Figure 75E:
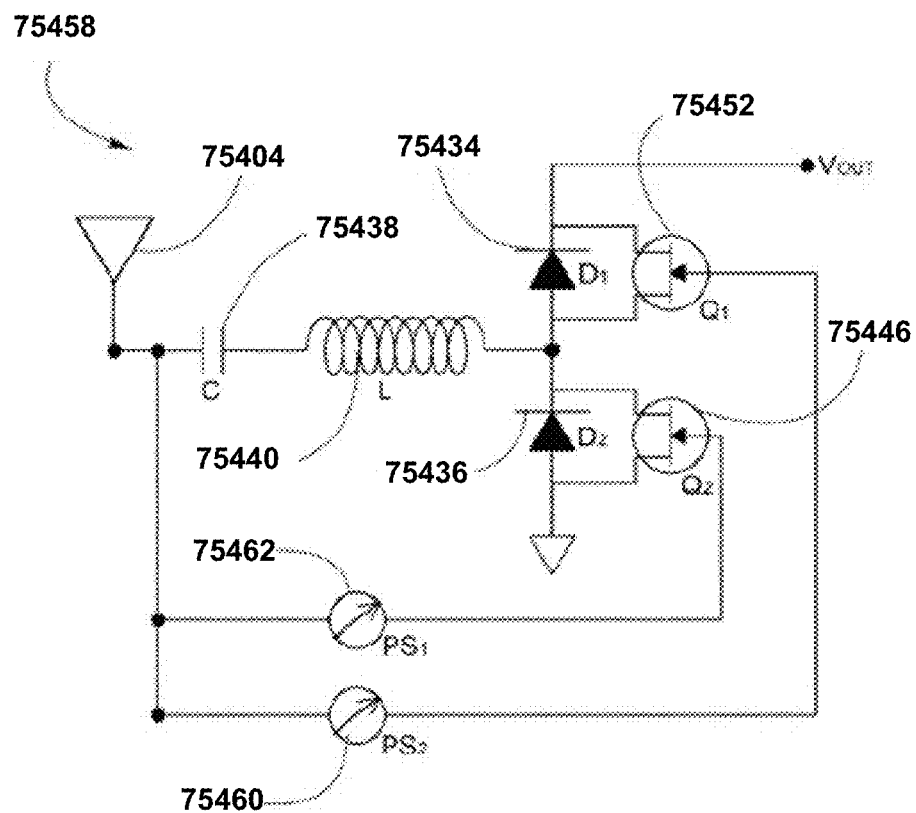

FIG. 75E depicts a circuit diagram 75458 of synchronous rectifier 75406 for wireless power receiver 75408, connected to antenna element 75404 and resonant filter including capacitor 75438 and inductor 75440, according to an embodiment. In this circuit, synchronous rectification may be enabled by a half-bridge rectifier configuration using diode 75434 coupled to FET transistor 75444 (Q1) and diode 75436 coupled to FET transistor 75446. This half-bridge rectifier configuration using synchronous rectification with coupled diode 75434 and FET transistor 75444, and coupled diode 75436 and FET transistor 75446 may be used to improve the efficiency limit which may result from using a half-bridge diode rectifier of prior art. As power conversion efficiency is primarily a function of the output voltage, output current, and the on-resistance and forward voltage drop of diodes 75434, 75436, adding FET transistors 75444, 75446 may provide significant improvement in power transfer from wireless transmitter 102 to wireless power receiver 75408. Replacing a half-bridge diode rectifier of prior art with a synchronous rectifier 75406 depicted in circuit diagram 75458 may introduce a synchronous rectifier possessing almost linear resistance characteristics and a lower forward-voltage drop. Consequently, the rectifier conduction loss may be reduced.

In this synchronous rectifier circuit topology, FET transistors 75444, 75446 may be driven by gate-drive signals derived from phase shifters 75460, 75462 for conduction control of synchronous rectification of a plurality of high-frequency signals received from wireless transmitter 102. In present embodiment, the level of high-frequency signals may be within the 900 MHz, 2.4 GHz, and 5.7 GHz unlicensed bands.

Phase shifters 75460, 75462 may be used to change the phase of the gate signal controlling FET transistors 75444, 75446 which may be phase-locked depending on the frequency of the signal received by antenna element 75404.

The accurate gate-drive timing provided by phase shifters 75460, 75462 may allow that when conduction through diode 75434 may be applied or terminated, at the same instant conduction through diode 75436 may be terminated or applied.

Switching controlling for a phase-shifted synchronous rectifier 75406 may start by developing two gate signal drives with a method of varying the phase relationship between them from 90º to 180°. Each gate signal drive from phase shifters 75460, 75462 may have an output which alternate with a 50% duty cycle to alternately drive FET transistor 75444, 75446. As the frequency of the incoming signal may change phase shifters 75460, 75462 may adapt to maintain the same level of current passing through diode 75434 and diode 75436, respectively, maintaining focus on high conduction times per switching control scheme previously described in FIG. 75D, so that they run at constant frequency and the phase relationship between the two complimentary gate signal may enable that both FET transistors 75444, 75446 may turn on and off with zero voltage across them, resulting in close to lossless switching when proper timing may be provided.

Therefore, the performance of SRs driven by phase shifters 75460, 75462 is strongly dependent on the timing of the gate drive signals that may be enabled, as seen in circuit diagram 75458. This may be seen in waveform 75454 for which a positive gate signal ($+V_{GS}$) may be applied from phase shifter 75460 to FET transistor 75444 for a conduction time, $t_C$, during which FET transistor 75446 is on off state. During FET transistor 75444 conduction time, losses due to voltage drop may be practically the voltage drop losses of FET transistor 75444, which are much lower than the voltage drop losses of diode 75434, thus allowing only current to flow through diode 75434 during the high conduction time. Similarly, since input voltage $V_A$ is from a monotonic power source, phase shifter 75462 have to phase shift current to turn on FET transistor 75446 at appropriate time once there is no current through diode 75434, then allowing current to flow through diode 75436 with a minimum level of voltage drop losses, which are mainly related to the voltage drop losses of FET transistor 75446, during the high conduction time during the negative voltage of gate signal ($-V_{GS}$).

Synchronous Rectifier Circuit Topology Including Wavelength Links

Figure 75F:
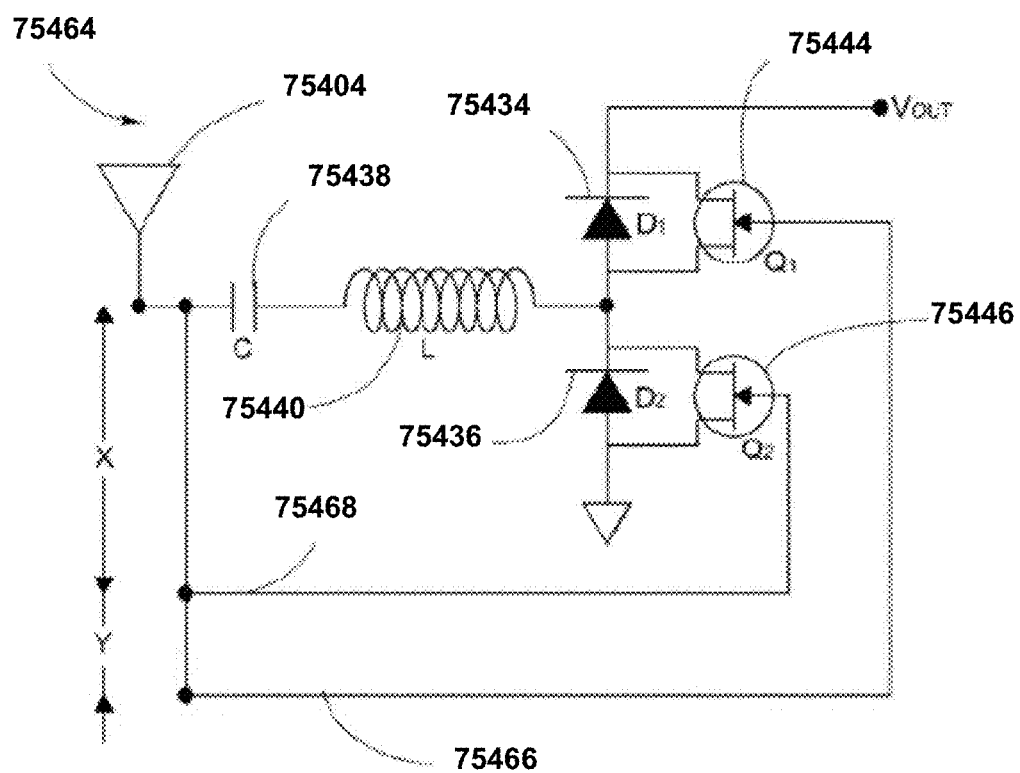

FIG. 75F depicts a circuit diagram 75464 of synchronous rectifier 75406 for wireless power receiver 75408, connected to antenna element 75404 and resonant filter including capacitor 75438 and inductor 75440. In this circuit, synchronous rectification may be enabled by a half-bridge rectifier configuration using diode 75434 coupled to FET transistor 75444 (Q1) and diode 75436 coupled to FET transistor 75446. This half-bridge rectifier configuration using synchronous rectification with coupled diode 75434 and FET transistor 75444, and coupled diode 75436 and FET transistor 75446 may be used to improve the efficiency limit which may result from using a half-bridge diode rectifier of prior art. As power conversion efficiency is primarily a function of the output voltage, output current, and the on-resistance and forward voltage drop of diodes 75434, 75436, adding FET transistors 75444, 75446 may provide significant improvement in power transfer from wireless transmitter 102 to wireless power receiver 75408. Replacing a half-bridge diode rectifier of prior art with a synchronous rectifier 75406 depicted in circuit diagram 75464 may introduce a synchronous rectifier possessing almost linear resistance characteristics and a lower forward-voltage drop. Consequently, the rectifier conduction loss may be reduced.

In this synchronous rectifier circuit topology, FET transistors 75444, 75446 may be driven by gate-drive signals derived from wavelength links 75466, 75468 for conduction control of synchronous rectification of a plurality of high-frequency signals received from wireless transmitter 102. In present embodiment, the level of high-frequency signals may be within the 900 MHz, 2.4 GHz, and 5.7 GHz unlicensed bands.

Wavelength links 75466, 75468 may be added as a frequency-division demultiplexing of the signal received by antenna element 75404 from wireless transmitter 102. Wavelength links 75466, 75468 may be of different wavelength spacing in order to have the required phase shifting to enable switching control of FET transistor 75444, 75446 and providing the proper timing for current to flow through diodes 75434, 75436 focusing on high conduction times per switching control scheme previously described in FIG. 75D, so that they run at constant frequency and the phase relationship between the two gate signals may enable that both FET transistors 75444, 75446 may turn on and off with zero voltage across them, resulting in close to lossless switching. Wavelength links 75466, 75468 may use spacing X and Y as shown in FIG. 75F within a range of about ¼ X to ½ X at about 5.7 GHz.

Therefore, the performance of SRs driven by wavelength links 75466, 75468 is strongly dependent on the timing of the gate drive signals that may be enabled, as seen in circuit diagram 75464. This may be seen in waveform 75454 for which a positive gate signal ($+V_{GS}$) may be applied from wavelength link 75466 to FET transistor 75444 for a conduction time, $t_C$, during which FET transistor 75446 is on off state. During FET transistor 75444 conduction time, losses due to voltage drop may be practically the voltage drop losses of FET transistor 75444, which are much lower than the voltage drop losses of diode 75434, thus allowing only current to flow through diode 75434 during the high conduction time. Similarly, since input voltage $V_A$ is from a monotonic power source, wavelength link 75468 have to phase shift current to turn on FET transistor 75446 at appropriate time once there is no current through diode 75434, then allowing current to flow through diode 75436 with a minimum level of voltage drop losses, which are mainly related to the voltage drop losses of FET transistor 75446, during the high conduction time during the negative voltage of gate signal ($-V_{GS}$).

FIGS. 75A-75F illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 75A-75F.

Presented below are example embodiments of the synchronous rectifier designs discussed above.

In some embodiments, an example receiver comprises an antenna configured to interface with a plurality of wireless power transmission waves, and a synchronous rectifier coupled to the antenna and configured to synchronously rectify an alternating current (AC) voltage of the power transmission waves to create a direct current (DC) voltage.

In some embodiments, the receiver further comprises a plurality of switches coupled to the synchronous rectifier. At least one of the switches is configured to control a conduction of the synchronous rectifier in accordance with at least one of a received voltage and a frequency of the power waves.

In some embodiments, at least one of the switches comprises a plurality of field effect (FET) transistors.

In some embodiments, the receiver further comprises a delay-locked loop coupled to at least one of the transistors. The loop is configured to control switching of the at least one of the transistors.

In some embodiments, the plurality of switches coupled to the synchronous rectifier further comprises a phase shifter. At least one of the switches is driven by a gate-drive signal derived from the phase shifter.

In some embodiments, the receiver further comprises an input boost converter coupled to the synchronous rectifier so that the synchronous rectifier is between the antenna and the input boost converter. The input boost converter is configured to increase the DC voltage from the synchronous rectifier.

In some embodiments, the receiver comprises an input boost converter includes a storage element coupled to the input boost converter and configured to store power from the DC voltage boosted by the input boost converter.

In some embodiments, the receiver comprises an input boost converter that includes a storage element further comprising an output boost converter coupled to the storage element. The output boost converter is configured to match an impedance of a load associated with the receiver.

In some embodiments, the receiver comprises an input boost converter that includes a storage element and comprises an output boost converter coupled to the storage element, further includes a processor configured to control an operation of the input boost converter and the output boost converter in accordance with the load associated with the receiver.

In some embodiments, the receiver comprises a plurality of switches coupled to the synchronous rectifier includes a wavelength link. At least one of the switches is driven by a gate-drive signal derived from the wavelength link.

In some embodiments, a method for receiving wireless power is described. The method comprises interfacing, by an antenna of a receiver, with a plurality of wireless power transmission waves; and synchronously rectifying, by a synchronous rectifier of the receiver, an AC voltage of the wireless power transmission waves to generate a DC voltage.

In some embodiments, the method further comprises controlling, by a switch of the receiver, a conduction of the synchronous rectification in accordance with at least one of a received voltage and a frequency of the power waves, where the switch is coupled to the synchronous rectifier.

FIGS. 76A-76E illustrate examples of an integrated rectifier and boost converter used for wireless power transmission, in accordance with some embodiments.

Figure 76A:
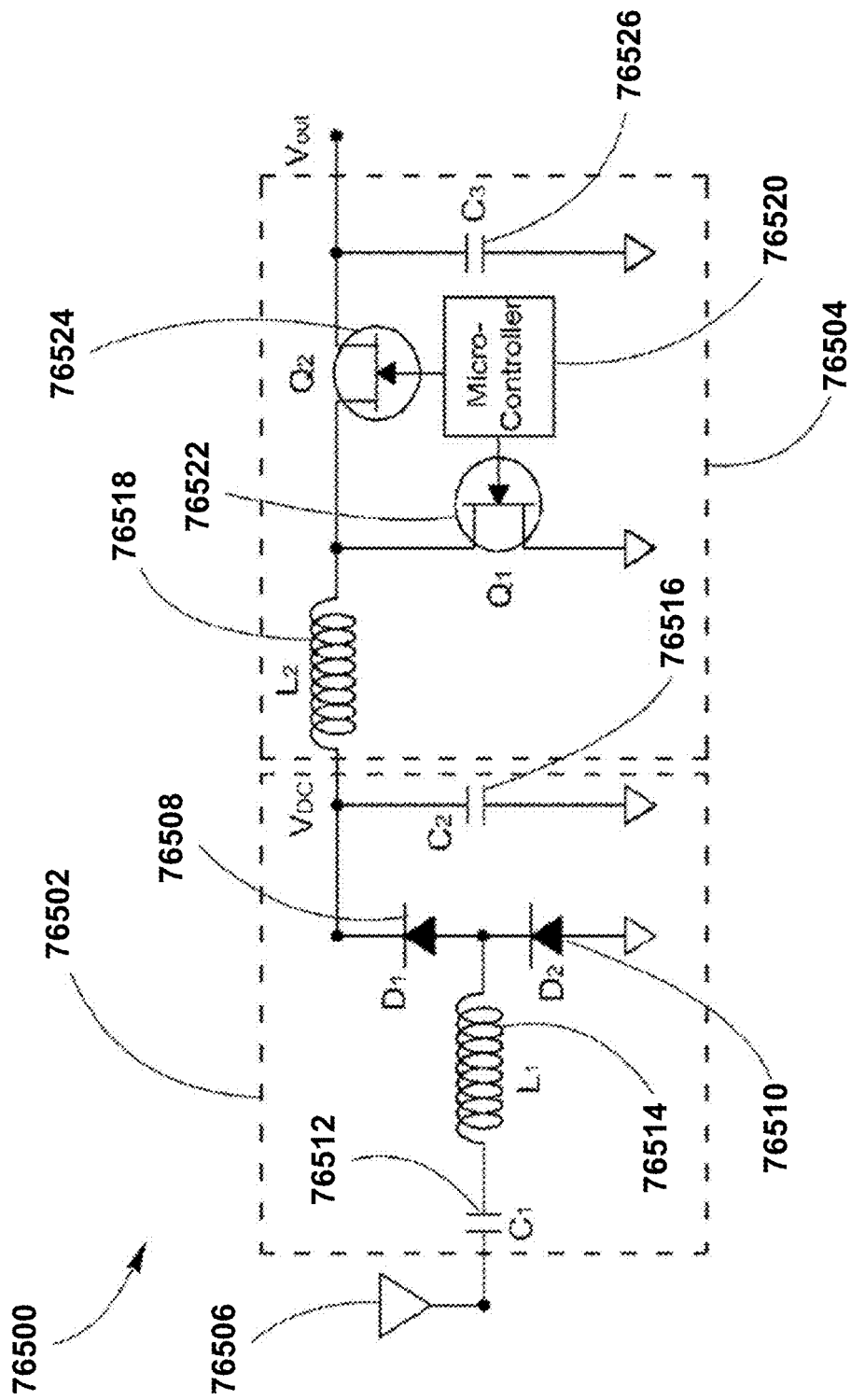
FIGS. 76A-76E illustrate examples of an integrated rectifier and boost converter used for wireless power transmission, in accordance with some embodiments

FIG. 76A illustrates a schematic diagram of a simplified circuit topology 76500 for an integrated rectifier 76502 and boost converter 76504.

Present embodiment may include at least one antenna element 76506 which may convert RF waves or pockets of energy into electrical power. Antenna element 76506 may be operatively coupled with one or more rectifiers 76502. RF waves may exhibit a sinusoidal shape within a voltage amplitude and power range that may depend on characteristics of a wireless power transmitter (not shown). Because of this sinusoidal nature of RF waves, the voltage or power generated by rectifier 76502 may be variable. As an illustrative embodiment, and not by way of limitation, the alternating current (AC) voltage or power generated by antenna element 76506 from transmitted RF waves or pocket of energy may vary from about 0 volts or 0 watt to about 5 volts at 3 watts.

Antenna element 76506 may include suitable antenna types for operating in frequency bands similar to frequency bands, such as 900 MHz, 2.4 GHz, and 5.7 GHz, amongst others, from the wireless transmitter. These frequency bands comply with Federal Communications Commission (FCC) regulations part 18(Industrial, Scientific and Medical equipment). Antenna element 76506 may include vertical or horizontal polarization, right hand or left hand polarization, elliptical polarization, or other suitable polarizations as well as suitable polarization combinations. Using multiple polarizations may be beneficial in devices where there may not be a preferred orientation during usage or whose orientation may vary continuously through time. For devices with well-defined orientations, there might be a preferred polarization for antennas which may dictate a ratio for the number of antennas of a given polarization. Suitable antenna types may include patch antennas with heights from about 1%8 inches to about 6 inches and widths from about 1%8 inches to about 6 inches. Patch antennas may have the advantage that polarization may depend on connectivity, i.e. depending on which side the patch is fed, the polarization may change.

Rectifier 76502 may include diodes, resistors, inductors, transistors and/or capacitors to rectify the AC voltage generated by antenna element 76506 to direct current (DC) voltage. Rectifier 76502 may be placed as close as technically possible to antenna element 76506 to minimize losses. In one embodiment, rectifier 76502 may operate in synchronous mode, in which case rectifier 76502 may include switching elements, transistors, which may improve the efficiency of rectification. Half-bridge rectifier 76502 may be used to produce an output with a fixed polarity that is independent of the polarity of the input.

Transmission of power converted by rectifier 76502 may be controlled using either an active-drive approach to provide control signals with electronic circuitry which may have timing information from voltage or current waveforms within the power circuit, or a passive-drive approach in which control signals may be directly provided or through passive circuit elements from a waveform in the power circuit.

When an alternating RF signal is received by antenna element 76506 from the wireless transmitter, a direct voltage output, $V_{DC}$, may be drawn from the output terminals of half-bridge rectifier 76502, including two diodes, $D_1$ and $D_2$, respectively identified as diode 76508 and diode 76510, which may be wired in series upstream and connected to the output terminal. Antenna element 76506 is connected in series to capacitor 76512, which is connected in series to inductor 76514, both acting as the resonant filter for the power signal being transferred from wireless transmitter and received by antenna element 76506. Additionally, rectifier 76502 may be connected in parallel to a second filter capacitor 76516 and in series with charging inductor 76518.

When the polarity of the alternating RF signal received may be positive, current flows through the first upstream diode 76508 and when the polarity of the alternating RF signal received is negative, current flows through second upstream diode 76510.

Boost converter 76504 may include charging inductor 76518, but it may be laid out internally of rectifier 76502. In the present embodiment inductor 76518 may be preferably laid out as an internal component of boost converter 76504 and may be designed with an appropriate, smaller form factor and scaled to a plurality of values, such that maximum power that may be converted may not saturate inductor 76518. Boost converter 76504 may convert the variable DC output voltage of rectifier 76502 into a more stable DC voltage that can be used by components of a wireless receiver and/or electronic device housing the wireless receiver. Boost converter 76504 may operate as a step-up DC-to-DC converter to increase the voltage from rectifier 76502 to a voltage level suitable for proper operation of other modules in the wireless receiver. In addition, boost converter 76504 may reduce or eliminate rail-to-rail deviations. Additional filtering capabilities, capacitor 76526, may be added at the output of boost converter 76504 as shown in FIG. 76A. In one embodiment, boost converter 76504 may exhibit a synchronous topology to increase power conversion efficiency.

As the voltage or power generated from RF waves may be zero at some instants of wireless power transmission, circuit topology 76500 may include circuit elements to store energy or electric charge from the output voltage produced by rectifier 76502. In this way, inductor 76518, may deliver continuous voltage or power to the output terminal of boost converter 76504, where a load (not shown) may represent a battery or internal circuitry of electronic device requiring continuous powering or charging.

When the required level of voltage may be present at the output terminal of rectifier 76502, micro-controller 76520 may turn switching transistor 76522, $Q_1$, on for current to flow through inductor 76518, which may start storing energy. Then, according to a predetermined control switching scheme in micro-controller 76520, switching transistor 76522 may be turned off. Subsequently, inductor 76518 may discharge its stored energy by sending current to switching transistor 76524, Q2, which may be presently in off state. Due to this current and the state of switching transistor 76524, the voltage may rise at the input of switching transistor 76524. At some level of voltage in accordance with the switching control scheme, micro-controller 76520 may turn switching transistor 76524 on for a particular amount of time allowing energy transmission at a level of voltage that is higher than the original voltage at capacitor 76516, $C_2$. Switching transistors 76522, 76524 may be identical field-effect transistors, bipolar junction transistors, insulated-gate bipolar transistors, or gallium nitride transistors, amongst others.

Micro-controller 76520 may be an integrated controller circuit driving switching transistor 76522, 76524 for power transfer to other modules of the wireless receiver and it may be a programmable or non-programmable type controller.

Circuit Architecture of an Integrated Rectifier and Boost Converter

Figure 76B:
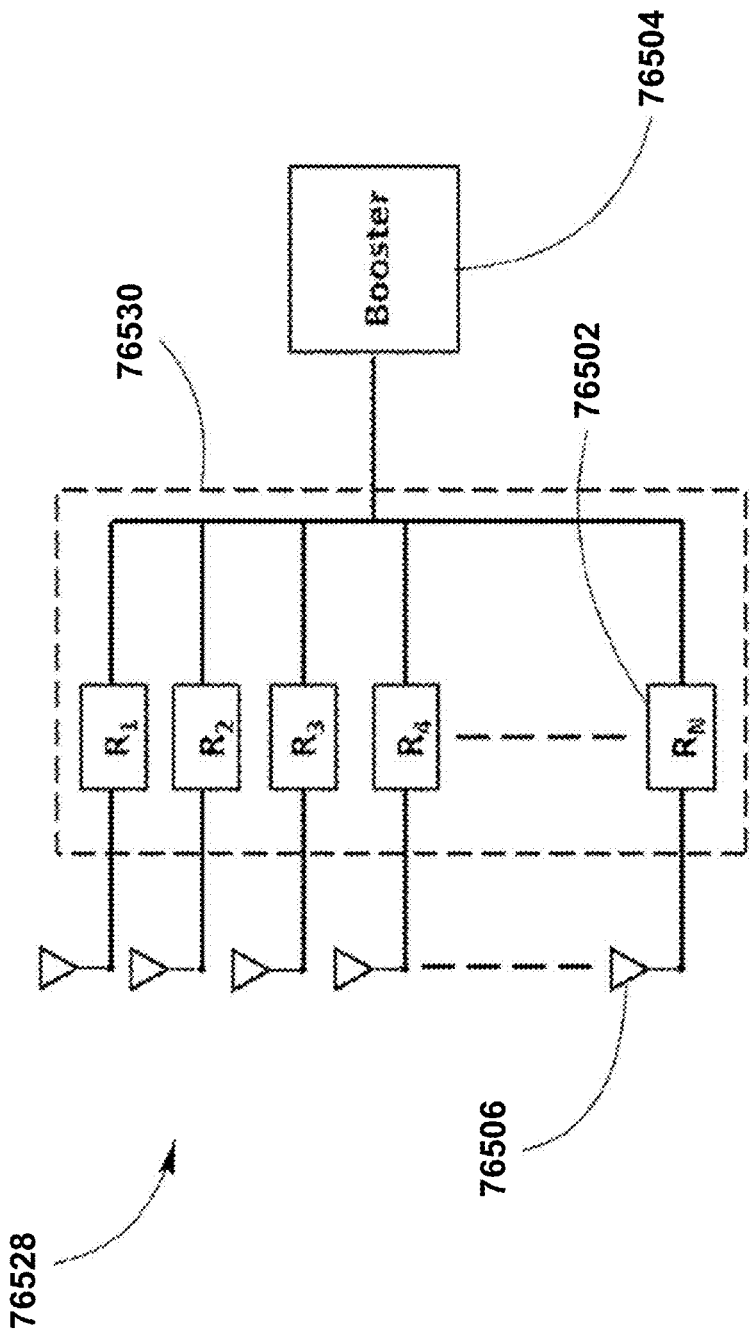

FIG. 76B depicts a block diagram of circuit architecture 76528 including antenna elements 76506 connected to integrated rectifier 76530 and boost converter 76504, according to an embodiment.

Better efficiency and power density may not be achieved using one sole rectifier 76502 as shown in FIG. 76A. The well-known problem of power availability at the output of a wireless receiver may be solved using circuit architecture 76528 including a plurality of identical rectifiers 76502, as described in circuit topology 76500, including same passive and active circuit components and switching control schemes, and integrated as rectifier 76530, connected to boost converter 76504. Accordingly, multiple configurations may be used to transfer wireless power from antenna elements 76506. This way, integrated rectifier 76530 may include as many identical rectifiers 76502 as required by the power level that may be needed for a wireless receiver to operate efficiently, as well as the electronic device housing the wireless receiver. Integrated rectifier 76530 may include from one to N identical rectifiers 76502, $R_1, R_2, R_3 \ldots R_N$, feeding one boost converter 76504.

In one embodiment, inductor 76518 may be included in the circuit topology of integrated rectifier 76530. In another embodiment inductor 76518 may be externally placed next to boost converter 76504. The size and shape of the external inductor 76518 may depend on the electrical constraints and parameters of the circuit.

As may be seen in FIG. 76B, circuit architecture 76528 may allow to have two rectifiers 76502, or four rectifiers 76502, or eight rectifiers 76502, as integrated rectifier 76530, each connected to a dedicated antenna element 76506 and the total power output feeding one boost converter 76504.

Integrated Circuit of Rectifiers and Boost Converter

Figure 76C:
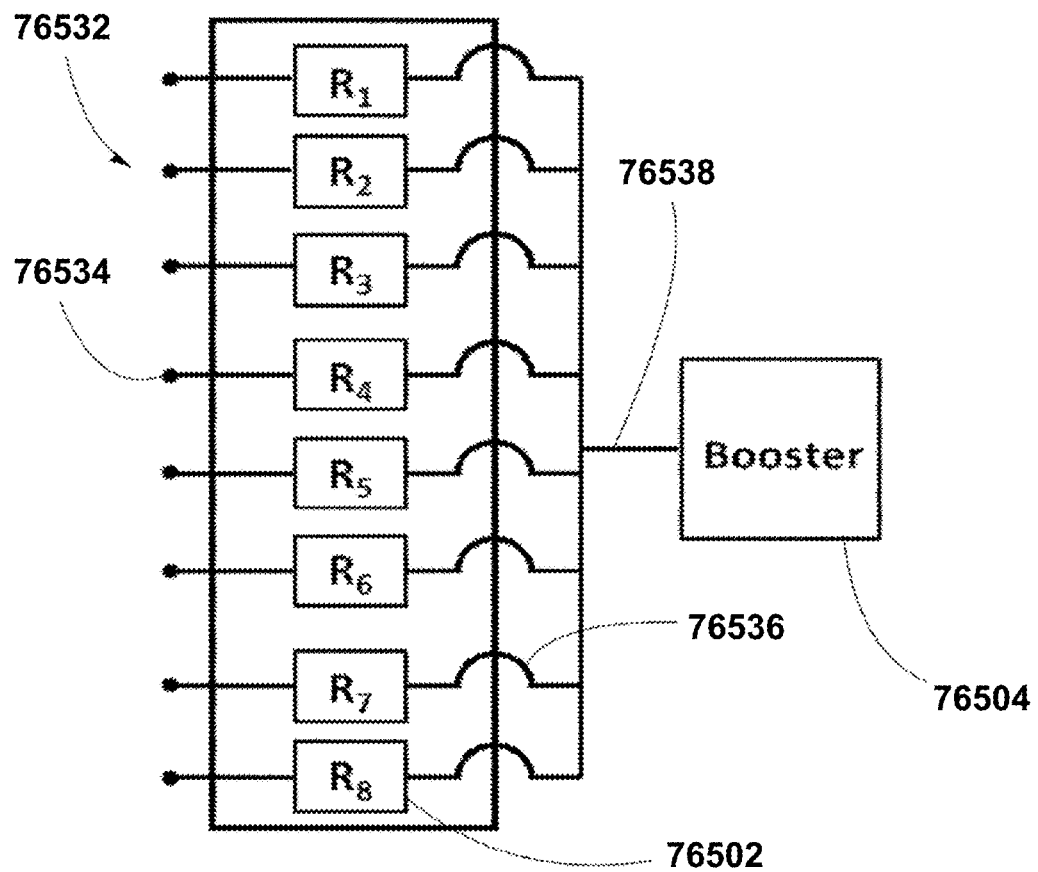

FIG. 76C shows a block diagram of integrated circuit 76532 of arrangement of rectifiers 76502, according to an embodiment.

Given that circuit architecture 76528, including rectifiers 76502 of circuit topology 76500, may be an expensive implementation using discrete components for rectifier 76502, a configuration of eight rectifiers 76502 may be enabled in integrated circuit 76532.

Integrated circuit 76532 may include eight RF input terminals 76534, eight rectifiers 76502, and eight DC output lines 76536 connected together to provide the total power extracted from RF signals received by antenna elements 76506 through a single feed line 76538 into boost converter 76504. Integrated circuit 76532 may also include synchronous half-bridge rectifiers 76502.

Additionally, integrated circuit 76532 may enable an implementation of circuit architecture 76528 that may be capable of operating over a large range of frequencies. This capability may not be possible using discrete components. Moreover, inductor 76518, shown in FIG. 76A, may be included in integrated circuit 76532 and physically sized to smaller form factor and value such that maximum power extracted and converted may not saturate inductor 76518.

Capacitor 76516 in each rectifier 76502 may be substituted in the package by the layout of bonded wires used for output lines 76536, thus significantly reducing the size of integrated circuit 76532 and increasing power transmission efficiency.

Control-Driven Integrated Rectifier and Boost Converter Circuit Topology

Figure 76D:
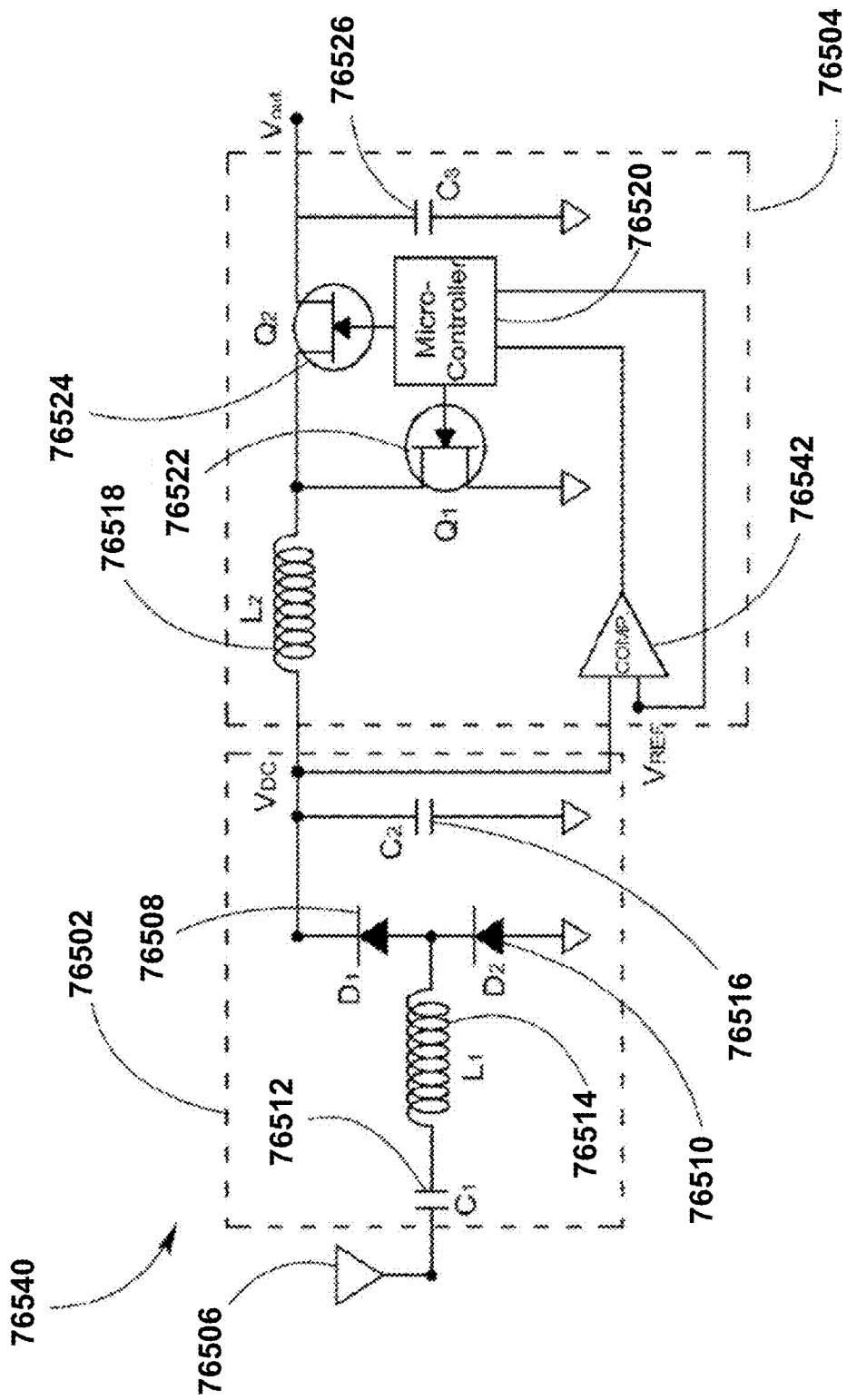

FIG. 76D represents a schematic diagram for a circuit topology 76540 of half-bridge rectifier 76502 power conversion controlled via a comparator 76542, according to an embodiment.

Circuit architecture 76528 may include micro-controller 76520, in boost converter 76504, to control the RF power that may be extracted. Micro-controller 76520 may drive comparator 76542 to which a reference signal, $V_{REF}$, may be fed to compare it with the extracted DC waveforms and enabling a proprietary algorithm to turn switch transistors 76522, 76524 on at the appropriate voltage point and particular amount of time to suit maximum power point tracking (MPPT) functionality, charging and discharging inductor 76518 as described in FIG. 76A. All other circuit elements in circuit topology 76540 are the same as in circuit topology 76500 in FIG. 76A. Directly sensing of the output voltage, $V_{DC}$, may be performed by comparator 76542 to see if it is below of a predetermined design voltage threshold.

Micro-controller 76520, based on voltage measurements, may control the power or voltage delivered at the output terminals of boost converter 76504, and therefore, adjust the current limits supplied to other modules in the wireless receiver.

An MPPT algorithm may be executed by micro-controller 76520 to control and optimize the amount of power that boost converter 76504 may pull from antenna elements 76506. Accordingly, MPPT functionality may be enabled having micro-controller 76520 to monitor the power levels converted. Subsequently, the comparison of DC voltage at the output terminal of rectifier 76502, $V_{DC}$, with the voltage reference, $V_{REF}$, may be used by micro-controller 76520 to detect the maximum power point in the RF signals received by antenna elements 76506 and for the proprietary algorithm to adjust the level of power extracted in conformity with the MPPT data in micro-controller 76520.

This active-drive approach of control may be also implemented including comparator 76542 in integrated circuit 76532.

Figure 76E:
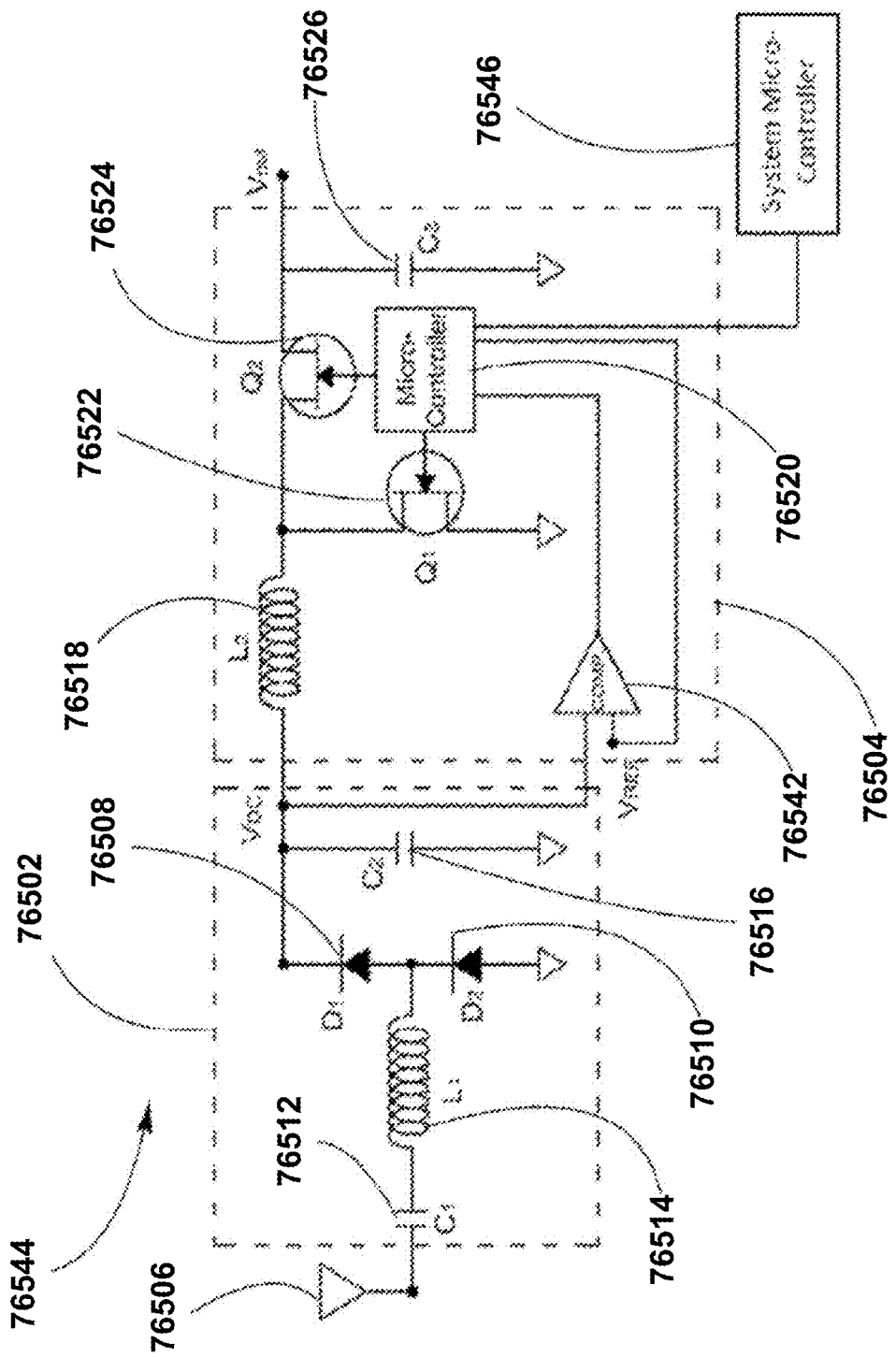

FIG. 76E represents a schematic diagram for a circuit topology 76544 of half-bridge rectifier 76502 power conversion including an additional external system micro-controller 76546, according to an embodiment.

Circuit topology 76544 may include all components in circuit topology 76540, to which the external system micro-controller 76546 may be added to provide additional control of boost converter 76504 in a wireless receiver (not shown).

Micro-controller 76520 in circuit topology 76540, may drive comparator 76542 to which a reference signal, $V_{REF}$, may be fed to compare it with the extracted DC waveforms and enabling a proprietary algorithm to turn switch transistors 76522, 76524 on at the appropriate voltage point and particular amount of time to suit maximum power point tracking (MPPT) functionality, charging and discharging inductor 76518. This active-drive approach of control may be also implemented including comparator 76542 in integrated circuit 76532.

System micro-controller 76546 may process information sent by the wireless receiver through its communications component for determining optimum times and locations for pocket-forming and may also operate in conjunction with an EEPROM module to run an algorithm for controlling the operation of boost converter 76504 according to load requirements. System micro-controller 76546 may actively monitor the overall operation of the wireless receiver by taking one or more power measurements at different nodes or sections of the wireless receiver. For example, system micro-controller 76546 may measure how much voltage or power is being delivered at rectifier 76502, boost converter 76504, and other components in the wireless receiver, including the connected load and may communicate these power measurements to the connected load so that electronic device may know how much power it can pull from the wireless receiver. System micro-controller 76546 may provide additional feedback to the boost converter 76504.

FIGS. 76A-76E illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 76A-76E.

Presented below are example embodiments of integrated rectifier and boost converter for wireless power transmission.

In some embodiments, an example receiver for providing power to a load includes a plurality of rectifiers, each comprising an antenna configured to convert electromagnetic energy from radio-frequency (RF) waves into AC voltage. Each of the plurality of rectifiers are configured to convert the AC voltage to a DC voltage and provide a DC voltage output to a common node; and a boost converter for increasing the DC voltage output, the boost converter comprising an inductor operatively coupled to the common node for receiving the DC voltage output, the boost converter further comprising a microcontroller for controlling an amount of power provided from the inductor.

In some embodiments, the receiver includes the microcontroller. The microcontroller is configured to control the amount of power provided by the inductor by controlling a plurality of transistors operatively coupled to the inductor.

In some embodiments, the boost converter further comprises a comparator operatively coupled to the microcontroller and the common node. The microcontroller controls the amount of power by comparing the DC voltage output to a reference voltage.

In some embodiments, the microcontroller controls the amount of power by comparing the DC voltage output to a reference voltage and the microcontroller is configured to provide a maximum power point tracking (MPPT) functionality to the amount of power extracted from the RF waves and provided from the inductor.

In some embodiments, the receiver further comprises a system microcontroller, operatively coupled to the microcontroller, and the system microcontroller is configured to control the operation of the boost converter according to load requirements.

In some embodiments, the receiver with a system microcontroller has the micro controller configured to monitor power measurements in the receiver for the load for controlling operation of the boost converter.

In some embodiments, the receiver with a system microcontroller has the micro controller further configured to configured to communicate power measurements to the microcontroller to provide feedback to the boost converter.

In some embodiments, a method for providing power in a receiver to a load comprises converting electromagnetic energy from radio-frequency (RF) waves into AC voltage in each of a plurality of antennas, converting each of the AC voltages to DC voltages in a plurality of rectifiers, each respectively coupled to one of the plurality of antennas, providing DC voltage outputs from each of the plurality of rectifiers to a common node, increasing the DC voltage output from the common node via a boost converter, and controlling an amount of power provided to the load via a microcontroller.

In some embodiments, a receiver for providing power to a load from wireless energy, comprises a plurality of synchronous rectifiers, each comprising an antenna configured to convert electromagnetic energy from radio-frequency (RF) waves into AC voltage. Each of the plurality of synchronous rectifiers are configured to convert the AC voltage to a DC voltage and provide a DC voltage output to a common node, and a boost converter for increasing the DC voltage output, the boost converter comprising an inductor operatively coupled to the common node for receiving the DC voltage output, the boost converter further comprising a microcontroller for controlling an amount of power provided from the inductor via a plurality of transistors operatively coupled to the inductor.

FIGS. 77A-77F illustrate examples of a boost-charger-boost system for enhanced power delivery, in accordance with some embodiments.

Wireless power transmission may include the use of RF waves for extracting power that may be used for charging or powering an electronic device. According to some aspects of wireless power transmission, a transmitter may send a beam of RF waves towards a receiver, where these RF waves may generate a 3-D pocket of energy that may be used by the receiver apparatus for charging or powering an electronic device. One challenge that may be present during wireless power transmission is that power or energy extracted from RF waves may be variable due to inherent characteristics of the medium. That is, the environment of transmission may be affected by changes to or movement of objects within the physical boundaries, or movement of the boundaries themselves. It may be also affected by changes to the medium of transmission; for example, changes to air temperature or humidity. Moreover, the power that can be extracted from RF waves may be zero at some instances of the wireless power transmission.

Figure 77A:
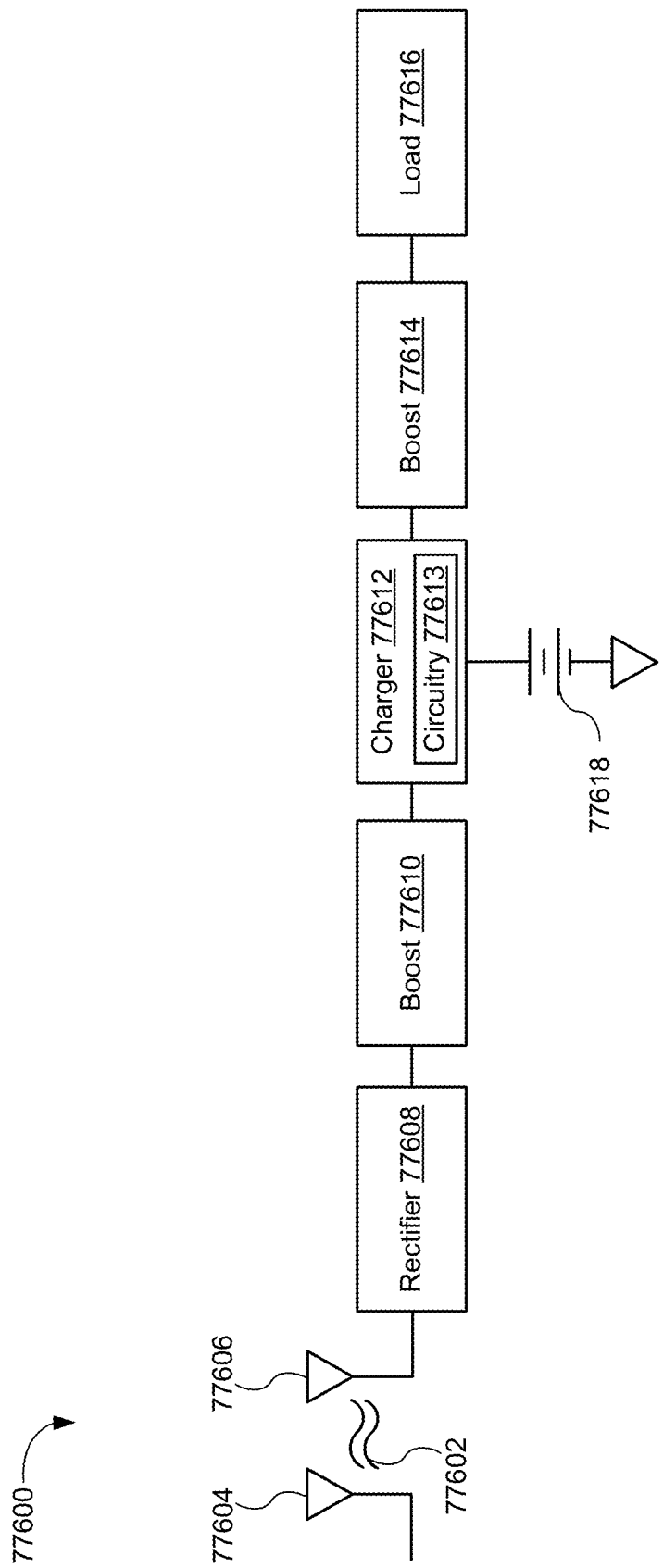
FIGS. 77A-77F illustrate examples of a boost-charger-boost system for enhanced power delivery, in accordance with some embodiments.

FIG. 77A shows a controlled-power delivery system 77600 for extracting power from a variable power source and delivering continuous voltage at suitable levels to load 77616. According to some aspects of this embodiment, a variable power source may be in the form of RF waves 77602 conveyed from one or more transmitting antennas 77604, where these RF waves 77602 may be collected by one or more receiving antennas 77606. In one embodiment, transmitting antenna 77604 may be part of a transmitter (not shown in FIG. 77A) capable of directing RF waves 77602 towards a receiver (not shown in FIG. 77A) for charging or powering an electronic device. Controlled-power delivery system 77600 may be part of a receiver suitably configured for wireless power transmission.

Receiving antenna 77606 may convert the electromagnetic energy from RF waves 77602 into AC voltage. Consequently, a rectifier 77608, operatively coupled with receiving antenna 77606, may convert this AC voltage into DC voltage. In one embodiment, rectifier 77608 may operate in synchronous mode, in which case rectifier 77608 may include switching elements that may reduce losses, thereby improving the efficiency of rectification. As an illustrative embodiment, and not by way of limitation, output of rectifier 77608 may vary from about 0 volts to about 5 volts DC.

A first boost converter 77610 may convert the variable DC output voltage of rectifier 77608 into a more stable DC voltage that may be used by a charger 77612 for charging storage element 77618. First boost converter 77610 may operate as a step-up DC-to-DC converter to increase the voltage from rectifier 77608 to a voltage level suitable for proper operation of charger 77612. As an illustrative embodiment, and not by way of limitation, first boost converter 77610 may operate with low input voltages of at least 0.4 volts to about 5 volts DC to produce an output voltage between about 4.2 volts and about 5.5 volts DC. In addition, first boost converter 77610 may reduce or eliminate rail-to-rail deviations. In one embodiment, first boost converter 77610 may exhibit a synchronous topology to increase power conversion efficiency. In another embodiment, first boost converter 77610 may use a maximum power point tracking (MPPT) algorithm run by microcontroller (not shown in FIG. 77A) to control and maximize the amount of power that first boost converter 77610 can pull from RF waves 77602.

Charger 77612 may include suitable components for controlling the power delivered to storage element 77618 and load 77616. Charger 77612 may include a low dropout (LDO) circuit and/or a synchronous DC-to-DC conversion circuit to charge storage element 77618 based on a charging algorithm. Storage element 77618 may include a battery, a capacitor, and the like. The charging algorithm used in charger 77612 may depend on the chemistry and operational specifics of storage element 77618. For example, a lithium-ion battery may require a constant current/constant voltage (CC/CV) algorithm to properly charge. In addition, charger 77612 may include circuitry 77613 (shown in FIGS. 77A-77F) that may allow power to take multiple paths throughout the controlled-power delivery system 200. For example, from input to output; from input to storage element 77618; from storage element 77618 to output; from input to output and from storage element 77618 to output; and from input to storage element 77618 and output.

The controlled-power delivery system 77600 may include second boost converter 77614 to match impedance and power requirements of load 77616. Second boost converter 77614 may also include a synchronous topology to increase power conversion efficiency.

Figure 77B:
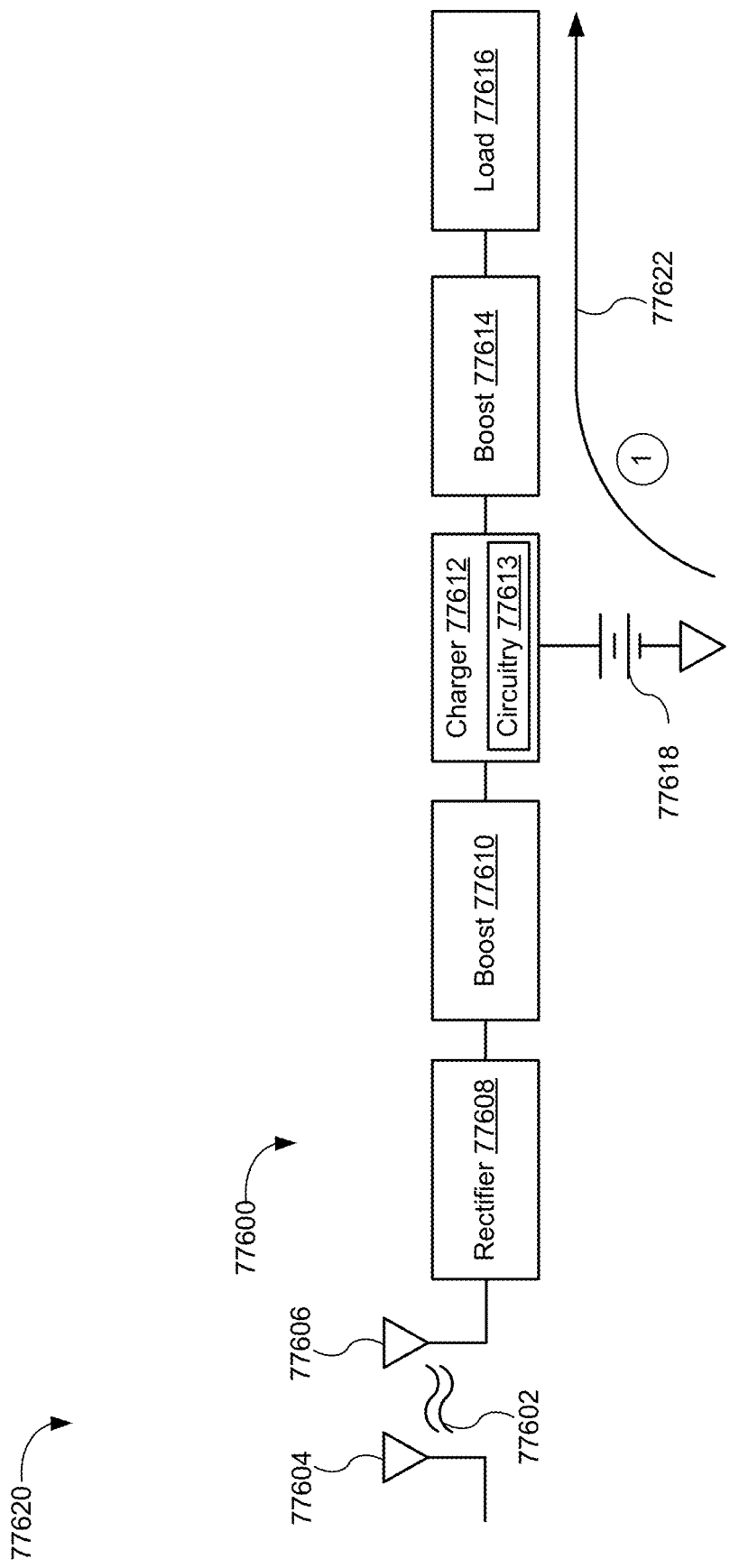

FIG. 77B illustrates an operation mode 77620 that may be implemented in controlled-power delivery system 77600 according to an embodiment. Operation mode 77620 may exhibit a current conduction path 77622 where the power delivered to load 77616 can be directly obtained from storage element 77618, passing through second boost converter 77614.

In one embodiment, current conduction path 77622 may be employed when there are power requirements at load 77616, but there is either none or not enough power available from in first boost converter 77610. Consequently, voltage can be drained from storage element 77618, as long as it is not below its set minimum. As previously explained, second boost converter 77614 may step up the voltage drained from storage element 77618 to suitable levels that can be used by load 77616.

Figure 77C:
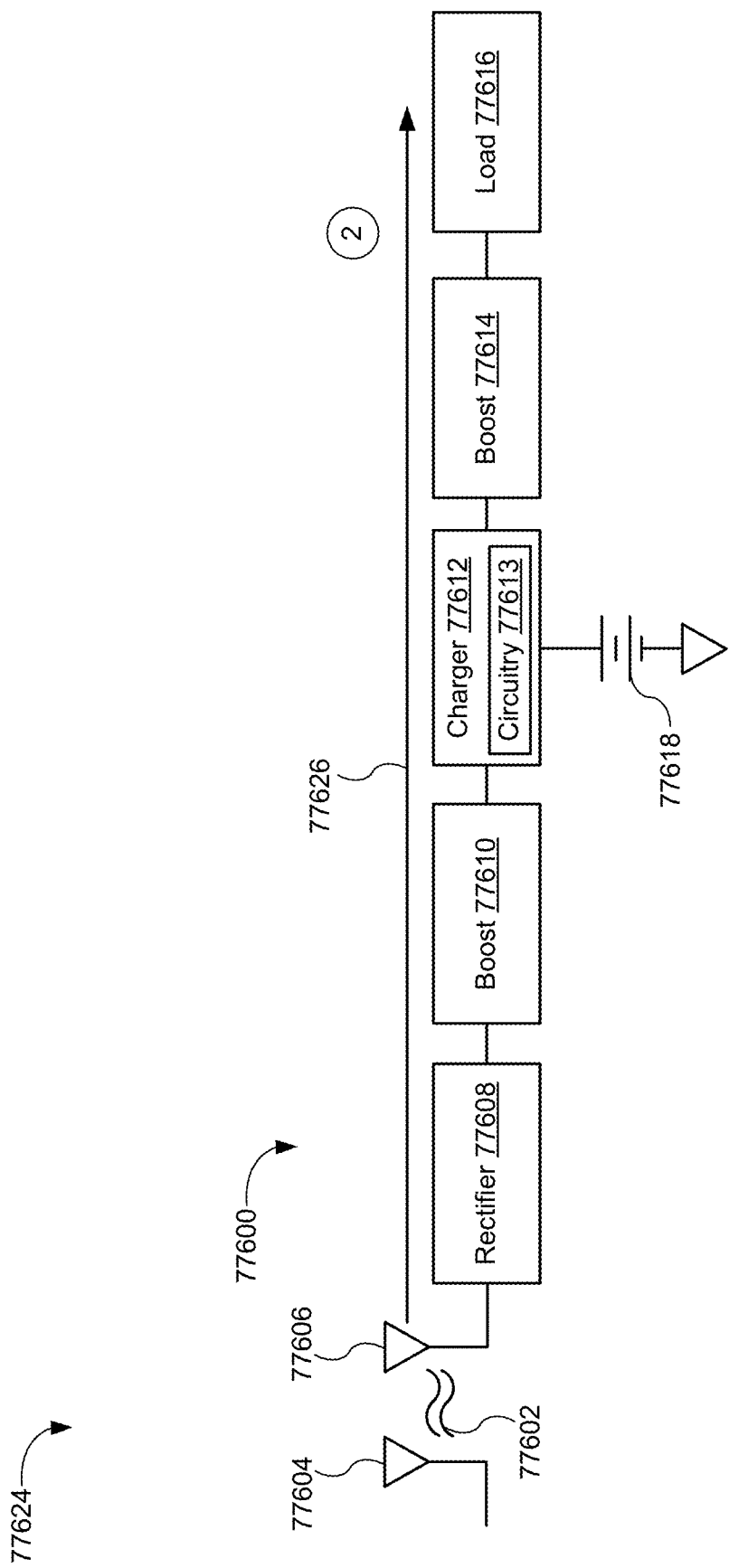

FIG. 77C depicts an operation mode 77624 that may be implemented in controlled-power delivery system 77600 according to an embodiment. Operation mode 77624 may exhibit a current conduction path 77626 where the power delivered to load 77616 can be directly obtained from transmitted RF waves 77602.

According to some aspects of this embodiment, current conduction path 77626 may be originated when transmitted RF waves 77602 may be converted into AC voltage by receiving antenna 77606, where this AC voltage can be converted into DC voltage by rectifier 77608. First boost converter 77610 and second boost converter 77614 may step up the rectified voltage to suitable levels that may be used by charger 77612 and load 77616. In this case, charger 77612 may determine that the power or voltage extracted from RF waves 77602 is suitable for powering load 77616, and/or that storage element 77618 may not require charging. In another embodiment, charger 77612 may determine that the power or voltage that can be extracted from RF waves 77602 is only sufficient for powering load 77616.

Figure 77D:
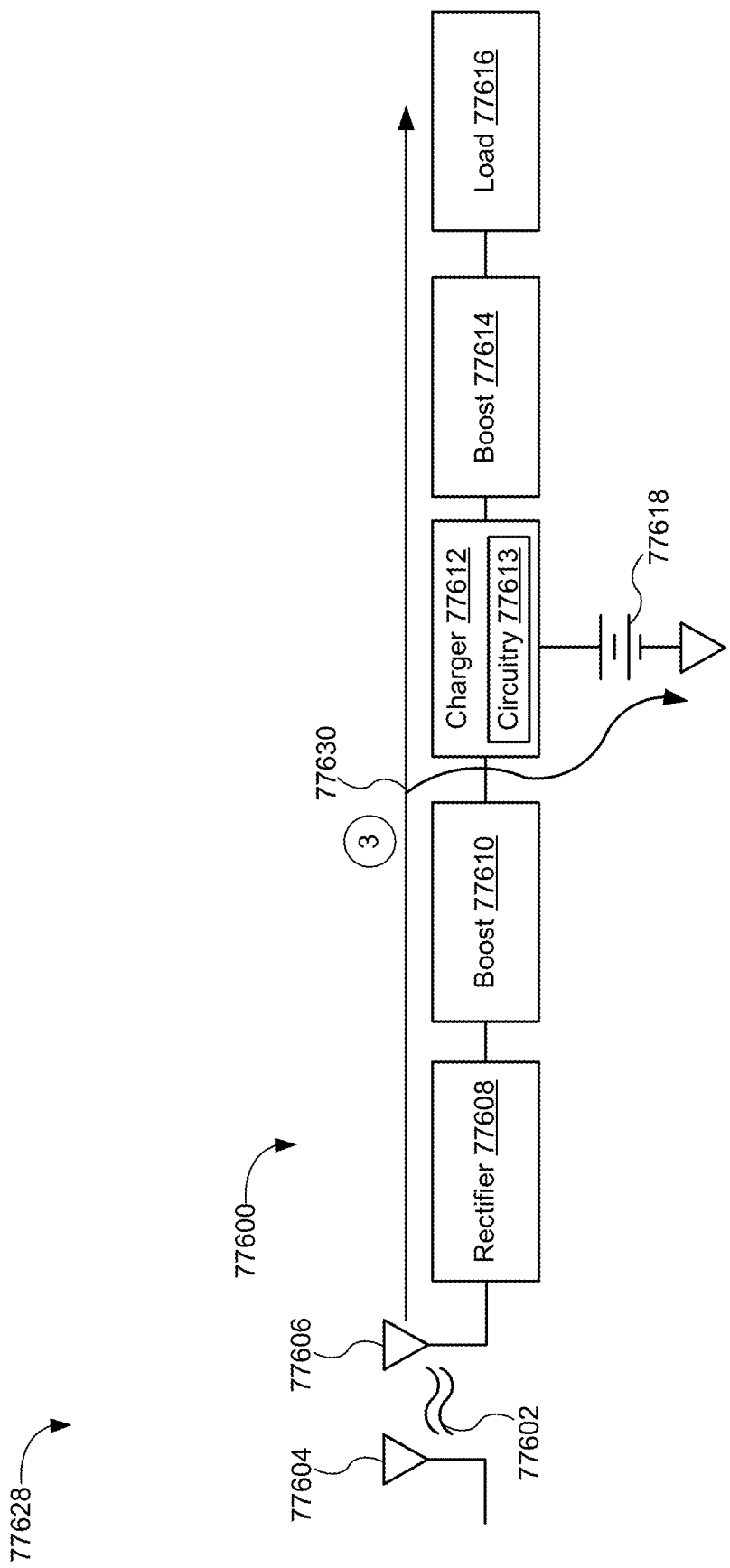

FIG. 77D shows an operation mode 77628 that may be implemented in controlled-power delivery system 77600 according to an embodiment. Operation mode 77628 may exhibit a current conduction path 77630 where power extracted from RF waves 77602 can be delivered to load 77616 and storage element 77618 simultaneously.

According to some aspects of this embodiment, when powering load 77616, if there is an excess of power available from rectifier 77608 and first boost converter 77610, then this excess of power may be used to charge storage element 77618. In this way, current conduction path 77630 may allow suitable powering of load 77616 and charging of storage element 77618.

Figure 77E:
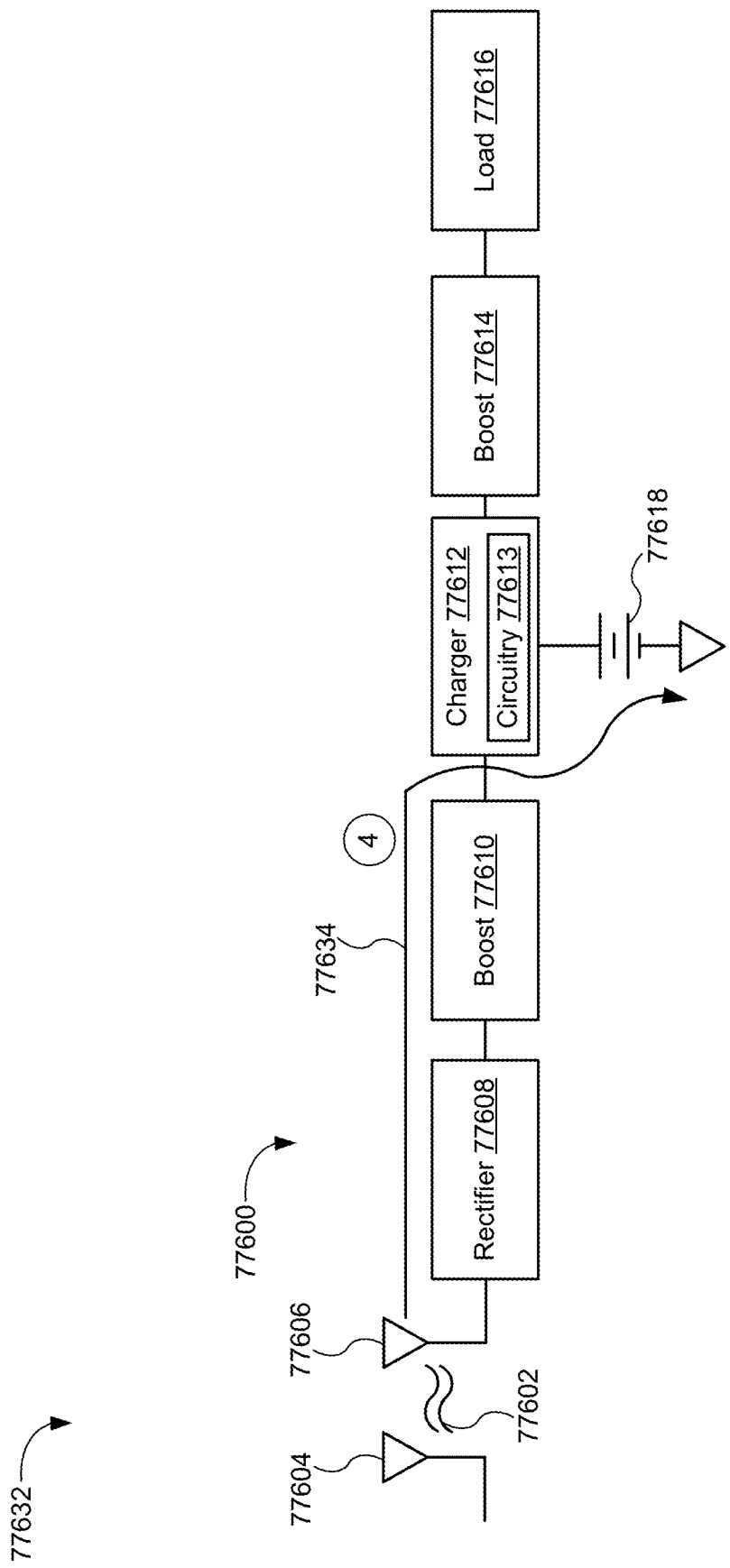

FIG. 77E shows an operation mode 77632 that may be implemented in controlled-power delivery system 77600. According to some aspects of this embodiment, if load 77616 does not require powering, then a current conduction path 77634 may be used, where power extracted from RF waves 77602 through receiving antenna 77606, rectifier 77608 and first boost converter 77610 can be delivered only to storage element 77618.

Figure 77F:
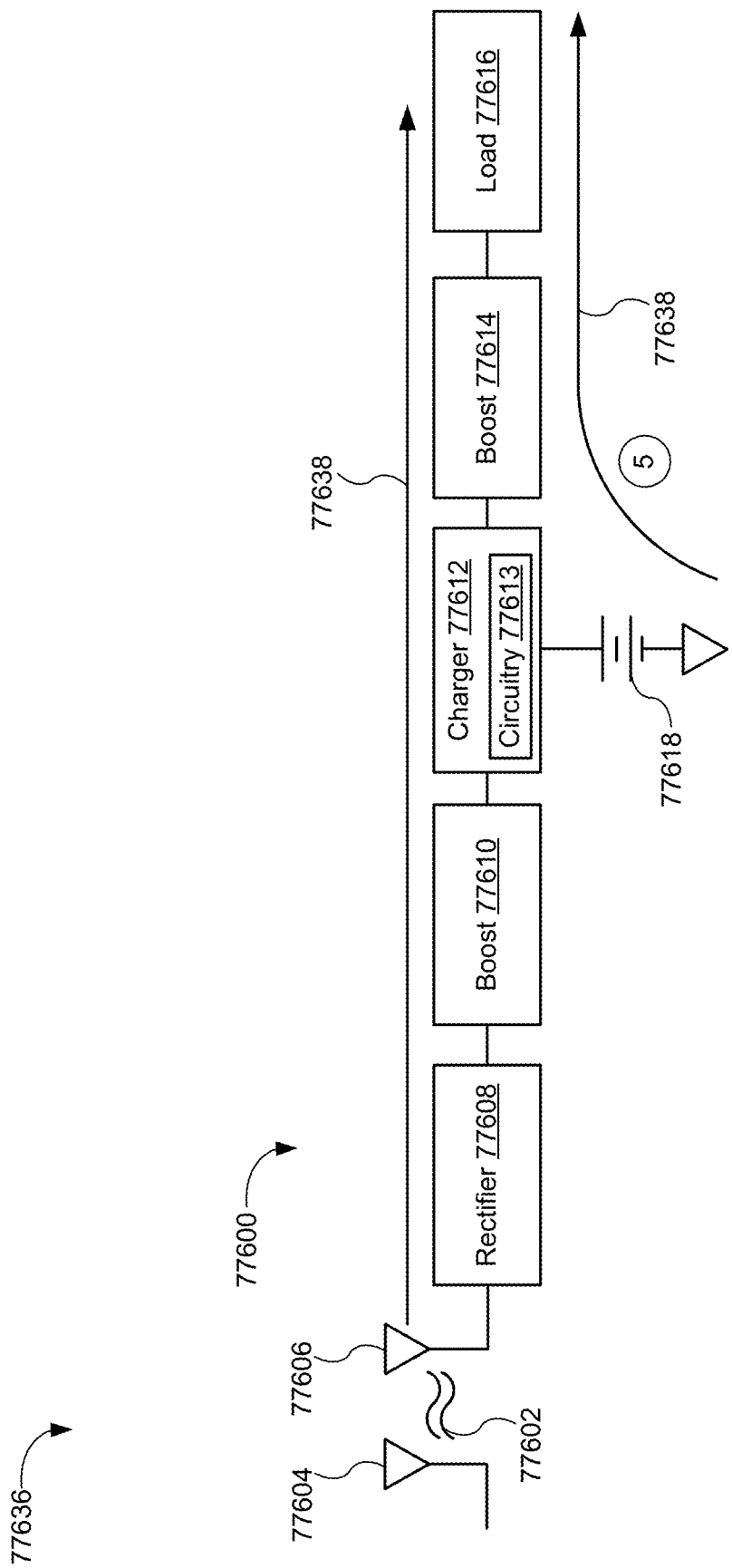

FIG. 77F shows an operation mode 77636 that may be implemented in controlled-power delivery system 77600. According to some aspects of this embodiment, a current conduction path 77638 may be operable in controlled-power delivery system 77600 when charger 77612 may be turned off for allowing current flow from storage element 77618 to load 77616. Simultaneously, power can also be applied from receiving antenna 77606, rectifier 77608, first boost converter 77610 and second boost converter 77614 to load 77616. Current conduction path 77638 may be applicable when the power or voltage that can be extracted from RF waves 77602 or storage element 77618 may not be sufficient for suitability powering load 77616, in which case it may be required to extract power from both, RF waves 77602 and storage element 77618, at the same time.

FIGS. 77A-77F illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 77A-77F.

Presented below are example embodiments of a boost-charger-boost system and associated methods for enhanced power delivery.

In some embodiments, an example receiver comprises an antenna configured to convert energy from a plurality of wireless power transmission waves into an alternating current (AC) voltage, a rectifier coupled to the antenna, where the rectifier is configured to rectify the AC voltage into a direct current (DC) voltage. The receiver further comprises a first boost converter coupled to the rectifier where the rectifier is electrically positioned between the antenna and the first boost converter, and where the first boost converter is configured to boost the DC voltage from the rectifier. The receiver also includes a charger coupled to the first boost converter, where the charger is configured to receive a first output from the first boost converter. The receiver also includes a storage element coupled to the charger, where the storage element is configured to receive a second output from the charger, and a second boost converter coupled to the charger where the charger is electrically positioned between the first boost converter and the second boost converter, and where the second boost converter is configured to match at least one of an impedance and a power requirement for a load associated with the receiver. The receiver is configured to function in an operational mode selected from a plurality of operational modes to provide a conduction path. The conduction path comprises at least one of (i) a first power flow from the storage element to the load, passed through the second boost converter, (ii) a second power flow from first boost converter to the load, passed through the second boost converter, (iii) a third power flow provided to the storage element via the charger, (iv) a fourth power flow simultaneously provided via a combination of (i) and (ii), (v) a fifth power flow simultaneously provided via a combination of (ii) and (iii).

In some embodiments, the antenna of the receiver is configured to convert the energy from a 3-D energy pocket defined via the wireless power transmission waves.

In some embodiments, the storage element of receiver comprises at least one of a battery and a capacitor.

In some embodiments, the receiver has the operational mode corresponding to the conduction path (v) selected by the receiver based on the receiver determining that an excess quantity of power for the load is available from the first boost converter.

In some embodiments, the receiver has the operational mode corresponding to the conduction path (iv) selected by the receiver based on the receiver determining that an insufficient quantity of power for the load is available from the first boost converter.

In some embodiments, the first boost converter is configured with a synchronous topology to increase a power conversion efficiency.

In some embodiments, the first boost converter comprises a controller configured to execute a maximum power point tracking (MPPT) process so that an amount of power that the first boost converter can pull from the signal waves is maximized.

In some embodiments, a method of providing power comprises converting, by an antenna of a receiver, energy from a plurality of wireless power transmission waves into an AC voltage, rectifying, by a rectifier of the receiver, the AC voltage into a DC voltage. The rectifier is coupled to the antenna, boosting, by a first boost converter of the receiver, the DC voltage provided from the rectifier. The first boost converter is coupled to the rectifier and the rectifier is electrically positioned between the antenna and the first boost converter; receiving, by a charger of the receiver, the DC voltage boosted by the first boost converter. The charger is coupled to the first boost converter, charging, by the charger of the receiver, a storage element coupled to the charger, matching, by a second boost converter of the receiver, at least one of an impedance and a power requirement for a load associated with the receiver. The second boost converter is coupled to the charger so that the charger is electrically positioned between the first boost converter and the second boost converter, and configuring the receiver to function in an operational mode selected from a plurality of operational modes to provide a conduction path. The conduction path comprises at least one of: (i) a first power flow from the storage element to the load, passed through the second boost converter, (ii) a second power flow from first boost converter to the load, passed through the second boost converter, (iii) a third power flow provided to the storage element via the charger, (iv) a fourth power flow simultaneously provided via a combination of (i) and (ii), (v) a fifth power flow simultaneously provided via a combination of (ii) and (iii).

In some embodiments, a receiver comprises an antenna configured to convert energy from a plurality of wireless power transmission waves into an AC voltage, a rectifier coupled to the antenna, where the rectifier is configured to rectify the AC voltage into a DC voltage, a first boost converter coupled to the rectifier. The rectifier is electrically positioned between the antenna and the first boost converter, and the first boost converter is configured to increase the DC voltage provided by the rectifier. The receiver further comprises a charger coupled to the first boost converter, where the charger is configured to receive the DC voltage increased by the first boost converter from the first boost converter, a storage element coupled to the charger, where the storage element comprises at least one of a battery and a capacitor. The storage element is configured to receive an output from the charger. The receiver also includes a second boost converter coupled to the charger where the charger is electrically positioned between the first boost converter and the second boost converter, and where the second boost converter is configured to match at least one of an impedance and a power requirement for a load associated with the receiver. The receiver is configured to function in an operational mode selected from a plurality of operational modes to provide a conduction path. The conduction path comprises at least one of: (i) a first power flow from the storage element to the load, passed through the second boost converter, (ii) a second power flow from the first boost converter to the load, passed through the second boost converter, (iii) a third power flow provided to the storage element via the charger, (iv) a fourth power flow simultaneously provided via a combination of (i) and (ii), (v) a fifth power flow simultaneously provided via a combination of (ii) and (iii).

Figures 78A, 78B:
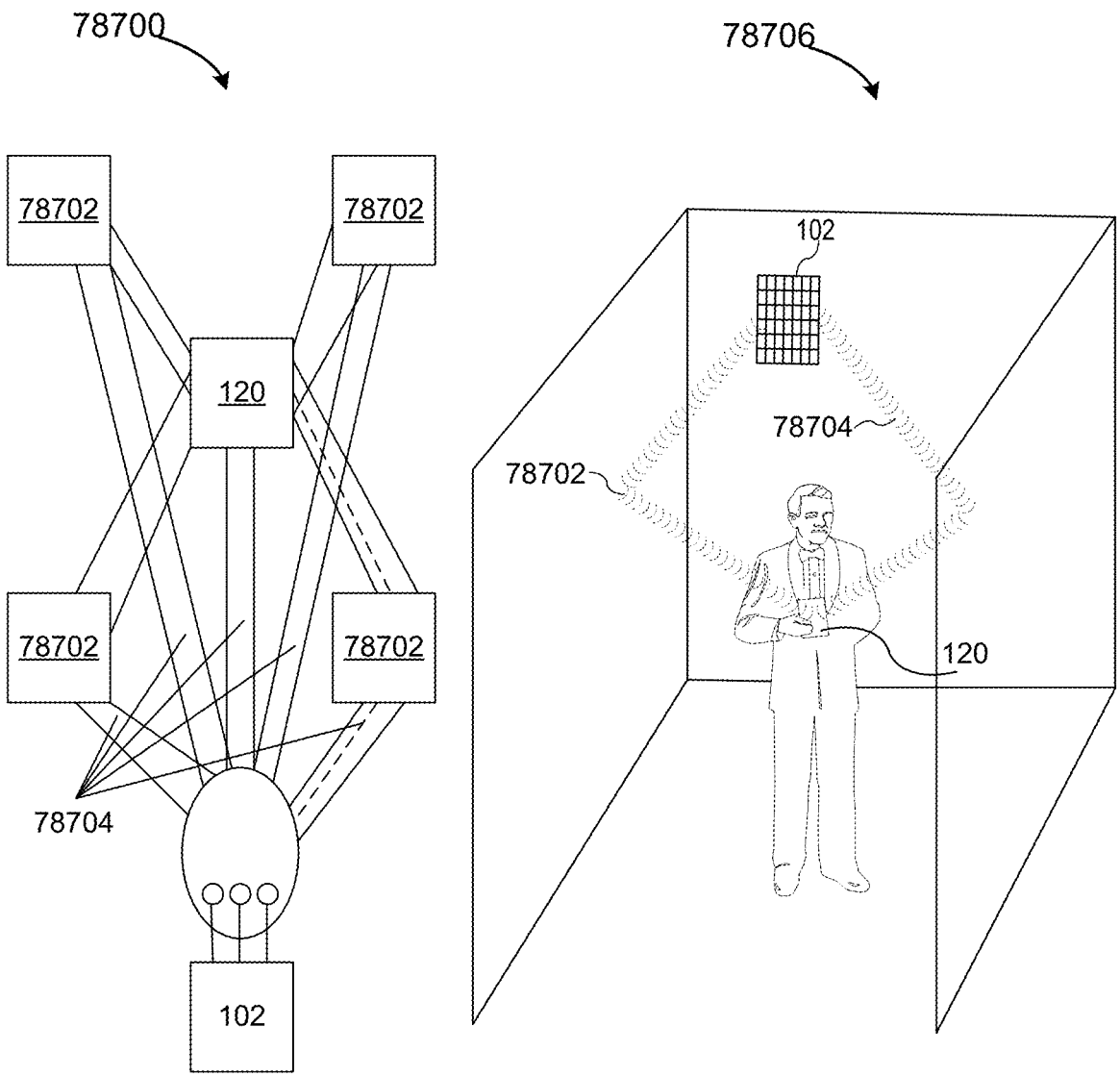
Figure 78C:
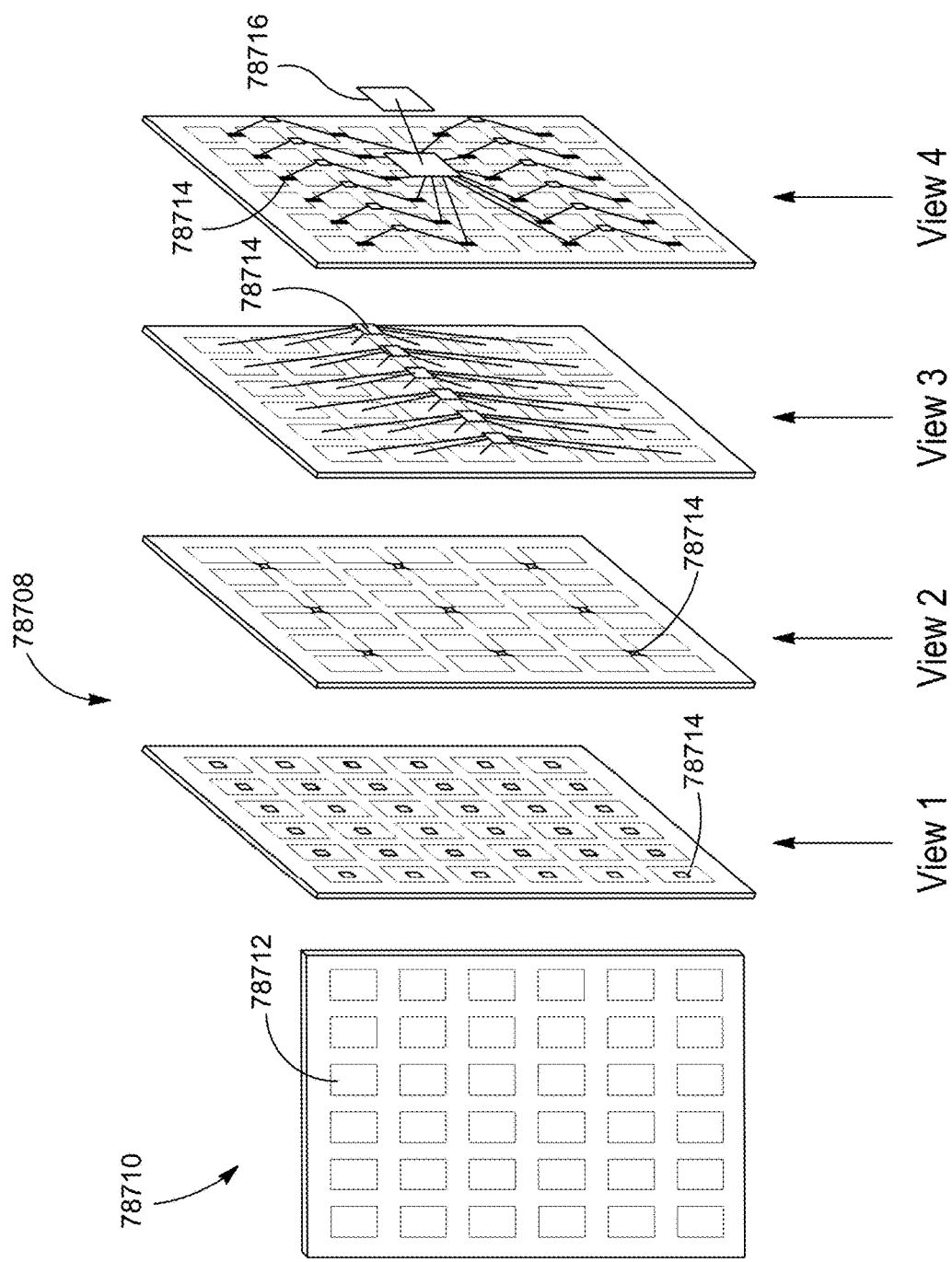
Figure 78E:
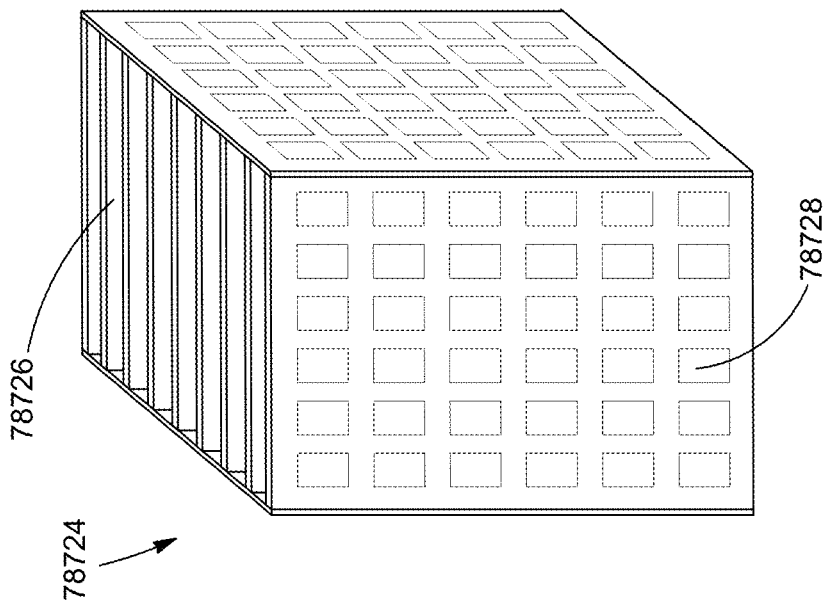
Figure 78D:
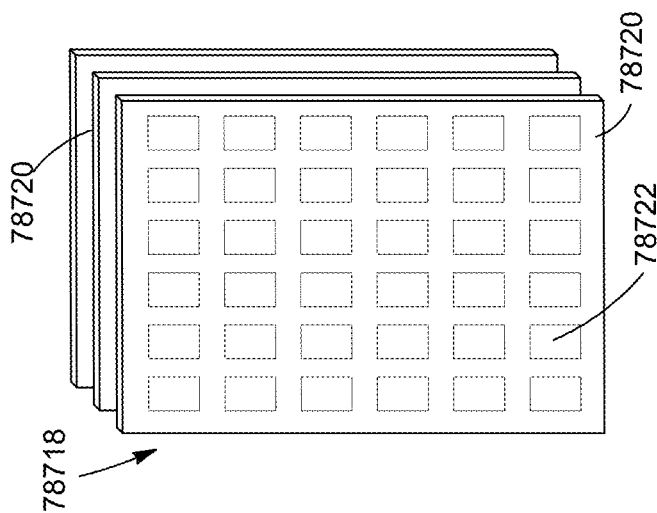
Figures 78F, 78G:
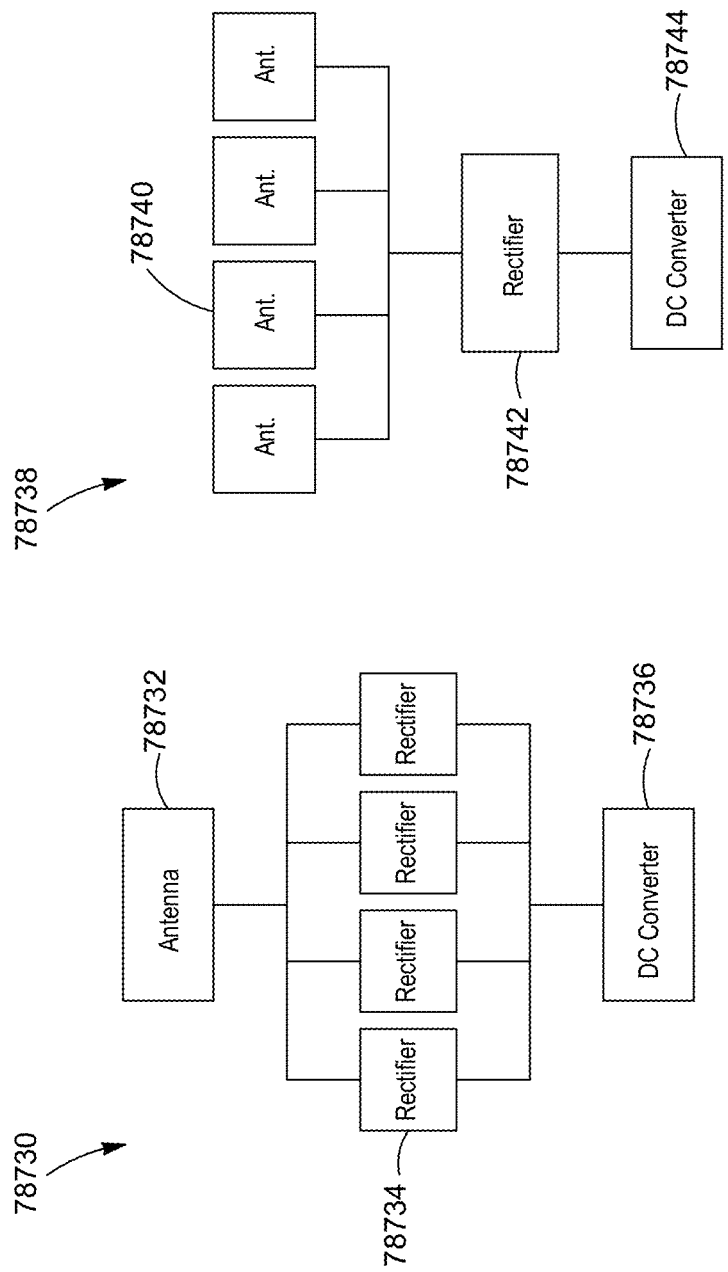
Figure 78I:
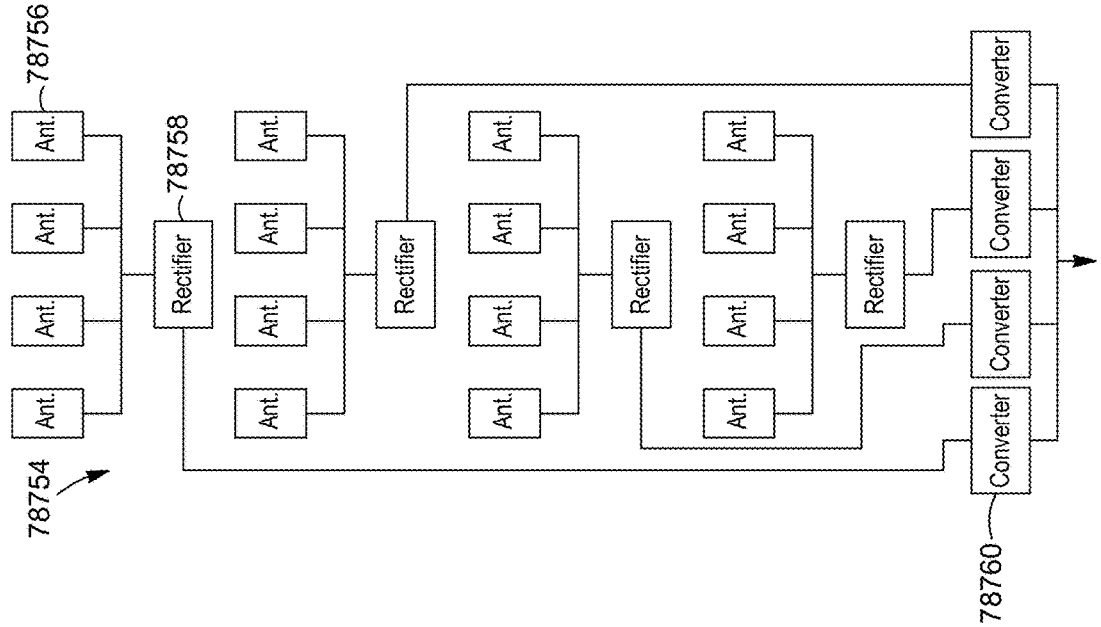
Figure 78H:
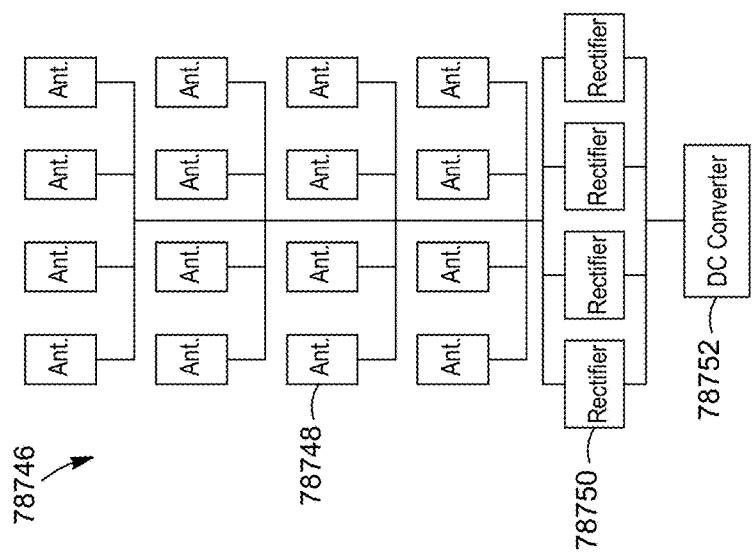
Figure 78J:
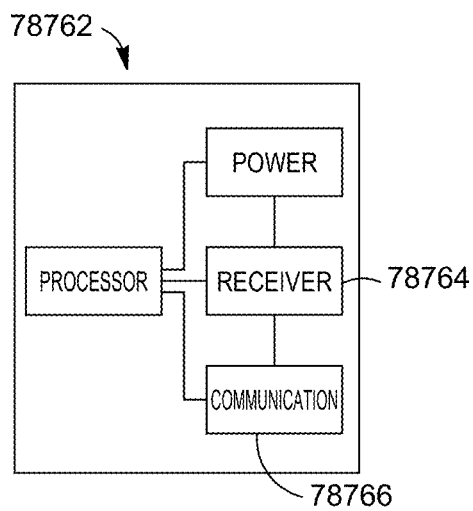
Figure 78L:
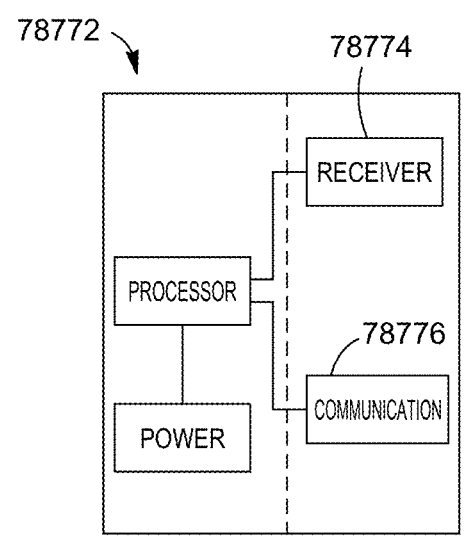
Figure 78K:
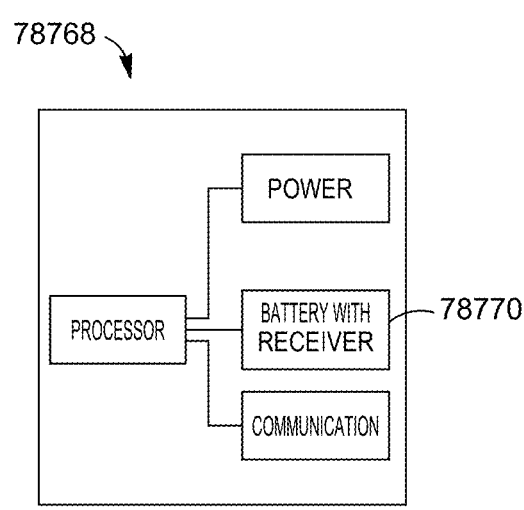
Figure 78N:
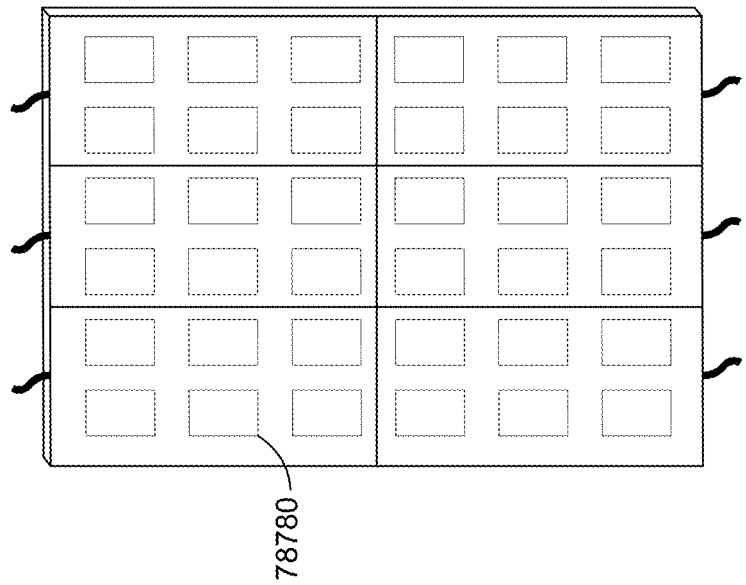

FIGS. 78A and 78N illustrate a diagram of architecture 78700, 78706 for a wireless charging client computing platform, according to an exemplary embodiment. In some implementations, a user may be inside a room and may hold in his hands an electronic device 122 (e.g. a smartphone, tablet). In some implementations, electronic device 122 may be on furniture inside the room. The electronic device 122 may include a receiver 120 either embedded to the electronic device or as a separate adapter connected to electronic device. Receivers 120 may include all the components described in FIG. 1. A transmitter 102 may be hanging on one of the walls of the room right behind user. Transmitters 102 may also include all the components described in FIG. 1.

As user may seem to be obstructing the path between receivers 120 and transmitters 102, RF waves may not be easily aimed to the receivers 120 in a linear direction. However, since the short signals generated from receivers 120 may be omni-directional for the type of antenna element used, these signals may bounce over the walls 78702 until they reach transmitters 102. A hot spot 78702 may be any item in the room which will reflect the RF waves. For example, a large metal clock on the wall may be used to reflect the RF waves to a user's cell phone.

A micro controller in the transmitter 102 adjusts the transmitted signal from each antenna based on the signal received from the receiver. Adjustment may include forming conjugates of the signal phases received from the receivers and further adjustment of transmit antenna phases taking into account the built-in phase of antenna elements. The antenna element may be controlled simultaneously to steer energy in a given direction. The transmitter 102 may scan the room, and look for hot spots 78702. Once calibration is performed, transmitters 102 may focus RF waves in a channel following a path that may be the most efficient paths. Subsequently, RF signals 78704 may form a pocket of energy on a first electronic device and another pocket of energy in a second electronic device while avoiding obstacles such as user and furniture.

When scanning the service area, the room in FIGS. 78A and 78B, the transmitter 102 may employ different methods. As an illustrative example, but without limiting the possible methods that can be used, the transmitter 102 may detect the phases and magnitudes of the signal coming from the receiver and use those to form the set of transmit phases and magnitudes, for example by calculating conjugates of them and applying them at transmit. As another illustrative example, the transmitter may apply all possible phases of transmit antennas in subsequent transmissions, one at a time, and detect the strength of the pocket of energy formed by each combination by observing information related to the signal from the receiver 120. Then the transmitter 102 repeats this calibration periodically. In some implementations, the transmitter 102 does not have to search through all possible phases, and can search through a set of phases that are more likely to result in strong pockets of energy based on prior calibration values. In yet another illustrative example, the transmitter 102 may use preset values of transmit phases for the antennas to form pockets of energy directed to different locations in the room. The transmitter may for example scan the physical space in the room from top to bottom and left to right by using preset phase values for antennas in subsequent transmissions. The transmitter 102 then detects the phase values that result in the strongest pocket of energy around the receiver 120 by observing the signal from the receiver 120. It should be appreciated that there are other possible methods for scanning a service area for heat mapping that may be employed, without deviating from the scope or spirit of the embodiments described herein. The result of a scan, whichever method is used, is a heat-map of the service area (e.g., room, store) from which the transmitter 102 may identify the hot spots that indicate the best phase and magnitude values to use for transmit antennas in order to maximize the pocket of energy around the receiver.

The transmitters 102 may use the Bluetooth connection to determine the location of the receivers 120, and may use different non-overlapping parts of the RF band to channel the RF waves to different receivers 120. In some implementations, the transmitters 102, may conduct a scan of the room to determine the location of the receivers 120 and forms pockets of energy that are orthogonal to each other, by virtue of non-overlapping RF transmission bands. Using multiple pockets of energy to direct energy to receivers may inherently be safer than some alternative power transmission methods since no single transmission is very strong, while the aggregate power transmission signal received at the receiver is strong.

FIG. 78B is an exemplary illustration of adaptive pocket-forming 78706. In this embodiment, a user may be inside a room and may hold on his hands an electronic device which in this case may be a tablet. Tablet may include a receiver 120 either embedded to it or as a separate adapter connected to tablet, Receiver 120 may include all the components described in FIG. 1. A transmitter 102 may be hanging on one of the walls of the room right behind user, as shown in 78B. Transmitter 102 may also include all the components described in FIG. 1. As user may seem to be obstructing the path between receiver 120 and transmitter 102, RF waves 78704 may not be easily aimed to receiver 120 in a linear direction. However, since the short signals generated from receiver 120 may be omni-directional for the type of antenna elements used, these signals may bounce over the walls until they find transmitter 102. Almost instantly, a micro-controller which may reside in transmitter 102, may recalibrate the signals, sent by receiver 120, by adjusting gain and phases and form conjugates taking into account the built-in phases of antenna elements. Once calibration is performed, transmitter 102 may focus RF waves 78704 in two channels following the path described in FIG. 78B, which may be the most efficient path. Subsequently, a pocket of energy may form on tablet while avoiding obstacles such as user. The foregoing property may be beneficial in that wireless power transmission using pocket-forming may inherently be safe as signals may never go through living tissue or other such obstacles.

Flat Transmitter

FIG. 78C depicts a flat transmitter 78710 in a front view and a several embodiments of rear views. Transmitter 78710 may include antenna element 78712 and RFIC 78714 in a flat arrangement. RFIC 78714 may be directly embedded behind each antenna element 78712; such integration may reduce losses due the shorter distance between components.

In one embodiment (i.e., View 1) in transmitter 78710, the phase and the amplitude of the pocket-forming for each antenna element 78712 may be regulated by the corresponding RFIC 78714 in order to generate the desired pocket-forming and transmission null steering. RFIC 78714 singled coupled to each antenna element 78712 may reduce processing requirement and may increase control over pocket-forming, allowing multiple pocket-forming and a higher granular pocket-forming with less load over MC 78716; thus, a higher response of higher number of multiple pocket-forming may be allowed. Furthermore, multiple pocket-forming may charge a higher number of receivers and may allow a better trajectory to such receivers. As described in the embodiment of FIG. 1, RFIC 78714 may be coupled to one or more MCs 78716, and microcontroller 78716 may be included into an independent base station or into the transmitter 78710.

In another embodiment (i.e., View 2), a subset of 4 antenna elements 78712 may be connected to a single RFIC 78714. The lower number of RFICs 78714 present in the transmitter 78710 may correspond to desired features such as: lower control of multiple pocket-forming, lower levels of granularity and a. less expensive embodiment. As described in the embodiment of FIG. 1, RFIC 78714 may be coupled to one or more MCs 78716, and microcontroller 78716 may be included into an independent base station or into the transmitter 78710.

In yet another embodiment (i.e., View 3), transmitter 78710 may include antenna element 78712 and RFIC 78714 in a flat arrangement. A row or column of antenna elements 78712 may be connected to a single MC 78716. The lower number of RFICs 78714 present in the transmitter 78710 may correspond to desired features such as: lower control of multiple pocket-forming, lower levels of granularity and a less expensive embodiment. RFIC 78714 connected to each row or column may allow a less expensive transmitter 78710, which may produce pocket-forming by changing phase and gain between rows or columns. As described in the embodiment of FIG. 1, RFIC 78714 may be coupled to one or more MCs 78716, and microcontroller 78716 may be included into an independent base station or into the transmitter 78710.

In some embodiments, (i.e., View 4), transmitter 78710 may include antenna element 78712 and RFIC 78714 in a flat arrangement. A cascade arrangement is depicted in this exemplary embodiment. Two antenna elements 78712 may be connected to a single RFIC 78714 and this in turn to a single RFIC 78714, which may be connected to a final RFIC 78714 and this in turn to one or more MCs 78716. Flat transmitter 78710 using a cascade arrangement of RFICs 78714 may provide greater control over pocket-forming and may increase response for targeting receivers. Furthermore, a higher reliability and accuracy may be achieved because multiple redundancy of RFICs 78714. As described in the embodiment of FIG. 1, RFIC 78714 may be coupled to one or more MCs 78716, and microcontroller 78716 may be included into an independent base station or into the transmitter 78710.

Multiple Printed Circuit Board Layers

FIG. 78D depicts a transmitter 78718, which may include a plurality of PCB layers 78720 that may include antenna element 78722 for providing greater control over pocket-forming and may increase response for targeting receivers. Multiple PCB layers 78720 may increase the range and the amount of power that could be transferred by transmitter 78718. PCB layers 78720 may he connected to a single MC or to dedicated MC. Similarly, RFIC may be connected antenna element 78722 as depicted in the foregoing embodiments. RFIC may be coupled to one or more MCs. Furthermore, MCs may be included into an independent base station or into the transmitter 78718.

Box Transmitter

FIG. 78E depicts a box transmitter 78724, which may include a plurality of PCB layers 78726 inside it, which may include antenna element 78728 for providing greater control over pocket-forming and may increase response for targeting receivers. Furthermore, range of wireless power transmission may be increased by the box transmitter 78724. Multiple PCB layers 78726 may increase the range and the amount of RF power waves that could be transferred or broadcasted wirelessly by transmitter 78724 due the higher density of antenna element 78728. PCB layers 78726 may be connected to a single MC or to dedicated MC for each antenna element 78728. Similarly, RFIC may control antenna element 78728 as depicted in the foregoing embodiments. Furthermore, box shape of transmitter 800 may increase action ratio of wireless power transmission; thus, box transmitter 78724 may be located on a plurality of surfaces such as, desks, tables, floors, and the like. In addition, box transmitter 78724 may comprise several arrangements of PCB layers 78726, which may be oriented in X, Y, and Z axis, or any combination these. The RFIC may, be coupled to one or more MCs. Furthermore, MCs may be included into an independent base station or into the transmitter 78724.

Multiple Rectifiers Connected in Parallel to an Antenna Element

FIG. 78F illustrates an arrangement 78730 where multiple rectifiers 78734 can be connected in parallel to an antenna element 78732. In this example, four rectifiers 78734 may be connected in parallel to antenna elements 78732. However, several more rectifiers 78734 may be used. Arrangement 78730 may be advantageous because each rectifier 78734 may only need to handle ¼ of the total power. If one watt is to be delivered to an electronic device, then each rectifier 78734 may only need to handle a quarter of a watt. Arrangement 78730 may greatly diminish cost because using a plurality of low-power rectifiers 78734 can be cheaper than utilizing one high-power rectifier 78734 while handling the same amount of power. In some embodiments, the total power handled by rectifier 78734 can be combined into one DC-DC converter 78736. In other embodiments, there may a DC-DC converter 78736 per rectifier 78734.

Multiple Antenna Elements Connected in Parallel to a Rectifier

FIG. 78G illustrates an arrangement 78738 where multiple antenna elements 78740 may be connected in parallel to a rectifier 78742, after which DC voltage may be regulated through a DC-DC converter 78744. In this example, four antenna elements 78740 may be connected in parallel to a single rectifier 78742. Arrangement 78738 may be advantageous because each antenna element 78740 may only handle ¼ of the total power. In addition, arrangement 78738 may enable usage of antenna element 78740 of different polarizations with a single rectifier 78742 because signals may not cancel each other. Because of the foregoing property, arrangement 78738 may be suitable for electronic devices with an orientation that is not well-defined or otherwise varies over time. Lastly, arrangement 78738 may be beneficial when using antenna element 78740 of equal polarization and configured for phases that do not differ greatly. In some embodiments, however, there can be a rectifier 78742 per antenna element 78740 or multiple rectifiers 78742 (as described in FIG. 78F) per antenna element 78740.

Multiple Antenna Elements Connected in Parallel to Multiple Rectifiers

FIG. 78H illustrates an arrangement 78746 where multiple antenna elements 78748 outputs can be combined and connected to parallel rectifier 78750 whose output may further be combined in one DC converter 78752. Arrangement 78746 shows, by way of exemplification, 16 antenna elements 78748 whose output may be combined at four parallel rectifiers 78750. In other embodiments, antenna elements 78748 may be subdivided in groups (e.g., four groups) and may connect to independent rectifiers as shown in FIG. 78I below.

Permutations of Groupings

FIG. 78I illustrates an arrangement 78754 where groups of antenna elements 78756 may be connected to different rectifiers 78758, which may in turn also be connected to different DC converters 78760. In arrangement 78754, four groups of antenna elements 78756 (each containing four antenna elements 78756 in parallel) may each connect independently to four rectifiers 78758. In this embodiment, the output of each rectifier 78758 may connect directly to a DC converter 78760 (four in total). In other embodiments, the output of all four rectifiers 78758 can be combined, before each DC converter 78760, to handle the total power in parallel. In other embodiments, the combined outputs of each rectifier 78758 may connect to a single DC converter 78760. Arrangement 78754 may be beneficial in that it allows great proximity between rectifier 78758 and antenna element 78756. This property may be desirable as it may keep losses at a minimum.

A receiver may be implemented on, connected to or embedded in electronic devices or equipment that may rely on power for performing its intended functions, for example a phone, laptop computer, a television remote, a children's toys or any other such devices. A receiver utilizing pocket-forming can be used to fully charge a device's battery while being "On" or "Off," or while being used or not. In addition, battery lifetime can be greatly enhanced. For example, a device operating on two watts utilizing a receiver that may deliver one watt may increase its battery duration up to about 50%. Lastly, some devices currently running on batteries can fully be powered using a receiver after which a battery may no longer be required. This last property may be beneficial for devices where replacing batteries can be tedious or hard to accomplish such as in wall-clocks. Embodiments below provide some examples of how integration of receivers may be carried out on electronic devices.

Embedded Receiver

FIG. 78J illustrates an implementation scheme where a device 78762 that may represent a typical phone, computer or other electronic device may include an embedded receiver 78764. Device 78762 may also include a power source, a communications component 78766, and a processor. Receiver 78764 way utilize pocket-forming for providing power to power source from device 78762. In addition, receiver 78764 can use built-in communications component 78766 of device 78762 (for example, Bluetooth) for communicating to a given transmitter based on requirements provided by processor such as battery level, user predefined charging profile or others.

Battery with an Embedded Receiver

FIG. 78K illustrates another implementation scheme where a device 78768 may include a battery with an embedded receiver 78770. Battery may receive power wirelessly through pocket-forming and may charge through its embedded receiver 78770. Battery may function as a supply for power source, or may function as back-up supply. This configuration may be advantageous in that battery may not need to be removed for charging. This may particularly be helpful in gaming controllers, or gaming devices where batteries, typically AA or AAA may be continuously replaced.

External Communication Component

FIG. 78L illustrates an alternate implementation scheme 78772 where receiver 78774 and a communications component 78776 may be included in an external hardware that may be attached to a device. Hardware can take appropriate forms such as cases that may be placed on phones, computers, remote controllers and others, which may connect thorough suitable interfaces such as Universal Serial Bus (USB). In other embodiments, hardware may be printed on flexible films, which may then be pasted or otherwise attached to electronic equipment. This option may be advantageous as it may be produced at low cost and can easily be integrated into various devices. As in previous embodiments, a communications component 78776 may be included in hardware that may provide communication to a transmitter or to electronic equipment in general.

Casing or Housing of Receiver Connecting to USB

Figure 78M:
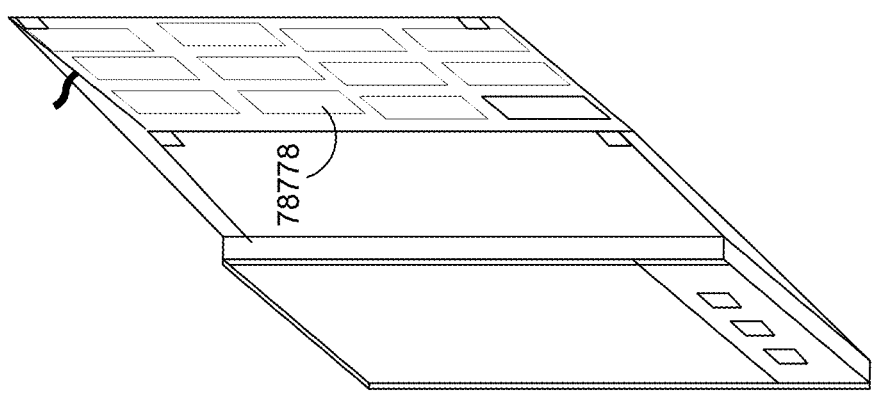

FIG. 78M illustrates hardware in the form of case including a receiver 78778 that may connect through flex cables or USB to a smartphone and/or any other electronic device. In other embodiments, the housing or case can be a computer case, phone case, and/or camera case among other such options.

PCB on Printed Film

FIG. 78N illustrates hardware in the form of a printed film or flexible printed circuit board (PCB) which may include a plurality of printed receivers 78780. Printed film can be pasted or otherwise attached to electronic devices and can connect trough suitable interfaces such as USB. Printed film may be advantageous in that sections can be cut from it to meet specific electronic device sizes and/or requirements. The efficiency of wireless power transmission as well as the amount of power that can be delivered (using pocket-forming) may be a function of the total number of antenna elements used in a given receiver and transmitter system. For example, for delivering about one watt at about 15 feet, a receiver may include about 80 antenna elements while a transmitter may include about 256 antenna elements. Another identical wireless power transmission system (about 1 watt, at about 15 feet) may include a receiver with about 40 antenna elements, and a transmitter with about 512 antenna elements. Reducing in half the number of antenna elements in a receiver may require doubling the number of antenna elements in a transmitter. In some cases, it may be cost-effective to put a greater number of antenna elements in a transmitter than in a receiver. However, the opposite can be achieved (placing more antenna elements on a receiver than on a transmitter), as long as there are at least two antenna elements in a transmitter.

FIGS. 78A-78N illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 78A-78N.

Presented below are example embodiments of a methodology for pocket-forming.

In some embodiments, an example method for transmitting wireless power, comprises generating two or more RF power waves from a transmitter having at least two RF transmit antennas for transmitting two separate RF power waves, forming controlled constructive interference patterns between the generated RF power waves to form pockets of energy, converging the pockets of energy in 3-D space to a targeted electronic device, and receiving the converged pockets of energy in a receiver having at least one antenna for charging or powering a targeted electronic device from the received pockets of energy.

In some embodiments, the forming controlled constructive interference patterns between the generated RF waves further comprises destructive interference patterns between the generated RF waves generating a null-space where pocket of energy do not form.

In some embodiments, converging the pockets of energy further comprises adjusting dynamically the pockets of energy to regulate the power to the targeted electronic device.

In some embodiments, generating two or more RF power waves comprises generating two or more RF power waves from at least one RF integrated circuit with at least one RF power wave being phase shifted and gain adjusted with respect to the other RF power waves.

In some embodiments, generating two or more RF power waves comprises operating antenna elements with polarization in frequency bands conforming to FCC regulations such as 900 MHz or 2.5 GHz or 5.8 GHz for transmitting the RF power waves.

In some embodiments, receiving the pockets of energy in the receiver with at least one antenna further comprises communicating between the receiver and transmitter operating on standard wireless communication protocol signals such as Bluetooth, Wi-Fi or ZigBee to transfer status information of the targeted electronic device regarding battery level and target location for directing desired pockets of energy to the targeted electronic device.

In some embodiments, the method for transmitting wireless power further comprises embedding the receiver in the targeted electronic device.

In some embodiments, the method for transmitting wireless power further comprises attaching electrically the receiver to the targeted electronic device.

In some embodiments, converging the pockets of energy in 3-D space to a targeted electronic device further comprises recalibrating the pockets of energy by adjusting gain and phases to focus RF power waves in two channels to follow a path that forms pockets of energy on the targeted electronic device without obstacles in the path.

In some embodiments, converging the pockets of energy in 3-D space to a targeted electronic device comprises energy pocket-forming with generally a wireless power transmission level directed by communication signals to avoid humans or other obstacles.

In some embodiments, wireless power transmission comprises a transmitter for generating two or more RF power waves having at least two transmit antennas, a controller for forming constructive and destructive interference patterns from the generated RF power waves, RF circuitry in the transmitter for generating energy in the form of constructive interference patterns between the RF power waves to form pockets of energy, a targeted electronic device for converging the pockets of energy in 3-D space, and a receiver with the RF circuitry and at least one antenna for receiving the pockets of energy for powering or charging the targeted electronic device.

In some embodiments, the method for wireless power transmission comprises generating a communication RF signal from a receiver with identifier information of a chargeable electronic device connected thereto, broadcasting the identifier RF signal through an antenna of the receiver, intercepting the identifier RF signal by an antenna of a power transmitter with a controller, decoding the identifier RF signal by the controller to ascertain the gain and phase of the identifier RF signal sent by the power receiver including the direction or spatial location of the power receiver, establishing a power channel or path between the transmitter and receiver from the identifier RF signal information, transmitting controlled RF power waves from the transmitter to the receiver along the established channel or path; controlling the phase and amplitude of the RF power waves by the controller to form constructive and destructive interference patterns generating pockets of energy in a 3-dimensional shape from the constructive patterns and generating null-spaces from the destructive patterns to aim the pockets of energy to the receiver in order to charge or power the electronic device, converging the channels of 3-dimensional pockets of energy at the power receiver antenna for power input to the receiver, and converting the received pockets of energy into DC voltages for charging or powering the electronic device.

Figure 79A:
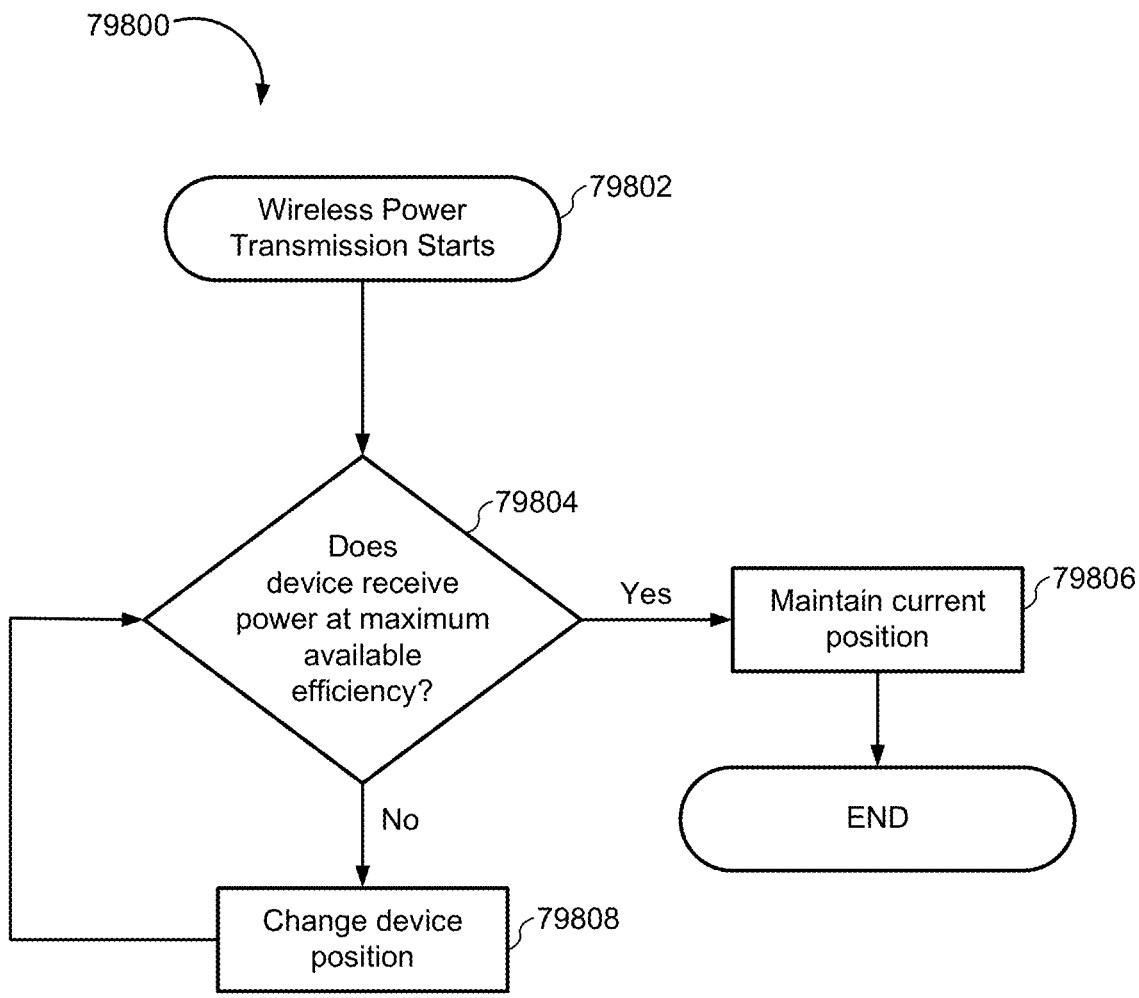
Figure 79B:
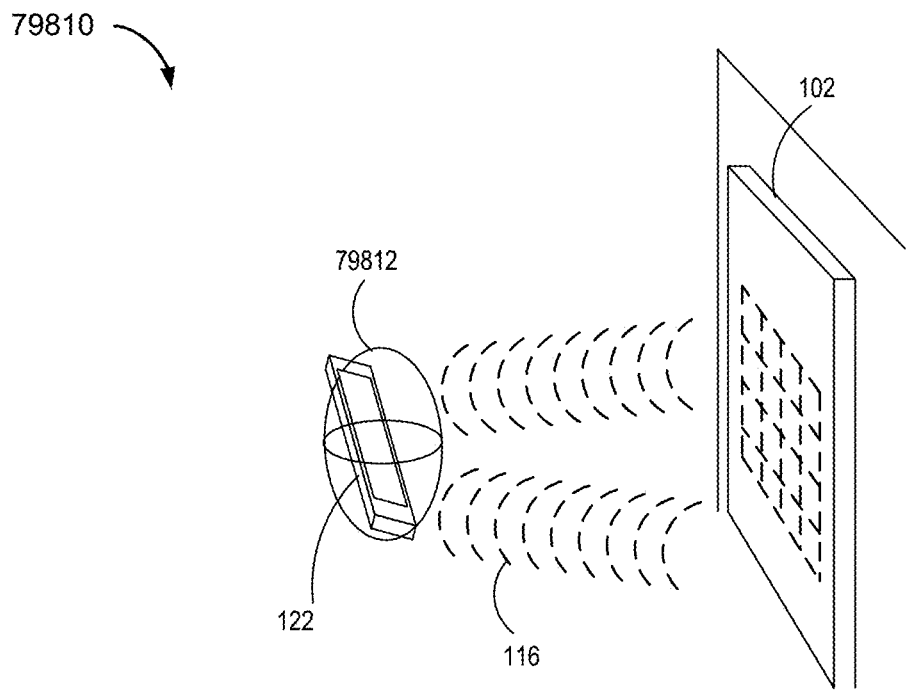
Figure 79C:
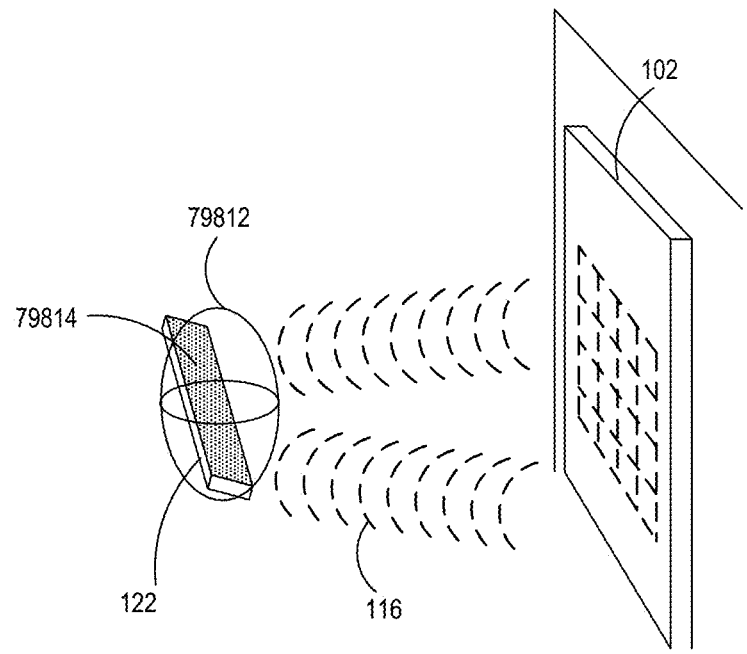

FIGS. 79A-79C illustrate examples of tracking surface for determining optimal charging position, in accordance with some embodiments.

FIG. 79A illustrates tracking and positioning flowchart 79800, which may be employed by an algorithm in a controller, CPU, processor, computer among others, for determining the optimal position and orientation of an electronic device which may receive power and/or charge through wireless power transmission.

In order to achieve the optimal efficiency, electronic device may use a variety of sensors for determining the voltage level in battery and/or the power level received when wireless power transmission starts 79802. Such sensors may indicate whether the device is receiving power at the maximum available efficiency 79804. Maximum available efficiency may depend on distance from transmitter, obstacles, temperature, among others. If the device is receiving power at maximum available efficiency, then an application, software or program installed on the electronic device and/or in the receiver 120 may aware and/or notify user to maintain current position 79806. Moreover, if the device is receiving power at a lower efficiency than the maximum available efficiency, then software or program may use a variety of sensors for tracking and determining the optimal position of electronic device in relation with transmitter 102 position and orientation. Sensors may include accelerometers, infrared, GPS, among others. Furthermore, a communication reciprocity may be used by the communication module for tracking and positioning. Communication module may include and combine Bluetooth technology, infrared communication, WI-FI, FM radio among others. By comparing voltage level and/or power received in each position and/or orientation of electronic device, the software and/or program may notify and/or guide user to change device position 79808 for looking the optimal position and/or orientation.

FIGS. 79B and 79C illustrates wireless power transmission 79810, where a transmitter 102 may produce pocket-forming over plurality of cellphones 122. As depicted in FIG. 79B, wireless power transmission 79810 may charge and/or power cellphone 122 at a low efficiency because antennas 79814 on the receiver 120 may be faced to the same direction of the RF waves 116, thus pocket of energy 79812 may provide less charge and/or power to antennas 79814. As shown in FIG. 79C. By turning cellphone 122 180° degrees, antennas 79814 may receive power at a higher efficiency, such efficiency may be achieved due the antennas 79814 orientation, which may be faced in the opposite direction of RF waves 116.

FIGS. 79A-79C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 79A-79C.

Presented below are example embodiments of tracking surface for determining optimal charging position.

In some embodiments, an example method for transmitting wireless power comprises generating two or more RF waves from a transmitter with at least two RF transmit antenna, forming controlled constructive and destructive interference patterns from the generated RF waves, accumulating energy or power in the form of constructive interference patterns from the RF waves to form pockets of energy, converging the pockets of energy in 3-d space to a targeted electronic device; sensing the converging pockets of energy for determining the power level and efficiency received by the targeted electronic device; and maintaining or changing the electronic device position for maximizing the efficiency of receiving the converged pockets of energy in a receiver connected to the electronic device with at least one antenna for powering the targeted electronic device from the pockets of energy.

In some embodiments, the sensing accomplished through accelerometers, infrared or GPS sensor circuits for tracking and positioning the electronic device.

In some embodiments, the method further comprises communicating circuitry in the transmitter and receiver for comparing the voltage level and power received to guide user for changing the device position to optimize position or orientation of the device for reception of the pockets of energy.

In some embodiments, communicating circuitry such as Bluetooth, infrared, Wi-Fi or FM radio signals is used for communication between the transmitter and the receiver.

In some embodiments, the method further comprises computing instructions for processing the sensed signals representing the power level and efficiency of the wireless transmitted power from. the received pockets of energy In some embodiments, a system for transmitting wireless power comprises a transmitter generating pockets of energy a receiver electrically connected to at least one electronic device for receiving the pockets of energy, a communication network on the transmitter and receiver controlled by a processor for determining a battery and power level of the electronic device and for tracking and positioning the electronic device to the optimal position or orientation for maximizing pockets of energy reception.

In some embodiments, the system for transmitting wireless power uses the transmitter to generate two or more RF waves from at least two RF transmit antennae to create constructive interference patterns from the RF waves to form. the pockets of energy.

In some embodiments, the system for transmitting wireless power has a receiver or electronic device includes sensors generating signals representing the battery level, power level, position and orientation of the device for feeding a processor including a set of instructions to maximize the efficiency for charging at least one electronic device from the sensor signals.

In some embodiments, the system for transmitting wireless power generates pockets of energy that are received by a plurality of electronic devices at a higher efficiency due to antennas orientation directed by the processor in response to the sensor signals.

In some embodiments, the system for transmitting wireless power determines the optimal position and orientation of the electronic device to receive the pockets of energy for charging the device.

In some embodiments, a system for transmitting wireless power, comprises a transmitter for generating two or more RF waves having at least two RF transmit antenna to form controlled constructive and destructive interference patterns from the generated RF waves, a processor within the transmitter controlling the constructive interference patterns from the generated RF waves to form pockets of energy; a receiver with at least one antenna for accumulating the pockets of energy converging in 3-d space to a targeted electronic device; a communication network connected to transmitter and receiver for utilizing the respective antennas for broadcasting signals from one or more sensors located on the transmitter, receiver or the electronic device for determining the power level and efficiency of the charging power received by the targeted electronic device; and where efficiency of the converged pockets of energy processed by the receiver connected to the electronic device are directly related to the sensor signals for determining the optimal position and orientation of the electronic device being charged.

In some embodiments, the system for transmitting wireless processes the sensor signals to determine the tracking and positioning of the electronic device.

In some embodiments, the system for transmitting wireless power senses information concerning a plurality of electronic devices ready to be charged.

In some embodiments, the system for transmitting wireless power produces pocket-forming over a plurality of electronic devices.

In some embodiments, the system for transmitting wireless power dynamically adjusts the pocket-forming to regulate power on one or more targeted electronic devices.

In some embodiments, the system for transmitting wireless power creates the pocket-forming pockets of energy to converge in 3-D space in a direction related to the sensor signals representing the tracking and orientation of the electronic device.

Figure 80A:
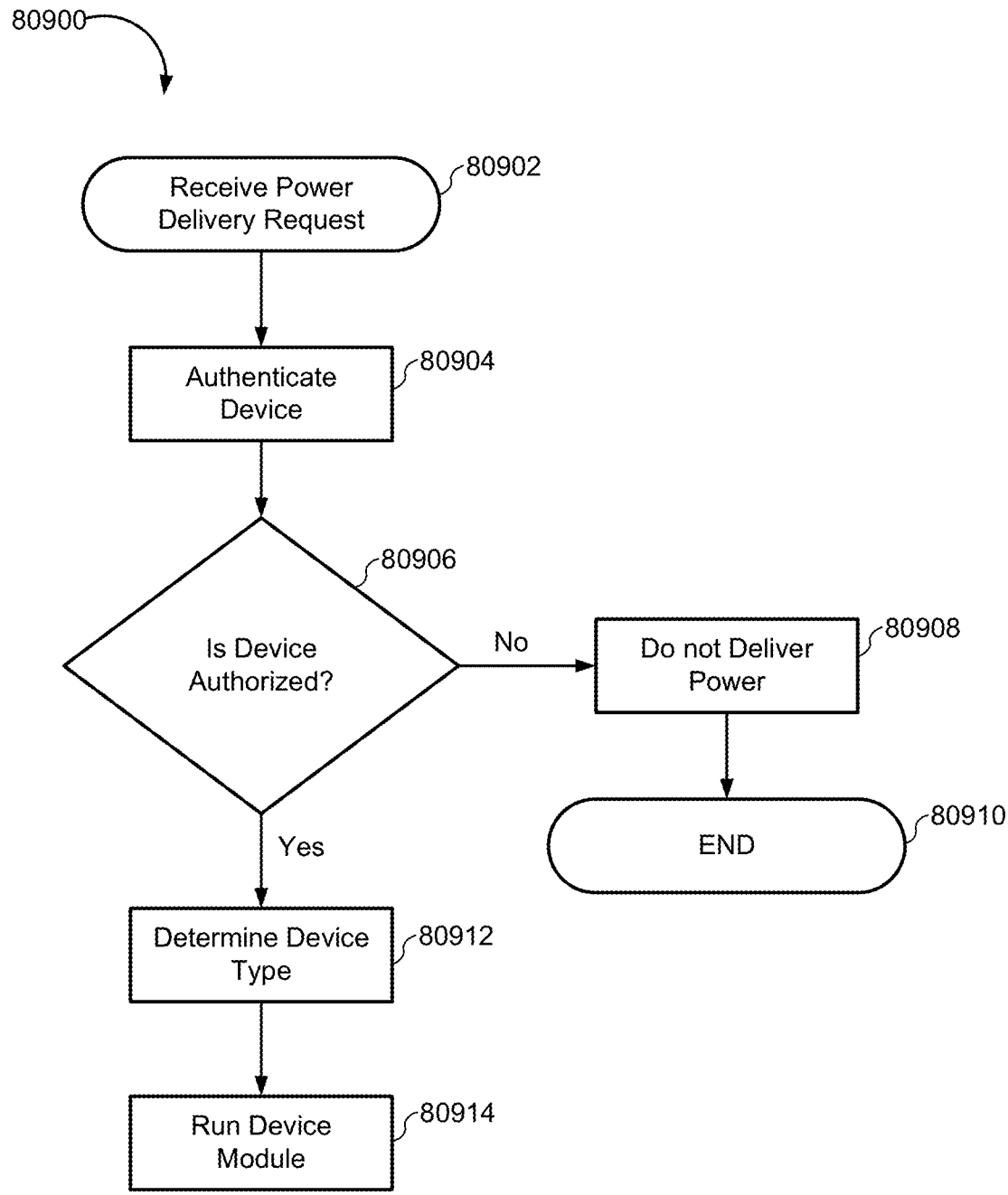
Figure 80B:
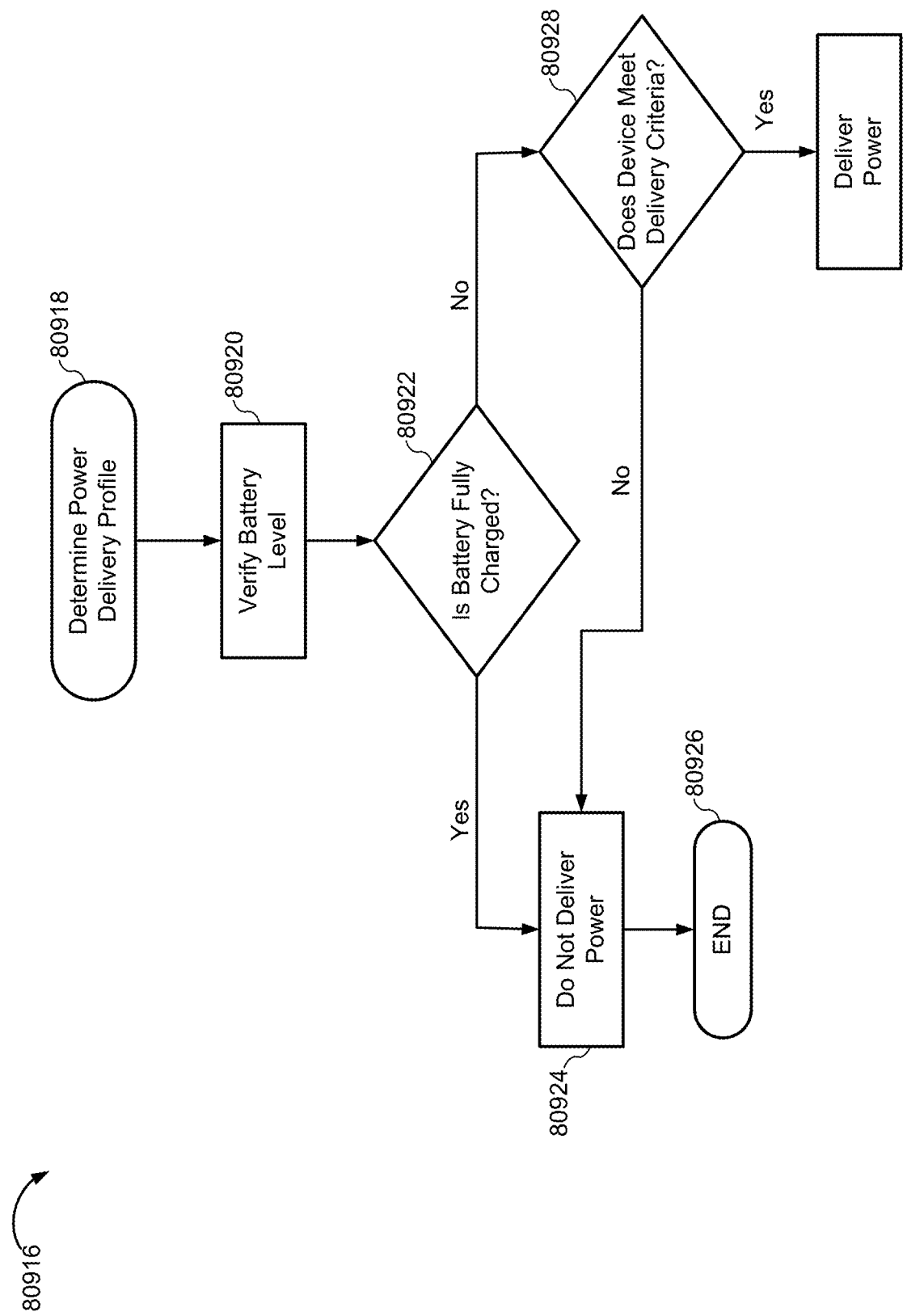

FIGS. 80A-80B illustrate examples of protocols for wireless power transmission, in accordance with some embodiments.

FIG. 80A illustrates an example routine 80900 that may be utilized by a micro-controller from the transmitter to control wireless power transmission. Routine 80900 may begin when transmitter receives a power delivery request 80902 from receiver 120. At Power delivery request 80902, receiver 120 may send a signature signal which may be coded using suitable techniques such as delay encoding, orthogonal frequency-division multiplexing (OFDM), code division multiplexing (CDM) or other suitable binary coding for identifying a given electronic device including receiver 120. At this stage, the micro-controller may proceed to authenticate 80904 where it may evaluate the signature signal sent by receiver 120. Based on authenticate 80904, the micro-controller may proceed to a decision 80906. If receiver 120 is not authorized to receiver power, the micro-controller may decide, at decision 80906, to don't deliver power 80908, and thus end routine 80900 at end 80910. On the other hand, if receiver 120 is authorized to receive power, the micro-controller may proceed to determine device type 80912. At this step, the micro-controller may obtain information from receiver 120 such as type of device, manufacturer, serial number, total. power required, battery level among other such information. Afterwards, the micro-controller may proceed to run device module 80914, where it may run a routine suited to the authenticated device. In addition, if multiple receivers 120 are requiring power, the micro-controller may deliver power equally to all receivers 120 or may utilize a priority status for each receiver 120. Such a priority status may be user defined. In some embodiments, the user may choose to deliver more power to its smartphone, than to its gaming device. In other cases, the user may decide to first power its smartphone and then its gaming device.

FIG. 80B illustrates an example of a routine 80916 that may be utilized by the transmitter micro-controller at device module 80914. Routine 80916 may start at determine power delivery profile 80918 Where it may decide to either run on a default power profile or a user custom profile. In the case of the former, the micro-controller may proceed to verify battery level 80920 where it may determine power needs of the electronic device including receiver 120. Afterwards, the micro-controller may proceed to a decision 80922. If the battery of the electronic device including receiver 120 is fully charged, at decision 80922, the micro-controller may proceed to don't deliver power 80924, and thus end routine 80916 at end 80926. On the other hand, if the battery of the electronic device including receiver 120 is not fully charged, the micro-controller may proceed to verify if such electronic device meets specific powering criteria at decision 80928. The foregoing powering criteria may depend on the electronic device requiring power. For example, smartphones may only receive power if are not being used, or maybe during usage but only if the user is not talking through it, or maybe during usage as long as Wi-Fi is not compromised among other such criteria. In the case of a user custom profile, the user may specify the minimum battery level its equipment can have before delivering power, or the user may specify the criteria for powering his or her device among other such options.

FIGS. 80A-80B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 80A-80B.

Presented below are example embodiments of protocols for wireless power transmission.

In some embodiments, an example method of control protocols for a wireless power transmission system comprises generating two or more RF waves from a transmitter having a micro-controller for digital signal processing in response to receiving a signature signal from a receiver requesting a power delivery, forming controlled constructive patterns from the generated RF waves controlled by the micro-controller, accumulating energy or power in the form of constructive interference patterns from the RF waves to form pockets of energy; converging the pockets of energy in 3-d space to a targeted electronic device connected to the receiver sending the signature signal, evaluating the signature signal sent by the receiver to authenticate the identification of the targeted electronic device for reception of the pockets of energy to charge the electronic device, and determining the power delivery profile of the targeted and authenticated electronic device to meet the request for power delivery by the receiver for charging or operating the electronic device.

In some embodiments, the transmitter forms controlled destructive patterns from the RF waves controlled by the micro-controller and accumulating energy or power in the form of destructive interference patterns from the RF waves to form null-space without pockets of energy. The signature signal further includes the method of delay encoding, orthogonal frequency-division multiplexing, code division multiplexing or other suitable binary coding for identifying the electronic device by the micro-controller.

In some embodiments, the method further comprises communicating circuitry in the transmitter and receiver for sending coded signature signals for authentication and power profile of the targeted electronic device.

In some embodiments, the communicating circuitry uses Bluetooth, infrared, Wi-Fi or FM radio signals for communication between the transmitter and the receiver.

In some embodiments, the method further comprises micro-controller computing instructions for processing the signature, signals from the requesting receiver representing the type of electronic device, manufacturer, serial number, total power required, battery level and other power profile requirements of each specific electronic device to adjust the received pockets of energy for each electronic device.

In some embodiments, a control protocol for a wireless power transmission system, comprises a transmitter for generating pockets of energy, a receiver electrically connected to at least one electronic device for receiving the pockets of energy, a micro-controller for receiving coded signature signals from the receiver and connected to a communication network between the transmitter and receiver for controlling an authentication and a power profile of each electronic device receiving the pockets of energy.

In some embodiments, the transmitter generates two or more RF waves from at least two RF transmit antennae to create constructive interference patterns from the RF waves to form the pockets of energy.

In some embodiments, the receiver generates the coded signature signals requesting power delivery from the transmitter to the receiver of the electronic device.

In some embodiments, the generated pockets of energy are received by a plurality of authenticated electronic devices according to the power profile of each electronic device.

In some embodiments, the micro-controller includes predetermined protocols for determining the proper authentication of the electronic device to receive the pockets of energy for charging or operating the electronic device.

In some embodiments, a system for wireless power transmission, comprises a transmitter for generating two or more RF waves to form controlled constructive interference patterns from the generated RF waves, a micro-controller within the transmitter controlling a predetermined configuration of the constructive interference patterns of BY waves to form pockets of energy, a receiver connected to at least one electronic device for accumulating the pockets of energy converging in 3-d space to the electronic device, communication protocols connected between the transmitter and receiver for processing a coded signature signal by the micro-controller to authenticate and to determine power level requirements of the electronic device.

In some embodiments, the coded signature signals include delay encoding, orthogonal frequency-division multiplexing, code division multiplexing or other suitable binary coding for identifying the electronic device by the micro-controller.

In some embodiments, the receiver provides the signature signals with information concerning the type of electronic device, the manufacturer of the device, the serial number of the device, power requirements of the device and battery level of the device for processing by the micro-controller.

In some embodiments, the transmitter produces pocket-forming over a plurality of electronic devices.

In some embodiments, the micro-controller stores power data, times requesting power, length of time for charging, amount of power delivered, priority status or other useful statistics for each charged or operated electronic device which electronic device data is capable of being wirelessly uploading to a base station. or Internet location for future reference or manipulation.

In some embodiments, the micro-controller dynamically adjusts the pocket-forming to regulate the delivery of power to one or more targeted electronic devices to monetize the amount of power received by a customer of the system.

Figure 81A:
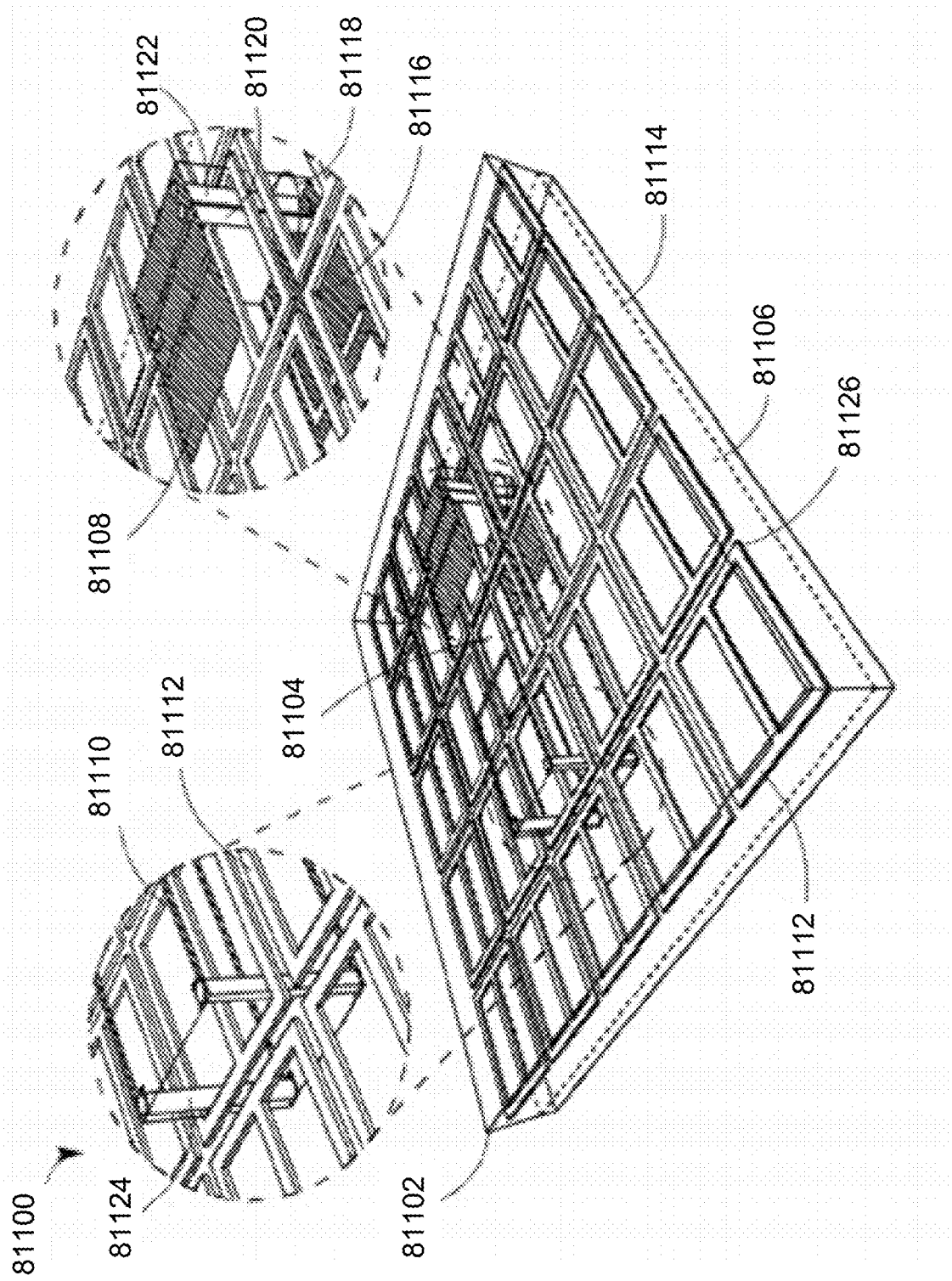

FIGS. 81A-81N illustrate examples of integrated antenna arrays for wireless power transmission, in accordance with some embodiments.

FIG. 81A illustrates an isometric view of an exemplary first integrated antenna structures 81100 that may include the integration of a PIFA 81104 with an AMC metamaterial 81102 layer for achieving a directional radiation pattern while maintaining a small form factor, according to an embodiment. Specifically, AMC metamaterial 81102 may exhibit a configuration of 5×5 arrays of AMC unit cells 81126, where these AMC unit cells 81126 may include an AMC metal layer 81112 and a backing metal layer 81114, and may exhibit a square e ring shape. Additionally, first integrated antenna structures 81100 may include a monolithic four layer PCB 81106 that may be used as a substrate to suitably integrate AMC metamaterial 81102 with PIFA 81104. For example, antenna element 81108 and folded ground 81110 of PIFA 81104 may be formed on the top layer of PCB 81106; AMC metal layer 81112 of AMC metamaterial 81102 may be formed in one of the inner layers of PCB 81106, and may exhibit a square A ring shape; backing metal layer 81114 of AMC metamaterial 81102 may be formed on the other available inner layer of PCB 81106; and ground element 81116 of PIFA 81104 may be formed on the bottom layer of PCB 81106.

According to some aspects of this embodiment, folded ground 81110 may allow to reduce the dimensions of PIFA 81104. PIFA 81104 dimensions in the x-axis, y-axis, and z-axis may be about 10 mm, 3.0 mm, and 2.4 mm respectively, for a system area of about 30 mm$^2$ and a system volume of about 72 mm$^3$.

A hole 81118 may be formed in backing metal layer 81114 for allowing signal via 81120 and ground via 81122 to pass through backing metal layer 81114 without electrically shortening it. As a result, ground element 81116 of PIFA 81104 shorted with backing metal layer 81114 may become the primary ground of the first integrated antenna structures 81100. At the opposite ends of this primary ground, folded ground vias 81124 may short-circuit backing metal layer 81114 at a crossing point. In another embodiment where PIFA 81104 has no folded ground 81110, folded ground vias 81124 may be also formed to electrically short backing metal layer 81114 and ground element 81116.

FIGS. 81B and 81C illustrate top and side views of first integrated antenna structures 81100. In some embodiments, as illustrated in FIG. 81B, PIFA 81104 may occupy about three AMC unit cells 81126 of the AMC metamaterial 81102 formed on PCB 81106. In some embodiments, as illustrated in FIG. 81B, first integrated antenna structures 81100 may include dimensions of about 18 mm and 18 mm for m and n respectively, for a system area of about 324 mm$^2$.

FIG. 81C shows a side view of first integrated antenna structures 81100 where it may be noticed how the AMC metamaterial 81102 is integrated with PIFA 81104. As shown in FIG. 81C, antenna element 81108 and folded ground 81110 may be formed on top side of PCB 81106, while ground element 81116 may be formed on the bottom side of PCB 81106. Backing metal layer 81114 and AMC metal layer 81112 may be formed in the inner layers of PCB 81106, between antenna element 81108 and ground element 81116. Folded ground vias 81124, signal via 81120, and ground via 81122 are also illustrated in FIG. 81C according to embodiments described herein. Thickness h of first integrated antenna structures 81100 may be about 2.4 mm.

Overall dimensions for first integrated antenna structures 81100 may vary according to the dimensions used for the AMC metamaterial 81102 and PIFA 81104, as well as the desired application.

Figure 81D:
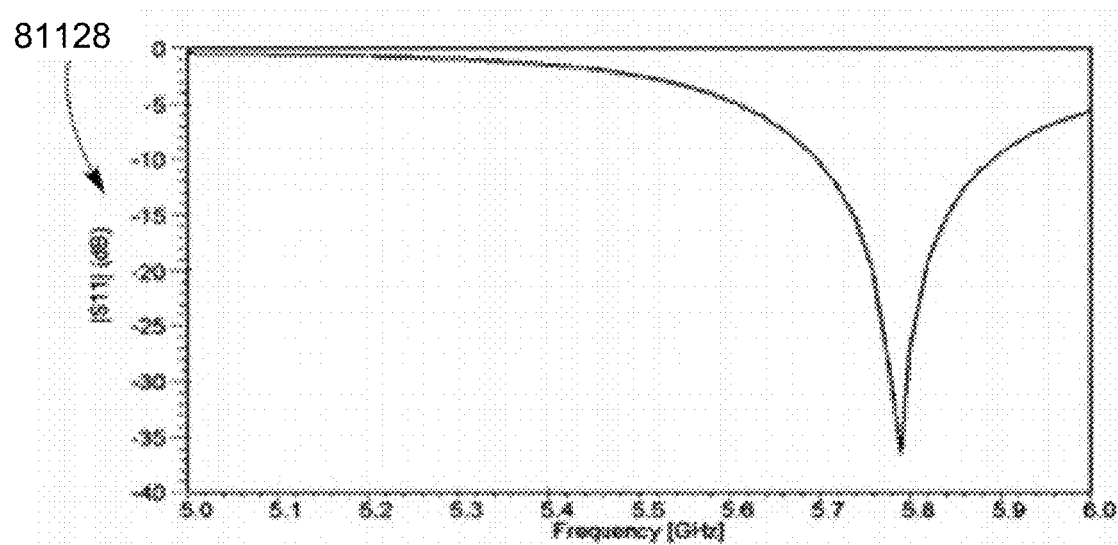
Figure 81E:
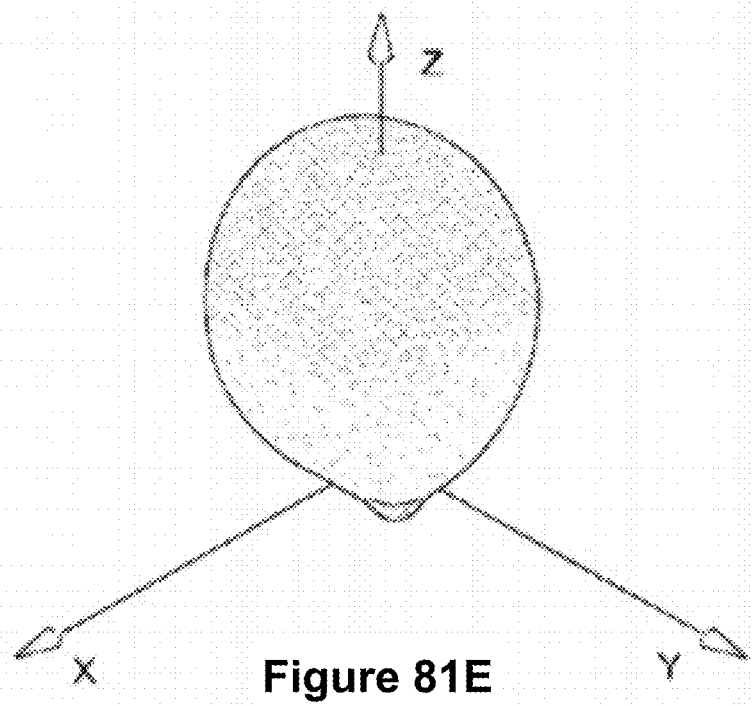

FIGS. 81D and 81E illustrate the return loss and radiation pattern 81128 of exemplary first integrated antenna structures 81100 when fed by a 50-Ohm port. As shown in FIG. 81D, first integrated antenna structures 81100 may exhibit an impedance bandwidth of about 160 MHz at −10 dB, where this bandwidth may provide sufficient margins for possible detuning upon integration of the exemplary first integrated antenna structures 81100 into an electronic device or a larger PCB. Radiation efficiency of first integrated antenna structures 81100 may be of about 72% at 5.8 GHz.

FIG. 81E illustrates the radiation pattern of first integrated antenna structures 81100, where the maximum gain may be of about 2.2 dBi at 5.8 GHz. First integrated antenna structures 81100 may exhibit a directional radiation pattern, more specifically, a directional broadside pattern that may be about twice of that of the omnidirectional radiation pattern exhibited by PIFA 81104 alone or without the AMC metamaterial 81102. In this way, by integrating the AMC metamaterial 81102 with PIFA 81104 in the first integrated antenna structures 81100, the omnidirectional pattern of PIFA 81104 may be changed to a directional pattern as exhibited in FIG. 81E, where the AMC metamaterial 81102 may operate as an artificial magnetic reflector, sending all the energy upwards. Still, the overall dimensions of first integrated antenna structures 81100 may be about 0.345×0.345×0.05 $\lambda^3$ which may significantly smaller compared to conventional directional antennas such as patch antennas, half-wave conductor-backed dipole. For example, a half-wave center-fed linear dipole with a quarter-wave backing metal reflector may need a system size of at least 0.5×0.5×0.25$\lambda^3$ to achieve a similar performance of first integrated antenna structures 81100.

Figure 81F:
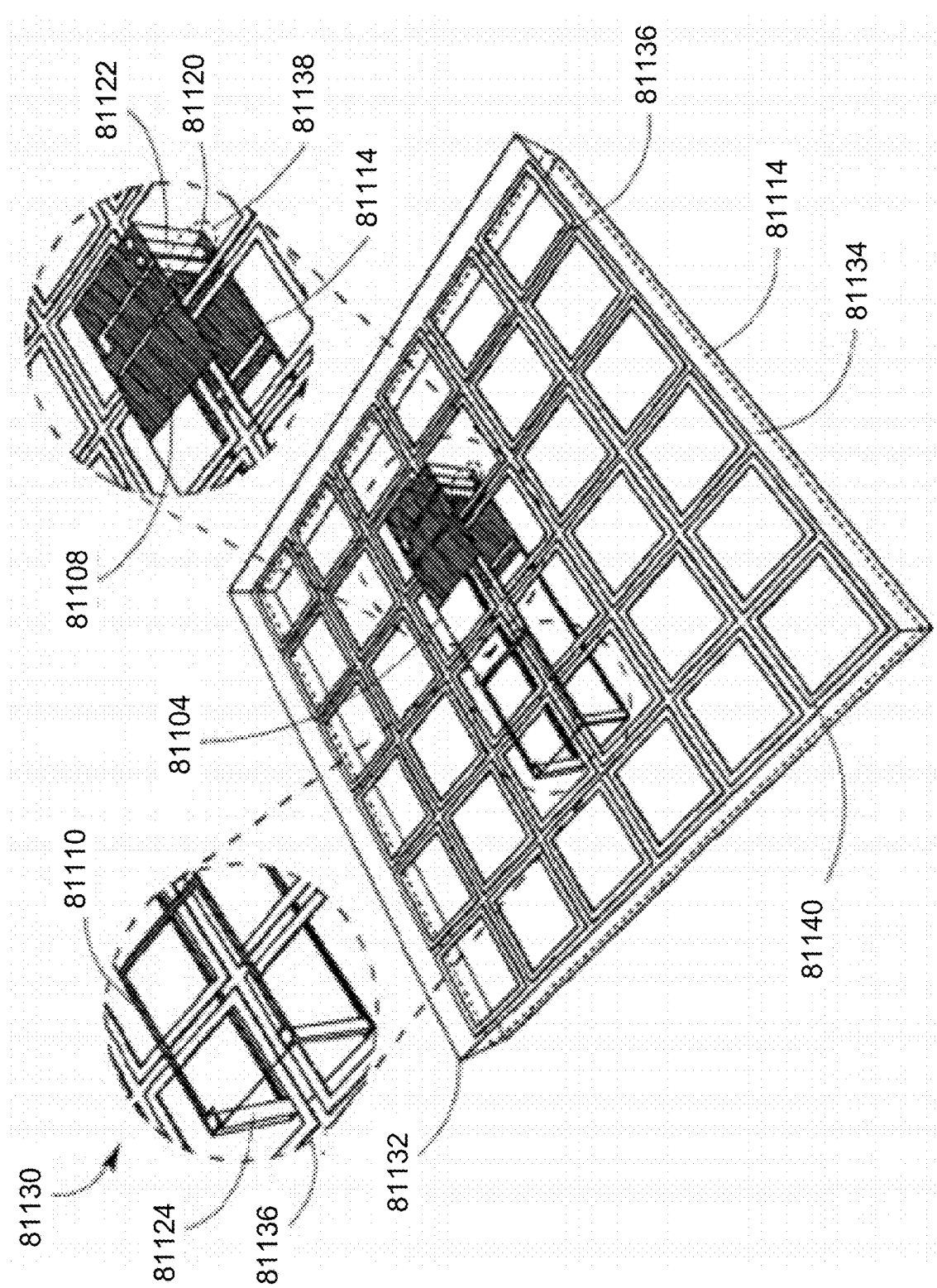

FIG. 81F illustrates an isometric view of an exemplary second integrated antenna structures 81130 that may include the integration of PIFA 81104 with an AMC metamaterial 81132 layer for achieving a directional radiation pattern while maintaining a small form factor, according to an embodiment. More specifically, AMC metamaterial 81132 may exhibit a configuration of 6×6 arrays of AMC unit cells 81140, where these AMC unit cells 81140 may include an AMC metal layer 81136 and backing metal layer 81114, and may exhibit a square ring shape. Additionally, second integrated antenna structures 81130 may include a monolithic four layer PCB 81134 that may be used as a substrate to suitably integrate AMC metamaterial 81132 with PIFA

81104. For example, antenna element 81108 and folded ground 81110 of PIFA 81104 may be formed on the top layer of PCB 81134; AMC metal layer 81136 of AMC metamaterial 81132 may be formed in one of the inner layers of PCB 81134 and may exhibit a square shape; backing metal layer 81114 of AMC metamaterial 81132 may be formed on the other available inner layer of PCB 81134; and ground element 81116 of PIFA 81104 may be formed on the bottom layer of PCB 81134.

A hole 81138 may be formed in backing metal layer 81114 for allowing signal via 81120 and ground via 81122 to pass through backing metal layer 81114 without electrically shortening it. As a result, ground element 81116 of PIFA 81104 shorted with backing metal layer 81114 may become the primary ground of the second integrated antenna structures 81130. At the opposite ends of this primary ground, folded ground vias 81124 may short-circuit backing metal layer 81114 at a crossing point. In another embodiment where PIFA 81104 has no folded ground 81110, folded ground vias 81124 may be configured to electrically short backing metal layer 81114 and ground element 81116.

Figure 81G:
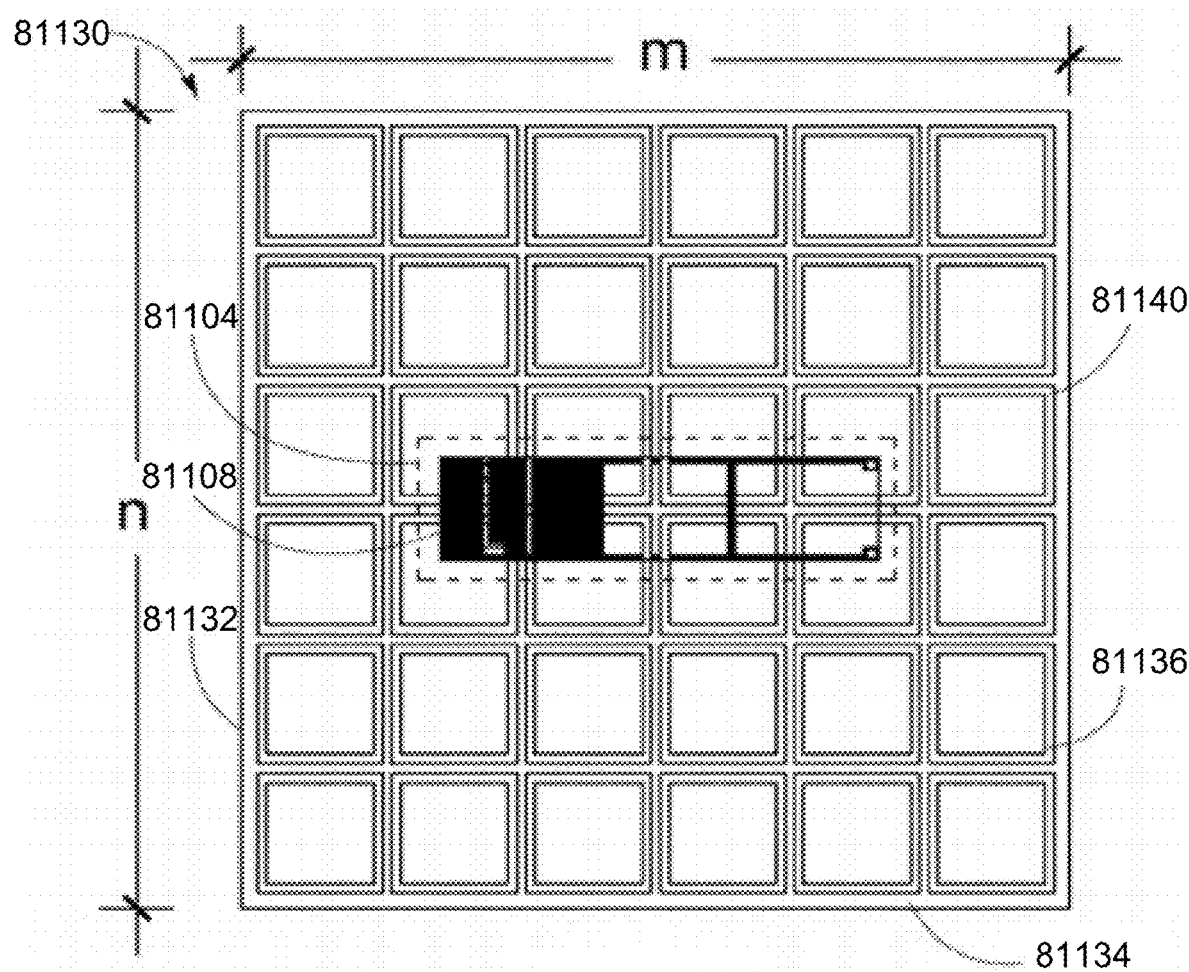
Figure 81H:
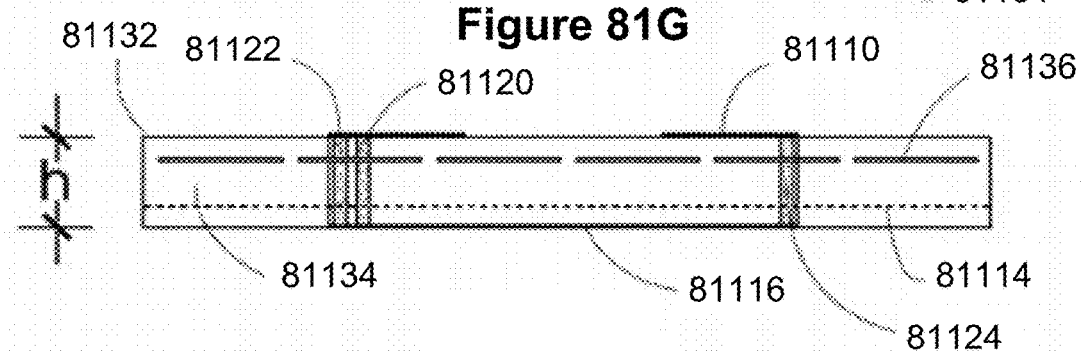

FIGS. 81G and 81H illustrate top and side views of second integrated antenna structures 81130. In some embodiments, as illustrated in FIG. 81G, PIFA 81104 may occupy about eight AMC unit cells 81140 of the AMC metamaterial 81132 formed on PCB 81134. In some embodiments, as illustrated in FIG. 81G, second integrated antenna structures 81130 may include dimensions of about 18 mm and 18 mm for m and n respectively, for a system area of about 324 mm$^2$.

FIG. 81H shows a side view of second integrated antenna structures 81130 where it may be noticed how the AMC metamaterial 81132 is integrated with PIFA 81104. As shown in FIG. 81H, antenna element 81108 and folded ground 81110 may be formed on top side of PCB 81134, while ground element 81116 may be formed on the bottom side of PCB 81134. Backing metal layer 81114 and AMC metal layer 81136 may be formed in the inner layers of PCB 81134, between antenna element 81108 and ground element 81116. Folded ground vias 81124, signal via 81120, and ground via 81122 are also illustrated in FIG. 81H according to embodiments described herein. Thickness h of second integrated antenna structures 81130 may be about 2.4 mm.

Overall dimensions for second integrated antenna structures 81130 may vary according to the dimensions used for the AMC metamaterial 81132 and PIFA 81104, as well as the desired application.

Figure 81I:
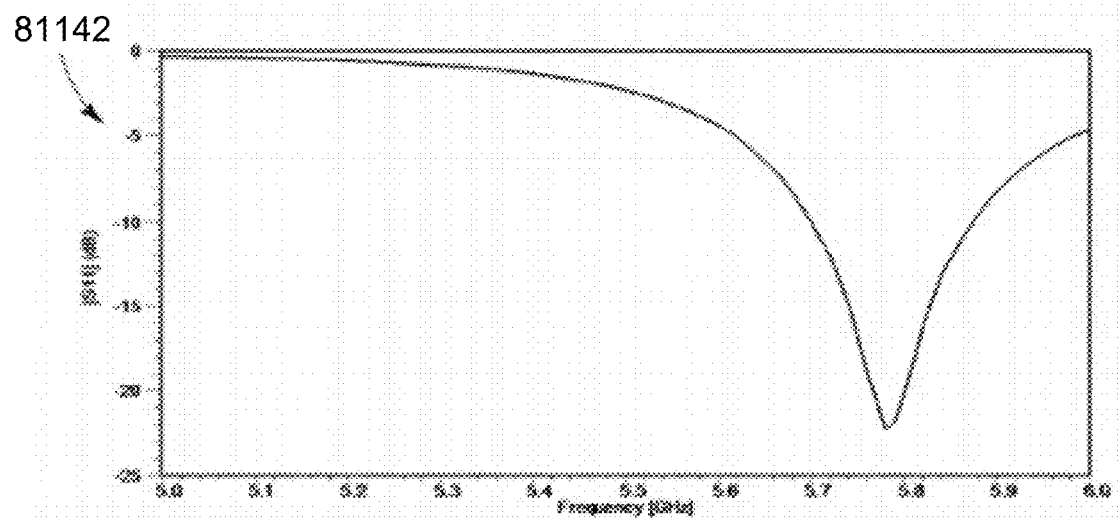
Figure 81J:
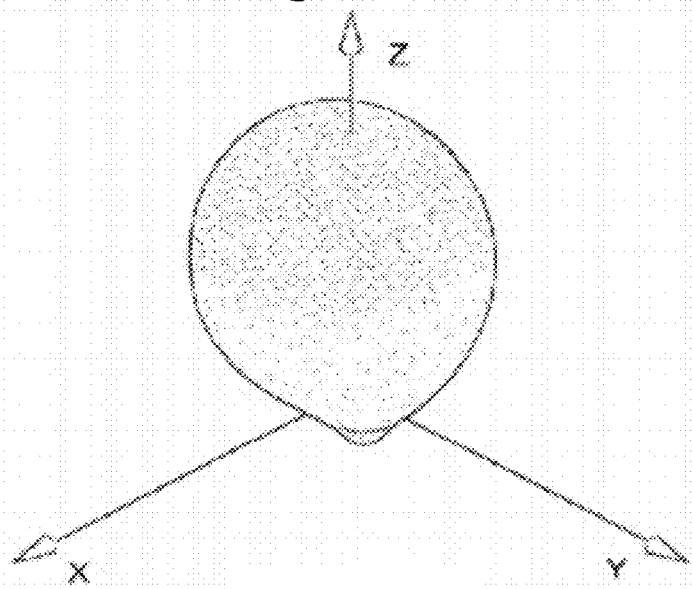

FIGS. 81I and 81J illustrate the return loss and radiation pattern 81142 of exemplary second integrated antenna structures 81130 when fed by a 50-Ohm port. As shown in FIG. 81I, second integrated antenna structures 81130 may exhibit an impedance bandwidth of about 160 MHz at −10 dB, where this bandwidth may provide sufficient margins for possible detuning upon integration of the exemplary second integrated antenna structures 81130 into an electronic device or a larger PCB. Radiation efficiency of second integrated antenna structures 81130 may be of about 67% at 5.8 GHz.

FIG. 81J illustrates the radiation pattern of second integrated antenna structures 81130, where the maximum gain may be of about 2.0 dBi at 5.8 GHz. Second integrated antenna structures 81130 may exhibit a directional radiation pattern, more specifically a directional broadside pattern that may be about twice of that of the omnidirectional radiation pattern exhibited by PIFA 81104 alone or without the AMC metamaterial 81132. In this way, by integrating the AMC metamaterial 81132 with PIFA 81104 in the second integrated antenna structures 81130, the omnidirectional pattern of PIFA 81104 may be changed to a directional pattern as exhibited in FIG. 81J, where the AMC metamaterial 81132 may operate as an artificial magnetic reflector, sending all the energy upwards. Still, the overall dimensions of second integrated antenna structures 81130 may be about 0.345× 0.345×0.05 X3 which may significantly smaller compared to conventional directional antennas such as patch antennas, and half-wave conductor-backed dipoles. For example, a half-wave center-fed linear dipole with a quarter-wave backing metal reflector may need a system size of at least 0.5×0.5×0.25 to achieve a similar performance of second integrated antenna structures 81130.

Given the compact form factors and the suitable directional radiation patterns exhibited by first integrated antenna structures 81100 and second integrated antenna structures 81130, they can be used in antenna arrays that may be included in transmitter 8112 for wireless power transmission as described in the following embodiments.

Figure 81K:
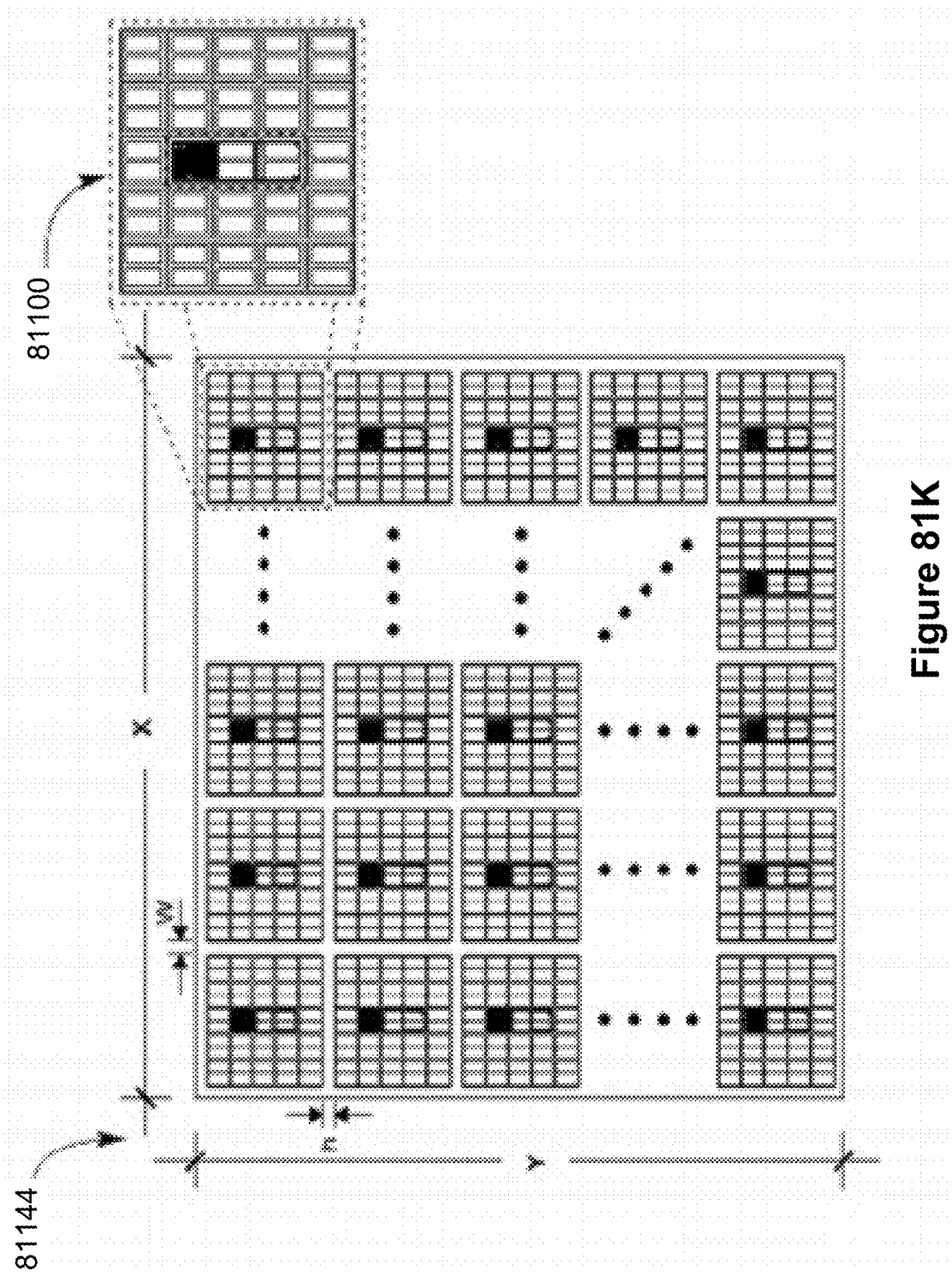

FIG. 81K illustrates an exemplary embodiment of a first flat panel antenna arrays 81144 that may include a plurality of first integrated antenna structures 81100, where this flat panel antenna arrays 81144 can be used in transmitter 8112 for sending focused RF waves towards a receiver for wireless power charging or powering, according to an embodiment.

Flat panel antenna arrays 81144 may include an N number of first integrated antenna structures 81100 distributed in an equally spaced grid. In one embodiment, flat panel antenna arrays 81144 may exhibit dimensions on the X and Y axis of about 16 inches and 14 inches respectively. First integrated antenna structures 81100 formed on flat panel antenna arrays 81144 may exhibit spacing h and w of about $\frac{1}{10}$ λ to about $\frac{1}{15}$ λ. This reduced spacing between first integrated antenna structures 81100 may be due to their high directionality. As a result, first integrated antenna structures 81100 can be placed very close together without or minimum coupling, thereby allowing a high density of first integrated antenna structures 81100 in flat panel antenna arrays 81144. In one embodiment, flat panel antenna arrays 81144 may fit about 418 first integrated antenna structures 81100.

Each first integrated antenna structures 81100 in flat panel antenna arrays 81144 may be operated independently, thus enabling an enhanced control over the pocket forming. For example, by individually controlling each first integrated antenna structures 81100, the gain and phase of each first integrated antenna structures 81100 can be adjusted for obtaining a narrower RF beam, and thereby allowing a higher coherent gain for flat panel antenna arrays 81144. In addition, the higher number of first integrated antenna structures 81100 may contribute to a higher gain for flat panel antenna arrays 81144.

In general, the number of first integrated antenna structures 81100 in flat panel antenna arrays 81144 may vary in relation with the desired range and power transmission capability for transmitter 8112. Additionally, the spacing between each first integrated antenna structures 81100 on flat panel antenna arrays 81144 may vary as well. Alternate configurations for flat panel antenna arrays 81144 may be considered, including circular patterns or polygon arrangements. Flat panel antenna arrays 81144 may also be broken into numerous pieces and distributed across multiple surfaces (multi-faceted). Shape and orientation of first integrated antenna structures 81100 may vary in dependency of the desired features of transmitter 8112, as well as various orientation types and combinations in three dimensional arrangements. Additionally, the AMC metamaterial 81102 in first integrated antenna structures 81100 may allow radio signal transmission with high efficiency, good heat dissipation and the like.

Moreover, first integrated antenna structures 81100 in flat panel antenna arrays 81144 may operate in frequency bands, such as 900 MHz, 2.5 GHz or 5.8 GHz as these frequency bands conform to Federal Communications Commission (FCC) regulations part 18 (Industrial, Scientific and Medical equipment). First integrated antenna structures 81100 may also operate in independent frequencies, allowing a multichannel operation of pocket-forming.

In other embodiments, shielding (not shown in FIG. 81K) may be applied between first integrated antenna structures 81100 in flat panel antenna arrays 81144 to eliminate or further reduce coupling.

Figure 81L:
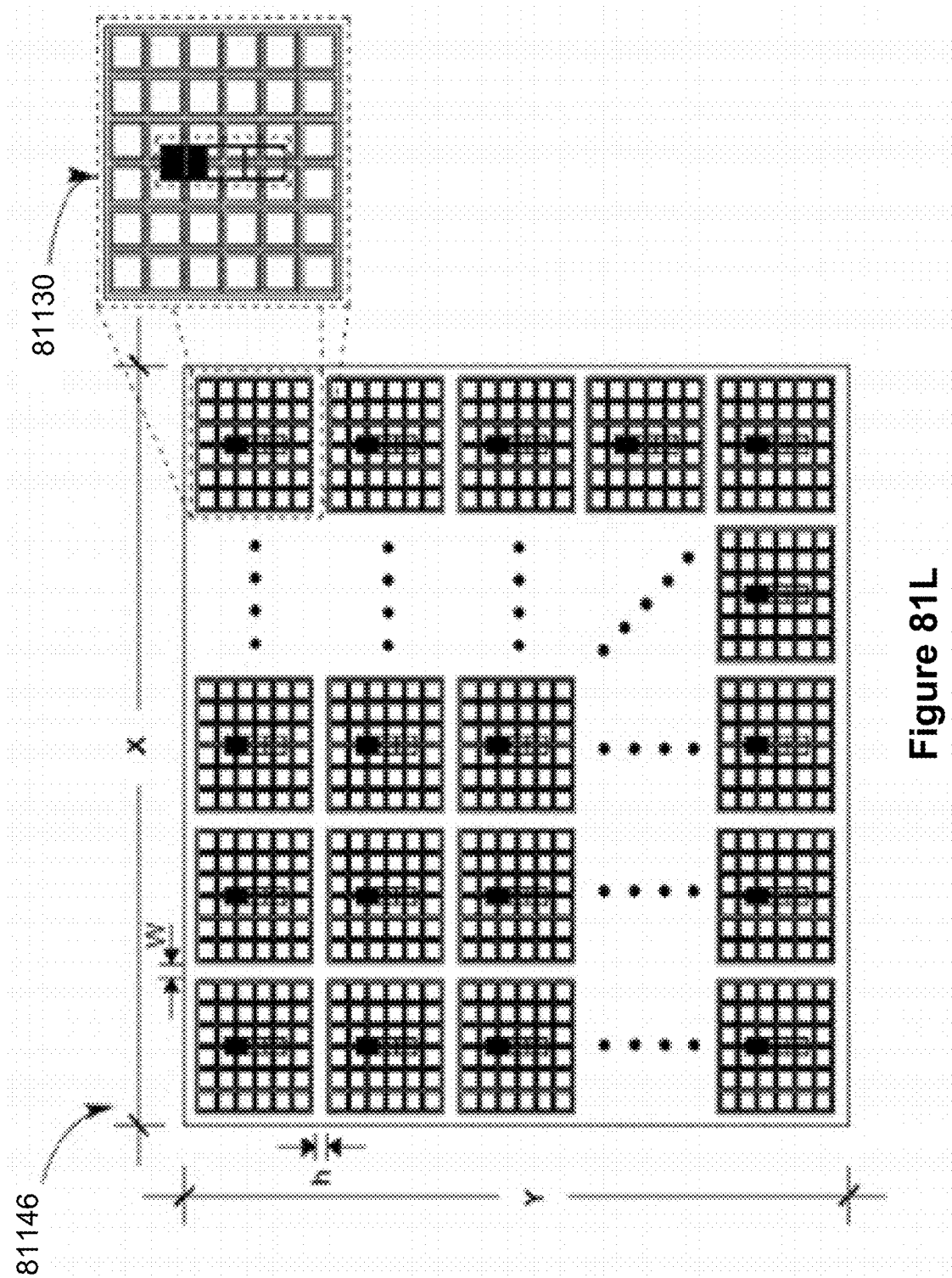

FIG. 81L illustrates an exemplary embodiment of a first flat panel antenna arrays 81146 that may include a plurality of second integrated antenna structures 81130, where this flat panel antenna arrays 81146 can be used in transmitter 8112 for sending focused RF waves towards a receiver for wireless power charging or powering, according to an embodiment.

Flat panel antenna arrays 81146 may include an N number of second integrated antenna structures 81130 distributed in an equally spaced grid. In one embodiment, flat panel antenna arrays 81146 may exhibit dimensions on the X and Y axis of about 16 inches and 14 inches respectively. Second integrated antenna structures 81130 formed on flat panel antenna arrays 81146 may exhibit spacing h and w of about $\frac{1}{10} \lambda$ to about $\frac{1}{15} \lambda$. This reduced spacing between second integrated antenna structures 81130 may be due to their high directionality. As a result, second integrated antenna structures 81130 can be placed very close together without or minimum coupling, thereby allowing a high density of second integrated antenna structures 81130 in flat panel antenna arrays 81146. In one embodiment, flat panel antenna arrays 81146 may fit about 418 second integrated antenna structures 81130.

Each second integrated antenna structures 81130 in flat panel antenna arrays 81146 may be operated independently, thus enabling an enhanced control over the pocket forming. For example, by individually controlling each second integrated antenna structures 81130, the gain and phase of each second integrated antenna structures 81130 can be adjusted for obtaining a narrower RF beam, and thereby allowing a higher coherent gain for flat panel antenna arrays 81146. In addition, the higher number of second integrated antenna structures 81130 may contribute to a higher gain for flat panel antenna arrays 81146.

In general, the number of second integrated antenna structures 81130 in flat panel antenna arrays 81146 may vary in relation with the desired range and power transmission capability for transmitter 8112. Additionally, the spacing between each second integrated antenna structures 81130 on flat panel antenna arrays 81146 may vary as well. Alternate configurations for flat panel antenna arrays 81146 may be considered, including circular patterns or polygon arrangements. Flat panel antenna arrays 81146 may also be broken into numerous pieces and distributed across multiple surfaces (multi-faceted). Shape and orientation of second integrated antenna structures 81130 may vary in dependency of the desired features of transmitter 8112, as well as various orientation types and combinations in three dimensional arrangements. Additionally, the AMC metamaterial 81132 in second integrated antenna structures 81130 may allow radio signal transmission with high efficiency, good heat dissipation and the like.

Moreover, second integrated antenna structures 81130 in flat panel antenna arrays 81146 may operate in frequency bands, such as 900 MHz, 2.5 GHz or 5.8 GHz as these frequency bands conform to Federal Communications Commission (FCC) regulations part 18 (Industrial, Scientific and Medical equipment). Second integrated antenna structures 81130 may also operate in independent frequencies, allowing a multichannel operation of pocket-forming.

In other embodiments, shielding (not shown in FIG. 81L) may be applied between second integrated antenna structures 81130 in flat panel antenna arrays 81146 to eliminate or further reduce coupling.

FIGS. 81M and 81N illustrate an isometric view of exemplary antenna arrangement configurations 81148 where one or more integrated antenna structures 81152 may be connected to at least one RFIC 81154. In one embodiment, a flat transmitter 8112 may include a plurality of integrated antenna structures 81152, such as first integrated antenna structures 81100 or second integrated antenna structures 81130, connected to one or more RFIC 81154 in a flat panel antenna arrays 81150 configuration.

For example, FIG. 81M illustrates a subset of 4 integrated antenna structures 81152, that may be connected to a single RFIC 81154.

In another embodiment, a row or column of integrated antenna structures 81152 may be connected to a single RFIC 81154, as shown in FIG. 81N.

In a further embodiment, 2 integrated antenna structures 81152 (not shown in FIGS. 81M and 81N) may be connected to a single RFIC 81154 and this in turn to a single RFIC 81154, which may be connected to a final RFIC 81154 and this in turn to one or more micro-controllers. Furthermore, a higher reliability and accuracy may be achieved because multiple redundancy of RFIC 81154.

In another embodiment, RFIC 81154 may be directly embedded behind each integrated antenna structures 81152 (not shown in FIGS. 81M and 81N); such integration may reduce losses due the shorter distance between components. Specifically, in flat panel antenna arrays 81150, the phase and the amplitude of each pocket-forming in each integrated antenna structures 81152 may be regulated by the corresponding RFIC 81154 in order to generate the desired pocket-forming and null steering. RFIC 81154 singled coupled to each integrated antenna structures 81152 may reduce processing requirement and may increase control over pocket-forming, allowing multiple pocket-forming and a higher granular pocket-forming with less load over microcontroller; thus, a higher response of higher number of multiple pocket-forming may be allowed. Furthermore, multiple pocket-forming may charge a higher number of receivers and may allow a better trajectory to such receivers.

In conclusion, integrated antenna structures 81152 may operate in single array, pair array, quad array, or any other suitable arrangement, which may be designed in accordance with the desired application. As described in FIG. 81M, RFIC 81154 may be coupled to one or more micro-controllers. Furthermore, micro-controllers may be included into an independent base station or into flat transmitter 8112.

FIGS. 81A-81N illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 81A-81N.

Presented below are example embodiments of integrated antenna arrays for wireless power transmission.

In some embodiments, an example flat panel antenna array for transmitting focused radio-frequency (RF) waves towards a receiver to provide wireless power thereto, which comprises N number of integrated antenna structures, distributed in an at least substantially equally spaced grid, said grid comprising spacing between the integrated antenna structures of about 1/10 λ to about 1/15 λ, and where N is varied with at least one of a desired range and power of the transmitting.

In some embodiments, the flat panel antenna array grid comprises a substantially rectangular shape, and the grid comprises dimensions of about 16 inches by about 14 inches.

In some embodiments, the flat panel antenna array grid spacing results from a high directionality of the integrated antenna structures.

In some embodiments, the flat panel antenna array grid spacing minimizes coupling between ones of the integrated antenna structures.

In some embodiments, the flat panel antenna array N comprises about 418 of the integrated antenna structures.

In some embodiments, the flat panel antenna array has each of the integrated antenna structures suitable for independent operation.

In some embodiments, the flat panel antenna array is capable of adjusting at least a gain and phase of each of the integrated antenna structures.

In some embodiments, the flat panel antenna array adjustment is suitable to provide a narrower beam of the RF.

In some embodiments, the flat panel antenna array grid comprises a circular arrangement of the integrated antenna structures.

In some embodiments, the flat panel antenna array grid comprises a polygonal arrangement of the integrated antenna structures.

In some embodiments, the flat panel antenna array grid comprises a multi-faceted arrangement of the integrated antenna structures.

In some embodiments, the flat panel antenna array integrated antenna structures operate in at least one frequency band of the RF selected from the group consisting of 900 MHz, 2.5 GHz, 5.8 GHz, and independent frequencies.

In some embodiments, the flat panel antenna array further comprises at least one RFIC connected to at least one of the integrated antenna structures.

In some embodiments, the flat panel antenna array has a grouped subset of the integrated antenna structures connected to a single RFIC.

In some embodiments, the flat panel antenna array has the grouped subset comprise 4 of the integrated antenna structures.

In some embodiments, the flat panel antenna array has the grouped subset comprise a row of the integrated antenna structures.

In some embodiments, the flat panel antenna array has the grouped subset comprise a column of the integrated antenna structures.

In some embodiments, the flat panel antenna array further comprises at least one second RFIC serially connected to the at least one RFIC.

In some embodiments, the flat panel antenna array further comprises at least one microcontroller connected to ones of the at least one RFIC.

In some embodiments, the flat panel antenna further comprises one RFIC connected to each of the integrated antenna structures.

FIGS. 82A-82D illustrate examples of devices, apparatus, and methods for 3 dimensional pocket-forming, in accordance with some embodiments.

Figure 82A:
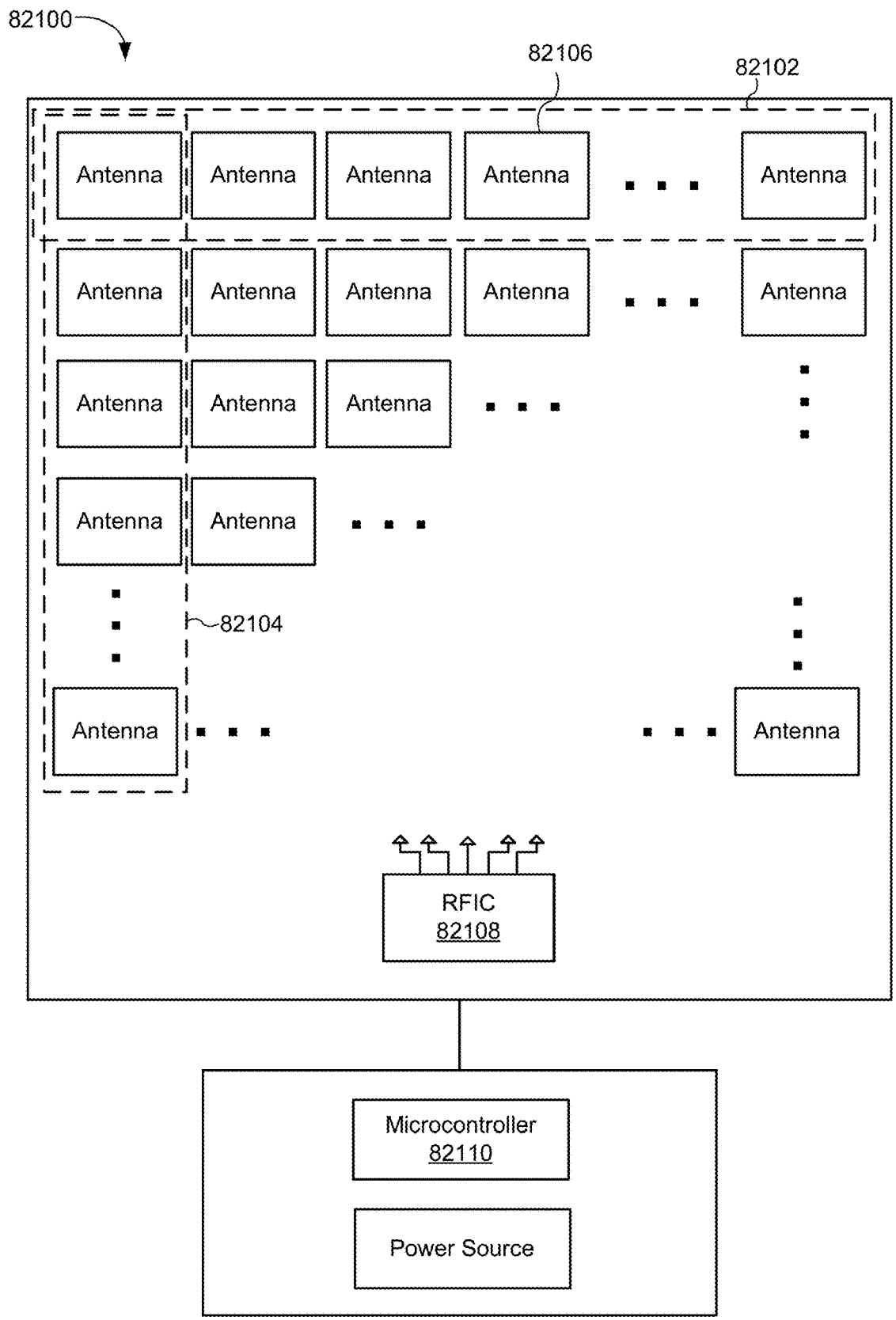

FIG. 82A is an example of a transmitter configuration 82100 that includes a plurality of antenna elements 82106. Antenna elements 82106 may form an array by arranging rows of antennas 82102 and columns of antennas 82104. Transmitter configuration 82100 may include at least one RFIC 82108 to control features of antenna elements 82106, such as gain and/or phase for pocket-forming and manage it through direction, power level, and the like. The array of antenna elements 82106 may be connected to a microcontroller 82110, which may determine optimum times and locations for pocket-forming, including the most efficient trajectory to transmit pocket forming in order to reduce losses because of obstacles. Such trajectory may include direct pocket-forming, bouncing, and distance discrimination of pocket-forming.

A transmitter 102 device may utilize antenna elements 82106 to determine the location of a receiver 120 in order to determine how to adjust antenna elements 82106 to form pockets of energy in the appropriate location. A receiver 120 may send a train signal to transmitter 102 in order to provide information. The train signal may be any conventional know signals that may be detected by antenna elements 82106. The signal sent by receiver 122 may contain information such as phase and gain.

Figure 82B:
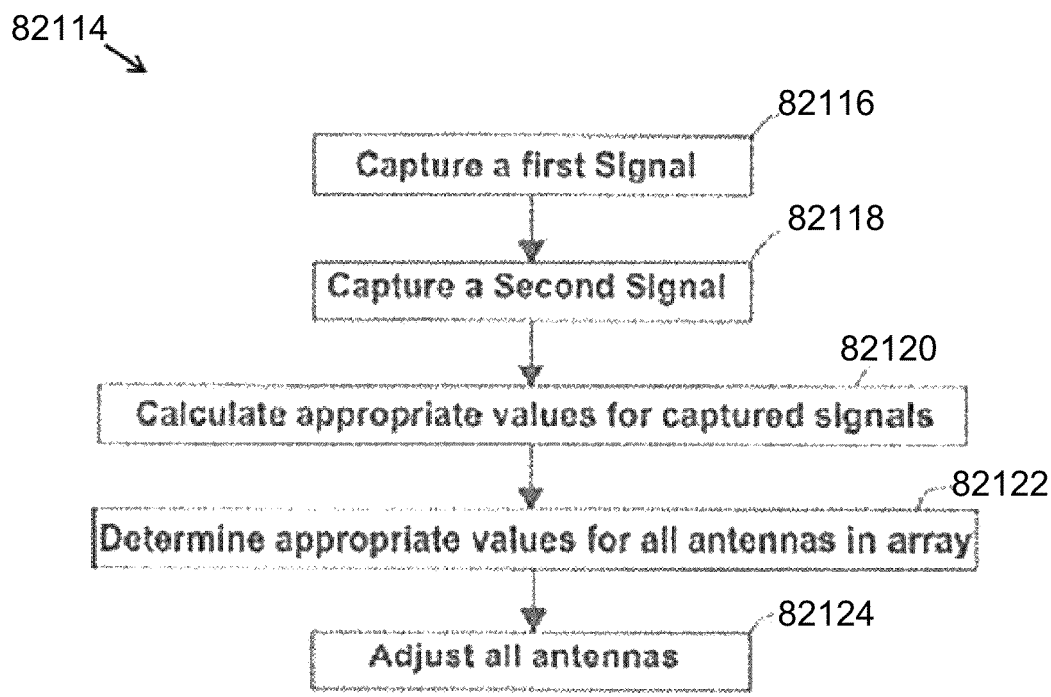

FIG. 82B is a method for determining receiver location 82114 using antenna elements 82106. Method for determining receiver location 82114 may be a set of programmed rules or logic managed by microcontroller 82110. The process may begin by capturing first signal 82116 with a first subset of antennas from the antenna array. The process may follow immediately by switching to a different subset of antenna. elements 82106 and capturing second signal 82118 with a second subset of antennas. For example, a first signal may be captured with a row of antennas 82102 and the second capturing may be done with a column of antennas 82104. A row of antennas 82102 may provide a horizontal degree orientation such an azimuth in a spherical coordinate system. A column of antennas 82104 may provide a vertical degree orientation such as elevation. Antenna elements 82106 used for capturing first signal 82116 and capturing second signal 82118 may be aligned in straight vertical, horizontal or diagonal orientation. The first subset and second subset of antennas may be aligned in a cross like structure in order to cover 360 degrees around transmitter 102.

Once both vertical and horizontal values have been measured, microcontroller 82110 may determine the appropriate values 82120 of phase and gain for the vertical and horizontal antenna elements 82106 used to capture the signal. Appropriate values for phase and gain may be determined by the relationship of the position of the receiver 120 to the antenna elements 82106 used. The values may be used by microcontroller 82110 in order to adjust antenna elements 82106 to form pockets of energy that may be used by a receiver 120 in order to charge an electronic device.

Data pertaining to initial values of all antenna elements 82106 in transmitter 102 may be calculated and stored previously for use by microcontroller 82110 in order to assist in the calculation of appropriate values for antenna elements 82106. After the appropriate values for the vertical and horizontal antennas used for capturing the signal have been determined, the process may continue by using the stored data to determine appropriate values for all the antennas in the array 82122. Stored data may contain initial test values of phase and gain for all antenna elements 82106 in the array at different frequencies. Different sets of data may be stored for different frequencies and microcontroller 82110 may select the appropriate data set accordingly.

Microcontroller 82110 may then adjust all antennas 82124 through RFIC 82108 in order to form pockets of energy at the appropriate locations.

Figure 82C:
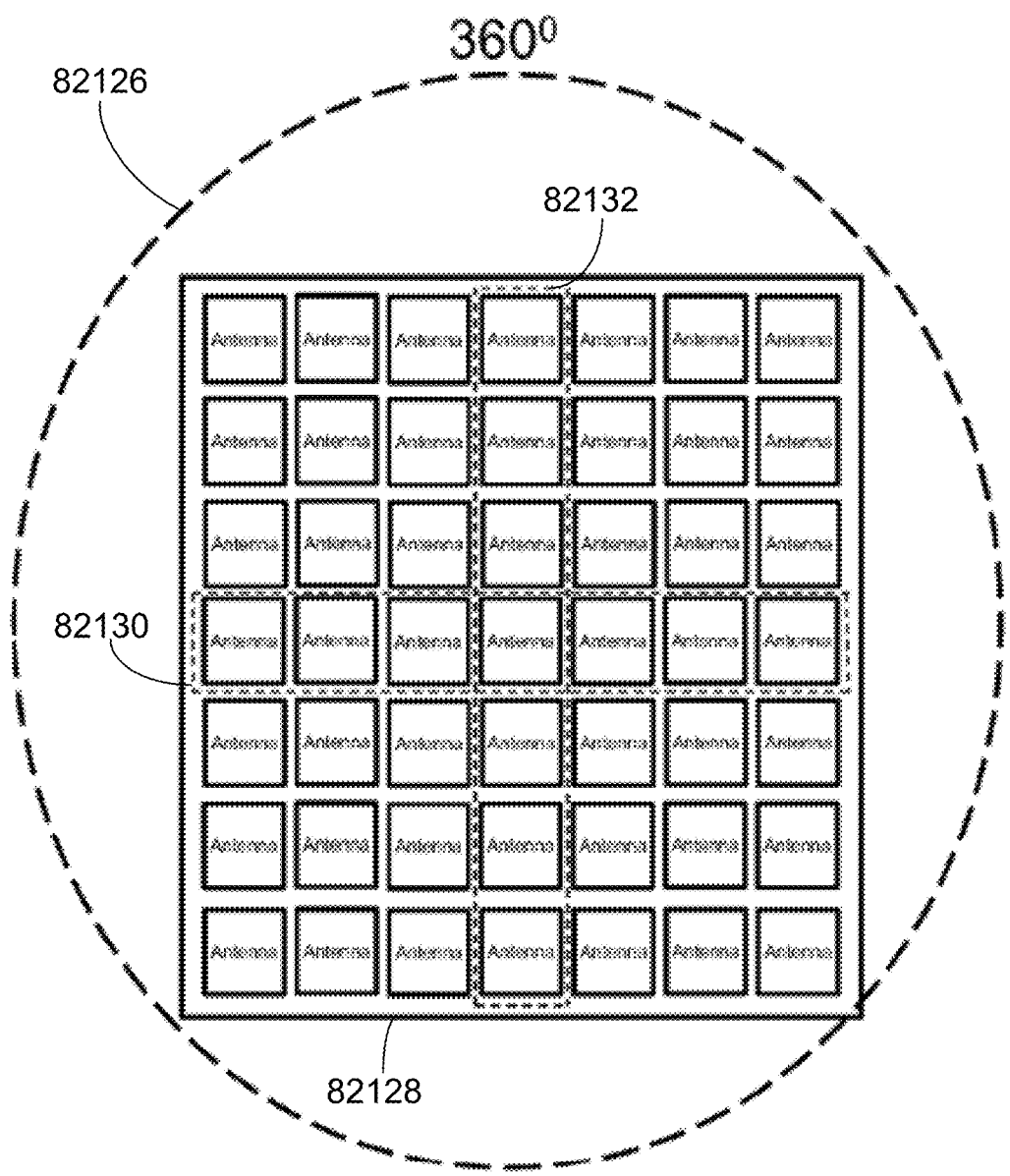

FIG. 82C illustrates an example embodiment of an array subset configuration 82126 that may be used in method for determining receiver location 82114. A transmitter may include an array of antennas 82128. A row of antennas 82130 may be used first for capturing a signal sent by a receiver 120. Row of antennas 82130 may then transfer the signal to the RFIC 82108 (not shown in FIG. 82C), where the signal may be converted from a radio signal to a digital signal and passed on to microcontroller 82110 for processing. Microcontroller 82110 may' then determine appropriate adjustments for phase and gain in row of antennas 82130 in order to form pockets of energy at the appropriate locations based on the receiver 120 locations. A second signal may be captured by a column of antennas 82132. Column of antennas 82132 may then transfer the signal to the RFIC 82108 (not shown in FIG. 82C), where the signal may be converted from a radio signal to a digital signal and passed on to microcontroller 82110 for processing. Microcontroller 82110 may then determine appropriate adjustments for phase and gain in column of antennas 82132 in order to form pockets of energy at the appropriate locations based on the receiver 120 locations. Once the appropriate adjustments have been determined for row of antennas 82130 and column of antennas 82132 microcontroller 82110 may determine the appropriate values for the rest of antenna elements 82106 in array of antennas 82128 by using previously stored data about the antennas and adjusting accordingly with the results from row of antennas 82130 and column of antennas 82132.

Figure 82D:
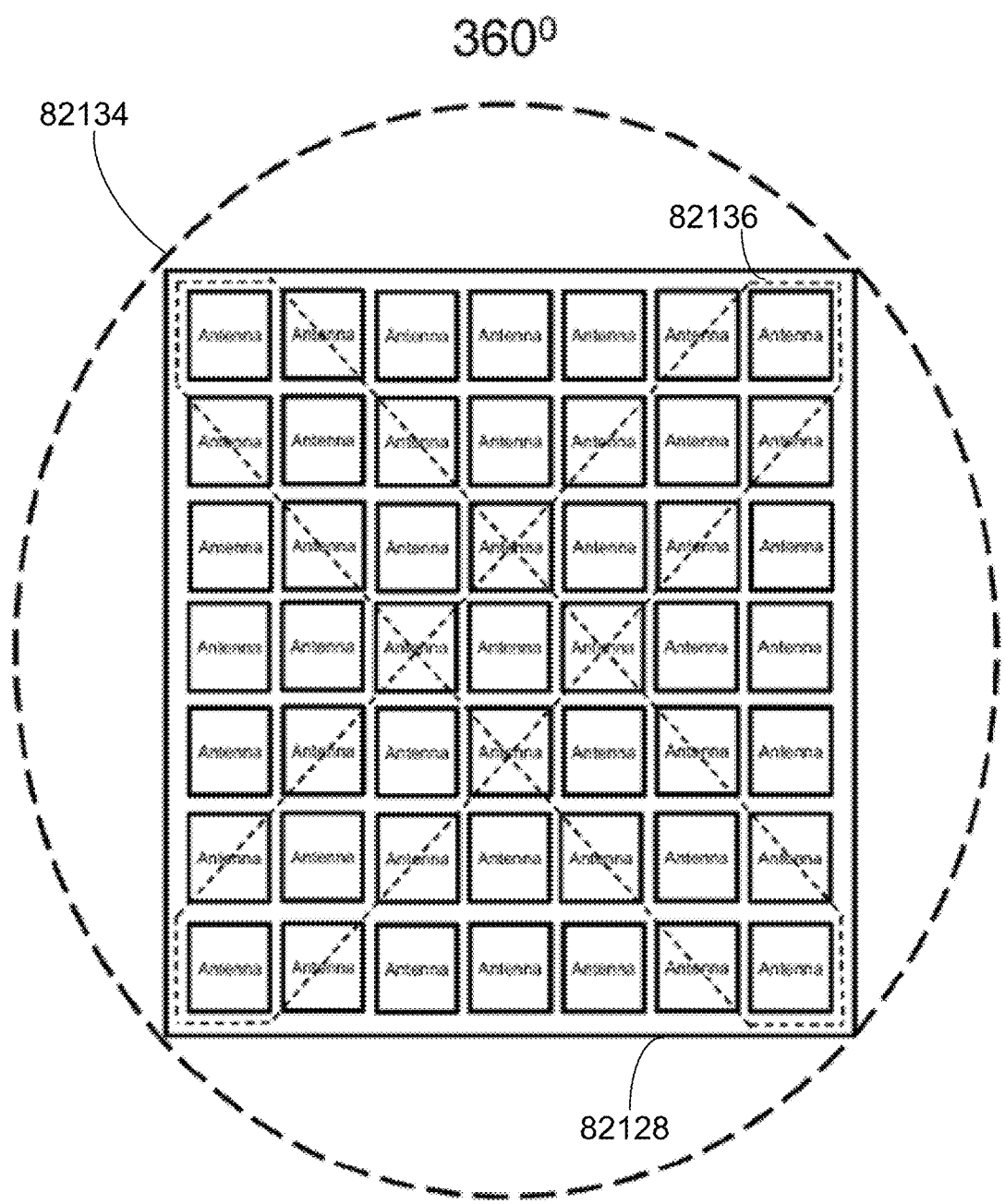

FIG. 82D illustrates another example embodiment of an array subset configuration 82134. In array subset configuration 82134 both initial signals are captured by two diagonal subsets of antennas 82136. The process follows the same path, such that each subset is adjusted accordingly. Based on adjustments made and the previously stored data, the rest of antenna elements 82106 in array of antennas 82128 are adjusted.

FIGS. 82A-82D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 82A-82D.

Presented below are example embodiments of 3-dimensional pocket-forming.

In some embodiments, an example method for 3-dimensional pocket-forming in wireless power transmission comprises the steps of capturing a first signal from a receiver with a first subset of antennas from an antenna array on a transmitter, switching to a different subset of antennas on the transmitter, capturing a second signal from the receiver with a second subset of antennas from the antenna array on the transmitter; and processing the first and second signals by a microprocessor on the transmitter in order to adjust the antenna array on the transmitter to form pockets of energy directed to the receiver to charge or power an electronic device.

In some embodiments, the first signal is captured with a row of antennas and the second signal is captured by a column of antennas in the transmitter array of antennas.

In some embodiments, the row of antennas provides a horizontal degree orientation such as an azimuth in a spherical coordinate system and has the column of antennas provide a vertical degree orientation such as elevation in the spherical coordinate system.

In some embodiments, the first and second subset of antennas aligned in a cross structure in order to cover 360 degrees around the transmitter.

In some embodiments, the method includes the step of measuring the horizontal and vertical values to determine appropriate values of phase and gain to determine a position of the receiver to the antenna array of the transmitter.

In some embodiments, the microprocessor uses the values of phase and gain to adjust transmitter antennas to form pockets of energy used by the receiver in order to charge or power the electronic device.

In some embodiments, the method further comprises the step of communicating between the electronic device receiver and the transmitter through short RF waves or pilot signals on conventional wireless communication protocols including Bluetooth, Wi-Fi, Zigbee or FM radio signal with the power level information for the electronic device to be charged.

In some embodiments, the method further comprises the steps of calculating the data pertaining to initial test values of all antennas in the transmitter and saving previously stored data of test values for use by the microprocessor to assist in the future calculation of appropriate values for the transmitter antennas in the array at different frequencies.

In some embodiments, the microprocessor determines appropriate adjustments for phase and gain in the row of transmitter antennas in order to form pockets of energy at the appropriate locations based on the receiver location.

In some embodiments, the method further includes the step of utilizing previously stored data about the transmitter antennas for adjusting the antenna array accordingly with the results from the row of antennas and from the column of antennas.

In some embodiments, the transmitter includes two diagonal subsets of antennas for capturing the first and second signals and based upon the signals captured, adjustments are made and data about the antennas are stored then the rest of the antenna in the array are accordingly adjusted.

In some embodiments, a device for 3-dimensional pocket-forming in wireless power transmission comprises a receiver connected to a portable electronic device to receive charging or powering from a transmitter with an antenna array, a first subset of antennas within the antenna array on the transmitter for capturing a first signal generated by the receiver, a second subset of antennas within the antenna array on the transmitter for capturing a second signal generated by the receiver, and a microprocessor mounted within the transmitter for processing the first and second signals in order to adjust the first and second subset of antennas within the antenna array to transmit pockets of energy to the receiver for charging or powering the electronic device.

In some embodiments, the microprocessor calculates the measurements of the horizontal and vertical values of the first and second signals for appropriate values of phase and gain to determine appropriate values for all antennas in the transmitter array in order to adjust all of the antennas in the transmitter array.

In some embodiments, each transmitter operates at different frequencies, power intensities and different ranges to power the electronic device.

In some embodiments, an apparatus for 3-dimensional pocket-forming in wireless power transmission comprises a receiver connected to an electronic device for communicating with a transmitter by generating first and second signals representative of horizontal and vertical orientation or values in a spherical system and a first and second subset of antenna elements for capturing the horizontal and vertical values of the receiver for the microprocessor to calculate the appropriate values of the phase and gain for the vertical and horizontal antenna elements used to capture the signals and used by the microprocessor to adjust antenna elements of the transmitter for forming pockets of energy used by the receiver to charge and power the electronic device.

In some embodiments, the apparatus further includes communication circuitry in the receiver and transmitter where the communication circuitry utilizes Bluetooth, infrared, Wi-Fi, FM radio or Zigbee for the communication protocols.

In some embodiments, the antenna elements are flat antenna elements, patch antenna elements, dipole antenna elements with heights from approximately ⅛ inches to about 1 inch and widths from approximately ⅛ inches to about 1 inch.

In some embodiments, the antenna elements of the transmitter operate in frequency bands of 900 MHz, 2.5 GHz or 5.8 GHz.

In some embodiments, the antenna elements of the transmitter operate in independent frequencies that allow a multichannel operation of pocket-forming in a single array, pair array, quad array or other suitable arrangement.

In some embodiments, the antenna elements of the transmitter include polarization of vertical pole, horizontal pole, circularly polarized, left hand polarized, right hand polarized or a combination of polarizations.

Figure 83A:
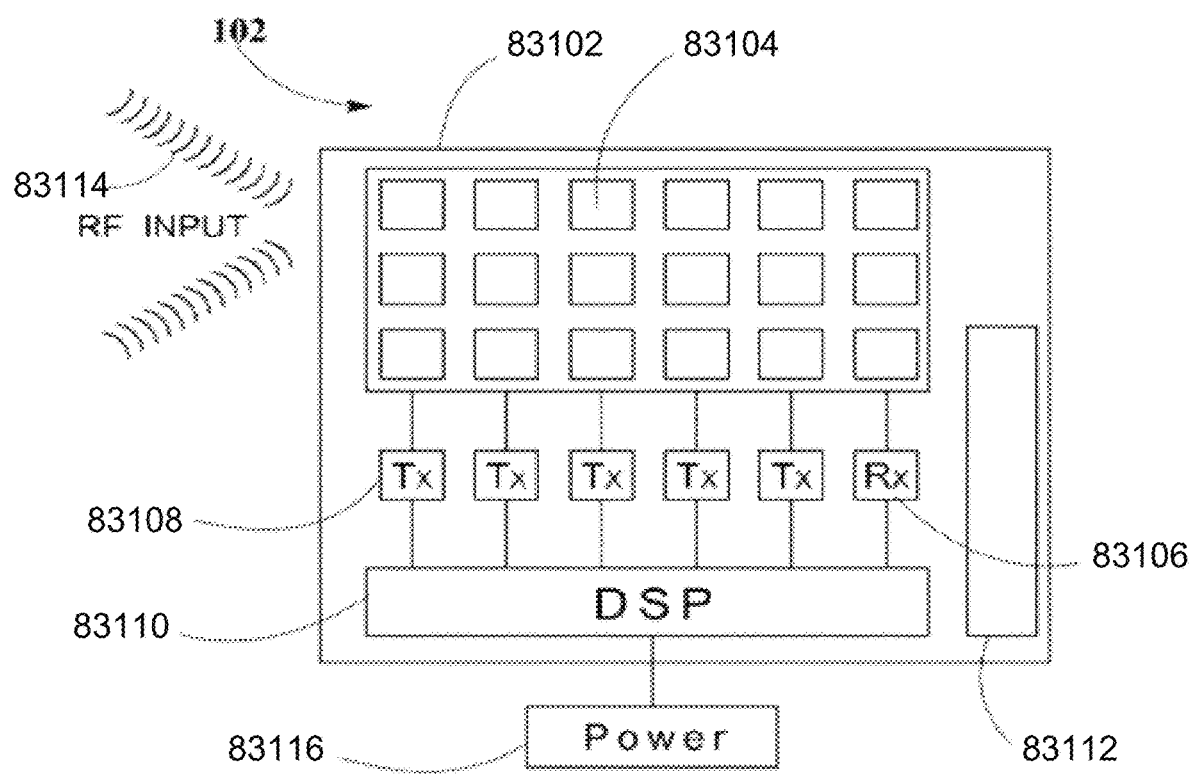
Figure 83B:
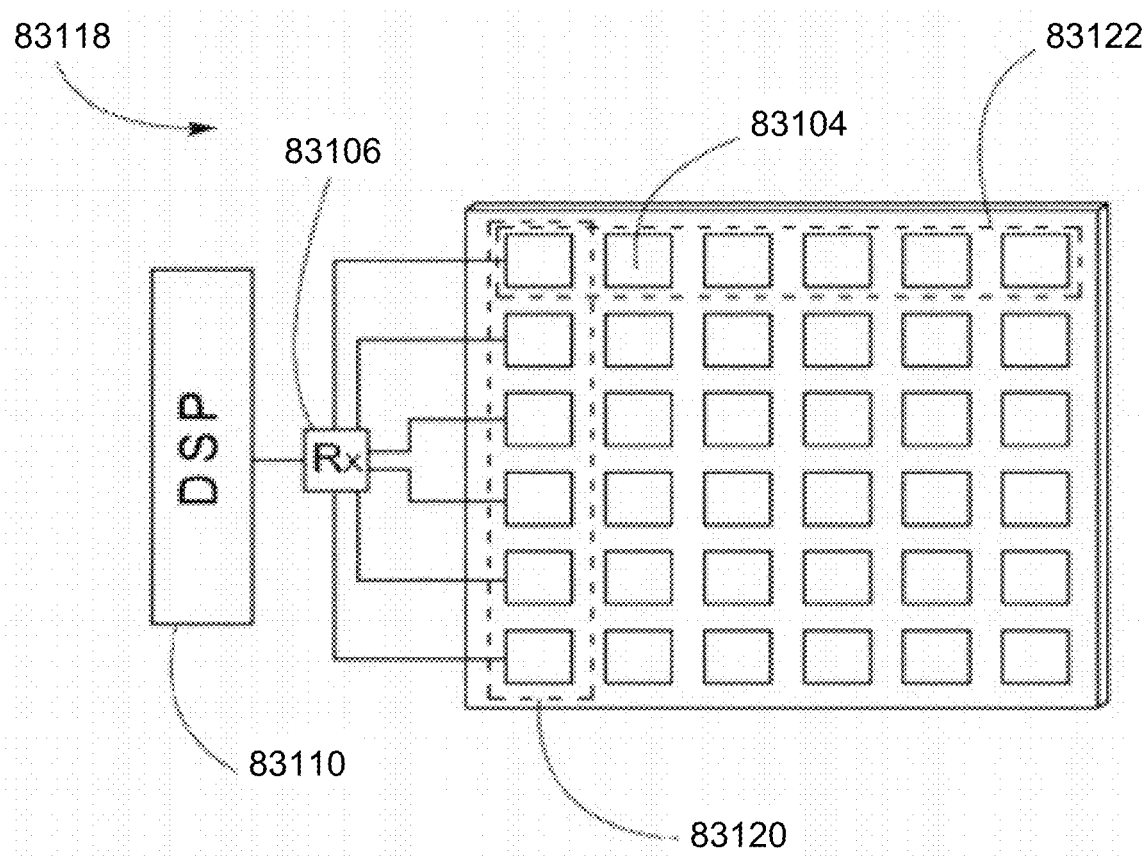
Figure 83C:
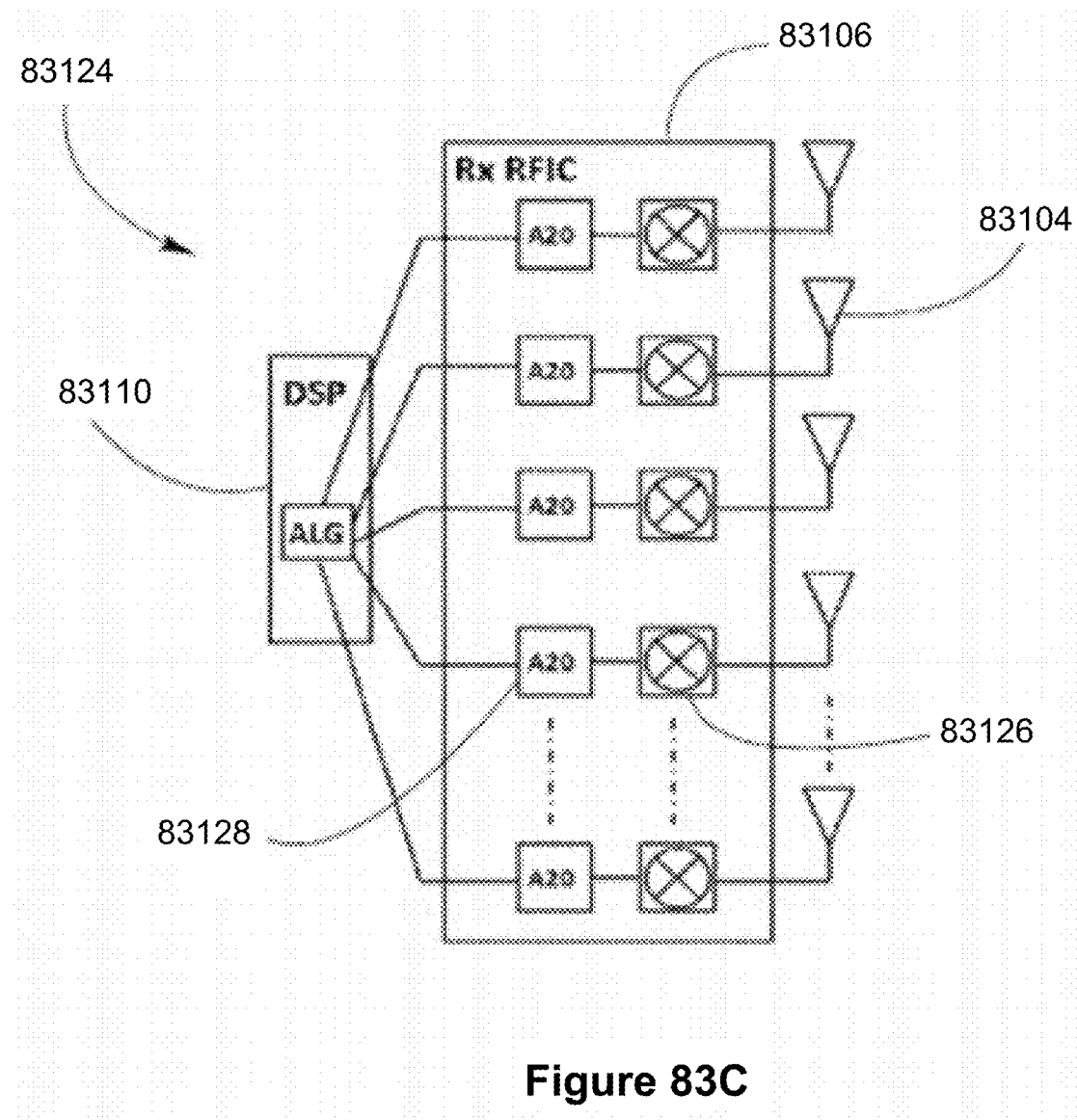

FIGS. 83A-83C illustrate examples of devices, apparatus, and methods for an enhanced transmitter for wireless power transmission, in accordance with some embodiments.

Enhanced Wireless Power Transmitter Hardware Configuration

FIG. 83A depicts the block diagram of an enhanced wireless power transmitter 102 which may be used in wireless power transmission 100. Transmitter 102 may include a housing 83102, at least two or more antenna elements 83104, at least one receiving (Rx) RF integrated circuit (RFIC) 83106, a plurality of transmitting (Tx) RF integrated circuit (RFIC) 83108, at least one digital signal processor (DSP) or micro-controller 83110, and one communications component 83112. Micro-controller 83110 may be included into an independent base station or into the transmitter 102.

RF input signals 83114 may be produced using a power source 83116 and a local oscillator chip (not shown) using a suitable piezoelectric material, or may be from other wireless sources (not shown), such as from a frequency chip, Bluetooth, and Wi-Fi.

Housing 83102 may be made of any suitable material which may allow for signal or wave transmission and/or reception, for example plastic or hard rubber. Antenna elements 83104 may include suitable antenna types for operating in frequency bands such as 900 MHz, 2.5 GHz or 5.8 GHz as these frequency bands conform to Federal Communications Commission (FCC) 47 CFR Part 18—Industrial, Scientific, and Medical Equipment. Antenna elements 83104 may include vertical or horizontal polarization, right hand or left hand polarization, elliptical polarization, or other suitable polarizations as well as suitable polarization combinations. Suitable antenna types may include, for example, patch antennas with heights from about ⅛ of an inch to about 8 inches and widths from about ⅛ of an inch to about 6 inches. Other antenna elements 83104 types that may be used include meta-materials based antennas, dipole antennas, and planar inverted-F antennas (PIFAs), amongst others.

Transmitter 102 may include a plurality of arrangements in which antenna elements 83104 may be connected to dedicated Rx RFIC 83106 or to Tx RFICs 83108. Arrangements may include different configurations, such as a dedicated row or column of antenna elements 83104 coupled to Rx RFIC 83106, and at least two or more rows or columns of antenna elements 83104 coupled to Tx RFICs 83108. Rx RFIC 83106 may include a proprietary chip for adjusting phases and/or relative magnitudes of frequency of RF input signals 83114 collected from the dedicated set/configuration antenna elements 83104 for reception of RF input signals 83114. Rx RFIC 83106 may be designed to include hardware and logic elements specifically dedicated for reception and processing of RF input signals 83114, which are not included as components of TX RFICs 83108.

In present embodiment of the enhanced wireless transmitter 102, 24 RFICs may be connected to 200 antenna elements 83104 and configured to allow operation of Rx RFIC 83106 as the dedicated receiver of RF input signals 83114 operatively coupled to a dedicated column of at least two or more antenna elements 83104, depending on the transmitter 102 configuration and operation, for example, eight antenna elements 83104. The remaining 23 Tx RFICs 83108 may be operatively coupled to a set/configuration of antenna elements 83104, other than those used to receive RF input signals 83114 by Rx RFIC 83106. Tx RFICs 83108 may be coupled to transmitting antenna elements 83104 depending on control signals from micro-controller 83110.

Micro-controller 83110 may include a proprietary algorithm to implement control of Rx RFIC 83106 and to allow operation of Rx RFIC 83106 using a switching control which enables monitoring of reception separately from transmission without overlapping in the operation of Rx RFIC 83106 and Tx RFICs 83108. RF input signals 83114 may be sampled at once after Rx RFIC 83106 may be allowed to receive by switching control in micro-controller 83110.

After the operation of Rx RFIC 83106, Tx RFICs 83108 may implement wireless power transmission 100 to receiver 120. Micro-controller 83110 may select a column of antenna elements 83104, a row of antenna elements 83104, or any interpolation of arrangement of antenna elements 83104 to couple with Tx RFICs 83108, depending on location from which wireless power is to be transmitted.

Micro-controller 83110 may also process information sent by receiver 120 through communications component 83112 for determining optimum times and locations for pocket-forming. Communications component 83112 may be based on standard wireless communication protocols which may include Bluetooth, Wi-Fi or ZigBee. In addition, communications component 83112 may be used to transfer other information, such as an identifier for the device or user, battery level, location, or other such information. Other communications component 83112 may be possible, including radar, infrared cameras or sound devices for sonic triangulation of electronic device 122 position.

Receiving Antenna Arrangement of an Enhanced Wireless Power Transmitter

FIG. 83B represents a transmitter arrangement 83118 of antenna elements 83104 which may be coupled to dedicated Rx RFICs 83106, according to an embodiment.

Depending on the location from which RF input signals 83114 may be received and information sent by receiver 120 to be processed by communications component 83112 regarding determination of optimum times and locations for pocket-forming, which may enhance efficiency of wireless power transmission 100, micro-controller 83110 may select Tx RFICs 83108 and the arrangement of antenna elements 83104 to maximize the transmission operation of transmitter 102. As seen in FIG. 83B, micro-controller 83110 may send switching control signals to Rx RFIC 83106 coupled to either antenna column 83120 or antenna row 83122 to include the antenna elements 83104 receiving RF input signals 83114, as described in FIG. 83A. After reception and processing of signals by Rx RFIC 83106, the remaining antenna elements 83104 may be coupled to Tx RFICs 83108 using a plurality of configurations of antenna elements 83104 as a result of an interpolation step which may be performed by micro-controller 83110 to control operation of Tx RFICs 83108 using the ARM micro-processor in micro-controller 83110 to enhance wireless power transmission performance of transmitter 102, directing transmission of wireless power to the appropriate location.

Antenna elements 83104 to connected to Rx RFIC 83106 may reduce processing requirement and may increase control over pocket-forming, allowing multiple pocket-forming and a higher granular pocket-forming with less load over micro-controller 83110; thus, a higher response of higher number of multiple pocket-forming may be allowed for transmission. Furthermore, multiple pocket-forming may charge a higher number of receivers 120 and may allow a better trajectory to such receivers 120 to provide a less expensive embodiment.

Integrated Circuit Configuration and Operation of a Receiving RFIC

FIG. 83C illustrates a block diagram 83124 of Rx RFIC 83106 in an enhanced wireless power transmitter 102, according to an embodiment.

RF input signals 83114 received by antenna elements 83104 dedicated for reception and operatively coupled to Rx RFIC 83106, depending on the location from which they may be radiated to transmitter 102, enable micro-controller 83110, as described in FIG. 83B. RF input signal 83114 may then be subject to frequency sampling by an array of down-converters 83126 included in Rx RFIC 83106 in which the range of frequencies of RF input signals 83114 of about 2.4 GHz or about 5.6 GHz may be shifted into RF signals of a new frequency range.

Down-converters 83126 may include a local oscillator (not shown) providing a signal of pre-determined frequency to mix with the RF input signals 83114 creating a sum heterodyne and a difference heterodyne from which one of the heterodyne may be filtered to provide the desired output frequency. In present embodiment a signal of about 5.8 GHz may be down-converted to an output signal of about 5.0 GHz. Output signal of 5.0 GHz from down-converters 83126 may then be fed to addressing lines (A20) 83128 at 10 MHz for processing by micro-controller 83110. Enhanced wireless power transmitter 102 may be receiving at one frequency, for example 2.4 GHz, and transmitting at a higher frequency, for example 5.7 GHz.

Micro-controller 83110 may be enabled to send control signals of about 1 msec or about 100 [isec to Rx RFIC 83106 and depending on how fast the RF input signals 83114 may be received, control may be enabled every msec or about 10 times/sec for 1 msec. If RF input signals 83114 may be constantly received, for example every 10 µsec, updating may be implemented to about 1,000 times/sec.

In micro-controller 83110, the proprietary algorithm may enable sampling of the incoming signals from each A20 83128 and may use an ARM micro-processor (not shown) to drive the required Tx RFICs 83108 coupled to the determined set/configuration of antenna elements 83104 to transmit wireless power to the appropriate location of receiver 120. The use of an ARM micro-processor may reduce cost, heat and power use, as it may be desirable for electronic devices 122 to be powered or charged using wireless power transmission 100. The instruction set architecture of the ARM micro-processor may allow higher processing power and energy efficiency for micro-controller 83110.

FIGS. 83A-83C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 83A-83C.

Presented below are example embodiments of an enhanced transmitter for wireless power transmission.

In some embodiments, an example apparatus for controlling transmission of pocket-forming wireless signals suitable for charging devices comprises a controller, at least one receiving circuit, operatively coupled to the controller, a plurality of transmitting circuits, operatively coupled to the controller, and an antenna array, comprising a plurality of antenna elements. A first portion of the plurality of antenna elements are respectively coupled to the at least one receiving circuit and a second portion of the plurality of antenna elements are respectively coupled to the transmitting circuits, the receiving circuit being configured to sample and process frequencies of incoming RF signals using the controller. The controller is configured to control operation of the transmitting circuit for pocket-forming based on the processed frequencies.

In some embodiments, the apparatus has the controller configured to control operation of the transmitting circuit by selecting at least some of the second portion of antenna elements for concentrating transmission of the pocket-forming wireless signals.

In some embodiments, the apparatus has the selected second portion of antenna elements concentrate transmission of the pocket-forming wireless signals by wirelessly broadcasting RF power waves that converge in 3-dimensional space to form pockets of energy in a 3-dimensional shape.

In some embodiments, the controller is one of a micro-controller, a digital signal processor and an ARM microprocessor.

In some embodiments, the apparatus has the receiving circuit configured to process frequencies by down-converting ranges of frequencies of the RF signals.

In some embodiments, the apparatus has the receiving circuit configured to adjust at least one of phase and relative magnitude of frequencies of the incoming RF signals.

In some embodiments, the apparatus has the antenna elements comprise patch antennas.

In some embodiments, the apparatus further comprises a communications component, operatively coupled to the controller. The communications component is configured to receive information for processing by the controller to optimize a time and one or more locations for the pocket-forming transmission.

In some embodiments, an apparatus for controlling transmission of pocket-forming wireless signals suitable for charging devices, comprises an antenna array, comprising a plurality of antenna elements. A first portion of the plurality of antenna elements is respectively coupled to at least one receiving circuit and a second portion of the plurality of antenna elements are respectively coupled to a plurality of transmitting circuits, and a controller, operatively coupled to the at least one receiving circuit and the plurality of transmitting circuits. The controller is configured to send switching signals to the at least one receiving circuit to select a sub-portion of the first portion of antenna elements to receive incoming RF signals. The controller is further configured to process frequencies of the received RF signals and control operation of the transmitting circuit for pocket-forming based on the processing.

In some embodiments, the apparatus sub-portion comprises at least one of rows and columns of antenna elements in the antenna array In some embodiments, the apparatus controller is configured to control operation of the transmitting circuit by selecting at least some of the second portion of antenna elements for concentrating transmission of the pocket-forming wireless signals.

In some embodiments, a method for providing wireless pocket-forming power, comprises transmitting and receiving, by one or more antennas in an antenna array coupled to a receiver circuit and a transmitter circuit, RF status signals, the RF status signals including location information of a device, processing the received RF status signals in a controller, controlling the generation RF power waves for the transmitter circuit via the controller, at least in accordance with the location information of the processed RF signals, and transmitting the generated RF power waves to the device.

In some embodiments, the method further comprises generating at least two RF power waves.

In some embodiments, the method further comprises phase shifting and gain adjusting one of the at least two RF power waves with respect to the other of the at least two RF power waves, to generate constructive and destructive interference patterns of RF power waves.

Figure 84A:
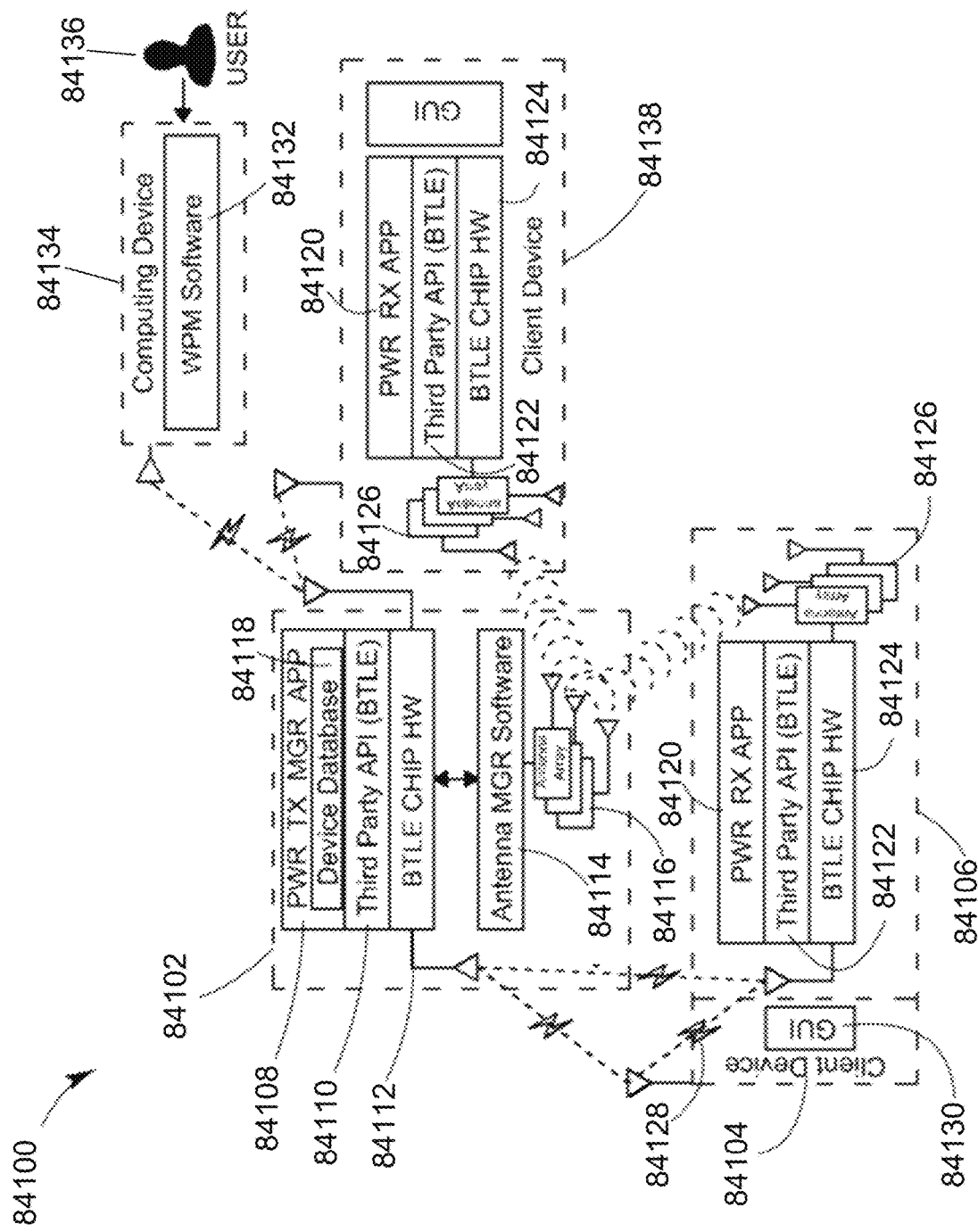
Figure 84B:
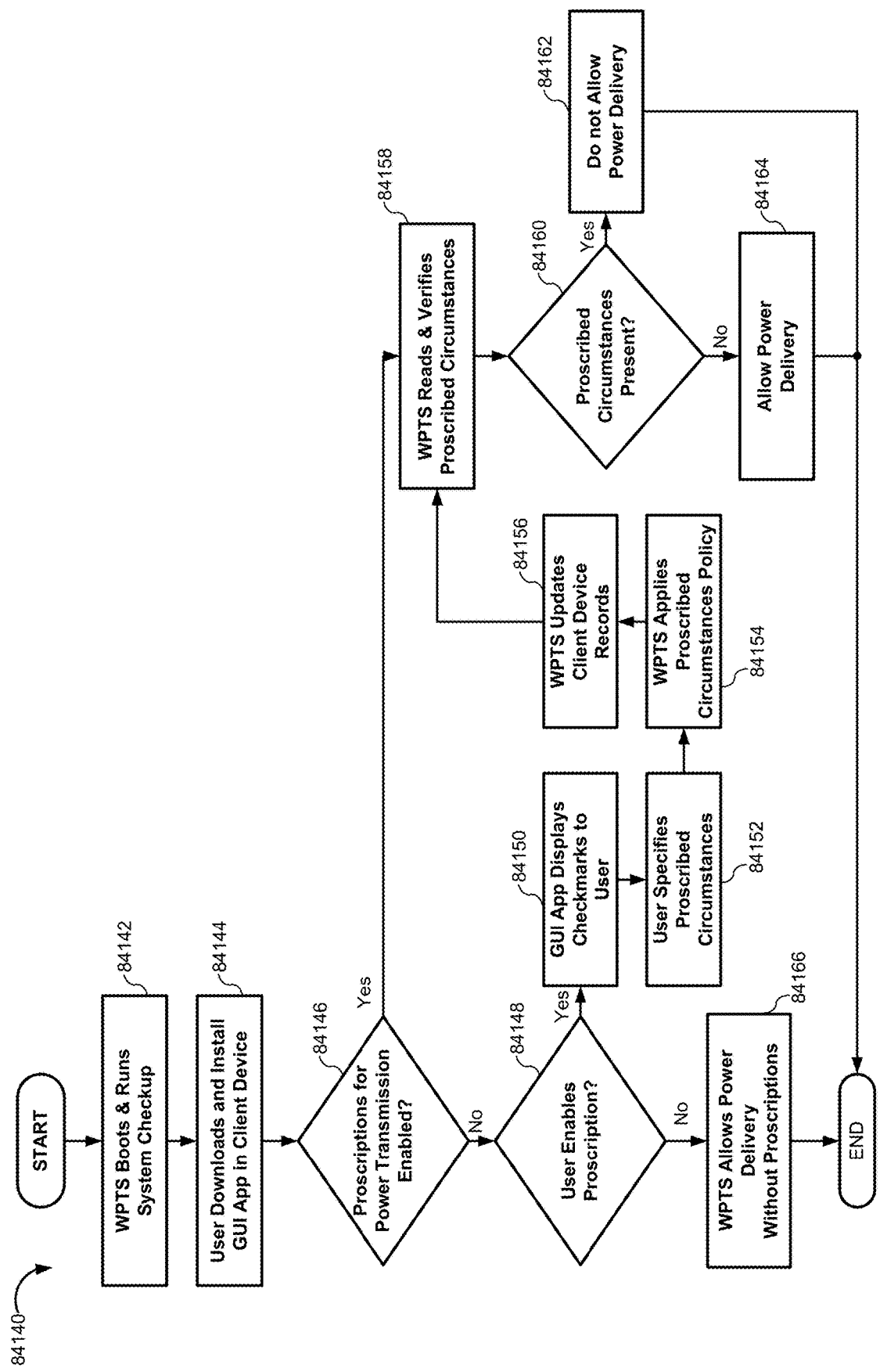

FIGS. 84A-84B illustrate examples of systems and methods for providing health safety in a wireless power transmission system, in accordance with some embodiments.

FIG. 84A shows an exemplary embodiment of a wireless power transmission system 84100 (WPTS) in which one or more embodiments of the present disclosure may operate. Wireless power transmission system 84100 may include communication between one or more wireless power transmitters 84102 and one or more wireless powered receivers 84106 and within client device 84138. Client device 84104 may be paired with an adaptable paired receiver 84106 that may enable wireless power transmission to the client device 84104. In another embodiment, a client device 84138 may include a wireless power receiver built in as part of the hardware of the device. Client device 84104 or 84138 may be any device which uses an energy power source, such as, laptop computers, stationary computers, mobile phones, tablets, mobile gaming devices, televisions, radios and/or any set of appliances that may require or benefit from an electrical power source.

In one embodiment, one or more wireless power transmitters 84102 may include a microprocessor that integrates a power transmitter manager app 84108 (PWR TX MGR APP) as embedded software, and a third party application programming interface 84110 (Third Party API) for a Bluetooth Low Energy chip 84112 (BTLE CHIP HW). Bluetooth Low Energy chip 84112 may enable communication between wireless power transmitter 84102 and other devices, including power receiver 84106, client device 84104 and 84138, and others. Wireless power transmitter 84102 may also include an antenna manager software 84114 (Antenna MGR Software) to control an RF antenna array 84116 that may be used to form controlled RF waves which may converge in 3-D space and create pockets of energy on wireless powered receivers. In some embodiments, one or more Bluetooth Low Energy chips 84112 may utilize other wireless communication protocols, including WiFi, Bluetooth, LTE direct, or the like.

Power transmitter manager app 84108 may call third party application programming interface 84110 for running a plurality of functions, including the establishing of a connection, ending a connection, and sending data, among others. Third party application programming interface 84110 may issue commands to Bluetooth Low Energy chip 84112 according to the functions called by power transmitter manager app 84108.

Power transmitter manager app 84108 may also include a distributed system database 84118, which may store relevant information associated with client device 84104 or 84138, such as their identifiers for a client device 84104 or 84138, voltage ranges for power receiver 84106, location of a client device 84104 or 84138, signal strength and/or any other relevant information associated with a client device 84104 or 84138. Database 84118 may also store information relevant to the wireless power network, including receiver ID's, transmitter ID's, end-user handheld devices, system management servers, charging schedules, charging priorities and/or any other data relevant to a wireless power network.

Third party application programming interface 84110 at the same time may call power transmitter manager app 84108 through a callback function which may be registered in the power transmitter manager app 84108 at boot time. Third party application programming interface 84110 may have a timer callback that may go for ten times a second, and may send callbacks every time a connection begins, a connection ends, a connection is attempted, or a message is received.

Client device 84138 may include a power receiver app 84120 (PWR RX APP), a third party application programming interface 84122 (Third party API) for a Bluetooth Low Energy chip 84124 (BTLE CHIP HW), and an RF antenna array 84126 which may be used to receive and utilize the pockets of energy sent from wireless power transmitter 84102.

Power receiver app 84120 may call third party application programming interface 84122 for running a plurality of functions, including establishing a connection, ending a connection, and sending data, among others. Third party application programming interface 84122 may have a timer callback that may go for ten times a second, and may send callbacks every time a connection begins, a connection ends, a connection is attempted, or message is received.

Client device 84104 may be paired to an adaptable power receiver 84106 via a BTLE connection 84128. A graphical user interface (GUI 84130) may be used to manage the wireless power network from a client device 84104. GUI 84130 may be a software module that may be downloaded from any suitable application store and may run on any suitable operating system, including iOS and Android, amongst others. Client device 84104 may also communicate with wireless power transmitter 84102 via a BTLE connection 84128 to send important data, such as an identifier for the device, battery level information, geographic location data, or any other information that may be of use for wireless power transmitter 84102.

A wireless power manager 84132 software may be used in order to manage wireless power transmission system 84100. Wireless power manager 84132 may be a software module hosted in memory and executed by a processor inside a computing device 84134. The wireless power manager 84132 may include a local application GUI, or host a web page GUI, from where a user 84136 may see options and statuses, as well as execute commands to manage the wireless power transmission system 84100. The computing device 84134, which may be cloud-based, may be connected to the wireless power transmitter 84102 through standard communication protocols, including Bluetooth, Bluetooth Low Energy, Wi-Fi, or ZigBee, amongst others. Power transmitter manager app 84108 may exchange information with wireless power manager 84132 in order to control access by and power transmission to client devices 84104. Functions controlled by wireless power manager 84132 may include scheduling power transmission for individual devices, prioritizing between different client devices, accessing credentials for each client, tracking physical locations of power receivers relative to power transmitter areas, broadcasting messages, and/or any functions required to manage the wireless power transmission system 84100.

FIG. 84B shows a flowchart of a method 84140 for proscribing client devices from receiving power from a wireless power transmission system, based on proscribed circumstances of heath safety. The disclosed method may operate in one or more components of a wireless power transmission system. The wireless power transmission system may include one or more system computers, GUI system management software running on client devices, one or more remote information service servers, and one or more system management servers, among others.

The remote information service server may be coupled to a system database which may be duplicated or distributed across all network computers operating in the wireless power transmission system. Said distributed system database along with the database distribution management software operating within all network computers may allow instant communication in the wireless power transmission system.

Examples of system computers may include wireless power receivers, wireless power transmitters, and system management servers, among others. Examples of client devices may include smartphones, tablets, and music players, among others.

The process may start at step 84142 when the wireless power transmission system (WPTS) boots up and runs a system checkup to make sure all communication channels work properly. Subsequently, at step 84144 the user may download and install the system management software app (GUI App) in client device for the WPTS, if this step has not already been done. This app may be made available at, downloaded, and installed from a public software app store or digital application distribution platform, such as Apple's iTunes, Google's Play Store, Amazon's Appstore, and the like. In other embodiments, the user may browse to a web page hosted by a computer or server where the user may command, control, or configure the WPTS. The app or web page may have a user interface that includes, but is not limited to, industry standard checkmark controls, or any other user interface control for specifying or controlling health safety operational parameters, displayed and described on the view screen of a client device, or web page served by a computer that manages the wireless power transmission system.

Following the process, at decision 84146, the GUI app verifies if there are any proscriptions for power transmission enabled in the WPTS. If proscriptions for power transmission have been enabled, continues to step 84158 below, otherwise proscriptions for power transmission have not yet been enabled, then at decision 84148, GUI may display a message to the user asking if the user desires to enable health safety operational parameters for wireless power transmission. If the user does not accept to enable proscriptions, then WPTS allows power delivery without proscriptions, at step 84166, and the process ends. If at decision 84148 the user accepts to enable proscriptions, then at step 84150, the GUI app may display a check list to user where he or she may specify the circumstances when wireless power should not be transmitted to the device in use by the user. Then, at step 84152, the user specifies the proscribed circumstances which may include, but are not limited to, the following criteria:

1) If the client device is presently in movement, indicating that the user has the device on the user's person or is holding or wearing the device.

2) If the client device is presently physically oriented in any attitude that is an indication that it is in use. For example, if the device is a mobile cell phone that is presently vertically oriented.

3) If the client device presently detects that it is within proximity to a user, such as if the device is being held to the user's face.

4) If the client device presently is placing a telephone call.

5) If the user is presently touching, tapping, or making finger gestures such as swiping, pinching, twirling, or interacting with the client device in any way.

6) If the client device is presently connected with a headset or any other external device.

Subsequently, at step 84154, after the user specifies proscribed circumstances or criteria, applies proscribed circumstances policy throughout all system computers. Then, at step 84156, WPTS updates Client Device data records in its distributed database. the WPTS reads and verifies proscribed circumstances associated with the client device. Subsequently, at step 84158, the WPTS reads and verifies proscribed circumstances associated with the client device. Next, at decision 84160, if proscribed circumstances are present, then at step 84162, power delivery is disabled, or if at decision 84160, proscribed circumstances are not present, then power delivery is enabled at step 84164. The process ends.

GUI app running on said client device may continually monitor the client device to detect if the present operation of said client device matches any of the proscribed circumstances of health safety. Monitoring the client device may include, but is not limited to, reading measurement hardware within said device that determines device's present velocity, yaw, pitch, or roll, or attitude by using accelerometers or gyroscopes internal to said client device, or a sensor that indices if device is help to face, or sensing any other aspect of the device that indicates if a proscribed circumstance is present The health safety determination, of whether or not the client device is presently in a circumstance proscribed from receiving power from said transmission system, may be stored by the GUI app within the data record that describes control and configuration of said client device. Said record may be part of the WPTS's distributed database, a copy of which resides within said client device's memory. GUI app and other computers within the wireless power transmission system then automatically distribute said updated record throughout said system to keep all copies of said database, throughout the WPTS, identical.

EXAMPLES

Example #1 describes how a decision is made to transmit power to a client device. Within the system database, the record of a paired client device is associated with the record of the wireless power receiver attached or built within said client device.

If the user uses any user interface (GUI or web page) of a WPTS to manually command said client device be charged (from power received by said wireless power receiver), or if the user has used said user interface to configure the record of said wireless power receiver to automatically charge said client device, such as by time, name, or physical location, or other method, then, the record of said wireless power receiver will be updated by the wireless power transmitter that has present control of the database record of said wireless power receiver because it is the nearest wireless power transmitter to said wireless power receiver, to indicate that said wireless power receiver should presently close its output switch to allow power to output to said client device. Said record of said wireless power receiver is also distributed, by said wireless power transmitter, throughout said system for other wireless power transmitters to read.

Once said wireless power transmitter that controls said wireless power receiver determines it should transmit power to said wireless power receiver, it next examines the record of the client device associated or paired with said wireless power receiver, and will only transmit power to said wireless power receiver if said health safety determination does not presently proscribe transmission of power to said client device. If power transmission is not proscribed, then power transmitter may take the following actions:

A) Begins real-time communication with said receiver to get continuous feedback of amount of power received, in order to keep transmission antennas aimed at said receiver.

B) Begins power transmission to said receiver.

C) Commands receiver to close its electrical relay switch to connect and transmit electrical energy to client device.

If user changes said safety proscriptions, then said wireless power transmitter will re-determine if said wireless power receiver should receive power or not.

FIGS. 84A-84B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 84A-84B.

Presented below are example embodiments of health safety in a wireless power transmission system.

In some embodiments, an example system for controlling wireless transmission of three-dimensional pockets of energy using pocket forming comprises a processing apparatus, a storage, operatively coupled to the processing apparatus, and one or more wireless power transmitters, communicatively coupled to the processing apparatus, the wireless power transmitters being configured to transmit the three-dimensional pockets of energy. The processing apparatus is configured to receive and process wireless power proscribing data relating to a device, where the proscribing data comprises at least one of (i) a device characteristic and (ii) time data, and where the processing apparatus is configured to transmit an operational command to the one or more power transmitter in response to processing the wireless power proscribing data.

In some embodiments, the system device characteristic comprises data relating to one of (a) movement of the device and (b) an orientation of the device.

In some embodiments, the device characteristic comprises data relating to proximity of the device to a user.

In some embodiments, the device characteristic comprises data relating to device usage by a user.

In some embodiments, the device characteristic comprises data relating to a peripheral device being connected to the device.

In some embodiments, the proscribing data comprises at least one of device sensor data and schedule data.

In some embodiments, the processing apparatus is configured to receive and process further wireless power proscribing data relating to the device and to transmit an updated operational command to the one or more power transmitter in response to processing the further wireless power proscribing data.

In some embodiments, an example method for controlling wireless transmission of three-dimensional pockets of energy using pocket forming comprises receiving and processing, in a processing device, wireless power proscribing data relating to a user device, where the proscribing data comprises at least one of (i) a user device characteristic and (ii) time data, and transmitting an operational command from the processing device to one or more power transmitters, configured to transmit the three-dimensional pockets of energy, in response to processing the wireless power proscribing data.

In some embodiments, the method further comprises the steps of receiving and processing further wireless power proscribing data relating to the user device and transmitting an updated operational command to the one or more power transmitter in response to processing the further wireless power proscribing data.

In some embodiments, an example processor-based method for controlling wireless reception of three-dimensional pockets of energy using pocket forming comprises generating proscribing data in a user device, where the proscribing data comprises at least one of (i) a user device characteristic and (ii) time data, transmitting the proscribing data from the user device to a wireless power system; receiving charging instructions from the wireless power system. The charging instructions include control data for controlling a manner in which the user device receives three-dimensional pockets of energy from the wireless power system.

Figure 85A:
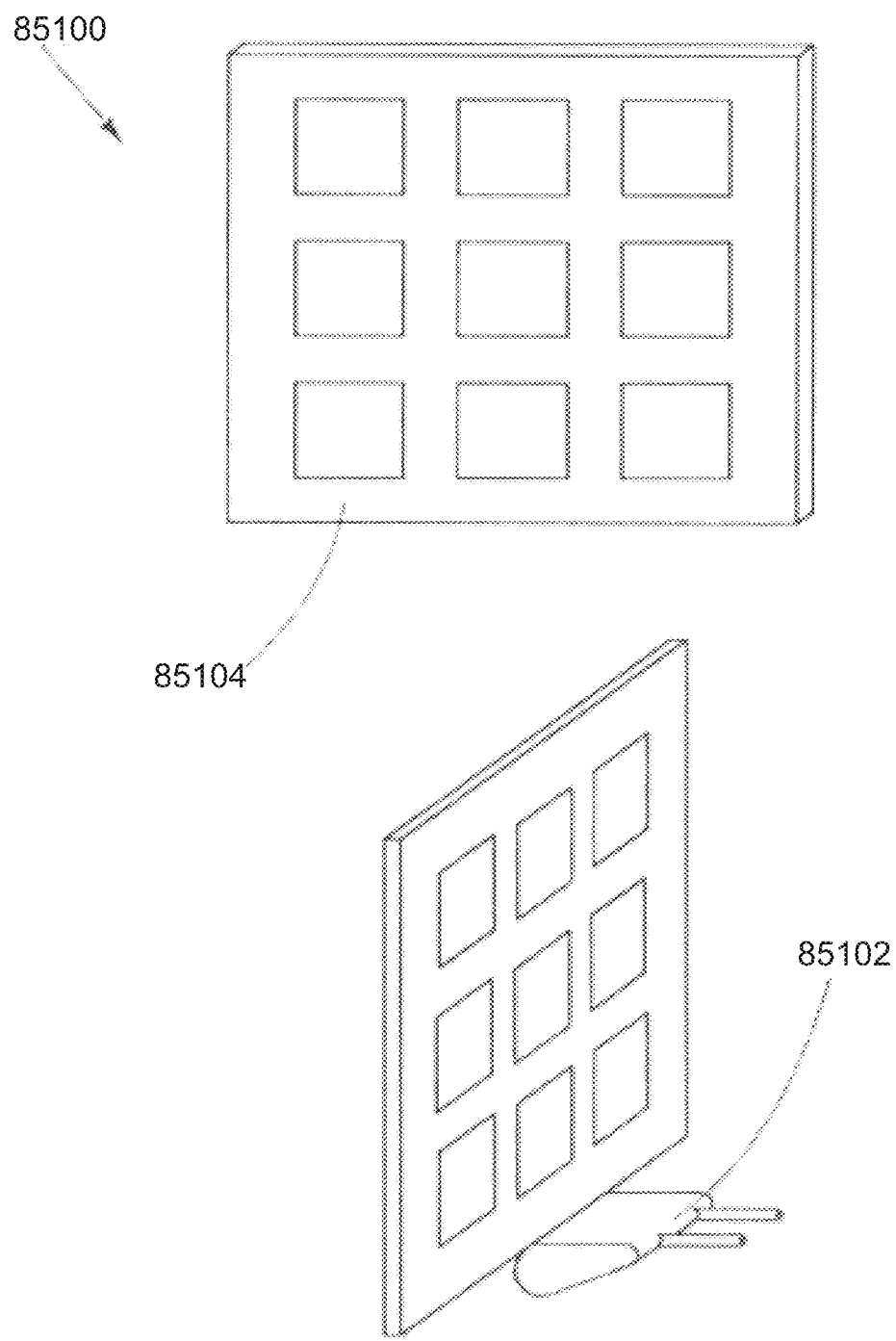
Figure 85B:
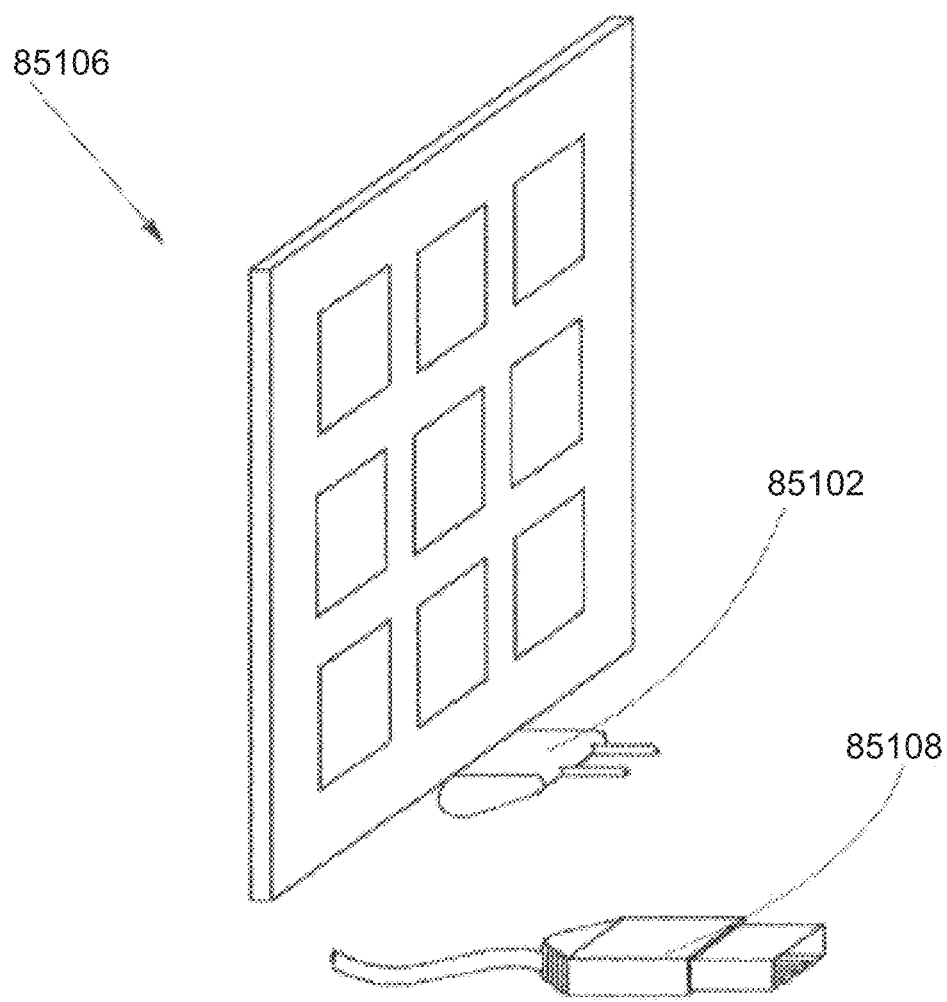

FIGS. 85A-85B illustrate examples of devices, apparatus, and methods for a portable transmitter for wireless power transmission, in accordance with some embodiments.

FIG. 85A depicts a portable wireless transmitter 85100 in a front view and a rear view. Portable wireless transmitter

85100 may include antenna elements in a flat arrangement. Portable wireless transmitter 85100 may he connected to a power source through one or more power plug 85102, such power plug 85102 may comply with the standard of each country and/or region. Power plug 85102 may be intended to connect portable wireless transmitter 85100 to one or more power outlet on the walls, floors, ceilings and/or electric adapters.

In order to increase portability of portable wireless transmitter 85100, power plug 85102 may be foldable, telescopic, ultra-compact and the like. Such features may reduce size for transportation and for pocketing.

Portable wireless transmitter 85100 may he built into a housing 85104, which may provide additional protection against water, high temperature, sand, bugs, shocks, vibration and other rough conditions which may be a threat to the integrity of portable wireless transmitter 85100. Thus, housing 85104 may be made using a plurality of materials which may provide the forgoing characteristics.

FIG. 85B depicts a portable wireless transmitter 85106 showing different power plugs 85102, such power plug 85102 may include a USB adapter 85108, and a cigarette lighter plug 85110. USB adapter 85108 may be used for receive power from any device having a USB port. These devices may include, laptops, Smart TVs, tablets and the like. Cigarette lighter plug 85110 may be used for receive power from any cigarette lighter socket, such as the used in cars. In addition, portable wireless transmitter 85106 may include a variety of power plugs 85102, such power plugs 85102 may vary in dependency with the final application.

FIGS. 85A-85B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 85A-85B.

Presented below are example embodiments of a portable transmitter for wireless power transmission.

In some embodiments, an example method for wireless power transmission by a portable transmitter comprises generating two or more RF waves from the transmitter with at least two RF transmit antennas connected to a radio frequency integrated circuit, managing the generation of RF waves by at least one microcontroller connected to the radio frequency integrated circuit, forming controlled constructive and destructive interference patterns from the generated RF waves by the radio frequency integrated circuit controlled by the microcontroller, accumulating energy or power in the form of constructive interference patterns from the RF waves to form pockets of energy; converging the pockets of energy in 3-d space to a targeted electronic device, and arranging the two antennas in an optimal array for charging or powering the targeted electronic device with the pockets of energy.

In some embodiments, an example method for wireless power transmission by a portable transmitter comprises the steps of: housing solid state circuits including an RF integrated circuit connected to at least two antennas in an enclosure resistant to water, shocks, vibration or adverse environmental conditions to increase the reliability of the portable transmitter, providing a power source through a variety of power plugs connected to the solid state circuits in the enclosure to generate RF waves from the RF integrated circuit, broadcasting the RF waves over the at least two antennas, controlling the generated RF waves by the solid state circuits and the RF integrated circuit to define pocket-forming for converging the RF' waves in 3-d space to form pockets of energy from the RF waves, and arranging the at least two antennas in an optimal array on a surface of the enclosure for wirelessly charging or powering a targeted electronic device with the pockets of energy.

In some embodiments, the power plug is attached to the enclosure and the solid state circuits is connected to a power outlet on a wall, floor, ceiling or other location.

In some embodiments, the method further includes the step of adaptive pocket-forming, to dynamically adjust the pocket-forming in order to regulate power or charging on one or more targeted electronic device.

In some embodiments, the pocket-forming is controlled through phase or gain adjustments of the RF waves to form constructive and destructive interference patterns.

In some embodiments, the method further includes the step of operating the antennas in independent frequencies to allow a multichannel operation of pocket-forming.

In some embodiments, the method uses the values of phase and gain with a microprocessor in the solid state circuits to adjust transmitter antennas to form pockets of energy used to charge or power the electronic device.

In some embodiments, the transmitter has components of the solid state circuits manufactured using meta-materials, micro-printing of solid state circuits, nano-materials to miniaturize and increase the portability of the transmitter.

In some embodiments, the antennas include antenna elements for operating in frequency bands of 900 MHz, 2.5 GHz or 5.8 GHz.

In some embodiments, the microprocessor determines appropriate adjustments for phase and gain in the transmitter antennas for the pocket-forming or for an adaptive pocket-forming or for a multiple pocket-forming to form pockets of energy at the appropriate locations based on the targeted electronic device location.

In some embodiments, the electronic device includes a laptop computer, a smartphone, a tablet, a music player, toys and wireless security cameras.

In some embodiments, the antenna elements include at least one polarization or a selection of polarizations to further include vertical pole, horizontal pole, circularly polarized, left hand polarized, right hand polarized, or a combination of polarizations where the antenna elements are configured to be located within the various surfaces of the wireless transmitter.

In some embodiments, an example wireless portable transmitter for power transmission comprises a housing for embedding analog or digital electrical circuits of the portable transmitter, at least two antennas connected to the electrical circuits, a RF integrated circuit connected to the electrical circuits; a microprocessor connected to the RF integrated circuit to control RF waves generated by the RF integrated circuit and to broadcast the controlled RF waves through the at least two antennas for pocket-forming to form pockets of energy consisting of constructive interference patterns of the controlled RF waves, and a power plug electrically connected to the electrical circuits within the housing for connecting an external power source to the electrical circuits in order to sustain the pockets of energy necessary for Charging or powering an electronic device.

In some embodiments, the wireless portable transmitter housing is generally a rugged, flat and rectangular shape of a predetermined thickness for protecting the electric circuits from rough environmental conditions.

In some embodiments, the wireless portable transmitter microprocessor controls the phase and gain of the RF waves to form constructive and destructive interference patterns resulting in the pockets of energy and null-spaces, respectively.

In some embodiments, the wireless portable transmitter microprocessor calculates the appropriate values of phase and gain to determine appropriate values for all antennas in the transmitter in order to adjust all of the antennas in a transmitter array.

In some embodiments, the wireless portable transmitter has each transmitter operate at different frequencies, power intensities and different ranges to power the electronic device.

In some embodiments, the wireless portable transmitter has power plug connected to the transmitter for delivering a power source is foldable, telescopic, ultra-compact a USB adapter, a cigarette lighter plug or other adapter configuration for a particular country or city code requirements.

In some embodiments, the wireless portable transmitter further includes communication circuitry in the transmitter for sending and receiving communication signals from the targeted electronic device in order to track and concentrate pockets of energy on the electronic device. The communication circuitry utilizes Bluetooth, infrared, FM radio or Zigbee for the communication protocols.

In some embodiments, the wireless portable transmitter housing is configured of a predetermined rugged material to withstand water, high or low temperatures, sand, hugs, shocks, vibration and other rough conditions which are a potential threat to the integrity of the portable wireless transmitter.

FIGS. 86A-86J illustrate examples of devices, apparatus, and methods for a compact PIFA antenna, in accordance with some embodiments.

Figure 86A:
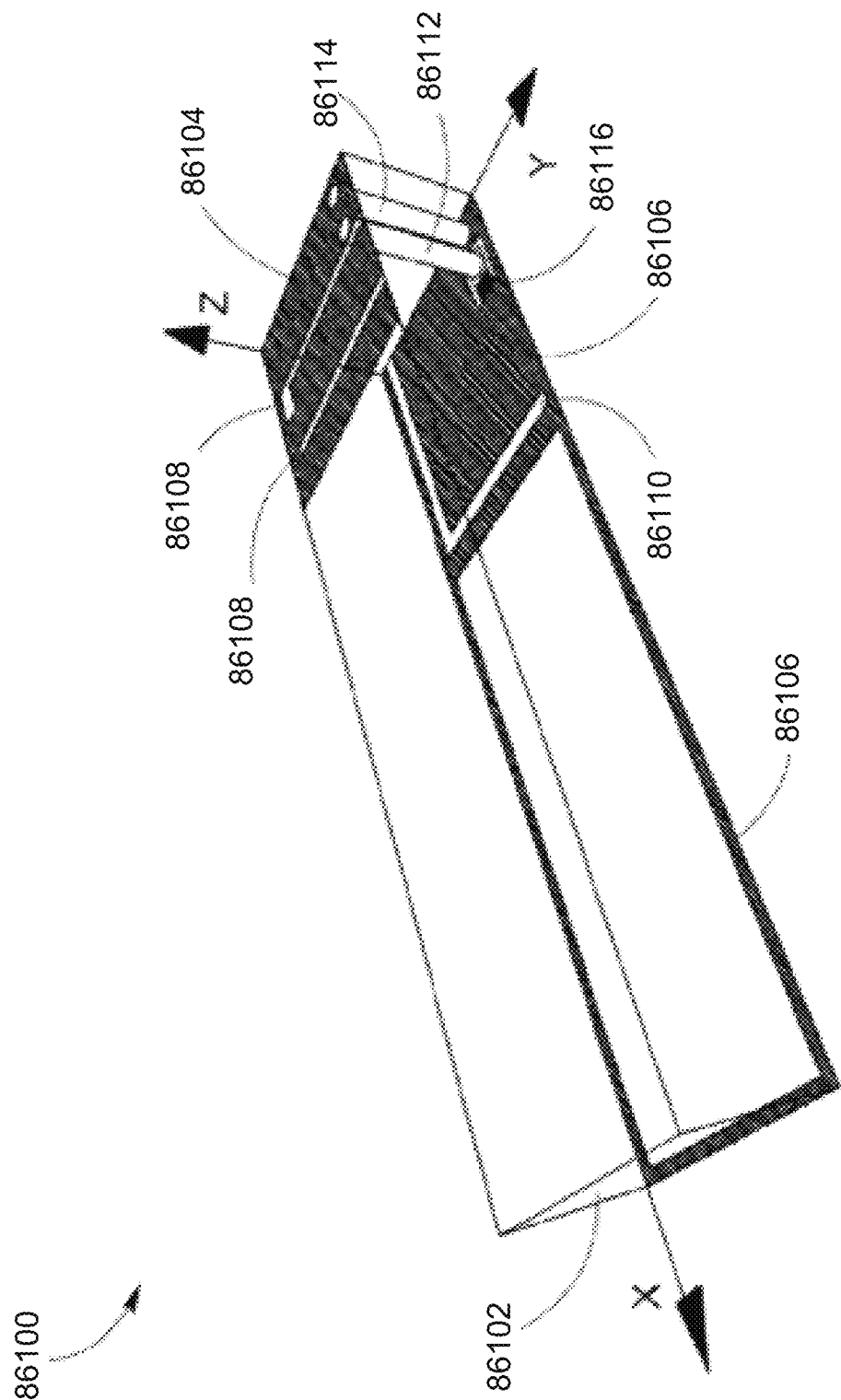

FIG. 86A shows a three-dimensional (3-D) view of a planar inverted-F antenna (PIFA) 86100 integrated in a printed circuit board (PCB) 86102. This PIFA 86100 may be designed to be as small as possible while maintaining a suitable performance for wireless power transmission, and it may be integrated in a double layer PCB for achieving a monolithic form. In one embodiment, PIFA 86100 may be formed on the PCB of an electronic device such as a smartphone, tablet, a laptop computer, a PDA, and the like. In another embodiment, PIFA 86100 may be formed on the PCB of a receiver that may be used for wireless power transmission. Yet in another embodiment, PIFA 86100 may be formed on its own PCB which may be connected to the PCB of an electronic device or a receiver.

PIFA 86100 may include an antenna element 86104 formed over the top layer of PCB 86102, and a ground element 86106 formed over the bottom layer of PCB 86102. Both PCB layers may be made of suitable metals such as copper of small metal thickness relative to the total PCB 86102 thickness. PCB 86102 may include a dielectric base with a suitable dielectric constant. In one embodiment, an Isola FR408HRIS may be used for PCB 86102 materials.

Antenna element 86104 may include two slots 86108 designed for reducing the area of antenna element 86104 while maintaining a suitable bandwidth operation. For example, PIFA 86100 may achieve a bandwidth of about 160 MHz. Without the two slots 86108, PIFA 86100 may still be able to achieve a similar bandwidth, but the area of antenna element 86104 may have to be increased about 34%. More slots may be introduced on antenna element 86104 for even further area reduction if necessary, according to application.

Similar to antenna element 86104, ground element 86106 may include a slot 86110 the main purpose of which may be to reduce the area of the ground element 86106 while reducing losses and increasing radiation efficiency. For example, by including slot 86110, PIFA 86100 may achieve a radiation efficiency of about 69%. In one embodiment, slot 86110 in ground element 86106 may increase the radiation efficiency of PIFA 86100 by about 22% and about 32% for PCB 86102 substrates having a thickness of about 1.4 mm and about 0.8 mm, respectively. In another embodiment, the combination of ground slot 86110 and ground element 86106 missing central area may increase the radiation efficiency by about 32% and about 54% for 1.4 mm-thick and 0.8 mm-thick PCB 86102 substrates, respectively, relative to designs with solid ground.

PIFA 86100 may also include a signal via 86112, a ground via 86114, and a RF port 86116 for electrical connection purposes. In one embodiment, a semi-rigid 50 Ohm coax cable can be connected to RF port 86116 for prototype measurements. For integration purposes, PIFA 86100 may be fed through RF port 86116 by a transmission line integrated in a larger PCB.

In an embodiment, dimensions of PIFA 86100 may be about 12 mm, 3.5 mm, and 1.4 mm in the x-axis, y-axis, and z-axis respectively, for an estimated system area of about 42 mm2 and a system volume of about 58.8 mm$^3$.

Figure 86B:
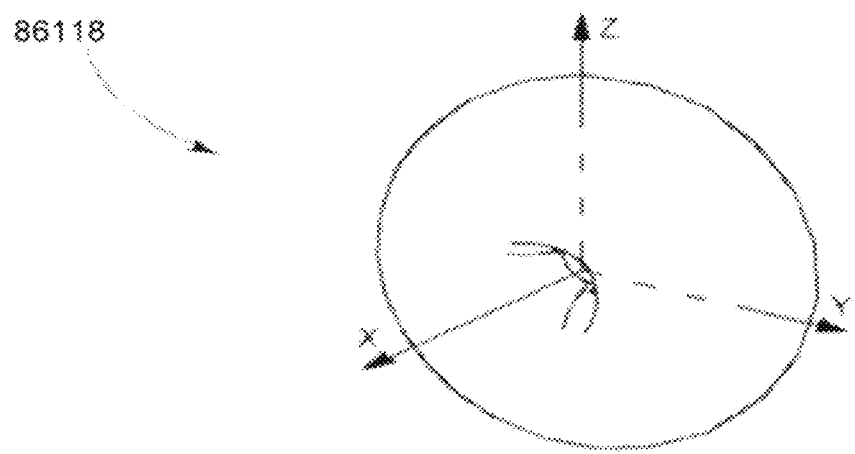
Figure 86C:
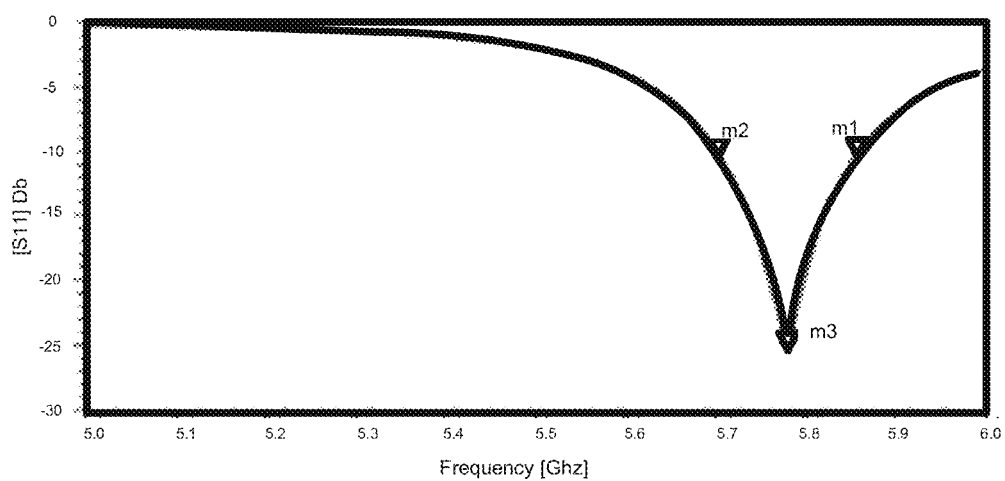

FIGS. 86B and 86C show the performance 86118 of PIFA 86100 according to embodiments described herein.

FIG. 86B shows an omnidirectional 3-D radiation pattern of PIFA 86100 oriented as shown in FIG. 86A. This omnidirectional radiation pattern in FIG. 86B may be similar to radiation patterns exhibited in dipole antennas, thereby allowing flexible placement or integration of PIFA 86100 into larger form factors, for example, a receiver PCB or an electronic device PCB. In one embodiment, PIFA 86100 may exhibit a maximum gain of about −0.0099 dBi at 5.8 GHz.

FIG. 86C illustrates the return loss of PIFA 86100 when fed by a 50-Ohm port. As seen from probes m1 and m2, PIFA 86100 may exhibit an impedance bandwidth of about 160 MHz at −10 dB, where this bandwidth may provide sufficient margins for possible detuning upon integration of PIFA 86100 into an electronic device or a larger PCB. Radiation efficiency of PIFA 86100 may be around 69% at 5.8 GHz.

Although PIFA 86100 may exhibit suitable characteristics for wireless power transmission, it may be an object of the following embodiments to provide PIFAs with a similar monolithic PCB form factor, but with a reduced size and a similar or improved performance in terms of impedance bandwidth, radiation pattern, and maximum radiation efficiency.

Figure 86D:
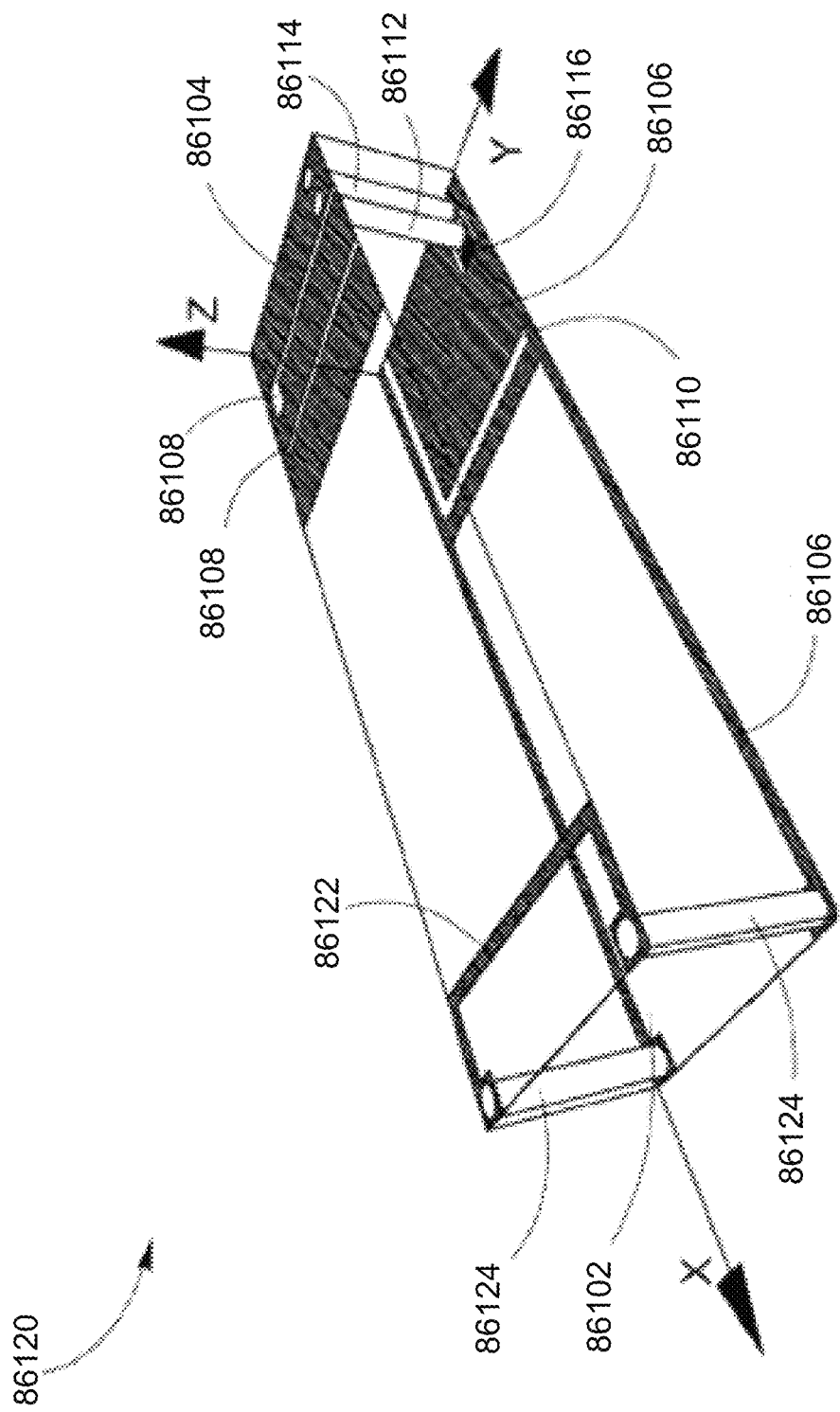

FIG. 86D is a 3-D view of a PIFA 86120 with a folded ground 86122, according to embodiments. This PIFA 86120 may be designed to be as small as possible while maintaining a suitable performance for wireless power transmission, and it may be integrated in a double layer PCB for achieving a monolithic form. In one embodiment, PIFA 86120 may be formed on the PCB of an electronic device such as a smartphone, tablet, a laptop computer, a PDA, and the like. In another embodiment, PIFA 86120 may be formed on the PCB of a receiver that may be used for wireless power transmission. Yet in another embodiment, PIFA 86120 may be formed on its own PCB which may be connected to the PCB of an electronic device or a receiver.

Similar to PIFA 86100, PIFA 86120 in FIG. 86D may include PCB 86102, antenna element 86104, ground element 86106, antenna slots 86108, ground slot 86110, signal via 86112 and ground via 86114. However, unlike PIFA 86100, PIFA 86120 may include folded ground 86122 which can be formed over an empty region of the top layer of PCB 86102 without interfering with the performance of antenna element 86104. Folded ground 86122 can be raised over the top layer of PCB 86102 and can be connected to ground element 86106 through folded ground vias 86124 which may not significantly affect the performance of PIFA 86120. Folded ground 86122 may act as an extension of ground element 86106.

According to some aspects of this embodiment, folded ground 86122 may allow the dimensions of PIFA 86120 to be reduced compared to the dimensions of PIFA 86100, while improving or at least maintaining similar performance characteristics. For example, PIFA 86120 dimensions in the x-axis, y-axis, and z-axis may be about 10 mm, 3.3 mm, and 1.4 mm respectively, for a system area of about 33 mm$^2$ and a system volume of about 46.2 mm$^3$. This can be translated to a 21% reduction in system area and volume as compared to PIFA 86100.

Figure 86E:
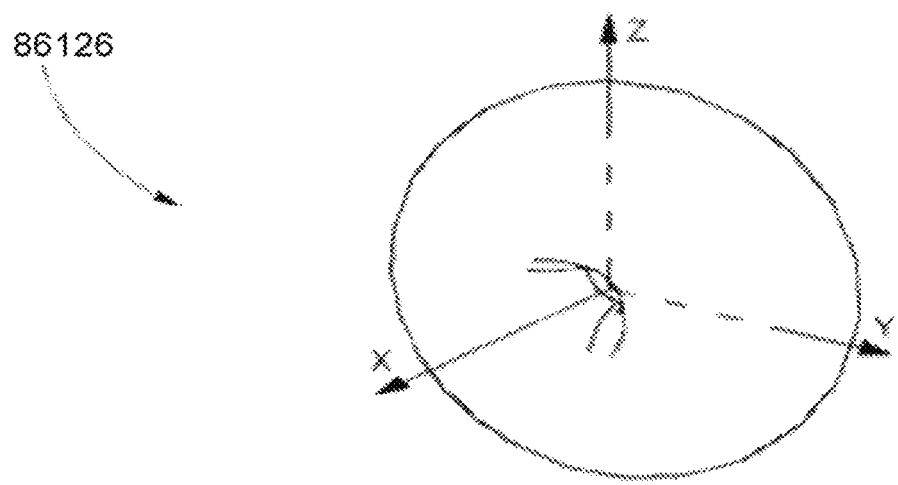
Figure 86F:
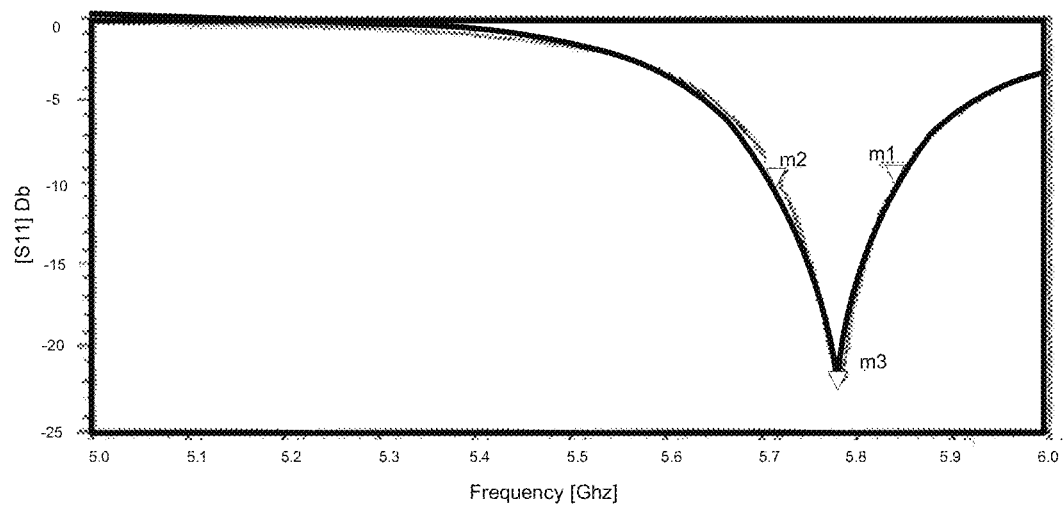

FIGS. 86E and 86F show the performance 86126 of PIFA 86120 according to embodiments described herein. Performance 86126 of PIFA 86120 may be fairly similar to performance 86118 of PIFA 86100, but significant reductions in size may be achieved as previously stated.

FIG. 86E shows an omnidirectional 3-D radiation pattern of PIFA 86120 oriented as shown in FIG. 86D. As seen in FIG. 86E, PIFA 86120 may still exhibit a suitable omnidirectional radiation pattern which may allow a flexible placement or integration of PIFA 86120 into larger form factors, for example, a receiver PCB or an electronic device PCB. In one embodiment, PIFA 86120 may exhibit a maximum gain of about −0.078 dBi at 5.8 GHz.

FIG. 86F illustrates the return loss of PIFA 86120 when fed by a 50-Ohm port. As seen from probes m1 and m2, PIFA 86120 may exhibit an impedance bandwidth of about 140 MHz at about −10 dB which may be slightly lower than the impedance bandwidth of PIFA 86100, but it may still be able to provide sufficient margins for possible detuning upon integration of PIFA 86120 into an electronic device or a larger PCB form. PIFA 86120 may exhibit a radiation efficiency of about 62% which may be slightly lower than the radiation efficiency exhibited by PIFA 86100, but it may be still suitable for effective wireless power transmission.

Figure 86G:
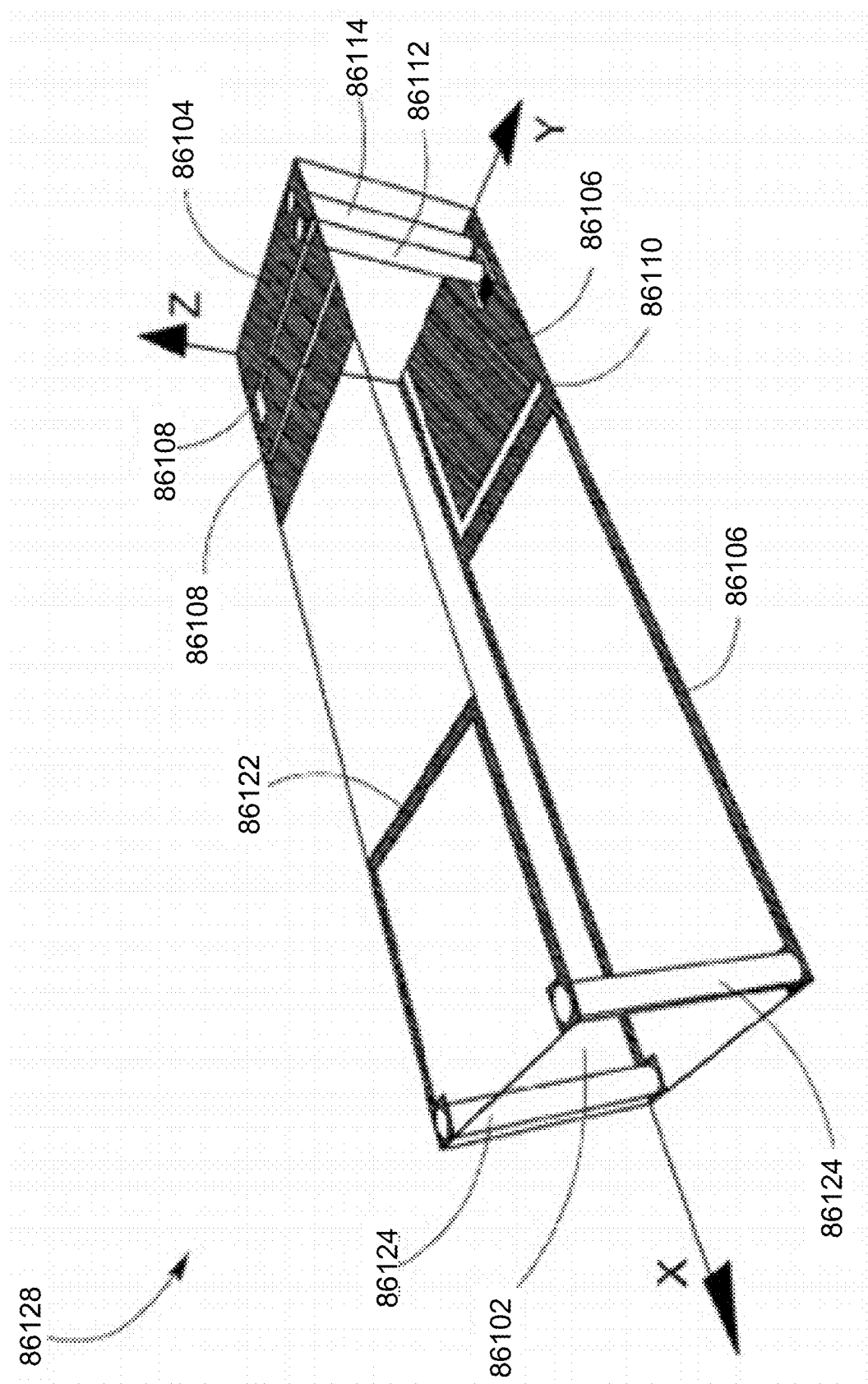

FIG. 86G illustrates a 3-D view of a PIFA 86128 with folded ground 86122 extended closer to antenna element 86104, according to embodiments of the present invention. This PIFA 86128 may be designed to be as small as possible while improving or at least maintaining a suitable performance for wireless power transmission. PIFA 86128 may be integrated in a double layer PCB for achieving a monolithic form. In one embodiment, PIFA 86128 may be formed on the PCB of an electronic device such as a smartphone, tablet, a laptop computer, a PDA, and the like. In another embodiment, PIFA 86128 may be formed on the PCB of a receiver that may be used for wireless power transmission. In yet another embodiment, PIFA 86128 may be formed on its own PCB which may be connected to the PCB of an electronic device or a receiver.

Similar to PIFA 86120, PIFA 86128 may include PCB 86102, antenna element 86104, ground element 86106, antenna slots 86108, ground slot 86110, signal via 86112, ground via 86114, folded ground 86122, and folded ground vias 86124. However, compared to PIFA 86120, folded ground 86122 in PIFA 86128 may be moved closer to antenna element 86104 as seen in FIG. 86G. In addition, the thickness of PIFA 86128 may be increased from about 1.4 mm to about 2.4 mm. PIFA 86128 dimensions in the x-axis, y-axis, and z-axis may be about 10 mm, 2.4 mm, and 2.4 mm respectively, for a system area of about 24 mm$^2$ and a system volume of about 57.6 mm$^3$.

According to some aspects of this embodiment, by extending folded ground 86122 towards antenna element 86104, the system area of PIFA 86128 can be reduced about 27% and 43% compared to PIFA 86120 and PIFA 86100 respectively. Moreover, by combining this extended folded ground 86122 with a slightly thicker PCB, the overall performance of PIFA 86128 may be significantly improved. For example, PIFA 86128 may achieve a radiation efficiency of about 82% at 5.8 GHz compared to about 69% in PIFA 86100 and 62% in PIFA 86120.

Figure 86H:
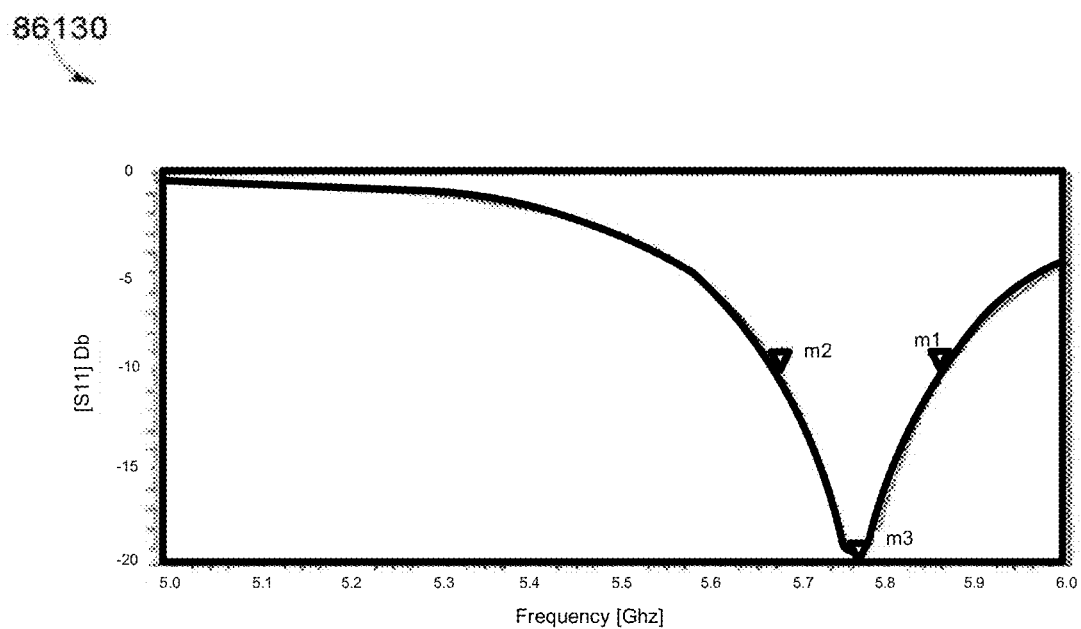

FIG. 86H shows the performance 86130 of PIFA 86128 according to embodiments described herein. Compared to PIFA 86100 and PIFA 86120, the performance of PIFA 86128 may be significantly improved, while also achieving significant reductions in system area as previously stated.

In addition to a higher radiation efficiency, the return loss of PIFA 86128 when fed by a 50-Ohm port, as shown in FIG. 86H, may exhibit a higher impedance bandwidth of about 180 MHz at −10 dB, compared to 160 MHz and 140 MHz for PIFA 86100 and PIFA 86120 respectively. This bandwidth may provide sufficient margins for possible detuning upon integration of PIFA 86128 into an electronic device or a larger PCB form factor.

As in PIFA 86100 and PIFA 86120, PIFA 86128 may still exhibit an omnidirectional radiation pattern (not shown in FIG. 86H) for allowing flexible placement or integration of PIFA 86128 into larger form factors, for example, a receiver PCB or an electronic device PCB. In one embodiment, PIFA 86128 may exhibit a gain of about +0.55 dBi at 5.8 GHz.

Figure 86I:
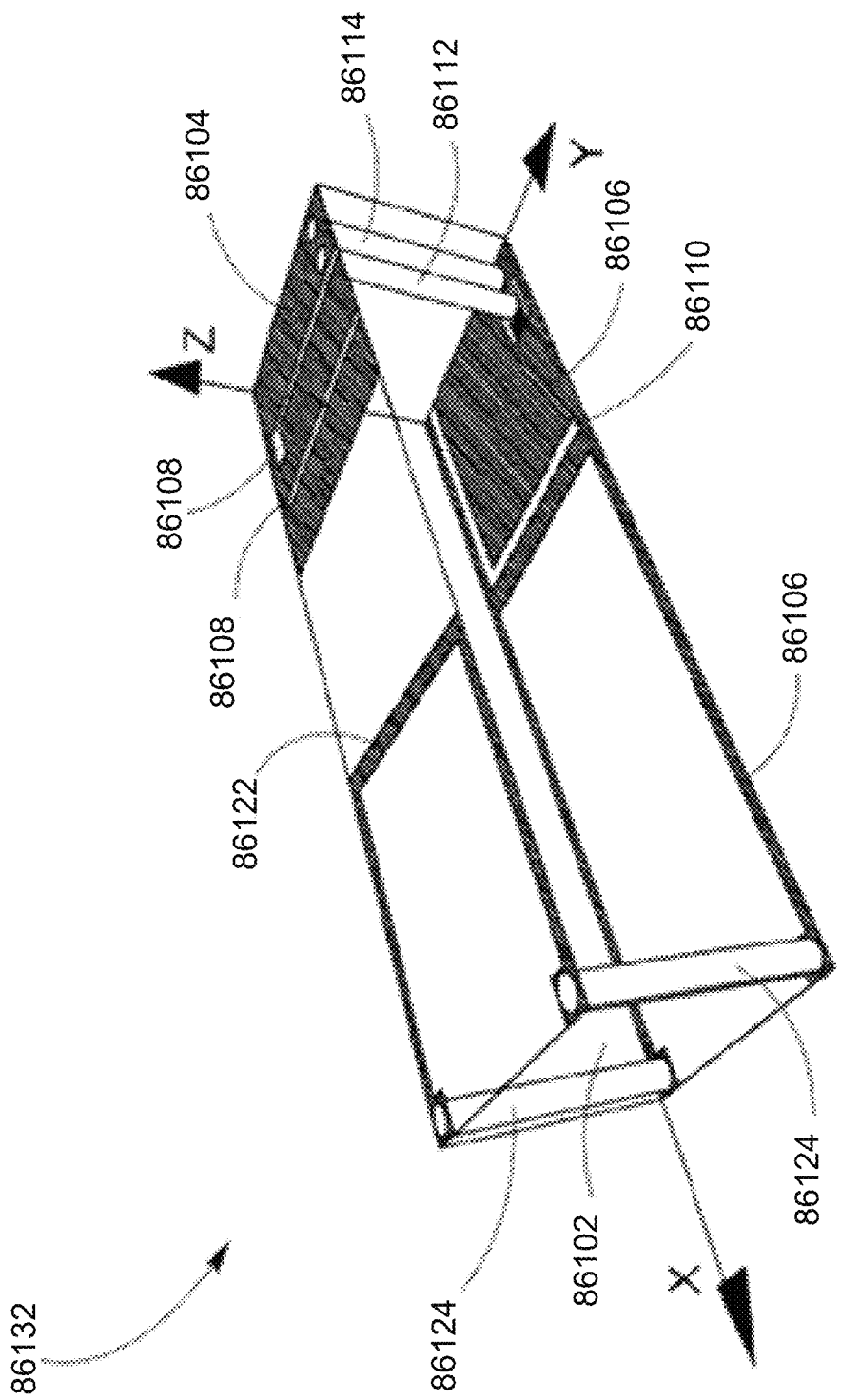

FIG. 86I shows a 3-D view of a PIFA 86132 where folded ground 86122 can be extended even closer to antenna element 86104, according to embodiments of the present invention. This PIFA 86132 may be designed to be as small as possible while improving or at least maintaining a suitable performance for wireless power transmission. PIFA 86132 may be integrated in a double layer PCB for achieving a monolithic form. In one embodiment, PIFA 86132 may be formed on the PCB of an electronic device such as a smartphone, tablet, a laptop computer, a PDA, and the like. In another embodiment, PIFA 86132 may be formed on the PCB of a receiver that may be used for wireless power transmission. Yet in another embodiment, PIFA 86132 may be formed on its own PCB which may be connected to the PCB of an electronic device or a receiver.

Similar as in PIFA 86120 and PIFA 86128, PIFA 86132 may include PCB 86102, antenna element 86104, ground element 86106, antenna slots 86108, ground slot 86110, signal via 86112, ground via 86114, folded ground 86122, and folded ground vias 86124. However, as seen in FIG. 86I, folded ground 86122 can be moved even closer to antenna element 86104 as compared to PIFA 86128 and PIFA 86120. In an embodiment, the thickness of PIFA 86132 may be about 2.4 mm. Overall PIFA 86132 dimensions in the x-axis, y-axis, and z-axis may be about 9 mm, 2.4 mm, and 2.4 mm respectively, for a system area of about 21.6 mm$^2$ and a system volume of about 51.8 mm$^3$.

According to some aspects of this embodiment, by extending folded ground 86122 even closer to antenna element 86104 as compared to PIFA 86128, the system area and volume area of PIFA 86132 may be reduced about 10% more, while maintaining a similar performance. For example, PIFA 86132 may exhibit a radiation efficiency of about 76%, at 5.8 GHz, just slightly lower than radiation efficiency in PIFA 86128, but higher compared to PIFA 86120 and PIFA 86100. In one embodiment, folded ground 86122 in PIFA 86132 may be at a maximum allowable distance from antenna element 86104 for maintaining a suitable performance for wireless power transmission.

Compared to PIFA 86120 and PIFA 86100, the system area reductions achieved in PIFA 86132 may be significantly higher, about 35% and 49% respectively. Similarly, PIFA 86132 may exhibit an enhanced performance in terms of higher impedance bandwidth and radiation efficiency as compared with PIFA 86120 and PIFA 86100.

Figure 86J:
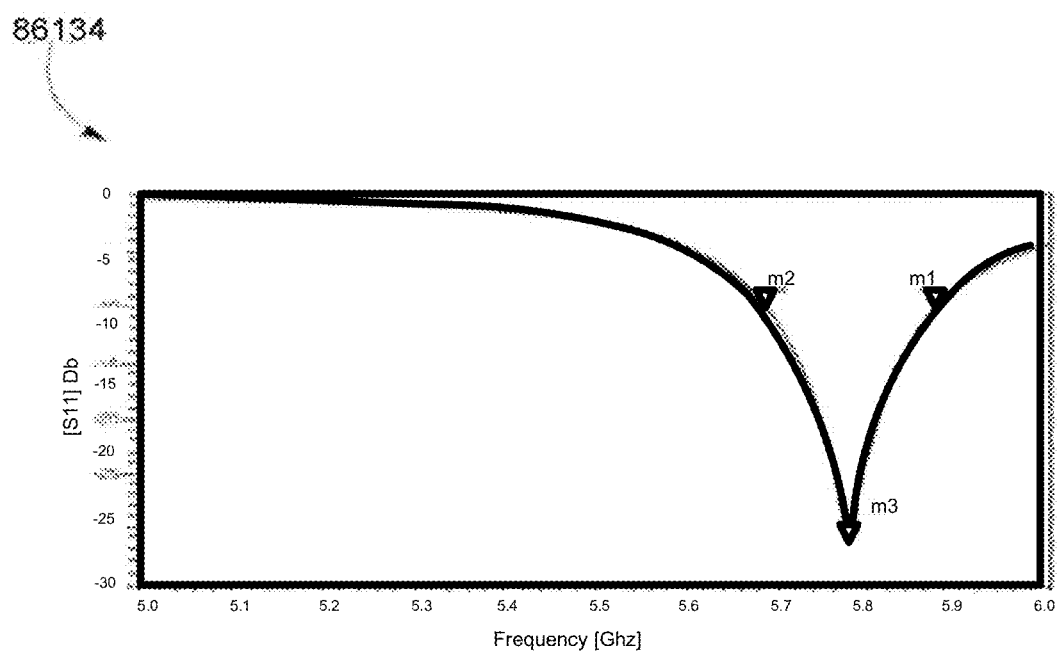

FIG. 86J shows the performance 86134 of PIFA 86132 according to embodiments described herein. Compared to PIFA 86100, PIFA 86120, and PIFA 86128, performance of PIFA 86132 may be maintained fairly similar and in some cases, it may be enhanced; all of this while achieving significant reductions in system area.

The return loss of PIFA 86132 when fed by a 50-Ohm port, as shown in FIG. 86J, may exhibit an impedance bandwidth of about 180 MHz at −10 dB, which is about the same bandwidth exhibited by PIFA 86128, but higher compared to 160 MHz and 140 MHz for PIFA 86100 and PIFA 86120 respectively. This bandwidth may provide sufficient margins for possible detuning upon integration of PIFA 86132 into an electronic device or a larger PCB form factor.

PIFA 86132 may still exhibit an omnidirectional radiation pattern (not shown in FIG. 86J) for allowing flexible placement or integration of PIFA 86132 into larger form factors, for example, a receiver PCB or an electronic device PCB. In one embodiment, PIFA 86132 may exhibit a maximum gain of about +0.019 dBi at 5.8 GHz.

In general, folded ground 86122 in PIFA 86120, PIFA 86128, and PIFA 86132 may allow significant reductions in the system area compared to the prior art. And by combining folded ground 86122 with a slightly thicker PCB, the performance in PIFA 86128 and PIFA 86132 may be improved even more.

It may be apparent to someone skilled in art that the selection of the optimal PIFA configuration may depend on the characteristics and form factor of a particular receiver or electronic device. For example, optimal configurations may be selected based on criteria of having a PIFA with the smallest system area; the higher impedance bandwidth; the higher radiation efficiency; the smallest system volume; or a combination of criteria as required by the application.]

FIGS. 86A-86J illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 86A-86J.

Presented below are example embodiments of a compact PIFA antenna.

In some embodiments, an example planar inverted-F antenna (PIFA), comprises a printed circuit board (PCB) formed of an electrically insulating material with a low electrical conductivity, the PCB having a top surface and a bottom surface, and a thickness defined by a shortest distance between the top surface and the bottom surface, an antenna element formed of an electrically conducting material with an electrical conductivity higher than that of the PCB, the antenna element disposed on the top surface of the PCB, the antenna element having a predetermined impedance bandwidth and a plurality of slots arranged to provide the antenna element with a surface area smaller than a surface area of an antenna element having the same impedance bandwidth but not having a plurality of slots, all other parameters relevant to the impedance bandwidth being equal, a ground element formed of an electrically conducting material with an electrical conductivity higher than that of the PCB, the ground element disposed on the bottom surface of the PCB and operatively coupled to the antenna element, the ground element having a continuous perimeter defining a central area at least a portion of which comprises a layer formed of the electrically conducting material that is substantially continuous, the layer having at least one internal slot arranged to provide the ground element with a layer smaller than a layer of a ground element providing the same radiation efficiency but not having at least one internal slot, all other parameters relevant to the radiation efficiency being equal.

In some embodiments, the PIFA has the ground element operatively coupled to the antenna element through a ground via and a signal via each defined by a respective hole through the PCB.

In some embodiments, the PIFA ground element perimeter encloses a portion of the central area that does not comprise a substantially continuous layer formed of the electrically conducting material.

In some embodiments, the PIFA ground element comprises a folded portion that extends from the bottom to the top of the PCB and toward the antenna element.

In some embodiments, the PIFA has the portion of the ground element on the top of the PCB operatively coupled to the portion of the ground element on the bottom of the PCB through folded ground vias each defined by a respective hole through the PCB.

In some embodiments, the PIFA antenna element is disposed substantially directly above the substantially continuous portion of the ground element, the portion of the ground element disposed on the top surface of the PCB is disposed substantially directly above a corresponding portion of the ground element disposed on the bottom surface of the PCB, and an area defined by the perimeter of the ground element viewed from a point on a line through the center of the ground element and normal to one of the surfaces of the PCB, is smaller than a corresponding area of a PIFA providing substantially similar radiation pattern, impedance bandwidth, and radiation efficiency, but having a ground element that does not include a folded portion.

In some embodiments, the PIFA has the thickness of the PCB greater than a corresponding thickness of the PIFA that does not include a folded portion.

In some embodiments, the PIFA has the distance between the antenna element and the portion of the ground element disposed on the top of the PCB, and the thickness of the PCB, are both configured to minimize the area defined by the ground element while providing at least a predetermined radiation pattern, impedance bandwidth, and radiation efficiency.

In some embodiments, the PIFA presents a monolithic form factor on a single double layer PCB.

In some embodiments, the PIFA PCB is dedicated to the PIFA and configured to be connected to the PCB of an electronic device.

In some embodiments, the PIFA PCB is physically coupled to at least one element of an apparatus that does not form part of the PIFA.

In some embodiments, the PIFA is incorporated into an electronic device.

In some embodiments, the PIFA is incorporated into an electronic device which is one of a receiver, a smartphone, a tablet computer, a laptop computer, and a personal digital assistant (PDA).

In some embodiments, the PIFA electronic device provides wireless power transmission.

In some embodiments, the PIFA during operation provides a radiation pattern that is substantially omnidirectional.

In some embodiments, the PIFA during operation provides sufficient margins for possible detuning upon integration into an electronic device.

In some embodiments, the PIFA provides a gain at 5.8 GHz of between about −0.078 dBi and +0.55 dBi.

In some embodiments, the PIFA exhibits an impedance bandwidth at 5.8 GHz and −10 dB of between about 140 MHz and 180 MHz.

In some embodiments, the PIFA exhibits a radiation efficiency at 5.8 GHz of between about 62% and 82%.

In some embodiments, the PIFA PCB thickness is one of 0.8 mm, 1.4 mm, and 2.4 mm, the width of the PIFA is between about 2.4 mm and 3.5 mm, and the length of the PIFA is between about 9 mm and 12 mm.

In some embodiments, the PIFA operation in other desired frequency bands may be obtained by suitably scaling the dimensions of antenna, antenna slots, ground, ground slot, PCB insulating material permittivity and PCB thickness.

FIGS. 87A-87E illustrate examples of devices, apparatus, and methods for a simultaneous power and payload receiver, in accordance with some embodiments.

Figure 87A:
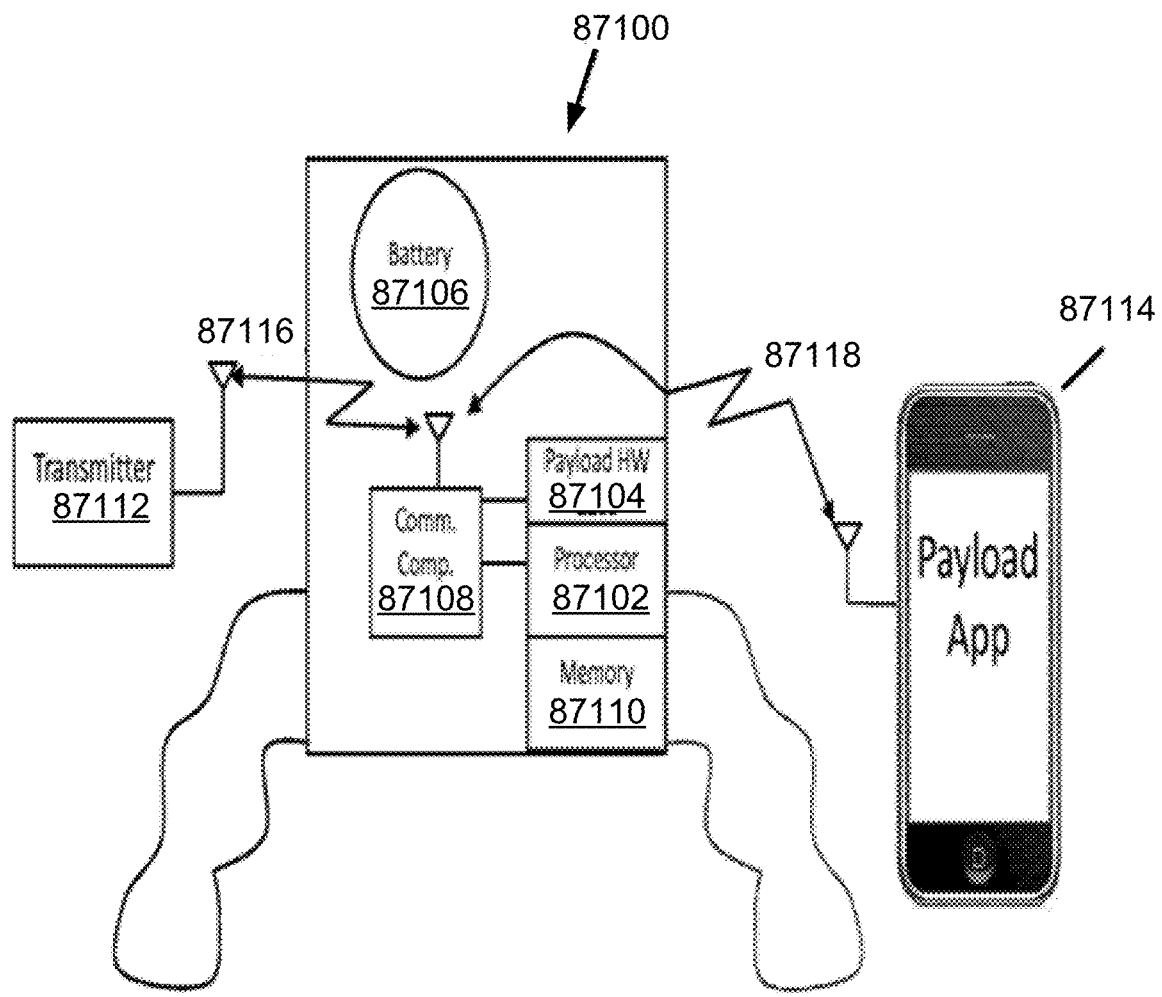

FIG. 87A shows a schematic representation of a wearable device 87100, which may be a type of computing device comprising a receiver, as described above. A wearable 87100 may be an article of clothing (e.g., shirt, hat, pants, shoes) or other personal accessory (e.g., jewelry, belt, book bag, wristband, watch, anklet) of a user, and may comprise a computing processor 87102, payload hardware 87104, a battery 87106, and a communication component, which in FIG. 87A is a Bluetooth® low-energy antenna and processor (BLE) 87108. The wearable 87100 may further comprise memory 87110 for storing the computer's programming and payload application data.

A computing processor 87102 of the wearable 87100 may be integrated circuitry capable of performing power and payload functionality for the wearable 87100. The wearable 87102 may communicate payload application data with a smart device 87114 to provide the user with the desired functionality, for which the wearable 87100 was designed. For example, if the wearable 87100 is a heart rate monitor, then the payload application executed by the smart device 87114 may be a software application that provides features such as heart rate tracking, dietary data, exercise data, among other heart health information and features. In this example, the payload application data may be heart rate measurements observed by the wearable 87100. The smart device 87114 may be any computing device comprising a processor capable of executing the payload application and that is capable of communicating payload application instructions and data over a wireless protocol, such as Bluetooth®, NFC, BLE, RFID, Wi-Fi, and the like. Non-limiting examples of the smart device 87114 may include a smartphone, laptop, or other computing device.

Payload hardware 87104 may be circuitry of the wearable 87100 capable of executing various processes and tasks in accordance with the features of the payload application and functional purpose of the wearable 87100. Returning to the example in which the wearable 87100 is a heart rate monitor, which may be worn on a user's wrist: in this example, the payload hardware 87104 may comprise components capable of measuring the user's heart rate and blood pressure. The processor 87102 of the wearable 87100 may receive the measurements from the payload hardware 87104 and then produce payload application data from the measurements. Although the examples of a wearable 87100 describe a heart rate monitor, it should be appreciated that the wearable 87100 may be any device that is worn by the user and provides various computing features (e.g., smart watches, smart glasses). As such, a wearable 87100 may comprise payload hardware 87104 rendering the wearable 87100 capable of the intended functionality.

In some embodiments, the wearable 87100 may comprise a battery 87106 capable of holding an electrical charge. The battery 87106 may power the computing processor 87102 and the payload hardware 87104. In some embodiments, the battery 87106 of the wearable 87100 may receive the electrical charge from the communications component 87108, which may comprise a receiver configured to harvest energy from pockets of energy produced by transmitters 87112. In some embodiments, the wearable 87100 may forego a battery 87106 and may be powered entirely by electrical energy harvested by a receiver of the communications component 87108.

A communications component 87108 may be circuitry of the wearable 87100 that may communicate control signals 87116 with a transmitter 87112 data using one or more wireless communications protocols (e.g., Bluetooth, BLE, Wi-Fi, NFC, RFID). The communications component 87108 may communicate payload application data over a second communication channel 87118 with a smart device 87114 executing a payload application associated with the functionality of the wearable 87100. The wearable 87100 may communicate control signals 87116 with a transmitter 87112 concurrently to communicating the payload application data to the smart device 87114 over the second communication channel 87118. In some embodiments, the wearable 87100 may communicate simultaneously with both the transmitter 87112 and the smart device 87114. In such embodiments, the communications component 87108 and the processor 87102 may be capable of receiving and processing the respective communications signals simultaneously. In some embodiments, the wearable 87100 may alternate communications between the transmitter 87112 and the smart device 87114. In such embodiments, the processor 87102 and communications component 87108 may communicate with each device for a predetermined period of time.

Control signals 87116 may contain control data produced by the processor 87102 and communications component 87108 of the wearable 87100, which the transmitter 87112 may use to adjust power transmission waves that the transmitter 87112 emits to generate pockets of energy. The control data of the control signals 87116 may contain, for example, data indicating the location of the wearable relative to the transmitter 87112, and data indicating the amount of power that the wearable 87100 has effectively harvested from a pocket of energy generated by the transmitter 87112. In some cases, the control signals 87116 may include an advertisement signal for establishing a first communication between the transmitter 87112 and the communications component 87108 of the wearable 87100.

Payload application data collected by the payload hardware 87104 may be transmitted to the smart device 87114, over a second communication channel 87118. The second communication channel 87118 hosting the payload application data may implement any wireless communication protocol capable of transmitting the payload application data from the wearable to the smart device 87114. In some embodiments, the communications component 87108 may transmit the payload application data at a given interval. In some embodiments, the payload application data may be transmitted at the moment the wearable 87100 and the smart device 87114 are brought into communicative proximity; in such embodiments, the second communication channel 87118 may be automatically established, and the smart device 87114 and wearable 87100 may then automatically exchange payload application data collected by the payload hardware 87104 of the wearable 87100.

In some embodiments, the wearable 87100 may comprise memory 87110, which may be a non-transitory machine-readable storage media that is capable of storing binary data. In some cases, the memory 87110 may store programming associated with the payload application that may be executed by the processor 87102 and/or the payload hardware 87104. When the processor 87102 executes the programming stored in the memory 87110, the payload hardware 87104 may collect measurements and perform various tasks intended to provide the intended functionality of the wearable 87100 and the associated payload application. In some cases, the memory 87110 may store control data that may inform transmitters 87112 of an optimal waveform and direction for transmitting power transmission waves to establish pockets of energy. In such cases, the wearable 87100 may transmit the control data for the transmitters 87112 to determine how the power transmission waves should be produced and transmitted. The processor 87102 may continuously update the memory 87110 with control data representing more effective ways for the transmitters 87112 to produce and transmit power control waves.

A smart device 87114 may be any computing device comprising a processor that executes a payload application associated with the wearable 87100, a communication component that communicates payload application data and instructions with the wearable 87100 over a second communications channel 87118. In some embodiments, communication between wearable and smart device 87114 may be through Bluetooth Low Energy (BLE), Wi-Fi, or other wireless communication protocol. Application payload data may include wearable 87100 status or usage reports, or payload application data generated by the wearable 87100. As an example, for embodiments in which the wearable 87100 is a heart rate monitor, the payload application data may include heart rate measurements or physical exertion data.

A transmitter 87112 may be any device that emits power transmission waves that establish a pocket of energy, which may be harvested by receivers and converted to electric energy. The transmitter 87112 may transmit power transmission waves to a wireless power receiver, which may be a component of the communications component 87108 of the wearable 87100 shown in FIG. 87A. In some embodiments, the wearable 87100 may communicate an advertisement signal to establish a first communication channel, which hosts control data 87116. After establishing the first communication channel hosting control data 87116, the transmitter 87112 may then begin communicating control data 87116 with the wearable 87100, to manage delivery of electrical energy to the battery 87106 of the wearable 87100. In some embodiments, the wearable 87100 may use the same or a different communication channel to upload application payload data to the transmitter 87112, which the transmitter 87112 may upload to a server of a computing service associated with the transmitters 87112. Control data may include wearable 87100 device status and usage reports.

Method of Programming Wearable Device

Figure 87B:
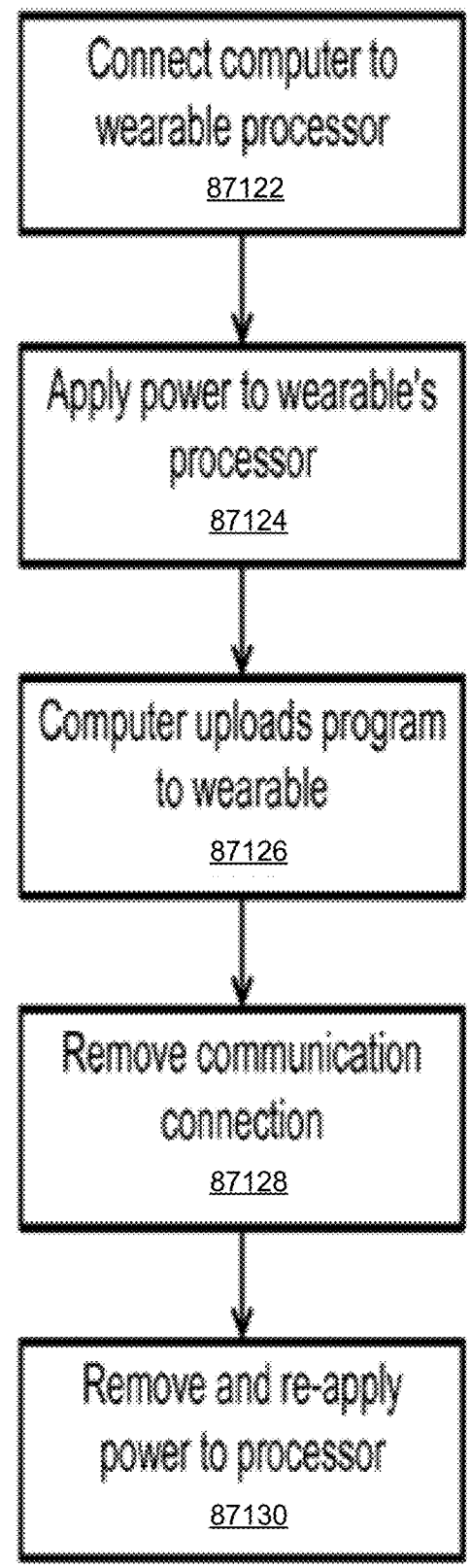

FIG. 87B shows steps of executed for programming a processor of a wearable and payload hardware of the wearable, according to an exemplary embodiment.

In a first step 87122, at manufacture time of the wearable, an external computing device may be communicatively coupled to the processor of the wearable. The computer may be coupled to the processor of the wearable using a communication connection capable of uploading binary data that programs the functionality of the wearable processor. Non-limiting examples of the connection may include a serial data connection, such as RS232, or universal service bus (USB) connection, and the like.

In a next step 87124, power (i.e., an electrical charge) may be applied to the wearable's processor, which may be "blank" or without prior programming. In some cases, the processor may be placed into a "programming mode" that will permit the processor to accept programming uploaded from the external computer.

In a next step 87126, after power is applied to the wearable's processor, the external computer may proceed to upload or transmit the binary data containing the programming, which may include an executable program or 'object code,' which instructs the wearable's processor on providing the intended functionality. The programming may be stored into non-transitory machine-readable storage memory accessible to the processor.

In a next step 87128, upon successful installation of the programming for the executable object code, the communication connection coupling the processor to the external computer may be removed.

In a next step 87130, the power supplied to the processor of the wearable may be removed or otherwise terminated. The power may then be re-applied to the wearable's processor, which may cause the processor to 'boot up,' during which time the processor may fetch and proceed to execute the executable program recently stored in the memory of the wearable.

Figure 87C:
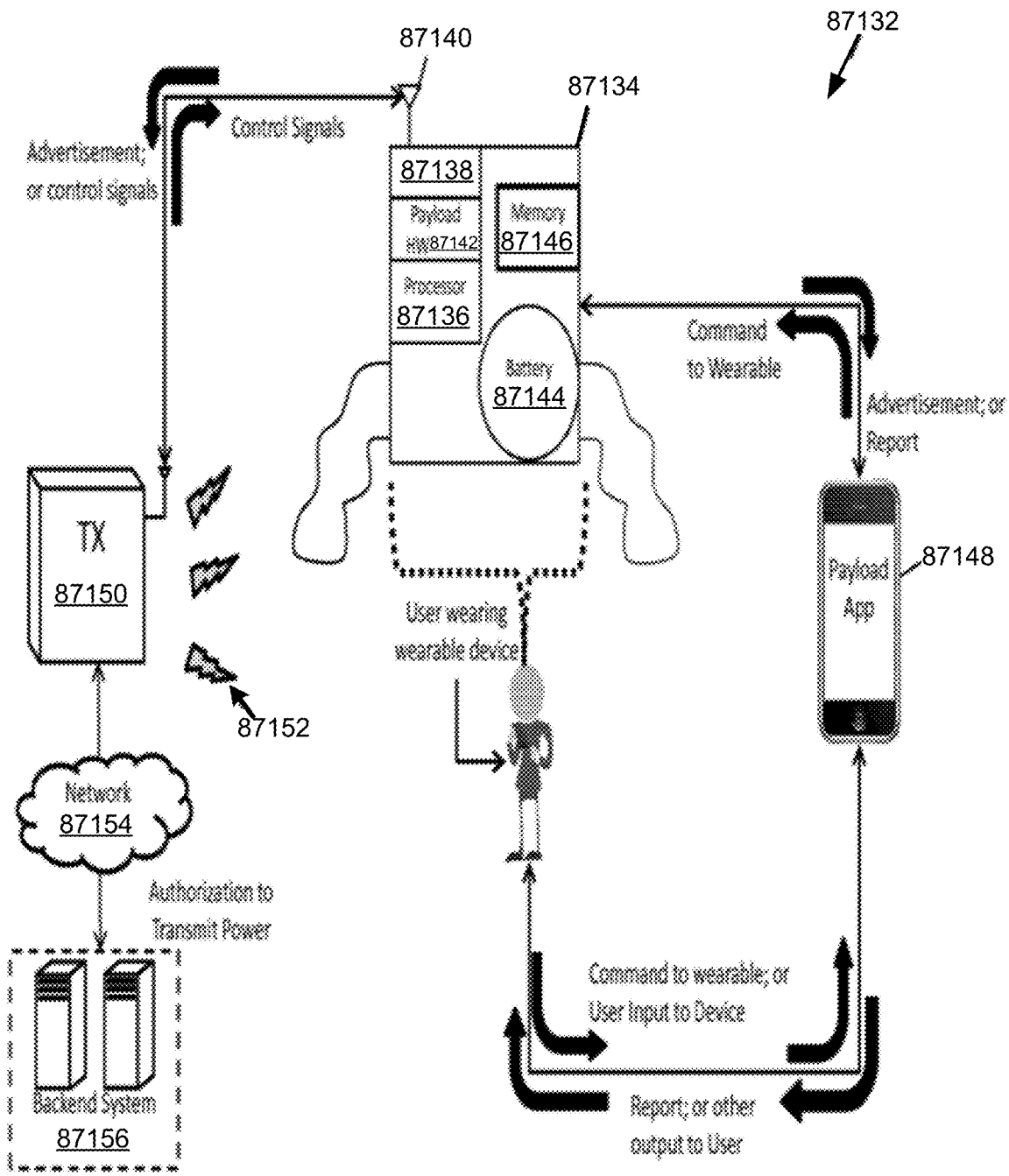

Simultaneous Power Control & Payload Functionality Receiver In A Wearable Device FIG. 87C shows components of an exemplary wireless power transmission system 87132. The system 87132 may comprise a wearable computing device 87134, a smart device 87148 executing a payload software application associated with the functionality of the wearable 87134, and one or more transmitters 87150 emitting power transmission waves 87152 that establish pockets of energy.

A smart device 87148 may be any computing device comprising a processor capable of executing the payload application and that is capable of communicating payload application instructions and data over a wireless protocol, such as Bluetooth®, NFC, BLE, RFID, Wi-Fi, and the like. Non-limiting examples of the smart device 87148 may include a smartphone, laptop, or other computing device.

In the exemplary system 87132, a wearable computing device 87134 may comprise a processor 87136 and communication hardware 87138, which may execute software modules facilitating concurrent communication between the wearable 87134 and the smart device 87148, and the between the wearable 87134 and the transmitters 87150. In the examplary system 87132 shown in FIG. 87C, concurrent communication may refer to the simultaneous or near-simultaneous communication among the devices 87134, 87148, 87150 of the system 87132. However, it should be appreciated that concurrent communication, as used herein, may refer to simultaneous or near-simultaneous communications, but may also refer to alternating communications among the devices 87134, 87148, 87150 of the system 87132.

A computing processor 87136 of the wearable 87134 may be integrated circuitry capable of performing power and payload functionality for the wearable 87134. The wearable 87134 may communicate payload application data with a smart device 87148 to provide the user with the desired functionality, for which the wearable 87134 was designed. Payload hardware 87142 of the wearable 87134 may be circuitry and other components that are capable of executing various processes and tasks in accordance with the features of the payload application and functional purpose of the wearable 87134. In some cases, the payload hardware 87142 may be capable of taking measurements or receiving inputs from a user, or executing instructions received from the smart device 87148 executing the payload application associated with the wearable 87134. In the exemplary system 87132, the wearable 87134 may comprise a battery 87144 capable of holding an electrical charge. The battery 87144 may power the computing processor 87136 and the payload hardware 87142. In some embodiments, the battery 87144 of the wearable 87134 may receive the electrical charge from the communications component 87138, which may comprise a receiver configured to harvest energy from pockets of energy produced by transmitters 87150. In some embodiments, the wearable 87134 may forego a battery 87144 and may be powered entirely by electrical energy harvested by a receiver of the communications component 87138.

A communications component 87138 may be circuitry of the wearable 87134 that may communicate control signals with a transmitter 87150 data using one or more wireless communications protocols (e.g., Bluetooth, BLE, Wi-Fi, NFC, RFID). The communications component 87138 may communicate payload application data over a second communication channel with a smart device 87148 executing a payload application associated with the functionality of the wearable 87134. The wearable 87134 may communicate control signals with a transmitter 87150 concurrently to communicating the payload application data to the smart device 87148 over the second communication channel. In some embodiments, the wearable 87134 may communicate simultaneously with both the transmitter 87150 and the smart device 87148. In such embodiments, the communications component 87138 and the processor 87136 may be capable of receiving and processing the respective communications signals simultaneously. In some embodiments, the wearable 87134 may alternate communications between the transmitter 87150 and the smart device 87148. In such embodiments, the processor 87102 and communications component 87138 may communicate with each device for a predetermined period of time.

Control signals may contain control data produced by the processor 87138 and communications component 87138 of the wearable 87134, which the transmitter 87150 may use to adjust power transmission waves 87152 that the transmitter 87150 emits to generate pockets of energy. The control data of the control signals may contain, for example, data indicating the location of the wearable relative to the transmitter 87150, and data indicating the amount of power that the wearable 87134 has effectively harvested from a pocket of energy generated by the transmitter 87150. In some cases, the control signals may include an advertisement signal for establishing a first communication between the transmitter 87150 and the communications component 87138 of the wearable 87134.

Payload application data collected by the payload hardware 87142 may be transmitted to the smart device 87148, over a second communication channel. The second communication channel hosting the payload application data may implement any wireless communication protocol capable of transmitting the payload application data from the wearable to the smart device 87148. In some embodiments, the communications component 87138 may transmit the payload application data at a given interval. In some embodiments, the payload application data may be transmitted at the moment the wearable 87134 and the smart device 87148 are brought into communicative proximity; in such embodiments, the second communication channel may be automatically established, and the smart device 87148 and wearable 87134 may then automatically exchange payload application data collected by the payload hardware 87142 of the wearable 87134.

In some embodiments, the wearable 87134 may comprise memory 87146, which may be a non-transitory machine-readable storage media that is capable of storing binary data. In some cases, the memory 87146 may store programming associated with the payload application that may be executed by the processor 87136 and/or the payload hardware 87142. When the processor 87136 executes the programming stored in the memory 87146, the payload hardware 87142 may collect measurements and perform various tasks intended to provide the intended functionality of the wearable 87134 and the associated payload application. In some cases, the memory 87146 may store control data that may inform transmitters 87150 of an optimal waveform and direction for transmitting power transmission waves 87152 to establish pockets of energy. In such cases, the wearable 87134 may transmit the control data for the transmitters 87150 to determine how the power transmission waves 87152 should be produced and transmitted. The processor 87136 may continuously update the memory 87146 with control data representing more effective ways for the transmitters 87150 to produce and transmit power control waves 87152.

A smart device 87148 may be any computing device comprising a processor that executes a payload application associated with the wearable 87134, a communication component that communicates payload application data and instructions with the wearable 87134 over a second communications channel. In some embodiments, communication between wearable and smart device 87148 may be through Bluetooth Low Energy (BLE), Wi-Fi, or other wireless communication protocol. Application payload data may include wearable 87134 status or usage reports, or payload application data generated by the wearable 87134. As an example, for embodiments in which the wearable 87134 is a heart rate monitor, the payload application data may include heart rate measurements or physical exertion data.

A transmitter 87150 (e.g., transmitter 102) may be any device that emits power transmission waves 87152 that establish a pocket of energy, which may be harvested by receivers and converted to electric energy. The transmitter 87150 may transmit power transmission waves 87152 to a wireless power receiver, which may be a component of the communications component 87138 of the wearable 87134 shown in FIG. 87C. In some embodiments, the wearable 87134 may communicate an advertisement signal to establish a first communication channel, which hosts control data.

After establishing the first communication channel hosting control data, the transmitter 87150 may then begin communicating control data with the wearable 87134, to manage delivery of electrical energy to the battery 87144 of the wearable 87134. In some embodiments, the wearable 87134 may use the same or a different communication channel to upload application payload data to the transmitter 87150, which the transmitter 87150 may upload to servers of a computing service 87156 associated with the transmitters 87150. Control data may include wearable 87134 device status and usage reports.

A network 87154 may be any combination of hardware and software modules capable of facilitating communication among computing devices, using any combination of wired and wireless communication protocols (e.g., TCP/IP, 803.11, 3G, 4G, LTE, WiMax). Non-limiting examples of networking hardware may include routers, firewalls, switches, trunks, cellular towers, and the like. In some embodiments, one or more transmitters 87150 may be connected with one another, over the network 87154. In some embodiments, the transmitters 87150 may be connected a backend computing system 87156 that manages the power transmission and pocket formation by the transmitters 87150. The smart device 87148 may communicate with the backend computing service 87156 to receive certain forms of information. For example, the user may access power usage statistics stored in the computing service 87156, which contains information regarding the amount of power previously spent and consumed by the wearable 87134 from the transmitters 87150.

A backend computing service 87156 may comprise one or more computing devices, such as server computers, providing one or more power transmission management functions for managing transmitters 87150 of the system 87132. Servers of the computing service 87156 may perform other functions as well, such as billing users for power consumption or managing user credentials. In some embodiments, the computing devices may host databases, which may be computing programs capable of storing, managing, and querying, data stored as database records in non-transitory machine-readable storage, according to a database management system (DBMS) of the particular database. The backend computing service 87156 may comprise a single computing device; or, the backend computing service 87156 may comprise a variety of computing devices, which may be found in disparate locations, thereby forming a distributed computing architecture.

As an example of a backend computing service 87156 function, in some cases the computing service 87156 may comprise an authentication server that may store user identifiers (e.g., billing information, usernames) and/or device identifiers (e.g., UUID, MAC address), which may be used to uniquely identify users and/or wearables 87134 that are authorized to receive energy from pockets of energy established by the transmitters 87150 of the system 87132. This authorization server belonging to the backend computing service 87156 may receive, over a network 87154, credentials associated with a wearable 87134 that were sent from a transmitter 87150 having just received an advertisement signal from the wearable 87134. The authorization server in the service 87156 may query the credentials associated with the wearable 87134 against a database storing the credentials of users and/or devices authorized to receive energy from transmitters 87150 of the system. In the case of a match, the authorization server of the backend service 87156 may instruct the transmitter 87150 to establish a communication channel with the wearable 87134 and begin transmitting power transmission waves 87152 to establish a pocket of energy for the wearable.

As another example of a backend computing service 87156 function, one or more servers in the backend service 87156 may receive power consumption data of the wearable, and generate an invoice based on the amount of energy consumed by the wearable 87134. The wearable 87134 may transmit this data in the control signals sent to the transmitter 87150, and the transmitter 87150 may then upload this data to the backend service 87156. Additionally or alternatively, such energy usage and consumption data may be uploaded to the smart device 87148, which may upload the data over the network 87154, to the computing service 87156. In some cases, the backend service may be communicatively coupled to the computing system of the user's bank (not shown), and may request funds from the user's account based on a card number provided by the customer, or based on a directly authorized account billing arrangement (e.g., ACH payment, wire transfer).

Simultaneous Communication Method

Figure 87D:
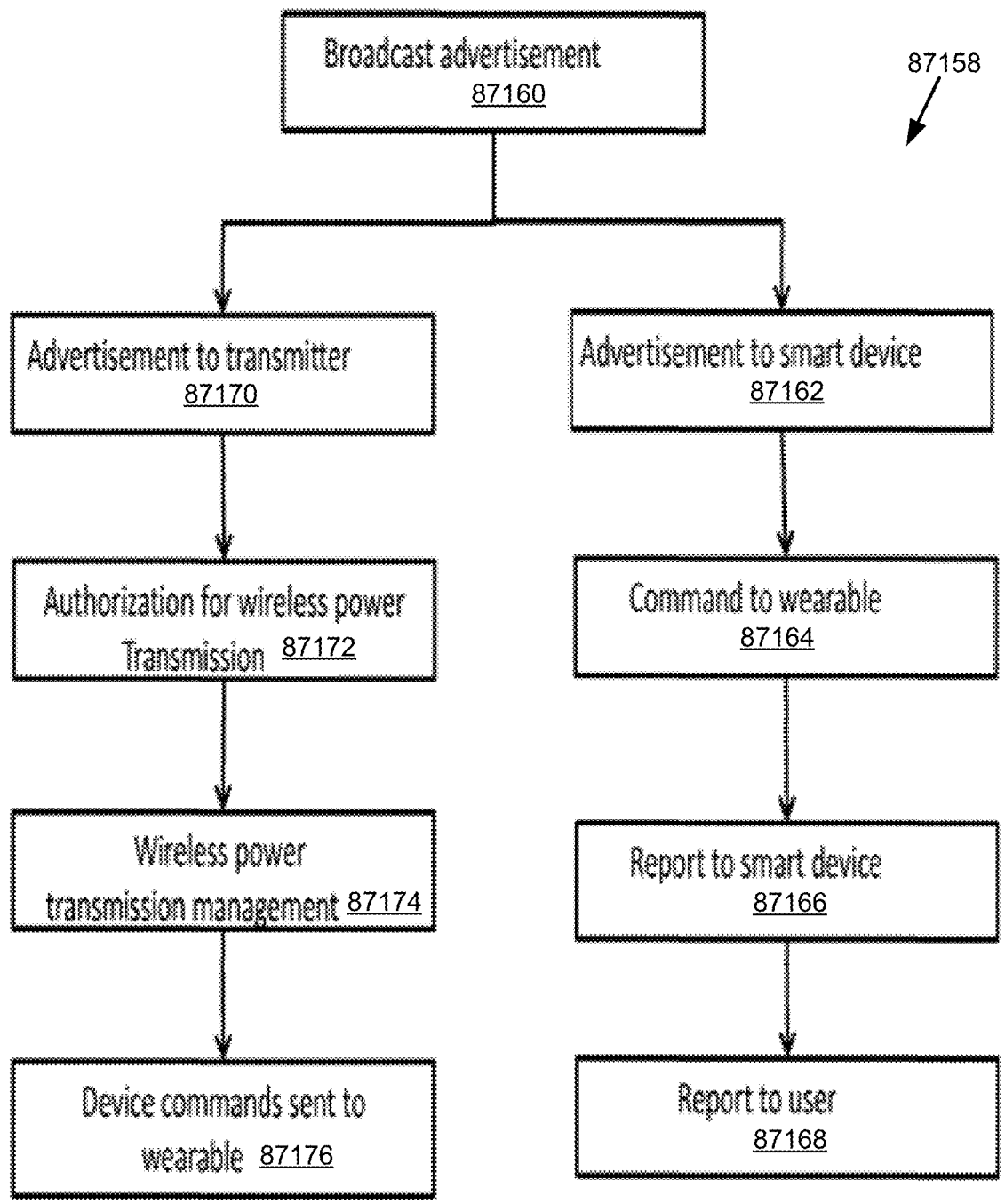

FIG. 87D shows steps of executing simultaneous or near-simultaneous communication between a wearable and a transmitter, and the wearable and a smart device, according to an exemplary method 87158 embodiment. The wearable may comprise a communication component and a processor capable of managing the simultaneous or near-simultaneous communication, and payload hardware may provide the wearable with components associated with the functionality of the wearable. The wearable may communicate data associated with power transmissions, with the transmitter, and the wearable may communicate payload data with the smart device that executes a payload application associated with the wearable. In some cases, the simultaneous or near-simultaneous communication may be accomplished using collision detection and correction techniques, or may be accomplished by interleaving individual communications, which may be in the form of data packets, such that the transmission and reception of each data packet by the wearable does not result in a collision of data packets arriving from or being transmitted to the transmitter and the smart device.

In a first step 87160, a wearable may broadcast an advertisement according to a wireless communication protocol implemented by the wearable to establish a communication channel with a transmitter, and to communicate power management data via control signals. The communication protocol may also communicate payload application data to the smart device. In some cases, the advertisement may be same for both transmitter and the smart device.

In a next step 87170, if the transmitter receives the advertisement signal from the wearable, then the transmitter and wearable may establish a communication connection, which may be established irrespective of whether the wearable has previously established a communication connection with the smart device. In a simultaneous or near-simultaneous step 87162, if the smart device receives the advertisement signal from the wearable, then the smart device and the wearable may establish a communication connection, irrespective of whether the wearable has already established a communication connection with the transmitter.

In a next step 87172, after establishing a communication connection with the transmitter, the transmitter may use information in the advertisement that identifies the wearable (e.g., MAC address, UUID) to authenticate the wearable. In some cases, the transmitter may require the user to enter more information (e.g., username, password) using the wearable or the smart device. The transmitter may transmit this information as credentials to authorize the wearable to receive power transmission waves. If the authentication fails, then the transmitter is prohibited from, or otherwise does not proceed with establishing a pocket of energy for the wearable device. On the other hand, if the credentials are successfully authenticated, then in a next step 87174, the transmitter and the wearable may communicate wireless power management data in control signals. The transmitter may use the controls signals to identify the relative location of the wearable, and determine a phase and a gain for transmitting power transmission waves, in order to establish a pocket of energy for the wearable to harvest electrical energy.

In a next step 87176, the user may issue commands to the wearable instructing the wearable to perform wireless power transmission functions. The wearable may continue to recharge a battery from the pocket of energy, irrespective of payload application functions being performed by the wearable or payload application data being communicated between the wearable and the smart device.

Returning to step 87162, in which the advertisement signal is received by the smart device, the wearable may establish a communication connection with the smart device and begin to communicate payload application data and receive payload application instructions from the smart device. This communication between the wearable and the smart device may proceed irrespective of the wearable's ongoing communication connection with a transmitter. As such, in a next step 87164, the smart device may issue a command to the wearable to execute one or more programmatic instructions associated with the wearable's intended function. For example, if the wearable is a pedometer measuring steps taken by the user, then the smart device may instruct the wearable to begin counting the number of steps at zero for a new day, or the smart device may instruct the wearable to upload data gathered from the previous day. These instructions may be received by the wearable and queued for execution, irrespective of instructions or control signals received from a transmitter. In a next step 87166, the wearable may provide payload application data to the smart device, which may be transmitted over the communication connection established between the smart device and the wearable. As previously mentioned, the simultaneous or near-simultaneous communication of data packets containing the payload application data and/or control signals may be accomplished by interleaving the transmission and/or reception of the respective data packets. In some embodiments, the communication component of the wearable may employ techniques for data packet collision detection and/or correction to preserve the information contained within any potentially lost data packets.

In a next step 87168, data reports relating to either the status of power transmission or the payload application may be presented to the user via a graphical user interface (GUI). In some embodiments, the smart device may generate a GUI to present the data report related to either power transmission or the payload application, in accordance with the payload application or an application associated with power transmission management. In some embodiments, the wearable may comprise a GUI, and may be capable of generating a GUI presenting the data report containing the power transmission data or the payload application data. The wearable may continue to concurrently communicate with each device (i.e., transmitter, smart device), until the wearable is out of range of either device, or until the user ends execution of either communication connection.

Alternating Communication Method

Figure 87E:
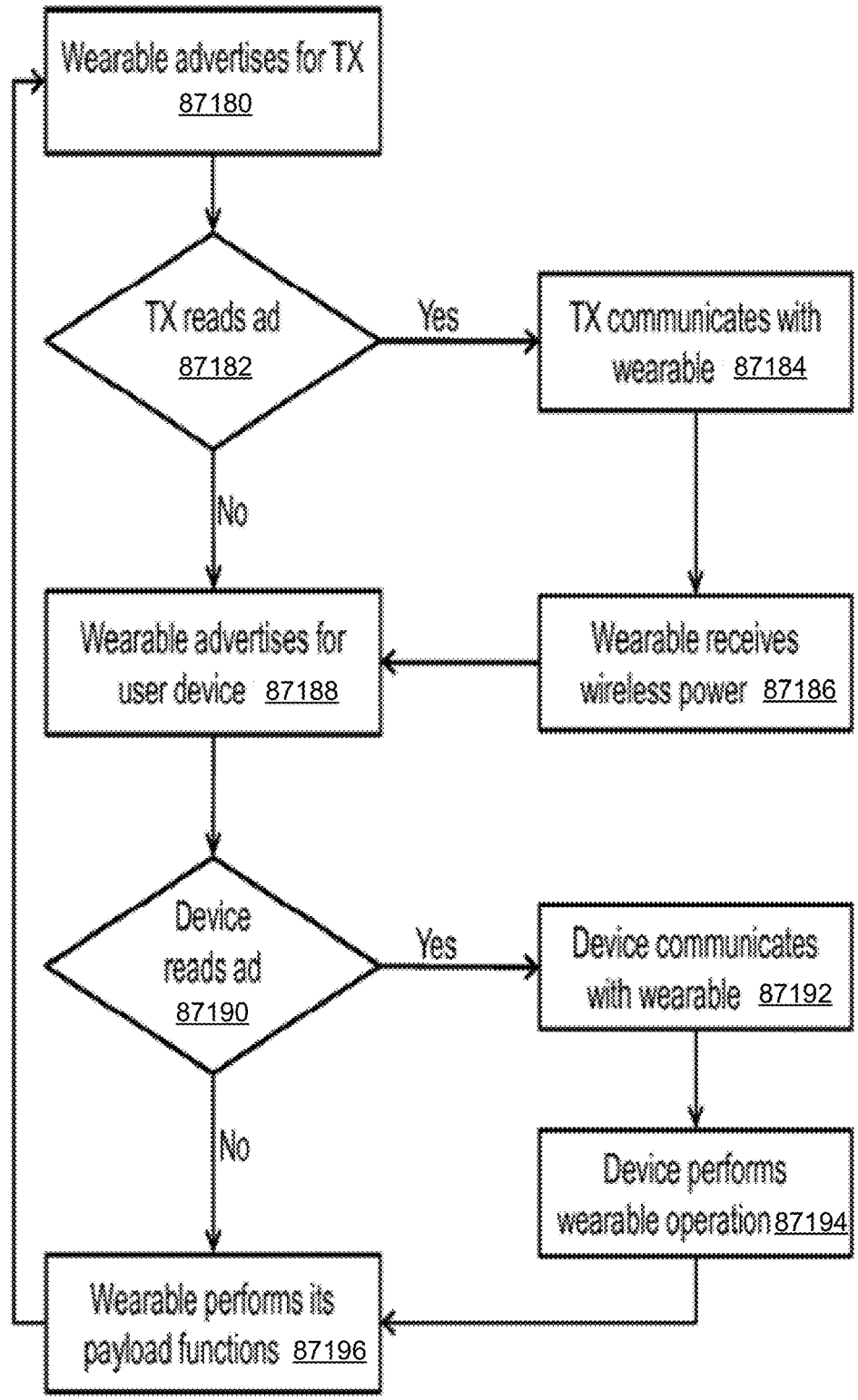

FIG. 87E shows steps of executing alternating communication between a wearable and a transmitter, and the wearable and a smart device, in accordance with an exemplary method 87178 embodiment. The wearable may comprise a communication component and a processor capable of managing the concurrent communication among the devices, and payload hardware comprising components capable of providing the intended functionality of the wearable. The wearable may communicate control signals containing data associated with power transmission management to and from the transmitter; and the wearable may communicate payload data with the smart device, which may execute a payload application associated with the wearable. In some cases, the alternating communication may be accomplished by assigning each communication connection a predetermine period of time for completing the relevant communication, which may be in the form of data packets. For example, for the prescribed period of time, the wearable may communicate data packets containing power transmission management data to and from the transmitter; and then the wearable may communicate data packets containing payload application data to and from the smart device, for the prescribed period of time. In some cases, this may be accomplished with time-division multiplexing (TDM) techniques for managing ongoing communications with multiple devices.

In a first step 87180, a wearable alternates between broadcasting an advertisement to a transmitter and broadcasting an advertisement to a smart device executing a payload application associated with the wearable. The advertisement may contain information identifying the wearable, which transmitters and smart devices may use determine whether the devices should establish a communication connection with the wearable.

In a next step 87182, the transmitter may receive the advertisement signal from the wearable, and parses the identifying information, and executes one or more authorization routines. In some embodiments, the transmitter may have a locally stored set of authorized credentials for determining whether to transmit power transmission waves and to establish a communication connection. In some embodiments, the transmitter may access a backend power management computing service that may determine whether the wearable and/or the user is authorized to receive power transmission waves.

If the device or user credentials are not authenticated in the prior step 87182, or if the transmitter does not receive the advertisement in the prior step 87182, the wearable may still proceed to establish a connection with a smart device, in a later step 87190. However, in the exemplary method 87178, the transmitter has received the advertisement and successfully authenticated the identifiers received from the wearable.

In a next step 87184, after the wearable is successfully authenticated, the wearable may communicate control signals containing data for wireless power management. This data may include an indication of the location of the wearable relative to the transmitter, billing data for the user, power consumption, and/or an amount of power being received by the wearable from power transmission waves. In the next step 87186, the transmitter may then begin transmitting power transmission waves based on the control signals received from the wearable. The transmitter may transmit the power transmission waves in one or more directions so that the power transmission waves converge to form a pocket of energy, from which a receiver in the wearable may harvest electrical energy. The wearable may then monitor the amount of power being harvested by the wearable, and generate data packets containing data related to wireless power management. As long as the period of time for communicating with the transmitter is active, the wearable may transmit data packets in a control signal, to the transmitter.

In a next step 87188, after the period of time to communicate with the transmitter lapses, the wearable may broadcast an advertisement for a smart device. That is, while re-charging a battery of the wearable, the wearable may break off communication with the transmitter in order to briefly advertise for a smart device, which may allow the user of the smart device to manage the wearable through various commands inputted through a GUI of the smart device. The user of the wearable and the smart device may issue commands to the wearable through a GUI presented by a payload application on the smart device. The commands may instruct the wearable to perform a payload application operation. Non-limiting examples such operations may include configuration of the wearable, read (i.e., fetch) payload data from the wearable, or initiate a payload application function to be performed by the wearable.

In a next step 87190, after the smart device receives the advertisement from the wearable, the payload application executed by the smart device may read identifying data in the advertisement signal, determine whether to the authorize the wearable based on a set of stored device identifiers or other user credentials, and may then establish a communication connection to begin wireless communication with the wearable.

In a next step 87192, the wearable and the smart device may then exchange data packets containing instructions for executing various tasks for the payload application and/or data packets containing data associated with the payload application.

In a next step 87194, the wearable may perform one or more operations as instructed by the user input, which the user inputted through the GUI of the payload application presented on the smart device. The wearable may perform the task, and may the send back payload application data based on the execution of the task, or other communication information (e.g., instructions) associated with the payload application.

In a next step 87196, the payload application may communicate with user by presenting an output to the user through a GUI. In some cases, smart device may cease communicating with the wearable, due to the end of a routine or due the close of the period of time for communications between the wearable and the smart device. That is, while performing operations based on instructions received from the smart device, the wearable may break off communication with smart device when the period of time has lapsed. The wearable may, in some embodiments, advertise for the transmitter, to allow the transmitter to continue communicating control signals.

In the exemplary method 87178, the Wearable may continue alternating advertisements and communication connections, from the transmitter to the smart device. In some embodiments, the wearable may communicate with the transmitter once the transmitter transmits a response indicating that wearable may communicate with the transmitter; and, in some embodiments, the wearable may communicate with the smart device once the smart device transmits a response indicting that the wearable may communicate with the smart device.

EXAMPLES

In an exemplary implementation of concurrent communication of a wirelessly powered wearable device, the wearable device may comprise a single battery and a single processor. The battery is configured to provide power to the processor, when the wearable is turn on by a user. The processor then broadcast an advertisement signal that contains a network address (e.g., IP address, Bluetooth UUID, device serial number, MAC address), and other information (e.g., user credentials, billing information), which facilitates the establishment of communication connections with both a transmitter emitting power transmission waves and a mobile device executing a software application that manages the intended payload functionality of the wearable device. The advertisement may also contain a request for wireless power to be provided by the transmitter.

In this example, after the transmitter detects the advertisement from the processor of the wearable, the transmitter determines whether the wearable needs power based on battery level data contained in the advertisement. The transmitter may then establish the communication connection for exchange power transmission data, and then transmits power transmission waves to establish pockets of energy. During this period of time in which the wearable and the transmitter are communicating, the wearable may not broadcast and other advertisements to establish communication connections with other devices. After a predetermine period for communication lapses, however, the wearable and/or the transmitter may disconnect from one another. The wearable may then proceed to advertise the necessary information to establish a connection with a smart device.

The user may then execute a management application and issues one or more payload commands, based on the user's interactions with a GUI of the application. In response to the command, the management application detects advertisement from wearable device, and may then establish a communication connection with the wearable. The wearable may not communicate with other devices during the predetermined period of time that the wearable and the smart device are intended to communicate. The application may then transmit to the wearable device the payload command. The wearable may process the payload command, which in this example, may instruct the wearable to execute tasks such as: send payload application data to the management application, execute a specific payload function, or receive payload data from the management application.

The payload application may display to the user the payload application data produced by the wearable and transmitted to the smart device. In some cases, the payload application may display the results or outcome of a command sent to the wearable.

After the lapse of the predetermined time, or after the management application releases the wearable, the application may disconnect the communication connection from the wearable. The exemplary alternating communication process may repeat continuously repeat until the devices are powered down, the devices are out of range of one another, or the user cease execution of the various processes.

FIGS. 87A-87E illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 87A-87E.

Presented below are example embodiments of a simultaneous power and payload receiver.

In some embodiments, an example computer-implemented method comprises receiving, by a transmitter, an advertisement signal from a wearable device, the advertisement signal containing binary data indicating a direction of the wearable relative to the transmitter, establishing, by a transmitter, a communication channel with the wearable device. The communication channel hosts control signals containing data associated with power transmission waves. The method firther compises transmitting, by the transmitter, one or more power transmission waves in the direction of the wearable device based on the advertisement signal, receiving, by the transmitter, from the wearable the control signals associated with the power waves, where the control signal indicate an amount to adjust antennas of the transmitter transmitting the one or more power waves, transmitting, by the transmitter, the one or more power transmission waves based on the amount to adjust the antennas of the transmitter, and ceasing, by the transmitter, the communication channel with the wearable device, where the transmitter continues to transmit the one or more power transmission waves.

In some embodiments, ceasing the communication channel with the wearable device further comprises determining, by the transmitter, whether a predetermined period of communication has lapsed.

In some embodiments, ceasing the communication channel with the wearable device further comprises receiving, by the transmitter, an instruction to cease the power transmission waves from a smart device associated with the wearable.

In some embodiments, the method further comprises retransmitting, by the transmitter, one or more data packets of the control signals to the wearable, responsive to determining the one or more data packets were not received, according to one or more collision detection techniques executed by the transmitter.

In some embodiments, the method further comprises authenticating, by the transmitter, the wearable based on one or more identifiers received in the advertisement. The transmitter establishes the communication connection and transmits power transmission waves in response to authentication of the wearable.

In some embodiments, authenticating the wearable further comprises transmitting, by the transmitter, the one or more identifiers to a computing service associated with the transmitter and configured to authenticate the one or more identifiers of the wearable.

In some embodiments, authenticating the wearable further comprises querying, by the transmitter, non-transitory machine-readable storage media storing one or more identifiers associated with one or more wearable devices.

In some embodiments, the one or more identifiers are selected from the group consisting of: an internet protocol (IP) address, a Bluetooth unique identifier, a universal unique identifier (UUID), a media access control (MAC) address, and a user identifier associated with the wearable.

In some embodiments, an example wireless power transmission system comprises a transmitter comprising a communications component configured to receive an advertisement signal from a wearable and communicates control signals with the wearable, and one or more antennas configured to transmit one or more power transmission waves to the wearable based on data containing in the advertisement signal and the control signals. The transmitter communicates with the wearable during a predetermined period of time, where the transmitter ceases communication with the wearable after the predetermined period of time, and where the transmitter continue to transmit the one or more power transmission waves after the predetermined period of time.

In some embodiments, the system transmitter further comprises a processor configured to determine a location of the wearable relative to the transmitter and a phase for the power transmission waves, based upon data contained in the advertisement signal and the control signals. The transmitter transmits the one or more based upon the location of the wearable, and the transmitter produces the power transmission waves to have the phase determined using the data in the control signals.

In some embodiments, the system transmitter continuously updates the location for transmitting the power transmission waves in response to receiving the control signals from the wearable.

In some embodiments, the system transmitter continuously updates the phase of the power transmission waves in response to receiving the control signals from the wearable.

In some embodiments, the system transmitter is configured to automatically transmit power transmission waves to the wearable in response to authenticating the wearable, based on one or more identifiers for the wearable received in the advertisement signal.

In some embodiments, the one or more identifiers are selected from the group consisting of: an internet protocol (IP) address, a Bluetooth unique identifier, a universal unique identifier (UUID), a media access control (MAC) address, and a user identifier associated with the wearable.

In some embodiments, the system transmitter is configured to automatically determine a power level of a battery of the wearable based on power level data contained in the advertisement signal. The transmitter transmits the power transmission waves to the wearable in response to determining the power level of the battery is below a threshold level.

In some embodiments, the system transmitter further comprises a network interface card configured to transmit to an authentication server one or more identifiers of the wearable received in the advertisement signal.

In some embodiments, the system transmitter is configured to automatically transmit the one or more power waves to the wearable upon authenticating the wearable.

In some embodiments, the system has a processor of the transmitter configured to detect one or more data packets lost during transmission to the wearable according to one or more collision detection algorithms executed by the processor, and where the transmitter is configured to automatically retransmit the one or more data packets in response to detecting the one or more data packets were lost during transmission to the wearable.

In some embodiments, the system further comprises one or more transmitters configured to continuously transmit one or more power transmission waves to establish a pocket of energy at a location relative to the wearable, and where only one transmitter of the one or more transmitters communicates with the wearable for the predetermined period of time.

FIGS. 88A-88M illustrate examples of devices, apparatus, and methods for proximity transmitters for wireless power charging systems, in accordance with some embodiments.

Figure 88A:
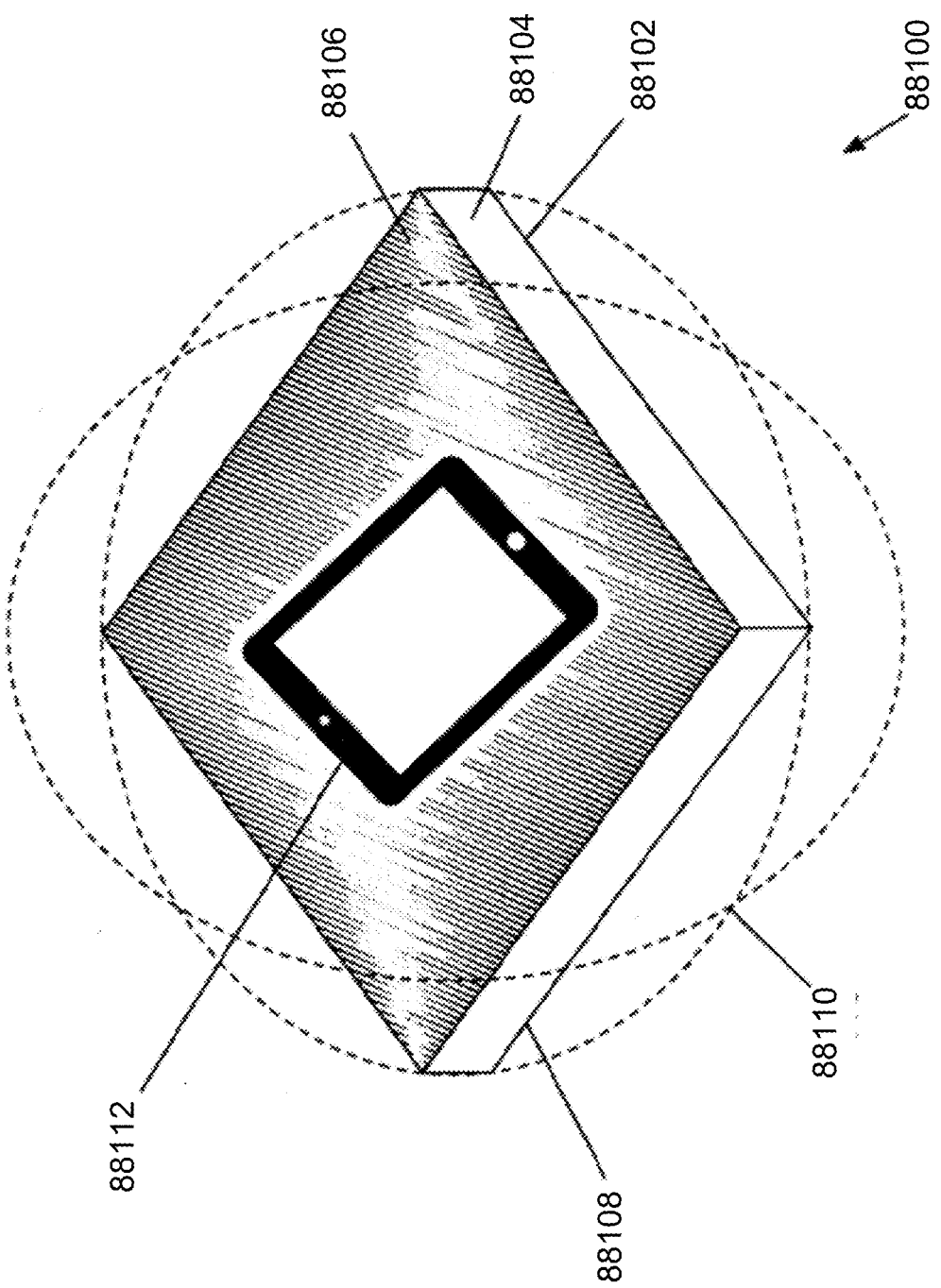

FIG. 88A illustrates a proximity transmitter 88100 transmitting one or more power waves such that the one or more power waves converge in a three dimensional space to form one or more pockets of energy, in accordance with an embodiment of the present disclosure. A proximity transmitter 88100 comprises a housing 88102 defined via a plurality of sidewalls 88104, a top 88106, and a bottom 88108. The top 88106 extends over the bottom 88108. The sidewalls 88104 span between the top 88106 and the bottom 88108. At least one of the sidewalls 88104, the top 88106, or the bottom 88108 includes a surface layer, whether internal to the housing 88102 or external to the housing 88102. The surface layer may be any size. For example, the surface layer can be 6 inches in length, 1 inch in height, and 0.5 inch thick (6"×1"×0.5"), but nearly any other combination of sizes may possible. Moreover, the surface layer and other components of the proximity transmitter 88100 can be of any shape or combination of shapes. For example, the surface layer or other component can be shaped as a rectangle, a triangle, a circle, an oval, a trapezoid, a parallelogram, or any other two dimensional (2D) shape. As another example, the top 88106 can comprise an upper squared surface layer and the bottom 88108 can having a rectangular shape that is comparatively broader and wider than the squared shape of the top 88106.

The housing 88102 comprises plastic, but can comprise at least one other material, whether additionally or alternatively, such as wood, metal, rubber, glass, or others. The housing 88102 has a shape of a cube, but other shapes are possible, such as a cuboid, a sphere, a hemisphere, a dome, a cone, a pyramid, or any other polygonal shape, whether having an open-shape or a closed-shape. In some embodiments, the housing 88102 is at least one of waterproof, water-repellant, or water-resistant.

The housing 88102 houses various components of a transmitter 88100, which transmits one or more controlled radio frequency (RF) waves in at least one direction. However, note that an omnidirectional transmission is possible as well. The RF waves may converge at a particular location in space. The RF waves may be controlled through phase and/or relative amplitude adjustments to form constructive and destructive interference patterns (pocket-forming) at specific locations in space. Accordingly, one or more pockets of energy 88110 are generated by forming constructive interference patterns, whereas null-spaces may be generated by forming destructive interference patterns. Therefore, if a device 88112 comprises a receiver, then the receiver may interface with the one or more pockets of energy 88110 generated by the transmitter and thus effectively receive wireless power transmission from the transmitter 88100.

The proximity transmitter 88100 may transmit or broadcast power waves to the receiver associated with the device 88112. Although some embodiments disclosed herein describe one or more power waves as radio frequency (RF) waves, power waves may be other types of waves capable of carrying energy, capable of being propagated through space, and capable of being converted into a source of electrical energy. The transmitter may transmit the power waves as a single collective of power waves directed at the receiver. In some embodiments, one or more transmitters may transmit a plurality of power waves that are propagated in multiple directions and may deflect off of physical obstructions, such as walls. The power waves may converge at a location in 3D space, forming the one or more pockets of energy 88110. The receiver of the device 88112, whether within a boundary of or via interfacing with the one or more pockets of energy 88110, may capture and covert the power waves into a useable source of energy. The transmitter may control pocket-forming based on phase and/or relative amplitude adjustments of power waves, to form constructive interference patterns.

Depending on the distance of the surface layer from the antennas or array of antennas, as well as other potential system parameters, the power waves may exhibit varying levels of convergence, or sometime none at all. For example, the power waves may converge to form a pocket of energy 88110 at the surface layer, or the power waves may loosely converge to form a general area at or near the surface layer in which the power waves are present. In some implementations, the device may receive a sufficient collection of waves directed at the receiver that the receiver may receive enough energy to charge the electronic device without requiring the power waves to form a constructive interference pattern or form a pocket of energy 88110.

Although some embodiments recite a use of RF wave transmission techniques, the wireless charging techniques should not be limited to RF wave transmission techniques. Rather, possible wireless charging techniques may include any number of alternative or additional techniques for transmitting energy to a receiver converting the transmitted energy to electrical power. Non-limiting example transmission techniques for energy that can be converted by a receiving device into electrical power may include: ultrasound, microwave, laser light, infrared, or other forms of electromagnetic energy or non-electromagnetic energy. In the case of ultrasound, for example, one or more transducer elements may be disposed so as to form a transducer array that transmits ultrasound waves toward a receiving device that receives the ultrasound waves and converts them to electrical power. In addition, although a transmitter can be shown as a single unit comprising potentially multiple transmitters (transmit array), both for RF transmission of power and for other power transmission methods mentioned in this paragraph, the transmit arrays can comprise multiple transmitters that are physically spread around a room rather than being in a compact regular structure.

The transmitter includes an antenna array where the antennas are used for sending the power waves. The surface layer can be proximate to the array of antennas. For example, the array of antennas can be positioned between the lower rectangular surface layer and the upper rectangular surface layer and along a plane parallel to the lower rectangular surface and the upper rectangular surface. Each antenna sends power transmission waves where the transmitter applies a different phase and amplitude to the signal transmitted from different antennas. Similar to the formation of pockets of energy, the transmitter can form a phased array of delayed versions of the signal to be transmitted, apply different amplitudes to the delayed versions of the signal, and send the signals from appropriate antennas. For a sinusoidal waveform, such as an RF signal, ultrasound, microwave, or other periodic signal, delaying the signal is analogous to applying a phase shift to the signal.

The one or more pockets of energy 88110 may be formed by creating constructive interference patterns of power waves transmitted by the transmitter. For example, the transmitter can be configured to transmit power waves which can converge in a constructive interference pattern at the surface layer of the housing 88102. For example, the constructive interference pattern is formed at the surface layer of the housing 88102 or the constructive interference pattern is formed proximate to the surface layer of the housing 88102. The pockets of energy 88110 may manifest from the constructive interference pattern as a three-dimensional field where energy may be harvested by the receiver located within the pocket of energy 88110. The pocket of energy 88110 produced by transmitter during pocket-forming may be harvested by the receiver, converted to an electrical current, and then provided to the device 88112 associated with the receiver. In some embodiments, there may be multiple transmitters. In some embodiments, a subset of the antennas of the antenna array can transmit the power waves to a receiver on the surface layer of the housing 88102. In some embodiments, the subset of the antennas of the array that transmit the power waves to the receiver on the surface layer of the housing 88102 are directly below the receiver. In some embodiments, at least one antenna of the subset of the antennas of the array that transmit the power waves to the receiver on the surface layer of the housing 88102 is not directly below the receiver. In some embodiments, the receiver is located externally to the device 88112, and may be connected to the device 88112 through one or more wires or otherwise attached to the device 88112. For instance, the receiver may be situated in an external case that is permanently or removably attached to the device 88112, thereby forming a connection with the device 88112 that allows the device 88112 to receive power from the receiver. Note that the power waves can comprise waves of various types, such as RF waves, ultrasound waves, microwaves, or others. In addition, in embodiments where RF waves are used, it should be appreciated that most any frequency for the waves may be used, including the range of roughly 900 MHz to roughly 100 GHz. For instance, one skilled in the art would appreciate that the power waves may be transmitted using nearly any industrial, scientific, and medical (ISM) radio band, such as 900MHZ, 2.4 GHZ, 5 GHz, 24 GHz, or more.

Note that although the device 88112 is a tablet computer, any type of any device, which comprises the receiver, can be placed on the housing 88102. Further, note that although the device 88112 is positioned centrally on the top 88106 of the housing 88102, the device 88112 can be positioned anywhere on the housing 88102 or in a local proximity of the housing 88102, such as within about twelve (12) inches or less from the housing 88102 in order to charge wirelessly. In some embodiments, the housing 88102 comprises at least two transmitters.

Figure 88B:
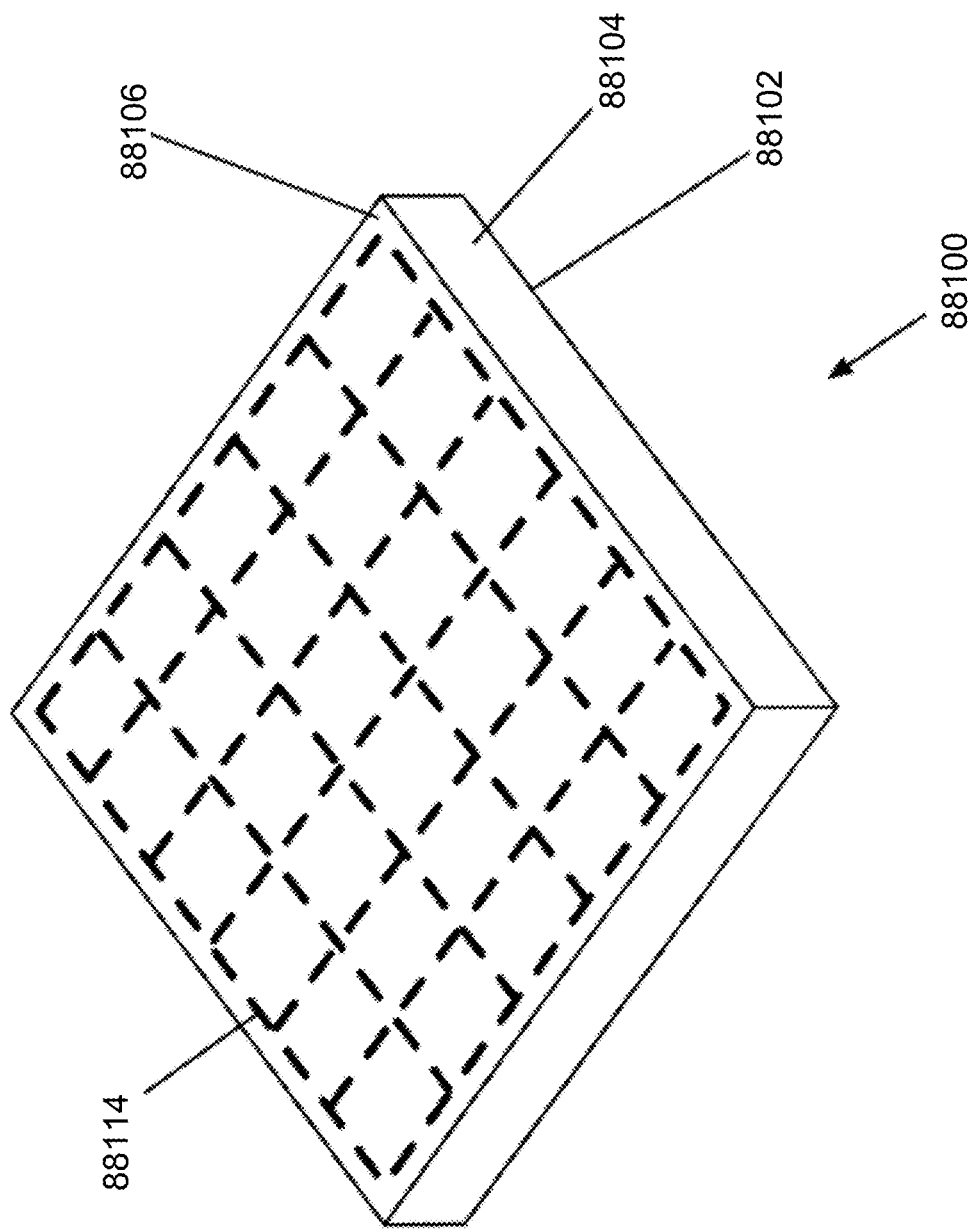

FIG. 88B illustrates a proximity transmitter 88100 comprising an antenna array positioned on a top of the proximity transmitter 88100, in accordance with an embodiment the present disclosure. The top 88106 comprises an array of antenna elements 88114, which can operate as a single antenna. Note that the array of antenna elements 88114 includes at least one antenna element, but array may comprise any number of antenna elements 88114. The top 88106 may comprise any number of arrays. In the exemplary embodiment, the top 88106 comprises a single array of antenna elements 88114. The array of antenna elements 88114 may be embedded into the structure of the top 88106 or may be coupled to the top 88106, which can be accomplished through any permanent or removable means, such as mating or fastening. The array of antenna elements 88114 are part of the transmitter 88100, such that the array of antenna elements 88114 transmit one or more RF waves, as described herein. In some embodiments, a transmitter 88100 may comprise multiple physically distinct arrays of antenna elements 88114, and may manage and feed power to each of the arrays. In yet other embodiments, the antenna elements may be located in, along, adjacent to or aligned with one or more sidewalls 88104.

In operation, one or more pockets of energy 88110 may be formed by creating constructive interference where the power transmission waves add constructively to form a pocket of energy within close proximity to the transmitter 88100. In some instances, the proximity is such that the constructive interference patterns may not accumulate to form a pocket of energy. But in such instances, the proximity transmitter 88100 may be configured to provide additional power waves to the receiver so that the receiver can receive and rectify enough energy for the electronic device coupled to the receiver. Through a separate communication channel from the power transmission waves, using any number of wireless communications protocols (e.g., Wi-Fi, Bluetooth®, ZigBee®) the receiver and transmitter 88100 may continually communicate the power levels being received by the receiver and the power levels required by the electrical device, to continually adjust which, if any, of the antennas should be transmitting power waves and how much energy those waves should contain.

Around pockets of energy, or at particular locations in space where pockets of energy are undesired, the proximity transmitter 88100 may generate and transmit power waves that result in one or more transmission nulls, which may be generated by creating destructive interference patterns. A transmission null in a particular physical location may refer to areas or regions of space where pockets of energy do not form because of destructive interference patterns of power transmission waves. In some embodiments, the housing 88102 contains an interior space, where one or more antennas or antenna elements are positioned. In some embodiments, the array of antenna elements 88114 can be at least partially invisible, such as via being positioned underneath an outermost surface of the top 88106. However, in some embodiments, the array of antenna elements 88114 can be at least partially visible, such as via being positioned on top of the outermost surface of the top 88106.

Figure 88D:
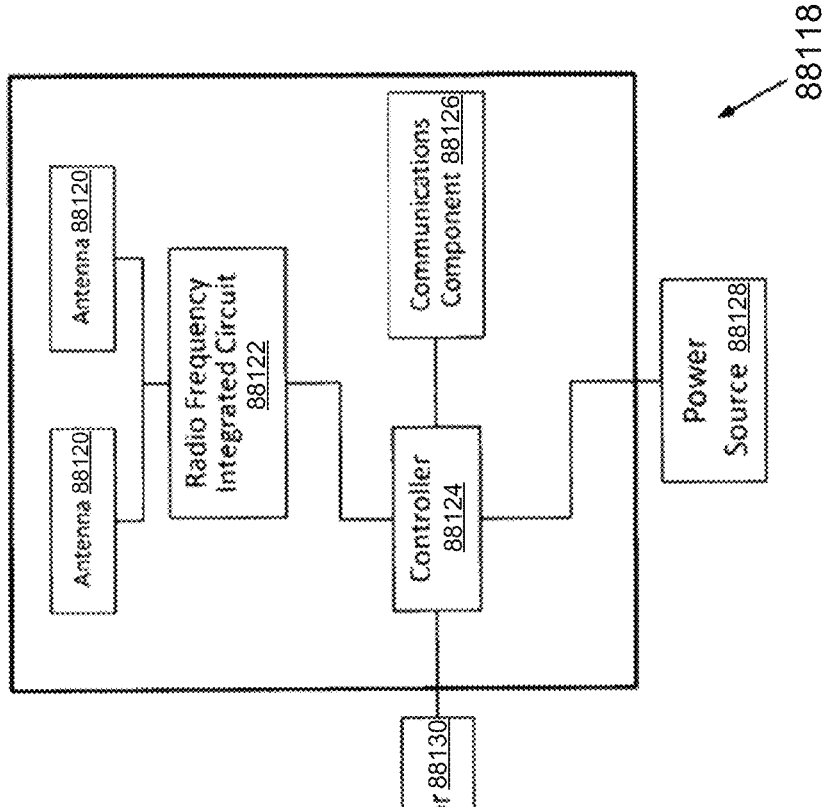
Figure 88C:
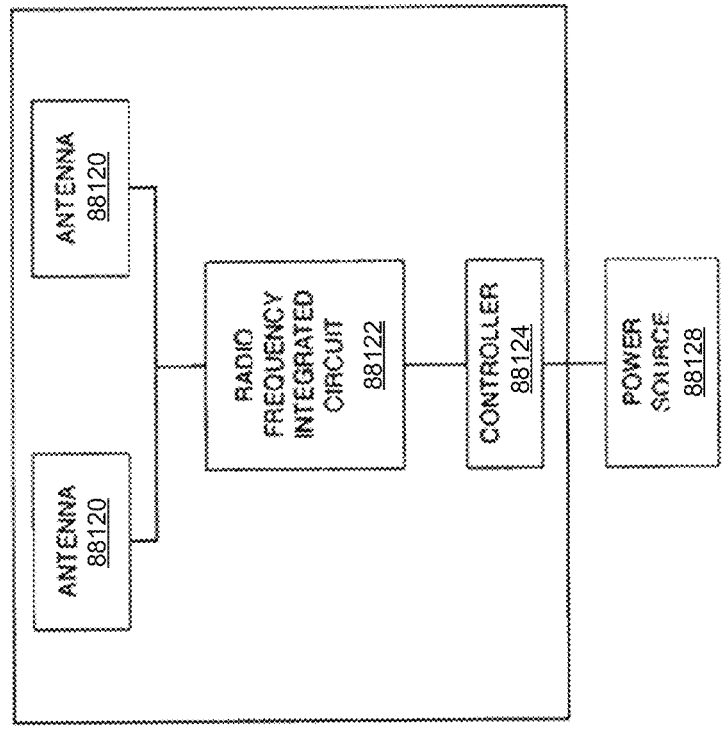

FIG. 88C illustrates a schematic diagram of a proximity transmitter 88116, in accordance with an embodiment of the present disclosure. A schematic diagram depicts a proximity transmitter 88116 capable of broadcasting wireless power waves, which may be RF waves, for wireless power transmission, as described herein. The transmitter 88116 may be responsible for performing tasks related to transmitting power waves, which may include pocket-forming, adaptive pocket-forming, and multiple pocket-forming. The transmitter 88116 includes one or more antenna elements 88120, one or more RFICs 88122, one or more controllers 88124, and one or more power sources 88128. The transmitter 88116 can include a housing or an enclosure to house or enclose the one or more antenna elements 88120, the one or more RFICs 88122, and the one or more controllers 88124. In some embodiments, the housing or the enclosure houses or encloses the one or more power sources 88128. The housing or the enclosure can be made of any suitable material which may allow for signal or wave transmission and/or reception, for example plastic or hard rubber. The various components of the transmitter 88116 may comprise, and/or may be manufactured using, meta-materials, micro-printing of circuits, nano-materials, and the like.

The one or more antenna elements 88120 can be structured as the array of antenna elements 88114, as described herein. At least one antenna element of the antenna elements 88120 can be used to transmit one or more power waves. In some embodiments, all of the array of the antenna elements 88114 is used to transmit one or more power waves.

The one or more RFICs 88122 is configured to control production and transmission of the power waves based on information related to power transmission and pocket-forming. The one or more RFICs 88122 may automatically adjust the phase and/or relative magnitudes of the power waves as needed. Pocket-forming is accomplished by the transmitter 88116 transmitting the power waves in a manner that forms constructive interference patterns.

The one or more controllers 88124 may comprise a processor running or having an ARM and/or a DSP architecture. ARM is a family of general purpose microprocessors based on a reduced instruction set computing (RISC). A digital signal processing (DSP) is a general purpose signal processing chip or technique which may provide a mathematical manipulation of an information signal to modify or improve the signal in some way, and can be characterized by the representation of discrete time, discrete frequency, and/or other discrete domain signals by a sequence of numbers or symbols and the processing of these signals. DSP may measure, filter, and/or compress continuous real-world analog signals. The first step may be conversion of the signal from an analog to a digital form, by sampling and then digitizing it using an analog-to-digital converter (ADC), which may convert the analog signal into a stream of discrete digital values. The one or more controllers 88124 may also run Linux and/or any other operating system. The one or more controllers 88124 may also be connected to Wi-Fi in order to provide information through a network.

The one or more controllers 88124 may control a variety of features of the one or more RFICs 88122, such as, time emission of pocket-forming, direction of the pocket-forming, bounce angle, power intensity and the like. Furthermore, the one or more controllers 88124 may control multiple pocket-forming over multiple receivers or over a single receiver. For example, the controller 88124 can be configured to transmit one or more power waves from the array of antennas that converges in a constructive interference pattern at the upper rectangular surface layer of the housing 88102 of the proximity transmitter 88100 upon a receiver being placed upon the upper rectangular surface layer. The proximity transmitter 88116 may allow distance discrimination of wireless power transmission.

The one or more power sources 88128 power the transmitter 88116. The one or more power sources 88128 may include AC or DC power supply. Voltage, power, and current intensity provided by the one or more power sources 88128 may vary in dependency with the required power to be transmitted. Conversion of power to radio signal may be managed by the one or more controller 88124 and carried out by the one or more RFICs 88122 that may utilize a plurality of methods and components to produce radio signals in a wide variety of frequencies, wavelength, intensities, and other features. As an illustrative use of a variety of methods and components for radio signal generation, oscillators and piezoelectric crystals may be used to create and change radio frequencies in different antenna elements 88114. In addition, a variety of filters may be used for smoothing signals or for shaping frequency spectrum of the signal as well as amplifiers for increasing power to be transmitted. The transmitter 88116 may emit RF power waves that are pocket-forming with a power capability from few watts to a predetermined number of watts required by a particular chargeable electronic device. Each antenna may manage a certain power capacity. Such power capacity may be related with the application. In some embodiments, the one or more power sources 88128 may be a mechanical power source, such as a crank, a chemical power source, such as a battery, or an electrical power source, such as a capacitor or a photovoltaic cell. In some embodiments, the proximity transmitter 88100 can be powered via mains electricity, such as via a power cord plugged into a wall outlet, which can be selectively detachable from the proximity transmitter 88100 or be permanently attached to the proximity transmitter 88100.

In one method of operation, the transmitter 88116 may transmit or otherwise broadcast controlled RF waves that converge at a location in three-dimensional space, thereby forming the one or more pockets of energy 88110. These RF waves may be controlled through phase and/or relative amplitude adjustments to form constructive or destructive interference patterns (i.e., pocket-forming). The one or more pockets of energy 88110 may be two or three-dimensional fields that are created by forming constructive interference patterns; whereas transmission nulls may be a particular two or three-dimensional physical location that are generated by forming destructive interference patterns. Accordingly, a receiver may harvest electrical energy from the one or more pockets of energy 88110 produced by pocket-forming for charging or powering a device coupled thereto.

In some embodiments, a communications component, as disclosed herein, is optional, but when used, the communication component is powered via the one or more power sources 88128 and can be used to identify a location of the receiver, such as via communicating with the receiver, such as via a directional antenna. For example, the communications component can be a chip or circuitry configured to communicate over a short range communication protocol.

FIG. 88D illustrates a schematic diagram of a proximity transmitter 88118 comprising or otherwise coupled to a communications component 88126 and a sensor 88130, in accordance with an embodiment of the present disclosure. One skilled in the art would appreciate that communications component 88126 and the sensor 88130 may be physically associated with the transmitter 88118 in any number of combinations, as the communications component 88126 and/or the sensor 88130 may be connected to the proximity transmitter 88118, or may be an integrated component of the proximity transmitter 88118.

In some embodiments, the proximity transmitter 88118 may comprise a communications component 88126, which may include integrated circuits and antennas configured to allow the proximity transmitter 88118 to communicate with receivers or other devices using any number of wired or wireless protocols. Non-limiting examples of wired communications may include Ethernet, USB, PCI, Firewire, and the like. Non-limiting examples of wireless protocols may include Wi-Fi, Bluetooth®, ZigBee®, NFC, RFID, and the like. In operation, the communications component 88126 of the proximity transmitter 88118 and a corresponding component of the receiver or electronic device may exchange communications signals containing operational data related to wireless charging and generating power waves, including operational instructions, measurements, and/or operational parameters. The controller 88124 of the proximity transmitter 88118 may determine various modes of operation and/or how to appropriately generate and transmit power waves based on the operational data received by the communications component 88126 via the communications signals.

As an example, the communications component 88126 of the proximity transmitter 88118 may include a Bluetooth-enabled communications chip and antenna, which may communicate operational data with a receiver using communications signals conforming to Bluetooth® technology and protocols. In this example, the communications component 88126 may detect the presence of the receiver based on Bluetooth-based data packets broadcasted by the receiver, or the receiver may transmit a "wake up" or "turn on" command to the proximity transmitter 88118, which is captured by the communications component 88126 and send to the controller 88124 of the proximity transmitter 88118 which may in turn activate various power wave generate routines. A processor or other component of the proximity transmitter 88118 may continuously monitor for signals triggering proximity transmitter 88118 operation (e.g., "wake up" or "turn on" signals), or may periodically poll for such signals. As the proximity transmitter 88118 may limit the distance at which the power waves may effectively charge the receiver, the communications component 88126 may determine whether the receiver is within a threshold distance from the proximity transmitter 88118 based on a signal strength of the communications signals or other parameters.

As another example, the communications component 88126 of the proximity transmitter 88118 may include a Bluetooth-enabled communications chip and antenna, which may communicate operational data with a receiver using communications signals conforming to Bluetooth® technology and protocols. In this example, the communications component 88126 may receive a number of operational parameters, such as a signal strength of the communications signals received from the receiver or an amount of power (e.g., voltage) being received by the receiver, to determine a location of the receiver with respect to the proximity transmitter 88118. These values and/or the determined location of the receiver may then be used by the proximity transmitter 88118 to determine which, if any, antennas 88120 to activate, and/or the physical characteristics of the power waves (e.g., frequency, amplitude, power level).

The sensor 88130 may receive raw sensor data from various types of sensors and then sends the sensor data to the one or more controllers 88124 of the proximity transmitter 88118. In some implementations, the sensor 88130 or related processor may execute a number of pre-processing routines on the raw sensor data. As such, the term "sensor data" may be used interchangeably with "raw sensor data" as it should be appreciated that the sensor data is not limited to raw sensor data and can include data that is processed by a processor associated with the sensor 88130, processed by the transmitter 88118, or any other processor. The sensor data can include information derived from the sensor 88130, and processed sensor data can include determinations based upon the sensor data.

In operation, the sensor data may help the transmitter 88118 determine various modes of operation and/or how to appropriately generate and transmit power waves, so that the transmitter 88118 may provide safe, reliable, and efficient wireless power to the receiver. As detailed herein, the sensor 88130 may transmit sensor data collected during sensor operations for subsequent processing by a processor of the transmitter 88118. Additionally or alternatively, one or more sensor processors may be connected to or housed within the sensor 88130. Sensor processors may comprise a microprocessor that executes various primary data processing routines, whereby the sensor data received at the transmitter processor has been partially or completely preprocessed as useable mapping data for generating power waves.

The sensor 88130 can be optionally coupled to the one or more power sources 88128. Alternatively or additionally, the sensor 88130 can comprise a power source, such as a mechanical power source, such as a crank, a chemical power source, such as a battery, or an electrical power source, such as a capacitor or a photovoltaic cell. For example, the housing 88102 can comprise the transmitter 88118, where the power source 88128 is a first power source and the sensor 88130 comprises a second power source, whether identical to or different from the first power source in power source manner, with the second power source being comprised in the housing 88102, whether internal to or external to the transmitter 88118. Alternatively or additionally, the sensor 88130 can operate without a power source, such as via being passive. However, note that the sensor 88130 can be a passive sensor or an active sensor.

The sensor 88130 can be positioned in any part or anywhere on or in the proximity transmitter 88100, whether unitary to or assembled therewith. For example, the housing 88102 comprises at least one of the interior space, the sidewall 88104, the top 88106, or the bottom 88108, where at least one of the interior space, the sidewall 88104, the top 88106, or the bottom 88108 comprises the sensor 88130. Alternatively the sensor can be positioned outside the housing in another enclosure, and may be connected to the controller of the proximity transmitter 88100 via a wired connection.

In some embodiments, the sensor 88130 is configured to sense the device 88112. Such sensing can be in the local proximity of the housing 88102, such as within about twelve (12) inches or less from the housing 88102. Accordingly, the sensor 88130 can be a pressure sensor, a contact sensor, a thermal sensor, a static electricity sensor, a motion sensor, a magnetic sensor, or an electromagnetic spectrum sensor. Note that such listing is an example and other types of sensors can be used additionally or alternatively. For example, the sensor 88130 can sense the device 88112 placed on the housing 88102 via a downward pressure of the device 88112, such as via a weight of the device 88112. For example, the sensor 88130 can sense the device 88112 via a contact of the device 88112 with the housing 88102. For example, the sensor 88130 can sense the device 88112 via a thermal signature or a thermal fingerprint from the device 88112, such as via a heat emitted from a battery or a human hand heat remaining on the device 88112 based on handling of the device 88112. For example, the sensor 88130 can sense a static electricity being emitted from or resulting from the device 88112 being placed in proximity with or contacting the housing 88102. For example, the sensor 88130 can sense a motion of the device 312 with respect to the housing 88102 or a motion resulting from the device 312 with respect to the housing 88102. For example, the sensor 88130 can sense the device 88112 via an electromagnetic radiation being emitted from the device 88112, such as a network signal, for instance a cellular signal, a Wi-Fi signal, a short range transmission protocol signal, or others. Note that a range of transmission of the transmitter 88118 and a range of sensing of the sensor 88130 can be identical to or different from each other, whether in a dependent or an independent manner. In some embodiments, the transmitter 88118 is configured to transmit one or more power waves based at least in part on the sensor 88130 sensing the device. For example, when the sensor 88130 senses the device 88112, the sensor 88130 communicates such information to the controller 88124, which in turn activates the one or more RFICs 88122 to emit one or more power waves via the one or more antennas 88120. For example, the transmitter 88118 can comprise a sensor configured to determine a presence of a receiver on the surface layer. For example, the transmitter 88118 can be configured to transmit power waves upon a receiver being placed upon the surface layer of the housing 88102, such via the sensor 88130, which can sense or determine a presence of a receiver on the surface layer of the housing 88102. Note that such sensing can occur without using the optional communications component, as disclosed herein.

In some embodiments, the sensor may be configured to detect humans or other living beings such as pets by detecting the heat generated using thermal sensors. This information may be used by the controller in deciding whether to transmit power transmission waves, whether to lower the transmit power, or it may be used to generate pockets of energy away from the living being, and/or to generate transmission nulls in locations of living beings in order to avoid sensing electromagnetic waves to that location.

Other types or configurations of sensors that can be used herewith are more fully described in U.S. patent application Ser. No. 14/861,285, filed on Sep. 22, 2015, entitled "Systems and Methods for Identifying Sensitive Objects in a Wireless Charging Transmission Field," which is incorporated by reference herein in its entirety.

In some embodiments, the one or more controllers 88124 can select which antenna elements in the array of antenna elements 88120 will transmit one or more power waves, such as via smart dynamic antenna selection, such as based on distance, transmission quality, or others. For example, the one or more controllers 88124 can select which antenna elements 88120 will transmit one or more power waves based on information received from the sensor 88130 or based on a detection of the receiver, such as via a placement of the receiver onto the housing 88102. For example, such selection can be in an alternating manner, where a first antenna element is used and a second antenna element is not used, and then based on an occurrence of a certain condition, the first antenna element is not used, whereas the second antenna element is used.

FIG. 88E illustrates a flowchart of a method of operating a proximity transmitter with a device sensor, in accordance with an embodiment of the present disclosure. A method 88132 comprises a plurality of blocks 88134-88140.

In block 88134, a receiver and associated electronic device may be positioned in proximity of the proximity transmitter. In some embodiments, proximity may include placing the receiver on top of, or otherwise in direct contact with, the proximity transmitter. And in some instances, proximity may include positioning the device within the local proximity of the proximity transmitter, such as within about twelve (12) inches of the proximity transmitter.

In block 88136, the communications component 88126 of the proximity transmitter may detect that the device is nearby or approaching based on communications signals received through a wired or wireless connection. The communications component may then determine whether the to begin generating power waves, which antennas should generate the power waves, and/or the characteristics of the power waves. In some instances, the controller may use this data collected by the communications component to determine whether the receiver has entered a threshold distance to begin transmitting power waves. The controller may then determine which antennas are generally proximate to or in contact with the receiver and thus which antennas should be activated.

In block 88138, the proximity transmitter may execute one or more instructions and/or determines transmission parameters based on operation data received by the communications component, from the receiver. For example, after the communications component detects or otherwise receives a wirelessly broadcasted data packet from the receiver, the controller may automatically begin determining the location of the receiver, or may begin transmitting power waves. As another example, the proximity transmitter may begin determining the location of the receiver, or the distance of the receiver, based on the signal strength of the communications signals or other data reported from the receiver. The proximity transmitter may also begin determining the effective antennas and waveform characteristics to use when transmitting power waves to the receiver.

In block 88140, the transmitter transmits one or more power waves to the device based on the operational data or operational parameters received by the communications component.

FIG. 88F illustrates a flowchart of a method of operating a proximity transmitter with a living tissue sensor, in accordance with an embodiment of the present disclosure. A method 88142 comprises a plurality of blocks 88144-88150.

In block 88144, the device is positioned in proximity of the proximity transmitter. Such positioning can be on the proximity transmitter 88100 or in the local proximity of the proximity transmitter, such as within about twelve (12) inches of the proximity transmitter.

In block 88146, the sensor of the proximity transmitter senses the living beings. For example, the sensor can be a pressure sensor, a contact sensor, a thermal sensor, a static electricity sensor, a motion sensor, or an electromagnetic spectrum sensor.

In block 88148, the sensor informs the transmitter of a presence of the living beings. Such informing can be wired or wireless.

In block 88150, the transmitter controls the one or more RFICs 88122 to emit away or around or in different direction or cease from emitting or not emit one or more power waves via the one or more antennas such that one or more power waves avoid the living beings. Therefore, the transmitter operates such that the one or more pockets of energy avoid the living beings based on being informed via the sensor.

Figure 88G:
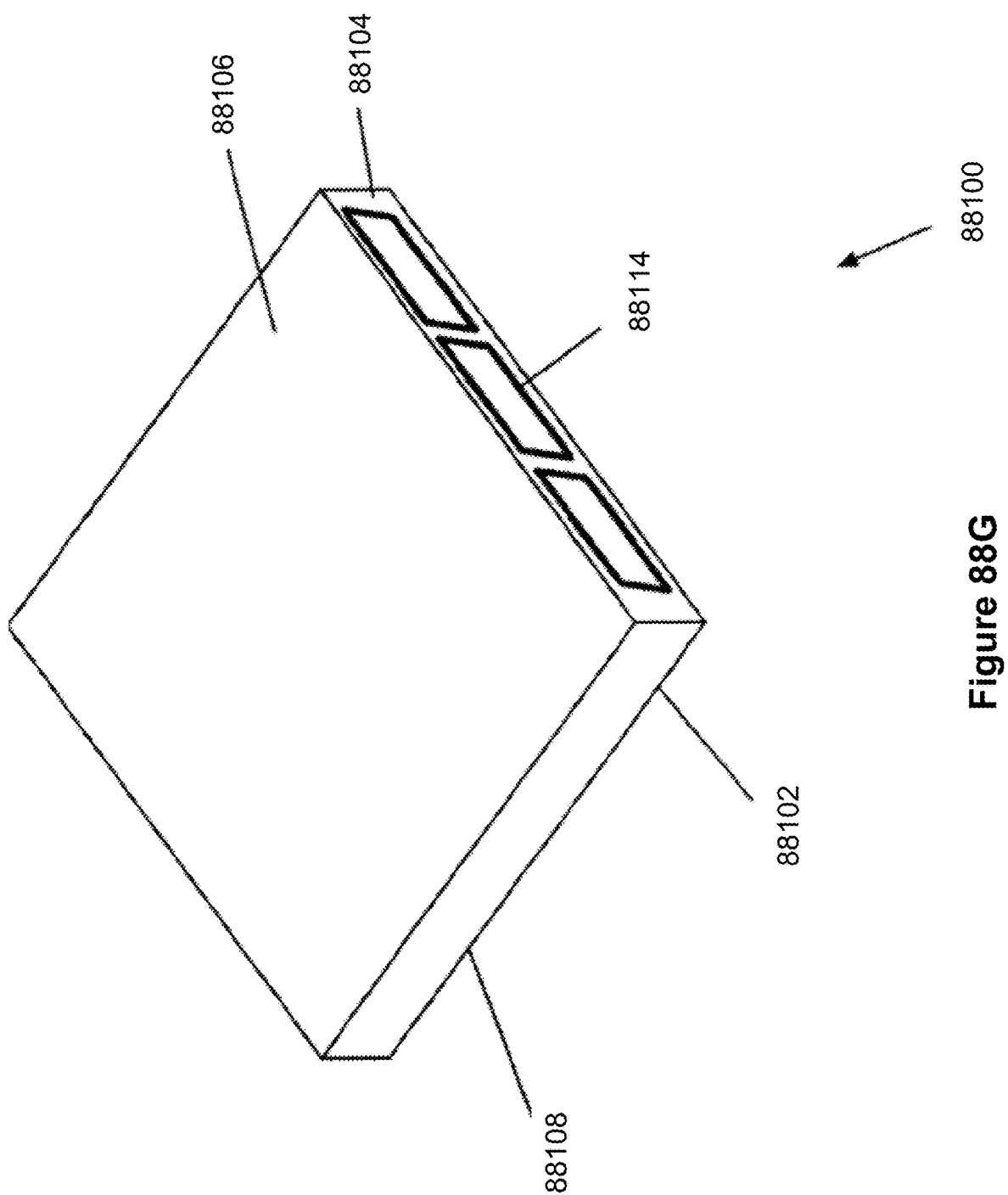

FIG. 88G illustrates a proximity transmitter 88100 comprising a sidewall 88104 with an antenna array, in accordance with an embodiment of the present disclosure. The sidewall 88104 of the housing 88102 comprises the array of antenna elements 88114, which can operate as a single antenna. Such configuration can be via the array of antenna elements 88114 being embedded in the sidewall 88104 or coupled to the sidewall 88104, which can be removable, such as via mating or fastening. Note that more than one sidewall 88104 can comprise the array of antenna elements 88114, in any permutation or combination. For example, opposing or adjacent sidewalls 88104 can comprise the array of antenna elements 88114. The array of antenna elements 88114 are part of the transmitter such that the array of antenna elements 88114 transmit one or more RF waves, as described herein. The one or more pockets of energy 88110 may be a 3D field of energy that are created by forming constructive interference patterns where the power transmission waves accumulate, around which one or more corresponding transmission null in a particular physical location may be generated by destructive interference patterns. A transmission null in a particular physical location may refer to areas or regions of space where pockets of energy do not form because of destructive interference patterns of power transmission waves.

In some embodiments, the bottom 88108 of the housing 88102 comprises the array of antenna elements 88114, which can operate as a single antenna. Such configuration can be via the array of antenna elements 88114 being embedded in the bottom 88108 or coupled to the bottom 88108, which can be removably, such as via mating or fastening.

In some embodiments, the array of antenna elements 88114 can be at least partially invisible, such as via being positioned underneath an outermost surface of at least one of the bottom 88108 or the sidewall 88104. However, in some embodiments, the array of antenna elements 88114 can be at least partially visible, such as via being positioned on top of the outermost surface of at least one of the bottom 88108 or the sidewall 88104.

Figure 88H:
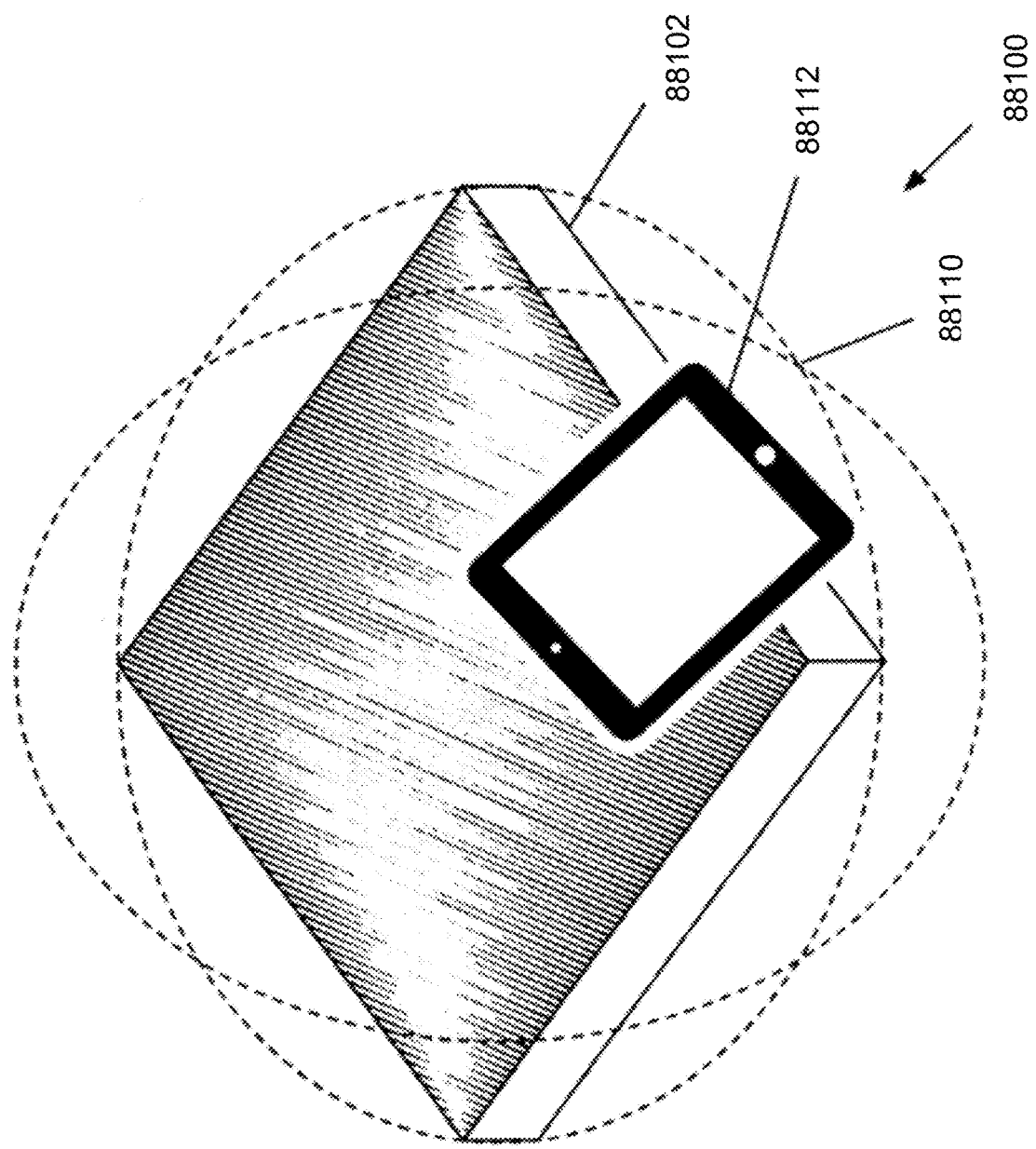

FIG. 88H illustrates a proximity transmitter transmitting one or more power waves such that the one or more power waves converge in a three dimensional space to form one or more pockets of energy, in accordance with an embodiment of the present disclosure. Note that the device 88112 is not centrally or specifically aligned/oriented/positioned on the housing 88102 to be wirelessly charged via the transmitter of the proximity transmitter 88100. Rather, the device 88112 can be positioned anywhere on the housing 88102 to be wirelessly charged or in the local proximity of the housing 88102 to be wirelessly charged, whether with a use of a sensor or communications component, or without the use of the sensor or communications component.

Figure 88I:
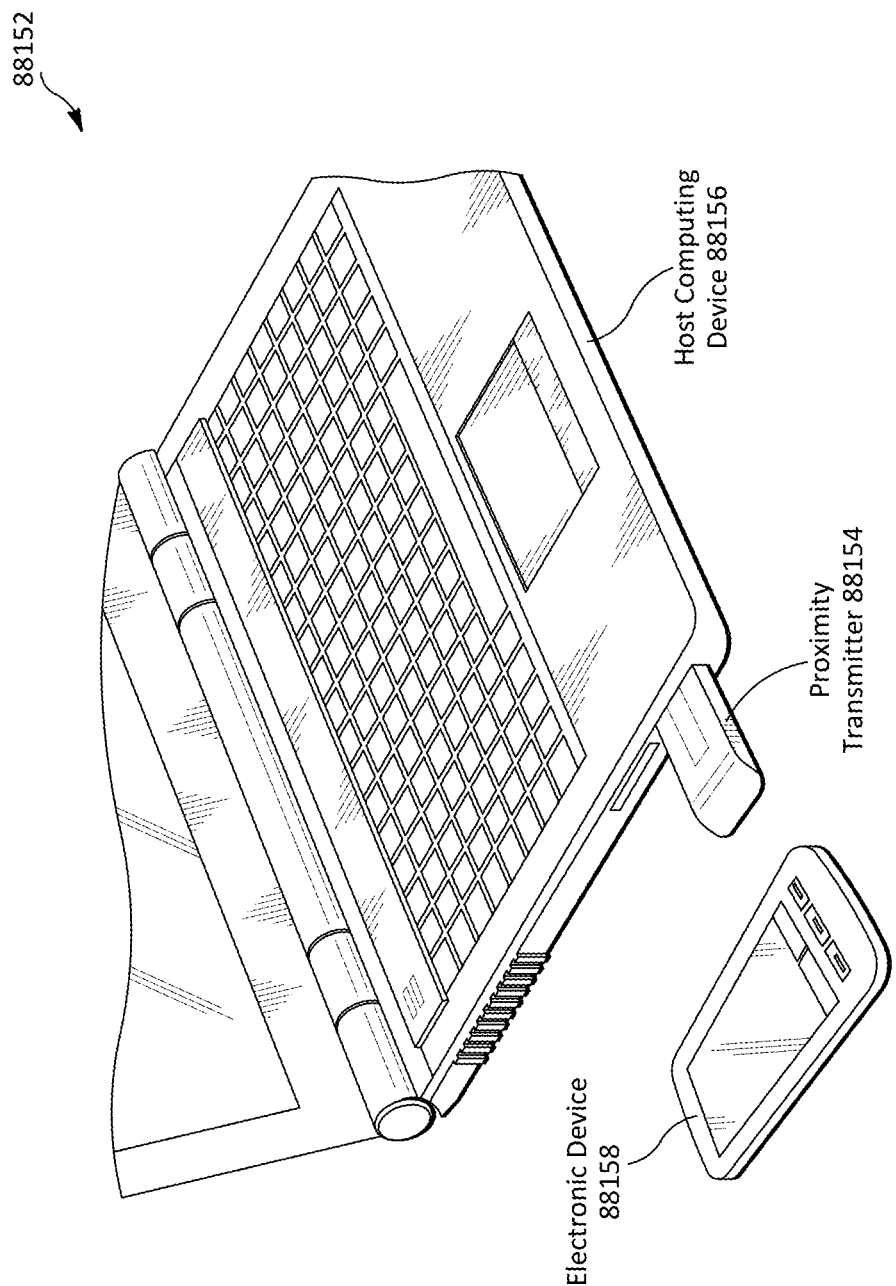

FIG. 88I shows a system 88152 for wireless power charging according to an exemplary embodiment. In the exemplary system 88152, the proximity transmitter 88154 may be a USB device that couples to a computer 88156 or other type of computing device, and may provide wireless power to an electronic device 88158, which in the exemplary system 88152 comprises an integrated receiver component.

A proximity transmitter 88154 may have nearly any form factor or shape. In the system 88152 shown in FIG. 88I, the proximity transmitter 88152 may be a USB device that couples to the computer 88156 through a USB port. The proximity transmitter 88152 may be directly coupled to the computer 88156, as the USB components and transmission components (e.g., antennas, integrated circuits, controller) are integrated into a common housing. However, in some embodiments, the transmission components may be in a separate housing, such that a USB wire couples the proximity transmitter 88154 to the computer 88156.

The proximity transmitter 88154 may comprise any number of wireless transmission components, but may additionally or alternatively capitalize on components of the computer 88156. For example, the proximity transmitter 88154 may not comprise a communications component, but may instead communicate operational data with the receiver through the computer's communications components, such as the computer's Bluetooth® or Wi-Fi antennas, among others. The proximity transmitter 88154 may also draw power from the computer 88156 as a power source. It should be appreciated that the proximity transmitter 88154 may be coupled to the computer 88156 through any type of data port of a computing device 88156 that may facilitate wired data and/or power exchanges between the proximity transmitter 88154 and the computing device 88156, and should not be considered to be limited solely to USB ports.

In some embodiments, the proximity transmitter 88154 may comprise an antenna array underneath or on the top surface that may transmit power waves within an inch from the top surface of the proximity transmitter 88154. In such embodiments, the proximity transmitter 88154 may function as a platform or stand for the electronic device 88158, and the antennas may transmit power waves to antennas of the receiver integrated into the electronic device 88158.

In some embodiment, the proximity transmitter 88154 may comprise antennas situated along the sidewalls of the proximity transmitter 88154, whereby the antennas may transmit power waves to the receiver of an electronic device 88158, in a direction other than or in addition to directly over top of the proximity transmitter 88154. Advantageously, this may allow the proximity transmitter to provide power to an electronic device 88158 situated nearby a proximity transmitter 88154 and computing device 88156, within a threshold distance of the proximity transmitter 88154. In many cases, the proximity transmitter 88154 may be configured with a threshold distance may be within the range of about one millimeter to about twelve inches. One having skill in the art would appreciate that the threshold distance may vary, and would not necessarily be limited to these distances. It should also be appreciated that the threshold distance in operation is not always exact, as there may be some slight natural variation in waves received and identified by the communications components. The communications components of the proximity transmitter 88154 and the receiver may exchange communications signals to determine whether the receiver of the electronic device 88158 is within the threshold distance to the proximity transmitter 88154. For embodiments where the receiver is an integrated component of the electronic device 88158, like the exemplary embodiment shown in FIG. 88I, the communications component of the receiver may include one or more of the native communications components of the electronic device 88158. Similarly, in some embodiments, the proximity transmitter 88154 may use one or more communications components native to the computing device 88156.

Figure 88K:
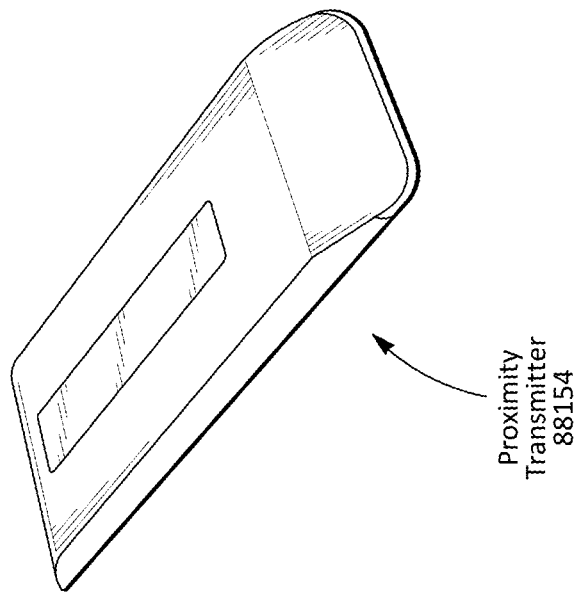
Figure 88J:
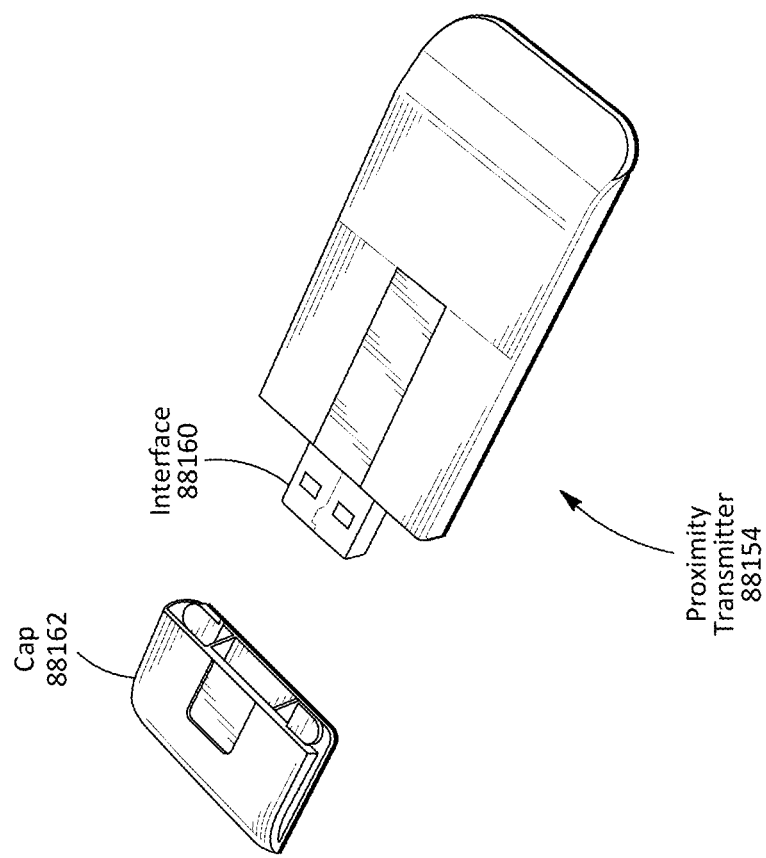

FIG. 88J and FIG. 88K are enlarged, perspective views of the exemplary proximity transmitter 88154 shown in FIG. 88I. FIG. 88J shows additional details for the proximity transmitter 88154, including an interface 88160 and a protective cap 88162. FIG. 88K shows an optional product form factor in which a cap 88162 may be placed over the interface 88160 to protect the operations of the interface 88160.

The interface 88160 of the exemplary transmitter 88154 is a "male" USB interface that allows the proximity transmitter to connect to any host device, such as a computer, through a corresponding USB port, either directly through a corresponding "female" USB interface on the host device or indirectly through a "female" to "male" connector. In some implementations, the proximity transmitter 88154 may draw power through the port connection from the host device, using the host device as a power source. In some implementations, the proximity transmitter 88154 may transmit data and/or instructions related to the operation of the power transmitter 88154. In some cases, in order to communicate data and/or instructions, the proximity transmitter 88154 may upload and install pre-stored drivers or other software modules to the electronic device, or may instruct the host device to download such drivers or software. One having skill in the art would recognize that the interface 88160 may be of any interface type and corresponding port that would allow the proximity transmitter 88154 to draw power from the host device and/or would allow the proximity transmitter 88154 and host device to exchange operational data and/or operational instructions. Non-limiting examples of the types of interfaces 88160 and corresponding ports and protocols allowing peripheral devices to interchangeably connect with host devices may include: Firewire, Thunderbolt, PCI, Ethernet, and the like. Furthermore, the proximity transmitter 88154 may operate by interfacing with computing devices of different operating systems, processors, or peripherals. This may involve installing or downloading drivers (e.g., software modules) that configure such devices to communicate with the proximity transmitter 88154.

Figure 88L:
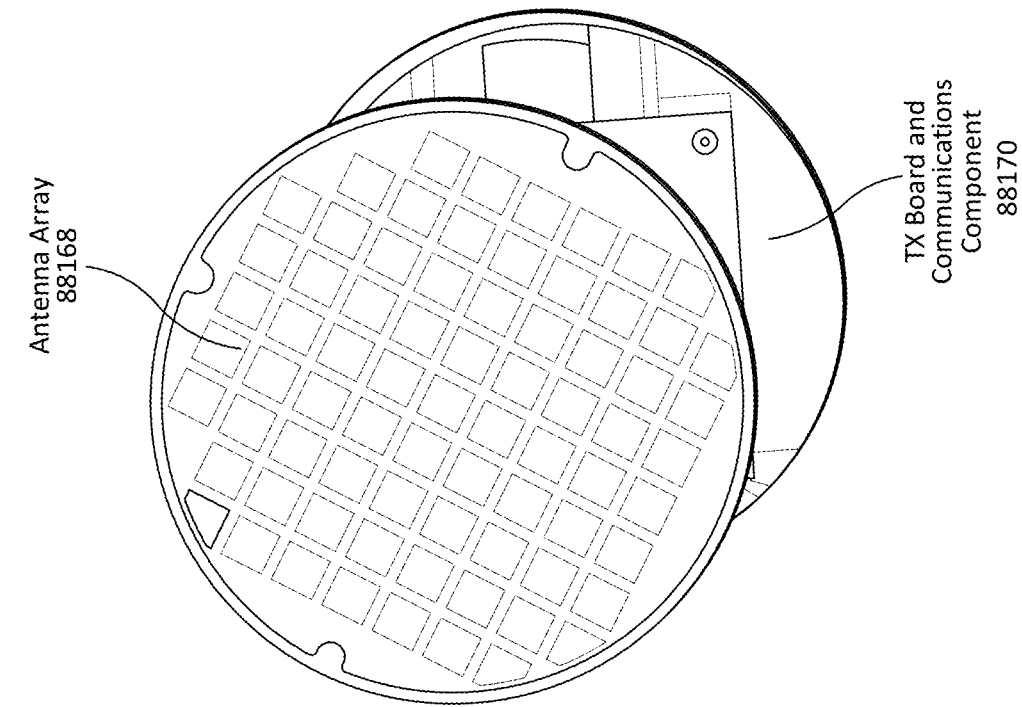
Figure 88L:
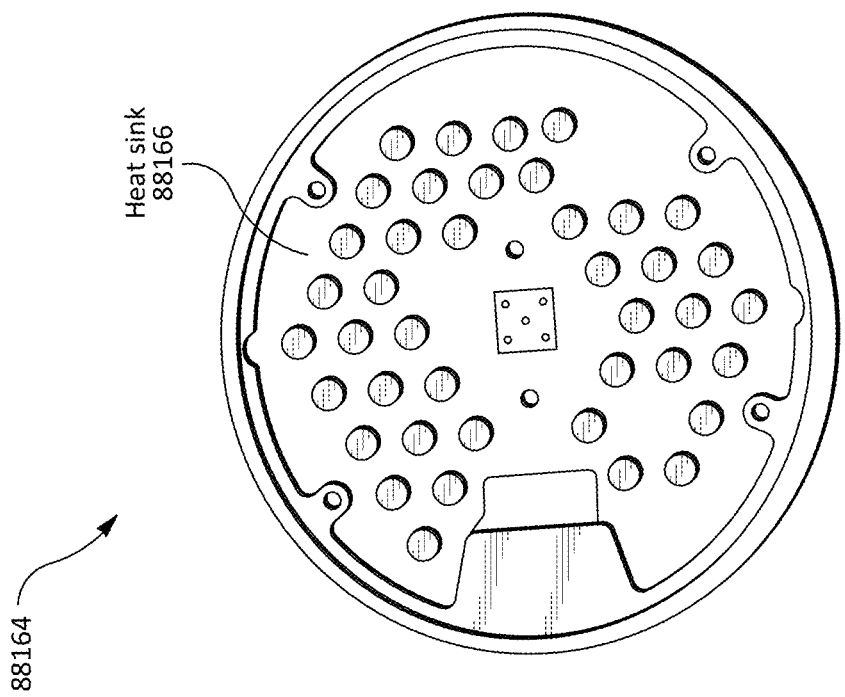

FIG. 88L shows components of a proximity transmitter 88164 device, according to an exemplary embodiment. The exemplary proximity transmitter 88164 may comprise a heat sink 88166, array of one or more antennas (antenna array 88168), and one or more circuit boards 88170. The circuit boards 88170 may comprise any number of circuits, antennas, processors, or other components capable of performing the various tasks described herein. For example, the circuit boards 88170 may include a controller that manages operation of the proximity transmitter 88164, such as determining which, if any, antennas of an antenna array 88168 should be transmitting power waves, and the characteristics of those power waves. As another example, the one or more circuit boards 88170 may include a communications component, such as a Bluetooth® chip and associated antenna, allowing the proximity transmitter to detect receivers, determine whether receivers are within a proximity threshold, and/or to exchange operational data with receivers through some wired-based or wireless communications protocol. It should be understood that additional or alternative components may be included on the one or more circuit boards 88170 of the exemplary proximity transmitter 88164.

An antenna array 88168 may comprise one or more antennas of one or more antenna types, each configured to transmit power waves generated by circuits, such as waveform generators, of a circuit board 88170. In some cases, the antenna array 88168 may transmit the power waves such that the power waves generate constructive interference patterns at some area in front of the antennas, and within some proximity of the proximity transmitter 88164. In some cases, rather than directing the power waves to some convergence point, the antenna array 88168 may transmit the power waves as a collection of power waves originating from one or more of the antennas. As an example, in some circumstances there may not be enough distance between the antennas and the receiver to allow the power waves to converge at a particular point, or the antennas may not be configured to adjust the vectors of the power waves, and so a subset of antennas in front of, or in contact with, the receiver may be selected to transmit power waves as a collection of power waves. In some embodiments, and in similar circumstances, the antenna array 88168 may be slightly concave with respect to a housing surface covering the antenna array 88168, and thus the power waves may be generally transmitted at slightly acute angles with respect a middle axis of the antenna array 88168, as opposed to alternative embodiments where the antennas are situated parallel to the housing surface covering the antenna array 88168.

A heat sink 88166 may be a metal construct or other material that may alleviate the amount of heat generated by components of the proximity transmitter 88164 during operation. In some circumstances, but not always, a proximity transmitter 88164 may generate heat due to the electrical current fed through the circuitry from a power source; this heat might eventually damage components of the transmitter 88164, such as the circuitry on the boards 88170. The heat sink 88166 may be a permanent or detachable component, and may comprise metal, ceramic or other material, configured to dissipate the heat generated by the proximity transmitter 88164 components.

Figure 88M:
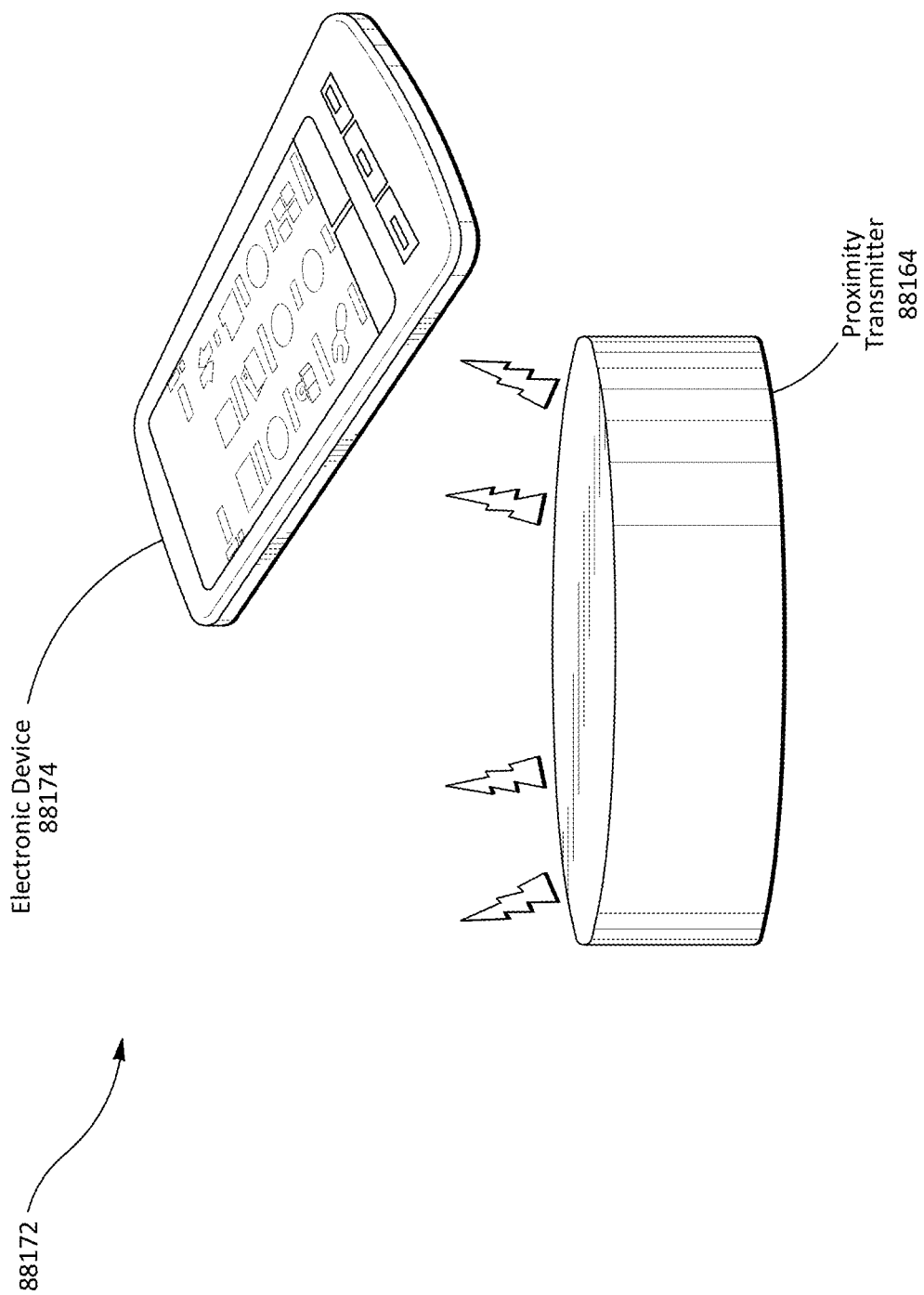

FIG. 88M shows a wireless charging system 88172, according to an exemplary embodiment. The exemplary system 88172 may comprise the exemplary proximity transmitter 88164 shown in FIG. 88L, and an electronic device 88174. The proximity transmitter 88164 may be the product of assembling the components shown in FIG. 88L, as well as any number of additional or alternative components. The electronic device 88174 may be any device requiring electric energy and capable of being coupled to or comprising a receiver. In the exemplary embodiment, the electronic device 88174 may be smartphone comprising an integrated receiver.

In operation, the proximity transmitter 88164 may detect the presence of the electronic device when the proximity transmitter 88164 receives one or more wireless communications signals, such as Bluetooth® or Wi-Fi signals. Based on operational data received in the communications signals, such as signal strength, response time, or some other location data indicating the location and/or proximity of the electronic device 88174, the proximity transmitter 88164 may determine whether the electronic device is within a proximity threshold distance from the antenna array. Additionally or alternatively, the proximity transmitter may comprise a sensor, such as a capacitive sensor to sense presence of the electronic device, magnetic sensor for detecting the magnetic waves produced by the electronic device 88174 or a pressure sensor, used to determine a proximity threshold or to determine that the electronic device is in contact with the exterior housing of the proximity transmitter 88164. When the proximity transmitter 88164 determines that the receiver is within the threshold proximity or is in contact with the proximity transmitter 88164 may generate and transmit power waves. In some cases, the proximity transmitter 88164 may identify a subset of antennas for transmitting power waves. This may be advantageous in circumstances where the electronic device 88174 does not cover the entire antenna array. This may also be advantageous in circumstances where the proximity transmitter 88164 comprises antenna arrays directed outward in different directions of the proximity transmitter 88164, thus power transmitter 88164 may identify which antenna array to activate based on where the electronic device is located with respect to the proximity transmitter 88164.

In some implementations, a receiver, such as the receiver integrated into the electronic device 88174, may be relocated away from the proximity transmitter 88164, but may then switch to receiving power waves from non-proximity transmitters (not shown), which may be transmitter devices configured to transmit power waves into a transmission field, but without the proximity limitations of a proximity transmitter 88164. Descriptions and examples of non-proximity transmitters may be found in U.S. patent application Ser. No. 14/860,991, filed Sep. 22, 2015, entitled "Systems and Methods for Generating and Transmitting Wireless Power Transmission Waves," which is incorporated by reference herein in its entirety. In such implementations, when the electronic device 88174 is moved away from the proximity of the proximity transmitter 88164, or when some other operational condition is violated (e.g., a person's hand is detected between the electronic device 88174 and the antenna array of the proximity transmitter 88164), the electronic device 88174 may then communicate with a non-proximity transmitter. When the electronic device 88174 enters the transmission field of the non-proximity transmitter, and when any operational conditions are satisfied (e.g., the person is not within a threshold distance to the power waves of the non-proximity transmitter), the receiver of the electronic device may then begin receiving power waves from the non-proximity transmitter. Conversely, when an electronic device 88174 receiving wireless power from a non-proximity transmitter is moved within proximity parameters (e.g., proximity threshold) of a proximity transmitter 88164, the receiver of the electronic device 88174 may discontinue receiving power from the non-proximity transmitter and start receiving power from the proximity transmitter 88164. Furthermore, in some embodiments, a receiver may receive power from both a non-proximity transmitter and a proximity transmitter 88164 at the same time. In such embodiments, the energy pocket formed at or about the receiver is a combination of the energy pocket created by the non-proximity transmitter as well as the pocket of energy created by the proximity transmitter. Additional descriptions and examples of receivers receiving power from one or more transmitters may be found in U.S. Provisional Patent Application Ser. No. 62/387,466, entitled "Cluster Management of Transmitters in a Wireless Power Transmission System," filed on Dec. 24, 2015.

FIGS. 88A-88M illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 88A-88M.

Presented below are example embodiments of proximity transmitters for wireless power charging systems.

In some embodiments, an example wireless charging proximity transmitter comprises an array of one or more antennas; and a surface layer proximate to the array of antennas. The transmitter is configured to transmit one or more power waves to a receiver in response to a device associated with the receiver being within a proximity threshold of the surface layer of the proximity transmitter.

In some embodiments, the proximity transmitter antenna array consists of one antenna, and the transmitter transmits one power wave.

In some embodiments, the proximity transmitter is further configured to transmit the one or more power waves to the receiver upon the device associated with the receiver being placed on the surface layer.

In some embodiments, the proximity transmitter has a constructive interference pattern formed within about twelve inches of the surface layer of the proximity transmitter.

In some embodiments, the proximity transmitter has subset of the antennas of the array transmit the one or more power waves to a receiver associated with a device on the surface layer.

In some embodiments, the subset of the antennas of the array that transmit the one or more power waves to the receiver are directly below the receiver.

In some embodiments, the proximity transmitter further comprising a sensor configured to determine the presence of the device associated with the receiver on the surface layer.

In some embodiments, the sensor is selected from the group consisting of a pressure sensor, a magnetic sensor, a contact sensor, a thermal sensor, a static electricity sensor, a motion sensor, and an electromagnetic spectrum sensor.

In some embodiments, the sensor is configured to sense a living being in a proximity to the proximity transmitter, and the transmitter is further configured to transmit the one or more power waves upon the sensor sensing the living being within the proximity to the proximity transmitter.

In some embodiments, the sensor is a passive sensor.

In some embodiments, the sensor is an active sensor.

In some embodiments, the one or more power waves comprise radio frequency waves.

In some embodiments, the one or more power waves comprise ultrasound waves.

In some embodiments, an wireless charging proximity transmitter comprises a housing comprising an upper surface layer, a lower surface layer, at least one side wall extending from the lower surface layer to the upper surface layer, an array of one or more antennas positioned between the lower surface layer and the upper surface layer, and a controller configured to transmit one or more power waves from the array of one or more antennas, the one or more power waves transmitted to converge at a location of a device associated with a receiver upon identifying the device within a proximity threshold from a portion of the upper surface layer of the proximity transmitter.

In some embodiments, the constructive interference pattern is formed proximate to the surface layer of the proximity transmitter.

In some embodiments, the proximity transmitter shape is selected from the group consisting of a circle, a rectangle, a square, a triangle, an octagon, or an oval.

In some embodiments, the array of antennas are arranged in a plane parallel to the lower surface or the upper surface.

In some embodiments, the array of antennas are arranged in a non-planar fashion forming a three dimensional placement of antennas inside the proximity transmitter housing.

FIGS. 89A-89I and 90A-90F illustrate examples of devices, apparatus, and methods of object detection in wireless power charging systems, in accordance with some embodiments.

Figure 89A:
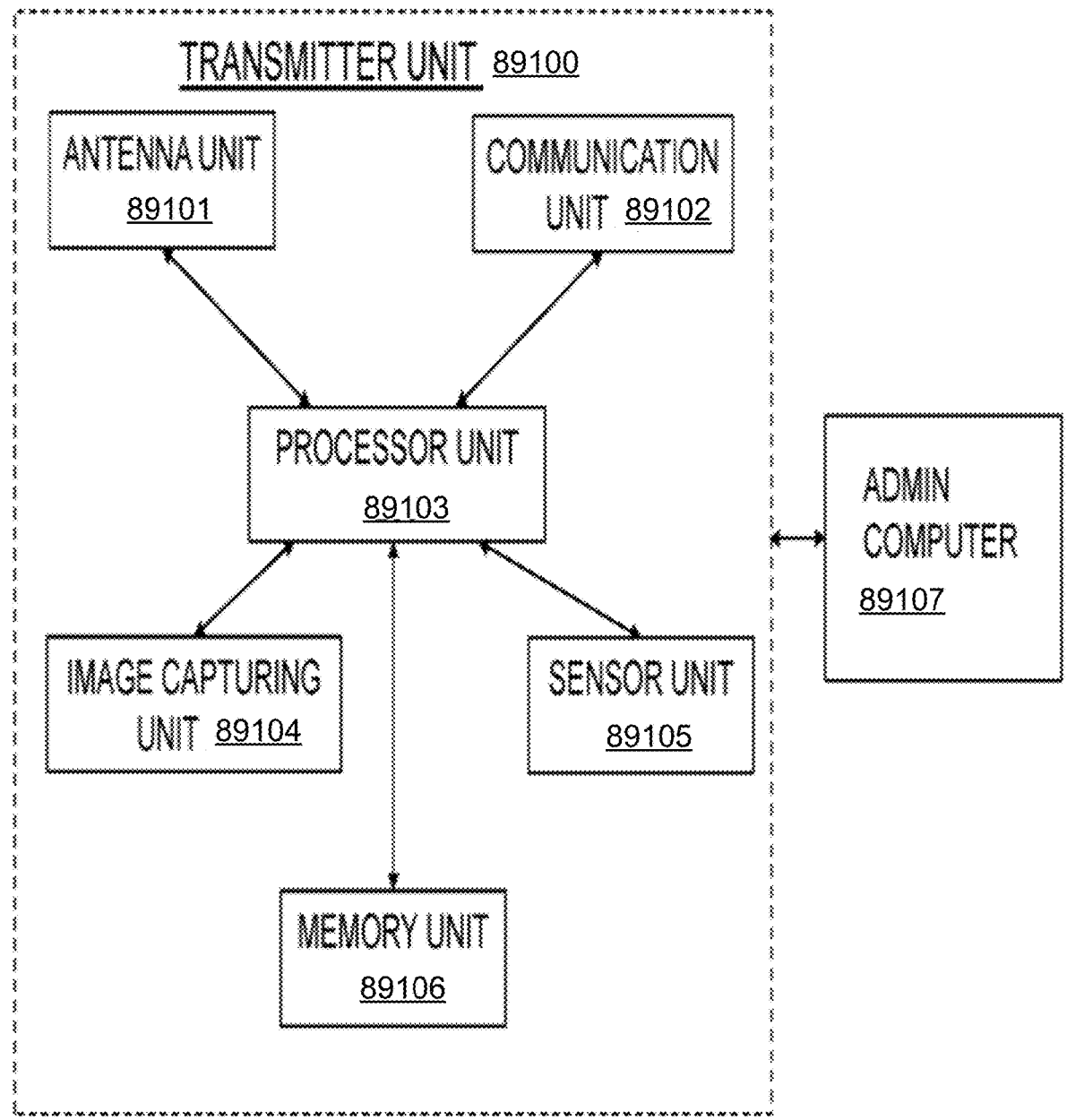

FIG. 89A illustrates a transmitter 89100 of a wireless power transmission system, according to an exemplary embodiment. The wireless power transmission system includes the transmitter 89100 and an admin computer 89107 (also referred to as administrator computer). The transmitter 89100 includes antennas 89101, a communication component 89102, a processor 89103, cameras 89104, sensors 89105, and a memory 89106. The transmitter 89100 may send various types of waves such as power waves into a transmission field of the transmitter 89100. The transmission field of a transmitter 89100 may be a two or three-dimensional space into which the transmitter 89100 may transmit the power waves.

The transmitter 89100 may be designed to function as a single transmitter. In another embodiment, there may be a plurality of transmitters where each of the plurality of transmitters are designed to work independently. The transmitter 89100 may include or be associated with the processor 89103 (or a microprocessor). The processor may control, manage, and otherwise govern the various processes, functions, and components of the transmitter 89100. The processor 89103 implements a system to control the operations of the transmitter 89100. The processor may be an integrated circuit that includes logic gates, circuitry, and interfaces that are operable to execute various processes and tasks for controlling the behavior of the transmitter 89100 as described herein. The processor may comprise or implement a number of processor technologies known in the art; non-limiting examples of the processor include, but are not limited to, an x86 processor, an ARM processor, a Reduced Instruction Set Computing (RISC) processor, an Application-Specific Integrated Circuit (ASIC) processor, or a Complex Instruction Set Computing (CISC) processor, among others. The processor may also include a Graphics Processor (GPI5) that executes the set of instructions to perform one or more processing operations associated with handling various forms of graphical data, such as data received from a visual or thermal camera, or to produce a graphical user interface (GUI) allowing a user to configure and manage operation of the transmitter 89100.

The processor 89103 may be configured to process and communicate various types of data (e.g., image data and/or video data obtained from video cameras of the cameras 89104, and/or sensor data obtained from the sensors 89105). Additionally or alternatively, the processor 89103 may manage execution of various processes and functions of the transmitter 89100, and may manage the components of the transmitter 89100. In one example, the processor 89104 may process the image data and/or video data of one or more objects captured by the cameras 89104, to identify human objects and/or receivers that may inhabit the transmission field of the transmitter 89100. In another example, the processor may process the sensor data of one or more objects captured by the sensors 89105, to identify human objects and/or receivers that may inhabit the transmission field of the transmitter 89100. In yet another example, the processor 89104 may generate heat-mapping data from communications signals received by the communications component 89102, and then, based upon the sensor data received from the sensor 89105, the processor 89104 may determine the safest and most effective characteristics for the power waves. Additional discussion and examples of functions related to determining how to formulate and transmit power waves, in order to effectively and safely provide energy to receivers, may be found in U.S. patent application Ser. No. 14/856,337, entitled "Systems and Methods for Wireless Power Charging," filed Sep. 16, 2015.

In an embodiment, the transmitter 89100 corresponds to a single transmitter that may include a single transmitter processor. However, it should be appreciated that, in some cases, a single transmitter processor may control and govern multiple transmitters. For example, the transmitters may be coupled to the admin computer 89107 comprising a processor that executes software modules instructing the processor of the admin computer 89107 to function as the transmitter processor capable of controlling the behavior of the various transmitters. Additionally or alternatively, the single transmitter 89100 may include multiple processors configured to execute or control specified aspects of the transmitter's behavior and components. For example, the transmitter 89100 may include an image processing processor and a sensor processor, where the sensor processor is configured to manage the sensors 89105 and process sensor data, and where the image processing processor is configured to process the image data produced by the cameras 89104 as well as manage the remaining functions of the transmitter 89100.

It should be appreciated that the wireless power transmission system may include any number of transmitters, such as a first transmitter and a second transmitter, which may transmit the power waves into one or more transmission fields of the transmitters. As such, the wireless power transmission system may include multiple discrete transmission fields associated with the transmitters, where the transmission field may or may not overlap, but may be managed discretely by the processors of the transmitters. Additionally or alternatively, the wireless power transmission system may include transmission fields that may or may not overlap, but may be managed by the processors of the transmitters as a unitary transmission field.

The antennas 89101 may be attached to antenna arrays. In an embodiment, each antenna array may include a set of one or more antennas configured to transmit one or more types of the power waves. In some embodiments, the antenna array may include antennas 89101 (antenna elements), and one or more integrated circuits controlling the behavior of the antennas, such as generating the power waves having predetermined characteristics (e.g., amplitude, frequency, trajectory, phase). An antenna of the antenna array may transmit the power waves having the predetermined characteristics, such that the power waves arrive at a given location within the transmission field, and exhibit those characteristics. The antennas of the antenna array may transmit the power waves that intersect at the given location (generally, where a receiver is recognized based on the image data obtained from the cameras 89104 and/or the sensor data obtained from the sensors 89105), and due to their respective characteristics, form a pocket of energy, from which the receiver may collect energy and generate electricity. It should be appreciated that, although the exemplary wireless power transmission system describes radio-frequency based power waves, additional or alternative transmitter antennas, antenna arrays, and/or wave-based technologies may be used (e.g., ultrasonic, infrared, magnetic resonance) to wirelessly transmit the power waves from the transmitter 89100 to the receiver. In an alternative embodiment using ultrasound for transmitting power waves, the antennas 89101 are configured as transducers, and other components may be modified to accommodate the differences between RF and ultrasound transmission and reception.

The transmitter 89100 may use the image data and/or the video data to determine where and how the antennas 89101 should transmit the power waves. In another embodiment, the transmitter 89100 may use the sensor data to determine where and how the antennas 89101 should transmit the power waves. In yet another embodiment, the transmitter 89100 may use the image data, the video data, and the sensor data to determine where and how the antennas 89101 should transmit the power waves. The image data, the video data, and/or the sensor data may indicate for the transmitter 89100 where the power waves should be transmitted and the pocket of energy should be formed, and, in some cases, where the power waves should not be transmitted. In an embodiment, the image data and/or the video data may be captured by the cameras 89104, and interpreted by the processor 89103 associated with the transmitter 89100, from which the transmitter 89100 may determine how the antennas 89101 should form and transmit the power waves. The sensor data may be captured by the sensors 89105, and interpreted by the processor 89103 associated with the transmitter 89100, from which the transmitter 89100 may determine how the antennas 89101 should form and transmit the power waves. When determining how the power waves should be formed, the transmitter 89100 determines the characteristics for each of the power waves to be transmitted from each of the respective antennas of the antennas 89101. The non-limiting examples of characteristics for the power waves may include: amplitude, phase, gain, frequency, and direction, among others. As an example, to generate the pocket of energy at a particular location, the transmitter 89100 identifies a subset of antennas from the antennas 89101, transmits the power waves to the predetermined location, and then the transmitter 89100 generates the power waves. The power waves transmitted from each antenna of the subset may have a comparatively different, e.g., phase and amplitude.

The antennas 89101 may include one or more integrated circuits that are associated with the antennas 89101 to generate the power waves. In some embodiments, integrated circuits are found on antennas 89101 that house an integrated circuit and the antennas 89101 associated with the integrated circuit. An integrated circuit may function as a waveform generator for an antenna associated with the integrated circuit, providing the appropriate circuitry and instructions to the associated antenna so that the antenna may formulate and transmit the power waves in accordance with the predetermined characteristics identified for the power waves based on the image data or some other data. The integrated circuits may receive instructions from the processor 89103 (e.g., transmitter processor) that determines how the power waves should be emitted into the transmitter's transmission field. The processor 89103, for example, may determine where to form a pocket of energy based on the image data and then may instruct the integrated circuits of the antennas 89101 to generate the power waves. The integrated circuits may then formulate the power waves and instruct their respectively associated antennas to transmit the power waves into the transmission field accordingly.

The communication component 89102 may effectuate wired and/or wireless communications to and from receivers of the wireless power transmission system. In one embodiment, the communications component 89102 may be an embedded component of the transmitter 89100; and in another embodiment, the communication component 89102 may be attached to the transmitter 89100 through any wired or wireless communications medium. In some embodiments, the communications component 89102 may be shared among a plurality of transmitters, such that each of the transmitters 89100 coupled to the communication component 89102 may use the data received within a communications signal, by the communication component 89102.

In some embodiments, the communication component 89102 may include electromechanical components (e.g., processor) that allow the communication component 89102 to communicate various types of data with one or more receivers, other transmitters of the wireless power transmission system, and/or other components of the transmitter 89100. In some implementations, these communications signals may represent a distinct channel for hosting communications, independent from the power waves. The data may be communicated using communications signals, based on predetermined wired or wireless protocols and associated hardware and software technology. The communication component 89102 may operate based on any number of communication protocols, such as Bluetooth®, Wireless Fidelity (Wi-Fi), Near-Field Communications (NFC), Zig-Bee, and others. However, it should be appreciated that the communication component 89102 is not limited to radio-frequency based technologies, but may include radar, infrared waves.

The data contained within the communications signals may be used by the wireless-charging devices to determine how the transmitter 89100 may transmit safe and effective power waves that generate a pocket of energy, from which the receiver may capture energy and convert it to useable alternating current or direct current electricity. In one embodiment, using the communications signal, the transmitter 89100 may communicate data that may be used, e.g., to identify receivers within the transmission field, determine whether electronic devices or users are authorized to receive wireless charging services from the wireless power transmission system, determine safe and effective waveform characteristics for the power waves, and hone the placement of pocket of energy, among other possible functions.

The cameras 89104 may include one or more video cameras. The cameras 89104 may be configured to capture image data in the transmission field of the transmitter 89100, and then transmit the image data to the processor 89103 of the transmitter 89100. The cameras 89104 may further be configured to capture image data in their field of view that overlapping the transmission field of the transmitter 89100, and then transmit the image data to the processor 89103 of the transmitter 89100. In one exemplary embodiment, the image data may be raw image data. It is intended that the image data is not limited to the raw image data, and the image data can include data that is processed by a processor associated within the cameras 89104 or an external processor such as the processor 89103 of the transmitter 89100, or any other suitable processor. The raw image data may include frames derived from the cameras 89104, and the processed image data may include for example symbolic data based upon the image data (or the raw image data). In one example, the one or more video cameras may provide the raw image data such as image/frame captures of the transmission field of the transmitter 89100 that may include receivers, humans, animals, and furniture present within the transmission field; and the processed image data from the one or more video cameras may include an orientation in X-plane, Y-plane, and Z-plane, and as well as a determination of the location of the receivers or a location of one or more receiver antennas, which may be based upon any number of features, characteristics, or current states of the receiver, such as data indicating an orientation of the receiver. In another example, the raw image data from the video camera of the cameras 89104 may provide thermal imaging information, and the processed image data may include an identification of the person or animal based upon the thermal imaging information obtained from the captured temperature data. As used herein, any reference to image data or raw image data can include data processed at the processor 89103 or other processing device.

The one or more video cameras may include infrared cameras, thermal cameras, ultrasound cameras, and visible light cameras. The infrared camera of the one or more video cameras is configured to produce the image data comprising an infrared image of a scene within the transmission field using only energy in an infrared portion of an electromagnetic spectrum. The images obtained using the infrared camera may assign colors or gray-levels to pixels composing the scene based on the intensity of an infrared radiation reaching the infrared camera or infrared camera's sensor elements. The resulting infrared image may be based on target's temperature; and the colors or levels displayed by the infrared camera typically correspond to the visible-light colors of the scene, to accurately relate features of interest (e.g. humans, animals, receivers) in the infrared scene with their corresponding locations in the visible-light scene.

The thermal camera of the one or more video cameras corresponds to thermal imaging cameras. The thermal imaging cameras uses an infrared spectrum to detect radiation coming from a determined area under control such as the transmission field of the transmitter 89100 and, based on the intensity of this radiation, there is a forming up of a map of temperatures in the zones placed under control. The detection activity, using the thermal imaging cameras, may be done continuously or dynamically in such a way that a passage of a flow of the one or more objects can be examined in real time. In other words, the one or more thermal imaging cameras control access zones transiting objects have to pass through; and these cameras use the infrared spectrum of the radiation received to assess the temperature gradients in the transmission field of the transmitter 89100 under control.

The operation of the thermal imaging camera may be similar to a standard camera that forms an image using visible light. In comparison with a visible light camera, which forms images with the 400-700 nanometer range of visible light, the thermal camera operates in wavelengths as long as 14,000 nm (14 p.m). The thermal camera may include a near-infrared camera that use the near-infrared part of the electromagnetic spectrum closest to visible light, and a thermal infrared camera that generally operate in the far infrared region. Thermal imaging, or thermography may rely on the principle that all objects emit a certain amount of black body radiation as a function of their temperatures. The higher an object's temperature, the more infrared radiation is emitted as black-body radiation, and the thermal cameras may be configured to detect the radiation in a way similar to the way an ordinary camera detects visible light. In an embodiment, there is a constant heat exchange between human body and environment due to differences in their temperatures. The radiation characteristics of any object can be analyzed using the black-body radiation curve governed by Planck's Law. Essentially all of the radiation of the human body is in the infrared region, with the peak radiation occurring at 9.55 p.m. These parameters are well suited to detection by the thermal cameras.

In one embodiment, the transmitter 89100 may include a single video camera 89104. In another embodiment, the transmitter 89100 may include an array of video cameras 89104. The video cameras may include infrared cameras, thermal cameras, ultrasound cameras, and visible light cameras. The array of video cameras may be positioned for viewing a region of the transmission field of the transmitter 89100. The region of interest may correspond to camera field view in the transmission field of the transmitter 89100. The array of video cameras may be arranged in a linear array in the transmitter 89100. In an alternate embodiment, the various other spatial arrangements including two-dimensional arrays of video cameras may be used.

When multiple cameras are used, each camera may be placed offset from the other cameras such that each camera has a different, possibly partially overlapping, viewpoints. Having cameras placed with offset spacing between them allows for computer vision algorithms to perform calculations and infer relative distances of objects in the two dimensional images captured by each camera.

The transmitter 89100 may have a trigger unit that may include a triggering mechanism to initiate capture of a set of frames by the one or more video cameras of the cameras 89104. In one embodiment, the triggering mechanism may include a central clock signal and an optional signal delivery unit. The central clock signal is delivered via the signal delivery unit to the one or more video cameras of the cameras 89104. In another embodiment, it is also possible to deliver the central clock signal directly to the one or more video cameras of the cameras 89104 either by a physical connection or by a wireless connection. In other embodiments, the one or more video cameras of the cameras 89104 may have their own internal synchronized clocks. A person of skill in the art will recognize that there are many ways to provide clock signal for the one or more video cameras of the cameras 89104 of the transmitter 89100 and will appreciate how to adjust the configuration of the transmitter 89100 depending on the actual way in which clock signal is generated and distributed to the one or more video cameras of the cameras 89104.

In some embodiments, the processor 89103 may be configured to combine and process data captured by the one or more cameras to generate an output of symbolic data. For examples, symbols may be a numerical value such as X, Y, Z coordinates of objects captured in the data, or temperature value that may be represented in numbers. The symbolic data may be obtained by processing the data (image data and/or video data). The processed image data will produce symbolic data that may include number of one or more objects captured in the image data, two-dimensional coordinates of the one or more objects captured in the image data, three-dimensional (XYZ) coordinates of the one or more objects (such as receivers and humans) captured in the image data, motion status of the one or more objects, and size of the one or more objects. The one or more objects may include receivers and humans. In another embodiment, the symbolic data may include three-dimensional (XYZ) coordinates of only one or more receivers, size of the one or more receivers, and angular orientation of the one or more receivers with respect to the transmitter captured in the image data.

In some embodiments, the image data obtained by the thermal imaging camera may include a map of temperatures (temperature data) of the transmission field of the transmitter 89100. During the step of identifying subjects from the image data, the processor 89103 analyzes the map of temperatures to identify a zone of interest that includes temperature values that correspond to body temperature values of the subjects being identified. For example, if the subject being identified is a human, then the processor 89103 may look for the zone of interest in the map that includes the temperature centered in the range of the temperature of the human body, i.e., between 35 and 40 degrees Celsius, 36-37 degrees Celsius being the nominal temperature, but the range can be expanded to include other living beings. After identifying the subjects, the processor 89103 then generates the symbolic data that may include the number of the identified subjects, three-dimensional (XYZ) coordinates of the identified subjects (such as receivers and humans), motion status of the identified subjects, size of the identified subjects, and shape of the identified subjects. In other words, the body temperature of a humans is measured by the thermal imaging camera. The analysis of thermal images captured by the thermal imaging camera by the processor 89103 can then distinguish human beings or other living beings from other parts of the thermal images based on detection of predetermined ranges of typical body temperatures. When viewed through the thermal imaging camera, warm objects stand out well against cooler backgrounds; humans and other warm-blooded animals become easily visible against the environment, during day or night.

The processor 89103 analyzes the map of temperatures to identify a zone of interest that includes temperature values that correspond to the body temperature values of the subjects (human body) being identified. The identification of the zone of interest by the processor 89103 may also depend upon the place in the body at which the measurement is made, the time of day, as well as the activity level of the person. For example, the typical cited values mentioned of temperatures of a human are: oral (under the tongue): 36.8±0.4° C. (98.2±0.72° F.); internal (rectal, vaginal): 37.0° C. (98.6° F.). The body temperature of a healthy person may vary during the day by about 0.5° C. (0.9° F.) with lower temperatures in the morning and higher temperatures in the late afternoon and evening; and body temperature also changes when a person is hungry, sleepy, sick, or cold. Other warm blooded animals may have different body temperatures than human body temperatures. For example, typical cited values of body temperatures include: dogs: 37.9-39.9° C. (100.2-103.8° F.); cats: 38.1-39.2° C. (100.5-102.5° F.); dairy cows: 38.0-39.3° C. (100.4-102.8° F.).

The sensors 89105 may include sensors that may be physically associated with the transmitter 89100 (i.e., connected to, or a component of), or devices may be configured to detect and identify various conditions of the wireless power transmission system and/or transmission field, and the sensor data may then be generated for the transmitter 89100, which may contribute to the generation and transmission of power waves by the transmitter 89100. The sensor data may help the transmitter 89100 determine various modes of operation and/or how to appropriately generate and transmit the power waves, so that the transmitter 89100 may provide safe, reliable, and efficient wireless power to receivers. As detailed herein, the sensors 89105 may transmit sensor data collected during sensor operations for subsequent processing by the processor 89103 of the transmitter 89100. Additionally or alternatively, one or more sensor processors may be connected to or housed within the sensors 89105. The sensor processors may include a microprocessor that executes various primary data processing routines, whereby the sensor data received at the transmitter processor has been partially or completely pre-processed as useable mapping data for generating power waves.

The sensors 89105 may transmit sensor data to the transmitter 89100. Although described in the exemplary embodiment as raw sensor data, it is intended that the sensor data is not limited to raw sensor data and can include data that is processed by a processor associated with the sensor, processed by the receiver, processed by the transmitter, or any other processor. The sensor data can include information derived from the sensor, and processed sensor data can include determinations based upon the sensor data. The processor 89103 can process sensor data received from a sensor of the transmitter or a sensor of a receiver (e.g., a gyroscope, accelerometer). For example, a gyroscope of a receiver may provide raw data such as an orientation in X-plane, Y-plane, and Z planes. In this example, the processor 89103 may generate processed sensor data from the gyroscope, which the processor 89103 may use to determine a location of a receiver antenna based upon the orientation of the receiver. In another example, raw sensor data from an infrared sensor of a receiver, and processed sensor data may determine presence of a person based upon the thermal sensor data. As used herein, any reference to sensor data or raw sensor data can include data processed at the sensor or other device. In some implementations, a gyroscope and/or an accelerometer of the receiver or electronic device associated with the receiver may provide sensor data indicating the orientation of the receiver or electronic device, which the transmitter 89100 may use to determine whether to transmit power waves to the receiver. The receiver may then transmit this sensor data to the transmitter 89100, via communications waves. In such implementations, the transmitter 89100 may transmit the power waves to the location of the receiver until the transmitter 89100 receives, via communications waves, the sensor data produced by the gyroscope and/or accelerometer, indicating that the receiver or electronic device is in motion or has an orientation suggesting that the electronic device is in use or nearby a person.

In some embodiments, the sensors 89105 may be devices configured to emit, receive, or both emit and receive sensor waves, which may be any type of wave that may be used to identify sensitive objects in a transmission field (e.g., a person, a piece of furniture). Non-limiting examples of sensor technologies for the sensors may include: infrared/pyro-electric, ultrasound, ultrasonic, laser, optical, Doppler, accelerometer, microwave, millimeter, and RF standing-wave sensors. Other sensor technologies that may be well-suited to secondary and/or proximity-detection sensors may include resonant LC sensors, capacitive sensors, and inductive sensors. Based upon the particular type of sensor waves used and the particular protocols associated with the sensor waves, the sensor may generate sensor data. In some cases, the sensor may comprise a sensor processor that may receive, interpret, and process sensor data, which the sensor may then provide to a transmitter processor.

In some embodiments, the sensors may be passive sensors, active sensors, and/or smart sensors. The passive sensors, such as tuned LC sensors (resonant, capacitive, or inductive) are a simple type of sensor and may provide minimal but efficient object discrimination. Such passive sensors may be used as secondary (remote) sensors that may be dispersed into the transmission field and may be part of the receiver or otherwise independently capture raw sensor data that may be wirelessly communicated a sensor processor. The active sensors, such as infrared (IR) or pyro-electric sensors, may provide efficient and effective target discrimination and may have minimal processing associated with the sensor data produced by such active sensors. Smart sensors may be the sensors having on-board digital signal processing (DSP) for primary sensor data (i.e., prior to processing by the transmitter processor). Such processors are capable of fine, granular object discrimination and provide transmitter processors with pre-processed sensor data that is more efficiently handled by the transmitter processor when determining how to generate and transmit the power waves.

In some implementations, the sensors may be configured for human recognition, and thus may discriminate a person from other objects, such as furniture. Non-limiting examples of the sensor data processed by human recognition-enabled sensors may include: body temperature data, infrared range-finder data, motion data, activity recognition data, silhouette detection and recognition data, gesture data, heart rate data, portable devices data, and wearable device data (e.g., biometric readings and output, accelerometer data).

The memory 89106 is a non-volatile storage device for storing data and instructions, to be used by the processor 89103. The memory 89106 is implemented with a magnetic disk drive, an optical disk drive, a solid state device, or an attachment to a network storage. The memory 89106 may comprise one or more memory devices to facilitate storage and manipulation of program code, set of instructions, tasks, pre-stored data including configuration files of receivers and electronic devices, and the like. Non-limiting examples of the memory 89106 implementations may include, but are not limited to, a random access memory (RAM), a read only memory (ROM), a hard disk drive (HDD), a secure digital (SD) card, a magneto-resistive read/write memory, an optical read/write memory, a cache memory, or a magnetic read/write memory. Further, the memory 89106 includes one or more instructions that are executable by the processor of the processor 89103 to perform specific operations. The support circuits for the processor include conventional cache, power supplies, clock circuits, data registers, I/O interfaces, and the like. The I/O interface may be directly coupled to the memory unit 89106 or coupled through the processor of the processor 89103.

In some embodiments, the transmitter 89100 may be associated with the memory 89106 that may further include one or more mapping-memories, which may be non-transitory machine-readable storage media configured to store the image data which may be data describing aspects of position of the receivers and the one or more objects within the transmission field associated with the transmitter 89100. The memory 89106 may also store mapping data that may comprise heat-map data and sensor data. The heat-map data may be generated by transmitter 89100 processors configured to identify receivers located in the transmission field; and the sensor data may be generated by transmitter 89100 processors and/or sensor processors to identify sensitive objects such as human beings and animals located in the transmission field. Thus, the image data and the mapping data stored in the memory unit 89106 of the wireless power transmission system may include information indicating the location of the receivers, the location of sensitive objects such as humans and animals, and other types of data, which may be used by the transmitter 89100 to generate and transmit safe and effective power waves. The transmitter 89100 may query the image data with the pre-stored data stored in the records of the memory unit 89106, so that the transmitter 89100 may use the image data as input parameters for determining the characteristics for transmitting the power waves and where to generate pocket of energy within the transmission field.

In some embodiments, the wireless power transmission system may include an external memory, which may be a database or a collection of machine-readable computer files, hosted by non-transitory machine-readable storage media of the admin computer 89107. In such embodiments, the external memory may be communicatively coupled to the transmitter 89100 by any wired or wireless communications protocols and hardware. The external memory may contain the pre-stored data comprising sample images and configuration files of the receivers and the one or more objects such as the humans and animals. The records of the external memory may be accessed by the transmitter 89100, which may update the pre-stored data when scanning the transmission field for the receivers or sensitive objects when determining safe and effective characteristics for the power waves that the transmitter 89100 is going to generate.

In some embodiments, the transmitter 89100 may comprise non-transitory machine-readable storage media configured to host an internal memory along with the memory unit 89106, which may store the mapping data within the transmitter 89100. The processor 89103 of the transmitter 89100, such as a transmitter processor, may update the records of the internal memory as new mapping data is identified and stored. In some embodiments, the mapping data stored in the internal memory may be transmitted to additional transmitters of the wireless power transmission system, and/or the mapping data in the internal memory may be transmitted and stored into an external memory at a regular interval or in real-time.

The administrative computer 89107 of the wireless power transmission system may be any computing device, which may comprise or may otherwise be coupled to a user interface allowing a user to control operations of the administrative computer 89107. The computing device refers to a computer with a processor/microcontroller and/or any other electronic component that performs one or more operations according to one or more programming instructions. The examples of the computing device include, but are not limited to, a desktop computer, a laptop, a personal digital assistant (PDA), a tablet computer, or the like. The computing device is capable of communicating with the transmitter 89100 and an external server through a network using wired or wireless communication capabilities. The network refers to a medium that also connects various computing devices and database of the wireless power transmission system. The examples of the network include, but are not limited to, LAN, WLAN, MAN, WAN, and the Internet. The network itself may include wired as well as wireless connections. The communication over the network may be performed in accordance with various communication protocols such as Transmission Control Protocol and Internet Protocol (TCP/IP), User Datagram Protocol (UDP), and IEEE communication protocols.

An input device may be a keyboard, mouse, pointer, touchscreen, or other input generating device to facilitate input of control instructions by a user to the processor 89103 and/or administrative computer 89107. In one embodiment, the input unit provides a portion of the user interface for the wireless power transmission system, and may include an alphanumeric keypad for inputting alphanumeric and other key information along with a cursor control device such as a mouse, a trackpad or stylus. A display unit of the wireless power transmission system may include a cathode ray tube (CRT) display, liquid crystal display (LCD), plasma, or light emitting diode (LED) display. A graphics subsystem may receive textual and graphical information, and processes the information for output to the display unit.

In an embodiment, the systems of the wireless power transmission system adhere to electromagnetic field (EMF) exposure protection standards for human subjects. Maximum exposure limits are defined by US and European standards in terms of power density limits and electric field limits (as well as magnetic field limits). These include, for example, limits established by the Federal Communications Commission (FCC) for MPE, and limits established by European regulators for radiation exposure. Limits established by the FCC for MPE are codified at 47 CFR § 1.1310. For electromagnetic field (EMF) frequencies in the microwave range, power density can be used to express an intensity of exposure. Power density is defined as power per unit area. For example, power density can be commonly expressed in terms of watts per square meter ($W/m^2$), milliwatts per square centimeter ($mW/cm^2$), or microwatts per square centimeter ($\mu W/cm^2$).

The present methods for the wireless power transmission incorporate various safety techniques to ensure that human occupants in or near a transmission field are not exposed to EMF energy near or above regulatory limits or other nominal limits. One safety method is to include a margin of error (e.g., about 10% to 20%) beyond the nominal limits, so that human subjects are not exposed to power levels at or near the EMF exposure limits. A second safety method can provide staged protection measures, such as reduction or termination of wireless power transmission if humans (and in some embodiments, other living beings or sensitive objects) move toward a pocket of energy with power density levels exceeding EMF exposure limits. A further safety method is redundant safety systems, such as use of power reduction methods together with alarms. Such safety methods employ the image processor 89104 including the one or more video cameras to capture images of objects within the transmission field and the sensors 89105, and subsequently processing the captured images and/or the senor data to identify the position of the humans and the receivers. Based on the determined positions of the humans and the receivers, the transmitter 89100 then transmit the power waves to the receivers and generate a null space in the positions of the humans.

Sensors Operation

The sensor 89105 may detect whether objects, such as person or furniture, enter a predetermined proximity of the transmitter 89100, power waves, and/or a pocket of energy. The sensor 89105 may detect whether objects, such as person or furniture, enter a transmission field of the transmitter 89100. In one configuration, the sensor 89105 may then instruct the transmitter 89100 or other components of the wireless power transmission system to execute various actions based upon the detected objects. In another configuration, the sensor 89105 may transmit sensor data generated upon detection of the objects to the processor 89103 of the transmitter 89100, and the processor 89103 of the transmitter 89100 may determine which actions to execute (e.g., adjust a pocket of energy, cease power wave transmission, reduce power wave transmission). For example, after one sensor identifies that a person has entered the transmission field, and then determines that the person is within the predetermined proximity of the transmitter 89100, the sensor 89105 could provide the relevant sensor data to the processor 89103 of the transmitter 89100, causing the transmitter 89100 to reduce or terminate transmission of the power waves. As another example, after identifying the person entering the transmission field and then determining that the person has come within the predetermined proximity of a pocket of energy, the sensor 89105 may provide sensor data to the processor 89103 of the transmitter 89100 that causes the transmitter 89100 to adjust the characteristics of the power waves, to diminish the amount of energy concentrated at the pocket of energy, generate a null, and/or reposition the location of the pocket of energy. In another example, the wireless power transmission system may comprise an alarm device, which may produce a warning, and/or may generate and transmit a digital message to a system log or administrative computing device configured to administer the system. In this example, after the sensor 89105 detects the person entering the predetermined proximity of the transmitter, power wave, and/or pocket of energy, or otherwise detects other unsafe or prohibited conditions of system, the sensor data may be generated and transmitted to the alarm device, which may activate the warning, and/or generate and transmit a notification to the administrator device. A warning produced by the alarm may comprise any type of sensory feedback, such as audio feedback, visual feedback, haptic feedback, or some combination.

The wireless power transmission system may include multiple transmitters 89100. For example, a first transmitter may include a first sensor that emits and/or receives sensor waves and generates sensor data, which may be stored on the first transmitter and/or a mapping memory; the wireless power transmission system may also have a second transmitter comprising a second sensor that emits and/or receives sensor waves and generates sensor data, which may be stored on the second transmitter and/or the mapping memory. In this example, both of the first and second transmitters may comprise processors that may receive sensor data from the first and second sensors, and/or fetch stored sensor data from the particular storage locations; thus, the sensor data produced by the respective first and second sensors may be shared among the respective first and second transmitters. The processors of each of the first and second transmitters may then use the shared sensor data, to then determine the characteristics for generating and transmitting the power waves, which may include determining whether to transmit the power waves when a sensitive object is detected. Multiple transmitters may interface with and may be controlled by the same processor.

As mentioned, the transmitter 89100 may comprise, or otherwise be associated with, multiple sensors or sensors from which the transmitter 89100 receives the sensor data. As an example, a single transmitter may comprise a first sensor located at a first position of the transmitter and a second sensor located at a second position on the transmitter. In this example, the sensors may be binary sensors that may acquire stereoscopic sensor data, such as the location of a sensitive object to the sensors. In some embodiments, such binary or stereoscopic sensors may be configured to provide three-dimensional imaging capabilities, which may be transmitted to an administrator's workstation and/or other computing device. In addition, binary and stereoscopic sensors may improve the accuracy of the receiver or the object location detection and displacement, which is useful, for example, in motion recognition and tracking.

In some implementations, the user may communicate to the transmitter 89100 tagging information that enables the transmitter 89100 to detect and confirm certain objects that the user wishes to exclude from receipt of wireless energy (i.e., power waves, pocket of energy). For example, the user may provide tagging information via a user device in communication with the controller of the transmitter 89100 via a graphical user interface (GUI) of the user device. Exemplary tagging information includes location data for an electrical device, which may include one-dimensional coordinates of a region in space containing the object, two-dimensional (2D) coordinates of a region in space containing the object, or three-dimensional (3D) coordinates of a region in space containing the object. One way to perform tagging may be to place the user device in close proximity to the object or location being tagged and use the location of the user device as a proxy for the location of the tagged object when recording the location to be tagged with the transmitter.

Additional details, discussion, and examples of the sensor operations in a wireless charging system may be found in U.S. patent application Ser. No. 14/861,285, entitled "Systems and Methods of Identifying Sensitive Objects in a Wireless Power Transmission Field," filed Sep. 22, 2015.

Cameras and Computer Vision Operation

The transmitter 89100 may include the cameras 89104. The cameras 89104 will capture the images of the objects within the transmission field of the transmitter 89100 and the images will be transmitted to the processor 89103. The processor 89103 may execute a computer vision software or any suitable software that is programmed to process the image data captured by the cameras 89104 to locate and recognize the receiver, living beings, and/or other sensitive objects from the captured images. In one example, the receiver, living being, and/or other sensitive object physical shape may be recognized first, and once the physical shape is recognized, it is matched with the pre-stored data. Once the matching is confirmed, then X, Y, Z coordinate of the receiver, living being, and/or other sensitive object will be determined.

In one embodiment, the transmitter 89100 uses two video cameras in stereo configuration that operate as stereoscopic vision, in side by side configuration. The images in the data captured by the two video cameras is processed in the computer vision software executed by the processor 89103 to search for visual patterns that it can recognize. The visual patterns are pre-programmed or preconfigured and saved in the pre-stored data in the memory 89106. In case of detecting presence of humans using visual light cameras, the pre-stored data may include all possible skin tones, hair color, and facial features, for instance, for purposes of matching. The computer vision software may also be trained to recognize different shapes of the receivers. There are several methods to train the computer vision software. One method to train the computer vision software is to hold up an object, for example, a cellphone, to the visual cameras and take snapshots of the object at different orientations and distances. The snapshots are saved in the memory 89106 and the computer vision software fills a configuration file for identifying the object by comparing the image data with the snapshots stored in the memory 89106. When the wireless power transmission system is running, and the computer vision software is receiving the image data from the cameras 89104, the computer vision software is executed by the processor 89103 to search for any portion within the image data that matches the pattern that was preprogrammed in a plurality of configuration files stored in the memory 89106.

In some implementations, the computer vision software may execute various algorithms enabling the software to intelligently learn the identity of various physical objects, based on certain characteristics of those objects, such as shape, orientation, movement, dimensions, emissions of RF radiation, emissions of light, heat, and the like. In operation, the computer vision software may identify an object when the characteristics of that object are within a threshold variance of the corresponding characteristics for baseline objects in the memory 89106. Allowing for some threshold variance when comparing characteristics may account for subtle changes in objects "seen" routinely by the cameras 89104, such as aging, erosion, or some forms of wear-and-tear on an object. Accordingly, when the computer vision software identifies, or "sees," an object in a still image or video, the computer vision may also update the parameters or characteristics of the corresponding baseline object in the memory 89106.

When the computer vision software recognizes an object in the image data from the configuration file stored in the memory 89106, then the computer vision software uses the image data to determine the X, Y, Z location of the object. Each video camera transmits X, Y coordinates of the object (which are called as pixels) to the processor 89103. The computer vision software after receiving the X, Y coordinates of the object from the two video cameras, compares the two copies of the X, Y coordinates of the object, and creates another dimension of the object which indicates the distance of each pixel of the object image from the two video cameras. In other words, the computer vision software compares the image data related to the object from each of the cameras 89104, to determine the comparable distance of each picture element (or pixel), and thereby determines an X, Y, Z coordinate of each picture element of the object. Determining the distance to such objects may include use of the sensor data in addition to the video data for triangularization purposes.

In an embodiment, the recognized object may be composed of many different pixels that may, in some cases, containing visual and/or thermal patterns, sometimes referred to as a "Binary Large Object" (BLOB) of visual data. A BLOB may be a region of an image where one or more characteristics of the image are substantially similar or substantially constant. The data underlying the pixels at these regions are therefore recognizable and understood to be one or more objects by the processor 89103, based on the underlying binary data generated for the pixels of that particular region of the image. It should be appreciated that this is merely a term of art referring to a contiguous set of image pixels, and should be not be considered limiting upon the operation of the transmitter 89100 or the nature of the items that can be identified or otherwise detected by the transmitter 89100. The computer vision software of the processor 89103 then determines a center coordinate of the BLOB of visual data, sometimes called a "centroid," and then the computer vision software executed by the processor 89103 determines the centroid X, Y, Z coordinate and uses the centroid X, Y, Z coordinate to activate the antennas 89101 for an optimal configuration or phase that will create the pocket of energy as close as possible to the identified object which is a receiver unit. Similarly, if a BLOB is determined to be a human, for instance, this information is used to control the phase and amplitude of power waves so as to avoid creating a pocket of energy in close proximity.

In an embodiment, the X, Y, Z coordinates determined may be relative to a frame of reference of the transmitter 89100. For example, if the transmitter 89100 has an X, Y, Z coordinate, then the receiver coordinate is relative to the transmitter 89100 with the frame of reference being the X, Y, Z coordinate. The computer vision software in conjunction with the cameras 89104 is continuously and/or periodically tracking the receivers and continuously and/or periodically determine the X, Y, Z coordinates for objects "seen" by the cameras 89104. The X, Y, Z coordinate data is immediately used by the transmitter 89100 to update the wireless power transmission antennas of the antennas 89101. For example, the phases of the wireless power transmission antennas may be a function of the X, Y, Z coordinates of the receiver, as detected by the computer vision software, and as determined and continuously updated by the processor 89103, based on the data received from the cameras 89104.

One having skill in the art would recognize that there are number of techniques for implementing the computer vision, and that there may be any number of software products that may be executed by the processor 89103 of the transmitter 89100 to configure the components of the transmitter 89100 to perform the various tasks associated with computer vision, as described herein. Non-limiting examples of such software that may be employed to instruct the processor 89103 and other components to execute processes associated with computer vision may include OpenCV, Fiji, Pfinder, Trax Image Recognition, Robot Operating System (ROS), and the like. It would also be appreciated that such underlying software modules may be configured or otherwise re-configured using libraries developed using C++, Python, MATLAB, LISP, and any other programming language capable of manipulating the behaviors of cameras, image processor, and/or processor 89103 when executing digital image processing and automated computer vision routines.

In operation, the cameras 89104 may be configured to report the X, Y, Z coordinate of every pixel of the image data sent from the cameras (e.g., visual video cameras, thermal cameras) transmitting images (e.g., continuous video, successive still frame images) to the cameras 89104. The programmatic modules may also have functions that can search for and detect visual BLOBs of pixels where a visual BLOB in the image data may be an object of interest. Thus, when the cameras 89104 see objects, for example, a human, a cell phone, a book, or a chair, such objects appear to the computer vision software executed by the processor 89103 as contiguous collections of pixels, usually of kind of a uniform color compared to the background, and the computer vision software can then determine the X, Y, Z coordinate of the centroid of these objects relative to the transmitter 89100. The computer vision software is further configured to operate for a stationary object or an object that's moving. The computer vision software is able to determine that an object is moving because the moving object may correspond to the contiguous pixels that are moving relative to a complete field of vision, whereas all the other pixels that are stationary are part of the background. Thus, the pixels that are in motion are easier to differentiate from the background pixels as the pixels that are in motion are the only pixels that are all moving in the same direction.

The computer vision software may use an open source software to determine the X, Y, Z coordinates of the object that's recognized as the receiver, for example the mobile device. The computer vision software of the transmitter 89100 may be trained by one or more techniques to identify the receivers. For example, the receivers for mobile devices where the receiver is embedded within the mobile devices such as a cell phone, the configuration files corresponding to shape, dimensions, and configuration of the mobile and/or the receiver may be stored in the memory 89106 of the transmitter 89100. The configuration files are stored so that when the transmitter 89100 is in operation, the configuration files are available for the computer vision software of to use, and then facilitate the communication between the computer vision software and may be an antenna management software of the antennas 89101. The communication by the computer vision software may include the X, Y, Z coordinates of the receivers over to the antenna management software of the antennas 89101. In another embodiment, when the antenna management software of the antennas 89101 is in direct communication with the receiver, and the transmitter 89100 is powering the receiver, then the antenna management software of the antennas 89101 will be able to determine the X, Y, Z coordinates of the receiver based on the settings of the phases of the antennas in 89101. In addition, the processor 89103 may use the determined location of the receivers based on the direct communication between the antenna management software of the antennas 89101 with the receiver, and compare the determined location with the location reported of the receiver by the computer vision software to verify that the computer vision software is recognizing the correct object as being the receiver.

In another example, if the antenna management software of the antennas 89101 detects an electronic device comprising a receiver where the computer vision software has not been programmed to recognize the electronic device. The computer vision software, or some other hardware and/or software component of the transmitter 89100, may determine the initial X, Y, X coordinates of the mobile device using sensor data received from sensors coupled to the transmitter 89100, or using a set of coordinates expressly inputted by a user through a user interface, enabling the computer vision software of the transmitter 89100 to continuously or periodically track the relative location of the mobile device, even though the computer vision software cannot initially recognize the electronic device using the pre-programmed database of objects. Where the computer vision software of the processor 89103 has not been programmed to recognize the pattern of the electronic device or a standalone receiver, the computer vision software executed by the processor 89103 of the transmitter 89100 will be unable initially to determine and report the X, Y, Z coordinates of the receiver coupled to the electronic device. In some cases, the unrecognized receiver may communicate various types of location data with the transmitter 89100 via a communications signal (e.g., Bluetooth®, ZigBee®, Wi-Fi, NFC), allowing the transmitter 89100 to detect the presence of the unrecognized receiver and determine the location of the receiver in the transmission field of the transmitter 89100. The processor 89103 of the transmitter 89100 may subsequently initiate antenna management software of the antennas 89101 to configure the power transmission antennas to transmit power waves to or proximate to the location of the receiver. Based on data received back from the receiver via the communications signal, the antenna management software of the transmitter 89100 may determine more specific X, Y, Z coordinates of the receiver being powered. The X, Y, Z coordinates of the receiver are then stored into non-transitory machine-readable storage of a memory unit 89106. The computer vision software, and the processor 89103 of the transmitter 89100 more generally, may then begin monitoring the location and movements (e.g., updated coordinates, updated location data) of the receiver and electronic device, using the coordinates stored in the memory unit 89106. Although the computer vision software of the processor 89103 may not initially recognize the pattern of an electronic device or a standalone receiver device, the electronic device or standalone receiver device may be recognized and serviced by the processor 89103 of the transmitter 89100 using location data received via a communications signal, location data received in user inputs from a user interface, and/or sensor data generated and/or received from sensors coupled to the transmitter 89100. After determining the initial location of the receiver, the transmitter 89100 may begin transmitting the power waves, provided no sensitive objects are detected in the path of the power waves to provide power to the electronic device comprising the receiver. The transmitter 89100 may then adjust the antenna configuration of the antennas 89101 to update the power waves based on receiver movement. Under these circumstances, the processor 89103 can determine the X, Y, Z coordinates of the receiver based on the antenna phases used to transmit power waves. The processor 89103 then uses the X, Y, Z coordinates of the receiver from the antenna management software of the antennas 89101 to calibrate the computer vision software to look for the receiver at that location of the X, Y, Z coordinates. If the receiver is subsequently moved, the computer vision software may then track the image of the receiver and report the image data to the processor 89103. The image will be depicted as a BLOB of pixels, and when the BLOB of pixels begins to move, the computer vision software in real time determines the X, Y, Z coordinates of the moving receiver, and continuously and/or periodically uses the determined X, Y, Z coordinates to update the phases of the antennas of the antennas 89101 to maintain the pocket of energy at the receiver.

The training functions of the computer vision software may have one or more parameters. The one or more parameters may be adjusted to optimize for the category of objects being recognized by the computer vision software. For example, different kinds of cell phones in general have a more unique kind of shape than an animal such as a dog or a cat. The cell phone may have more angular features and usually rectangular and flat shape. The computer vision software of may be trained to more readily, efficiently, and in a faster way recognize the objects such as cell phones due to the unique shape patterns of the cell phones. In one example, the objects may be recognized by the computer vision software by identifying visual patterns such as points, colors, and letters on the objects. In another example, the objects may be recognized by the computer vision software by identifying any kind of specific labeling on the body of the object. In yet another example, the objects may be recognized by the computer vision software by identifying configuration of distinctive visual patterns of the object, for example, location of a keyboard may be detected by locating keys on it. In another example, a TV remote control may be located by identifying the colors of the different buttons on the TV remote control, or a cell phone may be located by identifying the location of the camera which is usually present as a small round object on the backside of the phone. In the example of recognizing the cell phone by the computer vision software, the computer vision software may initially process an overall three-dimensional rectangular shape of the cell phone, and then recognize the smaller hole which will be the lens of the camera in the cell phone. In other words, the computer vision software may be trained to determine the relationship between the rectangular box that forms the cell phone itself and for all the features that are on the cell phone like the buttons to correctly identity or recognize the cell phone as an object of interest.

In an embodiment, the computer vision software is also trained to recognize the receiver when the receiver is placed external to the electronic device such as the cell phone in the image data captured by the cameras 89104. In such a case, the computer vision software of the processor 89103 is trained to recognize the lines that form the basic shape of the receiver. For example, if the receiver is in rectangular in shape, the computer vision software may be trained to identify the overall three-dimensional rectangular shape. In another example, the computer vision software may be trained to recognize the color of the receiver or any patterns, sub-color patterns if the receiver has multiple colors or lettering. The color is unique way to recognize the receiver by the computer vision software as the receiver may be marked with a trademark having colors, and the computer vision software may be pre-programmed to identify the trademark to the RGB color.

Using Multiple Transmitters to Model Objects in a Shared Transmission Field

In an embodiment, the wireless power transmission system may include multiple transmitters where each transmitter 89100 may include the cameras 89104. Each of the multiple transmitters may have their own transmission field or the energy zone, where the antennas of each transmitter 89100 may transmit power waves to charge the electronic devices. In another example, each of the multiple transmitters 89100 may have a same transmission field or the energy zone, where the antennas of each of the transmitter 89100 may transmit power waves to charge the electronic devices. In such a case, the video cameras of the multiple transmitters monitor and capture the image data of the same transmission field (transmission area). The multiple transmitters may be configured to communicate with each other directly through a wired means, or communicate to each other through a backend wireless server, to share the image data captured by each of the transmitters. The backend wireless server may by a server computer comprising a processor capable of performing communication between the multiple transmitters. Each of the transmitters may transmit the image data captured by their cameras to their own processors or a central processor. The processors of the transmitters may generate symbolic data from the image data captured by the video cameras of each of the multiple transmitters. The symbolic data obtained from the multiple different perspectives at each transmitter may then be combined to generate a visual model of all the objects and the receivers within the transmission field.

The multiple transmitters may be used in order to improve the accuracy of monitoring and detecting the receivers and the sensitive objects, such as humans. In a room having multiple transmitters where each of the multiple transmitters has video cameras, the multiple transmitters may be located in the room such that the images captured by the video cameras of each of the multiple transmitters is captured from different angles and perspectives. For example, in a room having a child that is hidden behind a chair, the video camera of a given transmitter may not be able to see the child because of the chair in the way, but the video camera of the transmitter located over in another part of the room may be able to recognize the child, and then all the image data captured from all the video cameras of all the transmitters may be analyzed to obtain the X, Y, Z coordinates of the child even though the video cameras of the given transmitter wasn't able to capture the image of the child.

In the above discussed example, the X, Y, Z coordinates of the child may be communicated between the wireless power transmitters, such that even the transmitters with video cameras that cannot view the child receive the X, Y, Z coordinates of the child from other transmitters, and then the transmitters with video cameras that cannot view the child can use the child's X, Y, Z coordinates to compare with the X, Y, Z coordinates of the receivers they are powering so that if the receiver being powered gets too close to the child, the transmission of power waves to the receiver may be reduced or ceased. Thus, in this case, the given transmitter may be receiving in real time the X, Y, Z coordinates of the given human or sensitive object and the given transmitter may adjust its antenna configuration phases to continuously and/or periodically keep the energy pocket away from the given human or sensitive object based on the X, Y, Z coordinates of the given human or sensitive object being received in real time from other transmitters. In some implementations, the transmitter may also adjust antenna configuration phases to transmit power waves that converge to from destructive interference patterns, resulting in nulls at or proximate to the location proximate of the human or other sensitive object.

In an embodiment, each video camera of the multiple transmitters may be producing the image data. The image data produced by video cameras of each transmitter is shared with the other transmitters operating in the same transmission field. The image data may be processed by the computer vision software executed by the processor of each transmitter such that the computer vision software compares all the image data produced by each camera of each transmitter to create a three dimensional cloud model of the transmission field area where all the transmitters are operating.

In another embodiment, in order to build the three dimensional cloud model, all the video cameras may send the image data to a central processor of the wireless power transmission system that is configured to create the three dimensional cloud model by using the X, Y, Z coordinates of each pixel in the image data captured by each video camera. In this case, each individual transmitter would be a client to the central processor that is generating the three dimensional cloud model. Each of the client transmitters will receive updated copies in real time of the three dimensional cloud model from the central processor, and at the same time continuously and/or periodically sending the image data from its own video cameras back to the central processor for updating the three dimensional cloud model. In other words, each transmitter is continuously and/or periodically transmitting its raw or processed image data to the central processor that is configured to generate the three-dimensional cloud model, and at the same time each individual transmitter is continuously and/or periodically downloading updates to the three-dimensional cloud model so that each individual transmitter can continuously and/or periodically have an accurate three-dimensional cloud model of the transmission field area to control the antenna configuration phases to maintain energy pocket at the receivers within the same transmission field area.

In yet another embodiment, the individual transmitters of the wireless power transmission system may be configured to use the antenna management software of their own antennas to communicate with the receivers to form an energy pocket for the receivers. The individual transmitters then subsequently determine the X, Y, Z coordinates of the receivers according to one or more methods of configuring the power transmission antennas to transmit power waves to or near the receivers. The individual transmitters may communicate the determined X, Y, Z coordinates of the receivers to a central processor of a device coupled to the transmitters, such as a master transmitter or a master server, where the X, Y, Z coordinates generated by each transmitter may be determined based on antennas phases and/or data received from the receiver through a communications signal (e.g., heat-mapping data). The central processor may be configured to generate a model of a common transmission field that is monitored by the various sensors and/or cameras of the transmitters.

A central processor may generate two or three-dimensional models of a common transmission field, based on inputs of various sensors and/or cameras. For example, the central processor may generate one model based on the image data obtained from the video cameras of multiple transmitters, and another model generated based on the phases of the antennas determined by the antenna management software of the respective transmitters. The central processor may be configured to compare the two models, and send signals to one or more transmitters containing data indicating or otherwise instructing a transmitter to adjust the power waves being produced, based on the optimal position of the receivers from a given transmitter determined by the comparison of the two models. In this case, the individual transmitters may not have to control the transmission of the power waves on their own, but instead the central processor may provide instructions/directions to form the energy pocket at locations of the receivers.

The individual transmitters of the wireless power transmission system may also be configured to transmit one or more parameters to the central processor in a decentralized model of operation of the wireless power transmission system. In one embodiment, the central processor may receive the raw image data captured by the video cameras of the individual transmitters. The raw image data from the video cameras is a steady stream of images generated by the video cameras, where a given video camera, inside its circuit, is creating multiple snapshots of a given scene, for example, at 10 frames per second. This implies that at 10 times per second, the camera will read the X, Y, Z coordinates of all the pixel colors, or in some cases temperatures, in the field of view of the camera. The X, Y, Z coordinates may be converted into numeric value (symbolic data) by a processor of the transmitter, and then the numeric value may be communicated back to the central processor. In another instance, the transmitters may directly send the raw image data captured by their own video cameras to the central processor.

The central processor may then receive the symbolic data that may be generated by each transmitter computer vision software from the raw image data. The symbolic data may include the X, Y, Z coordinates of the receivers, the sizes of the receivers, and the velocity of the receivers if the receivers are moving. In this case, the computer vision software of each transmitter may be programmed to analyze the raw image data and search for object patterns. The stationary objects may be recognized as contiguous BLOBs of pixels near the same background color, or the moving BLOBs of pixels which are contiguous pixels near the same background color that are moving relative to the field of view of the transmitter as well as relative to the background pixels of the field of view. The computer vision software then recognizes the BLOBs and generate the symbolic data that comprises the X, Y, Z coordinates of the center or the centroid of the BLOB, the size of the BLOB in terms of the number of pixels or a percentage of the pixels compared to the field of view, or the velocity of the BLOB, and the duration of the visibility of the BLOB in seconds. All the symbolic data may then be sent to the central processor. The central processor may use all the symbolic data and/or the raw image data being continuously and/or periodically received to generate the three-dimensional cloud model which is a data structure that may be useful for all the transmitters to use for wireless power transmission by controlling the antenna phases of their antennas to form the optimal energy pocket at each receiver location within the same transmission field area. The three-dimensional cloud model may be data structure that includes a list of X, Y, Z coordinates of all visually recognized objects (such as humans and furniture) and the X, Y, Z coordinates of all the receivers as determined by either the computer vision software of each transmitter and/or the antenna management software at each transmitter. Along with the X, Y, Z coordinates of each object, the model may contain other details associated with the objects such as the BLOB size or average pixel color.

One advantage of the wireless power transmission system of the present disclosure is that the cameras 89104 along with the computer vision software of each transmitter sees the object, recognizes the location of the object, determines the X, Y, Z coordinates in less than a second, and then an antenna management software of the antennas 89101 may rapidly configure the phases of all the transmission antennas to aim the transmission of the power waves and form the pocket of energy at the location of the object if the object is the receiver. Another advantage is that when a receiver is in motion, the antennas 89101 may rapidly configure the phases of all the transmission antennas in real time to follow the moving receiver. If the receiver is a cellphone carried by a human, the transmitter may transmit to the receiver location once the human is no longer carrying the cellphone. Using the cameras 89104 along with the computer vision software of the transmitter, the system is able to re-aim the transmission antennas in real time so that the energy pocket can efficiently move along with the receiver, and thus the receiver keeps receiving power.

In an embodiment, if the user has a device without a battery and the device needs to have continuous power, for example, a LED light mounted on a wall in a room, then the LED light or similar device lacking a battery would only operate as long as there is a pocket of energy formed at the device or a receiver coupled to the device. In one scenario, if a user walks into the room, and stands between the transmitter 89100 and the LED light, the LED light may go off until the transmitter 89100 can readjust the phase of the transmission antenna of the antennas 89101 to bounce the wireless power from a different route around the room to the LED light. In other words, the wireless power transmission system can power a device by being directly at the device and if there's something intervening then the wireless power of the wireless power transmission system can bounce off other objects in the room. Using the cameras 89104 along with the computer vision software, the wireless power transmission system responds a lot faster in case there's a person or something intervening between the transmitter 89100 and the receiver as the computer vision software of the transmitter 89100 always monitors exactly where the receiver is located, especially if the receiver has been moved or if the receiver unit is moving. The cameras 89104 always visually view the receiver, and then the computer vision software of the processor 89103 in real time keeps calculating the X, Y, Z coordinates of that receiver and send a signal to the antennas based on the location of the receiver to change its phases to continuously and/or periodically power the receiver.

Exemplary System Components with Thermal Camera Operations

Figure 89B:
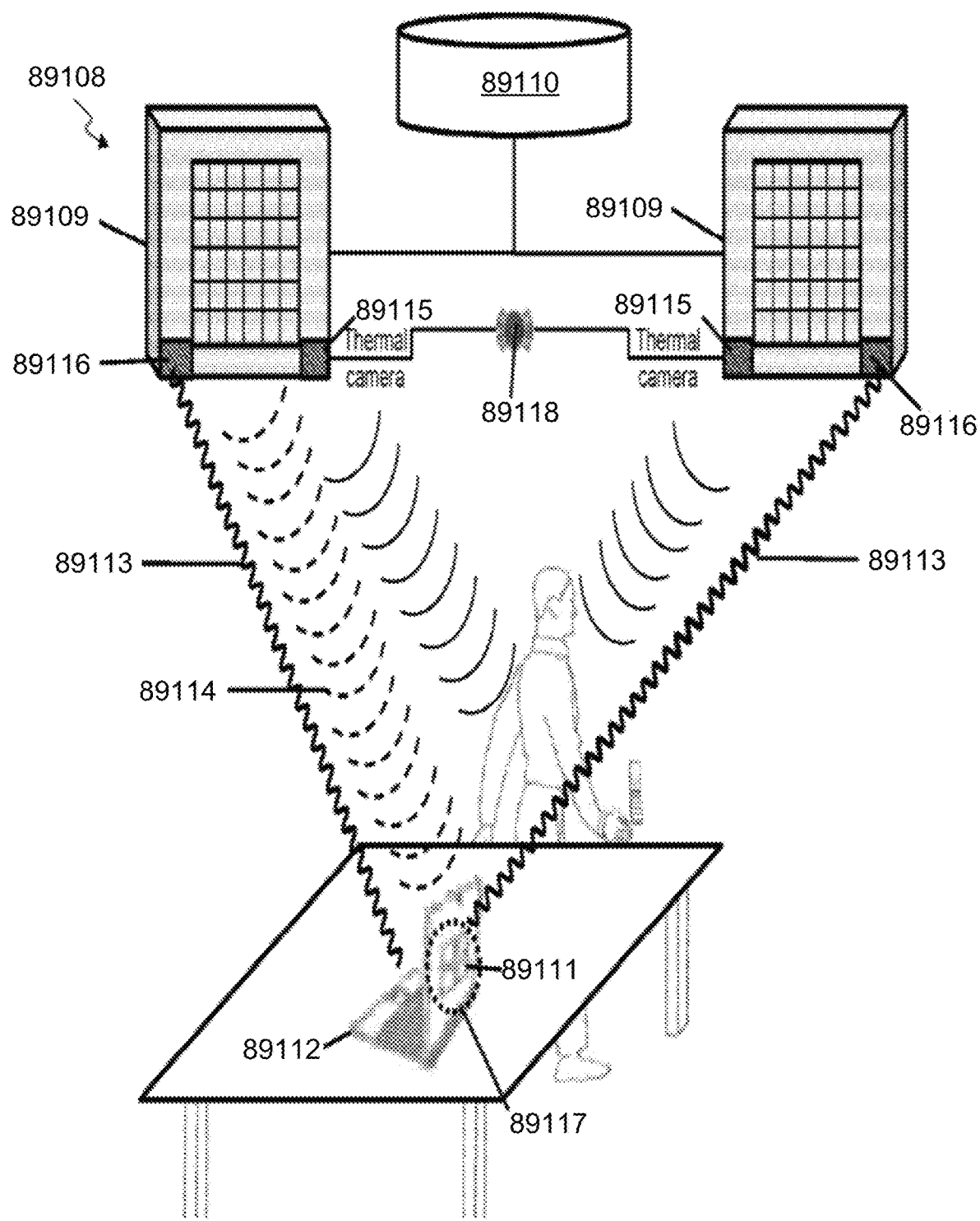

FIG. 89B shows components of an exemplary wireless power transmission system 89108 for identifying objects within a transmission field of a transmitter using thermal imaging cameras, according to an exemplary embodiment. FIG. 89B will be explained in conjunction to FIG. 89A. The wireless power transmission system 89108, using the thermal imaging cameras 89115 associated with the transmitters 89109, may determine the safest and most effective characteristics for wireless power transmission, taking into account the presence of humans and other living beings, such as domestic animals within the transmission field of the transmitter. In addition, the wireless power transmission system 89108 using the thermal imaging cameras 89115 may determine the characteristics for wireless power transmission, taking into account the presence of other sensitive objects, which may include certain equipment and other valuable objects that are sensitive to electromagnetic energy in power waves.

The wireless power transmission system 89108 includes transmitters 89109, an external mapping memory 89110, a receiver 89111 integrated in an electronic device 89112 to be charged. The transmitters 89109 may send various types of waves, such as communication signals 89113, and power waves 89114, into a transmission field, which may be the two or three-dimensional space into which the transmitters 89109 may transmit power waves 89114.

In addition, the wireless power transmission system 89108 includes thermal cameras 89115 that may receive thermal radiation from fields of view overlapping the transmission field of the transmitters 89109 and generate a thermal image. The thermal image may include temperature data (thermal imaging data) obtained from the thermal radiation. The overlap between the fields of view and the transmission field means that at least some portions of the fields of view are also within the transmission field of the transmitters 89109, Although, in some embodiments, the fields of view may extend beyond the transmission field. Additionally, the transmission field of the transmitters 89109 may extend beyond the fields of view. The thermal cameras 89115 form thermal images of their respective fields of view.

The transmitters 89109 may include one or more transmitter processors that may be configured to process and communicate various types of data (e.g., heat-mapping data, thermal imaging data). For example, the transmitter processor may generate heat-mapping data from the communications signals 89113 received by communications components 89116, and then, based upon thermal imaging data received from the thermal cameras 89115 (or thermal camera processor), the transmitter processors may determine the safest and most effective characteristics for the power waves 89114.

In one embodiment, the thermal imaging cameras 89115 may be physically associated with the transmitters 89109 (i.e., connected to, or a component of), or devices may be configured to detect and identify various conditions of the system 89108 and/or transmission field. Thermal imaging data may then be generated for the transmitters 89109, which may contribute to the generation and transmission of the power waves 89114 by the transmitters 89109. The thermal imaging data may help the transmitters 89109 determine various modes of operation and/or how to appropriately generate and transmit the power waves 89114, so that the transmitters 89109 may provide safe, reliable, and efficient wireless power to the receiver 89111 and avoid transmitting power waves to locations where humans or other sensitive objects are present. As detailed herein, the thermal imaging cameras 89109 may transmit the thermal imaging data derived from thermal images formed during thermal imaging camera operations for subsequent processing by transmitter processors of the one or more transmitters 89109. Additionally or alternatively, one or more thermal imaging camera processors may be connected to or housed within the thermal imaging cameras 89115. The thermal imaging camera processors may comprise a microprocessor that executes various primary data processing routines, whereby the thermal imaging data received at the transmitter processor has been partially or completely pre-processed as useable mapping data for generating the power waves 89114.

The thermal images in the field of view of the thermal cameras 89115 typically are recorded by two-dimensional (X by Y) pixel arrays. Specialized thermal imaging cameras 89115 use focal plane arrays (FPAs) that respond to longer wavelengths (mid- and long-wavelength infrared). The most common types are InSb, InGaAs, HgCdTe and QWIP FPA. FPAs resolution typically is considerably lower than that of optical cameras, mostly 160×120 or 320×240 pixels. The thermal imaging cameras 89115 tend to have a single color channel because the cameras generally use an image sensor that does not distinguish different wavelengths of infrared radiation. Sometimes the resulting monochromatic images are displayed in pseudo-color, in which changes in color are used rather than changes in intensity to display changes in the signal.

Specifications of the thermal imaging camera 89115 may be selected for detection of objects within fields of view overlapping the transmission field of the transmitter 89109. Specification parameters may include for example: number of pixels; ranging limit, or distances from the thermal imaging camera 89115 for effective detection of objects; frame rate of the thermal imaging camera 89115 operated to provide video output; angular field of view (measured horizontally and vertically); minimum resolvable temperature difference (MRTD); spectral band; and dynamic range. With reference to FIG. 89B, it should be understood that the field of view of the thermal imaging cameras 89115 is the extent of the observable environment of the transmitters 89109 that is seen at any given moment, which overlaps the transmission field of the transmitters 89109. In an embodiment, the field of view may be a solid angle within which a thermal imaging camera is sensitive to thermal radiation.

Thermal imaging data may be obtained from the thermal imaging cameras 89115 which is in the form of a two dimensional X by Y array of pixels includes at a basic level, analog and/or digital visual image data for each pixel in the array. In an embodiment, data captured by the thermal imaging camera 89115 includes infrared energy intensities detected by each pixel in the array, and individual temperature values for each pixel based on transformation of the infrared energy to form the temperature data. The thermal imaging data also can include data derived from this basic pixel data, e.g., to analyze objects in the field of view of the imaging sensor. This derivative thermal imaging data is generally symbolic in nature, such as a number representing area of an object, or an array containing location components for an object. Because there are multiple sources of the infrared energy, it can be difficult to get an accurate temperature of an object using thermal imaging. The thermal imaging cameras 89115, and computer vision processors (processors executing computer vision software's) incorporated in or communicating with the thermal imaging cameras 89115, are capable of performing algorithms to interpret the thermal imaging data and build an image. Often, the computer vision techniques that have been developed for visible light imaging, also can be applied to infrared imaging.

A plurality of the thermal imaging cameras 89115 may be deployed for detection of humans and other living beings within the transmission field of one or more transmitters 89109. As shown in FIG. 89B, the thermal imaging cameras 89115 are respectively physically associated with the transmitters 89109, which effect thermal imaging of objects within the transmission field of the transmitters 89109 from different directions, i.e., stereoscopic imaging. The thermal imaging cameras 89115 form thermal images with different fields of view, overlapping the transmission fields of the transmitters 89109. Disparity analysis techniques can be employed to determine three dimensional (3D) coordinates of objects detected by the two or more thermal imaging cameras 89115. In an embodiment, a first thermal imaging cameras of the two or more thermal imaging cameras 89115 may have a field of view in which an object in motion appears in changes across the field of view (lateral motion), wherein a second thermal imaging cameras of the two or more thermal imaging cameras 89115 may have a field of view in which motion of the object appears in near-far image changes, providing less accurate measurements of movement. Image processing associated with one or both of the thermal imaging cameras 89115, and imaging processing of one or both of the transmitters 89109, may calculate 3D locations of objects such as a living being detected by the thermal imaging cameras 89115 within a global coordinate system of the transmitters 89109. Transmitter(s) 89109 may compare the calculated 3D locations of objects detected by the thermal imaging cameras 89115 with 3D locations of other entities of the wireless transmission system 89108, such as the transmitters 89109, receiver 89111, and pocket of energy 89117. Transmitters 89109 may use a 3D location comparison in determining whether to adjust a power level of the power waves 89114, e.g., if the comparison indicates that a detected living being is within predetermined proximity to the transmitters 89109, or is in predetermined proximity to the pocket of energy 89117. Upon detecting that a living being or another sensitive object is within a predetermined proximity of the transmitter, the transmitter reduces or ceases transmission of power waves. Also, upon detecting that a living being or another sensitive object is between the transmit array and the receiver, or detecting that a living being or other sensitive object is within a predetermined proximity of a receiver, the transmitter reduces or ceases transmission of power waves to that receiver. Thermal imaging data and video imaging data are superimposed on the same 2D or 3D coordinates to identify the locations of living beings. One feature of the system described is that it prevents exposing of living beings to EM radiation from power wave transmissions.

In alternative embodiments, the plurality of thermal imaging cameras 89115 may be physically associated with the single transmitter 89109; or at least one of the plurality of thermal imaging cameras 89115 may be located remote from the transmitter 89109 but communicatively coupled to the transmitter 89109. The plurality of thermal imaging cameras 89115 may be located at the same height (e.g., both physically associated with floor mounted transmitters), or at different heights (e.g., associated respectively with floor and ceiling mounted transmitters). Stereoscopic imaging using the plurality of thermal imaging cameras 89115 may improve the accuracy of object location detection and detection of object displacements, which is useful, for example, in motion recognition and tracking. For example, two thermal imaging cameras 89115 can provide improved sensitivity in detecting distances of living beings from the transmitter 89109, in comparison to a single thermal imaging camera 89115 physically associated with that transmitter 89109.

Another advantage of stereoscopic imaging of the transmission field of the one or more transmitter 89109 is that obstacles (such as table) may partially or completely obstruct the view of the living being or other object in the transmission field of the transmitter 89109 by a first thermal imaging camera of the thermal imaging cameras 89115, but the object may be clearly visible to a second thermal imaging camera of the thermal imaging cameras 89115 that views the scene from a different direction. For example, a child may be blocked from the field of view of the first thermal imaging camera of the thermal imaging cameras 89115 by an obstacle such as furniture, but may be visible to the second thermal imaging camera of the thermal imaging cameras 89115. The system can share coordinates of the child obtained by the second thermal imaging camera of the thermal imaging cameras 89115 with the first thermal imaging camera of the thermal imaging cameras 89115.

One technique used in the present disclosure identifies a spatially contiguous area of pixels having temperature values meeting predetermined criteria, such as pixels with temperature values falling within a predetermined temperature range, or pixels with temperature values falling within local temperature maxima. In the present disclosure, the term "visually contiguous pixels" is sometimes used for a spatially contiguous area of pixels in a thermal image having temperature values meeting predetermined criteria. The local coordinates of the visually contiguous pixels represent the position of an associated object in the field of view. As previously mentioned, the image information contained in the selected image detail corresponding to the visually contiguous pixels can be treated in the image processing software as a "Binary Large Object" (BLOB). A BLOB or predetermined characteristics of a BLOB can be stored in databases (e.g., a database within or coupled to the transmitter 89109) as a single object; and can be treated as a pattern in thermal imaging software. For example, the BLOB can represent a pattern of thermal imaging data that can be relocated in thermal images recorded later.

Thermal imaging data associated with visually contiguous pixels can include various geometric characteristics of the set of visually contiguous pixels. One geometric characteristic is the centroid, the center of mass of a two-dimensional planar lamina or a three-dimensional solid. Another characteristic is size, which may be estimated by an area measured by the number of pixels in the set of visually contiguous pixels; by length and width of the visually contiguous pixels; or by radius of a round pattern of visually contiguous pixels. In some embodiments, upon identification of a human or other sensitive object covering a certain percent of the field of view of a camera co-located with the transmitter, the transmitter ceases transmission of power waves. This is done in anticipation of scenarios where a human may walk in front of a transmitter at close range, and hence represent a certain percent of the pixels of the field of view, and it would be necessary to avoid transmitting any power waves in order to assure complete safety of the human.

A further characteristic is shape, which may for example be a configuration file selected from an appearance pattern library. The appearance pattern library may include multiple configuration files for the same object taken from different orientations and different distances, which provides greater flexibility in recognizing that object. Further, when using stereoscopic imaging, the system may compare patterns of visually contiguous pixels, such as visually contiguous body temperature pixels, acquired by multiple thermal imaging cameras from different perspectives. The system can compare these pixel patterns with different configuration files in the appearance pattern library, to confirm identification of a given object or a given object category. Configuration files of an appearance pattern library may be stored in databases within the transmitters 89109, and/or within the external mapping memory 89110, for ready access to these files following boot up of the transmitters 89109. Configuration files may include patterns of temperature, color such as skin tone and hair color, or facial features such as eyes and mouth, representing visual patterns of a person.

A pattern of visually contiguous pixels can indicate the presence of a living being in the field of view of a thermal imaging camera. As used in the present disclosure, "visually contiguous body temperature pixels" refers to a spatially contiguous area of pixels in a thermal image having temperature values that correspond to a temperature or range of temperatures indicating presence of humans and/or other living beings. As a non-limiting example, visually contiguous body temperature pixels for detection of humans may be defined as pixels with temperature values in and around the range of about 36.5 C (97.7° F.) to about 37.5° C. (99.5 F). In addition or as an alternative to temperatures based on body temperature, In some embodiments, "visually contiguous body temperature pixels" may include temperatures of humans that are lower than normal body temperatures, such as detected temperatures of clothing worn by a human.

Techniques for detecting living beings based upon visually contiguous body temperature pixels may be based not only on temperature contrasts between visually contiguous body temperature pixels as warm objects, versus cooler backgrounds, but also other computer vision techniques such as shapes of visually contiguous body temperature pixel patterns (e.g., human upper body shape detection); movement of a pattern of visually contiguous body temperature pixels tracked over time (e.g. walking human detection and detection of other human motions); and biometrics techniques (e.g., filtering visually contiguous body temperature pixel patterns based upon human height). In general, a BLOB representing temperatures near human body temperatures are considered to represent a human with high likelihood if they are not stationary, and the transmission of power waves is reduced or ceased in response.

Various computer vision techniques for detection and recognition of humans and other living beings may be applied to thermal imaging in the wireless power transmission system 89108. For example, the transmitter 89109 may implement tracking algorithms to determine whether an object associated with visually contiguous body temperature pixels is in motion (e.g., determine displacement). In some embodiments, multiple frames of thermal images may display a changing pattern of visually contiguous body temperature pixels against a static background image. An object near body temperatures that moves is considered to be a sensitive object, such as a human, and power wave transmission is reduced or ceased.

System 89108 may employ a variety of computer vision techniques for detecting the presence and/or location of living being based upon thermal images formed by the thermal imaging cameras 89115, wherein resulting thermal imaging data embodies visually contiguous body temperature pixels. Suitable human detection and recognition techniques include for example human appearance patterns, sometimes called human shape detection (e.g., head detection, face detection, hand detection, human upper body detection); human biometric attributes (e.g., human height); human motion detection; human activity detection (e.g., static posture, motion, and offset); and body temperature detection (e.g., skin detection).

The system 89108 may employ object tracking and recognition methods based upon 2D thermal imaging data, or based upon 3D imaging data incorporating depth information. The system 89108 may utilize object detection methods that provide location information about living beings, or may utilize object recognition methods that do not provide the location information. In an embodiment, techniques for detecting living beings in the system 89108 do not identify particular humans and do not classify humans. Alternatively, the system 89108 provides human identification data and/or human classification data for controlling wireless power transmission. Examples include distinguishing infants or children from adults, or distinguishing mobile humans from immobile humans, in determinations whether to adjust wireless power levels.

System 89108 may employ indoor 3D mapping to reconstruct a digital presentation of the environment overlapping the transmission field of the transmitters 89109. For example, thermal images formed by the multiple thermal imaging cameras may be processed to generate a 3D mapping field, in which point depth (i.e., a location of a point in a 3D mapping field) is computed using stereo matching techniques. Each transmitter 89109 may maintain in its database a 3D image map, such as a point cloud model, based on thermal imaging data of the transmitter's service area (transmission field). In addition, each transmitter 89109 may generate heat-mapping data from the communications signals 89113 to create a second type of 3D map of the transmission field. Multiple transmitters 89109 may upload their visual imaging data and/or heat map data to the external mapping memory 89110, which may act as a 3D model server that maintains a three dimensional point cloud model incorporating thermal imaging data received from all the transmitters 89109 at a location. Individual transmitters 89109 may download the 3D models from the 3D model server to provide more accurate 3D coordinates of objects detected by all thermal imaging cameras and other sensors. These image models may be used in feature matching of objects within the transmission field, including living beings and other objects such as table and receiver 89109. In an exemplary embodiment, the system 89108 effects indoor 3D mapping using sparse feature matching, in which a number of distinct points are extracted from successive frames and the geometric relationship between them is found.

System 89108 may embody a library of programming functions used in computer vision. For example, the system 89108 may incorporate programming functions from the OpenCV (Open Source Computer Vision) open source computer vision library; or may incorporate programming functions customized for wireless power transmission installations. For example, different computer vision functions may be used in floor-level thermal imaging systems (e.g., height recognition functions), as compared with thermal imaging systems physically associated with ceiling-mounted transmitters (e.g., head detection functions); or different computer vision functions may be used at different ranges of distance of detected objects from the transmitter.

In operation, the thermal imaging cameras 89115 may detect whether living beings, such as person, enter a predetermined proximity of the transmitter 89109, power waves 89114, and/or the pocket of energy 89117. In one configuration, the thermal imaging camera 89115 may then instruct the transmitter 89109 or other components of the system 89108 to execute various actions based upon the detected objects. In another configuration, the thermal imaging camera 89115 may transmit thermal imaging data to the transmitter 89109, and the transmitter 89109 may determine which actions to execute (e.g., adjust a pocket of energy, cease power wave transmission, reduce power wave transmission). For example, after the thermal imaging camera 89115 identifies that the person has entered the transmission field, and then determines that the person is within the predetermined proximity (pre-defined distance) of power waves 89114 and/or the transmitter 89109, the thermal imaging camera 89115 could provide the relevant thermal imaging data to the transmitter 89109, causing the transmitter 89109 to reduce or terminate transmission of the power waves 89114. As another example, after identifying the person entering the transmission field and then determining that the person has come within the predetermined proximity of the pocket of energy 89117, the thermal imaging camera 89115 may provide thermal imaging data to the transmitter 89109 that causes the transmitter 89109 to adjust the characteristics of the power waves 89114, to diminish the amount of energy concentrated at the pocket of energy 89117, generate a null, and/or reposition the location of the pocket energy 89117. In another example, the system 89108 may comprise an alarm device 89118, which may produce a warning, and/or may generate and transmit a digital message to a system log or administrative computing device configured to administer the system 89108. In this example, after the thermal imaging camera 89115 detects the person entering the predetermined proximity (pre-defined distance) of the transmitter 89109, the power waves 89114, and/or the pocket of energy 89117, or otherwise detects other unsafe or prohibited conditions of the system 89108, the sensor data may be generated and transmitted to the alarm device 89118, which may activate the warning, and/or generate and transmit a notification to the administrator device. A warning produced by the alarm device 89118 may comprise any type of sensory feedback, such as audio feedback, visual feedback, haptic feedback, or some combination.

In an example, a single thermal imaging camera 89115 forms a plurality of thermal images over time, and these images are analyzed to detect a pattern of visually contiguous body temperature pixels and to determine the area of this pattern. If the area of the pattern of visually contiguous body temperature pixels exceeds a prescribed threshold value, the system 89108 terminates wireless power transmission by the transmitter 89109 as representing prohibited proximity to the transmitter 89109 of the living being associated with pattern of visually contiguous body temperature pixels. In a variation of this embodiment, the transmitter 89109 determines the total number of pixels within the field of view of the thermal imaging camera 89115 that fall within the predetermined body temperature range regardless of whether these pixels are spatially contiguous, and terminates wireless power transmission if this pixel count exceeds a predetermined threshold. In another variation of this embodiment, based upon a series of image frames over time the transmitter 89109 determines the trend over time of the total number of pixels within the field of view of the thermal imaging camera 89115 that fall within the predetermined body temperature range, and terminates wireless power transmission if the increase of this total number of pixels exceeds a predetermined threshold.

In another example, the plurality of thermal imaging cameras 89115 form thermal images including visually contiguous body temperature pixels. A processor of the transmitter 89109 receives thermal imaging data from the thermal imaging cameras 89115 and applies stereoscopic vision analysis to determine three dimensional coordinates of the pattern of visually contiguous body temperature pixels. The processor determines a centroid of the pattern of visually contiguous body temperature pixels, and calculates the distance between that centroid and a predetermined 3D location of the pocket of energy 89117. If the distance is less than a first predetermined threshold value, the system reduces the power level of the power waves 89114. If the distance is less than a second predetermined threshold value lower than the first predetermined threshold value, the system terminates transmission of the power waves 89114.

In a further example, each of the plurality of thermal imaging cameras 89115 forms a series over time of thermal images including visually contiguous body temperature pixels. A processor of the transmitter 89109 receives thermal imaging data from the thermal imaging cameras 89115 and applies motion tracking analysis contrasting the visually contiguous body temperature pixels from background image elements in the thermal image frame, to detect motion of the object associated with visually contiguous body temperature pixels. Additionally, the processor applies stereoscopic vision analysis to determine three dimensional coordinates of the pattern of visually contiguous body temperature pixels, calculating a centroid of the pattern of visually contiguous body temperature pixels. If the motion tracking analysis concludes that a living being associated with the visually contiguous body temperature pixels is moving toward the pocket of energy 89117, the system reduces the power level of the power waves 89114. If the stereoscopic vision analysis determines that the distance between the living being and a predetermined 3D location of the pocket of energy 89117 is less than a predetermined threshold distance, the system terminates transmission of the power waves 89114.

Figure 89C:
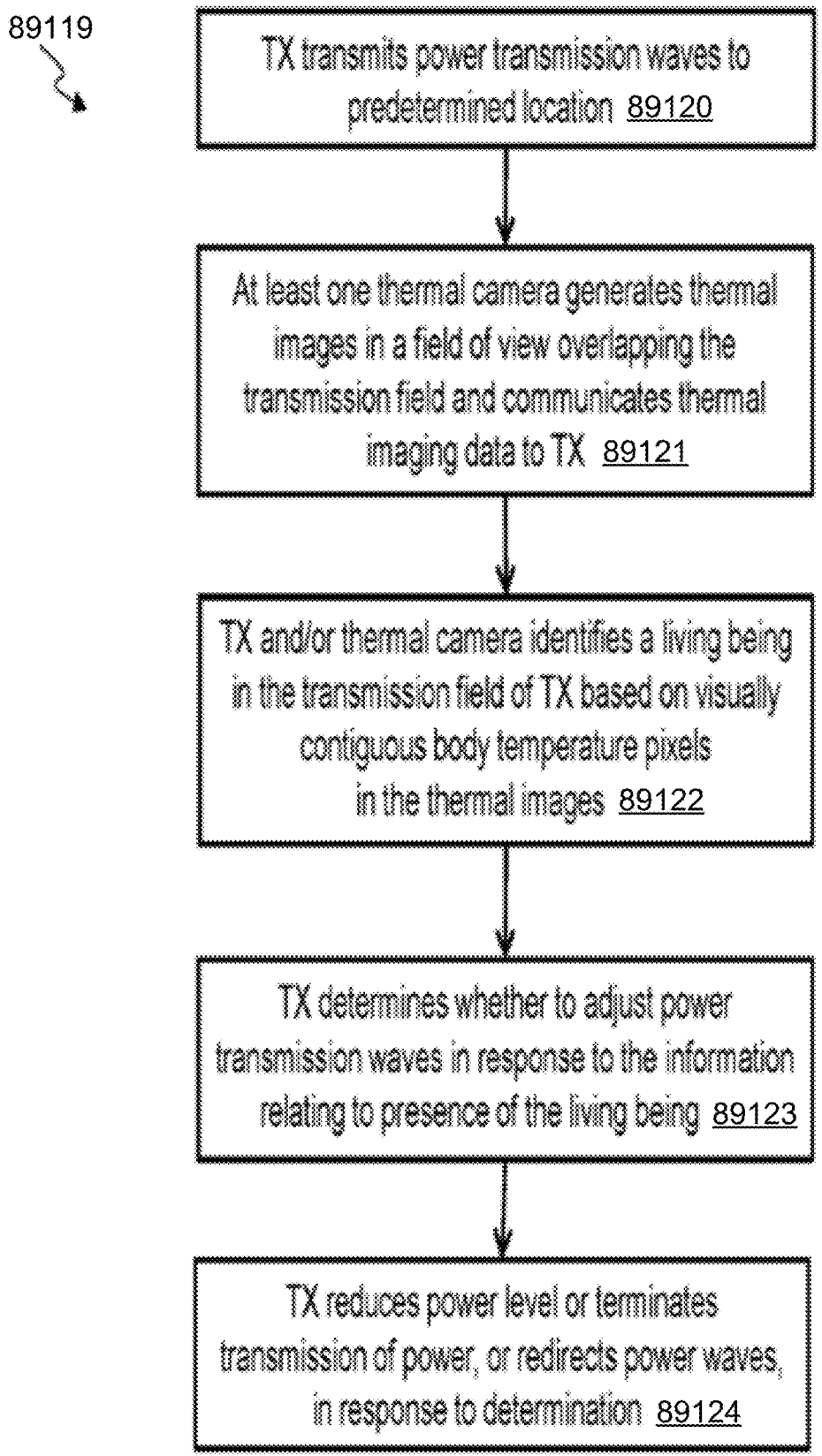

FIG. 89C is a flow diagram illustrating a method 89119 of identifying objects within a transmission field of a transmitter of a wireless power transmission system using thermal imaging cameras, according to an exemplary embodiment.

At a first step 89120, a transmitter transmits power waves to a predetermined location. The power waves transmitted at this step 89120 may converge into a three-dimensional constructive interference pattern, eventually forming one or more pocket of energy at the predetermined location. In one example, the pre-determined location is the location associated to a receiver. The predetermined location may be included in mapping data, such as thermal imaging data or heat-map data, used for determining where in a transmission field to transmit power waves. In some implementations, the mapping data containing the predetermined location may be stored in a mapping memory that is internal or external to the transmitter. In some implementations, the mapping data may be generated in real-time or near real-time, by a transmitter processor or a sensor processor. In addition, in some implementations, the mapping data containing the predetermined location may be provided from a user device, through a software application associated with the wireless charging system.

In some embodiments, of step 89120, the transmitter transmits power waves that converge in the transmission field to form a pocket of energy at the predetermined location, and also power waves that converge to form a second pocket of energy at a second location in the transmission field, which is separate from the predetermined location for the first pocket of energy. That is, in some instances, power waves may result in the generation of side lobes of power waves, which causes the formation of one or more second pocket of energy, in addition to the first pocket of energy generated at the predetermined location. In some implementations, the predetermined location for the first pocket of energy and the second location having the second pocket of energy, are both included in mapping data (e.g., thermal imaging data, heat-map data), tracking the locations of pocket-forming for the transmitter. Although waveform generation and transmission techniques may be employed to avoid or reduce formation of side lobes, various embodiments of wireless power transmission disclosed herein, such as the exemplary method 89119, may intelligently protect living beings and sensitive objects when these and other types of second pocket of energy are present in a transmission field.

At a next step 89121, one or more thermal imaging cameras generate thermal images in transmission field of the transmitter. The thermal imaging camera, or primary processing circuitry associated with the thermal imaging camera, communicates thermal imaging data to the transmitter. In an embodiment, a thermal imaging camera may communicate to the transmitter thermal imaging data including visually contiguous body temperature pixels. In an embodiment, the thermal imaging cameras may communicate to the transmitter location-related thermal imaging data concerning the presence and/or location of objects, such as a living being associated with visually contiguous body temperature pixels in the thermal images.

In an embodiment of step 89121, a first thermal imaging camera is located at a first position on the transmitter, and a second thermal imaging is located at a second position on the transmitter separated from the first position. In an embodiment, the first and second sensors acquire stereoscopic data indicating location of a pattern of visually contiguous body temperature pixels in the thermal images.

In an embodiment, a thermal imaging camera forms a plurality of thermal images over time of one or more field of view overlapping the transmission field of the transmitter. In an embodiment, the thermal imaging camera communicates to the transmitter thermal imaging data indicating motion of visually contiguous body temperature pixels in the thermal images.

At a next step 89122, the transmitter identifies a living being in the transmission field based on temperature data in the thermal images. In another embodiment, the transmitter and/or the thermal camera identifies a living in the transmission field based on visually contiguous body temperature pixels in the thermal images. As an example, one or more thermal imaging cameras may acquire raw thermal imaging data including a pattern of visually contiguous body temperature pixels, process the raw thermal imaging data, and then generate thermal imaging data containing information indicating the presence or location of a living being associated with the pattern of visually contiguous body temperature pixels.

In an embodiment of step 89122, a plurality of thermal imaging cameras communicates stereoscopic thermal imaging data to the transmitter, and either one or both of the thermal imaging cameras, or the transmitter, applies disparity analysis to determine three dimensional coordinates of a living being associated with the pattern of visually contiguous body temperature pixels.

A further embodiment, one or more thermal imaging cameras may acquire thermal imaging data containing information indicating the displacement or motion of a living being, based upon a series at different times of thermal images including a pattern of visually contiguous body temperature pixels indicating the presence of the living being. In an example, the transmitter uses this motion information to sense movement of the living being relative to the other objects of the wireless power transmission system, such as the transmitter, or the predetermined location of pocket of energy formed by the transmitter. In some embodiments, one or more thermal imaging cameras, the transmitter, or both, may calculate characteristics of the pattern of thermally contiguous body temperature pixels, such as centroid, area, length and width, radius, velocity (for a time series of thermal images) and shape.

At a next step 89123, transmitter determines proximity of identified living being to power waves. In order to calculate the proximity, the transmitter calculates a distance between location of identified living being and power waves being transmitted in the transmission field of the transmitter. The transmitter then adjusts the power level of the power waves upon determining that the proximity of the living being is within a pre-defined distance from the power waves. In one example, the pre-defined distance corresponds to distance from the living being to the transmitter. In another example, the pre-defined distance corresponds distance from the living being to the receiver.

In another embodiment, the transmitter determines whether to adjust the characteristics of the power waves, based upon information indicating the presence of a living being based upon visually contiguous body temperature pixels. In an embodiment, the transmitter compares location data for the living being obtained at step 89122, with coordinates (e.g., one-dimensional coordinates, two-dimensional coordinates, three-dimensional coordinates) of the transmitter. In another embodiment, transmitter compares information concerning the location data for the living being, obtained at step 89122, with coordinates (e.g., one-dimensional coordinates, two-dimensional coordinates, three-dimensional coordinates, polar coordinates) of the predetermined location of power transmission waves. In an embodiment, the transmitter calculates a distance of the living being from the transmitter, and reduces or terminates power in the event that distance falls below a threshold proximity value. In an embodiment, the transmitter calculates a distance of the living being from the location of the pocket of energy, and reduces or terminates power in the event that distance falls below a threshold proximity value.

In another embodiment of step 89123, the transmitter compares information concerning the location data for the living being, obtained at step 89122, with coordinates (e.g., one-dimensional coordinates, two-dimensional coordinates, three-dimensional coordinates, polar coordinates) of the location of the pocket of energy; and analyzes information concerning motion of the living being, obtained at step 89122. If the information concerning motion of the living being indicates motion of the living being toward the location of the pocket of energy, the transmitter reduces the power level of power transmission waves; and if the information concerning the location of the living being indicates less than a threshold distance from the location of the pocket of energy, the transmitter terminates wireless power transmission.

In some implementations, in step 89122, the transmitter may apply safety techniques to the determination of whether to adjust the power waves, using the location data in the sensor data associated with the living being or sensitive object. One safety technique is to include a margin of error (e.g., a margin of 10%-20%) beyond the regulatory limits or other limits on maximum permissible power level or on EMF exposure, to ensure living beings are not exposed to power levels at or near the limits. Another safety technique is to make a determination to adjust the power waves in the event an obstacle obstructs the field of view of a thermal imaging camera.

At a next step 89124, the transmitter may execute one or more actions, if the transmitter determines at a previous step 89123 to adjust power waves based on the information relating to presence of the living being. In some cases, the transmitter reduces the power level of the power waves at the predetermined location, when the transmitter determines at a previous step 89123 to adjust the power waves. In some cases, the transmitter terminates transmission of the power waves to the predetermined location, when the transmitter determines at a previous step 89123 to adjust or terminate the power waves. In some cases, the transmitter diminishes the amount of energy of the power waves at the predetermined location, when the transmitter determines at a previous step 89123 to adjust the power waves. In some embodiments, the transmitter redirects the transmission of the power waves around the living being or sensitive object, when the transmitter determines at a previous step 89123 to adjust the power waves. Additionally or alternatively, the transmitter may activate an alarm of the transmitter or wireless charging system, when the transmitter determines at previous step to adjust the power waves.

Exemplary System Components with Visual & Ultrasonic Devices

Figure 89D:
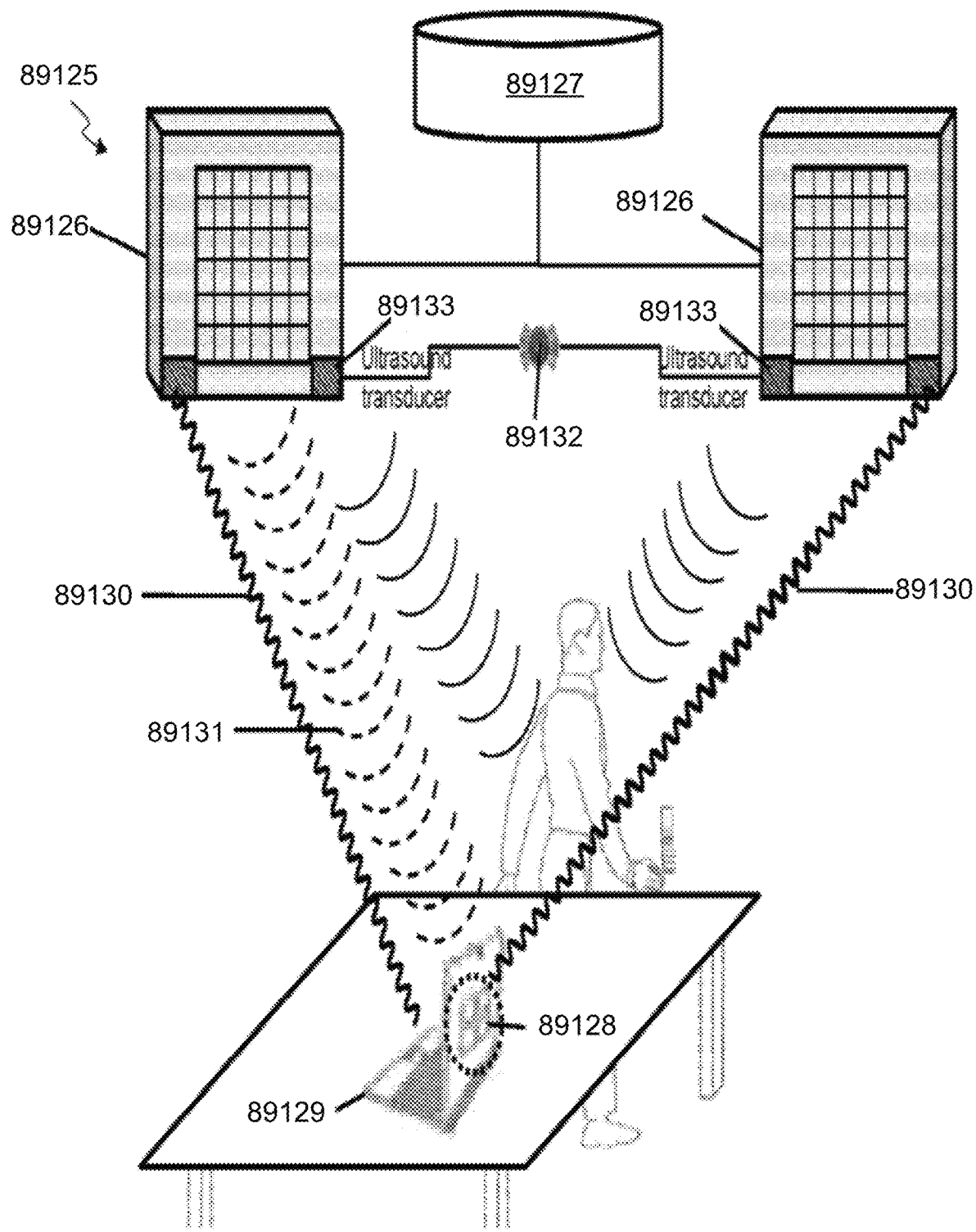

FIG. 89D shows components of an exemplary wireless charging system for identifying objects within a transmission field of a transmitter using a thermal imaging camera with ultrasonic transducers, according to an exemplary embodiment. FIG. 89D will now be explained in conjunction with FIG. 89A-89B.

The system 89125 may include transmitters 89126, an external mapping memory 89127, a receiver 89128, and an electronic device 89129 to be charged. Transmitters 89126 may send various types of waves, such as communication signals 89130, and power waves 89131, into a transmission field, which may be the two or three dimensional space into which the transmitters 89126 may transmit the power waves 89131.

System 89125 includes an imaging sensor 89132 that generates visual imaging data for a living being or sensitive object within at least a portion of a transmission field of the transmitter together with one or more ultrasonic transducers 89133 that generates ultrasound detection data to detect living beings and other sensitive objects within the transmission field of the transmitter 89126. The location of the living being and/or the sensitive object is then determined based on the visual imaging data and the ultrasound detector data. In another embodiment, this combination of detection devices can generate three dimensional location information for the living beings and other sensitive objects, which can be used by the transmitter 89126 in controlling wireless power transmission. The combined detection devices provide significantly more effective object detection and location than would be achieved using only ultrasound, or using only a single camera or other imaging sensor, enabling reliable detection of certain objects near the transmitter 89126 that may not be amenable to visual detection alone, or that may not be amenable to ultrasound detection alone. For example, ultrasound with no camera may not effectively discriminate between humans and other living beings, versus other objects. A single camera without ultrasound generally would not detect the distance from the transmitter 89126 of an object in two dimensional image data, and therefore may not detect unsafe proximity to the transmitter 89126 of a living being or other sensitive object.

System 89125 includes the imaging sensor 89132 that may receive radiation from a field of view overlapping the transmission field of the transmitters 89126. In one embodiment, the imaging sensor 89132 may be a video camera. In the embodiment of FIG. 89D, the imaging sensor 89132 may be a thermal imaging camera that may receive thermal radiation from the field of view. However, it should be understood that the imaging sensor includes other devices that can acquire two dimensional (2D) visual imaging data based upon other types of radiation within the field of view of the imaging sensor. In yet another embodiment, the imaging sensor is a visible light camera. The overlap between the field of view and the transmission field of the transmitter 89126 means that at least some portions of the field of view are also within the transmission field of the transmitters 89126, although in some embodiments, the field of view may extend beyond the transmission field. Additionally, the transmission field of the transmitters 89126 may extend beyond the field of view.

Additionally, the system 89125 includes the ultrasound transducers 89133, which capture ultrasonic detection data of objects in an ultrasound scan region that overlaps the field of view of the imaging sensor 89132, and that overlaps the transmission field of the transmitters 89126. The overlap between ultrasound scan region and the field of view means that at least some portions of the ultrasound scan region are also within the field of view, although in some embodiments, the ultrasound scan region may extend beyond the field of view. The overlap between the ultrasound scan region and the transmission field means that at least some portions of the ultrasound scan region are also within the transmission field, although in some embodiments, the ultrasound scan region may extend beyond the transmission field.

In an embodiment, the ultrasound transducers 89133 generate ultrasound energy for range finding of objects within the ultrasound scan region. Although the following discussion refers to ultrasound pulses, it should be understood that the ultrasound energy transmitted and received by the ultrasound transducers 89133 also may take the form of continuous waves. Ultrasound pulses are generated within the ultrasound scan region, overlapping the field of view. If there is an object in the path of these pulses, part or all of the pulses will be reflected back to the transmitter as an echo and can be detected through the receiver path. By measuring the difference in time between the ultrasound pulses transmitted and the echo received, the system can determine the distance of the object. By measuring a phase difference between the two echoes, the system can calculate the angle of the objects, e.g., as measured from a reference angle. A calculated distance and angle of an object can be represented as a vector from a reference point, such as a midpoint between the ultrasound transducers 89133 (in the present disclosure such a vector is sometimes called a "location vector" for the object).

In one embodiment, the imaging sensor, such as the thermal imaging camera 89132, is communicatively coupled to the transmitters 89126 and may be physically associated with the transmitters 89126 (i.e., connected to, or a component of). Although in some instances, the thermal imaging camera 89132 is shown positioned between the transmitters 89126, in various embodiments the thermal imaging camera 89132 would be positioned on or within a housing of the transmitter 89126. The imaging sensor 89132 generates two dimensional imaging data, such as thermal imaging data, for the transmitters 89126, which may contribute to the generation and transmission of the power waves 89131 by the transmitters 89126. Additionally, the one or more ultrasound transducers 89133, are communicatively coupled to the transmitters 89126 and may be physically associated with the transmitters 89126 (i.e., connected to, or a component of). The ultrasound transducers 89133 generate ultrasound detection data for the transmitters 89126, which may contribute to the generation and transmission of the power waves 89131 by the transmitters 89126. Transmitters 89126 may use the combination of the thermal imaging data from the thermal imaging camera 89132 with the ultrasonic detection data to determine various modes of operation and/or to appropriately generate and transmit the power waves 89131. For example, as further described below, the combination of the thermal imaging data from the thermal imaging camera 89132 with the ultrasonic detection data may determine three dimensional location information for a living being or sensitive object within the field of view of the thermal imaging camera 89132, in controlling generation and transmission of the power waves 89131, so that the transmitters 89126 may provide safe, reliable, and efficient wireless power to the receiver 89128.

In an illustrated embodiment, such as the exemplary system 89125, the one or more ultrasound transducers 89133 are internal components of the transmitter 89126. In some embodiments, the one or more ultrasound transducers 89133 may be external to the transmitter 89126 and may communicate, over a wired or wireless connection, ultrasonic detection data to the one or more transmitters 89126. The thermal imaging camera 89132 and the ultrasound transducers 89133 may provide the thermal imaging data and the ultrasound detection data, respectively, to the one or more transmitters 89126, and the processors of the transmitters 89126 may then share this data to determine the appropriate formulation and transmission of the power waves 89131. Host transmitters 89126 may send and receive object detection data with other detection devices, and/or with other host transmitters in the system 89125. Additionally or alternatively, the thermal imaging camera 89132, the ultrasound transducers 89132, or the host transmitters 89126 may transmit or retrieve one or more of visual imaging data, ultrasound detection data, and data derived from the processing of visual imaging data with ultrasound detection data, to or from one or more mapping memories 89127.

The ultrasound transducers 89133 may transmit ultrasound detection data for subsequent processing by a transmitter processor of the transmitter 89126. Additionally or alternatively, an ultrasound detection processor may be connected to or housed within one or more ultrasound transducers 89133. An ultrasound detection processor may comprise a microprocessor that executes various primary data processing routines, whereby the ultrasound detection data received at the transmitter processor has been partially or completely pre-processed as useable mapping data for generating the power waves 89131.

In another embodiment, the thermal imaging camera 89132 and the ultrasound transducers 89133 may include a processor that receives detection data from other detection devices, wherein detection data received at the transmitter processor from a combination of detection devices has been partially or completely pre-processed as useable mapping data for generating the power waves 89131. For example, the thermal imaging camera 89132 and the ultrasound transducers 89133 may include a processor that receives both two dimensional imaging data from the thermal imaging camera 89132, and the ultrasound detection data from the ultrasound transducers 89133, and that determines three dimensional location information for a living being or sensitive object within a field of view of the thermal imaging camera 89132.

With reference to FIG. 89D, it should be understood that the ultrasound scan region is not limited to the region of the ultrasound waves but may include other directions from ultrasound transducers 89133 and may extend further than the cross sectional plane from the imaging sensor's field of view. The ultrasound scan region overlaps the transmission field of the transmitters 89126 and the field of view of thermal imaging camera 89132 but may have a greater or lesser extent than these other regions. Generally, ultrasound signal wavelengths have a relatively short reach, and ultrasound is well suited to range finding in indoor environments.

The ultrasound transducers 89133 are physically associated with the transmitters 89126, respectively and transmit ultrasound waves, in an ultrasound scan region that overlaps the field of view of the thermal imaging camera 89132, and that overlaps the transmission field of the transmitters 89126. Echoes of the ultrasound waves may be reflected by one or more objects within the ultrasound scan region, such as a living being or sensitive object. In an embodiment, each of the ultrasound transducers 89133 transmits ultrasound pulses, and the time required to receive echoes of transmitted pulses is used to determine distance of objects. Ultrasound software receives object detection data from both the ultrasound transducers 89133, and may perform a disparity analysis based on phase differences of ultrasound detection measurements from the ultrasound transducers 89133. Based on this analysis, the system generates a location vector for each detected object. In an embodiment, the location vector is a location within a global coordinate system that can be used to specify three dimensional location information for objects within the field of view of the transmitters 89126.

In an embodiment, the ultrasound transducers 89133 are located along a line parallel to the X-Y area of the field of view of the imaging sensor 89132. In an embodiment, the imaging sensor 89132 is located substantially at a midpoint between the ultrasound transducers 89133. In another embodiment not shown, the ultrasound transducers 89133 may be located near the right and left edges of the transmitter housing of the transmitters 89126, and the imaging sensor 89132 may be located in line with the ultrasound transducers 89133, substantially at a midpoint between them.

Figure 89E:
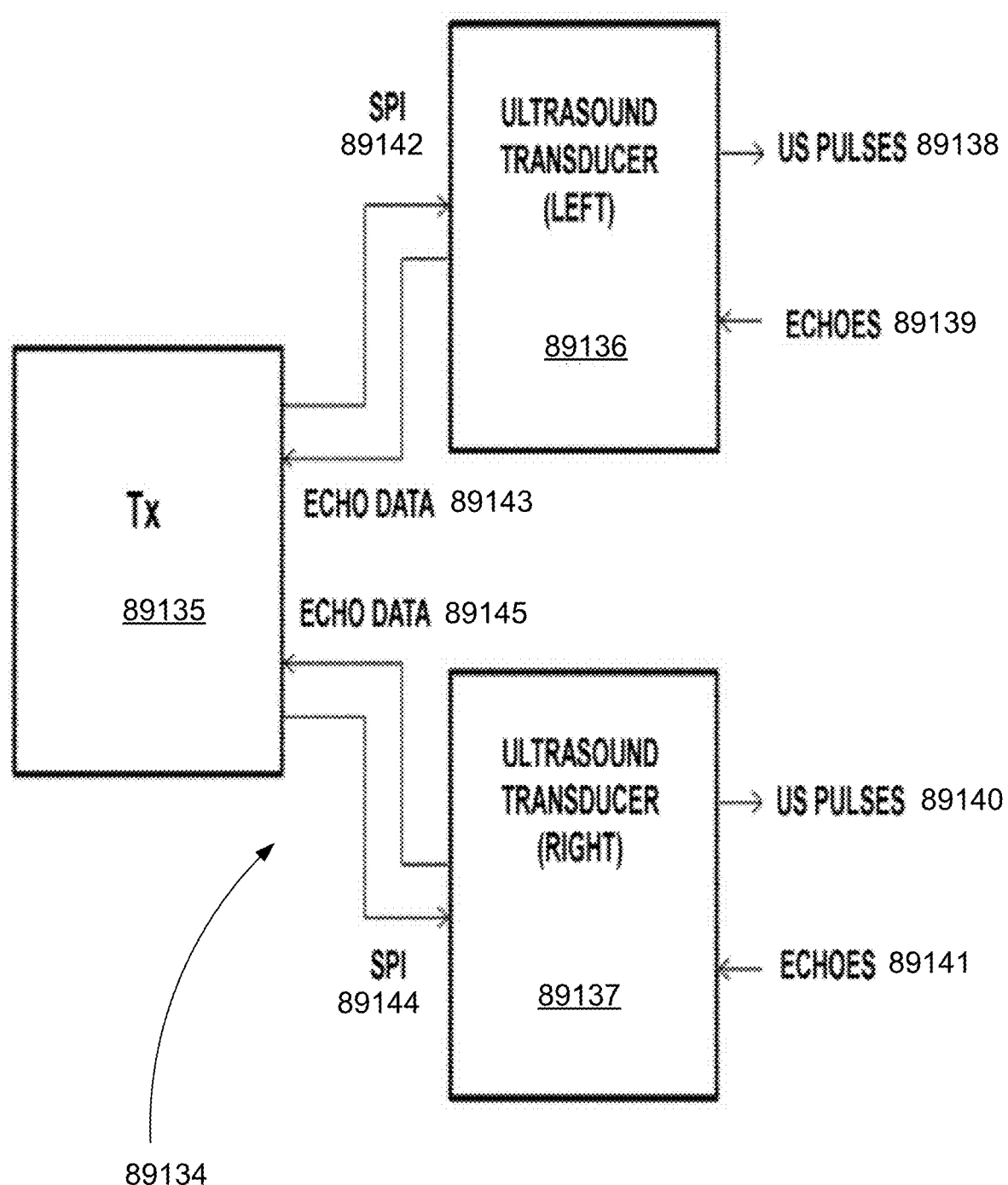

FIG. 89E illustrates components of a wireless power transmission system 89134 for identifying objects within a transmission field of a transmitter using ultrasonic transducers, according to an exemplary embodiment.

In an embodiment, a sensor processor, or ASIC, is integrated within transmitter (Tx) 89135. In some embodiments, the ASIC and/or sensor processor of Tx 89135 communicates commands to, and receives data from, ultrasound transducer 89136 (left transducer; "UT-L") and ultrasound transducer 89137 (right transducer; "UT-R") using Serial-Peripheral-Interface (SPI) interface.

In various embodiments, the ultrasound sensor components provide a timed sequence of steps in transmitting ultrasound pulses (or pings) and receiving echoes of these pulses from objects in an ultrasound scan region of transducers 89136, 89137. In an embodiment, the sequence includes the following steps, in timed sequence: (1) UT-L 89136 transmits ultrasound pulses (pings) 89138, as commanded by SPI 89142; (2) UT-L 89136 receives echoes 89139 of the ultrasound pulses; (3) UT-R 89137 transmits ultrasound pulses (pings) 89140, as commanded by SPI

89144; (4) UT-R 89137 receives echoes 89141 of the ultrasound pulses. In an embodiment, steps (2) and (4) are allocated sufficient time to complete collection of echoes from any objects within the transmission field, and then are followed immediately by the next transmission step. After step (4) is concluded, the sequence is repeated.

In an embodiment, during steps (3) and (4) when UT-R 89137 is transmitting pings and receiving echoes, UT-L 89136 may communicate echo data 89143 to Tx 89135 based on the echoes 89139 previously received during steps (1) and (2). Similarly, during steps (1) and (2) when UT-L 89136 is transmitting pings and receiving echoes, UT-R 89136 may communicate echo data 89144 to Tx 89135 based on the echoes 89141 previously received during steps (3) and (4).

This timed sequence permits ultrasound transducers 89136 and 89137 to transmit and receive signals using the same frequency, without interference with each other. Alternatively, ultrasound transducers 89136 and 89137 may operate on different frequencies.

In an embodiment, ultrasound transducers operate asynchronously with thermal imaging manager, but these devices time stamp reports to transmitters of thermal imaging data and ultrasound data in order to identify contemporaneously acquired data. In an embodiment, computer vision processing for thermal imaging camera, and ultrasound processing for ultrasound transducers, collectively operate within short cycle times. In exemplary embodiments, the cycle time of system for visual imaging and ultrasound detection may be between 9 cycles per second and 30 cycles per second. Advantageously, the system recognizes a living being or sensitive object and rapidly adjusts transmission of power waves based on this information. In an embodiment, the system terminates or limits the power level of wireless power transmission within 90 milliseconds of identifying an electromagnetic field (EMF) exposure risk via visual imaging and/or ultrasound detection.

In another embodiment, system includes a global coordinate system that is defined with respect to a transmitter. In this global coordinate system, a location vector for a detected object can measure a distance between the object and transmitter. In an embodiment, the global coordinate system is a Cartesian coordinate system in which transmitter is associated with coordinates (0, 0, 0). Two dimensional visual imaging data from imaging sensor may be correlated with ultrasound detection data from ultrasound transducers within the global coordinate system, to derive three dimensional location information for detected objects (such as living beings or sensitive objects) within the field of view of imaging sensor.

Figure 89F:
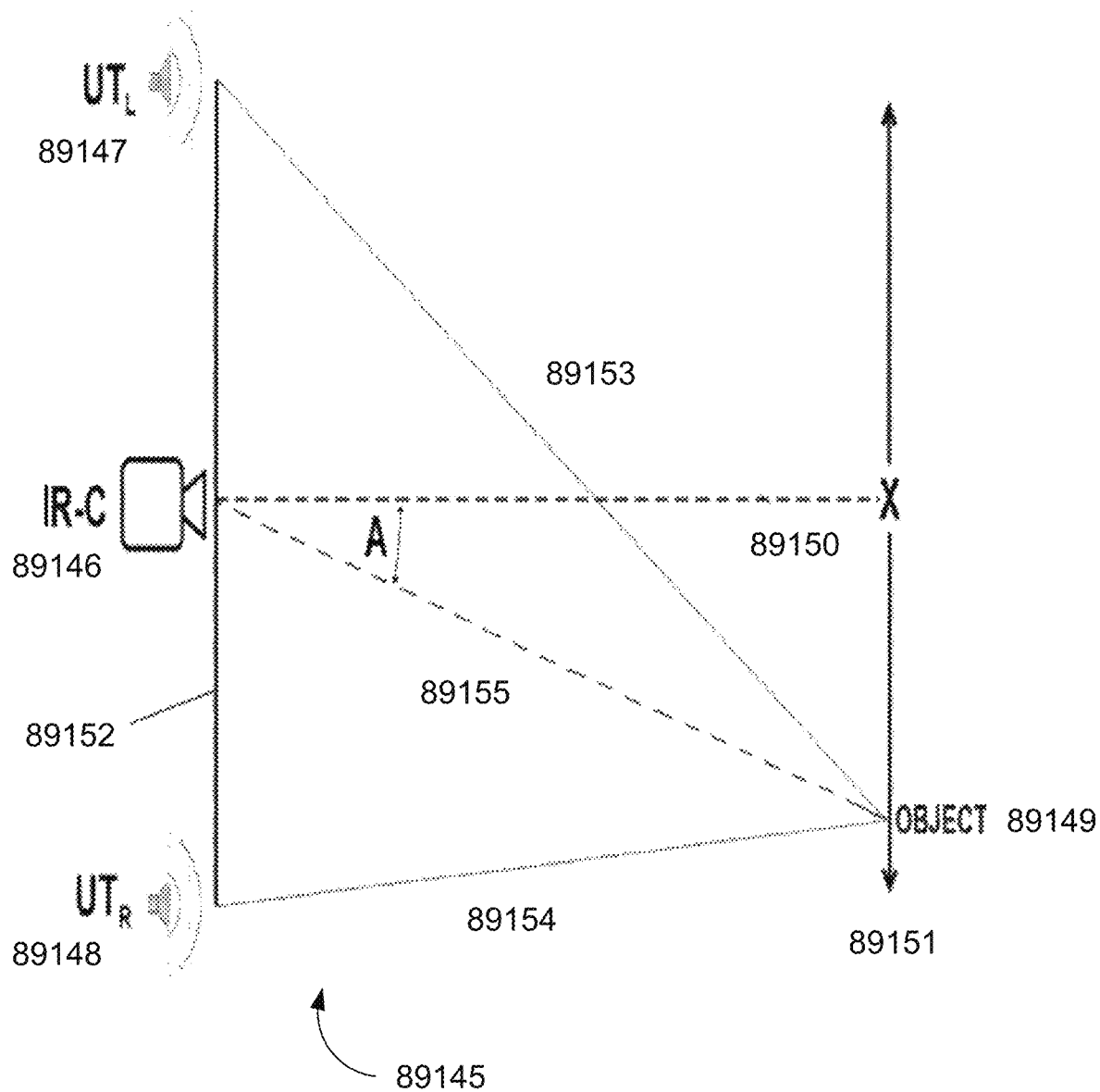

FIG. 89F is a schematic diagram of a wireless power transmission system 89145 with thermal imaging camera and ultrasonic transducers, according to an exemplary embodiment.

Left ultrasonic transducer 89147, right ultrasonic transducer 89148, and thermal imaging (infrared) camera 89146 are located in-line along axis 89152. Infrared camera is located substantially at a midpoint between ultrasonic transducers 89147 and 89148. Each of ultrasonic transducers 89147 and 89148 transmits ultrasound pulses that are reflected off object 89149, with echoes of these pulses reflected back to the transducers. Each transducer detects the amplitude and elapsed time of received echoes. The elapsed time of return of an ultrasound pulse indicates distance of an object from the ultrasound transducer. Triangulation algorithms may be employed to identify an "ultrasound angle" of object 89149 based on an offset of time as between the readings by transducers 89147, 89148. In the present disclosure "ultrasound angle" refers to the angle of a vector to an object's location as detected by the ultrasound sensors. Thus in the exemplary configuration of FIG. 89F, object 89149 is closer to transducer 89148 than to 89149, as indicated by a commensurately greater time for the echo to return to transducer 89147. In processing the echoes from object 89149, therefore, the system determines a vector 89153 from the left ultrasound transducer 89147 to the object 89149, and determines a vector 89154 from the right ultrasound transducer 89153 to the object 89149.

An ultrasound transducer operating as a ranging device may detect echoes from numerous objects within its ultrasound scan region, maintaining a list of these echoes with associated distance measurements. Given objects, however, can provide ultrasound echo of an amplitude that is characteristic of that object. Echo readings from transducers 89147, 89148 can be compared to identify echoes that were generated by the same object. In this manner, the system can identify and analyze pairs of corresponding echoes associated with a common object such as object 89149.

An object detected by infrared camera 89146 may be defined by a horizontal location, i.e. location along the X-axis 89151 from the field of view of the infrared camera. For example, the horizontal location may be the X-coordinate a centroid of a pattern of visually contiguous pixels detected by thermal imaging camera 89146, as further described below. A reference line, or normal, 89150 extends from the infrared camera 89146 perpendicular to the axis 89152. Horizontal angles of objects within the field of view of infrared camera 89146 may be defined with respect to the normal 89150; for example, an object located on the normal 89150 is at the center of the field of view. In the present disclosure, the angle to the horizontal location of an object within the field of view of thermal imaging camera 89146, e.g., angle A of the line 89155, is called the "visual angle".

In an embodiment in which the thermal imaging camera is located at the midpoint between the ultrasound transducers, the "ultrasound angle" can be defined with reference to the same normal 89150 in the global coordinate system that is used to define the visual angle. An object located on the normal 89150 is equidistant from ultrasonic transducers 89147 and 89148, hence echoes from this object would have the same elapsed time measurement. In the configuration of FIG. 89F, the system 89145 would determine ultrasound angle A based upon the triangulation of object 89149.

Visual angles can be compared with ultrasound angles in identifying objects. If the visual angle of an object 89149 detected by the thermal imaging camera 89146 substantially corresponds to the ultrasound angle of an object detected by ultrasound transducers 89147, 89148, it is highly probable that the object detected by the ultrasound transducers is the same as the object detected by the thermal imaging camera.

Figure 89G:
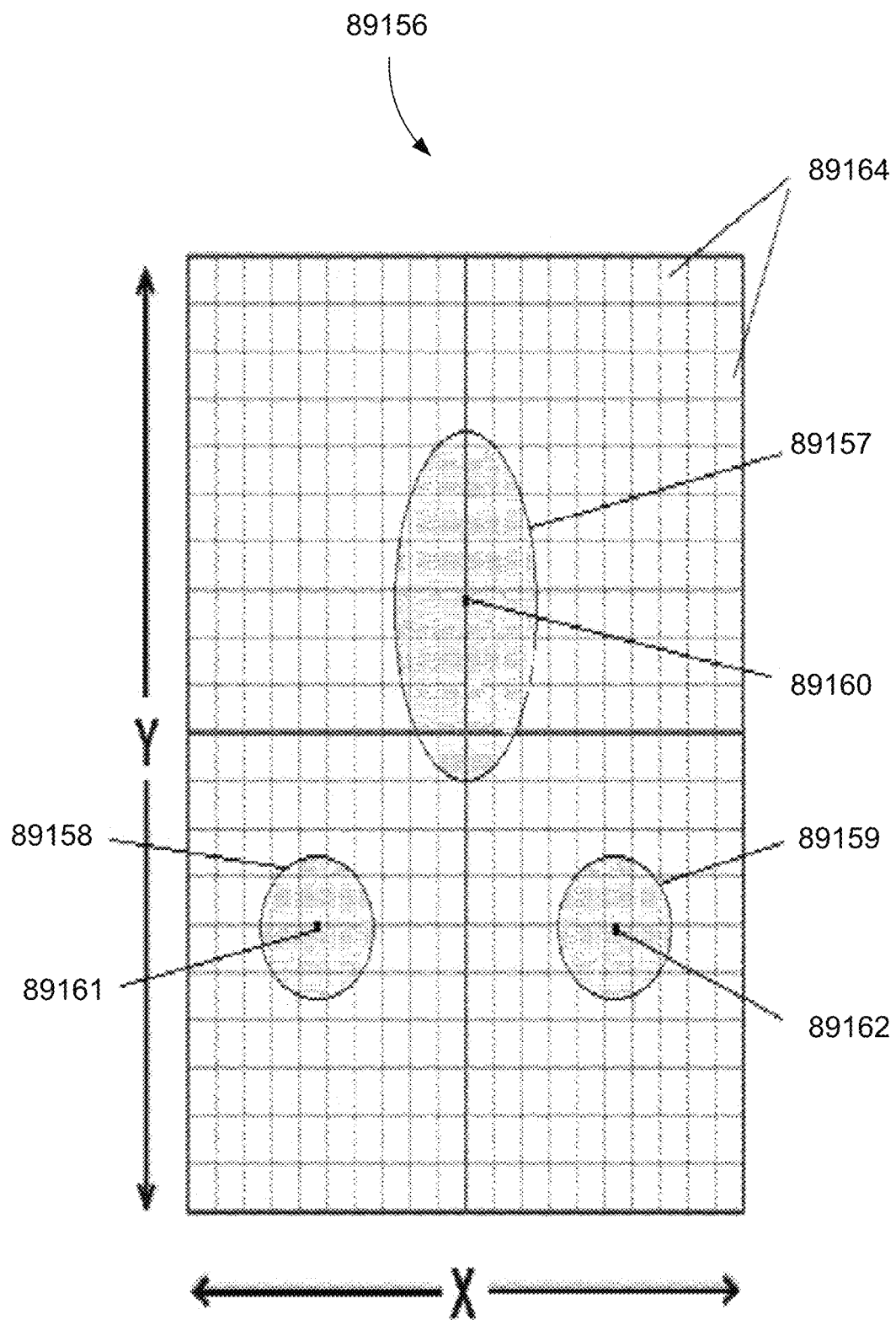

FIG. 89G is a two dimensional, X-Y grid of the field of view of a thermal imaging camera displaying several visually contiguous human temperature pixel patterns.

An exemplary thermographic image 89156 within the field of view of a thermal imaging camera is shown. The thermographic image 89156 includes a rectangular grid of pixels 89164 arrayed along an X axis and Y axis. Each of the pixels has an associated numerical value based on measurement of infrared energy, wherein this value indicates a corresponding temperature. In an embodiment, pixels of varying temperature values are displayed in a thermogram using pseudo-colors. In an embodiment, the thermal imaging data is analyzed to identify patterns of pixels having temperature values within defined ranges. Pixels within defined temperature ranges are grouped in patterns of visually contiguous pixels. In an embodiment, a temperature range is selected to identify with temperature values characteristic of human body temperatures, i.e. visually contiguous body temperature pixels.

Multiple patterns of visually contiguous body temperature pixels may be arrayed in the field of view of thermal imaging camera. The thermographic image of field of view 89156 includes three patterns of visually contiguous body temperature pixels, including a larger, higher central pattern 89157 and smaller, lower side patterns 89158, 89159 of visually contiguous body temperature pixels. The thermographic image 89156 might for example indicate features of a human, such as a human head corresponding to pattern 89157, and human hands corresponding to patterns 89158, 89159.

In an embodiment, the system analyzes the patterns of visually contiguous body temperature pixels for various characteristics (symbolic thermal imaging data). These characteristics may include for example, two dimensional locations of the centroid 89160 of visually contiguous body temperature pixels 89157; two dimensional locations of the centroid 89161 of visually contiguous body temperature pixels 89158; and two dimensional locations of the centroid 89162 of visually contiguous body temperature pixels 89159.

In an embodiment, the system 89125 of FIG. 89D combines these two-dimensional thermal imaging data with sensor measurements by ultrasound transducers 89133 of objects corresponding to the visually contiguous body temperature pixels (such as living beings, or limbs or features of living beings) to obtain three dimensional locations. Each of these ultrasound measurements identifies a distance to one of the objects corresponding to patterns 89157, 89158, and 89159. Ultrasound angles may be correlated with visual angles corresponding to horizontal locations of the centroids 89160, 89161, and 89162 to confirm that a given ultrasound reading corresponds to one of the objects associated with the thermal imaging data. Ultrasound amplitude measurements also may be used in confirming correspondence of detected objects. In an embodiment, distances determined by ultrasound ranging are combined with the X and Y coordinates of centroids 89160, 89161, and 89162 to determine three dimensional (X, Y, Z) coordinates for each of the visually identified objects.

Exemplary Embodiments Using Decision Manager Component

Figure 89H:
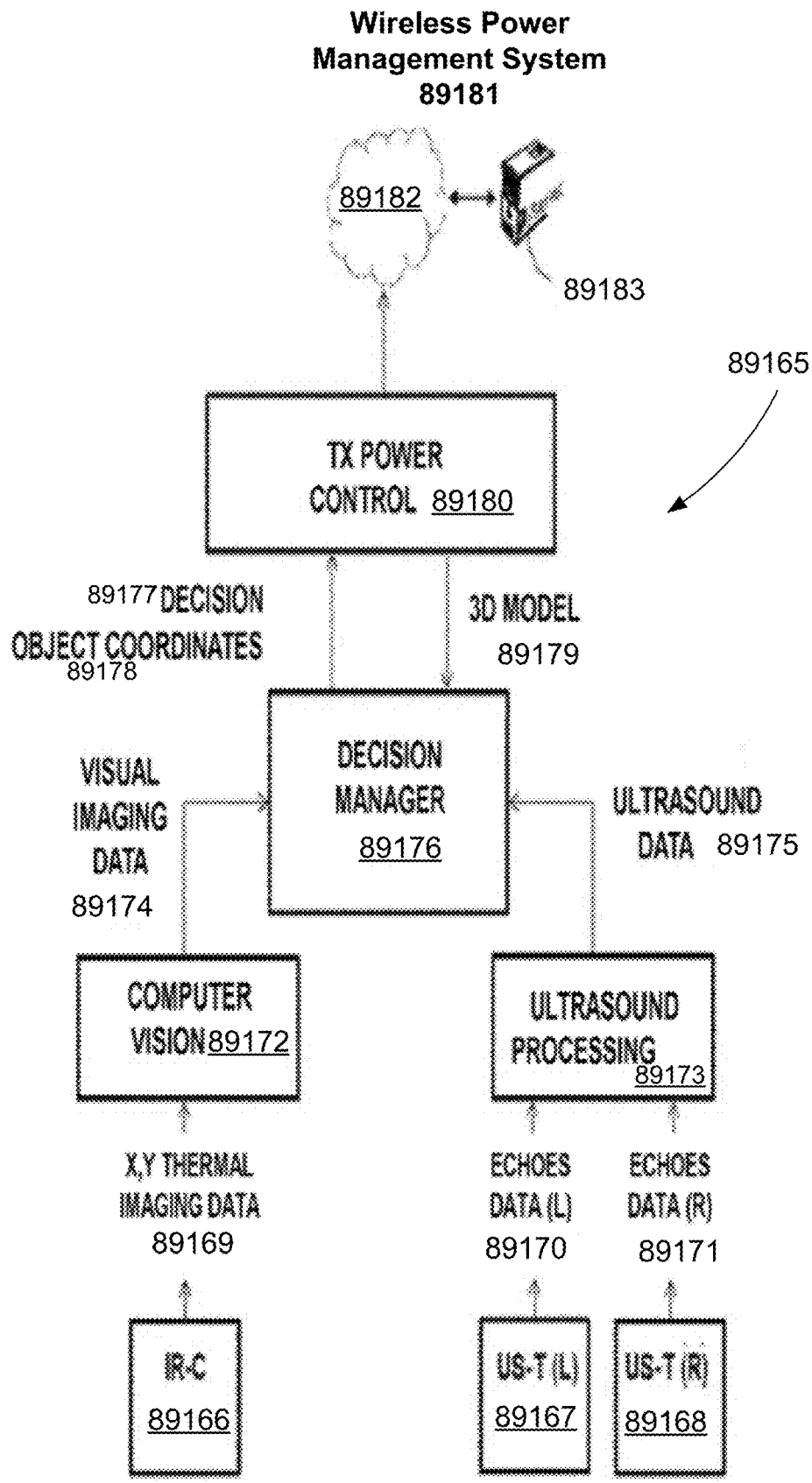

FIG. 89H illustrates an architecture of components of a wireless power transmission system 89165, according to an exemplary embodiment.

The components of the wireless power transmission system 89165 may include an imaging sensor, two ultrasound transducers, and a decision manager that processes outputs of these devices. In one embodiment, the image sensor may operate as a video camera. TX power control 89180 is configured to control power waves transmitted by a transmitter. In an embodiment, the transmitter transmits the power waves through at least two antennas. The power waves converge in a three dimensional space to form pocket of energy for receiving by an antenna element of a receiver, wherein the receiver is configured to harvest power from the pocket of energy. Decision manager 89176 is configured to communicate a decision 89177 to the TX power control 89180. In an embodiment, the decision 89177 instructs the TX power control 89180 whether to adjust a power level of the power waves based upon three dimensional location information determined by the decision manager 89176 for one or more object within the transmission field of the transmitter (e.g. living being, obstacle). Additionally, the decision manager 89176 may communicate to the TX power control 89180 three dimensional coordinates 89178 of the one or more object within the transmission field.

In an embodiment, the decision 89177 communicated by decision manager 89176 to the TX power control 89180 is one of the following: (a) a decision to maintain full power level of the power waves; (b) a decision to reduce the power level of the power waves; or (c) a decision to terminate transmission of power waves. In options (b) or (c), immediately upon receipt of the decision 89177, the TX power control 89180 reduces or terminates transmission of power waves by controller, thereby enhancing system safety. The decision to reduce the power level of power waves, option (b), may include different levels of reduction of power level, for example based on different calculated distances of a living being from a transmitter based upon the three dimensional location information calculated by the decision manager 89176.

To summarize the architecture and functions of the system 89165, the decision manager 89176 receives visual imaging data 89174 (image data captured by camera) from a computer vision (CV) module 89172, and receives ultrasound data 89175 from an ultrasound processing (US) module 89173. The decision manager 89176 comprising a processor processes the visual imaging data 89174 to identify a first set of coordinates of an object in the image data captured by the video camera with respect to location of the video camera, and the ultrasound data 89175 to identify a second set of coordinates to identify a second set of coordinates of an object in the image data captured by the ultrasound sensors with respect to location of the video camera. In one embodiment, the processor of the decision manager 89176 processes the visual imaging data 89174 and the ultrasound data 89175 to calculate three dimensional location information for the object within the transmission field of transmitter. In another embodiment, processor of the decision manager 89176 calculate three dimensional location information for the object within the transmission field of transmitter based on the first and second set of coordinates.

The decision manager 89176 may apply predetermined criteria to the calculated three dimensional location information to provide the decision 89177. CV 89172 generates the visual imaging data 89174 based upon two dimensional imaging data (e.g., X-Y thermal imaging data) 89169 that the CV 89172 receives from an infrared camera 89166. US 89173 generates the ultrasound data 89175 based upon echoes data (left) 89170 and echoes data (right) 89171 that US 89173 receives respectively from left ultrasound transmitter 89167 (US-T (L) 89167) and from right ultrasound transmitter 89168 (US-T (R) 89168).

In an embodiment, the TX power control 89180 and the decision manager 89176 are physically associated with wireless power transmitter (i.e., connected to, or a component of). Infrared camera 89166 is communicatively coupled to transmitter and may be physically associated with transmitter (i.e., connected to, or a component of). The IR-C 89166 may be positioned on or within a housing of a transmitter, or may be communicatively coupled to the transmitter but physically separated from transmitter. Likewise, the US-T (L) 89167 and the US-T (R) 89168 may be positioned on or within a housing of a transmitter, or may be communicatively coupled to the transmitter but physically separated from transmitter. In an embodiment, the IR-C

89166, the US-T (L) 89167, and the US-T (R) 89168 are mounted to a housing of the transmitter, with the IR-C 89166 located substantially at a midpoint between the US-T (L) 89167 and the US-T (R) 89168. The computer vision module 89172 may be connected to or housed within the infrared camera 89166, or may be physically separated from the IR-C 89166. Similarly, the ultrasound processing module 89170 may be one or more processor module connected to or housed within one or both of the US-T (L) 89167 and the US-T (R) 89168, or may be physically separated from the ultrasound transducers.

The infrared camera 89166 forms two dimensional images using infrared radiation. The infrared camera 89166 may be a near-infrared camera that use the near-infrared part of the electromagnetic spectrum closest to visible light, or may be a thermal infrared camera that generally operates in the far infrared region. In an embodiment, the IR-C 89166 captures thermal images of the objects within the camera's field of view and records these thermal images in two dimensional pixel arrays as X, Y thermal imaging data 89169. Each pixel or photo site in the array detects infrared energy intensities, and the IR-C 89166 stores individual temperature values for each pixel based on transformation of the infrared energy. Additional details of infrared imaging are described above.

The visual imaging data 89174 of particular significance in the operations of the decision manager 89176 include data indicating the presence of a living being or sensitive object within the transmission field of transmitter, and as well as data indicating presence of an obstacle within the transmission field of transmitter. Thermal imaging is especially useful in identifying living beings as warm objects within the field of view of the infrared camera 89166, but thermal imaging also can be used to identify obstacles. Additionally, ultrasound imaging can provide useful ultrasound data 89175 about presence, configuration, and location of obstacles to complement the visual imaging data 89174.

The computer vision module 89172 applies computer vision techniques to obtain the visual imaging data 89174 based upon the X, Y thermal imaging data 89174. Generally, the visual imaging data 89174 relates to two dimensional or one dimensional characteristics of the X, Y thermal imaging data 89169, since the thermal imaging data 89169 does not include three dimensional imaging data. In an embodiment, the CV 89172 analyzes the thermal imaging data 89169 to detect one or more object within the field of view of the IR-C 89166 (in the present disclosure, such visually identified objects are sometimes called "visual objects"). In one embodiment, the CV 89172 analyzes the thermal imaging data 89169 to detect patterns of visually contiguous pixels. For example, the CV 89172 may analyze the thermal imaging data 89169 to detect one more pattern of visually contiguous body temperature pixels, such as the patterns 89157, 89158, 89159 shown in FIG. 89G. The CV 89172 may analyze any identified patterns visually contiguous body temperature pixels for geometric characteristics such as area, centroid, length and width, and may provide visual imaging data based on this analysis to the decision manager 89176.

In addition, the CV 89172 may compare the visually contiguous pixel files with configuration files to look for a match with stored configurations. For example, the CV 89172 may compare the configuration of visually contiguous body temperature pixels with human appearance patterns, sometimes called human shape detection (e.g., head detection, face detection, hand detection, human upper body detection). Alternatively, some of these computer vision analyses, such as human appearance pattern analysis, may be carried out by the decision manager 89176. In addition, the decision manager 89176 may use other computer vision techniques for human recognition such as human biometric attributes (e.g., human height); human motion detection; human activity detection (e.g., static posture, motion, and offset), and body temperature detection (e.g., skin detection). The combination of two-dimensional visual imaging data 89174 with depth information obtained from the ultrasound data 89175 to derive three dimensional location information can be critical to some of these techniques.

Ultrasound processing module 89173 analyzes echoes data (left) 89170 obtained from US-T (L) 89167 and echoes data (right) 89171 obtained from US-T (R) 89168 to derive ultrasound data 89175 for objects within ultrasound scan regions of US-T (L) 89167 and US-T (R) 89168. Typically, ultrasound data includes vector data for a list of objects detected by US-T (L) 89167 and US-T (R) 89168 (in the present disclosure, such objects identified through ultrasound are sometimes called "ultrasound objects"). In an embodiment, vector data for each ultrasound object includes distance and ultrasound angle, for each of the detected objects. In an embodiment, the ultrasound processing module 89173 pairs object detection data from US-T (L) 89167 with object detection data from US-T (R) 89168, based on determination that the paired data are associated with the same ultrasound object.

In an embodiment, the decision manager 89176 compares the visual imaging data 89174 for visual objects, with the ultrasound data 89175 for ultrasound objects. The decision manager 89176 may use various techniques to associate visual objects with ultrasound objects, as discussed above with reference to FIG. 89F. For example, the decision manager 89176 may look for correspondence between a visual angle for a given visual object within the field of view of the IR-C 89166, with an ultrasound angle for a given ultrasound object. In an embodiment, the decision manager determines a visual angle to a visual object using a horizontal location corresponding to X, Y coordinates of a centroid of the visual object received from the computer vision module 89172, calculating the visual angle to that X, Y location. If the visual angle corresponds to the ultrasound angle, decision manager may determine that the visual object corresponds to the ultrasound object.

In an embodiment, the comparison by the decision manager 89176 of X-Y location information included in the visual imaging data 89174 with ultrasound vectors contained in the ultrasound data 89175, is based predominantly on a basis of substantially horizontal location information. In an embodiment, visual angles of visual objects included in the visual imaging data 89174 correspond to substantially horizontal, X-axis, locations of the visual objects. Similarly, in an embodiment, ultrasound angles of ultrasound objects included in the ultrasound data 89175 correspond to locations within a horizontal zone of the ultrasound transducers 89167 and 89168 and of the ultrasound scan regions of these ultrasound transducers. In an embodiment, these sensing characteristics are designed to sense most accurately objects that are at the same general height as the transmitter and the transmission field of transmitter; e.g. ground-level power transmission.

When the decision manager 89176 determines that a visual object corresponds to an ultrasound object, it may use the related visual imaging data 89174 and the ultrasound data 89175 to calculate three dimensional location information, such as X, Y, Z location coordinates, for the object in question. The three dimensional location information can include various other three dimensional information beyond X, Y, Z location coordinates of objects, such as three dimensional data on movement of an object obtained by analyzing a series of frames of X, Y thermal imaging data 89169; areas, length and widths of objects; pattern recognition data; etc.

In another embodiment, the decision manager 89176 may identify multiple visual objects within the field of view of IR-C 89166 and may analyze the visual objects to look for relationships. For example, decision manager may analyze whether multiple visually contiguous body temperature pixels correspond to different features of a given living being (such as head and hands) or whether the multiple patterns visually contiguous body temperature pixels correspond to more than one living being. Comparison by the decision manager 89176 of the visual imaging data 89174 with the ultrasound data 89175 can an important element of this analysis. For example, a comparison with the ultrasound data 89175 may show that a first pattern of visually contiguous body temperature pixels is located at a significantly different distance from the IR-C 89166 than a second pattern of visually contiguous body temperature pixels, indicating that these patterns identify different physical objects.

In an embodiment, decision manager also may receive a 3D model 89179 from Tx power control or from another component of the wireless power transmission system, such as external mapping memory. For example, multiple transmitters may communicate with one or more decision manager 89176 to maintain a 3D image map, such as a point cloud model, based in part on three dimensional location information derived from visual imaging data and ultrasound data. In addition, each transmitter may generate heat-mapping data from communications signals to create a second type of 3D map of the transmission field. Multiple transmitters may upload their visual imaging data and/or heat map data to external mapping memory, which may act as a 3D model server that maintains a three dimensional point cloud model incorporating thermal imaging data received from all transmitters at a location. Individual transmitters may download the 3D models from the 3D model server to provide more accurate 3D coordinates of objects detected by all thermal imaging cameras and other sensors. Decision manager 89176 may compare this 3D model with three dimensional location information obtained from analyzing the visual imaging data 89174 and the ultrasound data 89175, in determining the decisions 89177.

In an embodiment, the decision manager 89176 may communicate notifications to components of the wireless power transmission system 89165. For example, a decision 89177 can be considered a notification by decision manager to the TX power control 89180. Tx power control may forward this and other information received from the decision manager 89176 to the wireless power transmission manager 89181, which oversees operations of the wireless power transmission system 89165 and optionally, to other elements of the wireless power transmission system such as a set of antennas. For example, the TX power control 89180 may communicate notifications to the wireless power transmission manager 89181 via the cloud 89182, which may be an internet cloud, a business cloud, or a service provider cloud. Wireless power management system may store these notifications and other information at the server 89183.

Figure 89I:
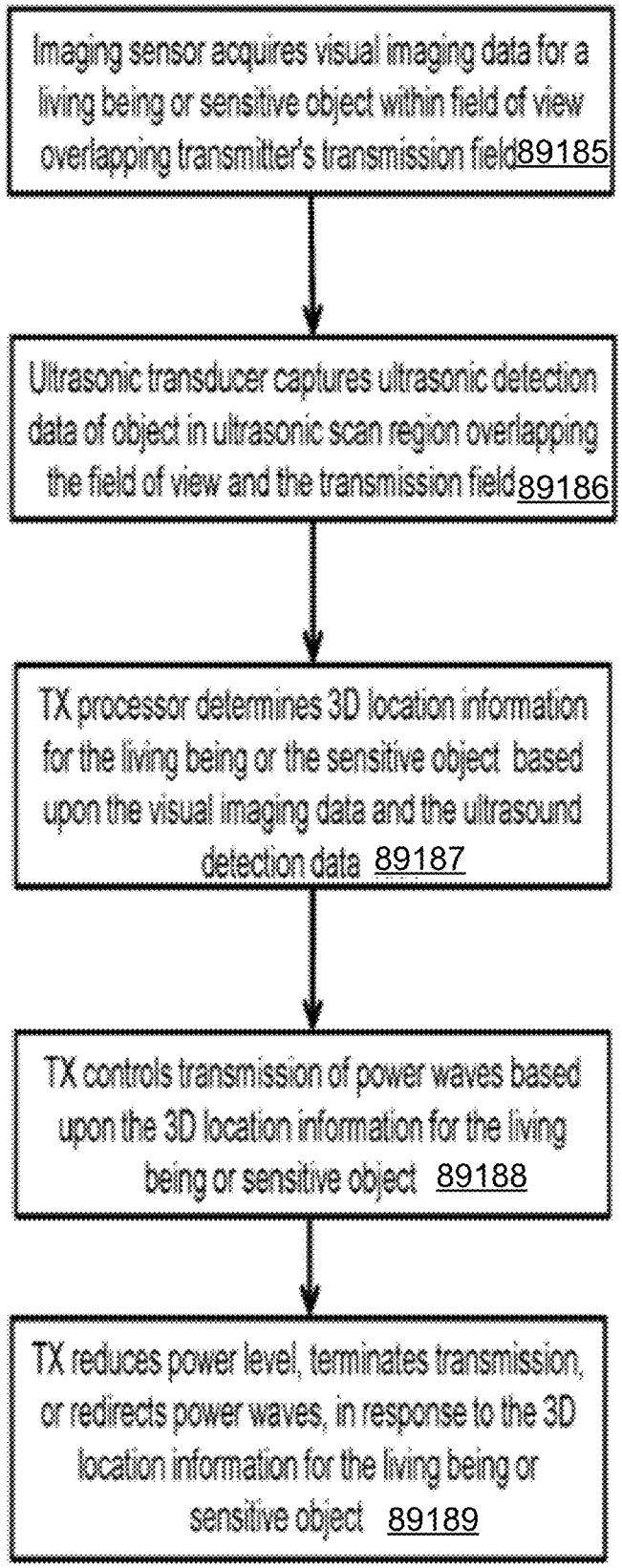

FIG. 89I is a flow diagram illustrating a method 89184 of identifying objects within a transmission field of a transmitter of a wireless power transmission system using a thermal imaging camera with ultrasonic transducers, according to an exemplary embodiment.

Transmitters of a wireless power system may comprise a thermal imaging camera and ultrasound detectors that collectively detect whether a living being is in proximity to one or more pocket of energy, power waves, and/or a transmitter. In these circumstances, the system may analyze thermal imaging data generated by the camera and ultrasound detection data generated by the ultrasound transducers, to determine 3D location information for a living being or sensitive object within the transmission field of the transmitter. This three dimensional location information may cause the transmitter to reduce or terminate power levels of power waves, among a number of additional or alternative actions.

At a first step 89185, a camera acquires thermal imaging data for a living being or sensitive object within a field of view of the camera. The field of view of the camera overlaps a transmission field of the transmitter. In some embodiments, the camera acquires two dimensional thermal imaging data. In an embodiment, the camera acquires two dimensional thermal imaging data for a living being or sensitive object within a field of view of the camera overlapping a transmission field of the transmitter.

In an embodiment of step 89185, the camera acquires thermal imaging data including visually contiguous pixels. In various embodiments, the camera is a thermal imaging camera. In an embodiment, the thermal imaging data includes visually contiguous body temperature pixels indicating a two dimensional location of the living being within the field of view of a thermal imaging camera. In an embodiment, the camera is a single thermal imaging camera, which may communicate to the transmitter two dimensional thermal imaging data concerning the presence and/or location of objects, such as a living being associated with visually contiguous body temperature pixels.

In an embodiment, the camera is a thermal imaging camera that forms a plurality of thermal images over time of one or more field of view overlapping the transmission field of the transmitter. In an embodiment, the thermal imaging camera communicates to the transmitter thermal imaging data indicating motion of visually contiguous body temperature pixels in the thermal images.

At a second step 89186, at least one ultrasound transducer in communication with the transmitter captures ultrasound detection data of one or more objects in an ultrasound scan region. In an embodiment, the ultrasound scan region overlaps the field of view of the imaging sensor and the transmission field of the transmitter.

In an embodiment of step 89186, a first ultrasound transducer captures first ultrasound detection data for one or more object in the ultrasound scan region, and a second ultrasound transducer captures second ultrasound detection data for the one or more object in the ultrasound scan region. In an embodiment, the first ultrasound detection data and the second ultrasound detection data is processed to provide ranging information for the one or more object. In an embodiment, the first ultrasound detection data and the second ultrasound detection data is processed to provide an ultrasound angle for the one or more object. In an embodiment, the camera of step 89185 is located substantially at a midpoint between the first ultrasound transducer and the second ultrasound transducer.

In an embodiment, at step 89185 the camera acquires the thermal imaging data for the living being or the sensitive object within an X-Y image area of the field of view of the imaging sensor; and at step 89186 a first ultrasound transducer and a second ultrasound transducer are located on a line parallel to the X-Y image area. The first ultrasound transducer and a second ultrasound transducer located on a line parallel to the X-Y image area capture ultrasound detection data for the one or more object in the ultrasound scan region.

At a next step 89187, a processor of the transmitter or in communication with the transmitter determines three dimensional location information for the living being or the sensitive object based upon the thermal imaging data and the ultrasound detection data.

In an embodiment of step 89187, two ultrasound transducers capture ultrasound detection data for the one or more object in the ultrasound scan region, and the processor determines an ultrasound angle for the one or more object. The processor determines, wherein the includes a visual angle of the living being or the sensitive object in the thermal imaging data from the camera and the ultrasound detection data includes an ultrasound angle of the one or more object from the camera. The processor of the transmitter or in communication with the transmitter determines correlating the visual angle of the living being or the sensitive object with the ultrasound angle of the one or more object to determine that the one or more object corresponds to the living being or the sensitive object.

In an embodiment of step 89187, a decision manager associated with the transmitter determines the three dimensional location information for the living being or the sensitive object based upon the thermal imaging data and the ultrasound detection data.

In a next step 89188, the transmitter controls the transmission of power waves based upon three dimensional location information for the living being or the sensitive object based upon the thermal imaging data and the ultrasound detection data. In an embodiment of step 89188, the transmitter compares the three dimensional location data for the living being or sensitive object obtained at step 89187, with coordinates (e.g., one-dimensional coordinates, two dimensional coordinates, three dimensional coordinates) of the transmitter. In an embodiment, the transmitter calculates a distance of the living being or sensitive object from the transmitter, and reduces or terminates power in the event that distance falls below a threshold proximity value. In another embodiment of step 89188, the transmitter compares information concerning the three dimensional location data for a living being or sensitive object, obtained at step 89188, with coordinates (e.g., one-dimensional coordinates, two dimensional coordinates, three dimensional coordinates, polar coordinates) of a predetermined location of a pocket of energy. In an embodiment, the transmitter calculates a distance of the living being from the predetermined location of the pocket of energy, and reduces or terminates power in the event that distance falls below a threshold proximity value.

In an embodiment of step 89188, a decision manager associated with the transmitter makes a decision whether to adjust the power level of the power waves based upon the three dimensional location information the three dimensional location information. In this embodiment, the decision whether to adjust the power level of the power waves may be one of a decision to maintain full power level of the power waves, a decision to reduce the power level of the power waves, or a decision to terminate the power waves.

In an embodiment of steps 89187 and 89188, a decision manager associated with the transmitter determines three dimensional location information for an obstacle within the transmission field of the transmitter, and determines to terminate transmission of power waves if this three dimensional location information indicates that the obstacle obstructs the field of view of the camera.

In some implementations, in step 89188 the transmitter, or the decision manager associated with the transmitter, may apply safety techniques to the determination of whether to adjust the power waves, using the location data in the sensor data associated with the living being or sensitive object. One safety technique is to include a margin of error (e.g., a nominal margin of 10%-20%) beyond the regulatory limits or other limits on maximum permissible power level or on EMF exposure, to ensure living beings are not exposed to power levels at or near the limits. Another safety technique is to make a determination to reduce or terminate the power waves in the event an obstacle obstructs the field of view of the camera.

At a next step 89189, the transmitter may execute one or more actions if the transmitter (or a decision manager associated with the transmitter) determines to adjust power waves based upon the three dimensional location information for the living being or the sensitive object based upon the thermal imaging data and the ultrasound detection data. In some cases, the transmitter reduces the power level of the power waves at the predetermined location. In some cases, the transmitter terminates transmission of the power waves. In some embodiments, the transmitter redirects the transmission of the power waves around the living being or sensitive object. Additionally or alternatively, the transmitter may activate an alarm of the transmitter or wireless charging system.

Figure 90A:
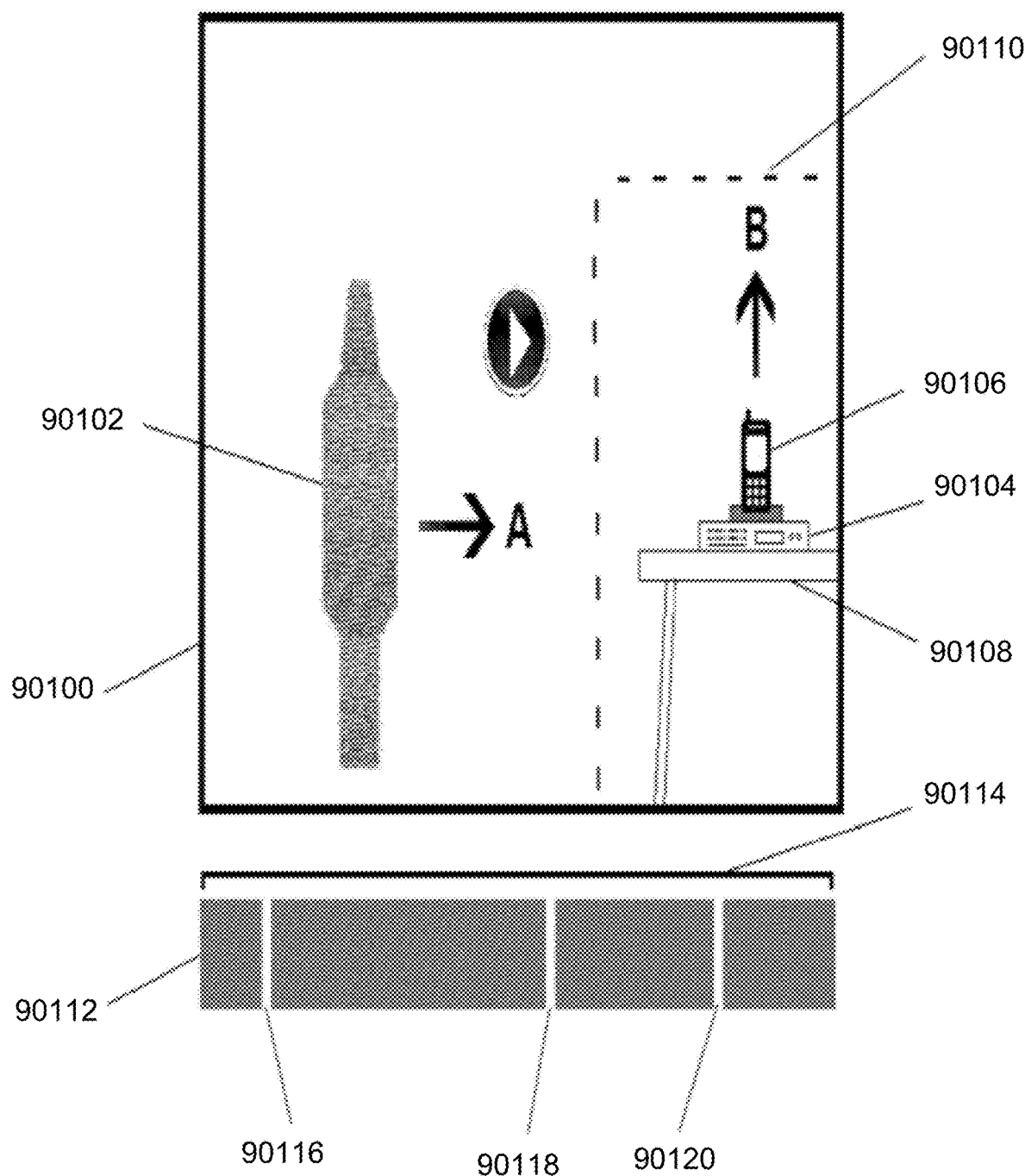

FIG. 90A shows an exemplary frame 90100 from a video captured by imaging sensor in a field of view overlapping the transmission field of a transmitter in a wireless power transmission system, according to an exemplary embodiment.

The imaging sensor such as a thermal imaging camera captures video imaging data of a scene including a human being 90102, wireless power receiver 90104, electronic device 90106, and table 90108 supporting the receiver 90104 and electronic device 90106. The system identifies human being 90102 as a selected object, and captures an extracted video segment in the form of a single frame showing biometric features and other visual features of the human being 90102. The "selected object" refers to an item of interest in video imaging data, usually captured within the transmission field of a wireless power transmission system. Examples of objects include a person, a pet, an electronic device that receives wireless power, a wireless power receiver, a wireless power transmitter, and an obstacle. In an embodiment, selected objects include living beings (such as human beings and animals) and other sensitive objects. Sensitive objects may include certain equipment and other valuable objects that are sensitive to electromagnetic energy in power waves. Selected objects may include object categories (such as human beings), and may include particular objects (such as a uniquely identified electronic device).

In the time indicator 90112, the system captures the single frame at time 90116. The system identifies the movement (indicated by arrow A) of human being 90102 toward wireless power receiver 90104 as a selected event, and extracts a video segment in the form of video clip showing this movement over the time span 90114. The system identifies certain activities of human being 90102 during this movement as additional selected events, and extracts an array of frames depicting these selected events. These additional selected events include human being 90102 entering a zone 90110 of defined proximity to the receiver 90104 (snapshot extracted at time 90118), and human being 90102 raising the electronic device 90106 off of the receiver 90104 (indicated by arrow B; snapshot extracted at time 90120).

The zone 90110 of proximity to the receiver 90104 is a selected location corresponding to a rectangular section of frame 90100, indicated schematically by dotted lines. It should be understood that although FIG. 90A illustrates the scene of frame 90100 in two dimensions, a plurality of imaging sensors may capture three dimensional video imaging data of a scene, and various objects and locations (such as human being 90102 and zone of proximity 90110) can be defined using three dimensional coordinates.

In an embodiment, the "selected event" refers to one or more objects engaged in an activity of interest. Selected events may be referenced with respect to a particular location or time. An "activity" refers to one or more action or composites of actions of one or more objects including interactions between objects. Examples of activities include entering; exiting; moving; stopping; raising; and lowering. Examples of selected events include a living being or sensitive object entering a location in close proximity to a transmitter or a pocket of energy 2337; video imaging data of a living being growing over time (indicating that the living being is moving toward the transmitter); and movement of furniture carrying a wireless power receiver 2303 that causes an obstacle to obstruct an imaging sensor's view of the receiver.

In an embodiment, the "selected location" refers to a space, usually within the transmission field of the wireless power transmission system, where an object of interest may be located or where an activity of interest may occur. A selected location can be scene-based or image-based. Examples of scene-based locations include a room; an enclosed area within a room; an area in which wireless power transmission is authorized; an area in which wireless power transmission is prohibited; physical extent of a transmission field of a wireless power transmitter; extent of overlapping transmission fields of multiple wireless power transmitters; a zone of defined proximity to a transmitter; a zone of defined proximity to a receiver or pocket of energy; a zone of proximity to an electronic device; three dimensional coordinates of a pocket of energy; three dimensional coordinates of multiple pocket of energy; a space obstructed by an obstacle; a vertically limited space such as an area under a table carrying a wireless power receiver; and a location tagged by a system user via a tagging device. Examples of image-based locations include: a video image; a line in a video image; an area in a video image; a rectangular or polygonal section of a video image; and visually contiguous pixels within a video image. A selected location can be a three dimensional space, two dimensional space, or one dimensional space.

In an embodiment, a processor that is communicatively coupled to imaging sensors receives video imaging data captured by one or more of imaging sensors, and analyzes this video imaging data to identify one or more selected features within the transmission field of transmitters. In an embodiment, based upon the identified selected features, the processor extracts from the video imaging data, one or more selected video segments depicting the one or more selected features.

As used in the present application, the term "selected features" refers to one or more features of video imaging data that are identified in order to select video segments to be extracted from the video imaging data. Selected features are sometimes called features of interest in the present disclosure. In one embodiment, selected features may include objects, events and locations, or combinations of these items, within video imaging data that are identified in order to select video segments to be extracted from the video imaging data. In an embodiment, the selected features are features of video imaging data captured within the transmission field, such as features that are particularly important or noticeable. In an embodiment, selected features are identified by analyzing video imaging data using predetermined criteria. In an embodiment, selected features are identified via computer analysis of the video imaging data using computer vision techniques, or other object recognition techniques. As used in the present application the term "selected video segments" refers to one or more video segments that are extracted from video imaging data, and that depict one or more selected features.

The processor issues a report including the extracted selected video segments. In an embodiment, the processor communicates this report to a wireless power management system, for example, hosted in a cloud or a server. In various embodiments, the cloud may be an internet cloud; a business cloud, or a service provider cloud. In another embodiment, the processor communicates the selected video segments to a transmitter, and the transmitter reports a report including the selected video segments to the wireless power management system.

Figure 90B:
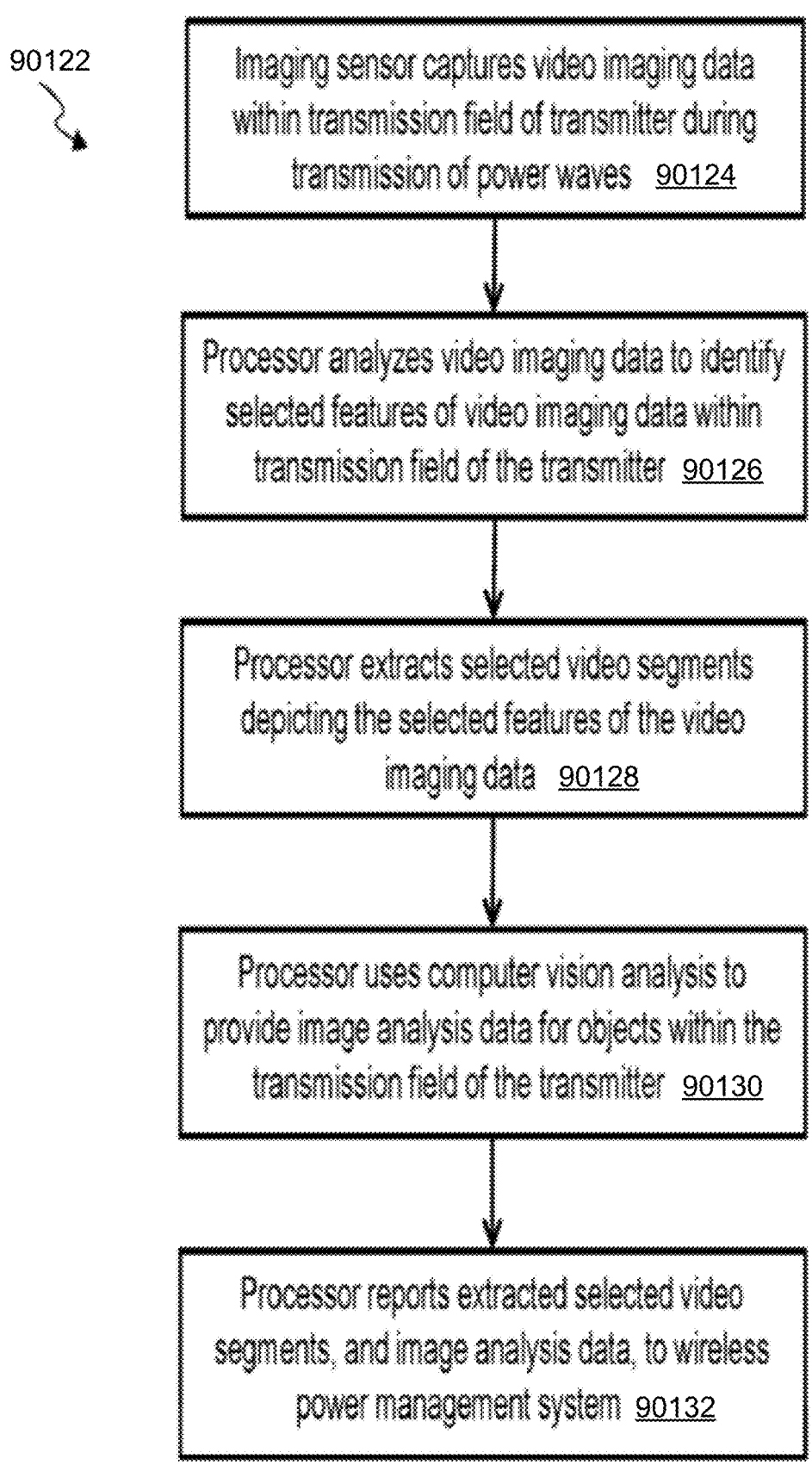

FIG. 90B is a flow diagram 90122 illustrating steps of computer video analytics of video imaging data captured during wireless power transmission in a wireless power transmission system, according to an exemplary embodiment.

Imaging sensors of a wireless power system may capture actual video images within a field of view overlapping a transmission field of transmitters during the transmission of power waves for receiving by an antenna element of a receiver. A processor analyzes the actual video images to identify selected features, such as selected objects and selected events, within the transmission field and to extract one or more selected video segments depicting the selected features. Selected video segments, and related image analysis data, may be reported to a wireless power management system for use in system analytics, troubleshooting, and other purposes.

At step 90124, an imaging sensor captures video imaging data with the field of view of one or more imaging sensor, overlapping the transmission field of a transmitter. The imaging sensor captures the video imaging data during the transmission by the transmitter of power waves that form one or more pocket of energy for receiving by an antenna element of a receiver. The receiver is configured to harvest power from the one or more pocket of energy, for example to charge or power an electronic device. In an embodiment, the imaging sensor is a thermal imaging camera that captures video imaging data in the form of thermal images. In another embodiment, the imaging sensor is an optical imaging camera that captures video imaging data in the form of visible light images. In an embodiment, a plurality of imaging sensors capture stereoscopic video imaging data. In an embodiment, the system converts video imaging data captured as analog video signals into video imaging data in digital form.

In various embodiments, the video imaging data may be video feeds or recorded video. The video imaging data captured by the imaging sensors may include two dimensional video images, or three dimensional video images. The video imaging data may consist of X by Y arrays of pixel data. In an embodiment in which the imaging sensor is a thermal imaging camera, the video imaging data includes X by Y arrays of pixel data representing temperatures. In an embodiment in which the imaging sensor is an optical imaging camera, the video imaging data includes X by Y arrays of pixel data representing individual color (e.g., RGB) values.

In an embodiment, the video imaging data includes a pattern of visually contiguous pixels corresponding to one or more objects within the field of view. In an embodiment, the video imaging data includes a pattern of visually contiguous body temperature pixels corresponding to one or more living being within the field of view.

At step 90126, a processor analyzes the video imaging data to identify one or more selected features within the transmission field of the transmitter. In an embodiment, the one or more selected features include one or more of a selected object, a selected event, and a selected location. In an embodiment, the one or more selected features include one or more of a transmitter, a receiver, an electronic device that receives power from a receiver, a living being, a sensitive object, and an obstacle.

In an embodiment, the selected feature includes a selected event, including one or more object engaged in an activity of interest. In an embodiment, the object is engaged in one or more of the following activities: entering; exiting; moving; stopping; raising; lowering; growing; and shrinking. In an embodiment, the selected event includes an object engaged in an activity of interest with respect to another object. In an embodiment, the selected event includes an object engaged in an activity of interest with respect to a location within transmission field of the transmitter.

In an embodiment, the selected feature includes a selected location within the transmission field of the transmitter. In an embodiment, the selected location includes one or more of an area of authorized power transmission; an area of prohibited power transmission; a zone of predefined proximity to a transmitter; a zone of predefined proximity to a receiver; or a zone of predefined proximity to an electronic device. In an embodiment, the selected location is an image-based location within video imaging data. The selected location may include a video image; a line in a video image; an area in a video image; a rectangular or polygonal section of a video image; or a visually contiguous pixels within a video image In an embodiment of the step 90126, the selected feature includes a selected event affecting exposure of a living being or sensitive object to the power waves that form the one or more pocket of energy for receiving by an antenna element of a receiver, or affecting efficiency of transmission by the transmitter of power waves that form one or more pocket of energy.

In an embodiment, the processor uses computer vision techniques to identify one or more selected features in the video imaging data. In an embodiment, the processor additionally uses data other than imaging data (such as data from a sensor other than an imaging sensor) to identify one or more selected features in the video imaging data.

At step 90128, the processor extracts from the video imaging data, one or more selected video segments depicting the selected features identified at step 90126. In an embodiment, the selected video segments include one or more of video clips; extracted video stills, frames or snapshots; and sequences or arrays of video stills or frames. In an embodiment, the selected video segment includes a timed sequence of snapshots.

In an embodiment, the selected video segments are extracted for reporting in real time. In another embodiment, the extracted video segments are recorded for later viewing. In various embodiment, the selected video segments are accompanied by other content. In one embodiment, embodiment, the selected video segments are accompanied by audio content such as audio feeds or extracted audio clips. In another embodiment, the selected video segments are accompanied by messages or text content. In an embodiment, selected video segments are accompanied by tags or metadata.

At step 90130, the processor uses computer vision analysis to provide image analysis data of objects within the transmission field of the transmitter. In an embodiment, the video segments extracted at step 90128 are accompanied by the image analysis data obtained from computer vision analysis of video imaging data in monitoring or analyzing operations of the wireless power transmission system. In an embodiment, the image analysis data is based on analysis of one or more of the selected features identified at step 90126. In an embodiment, the image analysis data includes a model of a visual scene overlapping the transmission field of the transmitter.

At step 90132, the processor reports selected video segments extracted at step 90128 to a wireless power management system. In an embodiment, the processor reports image analysis data provided at step 90130 to a wireless power management system, along with the selected video segments. In an embodiment, the processor reports the selected video segments the wireless power management system in real time, for current monitoring of the wireless power transmission system. In an embodiment, the processor reports recordings of selected video segments to the wireless power management system, for review at a later time.

Exemplary Method of Generating Symbolic Data

Figure 90C:
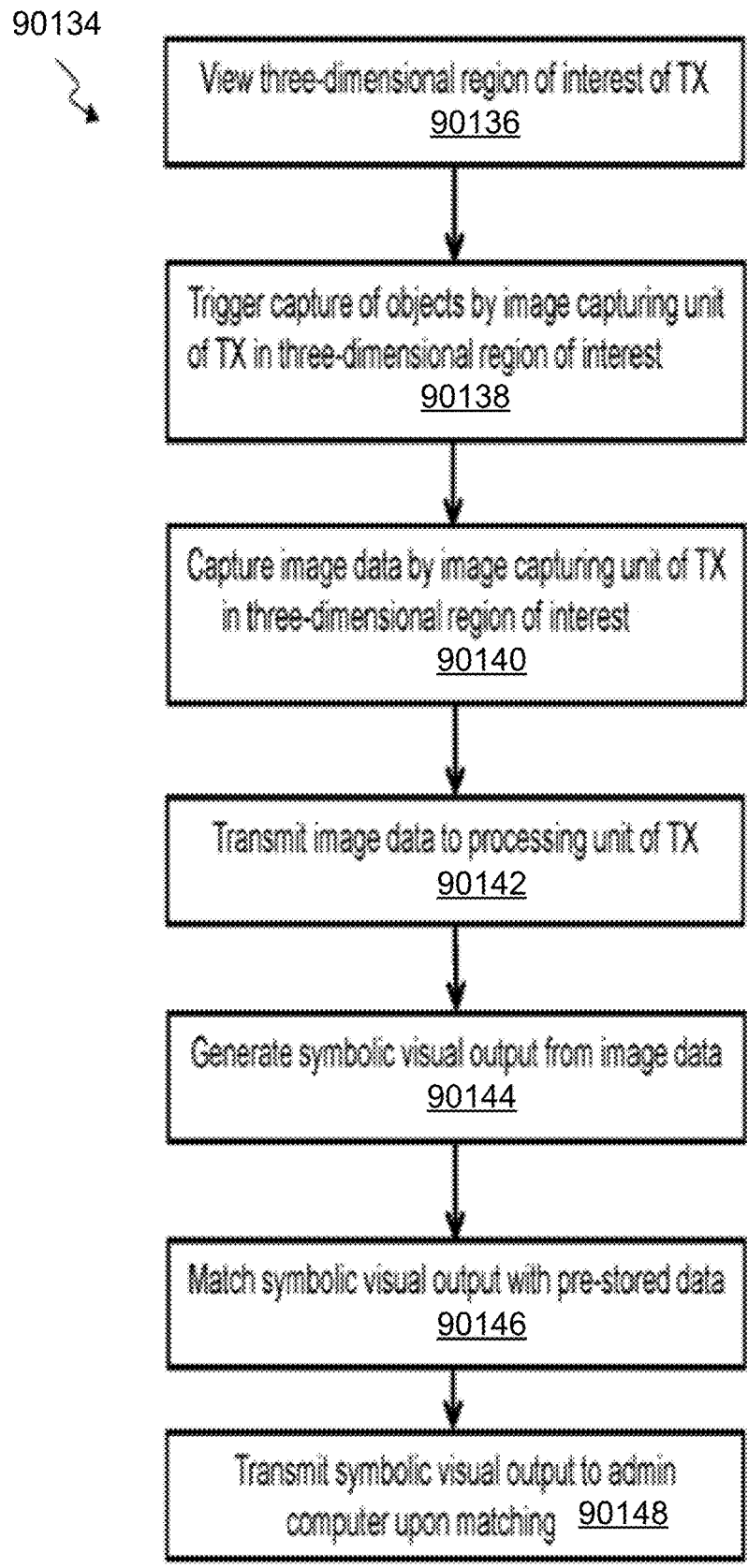

FIG. 90C is a flow diagram illustrating a method of identifying objects within a transmission field of a transmitter of a wireless power transmission system, according to an exemplary embodiment.

At step 90136, cameras and/or sensors coupled to a transmitter may capture location data for objects and/or receivers within a three-dimensional region of interest of a transmitter, such as the transmission field of the transmitter and/or some region beyond the transmission field. The transmitter may include one or more cameras that are configured to view the three-dimensional region of interest of the transmitter. The cameras may include one or more video cameras. The one or more video cameras may include but not limited to infrared cameras, thermal cameras, and visible light cameras.

In some embodiments, the transmitter may include a single video camera. In another embodiment, the transmitter may include an array of video cameras of same or different types such as infrared cameras, thermal cameras, and visible light cameras. The array of video cameras may be positioned for viewing a region of interest of the transmitter. In some cases, the region of interest corresponds to a transmission field (or transmission field area) of the transmitter. The array of video cameras may be arranged in a linear array in the transmitter. In an alternate embodiment, the various other spatial arrangements including two-dimensional arrays of video cameras may be used.

In some embodiments, such as an exemplary system, the cameras may be a component of the transmitter, housed within the transmitter. In some embodiments, the cameras may be external to the transmitter and may communicate, over a wired or wireless connection with one or more transmitters.

At step 90138, an image processor controlling operations of the one or more cameras of the transmitter may capture image data of one or more objects within the three-dimensional region of interest. The transmitter may comprise a separate distinct image processor, or the image processor may be the same processor of the transmitter used to manage other transmitter functions. In some implementations, the image processor may have a triggering mechanism for capturing a set of one or more image frames containing image data of one or more areas within the three-dimensional region of interest by the one or more video cameras. The triggering mechanism may have a central clock signal and an optional signal delivery unit. The central clock signal is delivered via the signal delivery unit to the one or more video cameras. In another embodiment, it is also possible to deliver the central clock signal directly to the one or more video cameras either by a physical connection or by a wireless connection. In other embodiments, the one or more video cameras may have their own internal synchronized clocks. A person of skill in the art will recognize that there are many ways to provide clock signal for the transmitter and will appreciate how to adjust the configuration of the transmitter depending on the actual way in which clock signal is generated and distributed to the one or more video cameras of the cameras of the transmitter.

The one or more objects may include electronic devices such as cell phones, laptops, humans, animals, furniture such as chairs, receivers embedded within the electronic devices, and receivers as individual components.

At step 90140, the image processor may capture image data within the three-dimensional region of interest. After a trigger signal is generated by the trigger mechanism of the transmitter, the one or more video cameras of the image processor initiates the capturing of the one or more objects in the transmission field area of the transmitter, and produces the image data capturing the one or more objects within the transmission field. The image data captured by the one or more video cameras of the image processor may include images/frames capturing the one or more objects within the transmission field of the transmitter.

In one embodiment, the trigger mechanism of the transmitter circuit may be configured such that each of the one or more video cameras of the image processor continuously and/or periodically capture the image data, video data, and audio data in the transmission field of the transmitter. In another embodiment, the trigger mechanism of the transmitter circuit may be configured such that each of the one or more video cameras of the image processor are activated at a different time with respect to each other to capture the image data in the transmission field of the transmitter.

At step 90142, the image processor may transmit the image data to a processor of the transmitter, in such embodiments where the image processor is a distinct processor from the transmitter processor. The cameras capture images within the three-dimensional region of interest of the transmitter, and transmits it to the processor of the transmitter. The processor processes the image data to generate symbolic data from the image data at step 90144. The symbolic data corresponds to data represented by a numerical value for each of the one or more objects in the image data, and the symbolic data varies depending on a video camera used from the one or more video cameras to capture the image data.

An image processor, as well as other potential processors of the transmitter, may include a single processor or a plurality of processors for configuring the transmitter as a multi-processor system, and may control functional aspects of the transmitter based on signal inputs and firmware programming. The processor includes suitable logic, circuitry, and interfaces that are operable to execute one or more instructions to perform predetermined operations. The processor can be realized through a number of processor technologies known in the art. The examples of the processor include, but are not limited to, an x86 processor, an ARM processor, a Reduced Instruction Set Computing (RISC) processor, an Application-Specific Integrated Circuit (ASIC) processor, or a Complex Instruction Set Computing (CISC) processor.

The processor may include a computer vision software or any suitable software that is programmed to recognize and locate the position of the one or more objects in the captured images. In order to recognize the one or more objects, the image data may be processed to generate the symbolic data. In one embodiment, the symbolic data may include a temperature value of each of the one or more objects in the image data when the image data is captured by a thermal camera. The symbolic data is analyzed to determine number of the one or more objects, three-dimensional (XYZ) coordinates of the one or more objects, motion status of the one or more objects, and size of the one or more objects.

At step 90146, the processor compares the symbolic data with pre-stored data. The symbolic data may be compared with the pre-stored data stored in a memory unit in order to identify each object in the one or more objects captured in the image data. In one embodiment, during the step of identifying the objects from the image data whose symbolic data is temperature values, the processor recognizes the face and/or other body characteristic of the object and then compares the face and/or another relevant body characteristic read with a corresponding face and/or other pre-memorized body characteristic stored as the pre-stored data to identify the object from the one or more objects within the image data. The objects identified based on comparison with the pre-stored data may include receivers, electronic devices, humans, and animals.

The processor is further configured to transmit a signal to antennas of the transmitter on identifying the given object. The antennas are configured to control the transmission of one or more power waves towards the given object. For example, the antennas is configured to transmit the one or more power waves towards the given object when the given object is identified as a receiver unit, and the antennas are configured to not transmit the one or more power waves towards the given object when the given object is identified as a living being.

At step 90148, the processor transmits the symbolic data to admin computer based upon matching. When the computer vision software of the processor recognizes the object in the image data based on the matching of the objects with the pre-stored data, then the computer vision software of the processor is also configured to transmit the symbolic data to the admin computer. In one embodiment, the computer vision software may transmit the raw image data of the matched objects to the admin computer. In another embodiment, the computer vision software may determine the X, Y, Z coordinates of the matched objects and transmits it to the admin computer.

Exemplary Method of Matching Visual Patterns

Figure 90D:
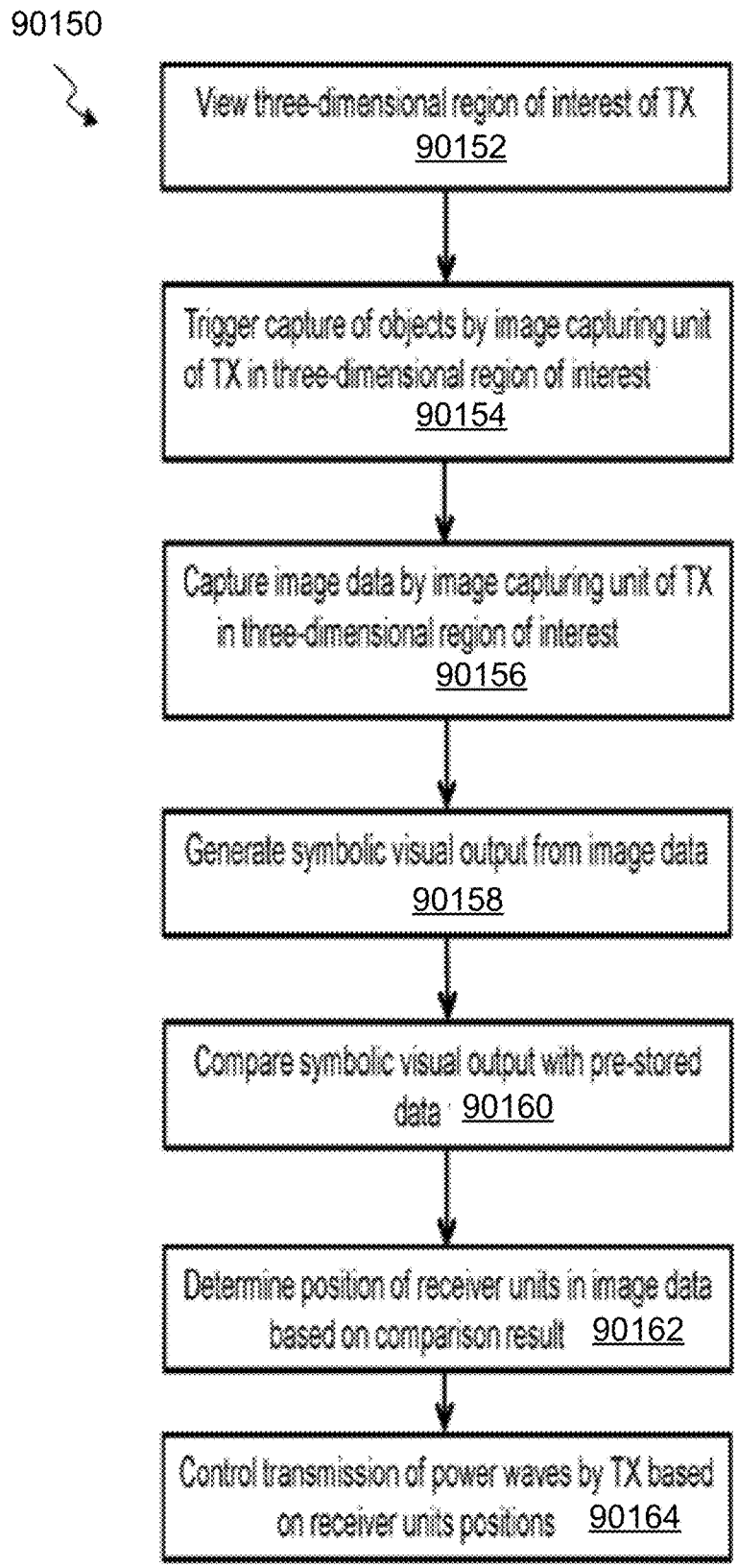

FIG. 90D is a flow diagram illustrating a method of identifying receivers within a transmission field of a transmitter of a wireless power transmission system, according to an exemplary embodiment.

At 90152, cameras and/or sensors coupled to a transmitter may capture location data for objects and/or receivers within a view a three-dimensional region of interest of a transmitter, such as the transmission field of the transmitter. The transmitter may include an cameras that is configured to view the three-dimensional region of interest of the transmitter. The cameras may include one or more video cameras. The one or more video cameras may include but not limited to infrared cameras, thermal cameras, and visible light cameras.

In some embodiments, the transmitter may include a single video camera. In another embodiment, the transmitter may include an array of video cameras of same or different types such as infrared cameras, thermal cameras, and visible light cameras. The array of video cameras may be positioned for viewing a region of interest of the transmitter. In some cases, the region of interest corresponds to a transmission field (or transmission field area) of the transmitter. The array of video cameras may be arranged in a linear array in the transmitter. In an alternate embodiment, the various other spatial arrangements including two-dimensional arrays of video cameras may be used.

In some embodiments, such as an exemplary system, the cameras may be a component of the transmitter, housed within the transmitter. In some embodiments, the cameras may be external to the transmitter and may communicate, over a wired or wireless connection with one or more transmitters.

At 90154, an image processor controlling operations of the one or more cameras of the transmitter may capture image data of objects by the cameras of the transmitter in the three-dimensional region of interest. The transmitter may comprise a separate distinct image processor, or the image processor may be the same processor of the transmitter used to manage other transmitter functions. In some implementations, the image processor of the transmitter may have a triggering mechanism for capturing a set of one or more image frames containing image data of one or more areas within the three-dimensional region of interest by the one or more video cameras. In one embodiment, the triggering mechanism may have a central clock signal and an optional signal delivery unit. The central clock signal is delivered via the signal delivery unit to the one or more video cameras. In another embodiment, it is also possible to deliver the central clock signal directly to the one or more video cameras either by a physical connection or by a wireless connection. In other embodiments, the one or more video cameras may have their own internal synchronized clocks. A person of skill in the art will recognize that there are many ways to provide clock signal for the transmitter and will appreciate how to adjust the configuration of the transmitter depending on the actual way in which clock signal is generated and distributed to the one or more video cameras of the cameras of the transmitter.

The one or more objects may include electronic devices such as cell phones, laptops, humans, animals, furniture such as chairs, receivers embedded within the electronic devices, and receivers as individual components.

At 90156, the image processor may capture image data within the three-dimensional region of interest. After a trigger signal is generated by the trigger mechanism of the transmitter, the one or more video cameras of the image processor initiates the capturing of the one or more objects in the transmission field area of the transmitter, and produces the image data capturing the one or more objects within the transmission field. The image data captured by the one or more video cameras of the image processor may include images/frames capturing the one or more objects within the transmission field of the transmitter.

In one embodiment, the trigger mechanism of the transmitter circuit may be configured such that each of the one or more video cameras of the image processor continuously and/or periodically capture the image data, video data, and audio data in the transmission field of the transmitter. In another embodiment, the trigger mechanism of the transmitter circuit may be configured such that each of the one or more video cameras of the image processor are activated at a different time with respect to each other to capture the image data in the transmission field of the transmitter.

At 90158, the image processor may receive the image data including visual patterns corresponding to each of the one or more objects from the one or more cameras. The image processor may capture the visual patterns corresponding to each of the one or more objects within the three-dimensional region of interest of the transmitter, and may transmit the image data to an image processor or other processor of the transmitter. The visual patterns may be selected from a group consisting of points, lines, colors, shape, and letters.

At 90160, the image processor or other processor of the transmitter may compare the visual patterns corresponding to each of the one or more objects with pre-stored data. The corresponding to each of the one or more objects is compared with the pre-stored data. The pre-stored data includes a list of visual patterns selected from a group consisting of points, lines, colors, shapes, and letters. In an embodiment, the computer vision software of the processor of the transmitter is trained by one or more techniques to perform the comparison of the visual patterns to identify the matching visual patterns. For example, the configuration files having the visual patterns of sample objects may be stored in the pre-stored data in a memory unit of the transmitter. The computer vision software of the processor compares the received visual patterns which may be in form of pixels with the configuration files of the sample object stored in the memory unit.

At 90162, the image processor or other processor of the transmitter may identify objects based on comparison result and determine location of identified objects. In an embodiment, the processor is configured to identify objects from the one or more objects when their corresponding one or more visual patterns matches with one or more visual patterns in the list of visual patterns in the pre-stored data. In another embodiment, the processor is configured to identify each of the one or more objects when their corresponding one or more visual patterns matches with one or more visual patterns in the list of visual patterns in the pre-stored data. In one example, the identified objects may correspond to receivers. In another example, the identified objects may correspond to electronic devices having an integrated receiver unit. In yet another example, the identified objects may correspond to humans or other sensitive objects.

After identifying the objects, the processor is further configured to determine the location of the identified objects. In one example, the processor is configured to receive two-dimensional coordinates of the identified objects from the cameras. In another example, the processor is configured to determine the two-dimensional coordinates of the identified objects based on pixels of the identified objects in the capture image received by the image captured unit. The processor is further configured to determine a third dimension coordinate for each of the identified objects using the transmitter as a frame of reference for each of the identified objects to generate three-dimensional coordinates of each the identified objects based on the two-dimensional coordinates (e.g., from cameras) and the third dimension coordinate (e.g., from a sensor) that correspond to the location of each of identified objects.

At step 90164, an antenna controlling processor or other processor of the transmitter may control transmission of power waves by the transmitter based on the location of objects identified by the same or different processor of the transmitter. In an embodiment, a processor of the transmitter may report the X, Y, Z coordinates of the identified objects that are recognized as the receiver unit to an antennas of the transmitter. Based on the received coordinates of the receiver unit, a processor of the antennas or the processor may instruct the transmitter or other components of the wireless power transmission system to execute various actions based upon the identified position of the receiver unit. The processor of the antennas or the processor of the transmitter may also receive data from one or more internal sensors, one or more external sensors, and heat mapping data regarding the location of the receiver unit. The processor of the antennas or the processor of the transmitter may then compare the location data provided by the one or more internal sensors, the one or more external sensors, and the heat mapping data with the determined location (X, Y, Z coordinates) of the identified object recognized as the receiver unit.

In one embodiment, based on the position of the identified receiver unit, the processor of the antennas or the processor of the transmitter may select a waveform (e.g., radio frequency waves, ultrasound waves) to be generated by a waveform generator of the wireless power transmission system that create an optimal pocket of energy for powering the identified receiver unit. For example, based on a first position of the receiver unit, the processor of the antennas or the processor of the transmitter may select chirp waves for transmission, and based on a second position of the receiver unit, the processor of the antennas or the processor of the transmitter may select sine waves for transmission. The processor of the antennas or the processor of the transmitter may select the chirp waves since the frequency of the chirp waves continuously and/or periodically increases or decreases with time, and the first position of the receiver unit may suggest signal parameters that do not have a fixed frequency over a period of time.

In another embodiment, based on the position of the identified receiver unit, the processor of the antennas or the processor of the transmitter may adjust spacing of antennas in the antennas that create an optimal pocket of energy for powering the identified receiver unit. For example, the antennas may include one or more antenna arrays. Each of the one or more antenna arrays may include one or more antennas to transmit one or more power waves. The spacing of antennas of the one or more antennas with respect to each other may be adjusted such that the one or more power waves transmitted by the plurality of antennas are directed to form the pocket of energy to power the identified receiver unit.

In yet another embodiment, the antennas may include a timing circuit. Based on the position of the identified receiver unit, the processor of the antennas or the processor of the transmitter may control the timing circuit such that the one or more antennas of each of the one or more antenna arrays are configured to transmit the one or more power waves at a different time from each other based on the position of the identified receiver unit. The timing circuit may also be used to select a different transmission time for each of the one or more antennas. In one example, the processor of the antennas or the processor of the transmitter may pre-configure the timing circuit with the timing of transmission of the one or more transmission waves from each of the one or more antennas. In another example, based on X, Y, Z coordinate calculated of the given object that is recognized as the receiver unit, the processor of the antennas or the processor of the transmitter may delay the transmission of few transmission waves from few antennas of the one or more antennas. In yet another example, based on the comparison result of the image data received from the image processor and the information received from the one or more internal sensors, the one or more external sensors, and the communication signal, the processor of the antennas or the processor of the transmitter may delay the transmission of few transmission waves from few antennas.

In yet another embodiment, based on the position of the identified receiver unit, the processor of the antennas or the processor of the transmitter may activate a first set of antennas of the one or more antennas for directing the pocket of energy using the one or more power waves at the position of the identified receiver unit. The first set of antennas may be selected from the one or more antennas based on distance between antennas of the first set of antennas that corresponds to the desired spacing of the antennas to form the pocket of energy. In other words, the distance selected between antennas of the first set of antennas may be such that the adjacent antennas are preferably far away from each other, and one or more power waves transmitting from the first set of antennas forms the pocket of energy to power the identified receiver unit.

In yet another embodiment, the antennas may include at least two antenna arrays. The at least two antenna arrays comprises a first antenna array and a second antenna array. It should be noted that for the simplicity of explanation only the antennas with the first antenna array and the second antenna array is being described, however more than two antenna arrays may be included in the antennas without moving out from the scope of the disclosed embodiments. Each of the first antenna array and the second antenna array may include one or more rows and one or more columns of antennas configured to transmit one or more power waves. The distance between the first antenna array and the second antenna array may be dynamically adjusted, by the processor of the antennas or the processor of the transmitter, depending on the location of the identified receiver unit such that the one or more power waves transmitted by antennas of the first antenna array and the second antenna array are directed to form the pocket of energy at the targeted receiver unit.

Figure 90E:
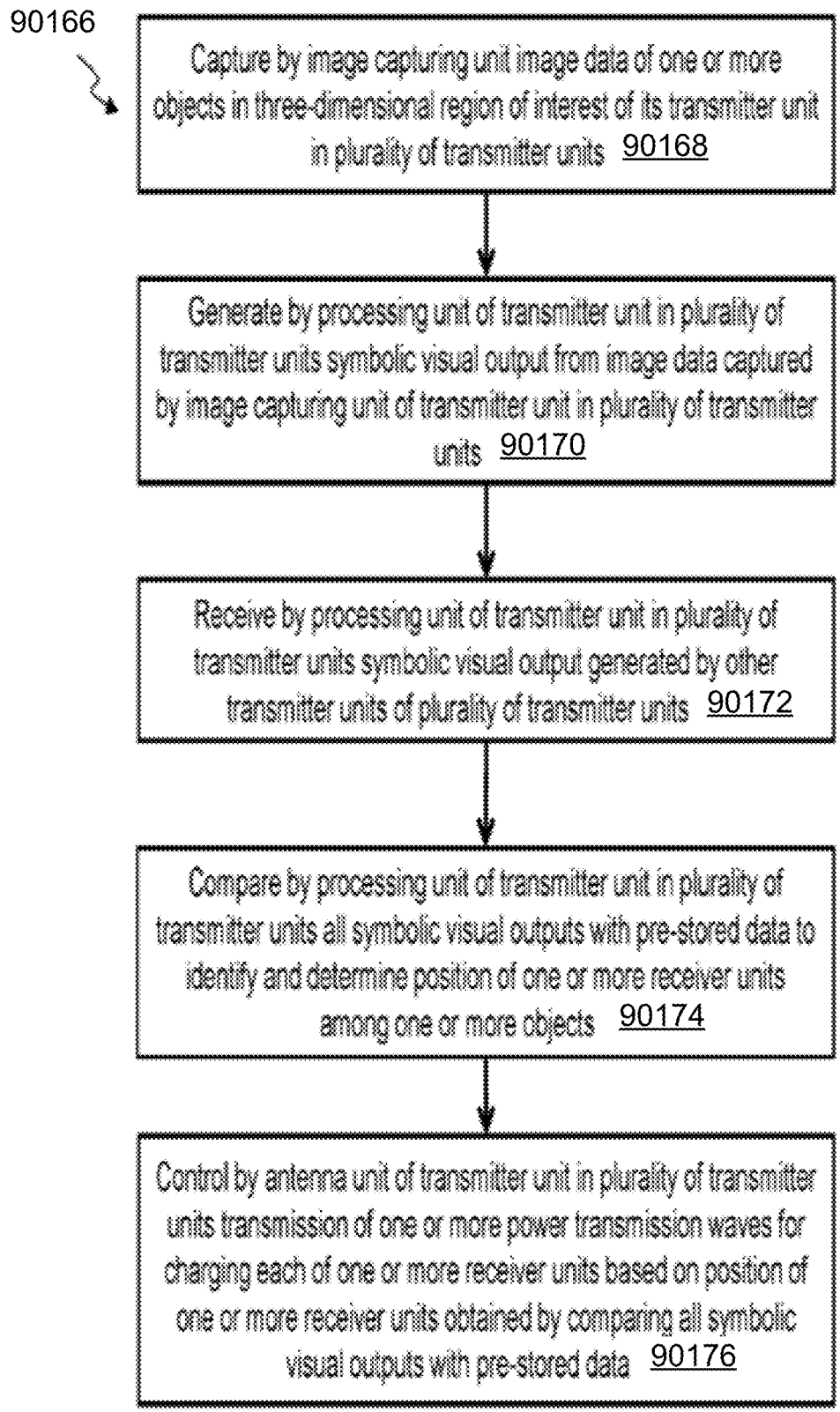

FIG. 90E is a flow diagram illustrating a method of identifying objects within a transmission field of one or more transmitters of a plurality of transmitters of a wireless power transmission system, according to an exemplary embodiment.

At step 90168, one or more cameras coupled to a transmitter may capture image data of one or more objects in a three-dimensional region of interest of a transmitter that is part of a plurality of transmitters. Each of the transmitters may include a processor, such as an image processor, configured to view the three-dimensional region of interest of the respective transmitter. The image processor may control or otherwise manage one or more video cameras. The one or more video cameras may include, but are not limited to, infrared cameras, thermal cameras, and visible light cameras, among others.

In some embodiments, a transmitter may include a single video camera. In some embodiments, the transmitter may include an array of video cameras. The array of video cameras are positioned for viewing a region of interest of the transmitter. The region of interest correspond to some portion, or all of, a transmission field (or transmission field area) of the transmitter. In some cases, the region of interest may stretch beyond the scope of the transmission field, so that the transmitter may identify objects before entering the transmission field. The array of video cameras may be arranged in a linear array in the transmitter. In an alternate embodiment, the various other spatial arrangements including two-dimensional arrays of video cameras may be used. In some embodiments, such as an exemplary system, the cameras is a component of the transmitter, housed within the transmitter. In some embodiments, the cameras may be external to the transmitter and may communicate, over a wired or wireless connection with one or more transmitters.

As mentioned previously, each of the transmitters may have a transmission field or energy zone where antennas of the respective transmitter may transmit power waves to charge the electronic devices. In some implementations, two or more transmitters may have the same transmission field or energy zone, or portions of the respective transmission fields may overlap. In such implementations, the video cameras of the transmitters having overlapping transmission fields may monitor and capture the image data of some portions of the overlapping regions of the transmission field (transmission area).

At step 90170, one or more processors of the transmitters may generate symbolic data from image data captured by the cameras of the transmitters. An image processor or other processor of a transmitter may capture image data for videos or still images within a three-dimensional region of interest of a transmission field of the transmitter, and may then transmit the image data to an image processor or other processor of the same transmitter, a different transmitter in the plurality of transmitters, or some central processor of a computing device configured to consume and process image data received from the transmitters. The particular processor receiving and processing the image data may generate symbolic data from the image data.

A processor may include a single processor or a plurality of processors for configuring the transmitter as a multi-processor system. The processor includes suitable logic, circuitry, and interfaces that are operable to execute one or more instructions to perform predetermined operations. The processor can be realized through a number of processor technologies known in the art. The examples of the processor include, but are not limited to, an x86 processor, an ARM processor, a Reduced Instruction Set Computing (RISC) processor, an Application-Specific Integrated Circuit (ASIC) processor, or a Complex Instruction Set Computing (CISC) processor.

The processor of the transmitter in the plurality of transmitters may include a computer vision software or any suitable software that is programmed to recognize and locate the position of the one or more objects from the captured images. In other words, the processor of the transmitter processes the captured images using a computer vision software such as but not limited to MATLAB or OpenCV. The software comprises programs configured to report X, Y, and, Z coordinates of every pixel in the captured images.

In order to recognize the one or more objects, the image data may be processed to generate the symbolic visual data. In one embodiment, the symbolic data may include a temperature value of each of the one or more objects in the image data. The symbolic data may also include data related to number of the one or more objects, three-dimensional (XYZ) coordinates of the one or more objects, motion status of the one or more objects, and size of the one or more objects.

At step 90172, a processor of a transmitter in the plurality of transmitters may receive the symbolic data generated by other transmitters of the plurality of transmitters or by a computing device coupled to the transmitters.

At step 90174, the processor of the transmitter may compare the symbolic data with pre-stored data to identify and determine position of one or more receivers among the one or more objects. The processor of each of the transmitter may include a computer vision software. The computer vision software of the processor is programmed to detect whether objects, such as person or furniture, enter a predetermined proximity of the transmitter, the receiver unit, the power waves, and/or a pocket of energy (energy pocket).

At step 90176, in one configuration, the processor may then instruct the antennas of the transmitter or other components of the system to execute various actions based upon the detected objects. For example, the processor may control the transmission of one or more power transmission waves for charging each of the one or more receivers based on position of the one or more receivers obtained by comparing all the symbolic data with pre-stored data.

In another configuration, the processor may transmit the image data to the antennas of the transmitter, and the processor of the antennas of the transmitter may determine which actions to execute (e.g., adjust a pocket of energy, cease power wave transmission, reduce power wave transmission). In one example, after the computer vision software of the processor identifies that a person has entered the transmission field of transmitted unit, and then determines that the person is within the predetermined proximity of the transmitter, the computer vision software of the processor could provide the relevant image data to the transmitter, causing the transmitter to reduce or terminate transmission of the power waves. In another example, after identifying the person entering the transmission field and then determining that the person has come within the predetermined proximity of the pocket of energy, the computer vision software of the processor may provide the image data to the antennas of the transmitter that causes the antennas to adjust the characteristics of the power waves, to diminish the amount of energy concentrated at the pocket of energy, generate a null, and/or reposition the location of the pocket energy.

In yet another example, the system may comprise an alarm device, which may produce a warning, and/or may generate and transmit a digital message to a system log or administrative computing device configured to administer the system. In this example, after the computer vision software of the processor detects the person entering the predetermined proximity of the transmitter, the power wave, and/or pocket of energy, or otherwise detects other unsafe or prohibited conditions of system, a signal may be generated and transmitted to the alarm device, which may activate the warning, and/or generate and transmit a notification to the administrator device. A warning produced by the alarm may comprise any type of sensory feedback, such as audio feedback, visual feedback, haptic feedback, or some combination.

In some embodiments, the cameras may be a component of the transmitter, housed within the transmitter. In some embodiments, the cameras may be external to the transmitter and may communicate, over a wired or wireless connection, the image data to one or more transmitters. The cameras, which may be external to one or more transmitters or part of a single transmitter, may provide the image data to the plurality of transmitters, and the processors of the plurality of transmitters may then share this image data with a central processor to determine the appropriate formulation and transmission of the power waves. Similarly, in some embodiments, multiple image processors may share the image data with multiple transmitters. In such embodiments, the cameras or host transmitters may send and receive the image data with other image processors or host transmitters in the system.

In one example of the exemplary system, a first transmitter may comprise a first cameras that captures image data, which may be stored on the first transmitter and/or a memory. The system may also have a second transmitter comprising a second cameras that captures the image data, which may be stored on the second transmitter and/or the memory of the system. In this example, both of the transmitters may comprise processors that may receive the image data from the first and second cameras, and thus, the image data captured by the respective first and second cameras may be shared among the respective first and second transmitters. The processors of each of the first and second transmitters may then use the shared image data to then determine the characteristics for generating and transmitting power waves, which may include determining whether to transmit power waves when a sensitive object such as a human is detected.

To enable the transmitter, to detect and confirm objects that the user wishes to exclude from receipt of wireless energy (i.e., power waves, pocket of energy), the user may communicate to the transmitter pre-stored data to be recorded in the memory unit of the transmitter. For example, the user may provide pre-stored data via a user device in communication with the processor of the transmitter via a graphical user interface (GUI) of the user device.

In some embodiments, tags may be assigned to particular objects and/or locations within a transmission field. During a tagging process, tagging data may be generated and stored into as the pre-stored data, and may inform the transmitter about how the transmitter should be behave with regards to specific objects or locations in the transmission field. The tagging data generated during a tagging process may inform transmitters whether to transmit power waves to an object or location, and/or where within a transmission field to transmit power waves or generate pocket of energy. For example, a record for a location in the pre-stored data may be updated or generated with the tagging data instructing the transmitter to never transmit power waves to the particular location. Likewise, in another example, tagging data may be populated into a record for a location, instructing the transmitter to always transmit power waves to that location.

In some implementations, the cameras may view sensitive objects within a transmission field that have been predetermined or "tagged" as being sensitive. In some cases, it may be desirable to avoid particular obstacles in the transmission field, such as furniture or walls, regardless of whether the cameras have identified a person or other sensitive object, entering within proximity to the particular obstacle. As such, an internal or external memory may store pre-stored data identifying the particular location of the particular obstacle, thereby effectively "tagging" the location of the particular location as being off-limits to the power waves. Additionally or alternatively, the particular object may be digitally or physically associated with a digital or physical tag that produces a signal or physical manifestation (e.g. heat-signature) detectable by the cameras of the transmitter. For example, as part of generating image data for the transmitter, the cameras may access an internal memory that stores pre-stored data comprising records of tagged obstacles to avoid, such as a table. In this example, the cameras would detect the table as a tagged obstacle, and generate the image data that causes the transmitters to reduce the amount of energy provided by the power waves where table is located, terminate the power waves being sent to the table, or redirect the power waves. Additionally or alternatively, in some implementations, the cameras may detect electrical devices that have been tagged (i.e., previously recorded in an internal memory or external memory) to receive wireless power waves.

Figure 90F:
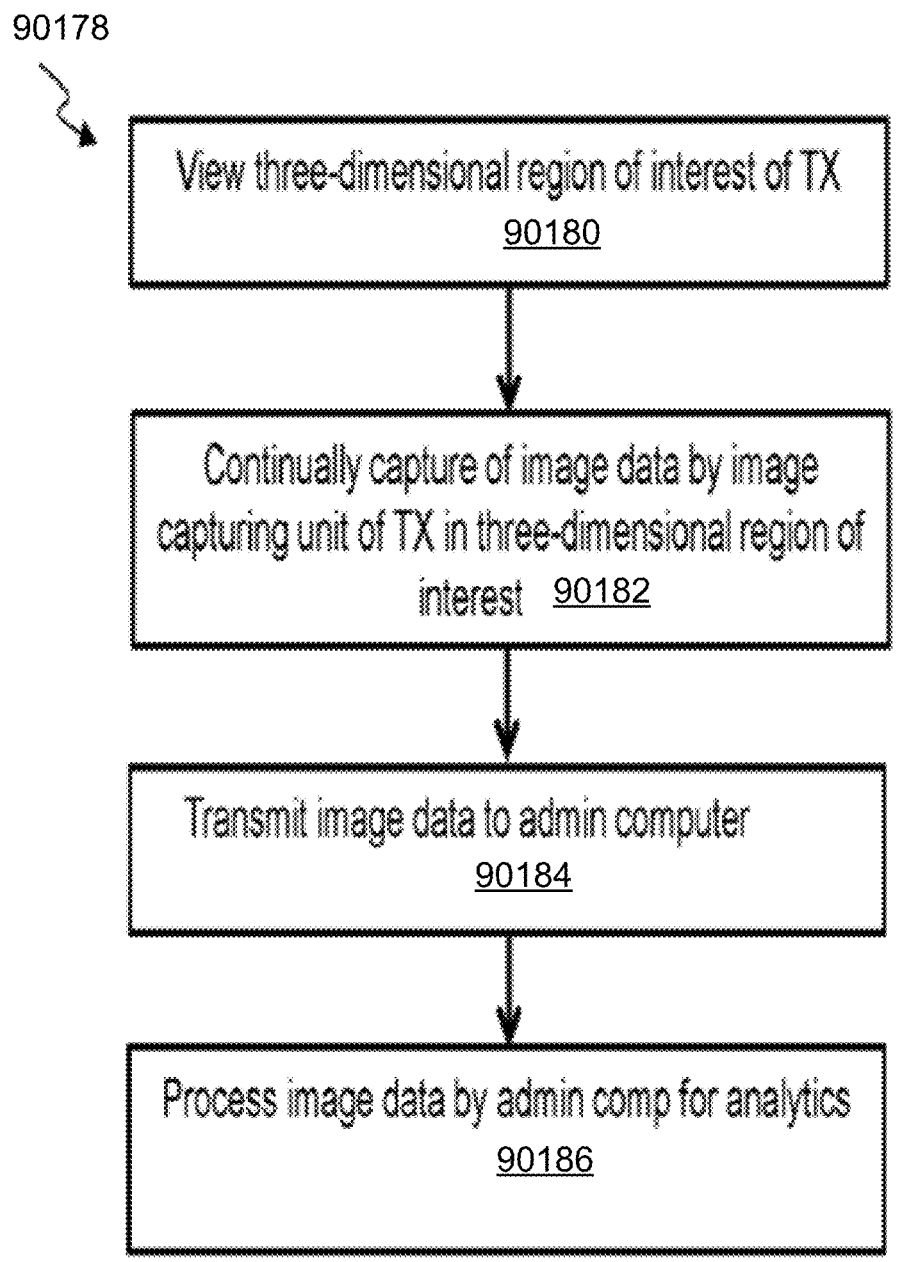

FIG. 90F is a flow diagram illustrating a method of identifying objects within a transmission field of a transmitter of a wireless power transmission system, according to an exemplary embodiment.

At step 90180, cameras and/or sensors coupled to a transmitter may capture location data for objects and/or receivers within a three-dimensional region of interest of a transmitter, such as the transmission field of the transmitter and/or some region beyond the transmission field. The transmitter may include cameras that is configured to view the three-dimensional region of interest of the transmitter. The cameras may include one or more video cameras. The one or more video cameras may include but not limited to infrared cameras, thermal cameras, and visible light cameras.

In some embodiments, the transmitter may include a single video camera. In another embodiment, the transmitter may include an array of video cameras of same or different types, such as infrared cameras, thermal cameras, and visible light cameras, among others. The array of video cameras may be positioned for viewing a region of interest of the transmitter. In some cases, the region of interest corresponds to a transmission field (or transmission field area) of the transmitter. The array of video cameras may be arranged in a linear array in the transmitter. In an alternate embodiment, the various other spatial arrangements including two-dimensional arrays of video cameras may be used.

In some embodiments, such as an exemplary system, the cameras may be a component of the transmitter, housed within the transmitter. In some embodiments, the cameras may be external to the transmitter and may communicate, over a wired or wireless connection with one or more transmitters.

At step 90182, an image processor controlling operations of the one or more cameras of the transmitter may continuously and/or periodically capture image data of objects within the three-dimensional region of interest of the transmission field of the transmitter. In some implementations, the image processor of the transmitter may have a triggering mechanism for capturing a set of one or more image frames containing image data of one or more regions within the transmission field by the one or more video cameras. The triggering mechanism may have a central clock signal and an optional signal delivery unit. The central clock signal is delivered via the signal delivery unit to the one or more video cameras. In another embodiment, it is also possible to deliver the central clock signal directly to the one or more video cameras either by a physical connection or by a wireless connection. In other embodiments, the one or more video cameras may have their own internal synchronized clocks.

In one embodiment, the trigger mechanism of the transmitter circuit may be configured such that each of the one or more video cameras of the image processor continuously and/or periodically capture the image data, video data, and audio data in the transmission field of the transmitter. In another embodiment, the trigger mechanism of the transmitter circuit may be configured such that each of the one or more video cameras of the image processor are activated at a different time with respect to each other to capture the image data in the transmission field of the transmitter.

The image data captured by the one or more video cameras of the image processor may include images/frame capturing one or more objects within the transmission field of the transmitter. The one or more objects may include electronic devices such as cell phones, laptops, humans, animals, furniture such as chairs, receivers embedded within the electronic devices, and receivers as individual components.

In one embodiment, the cameras may include a pair of thermal infrared cameras that are configured to recognize an object such as the human based on the body temperature of the humans. The pair of the thermal infrared cameras transmit the image data to a computer vision software of a processor of the transmitter, and then the computer vision software perform the mapping between the image data collected from the two thermal infrared cameras to provide depth perception of the objects from the location of the transmitter. In another embodiment, the cameras may include a pair of visual cameras that are configured to recognize the objects such as the human based on the pixels. The pixels in the image data captured by the pair of the visual cameras may represent a frequency of visual light which may be scaled to a thermal scale such as Fahrenheit and Celsius.

At step 90184, a processor of the transmitter may transmit the image data to an administrative computer or other central server of the wireless charging system. In some cases, so-called "raw" image data, which may be image data captured directly from a camera before any data processing or analytics have been performed, is sent to the administrative computer for processing. Where a camera is a video camera, the raw image data from the video camera may be received via a data "stream" generated and received from the video camera. One having skill in the art would appreciate the underlying technologies used for generating, compressing, and/or transmitting a data stream for binary data representing a video. One having skill in the art would also appreciate the underlying technologies used for generating, compressing, and/or transmitting independent computing files containing one or more still images (e.g., JPG, PDF, PNG, GIF) or videos (e.g., MP4, GIF, WMV, MOV, AVI).

In another embodiment, a symbolic data of the image data is generated by the processor of the transmitter, and the symbolic data is transmitted to the admin computer. The symbolic data may include X, Y, Z coordinates of the one or more objects within the raw image data, the sizes of the one or more objects, and the velocity of the one or more objects if the one or more objects are moving. In this case, the processor may include a computer vision software that may be programmed to analyze the raw image data and search for object patterns. The stationary objects may be recognized as contiguous BLOBs of pixels of near the same background color or the moving BLOBs of pixels which are contiguous pixels near the same background color that are moving relative to the field of view as well as relative to the background pixels of the field of view. The computer vision software recognizes the BLOBs and then generate the symbolic data that comprises the X, Y, Z coordinates of the center or the centroid of the BLOB, the size of the BLOB in terms of the number of pixels or a percentage of the pixels compared to the field of view, the velocity of the BLOB, and the duration of the visibility of the BLOB in seconds.

At step 90186, the administrative computer or other computing device of the system may process the image data generated and received from the cameras. The image data may be received as the raw image data or the symbolic data generated from the raw image data, or both. The administrative computer may include software that is configured to process the image data. For instance, the software may be programmed to identify, and in some cases differentiate between, "non-receiver" objects, such as sensitive objects (e.g., people), receivers, and objects comprising receivers (e.g., laptops, tablets, smartphones). For example, if a non-receiver object is a human being or an animal within a predetermined threshold proximity to power waves servicing a particular receiver, the administrative computer or computing device may transmit a signal to the appropriate transmitter, instructing the transmitter to reduce the power level of the power waves servicing the receiver, redirect the power waves to a new location, or cease transmitting the power waves altogether. The software, thereby, monitors the non-receiver objects, and when the human or the animal gets near the receiver unit, the admin computer may send a message to the transmitter to change the phases of the antennas that transmit the power waves to reduce the power being transmitter to stay within FCC power absorption limits.

The monitoring of the non-receiver objects by the admin computer of the wireless power transmission system may also be used for security purpose. In one example, if the non-receiver object such as the human is seen in a room when the room is locked up and there shouldn't be anyone in the room, then the administrator of the system can take necessary action. In another example, if the non-receiver object such as the human falls to the floor and is immobile longer than a certain minimum amount of time, then the information about that human such as the length of the human (for instance is it a child of four feet or an adult that's five and a half feet), snap shot of the human lying on the floor, the date and time of when the object first became prone and how long it's been lying on the ground may be used by the administrator of the system to alert authorities to go investigate and see if the fallen person is in medical trouble.

In yet another example, the symbolic data generated from the raw image data may also include information related to the temperature of the non-receiver object such as a person. For example, the person may have a fever and the person's temperature may be recorded as 103 or 104 degree centigrade. The temperature data may be used by the administrator of the system to alert authorities to call a doctor.

In yet another example, the software in the admin computer is programmed to recognize the humans either near the transmitter or near the receiver unit, and then send a message to the transmitter to control the transmitted power towards the receiver unit based on proximity of the human to the receiver unit or the transmitter. Also, the transmitter may be shut down by the administrator of the system within a specific maximum amount of time from detection of the human nearby the receiver unit or the transmitter.

FIGS. 89A-89I and 90A-90F illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 89A-89I and 90A-90F.

Presented below are example embodiments of object detection in wireless power charging systems.

In some embodiments, an example system for wireless power transmission comprises a video camera for capturing image data of at least a portion of a transmission field of the transmitter, where the image data comprises a visual pattern. The system further includes a processor of the transmitter configured to identify an object when the visual pattern matches a pre-stored visual pattern representing the object, and control transmission of one or more power transmission waves based on a location of the identified object.

In some embodiments, the system video camera is selected from a group consisting of infrared cameras, thermal cameras, and visible light cameras.

In some embodiments, the system video camera is an integral component of the transmitter.

In some embodiments, the system pre-stored visual patterns are selected from a group consisting of points, lines, colors, shape, and letters.

In some embodiments, the system further comprises one or more video cameras, and where a trigger unit for triggering the capture of the image data by the one or more video cameras. The one or more video cameras are triggered in a sequence by a central clock signal generated by the trigger unit.

In some embodiments, each of the one or more video cameras of the system have their own synchronized clocks.

In some embodiments, the system processor is further configured to receive two-dimensional coordinates of the identified object from the video camera.

In some embodiments, the system processor is further configured to create a third dimension coordinate for the identified object based on the two-dimensional coordinates and using the transmitter as a frame of reference for the identified object to generate three-dimensional coordinates of the identified object.

In some embodiments, the system identified object corresponds to a receiver.

In some embodiments, the system identified object corresponds to a living being.

In some embodiments, an example computer-implemented method for wireless power transmission comprises generating, by a video camera of a transmitter, image data of at least a portion of a transmission field, where the image data comprises a visual pattern. The method further comprises identifying, by a processor of the transmitter, an object when the visual pattern matches a pre-stored visual pattern representing the object, and controlling, by the processor, transmission of one or more power transmission waves based on a location of the identified object.

In some embodiments, an example method for wireless power transmission comprises transmitting, by a transmitter, power waves that converge to form constructive interference at a location associated with a receiver, generating, by at least one thermal imaging camera in communication with the transmitter, a thermal image of at least a portion of a transmission field of the transmitter, identifying, by the transmitter, a living being in the transmission field of the transmitter based upon temperature data in the thermal image, determining, by the transmitter, a proximity of the identified living being to the power waves; and adjusting, by the transmitter, a power level of the power waves upon determining that the proximity of the living being is within a predefined distance from the power waves.

In some embodiments, the pre-defined distance corresponds to distance from the living being to the transmitter.

In some embodiments, the pre-defined distance corresponds to distance from the living being to the receiver.

In some embodiments, the at least one thermal imaging camera generates the thermal image of its field of view overlapping the transmission field of the transmitter. The temperature data of the thermal image corresponds to visually contiguous body temperature pixels.

In some embodiments, identifying the living being further comprises detecting information relating to the presence of the living being within the transmission field of the transmitter based upon the temperature data.

In some embodiments, the information relating to presence of the living being based upon the thermal imaging data comprises one or more of face detection information, head detection information, hand detection information, skin detection information, human shape information, human appearance patterns, human biometric attributes, human motion information, and human activity information.

In some embodiments, the method further comprises generating, by a plurality of thermal imaging cameras in communication with the transmitter, a plurality of thermal images of their corresponding plurality of field of views overlapping the transmission field of the transmitter.

In some embodiments, a movement of living being towards the transmitter is detected by identifying a growing pattern of visually contiguous body temperature pixels in the thermal image over a period of time.

In some embodiments, the method further comprises reducing, by the transmitter, the power level of the power waves based on the detection of movement of the growing pattern of visually contiguous body temperature pixels in the thermal image over the period of time towards the transmitter.

In some embodiments, the method further comprises terminating, by the transmitter, the power waves based on the detection of movement of the growing pattern of visually contiguous body temperature pixels in the thermal image over the period of time towards the transmitter.

In some embodiments, an example transmitter for wireless power transmission comprises a thermal imaging camera configured to generate a thermal image of at least a portion of a transmission field of the transmitter, a controller configured to receive a thermal image from the thermal imaging cameras, identify a living being in the transmission field of the transmitter based upon temperature data in the thermal image, determine a proximity of the identified living being to power waves generated by the transmitter, and adjust a power level of the power waves upon determining that the proximity of the living being is within a predefined distance from the power waves.

FIGS. 91A-91D illustrate examples of devices, apparatus, and methods of providing wireless power using receiver device sensor inputs, in accordance with some embodiments.

Figure 91A:
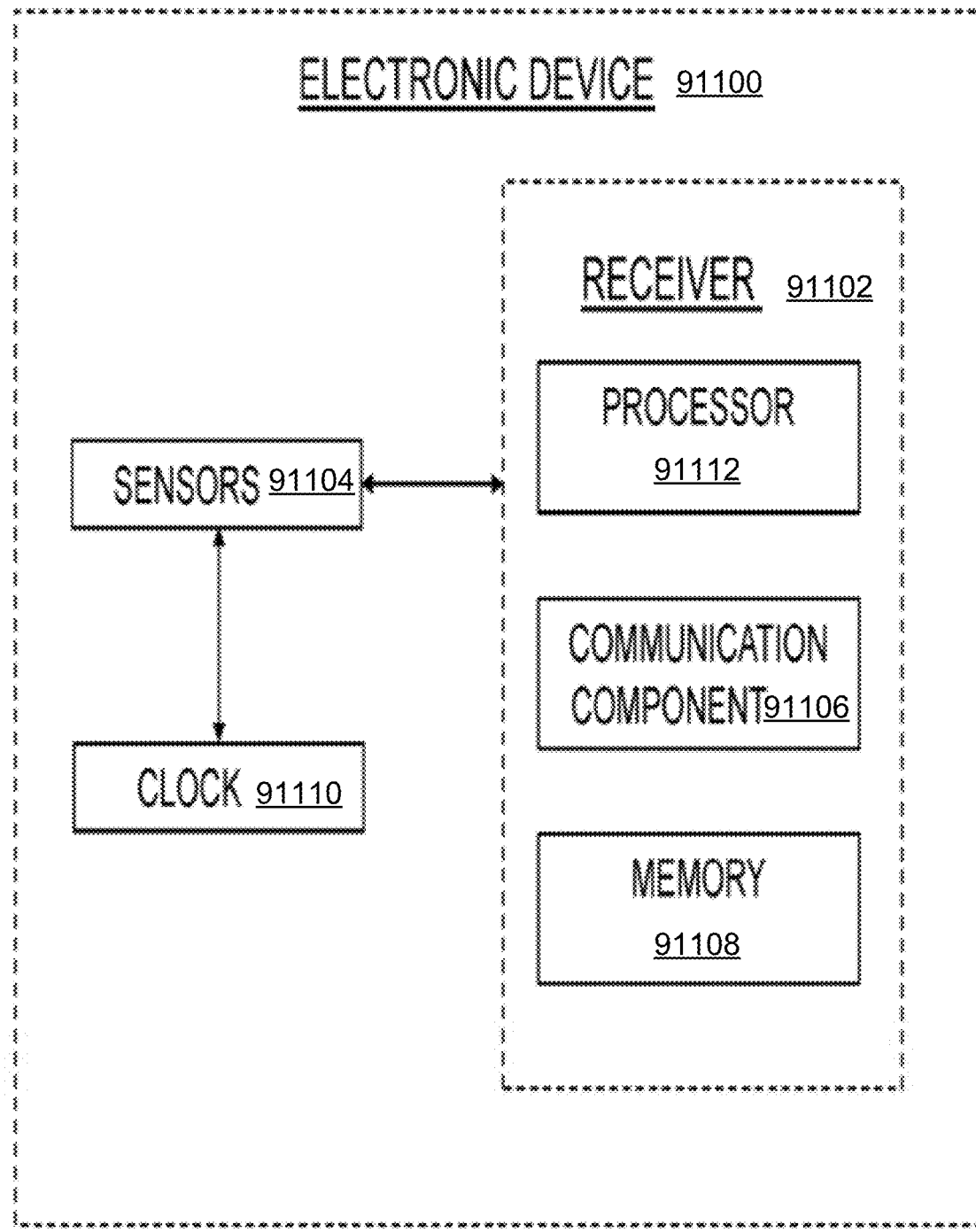

FIG. 91A shows an exemplary electronic device 91100 having a receiver 91102 of a wireless power transmission system, according to an exemplary embodiment. The electronic device 91100 coupled to the receiver 91102 may be any electrical device that requires continuous electrical energy or that requires power from a battery. The receiver 91102 may be permanently integrated into the electronic device 91100, or the receiver 91102 may be detachably coupled to the electronic device 91100, which, in some cases, may result in a single integrated product or unit. As an example, the electronic device 91100 may be placed into a protective sleeve comprising embedded receivers 91102 that are detachably coupled to the device's power supply input. Non-limiting examples of electronic devices 91100 may include laptops, mobile phones, smartphones, tablets, music players, toys, batteries, flashlights, lamps, electronic watches, cameras, gaming consoles, appliances, GPS devices, and wearable devices or so-called "wearable" (e.g., fitness bracelets, pedometers, smart watch), among other types of electrical devices 91100.

Electronic devices 91100 may comprise embedded or associated sensors 91104 such as accelerometers, gyroscopes, and/or ambient light sensors, which may act as a sensor data source for a transmitter. Electronic device 91100 may further include a clock 91110, which determines the pas-sage of time between various sensor related circumstances, such as motion, orientation, acceleration, and/or changes in lighting circumstances. In some embodiments, the sensor data can supplement heat-map data and/or mapping data, as generated by sensors associated with the transmitter, to determine how the transmitter may safely and effectively transmit power waves. In some embodiments, heat-map data may be generated by transmitter processors to identify receivers located in a transmission field. For example, the transmitter processor may determine an interval at which a beacon signal may be broadcast by a communications component of the transmitter, to identify receivers that may inhabit the transmission field. The transmitter processor may generate heat-mapping data from communications signals received by the communications component. Determinations of how to adjust power wave transmissions may be based up-on the clock and/or sensor data from one or more sensors, and proscribed circumstances may be based upon sensor data from one or more sensors.

The accelerometer may provide sensor data to indicate that the electronic device is moving, whereby the transmitter may determine that it should cease transmission when it appears that a human or other sensitive object is moving the electronic device. Even small movements detected by an accelerometer may indicate that the electronic device may be in the presence or being held by a human being, so transmission should cease. The accelerometer of the electronic device 91100 can be a Micro-Electro-Mechanical Sensors (MEMS) used to detect motion and/or measure non-gravitational acceleration of the electronic device 91100. The accelerometer may measure acceleration of the electronic device 91100 in one, two, or three orthogonal axes. When the electronic device 91100 goes from a standstill to any velocity, the accelerometer responds to the vibrations associated with such movement. The accelerometer may use microscopic crystals that go under stress when vibrations occur, and from that stress, a voltage is generated to create a reading on any acceleration, and thereby measure linear acceleration of movement of the electronic device 91100. Accordingly, the accelerometer can gauge the movement of an electronic device 91100.

The output of the accelerometer of the electronic device 91100 can be processed to determine if the sensor data is substantially similar to a proscribed motion circumstance of the electronic device 91100, which may correspond to any motion or a particular motion of the electronic device 91100. The detection of motion of the electronic device 91100 may indicate that the electronic de-vice 91100 is being moved by its user. The proscribed motion circumstance may indicate a risk that the transmission of power waves to charge or power the electronic device 91100 may expose the user to unsafe or undesirable radiation levels as the user is less than a pre-defined proximity to the electronic device 91100.

A gyroscope can determine orientation of the electronic device, whereby a particular orientation may be associated with an interaction with a sensitive object (e.g., a human holding a phone to his head or a phone in a pocket), whereas other orientations may be associated with a lack of interaction with a sensitive object (e.g., laying horizontal, especially when in conjunction with lack of movement determined by the accelerometer and further when in conjunction with the passage of a threshold time period since movement last occurred). The time-period of the lack of movement of the electronic device may be determined by the clock 91110. Even small movements detected by a gyroscope may indicate that the electronic device may be in the presence of or may being held by a human being, so transmission should cease. The gyroscope of the electronic device 91100 can measure a rate of rotation of the electronic device 91100 around a particular axis and is able to sense motion including both vertical and horizontal rotation of the electronic device 91100. When gauging the rate of rotation around the roll axis of the electronic device 91100, the gyroscope identifies an actual value until the electronic device 91100 stabilizes out. Accordingly, by using the principles of angular momentum, the gyroscope can indicate orientation of the electronic device 91100. The gyroscope can provide data over a period of time to indicate a rotation of the electronic device over that period, whereby a rotation may indicate that it is in the presence of a human or other sensitive object. The period or passage of time that corresponds to period of the rotation of the electronic device may be measured by the clock 91110. The clock 91110 may further measure the passage of time between various other sensor related circumstances, such as motion, orientation, acceleration, and/or changes in lighting circumstances. The measured period of the time by the clock 91110 may indicate a time-period during which there is a risk that the transmission of power waves to charge or power the electronic device 91100 may expose the user to unsafe or undesirable radiation levels as the user may be less than a pre-defined proximity to the electronic device 91100.

Although described in the exemplary embodiment as sensor data, it is intended that the sensor data is not limited to raw sensor data and can include data that is processed by a processor associated with the sensor, processed by the receiver, processed by the transmitter, or any other processor. The sensor data can include information derived from the sensor, and processed sensor data can include determinations based upon the sensor data. For example, the gyroscope of the electronic device 91100 may provide raw data such as an orientation in X-plane, Y-plane, and Z planes, and processed sensor data from the gyroscope may include a determination of the orientation or a circumstance involving that orientation of the electronic device 91100.

The use of the accelerometer and/or gyroscope data of the electronic device 91100 may generate a proscribed orientation circumstance of the electronic device 91100 that corresponds to a substantially vertical orientation of the electronic device 91100. In one instance, a vertical or near vertical orientation of the electronic device 91100 indicates that the electronic device 91100 is being held in the vertical orientation by a user near the user's head. In another instance, a vertical or near vertical orientation of the electronic device 91100 indicates that the electronic device 91100 is being carried by a user in the vertical orientation, e.g., in the user's pocket or in a case, holster, or other carrier. In another instance, a vertical orientation indicates that the electronic device is in a cradle for charging, so accelerometer data, particularly when combined with clock data obtained from the clock 91110, will indicate that despite the vertical orientation, the electronic de-vice is stationary. In another instance, a near perfect horizontal orientation of the electronic de-vice 91100 may indicate that the device is positioned on top of a surface, such as a table, counter or desk. The proscribed orientation circumstance may then be used to determine risk regarding the transmission of power waves to charge or power the electronic device 91100 that may expose the user to unsafe or undesirable radiation levels.

In order to simplify the description above, reference has been made to an accelerometer and gyroscope, each in a singular sense. In practice, the electronic device 91100 may have a three-dimensional accelerometer or three accelerometers with mutually orthogonal sensitive axes, often referred to as a 3-D accelerometer. The electronic device may have an X-axis accelerometer, Y-axis accelerometer, and Z-axis accelerometer. Similarly, the electronic device 91100 also has a 3-D gyroscope or an X-axis gyroscope, Y-axis gyroscope, and Z-axis gyroscope.

The ambient light sensor measures intensity of visible light received by the sensor, and a lack of ambient light may indicate that the electronic device is in a pocket or may be face-down on a table. In an embodiment, the ambient light sensor includes photo diodes that are sensitive to different spectra of visible light, to more accurately measure intensity of light received by the ambient light sensor. The output of the ambient light sensor includes a proscribed ambient light circumstance of the electronic device. The proscribed ambient light circumstance includes an ambient light reading that has a low intensity in comparison with one or more other ambient light readings acquired near the electronic device. A low intensity measurement by an ambient light sensor indicates low ambient light in a room, and the electronic devices including the ambient light sensors may increase screen brightness to compensate. However, where an ambient light sensor from an electronic device detects a low intensity of light, whereas one or more ambient light readings acquired near the electronic device have a higher intensity, the low intensity light reading from the user light may indicate that the electronic device is in a user's pocket or otherwise carried by the user with the electronic device covered. The ambient light sensor can provide data over a period of time to indicate whether the electronic device has a changed amount of ambient light, which may indicate, for example, that the electronic device has be-come or is no longer in a pocket or face down on a table. Such data may also be combined with clock data to determine whether a threshold passage of time has elapsed in which no change in ambient light has been observed. The proscribed ambient light circumstance therefore may indicate a risk that the transmission of the power waves to charge or power the electronic device may expose the user to unsafe or undesirable radiation levels.

The electronic device 91100 or the associated receiver 91102, are also associated with a communications component 91106 capable of communicating with a transmitter. The communications component 91106 may use communications signal to communicate data obtained from the sensors 91104 that may be used to, e.g., alert transmitters of the proscribed orientation circumstance of the electronic device 91100, the proscribed motion circumstance of the electronic device 91100, and the proscribed ambient light circumstance of the electronic device 91100 to determine how the transmitter may safely and effectively transmit power waves. On receiving the proscribed orientation circumstance of the electronic device 91100, the proscribed motion circumstance of the electronic device 91100, and/or the proscribed ambient light circumstance of the electronic device 91100, and/or data regarding the temporal nature of such circumstances, the transmitter can adjust or cease transmission of the power waves.

To enable the transmitter to locate and identify the electrical device 91100, a user may communicate to the transmitter, data obtained from the sensors 91104 which may be recorded into an memory 91108. For example, the user may provide data using the communications component 91106 or may provide data via an electronic device (e.g., laptop, smartphone, administrative computer or server) that is in communication with the transmitter or memory 91108. The electronic device may execute an administrative software application that permits the user, via a graphical user interface (GUI), to generate information of the proscribed orientation circumstance of the electronic device 91100, the proscribed motion circumstance of the electronic device 91100, and the proscribed ambient light circumstance of the electronic device 91100, and/or data regarding the temporal nature of such circumstances. The information of the proscribed orientation circumstance of the electronic device 91100, the proscribed motion circumstance of the electronic device 91100, and the proscribed ambient light circumstance of the electronic device 91100 may then be stored as mapping data (e.g., sensor data) into the memory 91108 for retrieval by one or more processors (e.g., receiver processor 91112, sensor processor, electronic device processor). In addition to proscribed orientation circumstance of the electronic device 91100, the proscribed motion circumstance of the electronic device 91100, and the proscribed ambient light circumstance of the electronic device 91100, exemplary information may also include location data for the electronic device 91100, level of power usage of the electronic device 91100, duration of power usage of the electronic device 91100, power transfer schedule of the electronic device 91100, data regarding the temporal nature of the sensor data, and authentication credentials of the electronic device 91100.

Figure 91B:
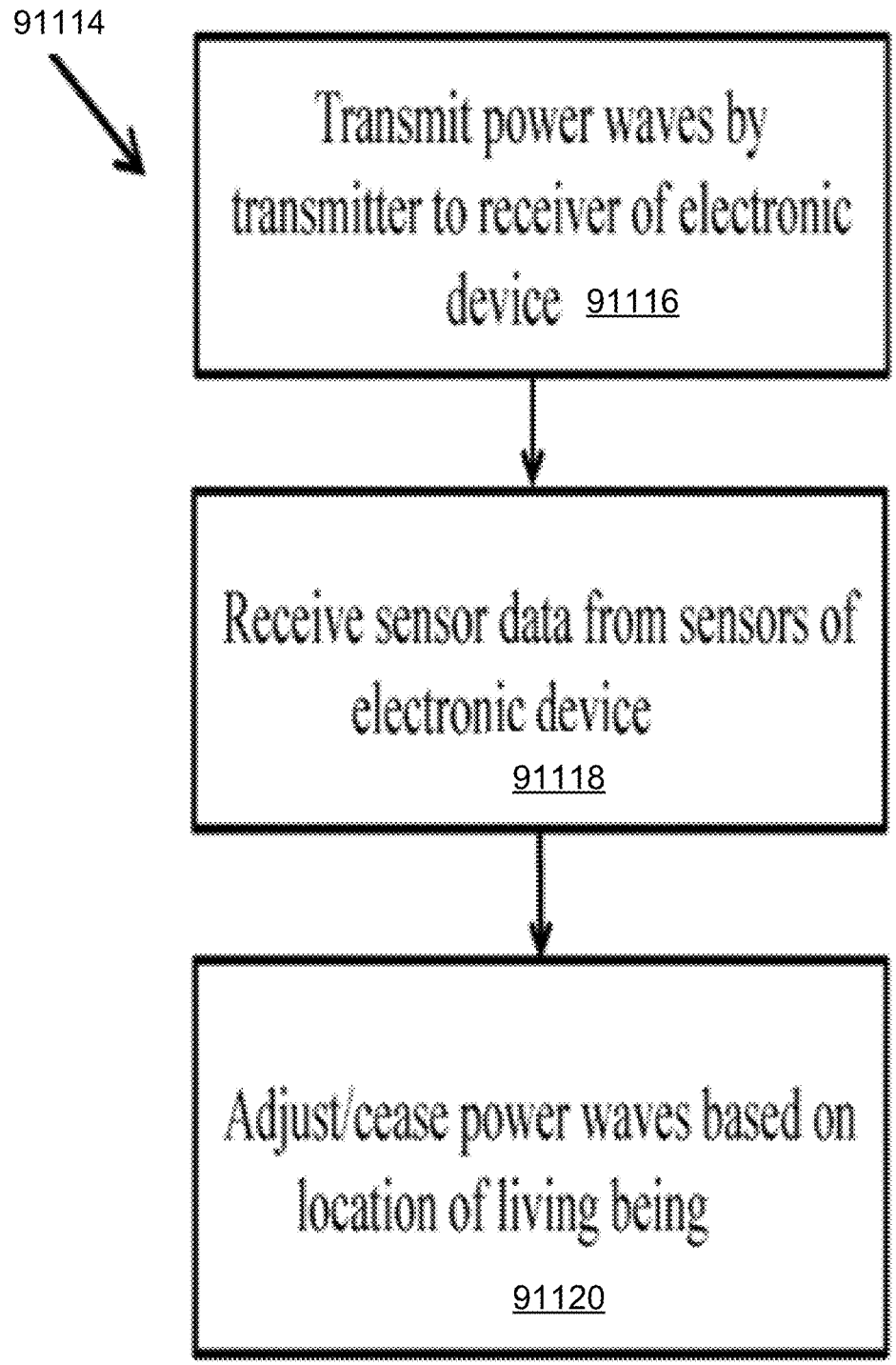

FIG. 91B is a flow diagram 91114 illustrating a method of adjusting transmission of power waves to receivers of electronic devices within a transmission field of a transmitter of a wireless power transmission system, according to an exemplary embodiment. The transmitter of the wireless power transmission system may receive sensor data from one or more sensors of the electronic device. The electronic device is operatively coupled to the receiver for receiving power waves transmitted by a transmitter. The sensor data from the electronic device may include orientation data, motion data, and/or ambient light data, or may be representative of one or more proscribed circumstance that may indicate when a living being or sensitive object, such as a human, may be interacting with the electronic device and thus in close proximity to a pocket of energy, power waves, and/or the transmitter. In some embodiments, the proscribed circumstances may include a proscribed orientation circumstance, a proscribed motion circumstance, and/or a proscribed ambient light circumstance of the electronic device. In response to the sensor data received from the sensors of the electronic device, a processor of the transmitter processes the sensor data and may reduce intensity of power waves, terminate transmission of power waves, or may form a null space at or near the electronic device, among a number of additional or alternative actions.

At step 91116, a transmitter transmits power waves that converge in three dimensional space to form a constructive interference pattern at the receiver. In some embodiments, multiple transmitters and/or multiple receivers may power various electronic devices. The receiver may be separable from the electronic device or integrated with the electronic device.

At step 91118, the transmitter receives sensor data from one or more sensors of the electronic de-vice. In an embodiment, the electronic device may include one or more sensors. The one or more sensors may be selected from a group consisting of an accelerometer, a gyroscope, and an ambient light sensor. Each of the one or more sensors may work independently to produce sensor data. In some embodiment, each of the one or more sensors work together to produce sensor data.

Operationally, before a link between the transmitter and the receiver is established and wireless power charging has commenced, the transmitter may request sensor data from the receiver, or may request a function of the sensor data that the electronic device is collecting, before starting sending wireless power waves to the receiver. If some of the proscribed conditions are met, the transmitter may decide that the receiver is near a human being or a sensitive object and may not initiate wireless power charging. Similarly, the receiver may make the determination that a human being is near and refrain from initiating wireless power transfer.

A proscribed orientation circumstance of the electronic device generated by the one or more sensors corresponds to an orientation of the electronic device. For example, the proscribed orientation circumstance may indicate that the electronic device is in a vertical or near vertical orientation, which could be indicative of cell phone being placed against the head of a human. In another instance, a vertical or near vertical orientation of the electronic device indicates that the electronic device is being carried by a user in the vertical orientation, e.g., in the user's pocket or in a case, holster, or other carrier. In another instance, a near perfect horizontal orientation of the electronic device 91100 may indicate that the device is positioned on top of a surface, such as a table, counter or desk. The proscribed orientation circumstance may then be used to determine risk regarding the transmission of power waves to charge or power the electronic de-vice that may expose the user to unsafe or undesirable radiation levels.

The orientation of the electronic device may indicate that the transmitter should increase the power waves transmitted to the electronic device. For example, an orientation circumstance of the electronic device generated by the one or more sensors corresponds to an orientation of the electronic device in which the electronic device has a substantially horizontal orientation. A horizontal orientation of the electronic device may indicate that the electronic device has been left at that location for a period of time and may require charging or powering, especially when the orientation remains unchanged for a period of time. Furthermore, this orientation circumstance tends to indicate that the electronic device is not being held or carried by a user, and the power waves may be transmitted.

A proscribed motion circumstance of the electronic device corresponds to motion of the electronic device. The motion of the electronic device is determined from processing of the sensor data obtained from an accelerometer of the electronic device. The detection of motion of the electronic device indicates that the electronic device is being moved by a user. The proscribed motion circumstance and other proscribed circumstances therefore may indicate a risk that the transmission of power waves to charge or power the electronic device may expose the user to unsafe or undesirable radiation levels. In another embodiment, a proscribed motion circumstance of the electronic device includes a motion of the electronic device represented by the sensor data received from the electronic device, in combination with one or more additional sensor data that indicate presence of a living being.

A proscribed ambient light circumstance of the electronic device includes an ambient light reading of an ambient light sensor that has a low intensity in comparison with one or more other ambient light readings acquired near the electronic device. A low intensity measurement by an ambient light sensor indicates low ambient light in a room, and the electronic devices including the ambient light sensors may increase screen brightness to compensate. However, where an ambient light sensor from an electronic device detects a low intensity of light, whereas one or more ambient light readings acquired near the electronic device have a higher intensity, the low intensity light reading from the user light may indicate that the electronic device is in a user's pocket or otherwise carried by the user with the electronic device covered. This proscribed ambient light circumstance therefore may indicate a risk that the transmission of the power waves to charge or power the electronic device may expose the user to unsafe or undesirable radiation levels.

It should be understood by someone skilled in the art that that proscribed conditions related to motion, orientation, ambient light, heat sensors, magnetic sensors, or any other kind of sensors may be used as individual indicators or may be used in combination to indicate proscribed conditions that indicate a human being or a sensitive object is near a receiver. One or more pro-scribed conditions of the sensors may be combined along with time lapse indicators also. In addition, the considering of proscribed conditions, or sensor outputs, generated by one or more sensors may be processed according to a function to obtain a proscribed condition indicative of a human being nearby. The function may be a single variable or multi variable function. The function may be a linear or non-linear function.

Temporal input to the decision making, regardless of what other sensors are used, may be a safety feature. The proscribed conditions may indicate that the receiver is placed on a horizontal surface and it is not moving, and therefore likely to have been placed on a table and may be appropriately charged. However the temporal input, such as a timer, which may also include a hysteresis, may also be included to assure that there was enough time for a human being to move away from the receiver after placing it on the table before generating the proscribed condition signal to trigger wireless charging.

It should be understood by someone skilled in the art that the sensors may be included in the electronic device or they may be included in the receiver, or both. It should also be understood that the receiver may be an integral part of the electronic device or may be removably connected to the electronic device. Communication of signals maybe from the electronic device to the transmitter or may be from a separate transmitter of the receiver to the transmitter of the power waves.

It should be understood by someone skilled in the art that the sensor outputs may be used in determining presence of proscribed conditions as the sensor data is generated, or a time average of multiple sensor outputs may be used in determining the proscribed condition exists.

In some embodiments, the transmitter receives the sensor data at different points in time from the one or more sensors of the electronic device. The one or more proscribed circumstances is then calculated based upon the sensor data obtained over a period of time. In one embodiment, a proscribed motion circumstance may be represented by a change of value of the sensor data over the different points in time and thereby indicating a motion of the electronic device. In an-other embodiment, a proscribed orientation circumstance of the electronic device is a change in orientation of the electronic device indicated by the sensor data at different points in time. In another embodiment, clocking data is generated to determine the period of time since the last change in any of the above described sensor circumstances described above.

In another embodiment, the transmitter receives the sensor data from the one or more sensors of the electronic device representative of at least two of the proscribed orientation circumstance of the electronic device, the proscribed motion circumstance of the electronic device, the pro-scribed ambient light circumstance of the electronic device and the time that has elapsed since the last change in the respective sensor circumstances described above. In another embodiment, the transmitter receives the sensor data from an orientation sensor of the electronic device, wherein the orientation sensor output is representative of both a proscribed orientation circumstance of the electronic device and a proscribed motion circumstance of the electronic device.

At step 91120, transmitter may adjust (e.g., increase, decrease, or cease) transmission based upon a likely proximity of a living being or sensitive object with the power waves or electronic de-vice. In some embodiments, the transmitter reduces the power level of the power waves. In other embodiments, the transmitter terminates transmission of the power waves. In other embodiments in this circumstance, the transmitter terminates transmission of the power waves to the location of the electronic device. In further embodiments, the transmitter forms a null space in the power waves at the location of the electronic device.

Figure 91C:
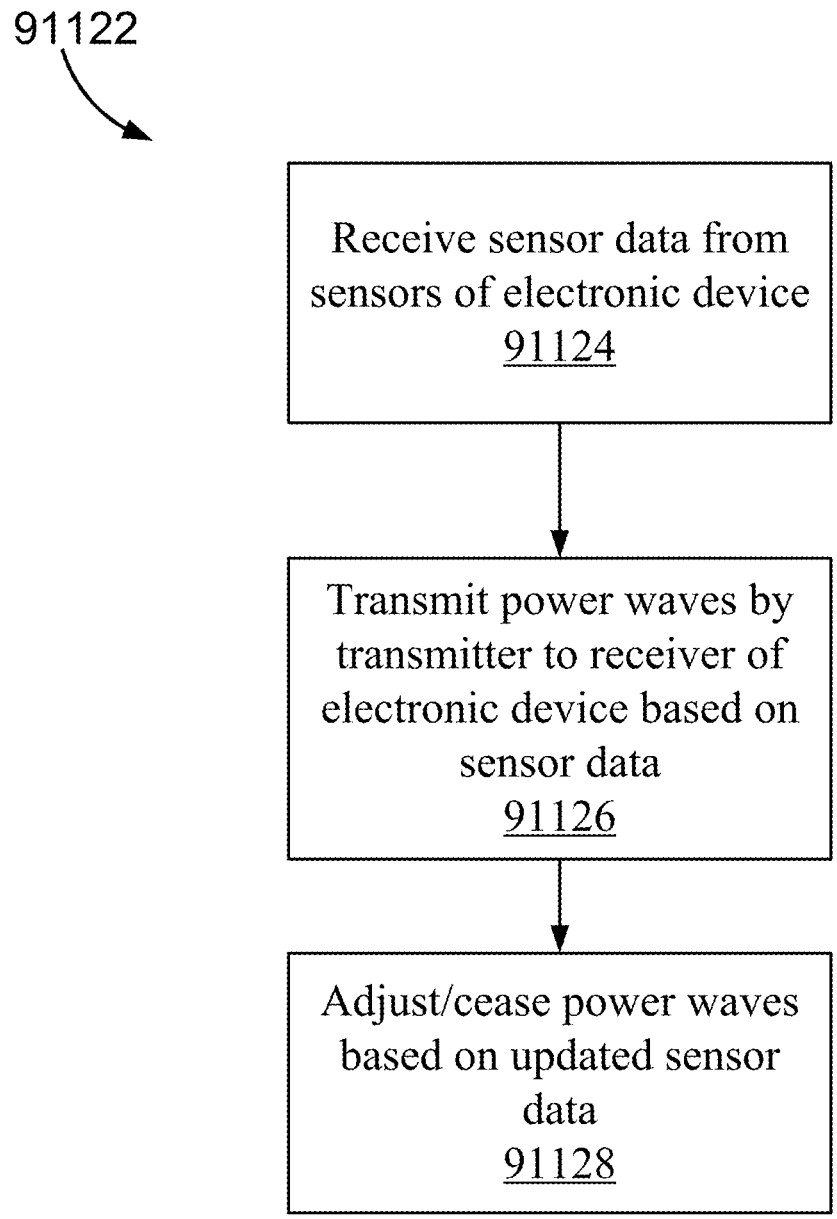

FIG. 91C is a flow diagram illustrating a method 91122 of transmitting power waves to or nearby receivers coupled to or integrated into electronic devices located within a transmission field of one or more transmitters of a wireless power transmission system, according to an exemplary. embodiment.

At step 91124, a transmitter receives sensor data from one or more sensors of the electronic de-vice. In an embodiment, the electronic device may include one or more sensors. It should be understood by someone skilled in the art that the sensors may be included in the electronic de-vice or they may be included in the receiver, or both. It should also be understood that the receiver may be an integral part of the electronic device or may be removably connected to the electronic device.

The one or more sensors may be selected from a group consisting of an accelerometer, a gyro-scope, and an ambient light sensor. Each of the one or more sensors may work independently to produce sensor data. In some embodiment, each of the one or more sensors work together to produce sensor data. The sensor data may be used in determining presence of proscribed conditions as the sensor data is generated, or a time average of multiple sensor outputs may be used in determining the proscribed condition exists.

In some embodiments, the transmitter receives the sensor data at different points in time from the one or more sensors of the electronic device. The one or more proscribed circumstances may then be calculated based upon the sensor data obtained over a period of time. In one embodiment, a proscribed motion circumstance may be represented by a change of value of the sensor data over the different points in time and thereby indicating a motion of the electronic device. In another embodiment, a proscribed orientation circumstance of the electronic device is a change in orientation of the electronic device indicated by the sensor data at different points in time. In another embodiment, clocking data may be generated to determine the period of time since the last change according to one or more sensor-related circumstances described above.

At step 91126, the transmitter transmits power waves that converge in a three dimensional space to form a constructive interference pattern at the receiver based on the sensor data. In some embodiments, multiple transmitters and/or multiple receivers may power various electronic devices. The receiver may be separable from the electronic device or integrated with the electronic device.

At step 91128, the transmitter may receive updated sensor data at different points in time from the one or more sensors of the electronic device, and may adjust (e.g., increase, decrease, or cease) transmission based upon the updated sensor data. For example, when the updated sensor data indicates a likely proximity of a living being or sensitive object with the power waves or electronic device, the transmitter may adjust (e.g., increase, decrease, or cease) transmission. In some embodiments, the transmitter reduces the power level of the power waves. In other embodiments, the transmitter terminates transmission of the power waves. In other embodiments in this circumstance, the transmitter terminates transmission of the power waves to the location of the electronic device. In further embodiments, the transmitter forms a null space in the power waves at the location of the electronic device.

Figure 91D:
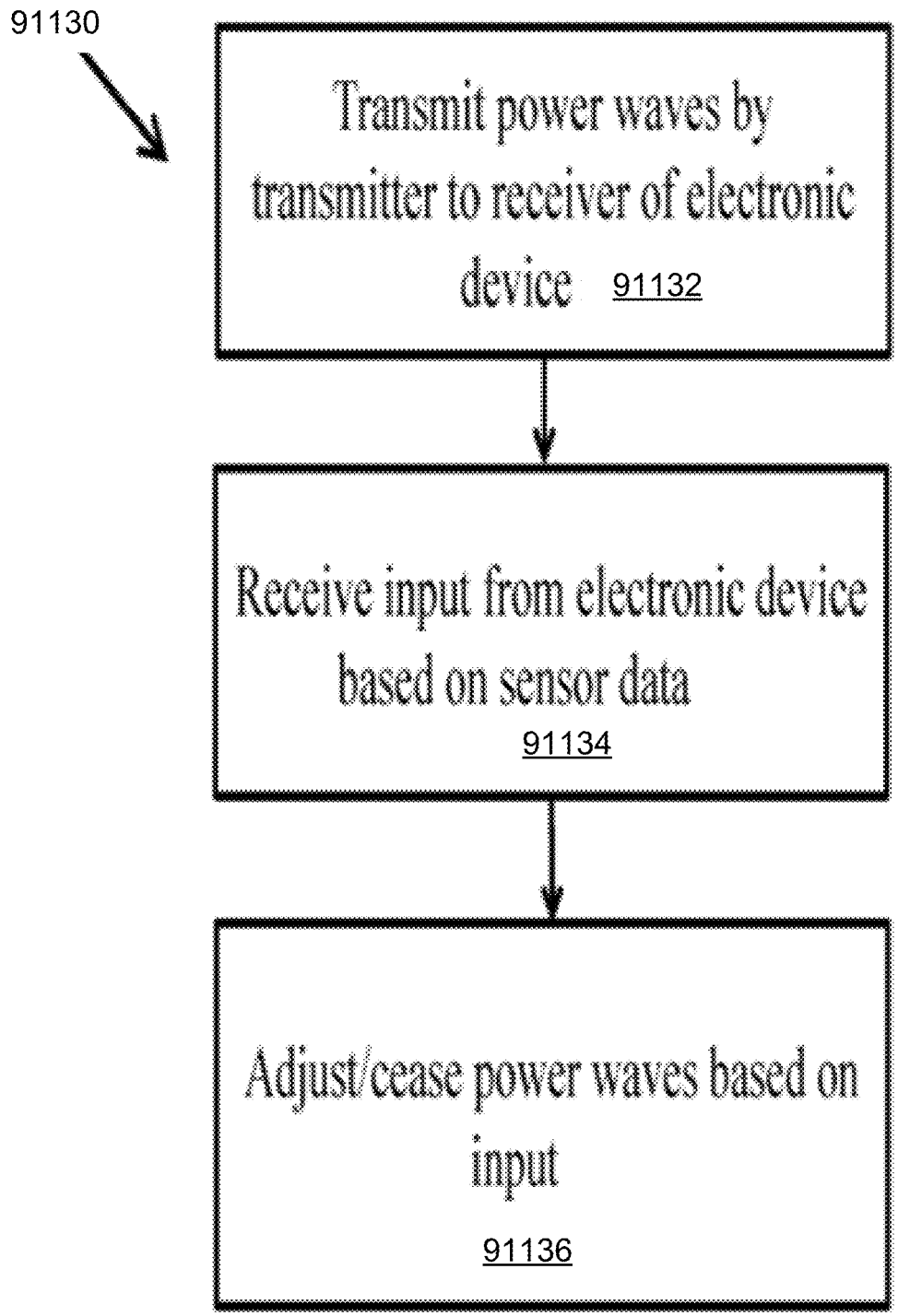

FIG. 91D is a flow diagram 91130 illustrating a method of transmitting power waves to receivers coupled to or integrated into electronic devices located within a transmission field of a transmitter of a wireless At step 91132, a transmitter transmits power waves that converge in three dimensional space to form a constructive interference pattern at or proximate to the location of the receiver. In some embodiments, multiple transmitters and/or multiple receivers may power various electronic de-vices. The receiver may be separable from the electronic device or integrated with the electronic device.

At step 91134, the transmitter receives input from the electronic device. The input is determined by the electronic device based on sensor data. In an embodiment, the electronic device may include one or more sensors. It should be understood by someone skilled in the art that the sensors may be included in the electronic device or they may be included in the receiver, or both. It should also be understood that the receiver may be an integral part of the electronic device or may be removably connected to the electronic device.

The one or more sensors may be selected from a group consisting of an accelerometer, a gyro-scope, and an ambient light sensor. Each of the one or more sensors may work independently to produce sensor data that is processed by the electronic device. In some embodiment, each of the one or more sensors work together to produce sensor data. The sensor data from the electronic device may include orientation data, motion data, and/or ambient light data, or may be representative of one or more proscribed circumstance that may indicate when a living being or sensitive object, such as a human, may be interacting with the electronic device and thus in close proximity to a pocket of energy, power waves, and/or the transmitter. In some embodiments, the proscribed circumstances may include a proscribed orientation circumstance, a proscribed motion circumstance, and/or a proscribed ambient light circumstance of the electronic device.

In response to the sensor data received from the sensors, a processor of the electronic device may process the sensor data and determine whether to reduce intensity of power waves, terminate transmission of power waves, or may form a null space at or near the electronic device, among a number of additional or alternative actions. Based on the determinations whether to reduce intensity of power waves, terminate transmission of power waves, or may form a null space at or near the electronic device, the electronic device generates an input comprising instructions to reduce intensity of power waves, terminate transmission of power waves, or may form a null space at or near the electronic device and send it to the transmitter.

At step 91136, the transmitter, based on the input received from the electronic device, adjust (e.g., increase, decrease, or cease) transmission based upon a likely proximity of a living being or sensitive object with the power waves or electronic device. In some embodiments, the transmitter reduces the power level of the power waves. In other embodiments, the transmitter terminates transmission of the power waves. In other embodiments in this circumstance, the transmitter terminates transmission of the power waves to the location of the electronic device. In further embodiments, the transmitter forms a null space in the power waves at the location of the electronic device.]

FIGS. 91A-91D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 91A-91D.

Presented below are example embodiments of providing wireless power using receiver device sensor inputs.

In some embodiments, an example method for wireless power transmission comprises transmitting, by a transmitter, power waves that converge to form constructive interference at a location associated with a receiver, receiving, by the transmitter, sensor data from one or more sensors of an electronic device representative of at least one of a proscribed orientation circumstance of the electronic device, a proscribed motion circumstance of the electronic device, and a proscribed ambient light circumstance of the electronic device, and adjusting, by the transmitter, a power level of the power waves upon receiving at least one of the proscribed orientation circumstance of the electronic device, the proscribed motion circumstance of the electronic device, and the proscribed ambient light circumstance of the electronic device.

In some embodiments, the one or more sensors are selected from a group consisting of an accelerometer, a gyroscope, an orientation sensor, and an ambient light sensor.

In some embodiments, the proscribed orientation circumstance of the electronic device comprises a substantially vertical orientation of the electronic device.

In some embodiments, the proscribed motion circumstance of the electronic device comprises motion of the electronic device determined from an accelerometer of the electronic device.

In some embodiments, the proscribed ambient light circumstance of the electronic device comprises an ambient light reading of an ambient light sensor that has a low intensity in comparison with one or more other ambient light readings acquired previously near the electronic device.

In some embodiments, the proscribed orientation circumstance is based on sensor data over a period of time.

In some embodiments, the proscribed motion circumstance is based on sensor data over a period of time.

In some embodiments, the proscribed ambient light circumstance is based on sensor data over a period of time.

In some embodiments, the proscribed orientation circumstance of the electronic device comprises a change in orientation of the electronic device indicated by the sensor data received from the one or more sensors at different points in time.

In some embodiments, the sensor data received from the one or more sensors has a change in value for at least two different points in time. The proscribed motion circumstance is a motion of the electronic device represented by the change in value of the sensor data.

In some embodiments, adjusting the power level comprises ceasing transmission of the power waves.

In some embodiments, the proscribed orientation circumstance of the electronic device comprises a substantially horizontal orientation of the electronic device.

In some embodiments, an example transmitter for wireless power transmission comprising: a processor configured to control transmission of power waves that converge to form constructive interference at a location associated with a receiver; and a memory operatively coupled with and readable by the processor and having stored therein machine-readable instructions that when executed by the processor cause the processor to: receive sensor data from one or more sensors of an electronic device representative of at least one of orientation, motion, and ambient light; and adjust a power level of the power waves upon receiving sensor data representative of at least one of orientation, motion, and ambient light and determining that the sensor data is indicative of a condition in which the power level of the power waves should be adjusted.

FIG. 92 shows a sequence diagram 92100 for a real time communication between wireless power transmitters and wireless power receivers, according to an embodiment.

Sequence diagram 92100 illustrates the interactions between objects or roles that allow the real time communication between a wireless power transmitter and one or more wireless power receivers. The objects or roles described here may include, but is not limited to, a GUI 92102, a third party API 92104 that controls a BTLE chip embedded on the power transmitter board, a power transmitter manager app 92106, a power receiver app 92108, and a power receiver API 92110 that controls a BTLE chip embedded on a wireless power receiver board.

Power transmitter manager app 92106 may first scan for power receivers ads every one second as long as its radio receiver is on. Power receiver app 92108 may continuously broadcast ads 92112 around its radio until a power transmitter manager app 92106 intercepts these ads 92112. Ads 92112 may include data such as unique IDs that may allow power transmitter manager app 92106 to identify the wireless power receiver to which is about to establish a connection. Once power transmitter manager app 92106 intercepts ads 92112, it may attempt connection one or more times until it gets connected. GUI 92102, at the same time, may continuously send ads 92114 to third party API 92104 on the transmitter board until it causes an add detection callback that may initiate timer callback 92116 in the third party API 92104. Ads 92114 may include data such as a list of power receivers to be tracked and which to be charged.

Timer callback 92116 may then trigger power transmitter manager app 92106 where power transmitter manager app 92106 may respond by sending a start communication 92118 write request message to power receiver app 92108 to initiate real time communication with power receiver app 92108. Then power receiver API 92110 may respond with a callback 92120 sent to power receiver app 92108 which may immediately trigger power receiver app 92108 by sending multiple messages including status and data 92122 of the wireless power receiver, at a rate of about 100 packets per second, to the power transmitter manager app 92106. Status and data 92122 may include data such as antenna voltage of the wireless power receiver, battery levels, and charging status among others. In other embodiments, the transfer rate may go up to 400 packets per second but there may be problems of communication at that rate.

After status and data 92122 is received at power transmitter manager app 92106, third party API 92104 sends a message received call back 92124 to power transmitter manager app 92106. Then power transmitter manager app 92106 processes the status and data 92122 message. This process may repeat every time a status and data 92122 is received. After a certain period of time, power receiver app 92108 may send a status indicating that power receiver API 92110 is running out of transmit buffers. Subsequently, power transmitter manager app 92106 may restore the buffers by sending back a start communication 92126 write request message to the power receiver app 92108. Once the buffers are restored, a callback 92128 from the power receiver API 92110 is sent to the power receiver app 92108, triggering the software to send status and data 92130 again back to power transmitter manager app 92106 at a rate of about 100 packets per second. Status and data 92130 may continue to send updates about antenna voltage of the wireless power receiver, battery levels, and charging status among others.

After status and data 92130 is received at power transmitter manager app 92106, third party API 92104 sends a message received call back 92132 to power transmitter manager app 92106. Then power transmitter manager app 92106 processes the status and data 92130 message. This process may repeat every time a status and data 92122 is received. After a certain period of time, power receiver app 92108 may send a status indicating that power receiver API 92110 is running out of transmit buffers. However, at this point, power transmitter manager app 92106 may check the time and realize that one second has gone since it started communication with power receiver app 92108, hence it may be time to check if there are other wireless power receivers that may need charge. Power transmitter manager app 92106 may then stop restoring buffers on power receiver API 92110 and set on a scanning mode where it listens for ads coming from GUI 92102 and power receiver APP 92108. Subsequently, GUI 92102 may send ads 92134 to third party API 92104 which my trigger a timer callback 92136. Ads 92134 may include data such as a list of power receivers to be tracked and which to be charged. Power transmitter manager app 92106 may then process ads 92134 and establish a real time communication with the next wireless power receiver available within a period of one second.

The above described systems and methods may allow wireless power transmitters to communicate with one or more wireless power receivers in real time within intervals of one second. The systems and methods described here may enable full control of the wireless power receivers by letting the user decide which wireless power receivers to charge, when to charge them, and set priorities and charging schedules among other functions. In other embodiments, the systems and methods described here may allow the wireless power transmitters to communicate with wireless power receivers simultaneously by adding multiple BTLE chips on the power transmitter board.

FIG. 92 illustrates examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIG. 92.

Presented below are example embodiments of wireless transmission of power.

In some embodiments, an example system for controlling communication between a wireless power transmitter and at least one wireless power receiver, the system comprises a wireless power transmitter that includes: a microprocessor running a power transmitter manager application, wireless communication hardware having an application programming interface (API) operatively coupled with the power transmitter manager application; a transmitter radio frequency (RF) antenna array controlled by transmitter antenna manager software running on the transmitter microprocessor, arranged to form controlled RF waves that converge to create pockets of energy in the space proximate the wireless power transmitter at least partially responsive to the power manager application, and at least one wireless power receiver that includes: a microprocessor running a power receiver application; wireless communication hardware having a receiver API operatively coupled to the power receiver application; a receiver RF antenna array arranged to receive and use RF power from the pockets of energy created by the wireless power transmitter at least partially responsive to the power receiver application.

In some embodiments, the communication protocol used by the wireless communication hardware is one of Bluetooth Low Energy (BTLE) and WiFi.

In some embodiments, the power transmitter manager application stores information obtained from the at least one wireless power receiver to facilitate communications between the wireless power transmitter and each respective wireless power receiver.

In some embodiments, the information includes an identifier and location of the wireless power receiver.

In some embodiments, the power transmitter manager application calls the transmitter API to perform a plurality of functions including: starting a connection; ending a connection; and sending data.

In some embodiments, the transmitter API commands the transmitter wireless communication hardware according to the functions called by the power transmitter manager application.

In some embodiments, the transmitter API calls the power transmitter manager application through a transmitter callback function.

In some embodiments, the transmitter callback function sends a callback every time a communication connection begins, a communication connection ends, a communication connection is attempted, and a message is received.

In some embodiments, the system has a callback sent ten times per second.

In some embodiments, the wireless power receiver is at least one of an energy consuming electronic device and a cover of an energy consuming electronic device.

In some embodiments, the power receiver application calls the receiver API to start a connection, end a connection, and send data.

In some embodiments, the receiver API calls the power receiver application through a receiver callback function.

In some embodiments, the receiver API sends a callback to the power receiver application when a connection begins, a connection ends, a connection is attempted, or a message is received.

In some embodiments, the receiver API sends a callback to the power receiver application ten times per second.

In some embodiments, the energy consuming device downloads a graphical user interface (GUI) from an application store to communicate with the power transmitter manager application.

In some embodiments, the wireless power receiver sends to the wireless power transmitter information of the receiver including an identifier and location of the wireless power receiver.

In some embodiments, an example wireless power transmitter comprises a microprocessor running a power transmitter manager application, wireless communication hardware having an application programming interface (API) operatively coupled with the power transmitter manager application, and a transmitter radio frequency (RF) antenna array controlled by transmitter antenna manager software running on the transmitter microprocessor, arranged to form controlled RF waves that converge to create pockets of energy in the area proximate the wireless power transmitter responsive to the power transmitter application, which is responsive to the API.

In some embodiments, an example wireless power receiver comprises a microprocessor running a power receiver application, wireless communication hardware having a receiver API operatively coupled to the power receiver application, a receiver RF antenna array arranged to receive and use RF power from the pockets of energy created by the wireless power transmitter responsive to the power receiver application, which is responsive to the API.

In some embodiments, an example method of wirelessly transmitting power comprises broadcasting ads by a power receiver, where the ads include an identifier of the power receiver, receiving, by a power transmitter, at least one of the power receiver ads, initiating, by the power transmitter, a communication connection with the power receiver, sending information of the power receiver, by the power receiver, to the power transmitter, determining whether the power receiver is to be charged; in the case the power receiver is to be charged, tracking a position of the power receiver by the power transmitter, sending, by the power transmitter, a plurality of radio frequency waves that interfere constructively at the location of the power receiver to form a pocket of energy at the power receiver's position, and receiving the pocket of energy by the power receiver.

In some embodiments, the method further comprises maintaining, by the power transmitter, information of a plurality of power receivers being tracked and which of the tracked power receivers are to be charged and sending power pockets by the power transmitter to the receivers to be charged.

FIG. 93 shows a sequence diagram 93100 for a real time communication between wireless powered transmitters and wireless powered receivers, according to an embodiment.

Sequence diagram 93100 illustrates the interactions between objects or roles in a wireless powered network. The objects or roles described here may include, but is not limited to, a user 93102 which manages the wireless power network, a wireless power manager 93104 which serves as a front end application for managing the wireless power network, power receiver devices with corresponding power receiver apps 93106 and transmitters with corresponding power transmitter manager apps 93108.

The process may begin when wireless power manager 93104 requests 93110 information from a power transmitter manager app 93108 hosted in a wireless transmitter. Request 93110 may include authentication security such as user name and password. Power transmitter manager apps 93108 may then verify the request 93110 and grant access to the wireless power manager 93104. Power. Wireless power manager 93104 may continuously request 93110 information for different time periods in order to continue updating itself. Power transmitter manager app 93108 may then send database records 93112 to the wireless power manager 93104. Wireless power manager 93104 may then display 93114 these records with options in a suitable GUI to a user 93102. User 93102 may then perform different actions in order to manage the wireless power network. For example and without limitation, a user 93102 may configure powering schedules 93116 for different devices, the user 93102 may also establish priorities depending on time 93118, type of client 93120, physical location 93122 or may even choose to broadcast a message 93124 to client devices. The wireless power manager 93104 may then send 93126 the updated database records back to the power transmitter manager apps 93108.

In a wireless network power grid more than one transmitter may be used. Power transmitter manager apps 93108 hosted on each transmitter may share updates 93128 to the device database. Power transmitter manager apps 93108 may then perform an action 93130 depending on the command and updates made by the user 93102 such as, charge a wireless device, send a message to the wireless devices, set a schedule to charge different devices, set power priority to specific devices, etc.]

FIG. 93 illustrates examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIG. 93.

Presented below are example embodiments of managing and controlling a wireless power network.

In some embodiments, an example wireless power network comprises at least one transmitter suitable for providing controlled radio frequency waves to produce a plurality of energy pockets suitable for receipt by a receiver at least one user device, and at least one power manager suitable for controlling at least the at least one transmitter, said at least one power manager further comprising at least one database comprising identification and attribute information of the at least one transmitter, the at least one receiver, and the at least one user device, where the control by the at least one power manager allows ones of the plurality of energy pockets to charge or power the at least one user device in accordance with the identification and attribute information of the at least one user device.

In some embodiments, the identification and attribute information comprise information indicative of the power usage of one of the at least one user device.

In some embodiments, the identification and attribute information comprise information indicative of the stored power available to one of the at least one user device.

In some embodiments, the identification and attribute information comprise information indicative of the number of power usage of one of the at least one user device.

In some embodiments, the identification and attribute information comprise at least one time related to the scheduling of a charge time for the at least one user device.

In some embodiments, the communication from the at least one transmitter to the at least one receiver is of a protocol selected form the group consisting of Bluetooth, Bluetooth Low Energy, WIFI, ZigBee, and combinations thereof.

In some embodiments, the at least one power manager communicates with a power transmitter manager application to provide for at least one device status, power schedule, authentication credentials, and combinations thereof.

In some embodiments, the at least one power manager performs one of the functions selected from the group consisting of allowing for the charging of at least one user device, and sending a message to ones of the at least one user device.

In some embodiments, the at least one power manager determines the charging time for each of the at least one user device.

In some embodiments, an example method for providing a wireless power network comprises transceiving controlled radio frequency waves to produce a plurality of energy pockets for receipt at a user device, and controlling the transmitting and receiving of said plurality of energy pockets using at least one power manager. Said controlling allows ones of the plurality of energy pockets to charge or power the at least one user device in accordance with identification and attribute information of the at least one user device.

In some embodiments, the communication protocol for said transceiving is selected form the group consisting of Bluetooth, Bluetooth Low Energy, WIFI, ZigBee, and or combinations thereof.

In some embodiments, an example wireless power network comprises at least one receiver at a user device suitable for receiving from a transmitter controlled radio frequency waves that produce a plurality of energy pockets, and at least one power manager suitable for controlling at least the at least one receiver, said at least one power manager further comprising at least one database comprising identification and attribute information of the transmitter, the at least one receiver, and the at least one user device. The control by the at least one power manager allows ones of the plurality of energy pockets to charge or power the at least one user device in accordance with the identification and attribute information of the at least one user device.

In some embodiments, the at least one receiver is not integral to the at least one user device.

In some embodiments, the at least one receiver is communicatively coupled to a power receiver application suitable for receiving instructions from the at least one power manager.

In some embodiments, the at least one user device is in communication with a graphical user interface providing the user of the at least one user device control over at least one task performed by the at least one power manager.

In some embodiments, the wireless power network has a user of an at least one user device control an aspect of the at least one power manager.

FIGS. 94 and 95 illustrate examples of systems and methods for power payment based on proximity, in accordance with some embodiments.

FIG. 94 is a flowchart of a power delivery and bill computing process 94100, according to an exemplary embodiment. Power delivery and bill computing process 94100 may start when a customer may approach 94102 the checkout of a service provider or goods-selling store, where the customer may pay 94104 for a first service or may purchase goods. The customer may need to charge an electronic device and may ask for power. Upon request, a cover may be associated 94106 in a database with a customer. In this step any needed customer information may be stored in the database, this information may include customer number, customer ID, name, credit card number and type of customer, amongst others.

Then, the customer may be given 94108 its associated cover and may attach 94110 the cover to an electronic device that needs to be charged. The electronic device may then begin 94112 to receive power. In some embodiments, the electronic device may receive power pre-stored in a battery included in the power receiver embedded in the attached cover. In other embodiments, the electronic device may receive power sent wirelessly by the power transmitter to the power receiver. The power transmitter may record 94114 the status of the power receiver, the ID of the power receiver and the time the customer device started charging. The power transmitter may store the records in a suitable database.

While the electronic device is being charged by the power receiver, the power transmitter may track 94116 the power receiver and keep a record of the power delivered to the electronic device.

When the electronic device is fully charged or the customer needs to leave the premises of the establishment, the customer may disconnect 94118 the power receiver and return it 94120 at the check-out. Upon request or automatically, the power transmitter may compute 94122 the bill for the customer based on the amount of power delivered to the electronic device. Subsequently, the power transmitter may update 94124 the database with the bill and any other suitable information and the process may end.

In some alternative embodiments, the customer's electronic device may have an embedded power receiver compatible with wireless charging system installed in the establishment. In this embodiment, the electronic device may be enrolled in the system and the customer's information may be associated with the device. In some cases, these electronic devices may be given limited permission to receive power.

In some exemplary embodiments, a customer may be able to purchase a predetermined amount of power. Additionally, it may be able to use only portions of the purchased power at a time.

In some exemplary embodiments, a customer may be able to have an account which provides access to wireless power delivery systems from the same service provider in more than one location.

FIG. 95 is a flowchart of a power delivery and bill computing process 94126, according to an exemplary embodiment. Power delivery and bill computing process 94126 may start when a customer may approach 94128 an establishment carrying an electronic device paired with a wireless power receiver. Then, a wireless power transmitter within the wireless power delivery system of the establishment may detect 94130 the customer's power receiver and may proceed to authenticate 94132 the customer's credentials. According to some embodiments, the power transmitter may use a suitable IP/TCP connection to connect to a suitable service provider server to authenticate 94132 the customer's credentials.

If the credentials are not valid 94134, process 94126 may end. If the customer's credentials are valid 94134 the power transmitter may start sending wireless power to the customer's power receiver to start charging 94136 customers' electronic device.

While the electronic device is being charged by the power receiver, the power transmitter may track 94138 the power receiver and keep a record of the power delivered to the electronic device.

Afterwards, when the customer wants to leave the establishment or the customer's electronic device is fully charged the wireless power transmitter may stop 94140 sending wireless energy to the customer's power receiver.

Then, the power transmitter may compute 94142 the amount of power delivered to the customer's electronic device and may send 94144 the information to a remote billing server and the customer may be billed 94146.

Subsequently, the power transmitter may update 94148 the database with the bill and any other suitable information and process 94126 may end.

EXAMPLES

In example #1 a customer enters a coffee shop and buys a cup of coffee. At checkout, the costumer asks for power to charge a smartphone. The customer's smartphone includes a suitable GUI for interacting with a wireless charging system. A cover with an embedded power receiver is associated with the customer and the customer receives the cover. Then, the smartphone is paired with a power receiver embedded in the smartphone cover. The smartphone starts receiving power and the power transmitter keeps records of the time, amount of power delivered to the smartphone, position of the power receiver and any suitable information needed. After some time, the smartphone reaches a desired level of charge and the customer disconnects the power receiver and returns it to the check-out. The power transmitter computes the bill based on the amount of power delivered to the smartphone and updates the database. The customer's electronic device is charged and the process ends.

In example #2 a customer enters a coffee shop and buys a cup of coffee. At checkout, the costumer asks for power to charge a smartphone. The customer's smartphone includes a suitable GUI and a power receiver for interacting with a wireless charging system. The smartphone is enrolled in the system using Near Field Communication (NFC). The smartphone starts receiving power and the power transmitter keeps records of the time, amount of power delivered to the smartphone, position of the power receiver and any suitable information needed. After some time, the smartphone reaches a desired level of charge and the customer returns to the check-out. The database is updated and the smartphone's permission to receive power is cancelled. The power transmitter computes the bill based on the amount of power delivered to the smartphone and updates the database. The customer's electronic device is charged and the process ends.

In example #3 a customer enters a coffee shop and buys a cup of coffee. The customer carries a smartphone paired with its own power receiver. A wireless power transmitter in the coffee shop detects the power receiver within the customer's smartphone. The power receiver reads the power receiver's unique identifier and using the coffee shop's network connects to a remote billing server to authenticate the unique ID of the power receiver. The device is authorized to receive wireless power and the power transmitter start delivering wireless energy to the smartphone. The power transmitter keeps records of the time, amount of power delivered to the smartphone, position of the power receiver and any suitable information needed. After some time, the customer leaves the establishment and the power transmitter computes the amount of energy delivered to the smartphone. The information is sent to a remote billing server, the customer is billed and the power transmitter updates its database.

FIGS. 94 and 95 illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 94 and 95.

Presented below are example embodiments of power payment based on proximity.

In some embodiments, an example apparatus for wirelessly providing power comprises a wireless power transmitter a wireless power transmitter manager, configured to control radio frequency (RF) waves to form three-dimensional pockets of energy for providing power from the wireless power transmitter to a receiver, and an interface for determining at least one of (i) the amount of power provided by the wireless power transmitter and (ii) a time period of power being provided by the wireless power transmitter. The interface is configured to communicate with the wireless power transmitter manager to calculate a billing amount based on the determination.

In some embodiments, the wireless power transmitter manager is configured to control RF waves via at least one of phase and relative amplitude adjustments to form constructive and destructive interference patterns.

In some embodiments, the wireless power transmitter comprises an antenna array comprising a plurality of antenna elements.

In some embodiments, the interface is configured to determine a total amount of power provided by the wireless power transmitter.

In some embodiments, the interface is configured to communicate with the wireless power transmitter to provide a predetermined amount of power.

In some embodiments, the wireless power transmitter manager is configured to determine an authorization for the receiver and provide power to the receiver when the authorization is valid.

In some embodiments, the apparatus further comprises communications for communicating over a computer network, the apparatus being configured to receive information regarding the receiver via the communications.

In some embodiments, an example method for wirelessly providing power via an apparatus, comprises controlling radio frequency (RF) waves in a wireless power transmitter of the apparatus, via a wireless power transmitter manager, to form three-dimensional pockets of energy for providing power from the wireless power transmitter to a receiver; determining, via an apparatus interface, at least one of (i) the amount of power provided by the wireless power transmitter and (ii) a time period of power being provided by the wireless power transmitter, and calculate a billing amount based on the determination.

In some embodiments, an example system for wirelessly providing power comprises a wireless power transmitter, a wireless power transmitter manager, configured to control radio frequency (RF) waves to form three-dimensional pockets of energy for providing power from the wireless power transmitter to a receiver, communications for receiving information regarding the receiver; and an interface for determining at least one of (i) the amount of power provided by the wireless power transmitter cased on the received information and (ii) a time period of power being provided by the wireless power transmitter. The interface is configured to communicate with the wireless power transmitter manager to calculate a billing amount based on the determination.]

FIGS. 96A-96H illustrate examples of devices, apparatus, and methods for antenna for near field wireless power charging, in accordance with some embodiments.

Figure 96B:
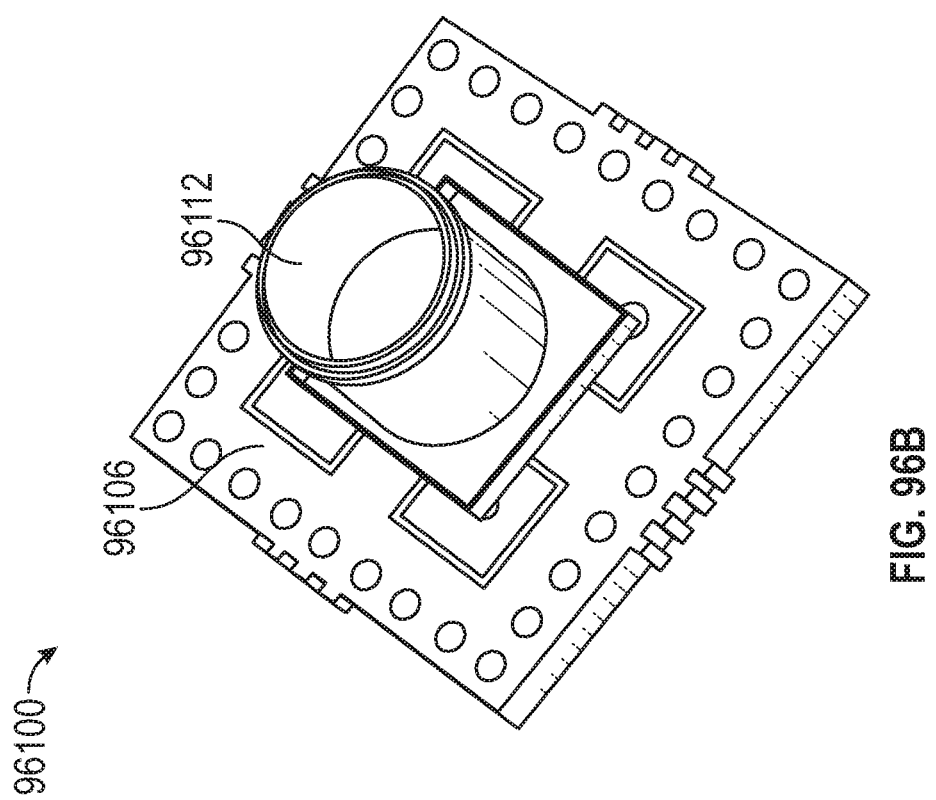
Figure 96A:
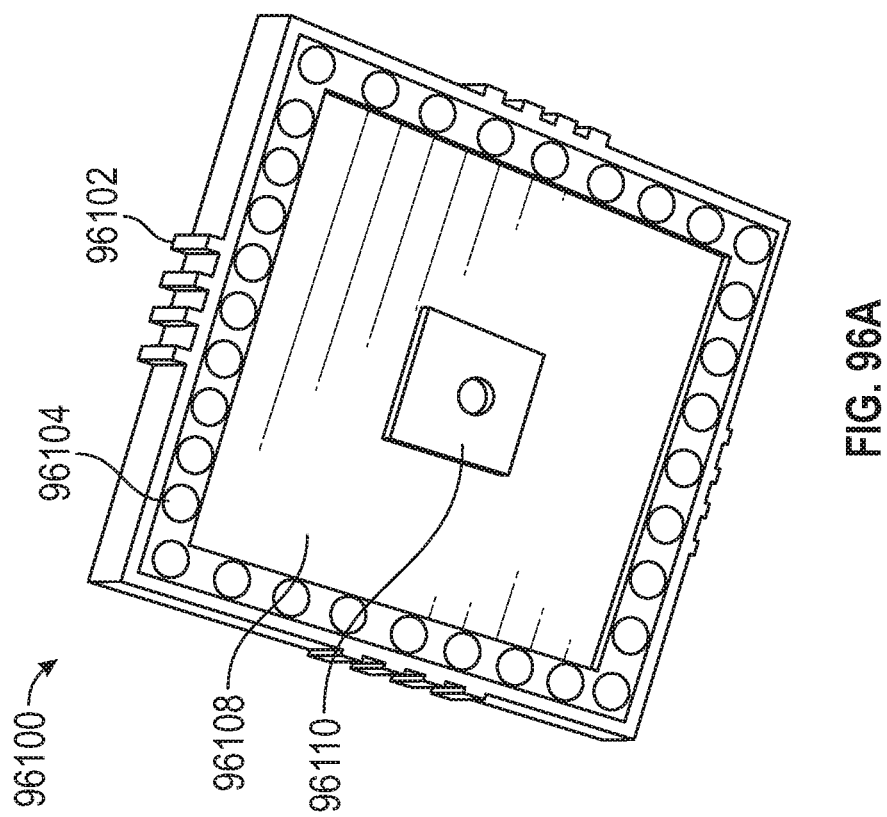

FIGS. 96A and 96B is a schematic diagram of a front view and a rear view respectively of a first coaxial structure 96100, in accordance with an embodiment of the present disclosure. In one embodiment, the first coaxial structure 96100 may be part of a charging device. In another embodiment, the first coaxial structure 96100 may correspond to or be associated with a charging device. In either case, the first coaxial structure 96100 may be in electrical communication with a charging device. As shown, the first coaxial structure 96100 is square, and includes a transmission line (TL) that produces a transmission-line RF field from a transmitter (i.e., coaxial mode), as further described in FIG. 96E. The shape of the first coaxial structure 96100 may alternatively be rectangular, circular, or any other geometric or non-geometric shape.

The first coaxial structure 96100 may include a housing defined by a plurality of sidewalls 96102, a top surface 96104, and a bottom surface 96106. The top surface 96104 extends over the bottom surface 96106. The sidewalls 96102 span between the top surface 96104 and the bottom surface 96106. The top surface may include vias, as shown, or not include vias. In some embodiments, the housing is formed of plastic, but alternatively or additionally can be formed of other materials, such as wood, metal, rubber, glass, or other material that is capable of providing for the functionality described herein. As illustrated in FIGS. 96A and 96B, the first coaxial structure 96100 has a square shape, but other two-dimensional or three-dimensional shapes are possible, such as a cube, a sphere, a hemisphere, a dome, a cone, a pyramid, or any other polygonal or non-polygonal shape, whether having an open-shape or a closed-shape. In some embodiments, the housing of the first coaxial structure 96100 is waterproof or water-resistant.

The first coaxial structure 96100 may be stiff or flexible and optionally include a non-skid bottom surface to resist movement. Similarly, the top surface 96104 may be or include non-skid region(s) or be entirely non-skid to resist motion between the top surface 96104 and an electronic device. Still yet, a bracket or other guide may be mounted to the top surface 96104 to assist a user with positioning of an electronic device. The housing may contain various components of the first coaxial structure 96100.

The first coaxial structure 96100 may include a substrate 96108. The substrate 96108. The substrate may include metamaterials, or traditional materials such as FR4 or any other material known in the art. The metamaterials of the present disclosure may be a broad class of synthetic materials that are engineered to yield permittivity and permeability characteristics compliant with the wireless charging system requirements. The metamaterials described herein radiate on their own, and act as very thin reflectors.

The first coaxial structure 96100 may be configured to keep desired currents inside and undesired current outside and thereby retaining the electric current in the first coaxial structure 96100. In the exemplary embodiment, the electric current is an RF signal that is carried on the first coaxial structure 96100. The first coaxial structure 96100 may further include a core 96110. The core 96110 is formed at a center of the substrate 96108. In one embodiment, the core 96110 is made up of metal to operate as an electrical conductor, as understood in the art. In another embodiment, the core 96110 may be made of any suitable material known in the art without moving out from the scope of the present disclosure.

The first coaxial structure 96100 may further include coaxial connector 96112 having two ends where one end of the coaxial connector 96112 may extend from the bottom surface 96106 and the other end of coaxial connector 96112 is connected to a ground terminal.

Figure 96D:
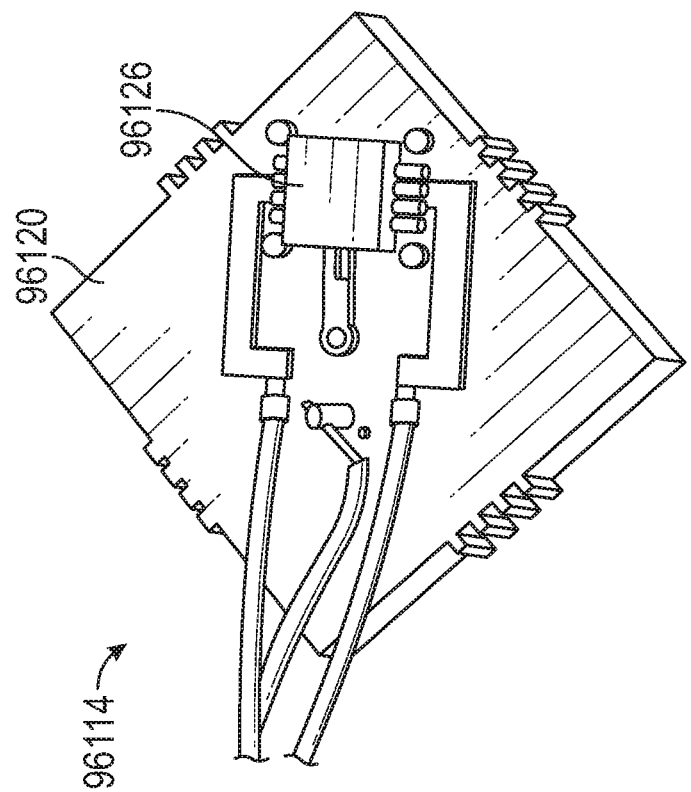
Figure 96C:
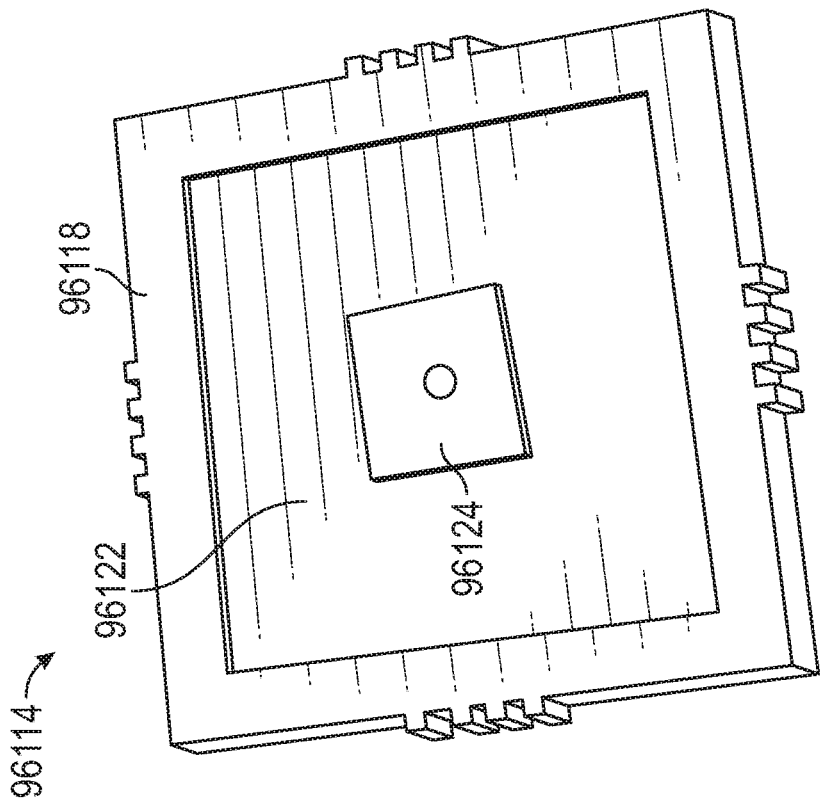

FIGS. 96C and 96D is a schematic diagram of a front view and a rear view respectively of a second coaxial structure 96114, in accordance with an embodiment of the present disclosure. In one embodiment, the second coaxial structure 96114 may be part of an electronic device, such as a mobile telephone, comprising a battery. In another embodiment, the second coaxial structure 96114 may be part of a portable battery device. In yet another embodiment, the second coaxial structure 96114 may be attached to an electronic device, such as wearable watch comprising a battery.

The second coaxial structure 96114 may include a housing defined by a plurality of sidewalls 96116, a top surface 96118, and a bottom surface 96120. The top surface 96118 extends over the bottom surface 96120. The sidewalls 96116 span between the top surface 96118 and the bottom surface 96120. In some embodiments, the housing is formed of plastic, but alternatively or additionally can be formed of other materials, such as wood, metal, rubber, glass, or other material that is capable of providing for the functionality described herein. As illustrated in FIGS. 96C and 96D, the second coaxial structure 96114 has a square shape, but other two-dimensional or three-dimensional shapes are possible, such as a cube, a sphere, a hemisphere, a dome, a cone, a pyramid, or any other polygonal or non-polygonal shape, whether having an open-shape or a closed-shape. In some embodiments, the housing of the second coaxial structure 96114 is waterproof or water-resistant.

The second coaxial structure 96114 may be stiff or flexible and optionally include a non-skid bottom surface to resist movement. Similarly, the top surface 96118 may be or include non-skid region(s) or be entirely non-skid to resist motion between the top surface 96118 and an electronic device. Still yet, a bracket or other guide may be mounted to the top surface 96118 to assist a user with positioning of an electronic device. The housing may contain various components of the second coaxial structure 96114.

The second coaxial structure 96114 may include a substrate 96122. The substrate may include metamaterials, or traditional materials such as FR4 or any other material known in the art. The metamaterials of the present disclosure may be a broad class of synthetic materials that are engineered to yield permittivity and permeability characteristics compliant with the wireless charging system requirements. The metamaterials described herein radiate on their own, and act as very thin reflectors.

The second coaxial structure 96114 may be configured to keep desired currents inside and undesired current outside and thereby retaining the electric current in the second coaxial structure 96114. In the exemplary embodiment, the electric current is an RF signal that is carried on the second coaxial structure 96114. The second coaxial structure 96114 may further include a core 96124. The core 96124 is formed at a center of the substrate 96122. In one embodiment, the core 96124 is made up of metal to operate as an electrical conductor, as understood in the art. In another embodiment, the core 96124 may be made of any suitable material known in the art without moving out from the scope of the present disclosure.

The second coaxial structure 96114 may further include circuitry 96126, such as a transducer device, to convert coaxial field radiation into energy to power or charge a battery of the electronic device.

Figure 96E:
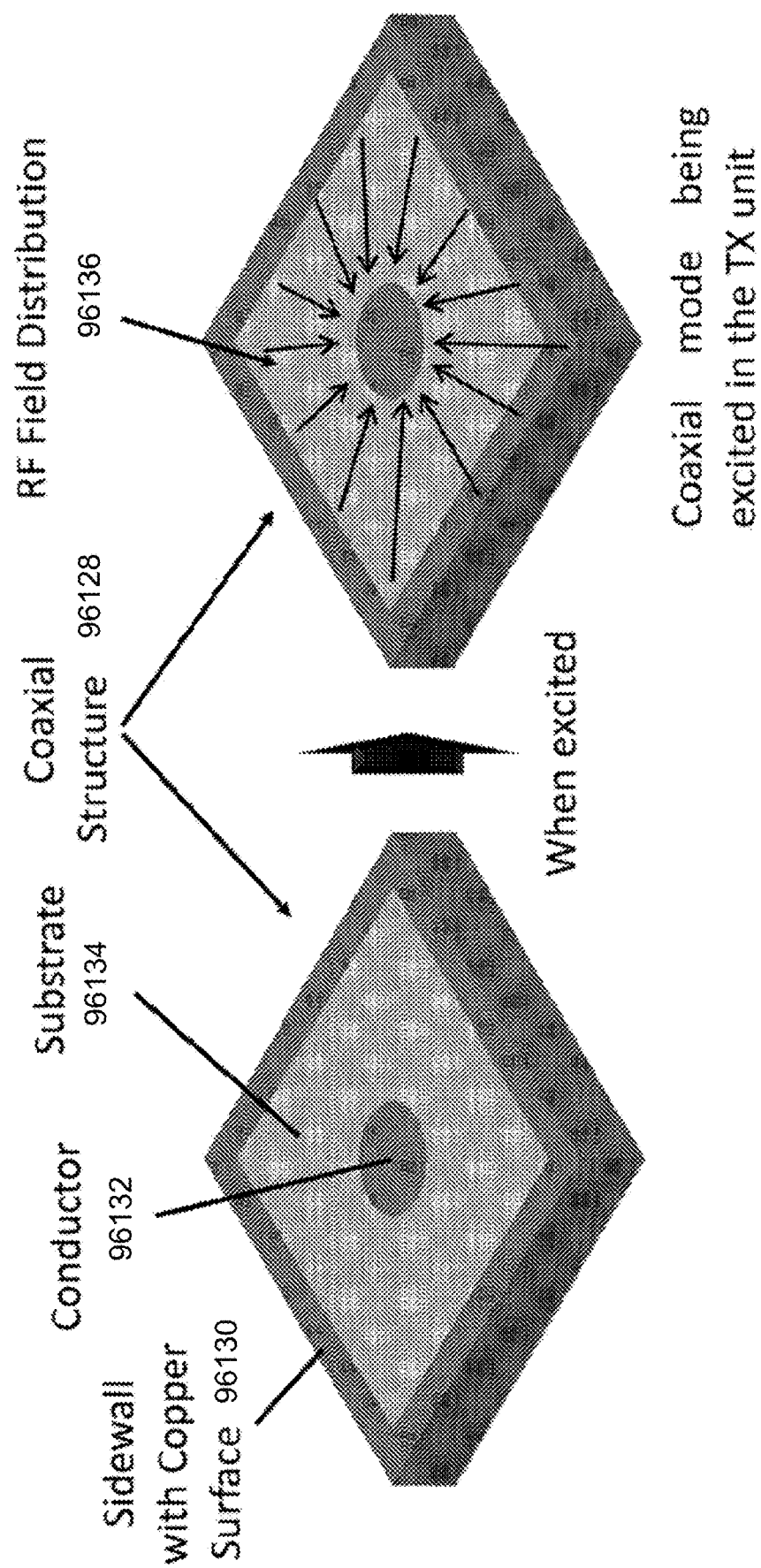

FIG. 96E is an illustration of showing a coaxial structure 96128 on a transmitter side. The coaxial structure 96128 is shown to include a sidewall with a copper surface 96130, conductor 96132, and substrate 96134, The substrate may be a conventional substrate or otherwise. When the coaxial structure 96128 is excited, an RF field distribution (mode) 96136 occurs in the substrate 96134 between the sidewall with copper surface 96130 and conductor 96132. Size of the coaxial structure 96128 may be scaled up or down without limit. The coaxial structures 96128 and 96138 may be identical and reciprocal in structure or be different in structure but be complementary in that the two coaxial structures 96128 and 96138 are able to connect or otherwise be arranged such that the RF field distribution 96136 is generated based on the coaxial structures 96128 and 96138 being near to one another. In one embodiment, especially if the coaxial structures 96128 and 96138 are small, magnet(s) may be integrated or attached to either or both of the coaxial structures 96128 and 96138 to help alignment and positioning to maintain the coaxial structures 96128 and 96138 being near to one another.

In operation, when a coaxial structure 96138 on the receiver side (see FIG. 96F) is not positioned near the coaxial structure 96128 of the transmitter side, as shown in FIG. 96E, the input impedance of the transmitter unit is akin to an open circuit (that is, the input impedance is infinite) and the receiver unit is not excited with the same RF field distribution (mode) so power is not leaked or otherwise transferred from the coaxial structure 96128. However, when the coaxial structure 96138 on a receiver side is positioned near the coaxial structure 96128, as shown in FIG. 96F, the receiver unit is excited with the same RF field distribution (mode).

Figure 96F:
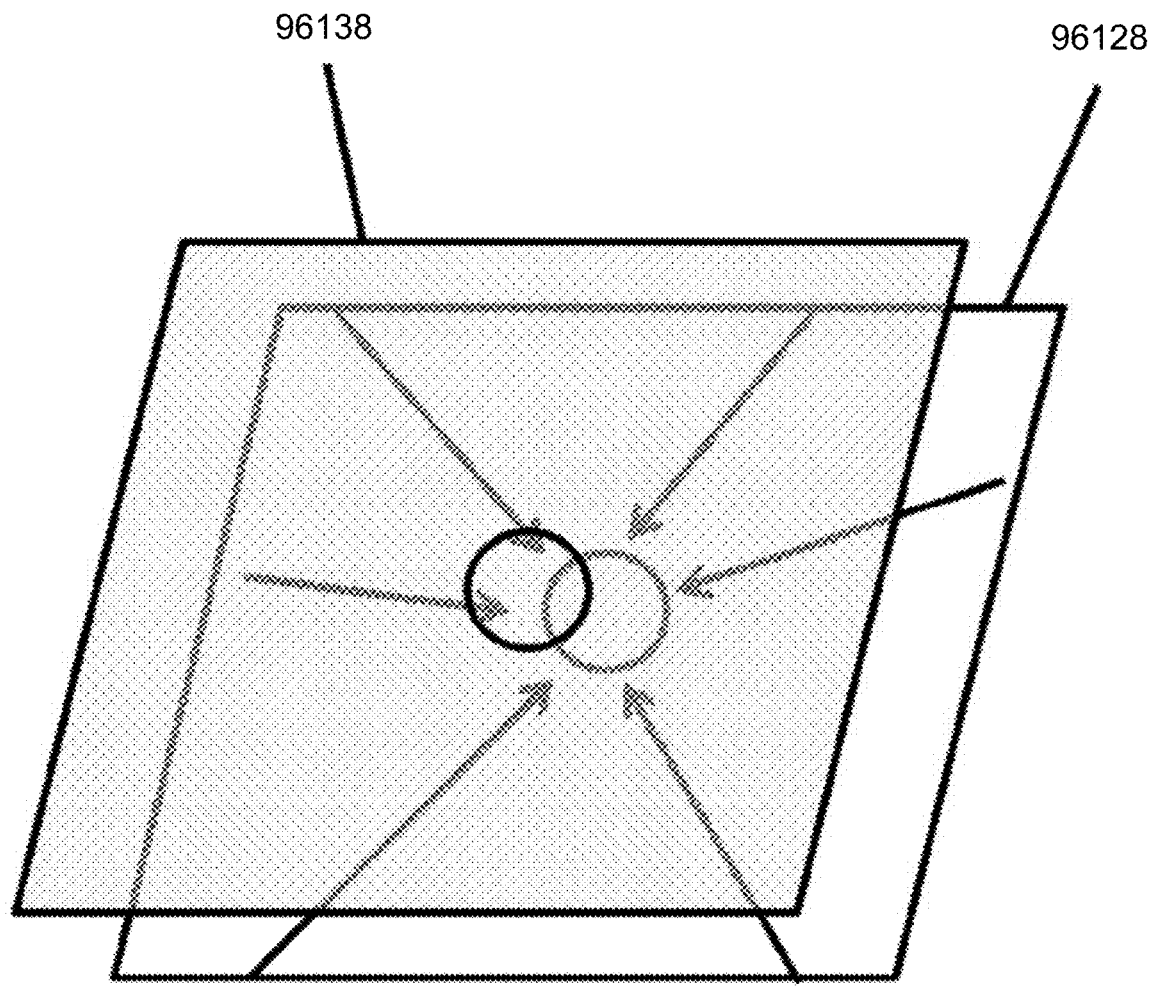

FIG. 96F is a schematic diagram showing the first coaxial structure 96128 of a transmitter and the second coaxial structure 96138 of a receiver, in accordance with an embodiment of the present disclosure. A more detailed construction of the first coaxial structure 96128 is presented in FIGS. 96A and 96B. A more detailed construction of the second coaxial structure 96138 is described in FIGS. 96C and 96D.

In illustrated embodiment, when the surfaces of the first coaxial structure 96128 and the second coaxial structure 96138 are positioned at a proximate distance from each other, a coaxial field radiation may be excited due to the presence of an electric current in each of the first coaxial structure 96128 and the second coaxial structure 96138. The coaxial field radiation that is excited or otherwise generated results in a distribution of the coaxial field radiation in an area around the first coaxial structure 96128 and the second coaxial structure 96138, and transfer of the current from the coaxial field radiation may be transferred from the first coaxial structure 96128 to the second coaxial structure 96138 for conversion by a receiver into power to charge a battery of an electronic device that is coupled to the second coaxial structure 96138. In the illustrated embodiment, the proximate distance may be any distance that is less than 10 mm, however it will be appreciated by a person having ordinary skill in the art that the proximate distance is not limited to 10 mm or less, and may be more than 10 mm without moving out from the scope of the disclosed embodiments.

In another embodiment, when the surfaces of the first coaxial structure 96128 and the second coaxial structure 96138 are touched to each other, a coaxial field radiation may be created due to the presence of electric current in each of the first coaxial structure 96128 and the second coaxial structure 96138. The coaxial field radiation is then distributed in an area around the first coaxial structure 96128 and the second coaxial structure 96138, and may be converted into power to charge a battery of an electronic device that is coupled to the second coaxial structure 96138.

In one embodiment, the surfaces of the first coaxial structure 96128 and the second coaxial structure 96138 may comprises magnetic properties and/or configured with magnets that may pull the surfaces of the first coaxial structure 96128 and the second coaxial structure 96138 towards each other such that the distance between the first coaxial structure 96128 and the second coaxial structure 96138 is less than a proximate distance. When the first coaxial structure 96128 and the second coaxial structure 96138 are proximately positioned, a coaxial field radiation may be generated due to the presence of current in the first coaxial structure 96128 and, optionally, the second coaxial structure 96138. When both coaxial structures 96128 and 96138 are in the same mode, as understood in the art, and placed in proximate position to one another, power transfers from the first coaxial structure 96128 to the second coaxial structure 96138. In an alternative embodiment, a structure, such as top surfaces 96104 and 96118 may have magnetic properties or be configured with magnets to provide attraction properties to bring and maintain the coaxial structures 96128 and 96138 in proximity to one another. The coaxial field radiation 96132 may then be converted into power to charge a battery of an electronic device using a suitable circuitry including a rectifier and a power converter.

Figure 96G:
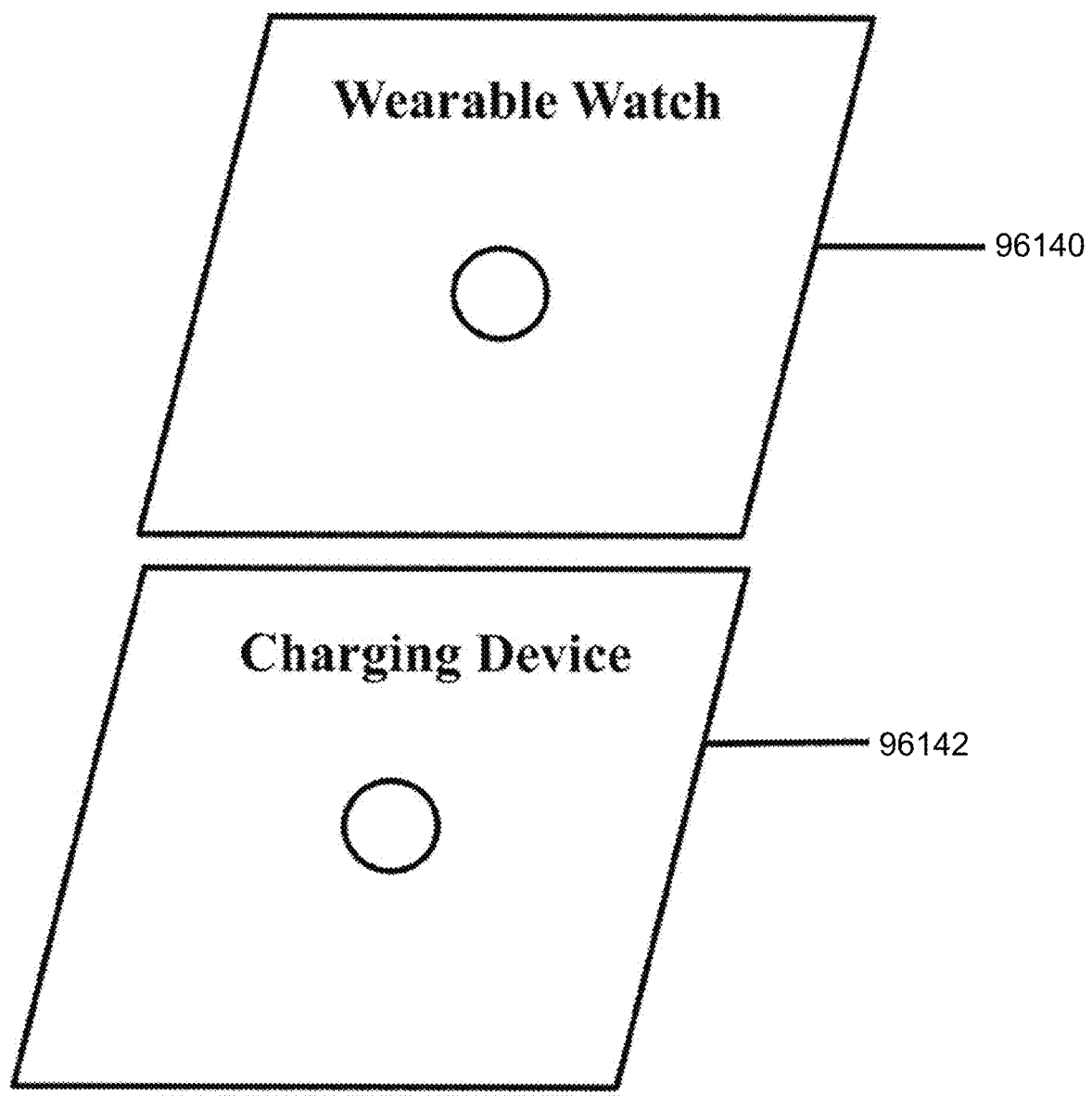

FIG. 96G is a schematic diagram showing an electronic device 96140, in accordance with an embodiment of the present disclosure. An exemplary electronic device 96140 may be positioned near a charging device 96142. The electronic device 96140 includes a second coaxial structure mounted on the electronic device 96140 for charging a battery in the electronic device 96140. The charging device 96142 includes a first coaxial structure. A more detailed construction of the first coaxial structure is described in FIGS. 96A and 96B. A more detailed construction of the second coaxial structure is described in FIGS. 96C and 96D.

The electronic device 96140 may include a second coaxial structure, as well as a battery that is to be charged in accordance with the present disclosure. In some embodiments, the electronic device 96140 comprises circuitry including one or more switch elements, a rectifier, and a power converter, where the rectifier and power converter may be combined. In some embodiments, the second coaxial structure may comprise circuitry including one or more switch elements, a rectifier, and a power converter, where the rectifier and power converter may be combined. The second coaxial structure may be positioned within the electronic device 96140 and connected to the battery.

The charging device 96142 may include a second coaxial structure. When the electronic device 96140 and the charging device 96142 are brought close to each other such that the distance between the electronic device 96140 and the charging device 96142 is less than the proximate distance, then a coaxial field radiation is generated due to presence of electric currents at least the first and second coaxial structure.

The switch elements may be capable of detecting coaxial field, and directing the radiations to the rectifier when the detected radiations correspond to a power level that exceeds a threshold. For example, in some embodiments, the switch may direct the received coaxial field to the rectifier when the coaxial radiations received is indicative of a wireless power transfer greater than a pre-defined threshold limit. In other embodiments, the switch may direct the received coaxial field when they are indicative of a wireless power transfer greater than a pre-defined limit. This switching acts to protect from damaging electronic components of the electronic device 96140 by preventing a power surge from being applied thereto.

The generated coaxial field is then converted to a power signal by a power conversion circuit, such as a rectifier circuit for charging a battery of the electronic device 96140. In some embodiments, the total power output is less than or equal to 1 Watt to conform to Federal Communications Commission (FCC) regulations part 15 (low-power, non-licensed first coaxial structures). In an embodiment, the rectifier may include diodes, resistors, inductors, and/or capacitors to rectify alternating current (AC) voltage generated to direct current (DC) voltage, as understood in the art. In some embodiments, the rectifier and switch may be placed as close as is technically possible to minimize losses. After rectifying AC voltage, DC voltage may be regulated and/or conditioned using power converter. Power converter can be a DC-DC converter, which may help provide a constant voltage output, regardless of input, to an electronic device or, as in this embodiment, to a battery.

Figure 96H:
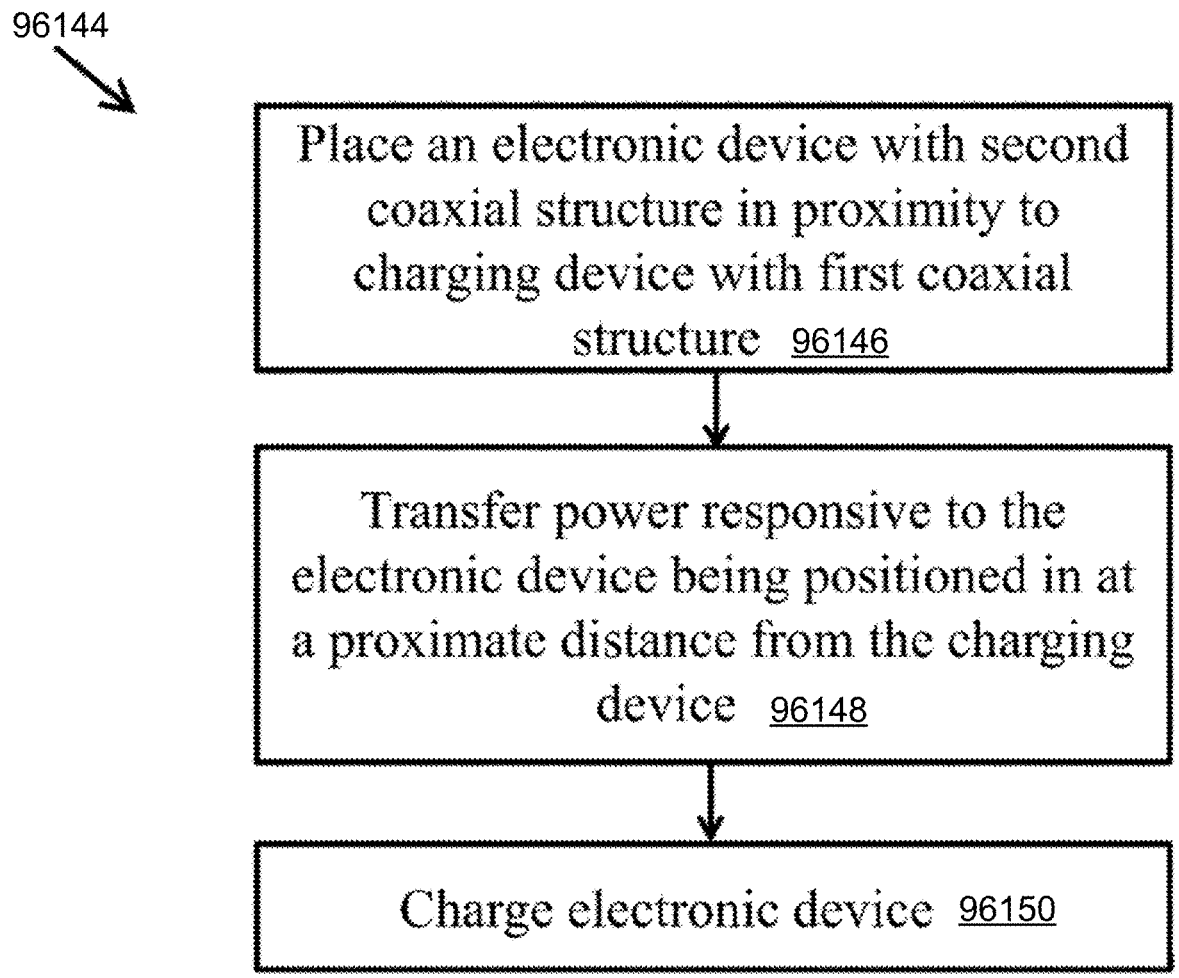

FIG. 96H is a flow diagram 96144 illustrating operation of charging of an electronic device in accordance with one or more embodiments of the present disclosure.

At step 96146, an electronic device with a second coaxial structure may be placed in proximity with a charging device. The second coaxial structure may be positioned within or attached to the body of the electronic device. The second coaxial structure may be configured to keep desired currents inside and undesired current outside and thereby maintaining an electric current in the second coaxial structure.

The charging device may be provided with a first coaxial. The first coaxial structure may be positioned within or attached to the body of the electronic device. The first coaxial structure may be configured to keep desired currents inside and undesired current outside and thereby maintaining an electric current in the first coaxial structure.

At step 96148, in response to the electronic device being positioned in a proximate distance to the charging device, power may be transferred from the charging device to the electronic device. In one embodiment, the proximate distance is less than about 10 mm. Other distances to be within a proximate distance are also possible. Upon a planar surface of the first coaxial structure being proximately positioned to a planar surface of the second coaxial structure, the first planar coaxial structure excites the same RF field distribution (mode) on the second coaxial structure to transfer a charge from the first coaxial structure to the second coaxial structure.

At step 96150, the electronic device may be charged by converting the coaxial field radiation into a suitable form of energy that is used to power the electronic device. The generated coaxial radiation may be converted to a power signal by a power conversion circuit for example rectifier circuit for charging a battery of the electronic device. The rectifier may include diodes, resistors, inductors, and/or capacitors to rectify alternating current (AC) voltage generated to direct current (DC) voltage, as understood in the art. In some embodiments, the total power output is less than or equal to 1 Watt to conform to Federal Communications Commission (FCC) regulations part 15 (low-power, non-licensed first coaxial structures).

FIGS. 96A-96H illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 96A-96H.

Presented below are example embodiments of antenna for near field wireless power charging.

In some embodiments, an example wireless charging system comprises a first coaxial structure configured to carry an RF signal present on a conductor, and a second coaxial structure configured to be excited by an RF signal from the first coaxial structure, power being transferred from the first coaxial structure to the second coaxial structure when the first coaxial structure and the second coaxial structure are placed in proximity to each other.

In some embodiments, the first coaxial structure is situated in a charging device and the second coaxial structure is situated in an electronic device, the power being transferred in response to a surface of the electronic device being touched to a surface of the charging device.

In some embodiments, the proximity of first and second coaxial structures is less than about 10 mm.

In some embodiments, the first and second coaxial structures include respective planar surfaces configured to be positioned in proximity to each other.

In some embodiments, the planar surfaces are positioned in proximity to each other and in parallel with one another.

In some embodiments, the first coaxial structure comprises a substrate, and where the substrate comprises a metamaterial.

In some embodiments, the has a metallic core formed at a center location of the substrate.

In some embodiments, the second coaxial structure comprises a substrate, and where the substrate comprises a metamaterial.

In some embodiments, the has a metallic core formed at a center location of the substrate of the second coaxial structure.

In some embodiments, the apparatus further comprises a magnet attached to each of the charging device and the electronic device so as to cause the electronic device and the charging device to be pulled towards each other to at least a proximate distance that causes excitation.

In some embodiments, the electronic device is a wearable watch.

In some embodiments, an example method for charging an electronic device in a wireless charging system, the method comprises upon a first planar coaxial structure being proximately positioned to a second planar coaxial structure, exciting the first planar coaxial structure to allow for the transfer power from the first planar coaxial structure to the second planar coaxial structure.

In some embodiments, the first coaxial structure is situated in a charging device and the second coaxial structure is situated in an electronic device. Power is transferred in response to a surface of the electronic device being proximately positioned to a surface of the charging device to charge a battery of the electronic device.

In some embodiments, an example wireless charging system comprises a second coaxial structure configured to be excited by an RF signal. Power is transferred from a first coaxial structure having an RF signal present to the second coaxial structure when the first coaxial structure and the second coaxial structure are placed in proximity to each other.

In some embodiments, an example wireless charging system comprises a first coaxial structure carrying an RF signal. Power is transferred from the first coaxial structure to a second coaxial structure when the first coaxial structure and the second coaxial structure are excited in proximity to each other.

Figure 97A:
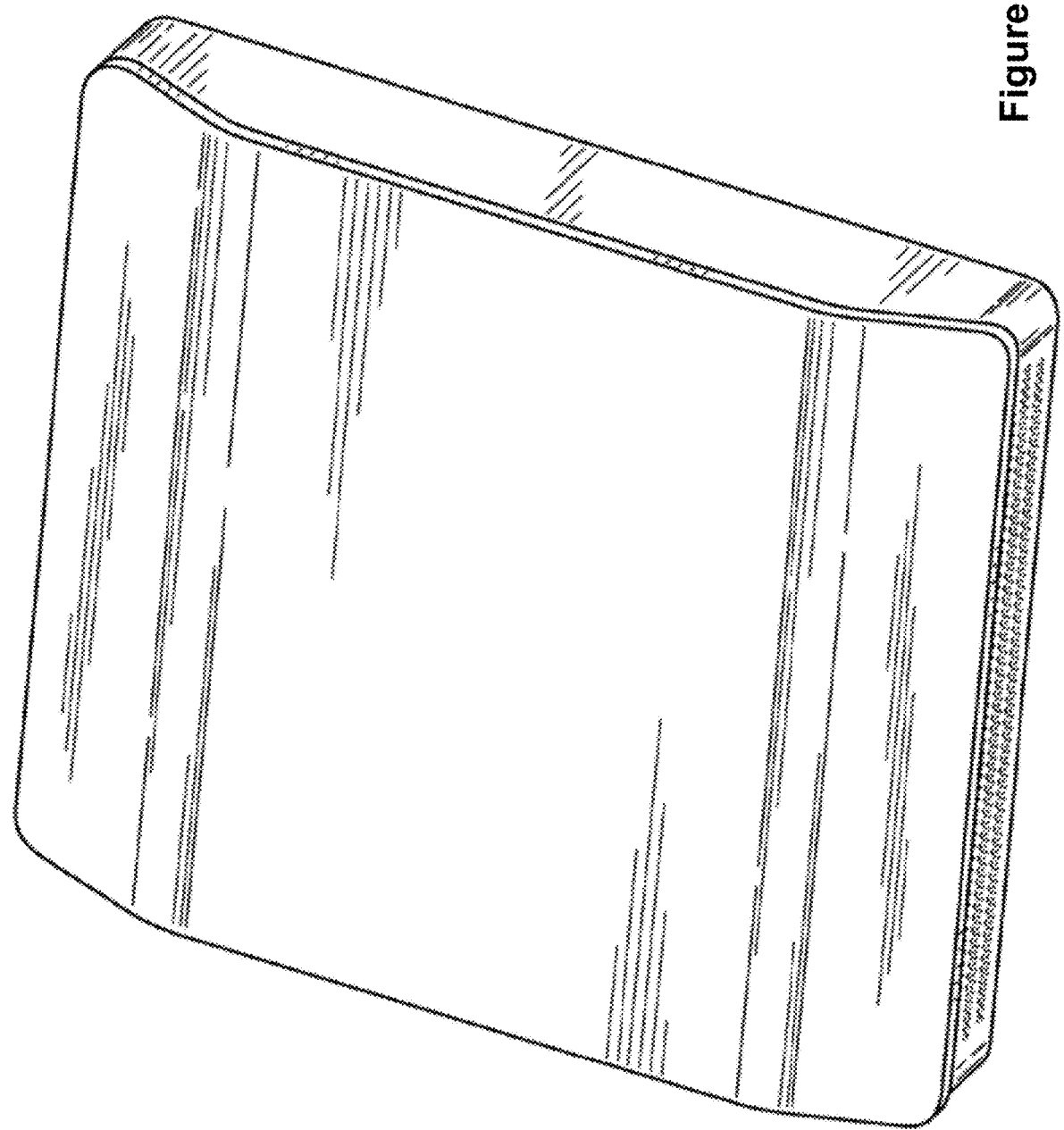
Figure 97C:
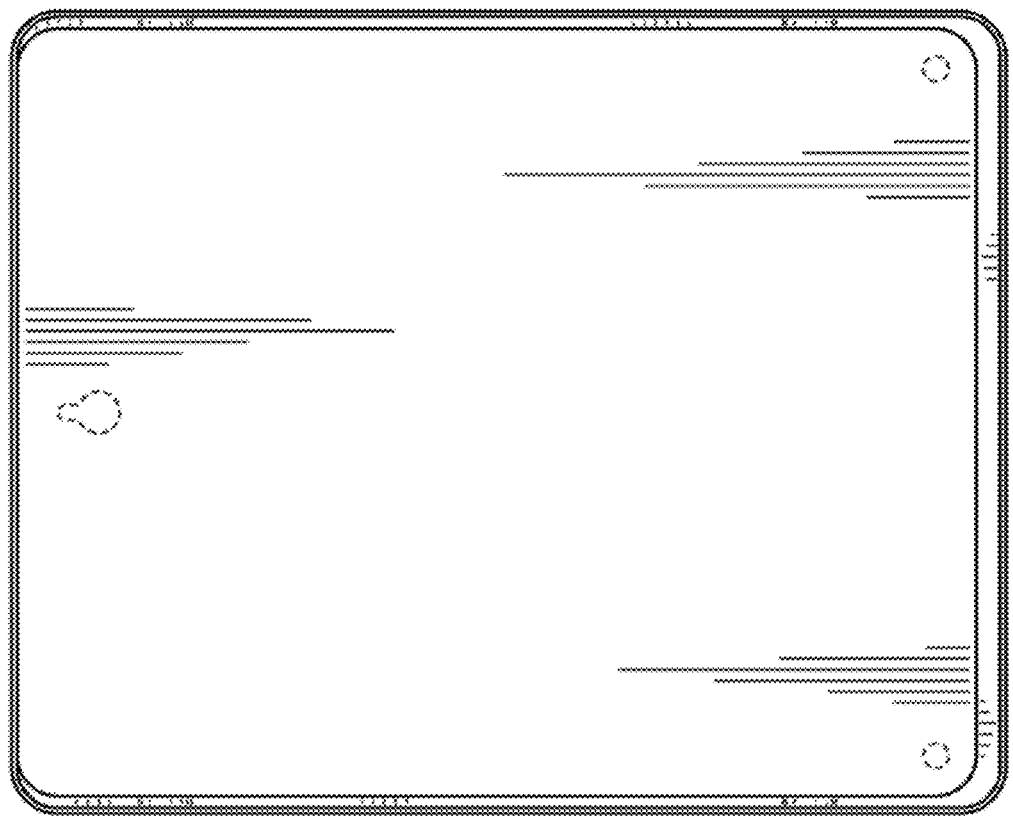
Figure 97B:
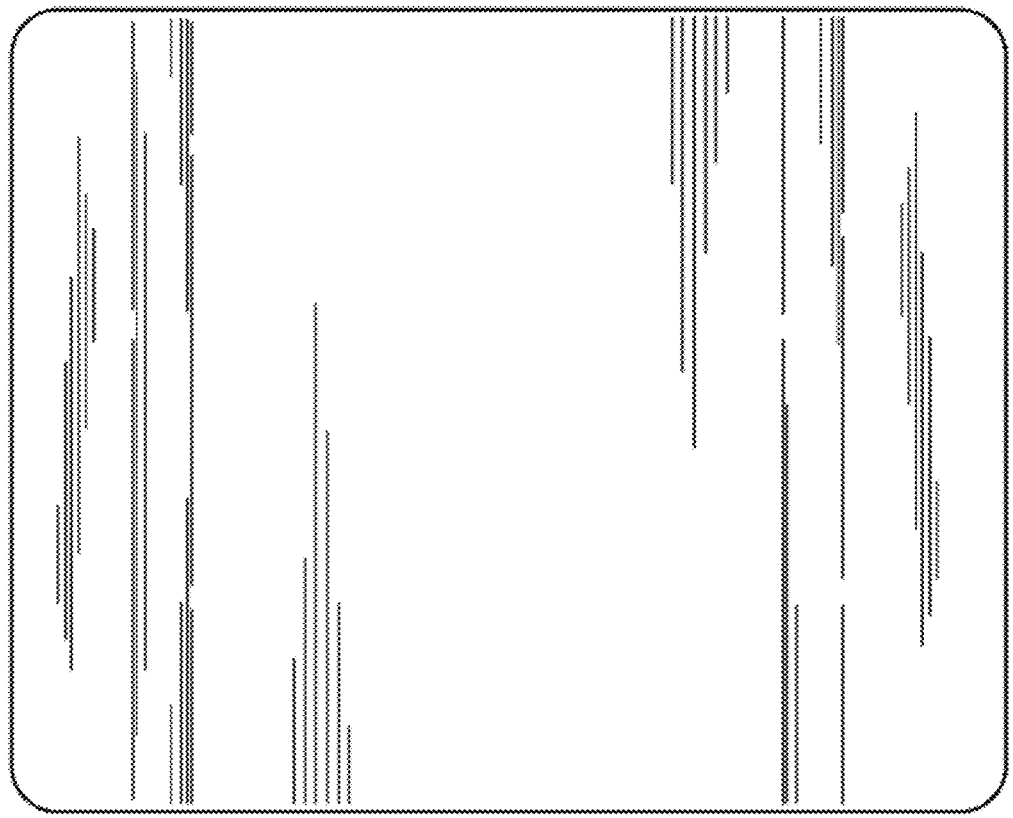
Figure 97F:
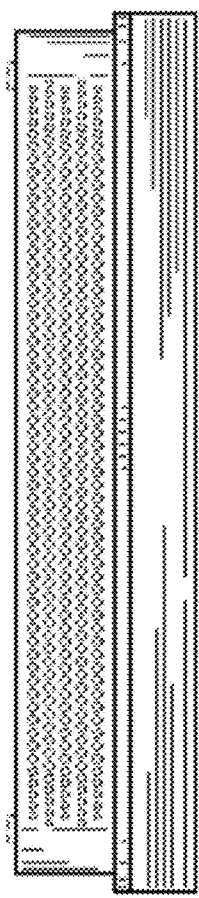
Figure 97G:
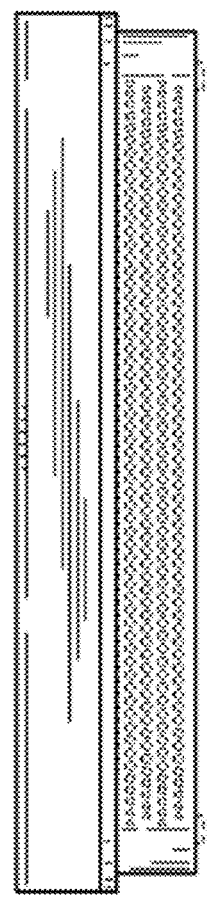
Figure 97E:
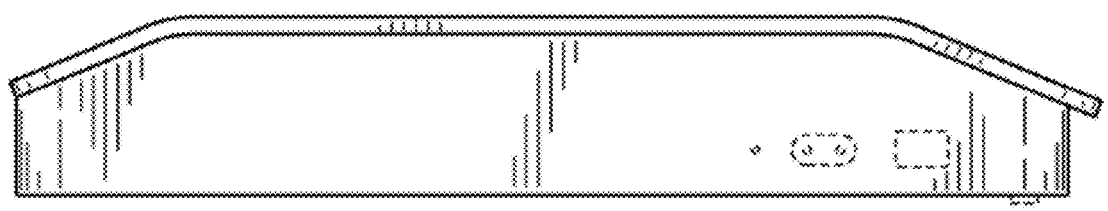
Figure 97D:
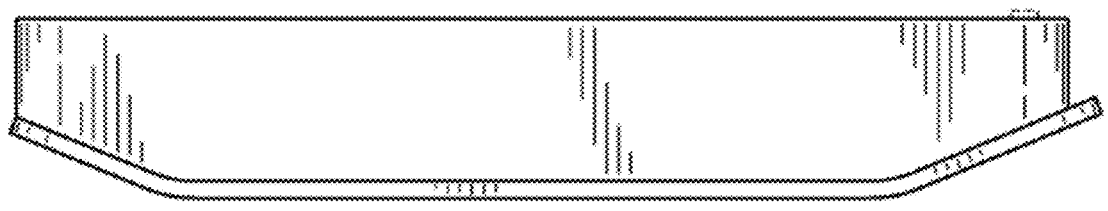

FIGS. 97A-97G illustrate examples of electronic devices, in accordance with some embodiments. Specifically, FIG. 97A is a perspective view of an electronic device showing our new design; FIG. 97B is a front view of the electronic device; FIG. 97C is a back view of the electronic device; FIG. 97D is a right-side view of the electronic device; FIG. 97E is a left-side view of the electronic device; FIG. 97F is a top view of the electronic device; and FIG. 97G is a bottom view of the electronic device. The broken lines are included for purposes of illustrating a portion of the electronic device that forms no part of the claimed design. The ornamental design for an electronic device, as shown and described.

FIG. 98 illustrates an example of display screen or portion thereof with a graphical user interface, in accordance with some embodiments. The sole figure (FIG. 98) is a front view of a display screen or portion thereof with a graphical user interface showing my new design. The broken lines illustrate numerous unclaimed features including the display screen, portions of the graphical user interface, and portions of an electronic device. In other words, none of the broken lines form part of the claimed design. The ornamental design for a display screen or portion thereof with a graphical user interface, substantially as shown and described.

FIGS. 99A and 99B illustrate examples of devices, apparatus, and methods for external or internal receiver for smart mobile devices, in accordance with some embodiments.

FIG. 99A illustrates internal hardware 99100, where receiver 99102 may be used for wireless power transmission in smartphones 99110. FIG. 3 then shows a first embodiment where smartphone 99110 may include receiver 99102, as the one described in FIG. 1, embedded around the internal edge of smartphone 99110's case. Receiver 99102 may include an array of antenna elements 99104 strategically distributed on the grid area shown in FIG. 99A. The number and type of antenna elements 99104 may be calculated according to smartphone 99110's design.

Particularly, internal hardware 99100 in the form of a printed film 99112 or flexible printed circuit board (PCB) may include different components, such as a plurality of printed antenna elements 99104 (connected with each other in serial, parallel, or combined), rectifier 99106, and power converter 99108 elements, as shown in FIG. 1. Printed film 99112 may be pasted or otherwise attached to any suitable electronic devices, such as smartphones 99110 or tablets and may be connected through any suitable interfaces such as flexible cables 99114. Printed film 99112 may exhibit some benefits, one of those benefits may be that sections can be cut from it to meet specific smart mobile device sizes and/or requirements.

According to one embodiment, the spacing between antenna elements 99104 for receivers 99102 may range from about 5 nm to about 12 nm, being most suitable about 7 nm. Additionally, the optimal amount of antenna elements 99104 that may be used in receivers 99102 for smartphones 99110 may be ranging from about 20 to about 30, being most suitable about 25; however, the amount of antennas within receivers 99102 may vary according to smartphone 99110's design and size. Antenna elements 99104 may be made of different conductive materials such as cooper, gold, and silver, among others. Furthermore, antenna elements 99104 may be printed, etched, or laminated onto any suitable non-conductive flexible substrate, such as flexible printed circuit board (PCB), among others. The disclosed configuration and orientation of antenna elements 99104 may exhibit a better reception, efficiency, and performance of wireless charging.

FIG. 99B illustrates external hardware 99116 in the form of cover 99118 including receiver 99102, which may be connected through flexible cables 99114 to battery of any suitable smart mobile device, such as smartphones 99110. In one embodiment, cover 99118 including receiver 99102 may be a laptop cover, camera cover, GPS cover, and tablet cover, among other such options.

Furthermore, FIG. 99B shows an embodiment where smartphone 99110 may include receiver 99102, as the one described in FIG. 1. However, in this embodiment, smartphone 99110 may include cover 99118 with receiver 99102 to provide wireless power to smartphone 99110. Cover 99118 may be made out of plastic rubber or any other suitable material for covers 99118, and may include an array of antenna elements 99104 located around the edges of cover 99118 for optimal reception. Number, spacing and type of antenna elements 99104 may be calculated according to smartphone 99110 design and size, as described in FIG. 99A.

FIGS. 99A and 99B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 99A and 99B.

Presented below are example embodiments of external or internal receiver for smart mobile devices.

In some embodiments, an example method for wireless power transmission to a smart mobile device, comprising the steps of: transmitting power RF waves from a pocket-forming transmitter having a radio frequency integrated circuit, antenna elements, a microprocessor and communication circuitry; generating pockets of energy from the transmitter to converge in 3-d space at a predetermined location; integrating a receiver having antenna elements and communication circuitry with the smart mobile device; converting the pockets of energy from the transmitter to the integrated receiver to power the smart mobile device.

In some embodiments, the receiver is embedded around an internal edge of the smart mobile device.

In some embodiments, the antenna elements are distributed on a grid around an internal edge of the smart mobile device.

In some embodiments, the receiver is embedded around an internal edge of the smart mobile device including an array of the antenna elements strategically distributed on a predetermined grid on an outwardly facing surface of the receiver.

In some embodiments, the receiver antenna elements number and type are calculated according to a smart mobile device configuration, In some embodiments, the further includes the step of connecting an output of the receiver to a battery for the smart mobile device.

In some embodiments, the receiver is formed on a printed film including printed antenna elements connected in serial, parallel or combination, a rectifier and a power converter and further including the step of pasting the printed film to an internal edge of the smart mobile device.

In some embodiments, the spacing between receiver antenna elements is approximately 5 mm to 12 mm with 7 mm most suitable for receiving the pockets of energy.

In some embodiments, the receiver antenna elements are made from conductive materials of copper, silver or gold further including the step of etching or laminating the receiver antenna elements onto a non-conductive flexible substrate band.

In some embodiments, the receiver is mounted on a. peripheral edge cover of a predetermined thickness and circumference conforming to generally an outer edge of the smart mobile device with an array of the antenna elements spaced apart from each other a predetermined distance on an inner surface of the cover.

In some embodiments, the spacing, type and number of antenna elements located around the edges of the inner surface of the cover are calculated according to the smart mobile device design, size and operating parameters.

In some embodiments, the method further includes the steps of selecting the transmitter to send pockets of energy to the receiver when the smart mobile device comes within a predetermined charging range of the transmitter; verifying a battery charge level of smart mobile device; and powering or charging the smart mobile device to a full battery charge level.

In some embodiments, the cover with the receiver is a laptop cover, camera cover, GPS cover, a tablet cover or an iPod cover.

In some embodiments, the computer system transmitter includes adaptive pocket-forming for dynamically adjusting pocket-forming to regulate power on the receiver of at least one peripheral electronic device within predetermined range of the transmitter through communication signals between the transmitter and receiver communication circuitry.

In some embodiments, an example receiver for wireless power transmission to a smart mobile device, comprising a flexible housing of a predetermined configuration mounted on the smart mobile device, an array of antenna elements spaced apart a predetermined distance from one another around the flexible housing for optimal reception of power RF waves in the form of pockets of energy generated by a pocket-forming transmitter, and a rectifier connected to a power convertor for converting the pockets of energy into a charging or powering voltage for the smart mobile device.

In some embodiments, the flexible housing is a flexible printed circuit board connected to the antenna elements, rectifier and power converter.

In some embodiments, the antenna elements are printed antenna elements on the flexible housing for collecting the power RF waves for charging the smart mobile device.

In some embodiments, the power converter is a DC-DC converter to provide a constant voltage output to the smart mobile device.

In some embodiments, the flexible housing includes a flexible cable for connection to a battery in the smart mobile device and provides a cover for a smartphone, iPad, iPod, tablet, a laptop computer, a camera, a GPS unit or other such smart mobile device requiring battery power.

In some embodiments, the antenna elements spaced apart a predetermined distance from each other and are facing out from an inner surface of the flexible housing when used as a cover for the mobile device and the antenna elements are facing out from the outer surface of the flexible housing when embedded around an internal edge of the smart mobile device for optimum reception of the power RF waves.

FIGS. 100A-100C illustrate examples of devices, apparatus, and methods for systems and methods for device and power receiver pairing.

FIG. 100A is a flowchart of a charge request process 10100, according to an exemplary embodiment. Process 10100 may start when an electronic device, which includes a GUI suitable for interacting with a wireless charging system, communicates 10102 with a power transmitter. During the communication the electronic device may send information to the power transmitter including device ID and charge status, amongst others. The power transmitter may update its database and may send a copy to the electronic device including the IDs of available power transmitters within the system.

Then, the electronic device may check 10104 if its ID is already associated with the ID of a power receiver.

If the electronic device is not already paired, the electronic device may start scanning 10106 for power receivers. All the power receivers in the system may broadcast advertisement messages at any time. The advertisement messages may include a unique 32-bit device ID and a system ID or UUID (Universally Unique Identifier). In some embodiments, the advertisement messages may include additional information. The electronic device may be capable of monitoring the signal strength of the ads being broadcasted by the different power receivers and keep track of the proximity of the power receivers to the electronic device.

When the electronic device detects that a power receiver is within a suitable range of proximity for a suitable amount of time, it may proceed to check the database to determine if the power receiver is not already paired with another electronic device. If the power receiver is not already paired with another device the electronic device may update the database with the association of electronic device's ID with the ID of the power receiver during pairing 10108. Then, the electronic device may send a copy of the updated database to the power transmitter.

Once the electronic device is paired, a user, through the GUI in the electronic device, or the electronic may send a power request 10110 to the power transmitter. If the power transmitter finds it suitable to provide power to the electronic device, it may turn on 10112 the power receiver.

Afterwards, the power transmitter may aim the antenna array to the power receiver associated with the electronic device and start sending energy to the power receiver. The power receiver may then start charging 10114 the electronic device. Once the electronic device is charged, the process may end.

FIG. 100B is a flowchart of a pairing process 10116, according to an exemplary embodiment. Pairing process 10116 may start when an electronic device identifies 10118 available power receivers in a system. Then, using the signal strength the electronic device may be capable of monitoring 10120 the proximity of each of the available power receivers. The electronic device may constantly check 10122 if one of the power receivers is within a suitable range of proximity to perform the pairing. If none of the power receivers is within the range, the electronic device may continue to monitor the proximity of the power receivers. If one of the power receivers is within range the electronic device may proceed to check the database 10124 to determine if the power receiver is already paired 10126. If the power receiver is associated with another electronic device, the electronic device may continue to scan for power receivers and track their proximity. If the power receiver has no associations, the electronic device may commence the pairing protocol, and may start 10128 a timer and continuously monitor 10130 the proximity of the power receiver. After a suitable time lapse the electronic device may check 10132 if the power receiver is still within the suitable range. If the power receiver is not within the suitable proximity range the electronic device may continue to track the proximity of the power receivers. If the power receiver is still within a suitable proximity range the electronic device may update 10134 the database, associating its ID with the ID of the power receiver.

In some embodiments, the GUI in the electronic device may analyze several signal strength measurements (RSSI) over the predetermined time lapse before updating the database. In some embodiments, the GUI may compute and average of the signal strength measurements and compare it with predefined reference values. After updating the information in an internal database, the electronic device may send 10136 a copy of the updated database to the power transmitter and pairing process 10116 may end.

FIG. 100C is a flowchart of an unpairing process 10138, according to an exemplary embodiment. Unpairing process 10138 may start when an electronic device that is paired to a power receiver is constantly monitoring 10140 the proximity of the power receiver to check 10142 if the power receiver is beyond pairing range. If there is no change, the electronic device may continue to monitor 10140 the proximity of the paired power receiver. If there is a change, the electronic device may start 10144 a timer. After a suitable time lapse the electronic device may check 10146 the signal strength of the ads broadcasted by the power receiver to determine 10148 if the power receiver is still within a suitable range. This may be done by the GUI in the electronic device. The GUI may analyze several signal strength measurements (RSSI) over the predetermined time lapse. In some embodiments, the GUI may compute and average of the signal strength measurements and compare it with predefined reference values.

If the electronic device determines that the power receiver is still within the suitable proximity range it may continue to normally monitor the proximity of the power receiver. If the electronic device determines that the power receiver is not within the suitable proximity range any more the electronic device may proceed to update 10150 the internal database and subsequently send 10152 the updated version of the data base to the power transmitter. In a parallel process, the electronic device may start to scan and identify 10154 available power receivers and continuously monitor 10156 the proximity of the available power receivers and the unpairing process 10138 may end.

EXAMPLES

In example #1 a smartphone including a suitable GUI for interacting with a wireless charging system is paired with a power receiver embedded in a cellphone cover. At a first moment, the smartphone communicates with the power transmitter, is authenticated, receives the power receivers' database and starts scanning for power receiver devices. After scanning, the smartphone finds 3 available power receivers. It tracks the proximity of the power devices based on signal strength. At a second moment, one of the power receivers is placed near the smartphone. The smartphone determines that the power receiver is within the suitable range and starts the pairing process. After a few seconds it checks the signal strength again and it determines that the power receiver is still within an acceptable distance for pairing. Then, the smartphone updates its internal database and sends a copy of the updated database to the power transmitter. At a third moment, the smartphone sends a power request to the power transmitter. The power transmitter searches the database to determine which power receiver is associated with the smartphone, then it directs the antenna array towards the power receiver that is associated with the smartphone, and starts transmitting power.

FIGS. 100A-100C illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 100A-100C.

Presented below are example embodiments of systems and methods for device and power receiver pairing.

In some embodiments, an example method for pairing a plurality of user devices and a plurality of transmitters in a wireless power network, comprising communicating through at least one user interface resident on ones of the user devices with at least one of the plurality of transmitters capable via provided controlled radio frequency waves that produce a plurality of energy pockets, providing to a database associated with the at least one of a plurality of network transmitters information regarding the ones of the user devices, and uniquely pairing the ones of the user devices with ones of the at least one of a plurality of network transmitters in accordance with the user device information and in order to receive, at the paired ones of the user devices, energy provided by the energy pockets.

In some embodiments, the user device information comprises at least one selected from the group consisting of a user device ID, current battery status, charge history information, proximity to the at least one transmitter, and combinations thereof.

In some embodiments, the method further comprises providing at least one advertisement for display on the user device.

In some embodiments, the pairing of the user device with the at least one of a plurality of network transmitters is in accordance with the proximately of the user device to ones of the at least one of In some embodiments, the method further comprises communicating a power request to ones of the at least one of a plurality of network transmitters.

In some embodiments, the user device comprises a power receiver identifiable by the at least one of a plurality of network transmitters.

In some embodiments, the pairing is effective after the user device has been in communication with the at least one of a plurality of network transmitters over a predetermined period of time.

In some embodiments, the predetermined period of time is set by the user.

In some embodiments, the predetermined period of time is greater than 5 seconds.

In some embodiments, the user device measures the signal strength of the at least one of a plurality of network transmitters during the predetermined period of time.

In some embodiments, an example system for pairing two devices in a wireless power network, comprising at least one user interface provided on a user device in communication with at least one of a plurality of network transmitters capable of providing controlled radio frequency waves to produce a plurality of energy pockets, at least one database associated with the at least one of a plurality of network transmitters and information regarding the user device, and at least one server for comparing the information comprising at least one user device identifier with at least one identifier of ones of the at least one of the plurality of network transmitters to facilitate pairing of the at least one user device and the at least one of a plurality of network transmitters.

In some embodiments, the user device information comprises at least one selected from the group consisting of a user device ID, current battery status, charge history information, proximity to the at least one transmitter, and combinations thereof.

In some embodiments, the system further comprises at least one advertisement for display on the user device.

In some embodiments, the pairing of the user device with the at least one of a plurality of network transmitters is in accordance with the proximately of the user device to ones of the at least one of a plurality of network transmitters.

In some embodiments, the at least one user interface resident on a user device communicates a power request to ones of the at least one of a plurality of network transmitters.

In some embodiments, the user device comprises a power receiver identifiable by the at least one of a plurality of network transmitters.

In some embodiments, the at least one user interface resident on a user device pairs the user device with the at least one of a plurality of network transmitters after a predetermined period of time.

In some embodiments, the user device measures the signal strength of the at least one of a plurality of network transmitters during the predetermined period of time.

Figure 101A:
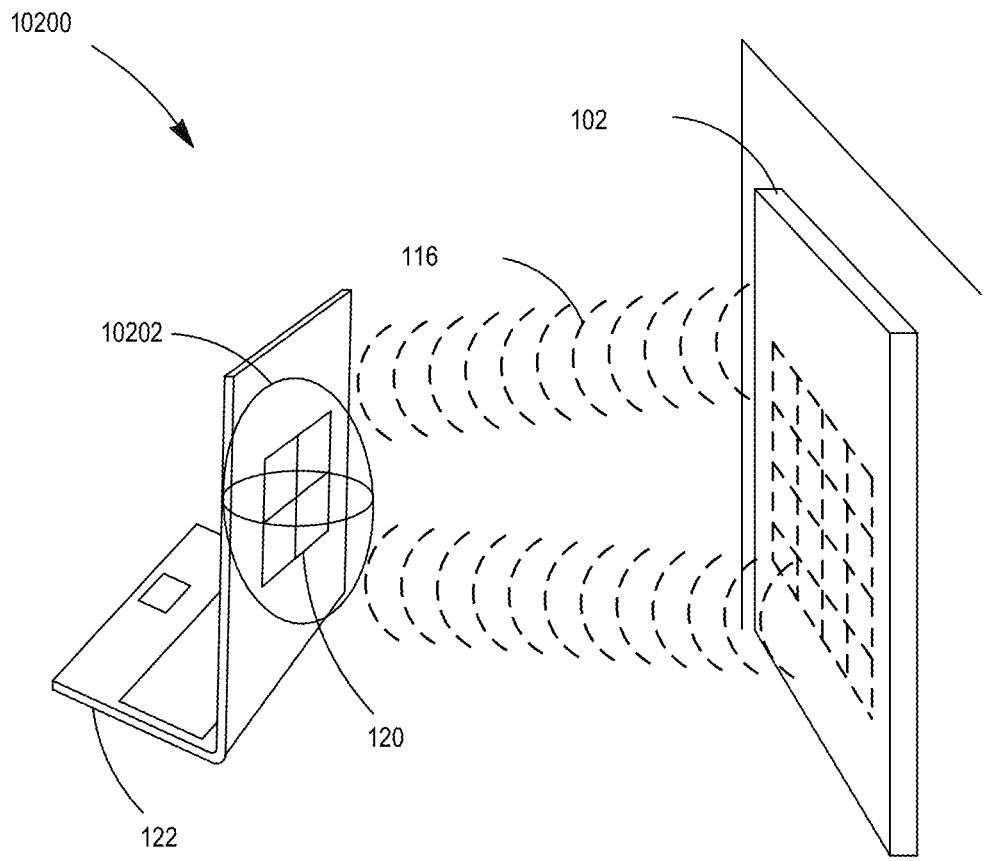

FIGS. 101A-11D illustrate examples of devices, apparatus, and methods for home base station for multiple room coverage with multiple transmitters, in accordance with some embodiments.

FIG. 101A illustrates wireless power transmission 10200 using pocket-forming. A transmitter 102 may transmit controlled Radio RF waves 116 which may converge in 3-d space. These Radio frequencies (RF) waves may he controlled through phase and/or relative amplitude adjustments to form constructive and destructive interference patterns (pocket-forming). Pockets of energy 10202 may he formed at constructive interference patterns and can be 3-dimensional in shape whereas null-spaces may be generated at destructive interference patterns. A receiver 120 may then utilize pockets of energy 10202 produced by pocket-forming for charging or powering an electronic device, for example a laptop computer 122 and thus effectively providing wireless power transmission 10200. In other situations, there can be multiple transmitters 102 and/or multiple receivers 120 for powering various electronic equipment for example smartphones, tablets, music players, toys and others at the same time. In other embodiments, adaptive pocket-forming may be used to regulate power on electronic devices.

Figure 101B:
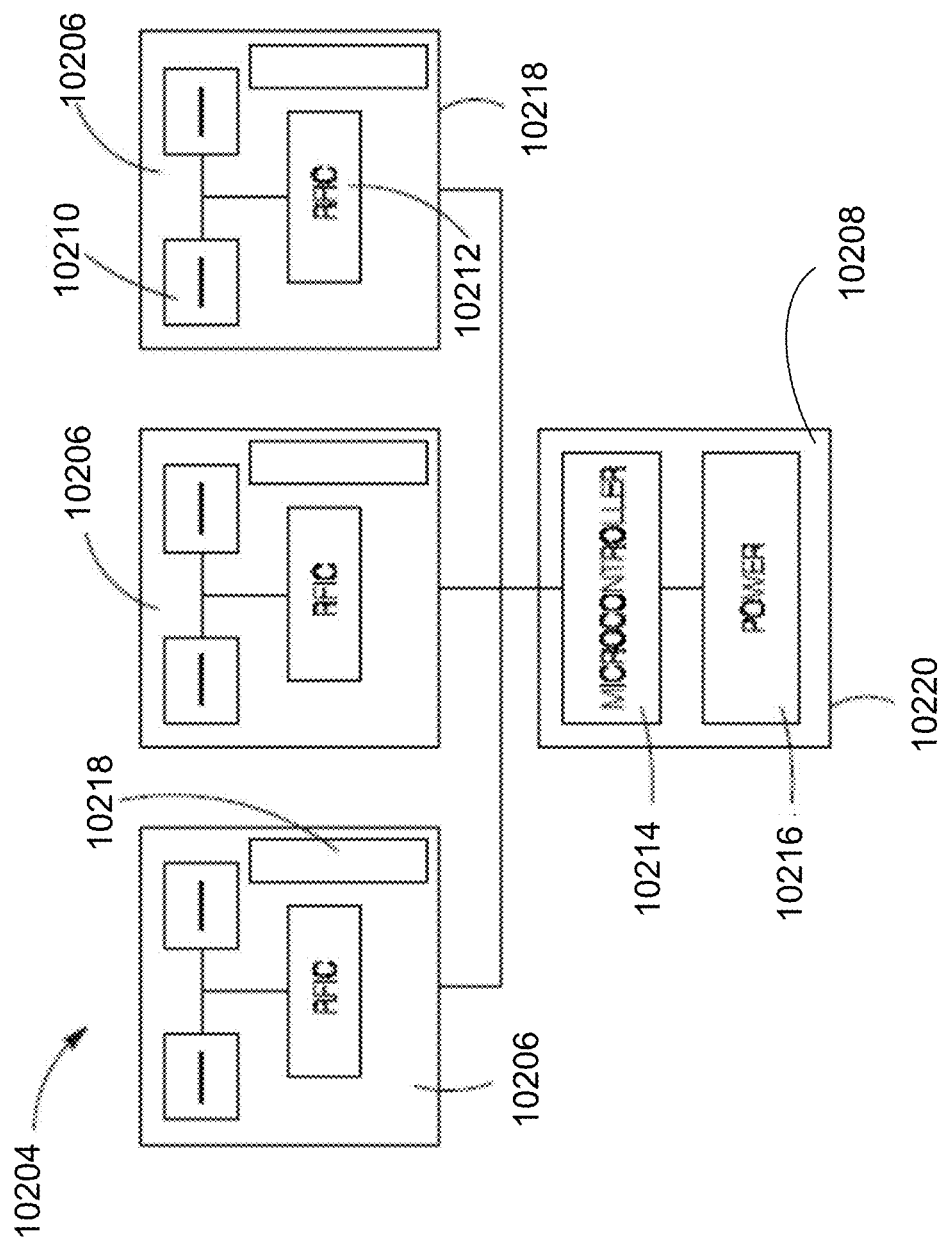

FIG. 101B depicts a block diagram of a wireless power system 10204, which may include a plurality of wireless power transmitter 10206 connected to a single base station 10208. transmitters 10206 may include one or more antenna elements 10210, one or more Radio frequency integrated circuit (RFIC) 10212, a communication component 10218 and a housing 10220, which may allocate all the components previously mentioned. Base station 10208 may include one or more microcontroller 10214, a power source 10216 and a housing 10220, which may allocate all the components previously mentioned. Components in wireless power system 10204 and base station 10208 may be manufactured using meta-materials, micro-printing of circuits, nano-materials, and the like.

Base station 10208 may be located. in variety of locations where transmitters 10206 may stay connected to it. Such connection may include a variety of connections, which may include coaxial cable, phone cable, LAN cable, wireless connection among others. The connection between base station 10208 and transmitters 10206 aims to establish a link between. RFC 10212 and microcontroller 10214, as well as the power source 10216 connection.

Microcontroller 10214 may control a variety of features of RFIC 10212 such as, time emission of pocket-forming, direction of the pocket-farming, bounce angle, power intensity and the like. Furthermore, microcontroller 10214 may control multiple pocket-forming over multiple receivers 10$ or over a single receiver 120. In addition, microcontroller 10214 may manage and control communication protocols and signals by controlling communication component 10218. Thus microcontroller 10214 may drive the foregoing features in several transmitters 10206 at the same time.

Base station 10208 may be fed by a power source 10216 which in turn may feed to transmitters 10206. Power source 10216 may include AC or DC power supply. Voltage, power and current intensity provided by power source 10216 may vary in dependency with the required power to be transmitted. Conversion of power to radio signal may be managed by microcontroller 10214 and carried out by RFIC 10212, which may utilize a plurality of methods and components to produce radio signals in a wide variety of frequencies, wavelength, intensities and other features. As an exemplary use of a variety of methods and components for radio signal generation, oscillators and piezoelectric crystals may be used to create and change radio frequencies in different antenna elements 10210. In addition, a variety of filters may be used for smoothing signals as well as amplifiers for increasing power to be transmitted.

Furthermore, RFIC 10212, microcontroller 10214, communication component 10218 and the rest of electronic components may be built in solid state circuits for increasing reliability in wireless power system 10204. Others techniques for increasing reliability of electronic components may be used.

Figure 101C:
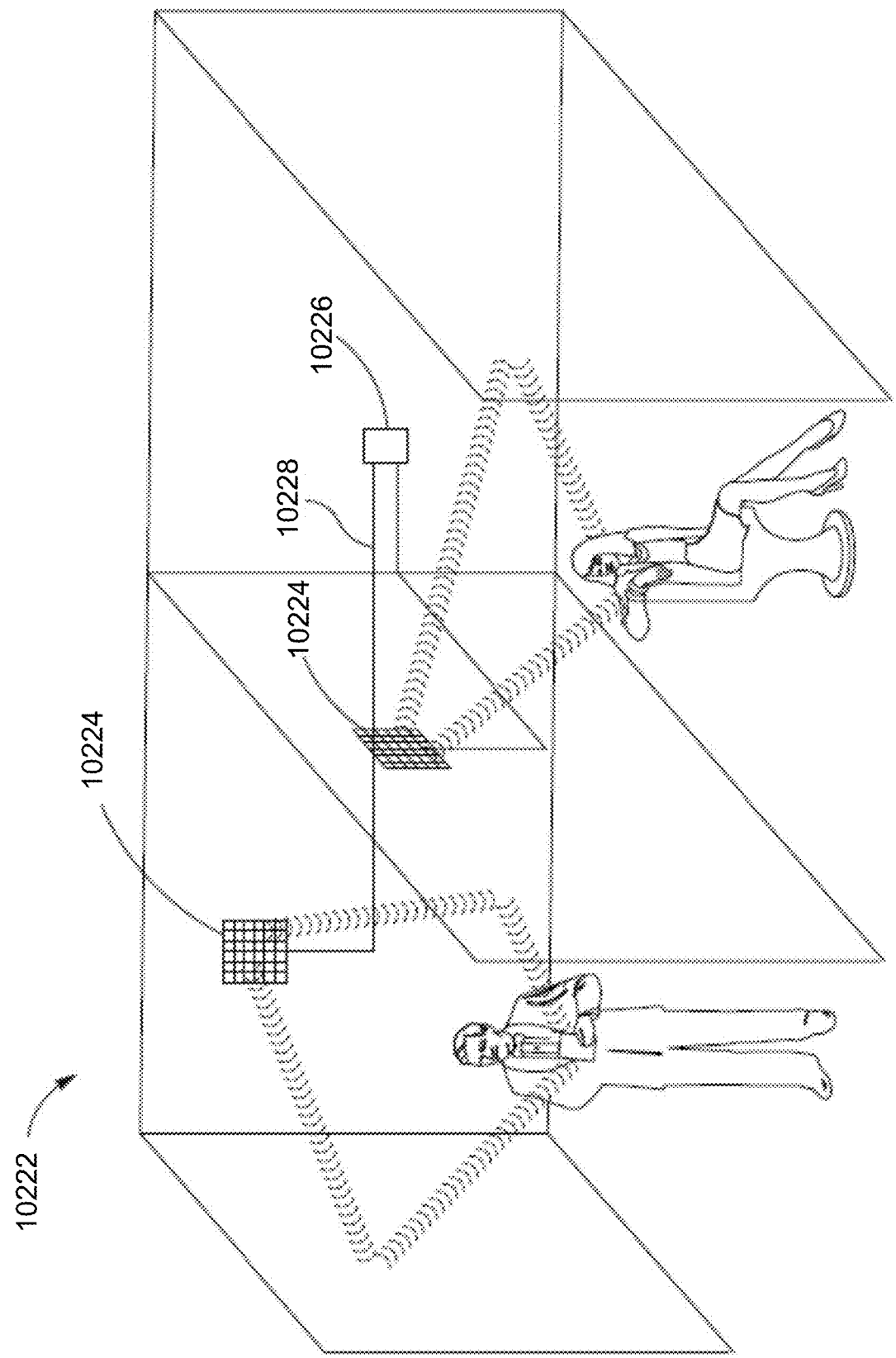

FIG. 101C depicts a wireless power system 10222, which. may include 2 transmitters 10224, a base station 10226 and connections 10228.

Base station 10226 may enable operation of different transmitters 10224 in different rooms or area coverages. Each transmitter 10224 may operate at different frequencies, power intensities and different ranges. In addition, each transmitter 10224 may provide power to a plurality of receivers 120. Furthermore, base station 10226 may enable a single operation of all transmitter 10224, thus may provide a higher capability for wireless charging by the use of each transmitter 10224 as a single one.

Figure 101D:
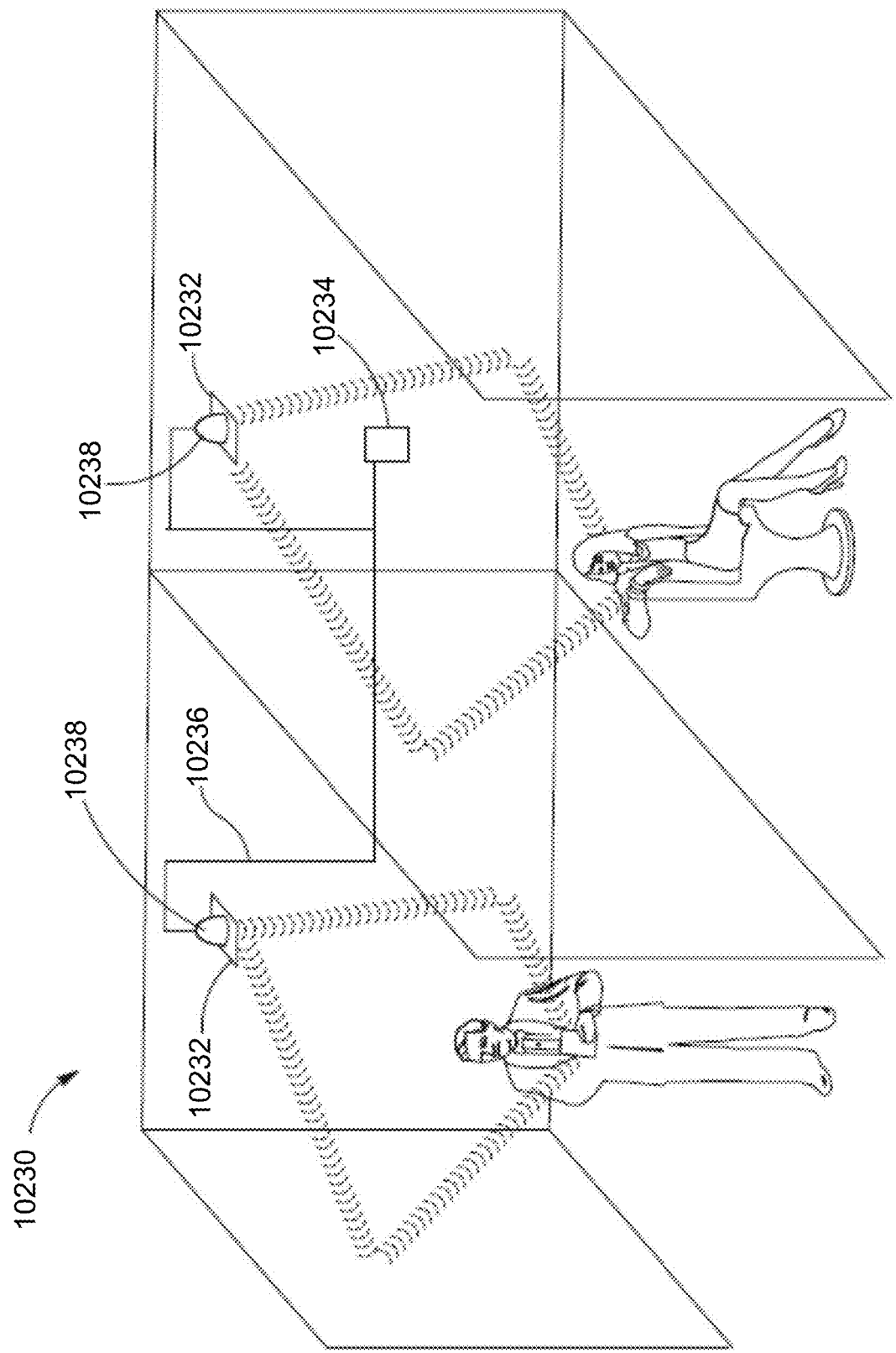

FIG. 101D depicts a wireless power system 10230, which may include 2 transmitters 10232, a base station 10234 and connections 10236.

Base station 10234 may enable operation of different transmitters 10232 in different rooms or area coverages. Each transmitter 10232 may operate at different frequencies, power intensities and different ranges. In addition, each transmitter 10232 may provide power to a plurality of receivers 120. Furthermore, base station 10234 may enable a single operation of all transmitter 10232, thus may provide a higher capability for wireless charging by the use of each transmitter 10232 as single one.

In addition, transmitters 10232 may be plugged into light sockets 10238. Such light sockets 10238 may increase the places where transmitters 10232 may be installed.

FIGS. 101A-101D illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 101A-11D.

Presented below are example embodiments of home base station for multiple room coverage with multiple transmitters.

In some embodiments, an example method for wireless power transmission, comprising the steps of providing at least one base station including a micro-controller connected to a power source, and connecting multiple transmitters to the base station having pocket-forming capabilities for generating pockets of energy to power an electronic device within range of at least one of the multiple transmitters.

In some embodiments, the base station includes a housing for the micro-controller and the power source.

In some embodiments, each of the portable transmitters includes antenna elements, a radio frequency integrated circuit for the pocket-forming, and a communication component for communicating with the electronic device within range to determine powering levels.

In some embodiments, each of the multiple transmitters includes a housing for the circuitry and components.

In some embodiments, the method further includes the step of establishing a link between the base station and multiple transmitters through a connection including coaxial cable, phone cable, LAN cable, Wi-Fi or other wireless connection.

In some embodiments, the method further comprises the step of communicating between the electronic device receiver and the transmitter through short RF waves or pilot signals on conventional wireless communication protocols including Bluetooth, Wi-Fi, Zigbee or FM radio signal with the power level information for the electronic device to be charged.

In some embodiments, the method further comprises the step of adjusting dynamically the pocket-forming to regulate power on one or more targeted electronic device within range of the multiple transmitters.

In some embodiments, the multiple transmitters are capable of powering multiple receivers connected to portable electronic devices including smartphones, tablets, music players, toys, game consoles and other similar devices. The transmitters are providing different powering or charging levels corresponding to the electronic device being powered within the range of the multiple transmitters.

In some embodiments, the components of the base station and the multiple transmitters are manufactured from meta-materials, micro-printing of circuits, nano-materials and other similar materials for integrated chips.

In some embodiments, the pocket-forming within the transmitters is controlled by a radio frequency integrated circuit utilizing components including oscillators and piezo-electric crystals to create and change radio frequencies in different antenna elements connected to the radio frequency integrated circuit.

In some embodiments, the micro-controller in the base station enables different transmitters of the multiple transmitters in different rooms or coverage areas in which each transmitter operates at a different frequency, different power intensity and different range to power the selected electronic device.

In some embodiments, the base station and multiple transmitters are built in solid state circuits to increase reliability.

In some embodiments, the multiple transmitters are plugged into a light socket in a. room for a power source.

In some embodiments, each transmitter operates at different frequencies, power intensities and different ranges to power the electronic device.

In some embodiments, an example wireless power transmission, comprises a base station having a micro-controller and a power source, and multiple transmitters electrically connected to the base station having pocket-forming capabilities for generating pockets of energy to power an electronic device within range of at least one of the multiple transmitters.

In some embodiments, the base station includes a housing for the micro-controller and the power source.

In some embodiments, each of the portable transmitters includes antenna elements, a radio frequency integrated circuit for the pocket-forming, and a communication component for communicating with the electronic device within range to determine powering levels.

In some embodiments, the electronic device communicates power requests to the transmitters for charging through communication protocols of Bluetooth, Wi-Fi, Zigbee or radio FM signals.

In some embodiments, the base station is electrically connected to the multiple transmitters through a connection including a coaxial cable, a phone cable, a LAN cable, a Wi-Fi or another wireless connection.

In some embodiments, each transmitter powers a plurality of receivers embedded within the electronic device. The base station enables a single of operation of the multiple transmitters to provide a higher capability for wireless charging by using several transmitters to act as a single charging transmitter with regard to the electronic device being charged.

FIGS. 102A-102K and 103A-103F illustrate examples of devices, apparatus, and methods for cluster management of transmitters in a wireless power transmission system, in accordance with some embodiments.

Figure 102A:
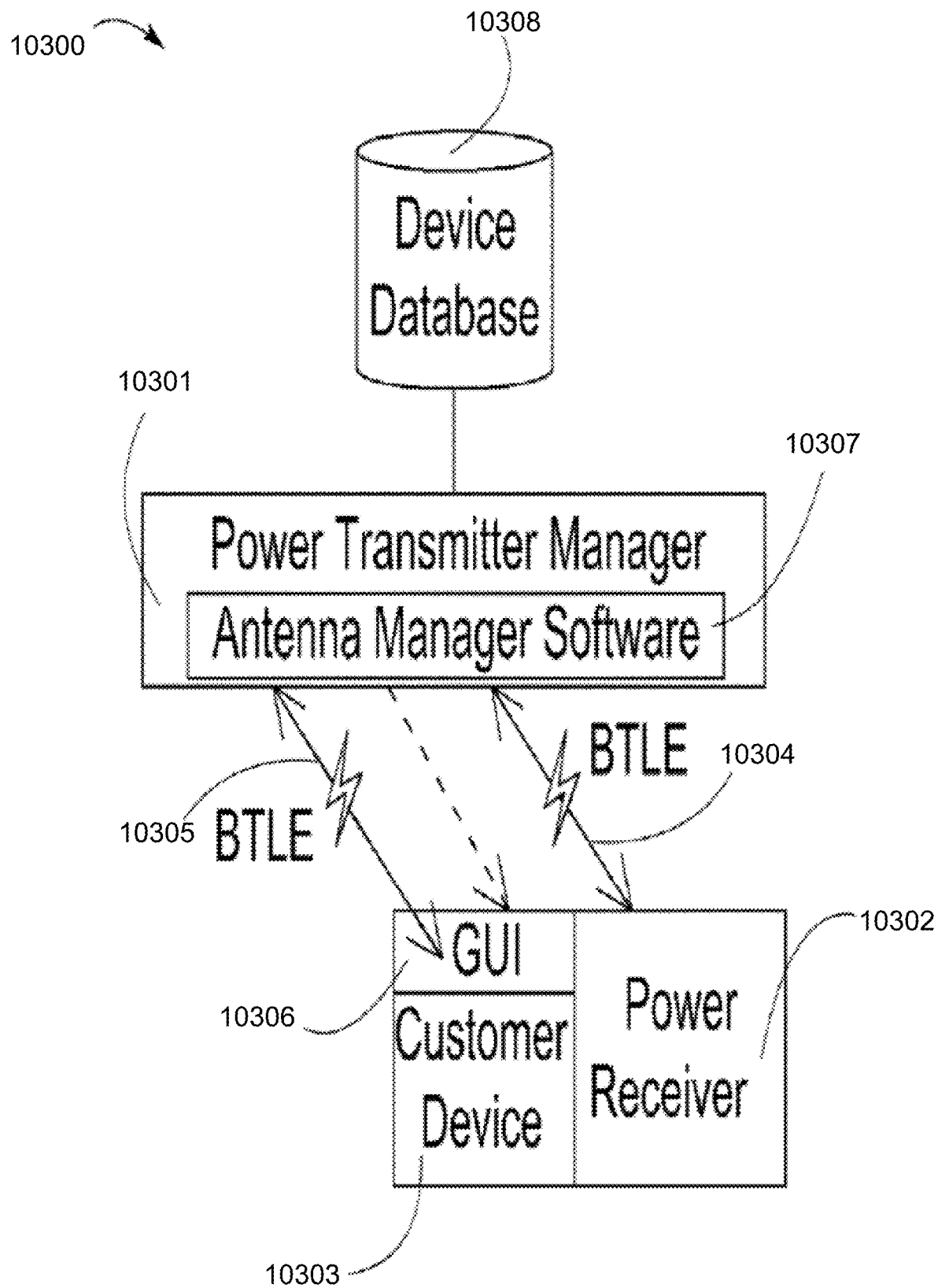

FIG. 102A shows a wireless power system 10300 using a wireless power transmitter manager device 10301, according to an embodiment. Wireless power transmitter manager device 10301 may include a processor with computer-readable medium, such as a random access memory (RAM) (not shown) coupled to the processor. Examples of processor may include a microprocessor, an application specific integrated circuit (ASIC), and field programmable object array (FPOA), among others. In some embodiments, a transmitter manager device 10301 or the various hardware and/or software components of the transmitter manager device 10301 may be integrated into one or more transmitters. In some embodiments, a transmitter manager device 10301 may be a distinct device comprising hardware and software components capable of performing the various tasks and processes described herein, including managing and controlling one or more transmitters coupled to the transmitter manager device 10301 through wired and/or wireless communications protocols.

Wireless power transmitter manager 10301 may transmit controlled RF waves that act as power waves that may converge in three-dimensional (3-D) space to a wireless power receiver 10302 for charging or powering a customer device 10303. Although the exemplary embodiment recites the use of RF waves as power waves, the power waves may include any number of alternative or additional techniques for transmitting energy to a wireless power receiver converting the transmitted energy to electrical power. These RF waves may be controlled through phase and/or relative amplitude adjustments to form constructive and destructive interference patterns (pocket-forming). Pockets of energy may form at constructive interference patterns and can be 3-D in shape, whereas null-spaces may be present outside the constructive interference patterns.

Wireless power receiver 10302 may be paired with customer device 10303 or may be built into customer device 10303. Examples of customer devices 10303 may include laptop computer, mobile device, smartphones, tablets, music players, and toys, among other. Wireless power transmitter manager 10301 may receive customer device's signal strength from advertisement emitted by wireless power receiver 10302 for the purpose of detecting if wireless power receiver 10302 is nearer to wireless power transmitter manager 10301 than to any other wireless power transmitter manager 10301 in system 10300.

Customer device 10303 may include a graphical user interface 10306 (GUI). Graphical user interface 10306 (GUI) may receive customer device's signal strength from advertisement emitted by wireless power receiver 10302 for the purpose of detecting if wireless power receiver 10302 is paired with graphical user interface 10306 (GUI).

According to some aspects of this embodiment, wireless power transmitter manager 10301 may include a device database 10308, where device database 10308 may store information about all network devices, such as universally unique identifier (UUID), serial number, signal strength, identification of paired partner device, customer device's power schedules and manual overrides; customer device's past and present operational status, battery level and charge status, hardware value measurements, faults, errors, and significant events; names, customer's authentication or authorization names, and configuration details running the system, among others. Device database 10308 may also store information about all system devices such as wireless power transmitter managers, wireless power receivers, end user hand-held devices, and servers, among others. Note that authentication of devices may be performed as well as authentication of users, giving the ability to charge an authorized device by anyone, or giving the ability to charge any compatible device by an authorized user.

Wireless power transmitter manager 10301, with control over wireless power receiver's power record, may allow sending power to a specific wireless power receiver 10302. In one embodiment, wireless power transmitter managers 10301 may need to fulfill two conditions to control wireless power receiver's power record in device database 10308; customer device's signal strength threshold has to be greater than 50% of the signal strength measured by all other wireless power transmitter managers 10301 and has to remain greater than 50% for a minimum amount of time. Note that in situations where charging of a customer's device is desired despite not meeting the conditions above, such as in emergency situations or in cases where the user belongs to a higher subscription class and need to be given priority, the power transmission manager may override the above conditions.

Wireless power transmitter manager 10301 may use, but is not limited to, Bluetooth low energy (BLE) to establish a communication link 10304 with wireless power receiver 10302 and a control link 10305 with customer device's graphical user interface (GUI). Wireless power transmitter manager 10301 may use control link 10305 to receive commands from and receive pairing information from customer device's graphical user interface (GUI).

Wireless power transmitter manager 10301 may include antenna manager software 10307 to track customer device 10303. Antenna manager software 10307 may use real time telemetry to read the state of the power received in customer device 10303.

Wireless power transmitter manager 10301 may create a wireless energy area model which includes information about all the movements in the system. This information may be stored in device database 10308.

In other situations, there can be multiple wireless power transmitter managers 2902 and/or multiple wireless power receivers 10302 for powering multiple and various customer devices 10303.

Figure 102B:
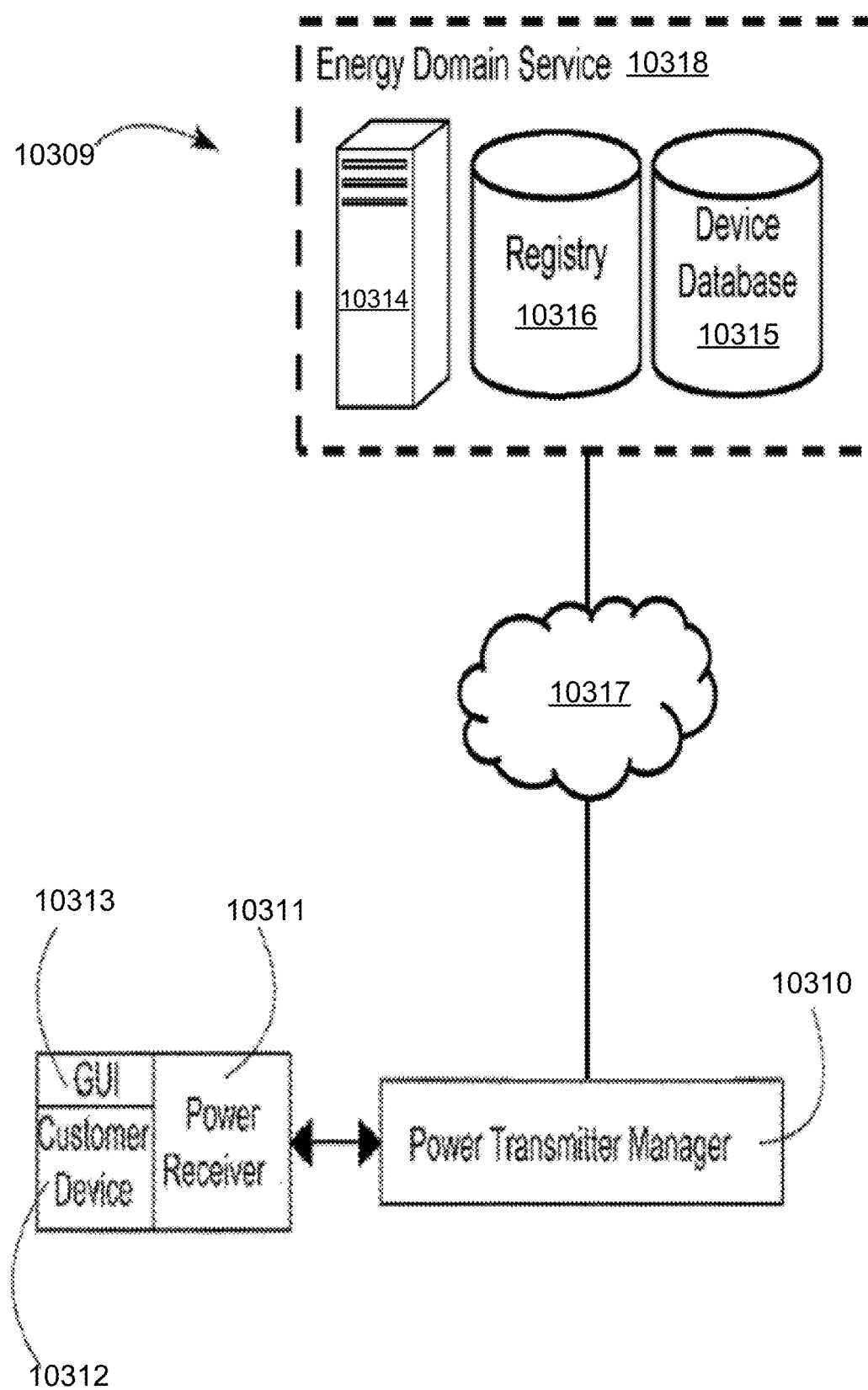

FIG. 102B illustrates a system architecture for smart registration 10309 of wireless power receivers within a wireless power network, according to another embodiment.

In a wireless power network, one or more wireless power transmitter managers and/or one or more wireless power receivers may be used for powering various customer devices.

Each wireless power device in the wireless power network may include a universally unique identifier (UUID). Examples of wireless power devices may include wireless power transmitter manager, wireless power receiver, end user hand-held or mobile devices, and servers, among others.

A wireless power transmitter manager 10310 may be any electronic device comprising a processor configured to execute software modules instructing the wireless power transmitter manager 10310 to execute various processes and tasks described herein. In operation, the hardware and software components of the wireless power transmitter manager 10310 may control the wireless power transmission behaviors of one or more transmitters. In some embodiments, a wireless power transmitter manager 10310 or the various hardware and/or software components of the wireless power transmitter manager 10310 may be integrated into one or more transmitters. In some embodiments, a transmitter manager device 10310 may be a distinct device, such as a computer (e.g., desktop, laptop, server), comprising hardware and software components capable of performing the various tasks and processes described herein through wired and/or wireless communications protocols.

A wireless power device bought by a customer may be registered with an energy domain service 10318 through some automated or manual process, such as using a publicly accessible web page or smart device application that communicates to an authentication and/or registration server 10314 of the energy domain service 10318. The device may be registered with the wireless power network, and authenticated via a registry database 10316, which may be a database hosted on one or more servers 10314 the energy domain service 10318, and configured to store data records regarding registered devices and/or users.

Energy domain service 10318 may be a network-based computing service comprising one or more servers 10314 comprising processors that execute software modules configured to control the flow of wireless energy transmissions by managing the transmitters via the power transmitter manager 10310. The servers 10314 may host a registry database 10316 configured to store information about each wireless power device registered with the energy domain service 10318 by a customer. The registry 10316 may be implemented through known-in-the-art database management systems (DBMS) such as, for example, MySQL, PostgreSQL, SQLite, Microsoft SQL Server, Microsoft Access, Oracle, SAP, dBASE, FoxPro, IBM DB2, LibreOffice Base, FileMaker Pro and/or any other type of database that may organize collections of data. The registry 10316 may store data about customers, such as a customer's name, customer's credit card, Pay Pal account, or any other method of payment, address; the registry 10316 may additionally or alternatively store data about a wireless power device, such as IP address, MAC address, and UUID, among others. The registry 10316 may also store data records for power transmitter manager devices 10310 that are controlled by the energy domain service 10318. For instance, the registry 10316 may indicate whether wireless power transmitter manager 10310 is for business, commercial, municipal, government, military, or home use. The registry 10316 records for power transmitter managers 10310 may also include various access policies for each wireless power transmitter manager 10310.

In a different aspect of this embodiment, a wireless power receiver 10311 may include a nonvolatile memory for storing a universally unique identifier (UUID) identifying a wireless power transmitter manager 10310 that may communicate with the receiver 10311. Examples of nonvolatile memory may include read-only memory, flash memory, ferroelectric RAM (F-RAM) hard disks, floppy disks, and optical discs, among others. Wireless power receiver 10311 may be paired with customer device 10312 or may be built into customer device 10312. Examples of customer devices 10312 may include laptop computer, mobile device, smartphone, tablet, music player, and toys, among other. Customer device 10312 may include a graphical user interface 10313 (GUI) as part of wireless power system software downloaded and installed from public application store.

A wireless power transmitter manager device 10310 may communicate a device database 10315, which may be hosted on any computing device comprising non-transitory machine-readable storage media that is accessible to the transmitter manager device 10310, via one or more networks 10317 or as an integrated component of the transmitter manager device 10310. A device database 10315 may store information about receivers 10311 and/or customer devices 10312 coupled to receivers 10311, such as universally unique identifier (UUID), serial number, signal strength, identification of paired partner device, customer device's power schedules and manual overrides; customer device's past and present operational status, battery level and charge status, hardware value measurements, faults, errors, and significant events; names, customer's authentication or authorization names, and configuration details running the system, among others. In some implementations, the wireless power transmitter manager 10310 may be configured to refer to this device database 10315 to determine whether the device is permitted to receive wireless power from the transmitters of the system 10309 that are controlled by a respective transmitter manager 10310.

A wireless power transmitter manager 10310 may detect a signal strength of a control signals received from a receiver 10311 or the customer device 10312 coupled to or comprising the receiver 10311. In some cases, the transmitter manager 10310 may detect the signal strength of the control signals received from the receiver 10311 based on an advertisement message emitted from the power receiver 10311 or customer device 10312. The wireless power transmitter manager 10310 may also detect if wireless power receiver 10311 is nearer to wireless power transmitter manager 10310 than to any other wireless power transmitter manager 10310 in the wireless power system 10309 through an analysis of each database records of receivers 10311 and 10312 in the wireless power system 10309 and a comparison of signal strength received at each wireless power transmitter manager 10310. Each record of a wireless power transmitter manager 10310 in the device database 10315 may include a list of each wireless power receiver 10311 and its signal strength relative to and detected by wireless power transmitter manager 10310. Then wireless power receiver 10311 may be assigned to wireless power transmitter manager 10310, which may have exclusive control and authority to change the record of the wireless power receiver 10311 in distributed system device database 10315 until wireless power receiver 10311 moves to a new location closer to another wireless power transmitter manager 10310.

As previously mentioned, a wireless power transmitter manager 10310 may verify with energy domain service 10318 whether one or more transmitters are authorized to send power waves to a wireless power receiver 10311. When the wireless power transmitter manager 10310 establishes a communications connection with a wireless power receiver 10311, the transmitter manager 10310 may request a universally unique identifier (UUID) identifying the power receiver 10311, and, in some cases, the transmitter manager 10310 may send the UUID of the transmitter manager 10310 to the power receiver 10311. The wireless power transmitter manager 10310 may establish communication connection with the energy domain service 10318 and then send the UUID of the transmitter manager 10310 and the UUID of the wireless power receiver 10311 to the energy domain service 10318, through one or more networks 10317, which may comprise any number wired and wireless communications connections between computers and/or networking devices. Non-limiting examples of networks 10317 may include intranets, local area networks (LAN), virtual private networks (VPN), wide area networks (WAN), and the Internet, among others. Once energy domain service 10318 receives the UUID of the wireless power transmitter 10310 and the UUID of the wireless power receiver 10311, one or more servers 10314 of the domain service 10318 may inspect the registry 10316 for a record of the wireless power transmitter manager 10310 using the corresponding UUID. The registry 10316 may store a record of the transmitter manager 10310, which may include an access policy for the wireless power transmitter manager 10310. The server 10314 of the energy domain service 10318 may determine whether the wireless power transmitter manager 10310 should instruct transmitters to transmit power to the receiver 10311, based on a set of rules indicated by the access policy in the registry 10316. For example, the record of the wireless power transmitter manager 10310 may store an access policy having an access control list of authorized receivers 10311 based on one or more identifiers (e.g., IP address, user identifier, MAC address, UUID), or the access policy references the server 10314 to a device database 10315 containing records of authorized receivers 10311 according to respective identifiers (e.g., IP address, user identifier, MAC address, UUID). In some implementations, the access policy of a transmitter manager 10310 states that a wireless power receiver 10311 with UUID needs to pay to receive power from transmitters controlled by the transmitter manager 10310. One or more servers 10314 of the energy domain service 10318 may comprise payment acceptance and/or verification software to verify whether payment was received from, for example, a credit card, Pay Pal, or other payment method. If a payment method is associated with wireless power receiver 10311, a server 10314 of the energy domain service 10318 may send a message to wireless power transmitter manager 10310 authorizing the power transfer to wireless power receiver 10311. In response, transmitter manager 10310 may instruct one or more transmitters to transmit power waves to the receiver 10311. In some implementations, the wireless power transmitter manager 10310 may report energy consumption statistics to energy domain service 10318 for subsequent billing of wireless power receiver's owner. Energy consumption statistics may be stored in device database 10315 and also may be sent to energy domain service 10318 for storage in a device database 10315 and/or a registry database 10316.

If no payment method is associated with wireless power receiver 10311, energy domain service 10318 may send a message to wireless power transmitter manager 10310 denying the power transfer to wireless power receiver 10311.

In the case wireless power transmitter manager 10310 access policy states that no charge will be applied to certain wireless power receivers 10311, then energy domain service 10318 may confirm if wireless power receiver 10311 is allowed to receive power from wireless power transmitter manager 10310. If wireless power receiver 10311 is allowed to receive power from wireless power transmitter manager 10310, then, energy domain service 10318 may send a message to wireless power transmitter manager 10310 authorizing the power transfer to wireless power receiver 10311. Otherwise energy domain service 10318 may send a message to wireless power transmitter manager 10310 denying the power transfer to wireless power receiver 10311.

In some implementations, a customer may access an webpage portal using a web browser of a customer device 10312, such as a computer or other computing device (e.g., smartphone, tablet, server), or the customer may download and install onto the customer device 10312 a software application associated with the energy domain service 10318 to select through a graphical user interface (GUI) 10313 which wireless power receivers 10311 may receive power waves from transmitters governed by the energy service 10318 and/or governed by particular wireless power transmitter managers 10310. In some implementations, the GUI 10313 may display each wireless power receiver 10311 near one or more wireless power transmitter managers 10310, then, customer may select which wireless power receivers 10311 are allowed to receive power waves from a particular wireless power transmitter manager 10310. This information may be stored in a device database 10315 and also may be sent to energy domain service 10318.

In some cases, a proprietor or clerk of a commercial or retail business establishment that owns a wireless power system 10309 may be able to select through the GUI 10313 a wireless power receiver 10311 to receive power from one or more wireless power transmitter managers 10310. The customer may be provided with a pre-authorized wireless power receiver 10311 at business establishment by proprietor or clerk. The wireless power receiver 10311 may be attached to customer's device 10312. The proprietor or clerks may specify to GUI 10313 the customer's method of payment (credit card, Pay Pal, cash, among others). The wireless power transmitter manager 10310 of the business establishment may start sending power to the customer device 10312 that is attached to pre-authorized wireless power receiver 10311. Customer may be billed on behalf of business establishment for power provided. Also in the GUI 10313, proprietor or clerk may be able to visualize power received by wireless power receiver 10311 and the amount to bill for power received. This information may be stored in distributed system device database 10315 and also may be sent to energy domain service 10318.

Figure 102C:
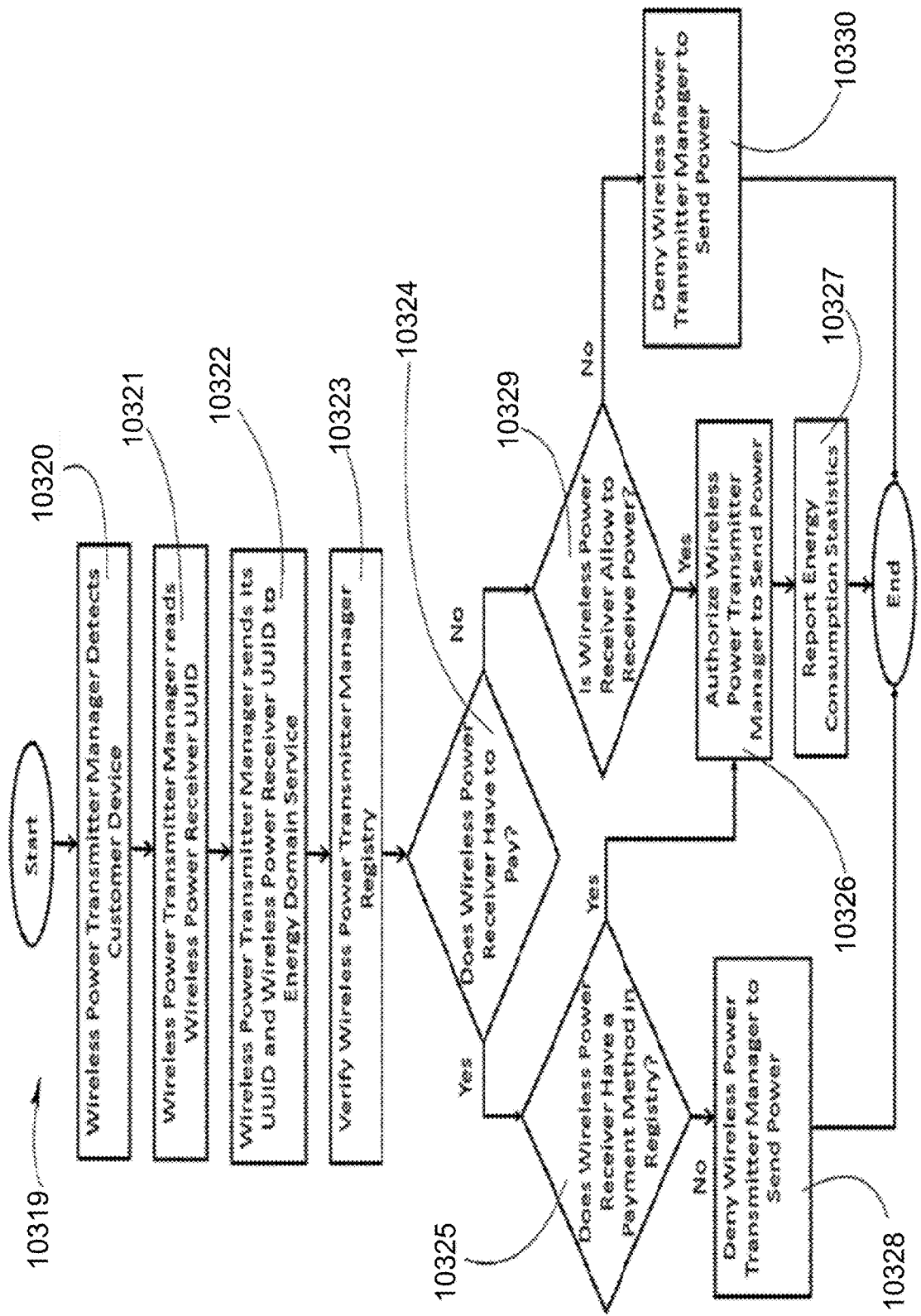

FIG. 102C is a flowchart of a method for smart registration 10319 of wireless power receivers within a wireless power network, according to a further embodiment.

In a wireless power network, one or more wireless power transmitter managers and/or one or more wireless power receivers may be used for powering various customer devices. Each wireless power device in the wireless power network may include a universally unique identifier (UUID). Examples of wireless power devices may include wireless power transmitter manager, wireless power receiver, end user hand-held or mobile devices and servers, among others. The wireless power managers may be software modules executed by electronic devices in the system. The software modules of the wireless power managers may control the operation of transmitters and may manage the interactions between receivers and the transmitters. For example, the wireless power managers may select which transmitters should transmit power waves to which receivers, if any, so that each transmitter is being utilized efficiently and so that each receiver is being serviced adequately. As another example, the transmitter managers may manage authorization and verification of receivers, and may capture payment from the receivers before instructing the transmitters to transmit power waves. In some cases, the wireless power transmitter managers may be integrated into transmitters; and in some cases, the wireless power transmitter managers may be installed and executed by a distinct electronic device, such as a server computer. In some cases, transmitters may be controlled by multiple transmitter managers that interact with one another; and in some cases, transmitters may be controlled by a single transmitter manager configured to control multiple transmitters. Data and instructions may be transmitted between transmitters and transmitter managers via one or more networks, using any number of networked-communications protocols.

The method may start at step 10320 when a wireless power transmitter manager detects a customer device. Customer device may be paired with wireless power receiver or wireless power receiver may be built in a customer device. Example of customer devices may include smartphones, mobile device, tablets, music players, toys and others at the same time. Customer device may include a graphical user interface (GUI) as part of wireless power system software downloaded and installed from public application store.

Wireless power transmitter manager may detect customer device's signal strength from advertisement emitted from the receiver or from a device coupled to the receiver. Wireless power transmitter manager may also detect if wireless power receiver is nearer to wireless power transmitter manager than to any other wireless power transmitter manager in the wireless power network through an analysis of each device database records in the wireless power system. Each record may include a list of each wireless power receiver and its signal strength relative to and detected by wireless power transmitter manager. Then wireless power receiver may be assigned to wireless power transmitter manager, which may have exclusive control and authority to change the wireless power receiver's record in distributed system device database until wireless power receiver moves to a new location closer to another wireless power transmitter manager.

According to some aspects of this embodiment, device database may store information about all network devices such as universally unique identifier (UUID), serial number, signal strength, identification of paired partner device, customer device's power schedules and manual overrides; customer device's past and present operational status, battery level and charge status, hardware value measurements, faults, errors, and significant events; names, customer's authentication or authorization names, and configuration details running the system, among others.

Wireless power transmitter manager may establish a communication connection with wireless power receiver indicating is within range to receive charge. Wireless power transmitter manager may then send power to receivers within a range (e.g., up to 30 feet from the power transmitters).

If wireless power receiver tries to obtain charge from wireless power transmitter manager, wireless power transmitter manager may verify with energy domain service if it is authorized to send power to wireless power receiver. Therefore, wireless power transmitter may establish a communication connection with wireless power receiver to request universally unique identifier (UUID). Wireless power receiver may send UUID to wireless power transmitter manager. Wireless power transmitter manager may read wireless power receiver UUID, at step 10364.

Energy domain service may be one or more cloud-based servers and each cloud-based servers may include a database that may store a registry for each wireless power device purchased by a customer. Cloud-based servers may be implemented through known in the art database management systems (DBMS) such as, for example, MySQL, PostgreSQL, SQLite, Microsoft SQL Server, Microsoft Access, Oracle, SAP, dBASE, FoxPro, IBM DB2, LibreOffice Base, FileMaker Pro and/or any other type of database that may organize collections of data. The registry may include customer's name, customer's credit card, address, and wireless power device UUID, among others. The registry may indicate whether wireless power transmitter manager is for business, commercial, municipal, government, military, or home use. The registry may also include different access policies for each wireless power transmitter manager, depending on it use, for example if wireless power transmitter manager will be for businesses use, the customer may need to define whether the power transfer will be charged or not.

According to some aspects of this embodiment, each wireless power device bought by a customer may be registered at the time of purchase, or registered later by the customer using public accessible web page or smart device application that communicates to energy domain service.

Wireless power transmitter manager may send its UUID and also wireless power receiver UUID to an energy domain service through the internet cloud, at step 10322. Internet cloud may be any suitable connections between computers such as, for example, intranets, local area networks (LAN), virtual private networks (VPN), wide area networks (WAN) and the internet among others.

Energy domain service may inspect the registry for wireless power transmitter manager using UUID, at step 10323. Registry may include access policy for wireless power transmitter manager.

Energy domain service may determine through the access policy whether wireless power transmitter manager needs to collect or verify payment from a receiver before transmitting power waves, at step 10324, where the transmitter manager or energy domain service determines whether the receiver is required to pay according to the access policy of the particular transmitter manager.

If wireless power transmitter manager access policy states that wireless power receiver with UUID needs to pay to receive power, energy domain service may verify whether a credit card, Pay Pal, or other payment method, may be denoted within wireless power receiver registry, at step 10325.

If a payment method is associated with wireless power receiver registry, energy domain service may send a message to wireless power transmitter manager authorizing the power transfer to wireless power receiver, at step 10326.

Wireless power transmitter manager may report energy consumption statistics to energy domain service for subsequent billing of wireless power receiver's owner, at step 10327. Energy consumption statistics may be stored in device database and also may be sent to energy domain service and saved in wireless power receiver's registry.

In the case no payment method is associated with wireless power receiver, energy domain service may send a message to wireless power transmitter manager denying the power transfer to wireless power receiver, at step 10328.

Else, if wireless power transmitter manager access policy states that no charge will be applied to a certain wireless power receiver which may be trying to obtain power from wireless power transmitter manager, energy domain service may confirm whether wireless power receiver is allowed to receive power from wireless power transmitter manager, at step 10329.

If wireless power receiver is allowed to receive power from wireless power transmitter manager. Energy domain service may send a message to wireless power transmitter manager authorizing the power transfer to wireless power receiver, at step 10326.

Wireless power transmitter manager may report energy consumption statistics to energy domain service, at step 10327. Energy consumption statistics may be stored in device database and also may be sent to energy domain service and saved in wireless power receiver's registry.

Otherwise if wireless power receiver is not allowed to receive power from the wireless power transmitter, energy domain service may send a message to wireless power transmitter manager denying the power transfer to wireless power receiver, at step 10330.

According to some aspect of this embodiment, a customer may be able to select through a GUI device which wireless power receivers may receive charge from wireless power transmitter manager. In the GUI device, customer may be able to visualize each wireless power receiver near to wireless power transmitter manager, then customer may select which wireless power receivers are allowed to receive charge from wireless power transmitter manager. This information may be stored in device database and also may be sent to energy domain service.

Example #1 is a wireless power network with components similar to those described in FIG. 102B. A customer may have a wireless power transmitter manager in his/her house. The customer invites three friends to watch a football game. Two of the three friends have a wireless power receiver cover paired with their cellphones. When both wireless power receivers are within the range of the wireless power transmitter manager, they may receive a message from wireless power transmitter manager indicating they are within range to receive power. One of the wireless power receivers may try to obtain power from wireless power transmitter manager, but first the wireless power transmitter manager may verify whether wireless power receiver is authorized to receive power. Therefore, wireless power transmitter manager may send its own UUID and wireless power receiver UUID to an energy domain service. Energy domain service may verify access policy for wireless power transmitter manager to determine if a billing charge has to be applied for using wireless power transmitter manager. The access policy for wireless power transmitter manager may indicate that no charge will be applied for using wireless power transmitter manager and that any wireless power receiver is able to receive charge from it. Energy domain service may verify wireless power receiver registry and then energy domain service may authorize wireless power transmitter manager to send power to wireless power receiver.

Example #2 is a wireless power network with components similar to those described in FIG. 102B. A restaurant may have a wireless power transmitter manager. A customer within the restaurant has a cellphone with a wireless power receiver cover. The customer may want to charge his/her cellphone while having dinner. The customer tries to charge his/her cellphone using wireless power transmitter manager, the wireless power transmitter manager may need to verify if wireless power receiver is authorized to receive power. Therefore, wireless power transmitter manager may send its own UUID and wireless power receiver UUID to an energy domain service. Energy domain service may verify access policy for wireless power transmitter manager to determine if a billing charge has to be applied for using wireless power transmitter manager. The access policy for wireless power transmitter manager may indicate that a charge will be applied for using wireless power transmitter manager. Then, energy domain service may verify wireless power register to determine whether a method of payment such as credit card or other method is associated with wireless power receiver. If a payment method is on the registry file, energy domain service may authorize wireless power transmitter manager to send power to wireless power receiver. Wireless power transmitter manager may track the amount of power sent to wireless power receiver. This information may be stored in device database and also may be sent to energy domain service to generate a bill, on behalf of the restaurant.

Figure 102D:
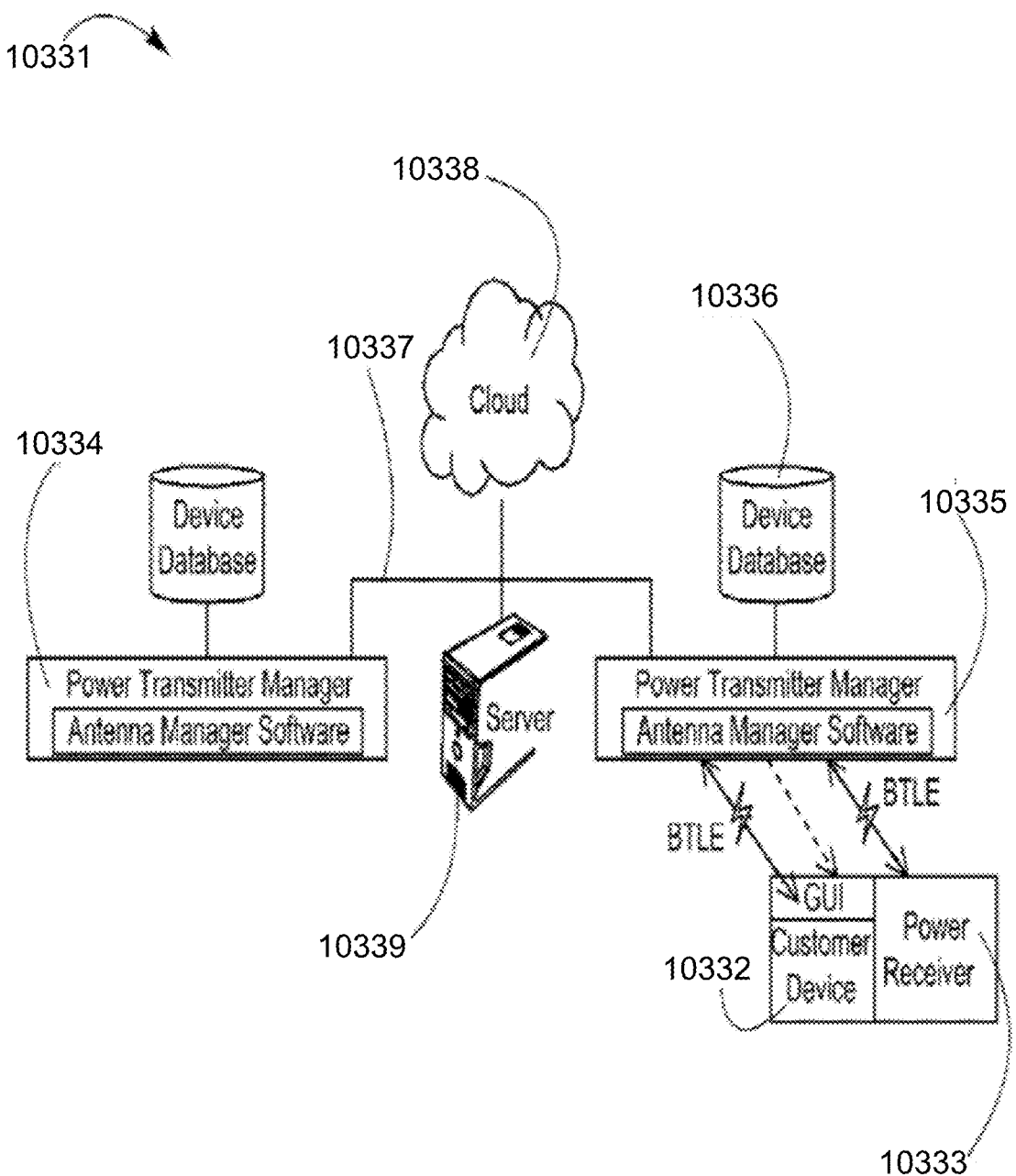

System and Method for Controlling Communication Between Wireless Power Transmitter Managers Based upon Power Transfer Proximity FIG. 102D illustrates a transmitter transition 10331; as used herein "transmitter transition" refers to transitioning wireless power transmission responsibilities from a first set of one or more transmitters to another set of one or more transmitters, or, in some cases, one or more wireless power receivers 10333. When transmitter transition commences, wireless power transmission to a given wireless power receiver 10333 is shifted from a first transmitter to a new, second transmitter. The first transmitter then ceases wireless power transmission to the given wireless power receiver.

In a wireless power transmission system, multiple wireless power transmitter managers and/or multiple wireless power receivers may be used for powering various customer devices 10332. A wireless power receiver 10333 may be paired with customer device 10332 or may be built into customer device 10332. Example of customer devices 10332 may include smartphones, tablets, music players, toys and others at the same time. Customer device 10332 may include a graphical user interface (GUI).

Each wireless power transmitter manager in the wireless power transmission system may receive customer device's signal strength from ads emitted by wireless power receiver 10333 and displayed in the graphical user interface (GUI).

In an embodiment, the customer's device's signal strength is represented as quality, in percentage terms. In another embodiment, the customer's device signal strength is measured using received signal strength indicator (RSSI) values. RSSI is received wireless signal strength in dBm, and indicates the power level being received by the antenna of the customer device. The higher the RSSI number, the stronger the signal. In the present disclosure, "power transfer proximity" (also called "power transfer proximity indicator") is sometimes used to describe proximity of transmitters (TX) for charging/power transfer to customer devices, wherein high RSSI values typically indicate in-close power transfer proximity.

Each wireless power transmitter manager in the wireless power transmission system may include a device database 10336. Device database 10336 may store customer device's power schedules, customer device's status, names, customer's sign names, and details running the system, among others, for each customer device 10332 in the wireless power transmission system near to a wireless power transmitter manager. Device database 10336 may also store information about all system devices such as wireless power transmitter managers, wireless power receivers, end user hand-held devices, and servers, among others.

A Wi-Fi connection 10337 may be established between a wireless power transmitter manager one 10334 and a wireless power transmitter manager two 10335 to share between system devices: device database's power records, quality control information, statistics, and problem reports, among others Each wireless power transmitter manager may create a wireless energy area model which includes information about all the movements in the system. Also this information may be stored at device database 10336. Wireless energy area model may be used in transmitter power transfer transitions, i.e., in transitioning communications and power transfer from wireless power transmitter manager one 10334 to wireless power transmitter manager two 10335. For example, if a customer device 10332 moves away from wireless power transmitter manager one 10334 and nearer to wireless power transmitter manager two 10335, this movement may be registered in the wireless energy area model.

In another aspect of this embodiment, wireless power transmitter managers may transfer power in a range between 15 feet to 30 feet, but only wireless power transmitter manager with control over wireless power receiver's power record, may be allowed to send power to a specific wireless power receiver. Furthermore, wireless power transmitter managers may share wireless power receiver's power record, but only the wireless power transmitter manager, with control over wireless power receiver's power record, can change the information stored for that power record in the device database 10336.

According to some aspects of this embodiment, wireless power transmitter managers may need to fulfill two conditions to control power transfer over a customer device; customer device's signal strength threshold has to be greater than a predetermined percentage of the signal strength measured by all the other wireless power transmitter manager; and it must exceed this threshold for a minimum amount of time. For example, in the case of a predetermined percentage of 50%, the signal strength threshold has to be greater than 55% of the signal strength measured by all the other wireless power transmitter managers, for a minimum amount of time. If multiple wireless power transmitter managers are within range to communicate with and transfer power to a given wireless power receiver, then only the closest wireless power transmitter manager or the last wireless power transmitter manager closest to wireless power receiver, has control of the wireless power receiver's power record in device database 10336, however each wireless power transmitter manager may individually and simultaneously transfer power to the power record. In this case, communication with the wireless power receiver is time-multiplexed (shared) between the multiple wireless power transmitter managers so that each can track the 3-D location of the wireless power receiver, in case it is in movement.

In another aspect of this embodiment, wireless power transmitter manager one 10334 and wireless power transmitter manager two 10335 may share customer device's information through a cloud 10338. Both wireless power transmitter managers may be connected to cloud 10338 through network connections (not shown in FIG. 102D). Network connections may refer to any suitable connections between computers such as, for example, intranets, local area networks (LAN), virtual private networks (VPN), wireless area networks (WAN) and the internet among others. Cloud 10338 may also be used to share between system devices: quality control information, statistics, and problem reports, among others.

According to some aspects of this embodiment, a server 10339 may be connected to cloud 10338 as a backup of device database 10336 shared by every wireless power transmitter manager in the wireless power transmission system.

Figure 102E:
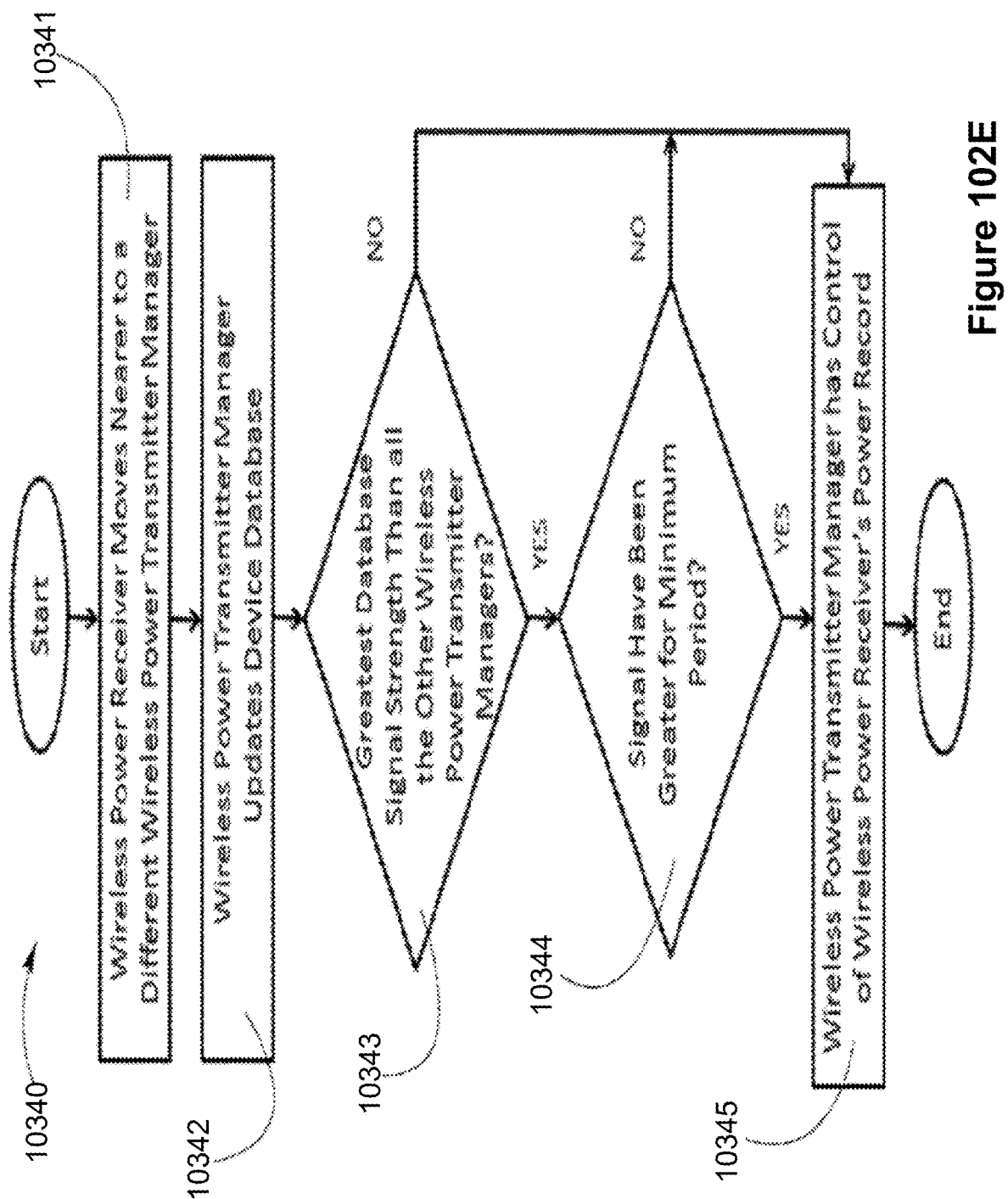

FIG. 102E is a flowchart 10340 of a transmitter power transfer transition, between one wireless power transmitter manager to another, in a wireless power transmission system, according to an embodiment.

In a wireless power transmission system with two wireless power transmitter managers the process may start when a wireless power receiver moves away from a wireless power transmitter and nearer to another transmitter, at step 10341. A customer device may be paired with the wireless power receiver. Example of customer devices may include smartphones, tablets, music players, and toys, among others. Customer device may include a graphical user interface (GUI).

Wireless power transmitter managers may receive customer device's signal strength from advertisement signals emitted by wireless power receiver. Subsequently, both wireless power transmitter managers may update a device database with the customer device's signal strength measured by each transmitter manager, at step 10342.

Each wireless power transmitter manager in the wireless power transmission system may include a device database. Device database may store customer device's power schedules, customer device's status, names, customer's sign names, and details running the system, among others, for each customer device in the power transmission system near to a given wireless power transmitter manager. Device database also may store information about all system devices such as wireless power transmitter managers, wireless power receivers, end user hand-held devices, and servers, among others.

According to some aspects of this embodiment, a wireless power transmitter manager, may instruct transmitters to send power waves to a specific wireless power receiver, based upon a record in a device database or registry database accessible to the wireless power transmitter manager. In some cases, wireless power transmitter managers in the system may share wireless power receiver's power records, which may allow a system to omit an energy service, or one or more databases, or may allow the transmitter managers to share information without need to reference central databases unnecessarily, thereby reducing the burden on the energy domain service.

According to some aspects of this embodiment, wireless power transmitter managers may need to fulfill two conditions to control power transfer over a customer device; customer device's signal strength threshold has to be greater than a predetermined percentage of the signal strength measured by all the other wireless power transmitter managers for a minimum amount of time. For example, in the case of a predetermined percentage of 50%, the signal strength threshold has to be greater than 55%. If multiple wireless power transmitter managers are within range to communicate with and transfer power to a given wireless power receiver, then only the closest wireless power transmitter manager or the last wireless power transmitter manager closest to wireless power receiver, has control of the wireless power receiver's power record in the device database, however each wireless power transmitter manager may individually and simultaneously transfer rights to read and manipulate the power record. In this case, communication with the wireless power receiver is time-phased (shared) between the multiple wireless power transmitter managers so that each can track the 3-D location of the wireless power receiver, in case it is in movement.

The wireless power transmitter manager that first receives the strongest signal strength from customer device may verify if the signal strength of customer device has been significantly greater than predetermined percentage (for example greater than 55%, for a predetermined percentage of 50%) for a minimum amount of time, at step 10344.

The wireless power transmitter manager that first receives the strongest signal strength from customer device for a minimum amount of time may take control of wireless power receiver's power records and power transfer, at step 10345.

Figure 102F:
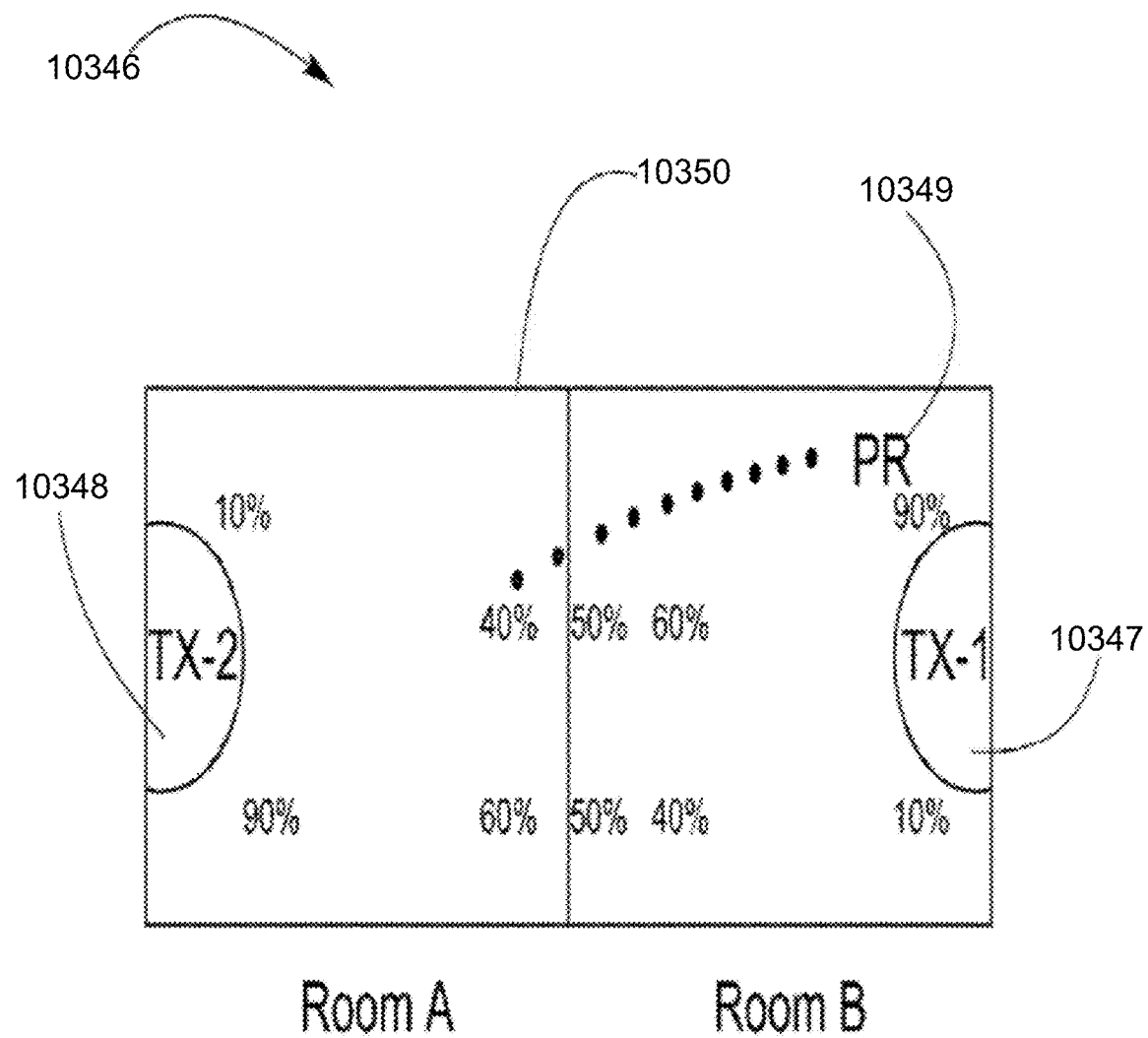

FIG. 102F is an exemplary embodiment 10346 of a transmitter power transfer transition, between one wireless power transmitter manager to another, in a wireless power transmission system, according to an embodiment.

In a wireless power transmission system 10350, multiple wireless power transmitter managers and/or multiple wireless power receivers may be used for powering various customer devices.

As an exemplary embodiment 10346, two wireless power transmitter managers may be in different rooms. Wireless power transmitter manager one 10347 may be located in room B and wireless power transmitter manager two 10348 may be located in room A. Room A and B may be next to each other.

Wireless power receiver 10349 may be located in room B and may receive power transfer from wireless power transmitter manager one 10347. A customer device may be paired with a wireless power receiver 10349. Example of customer devices may include smartphones, tablets, music players, toys and others at the same time. Customer device may include a graphical user interface (GUI).

Each wireless power transmitter manager or transmitter near to customer device may receive customer device's signal strength from advertisement signals emitted by wireless power receiver 10349.

Each wireless power transmitter manager in the power transmission system 10350 may have a device database. Device database may store customer device's power schedules, customer device's status, names, customer sign names, and details running the system, among others, for each customer device in the power transmission system 10350 near to any wireless power transmitter manager. Device database also may store information about all system devices such as wireless power transmitter managers, wireless power receivers, end user hand-held devices, and servers, among others.

Each wireless power transmitter manager may create a wireless energy area model which includes information about all the movements in the system. This information may be used to effect a transmitter power transfer transition involving control of power transfer from wireless power transmitter manager one 10347 to wireless power transmitter manager two 10348. Wireless energy area model may be stored in the corresponding device database for each wireless power transmitter manager.

If wireless power receiver 10349 starts moving from room B to room A, wireless power transmitter manager one 10347 may take control over power transfer for wireless power receiver 10349 and wireless power transmitter's power records if customer device's signal strength threshold is significantly greater than 50% of the signal strength measured by all other wireless power transmitter managers. For example, if wireless power transmitter manager one 10347 receives 90% signal strength from customer device, wireless power transmitter manager one 10347 may still have control over power transfer and wireless power receiver's power records.

If wireless power receiver 10349 continues moving toward room A, but wireless power transmitter manager one 10347 receives 60% signal strength from customer device, wireless power transmitter manager one 10347 may still have control over power transfer and wireless power receiver's power records.

Wireless power receiver 10349 may move until mid-way between room A and room B. If wireless power transmitter manager one 10347 and wireless power transmitter manager two 10348 receives 50% signal strength from customer device, wireless power transmitter manager one 10347 may still have control over power transfer and wireless power receiver's power records.

Wireless power receiver 10349 continues moving towards room A. If wireless power transmitter manager one 10347 may receive 40% or 45% signal strength from customer device and wireless power transmitter manager two 10348 may receive 55% or 60% signal strength from customer device for a minimum amount of time, wireless power transmitter manager one 10347 may effect a transmitter power transfer transition, transferring control of power transfer, and may provide wireless power receiver's power record to wireless power transmitter manager two 10348. Wireless power transmitter manager two 10348 may take control over power transfer and wireless receiver power's power record.

If wireless power receiver 10349 moves back from room A to room B, wireless power transmitter manager two 10348 may have control over power transfer for wireless power receiver 10349 until signal strength drops to 45% or less for a minimum amount of time. Wireless power transmitter manager one 10347 may take control over power transfer until customer device's signal strength reaches 55% or more for a minimum amount of time.

Example #1 is an application of the system described in FIG. 102D. First wireless power transmitter manager may be located in a living room and a second wireless power transmitter manager may be located in a bedroom. A customer may be watching television in the living room, and at the same time the customer may be charging his cellphone using the wireless power transmitter manager located in the living room. The customer's cellphone may be paired with a wireless power receiver. Wireless power transmitter manager located in the living room and wireless power transmitter manager located in the bedroom may receive customer cellphone's signal strength from advertisements emitted by wireless power receiver. The customer may go to sleep and may take his cellphone with him; the customer's cellphone may continue charging using the wireless power transmitter manager located in the living room until his/her cellphone's signal strength drops to 45% or less. When the cellphone's signal strength drops to 45% or less for wireless power transmitter manager located in the living room, wireless power transmitter manager located in the bedroom may take control over power transfer without power transfer interruption, after it receives 55% or more signal strength for a minimum amount of time. Customer cellphone may continue charging using wireless power transmitter manager located in the bedroom. A transmitter power transfer transition between wireless power transmitter managers located in the living room and wireless power transmitter manager located in the bedroom may not be noticed by customer.

B. Cluster Management of Transmitters

The wireless power management system provides cluster management of a plurality or cluster of transmitters at a location, facilitating the transfer of power from two or more transmitters in the cluster of transmitters to a power receiver. In cluster management of a plurality of transmitters, transmitter power transfer transition as used herein refers to transition of wireless transfer of power by one or more transmitter of a plurality or cluster of transmitters to a given wireless power receiver. The transmitter power transfer transition commences wireless power transmission to the given wireless power receiver from a new transmitter, ceases wireless power transmission to the given wireless power receiver from a transmitter that was previously wirelessly transmitting power, or both.

In an embodiment, the power receiver receives power only from a single transmitter during a given time period. A transmitter power transfer transition effects a transition of wireless transfer of power to the wireless power receiver from one wireless power transmitter to another wireless power transmitter of the plurality or cluster of transmitters. Alternatively, if there is no available transmitter of the plurality or cluster of transmitters that can transmit power to the wireless power receiver following the transmitter power transfer transition, wireless power transmission by the plurality or cluster of transmitters to the wireless power receiver may cease altogether. The latter situation may arise for example when a mobile device associated with the power receiver moves out of the transmitter cluster location.

In another embodiment, the power receiver may receive wireless transfer power from more than one transmitter during a given time period, sometimes called additive power in the present disclosure. In this embodiment, a transmitter power transfer transition includes a number of possible scenarios: (a) adding a given transmitter within the plurality or cluster of transmitters to a set of one or more transmitters that was previously wirelessly transmitting power to the power receiver wherein the given transmitter was not previously wirelessly transmitting power to the wireless power receiver; (b) ceasing wireless power transfer by a transmitter from a set of one or more transmitters that were previously wirelessly transmitting power to the wireless power receiver; and (c) transitioning the wireless transfer of power to the wireless power receiver between one wireless power transmitter of a set of one or more transmitter that was previously wirelessly transmitting power to the wireless power receiver, to another wireless power transmitter of the plurality or cluster of transmitters that was not previously wirelessly transmitting power to the wireless power receiver. In wireless power transfer transition scenario (b), if the wireless power receiver had been receiving wireless power from a single transmitter, wireless power transmission by the plurality or cluster of transmitters to the wireless power receiver may cease altogether.

In an embodiment, a plurality of transmitters are communicatively coupled to at least one wireless power transmission manager, and the transmitter power transfer transition is effected by the at least one wireless power transmission manager. For example, a transition of wireless transmission responsibilities to the particular wireless power receiver may be effected by a wireless power transmitter manager of a transmitter of the plurality or cluster of transmitters that was previously wirelessly transmitting power to the wireless power receiver, and by a wireless power transmitter manager of another transmitter of the cluster of transmitters that was not previously wirelessly transmitting power to the wireless power receiver.

In an embodiment, a transmitter power transfer transitions occur as a mobile device associated with a power receiver moves to, from, or within the transmitter cluster location.

In an exemplary transmitter and receiver embodiment, a receiver is embedded in or otherwise joined to a device such as a mobile phone. In the embodiment described below, status communications between transmitter and receiver are hosted using the Bluetooth Low Energy (BLE) wireless communications protocol. BLE is exemplary of a broad range of wireless communications protocols that are capable of hosting status communications between the transmitters and receivers (for example, Wi-Fi (IEEE 23A02.11), Near Field Communication (NFC), radio frequency identification (RFID), iBeacon), and the present transmitter cluster management method is not limited to a particular status communication protocol. The transmitter and receiver each has a Bluetooth low energy (BLE) processor. In use, the transmitter's BLE processor scans for Bluetooth devices. When the receiver's Bluetooth processor powers up, it begins advertising that it is a Bluetooth device. The advertisement includes a unique identifier so that when the transmitter scans the advertisement, it will distinguish that receiver's advertisement from all other Bluetooth devices in range. In response to this identification, the transmitter immediately forms a communication connection with the receiver and will command the receiver.

After forming the BLE communication connection between transmitter and receiver, the transmitter commences sending power transfer signals to the receiver (for example, at a rate of 300-400 times a second), and the receiver sends voltage sample measurements back to the transmitter. The transmitter analyzes these voltage measurements while varying the configuration of the transmitter antennas in phase and gain, until achieving a maximum voltage level. At this level, there is maximum energy in the pocket around the receiver. The wireless power transfer management system continually receives status and usage data from the transmitter, and through the transmitter, obtains status and usage information from the receiver, as with all other transmitters and receivers in the system. For example, as applied to energy harvest, the receiver communicates the updated energy harvest value to the transmitter, once a second. The transmitter accumulates data such as energy harvest values from the receiver, and from any other receiver with which it communicates. Periodically, the transmitter uploads accumulated energy information to the wireless power management system.

The present transmitter cluster management method addresses situations in which a plurality or cluster of transmitters provides power to a given receiver at a location using pocket-forming. Two or more transmitters each may execute an additive power procedure for pocket-forming at the given receiver, as multiple pockets formed at the receiver by the two or more transmitters generally would improve power transfer efficiency or control for that receiver.

In transferring power to a given receiver with a plurality of transmitters, each transmitter will execute the same general communication procedure that applies to power transfers between a single transmitter and receiver. After forming a BLE communication connection between the respective transmitter and receiver, the transmitter begins sending power transfer signals to the receiver (e.g., 3400 times a second), and the receiver sends voltage sample measurements back to the transmitter. Each of the plurality of transmitters may analyze these voltage measurements while varying the configuration of the transmitter antennas in phase and gain, until achieving a maximum voltage level. At this level, there is maximum energy in the pocket formed by that respective transmitter around the receiver. Each transmitter that is executing power transfers to the receiver will periodically communicate accumulated energy information for the receiver, and other status and usage information, to the wireless power management system.

Figure 102G:
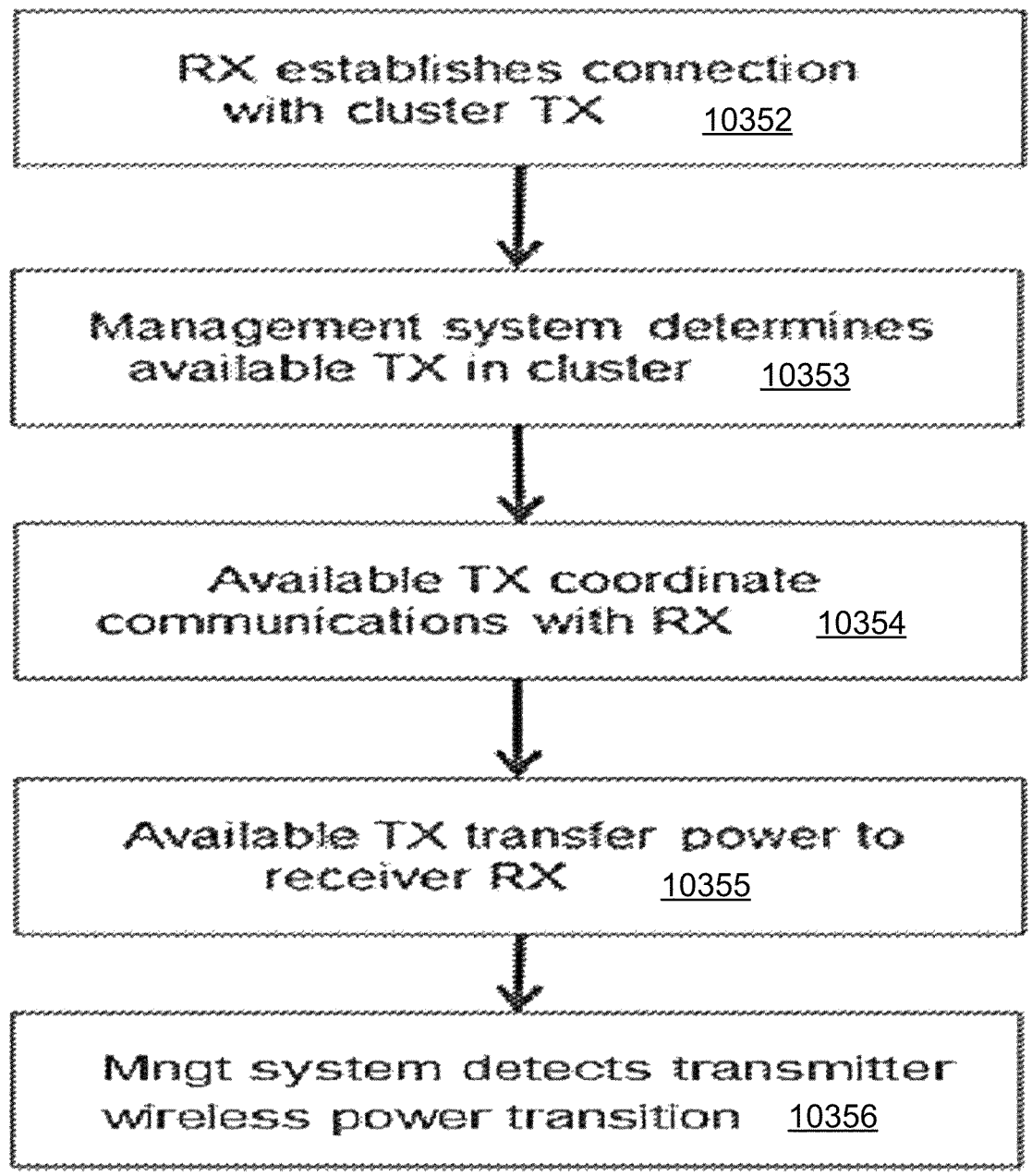

FIG. 102G illustrates steps of cluster management of a plurality or cluster of transmitters TX at a location, to facilitate power transfer to a receiver RX. In the initial step 10352, receiver RX establishes communications with a transmitter TX within the cluster. Upon establishing communications with receiver RX, the transmitter TX communicates the unique identifier of the newly identified power receiver RX to the wireless power management system. In one embodiment transmitter TX is a master transmitter that has been designated to manage communications for the cluster of transmitters. At step 10353, the wireless power management system determines which transmitters within the cluster at that location are available to transfer power to receiver RX.

In one embodiment, the available transmitters TX will include any transmitter within the cluster capable of transferring power to receiver RX, including the transmitter of step 10352 and any other TX within range of the receiver as reported to the management system. One or more wireless power transmitters may automatically transmit power to any single wireless power receiver that is close enough for it to establish a communication connection using a suitable communication technology, including Bluetooth Low Energy (BLE), or the like. The wireless power receiver may then power or charge an electrically connected client device.

However, this may not be the case at some locations with a cluster of transmitters. The system can be configured by the wireless power management system to transmit power only to specific wireless power receivers depending on specific system criteria or conditions, such as the time or hour of the day for automatic time-based scheduled power transmission, wireless power receiver physical location, owner of client device, or other suitable conditions and/or criteria. For example, a transmitter TX of the cluster of transmitters may be dedicated to powering one or more device of a particular user, wherein other devices and receivers are not authorized to receive power from that transmitter. In the following discussion, references to available transmitters or to transmitters available to a given receiver mean transmitters that are within power transfer range of that receiver, and that can be used to transfer power to that receiver based upon all other considerations, such as any limitation on transmitter use in specific system criteria or conditions recorded in the wireless power management system.

At step 10354, it is assumed that two or more transmitters TX are available to transfer power to receiver RX. At this step, the two or more transmitters coordinate communications with receiver RX in an embodiment (such as Bluetooth® communications) in which only one transmitter TX can communicate with receiver RX at a time. In one embodiment as explained below, communications are coordinated by one of the two or more transmitters which is selected as a master transmitter. At step 10355, the available transmitters TX transfer power to receiver RX, subject to the coordination of communications at step 10354. At step 10356, the management system detects a transmitter power transfer transition within the cluster of transmitters that are in communication with receiver RX. This transmitter power transfer transition may involve one of the available transmitters ceasing its communications with receiver RX (e.g., due to receiver RX moving out of range of that transmitter); a new transmitter TX establishing communications with receiver RX; or a combination of these occurrences. Typically, in this event, unless the transmitter power transfer transition entails the end of all connections of receiver RX with transmitters in the cluster, the power transfer management system and the transmitter(s) available after the transition will repeat steps 10353 through 10356 of this cluster management method.

Figure 102H:
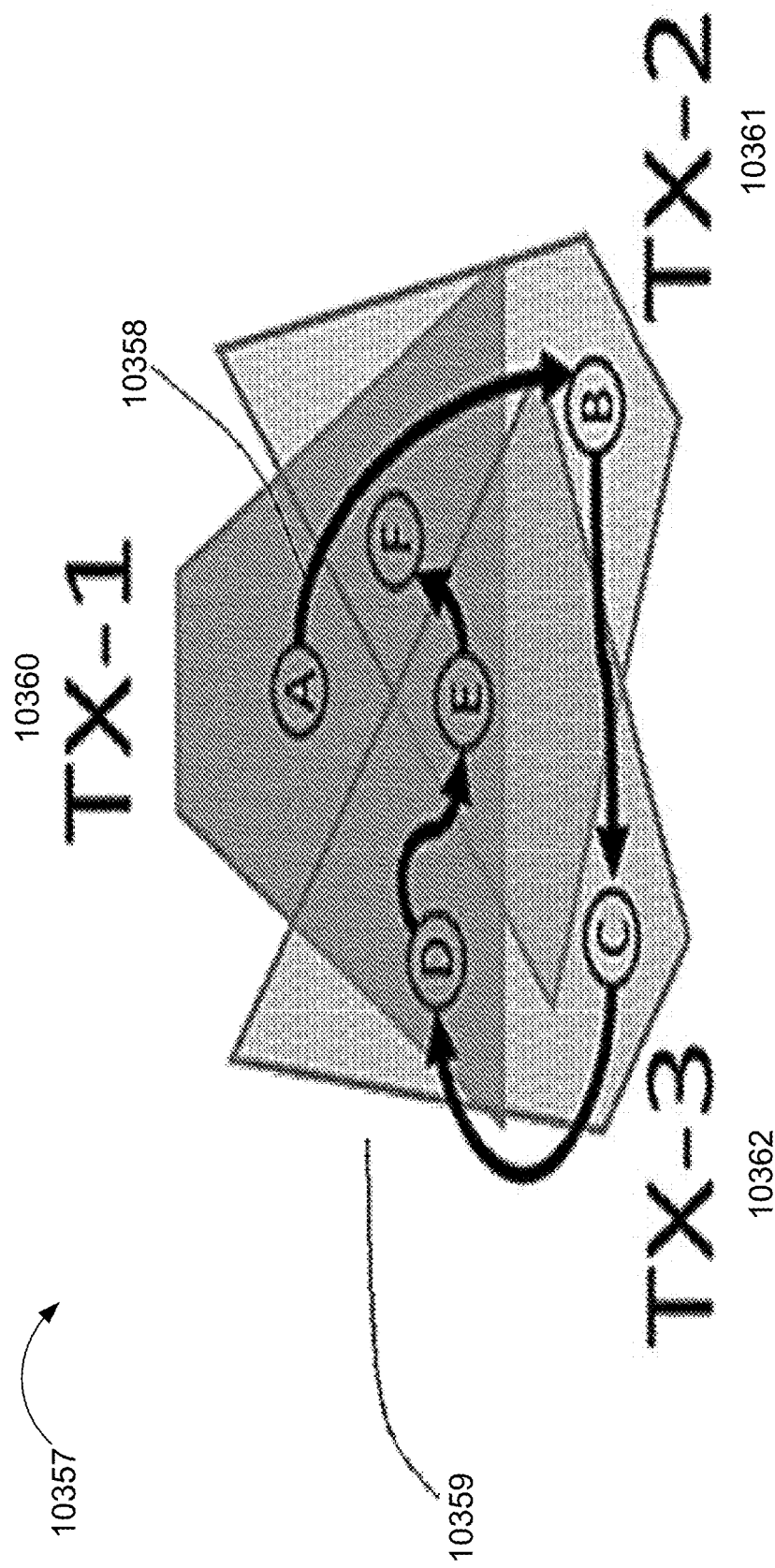

FIG. 102H shows the path 10358 of a user with mobile phone in hand, who enters and travels through a location 10359 including a cluster of transmitters TX1 10360, TX2 10361, and TX3 10362, As the device and receiver 10358 travel the path 10358 through nodes A→B→C→D→E→F, transmitters TX1 10360, TX2 10361, and TX3 10362 undergo the following transmitter power transfer transitions: (A) TX1 10360 detects the receiver and starts transmitting power; (B) The receiver moves out of range of TX1 10360 which ceases power transfer; TX2 10361 detects the receiver and starts transferring power; (C) The receiver moves out of range of TX2 10361 which ceases power transfer; TX3 10362 detects the receiver and starts transferring power; (D) The receiver remains within range of TX3 10362 which continues power transfer; TX1 10360 detects the receiver and re-starts transferring power; (E) The receiver remains within range of TX1 10360 and TX3 10362, which continue power transfer; TX2 10361 detects the receiver and re-starts transferring power, so that all three transmitters are transferring power; and (F) The receiver moves out of range of TX3 10362 which ceases power transfer; the receiver remains within range of TX1 10360 and TX2 10361, which continue power transfer.

Wireless communications, such as BLE, between transmitters TX1 10360, TX2 10361, and TX3 10362 and the receiver 10358 may operate at a greater distance than the power transfer range of the transmitters. In this case, a transmitter power transfer transition in FIG. 102H may not be caused by a transmitter's detection of receiver 10358, but by receiver 10358 entering, or exiting, the transmission range of the transmitter.

When multiple wireless power transmitters are executing power transfers to a single receiver using BLE communications between transmitters and receiver, one or more wireless power transmitter managers embedded in the wireless power transmitters coordinate communications between the respective transmitters and the receiver. Bluetooth protocols only permit one communication connection at a time between the wireless power receiver and the multiple wireless power transmitters. Wireless power manager application software within the wireless power transmitter managers may carry out a routine, as a set of instructions and/or algorithm, for coordinating communication between communication managers of the multiple wireless power transmitters (wireless power transmitter cluster). This routine coordinates contemporaneous communications of the respective wireless power transmitters with the power receiver. As used in this description of cluster management of wireless power transmitters, contemporaneous means that at least two wireless power transmitters communicate with a power receiver during the same general period of time, but it does not mean that more than one wireless power transmitter communicate with the power receiver at exactly the same time. In an embodiment, the routine carried out by the wireless power manager application employs time division multiplexing (TDM) of contemporaneous communications between at least two wireless power transmitters and the power receiver.

During the general period of time of contemporaneous communications of the wireless power transmitters with the power receiver, multiple wireless power transmitters within the cluster can simultaneously send power to the power receiver. In an embodiment, system management may limit the total amount of power transmitted by the multiple wireless power transmitters to the power receiver.

In one embodiment involving a centralized control method, the wireless power management system selects one of the transmitters as a master transmitter. The master transmitter controls the order and timing of communications with the receiver among the plurality of transmitters that are executing power transfers to the receiver. Alternative methods for coordinating communications also are possible besides this centralized control method, such as methods involving decentralized control among the plurality of transmitters.

Figure 102I:
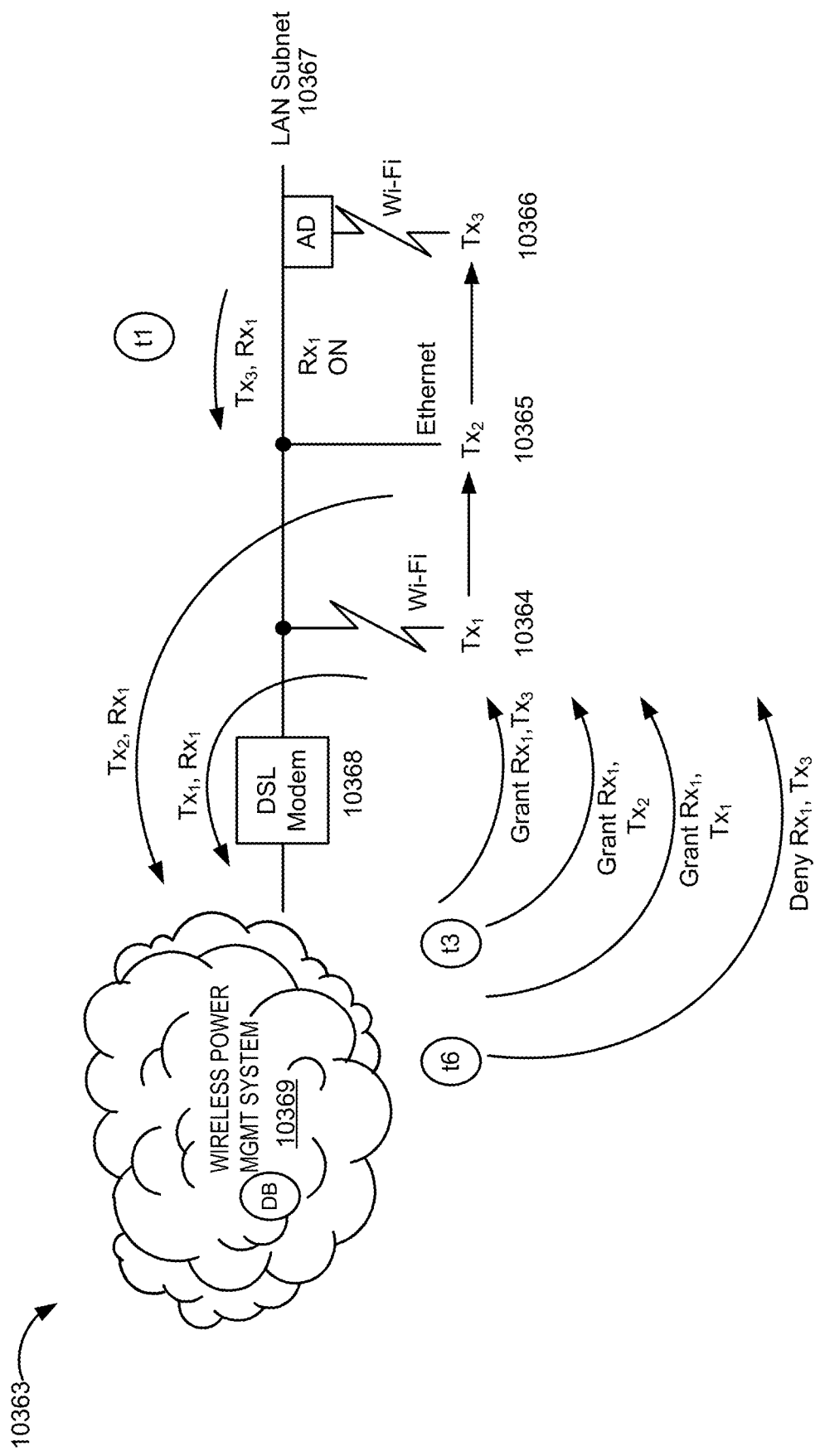

In a system 10363 illustrated in FIG. 102I, each of a plurality or cluster of transmitters TX1 10364, TX2 10365, TX3 10366 is connected with an enterprise bus 10367 such as Wi-Fi or Ethernet. When the system 10363 is installed, it is configured for network control, e.g., via a local area network subnet. Transmitters TX1 10364 and TX3 10366 are connected to LAN 10367 by Wi-Fi, and TX2 10365 is connected by Ethernet. An access point is included at 10368. Thus, the transmitters can exchange communications across a TCP/IP local area subnet, ensuring guaranteed communication using TCP sockets. This arrangement also allows the transmitters to broadcast information using an Internet protocol such as the User Datagram Protocol (UDP), providing communications analogous to Bluetooth advertising.

When transmitters TX1 10364, TX2 10365, TX3 10366 power up, each of the transmitters begins regularly to broadcast across the network a message including its IP address and other information identifying the transmitter. Each transmitter in the network has access to broadcasts of the other transmitters, and each transmitter builds a list of all transmitters of the network, including identification of one of the transmitters as master transmitter. In a first embodiment of centralized control, the system identifies as master transmitter the transmitter with the lowest IP number, here shown as TX3 with IP address 192.168.000.3. Within the general approach of centralized control of transmitter-receiver communications by a master transmitter, other algorithms besides lowest IP number can be used to determine the master transmitter.

The system repeats this procedure regularly, so that if master transmitter TX3 went off line, the remaining transmitters may recalculate and assign one of the remaining transmitters as master. If the other transmitters did not see a UDP broadcast message from the master transmitter within a set period of time (e.g., 15 seconds), these remaining transmitters may recalculate the list of available transmitters and may assign one of the remaining transmitters as master based upon the applicable algorithm (in this embodiment, lowest IP number).

Figure 102J:
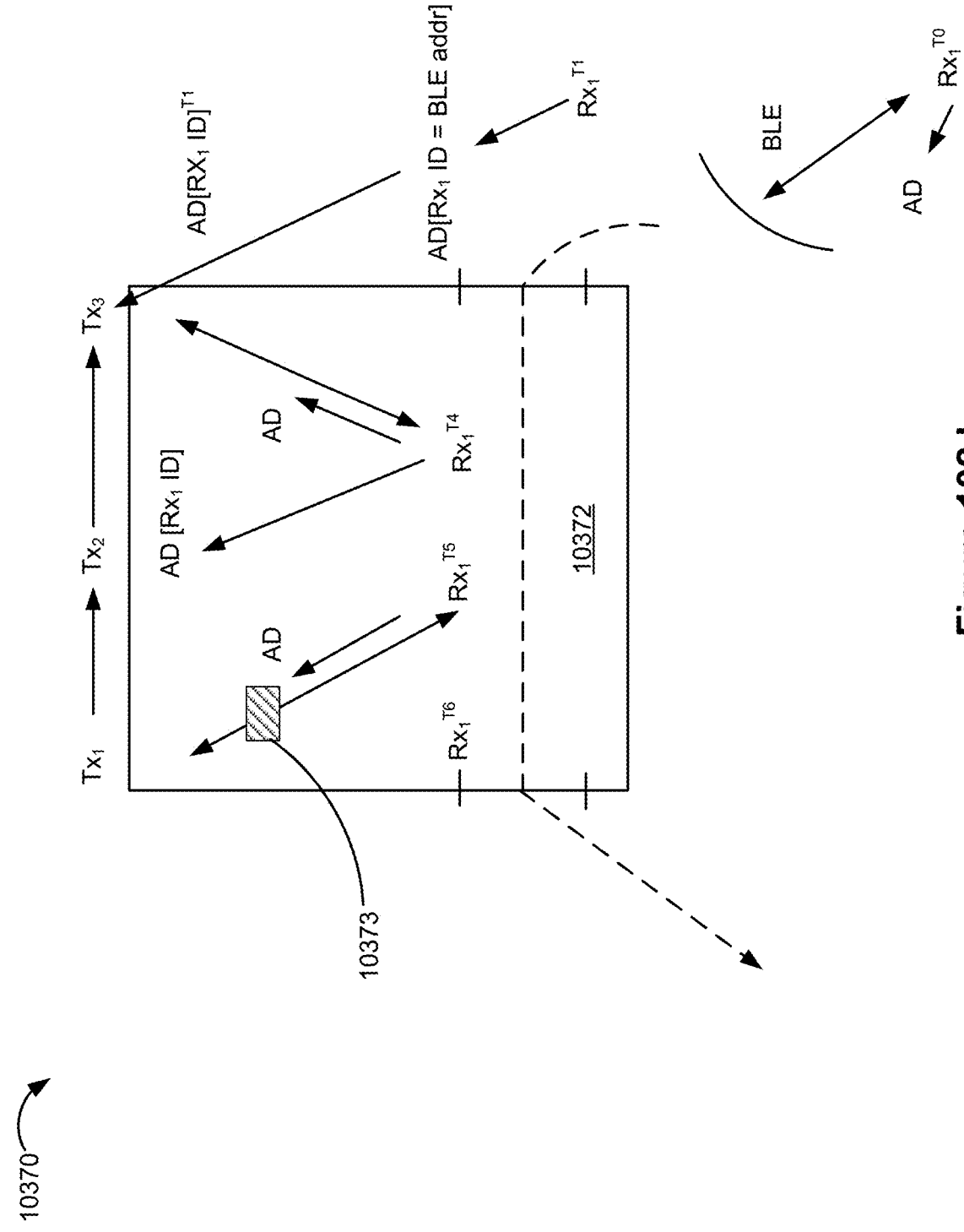

Receiver RX1 periodically broadcasts Bluetooth advertisements as the device with receiver approaches location 10372. In FIG. 102J the receiver first approaches location 10372 at time T0, as shown at 10371. Transmitter TX3 10366 first detects a BLE advertisement from receiver RX1 at time T1 (location 10371 in FIG. 102J). At this time, transmitter TX3 acquires the receiver's unique ID (e.g., Bluetooth unique identifier, MAC address), and TX3 transmits this information to the management system 10369 via modem 10368 (both communications are shown schematically in FIG. 102I at time T1). Management system 10369 can reference information on the identified receiver; the local power management facility including all transmitters; information pertinent to authorization of the receiver (such as the enterprise or account associated with the receiver); pricing information; and other applicable information such as information on the transmitter TX3 that initiated the communication. In this embodiment, the management system 10369 determines that all transmitters in the cluster TX1, TX2, and TX3 are available for power transfers to receiver RX1, and sends this message to the master transmitter (step 10353 in the method of FIG. 102G).

FIGS. 102I and 102J schematically illustrate a method of transmitter cluster management at a location (e.g., room 10372). At time T3, management system 10369 sends the master transmitter a message granting receiver RX1 access to wireless power transmission by transmitters TX1 10364, TX2 10365, TX3 10366. After the initial authorization of transfer of power to receiver RX1 at time T3, in FIG. 102J receiver RX1 is shown entering and moving across room 10372 at various times T4, T5, and T6. At time T4, receiver RX1 is in range of transmitters TX2 and TX3. At time T5, receiver RX1 enters the range of transmitter TX1 and is in range of all three transmitters TX1, TX2 and TX3. When transmitter TX1 first detects receiver RX1, it sends a message to management system 10369, which sends the master transmitter TX3 a return communication granting transmitter TX1 power transfer to receiver RX1.

During a period following time T5, all three transmitters TX1, TX2, and TX3 are available to transfer power to receiver RX1, subject to coordination of communications of the three transmitters with receiver RX1 by the master transmitter TX3 (step 10354 in the method of FIG. 102G). In one embodiment, master transmitter TX3 commands transmitters TX1 and TX2 to limit their communications with the receiver to one second of every period of three seconds (i.e., so that transmitters TX1, TX2, and TX3 each is allotted one second from the three second period). This could be done for example by master transmitter TX3 sending one of the other transmitters an "on" signal at the beginning of the one second period for which communications are to occur for that other transmitter, and transmitter TX3 sending an "off" signal at the end of that period. Alternatively, master transmitter TX3 could send an "on" signal at the beginning of the "on" period for communications, coupled with the duration of that "on" period. During time periods in which a given transmitter is not communicating with receiver RX1, the transmitter will control the phase of its transmit antennas based upon the most recent communications obtained from the receiver. Given the high volume of communications transmitted by receiver RX1 during each one second "on" period, such intermittent time periods for communications have been observed to be sufficient to permit each transmitter to adjust its antenna phases to regulate power transfer (step 10355 in the method of FIG. 102G), when transmitting power to a receiver in motion.

At time T6, receiver RX1 has left the range of transmitter TX3, while remaining within the range of transmitters TX1 and TX2. During the period in which a transmitter has been authorized to transmit power to an identified receiver, among other data the transmitter communicates to management system 10369, are data on the signal strength of its communications with the receiver, so that by time T6, the management system 10369 detects that transmitter TX3 is out of range for receiver RX1 (step 10356 in the method of FIG. 102G). Management system 10369 thereupon sends a deny access message for receiver RX1 to transmitter TX3, and selects one of the remaining transmitters (transmitter TX1, which has the lower IP number) as master transmitter. Thereafter, transmitter TX1 controls communications between receiver RX1 and the transmitters TX1 and TX2 that are still transferring power to receiver RX1.

In addition to tracking which transmitters are within range of a given receiver, the management system 10369 can limit the power output to given receivers and devices, e.g., based upon safety concerns. Various mobile phones have maximum DC power levels at or just under 4.0 watts (e.g., 3.96, 3.97, 3.98 or 3.99 watts). In the event of a transmitter cluster management transition, i.e., a change to the set of transmitters in communication with a given receiver, management system 10369 can send a message to the master transmitter to ensure compliance with any applicable maximum power level. This message would instruct available transmitters to limit power transfer from individual transmitters among the cluster of transmitters, thereby to ensure safe power transfers from each transmitter.

The above discussion assumed that power transmission between receiver RX1 and transmitters TX1, TX2, and TX3 was governed by the power transfer proximity of the receiver to the respective transmitters. In operation of the management system 10369, additional factors besides power transfer proximity may determine the capability of a given transmitter to transfer power to a receiver and associated user device; collectively these factors are sometimes called "power transfer attributes" in the present disclosure. In addition to power transfer proximity, power transfer attributes include power transfer capacity of a transmitter; power transfer availability, which includes authorization to transfer power to a receiver and scheduling; and transmission path obstruction, i.e., line of sight paths versus path obstructed by an obstacle. For example, as seen in FIG. 102J, obstacle 10373 may obstruct power transfer from transmitter TX1 to receiver RX1. In another example, transmitter TX2 may have significantly lower power transfer capacity than transmitter TX3. Metrics of these other power transfer attributes, in addition to power transfer proximity indicators, can be included in the data processed by management system 10369 in managing transmitter power transfer transitions.

The foregoing discussion describes controlling cluster management of transmitters through the interaction of a cluster of transmitters with a wireless power management system, preferably a cloud computing management system with networked remote servers are networked for centralized data storage and online access to data management services. In an alternative embodiment, the cluster of transmitters achieves transmitter cluster management under the control of the transmitters themselves, without oversight by a wireless power management system. This is possible since the transmitters themselves can replicate most of the management information and functionality used by the wireless power management system in transmitter cluster management.

The transmitter cluster management scheme discussed above involves hierarchical management of all transmitters at given locations, sometimes herein called a transmitter cluster, in controlling power transfer by the transmitters to a receiver at that location. Other transmitter cluster management schemes are possible, which may manage transmitter-receiver connections at any level of a hierarchical structure. For example, the management system may define a given transmitter cluster as a subset of all transmitters at a location, and manage receiver interactions only with these transmitters separate from other transmitters at the location. Furthermore, the transmitter cluster management scheme may manage transmitter-receiver power transfers and communications across multiple, neighboring locations. For example, two neighboring households each may have two transmitters, which may be organized into one or two clusters managed by the cloud based power transfer management system. The system could manage neighboring locations as clusters, so all four transmitters would be part of one cluster; or, the system could manage each billing address as a separate cluster, so there would be two clusters each with two transmitters.

FIGS. 102K-103D illustrate system and methods for wirelessly powering one or more devices that are stationery or in movement within the service zone of a cluster of transmitters. Transmitters TX within the cluster collectively can deliver power to receivers within the service zone, and these transmitters are in communication with a master transmitter that coordinates power transmission by transmitters of the cluster.

In an embodiment, a plurality of transmitters of the cluster may form an energy pocket at a device to receive power, wherein there are multiple pockets of energy at the device. The use of multiple pockets of energy can be useful, for example, with devices (such as LED lighting fixtures) that do not include batteries, and that require continuous and uninterrupted power to ensure device operation, or sensors for security applications.

In an embodiment, transmitters within the cluster communicate with each other via a common computer network or subnet. Transmitters of the cluster inter-communicate power authorization data and receiver communication assignments in order to maintain sufficient power for continuous and uninterrupted device operation when a device moves out of range or into range of any transmitter. Furthermore, coordinated transfer of power by multiple transmitters can prevent inefficiencies such as destructive interference of pockets of energy formed at a device by multiple transmitters.

Figure 102K:
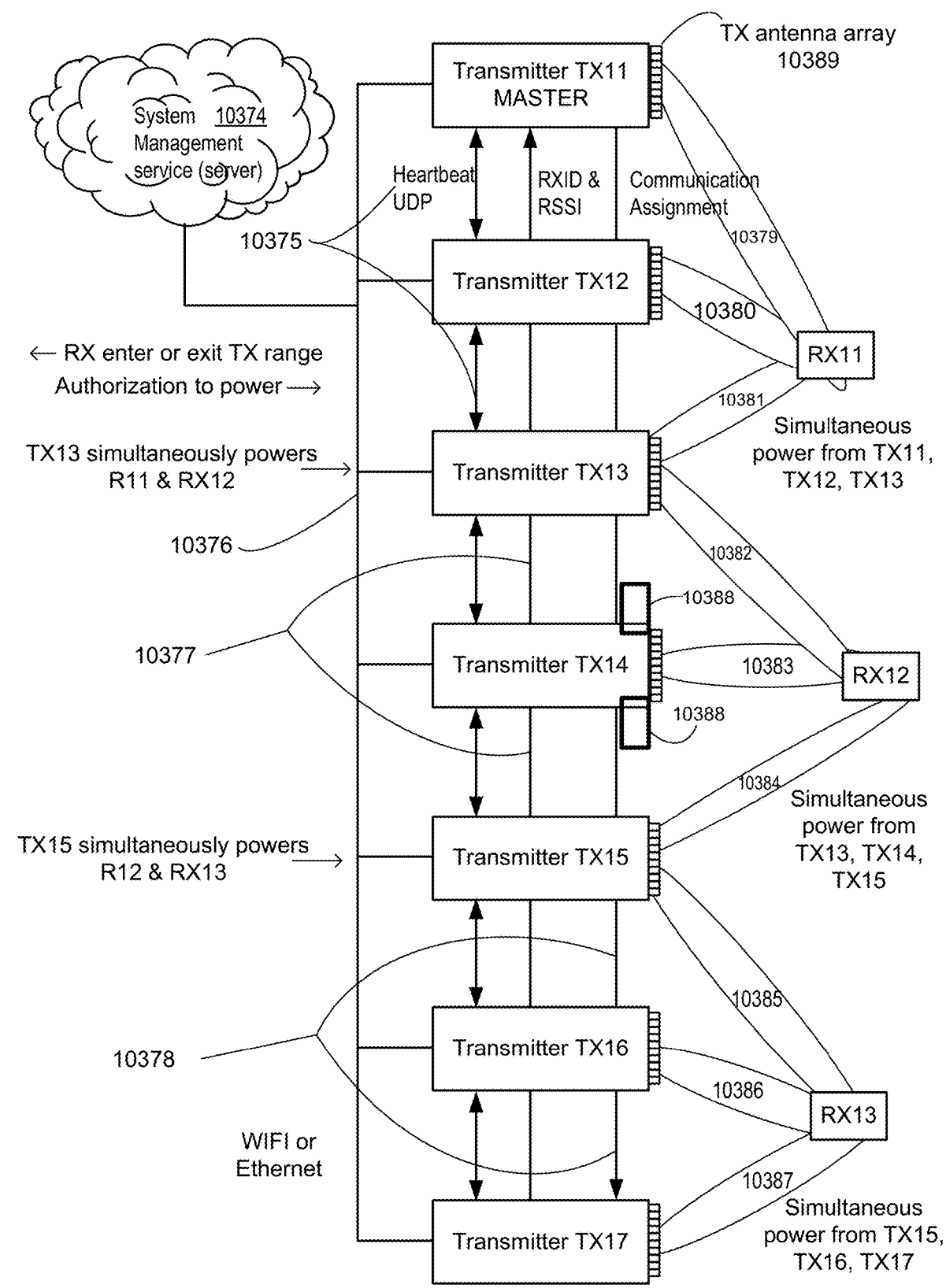

FIG. 102K is a system block diagram of a wireless power network for wirelessly powering devices associated with receivers RX11, RX12, and RX13 within the service zone of a cluster of transmitters TX11-TX17. System management service 10374 may include a local server, or (as shown here) cloud based server that manages the wireless power transmission system. System management service 10374 manages communications from transmitters TX to system management, for example during transmitter power transfer transitions. Each of the wireless power transmitters TX11-TX17 may include an embedded wireless power transmitter manager (not shown). Each embedded wireless power transmitter manager may include a wireless power manager application, communicatively coupled to an embedded database (cf. FIG. 102D), to effect methods of FIGS. 103A-103D for wirelessly powering devices within the service zone of the cluster of transmitters TX11-TX17.

Transmitter TX11 is the master transmitter of the transmitter cluster TX11-TX17. In an embodiment, the master transmitter TX11 controls communication assignments between transmitters and receivers in the service zone of the cluster. As used in the present disclosure, the transmitter cluster consists of "worker" transmitters, i.e., transmitters with assigned RX's that perform wireless power transfer to these RX's. In an embodiment, the master transmitter TX11 also is a worker transmitter.

Each of TX11-TX17 includes a TX antenna array 10389, an array of transmission antennas that transmits wireless energy to form energy pockets at a power receiver RX. Generally, transmission of energy from multiple TX antenna arrays to a receiver provides additional available power for the receiver; for example, pockets of energy 10379, 10380, and 10381 at receiver RX11.

A communication network of the wireless power system includes a Wi-Fi or Ethernet communication network 10376 between the transmitters and the system management service 10374. Each of transmitters TX11-TX17 broadcasts a heartbeat User Datagram Protocol (UDP) 10375 datagram throughout the network. The heartbeat is a signal generated by transmitter managers of transmitters TX11-TX17, which communicates to other system processors that the first transmitter manager is still online or performing its normal function. In an embodiment, the heartbeat of a transmitter manager for a given TX contains the network IP address of that TX, and whether the TX is the master TX, among other information.

System communications also includes, at 10377, receiver data and RSSI from each of transmitters TX12-TX17 to the master transmitter TX11. RX information can include the receiver's unique ID, such as Bluetooth Low Energy address, MAC address, or serial number. RSSI or signal strength is measured at each of the transmitters.

In an embodiment, communication assignments 10378 are sent by master transmitter TX11 to all other transmitters. These assignments specify which RX (or multiple RX's) each TX is assigned for communications. In an embodiment, no two transmitters communicate with the same RX at the same time. Table 1 is an exemplary communication assignment list for the power transmission configuration shown in FIG. 102K.

TABLE 1

Communication Assignment List

| Transmitter | Receiver |
|---|---|
| TX11 | RX11 |
| TX12 | RX11 |
| TX13 | RX11, RX12 |
| TX14 | RX12 |
| TX15 | RX12, RX13 |
| TX16 | RX13 |
| TX17 | RX13 |

During each heartbeat period, the master TX broadcasts a list of receivers authorized for power from each transmitter, including the master TX. Each receiver is assigned to only one transmitter at a time. A specific transmitter TX may power one or more receiver. Communication assignments may be changed by the master TX at each heartbeat period. At each heartbeat period the master TX builds the latest list of RX communication assignments to TX's, and any RX not authorized by System Management 10401 to receive power is ignored. The new list is broadcast at each heartbeat period.

In an embodiment of master communication assignments to TX's of the cluster, at every heartbeat period an RX in communication range of multiple TX's is assigned to the next TX if the latest TX has not had time to communicate with the RX. Each TX in communication range has a turn to communicate with RX (10415, FIG. 103A), and the communication cycle repeats. The list of TX's powering a given RX may change as the RX moves in and out of range of TX's. This process continues until the RX is no longer authorized, is out of range, or no longer needs power.

For maximum power to a device, multiple transmitters that power a specific RX take turns at communication because only one TX may communicate with RX at same time. This is controlled by master TX, which moves the communication assignment of specific RX sequentially, one TX at a time, to each TX that powers RX, assignment being sent every heartbeat period of time. Master may assign a specific RX to a specific TX for more than one heartbeat period of time if TX has not yet communicated with RX. This may occur in the case of TX that concurrently powers more receivers than its maximum number of simultaneous communication connections.

The following is a summary of cluster management of transmitter power transfer transitions in the system of FIG. 102A. One transmitter (TX11) of the cluster of transmitters has the designation of "master transmitter", and controls communications between transmitters TX11-TX17 and receivers in the service zone of the cluster. Whenever a receiver RX moves within communication range of a transmitter, which detects that communication has become available with receiver, the transmitter communicates this state to system management 10374 in order to obtain authorization to power receiver. When system management communicates authorization to the transmitter, the transmitter forwards this authorization to the master TX, which may communicate to TX that it is assigned communication rights with the RX for the purpose of wireless power transmission to receiver. Whenever a receiver moves out of communication range of a transmitter, and communication between RX and TX is no longer available, the transmitter reports this state to system management and the master TX. Thereafter the master transmitter will no longer command that TX to communicate with and power the RX.

Figure 103A:
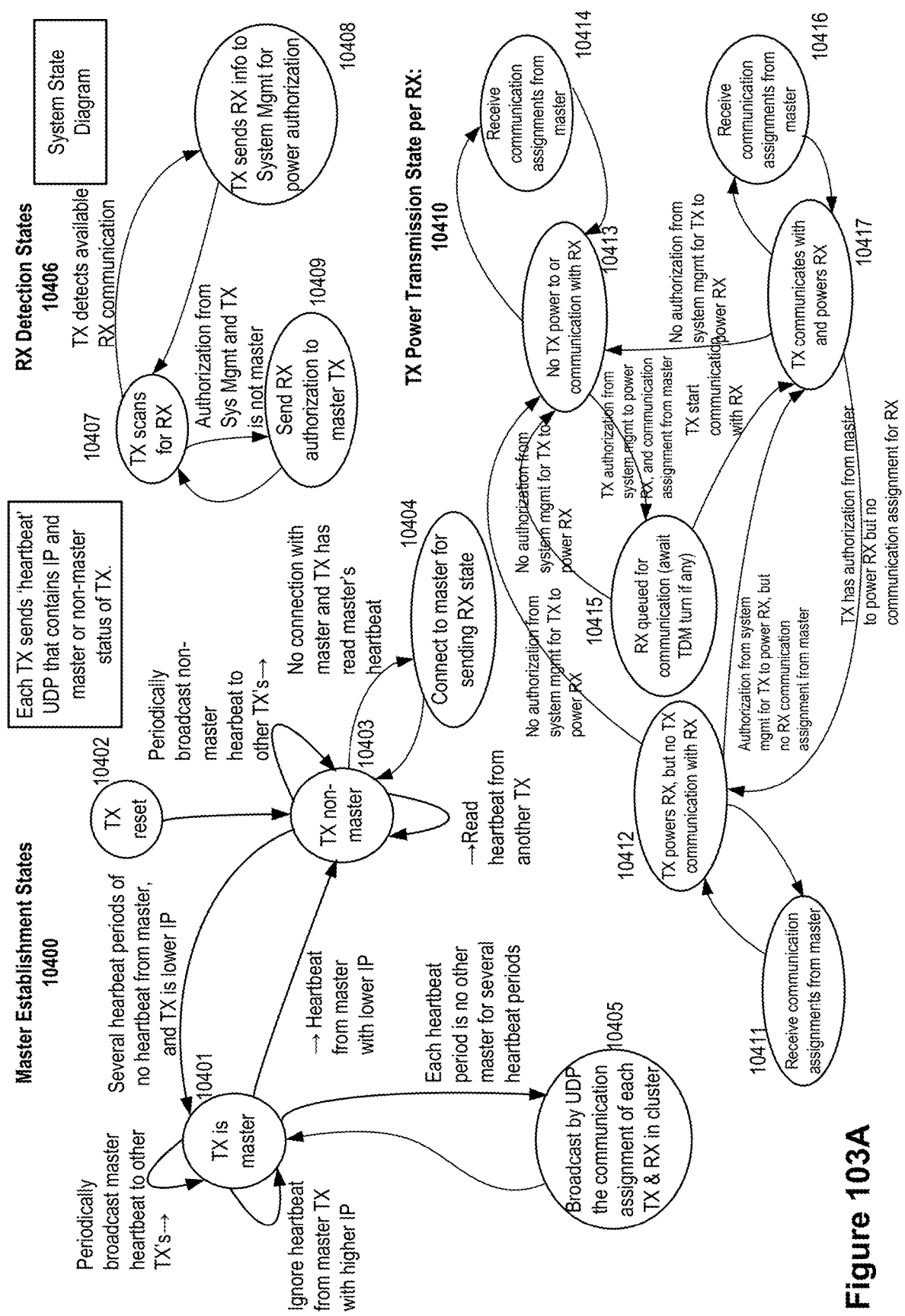

FIG. 103A is a system state diagram showing states of wireless power transmitter software of the system of FIG. 102K, for wirelessly powering receiver devices within the service zone of a cluster of wireless power transmitters. Referring to the state diagrams RX Detection States 10406, and TX Power Transmission State Per RX 10410, a transmitter TX may not power a receiver RX until RX is close enough for communication with the TX. When TX detects an RX 10407 within communications range that was not previously within range, then TX may communicate this to system management for power authorization 10408. TX may not power RX until system management communicates authorization to TX. When TX that is not master receives this authorization, it communicates it to the master TX 10409. Thus the master TX knows which authorized RX's should be assigned to TX's.

Referring to TX Power Transmission State per RX 10410, upon receiving a communication assignments list from the master TX 10414, TX ends communication with any RX not in the list of RX's for that TX (10414, 10413). TX enables communication with RX's in its list (10416, 10417).

Each TX may communicate with more than one receiver simultaneously. If number of RX's assigned to TX exceeds this maximum, then TX may employ Time-Division Multiplexing (TDM) communication. In this case, TX may not communicate right away with RX. RX is queued for communication 10415 and TX uses Time-Division Multiplexing (TDM) to manage the RX with which TX communicates. Once TX has a communications connection available for RX, TX starts communication with RX 10417.

If TX Power Transmission State per RX 10410 is "RX queued for communication" 10415 or "TX communicates with and powers RX" 10417, but there is no longer authorization from system management for TX to power RX, the TX Power Transmission State per RX reverts to "No TX power to or communication with RX" state 10413. If RX is no longer authorized by system management to receive power from TX, TX communicates this change in authorization to the master TX, which will remove RX from list of communication assignments that will be sent to TX at next heartbeat period.

Referring to the TX Power Transmission Flowchart 10445 of FIG. 103D, when TX receives communication assignments from the master transmitter 10449, and there is no longer a communication assignment to an RX for which it is still authorized to power 10450, then if TX is still in communication with Rx then TX ends communication with RX 10450. TX will not again communicate until RX is re-assigned to TX 10452, 10453 by the master transmitter.

When TX receives communication assignments from the master transmitters, and the communication assignments include the same receiver RX with which TX was previously in communication, then TX starts communication with RX (10416, 10417). TX will continue communication until RX is re-assigned to another TX by the master TX (10414, 10413), or until TX no longer has authorization from system management to power receiver RX (10417, 10413).

Figure 103B:
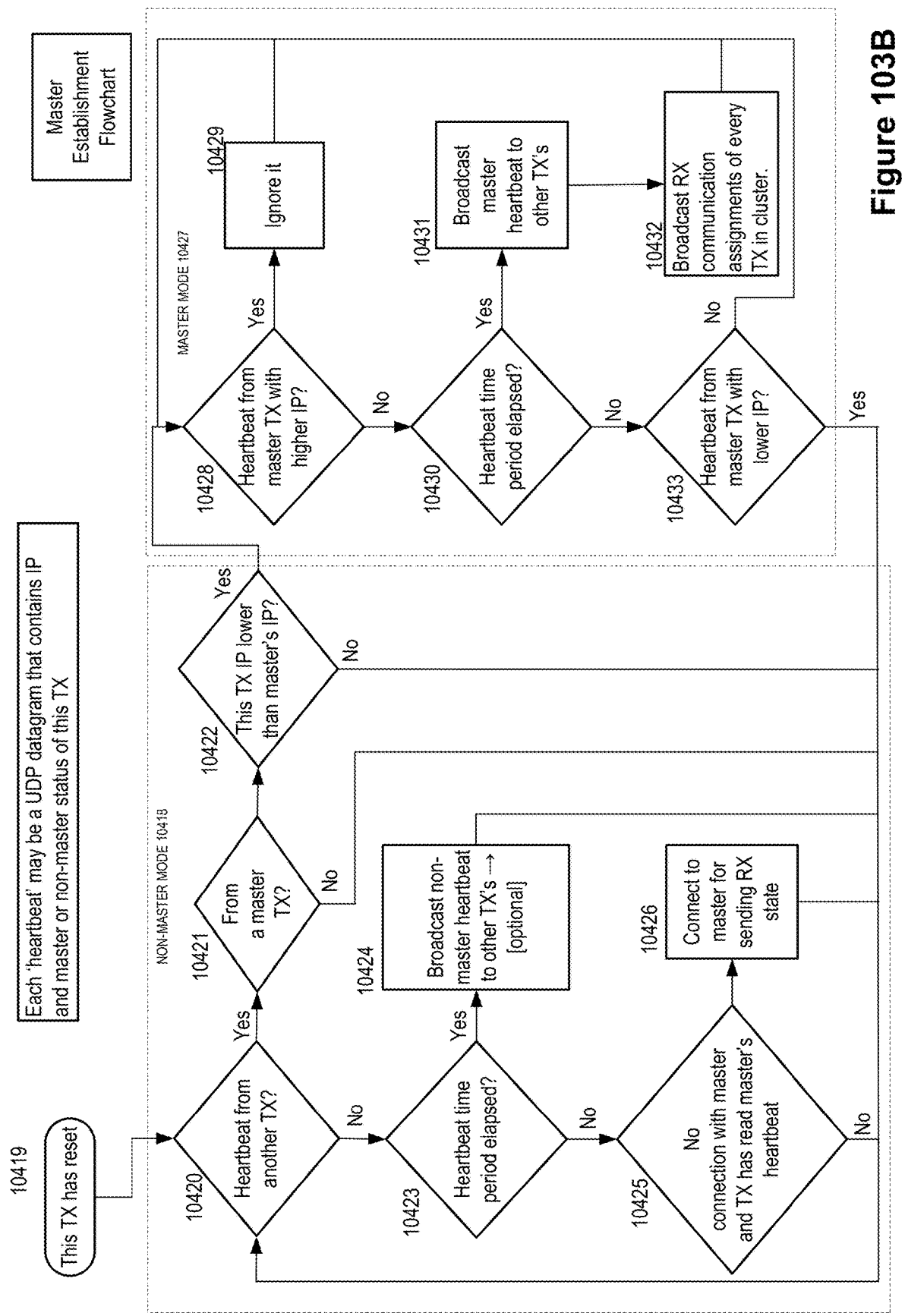

Turning to the Master Establishment Flowchart of FIG. 103B, and the Master Establishment States diagram 10400 of FIG. 103A, there can only be a single master transmitter of the cluster. Whenever the software of a transmitter starts or resets 10419 (state 10402, FIG. 103A), it performs the default role of non-master mode 10418 (state 10403, FIG. 103A). In non-master mode 10418 (Master Establishment state 10403), a non-master TX begins periodically broadcasting its heartbeat. Heartbeat broadcast may be by UDP datagram 10375 (FIG. 102K), or other communication method.

The non-master TX begins reading heartbeats 10420 from any other TX in the cluster (state 10403, FIG. 103A). If a heartbeat is received from the master 10425, and non-master TX does not already have communication connection with master, then TX starts communication connection with the master TX to periodically receive assignments to communicate with one or more RX's that TX is authorized to power (state 10404, FIG. 103A).

If non-master TX does not receive heartbeat from a master for a predetermined period of time (e.g., 10 seconds), and the network address, or IP, of TX is numerically lower than any other TX of the cluster 10422, than TX may change to the master role 10427 becoming the cluster master (Master Establishment State transition from 10403 to 10401, FIG. 103A). Non-master TX learns the network address of other TX's by reading their heartbeat broadcasts.

Master mode process 10427 prevents multiple masters within a cluster of TX's. A master TX periodically broadcasts its master heartbeat to the other transmitters of the cluster (state 10401, FIG. 103A). If a master TX receives a heartbeat from another TX of the cluster that also is in the master role and the other TX has a numerically lower network address than the first TX (yes at 10433), then the first TX will change to the non-master role (Master Establishment State transition from 10401 to 10403, FIG. 103A). The other TX will continue as master, broadcasting a master heartbeat to other TX's 10431.

A master TX will ignore a heartbeat from another master with a numerically greater network address (10429; 10401 in FIG. 103A), because the TX master with greater address will eventually detect the TX master with lower address, and switch to non-master mode.

If a master TX detects no other master for a predetermined heartbeat time period (e.g., 10 heartbeat periods), then after the predetermined heartbeat time period the master broadcasts 10432 the communication assignments of each TX and RX in the cluster (state 10405, FIG. 103A).

Figure 103C:
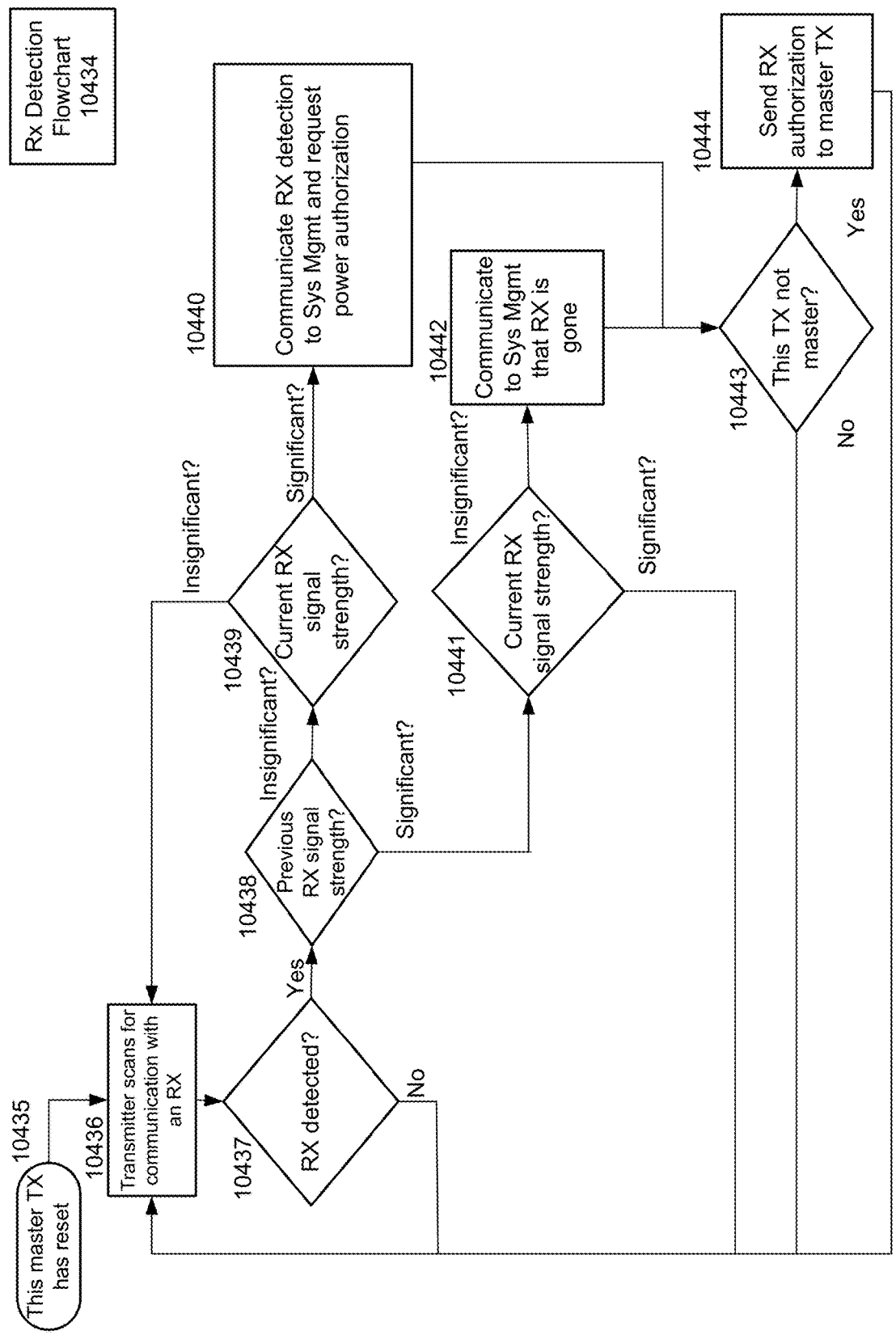

The RX Detection Flowchart 10434 of FIG. 103C, and RX detection states diagram 10400 of FIG. 103A, show states of a worker transmitter TX in detection of receiver RX. Whenever the software of a transmitter starts or resets 10419, the transmitter scans 10436 for receivers RX in communication range (state 10407, FIG. 103A). On detecting RX 10437 the TX determines 10438 whether a previous RX signal strength exceeds a required threshold ("significant") or is below the threshold ("insignificant"); and TX determines 10439 whether current RX signal strength reading stored by TX. In an embodiment, the current and previous signal strengths are communicated by power receiver 10333 to transmitter TX and stored in a device database 10336 associated with transmitter manager 10335 of transmitter TX (FIG. 102D).

In the event current signal strength is above a particular threshold whereas previous signal strength was below a particular threshold, at 10440 the transmitter manager of worker transmitter TX communicates the detection of receiver RX to system management, and requests power authorization (state 10408, FIG. 103A). On receiving power authorization if the worker transmitter is not master (yes at 10443), the worker TX sends 10444 power authorization to the master TX (state 10409 in FIG. 103A). Thereafter worker TX transmits power to RX as long as it continues to detect receiver RX (10437) and current signal strength readings remain significant (10438, 10441).

In the event current signal strength is below a particular threshold, whereas previous signal strength was above a particular threshold, at 10440 the transmitter manager of worker transmitter TX, at 10442 TX communicates to system management 10401 that the RX signal strength has dropped below threshold, and a worker transmitter transmits this state change to the master TX 10444. Thereafter the master transmitter will no longer command that TX to communicate with and power the RX.

In the above described RX detection state embodiment, control logic for RX communication and power authorization are based on signal strength levels (i.e., power transfer proximity thresholds). In further embodiments, RX power authorization may be based upon predetermined standards of other power transfer attributes besides power transfer proximity. In an embodiment, power transfer attributes include power transfer proximity; power transfer capacity of a transmitter; power transfer availability (e.g., authorization to transfer power to a receiver, and power scheduling); transmission path obstruction (line-of-sight power transmission vs. obstructed power transmission); and combinations of two or more of these power transfer attributes. In an embodiment, RX power authorization is based upon at least three power transfer attributes.

Power transfer attributes (also herein called power transfer attributes data) may be used in managing transmitter power transfer transitions and other power transfer events in a wireless power transmission system. In a control architecture such as that of FIG. 102D, at least one of transmitter managers 10334, 10335 may receive data representing a plurality of power transfer attributes of one or more of the power transmitters from one or more sources within the wireless power transmission system. The sources of power transfer attributes data may include one or more of the power receiver 10333; a customer device 10332 (also called user device); a management control system 10339 of the plurality of power transmitters (e.g., a local server or cloud base server); as well as other transmitter managers. The sources of power transfer attributes data also may include sensors, such as sensors 10388 that may be mounted at the front of transmitter TX14 and that are communicatively coupled with a transmitter manager of TX14 (FIG. 102K).

Power transfer attributes data may be stored in device databases 10336 associated with transmitter managers 10334, 10335, and in management control system 10339. In an embodiment, one of the transmitter managers is a master transmitter, which processes power transfer attributes in managing the transition of transmission responsibilities between transmitters within a cluster of wireless power transmitters. In an embodiment, the database stores weighting factors for each of the power transfer attributes data, which may be used in calculating and storing power transfer ratings based upon the power transfer attributes data. In an embodiment, the device databases include audit and logging information to track increases and decreases over time of the power transfer attributes data, weighting factors, and power transfer ratings; and to track events of the wireless power transmitter cluster such as transmitter power transfer transitions.

In an example of acquisition of power transfer attributes, a transmitter manager may receive power transfer proximity data (e.g., RSSI) from power receivers and from other transmitter managers. In another example, a transmitter manager may receive power transfer availability data (e.g., authorization to transfer power to a receiver, and power scheduling data) from management control system 10339. In a further example, a transmitter manager may receive transmission path obstruction attributes from one or more sensors, as sensor data indicating the location and dimensions of an obstacle obstructing power transmission by a given transmitter TX to a given receiver RX (e.g., obstacle 10373, FIG. 102J).

Figure 103E:
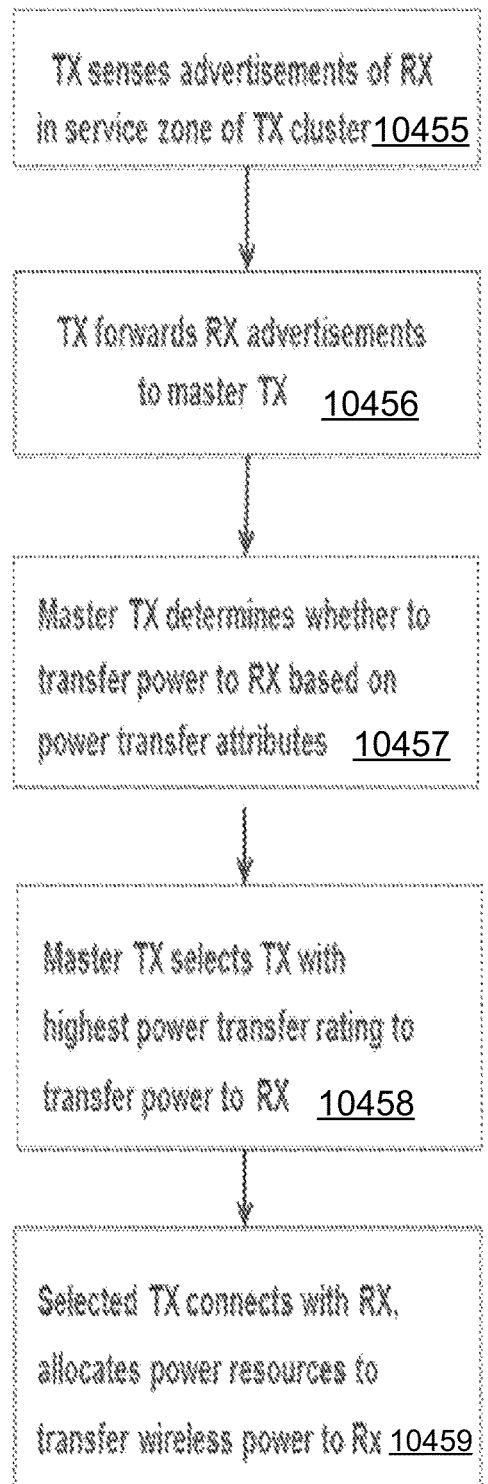

FIG. 103E is a flowchart of a method for determining whether to transfer power to a receiver, and selecting a transmitter to transfer power to a receiver, in a system for wirelessly powering receiver devices within the service zone of a cluster of wireless power transmitters. Besides Bluetooth®, RX communications may use other communication medium or protocol capable of communicating data between processors, such as RFID, infrared, near-field communication (NFC). The cluster is a set or plurality of TX(s) that collectively can deliver power to a RX within the service zone. Master TX refers to an TX that coordinates communication and power delivery by TX(s) within the cluster.

At step 10455, TX detects BLE advertisements of RX within the service zone of the cluster. In an embodiment, RX sends periodic BLE advertisements, and enters the service zone covered by a cluster of TX. At step 10456, any TX within communication range of the BLE advertisements forward the advertisements to the master TX.

At step 10457, the master TX determines whether to transfer power to RX based upon power transmitter attributes relating to RX. In an embodiment, power transfer attributes include a plurality of the following attributes:

(a) Power transfer proximity, or in-close charging/power proximity of TX within the service zone. In an embodiment, high power transfer proximity is reflected in strong RSSI;

(b) Authorization (whether RX is allowed to be charged/receive power from a given TX);

(c) Power scheduling, i.e., scheduling of RX for power (e.g., start time and stop time of power transfer or duration of power transfer). In an embodiment, (b) authorization and (c) power scheduling are power transfer availability attributes, which may be received by the master transmitter from system management of the wireless transmission system;

(d) Power availability, i.e., whether TX has available power capacity (e.g., based upon antenna configuration) and/or whether TX has sufficient resources to transmit power waves to RX. Power availability can be a consideration for example when a given TX already has power allocated to charge or one or more other RX;

(e) RX power requirements;

(f) Power transmission obstruction, i.e., line of sight transmission path vs. obstructed path.

At step 10458, the master TX selects an TX within the cluster to transfer power to RX based upon the power transfer attributes. In an embodiment, the master TX determines a power transfer rating from one or more TX capable of transmitting power to RX, and selects the TX with highest power transfer rating to transfer power to RX. In another embodiment, the master TX selects the TX with highest transfer rating as primary TX to transfer power to RX, but also another TX with a lower power transfer rating to transfer power to RX (additive power, e.g., for RX with high power requirements). In an embodiment, the master TX selects an TX within the cluster to transfer power to RX based upon at least three power transfer attributes.

In an embodiment, at step 10458 the master TX uses a heuristic process to determine power transfer rating for TX selection, in order to select an TX that can provide optimal power service to RX. The heuristic process may use a list of sorted, weighted metrics based upon relevant power transfer attributes, in determining the power transfer rating. For example, each metric may be assigned a weighted score, and these scores may be summed to determine a total score, i.e., power transfer rating, for an TX. In an embodiment, given metrics may have positive or negative scores, and the highest power transfer rating based on summing these metrics determines the selection of TX to transfer power. The heuristic process may penalize the TX power transfer rating due to certain data or events; for example, a failed connection event may be included as a metric with a negative score. The heuristic process may increase or reduce the weight of metrics due to certain data or events; for example, sensor data indicating a substantial obstacle obstructing transmission between TX and an RX in motion, may result in an increased weight of a power transmission obstruction metric.

At 10459 the selected TX connects with RX, and allocates power resources to transfer wireless power to RX. In an embodiment, the master TX sends a connection command to the selected TX. In an embodiment, the master TX sends a power allocation command to the selected TX.

In an embodiment, after allocating power resources to RX, the TX sends its power status (measuring amount of power delivered) to the TX master. The master TX determines whether this power status is sufficient to meet RX power requirements. If the power status is sufficient the master TX maintains the TX-RX connection and current power allocation, but if the power status is insufficient the master TX may command a transmission power transfer transition and/or may command an adjusted TX-RX power allocation.

Figure 103F:
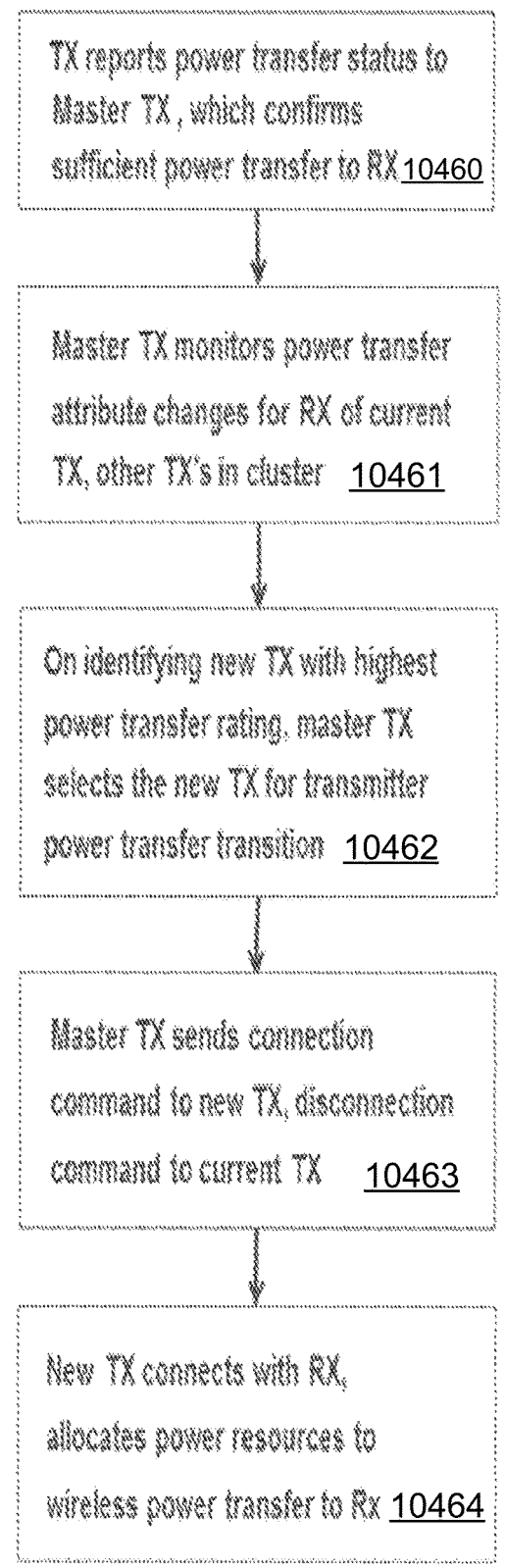

FIG. 103F is a flowchart of a method by a master transmitter for monitoring power transfer attributes of transmitters within a cluster of wireless power transmitters to a receiver device, and for transitioning power transfer authorization from a current transmitter to a new transmitter. The method applies to TX currently transferring power to RX, e.g., following selection of TX based upon the method of FIG. 103E. At 10460 the TX reports its power status for transfer of power to RX to the TX master. In an embodiment, the TX power status reports to TX master are periodic reports. If the power status is sufficient the master TX maintains the TX-RX connection and current power allocation, but if the power status is insufficient the master TX may command a transmission power transfer transition and/or may command an adjusted TX-RX power allocation.

At 10461, the master TX monitors power transfer attributes changes of the current TX for power transfer to RX, as well as power transfer attributes of other transmitters in the cluster. In an embodiment, the master TX updates its database of power transfer changes in the case of changes that exceed a minimum difference, such as power transfer proximity changes that exceed a minimum percentage difference. In an embodiment, the master TX calculates power transfer ratings of transmitters in the cluster, for example when the power transfer attributes of the current TX are decreasing gradually or sharply (e.g., due to RX movement away from TX).

At 10462 the master transmitter identifies a new TX with the highest power transfer rating in the cluster. The master transmitter selects the new TX for power transfer to RX. At 10463 the master TX sends a connection command to the new TX, and a disconnection command to the TX currently transferring power to RX. In another embodiment, the current TX maintains its connection to RX, for additive power to RX by the current TX and the new TX. In an embodiment, RX enters a transmission power transfer transition state in which its BLE advertisement rate increases above normal advertisement rate, in order to facilitate the change of connection to the new TX. At 10464, the new TX connects with RX, allocates power resources for wireless power transfer to RX. The method steps of FIG. 103F may then repeat, starting with the new RX reporting power transfer status to the master transmitter 10460.

In a further embodiment, the process of connecting an optimal TX to RX includes a security pairing process, to secure the communications link from attacks.

FIGS. 102A-102K and 103A-103F illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 102A-102K and 103A-103F.

Presented below are example embodiments of cluster management of transmitters in a wireless power transmission system.

In some embodiments, an example system for providing wireless power delivery, comprising a master transmitter manager configured to communicate with a plurality of transmitter managers communicatively coupled with a plurality of transmitters. The master transmitter manager is configured to control the transmission of power waves by at least one of a plurality of power transmitters to a receiver based upon a strength of a communication signal received by each transmitter manager from the receiver.

In some embodiments, the master transmitter manager is configured to select a transmitter of the plurality of transmitters when that transmitter is associated with a transmitter manager that received a communication signal having a higher strength than any other transmitter manager associated with another transmitter.

In some embodiments, the master transmitter manager is configured to compare the strength of the communication signal received by each transmitter manager from the receiver.

In some embodiments, the master transmitter manager is configured to provide to the plurality of transmitter managers information related to a power record of the receiver.

In some embodiments, the master transmitter manager is configured to communicably deliver to at least one remote server information related to the at least one of the plurality of transmitters or a power record of the receiver.

In some embodiments, each of the plurality of transmitter managers is configured to broadcast a datagram including a master/non-master state and an IP address of the transmitter manager broadcasting the datagram.

In some embodiments, each transmitter manager is configured to receive the datagram broadcast from the other transmitter managers.

In some embodiments, the master transmitter manager is configured to determine that a first transmitter manager is to decrease a transmission of power waves and a second transmitter manager is to increase a transmission of power waves upon the second transmitter manager receiving a higher strength communication signal than the first transmitter manager.

In some embodiments, the master transmitter manager is configured to select at least two of the plurality of transmitter managers of at least two of the plurality of transmitters to control the transmission of power waves to the receiver.

In some embodiments, the transmitter manager is configured to coordinate contemporaneous communication of the plurality of power transmitters with the receiver via time division multiplexing (TDM) of such contemporaneous communication.

In some embodiments, the master transmitter manager is configured to communicate to the plurality of transmitter managers a communications assignment list specifying which of the plurality of transmitter managers are assigned for communication with the receiver.

In some embodiments, an example method for providing wireless power delivery, comprising receiving, by a master transmitter manager, a signal strength of a communication signal from a receiver to a plurality of transmitters, and selecting, by the master transmitter manager, at least one of the plurality of transmitters to generate power waves that form constructive interference to the receiver based upon the communication signal strength.

In some embodiments, the communication signal strength is based upon a power transfer proximity indicator indicative of at least one of proximity of the receiver relative to the at least one of the plurality of power transmitters.

In some embodiments, each of the plurality of transmitter managers communicates to others of the plurality of transmitter managers a datagram including a master/non-master state and an IP address.

In some embodiments, the method further comprises selecting a second transmitter of the at least one of the plurality of transmitters respectively communicatively coupled to the plurality of transmitter managers, whereby the receiver continuously receives power waves from at least one of the plurality of transmitters.

In some embodiments, the master transmitter manager selects at least two of the plurality of transmitters respectively communicatively coupled to the plurality of transmitter managers.

In some embodiments, the method further comprises coordinating contemporaneous communication of the at least two of the plurality of transmitters respectively communicatively coupled to the plurality of transmitter managers with the power receiver via time division multiplexing (TDM) of such contemporaneous communication.

In some embodiments, the method further comprises receiving a plurality of power transfer attributes of the plurality of power transmitters with respect to the receiver. The master transmitter manager selects the at least one of the plurality of transmitters respectively communicatively coupled to the plurality of transmitter managers in accordance with the plurality of power transfer attributes.

A method for providing wireless power delivery, comprising transmitting, by a master transmitter manager to a plurality of transmitter managers communicatively coupled to a plurality of power transmitters, a selection of at least one of the plurality of power transmitters to generate power waves that form a constructive interference pattern at a receiver, monitoring, by the master transmitter manager, a location information of the receiver with respect to each of the plurality of power transmitters, and changing, by the master transmitter manager, the selection of the at least one of the plurality of power transmitters based upon the location information of the receiver, whereby at least one of the plurality of power transmitters continues to generate power waves during the change.

In some embodiments, the method further comprises determining, by the master transmitter manager, the location information of the receiver based upon a communication signal transmitted from the receiver.

FIGS. 104A-104B illustrate examples of devices, apparatus, and methods for radar motion detection using stepped frequency in wireless power transmission system, in accordance with some embodiments.

FIG. 104A shows a method of transmission of power waves in a wireless power transmission system, according to an exemplary embodiment.

At step 10502, a receiver (RX) generates location data associated with one or more objects. In one example, the receiver generates the location data associated with the one or more objects when the receiver is receiving power waves from a transmitter and the one or more objects enter within a pre-defined distance from the receiver. In another example, the receiver is configured to continuously or periodically generate and update location data associated with the one or more objects.

The receiver generates the location data associated with one or more objects based upon one or more object detection signals reflected from each object. The object detection signals received back from a particular object indicate a location of the particular object in relation to the receiver, allowing the receiver to generate location data based upon this relative location determined by the receiver. Because the transmitter may be aware of the location of the receiver, the location data of the particular object indicates to the transmitter the location of the respective object in relation to a transmitter. In some implementations, an object detection antenna coupled to the receiver may emit a plurality of object detection signals, where each respective object detection signal has a successively stepped frequency. The object detection antenna then receives at least one object detection signal reflected back from the object. In one example, a single object detection antenna or a set of object detection antennas may be utilized for both transmitting object detection signals and receiving reflected object detection signals. In another example, one set of object detection antennas may be utilized for transmitting object detection signals and another set of object detection antennas may be utilized for receiving reflected object detection signals.

A processor configured to control the receiver, then generates the location of the object in relation to the receiver based on the at least one object detection signal being reflected back from the object. In one example, the location data of the object may be determined by measuring the lag time of reflected object detection signals from the object. The determined location of the object may then be saved in a memory of the receiver by the processor.

At step 10504, the receiver transmits the location data associated with the object to the transmitter (TX). The location data of the object is then transmitted by the receiver via one or more communications signals generated by a communication component of the receiver containing the location data to the transmitter. In an embodiment, the communication component may send the location data of the object to the transmitter on receiving a request from the transmitter.

At step 10506, the receiver receives from one or more antennas of the transmitter, one or more power waves having one or more waveform characteristics causing the one or more power waves to converge at a location proximate to the receiver based on the location data generated for each respective object. The one or more power waves may also converge destructively to form one or more null spaces based on the one or more waveform characteristics of the one or more power waves. The receiver may be embedded in an electronic device that is being charged by the one or more power waves received from the one or more antennas of the transmitter. Alternatively, the receiver may stop receiving power waves altogether based on the sensed location of the object to the receiver.

FIG. 104B illustrates a method of transmission of power waves in a wireless power transmission system, according to an exemplary embodiment.

At step 10510, a first set of one or more object detection antennas of a receiver (RX) emits a plurality of outbound object detection signals, where each respective object detection signal has a successively stepped frequency with respect to a preceding object detection signal.

In an embodiment, a signal generator of the receiver may be configured to generate object detection signals. In one example, the object detection signals generated may be tone waves that require minimal filtering. In another example, each object detection signal generated may not modulated. In yet another example, the object detection signals generated may be non-linear chirp signals, where the non-linear chirp signals are selected from the group consisting of exponential, logarithmic, and arbitrarily formulated chirp waveform. The signal generator may also randomly change a frequency of one or more outbound detection signals of the plurality of outbound detection signals. The frequency of the one or more outbound detection signals may be randomly changed at a random interval range of, for example, 1 to 1000 times per second.

At step 10512, a second set of one or more object detection antennas of the receiver receives one or more inbound object detection signals that are reflected from one or more objects. The characteristics and timing of inbound object detection signals may be used to determine various aspects of location data for an object, such as range or distance from the receiver. More antennas and more inbound object detection signals may permit the receiver to generate more sophisticated forms of location data, such as multiple dimensions and greater accuracy. For example, an inbound object detection signal reflected back from an object indicates a location of the object in relation to the receiver; in this case, the range or distance from the receiver. In some cases, multiple inbound object detection signals reflected back from an object may have different phase positions in relation to one another based on an angular position of the object in a spatial direction in relation to the receiver.

At step 10514, a processor of the receiver generates location data associated with each object based on the one or more inbound object detection signals reflected back from the particular object. The inbound object detection signals may be the result of the location of the object in relation to the receiver, and thus the receiver may generate the location data based on the location of the object in relation to the receiver. When received by the transmitter, the location data associated• with each respective object indicates to the transmitter the location of each respective object in relation to a transmitter. In an embodiment, the processor of the receiver generates the location data of each respective object by determining a lag time between emitting the plurality of outbound object detection signals and receiving the at least one inbound object detection signal reflected from the respective object. The processor of the receiver also generates the location data associated with the object based on the different phase positions of each of the at least one inbound object detection signal.

At step 10516, a communications component of the receiver transmits communication signals containing the location data associated with each of the one or more objects to a transmitter (TX). In some implementations, the communications component of the receiver automatically transmits communication signals containing the location data associated with each of the one or more objects to the transmitter. In some implementations, the communications component of the receiver transmits communication signals containing the location data associated with each of the one or more objects to the transmitter on receiving a request from the transmitter.

At step 10518, another antenna of the receiver receives from the transmitter one or more power waves having one or more characteristics based on the location data associated with the one or more objects. In an embodiment, based on the location of the object, the transmitter may vary the one or more characteristics, e.g., frequency, amplitude, phase, gain, direction of the power waves that are being transmitted by the transmitter towards the location of the receiver and/or location of the object. In one example, when the location of the object is within a pre-defined proximity to the receiver, a null space may be formed at the location of the object caused by destructive interference of waves at that location. The destructive interference may occur when power waves destructively converge at the object location and their respective waveform characteristics are opposite each other (i.e., waveforms cancel each other out), thereby diminishing the amount of energy concentrated at the object location. In another example, the transmitter may form a null space at the location of the object irrespective of whether the object is within a pre-defined proximity or not. In yet another embodiment, the transmitter may reduce the intensity of the power waves that are being transmitted to the receiver. In another example, the receiver may stop receiving power waves altogether based on the sensed location of the object to the receiver.

FIGS. 104A-104B illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 104A-104B.

Presented below are example embodiments of radar motion detection using stepped frequency in wireless power transmission system.

In some embodiments, an example method of wireless power transmission, the method comprises generating, by a receiver, location data associated with one or more objects based upon one or more object detection signals reflected from the one or more objects and indicating a location of each respective object in relation to the receiver, transmitting, by the receiver, one or more communications signals containing the location data to the transmitter, and receiving, by the receiver, from one or more antennas of the transmitter one or more power waves having one or more waveform characteristics. The characteristics are based on the location data generated for each respective object.

In some embodiments, generating the location data for the respective object further comprises emitting, by a detection antenna coupled to the receiver, a plurality of object detection signals, each respective object detection signal having a successively stepped frequency.

In some embodiments, the method further comprises receiving, by the detection antenna coupled to the receiver, at least one detection signal reflected back from the object.

In some embodiments, the method further comprises determining, by a processor configured to control the receiver, the location of the object in relation to the receiver based on the at least one object detection signal reflected back from the object.

In some embodiments, the one or more power waves converge destructively to form one or more null spaces based on the one or more waveform characteristics of the one or more power waves.

In some embodiments, the receiver is coupled to a communications component configured to transmit the one or more communications signals containing the location data of each object to the transmitter.

In some embodiments, the receiver is embedded in an electronic device that is being charged by the one or more power waves received from the one or more antennas of the transmitter.

In some embodiments, an example method of wireless power transmission, the method comprises emitting, by a first antenna of a receiver, a plurality of outbound object detection signals, each respective object detection signal having a successively stepped frequency with respect to a preceding object detection signal, receiving, by a second antenna of the receiver, one or more inbound object detection signals that are reflected from one or more objects. At least one inbound object detection signal is reflected from an object, and at least one inbound object detection signal indicates a location of the object in relation to the receiver, generating, by a processor of the receiver, location data associated with each respective object based on the one or more inbound object detection signals. The method further comprises transmitting, by a communications component of the receiver, to a transmitter one or more communication signals containing the location data associated with each of the one or more objects, and receiving, by a third antenna of the receiver, from the transmitter one or more power waves having one or more characteristics. The characteristics are based on the location data associated with the one or more objects.

In some embodiments, each of the at least one inbound object detection signals received from the object has a phase position based on an angular position of the object in relation to the receiver, and a spatial direction in relation to the receiver.

In some embodiments, the method further comprises determining, by the receiver, the location data associated with the object based on the different phase positions of each of the at least one inbound object detection signal.

In some embodiments, generating the location data of each respective object further comprises determining, by the receiver, a lag time between emitting the plurality of outbound object detection signals and receiving the at least one inbound object detection signal reflected from the respective object.

In some embodiments, the plurality of outbound object detection signals are generated as non-linear chirp signals. The non-linear chirp signals are a waveform selected from the group consisting of exponential, logarithmic, and arbitrarily formulated.

In some embodiments, emitting the plurality of outbound detection signals further comprises randomly changing, by the first antenna of the receiver, a frequency of one or more outbound detection signals of the plurality of outbound detection signals. The frequency of the one or more outbound detection signals is randomly changed at a random interval range of 1 to 1000 times per second.

In some embodiments, the plurality of outbound detection signals are not modulated.

In some embodiments, an example receiver in a wireless power transmission system comprises a first antenna configured to emit a plurality of outbound detection signals, each outbound detection signal having a successively stepped frequency, a second antenna configured to receive a plurality of inbound detection signals reflected from one or more objects, where one or more detection signals are reflected from an object. The receiver further comprises a processor configured to generate location data associated with each respective object based on the one or more inbound detection signals received from the respective object, where the location data of each respective object indicates the location of the respective object in relation to the receiver, a communications component configured to transmit to the transmitter communications signals containing the location data associated with the one or more objects, and a third antenna configured to receive from the transmitter one or more power waves having one or more characteristics causing the one or more power waves to converge at a location proximate to the receiver based on the location data associated with the one or more objects.

In some embodiments, the plurality of outbound detection signals corresponds to chirp waves having a frequency that is continually varied.

In some embodiments, the one or more inbound object detection signals reflected back from the object have a phase position based on an angular position of the object in relation to the receiver, and a spatial direction of the object in relation to the receiver.

In some embodiments, the processor is further configured to determine the location data associated with the object based on the different phase positions of the one or more inbound object detection signals.

In some embodiments, the processor is further configured to determine the location data of each respective object by measuring a lag time between emitting the plurality of outbound object detection signals and receiving the inbound detection signals reflected from the respective object.

In some embodiments, the one or more power waves are selected from the group consisting of electromagnetic wave, radio wave, microwave, acoustics, ultrasound, and magnetic resonance.

Figure 105A:
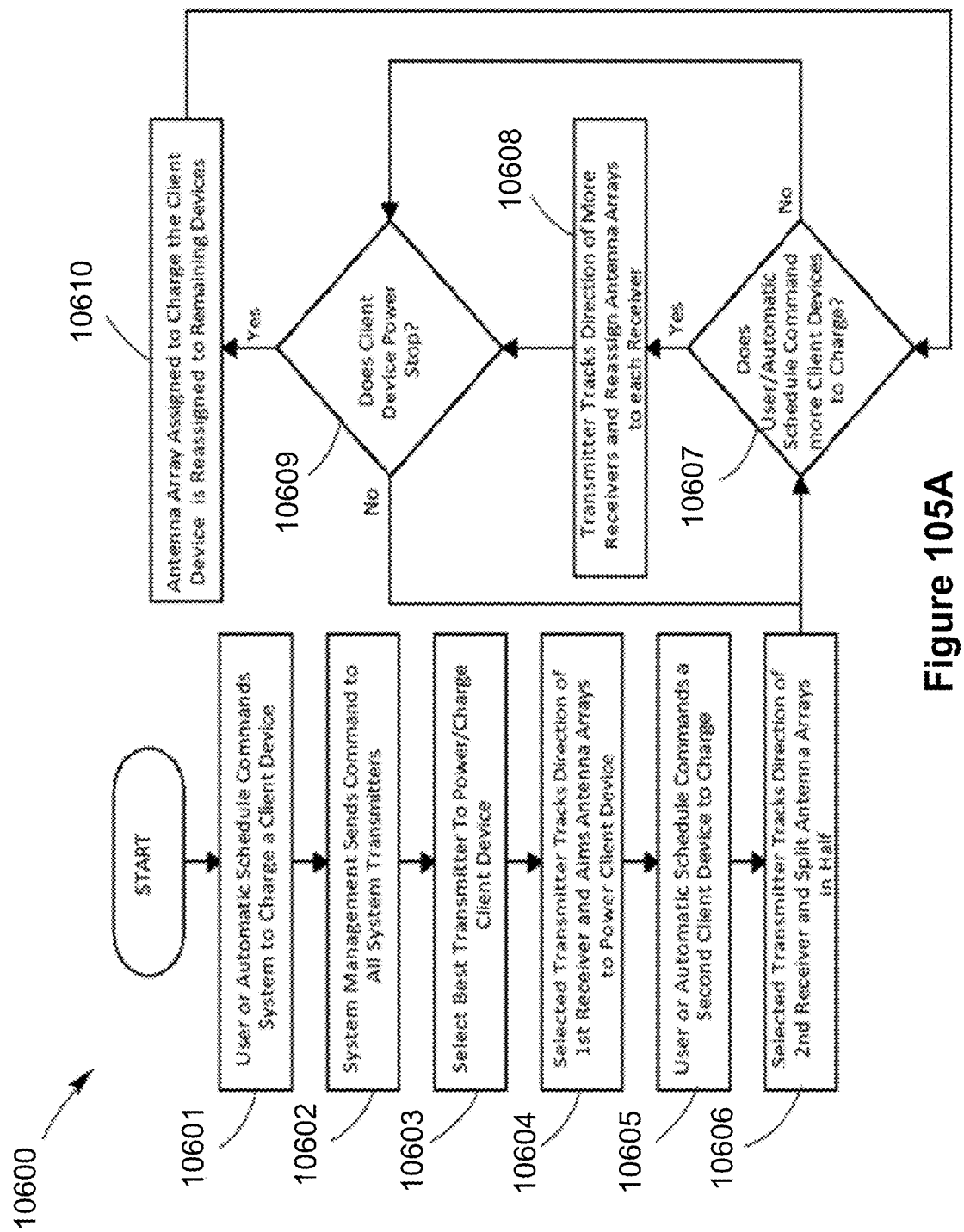

FIGS. 105A-105M illustrate examples of devices, apparatus, and methods for systems and methods for wireless power transmission, in accordance with some embodiments. Powering Multiple Devices Utilizing Time Division Multiplexing FIG. 105A illustrates a flowchart showing a method for automatically assigning subsets of antenna arrays for simultaneously powering two or more client devices, according to an exemplary embodiment.

Method 10600 may start when a user or system operator accesses the system management GUI, through a web site or on a client computing device, to command 10601 the wireless power transmission system to charge a client device that may be paired with an adaptable paired receiver or a client device that may include a wireless power receiver built in as part of the hardware of the device. In other embodiments, the system automatic charge schedule may also command the wireless power transmission system to charge a client device. Subsequently, the system management may send charging command 10602 to all system transmitters. Each system transmitter may determine if it is within power range of said power receiver, and, if not, may select 10603 best transmitter to control wireless power receiver of client device to power, subsequently, selected transmitter may start real-time communication with wireless power receiver to track 10604 direction of wireless power receiver relative to transmission antenna array, aims entire power transmission antenna array at wireless power receiver, and starts power transmission. Wireless power receiver may then receive said power, and subsequently power client device.

Following method 10600, user or automatic schedule software may command 10605 a second client device to charge, subsequently, selected transmitter may start real-time communication with second client device's receiver to track direction of second wireless power receiver and split 10606 transmitter's antenna array in half so that the transmitter may aim and use half, or a subset of, the power antenna array to power first client device, and aim and use the remaining antennas to power second client device, so that both client devices may continually receive power. Then, if the user or automatic schedule software command more client devices to charge, at decision 10607, then selected transmitter may start real-time communication with a third or more client devices and reassign 10608 its antenna arrays by splitting said antenna arrays in subsets of antennas to aim and power each receiver. If there are no more client devices to charge, the system manager may check if any of the client devices being charged or powered stops powering, at decision 10609, subsequently, if one or more client devices stops power, then the subset of antenna arrays assigned to power said client device's receiver may be re-distributed 10610 among the remaining client devices' receivers to continue powering said receivers. This process may happen almost instantaneously for the devices being powered because the transmitter software is already tracking and immediately uses their exact direction relative to the antenna array. If no client device stops power, then the system manger may check again, at decision 10607, if there are more client devices to charge and follow the same steps previously described. This method may continue in a loop as long as the wireless power system is charging or powering one or more client device's receiver.

Figure 105B:
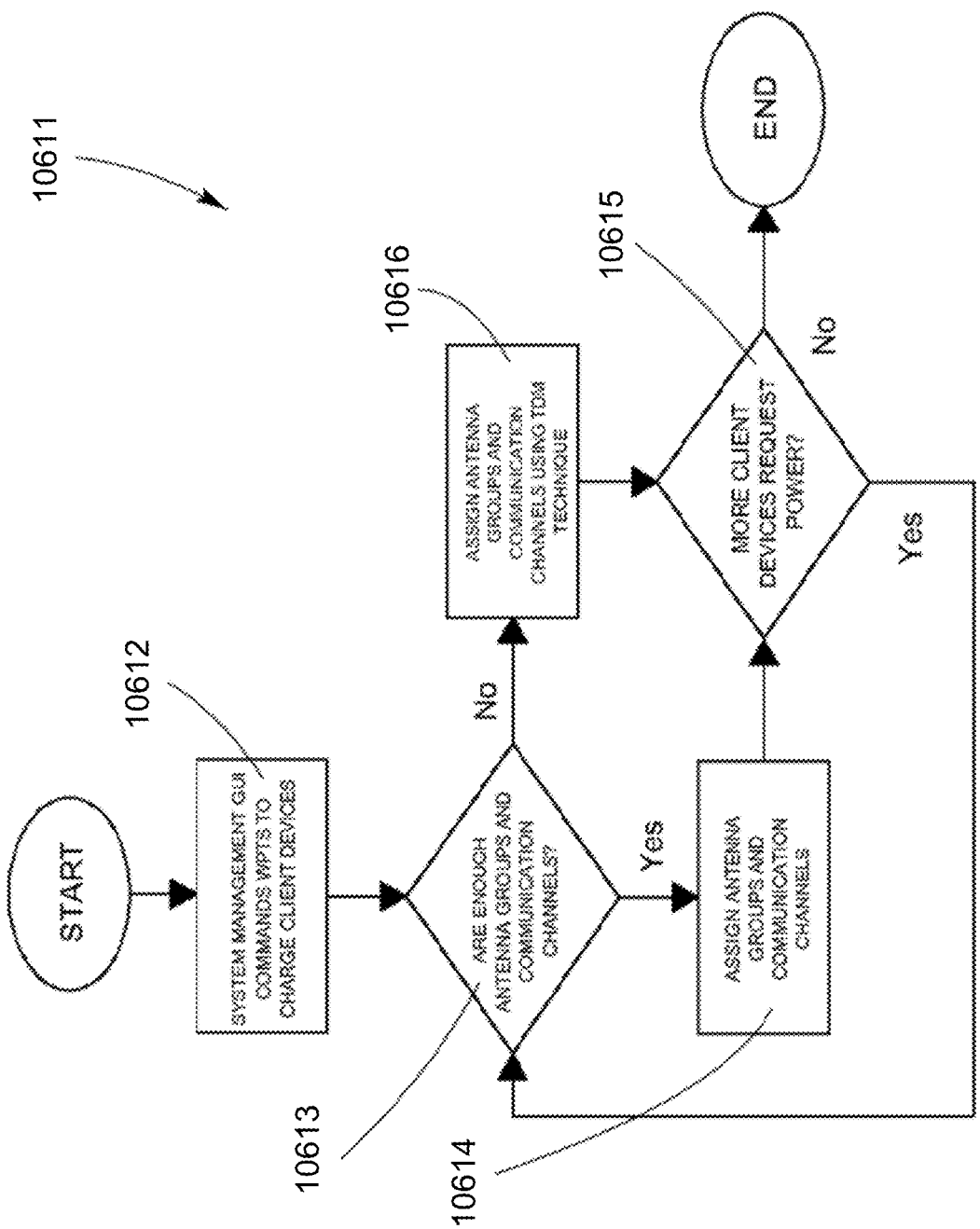

FIG. 105B illustrates a flowchart of an exemplary routine 10611 that may be utilized by wireless power management software, which may be initiated by system management GUI to command system to charge one or more client devices at step 10612. System management may distribute command to all system transmitters managed by wireless management software. Then, based on the number of client devices to be charged, management software may determine if there are enough antennas and communication channels available, at decision 10613. If there are enough antennas and communication channels for charging the client devices, then at step 10614, management software may assign the closest transmitter to charge client device and may assign a dedicated communication channel to start communication with the client device, which may be to continuously track client device direction from power transmission antenna array, or to monitor battery levels, or to receive measurements or other telemetry or meta data from receiver, or any other functionality to support wireless power transmission. Dedicated communication channel may be selected from available channels for communication with client devices.

Subsequently, wireless management software may continue charging client devices until more devices request power, at decision 10615. If there are no additional client devices requesting power, then routine 10611 may end. However, if more devices are requesting power, then at decision 10615, wireless power manager may determine if there are enough antennas and communication channels available for the new client devices. If there are not enough antennas and communication channels, then at step 10616, wireless power manager may assign all or groups of antennas from the antenna array and communication channels by employing Time Division Multiplexing (TDM).

TDM is used for transmitter communication with more power receivers than it has channels for, by sharing the available channels over time. It takes turn communicating to each receiver, communicating with each one for a finite amount of time, which may be a short amount of time such as 1 second or less. By allowing frequent communication with all receivers, by sharing the limited number of transmitter communication channels, the transmitter can then track and/or power all those receivers (and subsequently the client devices that power receivers transmit electrical power to).

TDM also supports sharing the power transmission from the entire transmitter antenna array between all the devices over time. That is, as the transmitter automatically switches communication throughout the receivers scheduled to receiver power, so that the transmitter can track receiver direction (angle) relative to transmitter antenna array, it also rapidly re-directs the antenna array from one receiver to another, so that each scheduled receiver periodically gets the antenna power, during its 'time slice.' The transmitter may also direct an individual group (sub-set) of antennas to a specific receiver while simultaneously directing one or more other groups to one or more other receivers.

TDM may be employed for allowing charge and more specifically communication between transmitters and power receivers of client devices, by using the existing communication channels, which may be shared by more than one device instead of being dedicated channels. By using TDM techniques wireless power transmitter may allow to re-assign one or more of its individual transmission antennas and communication channels to certain group of client devices, which may be in an online mode, consequently, being simultaneously powered. The remaining client devices may be turned in an offline mode, while online client devices are powered and hold a communication channel in a limited interval of time.

Subsequently, wireless power manager may continue charging client devices until more devices request power, at decision 10615. Finally, if there are no additional client devices requesting power at decision 10615, then routine 10611 may end.

Figure 105C:
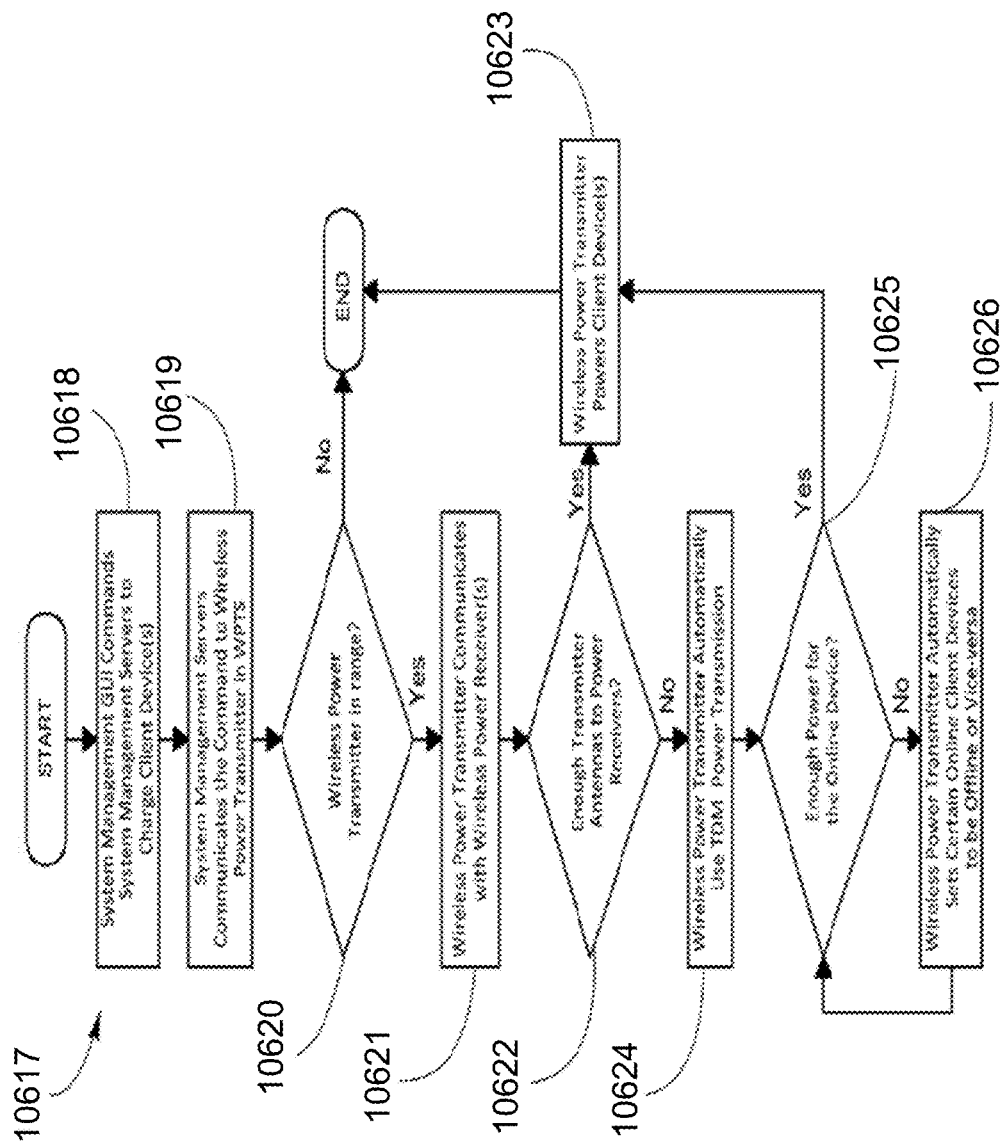

FIG. 105C is a flowchart of a process 10617 to power a plurality of client devices using a time division multiplexing (TDM) method in a wireless power transmission system, according to an embodiment. Process 10617 may start when a system management GUI operated by a user in a wireless power transmitter system may command a system management server to manually or automatically power one or more client devices from wireless power receivers, at step 10618. Subsequently, the system management server may communicate the commands to one or more wireless power transmitters in the wireless power transmission system, at step 10619.

Each wireless power transmitter may examine a local system distributed database or other storage means of system status, control and figuration to determine if the transmitter is within the power range of client device, at step 10620, and may control the wireless power receiver of the client device that has been commanded to receive power. If the wireless power receiver of the client device is not within the power range of wireless power transmitters, then the process may end. However, if the wireless power receiver of the client device is within the power range of any wireless power transmitter, then said wireless power transmitter may start real-time communication with the wireless power receiver of the client device, at step 10621. Each time that there is one or more client devices commanded for wireless power transmitters to be powered, then wireless power transmitters may re-divide its power transmission antennas into groups, where each group may be assigned for each client device allowing to power all client devices at the same time.

Afterwards, system management server within the wireless power transmission system may command to wireless power transmitters if there are enough transmitter antennas to power all the wireless power receivers of the client devices within the power range, at step 10622. If transmitter antennas within the wireless power transmitters, are able to meet the power demand of all wireless power receivers, then the wireless power transmitters may continue powering all client devices, at step 10623. However, if the present power resources of wireless power transmitter do not meet the power demand of all wireless power receivers, then system management server may command to power transmitter manager to implement the TDM power transmission within the wireless power transmitters, at step 10624. The wireless power manager within the wireless power transmitter may receive the command about the client device to be powered, and may determine which wireless power receiver is associated with the client device.

Wireless power transmitter by using TDM power transmission groups or reassigns one or more of its transmission antennas so that each group sends power to a different wireless power receiver, so that the client devices of the receivers simultaneously receiver power. The remaining client devices with wireless power receivers may be set to offline mode, while online client devices are powered. TDM power transmission system may determine if there is enough power for the online client devices, at step 10625. If there is not enough power for the online client devices, that is, one or more client devices may not be receiving enough power, then the wireless power transmitter will set one or more online client device to be offline, and try again, and then proceed by taking more devices offline until all the online client devices receive enough power.

The TDM power transmission process may allow wireless power transmitter to power all client devices enough at regular intervals of time (or time slots) using an automatic on/off line process, at step 10626.

Similarly, if there is not enough power for the present online client devices, then one by one the client devices that have been online for the longest may be turned offline until all online client devices get enough power. However, if the client devices that are in the online mode receive enough power, then the TDM power transmission may decide to keep the same amount of client devices in online mode and power them, at step 10623.

Figure 105D:
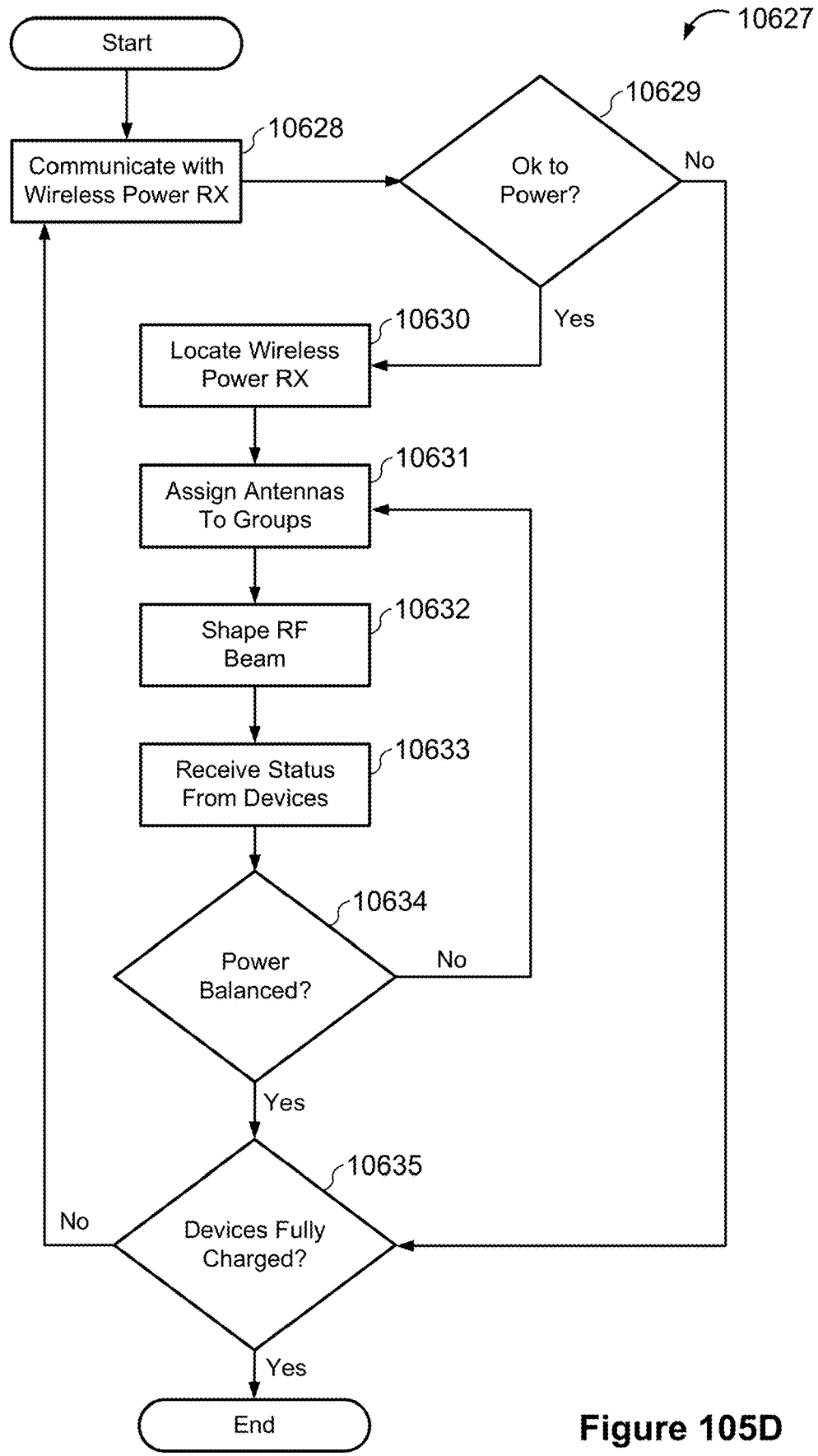

FIG. 105D is a flowchart of a process 10627 for adjusting the numbers of antennas assigned to a wireless power receiver so power transmission from a wireless power transmitter to a receiver is more balanced. Process 10627 may be part of an overall process for wireless power transmission, and may performed by a microprocessor, that may be part of system architecture. Process 10627 may be performed by the processor by executing software code in a power transmission management application such as power transmitter manager app. In some embodiments, the processor may perform process 10627 by executing instructions laid out in a wireless power manager application, in yet other embodiments, the processor may perform process 10627 by executing instructions laid out in a software application that may not be part of system architecture.

The code executed by the microprocessor may cause several components included in system architecture to initiate or terminate an activity. Hardwired circuitry, alternative to those shown in system architecture, may be used in place of or in combination with software instructions to implement processes described here. Thus, implementations described here are not limited to any specific combination of hardware circuitry and software. While the blocks in the disclosed process 10627 are shown in a particular order, the actual order may differ. In some embodiments, some steps may be performed in parallel.

The process may begin at step 10628, when a processor commands a wireless power transmitter (WPT) communicates with a wireless power receiver (WPR) that is close enough to establish communication with the WPT. The WPR may communicate data to the WPT that may include the WPR's identification number, WPR's approximate spatial location, and WPR's power status, among others. At step 10629, the processor may determine from the received data and additional data that may be stored in a database, such as database, whether the WPT should transmit power to the WPR. If the processor determines that the WPT should not power the WPR, it may continue to look, at step 10635, for more wireless power receivers that are in range and should be powered. If the processor determines that the WPT should power the WPR, then at step 10630, the processor may calculate a better approximation of the location of the WPR by using the approximate spatial location data received from the WPR and additional metrics that may include signal strength, WPT type, and device type that the WPR may be attached to, among others.

At step 10631, the processor may command the WPT to assign a set of antennas, from the antenna array, which may be used to transmit RF waves to the WPR. At step 10632, the processor may command the WPT to modify amplitude, and phase, among other parameters of the transmitted RF waves to shape a beam that may be focused on the WPR. At step 10633, the processor may read status data that may come from the WPR. Status data coming from the WPR may include, measurement of energy being received by the WPR, power level of the WPR, the perceived spatial location of the WPR, and the minimum power that is enough to power the electronic device to which the WPR may be attached, among other operational parameters. In some embodiments, the minimum power setting may come from other source, such as look-up tables elsewhere in the system.

At step 10634, the processor may use the information read and determine if the power transmitted to a WPR is unbalanced compared to other WPR's, or if any WPR is getting too much or too little power. If the power received by the WPR is less than the minimum power, the processor may command the WPT, back at step 10631, to assign more antennas to the set of antennas that may be in use to power the WPR. In some embodiments, if the number of antennas available is not enough to power the WPR, the WPT may utilize techniques such as time division multiplexing, to share more antennas with the WPR to meet the power demand of the WPR that may be within the power range of one or more wireless power transmitters. A technique such as time division multiplexing may allow to charge multiple WPR's through regular intervals of time or slot time during an automatic online mode and offline mode sequence.

If the power received by a WPR is substantially more than its required minimum power, the processor may command the WPT, back at step 10631, to reduce the number of antennas assigned to the WPR, and use the de-assigned antennas to power other WPR's, allowing the first WPR to continue to be wirelessly powered simultaneously. At step 10635, the processor may look for another wirelessly powered receiver that is in range and should be powered, and if found, the process may initiate communication with the new WPR, back at step 10629, and process from step 10629 may repeat. When the processor determines from communication with the WPR, that the WPT is done transmitting power the WPR, it may communicate to the WPR, back at step 10628, that the power transmission has ended, and may disconnect communication at step 10629. The WPT may then, at step 10635, examine the database to determine which, if any, WPR is in range that the WPT should transmit power to.

Figure 105E:
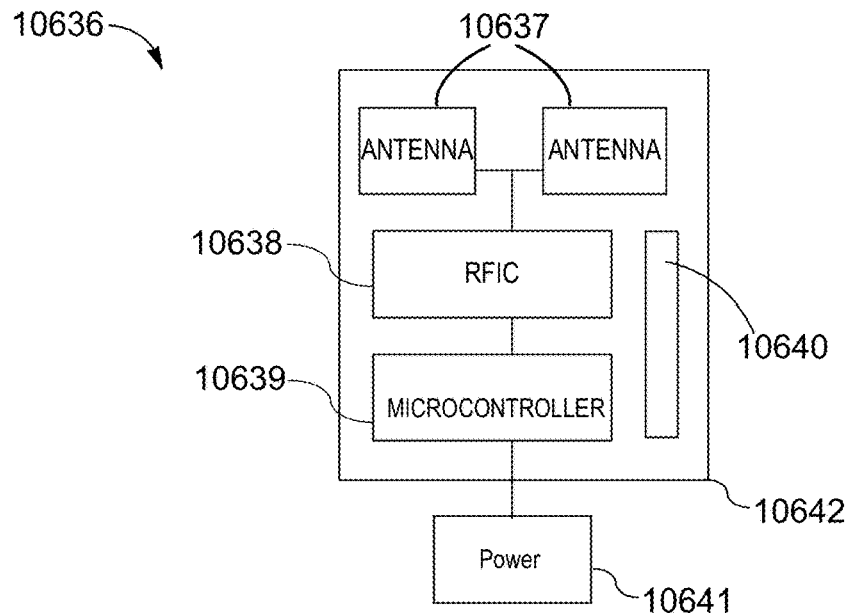

FIG. 105E depicts a block diagram of a transmitter 10636 which may be utilized for wireless power transmission. Such transmitter 10636 may include one or more antenna elements 10637, one or more Radio frequency integrated circuit (RFIC) 10638, one or more microcontroller 10639, a communication component 10640, a power source 10641 and a housing 10642, which may allocate all the requested components for transmitter 10636. Components in transmitter 10636 may be manufactured using meta-materials, micro-printing of circuits, nano-materials, and the like.

Transmitter 10636 may be responsible for the pocket-forming; adaptive pocket-forming and multiple pocket-forming through the use of the components mentioned in the foregoing paragraph. Transmitter 10636 may send wireless power transmission to one or more receivers in form of radio signals, such signals may include any radio signal with any frequency or wavelength.

Figure 105F:
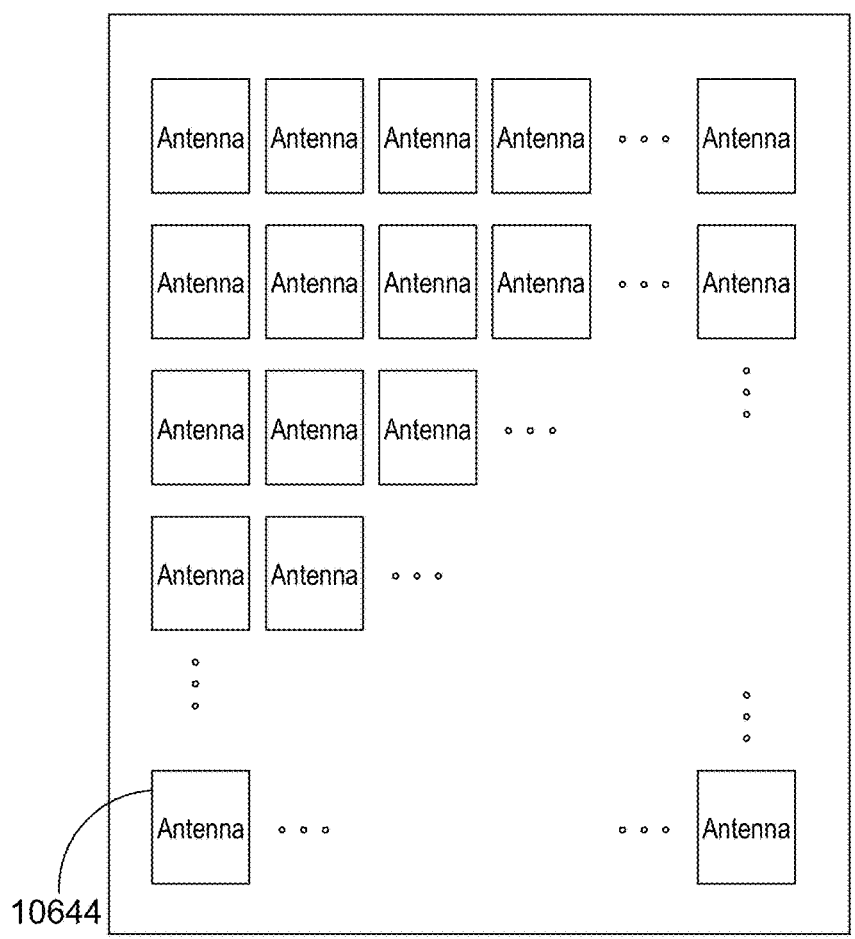

FIG. 105F is an exemplary illustration of a flat panel antenna array 10643 that may be used in transmitter 10636. Flat panel antenna array 10643 may then include an N number of antenna elements 10644 where gain requirements for power transmitting may be from 64 to 256 antenna elements 10644 which may be distributed in an equally spaced grid. In one embodiment, flat panel antenna array 10643 may have a 8×8 grid to have a total of 64 antenna elements 10644. In another embodiment, flat panel antenna array 10643 may have a 16×16 grid to have a total of 256 antenna elements 10644. However, the number of antenna elements 10644 may vary in relation with the desired range and power transmission capability on transmitter 10636, the more antenna elements 10644, the wider range and higher power transmission capability. Alternate configurations may also be possible including circular patterns or polygon arrangements. Flat panel antenna array 10643 may also be broken into numerous pieces and distributed across multiple surfaces (multi-faceted).

Antenna elements 10644 may include flat antenna elements 10644, patch antenna elements 10644, dipole antenna elements 10644 and any suitable antenna for wireless power transmission. Suitable antenna types may include, for example, patch antennas with heights from about ½ inch to about 6 inches and widths from about ½ inch to about 6 inches. Shape and orientation of antenna elements 10644 may vary in dependency of the desired features of transmitter 10636, orientation may be flat in X, Y, and Z axis, as well as various orientation types and combinations in three dimensional arrangements. Antenna elements 10644 materials may include any suitable material that may allow radio signal transmission with high efficiency, good heat dissipation and the like.

Antenna elements 10644 may include suitable antenna types for operating in frequency bands such as 900 MHz, 2.5 GHz or 5.8 GHz as these frequency bands conform to Federal Communications Commission (FCC) regulations part 18 (Industrial, Scientific and Medical equipment). Antenna elements 10644 may operate in independent frequencies, allowing a multi-channel operation of pocket-forming.

In addition, antenna elements 10644 may have at least one polarization or a selection of polarizations. Such polarization may include vertical pole, horizontal pole, circularly polarized, left hand polarized, right hand polarized, or a combination of polarizations. The selection of polarizations may vary in dependency of transmitter 10636 characteristics. In addition, antenna elements 10644 may be located in various surfaces of transmitter 10636.

Antenna elements 10644 may operate in single array, pair array, quad array and any other suitable arrangement, which may be designed in accordance with the desired application.

Figure 105G:
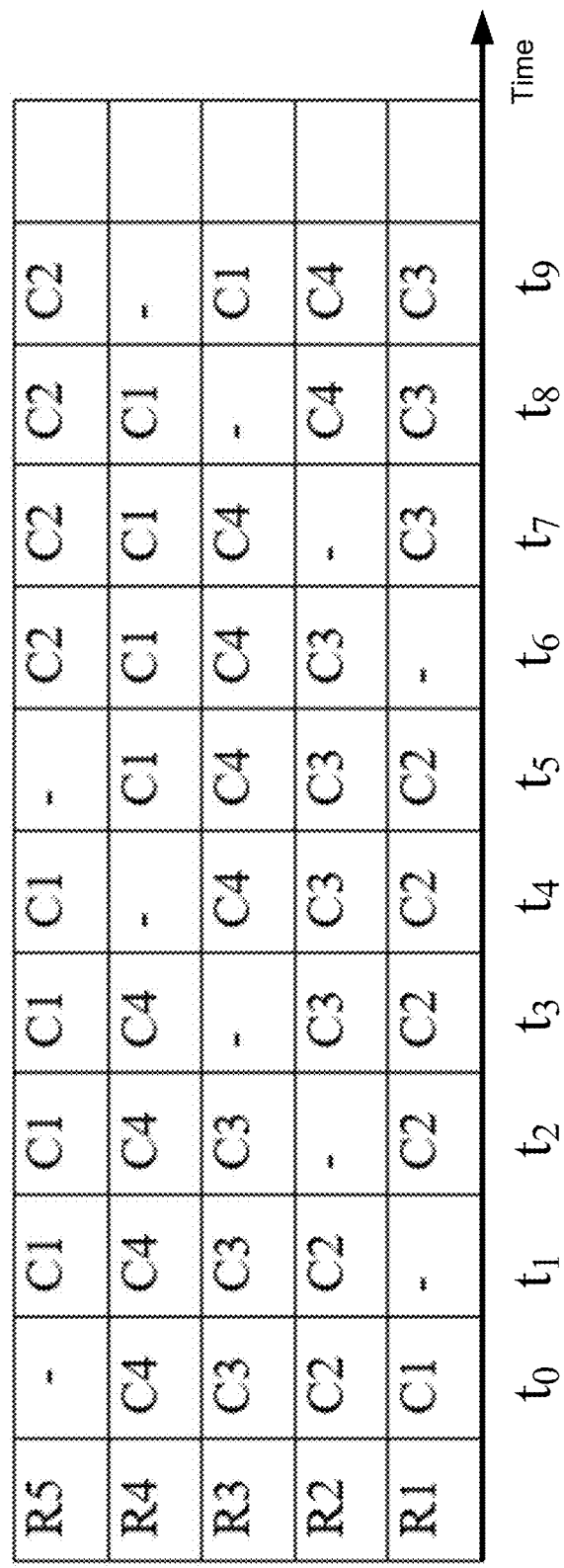

FIG. 105G is a chart depicting an exemplary distribution of communication channels 10645 over time, employing TDM in wireless power transmission. More specifically, FIG. 105G depicts a table with channels assignment for 5 client devices while the wireless power transmitter only allows 4 communication channels.

FIG. 105G chart shows over time how the transmitter's limited number of 4 communication channels may be used to communicate with 5 receivers—more receivers than the transmitter has channels for. Time advances from left to right, and 10 time slices are represented. Each time slice represents a finite amount of clock time, for example 1 second. Each 'Cn' denotes one of the transmitter's communication channels. Each 'Rn' denotes one of the wireless power receivers that receive power from wireless transmitter and then subsequently transmit electrical power to client devices.

During time-slice $t_0$, transmitter uses channel C1 to communicate with receiver R1, channel C2 to communicate with receiver R2, C3 for R3, and C4 for R4, and there is no communication with receiver R5.

During time-slice $t_1$, transmitter now uses channel C1 to communicate with receiver R5, so that R5 gets a turn receiving power, receiver R2 continues communication with transmitter through channel C2, receiver R3 continues with channel C3, and receiver R4 continues with channel C4. There is no communication with receiver R1.

During time-slice $t_2$, transmitter now uses channel C2 to communicate with receiver R1, so that R1 gets a turn receiving power, receiver R3 continues communication with transmitter through channel C3, receiver R4 continues with channel C4, and receiver R5 continues with channel C1. There is no communication with receiver R2.

During a time slice while transmitter is in communication with a specific receiver, it may use that communication to get receiver power status from the receiver, which values transmitter uses to aim transmitter antennas at that receiver, to power receiver's client device. The system may use other methods to control aiming antennas at receivers, such as receiver beacon signal transmission and transmitter beacon signal reception. Transmitter may aim a subset of array antennas at each of the four receivers in communication.

The pattern continues through time while the receivers are schedule by the user to receiver power. More receivers may be added to those scheduled, or some may be removed. When there are more than the available transmitter channels (in this example 4), then the channels are shared over time (TDM) so that transmitter may communicate with any number of receivers. When there are not more, then the transmitter dedicates each channel to a specific receiver.

An exemplary distribution of communication channels employing TDM in wireless power transmission is depicted in a table with channels assignment for 5 client devices while the wireless power transmitter only allows 4 communication channels. Wireless power manager may employ TDM technique when a fifth client device R5 is commanded to begin charge at time stage $t_1$. Subsequently, at time stage $t_1$, wireless power manager may command wireless power transmitter to cease communication using first communication channel C1 with first client device R1, and starts real-time communication using first communication channel C1 with fifth client device R5. Afterwards, finite amount of time later at time stage $t_2$, wireless power manager may order wireless power transmitter to cease communication using second communication channel C2 with second client device R2, and then wireless power transmitter may use second communication channel C2 to restart communication with first client device R1, and aims an antenna group at first client device R1. Subsequently, finite amount of time later at time stage $t_3$, wireless power manager may order wireless power transmitter to cease communication with third client device R3 which was using third communication channel C3. Wireless power transmitter may now use third communication channel C3 to restart communication with second client device R2, and aims an antenna group at second client device R2. This process may continue until the amount of client devices to be powered changes.

Figure 105H:
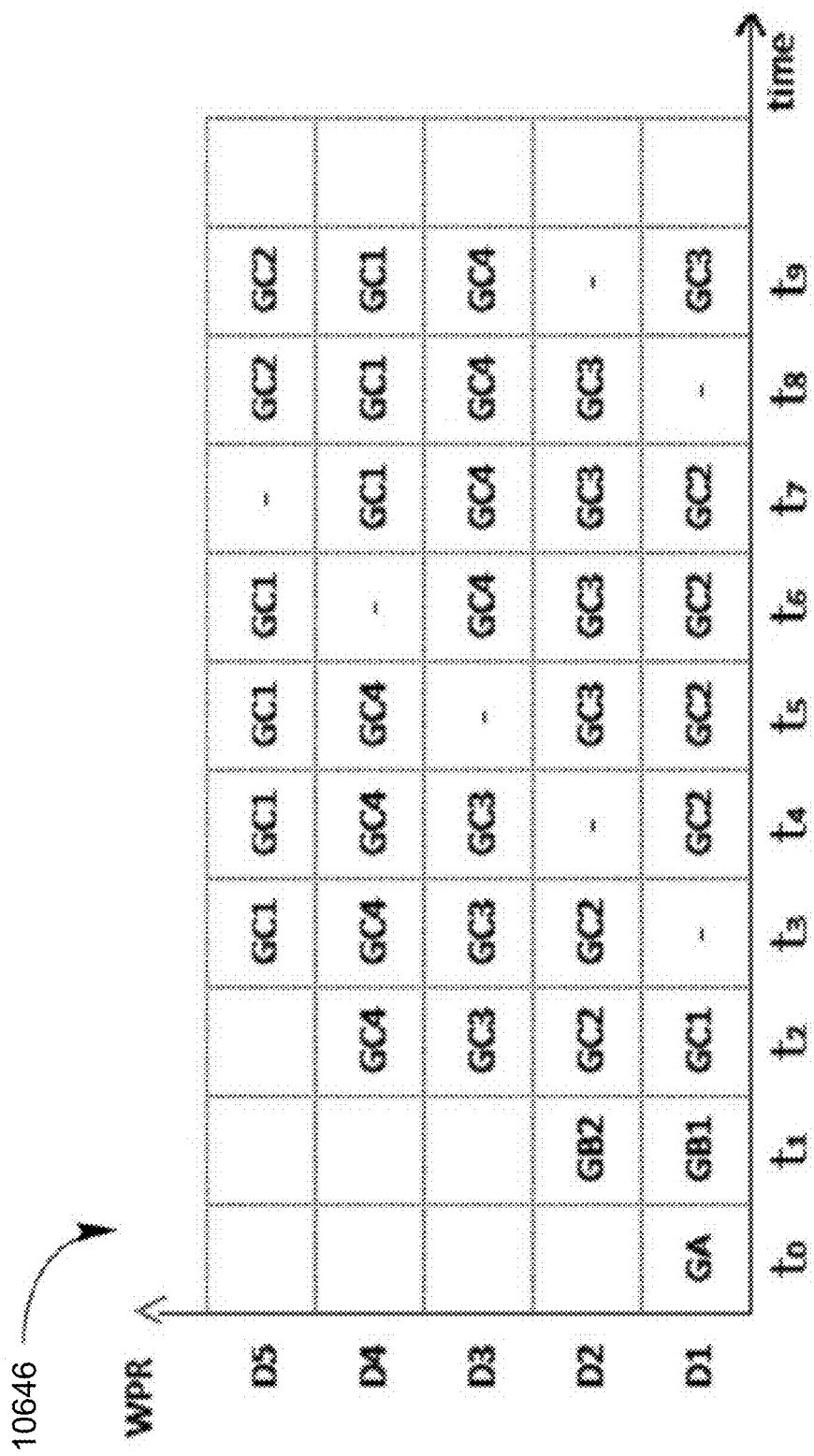

FIG. 105H is a diagram 10646 of an exemplary potential interaction between wireless power receivers and wireless power transmitters, according to some embodiments. Diagram 10646 may describe a process about how TDM power transmission (software module) may operate in a wireless power transmitter. Specifically, the process may start at time $t_0$, where a wireless power device (D1) may be in reach of a wireless power transmitter, TDM power transmission may command the wireless power transmitters to assign an antenna group (GA) to power D1.

If D1 moves from the initial position, at time $t_1$, TDM power transmission may command the wireless power transmitter to change the numbers of antennas from the original group and assign an antenna group (GB1) to power D1. If at the same time another wireless power device (D2) comes in reach of a wireless power transmitter, the TDM power transmission may command the wireless power transmitter to assign another antenna group (GB2) to power D2. The wireless power transmitter may now be powering two wireless power receivers.

If both D1 and D2 move from their position, at time $t_3$, TDM power transmission may command the wireless power transmitter to change the numbers of antennas from the original group and assign an antenna group (GB1) to power D1, and assign another antenna group (GC2) to power D2. If two more wireless power devices (D3 and D4) come in reach of the wireless power transmitter, the TDM power transmission may command the wireless power transmitter to assign two more antenna groups (GC3 and GC4) to power D3 and D4. The wireless power transmitter may now be powering four devices and may have no more transmitting antennas available for additional wireless power receivers.

If an additional wireless power receiver (D5) comes in range of the wireless power transmitter, at time $t_3$ and no additional antennas are available for dedicating a new group to power D5, TDM power transmission may employ an antenna sharing techniques to make sure that all devices are receiving power. For example, TDM power transmission may switch antenna groups from one device to another at regular time intervals. If no other changes in location occur, for example from times $t_4$ to $t_9$, TDM power transmission may continue to switch groups from the wireless power receiver being transmitted power the most of the time, to the wireless power receiver being transmitted the least of the time.

FIG. 105I illustrates a diagram 10647 or exemplary potential interaction of wireless power receivers and wireless power transmitters that may be part of wireless power transmission system architecture. Diagram 10647 may provide an example of a wireless power receiver being served by a wireless power transmitter. Additional wireless power receivers may be served as they come in reach of the wireless power transmitter, according to some embodiments.

According to another embodiment, multiple wireless power transmitters may power together one or more receivers. At time $t_0$, a wireless power device (D1) may come in range of the wireless power transmitter. A processor may command the wireless power transmitter to assign an antenna group (GA) of all transmitter antennas to power client device D1.

At time $t_1$, the system begins to also power client device D2, and so transmitter replaces previous antenna group GA with two new antenna groups GB1 for D1, which continues to be powered, and group GB2 for newly powered device D2. Since there are two groups, each gets half of the entire transmitter antenna array.

At time $t_2$, two more devices D3 and D4 begin to receiver power, so transmitter replaces previous two antenna groups GB1 and GB2 with four antenna groups, one for each client device (D1 D2 D3 D4) presently being powered: GC1 GC2 GC3 GC4.

At time $t_3$, a fifth client device D5 is configured to receive power. However, the maximum allowed simultaneous antenna groups is 4. So, to power the 5 devices, Time Division Multiplexing must be used to simultaneously power 4 devices at once using the 4 antenna groups, with one of the 5 devices being not powered during each subsequent time interval tn. Thus, at time $t_3$ the maximum of four antenna groups GC1 GC2 GC3 GC4 power client devices D5, D2, D3, D4 respectively. At time $t_4$, power stops to D2, power re-starts to D1, and D3, D4, D5 continue to receive power. The cycle pattern continues indefinitely until devices are charged.

Power Transmission Management

Figure 105J:
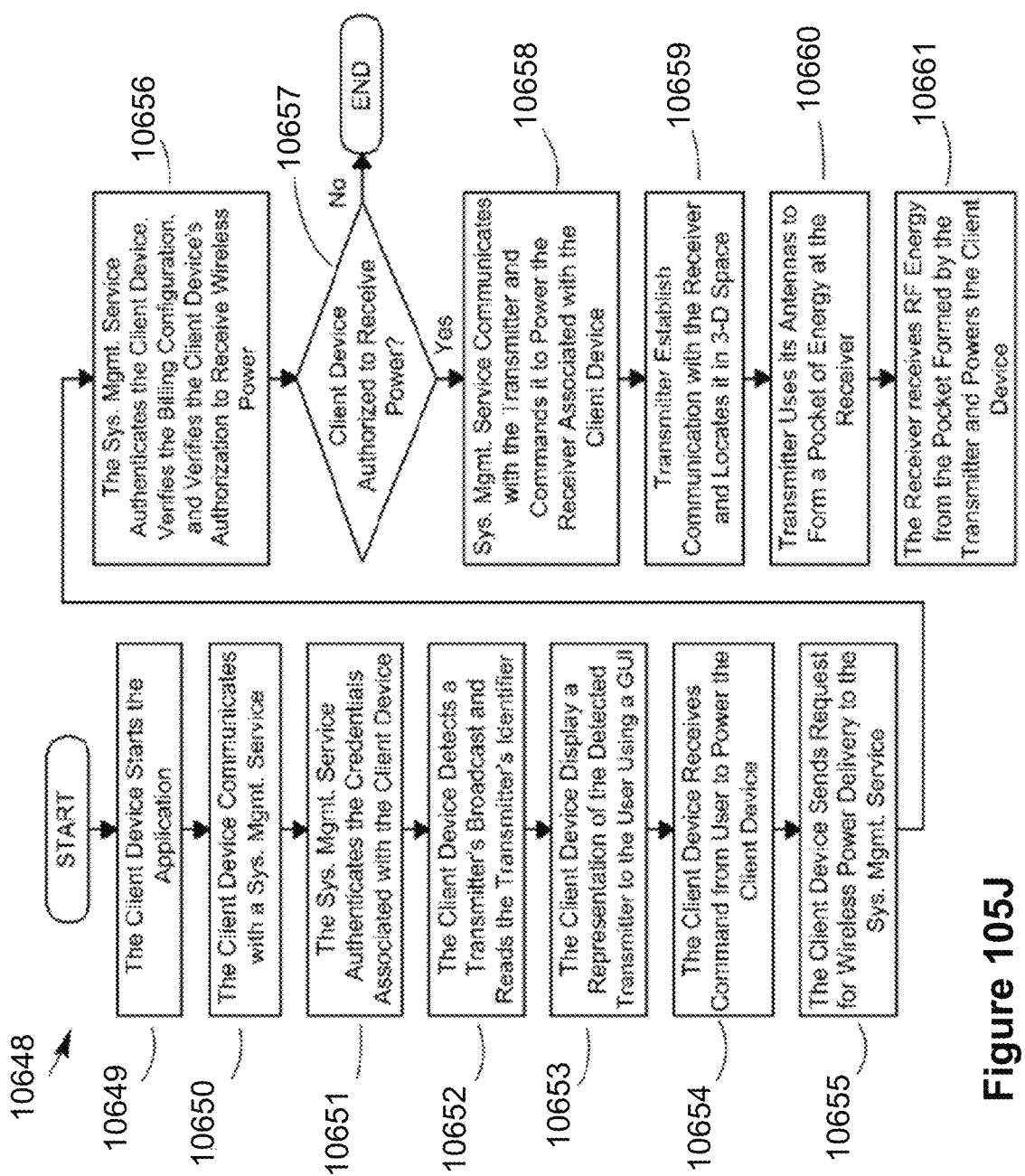

FIG. 105J is a flow diagram 10648 generally illustrating an exemplary method for transmitting wireless power to a device. The steps of this exemplary method are embodied in a computer readable medium containing computer readable code such that the steps are implemented when the computer readable code is executed by a computing device. In some implementations, certain steps of the method can be combined, performed simultaneously, performed in a different order, or omitted, without deviating from the objective of the method.

In FIG. 105J, the process begins when the client device starts 10649 the application on request from the user. In some embodiments, client device detects a receiver it is coupled to, and reads from receiver an identifier associated with receiver. In other embodiments, receiver is an inherent to client device and consequent client device already includes the identifier associated with receiver. In yet other embodiments, client device broadcasts or otherwise advertises the identifier associated with receiver to other devices in range.

Next client device communicates 10650 with a system management service through a suitable network connection, including intranets, local area networks (LAN), virtual private networks (VPN), wireless area networks (WAN), Bluetooth, Bluetooth Low Energy, Wi-Fi, ZigBee, and the like. In some embodiments, client device communicates the credentials associated with the user of client device, the identifier of receiver associated with the client device, and the like. system management service then authenticates 10651 the credentials associated with client device. In some embodiments, if the credentials cannot be authenticated the user is directed to register. In other embodiments, if the authentication fails the system management service denies access to the user.

Client device then detects 10652 a broadcast from transmitter and reads an identifier associated with transmitter. In some embodiments, transmitter broadcasts its presence and an identifier associated with it using Bluetooth, Bluetooth low energy (BTLE), Wi-Fi, or the like. Identifiers associated with transmitter can include the transmitter's MAC address, network address, serial number, and the like. client device displays 10653 a representation of transmitter to the mobile device user via GUI. In some embodiments, GUI produces the representation of transmitter allowing a mobile device user to request power transmission from transmitter to client device. In other embodiments, GUI displays additional information, such as, for example the distance from transmitter to client device, the cost associated with receiving power from transmitter, and the like.

Next, client device receives 10654 a command from the mobile device user to being powering client device. client device sends request 10655 for wireless power delivery to system management service. In some embodiments, the request sent by client device includes credentials (e.g., user account credentials) associated with client device, an identifier associated with one or more nearby Transmitters, an identifier associated with client device, an identifier associated with a receiver coupled to the client device (if not integral to the device), billing instructions, and the like.

System management service then authenticates 10656 client device, verifies the billing configuration, and verifies if client device is authorized to receive wireless power. In some embodiments, system management service authenticates client device by comparing credentials contained within the request (e.g. user account credentials) and the identifier associated with client device to data stored in a database within cloud service provider. In other embodiments, system management service additionally verifies that the user's billing configuration is valid. system management service then determines 10657 if client device is authorized to receive power. In some embodiments, if the client device is not authorized the process ends. In other embodiments, the process continues to another process allowing the mobile device user to authorize the client device by adding additional funding to the account, request authorization from a third party, or the like.

System management service communicates 10658 with transmitter and commands it to power receiver associated with client device. In some embodiments, the system management service communicates with the transmitter using a suitable network connection, including intranets, local area networks (LAN), virtual private networks (VPN), wireless area networks (WAN), Bluetooth, Bluetooth Low Energy, Wi-Fi, ZigBee, and the like. In other embodiments, the command includes any number of suitable parameters for carrying out a desired method of charging, including desired power output, amount of time to charge, amount of power to transmit, and the like. In some embodiments, receiver is integral to client device. In other embodiments, receiver is a wireless receiver coupled and in electrical communication with one or more client devices.

Transmitter establishes 10659 communication with receiver and locates it in 3-D space. transmitter then uses its antennas to form a pocket of energy at the receiver 10660. Next, receiver receives 10661 RF energy from the pocket formed by the transmitter and powers the client device.

Figure 105K:
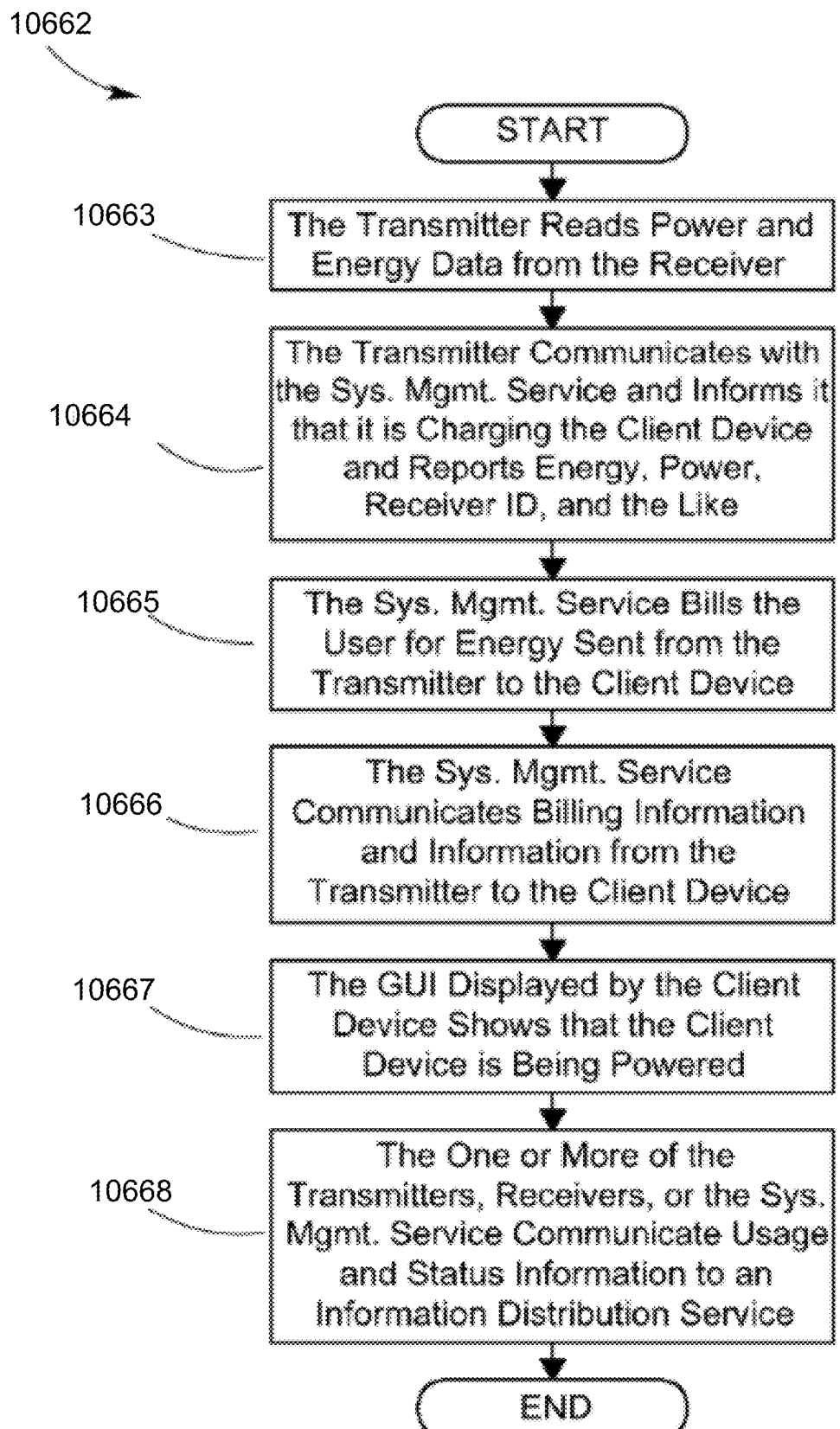

FIG. 105K is a flow diagram 10662 generally illustrating an exemplary method for monitoring wireless power transmitted to a device. The steps of this exemplary method are embodied in a computer readable medium containing computer readable code such that the steps are implemented when the computer readable code is executed by a computing device. In some implementations, certain steps of the method can be combined, performed simultaneously, performed in a different order, or omitted, without deviating from the objective of the method.

In FIG. 105K, the process begins with transmitter reading 10663 power and energy data from receiver. In some embodiments, receiver is integral to client device. In other embodiments, receiver is a wireless receiver coupled and in electrical communication with one or more client devices. In some embodiments, the data includes the rate of power delivered from Wireless Power transmitter to receiver, the total energy transferred from Wireless Power transmitter to receiver, the current battery power level of client device, and the like.

Transmitter then communicates 10664 with system management service and informs it that it is charging client device. In some embodiments, transmitter additionally reports energy/power transmitted to fulfill the charging request for client device, the identifier of receiver, and the like.

Next, system management service bills 10665 the mobile device user for the energy sent from transmitter to client device, if required. system management service then communicates 10666 account information to client device. In some embodiments, account information includes billing information and other information associated with the current charging session, information from previous charging sessions, account balance information, charges associated with receiving wireless power during the current charging session, rate of power transmission from transmitter, and the like.

GUI displayed by client device shows 10667 that client device is being powered. In some embodiments, GUI displays the aforementioned account balance information, account information, and the like.

One or more of the wireless power transmitters, receivers, and/or the system management service then communicate 10668 usage and status information to information distribution service. In some embodiments, the usage and status information is used for running analytics on customer behavior, demographics, service quality, and the like. In some embodiments, information distribution service is hosted in a remote cloud. In other embodiments, information distribution service is hosted in a local network.

For example, a user having a smartphone walks into a coffee shop. The smartphone detects a wireless power transmitter operated by the coffee shop and reads transmitter's ID. The user then notices that the smartphone is low on power, and proceeds to command a mobile app to request local wireless power. The user may also have configured wireless power system management to do this automatically whenever and/or wherever wireless power is available. The smartphone then communicates its ID, its receiver's ID, and the transmitter's ID to the system management service. The system management service reviews its system database and finds the smartphone or its receiver, as well as the transmitter. The system management service then communicates with the transmitter and commands it to power the user's smartphone receiver. Transmitter then communicates with the receiver to determine the receiver's location, and transmits wireless energy to the receiver using pocket-forming techniques. The receiver proceeds to power the smartphone with this energy.

In another example, a user with a wearable device having a built-in wireless power receiver visits a friend's house, where the house equipped with a wireless power transmitter. The wearable device detects the house's wireless power transmitter and reads the transmitter's ID, and the homeowner's transmitter has configured the system management service to automatically power any wireless power receiver. The wearable device's receiver communicates its ID and transmitter's ID to the system management service, and the system management service then reviews its system database and finds the wearable device, its receiver, and the transmitter. The system management service then communicates with the transmitter and commands it to power the wearable device's receiver. The transmitter then communicates with the receiver to determine receiver's location, and transmits wireless energy to the receiver using adaptive 3-D pocket-forming techniques. The receiver then powers the wearable device with this energy.

Measuring and Reporting Power Level

Figure 105L:
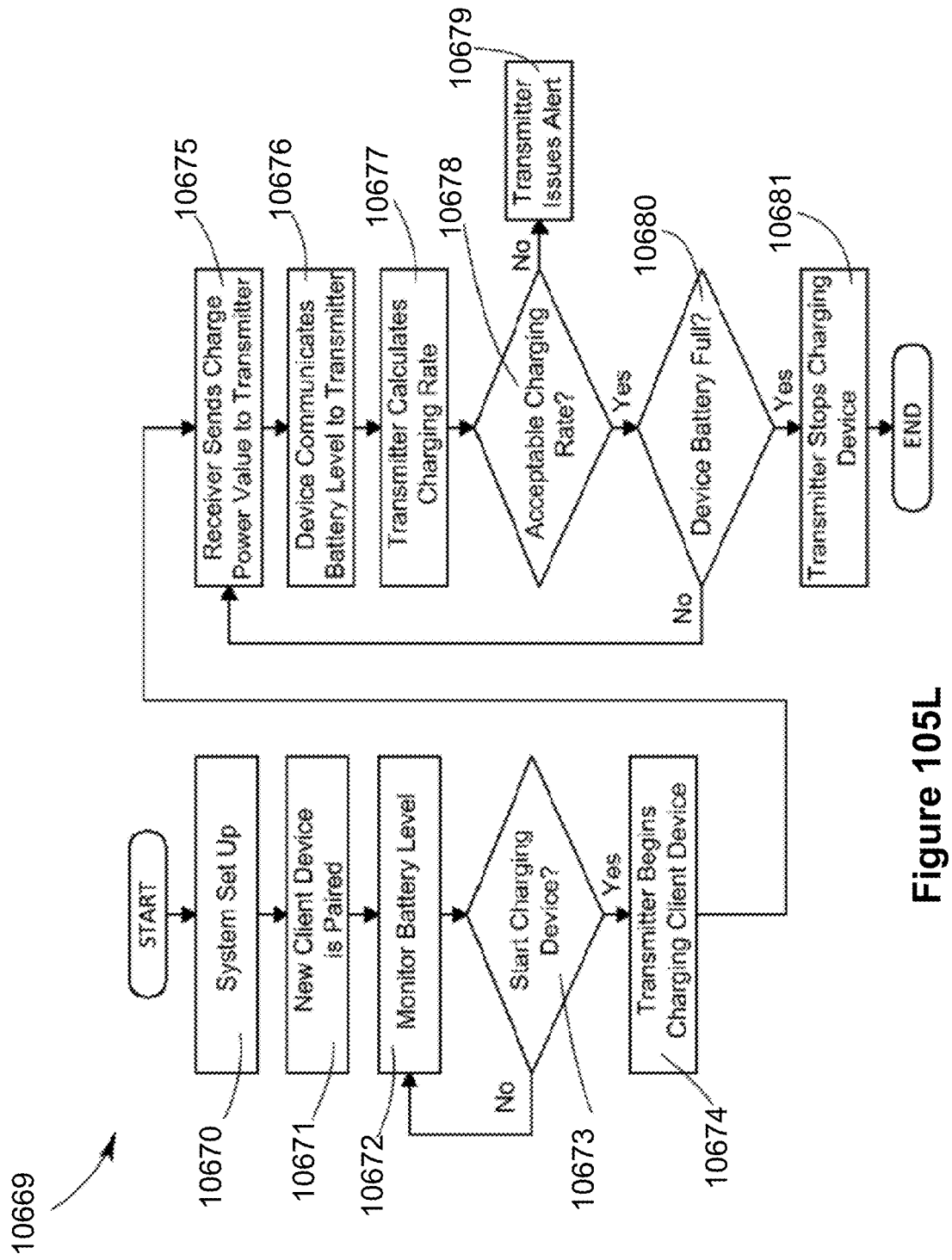

FIG. 105L is a flowchart of a method for monitoring battery performance 10669 in a wireless power transmission system, according to an embodiment. In some exemplary embodiments, the Wireless Power transmission system is capable of determining the present or actual rate at which the battery of an electronic device is charging, and compare that value with the expected reference rate. If the present rate is significantly less than the expected reference rate then the battery or related charging circuit within the electronic device may be malfunctioning and causing significantly less charging efficiency or performance.

When the Wireless Power transmission system detects this error condition, the system may then alert the system operator or user of the client device, or any other suitable party, so that the problem may be corrected and the electronic device battery charging system may no longer waste power when charging or stops taking longer periods of time to charge than it should.

In an alternative embodiment, the wireless power transmission system to monitors the charging rate of the client device from when the device was first put into service with the system, and then use this as a reference to compare against the present rate of charge for the device, so that if ever the present rate of charging for the device becomes less than the reference rate that was based on the initial rate of charge, then alerts would be generated by the system indicating that something is wrong with the device and it is taking too long to charge or wasting power when it is being charged.

In some exemplary embodiments, method for monitoring battery performance 10679 may start with step 10670, where an operator or user installs and operates a wireless Power transmission system. Then, a client device may be paired with a wireless power receiver within the system, at step 10671. Pairing may occur when a client electronic device detects that a power receiver is within a suitable range of proximity for a suitable amount of time. Then, it may proceed to check an internal database to determine if the power receiver is not already paired with another electronic device. If the power receiver is not already paired with another device, the client electronic device may associate its ID with the ID of the power receiver and update the internal database. Then, the electronic device may send a copy of the updated database record to the power transmitter. In this way the device may be ready to start changing wirelessly.

At step 10672, the wireless power transmitter may continuously monitor the battery level of the client device to determine, at step 10673, if the battery needs to be charged. In other embodiments, the wireless power transmitter may charge the client device according to a predefined schedule. The wireless power transmission system may automatically charge the battery of the client device whenever it is time to do so, or if the battery level is below full and the battery needs to be charged, or system may automatically charge battery in response to some other condition or situation that may be built into the system, or configured by the operator or user, or other.

If the wireless power transmitter determines that the client device needs to be charged, it may start transmitting power to the wireless power receiver connected to the client device, at step 10674. To do so, the wireless power transmitter continuously communicate in real-time with the wireless power receiver.

During the charging period, at step 10675, the receiver constantly sends the charge power values to the wireless power transmitter. Additionally, the client device may constantly send the battery level values to the wireless power transmitter, at step 10676.

Using the values received at steps 10675 and 10676, the wireless power transmitter is capable of calculating the charging rate of the client device, at step 10677. In some embodiments, the wireless power transmitter will monitor his own real time clock circuit or other, to measure present real-time or clock time, in order to calculate the charging rate of the client device battery.

Then, at step 10678, the wireless power transmitter may determine if the rate of charge of the client device is within an acceptable range or if it's not. In some exemplary embodiments, the wireless power transmitter will look up in a reference table the expected charging rate for the particular client device; the unique identification or category of the device previously made known to the system either by operator, or user, or automatically by the client device communication of said categories from client device directly to the wireless power transmitter or other system computer of the wireless power transmission system. Said reference table is located within transmitter memory, or local database, or downloaded or communicated to transmitter from remote management or information service on a remote server.

In some embodiments, the reference charging rate expected of a particular client device is already stored in the transmitter's memory. Also, the rate of each category or model of client device that the transmitter is expected to charge, are all also stored in memory. These rates may have been already stored in memory of transmitter at the time of transmitter manufacture, or may have been uploaded to or communicated to transmitter from another system computer, such as a system management server that contains updated rates for all types, categories, or models of client devices that the wireless power transmission system is expected to charge.

If the wireless power transmitter detects that actual charging performance of device is below expected charging performance, then transmitter may alert a system operator, or the client device user, that battery or charging circuit or other of client devices is malfunctioning, may be losing power, may be taking too long to charge, and needs to be investigated or repaired or replaced, at step 10679. In some embodiments, the wireless power transmitter is also capable of determining the root cause of the system malfunction, when the battery of the client device is not causing the low charging rate or loss of power.

In some embodiments, the wireless power transmitter communicates this information through automatic database replication, sending message across the system network between the transmitter and other system computers or through other suitable communication means. Furthermore, the operator or user may receive the alert and respond by configuring the wireless system to no longer wirelessly charge the client device, and then removing the client device from service so that it may be investigated, repaired or replaced or other suitable solutions.

If the wireless power transmitter determines that no evidence of a system or component fault is found in the data analyzed, the wireless power transmitter may continue to charge the client device, and continuously check, at step 10680, if the battery level of the client device is full. If the battery of the client device is not full, the wireless power transmitter may continue to transmit wireless power to the wireless power receiver connected to the client device to keep charging the client device. If the battery of the client device is already full or its time to stop charging the device, the wireless power transmitter stops charging the device, at step 10681, and the process may end.

Figure 105M:
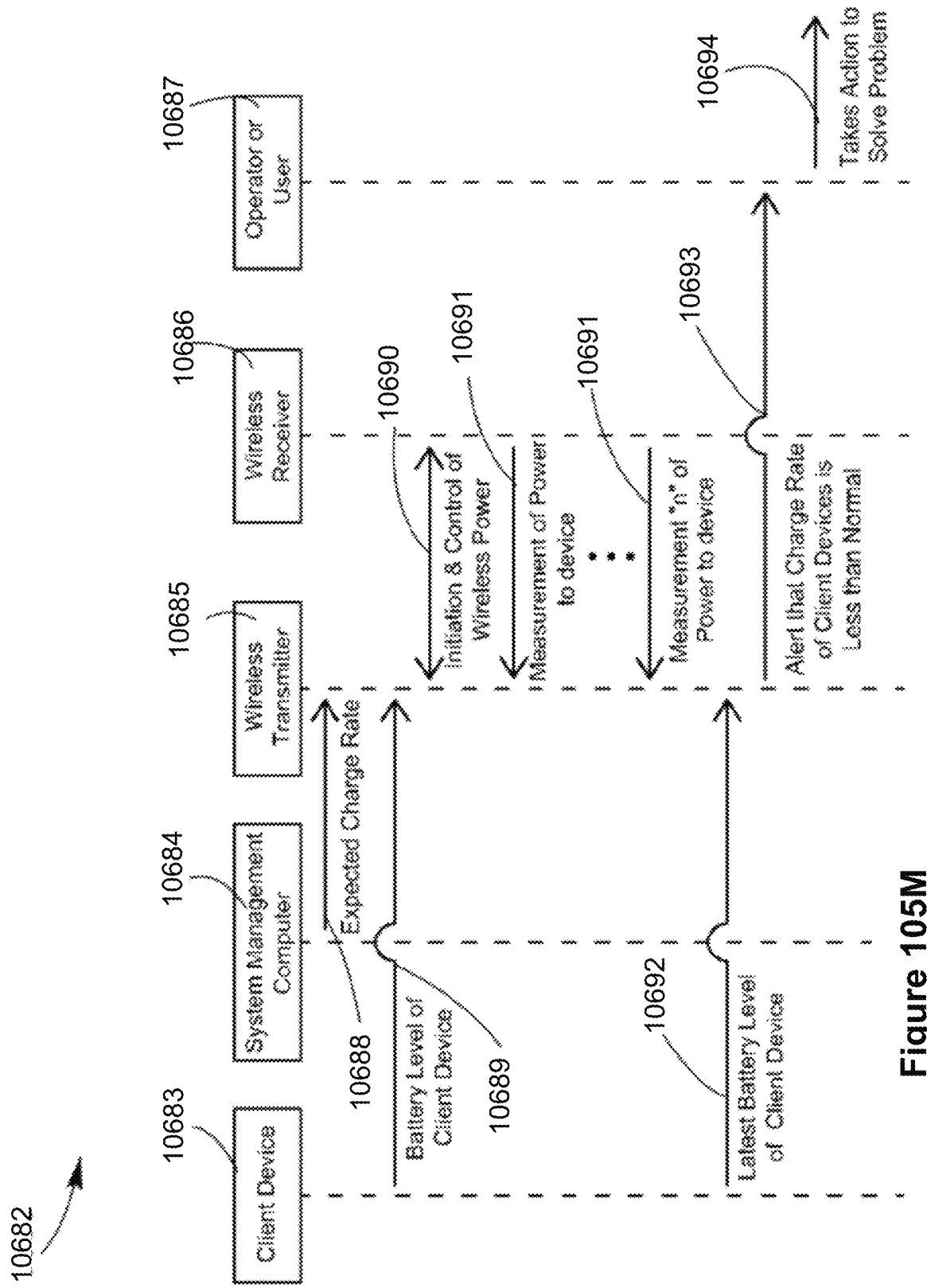

FIG. 105M is a sequence diagram 10682 of a method for monitoring battery performance, according to exemplary aspects of the present disclosure. Sequence diagram 10682 includes a client device 10683, a system management computer 10684, wireless power transmitter 10685, wireless power receiver 10686 and user or operator 10687.

System management computer first sends the expected charge rate 10688 of client device 10683 to the wireless power transmitter 10685. Then, client device 10683 sends information about client device's 10684 battery level 10689. Afterwards, wireless power transmitter 10685 starts delivering wireless power 10690 to wireless power receiver 10686, which is connected to client device 10683. Then, wireless power receiver constantly sends measurements 10691 of the amount power delivered to client device 10683. Subsequently, client device 10683 sends latest battery level 10692 to wireless power transmitter 10685. Using the measurements 10691 of the amount power delivered to client device 10683 and latest battery level 10692, wireless power transmitter 10685 calculates the rate of charge of client device 10683. In case the rate of charge of client device 10683 is below the threshold, wireless power transmitter sends and alert 10693 to user or operator 10687. Then, user or operator 10687 takes an action 10694 in order to correct the error.

For example, a family has a wireless power transmission system installed in their home. One member of their family configures the system to wirelessly power and charge a smartphone. The smartphone is several years old. The system automatically charges the smartphone whenever the smartphone is within power range of the system and the battery level of the smartphone is low enough to warrant charge. The family has installed into the smartphone the software app downloaded from a public app store, which is the system management app for the wireless power transmission system. This app automatically communicates value of the battery level of the smartphone to the system. After charging the smartphone, the system observes that the smartphone took three times longer than it should have to completely charge up. The system then communicates an alert of this problem to the owner of the family system by sending the owner a text message with the name of the smartphone and a brief description of the problem. The owner subsequently purchases a replacement smartphone.

In another example, a user purchases a wearable product that goes on user's wrist. The product contains wireless power receiver. The wireless power transmitter is in user's bedroom, and each night user goes to bed wearing product the wearable on the wrist of user. The wireless power transmission system then automatically charges the battery within the wearable by transmitting power from the transmitter in the bedroom a distance away from the power receiver, to the power receiver within the wearable on the wrist of the user. Each night, the wearable battery charges back up.

Beginning with the first time that the transmitter charged the wearable client device, the transmitter computed the charge rate of the wearable's battery. The wireless power transmission system has no reference information about the battery's charge rate for this particular wearable product.

After over a year, the wireless power transmission system detects that the amount of time to charge the wearable battery is now longer than it took when the user first began wirelessly charging the wearable with the system. Subsequently, the system issues an alert to the user by sending an e-mail containing a message that the wearable of the user is now taking longer to charge. Subsequently, the user replaces the wearable product with the latest model.

FIGS. 105A-105M illustrate examples of or relate to the wireless power transmission environment 100 described above with reference to FIG. 1. For the sake of brevity, certain details related to techniques for wirelessly delivering power described above in reference to FIG. 1 are not repeated here, as one of skill in the art will appreciate that these techniques apply to the embodiments of FIGS. 105A-105M.

Presented below are example embodiments of systems and methods for wireless power transmission.

In some embodiments, an example method for transmitting wireless power comprises identifying, by a transmitter, a first wireless power receiver coupled to a first electronic device within range of the transmitter, receiving, by the transmitter, a communication signal from the first power receiver comprising a battery power level of the first electronic device, receiving, by the transmitter from the first power receiver, a request to charge the first electronic device upon the first power receiver determining the battery power level in the first electronic device is below a predetermined threshold, generating, by the transmitter, two or more power transmission waves from a plurality of antennas forming controlled constructive interference patterns that converge at the first wireless power receiver, receiving, by the transmitter from the first power receiver, a request to stop charge of the first electronic device upon determining the battery power level is at a predetermined threshold, and stopping generation, by the transmitter, of the two or more power transmission waves from a plurality of antennas forming controlled constructive interference patterns that converge at the first wireless power receiver.

In some embodiments, the method further comprises receiving, by the transmitter, constant charge power values from the first electronic device.

In some embodiments, the method further comprises receiving, by the transmitter, constant communication signals comprising battery power level values from the first electronic device.

In some embodiments, the method further comprises calculating, by the transmitter, a present charging rate based on the battery power level values of the first electronic device.

In some embodiments, the method further comprises searching, by the transmitter, a reference table for an expected charging rate for the first electronic device.

In some embodiments, the method where when the present charging rate is less than the expected reference rate, transmitting an alert to the first electronic device.

In some embodiments, the method where when the present charging rate is less than the expected reference rate, discontinuing generation of two or more power transmission waves from the plurality of antennas that converge at the first wireless power receiver.

In some embodiments, the method further comprises determining, by the transmitter, a second wireless power receiver coupled to a second electronic device within range of the transmitter, receiving, by the transmitter, a communication signal from the second power receiver comprising a battery power level of the second electronic device, and receiving, by the transmitter from the second power receiver, a request to charge the second electronic device upon the second power receiver determining the battery power level in the second electronic device is below a predetermined threshold.

In some embodiments, the method further comprises assigning, by the transmitter, the plurality of antennas into a first group and a second group, and assigning, by the transmitter, a second group of the plurality of antennas to the second power receiver coupled to the second electronic device.

In some embodiments, an example system for transmitting wireless power comprises a transmitter configured to identify a first wireless power receiver coupled to a first electronic device within range of the transmitter, receive a communication signal from the first power receiver comprising a battery power level of the first electronic device, receive from the first power receiver, a request to charge the first electronic device upon the first power receiver determining the battery power level in the first electronic device is below a predetermined threshold, generate two or more power transmission waves from a plurality of antennas forming controlled constructive interference patterns that converge at the first wireless power receiver, receive from the first power receiver, a request to stop charge of the first electronic device upon determining the battery power level is at a predetermined threshold, and stop generation of the two or more power transmission waves from a plurality of antennas forming controlled constructive interference patterns that converge at the first wireless power receiver.

In some embodiments, the system transmitter further configured to receive communication comprising constant charge power values from the first electronic device.

In some embodiments, the system transmitter further configured to receive communication comprising constant battery power level values from the first electronic device.

In some embodiments, the system transmitter further configured to calculate a present charging rate based on the battery power level values of the first electronic device.

In some embodiments, the system transmitter further configured to search a reference table for an expected charging rate for the first electronic device.

In some embodiments, the system where when the present charging rate is less than the expected reference rate, the transmitter is further configured to transmit an alert to the first electronic device.

In some embodiments, the system where when the present charging rate is less than the expected reference rate, the transmitter is further configured to discontinue generation of two or more power transmission waves from the plurality of antennas to converge at the first wireless power receiver.

In some embodiments, the system transmitter further configured to determine a second wireless power receiver coupled to a second electronic device within range of the transmitter, receive a communication signal from the second power receiver comprising a battery power level of the second electronic device, receive from the second power receiver a request to charge the second electronic device upon the second power receiver determining the battery power level in the second electronic device is below a predetermined threshold.

In some embodiments, the system transmitter further configured to assign the plurality of antennas into a first group and a second group; and assign a second group of the plurality of antennas to the second power receiver coupled to the second electronic device.

Features of the present invention can be implemented in, using, or with the assistance of a computer program product, such as a storage medium (media) or computer readable storage medium (media) having instructions stored thereon/in which can be used to program a processing system to perform any of the features presented herein. The storage medium (e.g., memory 106) can include, but is not limited to, high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. Memory 106 optionally includes one or more storage devices remotely located from the CPU(s) 104. Memory 106, or alternatively the non-volatile memory device(s) within memory 106, includes a non-transitory computer readable storage medium.

Stored on any one of the machine readable medium (media), features of the present invention can be incorporated in software and/or firmware for controlling the hardware of a processing system (such as the components associated with the transmitters 102 and/or receivers 120), and for enabling a processing system to interact with other mechanisms utilizing the results of the present invention. Such software or firmware may include, but is not limited to, application code, device drivers, operating systems, and execution environments/containers.

Communication systems as referred to herein (e.g., communications component 112, FIG. 1) optionally communicate via wired and/or wireless communication connections. Communication systems optionally communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. Wireless communication connections optionally use any of a plurality of communications standards, protocols and technologies, including but not limited to radio-frequency (RF), radio-frequency identification (RFID), infrared, radar, sound, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), ZIGBEE, wideband code division multiple access (W-CDMA), code division multiple access (CDMA), time division multiple access (TDMA), BLUETOOTH, Wireless Fidelity (WI-FI) (e.g., IEEE 102.11a, IEEE 102.11ac, IEEE 102.11 ax, IEEE 102.11 b, IEEE 102.11 g and/or IEEE 102.11 n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A wireless-power transmitter configured to wirelessly power a security camera, comprising:
   a processor in communication with a wireless-power transmitter; and
   one or more programs, wherein the one or more programs are configured to be executed by the processor, the one or more programs including instructions for causing the wireless-power transmitter to:
      emit a first set of one or more radio frequency (RF) signals to a security camera coupled to a wireless-power receiver, wherein:
         the wireless-power receiver is configured to receive the first set of one or more RF signals from the wireless-power transmitter;
         the security camera includes at least one component for converting energy from the first set of one or more RF signals into usable power to power the security camera, and
         the usable power is a primary source of power for the security camera; and
      in accordance with a determination that the security camera has moved relative to the wireless-power transmitter, adjust transmission characteristics used to emit a second set of one or more RF signals from the wireless-power transmitter to continue providing usable power to the security camera.

2. A system for wirelessly powering a security camera, comprising:
   a wireless-power transmitter configured to emit a first set of one or more radio frequency (RF) signals;

a security camera coupled to a wireless-power receiver, wherein:
- the wireless-power receiver is configured to receive the first set of one or more RF signals from the wireless-power transmitter;
- the security camera includes at least one component for converting energy from the first set of one or more RF signals into usable power to power the security camera, and
- the usable power is a primary source of power for the security camera; and a processor in communication with the wireless-power transmitter configured to:
- in accordance with a determination that the security camera has moved relative to the wireless-power transmitter, adjust transmission characteristics used to emit a second set of one or more RF signals from the wireless-power transmitter to continue providing usable power to the security camera.

3. The system of claim 2, wherein:
the wireless-power transmitter is configured to receive, from the wireless-power receiver, a communication signal indicating a power requirement of the security camera;
the wireless-power transmitter is configured to, in response to receiving the communication signal from the wireless-power receiver:
- determine a location of the security camera based on the communication signal;
- generate a plurality of RF waves; and
- control transmission of the RF waves through at least two antenna elements coupled to the transmitter, wherein the transmitter is configured to shift a phase and a gain of a respective RF wave with respect to other respective RF waves so that the plurality of RF waves converge to form a constructive interference pattern in proximity to the location of the security camera.

4. The system of claim 2 wherein the wireless-power receiver is embedded in a RF transparent housing that is adapted to electrically connect the security camera with the receiver.

5. The system of claim 4, wherein the wireless-power receiver is separated from the wireless-power transmitter by a non-zero distance.

6. The system of claim 4, wherein the RF transparent housing supports the security camera.

7. The system of claim 2, further comprising: a plurality of security cameras, each security camera of the plurality of security cameras is coupled to a respective wireless-power receiver, wherein each respective wireless-power receiver is configured to receive one or more respective additional RF signals from the wireless-power transmitter, wherein the one or more additional RF signals are distinct from the one or more RF signals.

8. The system of claim 7, wherein each respective wireless-power receiver is configured to receive energy from one or more respective additional RF signals from the wireless-power transmitter simultaneously.

9. The system of claim 7, wherein the processor is further configured to:
in accordance with a determination that another security camera of the plurality of security cameras has moved relative to the wireless-power transmitter, cause adjustment to a transmission characteristic of at least one of the one or more additional RF signals from the wireless-power transmitter to continue providing usable power to the other security camera.

10. The system of claim 9, wherein the processor is further configured to:
in accordance with the determination that another security camera of the plurality of security cameras has moved relative to the wireless-power transmitter, cause a remainder of the plurality of security cameras continue to receive the one or more additional RF signals from the wireless-power transmitter.

11. The system of claim 2, further comprising:
a second wireless-power transmitter, in communication with the processor, configured to emit a third set of one or more RF signals; and
the processor in communication with the wireless-power transmitter further configured to:
- in accordance with a determination that the security camera has moved outside of a transmission range of the wireless-power transmitter, stop the wireless-power transmitter from emitting RF signals to stop providing usable power to the security camera; and
- in accordance with a determination that the security camera has moved into a transmission range of the second wireless-power transmitter, adjust a transmission characteristic of the second wireless-power transmitter used to emit a third set of one or more RF signals from the second wireless-power transmitter to provide usable power to the security camera.

12. The system of claim 2, wherein:
the wireless-power transmitter is configured to:
control creation of constructive interference patterns from a convergence of two or more RF waves to form a pocket of energy in 3D space at the security camera.

13. The system of claim 2, wherein the determination that the security camera has moved relative to the wireless-power transmitter is at least partially based on the wireless-power receiver communicating location data to the wireless-power transmitter.

14. The system of claim 2, wherein the adjusting the transmission characteristic used to emit the one or more RF signals from the wireless-power transmitter to continue providing usable power to the security camera includes changing phase and gain in at least one antenna of the wireless-power transmitter.

15. The system of claim 2, wherein the wireless-power receiver is integrated with the with the security camera.

16. The system of claim 2, wherein energy from RF signals emitted by the wireless-power transmitter is a sole source of power the security camera.

17. A non-transitory computer-readable storage medium comprising instructions that, when executed by a processor in communication with a wireless-power transmitter, the wireless power transmitter configured to wirelessly power a security camera, cause the wireless-power transmitter to:
emit a first set of one or more radio frequency (RF) signals to provide usable power to a security camera coupled to a wireless-power receiver, wherein:
- the wireless-power receiver is configured to receive the first set of one or more RF signals from the wireless-power transmitter, and
- the security camera includes at least one component for converting energy from the first ser of one or more RF signals into usable power to power the security camera;
- the usable power is a primary source of power for the security camera; and in accordance with a determination that the security camera has moved relative to the wireless-power transmitter, adjust transmission characteristic used to emit a second set of one or more RF signals to continue to provide usable power to the security camera.

\* \* \* \* \*